United States Patent
Chen et al.

(10) Patent No.: US 10,529,928 B2
(45) Date of Patent: Jan. 7, 2020

(54) COMPOUND AND ORGANIC ELECTRONIC DEVICE USING THE SAME

(71) Applicant: NICHEM FINE TECHNOLOGY CO., LTD., Jhubei, Hsinchu County (TW)

(72) Inventors: Chi-Chung Chen, Jhubei (TW); Shwu-Ju Shieh, Jhubei (TW); Liang-Di Liao, Jhubei (TW); Hui-Ling Wu, Jhubei (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 374 days.

(21) Appl. No.: 15/466,319

(22) Filed: Mar. 22, 2017

(65) Prior Publication Data
US 2017/0279050 A1    Sep. 28, 2017

Related U.S. Application Data

(60) Provisional application No. 62/312,948, filed on Mar. 24, 2016.

(51) Int. Cl.
*H01L 51/54* (2006.01)
*C09K 11/06* (2006.01)
(Continued)

(52) U.S. Cl.
CPC .......... *H01L 51/006* (2013.01); *C07C 211/61* (2013.01); *C07D 307/77* (2013.01); *C07D 307/91* (2013.01); *C07D 333/50* (2013.01); *C07D 409/12* (2013.01); *H01L 51/0056* (2013.01); *H01L 51/0061* (2013.01); *H01L 51/0073* (2013.01); *H01L 51/0074* (2013.01); *C07C 2603/18* (2017.05);
(Continued)

(58) Field of Classification Search
CPC ............... C07C 211/61; C07C 2603/18; C07C 2603/98; C07D 307/77; C07D 307/91; C07D 333/50; C07D 409/12; H01L 51/0032; H01L 51/005; H01L 51/0056; H01L 51/0058; H01L 51/006; H01L 51/0072; H01L 51/0073; H01L 51/0074; H01L 51/50; H01L 51/5012; H01L 51/5016; H01L 51/5056; H01L 51/5064
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

2014/0312311 A1* 10/2014 Chen .................... H01L 51/006 257/40
2017/0317283 A1* 11/2017 Mujica-Fernaud ................. H01L 51/006

FOREIGN PATENT DOCUMENTS

CN            106432107 A    †  2/2017
WO    WO 2016/087017 A1       6/2016

OTHER PUBLICATIONS

Evidence-16: Doubly Ortho-linked Quinoxaline/Triarylamine Hybrid as a Bifunctional, Dipolar Electroluminescent Template for Optoelectronic Applications, pp. 1-12, by Chien-Tien Chen et al., Publication Date: 2005, which is 1H NMR spectroscopic data (pp. 5 and 6) in Supporting Information from Evidence-15. Pages/Lines Cited: p. 5 and 6.†
Evidence-15: Doubly ortho-linked quinoxaline/triarylamine hybrid as a bifunctional, dipolar electroluminescent template for optoelectronic applications, pp. 3980-3982, Chien-Tien Chen et al., Chem. Commun, Publication Date: Jul. 8, 2005. Pages/Lines Cited: p. 3980 printed on bottom left corner.†
Evidence-14: Supplementary Information—Polycationic ligands in gold catalysis: Synthesis and applications of extremely π-acidic catalysts, pp. S1-S231, by Javier Carreras et al., Publication Date: 2013, which is 1H NMR spectrum (p. S200) in Supporting Information from Evidence-13. Pages/Lines Cited: S200 printed on bottom right corner.†

(Continued)

*Primary Examiner* — Andrew K Bohaty
(74) *Attorney, Agent, or Firm* — Birch, Stewart, Kolasch & Birch, LLP

(57) ABSTRACT

Provided are a novel compound and an organic electronic device using the same. The novel compound is represented by the following Formula (I):

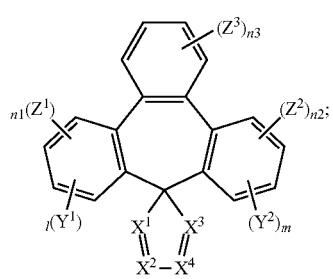

Formula (I)

wherein $X^1$ and $X^2$ are each independently $C(R^a)$, and the two $(R^a)$s are the same or different; $X^3$ and $X^4$ are each independently $C(R^b)$, and the two $(R^b)$s are the same or different; the two $(R^a)$s are joined together to form an aryl ring and the two $(R^b)$s are joined together to form an oxygen-containing heteroaryl ring, a sulfur-containing heteroaryl ring, or a polycyclic aromatic ring; wherein $Y^1$ and $Y^2$ are the same or different; $Y^1$ and $Y^2$ are each represented by NR'R"; R' and R" are the same or different; at least one of R' and R" is an aryl group.

20 Claims, 18 Drawing Sheets

(51) Int. Cl.
H01L 51/00 (2006.01)
C07C 211/61 (2006.01)
C07D 307/77 (2006.01)
C07D 307/91 (2006.01)
C07D 333/50 (2006.01)
C07D 409/12 (2006.01)
H01L 51/50 (2006.01)

(52) U.S. Cl.
CPC ...... C07C 2603/98 (2017.05); H01L 51/0058 (2013.01); H01L 51/5056 (2013.01); H01L 51/5064 (2013.01)

(56) References Cited

OTHER PUBLICATIONS

Evidence-13: Polycationic Ligands in Gold Catalysis: Synthesis and Applications of Extremely π‑Acidic Catalysts, pp. 18815-18823, by Javier Carreras et al., Journal of the American Chemical Society, Publication Date: Dec. 5, 2013. Pages/Lines Cited: p. 18817 printed on bottom.†
Evidence-12: The Synthesis of Novel p-Quinone Methides: O-Dealkylation of 5-(p-Alkyloxyaryl)-10,11-dihydrodibenzo[a,d]cyclohepten-5-ols and Related Compounds, pp. 2607-2619, by Benjamin Taljaard et al., Eur. J. Org. Chem., Publication Date: Dec. 31, 2005. Pages/Lines Cited: p. 2612 printed on bottom left corner, right col.†
Evidence-11: Supporting Information for: Switching of Non-Helical Overcrowded Heptafulvalene Derivatives, pp. 1-59, by Jiye Luo et al., Publication Date: 2011, which is 1H NMR spectrum (p. 30) in Supporting Information from Evidence-10. Pages/Lines Cited: p. 30.†
Evidence-10: Switching of non-helical overcrowded tetrabenzoheptafulvalene derivatives, pp. 2029-2034, by Jiye Luo et al., Chemical Science, Publication Date: Jul. 21, 2011. Pages/Lines Cited: p. 2031 printed on bottom right corner, left col.†
Evidence-9: Doubly Ortho-linked cis-4,4'-Bis(diarylamino)stilbene/ Fluorene Hybrids as Efficient Non-doped, Sky-blue Fluorescent Materials for Optoelectronic Applications, pp. S1-S22, by Yi Wei et al., 2007, which is 1H NMR spectrum (p. S16) in Supporting Information from Evidence-8. Pages/Lines Cited: S16 printed on top right corner.†
Evidence-8: Doubly Ortho-Linked cis-4,4'-Bis(diarylamino)stilbene/ Fluorene Hybrids as Efficient Nondoped, Sky-Blue Fluorescent Materials for Optoelectronic Applications, pp. 7478-7479, by Yi Wei et al., J. Am. Chem. Soc., Publication Date: May 25, 2007. Pages/Lines Cited: p. 7478 printed on bottom left corner, right col.†
Evidence-7: Doubly Ortho-linked Quinoxaline/Diphenylfluorene Hybrids as Bipolar, Fluorescent Chameleons for Optoelectronic Applications, pp. S1-S23, by Chien-Tien Chen et al., Publication Date: 2006, which is 1H NMR spectrum (p. S20) in Supporting Information from Evidence-6. Pages/Lines Cited: S20 printed on top right corner.†
Evidence-6: Doubly Ortho-Linked Quinoxaline/Diphenylfluorene Hybrids as Bipolar, Fluorescent Chameleons for Optoelectronic Applications, pp. 10992-10993, Chien-Tien Chen et al., J. Am. Chem. Soc., Publication Date: Aug. 8, 2006. Pages/Lines Cited: p. 10992 printed on bottom left corner, right col.†
Evidence-5: hint of step 4 "Check that the integration of the peak matches the number of hydrogens in the molecule", webpage of Golden Rules to Nuclear Magnetic Resonance Spectroscopy (NMR) Analysis, 1 page, by Dr. Madalee Gassaway, Publication Date: Oct. 23, 2017 (from http://blog.cambridgecoaching.com/golden-rules-to-nuclear-magnetic-resonance-spectroscopy-nmr-analysis-part-1-0); Pages/Lines Cited : hint of step 4, webpage of Golden Rules to Nuclear Magnetic Resonance Spectroscopy (NMR) Analysis.†
Evidence-4: Proton Nuclear Magnetic Resonance Spectroscopy, Lecture of Structure Determination Using Spectroscopic Methods at University of Wisconsin, pp. 1-38, by Dr. Hans J. Reich, 2017 (from https://www.chem.wisc.edu/areas/reich/nmr/Notes-05-HMR-v26-part1.pdf); Pages/Lines Cited: p. 8, lines 3-4, Proton Nuclear Magnetic Resonance Spectroscopy.†
Evidence-3: Real-Time Enzyme Kinetics by Quantitative NMR Spectroscopy and Determination of the Michaelis−Menten Constant Using the Lambert‑W Function, pp. 1943-1948, by Cheenou Her et al., J. Chem. Educ., 2015; Pages/Lines Cited: p. 1946 printed on bottom, right col., lines 13-17.†
Evidence-2: Integration of 1H NMR spectra (proton) from NMR theory of Spectroscopy of Organic Chemistry Lecture Website at University of Colorado Boulder, which was built by Dr. Patty Feist et al. (from < http://www.orgchemboulder.com:80/Spectroscopy/ nmrtheory/NMRtutorial.shtml> 1 page, Dec. 14, 2016, retrieved from Internet Wayback Machine < http://web.archive.org/web/20161214110543/http://www.orgchemboulder.com:80/Spectroscopy/nmrtheory/NMRtutorial.shtml> on Feb. 7, 2018); Pages/Lines Cited: lines 2-3 & 4-5.†
Evidence-1: Organic Chemistry (eighth edition), Paula Yurkanis Bruice, Global Edition, pp. 660, 661, 668, 678, Publication Date: Jan. 15, 2016, Pearson Education, Inc., NJ, USA; Pages/Lines Cited: pp. 660, 661, 668, 678.†

\* cited by examiner
† cited by third party

COMPOUND AND ORGANIC ELECTRONIC DEVICE USING THE SAME

CROSS-REFERENCE TO RELATED APPLICATION

Pursuant to 35 U.S.C. § 119(e), this application claims the benefits of the priority to U.S. Provisional Patent Application No. 62/312,948, filed Mar. 24, 2016. The contents of the prior applications are incorporated herein by its entirety.

BACKGROUND OF THE INVENTION

1. Field of the Invention

The present invention relates to a novel compound and an organic electronic device using the same, more particularly to a novel compound as hole-transporters and an organic electronic device using the same.

2. Description of the Prior Arts

With the advance of technology, various organic electronic devices that make use of organic materials have been energetically developed. Examples of organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching Tang and Steven Van Slyke of Kodak Company deposited an electron transport material such as tris(8-hydroxyquinoline)aluminum(III) (abbreviated as $Alq_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons, thereby emitting a light when the excitons decay from excited state to ground state.

Another approach is to modify the material of HTL to exhibit electron-blocking ability. Examples of conventional hole transport materials include $N^1,N^{1'}$-(biphenyl-4,4'-diyl)bis($N^1$-(naphthalen-1-yl)-$N^4,N^{4'}$-diphenylbenzene-1,4-diamine); or $N^4,N^{4'}$-di(naphthalen-1-yl)-$N^4,N^{4'}$-diphenylbiphenyl-4,4'-diamine (NPB).

However, even using the foresaid hole transport materials, the current efficiency of OLEDs still needs to be improved.

Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to improve the efficiency of the organic electronic device.

To achieve the foresaid objectives, the present invention provides a novel compound represented by the following Formula (I):

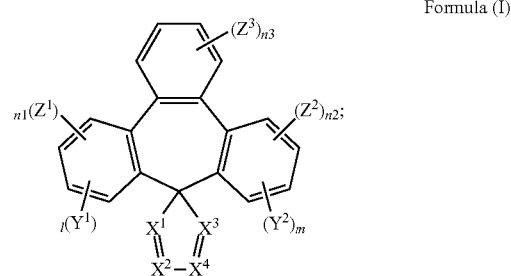

Formula (I)

wherein $X^1$ and $X^2$ are each independently $C(R^a)$, and the two $(R^a)$s are the same or different; $X^3$ and $X^4$ are each independently $C(R^b)$, and the two $(R^b)$s are the same or different; the two $(R^a)$s are joined together to form an aryl ring and the two $(R^b)$s are joined together to form an oxygen-containing heteroaryl ring, a sulfur-containing heteroaryl ring, or a polycyclic aromatic ring;

wherein $Y^1$ and $Y^2$ are the same or different; $Y^1$ and $Y^2$ are each represented by NR'R"; R' and R" are the same or different; at least one of R' and R" is an aryl group;

wherein $Z^1$ to $Z^3$ are each independently selected from the group consisting of: a deuterium atom, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 carbon atoms, a heterocycloalkyl group having 3 to 60 carbon atoms, an aryl group having 6 to 60 carbon atoms, a heteroaryl group having 3 to 60 carbon atoms, an alkoxy group having 1 to 40 carbon atoms, an aryloxy group having 6 to 60 carbon atoms, an alkylsilyl group having 1 to 40 carbon atoms, an arylsilyl group having 6 to 60 carbon atoms, an alkylboron group having 1 to 40 carbon atoms, an arylboron group having 6 to 60 carbon atoms, a phosphine group having 1 to 40 carbon atoms, and a phosphine oxide group having 1 to 40 carbon atoms;

wherein l is an integer from 1 to 4; m is an integer from 0 to 4; n1 is an integer from 0 to 3; n2 is an integer from 0 to 4; n3 is an integer from 0 to 4; the total of n1 and l is not more than 4; the total of n2 and m is not more than 4.

Preferably, $Z^1$ to $Z^3$ are each independently selected from the group consisting of: a deuterium atom, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 30 carbon atoms, an alkoxy group having 1 to 12 carbon atoms, an aryloxy group having 6 to 30 carbon atoms, an alkylsilyl group having 1 to 12 carbon atoms, an arylsilyl group having 6 to 30 carbon atoms, an alkylboron group having 1 to 12 carbon atoms, an arylboron group having 6 to 30 carbon atoms, a phosphine group having 1 to 12 carbon atoms, and a phosphine oxide group having 1 to 12 carbon atoms.

Preferably, the oxygen-containing heteroaryl ring contains at least one furan group.

For example, the compound is represented by any one of the following Formulae (I-I) to (1-VI):

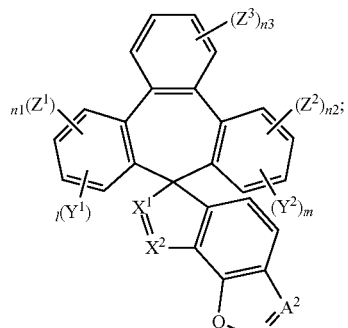

Formula (I-I)

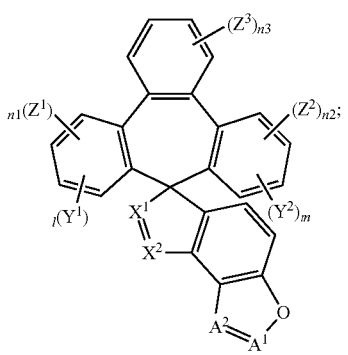

Formula (I-II)

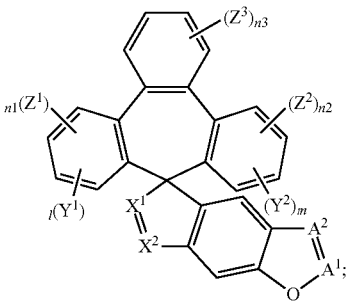

Formula (I-III)

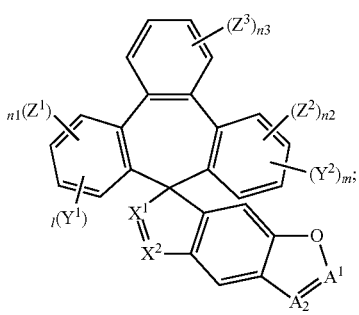

Formula (I-IV)

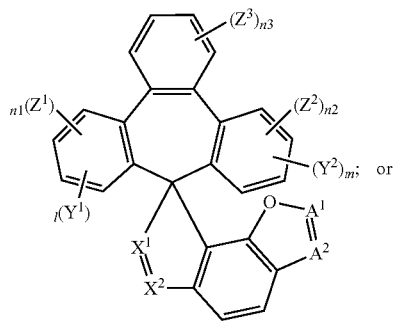

Formula (I-V)

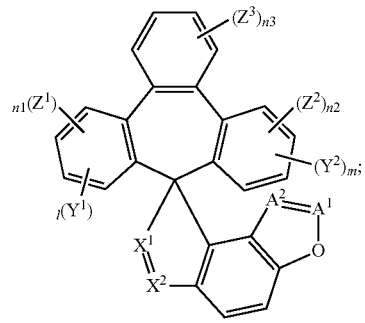

Formula (I-VI)

wherein $A^1$ and $A^2$ are each independently) $C(R^c)$; the two $(R^c)$s are the same or different, and the two $(R^c)$s are joined together with the double bond of $A^1$ and $A^2$ to form an aromatic structure contained in the oxygen-containing heteroaryl ring.

Preferably, the aromatic structure contained in the oxygen-containing heteroaryl ring, which is formed by the two joined $C(R^c)$s and the double bond of $A^1$ and $A^2$, may be a substituted or unsubstituted 6 to 20-membered carbon cyclic structure, for example, but not limited to, a substituted or unsubstituted benzene structure. The substitution group on the 6 to 20-membered carbon cyclic structure may be, but not limited to, a halogen group, a cyano group, a nitro group, an alkyl group having 1 to 12 carbon atoms, an alkenyl group having 2 to 12 carbon atoms, or an alkynyl group having 2 to 12 carbon atoms.

Preferably, the sulfur-containing heteroaryl ring contains at least one thiofuran group.

For example, the compound is represented by any one of the following Formulae (II-I) to (II-VI):

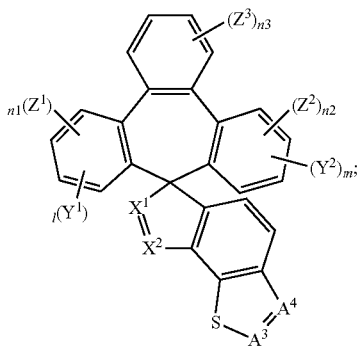

Formula (II-I)

-continued

Formula (II-II)
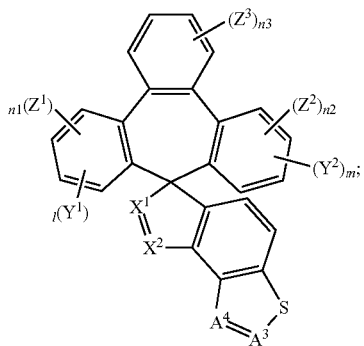

Formula (II-III)
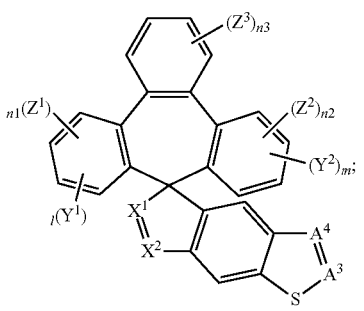

Formula (II-IV)
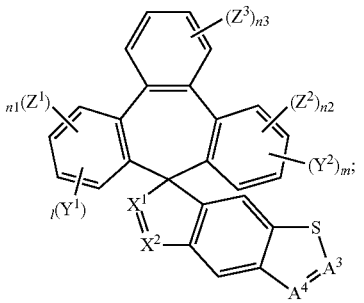

Formula (II-V)
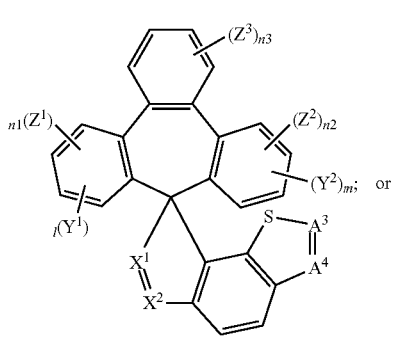

Formula (II-VI)
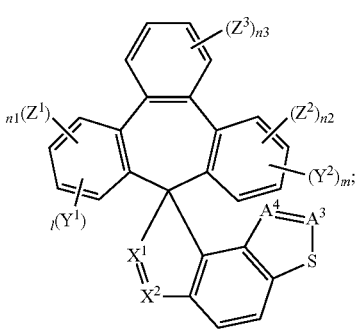

wherein $A^3$ and $A^4$ are each independently $C(R^d)$, the two $(R^d)$s are the same or different, and the two $(R^d)$s are joined together with the double bond of $A^3$ and $A^4$ to form an aromatic structure contained in the sulfur-containing heteroaryl ring.

Preferably, the aromatic structure contained in the sulfur-containing heteroaryl ring, which is formed by the two joined $C(R^d)$s and the double bond of $A^3$ and $A^4$, may be a substituted or unsubstituted 6 to 20-membered carbon cyclic structure, for example, but not limited to, a substituted or unsubstituted benzene structure. The substitution group on the 6 to 20-membered carbon cyclic structure may be, but not limited to, a halogen group, a cyano group, a nitro group, an alkyl group having 1 to 12 carbon atoms, an alkenyl group having 2 to 12 carbon atoms, or an alkynyl group having 2 to 12 carbon atoms.

Preferably, the polycyclic aromatic ring, which is formed by the two joined $C(R^b)$s and the double bond of $X^3$ and $X^4$, is selected from the group consisting of: a benzene ring, a dimethylfluorene, a naphthalene ring, an anthracene ring, a phenanthrene ring, a tetracene ring, a chrysene ring, a triphenylene ring, a pyrene ring, a perylene ring, a pentacene ring, a benzopyrene ring, a corannulene ring, a benzoperylene ring, a coronene ring, an ovalene ring, and a benzofluorine ring, an indene ring, a fluoranthene ring, and a benzofluoranthene ring.

For example, the compound is represented by any one of the following Formulae (III-I) to (III-XVIII):

Formula (III-I)
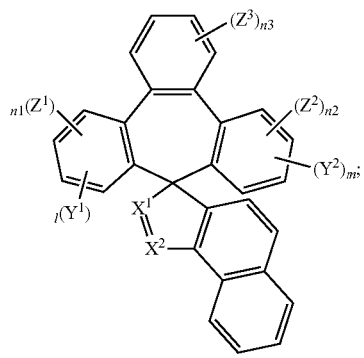

Formula (III-II)
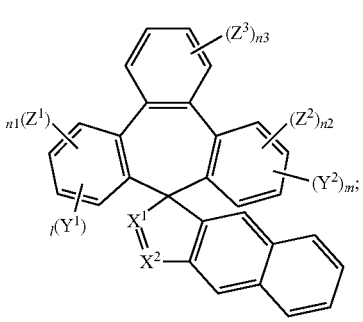

Formula (III-III)
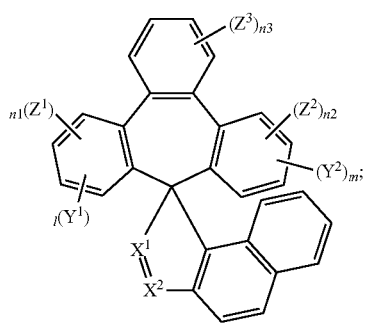
Formula (III-IV)
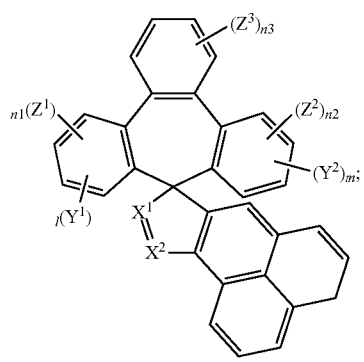
Formula (III-V)
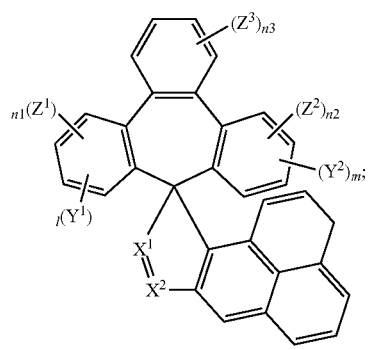
Formula (III-VI)
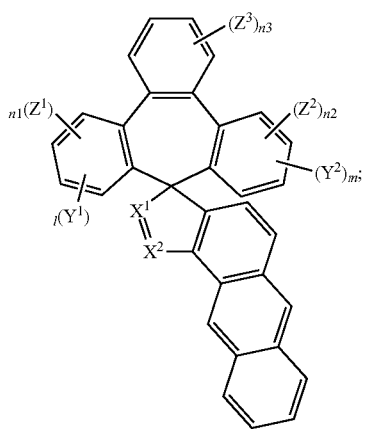
Formula (III-VII)
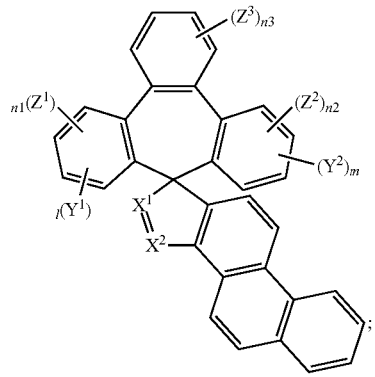
Formula (III-VIII)
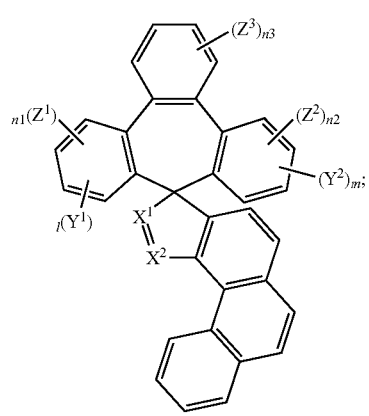
Formula (III-IX)
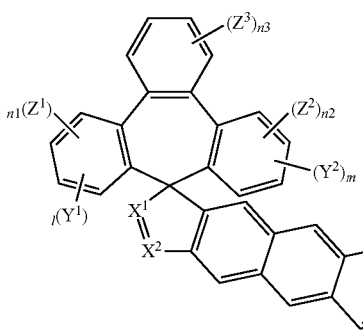
Formula (III-X)
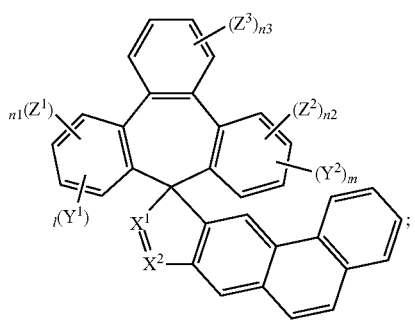

Formula (III-XI)
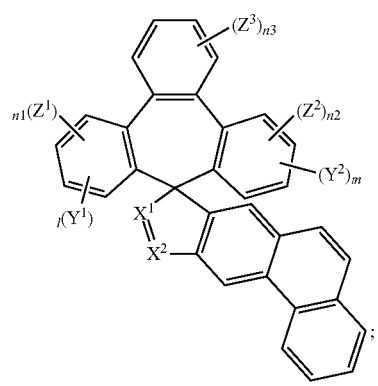
Formula (III-XII)
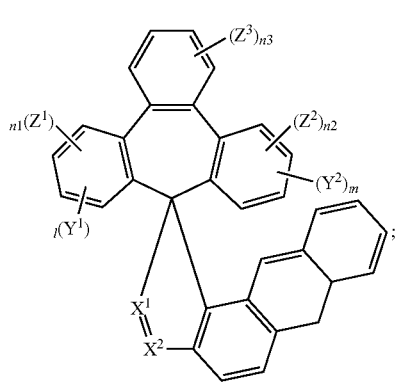
Formula (III-XIII)
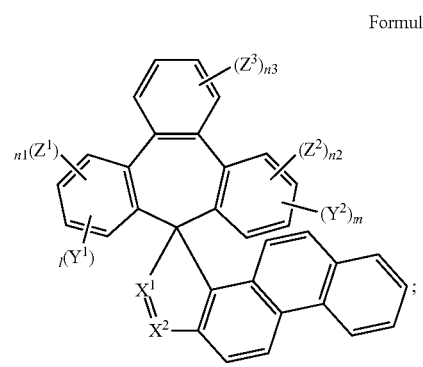
Formula (III-XIV)
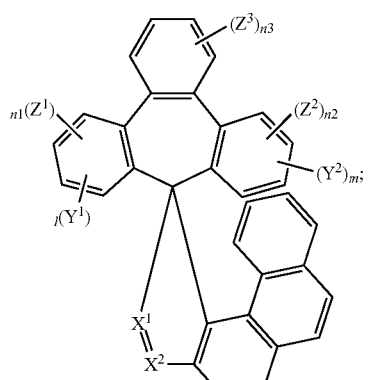
Formula (III-XV)
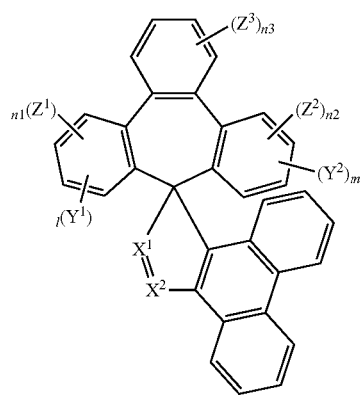
Formula (III-XVI)
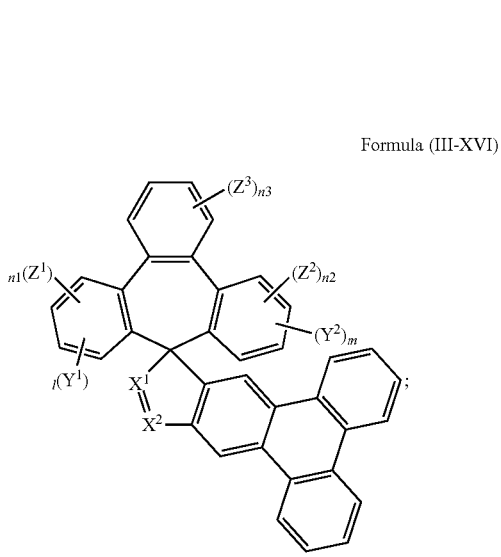
Formula (III-XVII)
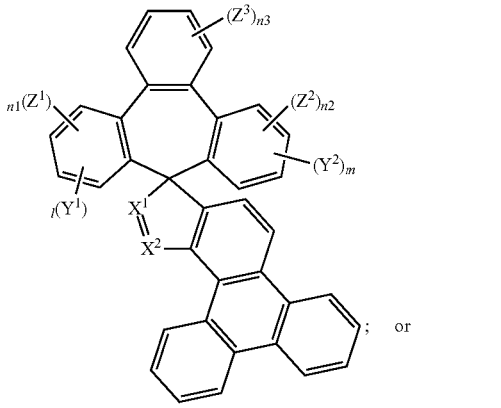
or Formula (III-XVIII)

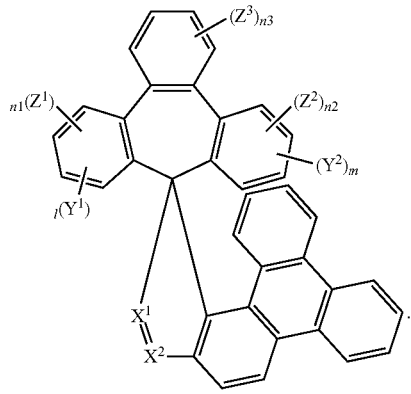

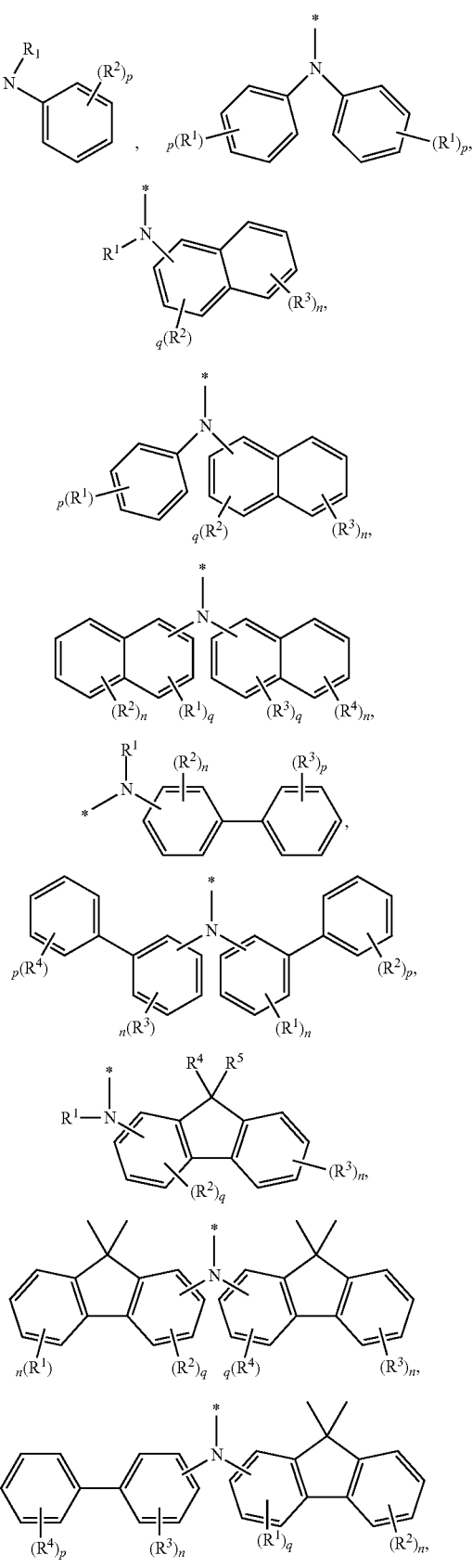

Preferably, the aryl ring formed by the two joined C(R$^a$)s and the double bond of X$^1$ and X$^2$ is selected from the group consisting of: a substituted or unsubstituted benzene ring, a substituted or unsubstituted dimethylfluorene, a substituted or unsubstituted naphthalene ring, a substituted or unsubstituted anthracene ring, a substituted or unsubstituted phenanthrene ring, a substituted or unsubstituted tetracene ring, a substituted or unsubstituted chrysene ring, a substituted or unsubstituted triphenylene ring, a substituted or unsubstituted pyrene ring, a substituted or unsubstituted perylene ring, a substituted or unsubstituted pentacene ring, a substituted or unsubstituted benzopyrene ring, a substituted or unsubstituted corannulene ring, a substituted or unsubstituted benzoperylene ring, a substituted or unsubstituted coronene ring, a substituted or unsubstituted ovalene ring, a substituted or unsubstituted benzofluorine ring, a substituted or unsubstituted indene ring, a substituted or unsubstituted fluoranthene ring, and a substituted or unsubstituted benzofluoranthene ring.

Preferably, the aryl ring formed by the two joined C(R$^a$)s and the double bond of X$^1$ and X$^2$ is a substituted or unsubstituted 6 to 60-membered aryl ring. The substitution group on the 6 to 60-membered carbon ring may be, but not limited to, a halogen group, a cyano group, a nitro group, an alkyl group having 1 to 12 carbon atoms, an alkenyl group having 2 to 12 carbon atoms, or an alkynyl group having 2 to 12 carbon atoms.

Preferably, R' contained in Y$^1$ and/or Y$^2$ is the aryl group and R" contained in Y$^1$ and/or Y$^2$ is selected from the group consisting of: an alkyl group having 1 to 40 carbon atoms, an alkenyl group having 2 to 40 carbon atoms, an alkynyl group having 2 to 40 carbon atoms, a cycloalkyl group having 3 to 60 carbon atoms, and an aryl group having 6 to 60 carbon atoms.

More preferably, R' and R" contained in Y$^1$ and/or Y$^2$ may each independently be the aryl group having 6 to 60 carbon atoms. The aryl group of R' and the aryl group of R" may be the same or different.

R' and R" contained in Y$^1$ and/or Y$^2$ are each independently selected from the group consisting of: an alkyl group having 1 to 40 carbon atoms, an alkenyl group having 2 to 40 carbon atoms, an alkynyl group having 2 to 40 carbon atoms, a cycloalkyl group having 3 to 60 carbon atoms, and an aryl group having 6 to 60 carbon atoms.

In addition, R' and R" contained in Y$^1$ and/or Y$^2$ can be joined together to form an aromatic cyclic structure.

Preferably, Y$^1$ and Y$^2$ in Formula (I) are each independently selected from the group consisting of:

-continued
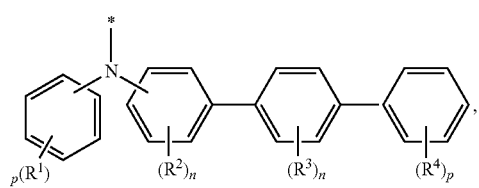
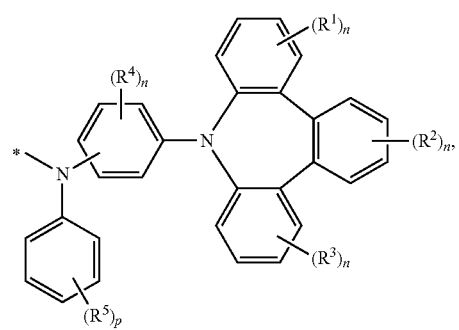
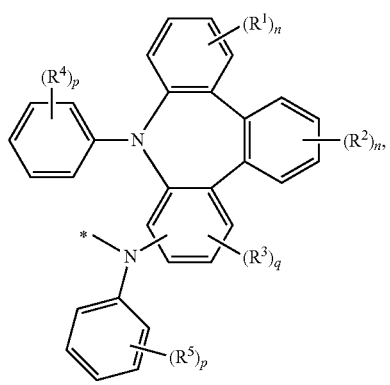
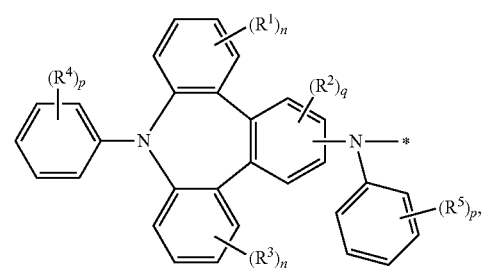
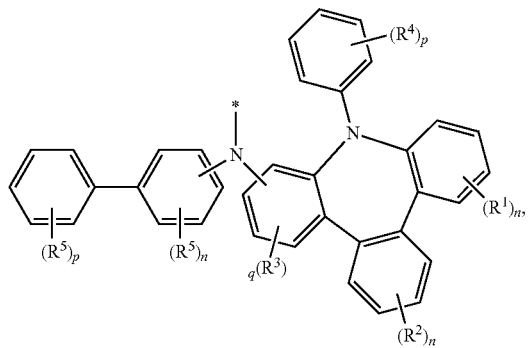
-continued
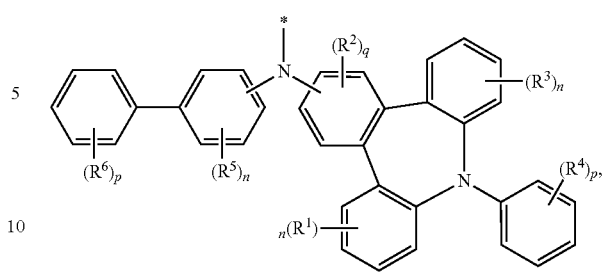
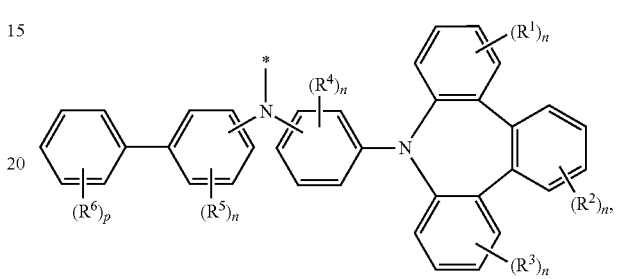
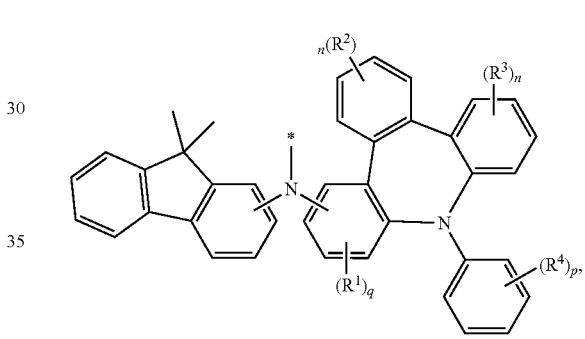
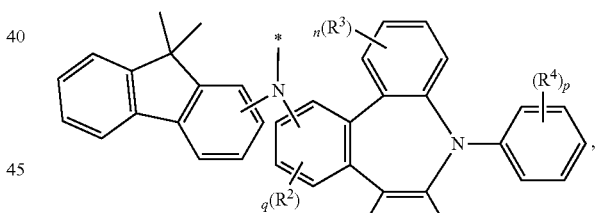
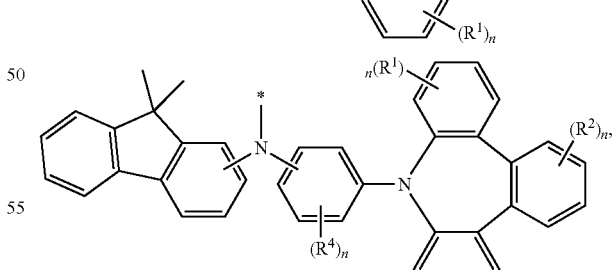
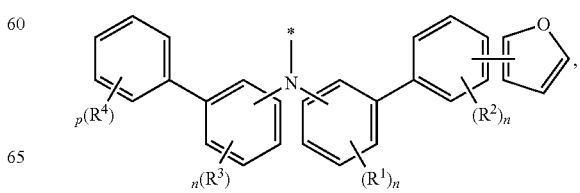

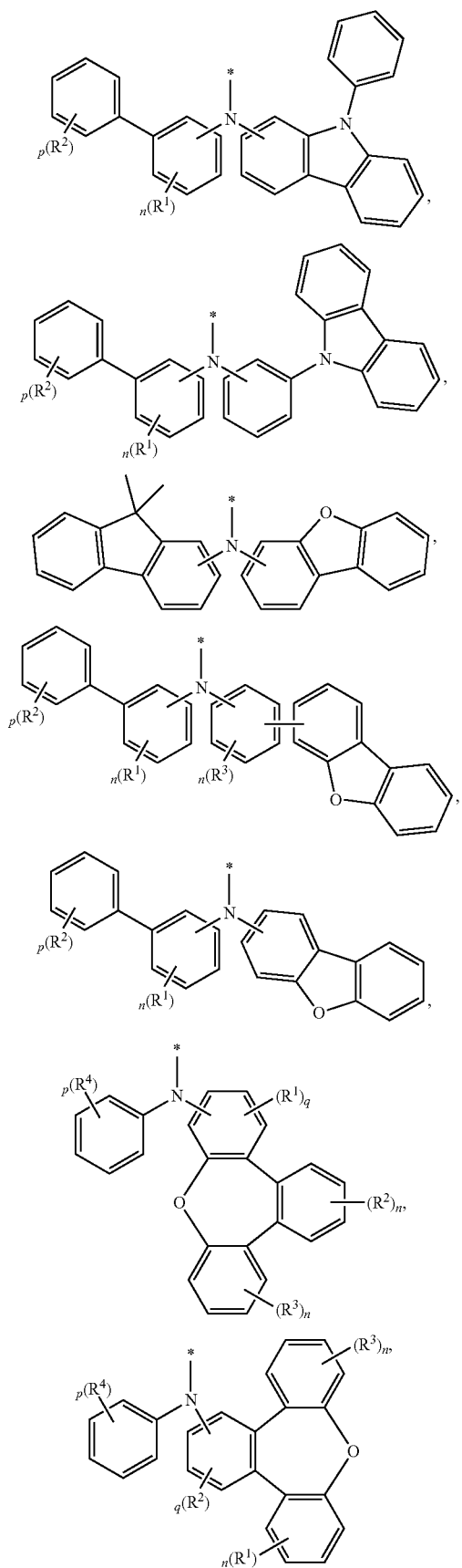
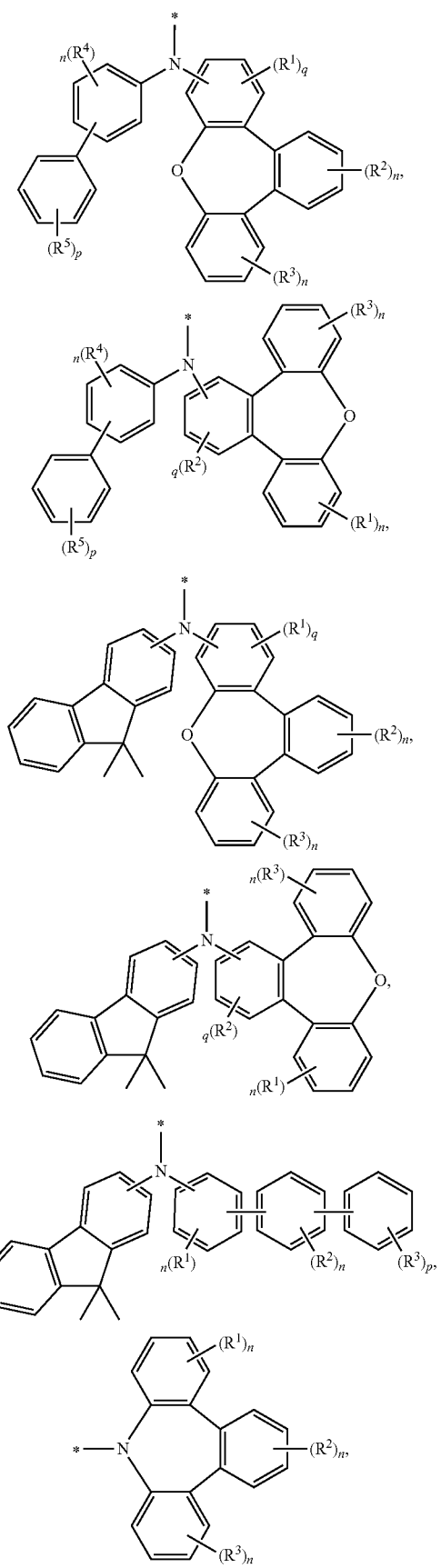

-continued

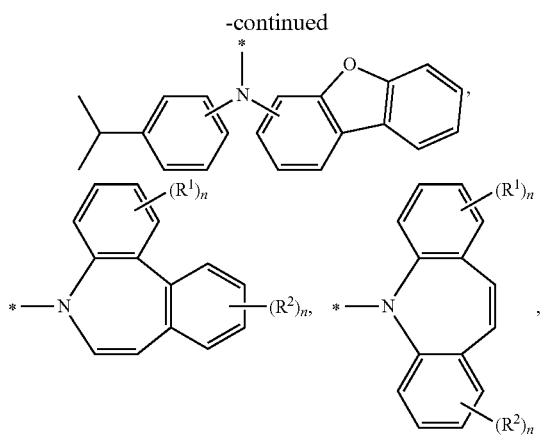

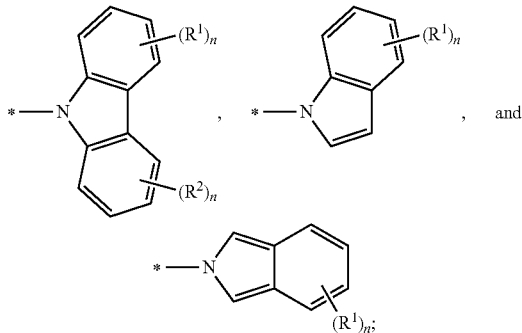

wherein * represents bonding positions;
wherein $R^1$ to $R^5$ are each independently selected from the group consisting of: a deuterium atom, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 30 carbon atoms, an alkoxy group having 1 to 12 carbon atoms, an aryloxy group having 6 to 30 carbon atoms, an alkylsilyl group having 1 to 12 carbon atoms, an arylsilyl group having 6 to 30 carbon atoms, an alkylboron group having 1 to 12 carbon atoms, an arylboron group having 6 to 30 carbon atoms, a phosphine group having 1 to 12 carbon atoms, and a phosphine oxide group having 1 to 12 carbon atoms;
wherein p is an integer from 0 to 5; n is an integer from 0 to 4; q is an integer from 0 to 3.

Preferably, the formula (I) may also be represented by the following Formula (I') marked with the serial number of the carbon atoms:

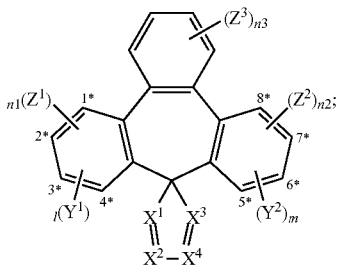

Formula (I')

wherein, $Y^1$ may be bonded on the 2* carbon atom or the 3* carbon atom and $Y^2$ may be bonded on the 6* carbon atom or the 7* carbon atom. In the case where l is 2, the two ($Y^1$)s may be bonded on both the 2* and 3* carbon atoms. In the case where m is 2, the two ($Y^2$)s may be bonded on both the 6* and 7* carbon atoms.

Preferably, the compound is selected from the group consisting of:

Compound 1

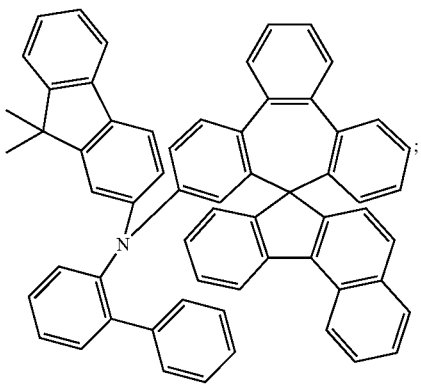

Compound 2

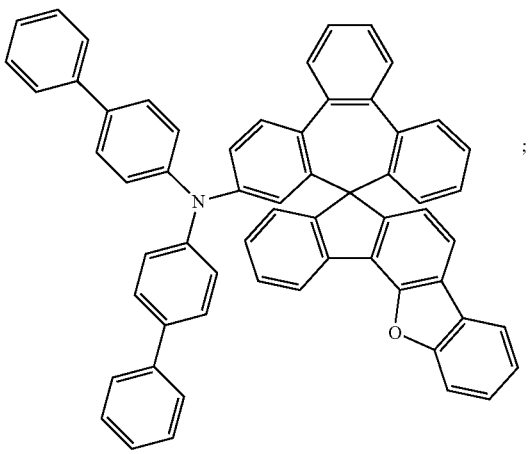

-continued
Compound 3
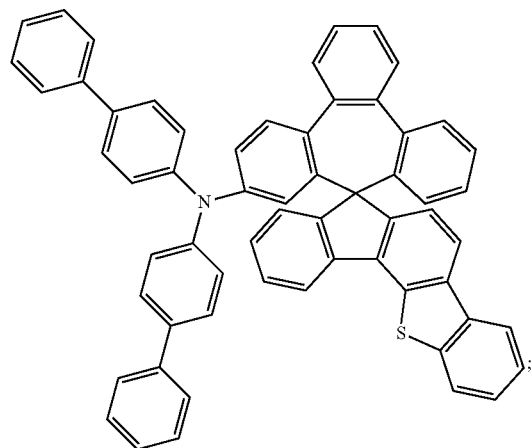
Compound 4
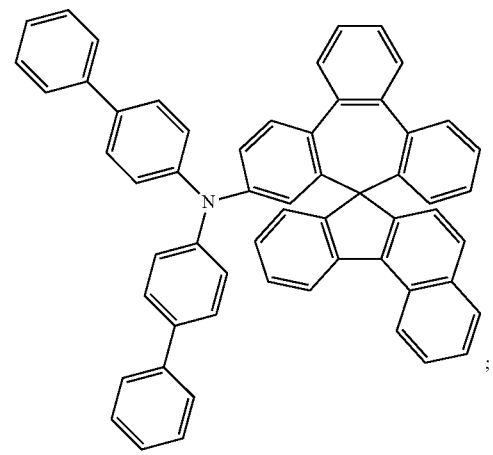
Compound 5
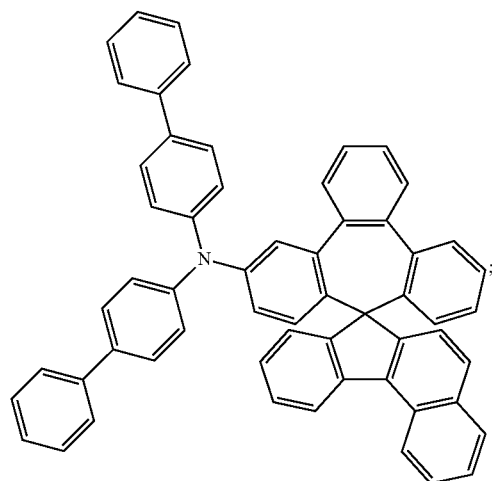
Compound 6
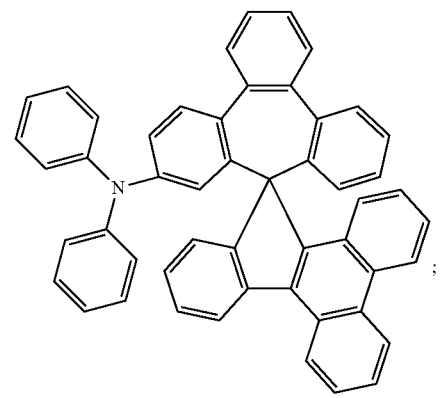
Compound 7
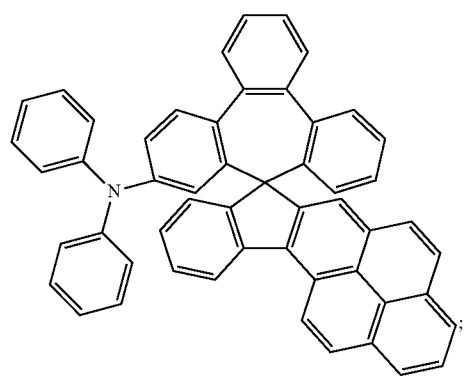
Compound 8
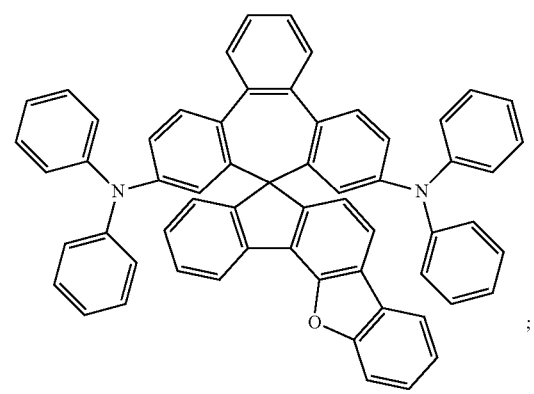

-continued
Compound 9
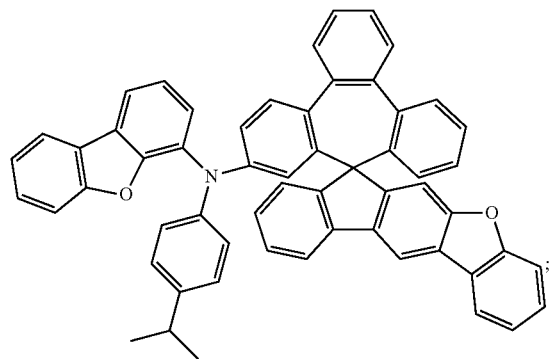
Compound 10
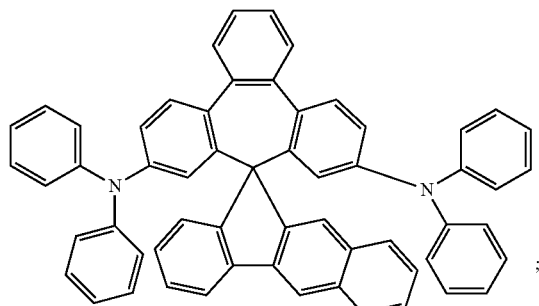
Compound 11
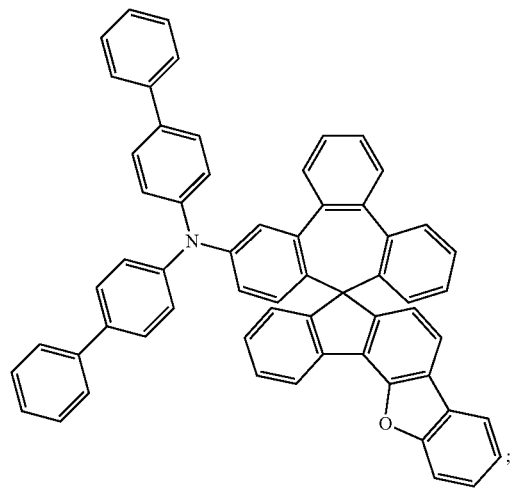
Compound 12
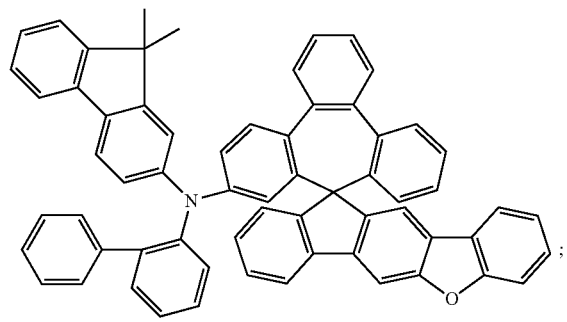
Compound 13
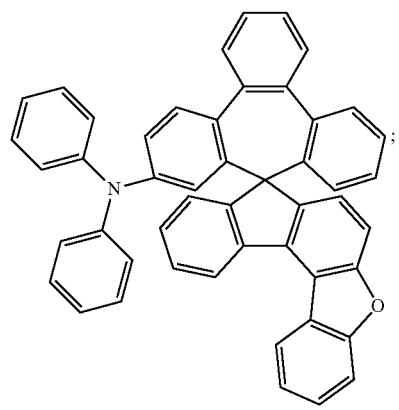
Compound 14
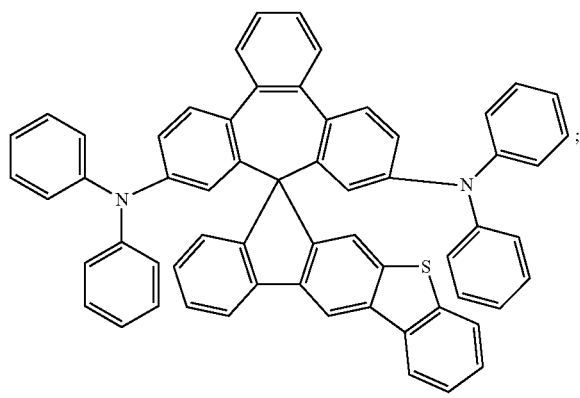

-continued
Compound 15
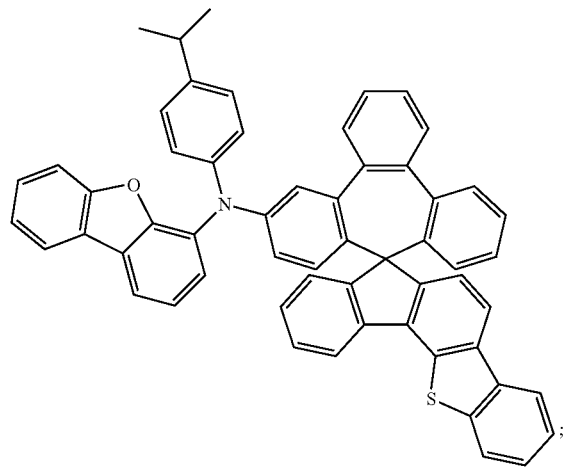
Compound 16
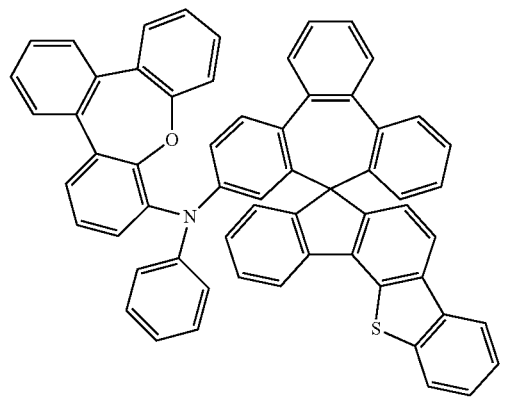
Compound 17
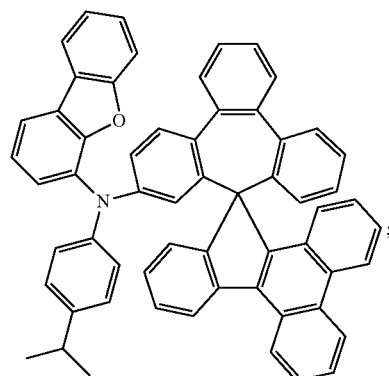
Compound 18
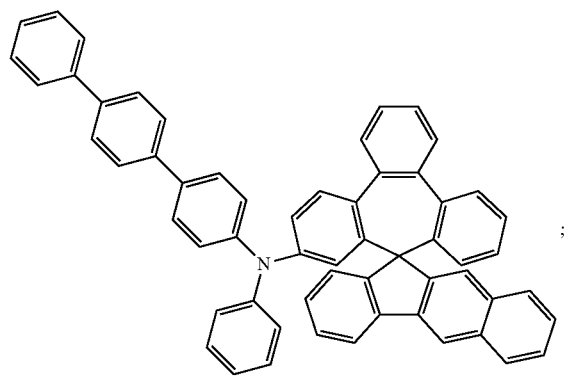
Compound 19
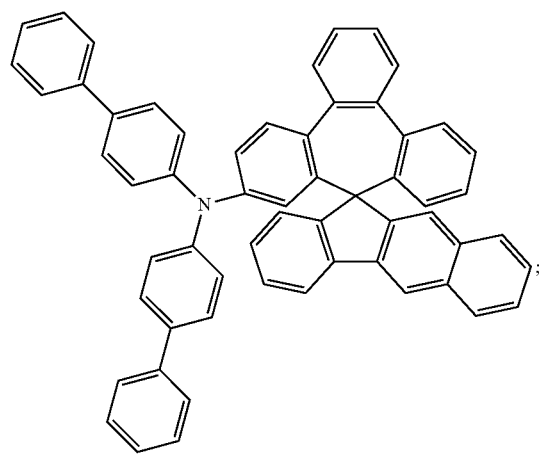
Compound 20
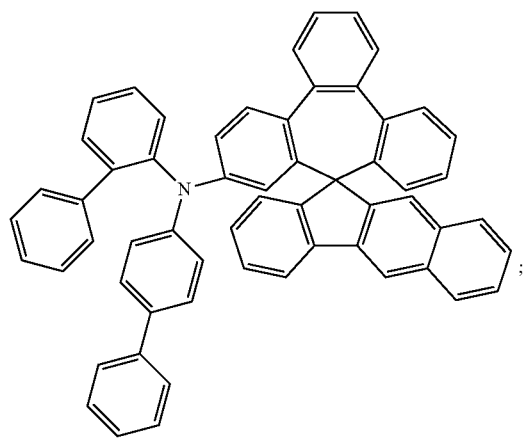

-continued
Compound 21
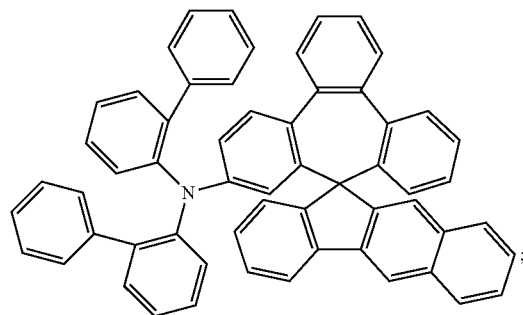
Compound 22
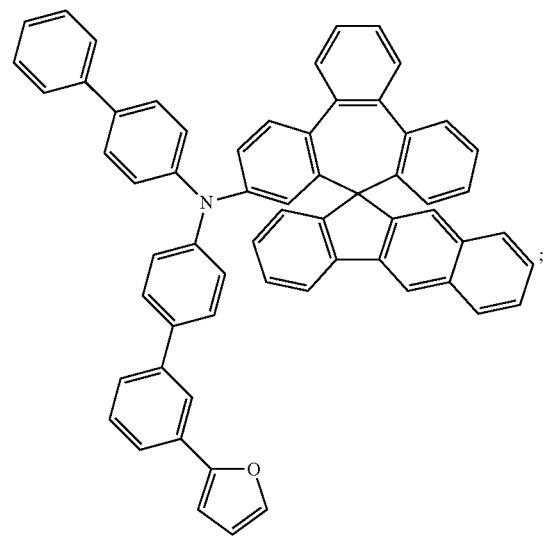
Compound 23
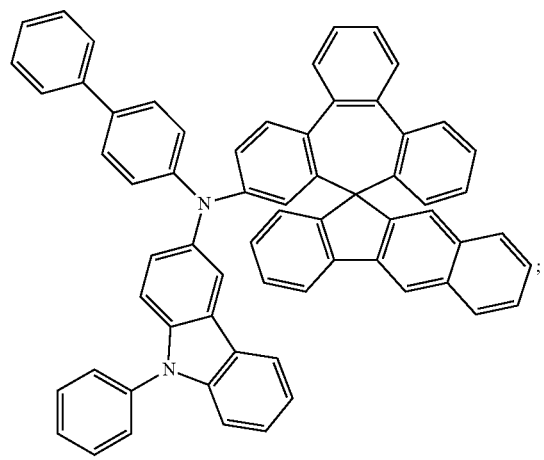
Compound 24
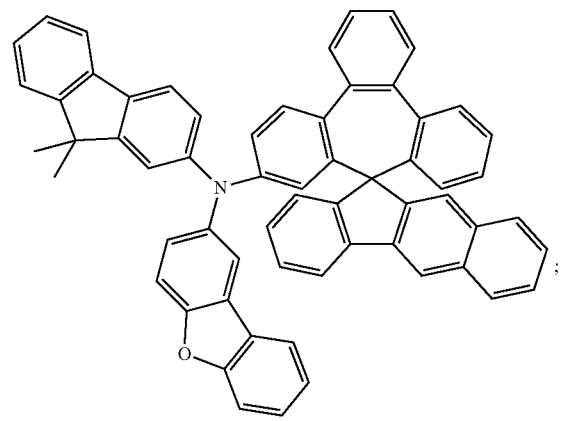
Compound 25
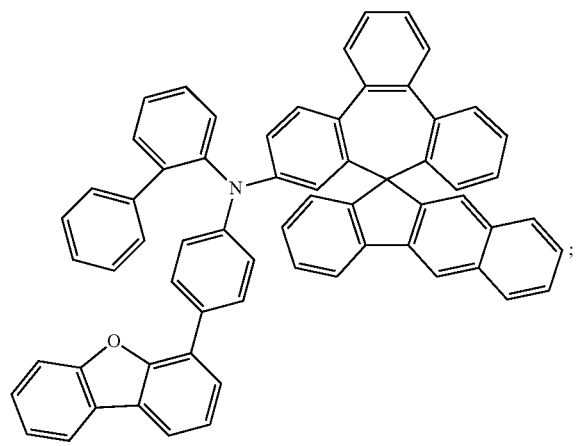
Compound 26
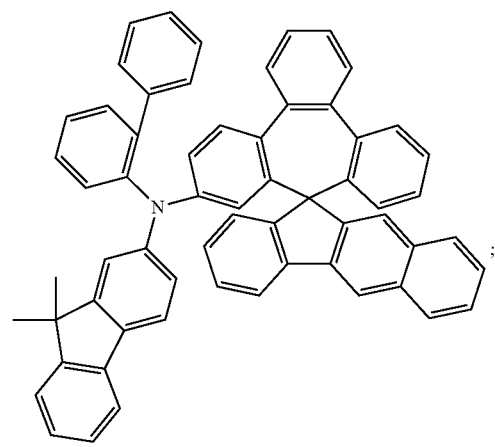

-continued
Compound 27
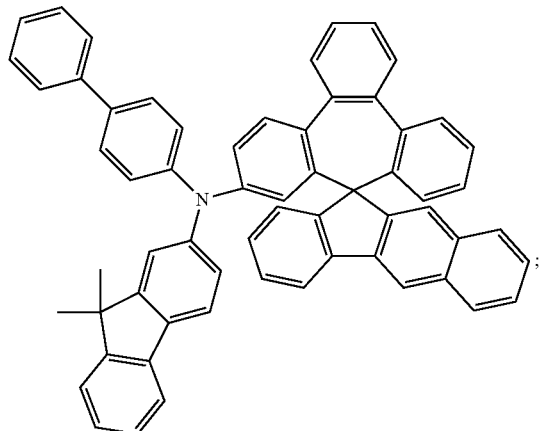
Compound 28
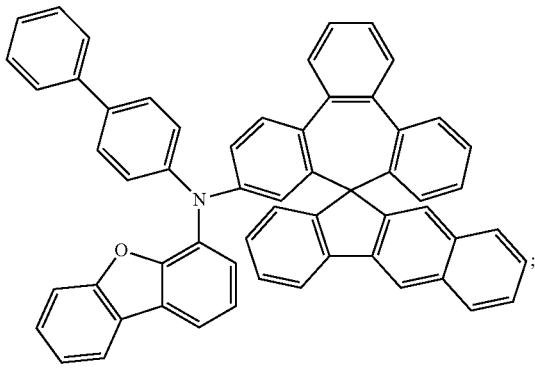
Compound 29
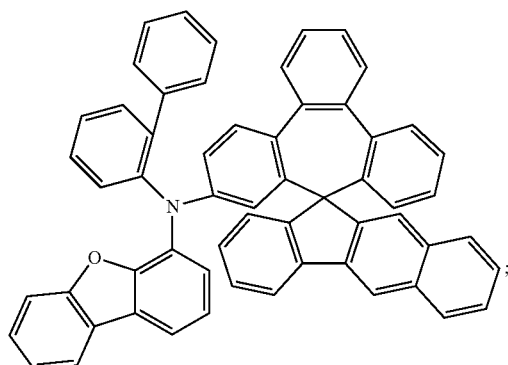
Compound 30
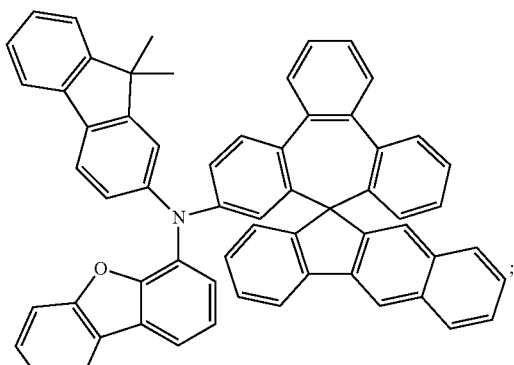
Compound 31
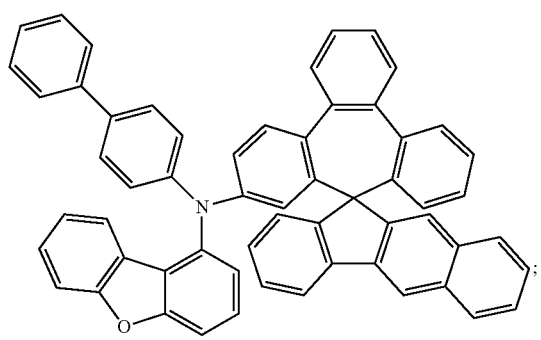
Compound 32
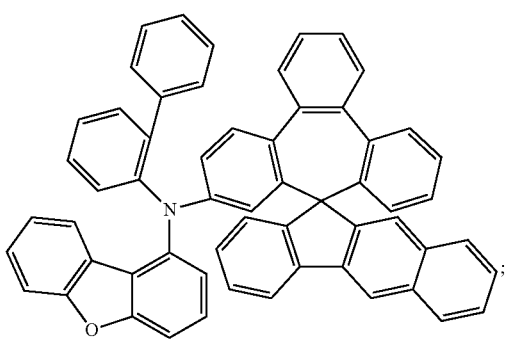
Compound 33
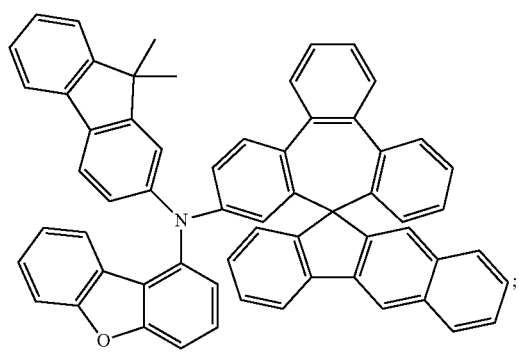
Compound 34
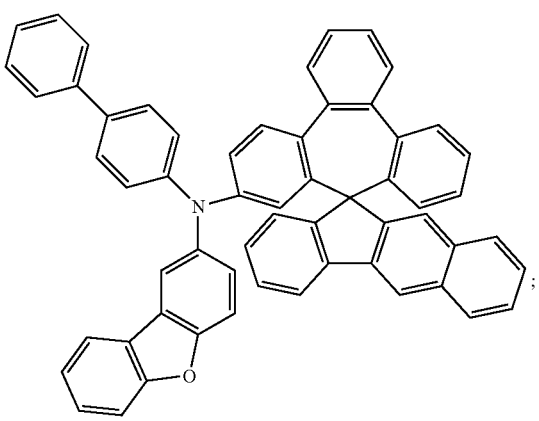

-continued
Compound 35
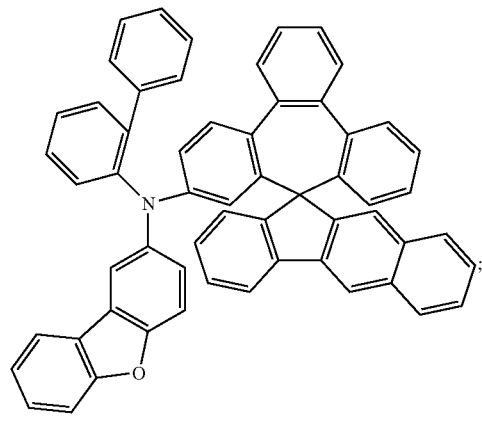
Compound 36
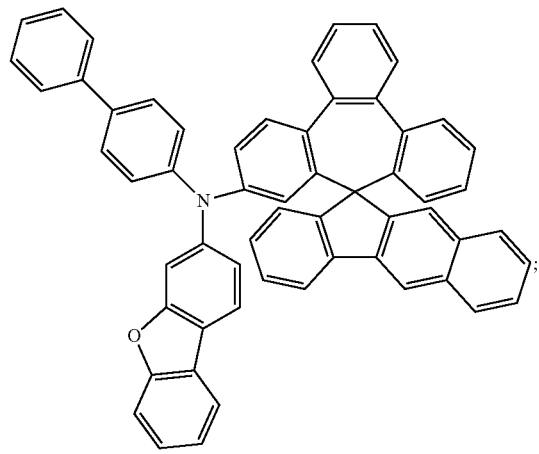
Compound 37
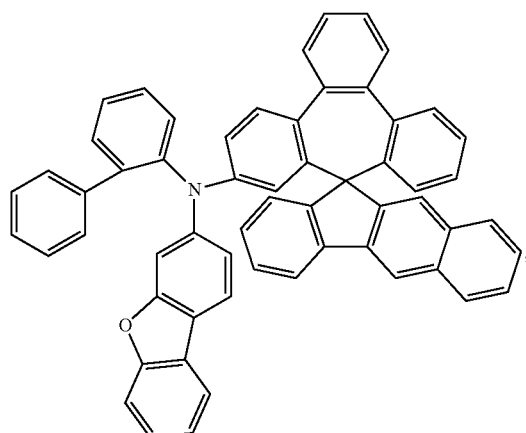
Compound 38
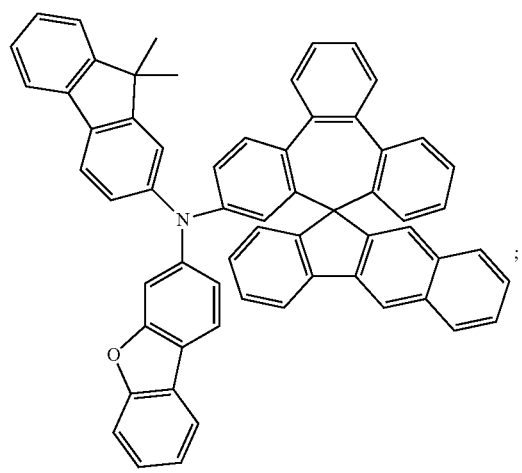
Compound 39
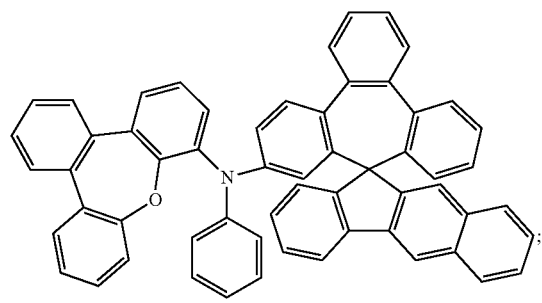
Compound 40
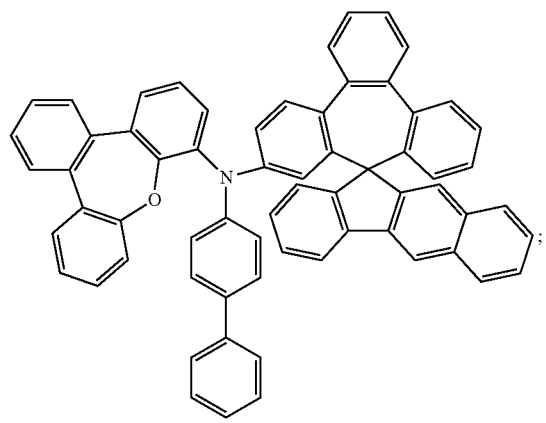

-continued
Compound 41
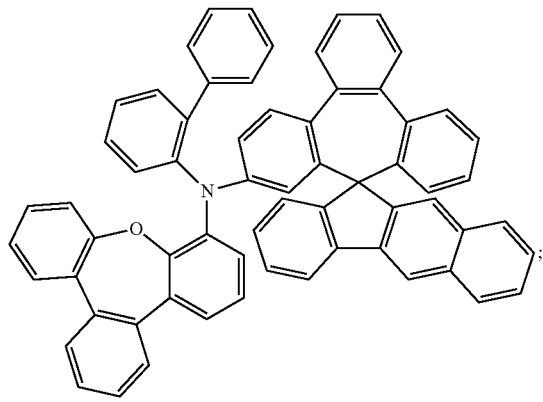
Compound 42
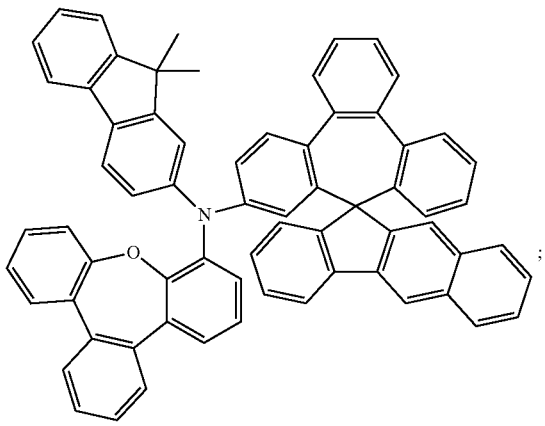
Compound 43
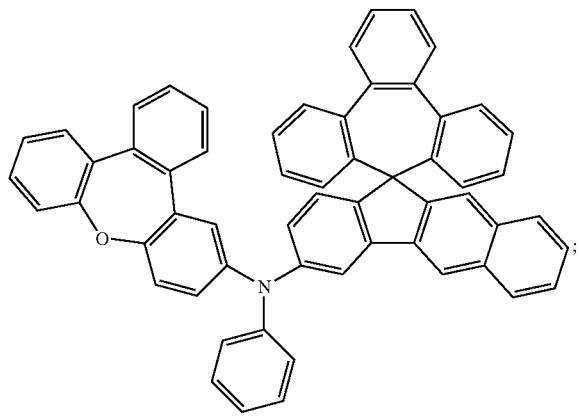
Compound 44
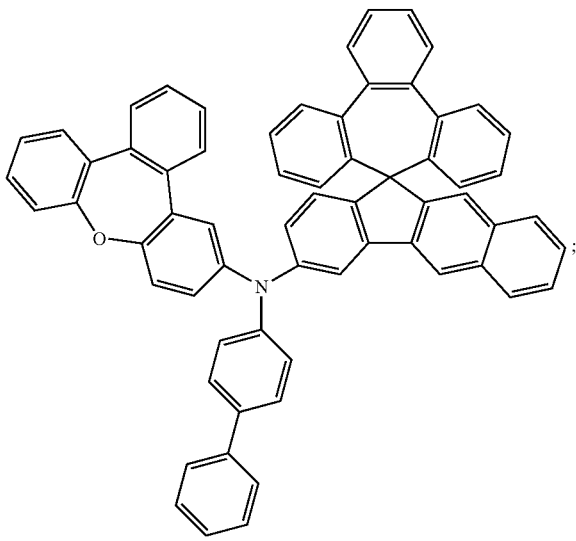
Compound 45
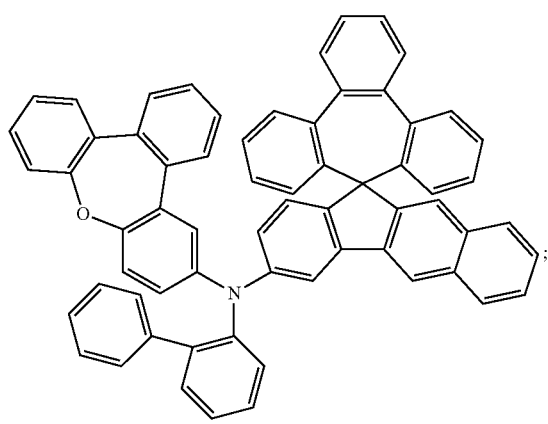
Compound 46
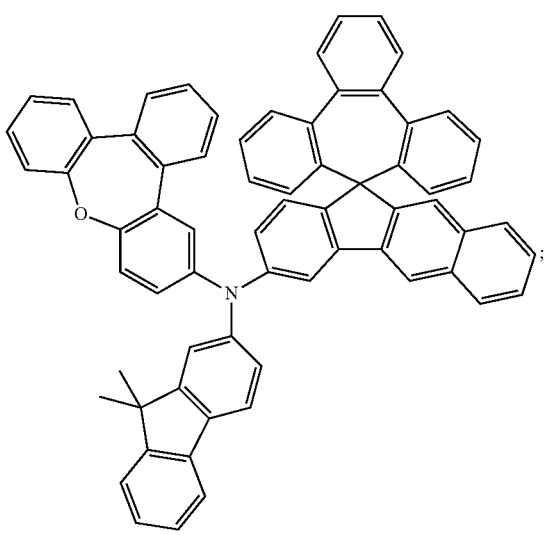

Compound 47
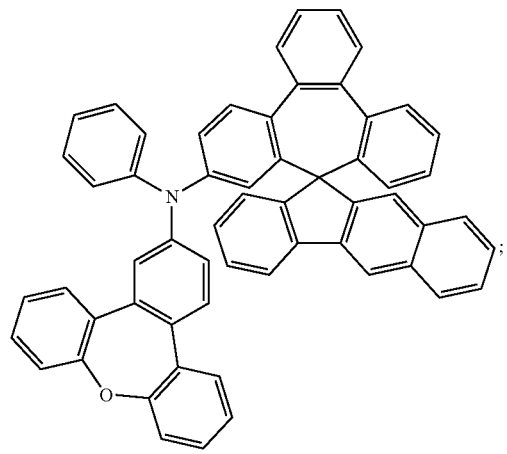
Compound 48
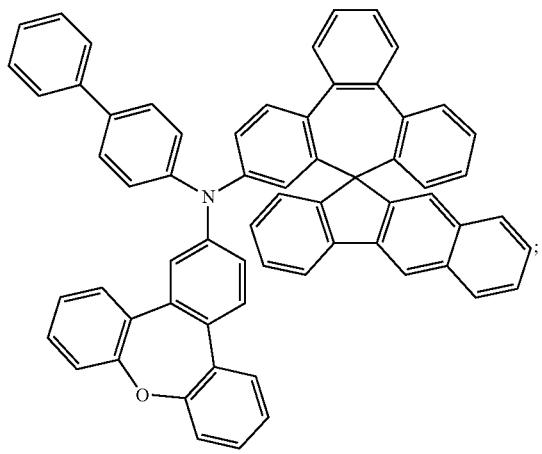
Compound 49
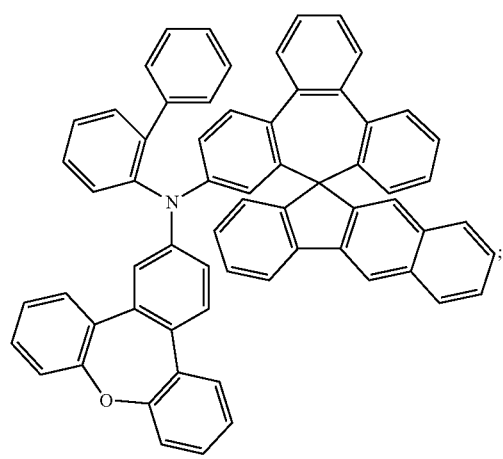
Compound 50
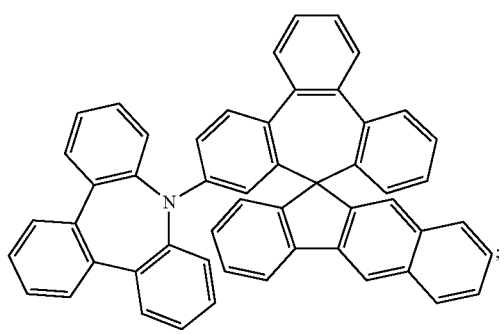
Compound 51
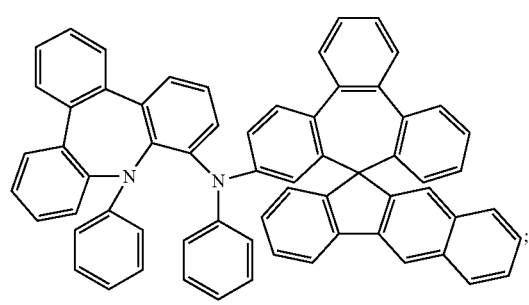
Compound 52
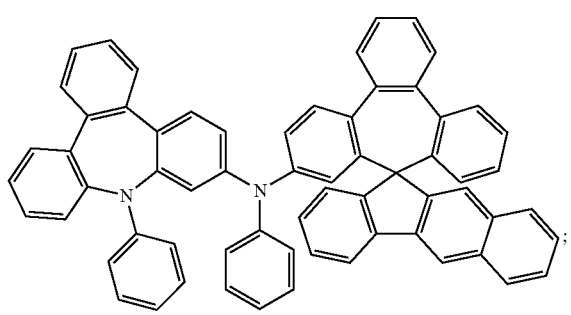

-continued
Compound 53
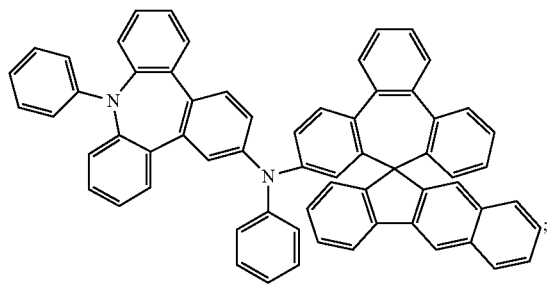
Compound 54
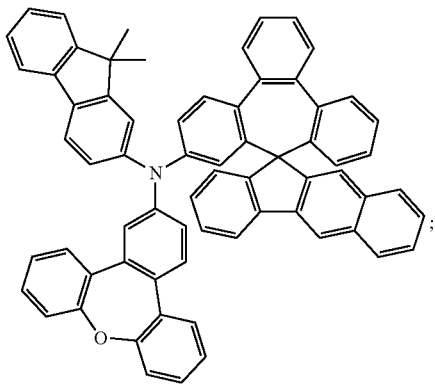
Compound 55
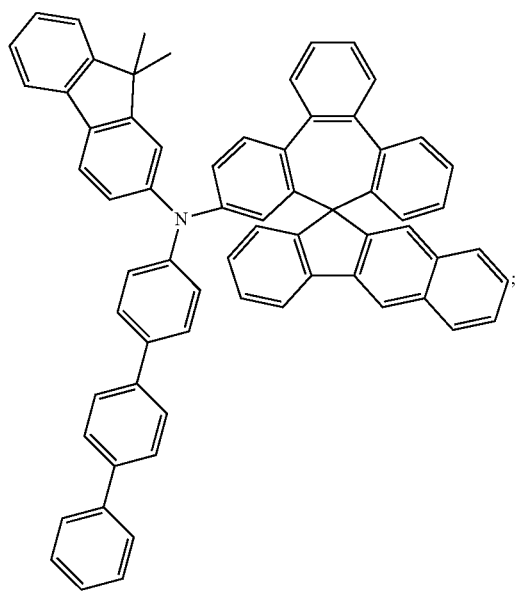
Compound 56
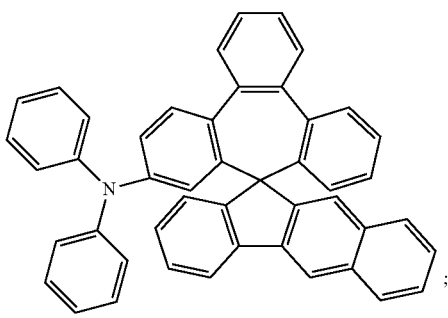
Compound 57
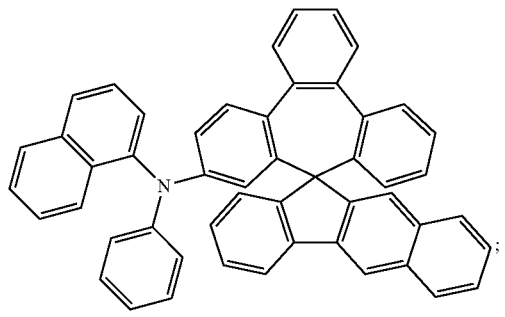
Compound 58
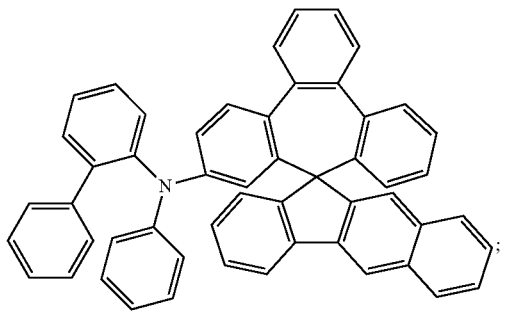

-continued
Compound 59
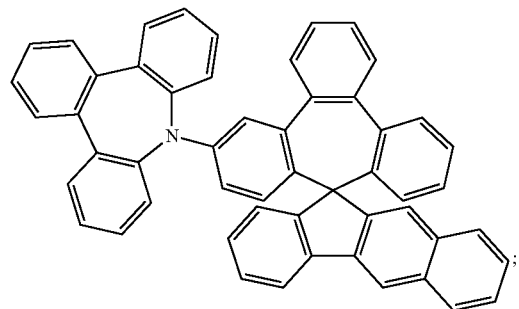
Compound 60
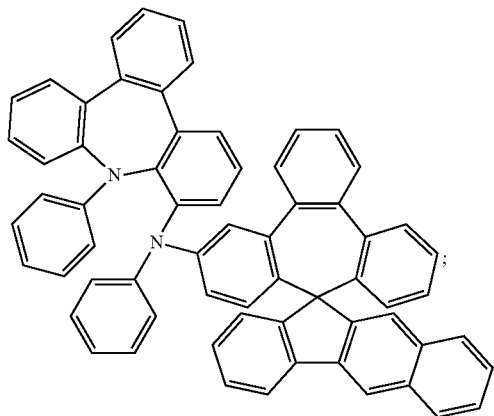
Compound 61
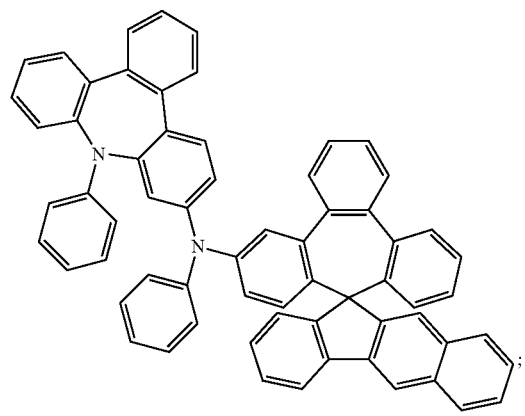
Compound 62
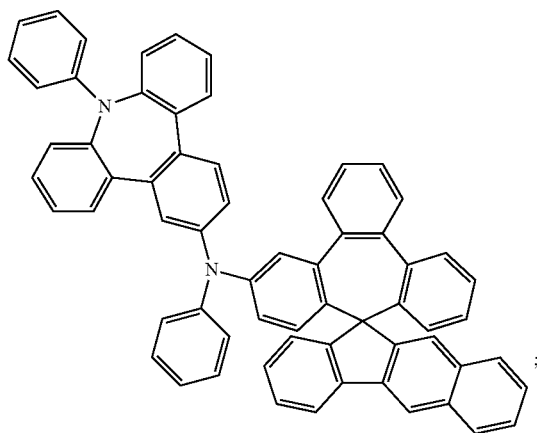
Compound 63
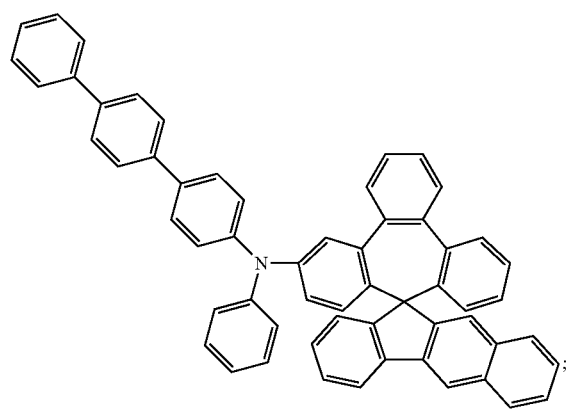
Compound 64
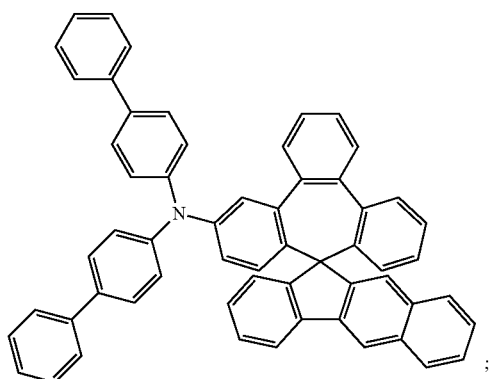

-continued
Compound 65
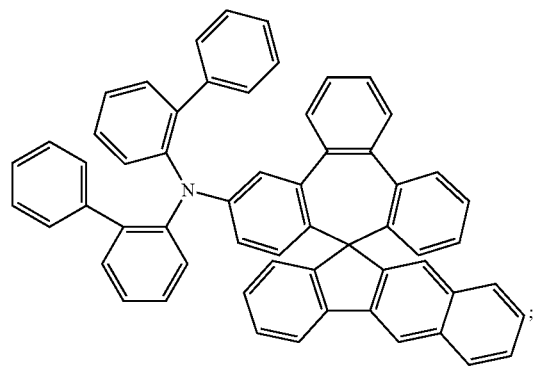
Compound 66
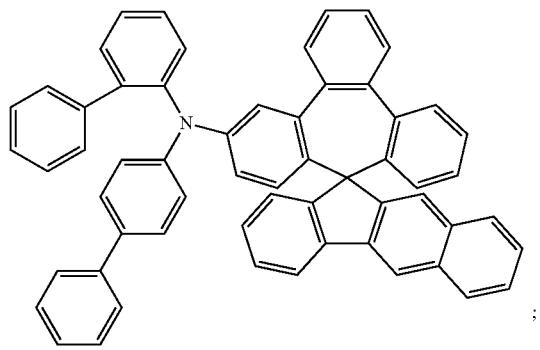
Compound 67
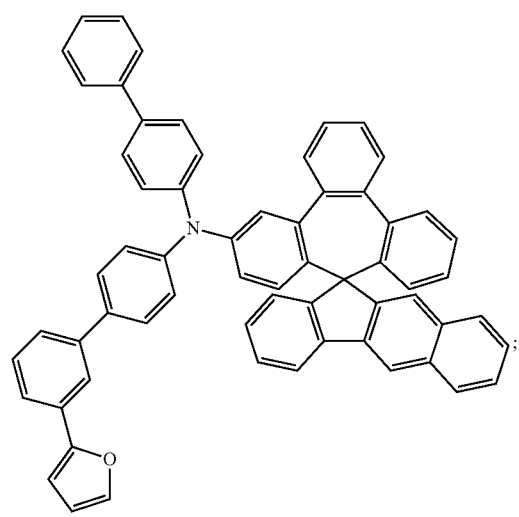
Compound 68
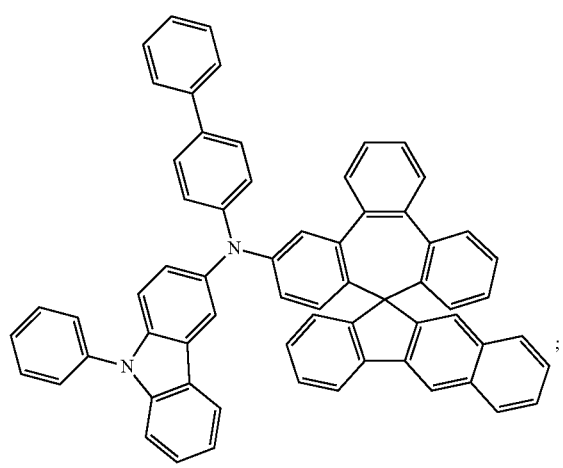
Compound 69
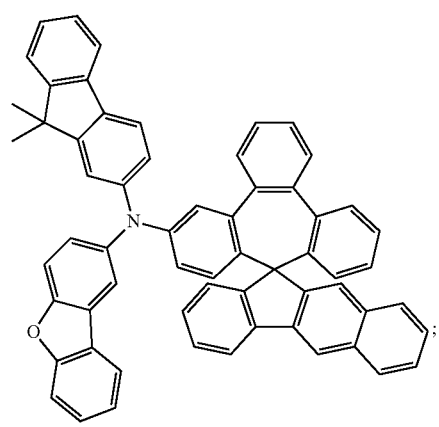
Compound 70
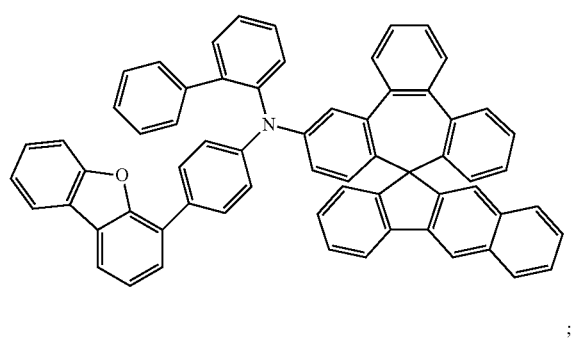

-continued
Compound 71
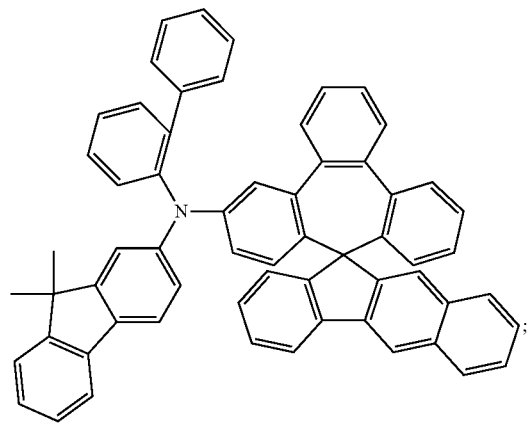
Compound 72
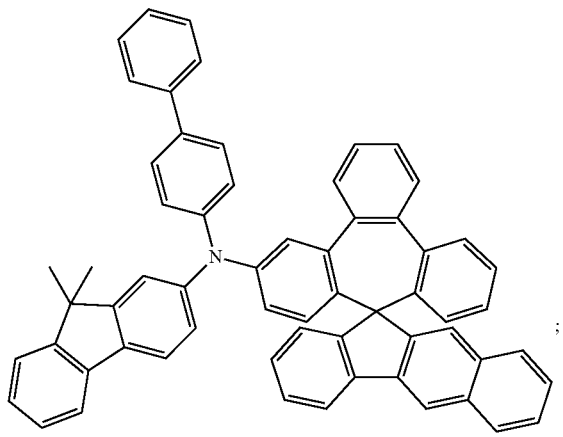
Compound 73
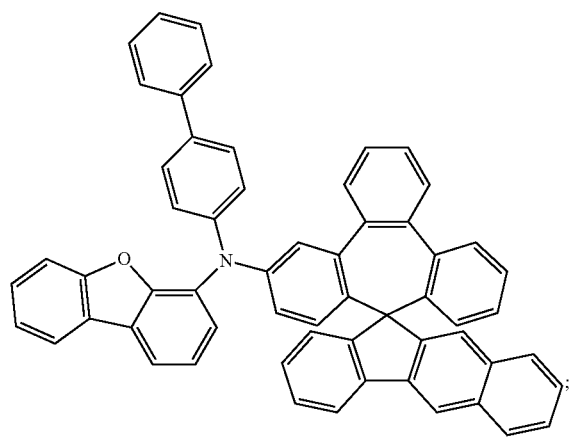
Compound 74
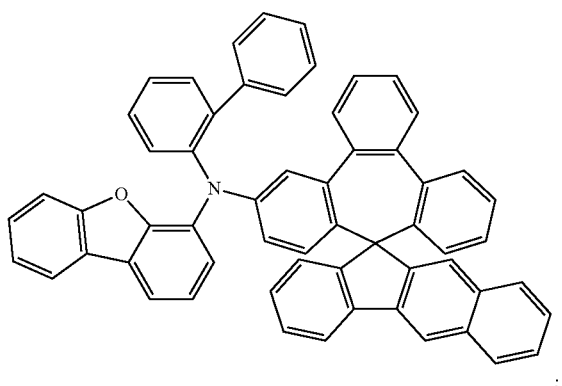
Compound 75
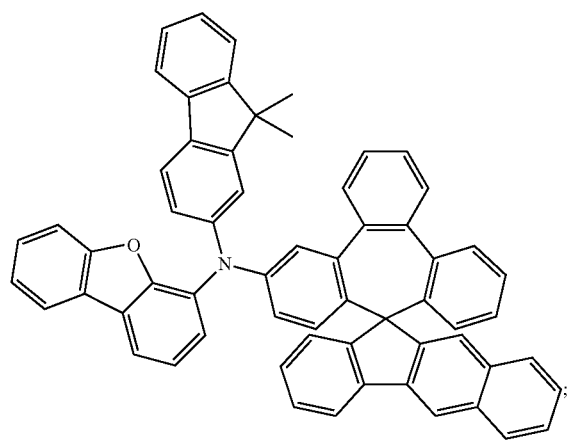
Compound 76
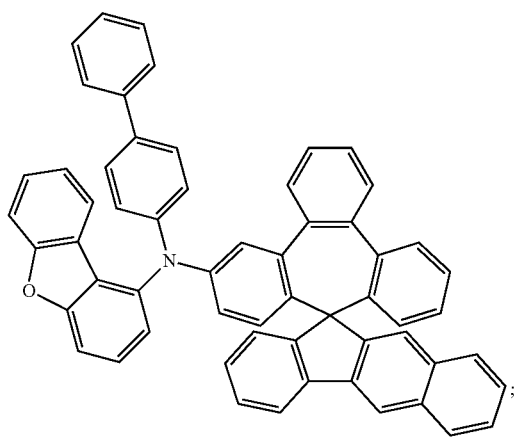

Compound 77
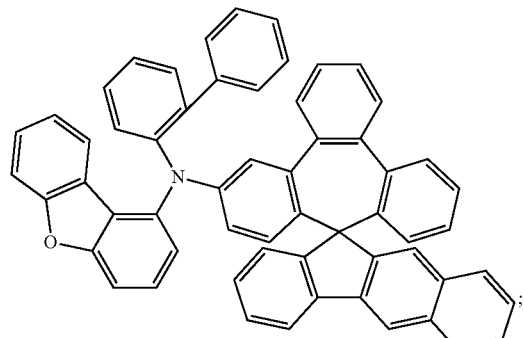
Compound 78
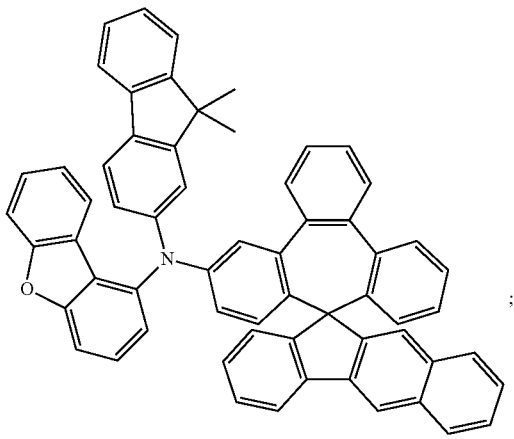
Compound 79
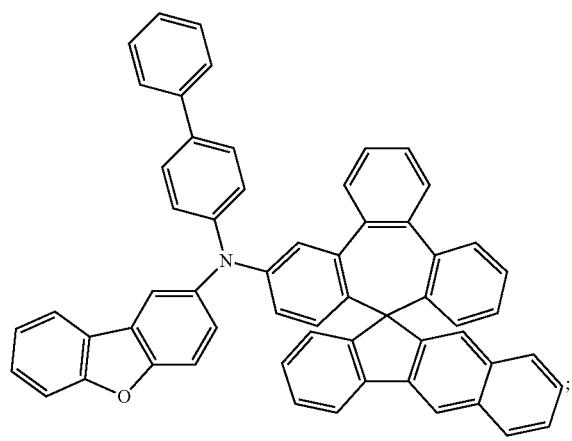
Compound 80
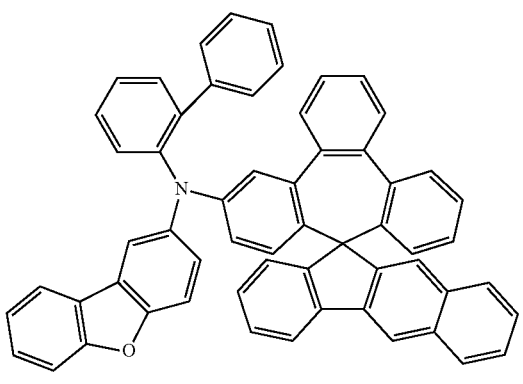
Compound 81
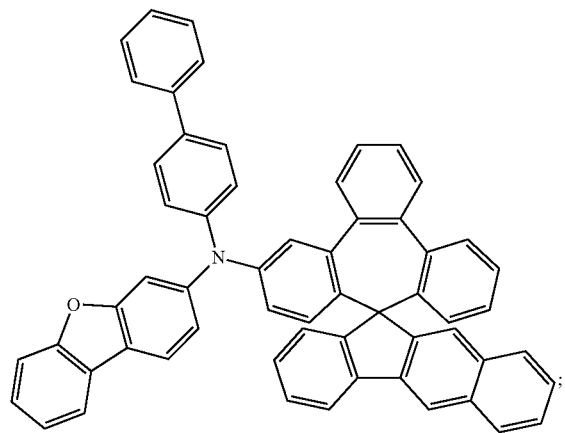
Compound 82
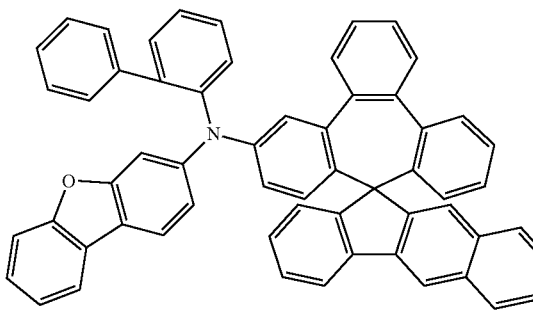

-continued
Compound 83
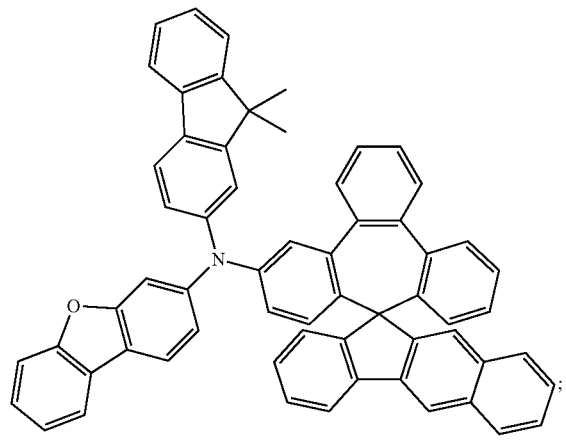
Compound 84
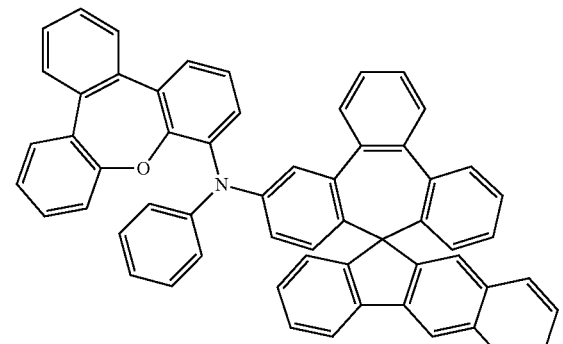
Compound 85
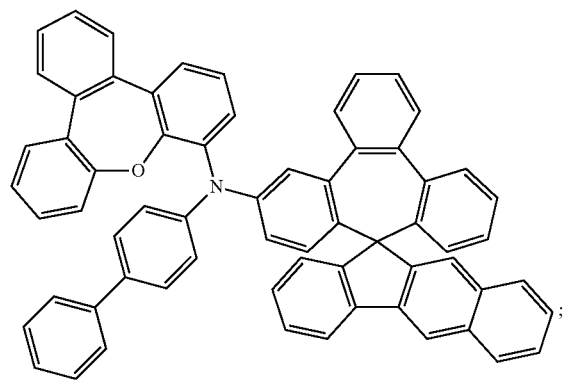
Compound 86
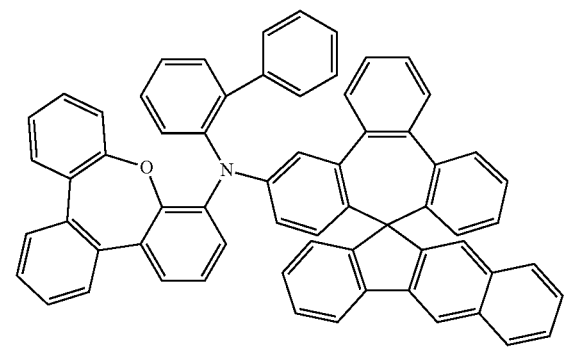
Compound 87
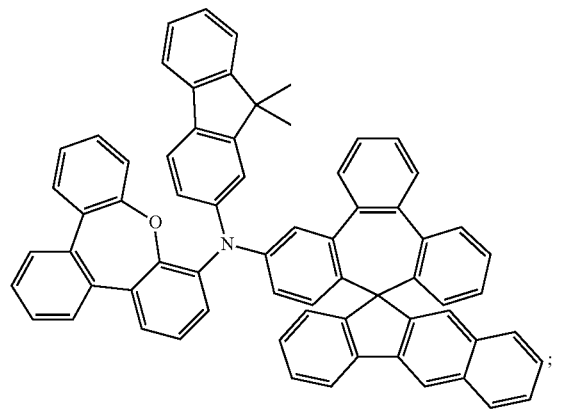
Compound 88
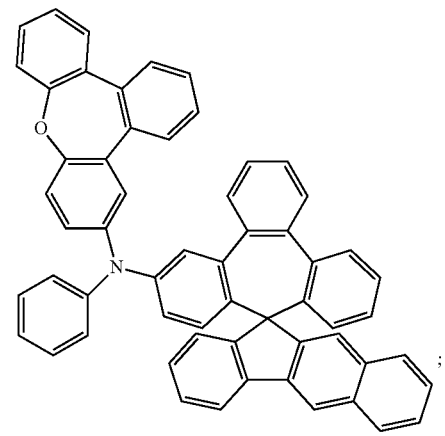

-continued
Compound 89
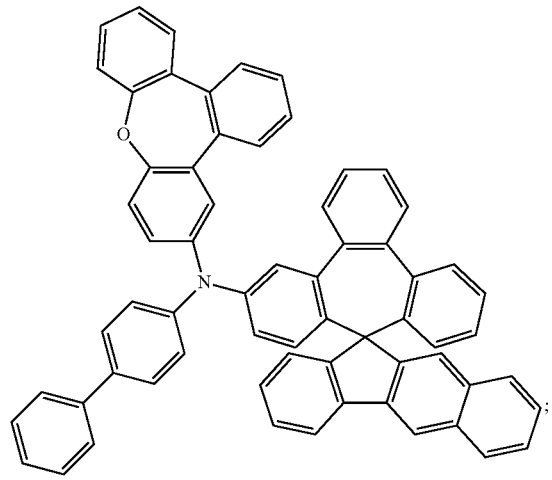
Compound 90
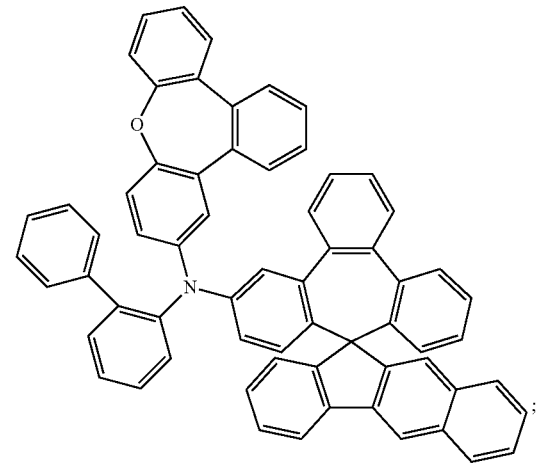
Compound 91
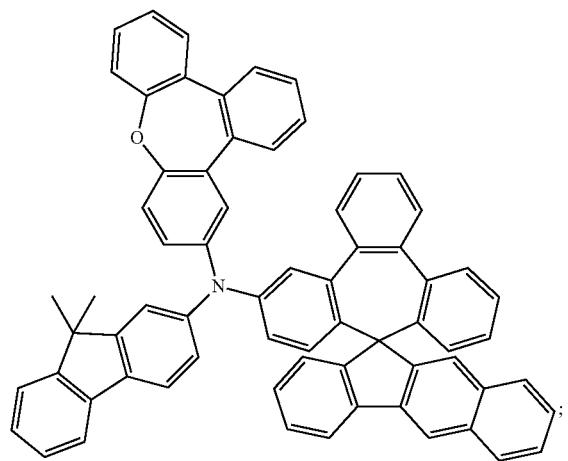
Compound 92
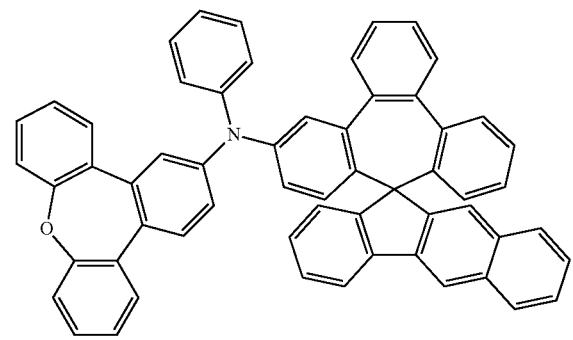
Compound 93
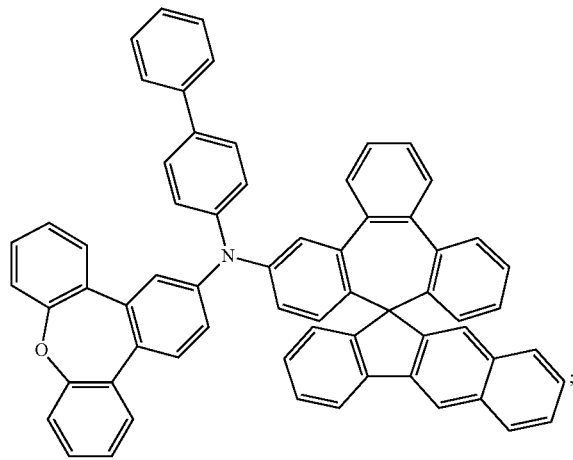
Compound 94
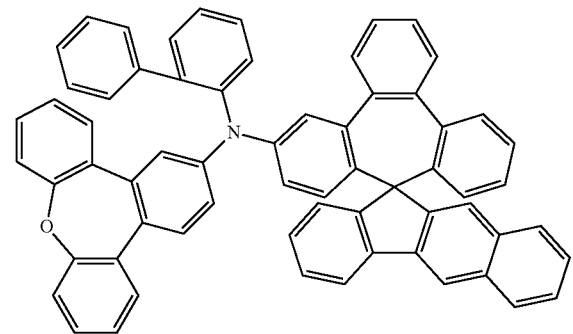

-continued
Compound 95
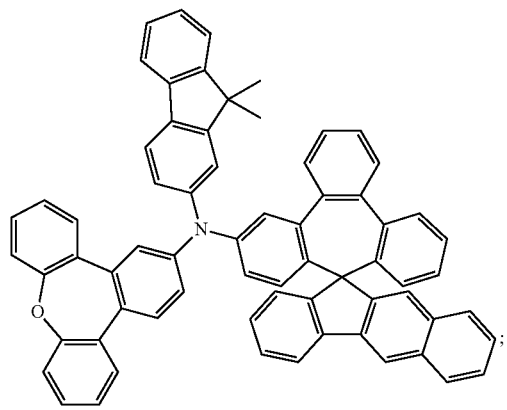
Compound 96
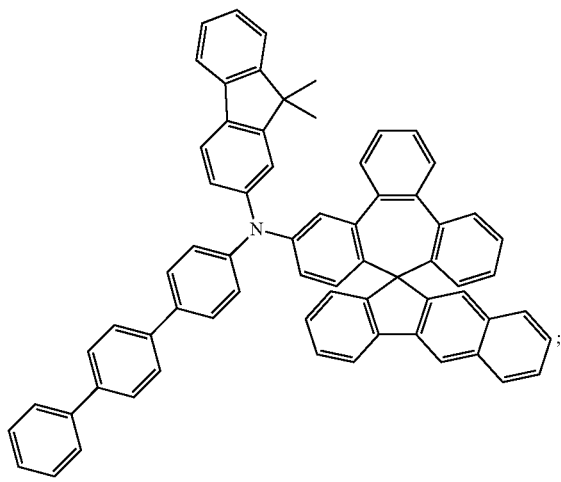
Compound 97
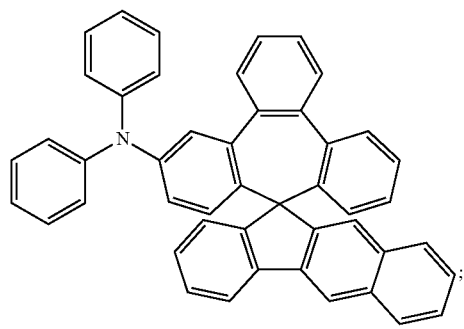
Compound 98
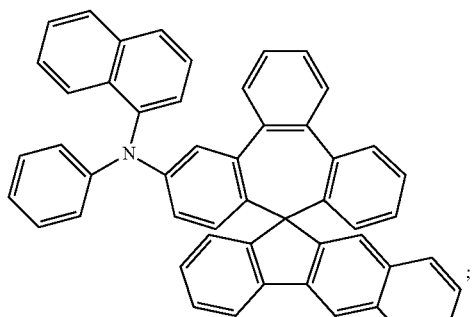
Compound 99
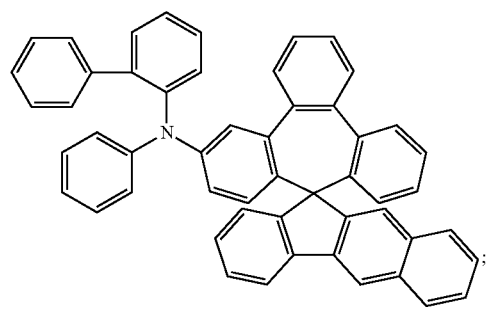
Compound 100
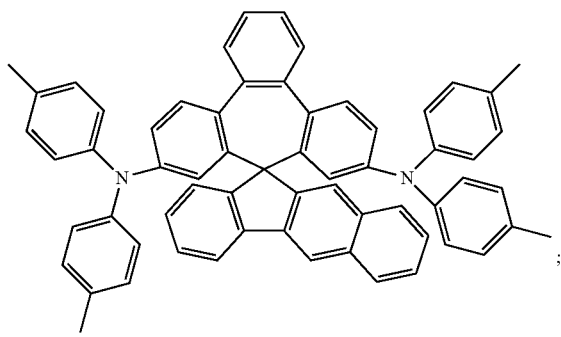
Compound 101
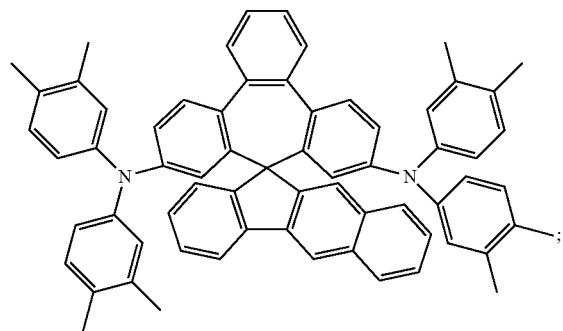
Compound 102
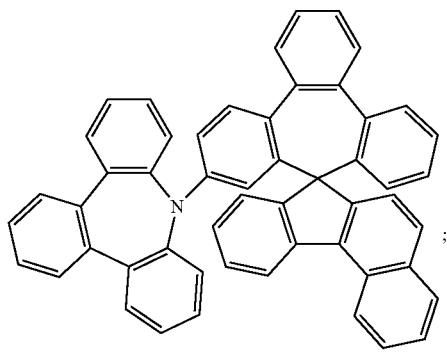

-continued
Compound 103
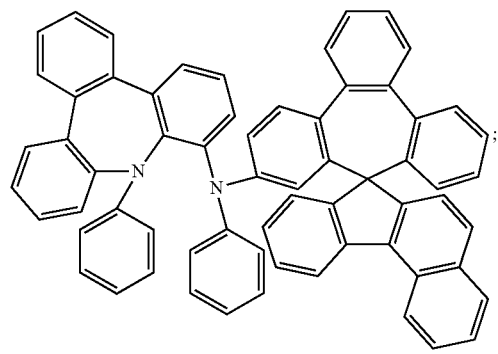
Compound 104
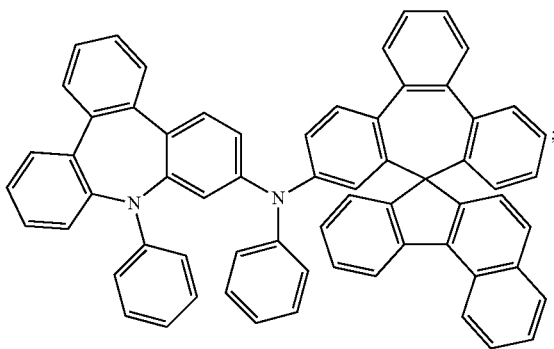
Compound 105
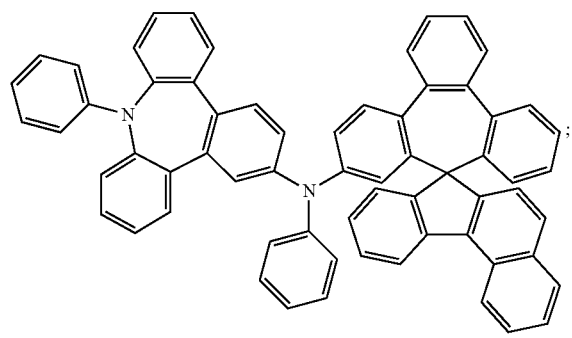
Compound 106
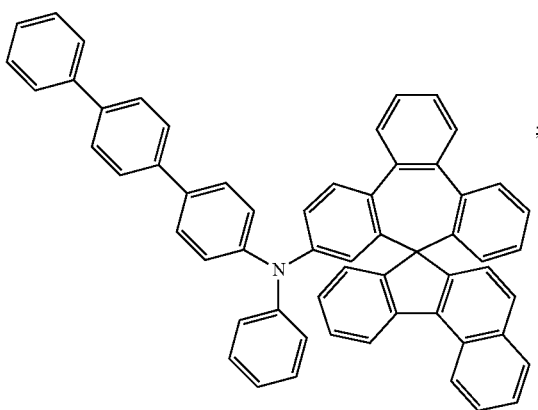
Compound 107
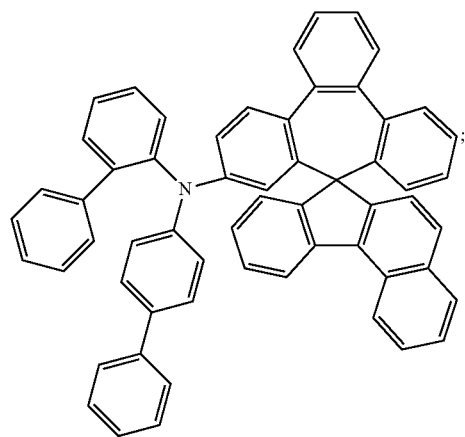
Compound 108
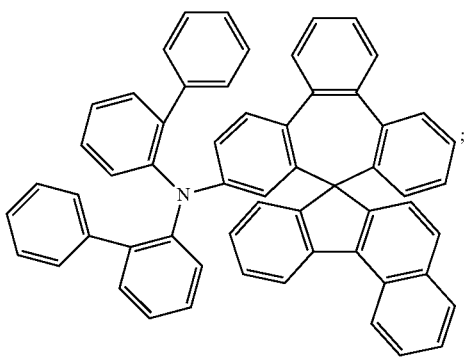

-continued
Compound 109
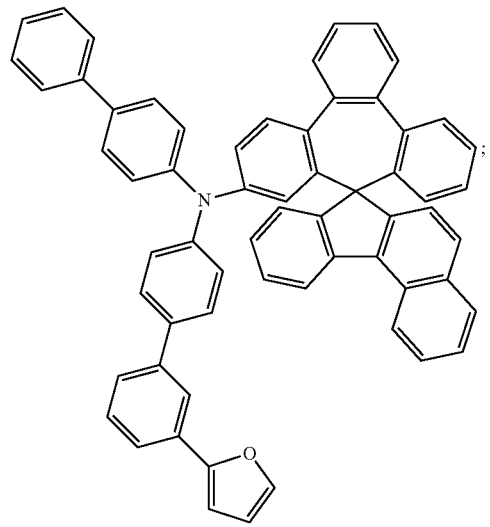
Compound 110
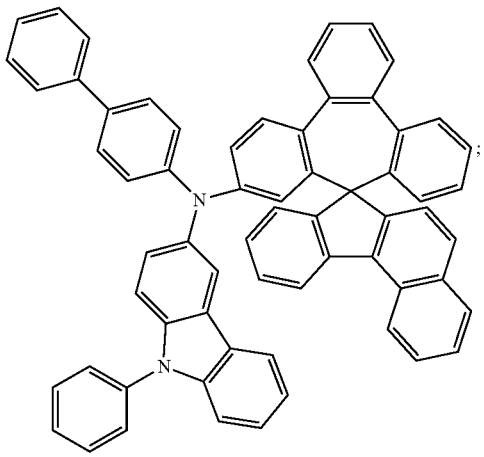
Compound 111
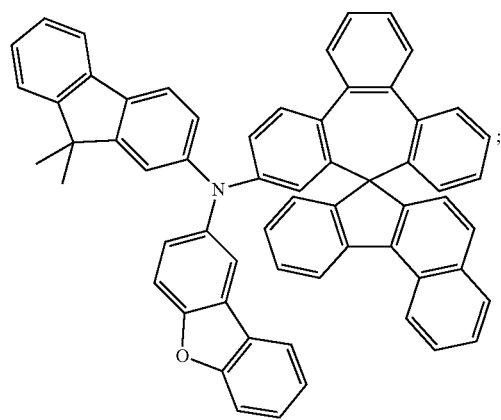
Compound 112
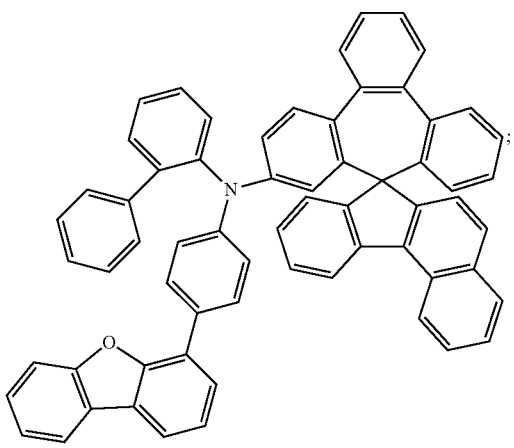
Compound 113
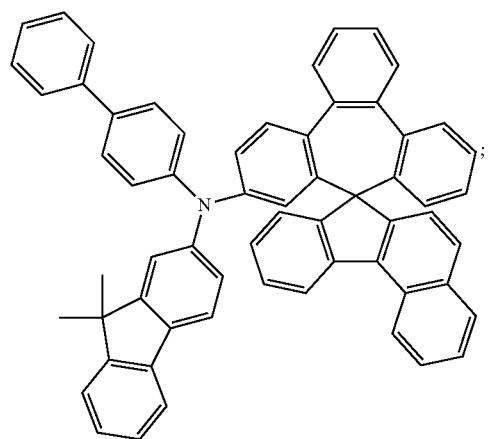
Compound 114
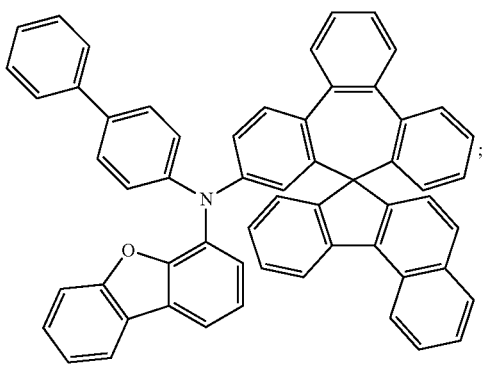

-continued
Compound 115
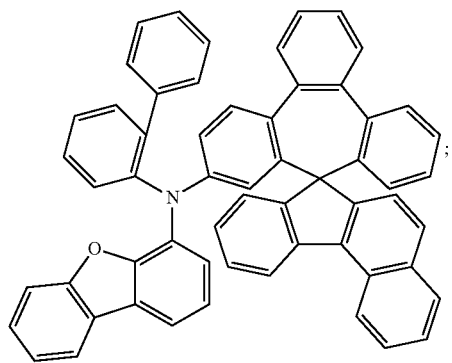
Compound 116
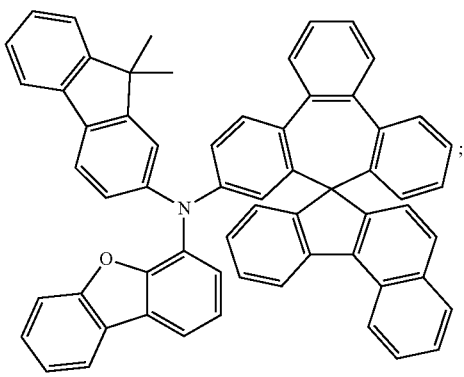
Compound 117
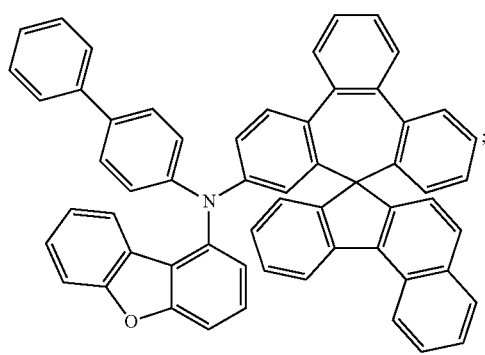
Compound 118
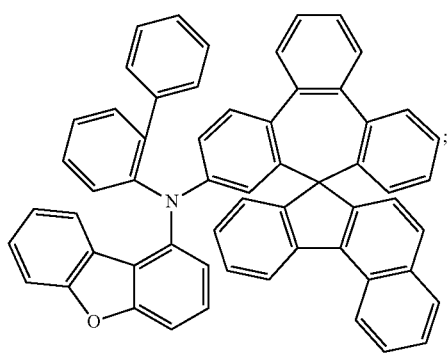
Compound 119
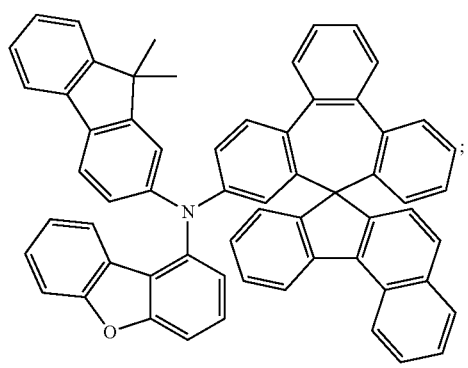
Compound 120
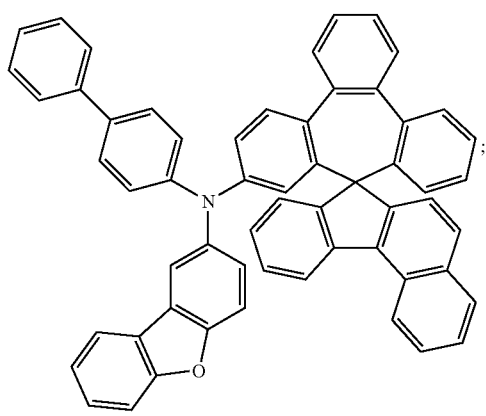

-continued
Compound 121
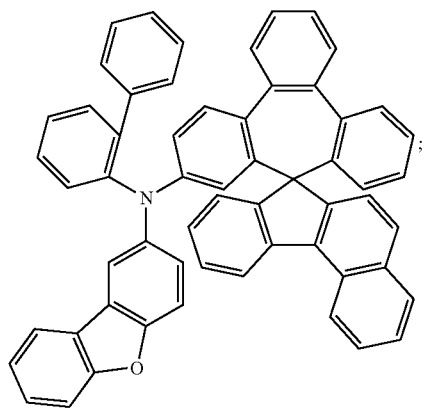
Compound 122
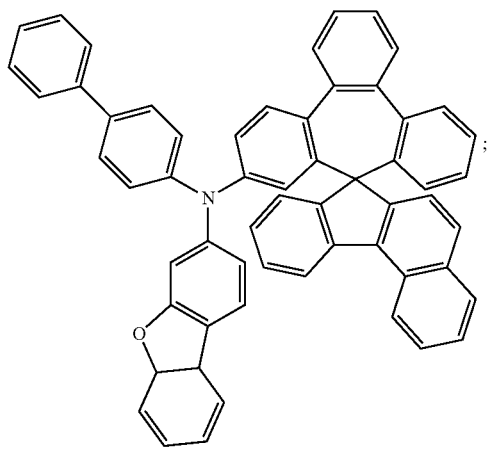
Compound 123
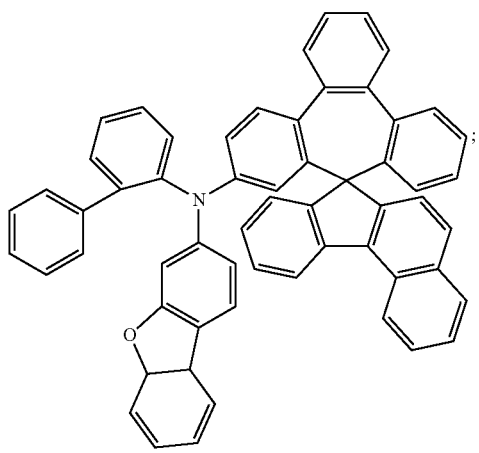
Compound 124
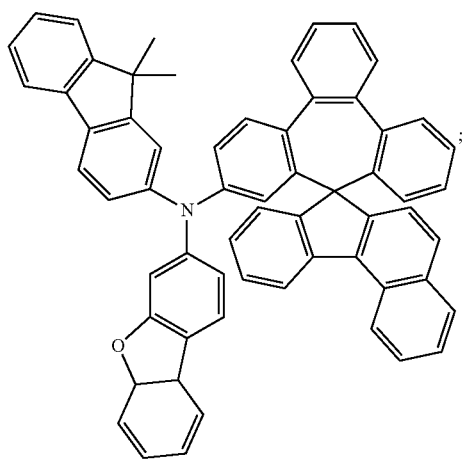
Compound 125
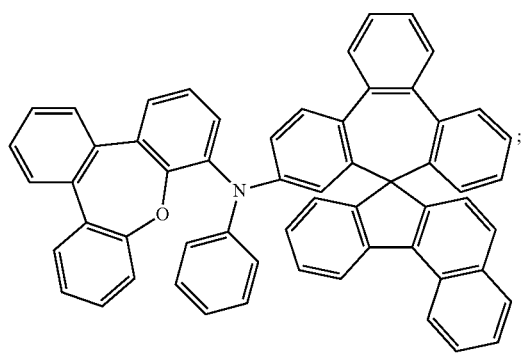
Compound 126
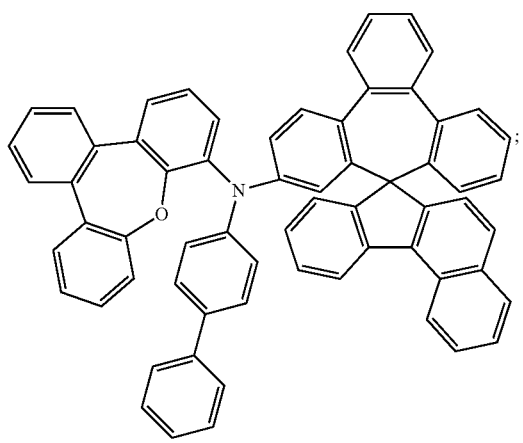

-continued
Compound 127
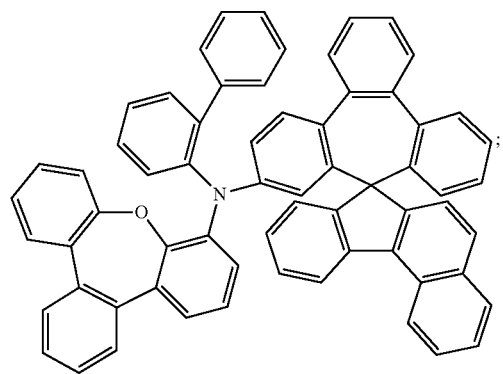
Compound 128
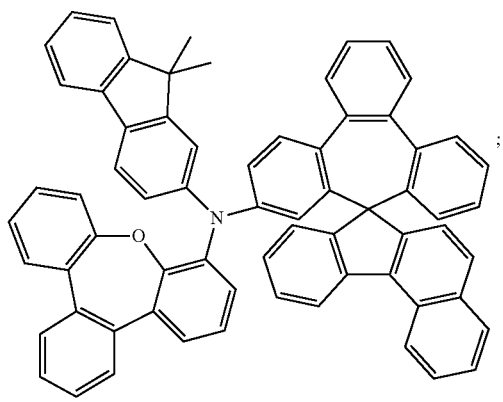
Compound 129
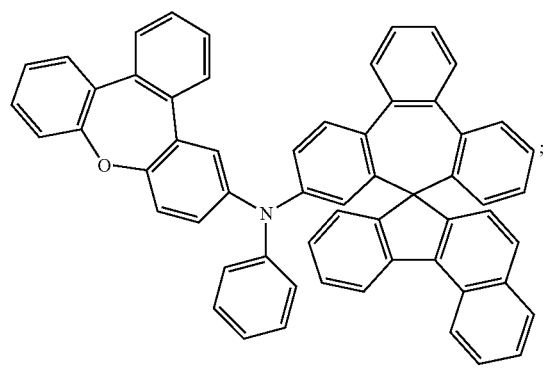
Compound 130
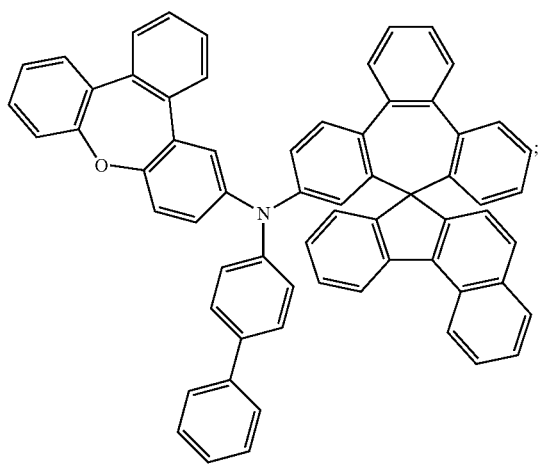
Compound 131
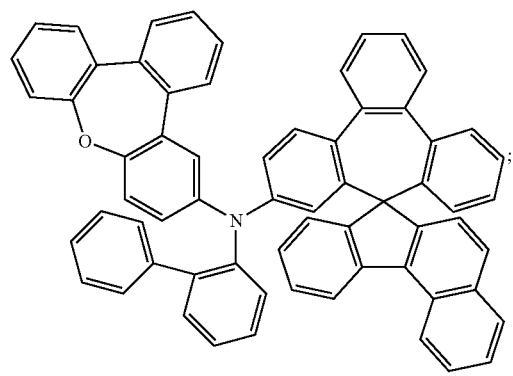
Compound 132
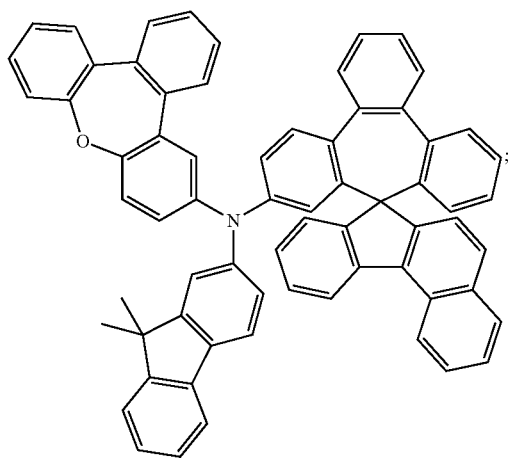

Compound 133
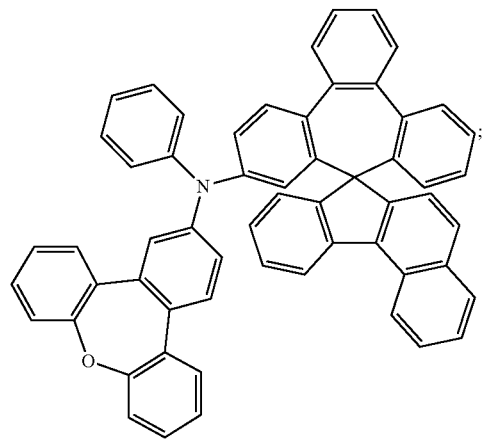
Compound 134
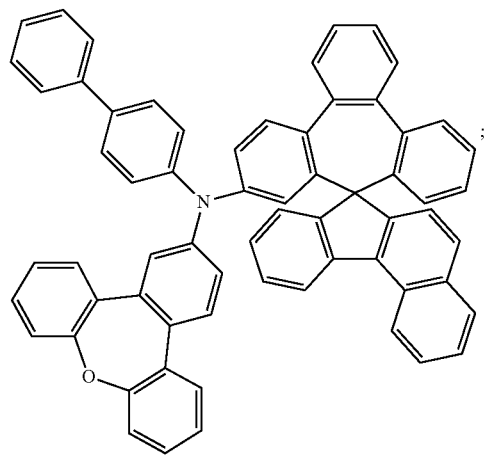
Compound 135
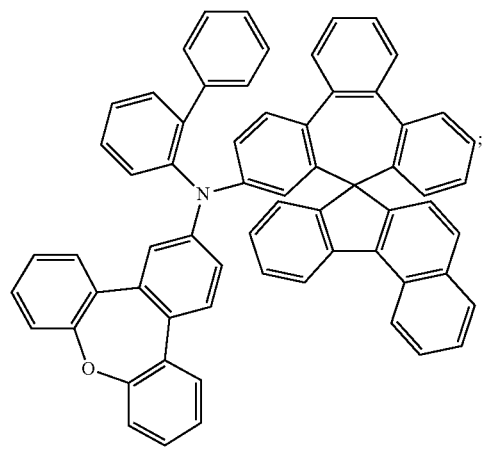
Compound 136
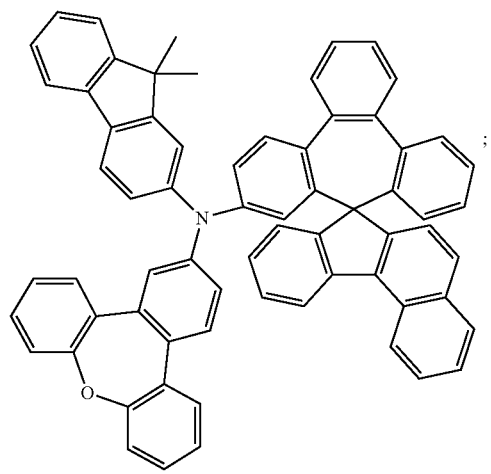
Compound 137
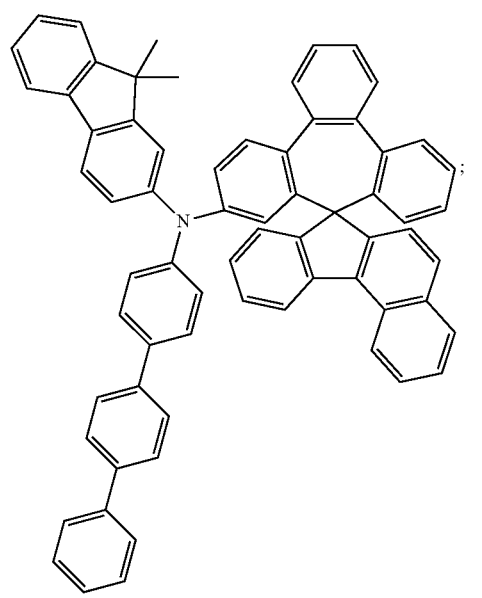
Compound 138
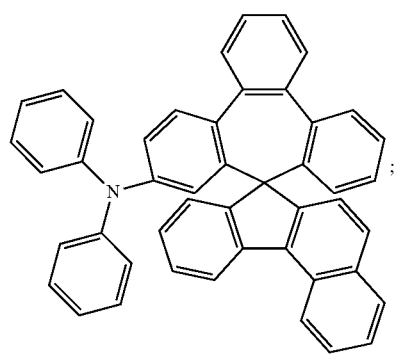

-continued
Compound 139
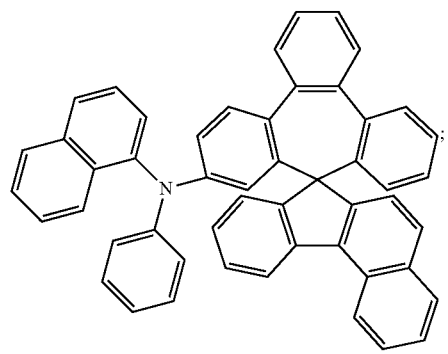
Compound 140
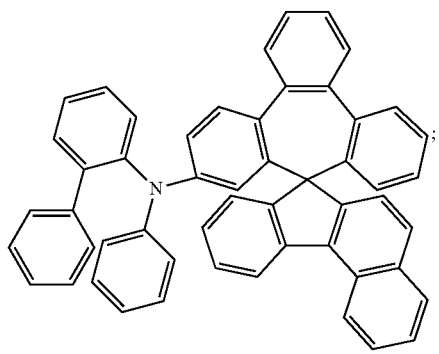
Compound 141
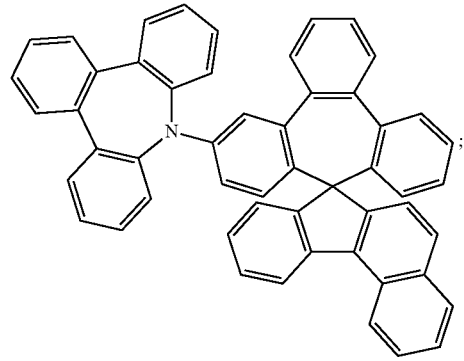
Compound 142
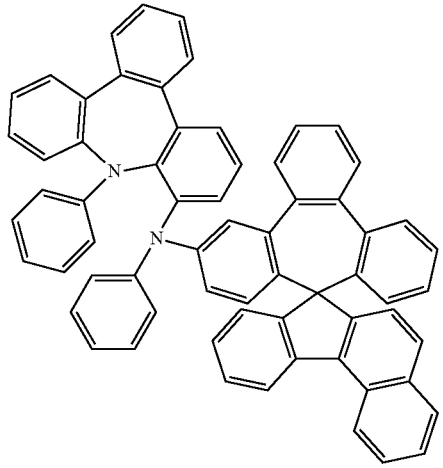
Compound 143
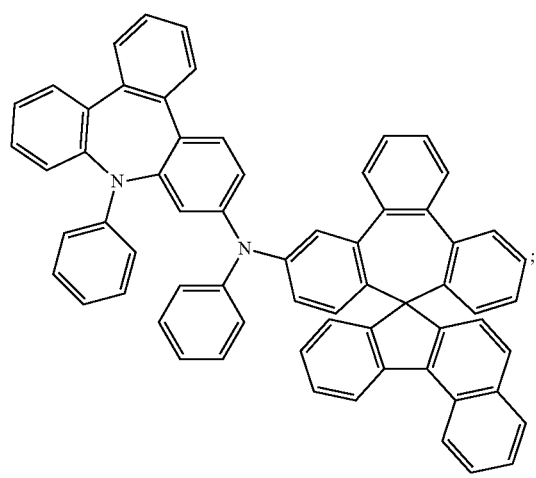
Compound 144
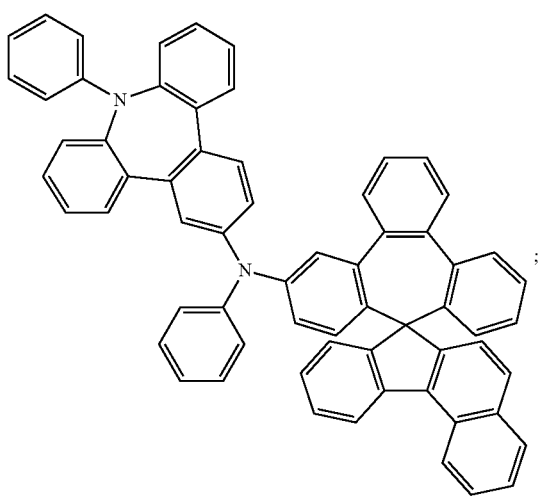

-continued
Compound 145
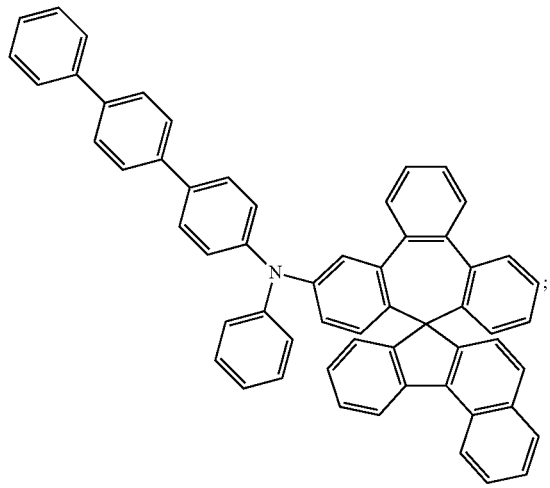
Compound 146
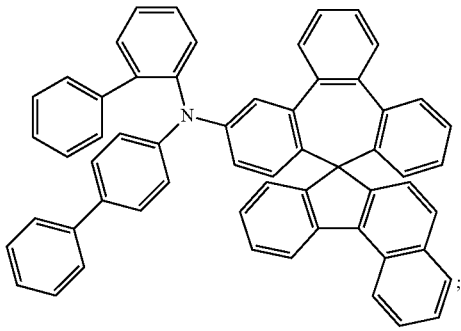
Compound 147
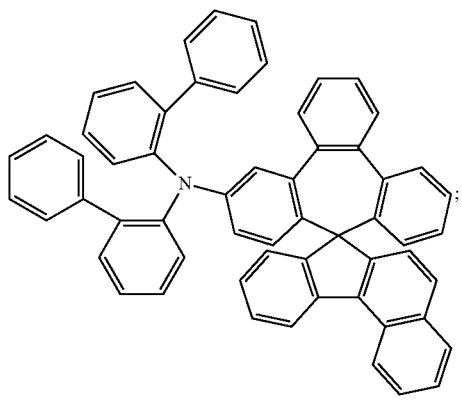
Compound 148
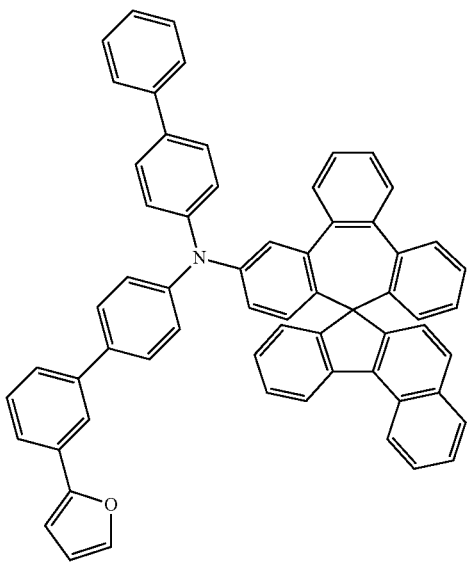
Compound 149
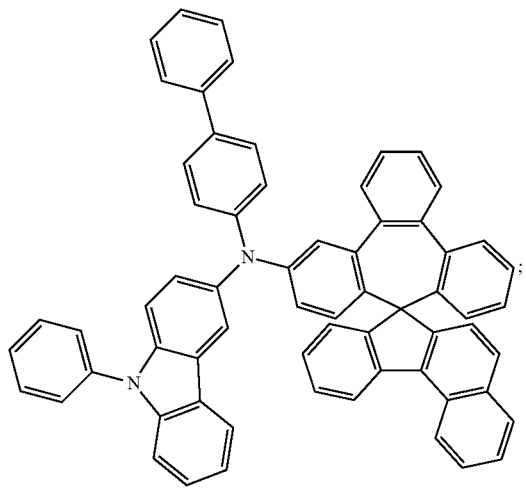
Compound 150
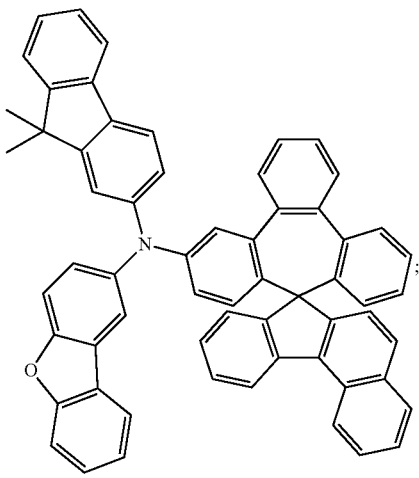

-continued
Compound 151
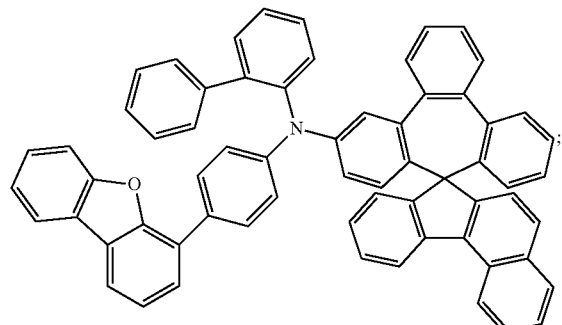
Compound 152
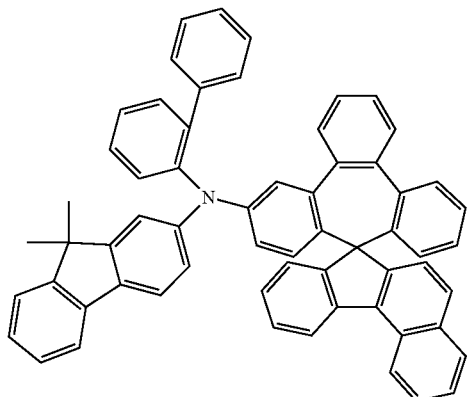
Compound 153
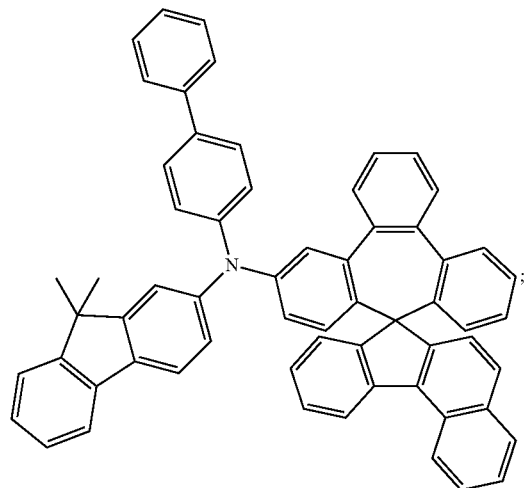
Compound 154
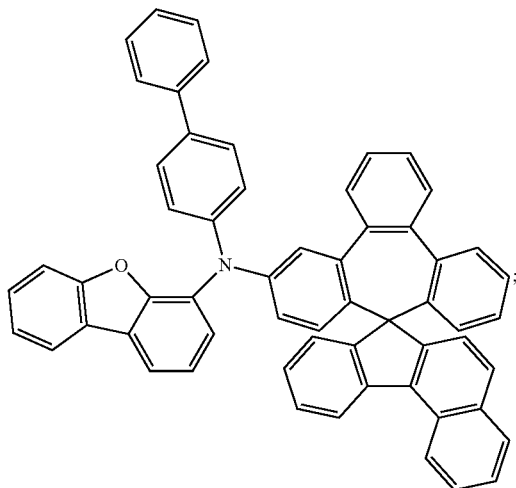
Compound 155
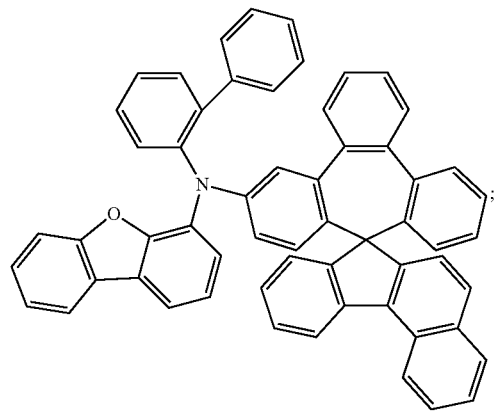
Compound 156
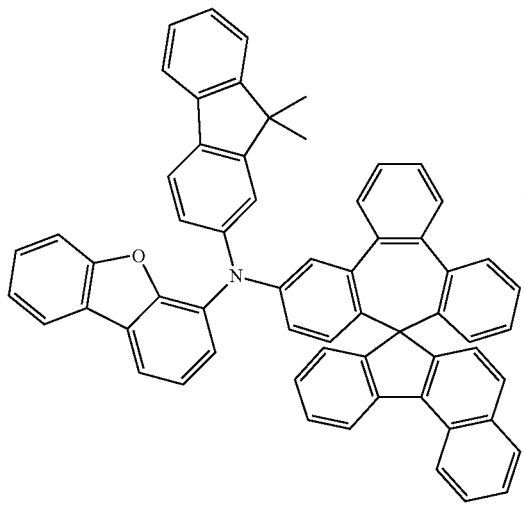

-continued
Compound 157
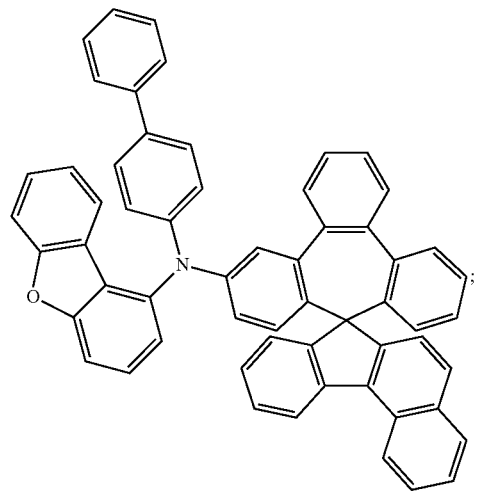
Compound 158
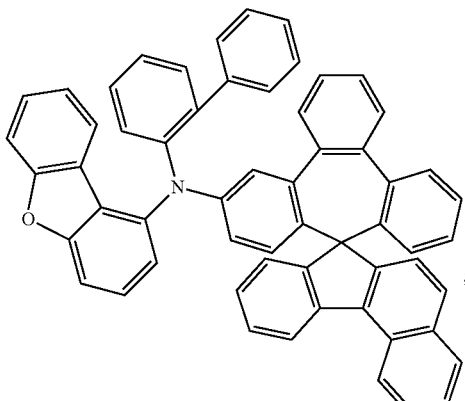
Compound 159
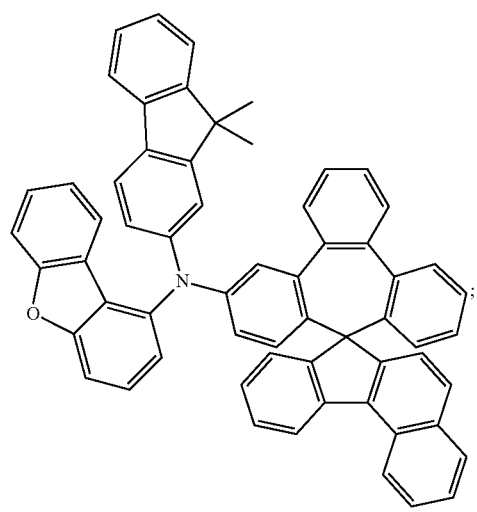
Compound 160
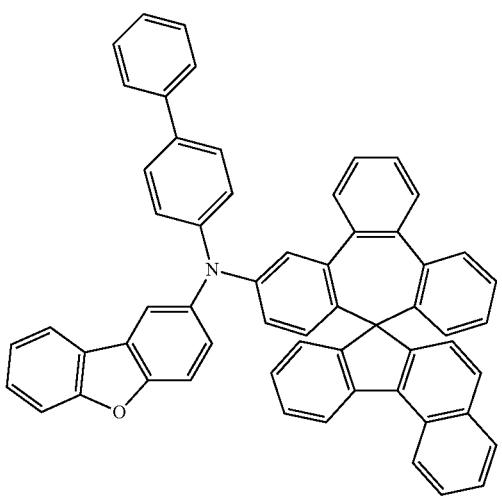
Compound 161
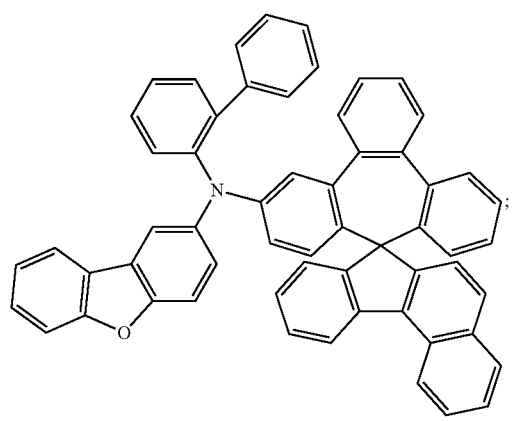
Compound 162
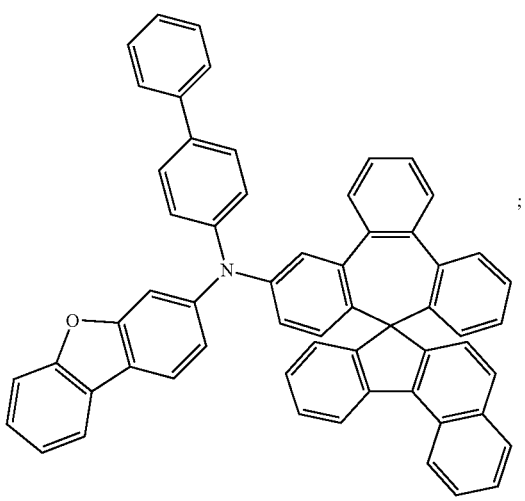

Compound 163
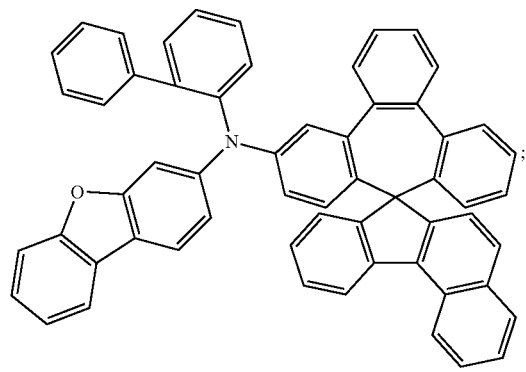
Compound 164
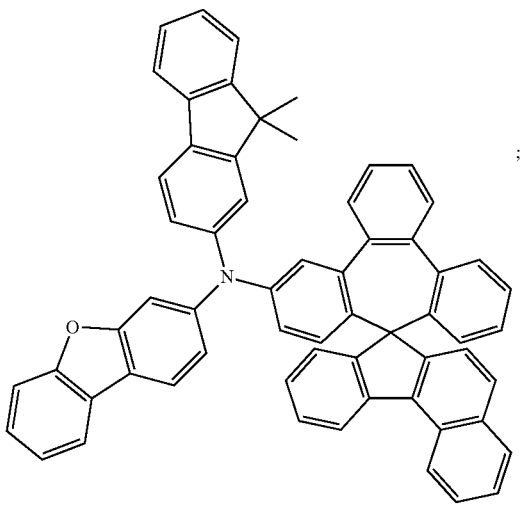
Compound 165
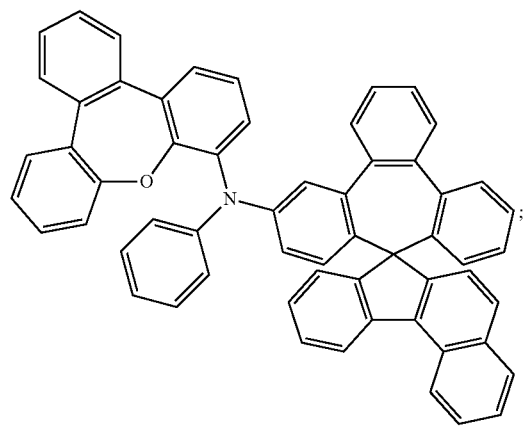
Compound 166
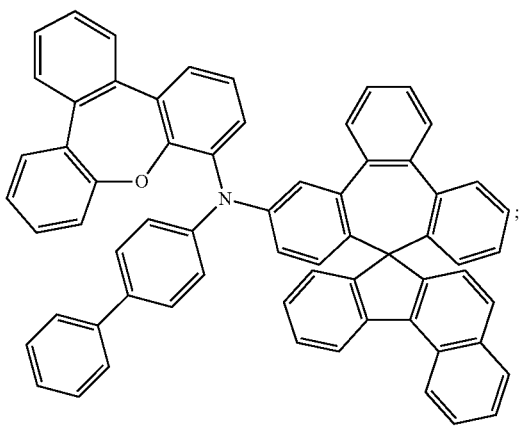
Compound 167
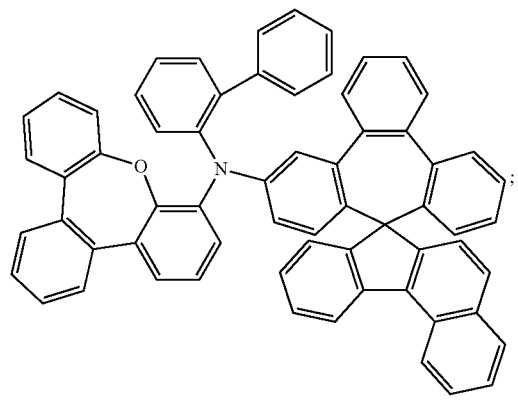
Compound 168
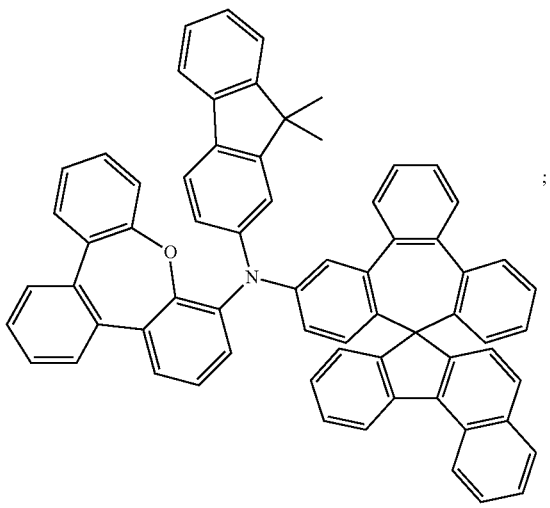

-continued
Compound 169
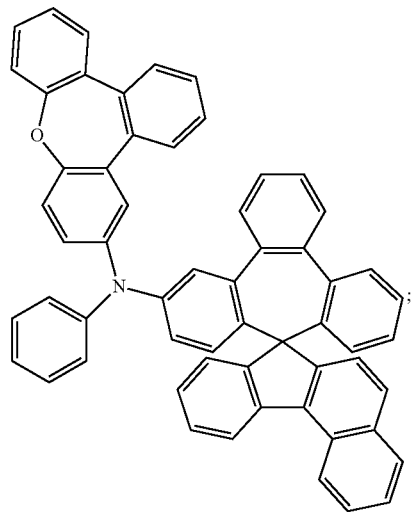
Compound 170
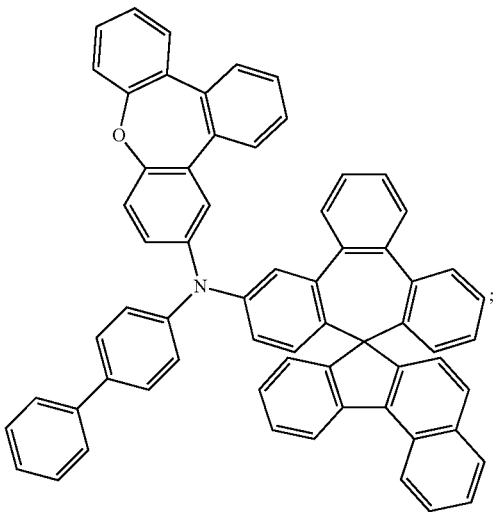
Compound 171
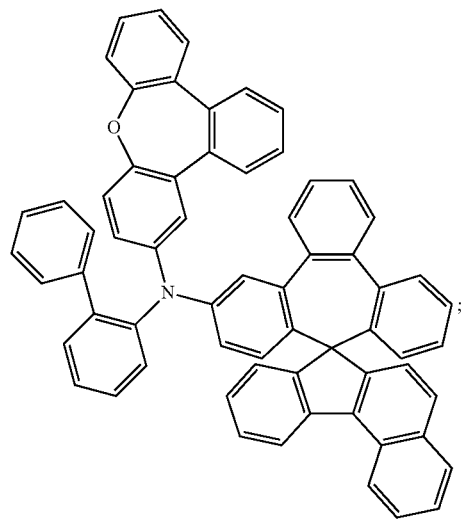
Compound 172
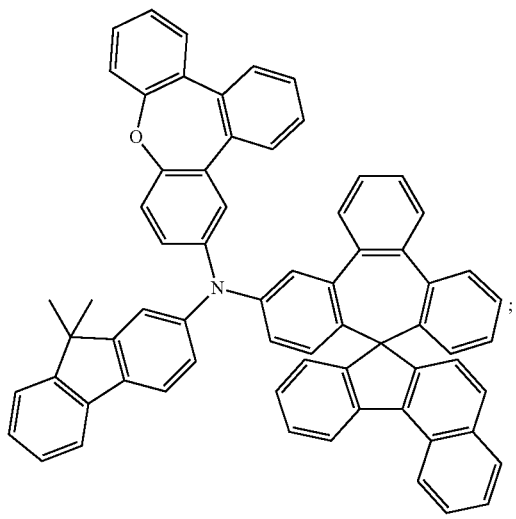
Compound 173
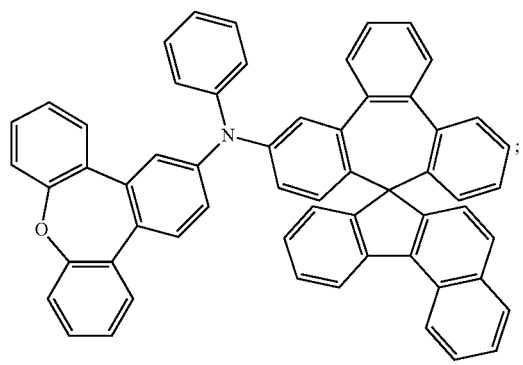
Compound 174
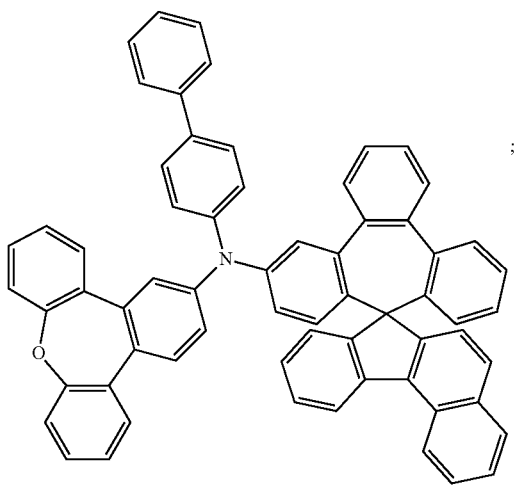

-continued
Compound 175
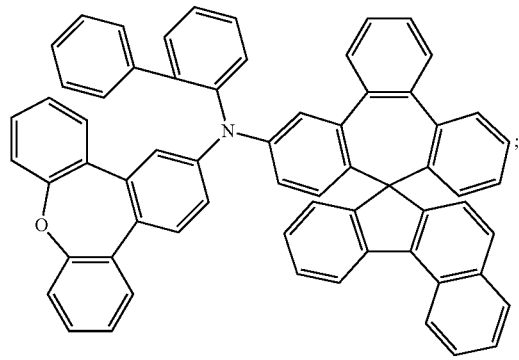
Compound 176
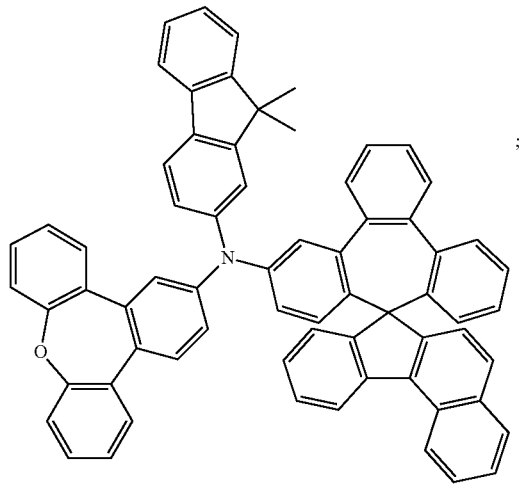
Compound 177
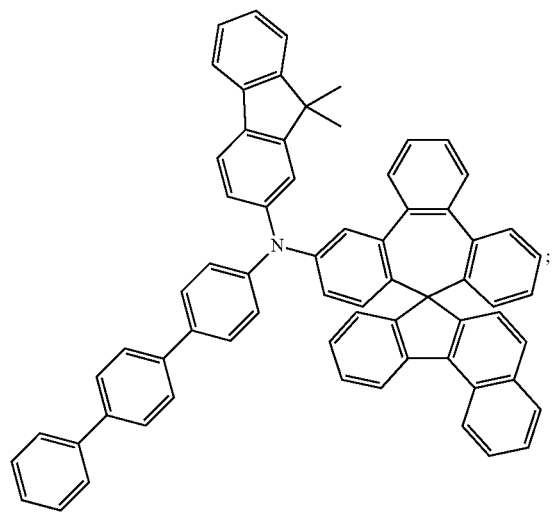
Compound 178
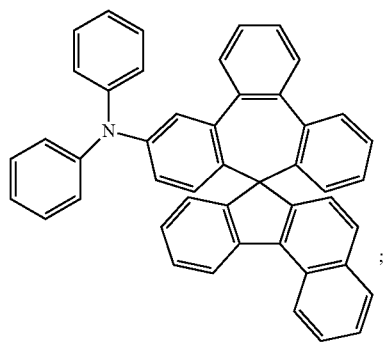
Compound 179
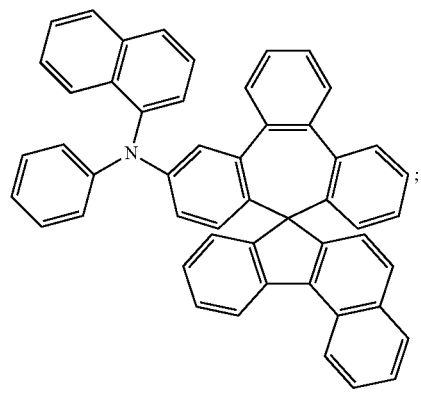
Compound 180
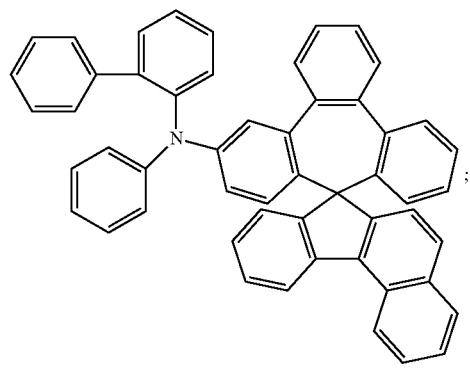

-continued
Compound 181
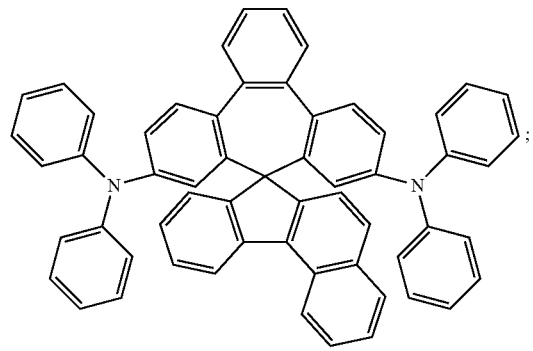
Compound 182
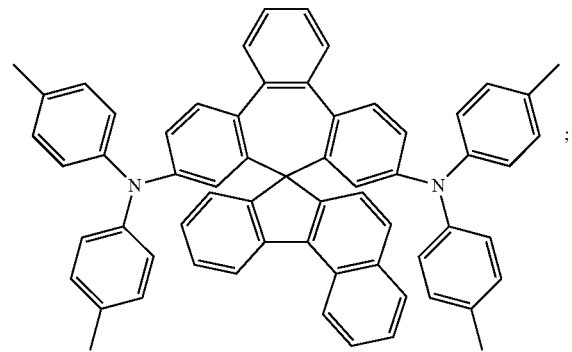
Compound 183
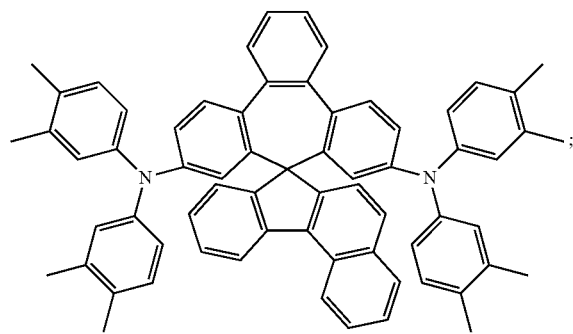
Compound 184
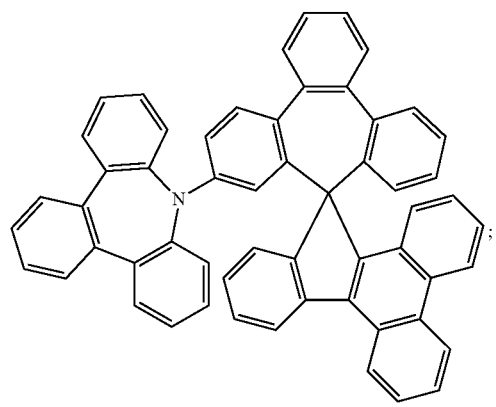
Compound 185
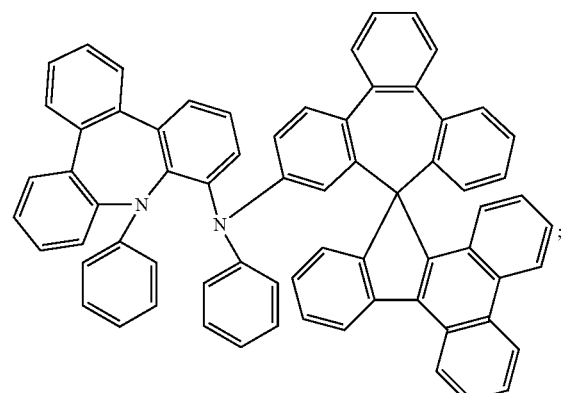
Compound 186
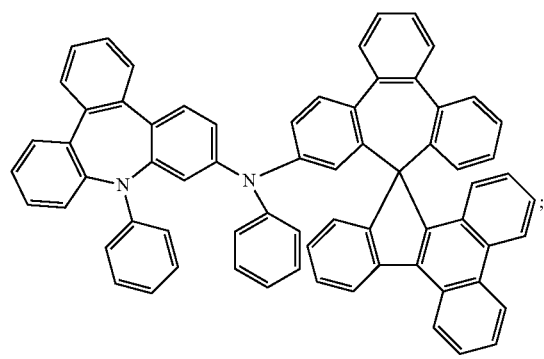
Compound 187
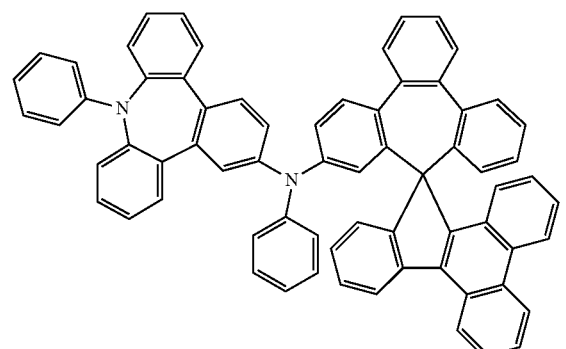

-continued
Compound 188
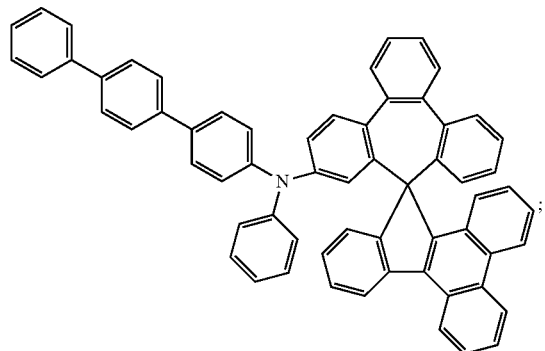
Compound 189
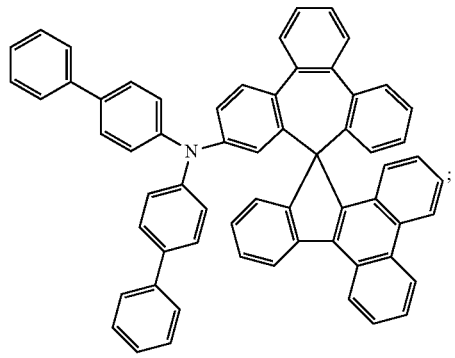
Compound 190
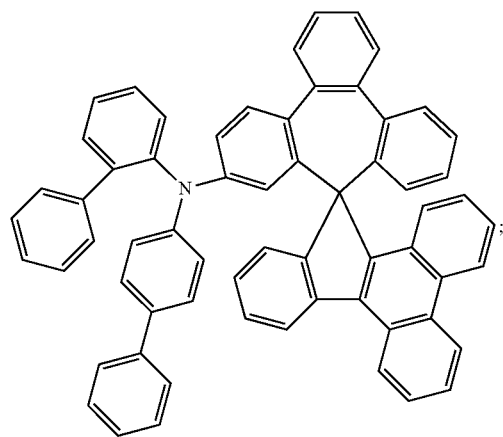
Compound 191
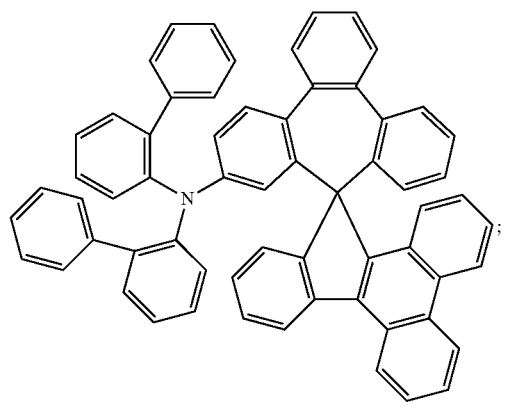
Compound 192
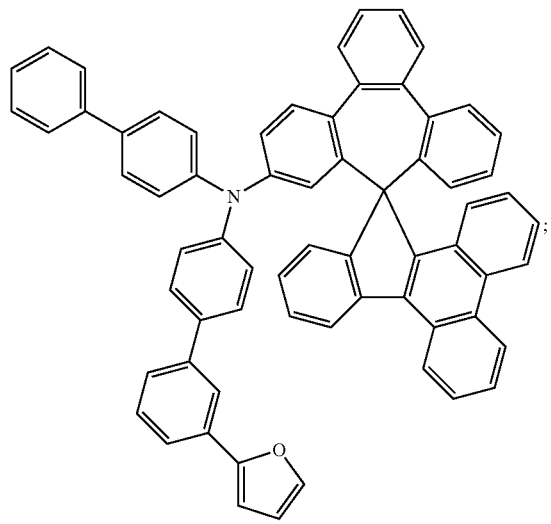
Compound 193
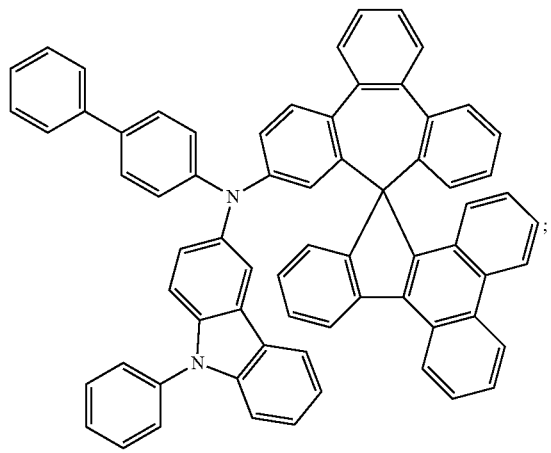

-continued
Compound 194
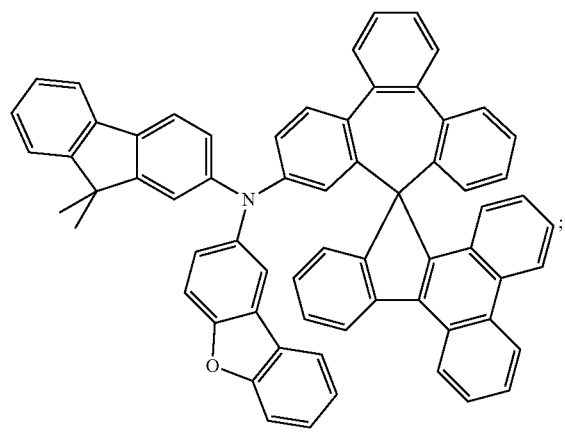
Compound 195
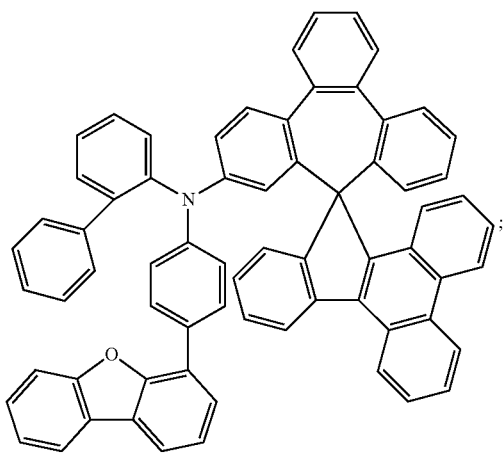
Compound 196
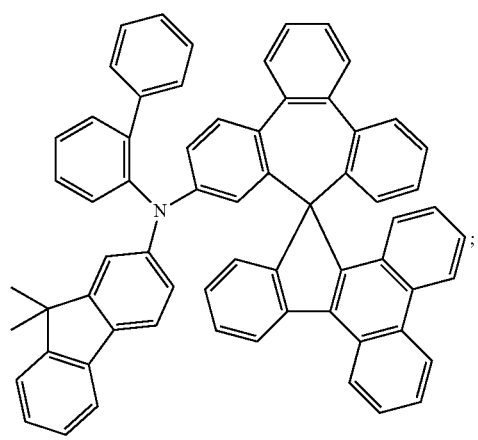
Compound 197
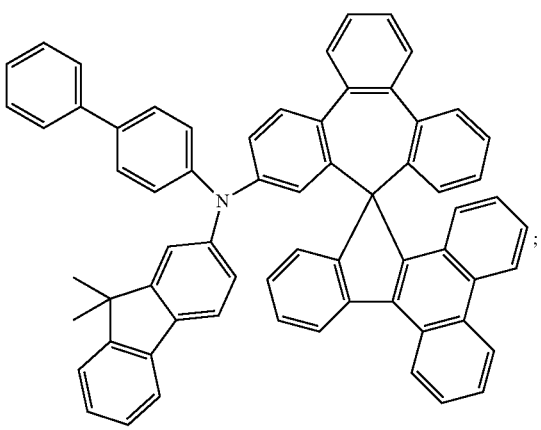
Compound 198
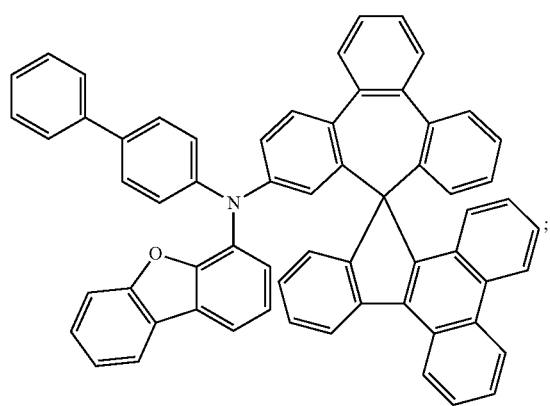
Compound 199
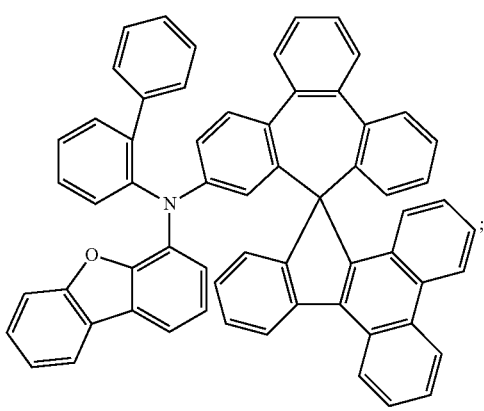

-continued
Compound 200
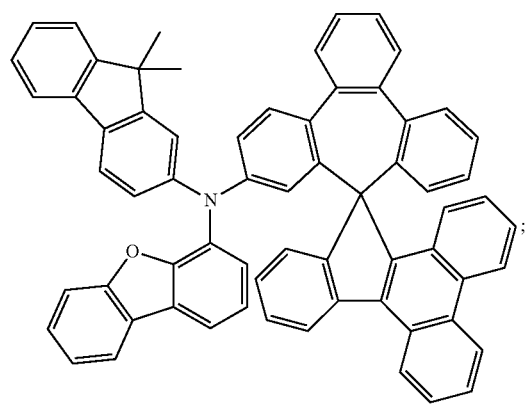
Compound 201
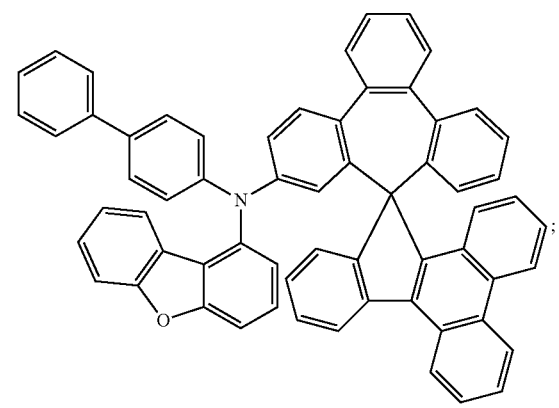
Compound 202
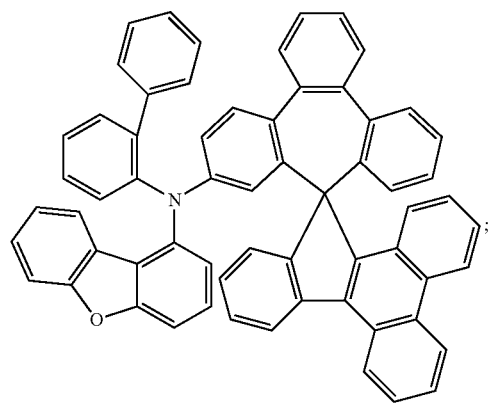
Compound 203
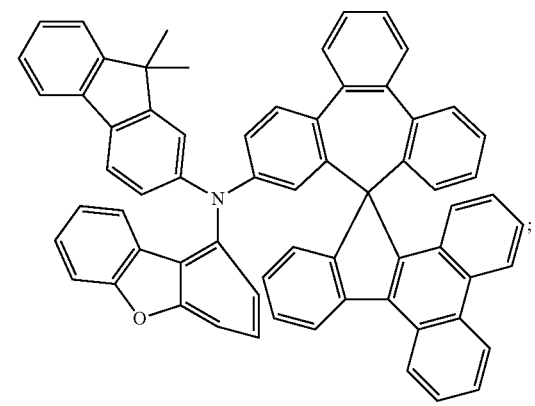
Comopund 204
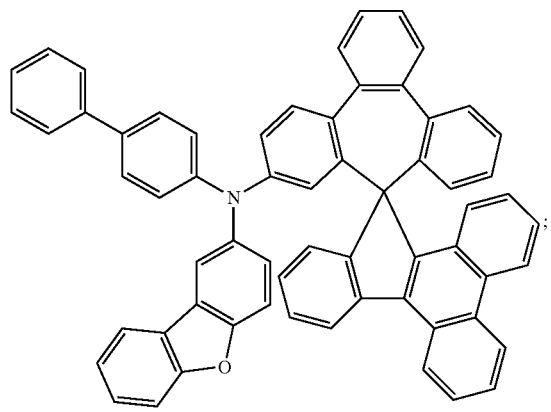
Compound 205
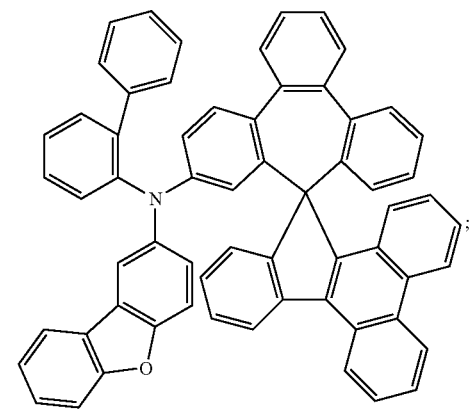

-continued
Compound 206
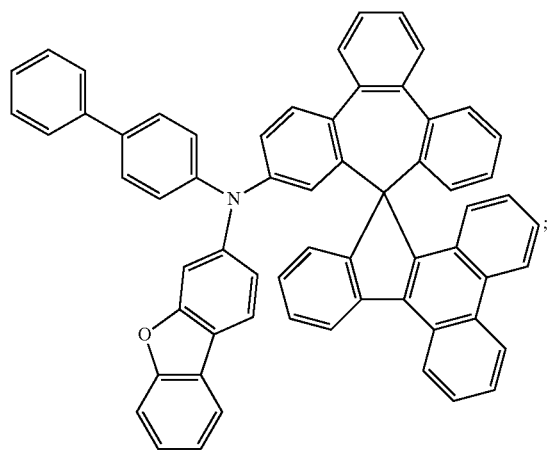
Compound 207
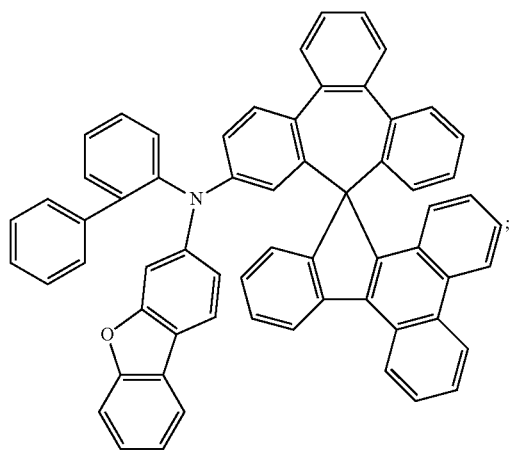
Compound 208
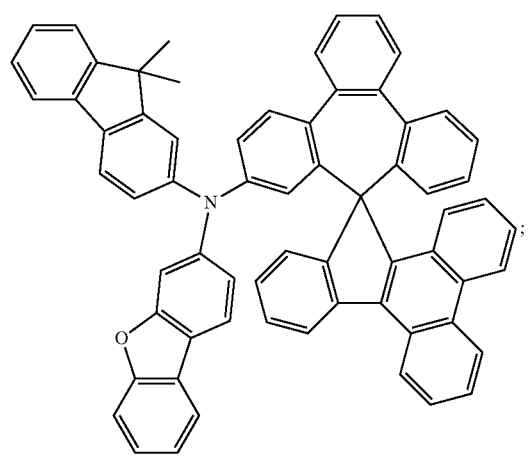
Compound 209
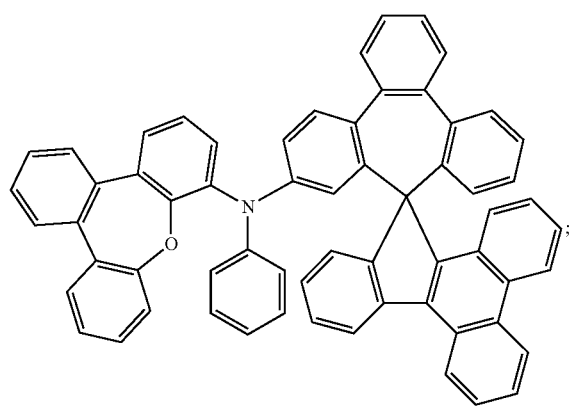
Compound 210
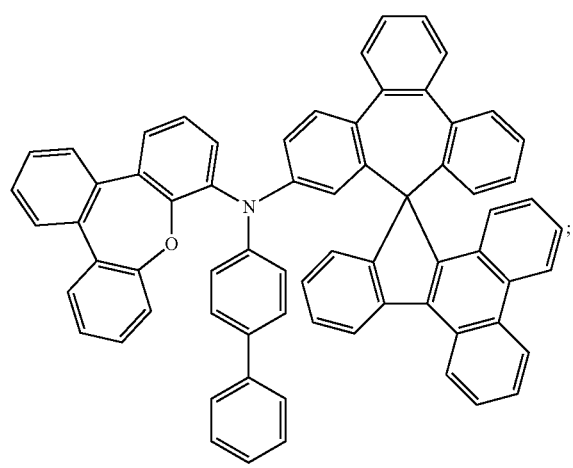
Compound 211
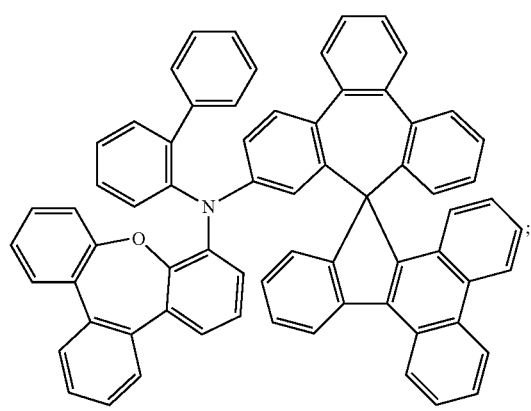

-continued
Compound 212
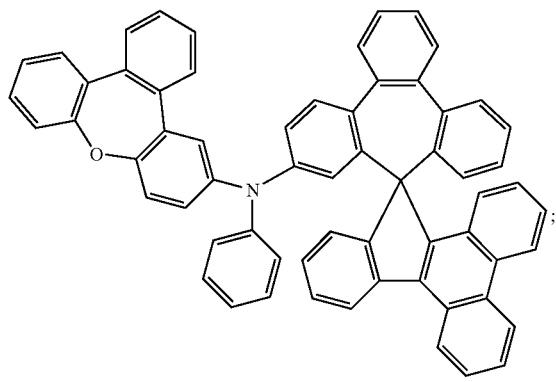
Compound 213
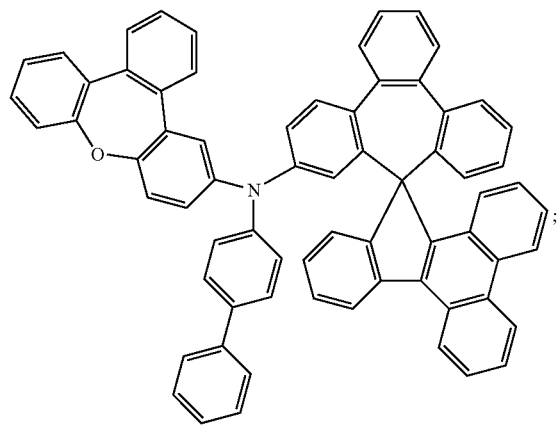
Compound 214
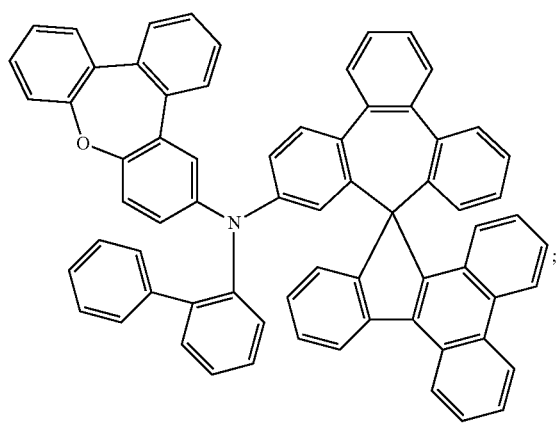
Compound 215
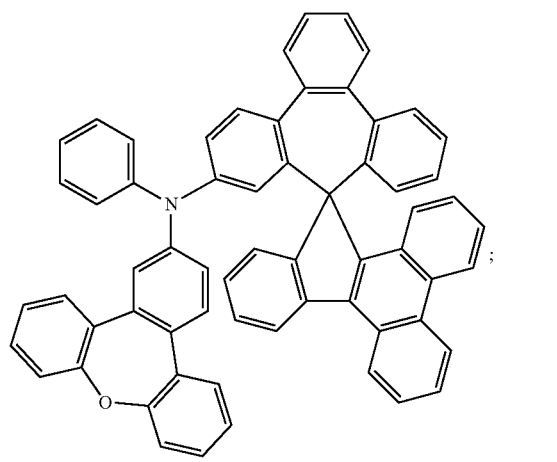
Compound 216
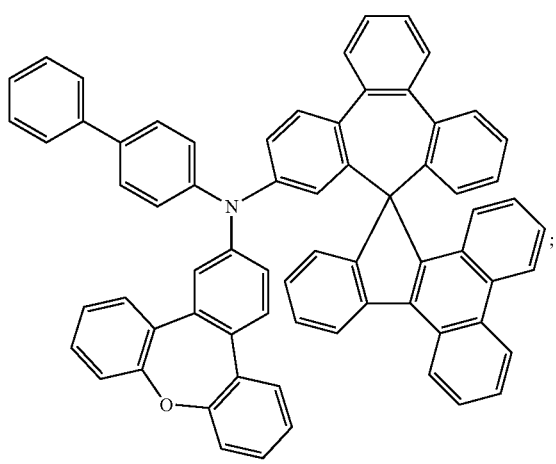
Compound 217
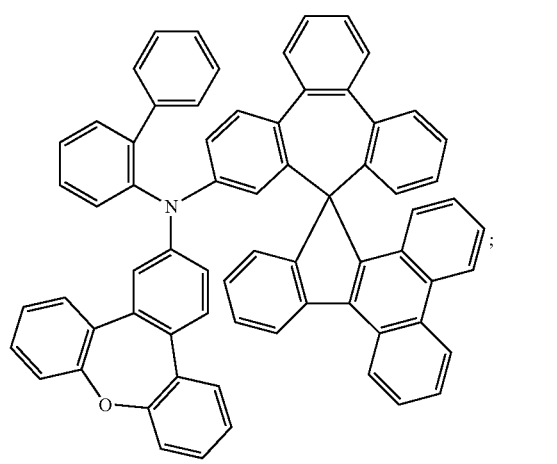

-continued
Compound 218
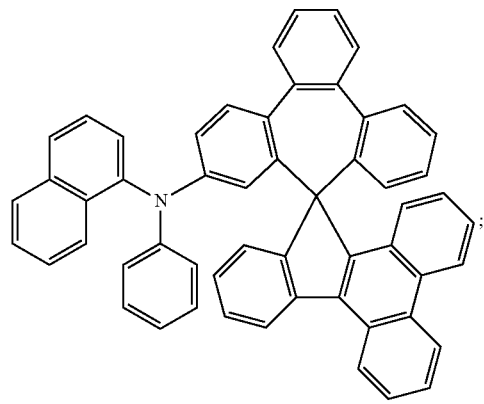
Compound 219
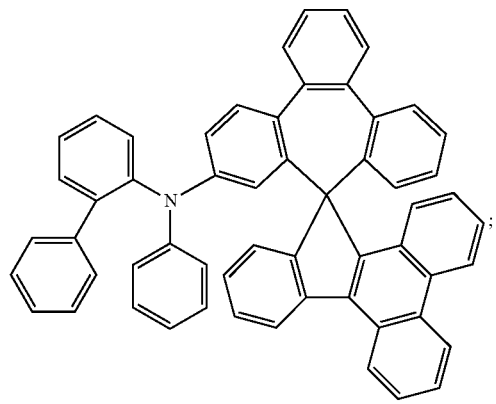
Compound 220
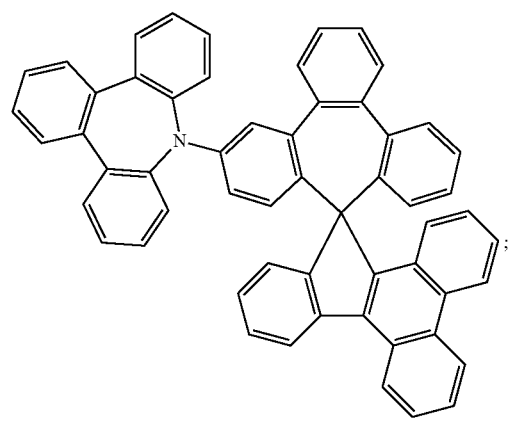
Compound 221
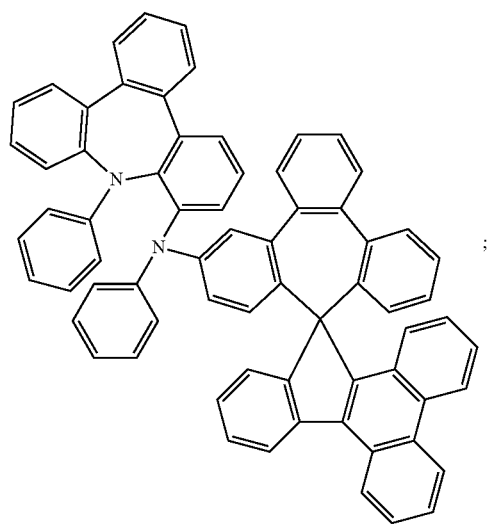
Compound 222
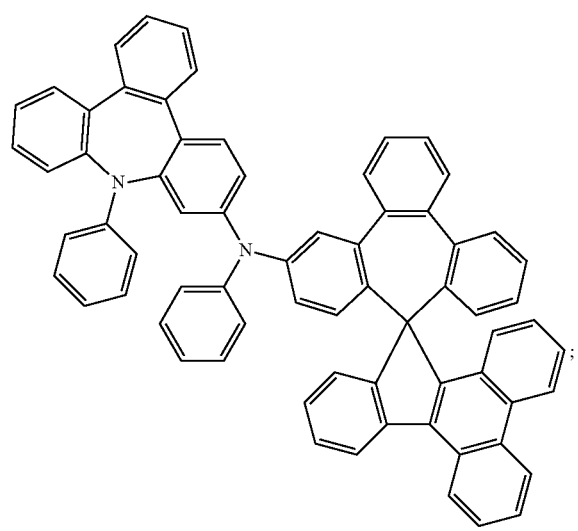
Compound 223
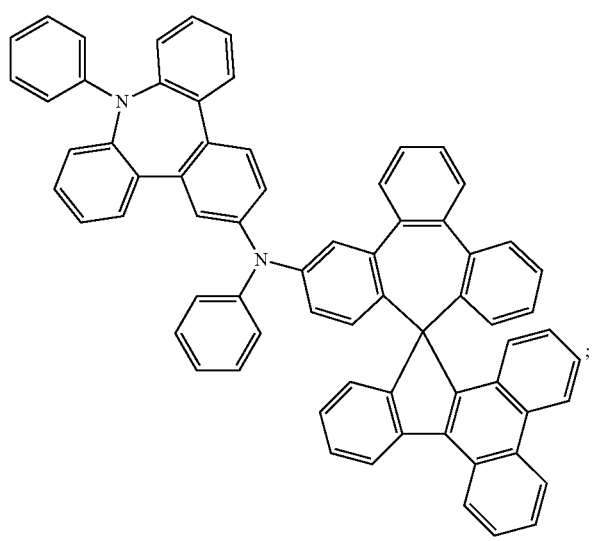

-continued
Compound 224
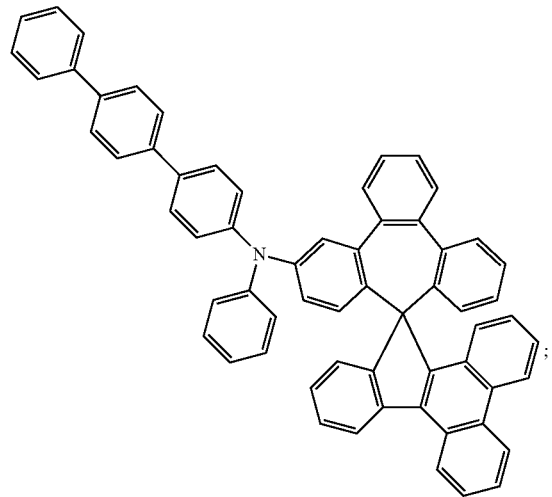
Compound 225
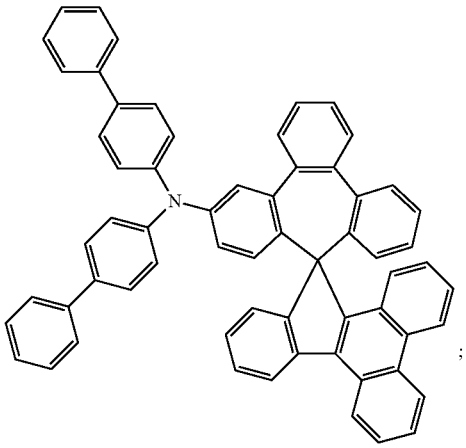
Compound 226
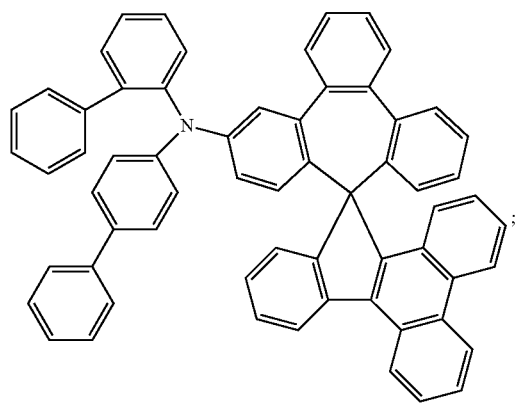
Compound 227
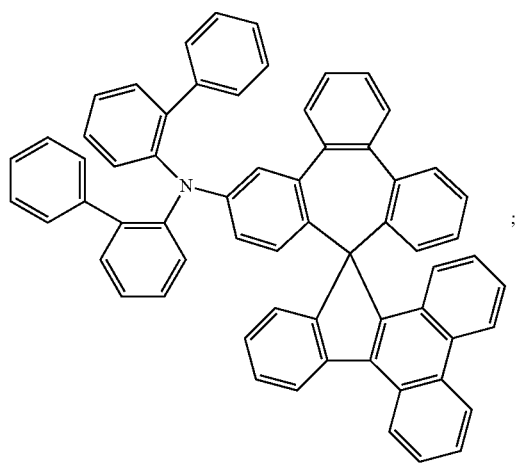
Compound 228
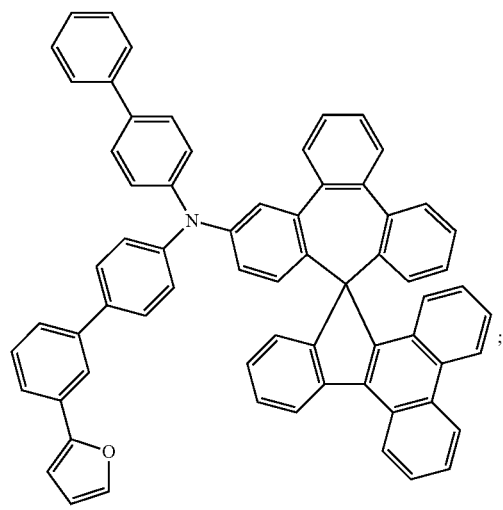
Compound 229
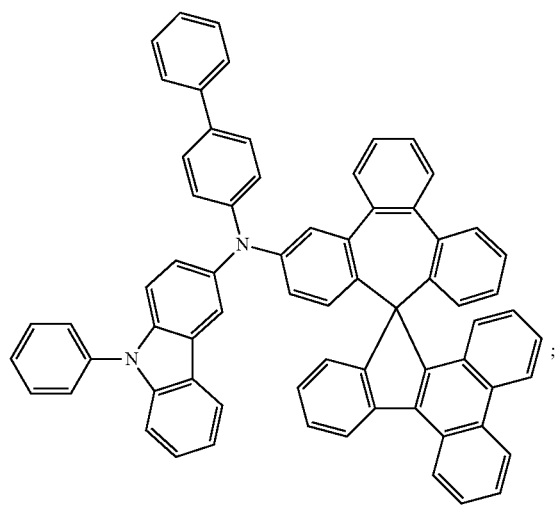

-continued
Compound 230
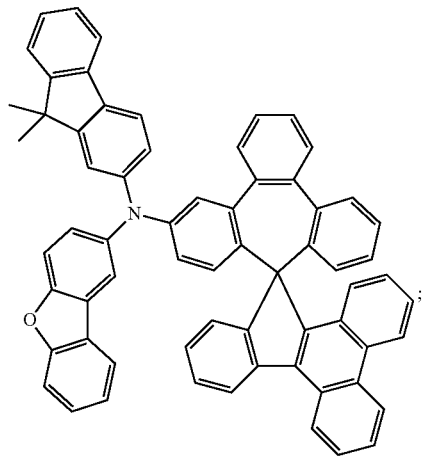
Compound 231
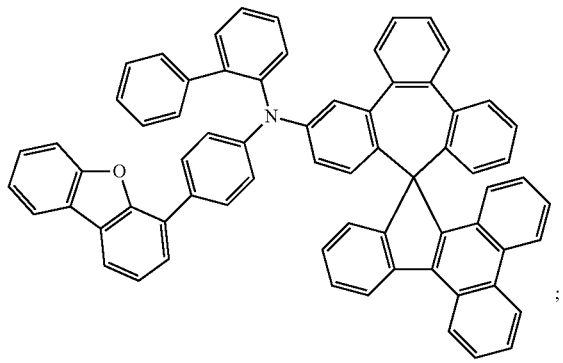
Compound 232
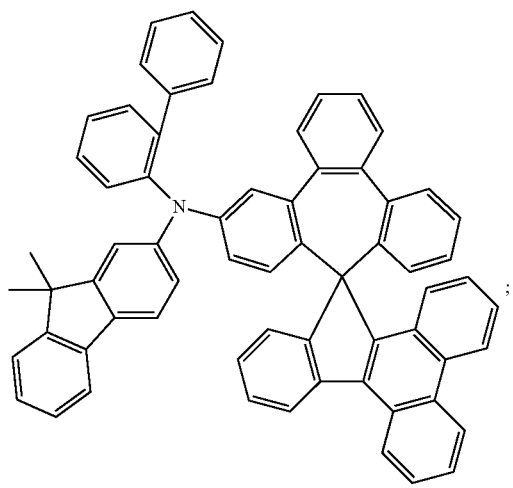
Compound 233
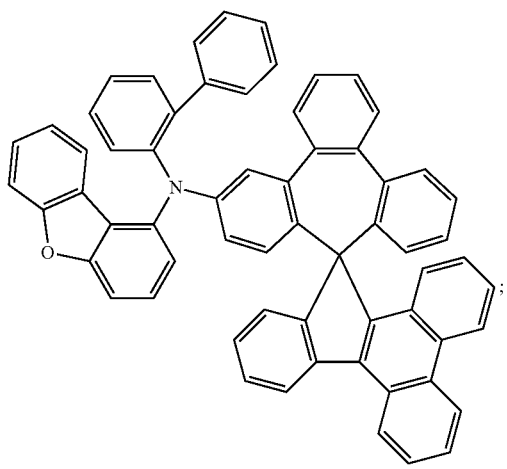
Compound 234
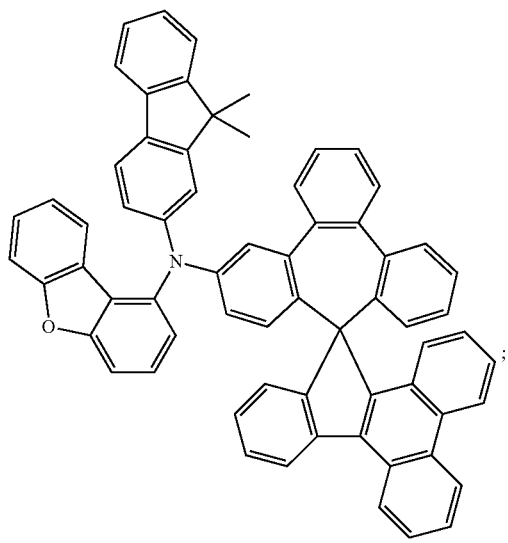
Compound 235
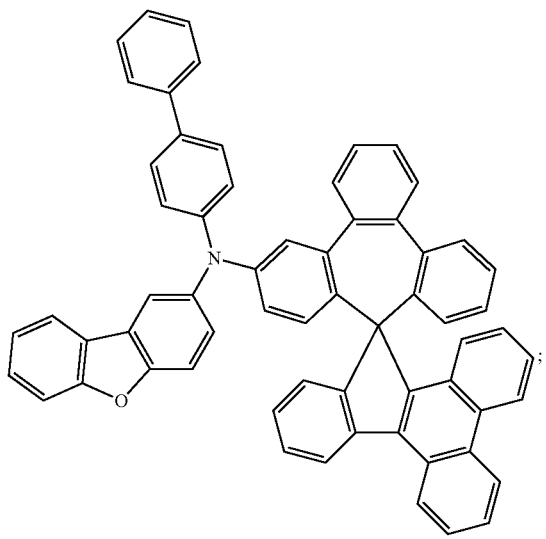

Compound 236
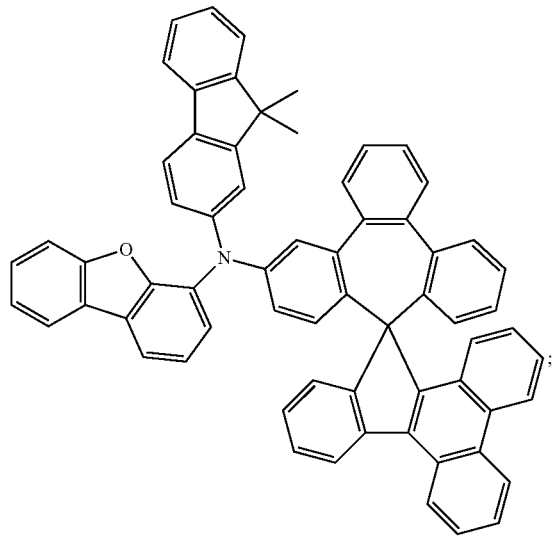
Compound 237
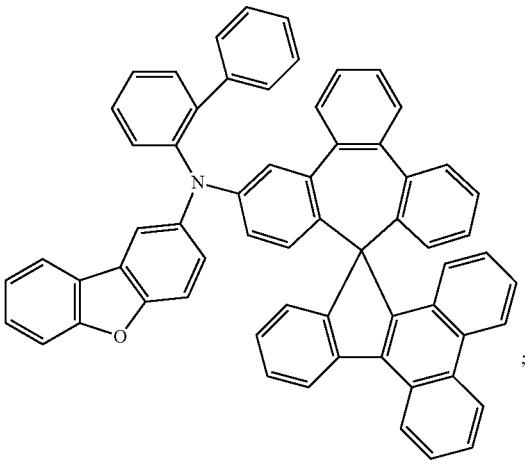
Compound 238
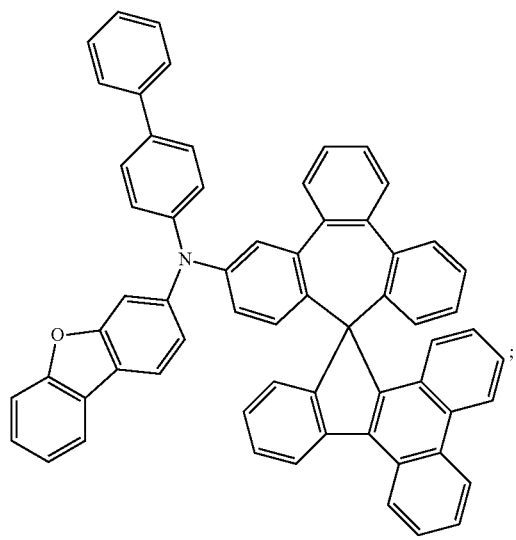
Compound 239
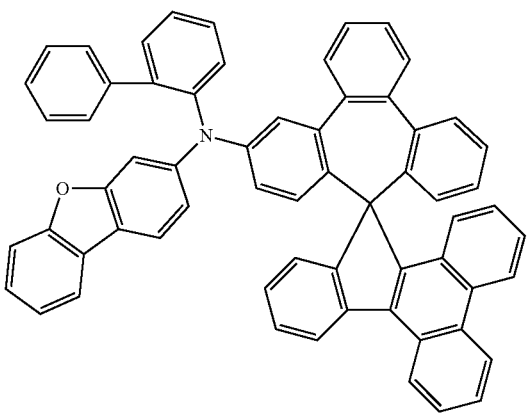
Compound 240
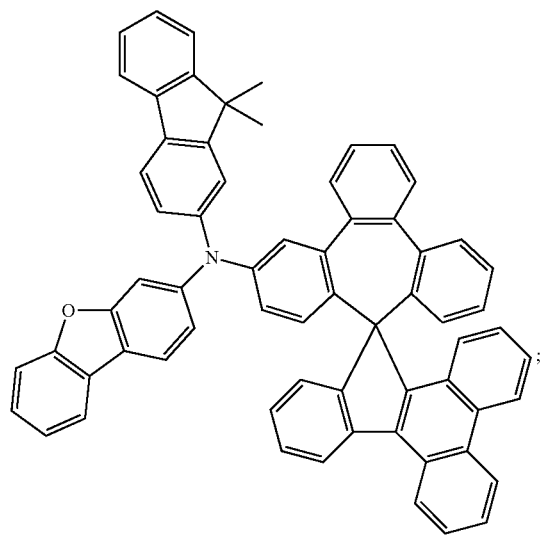
Compound 241
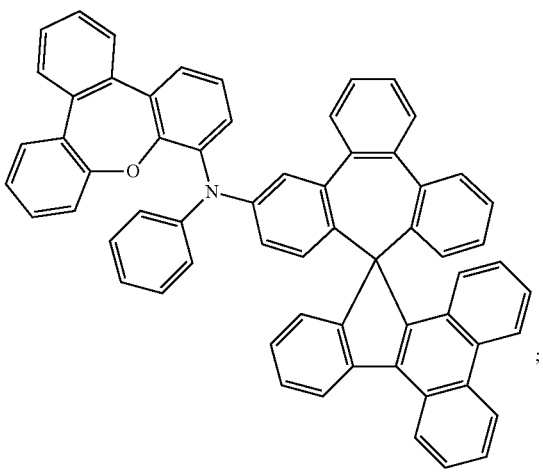

-continued
Compound 242
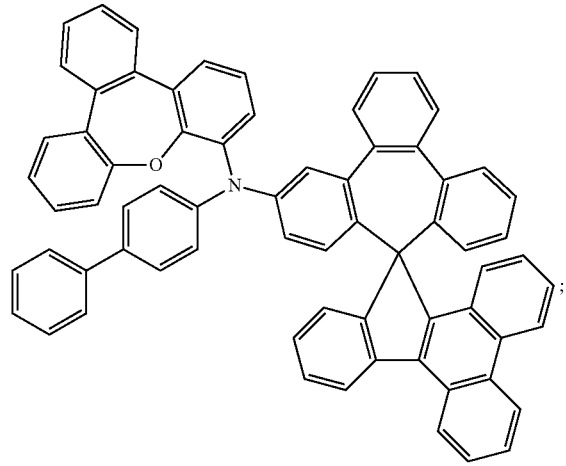
Compound 243
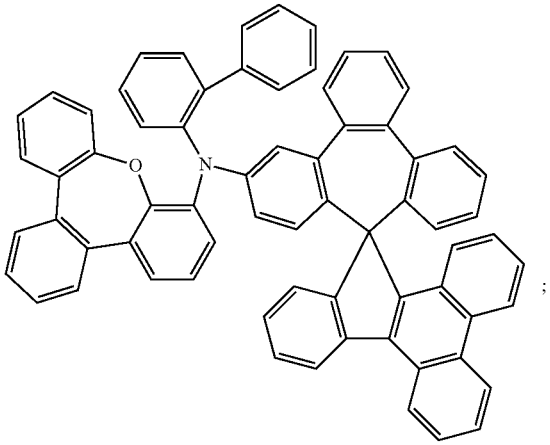
Compound 244
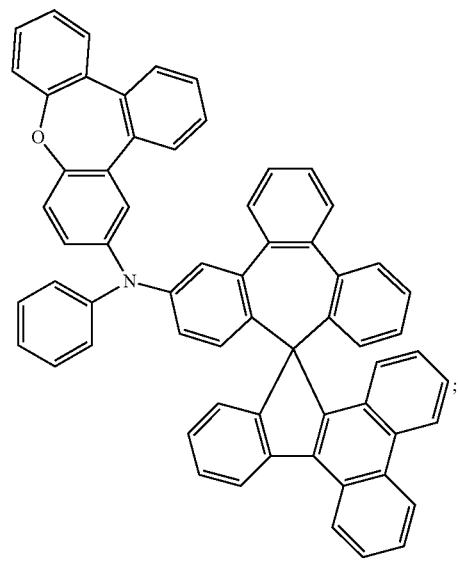
Compound 245
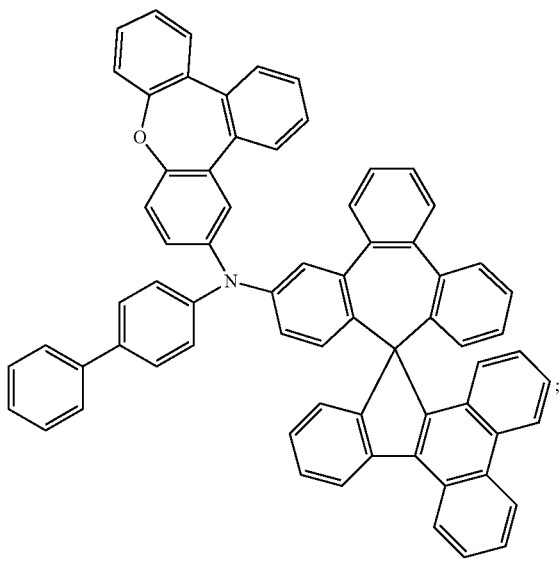
Compound 246
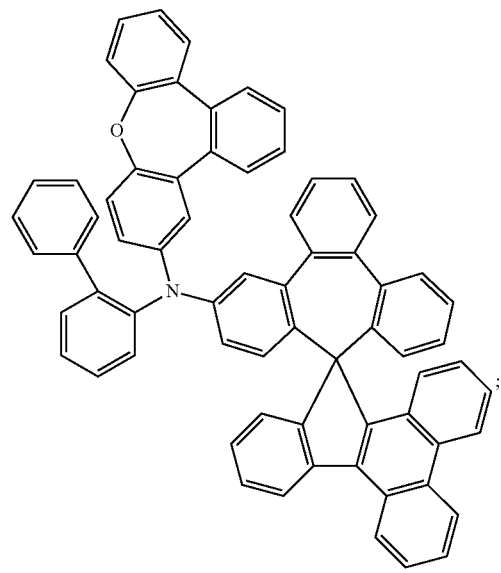
Compound 247

-continued
Compound 248
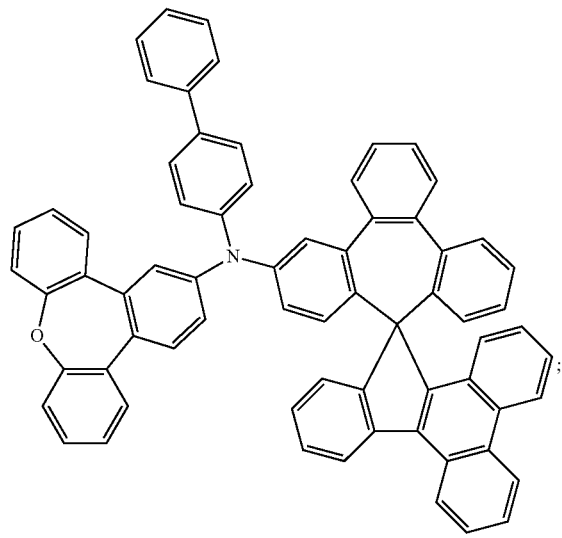
Compound 249
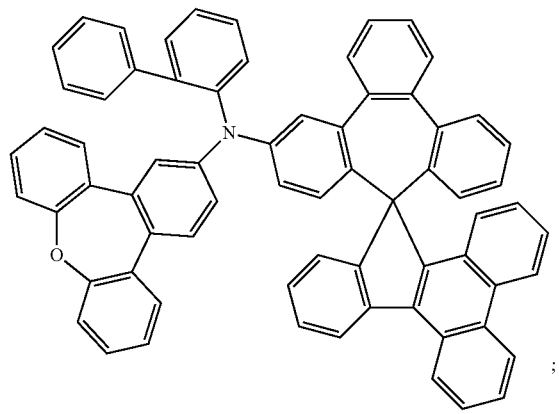
Compound 250
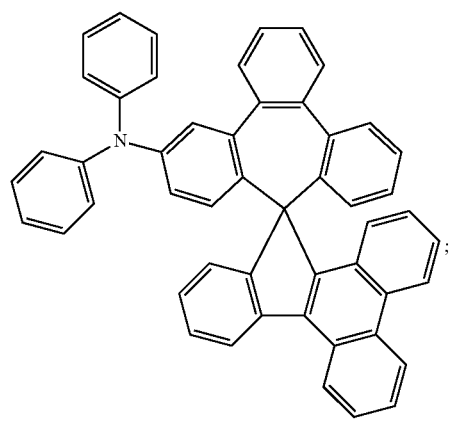
Compound 251
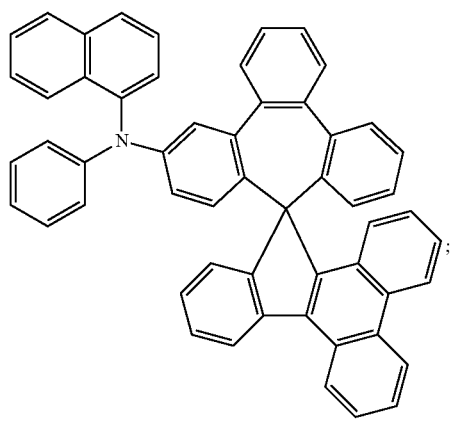
Compound 252
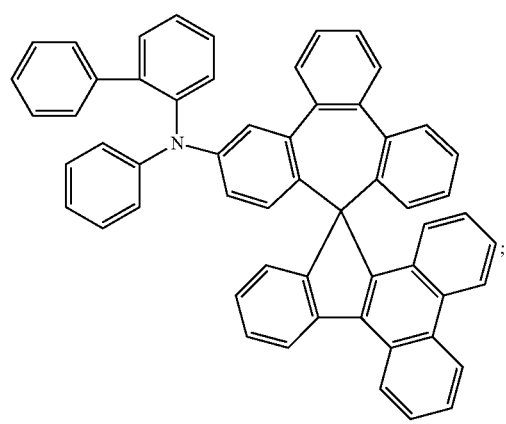
Compound 253
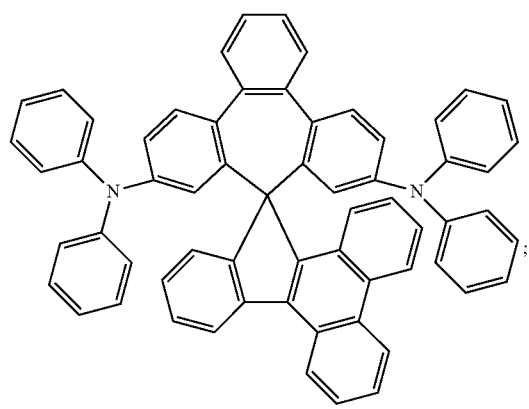

-continued
Compound 254
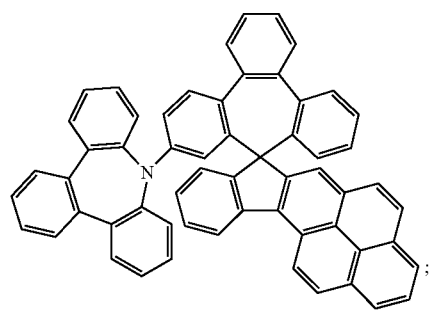
Compound 255
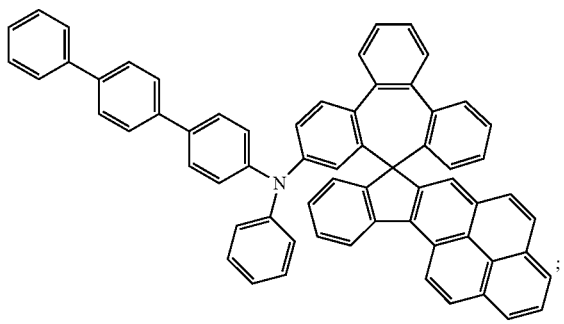
Compound 256
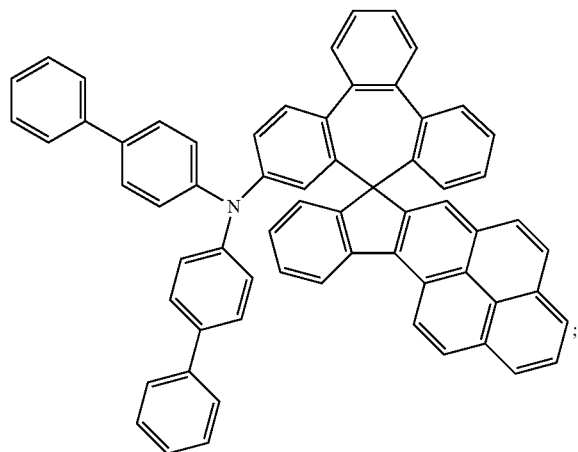
Compound 257
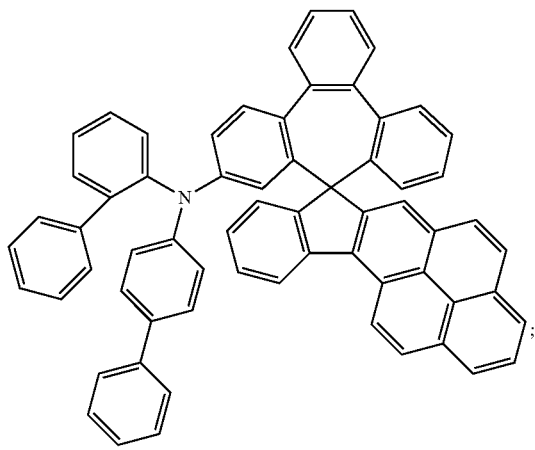
Compound 258
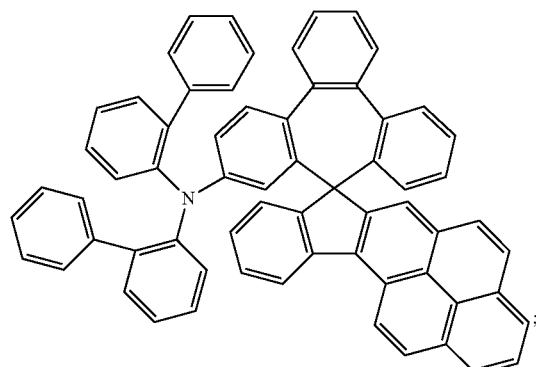
Compound 259
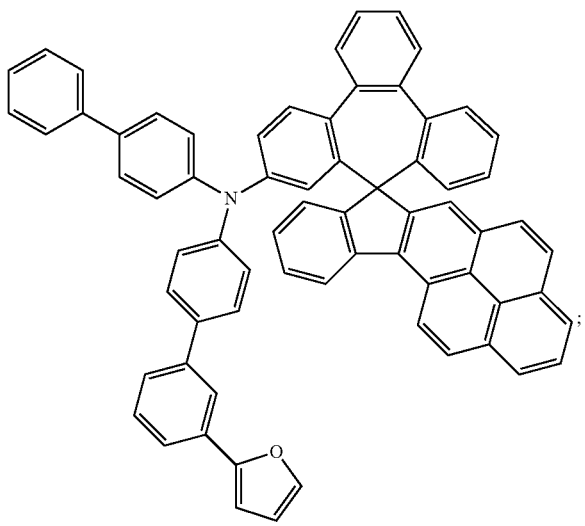

Compound 260
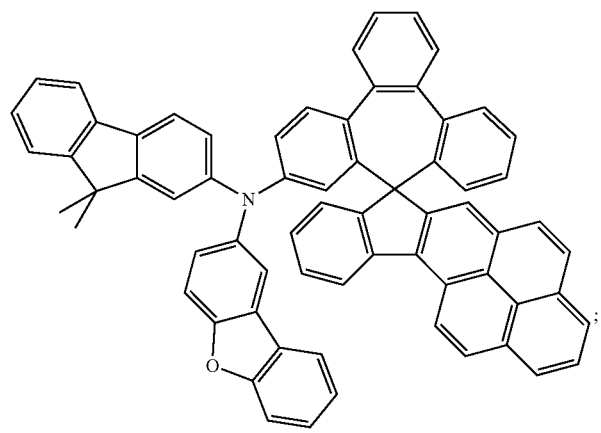
Compound 261
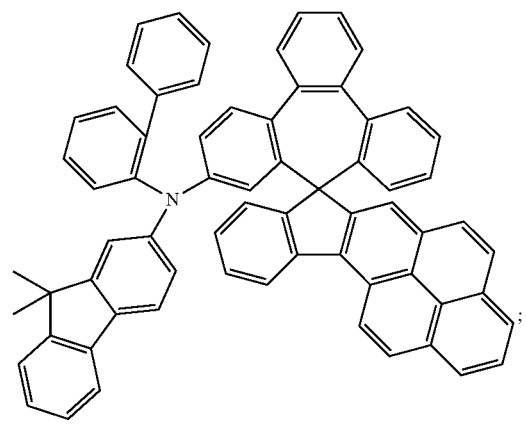
Compound 262
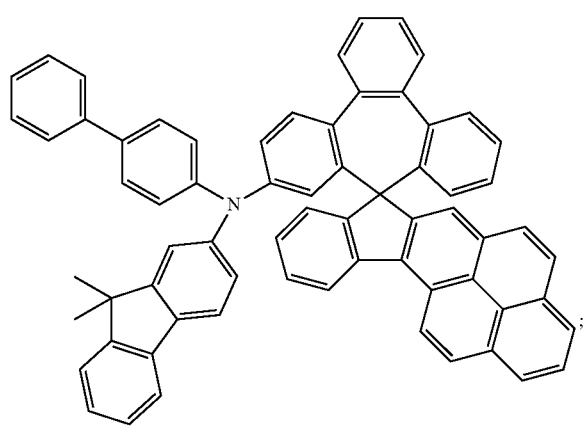
Compound 263
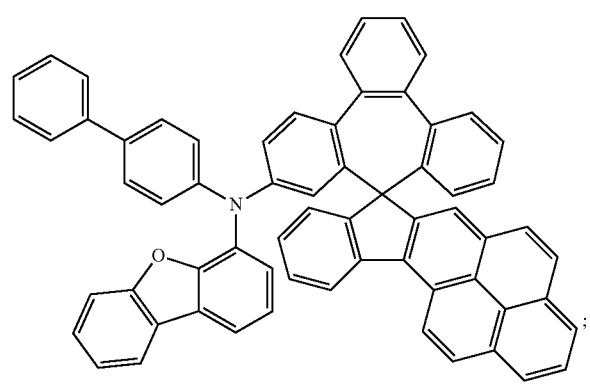
Compound 264
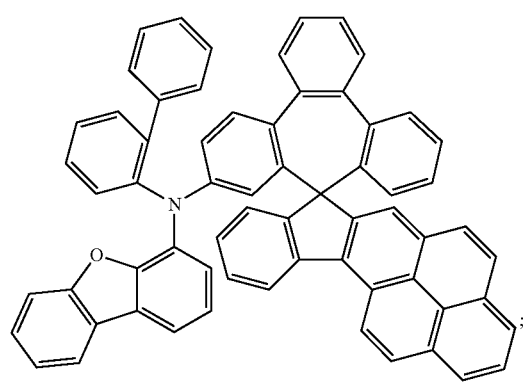
Compound 265
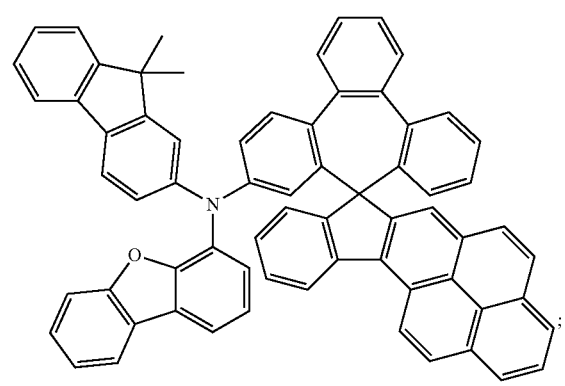

-continued
Compound 266
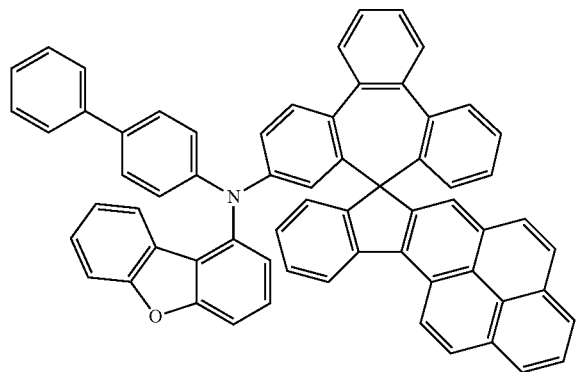
Compound 267
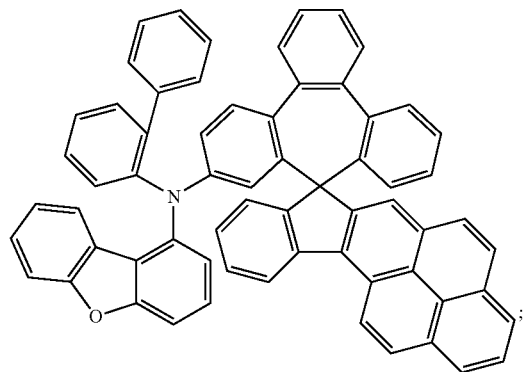
Compound 268
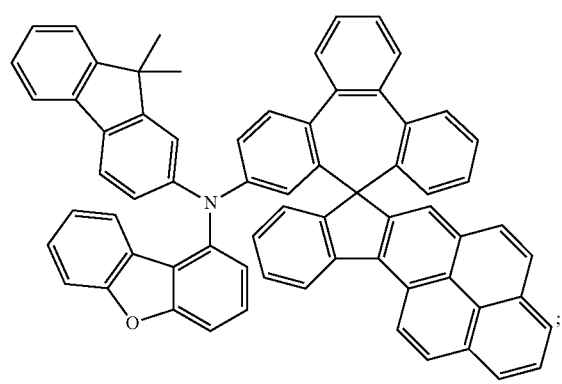
Compound 269
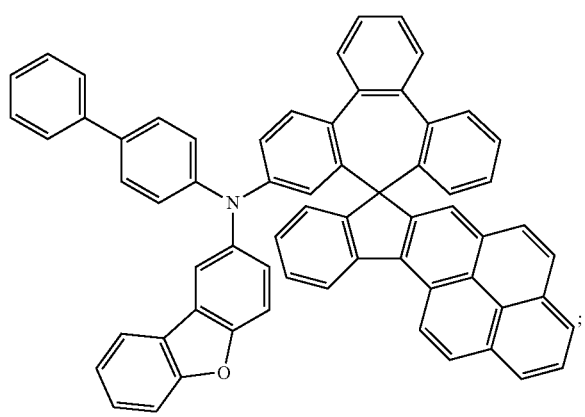
Compound 270
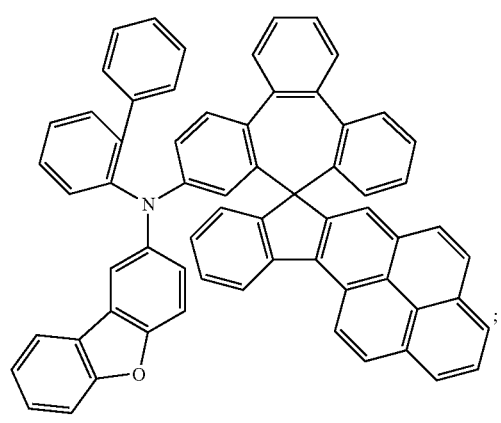
Compound 271
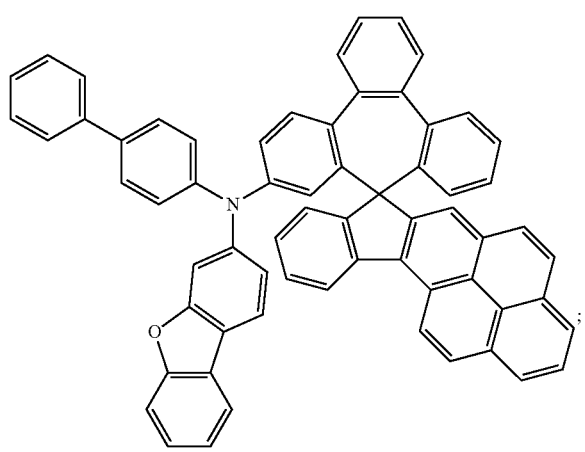

-continued
Compound 272
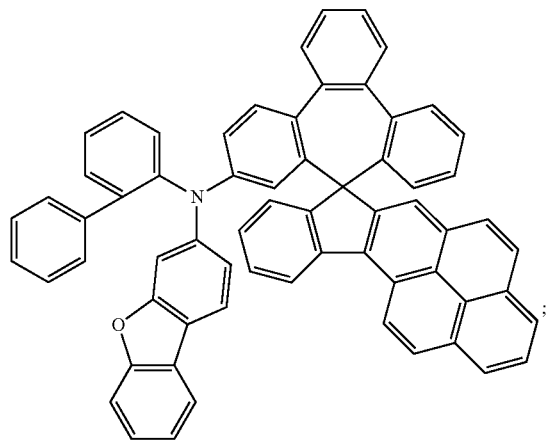
Compound 273
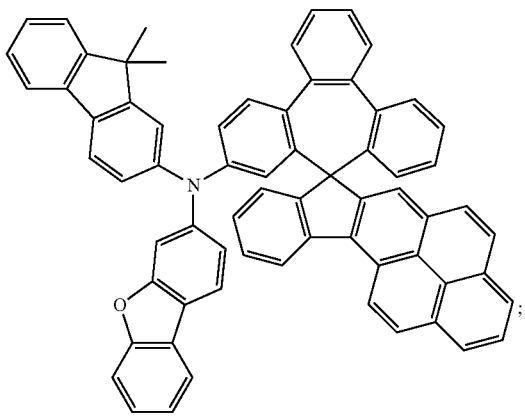
Comopund 274
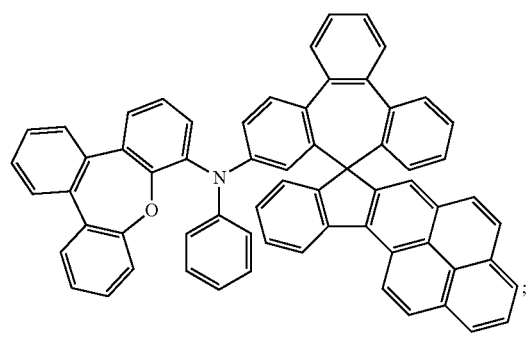
Compound 275
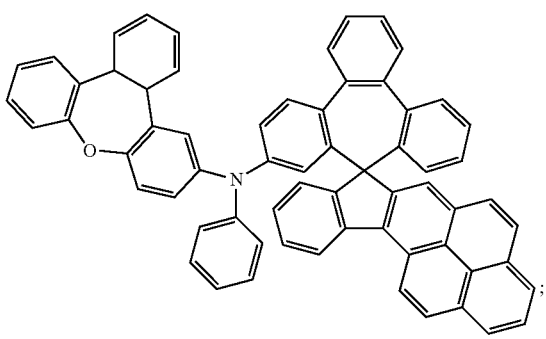
Compound 276
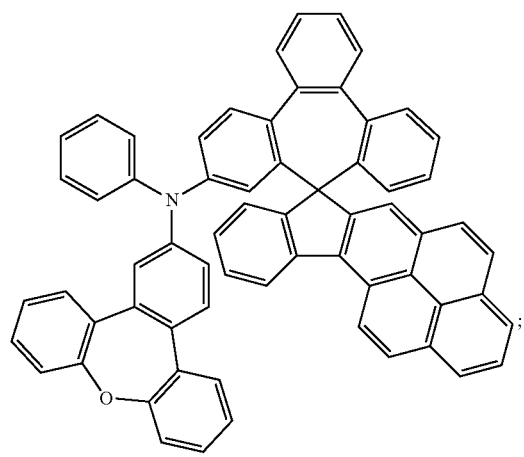
Compound 277
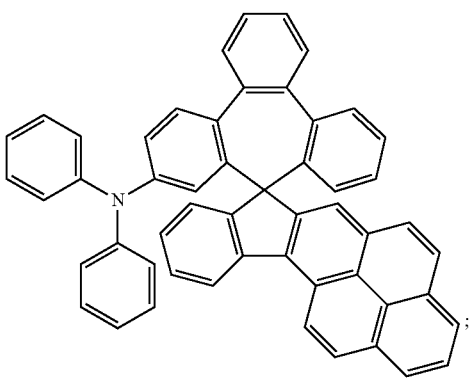

-continued
Compound 278
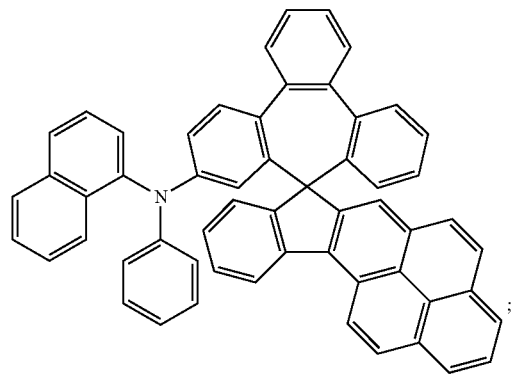
Compound 279
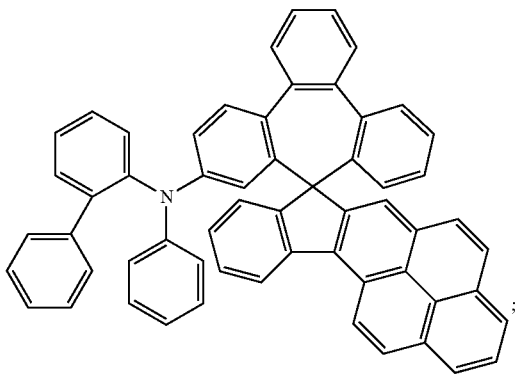
Compound 280
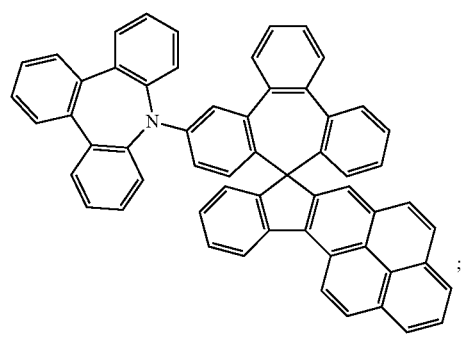
Compound 281
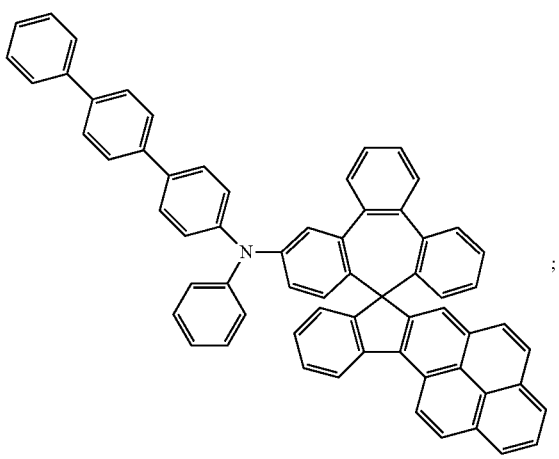
Compound 282
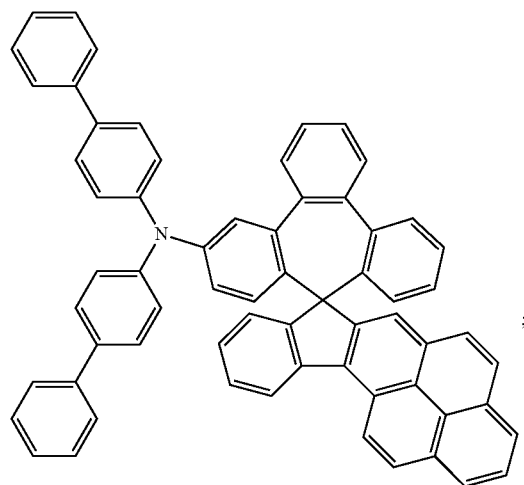
Compound 283
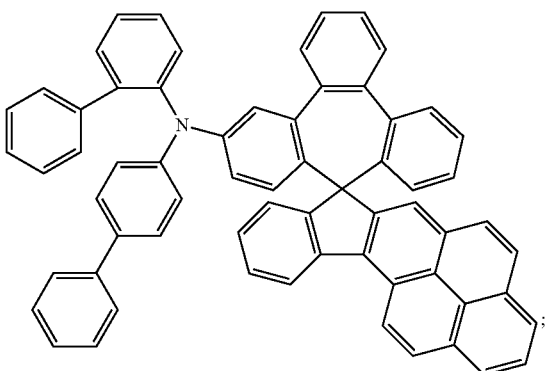

Compound 284
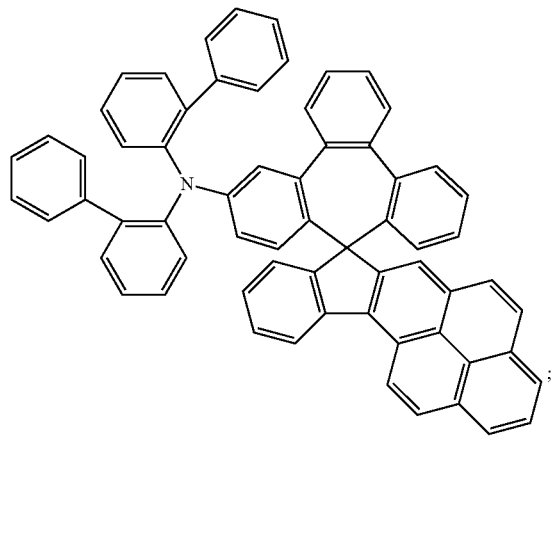
Compound 285
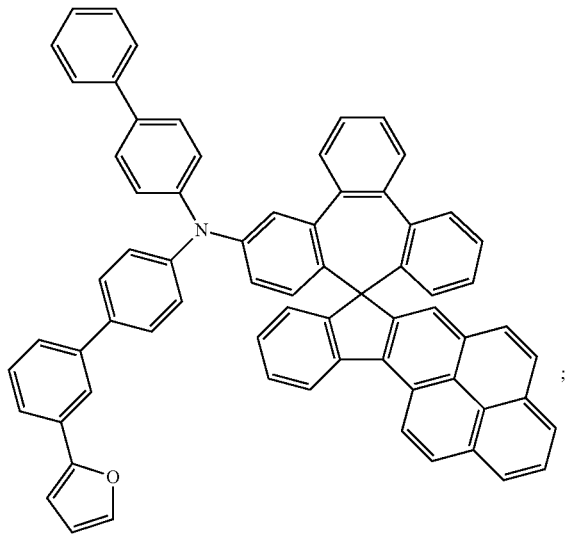
Compound 286
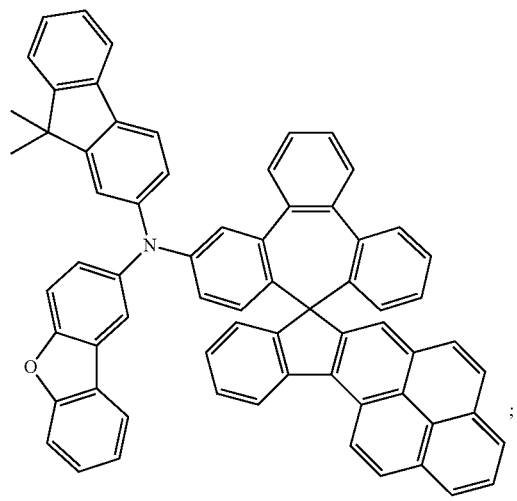
Compound 287
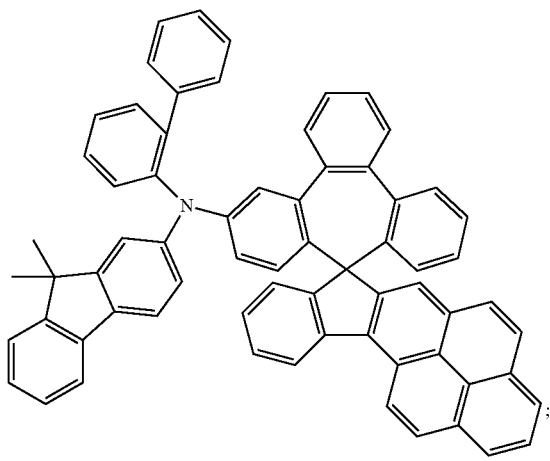
Compound 288
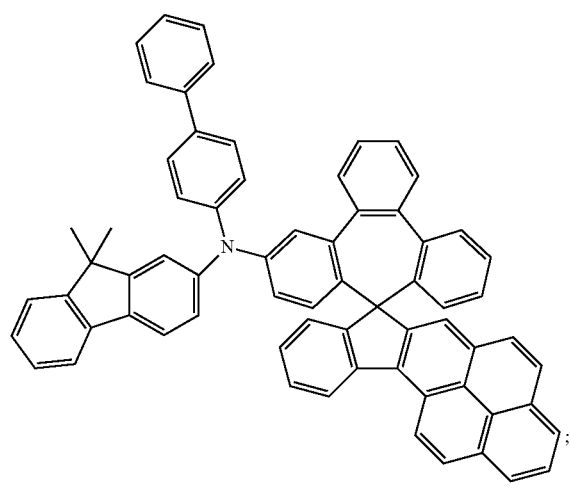
Compound 289
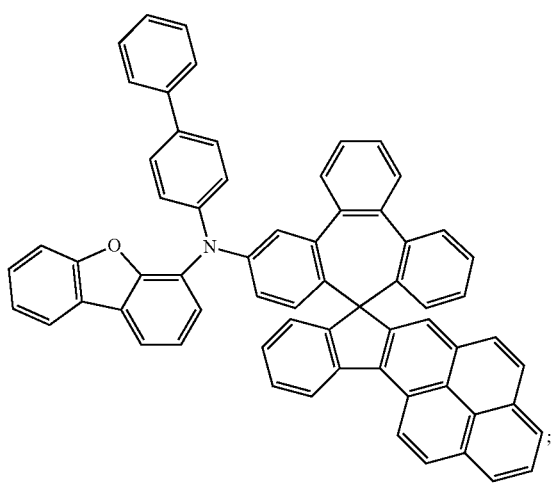

-continued
Compound 290
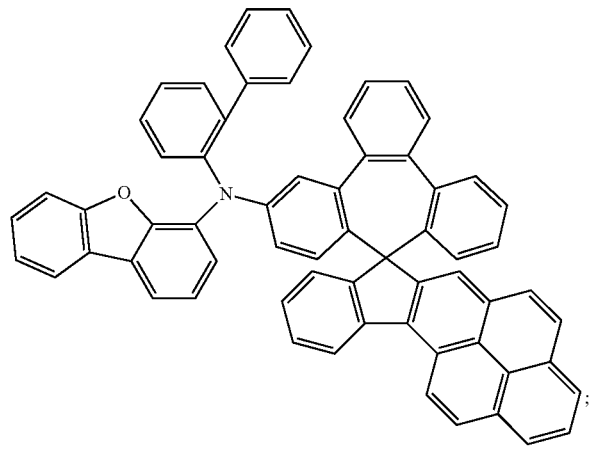
Compound 291
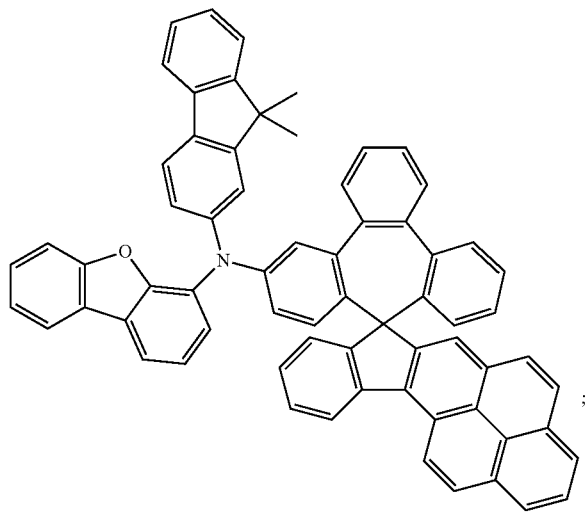
Compound 292
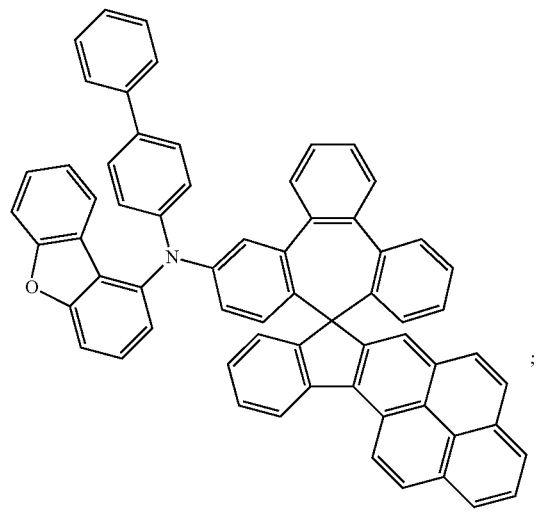
Compound 293
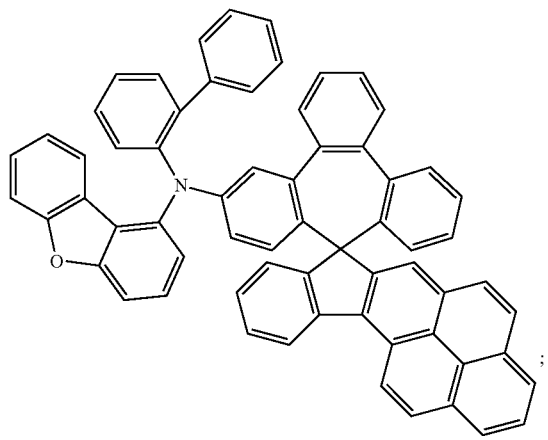
Compound 294
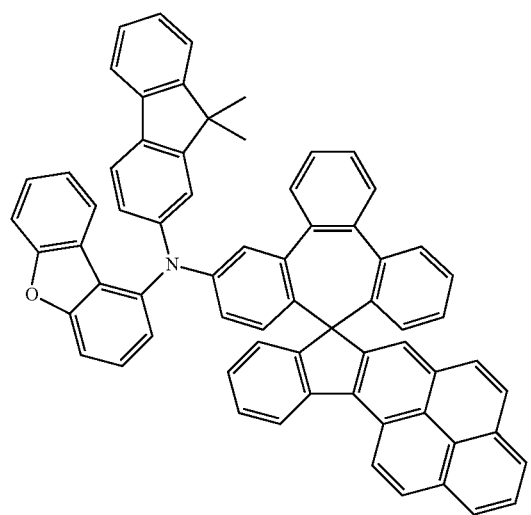
Compound 295
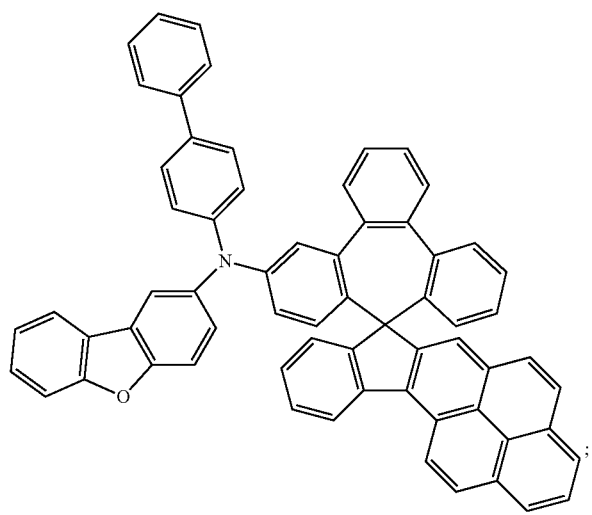

-continued
Compound 296
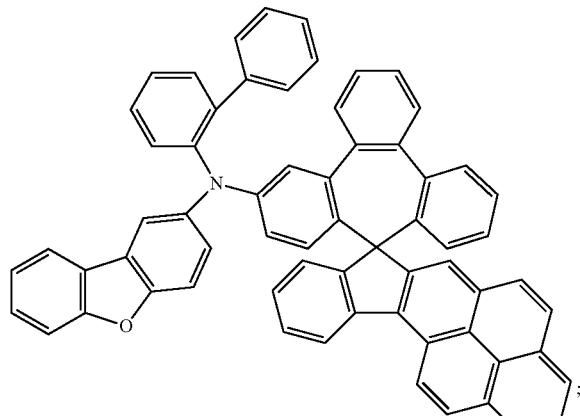
Compound 297
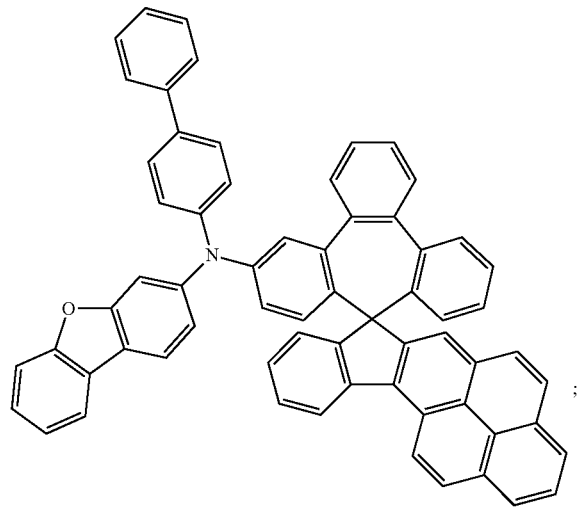
Compound 298
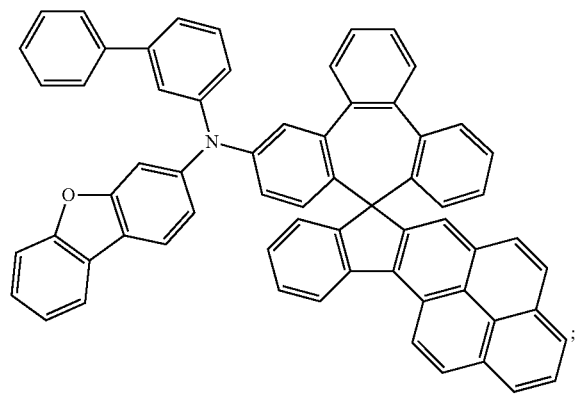
Compound 299
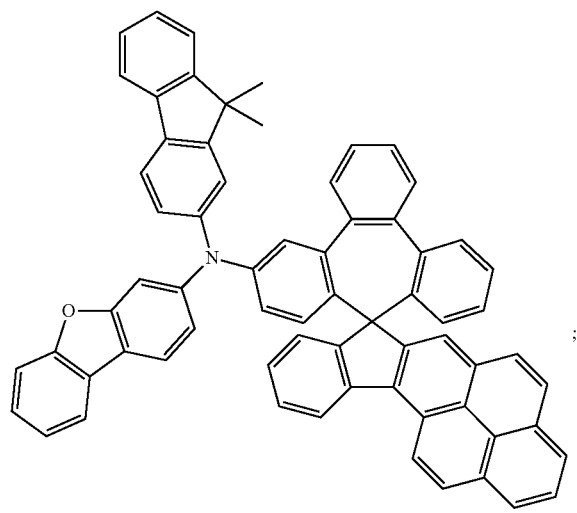
Compound 300
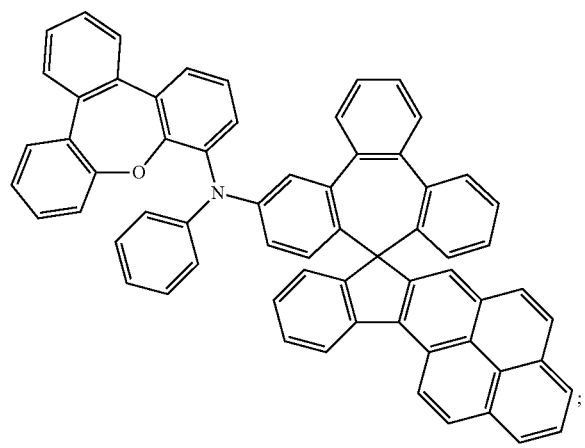
Compound 301
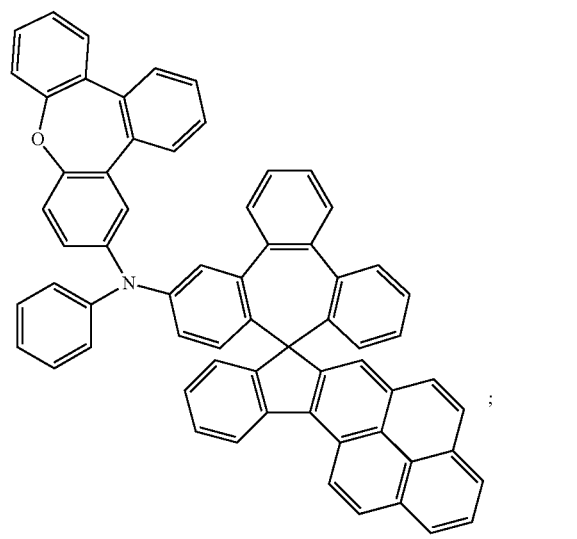

-continued
Compound 302
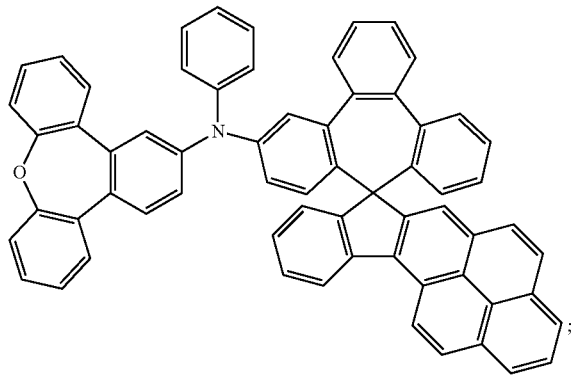
Compound 303
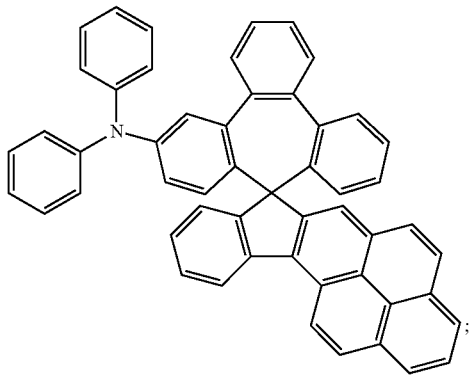
Compound 304
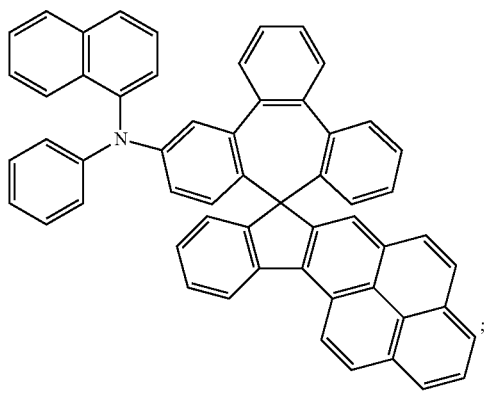
Compound 305
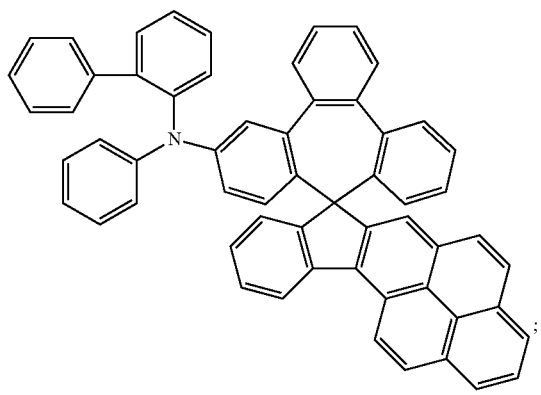
Compound 306
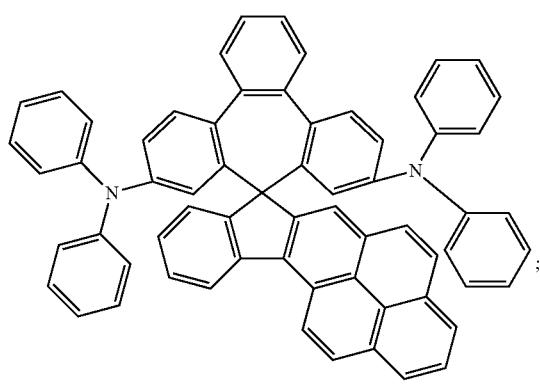
Compound 307
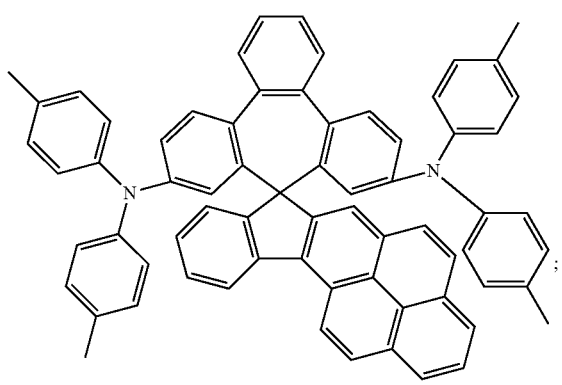

-continued
Compound 308
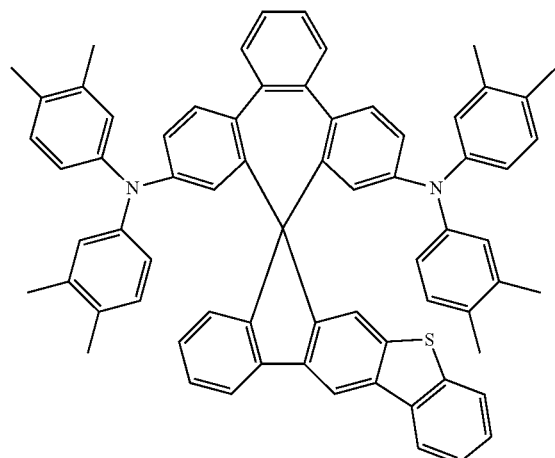
Compound 309
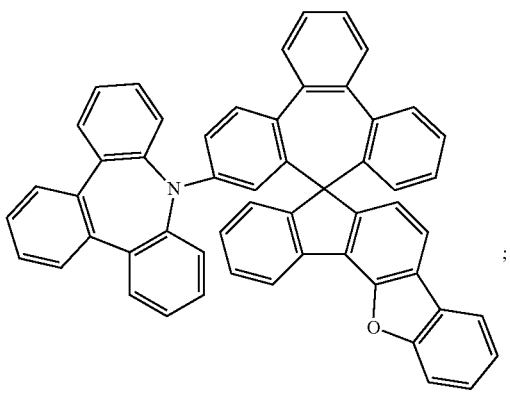
Compound 310
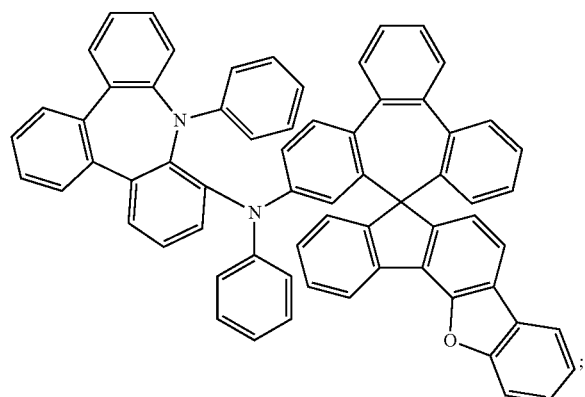
Compound 311
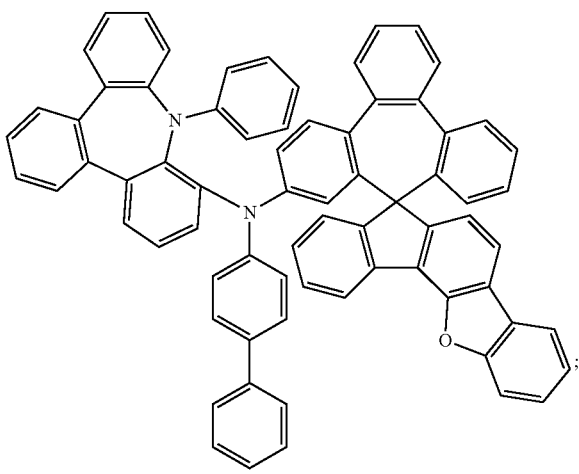
Compound 312
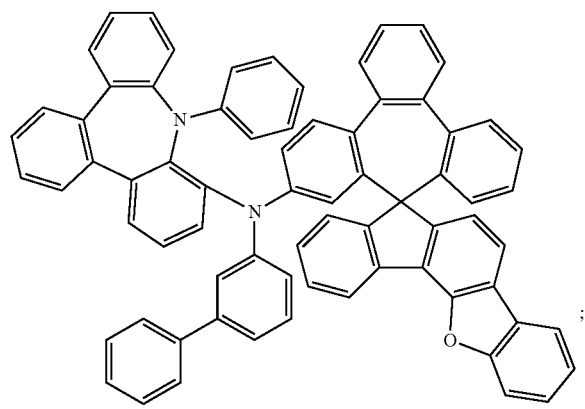
Compound 313
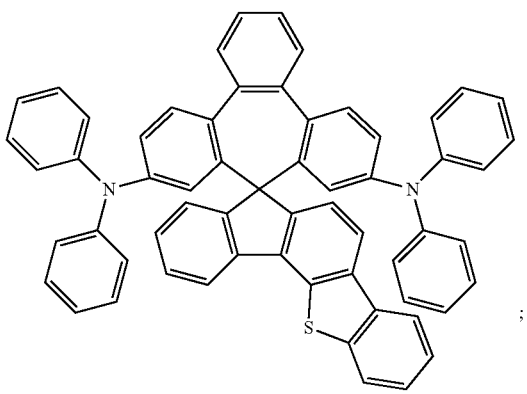

-continued
Compound 314
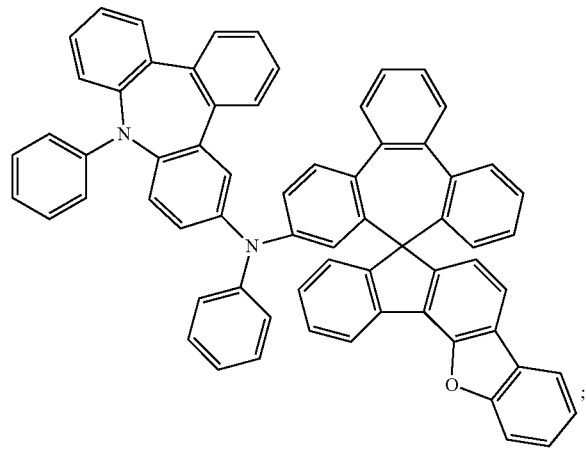
Compound 315
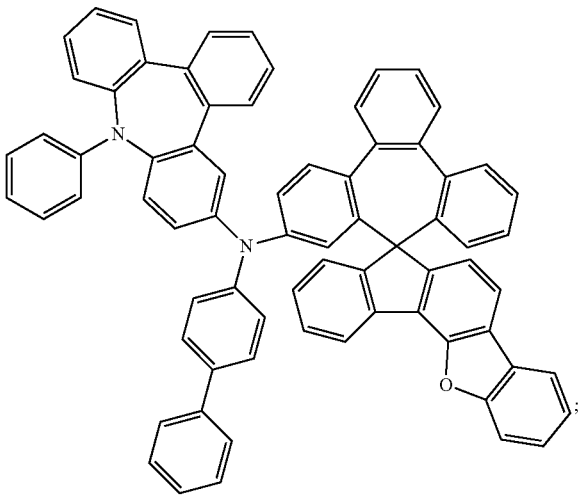
Compound 316
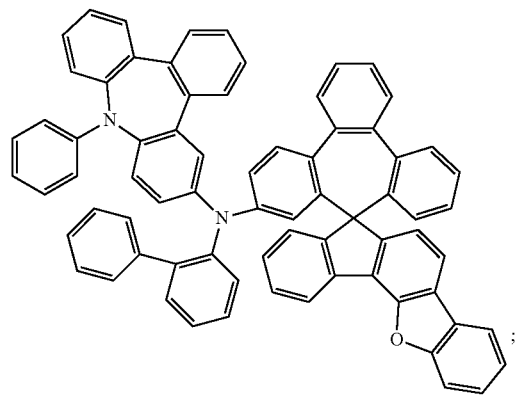
Compound 317
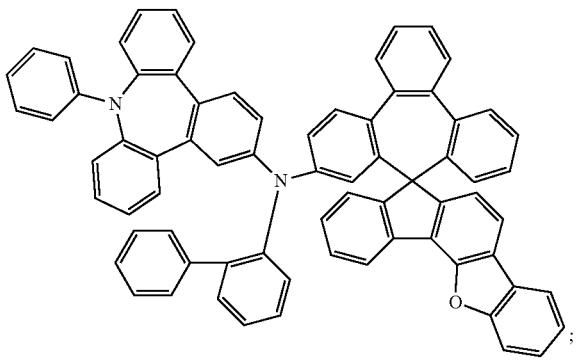
Compound 318
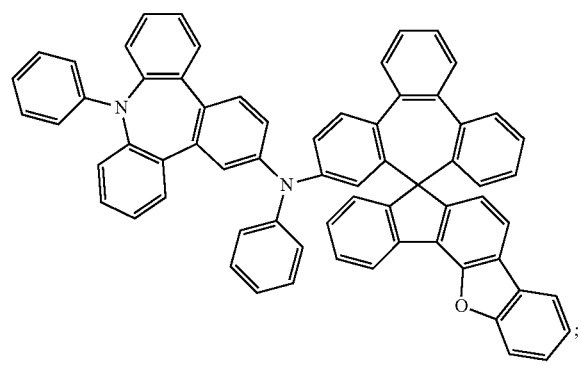
Compound 319
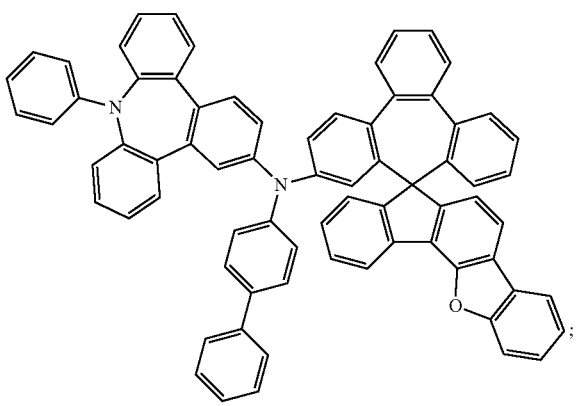

-continued
Compound 320
Compound 321
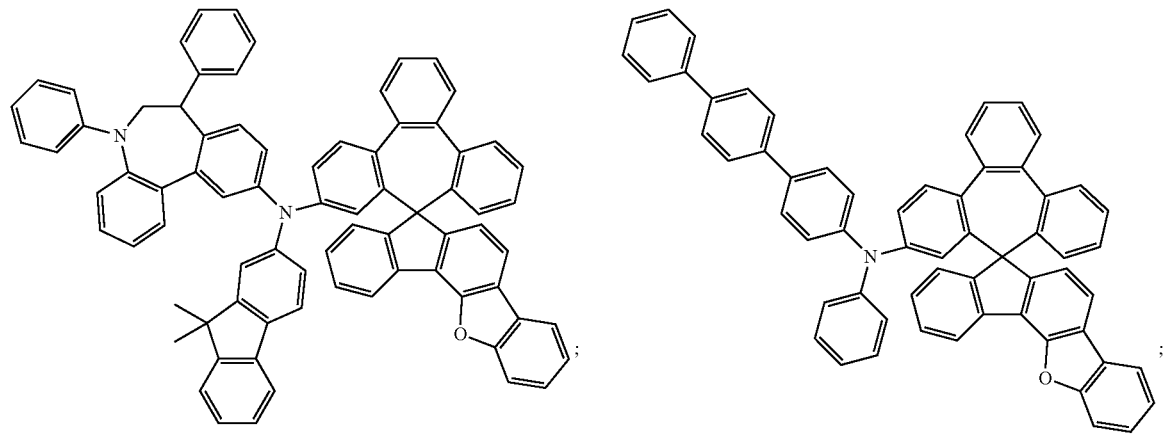
Compound 322
Compound 323
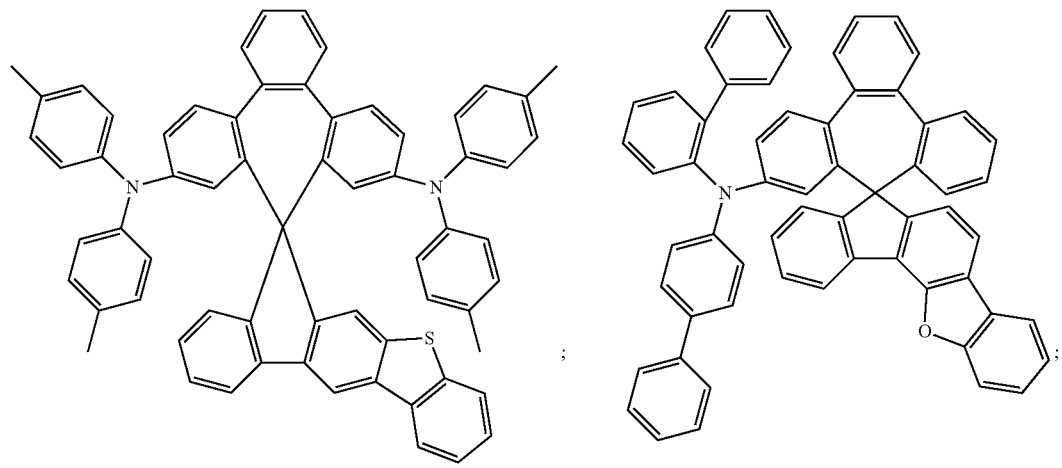
Compound 324
Compound 325
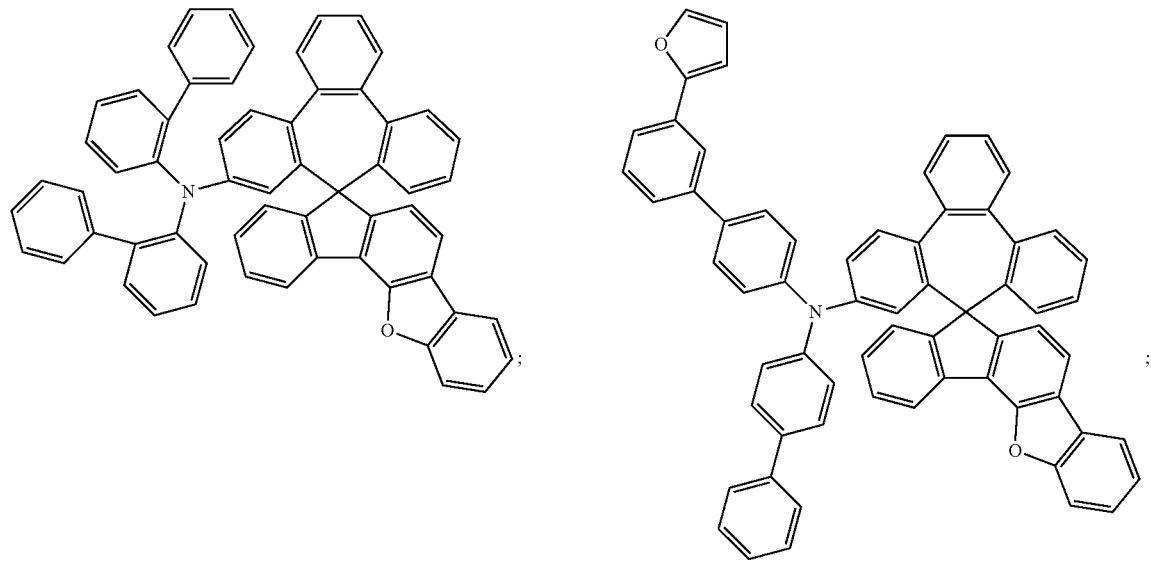

-continued
Compound 326
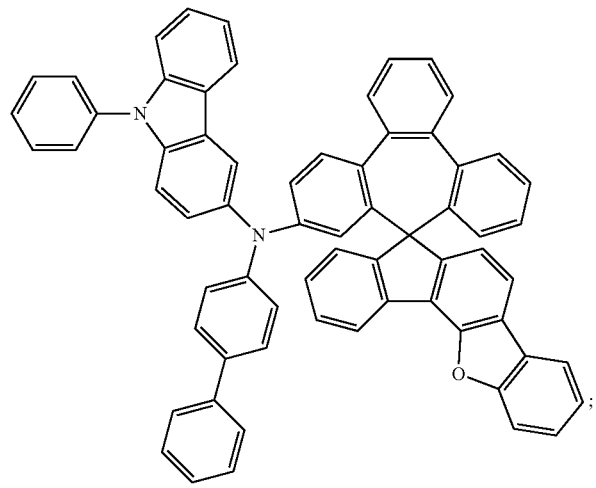
Compound 327
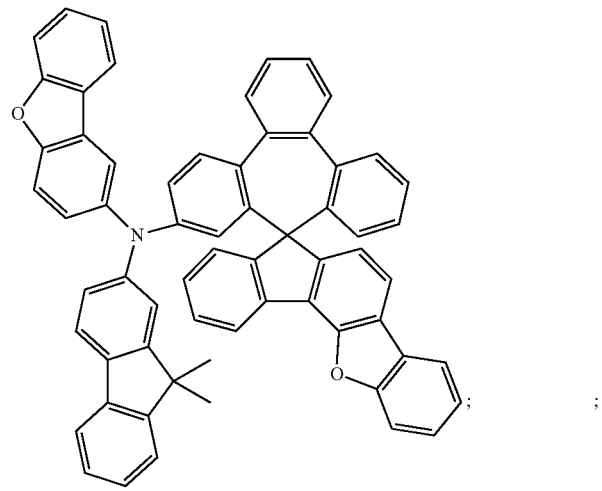
Compound 328
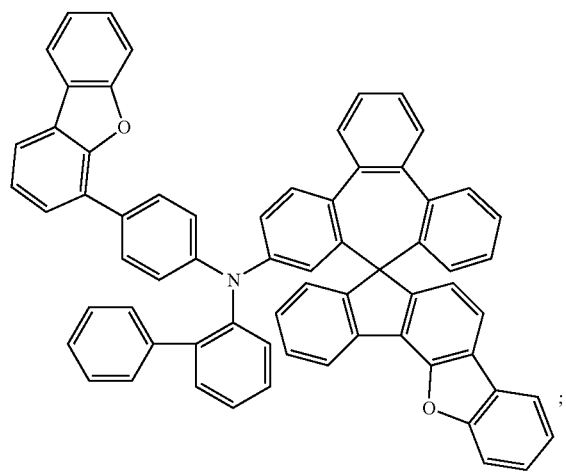
Compound 329
Compound 330
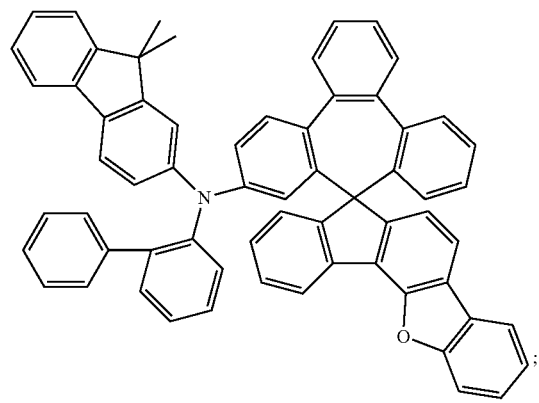
Compound 331
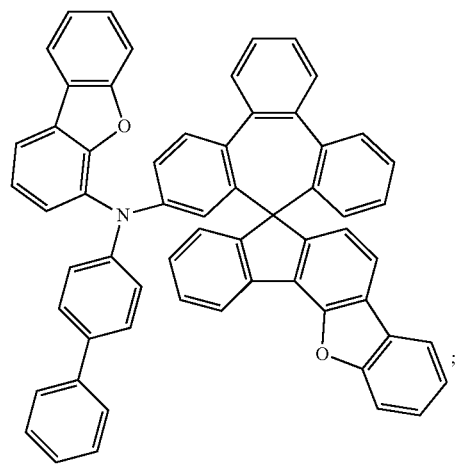

-continued
Compount 332
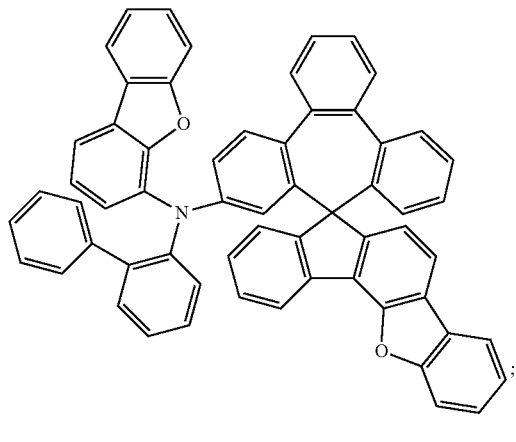
Compound 333
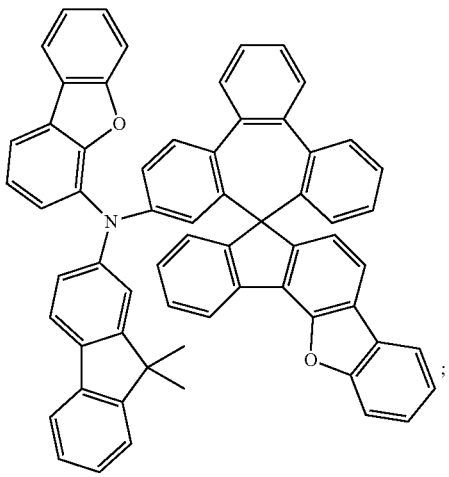
Compound 334
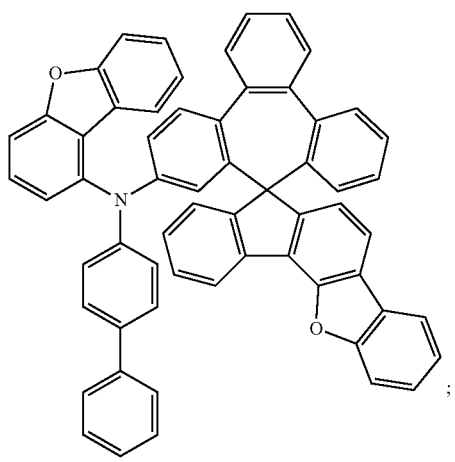
Compound 335
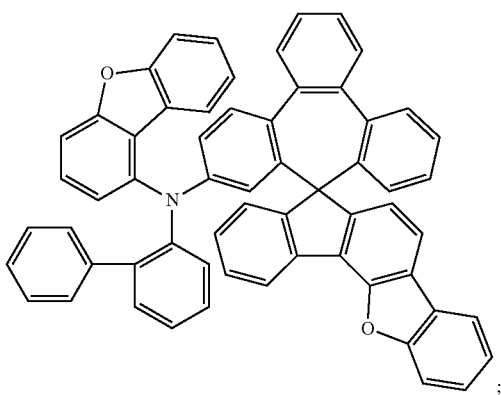
Compound 336
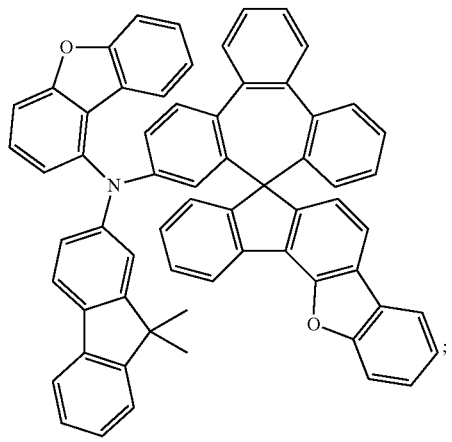
Compound 337
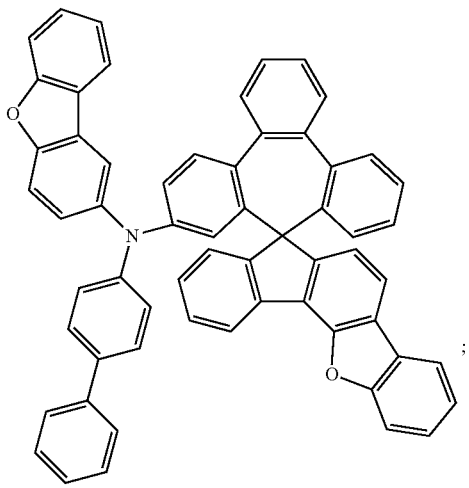

-continued
Compound 338
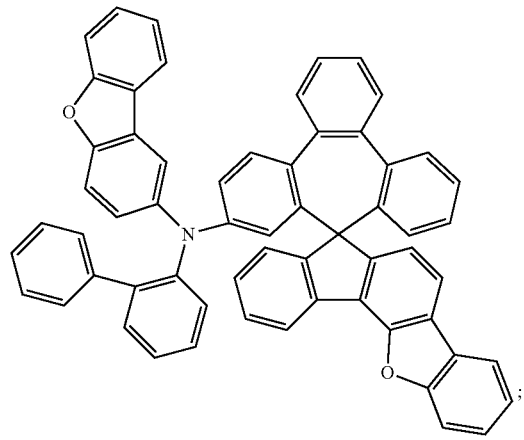
Compound 339
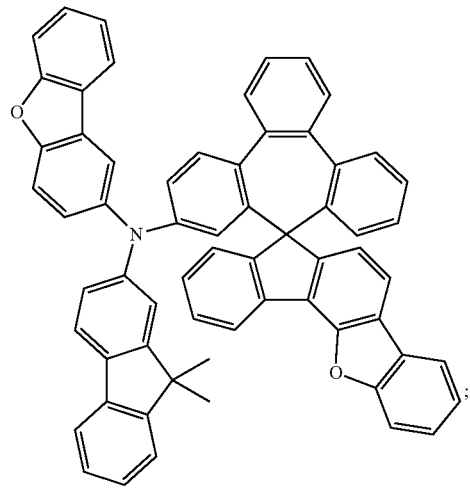
Compound 340
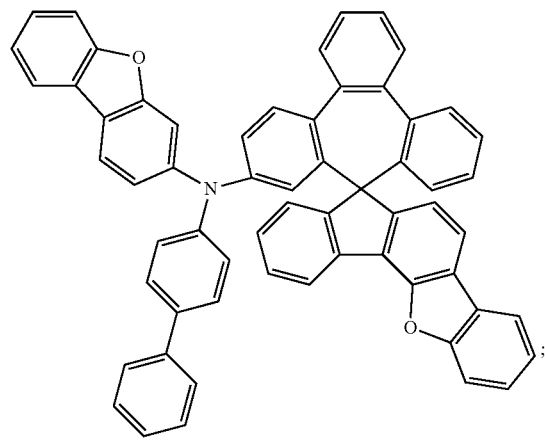
Compound 341
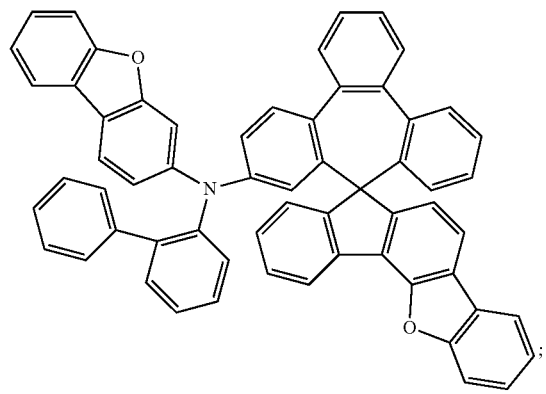
Compound 342
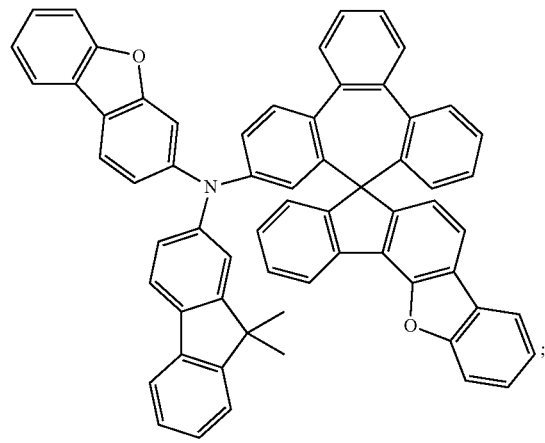
Compound 343
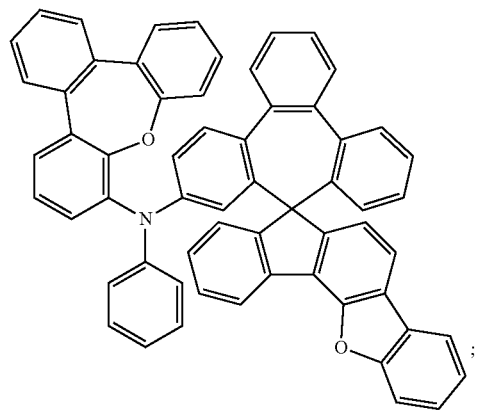

-continued
Compound 344
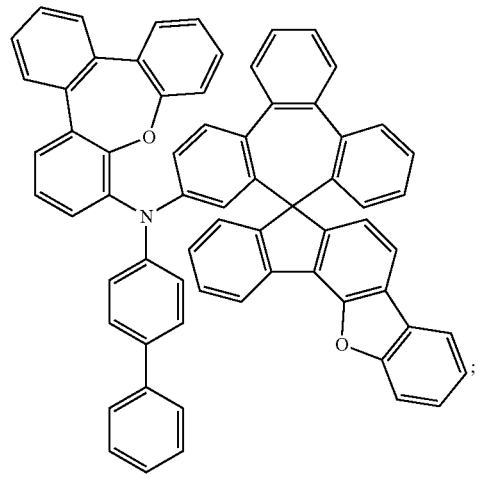
Compound 345
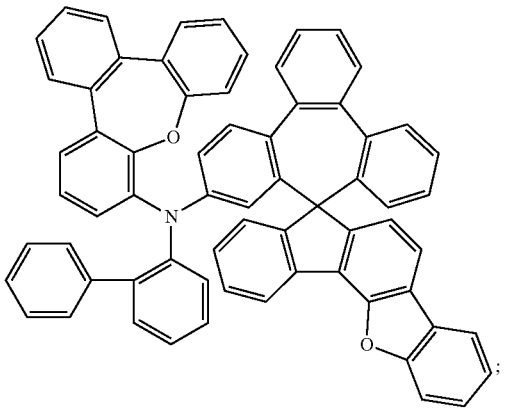
Compound 346
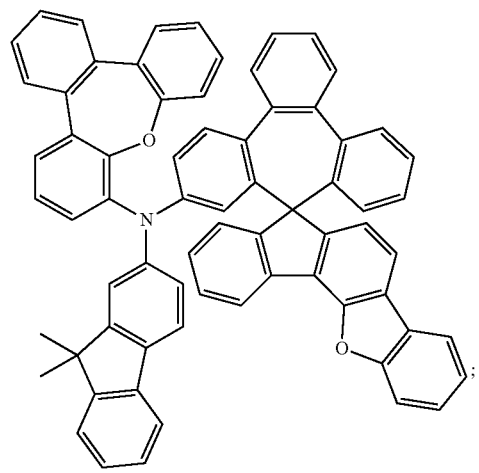
Compound 347
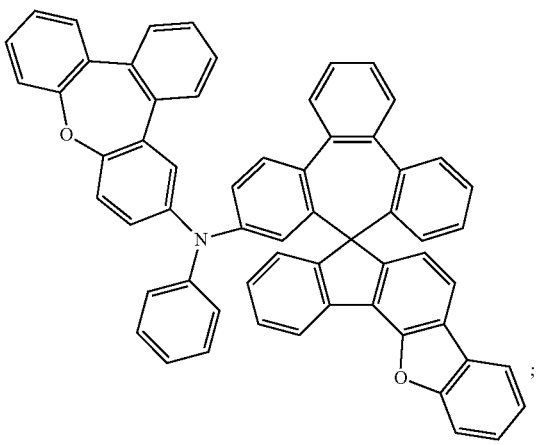
Compound 348
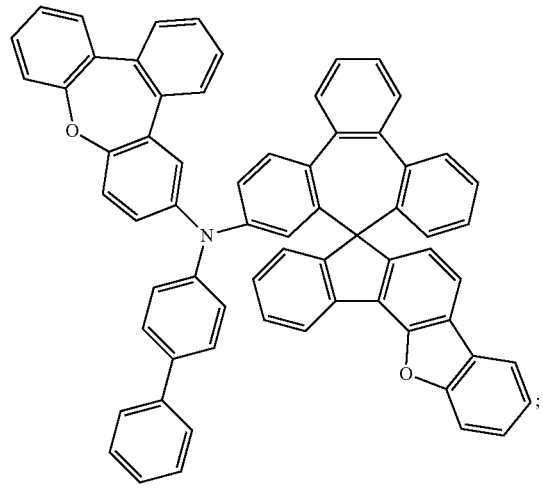
Compound 349
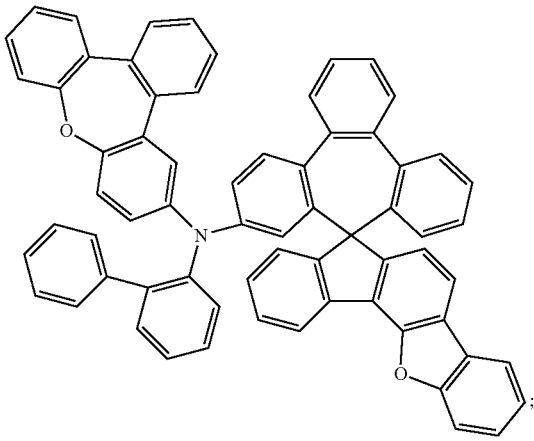

-continued
Compound 350
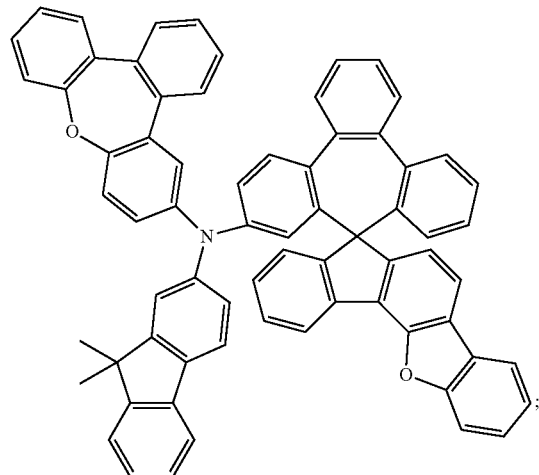
Compound 351
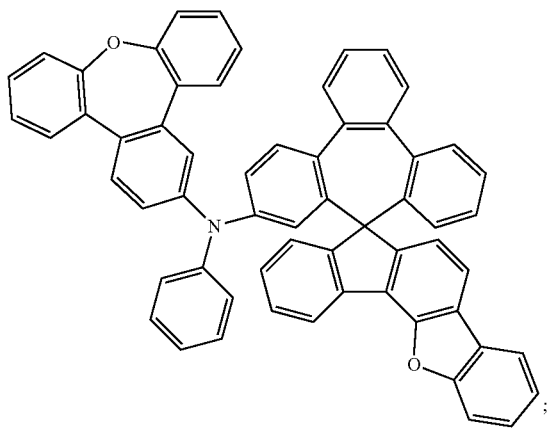
Compound 352
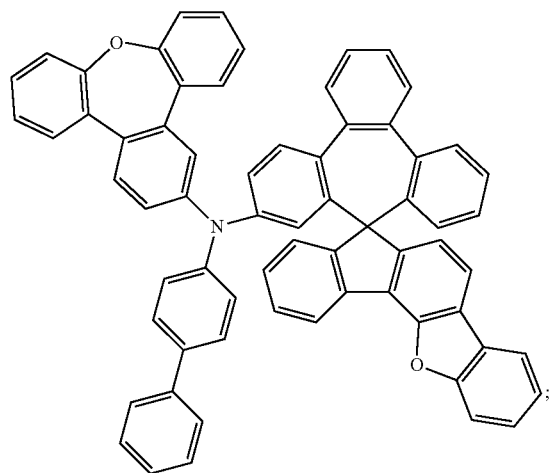
Compound 353
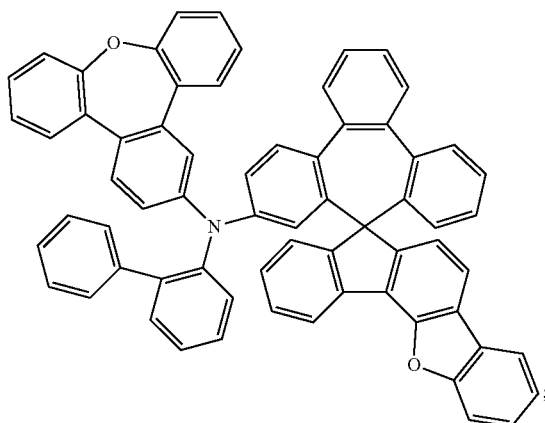
Compound 354
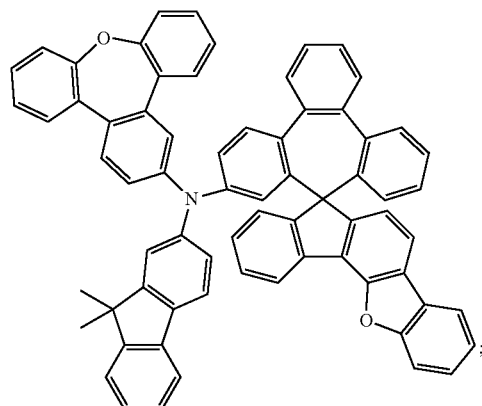
Compound 355
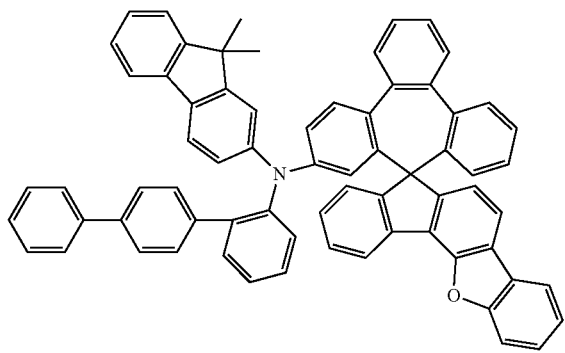

-continued
Compound 356
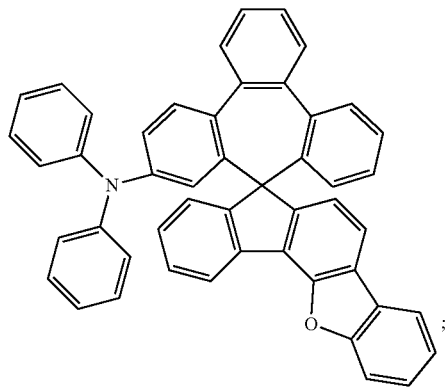
Compound 357
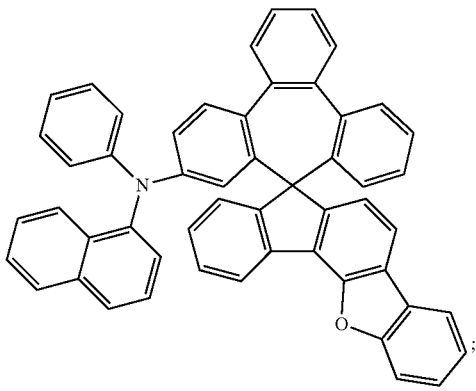
Compound 358
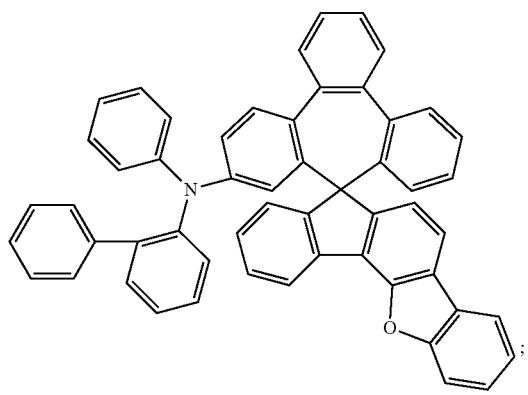
Compound 359
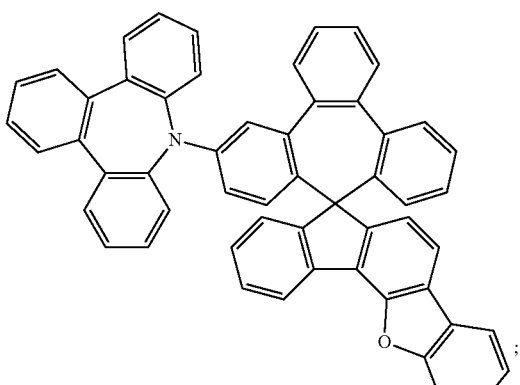
Compound 360
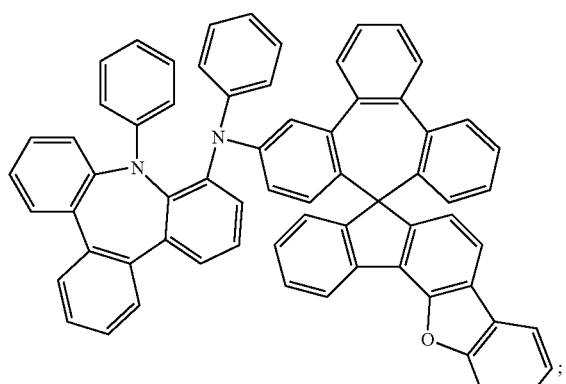
Compound 361
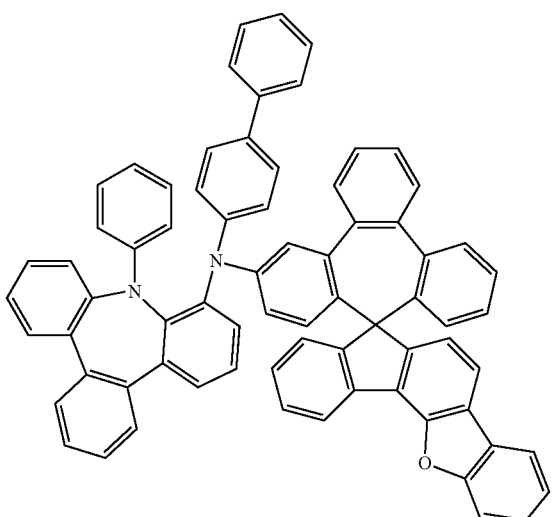

Compound 362
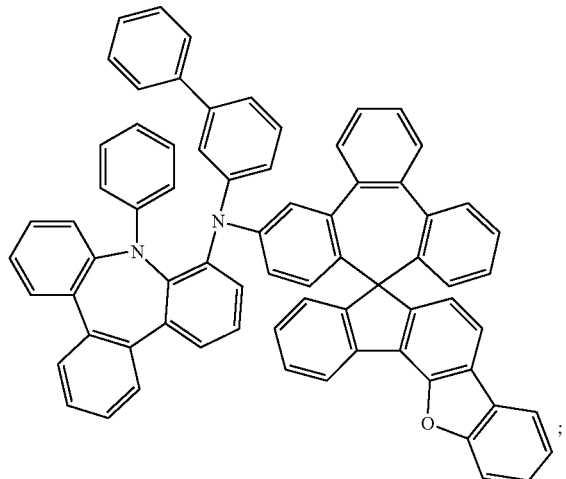
Compound 363
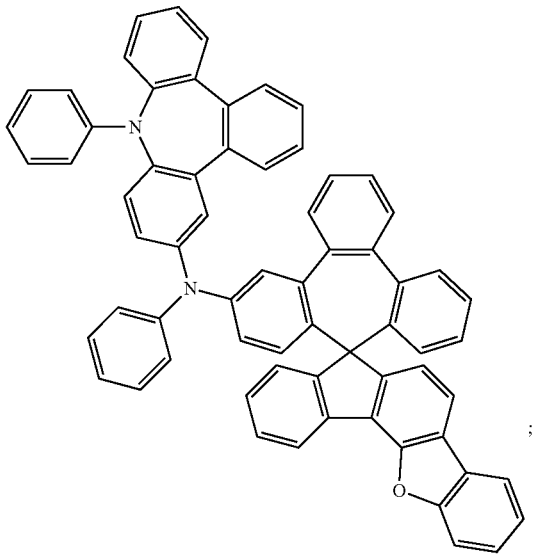
Compound 364
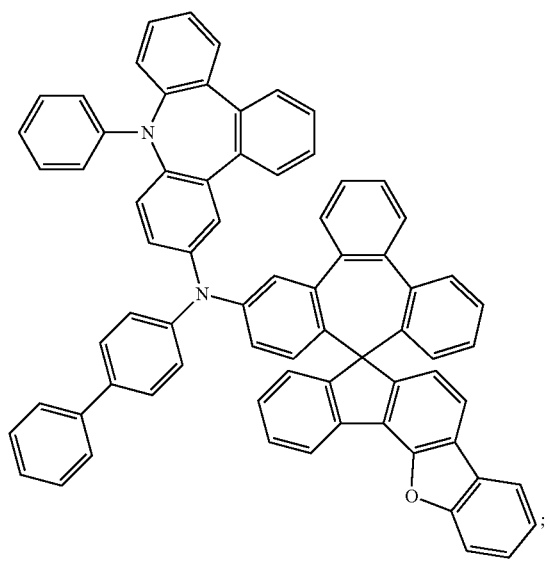
Compound 365
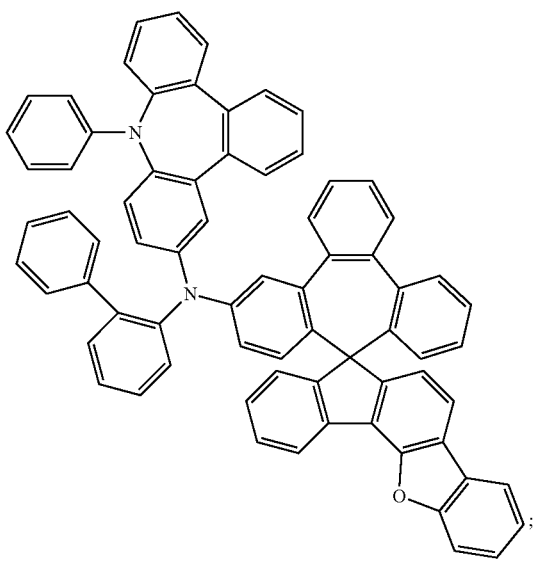

Compound 366
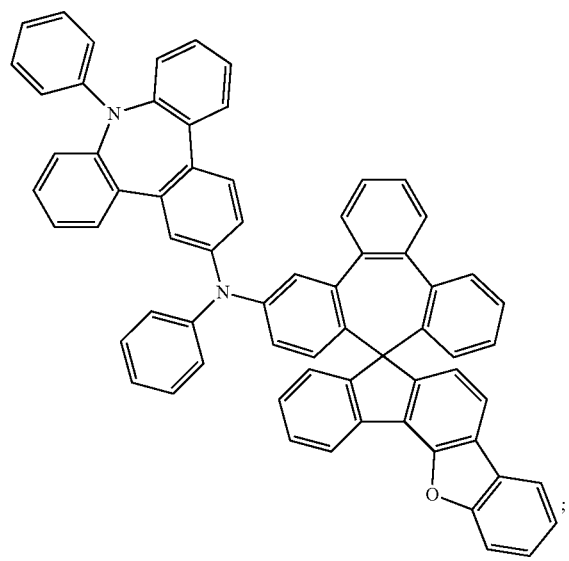
Compound 367
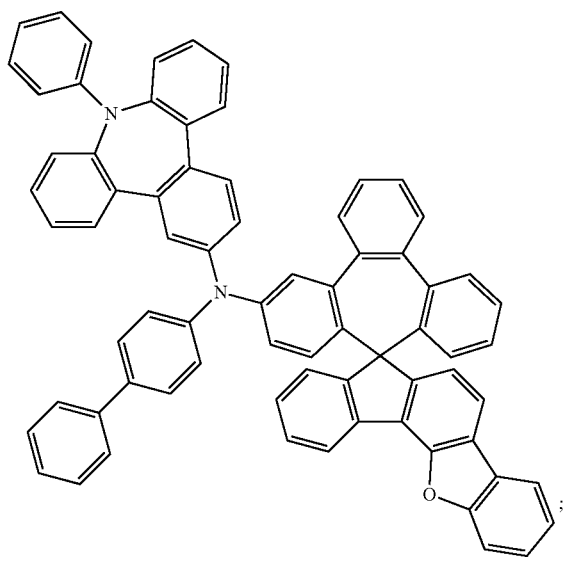
Compound 368
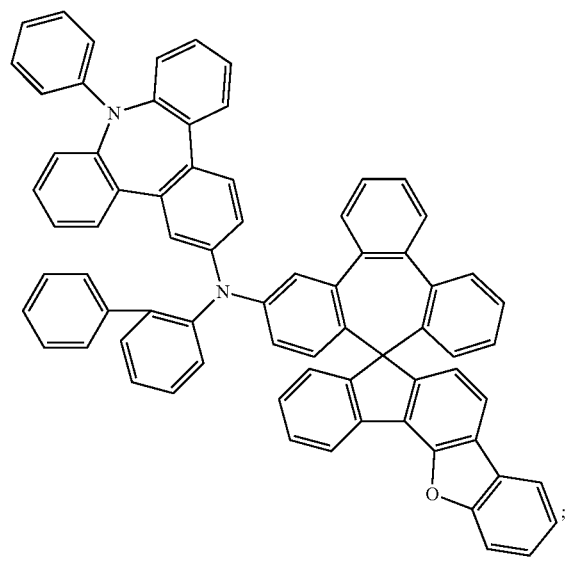
Compound 369
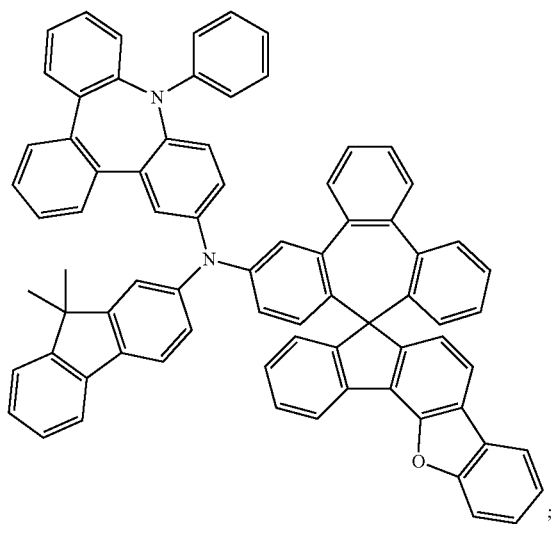

-continued
Compound 370
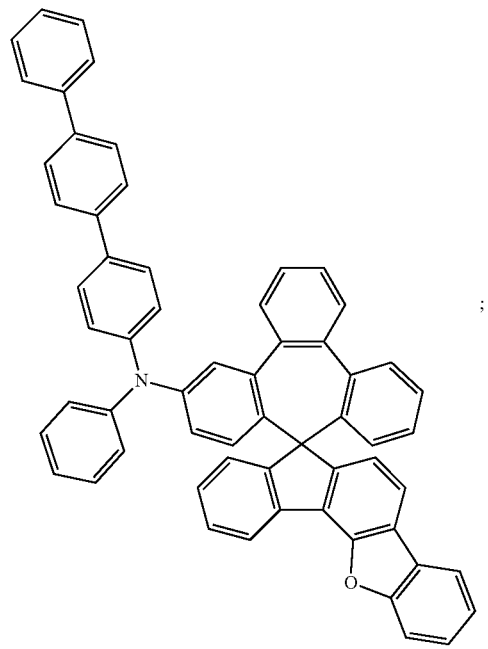
Compound 371
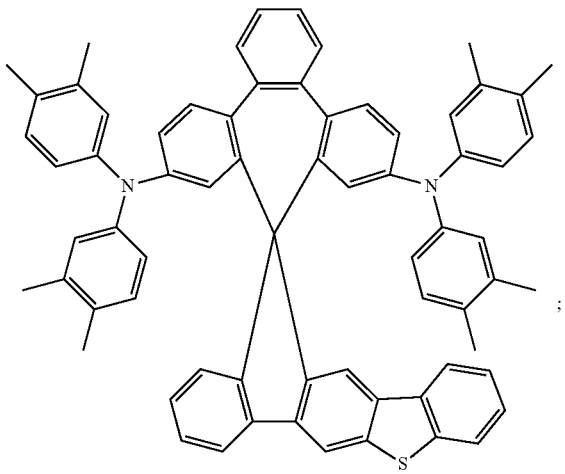
Compound 372
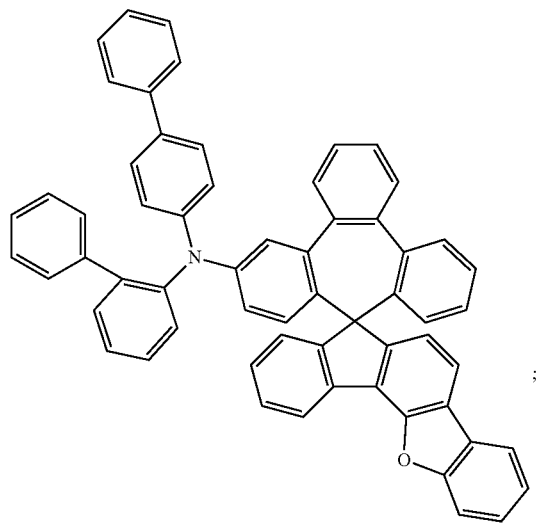
Compound 373
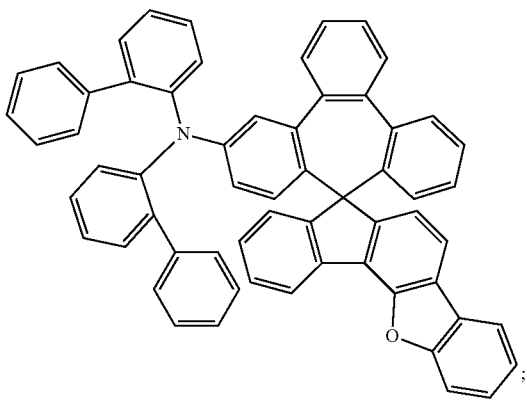

-continued
Compound 374
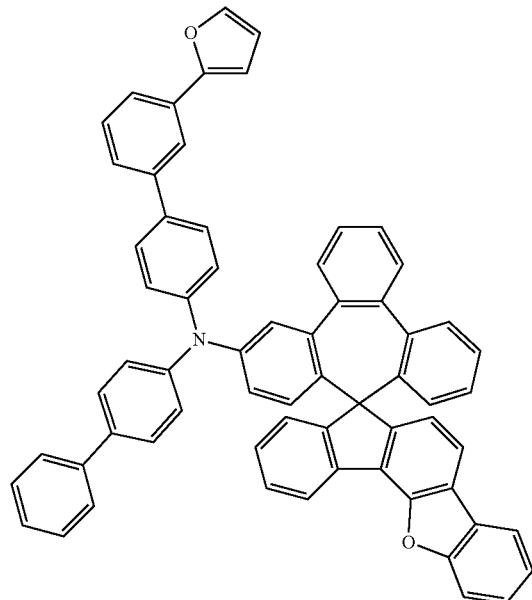
Compound 375
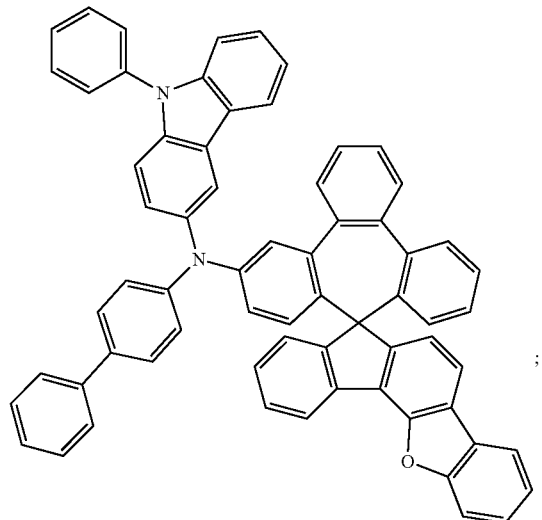
Compound 376
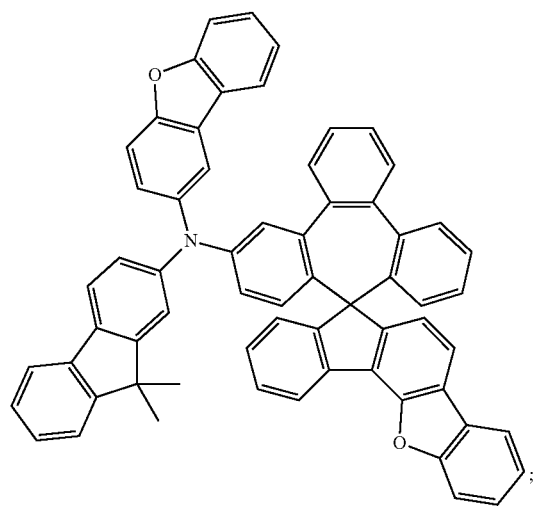
Compound 377
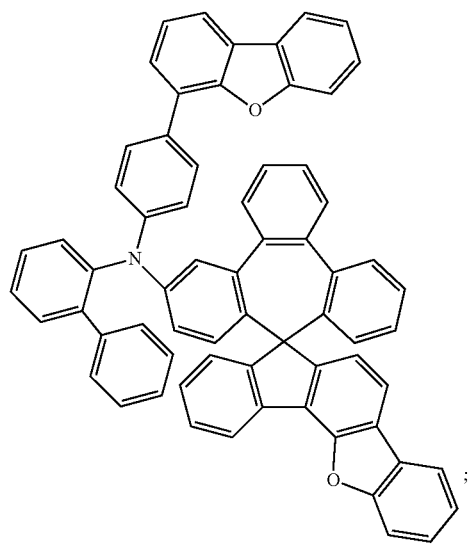

-continued
Compound 378
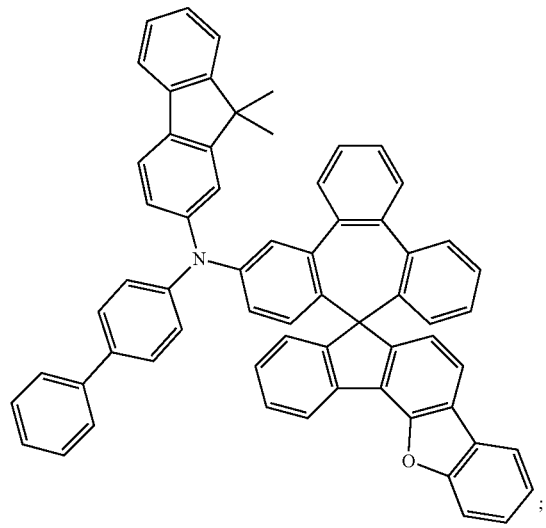
Compound 379
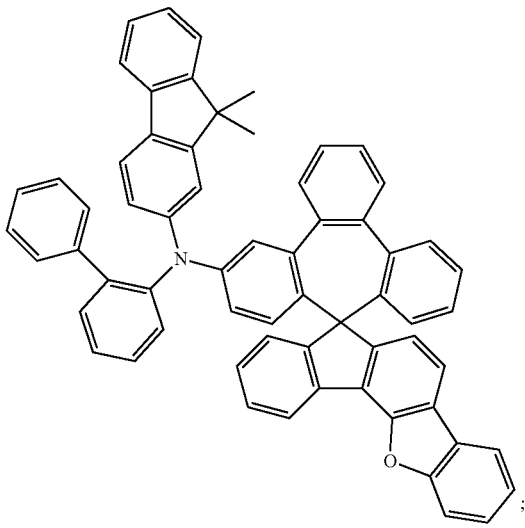
Compound 380
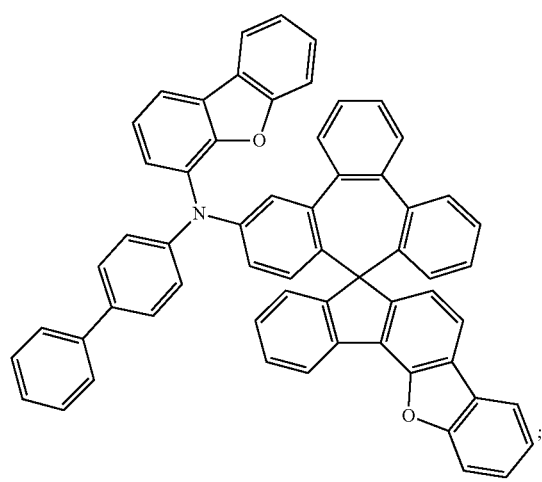
Compound 381
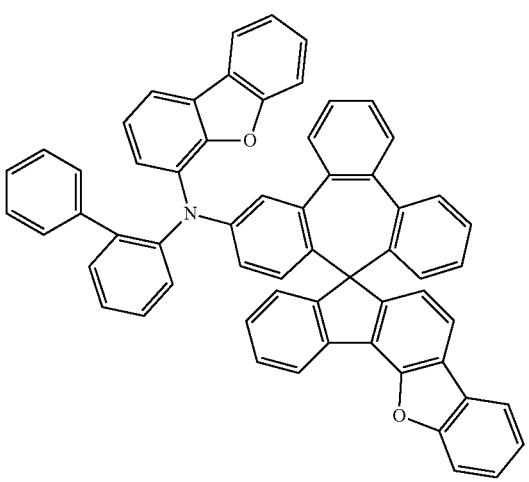
Compound 382
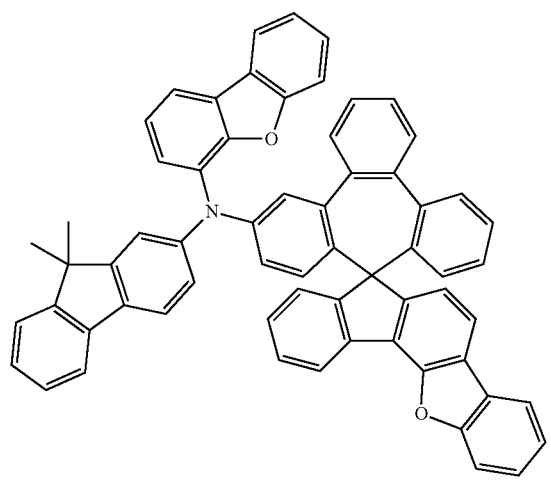
Compound 383
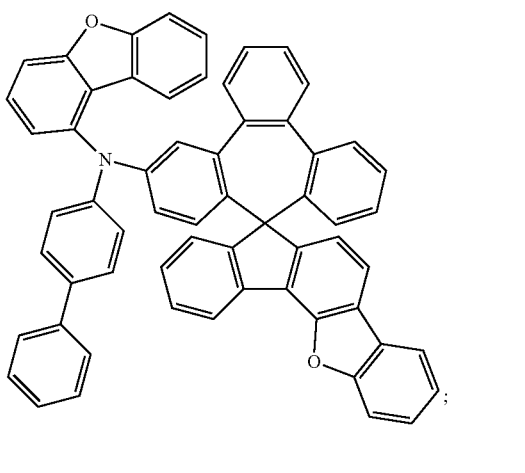

-continued
Compound 384
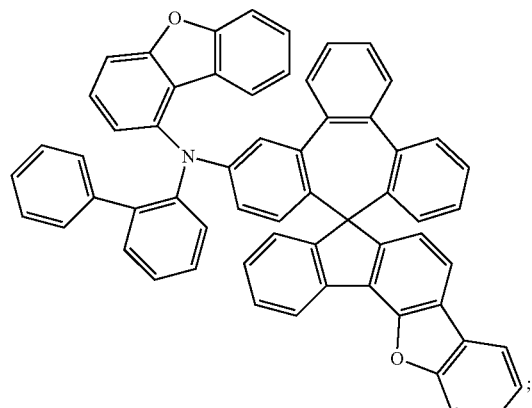
Compound 386
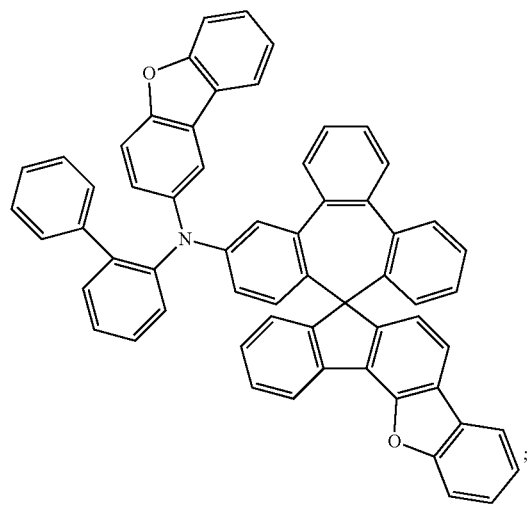
Compound 388
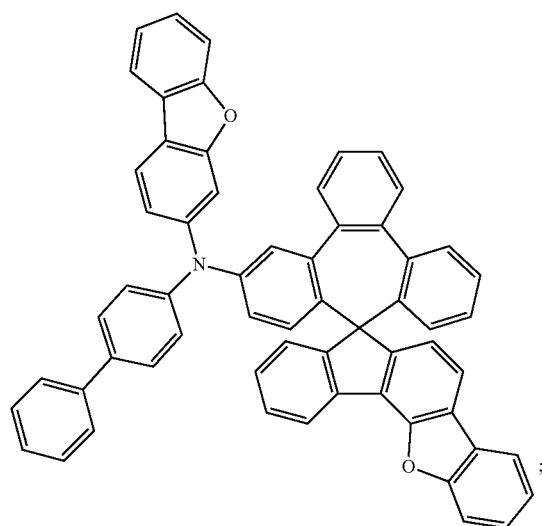
Compound 385
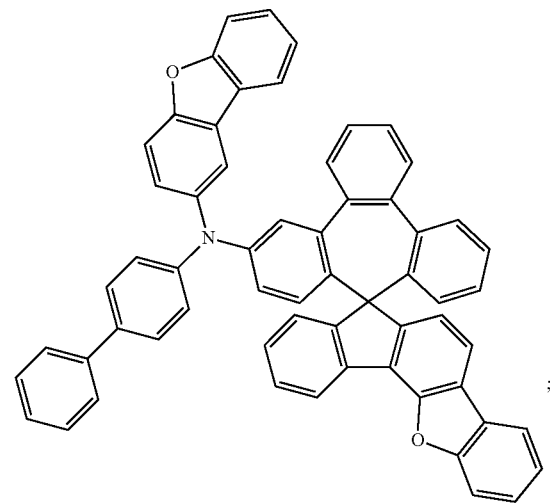
Compound 387
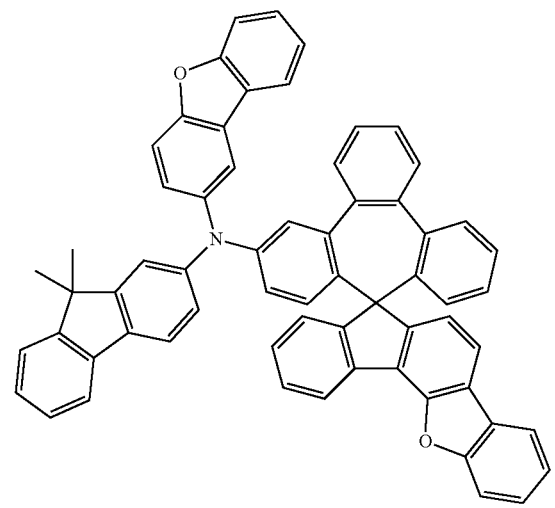
Compound 389
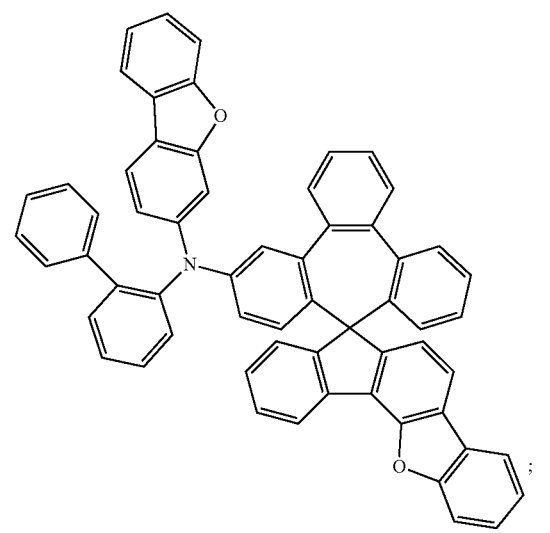

-continued
Compound 390
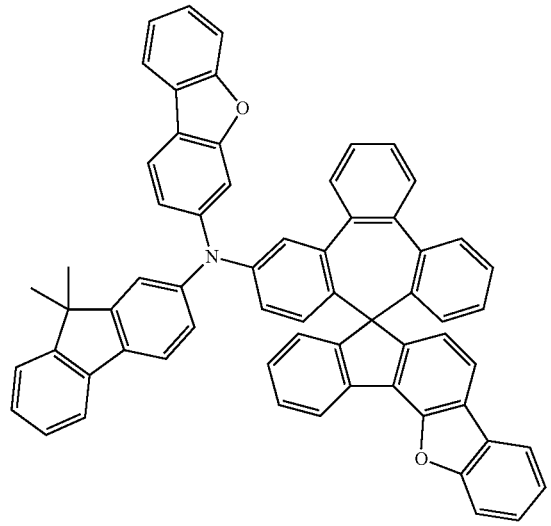
Compound 391
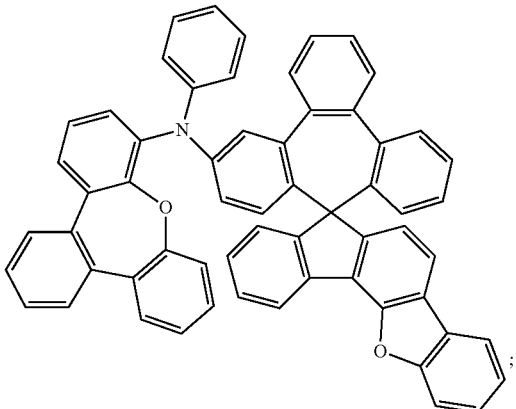
Compound 392
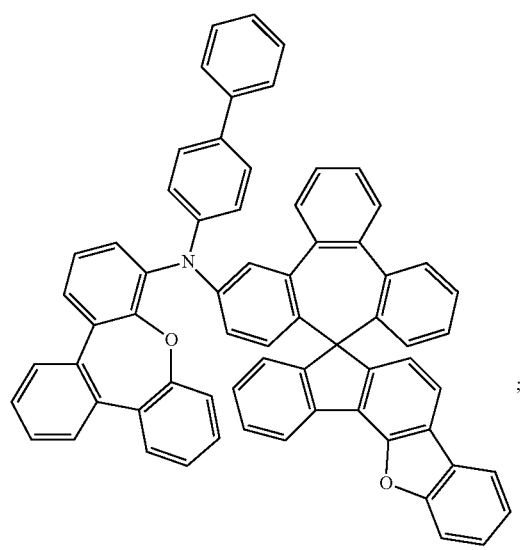
Compound 393
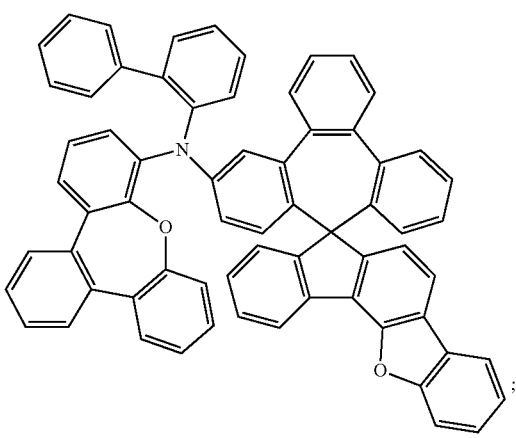
Compound 394
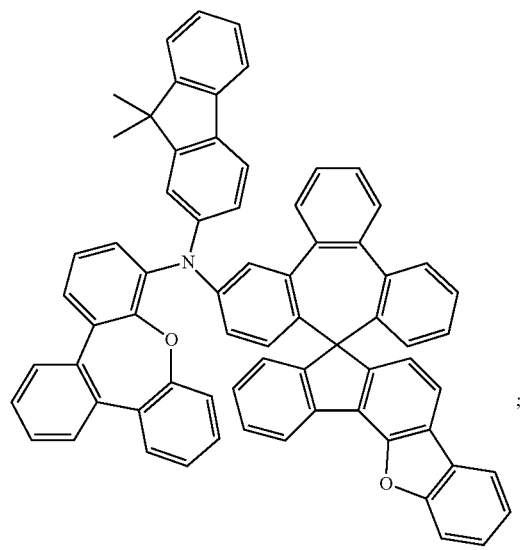
Compound 395

-continued
Compound 396
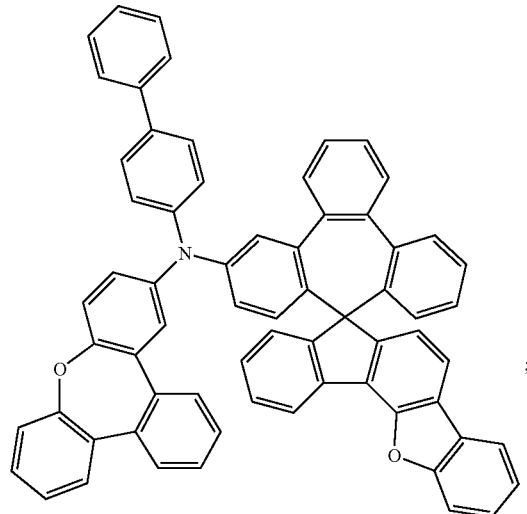
Compound 398
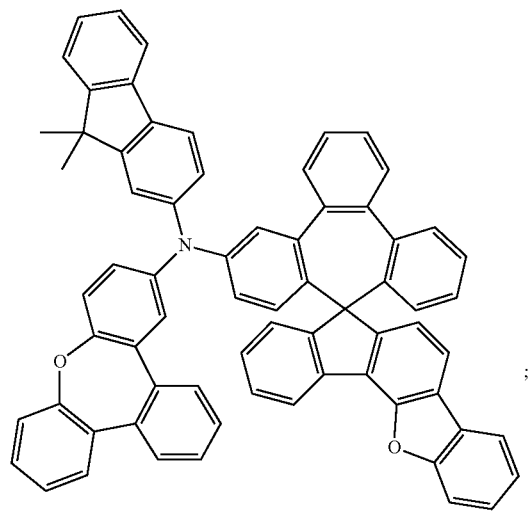
Compound 400
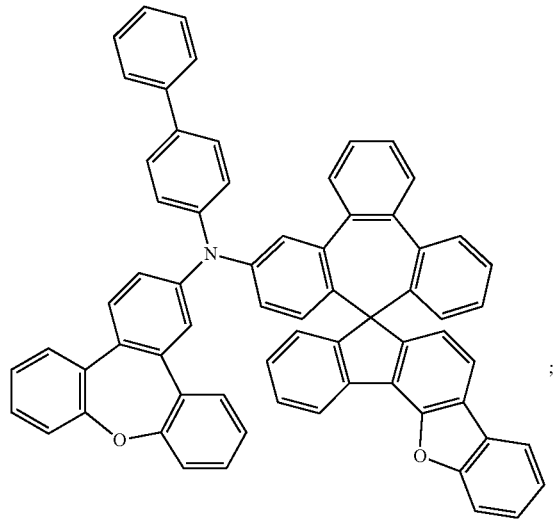
Compound 397
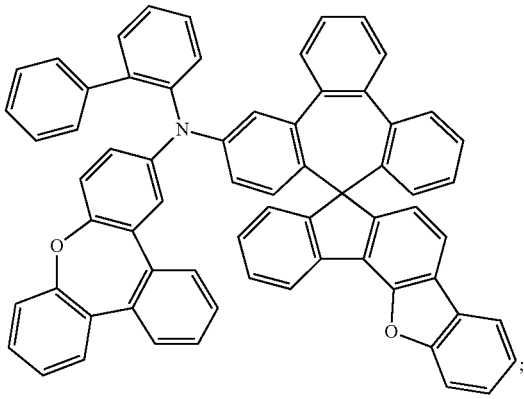
Compound 399
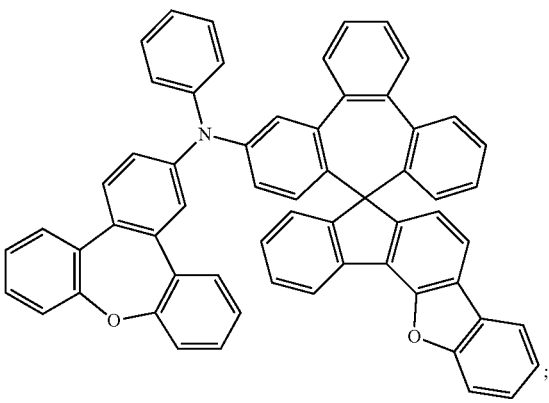
Compound 401
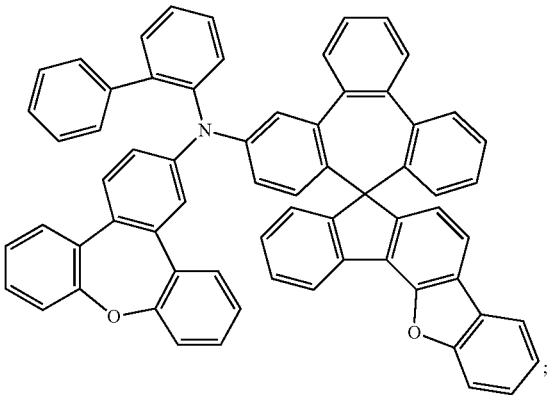

-continued
Compound 402
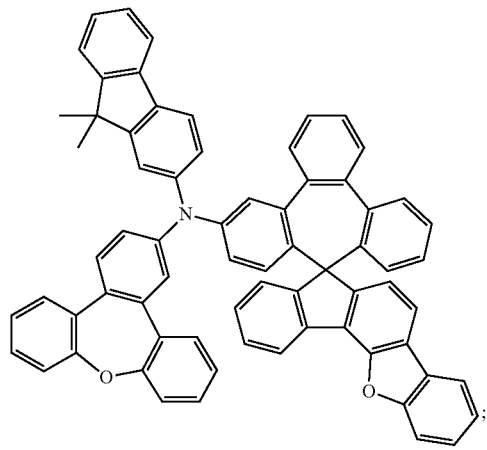
Compound 403
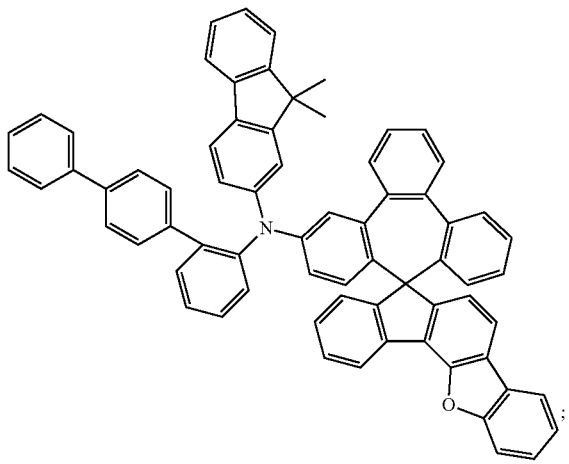
Compound 404
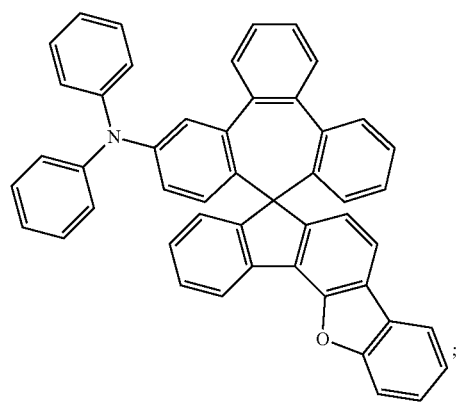
Compound 405
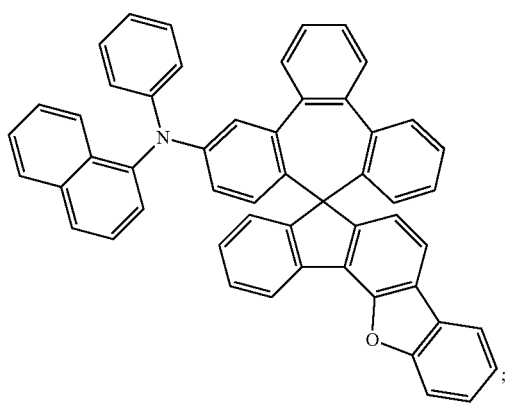
Compound 406
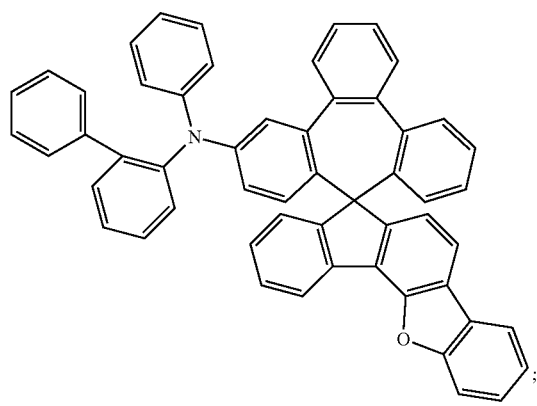
Compound 407
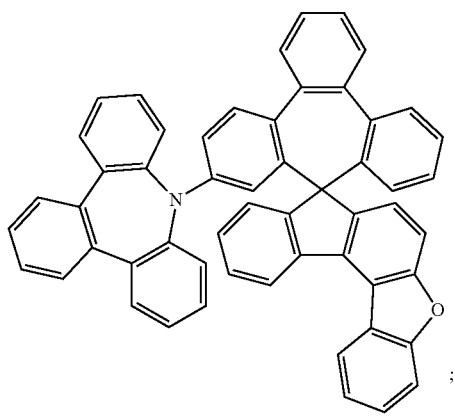

-continued
Compound 408
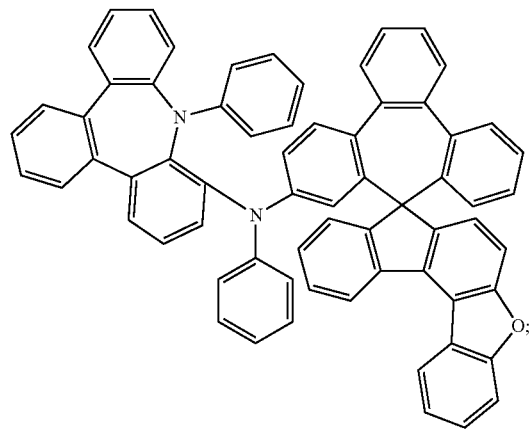
Compound 409
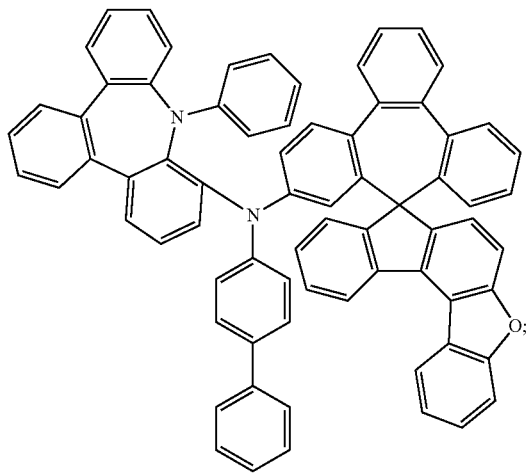
Compound 410
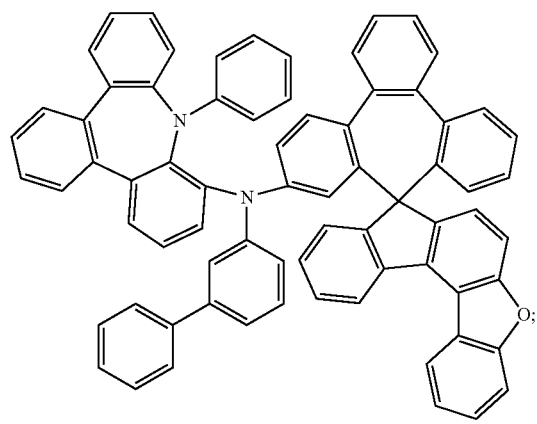
Compound 411
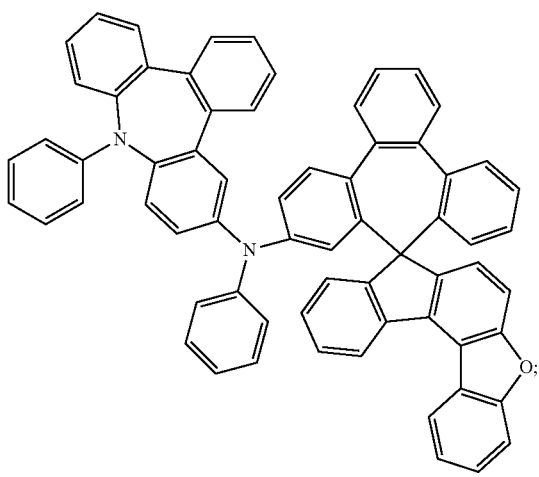
Compound 412
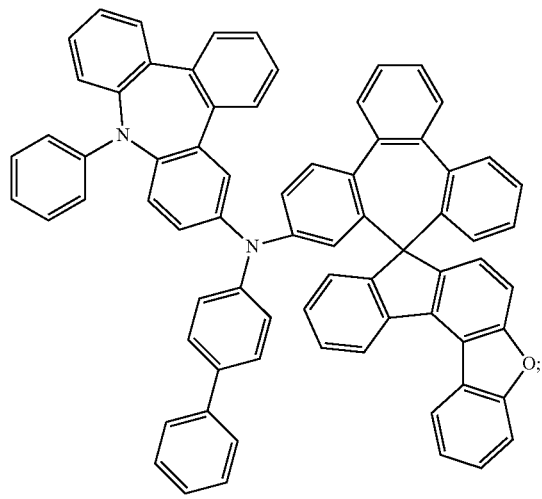
Compound 413
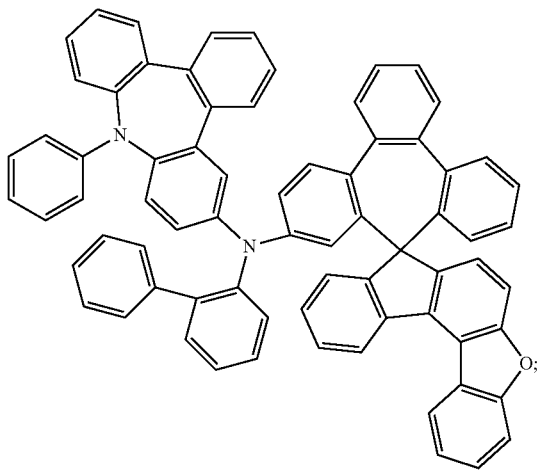

-continued

Compound 414

Compound 415

Compound 416

Compound 417

Compound 418

Compound 419

-continued
Compound 420
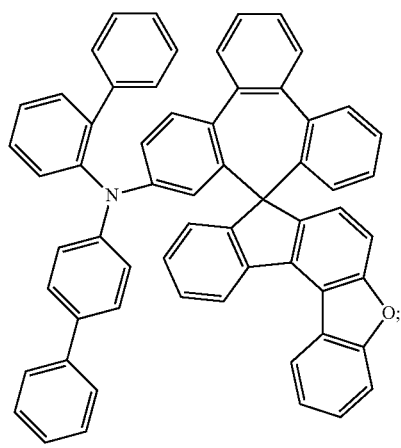
Compound 421
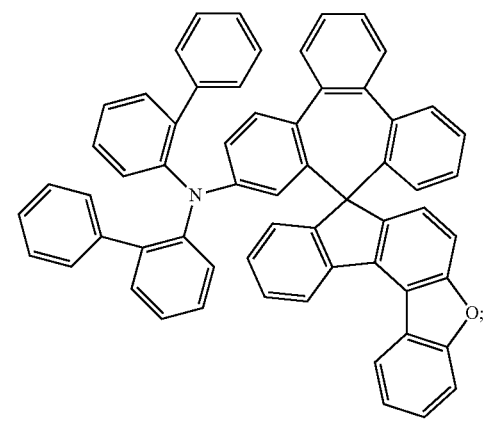
Compound 422
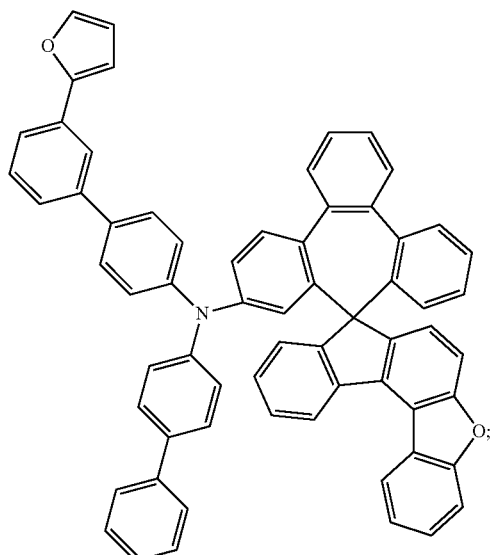
Compound 423
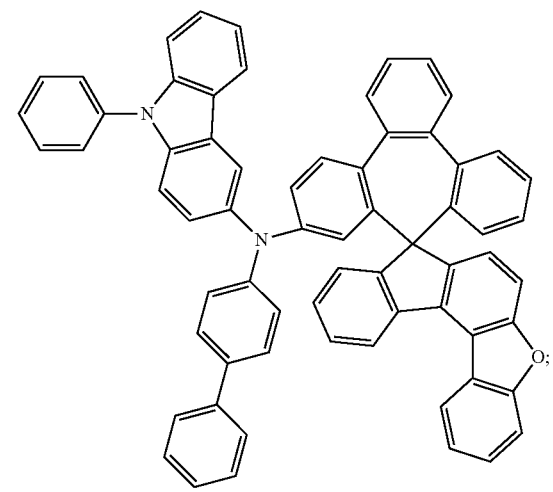
Compound 424
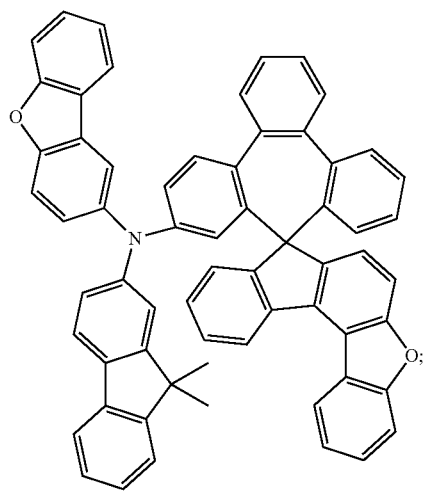
Compound 425
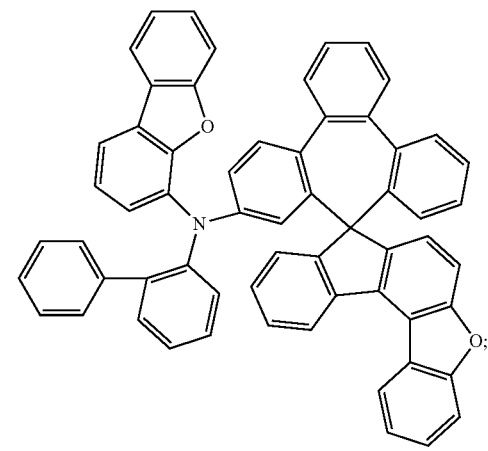

-continued
Compound 426
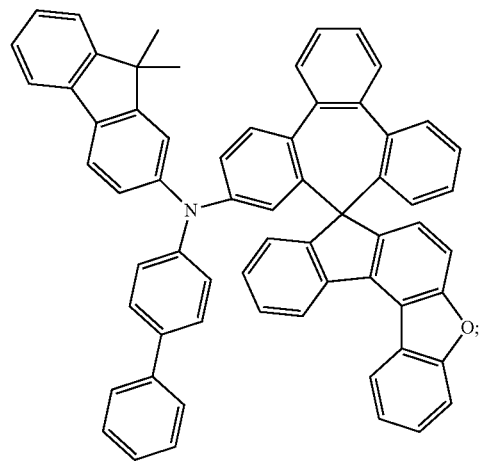
Compound 427
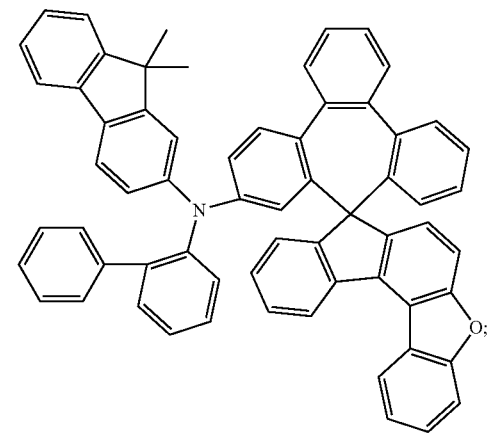
Compound 428
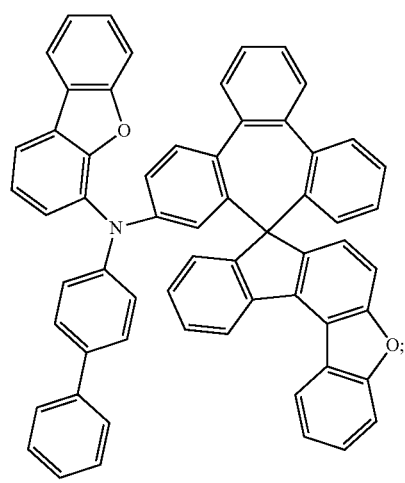
Compound 429
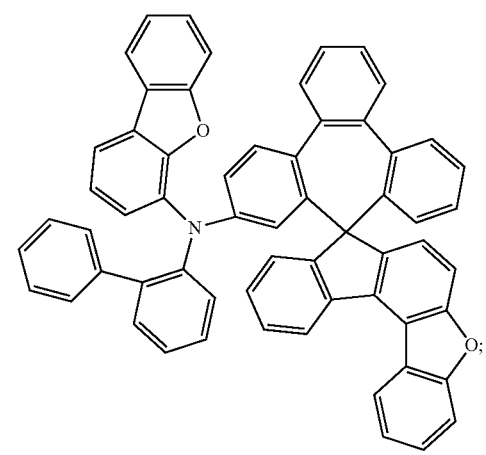
Compound 430
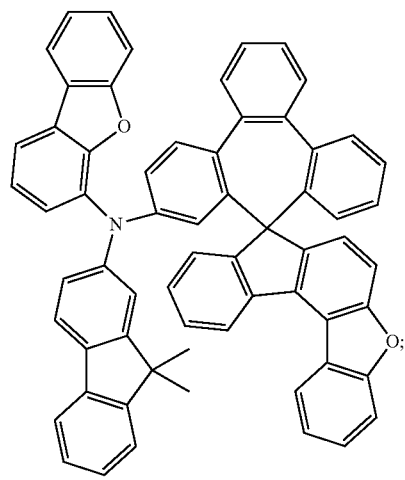
Compound 431
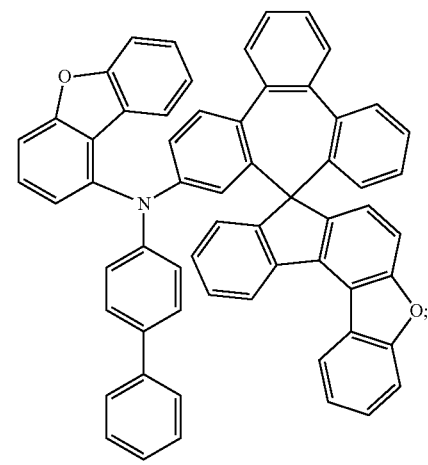

-continued
Compound 432
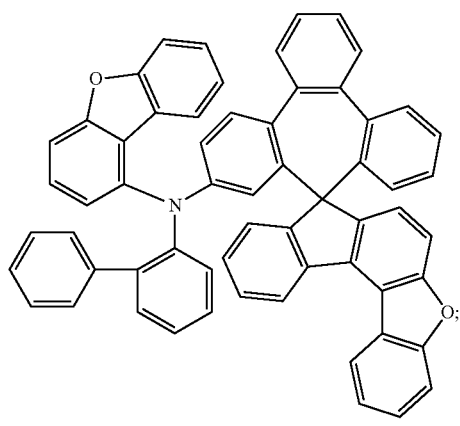
Compound 433
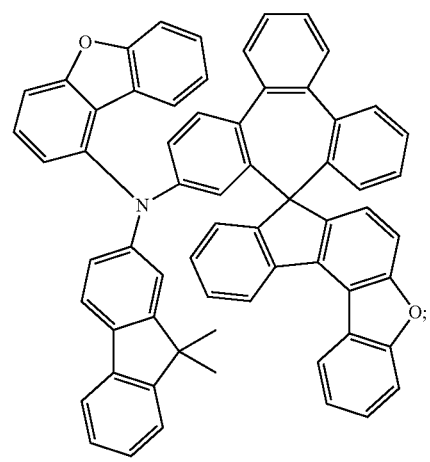
Compound 434
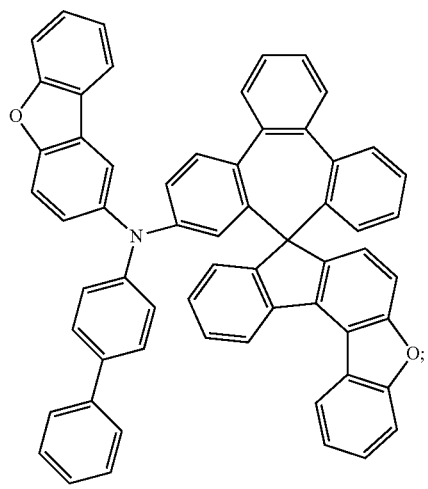
Compound 435
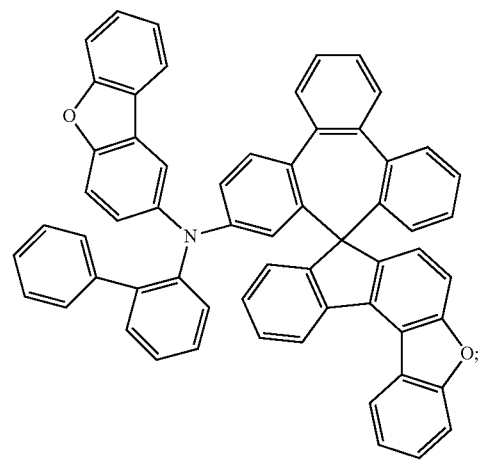
Compound 436
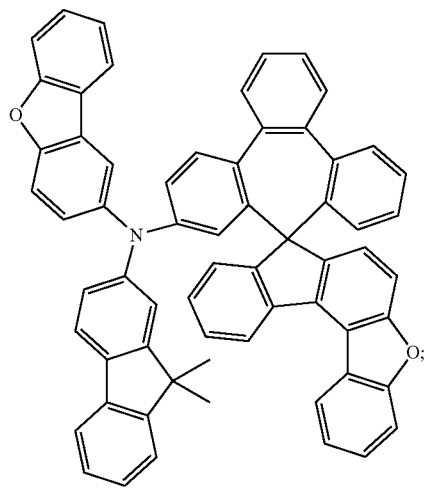
Compound 437
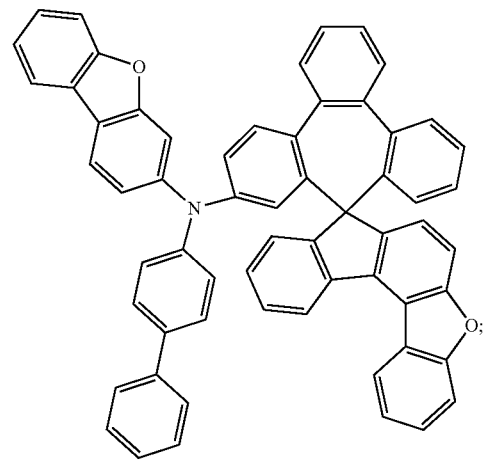

-continued
Compound 438
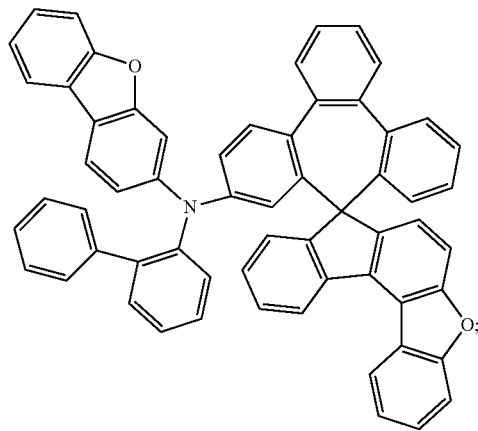
Compound 439
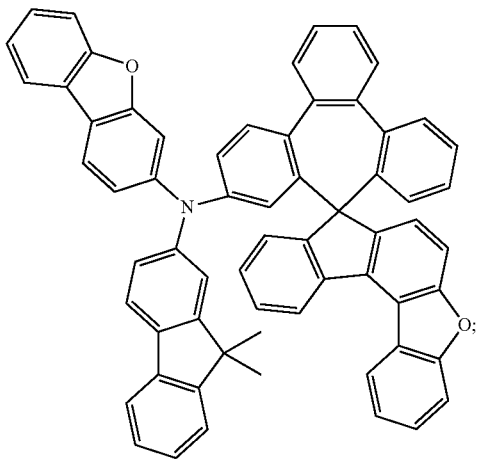
Compound 440
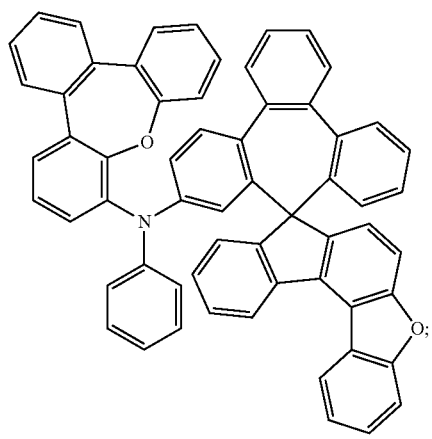
Compound 441
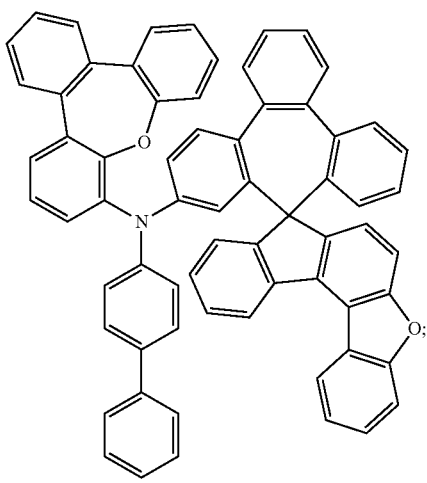
Compound 442
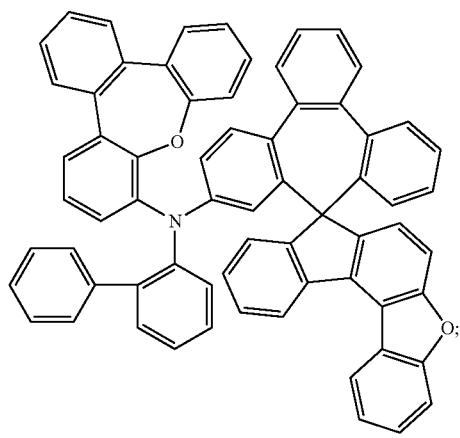
Compound 443
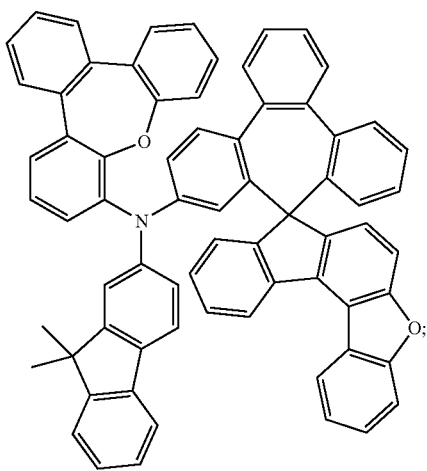

-continued
Compound 444
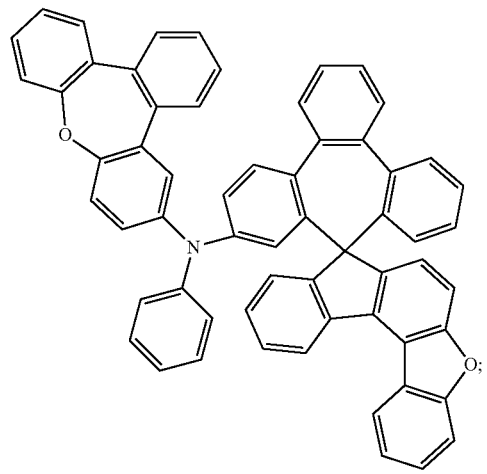
Compound 445
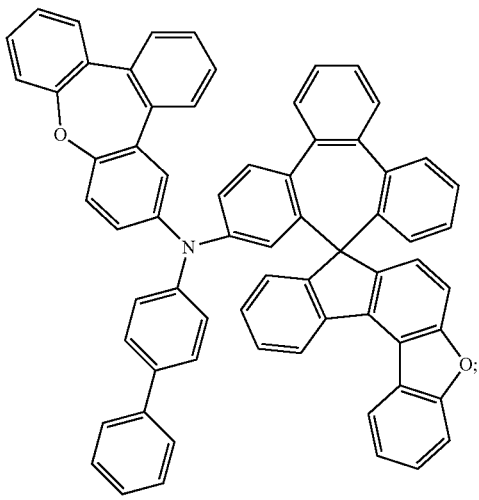
Compound 446
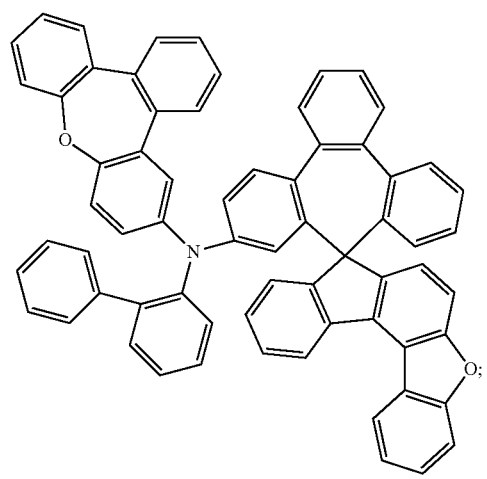
Compound 447
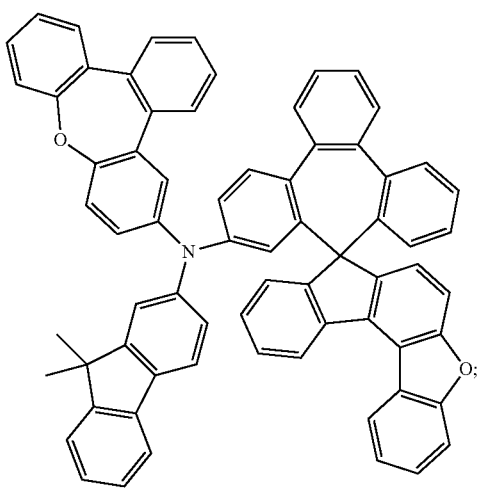
Compound 448
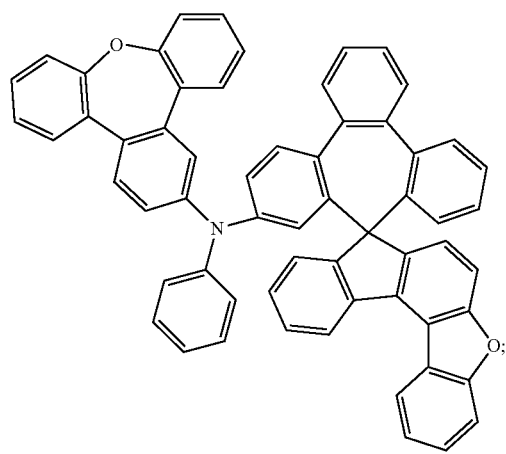
Compound 449
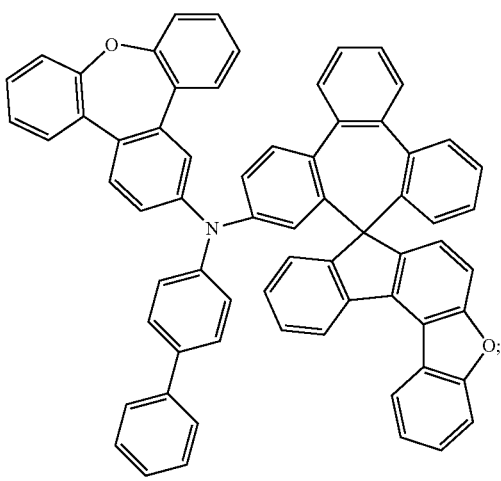

-continued
Compound 450
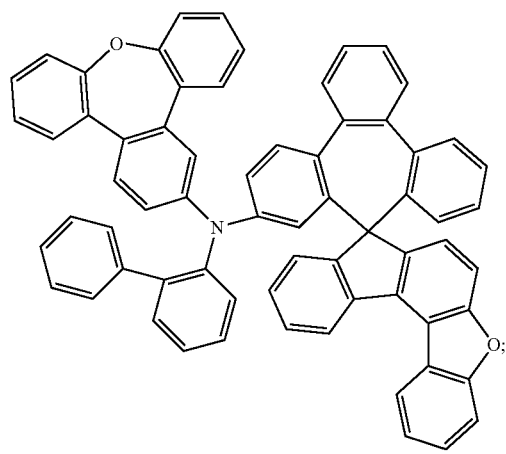
Compound 451
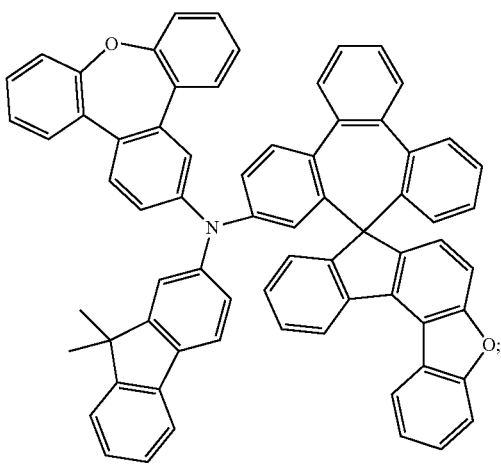
Compound 452
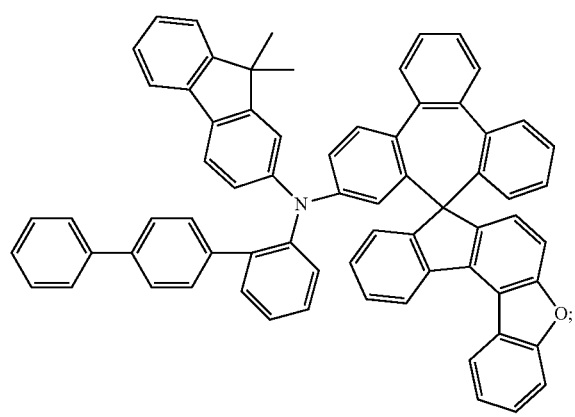
Compound 453
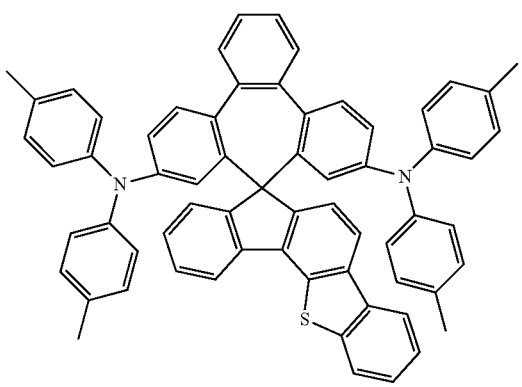
Compound 454
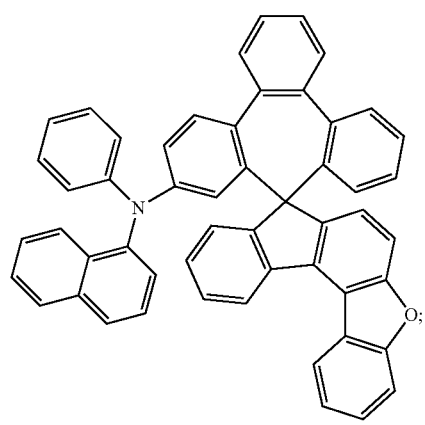
Compound 455
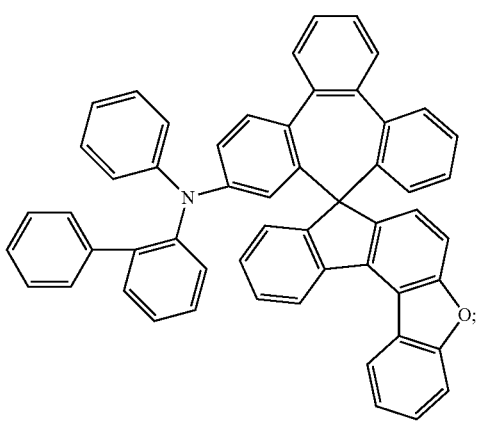

-continued
Compound 456
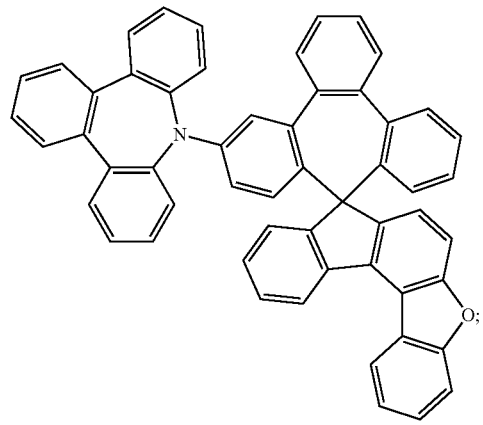
Compound 457
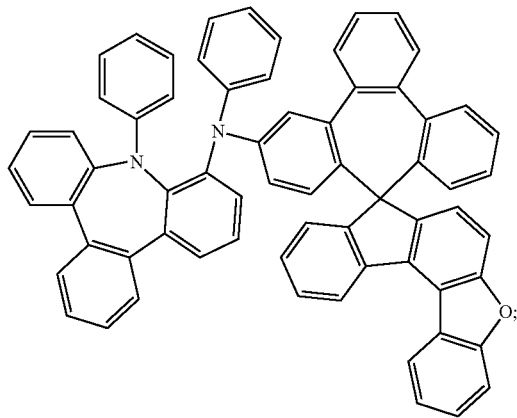
Compound 458
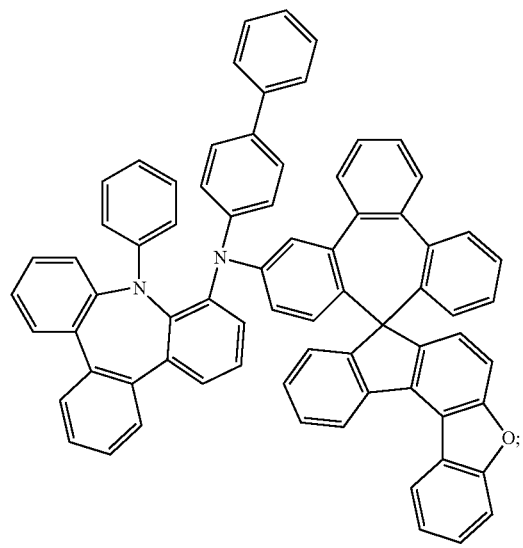
Compound 459
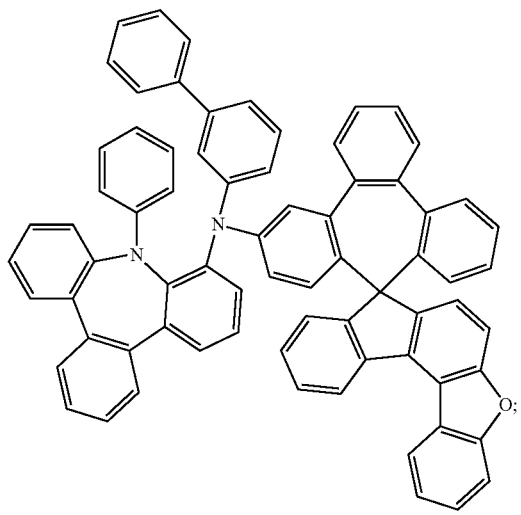
Compound 460
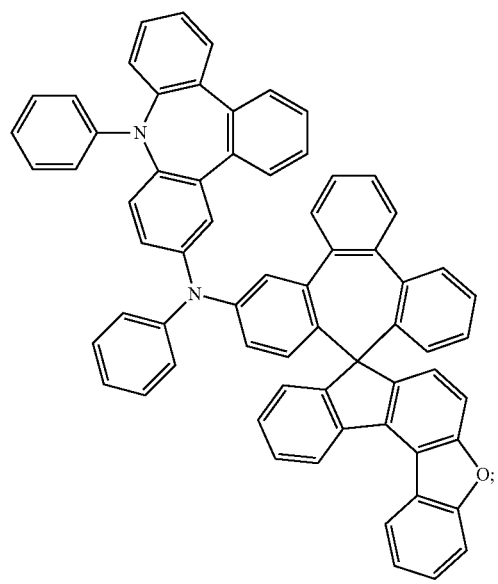
Compound 461
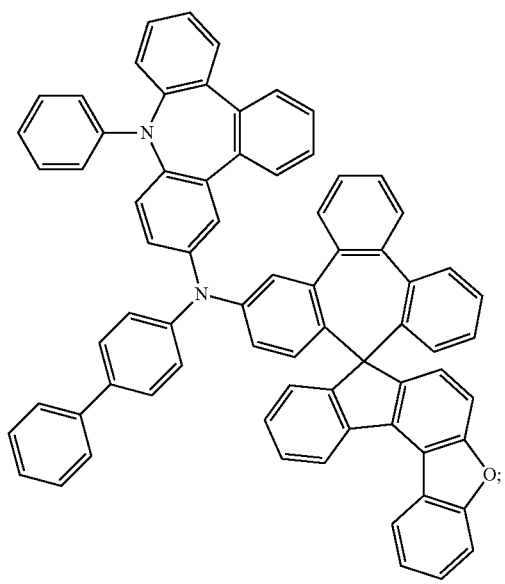

-continued
Compound 462
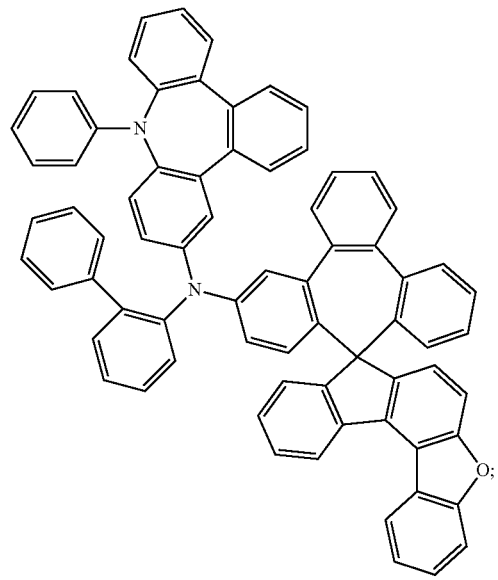
Compound 463
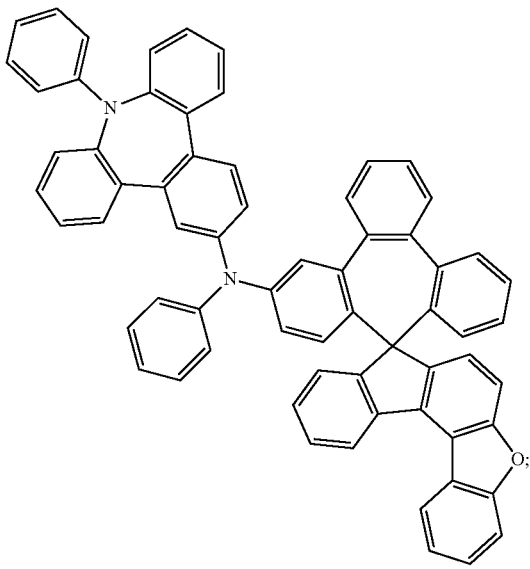
Compound 464
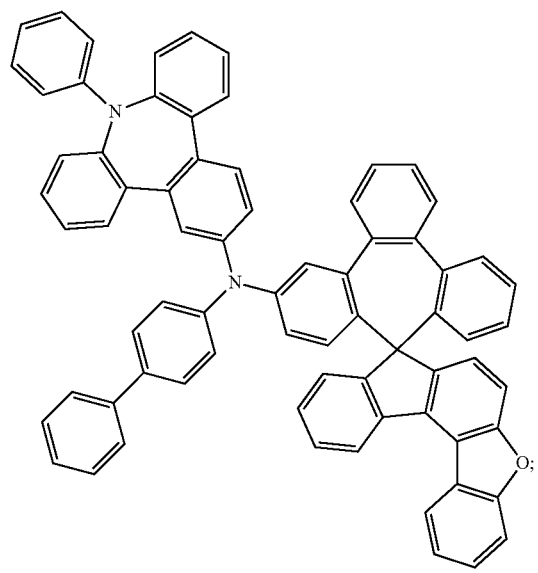
Compound 465
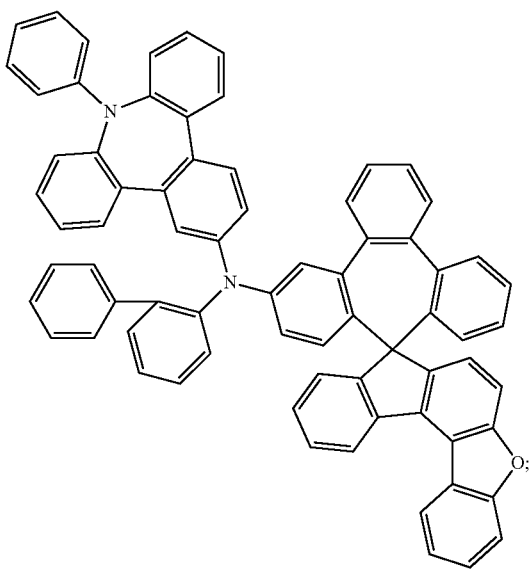

-continued
Compound 466
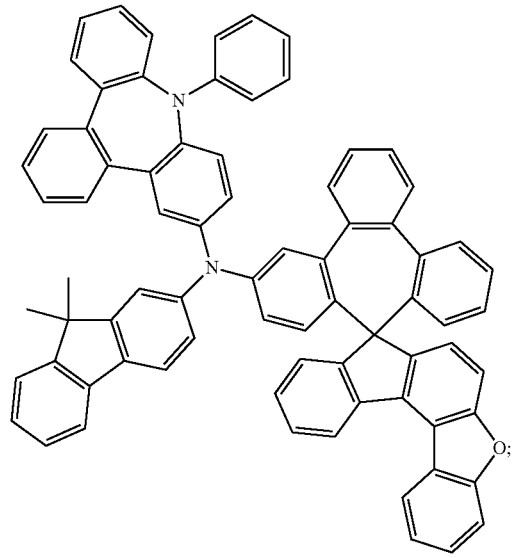
Compound 467
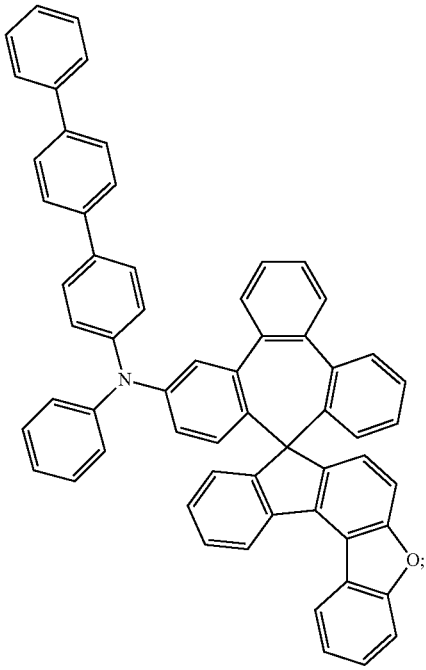
Compound 468
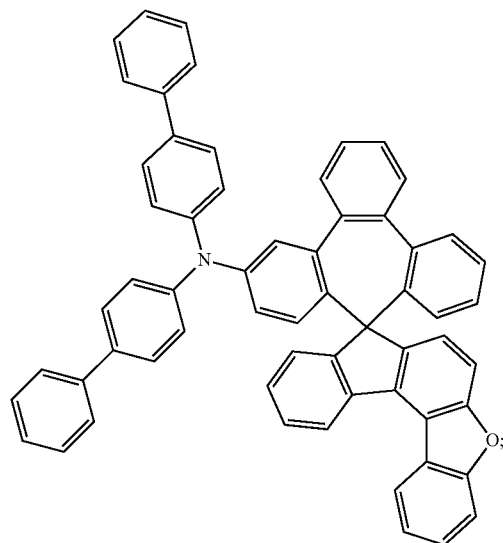
Compound 469
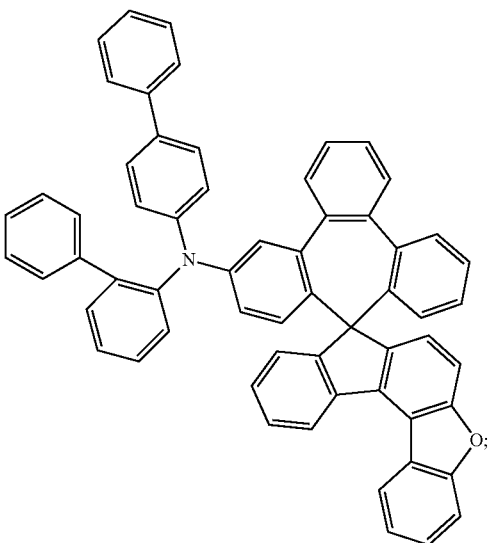

-continued
Compound 470
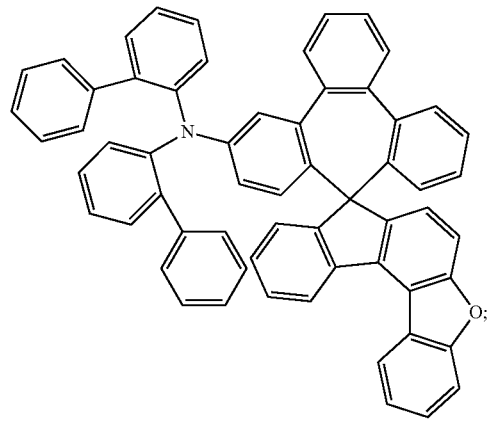
Compound 471
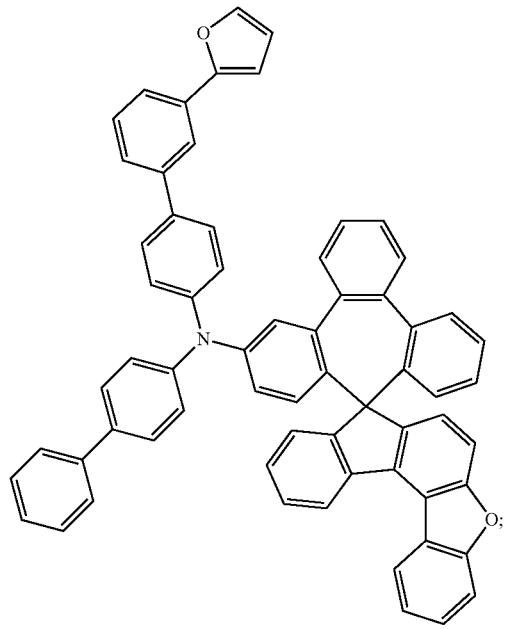
Compound 472
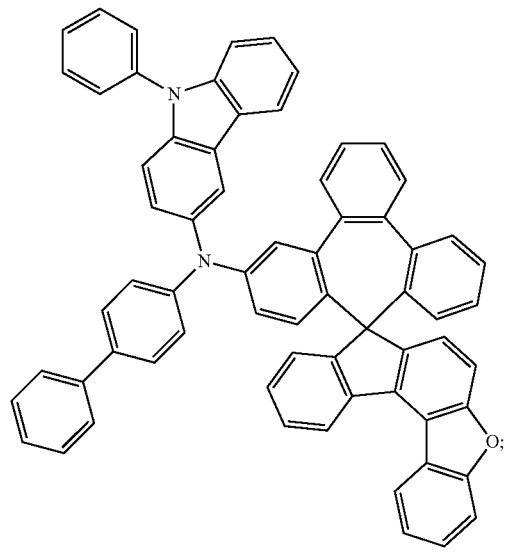
Compound 473
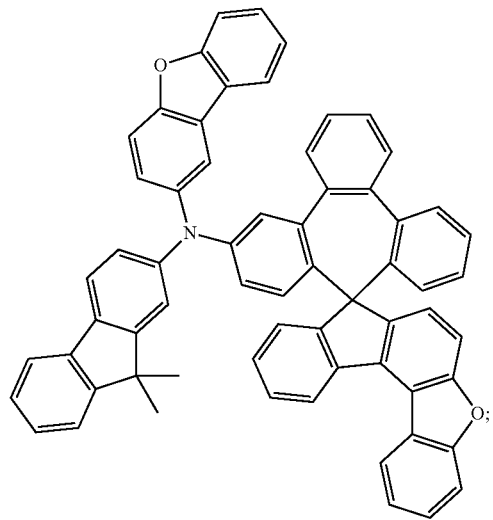

-continued
Compound 474
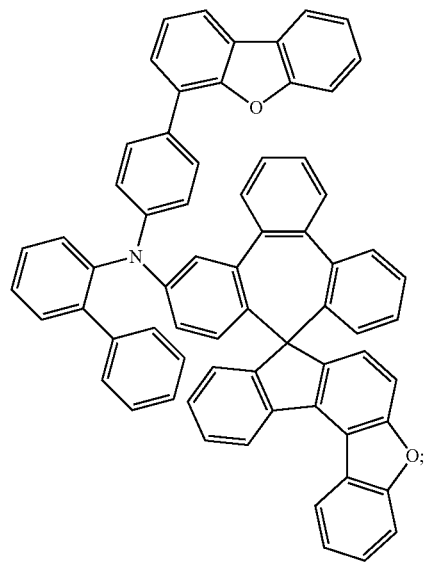
Compound 475
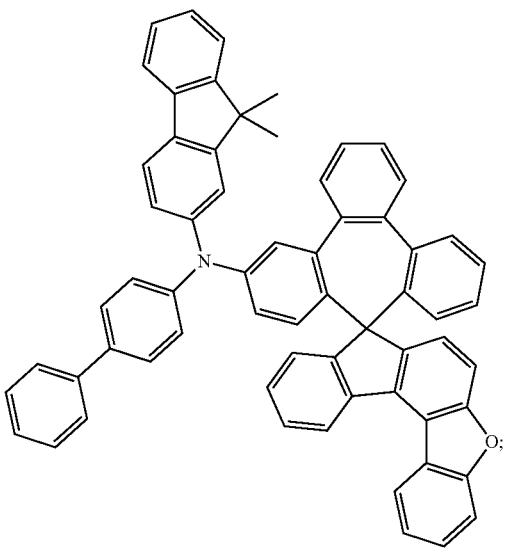
Compound 476
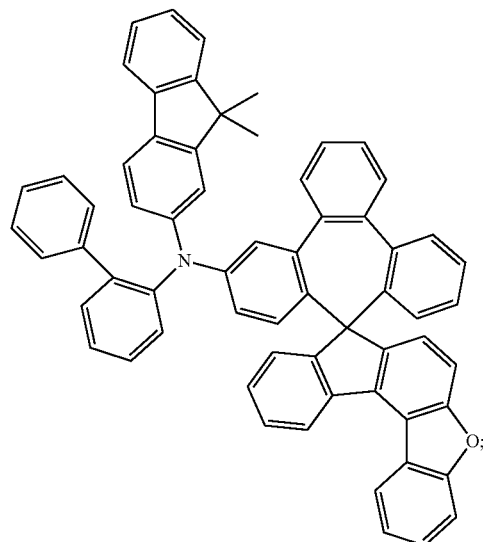
Compound 477
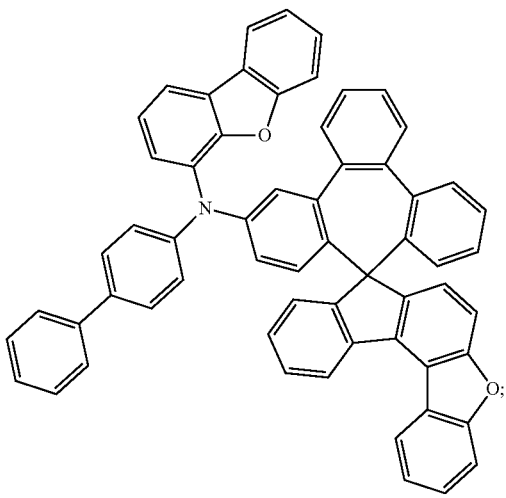
Compound 478
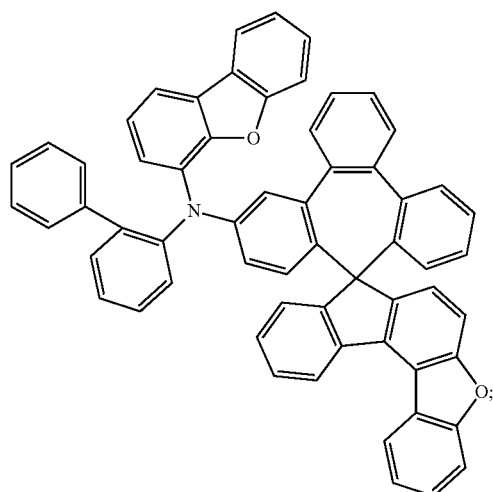
Compound 479
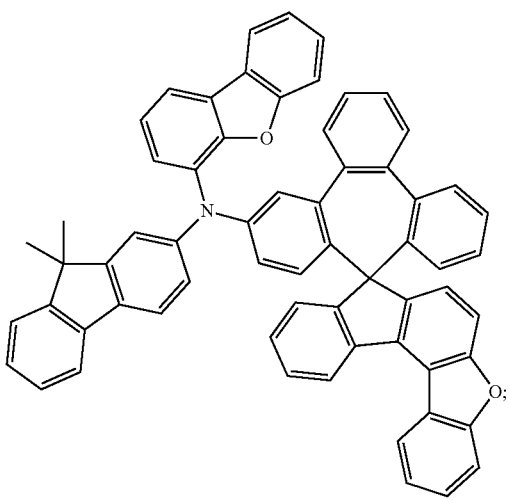

-continued
Compound 480
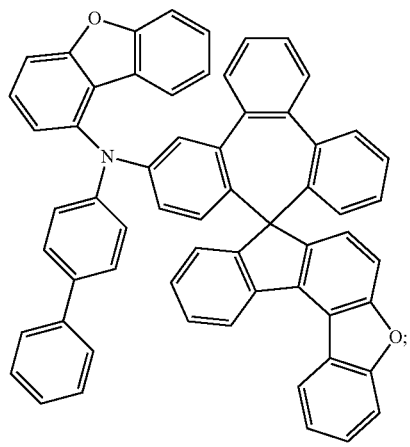
Compound 481
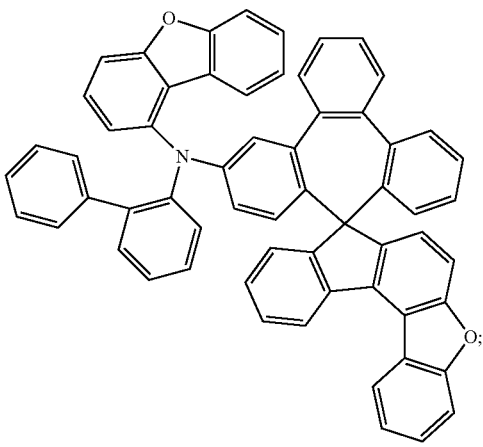
Compound 482
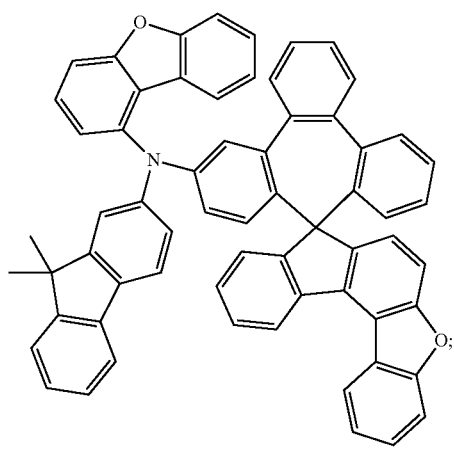
Compound 483
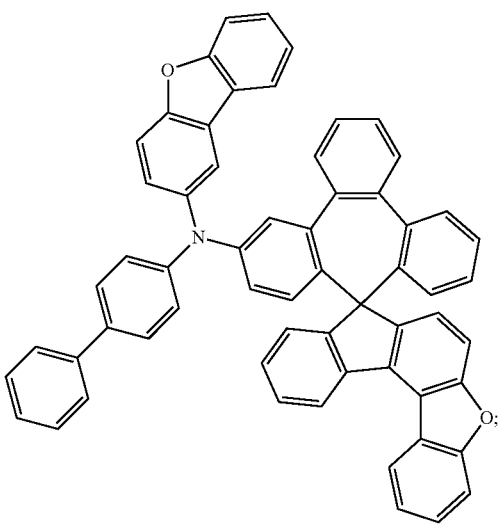
Compound 484
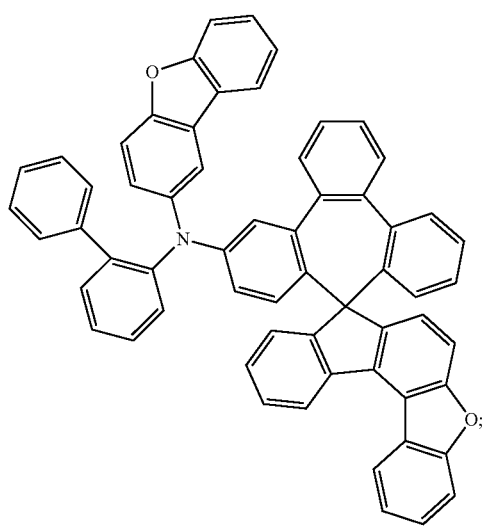
Compound 485
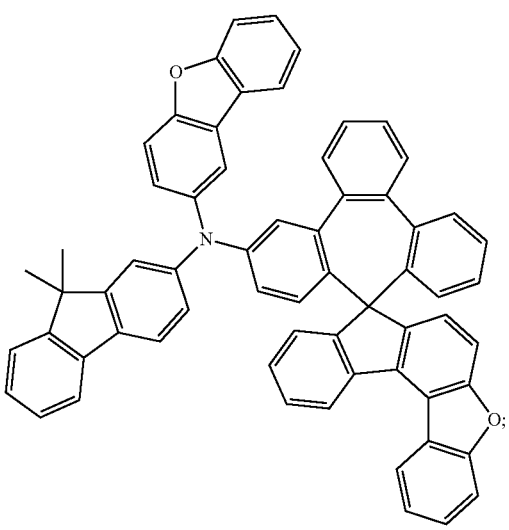

-continued
Compound 486
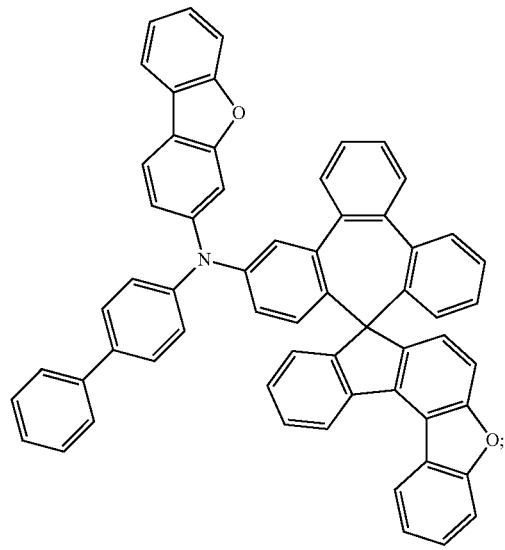
Compound 487
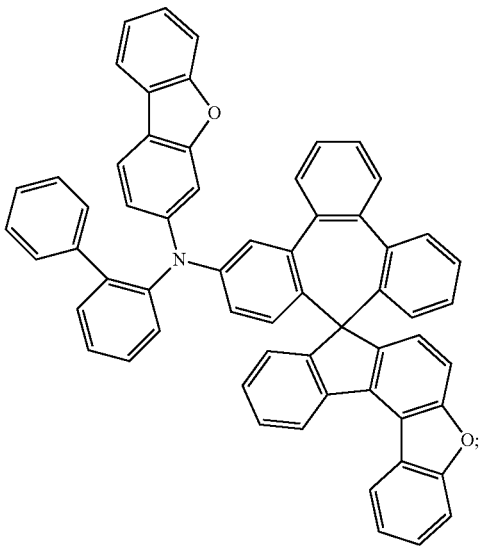
Compound 488
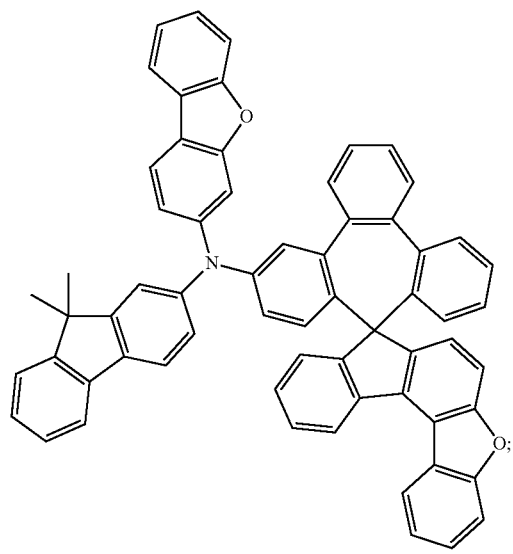
Compound 489
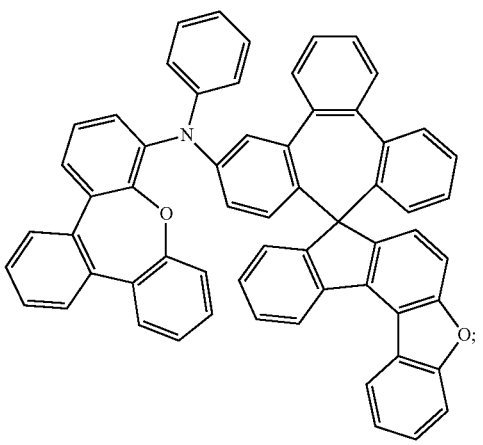

-continued
Compound 490
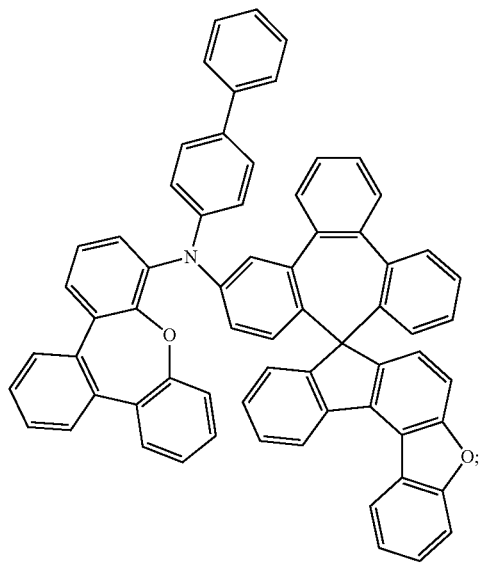
Compound 491
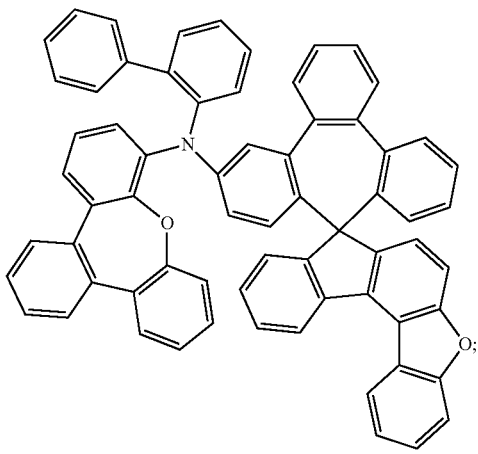
Compound 492
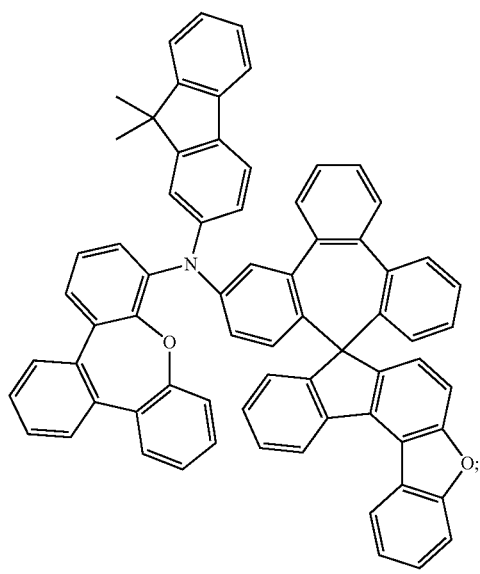
Compound 493
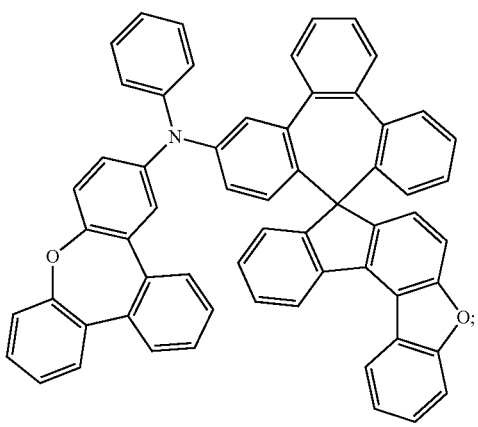

-continued
Compound 494
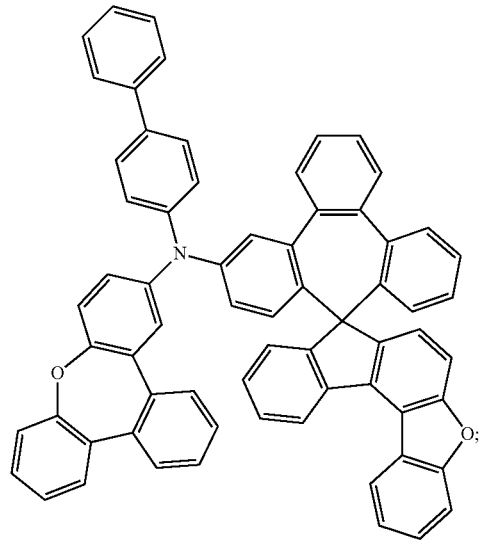
Compound 495
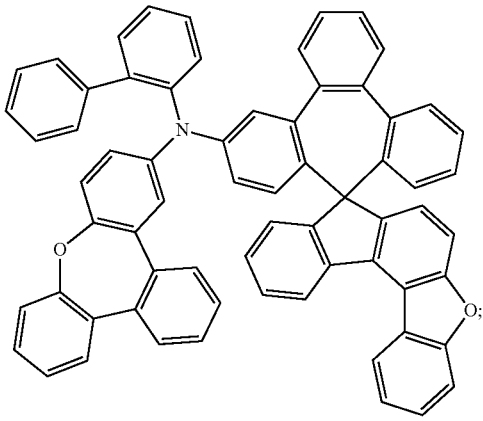
Compound 496
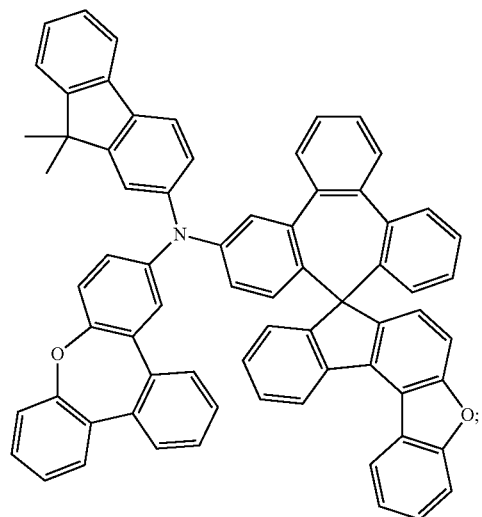
Compound 497
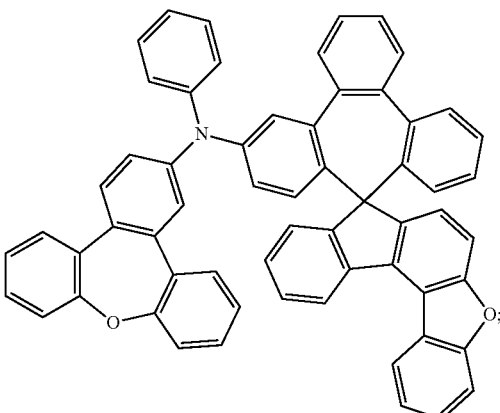
Compound 498
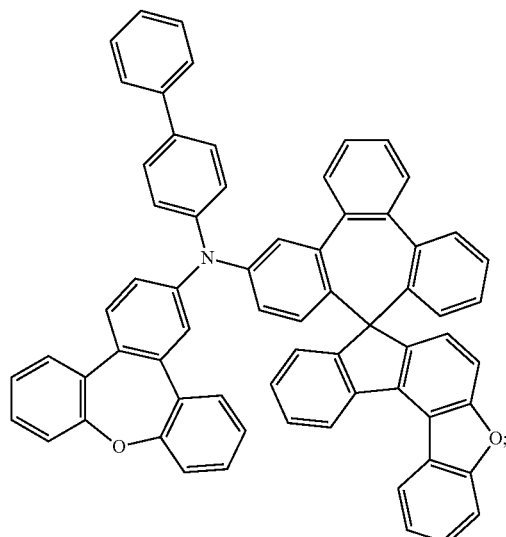
Compound 499
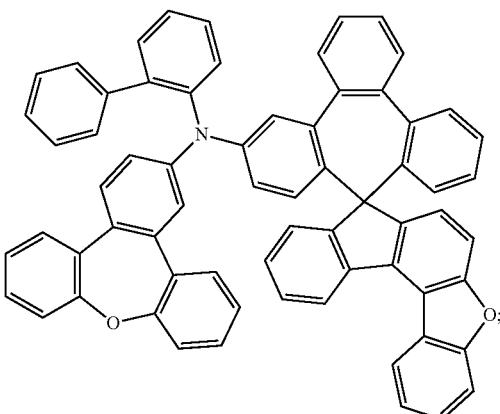

-continued
Compound 500
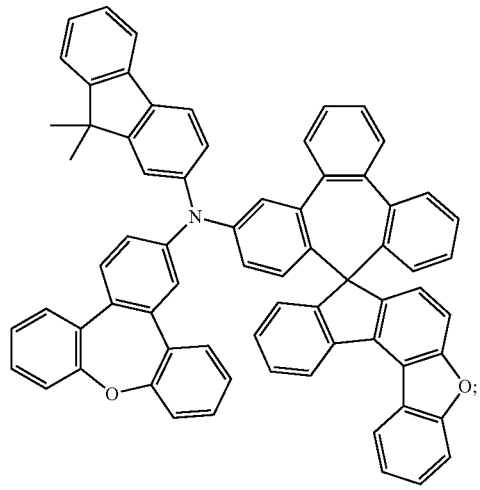
Compound 501
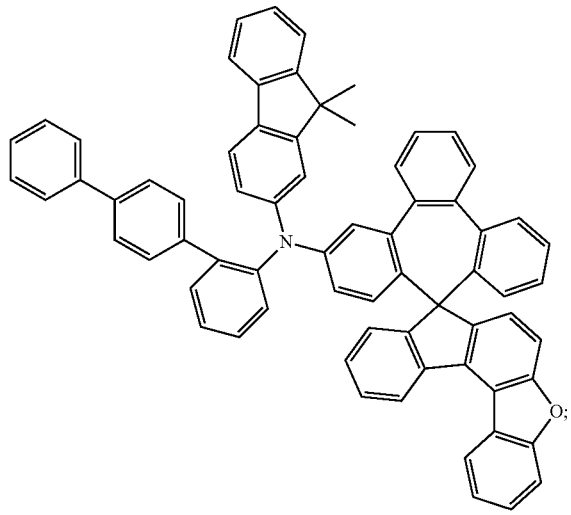
Compound 502
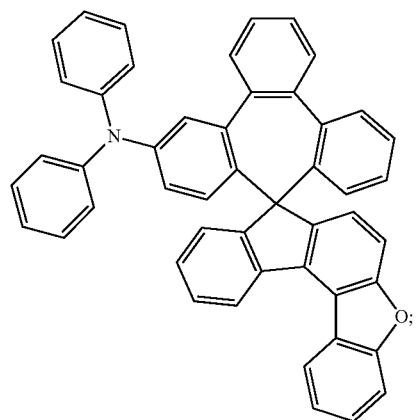
Compound 503
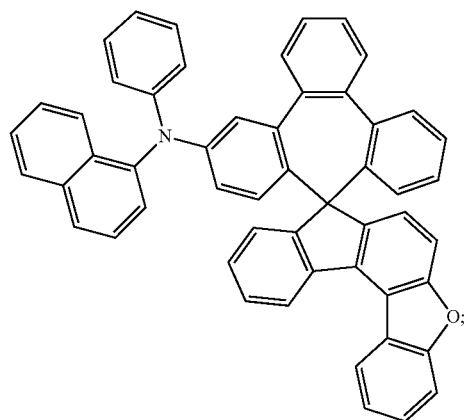
Compound 504
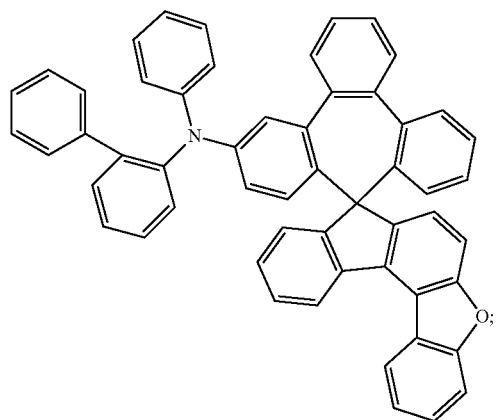
Compound 505
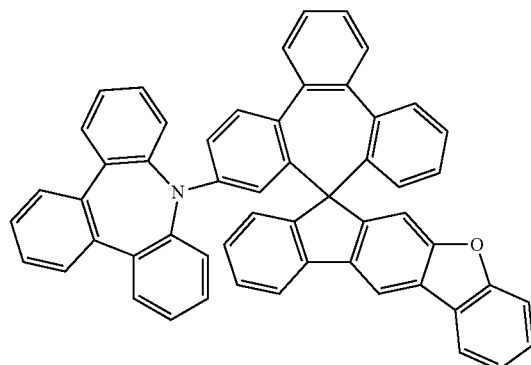

-continued
Compound 506
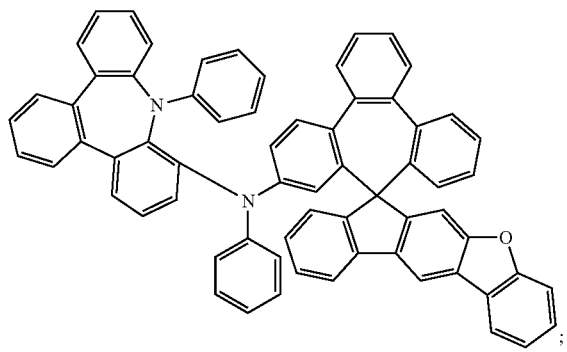
Compound 507
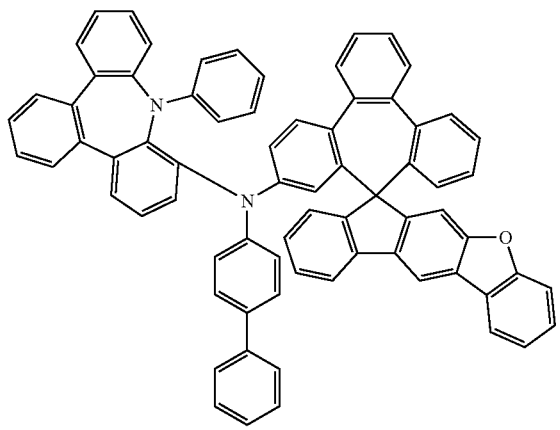
Compound 508
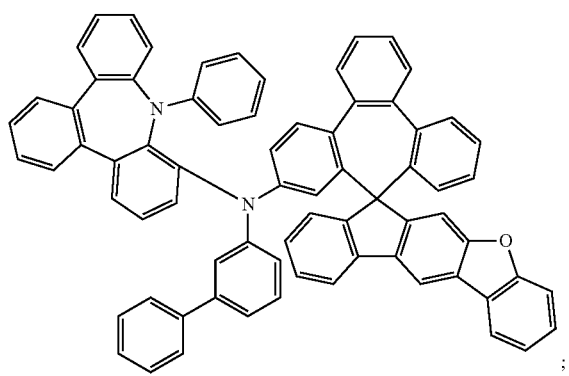
Compound 509
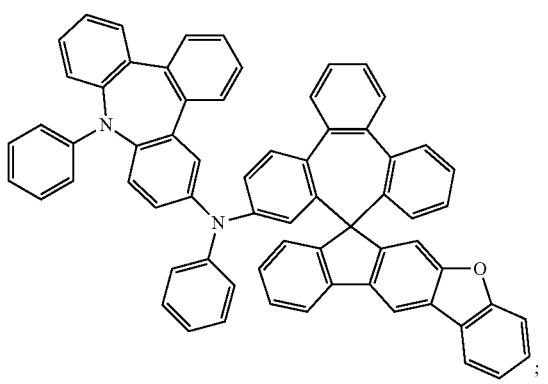
Compound 510
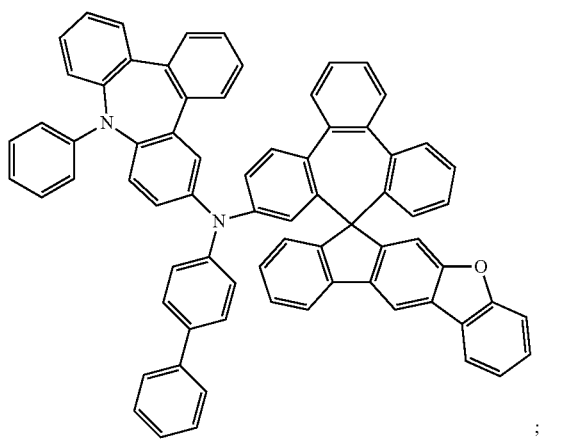
Compound 511
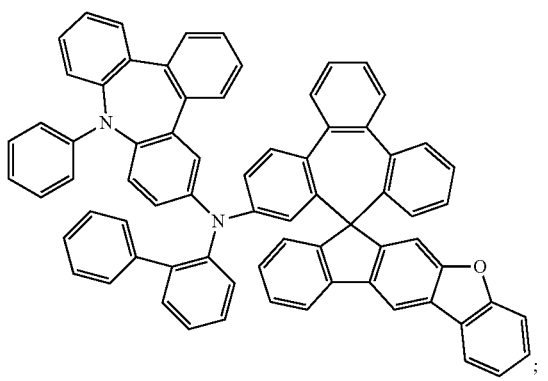

-continued
Compound 512
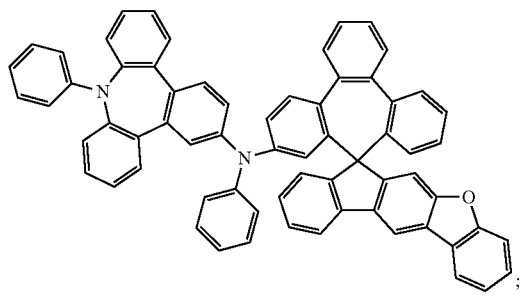
Compound 513
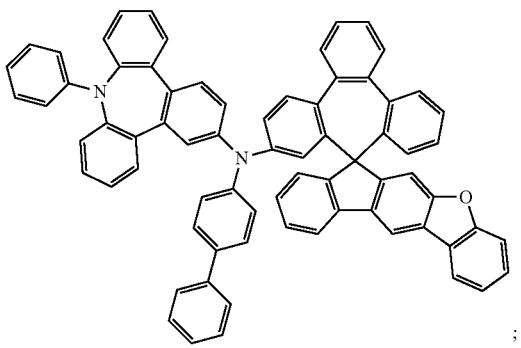
Compound 514
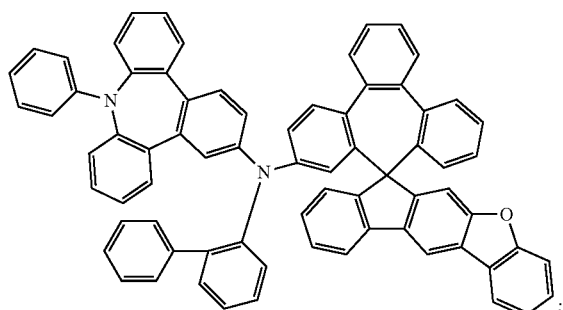
Compound 515
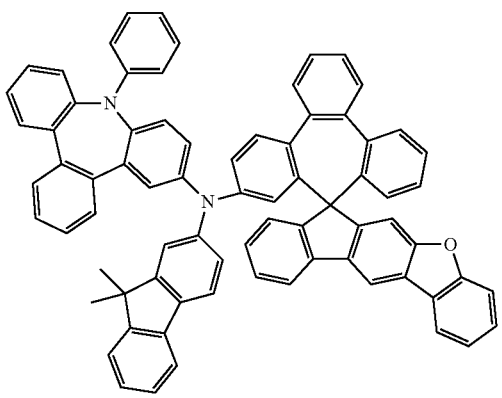
Compound 516
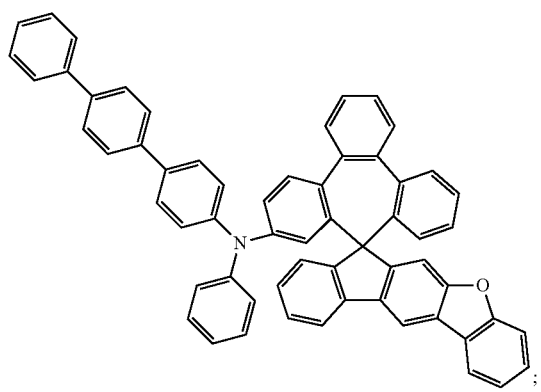
Compound 517
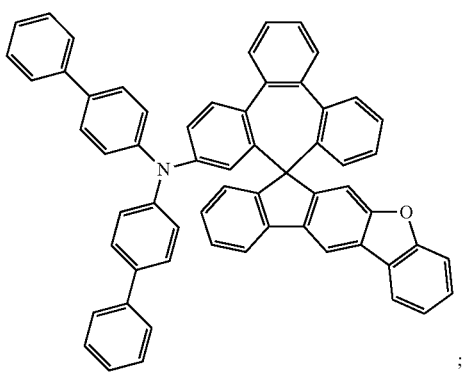
Compound 518
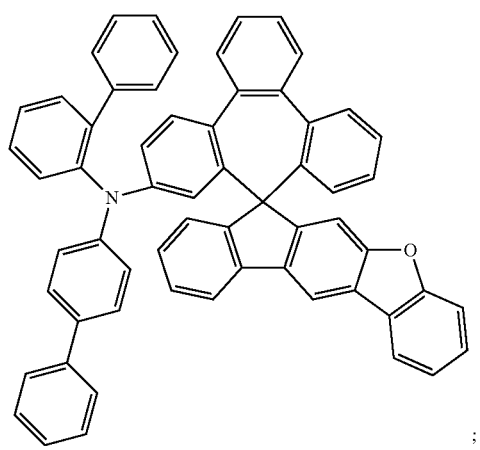
Compound 519
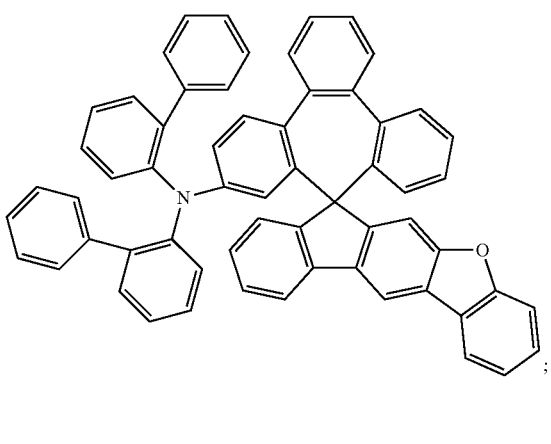

Compound 520
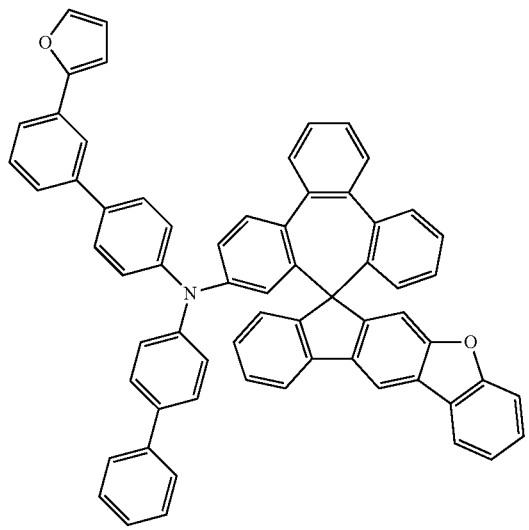
Compound 522
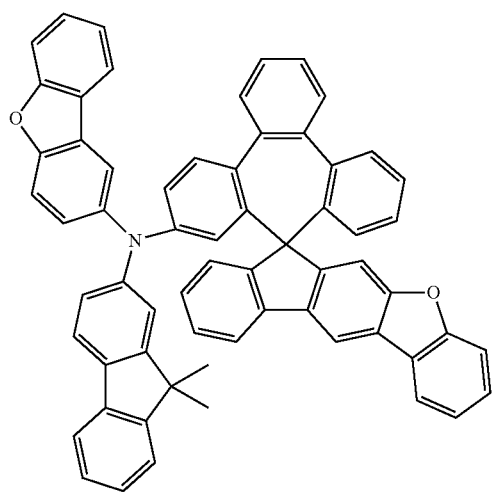
Compound 524
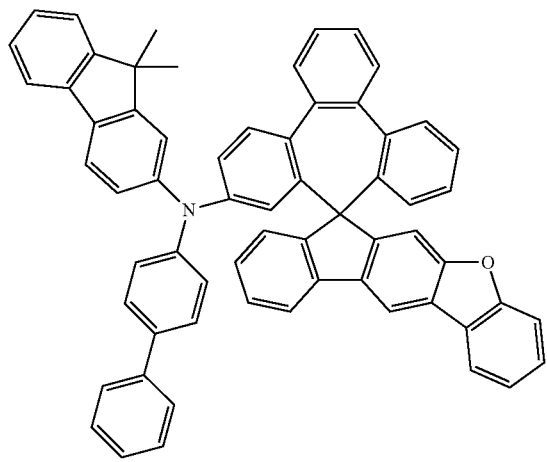
Compound 521
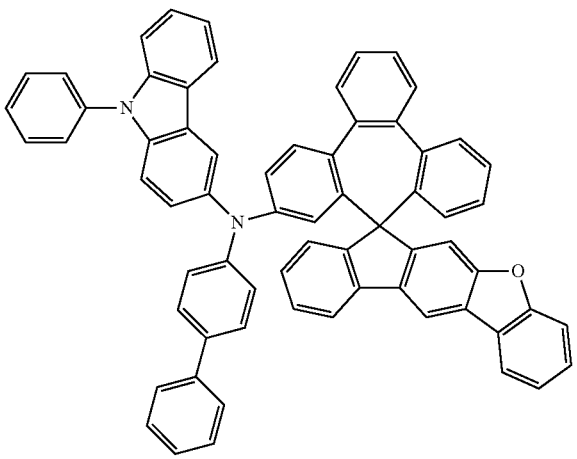
Compound 523
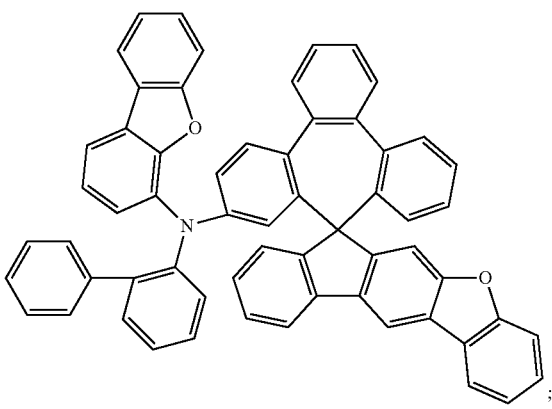
Compound 525
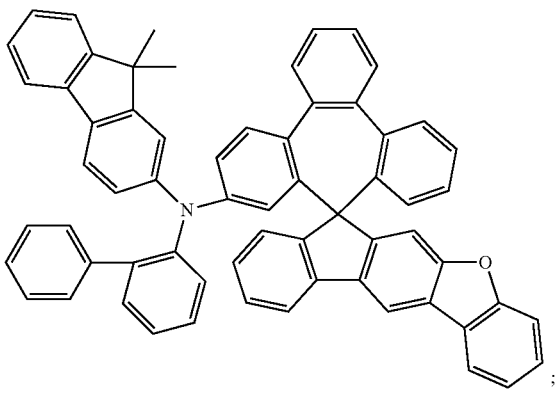

-continued
Compound 526
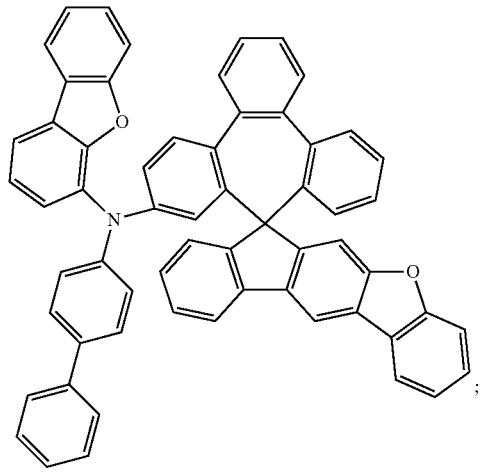
Compound 527
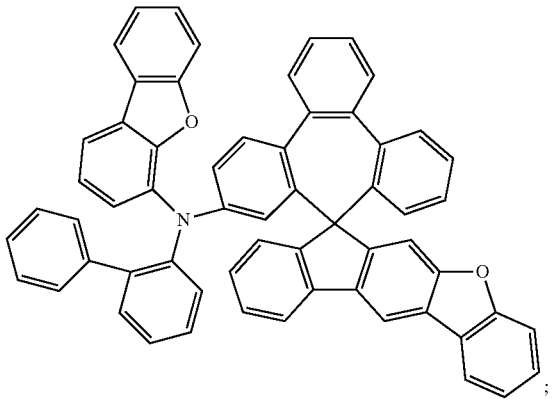
Compound 528
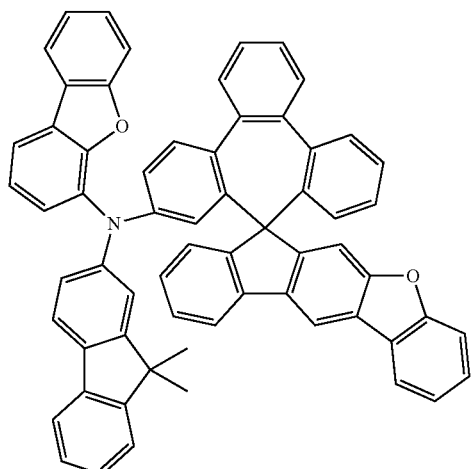
Compound 529
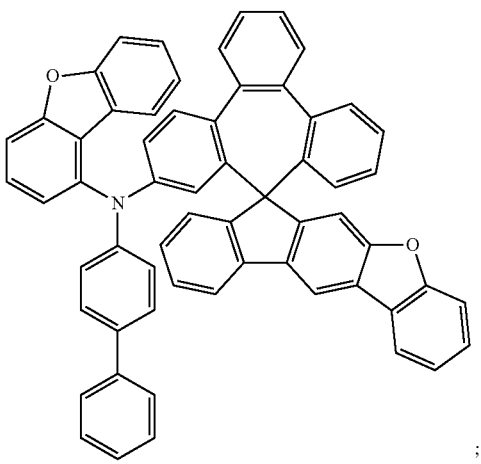
Compound 530
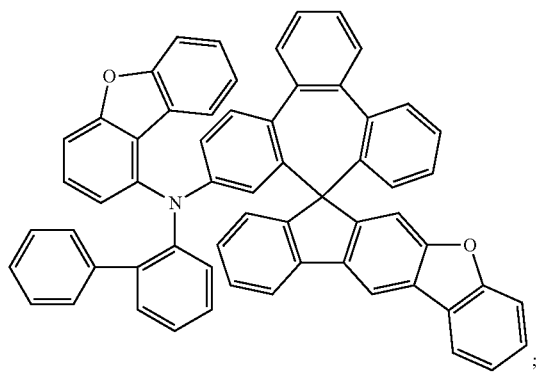
Compound 531
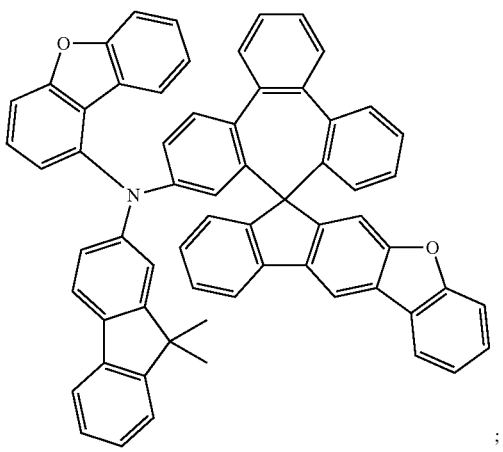

Compound 532
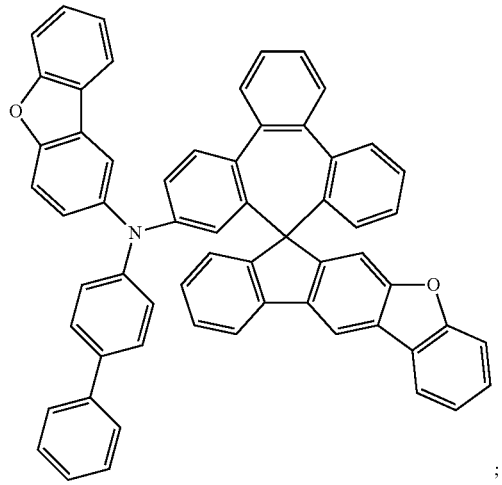
;
Compound 533
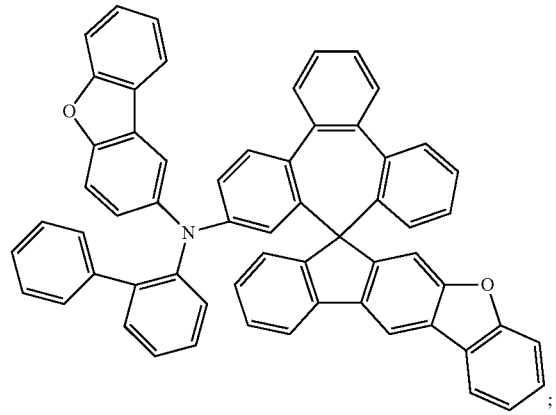
;
Compound 534
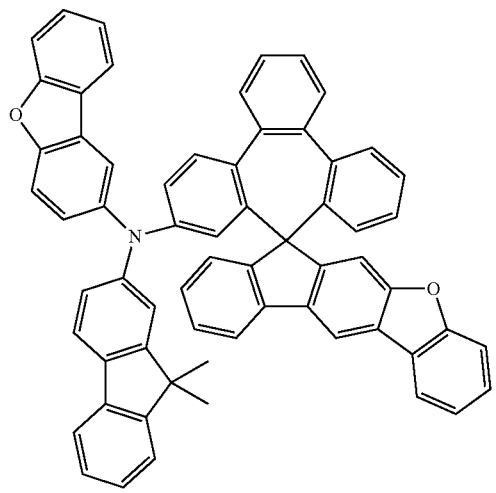
;
Compound 535
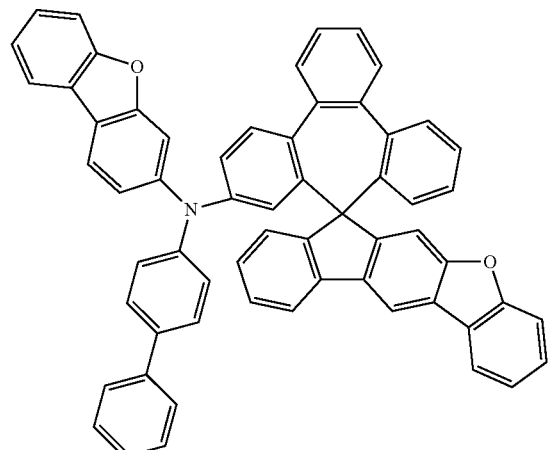
;
Compound 536
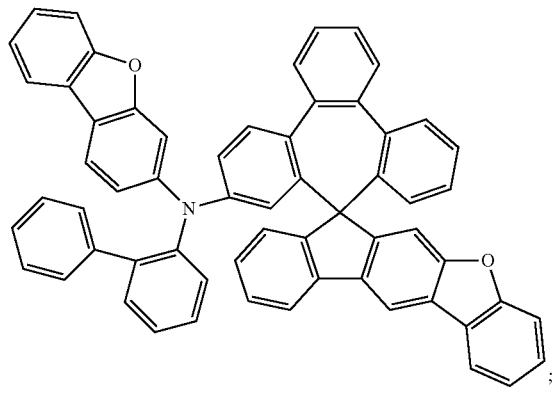
;
Compound 537
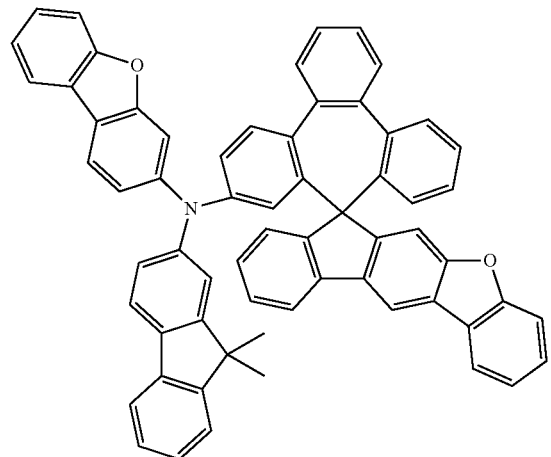
;

-continued
Compound 538
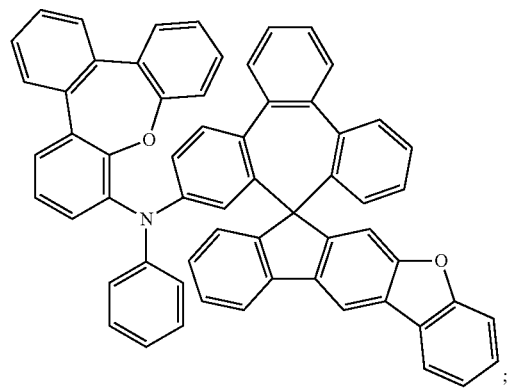
Compound 539
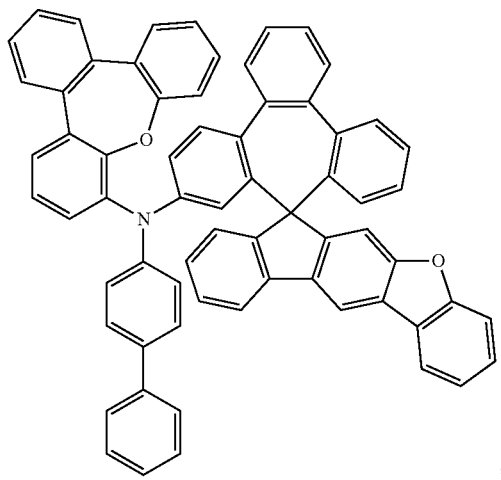
Compound 540
Compound 541
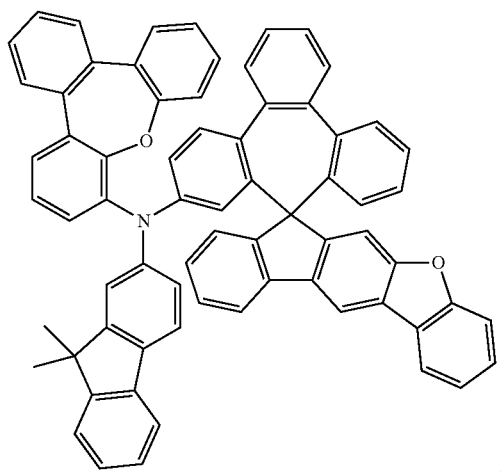
Compound 542
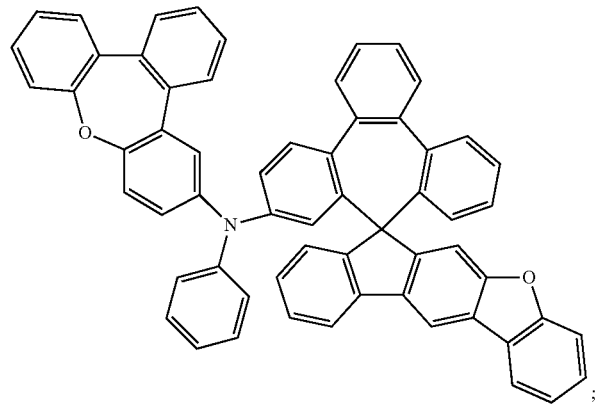
Compound 543
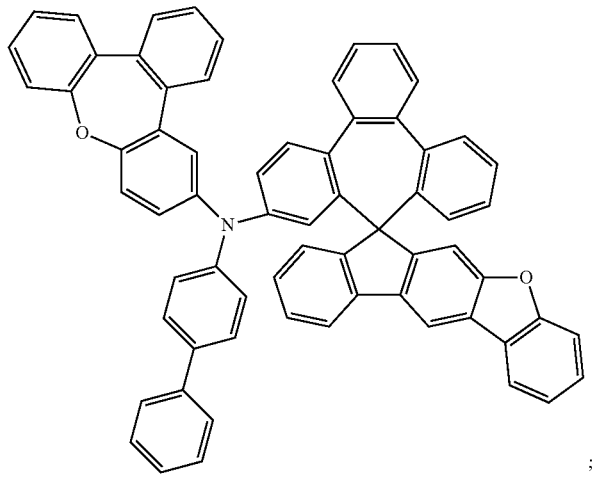

Compound 544
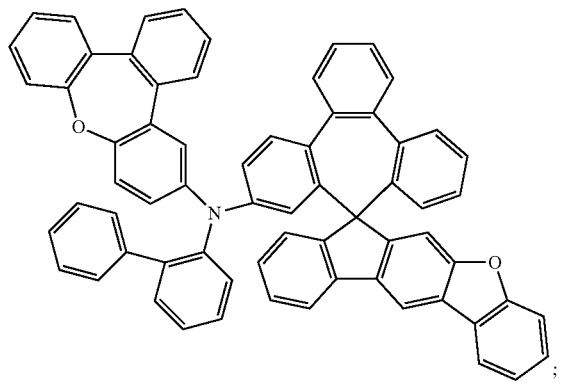
Compound 545
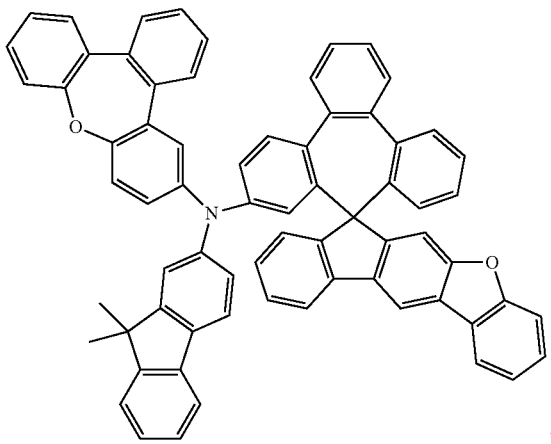
Compound 546
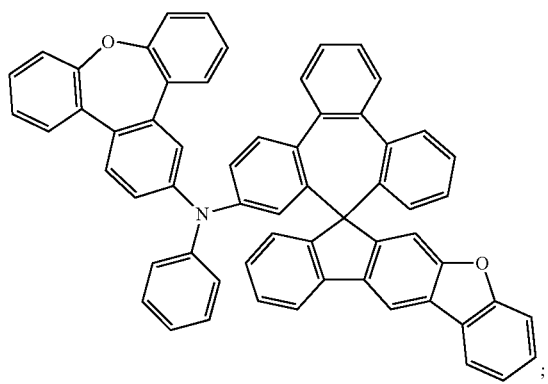
Compound 547
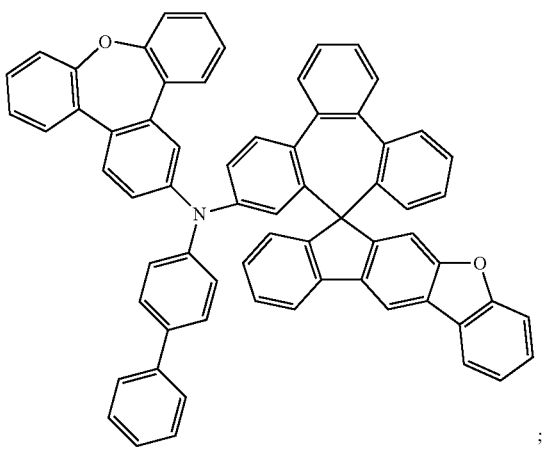
Compound 548
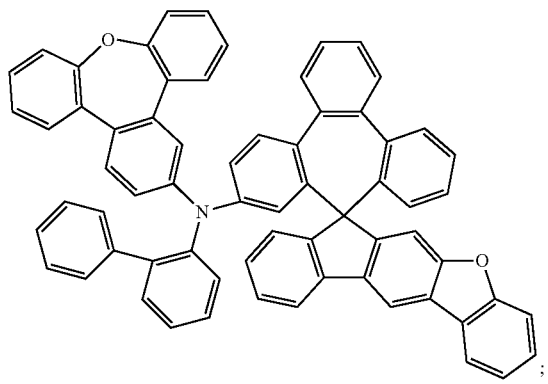
Compound 549
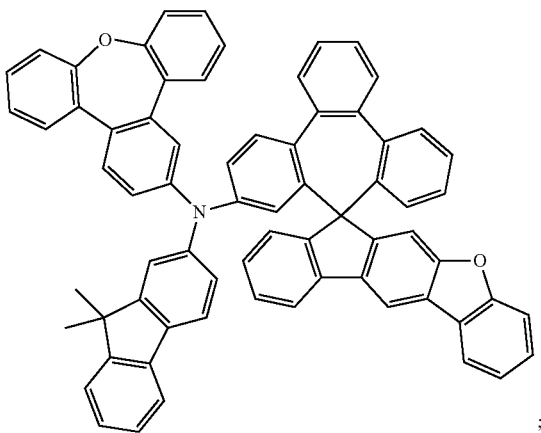

-continued
Compound 550
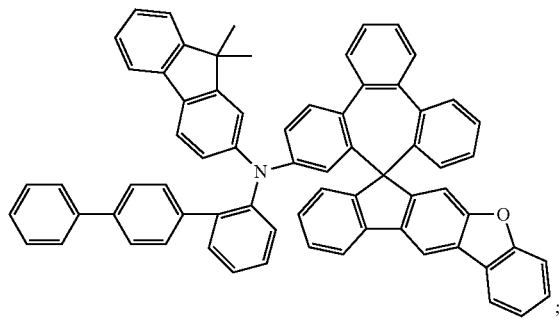
Compound 551
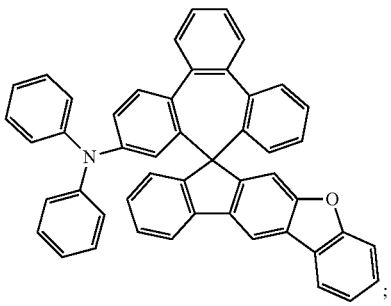
Compound 552
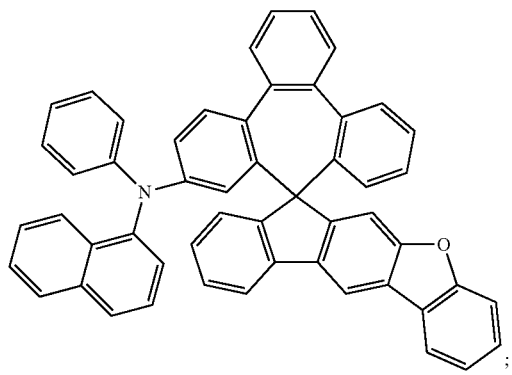
Compound 553
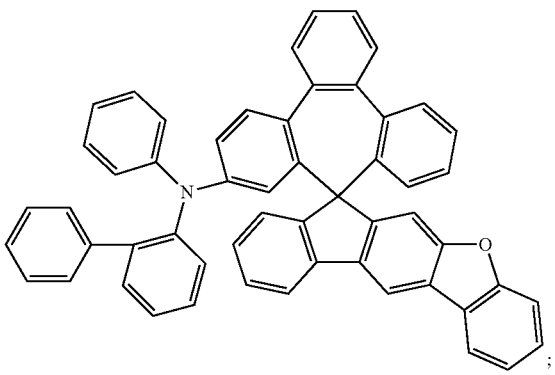
Compound 554
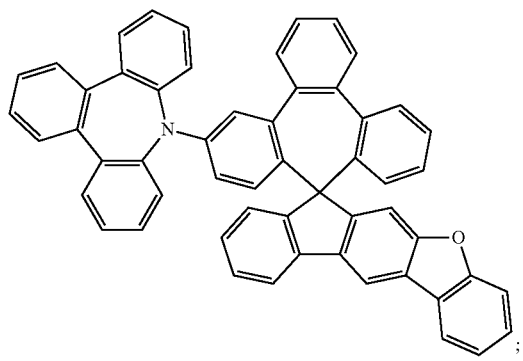
Compound 555
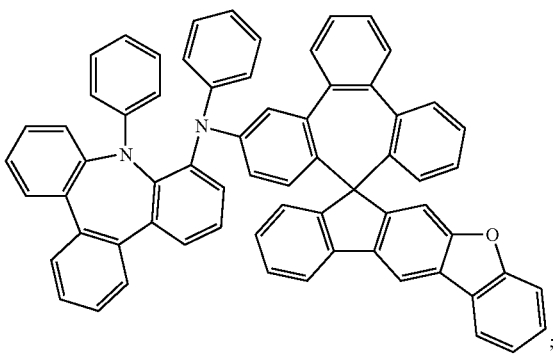
Compound 556
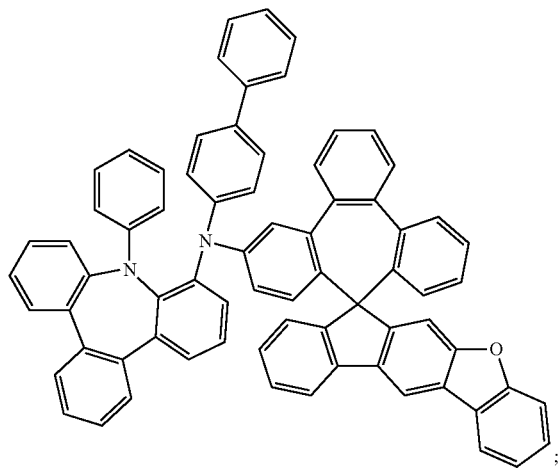
Compound 557
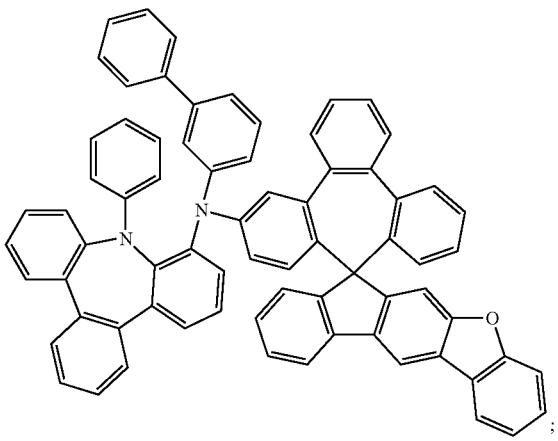

-continued
Compound 558
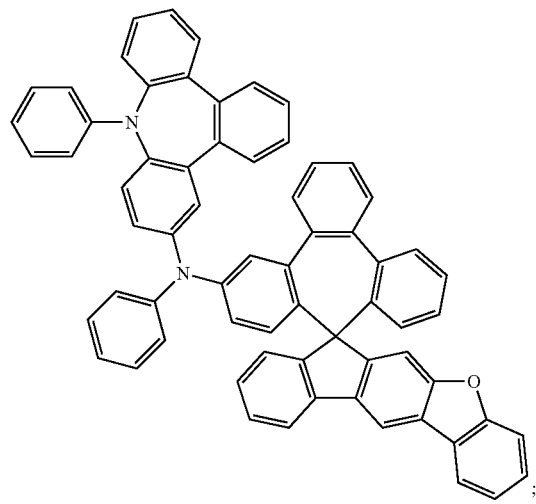
Compound 559
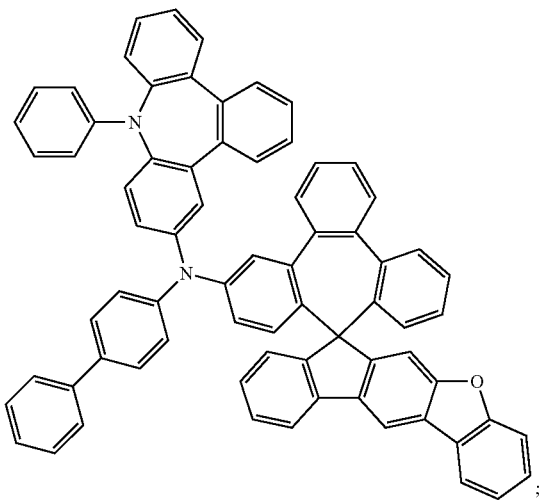
Compound 560
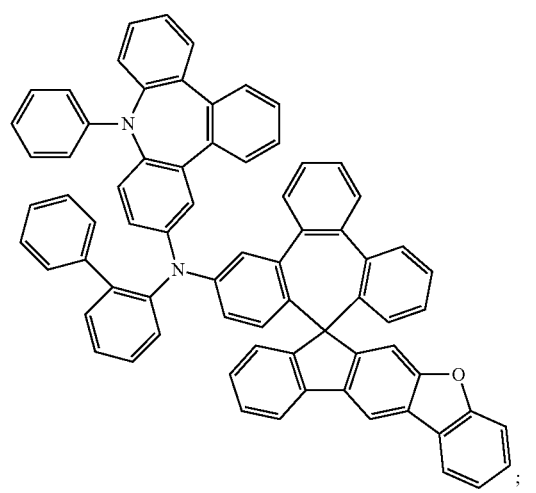
Compound 561
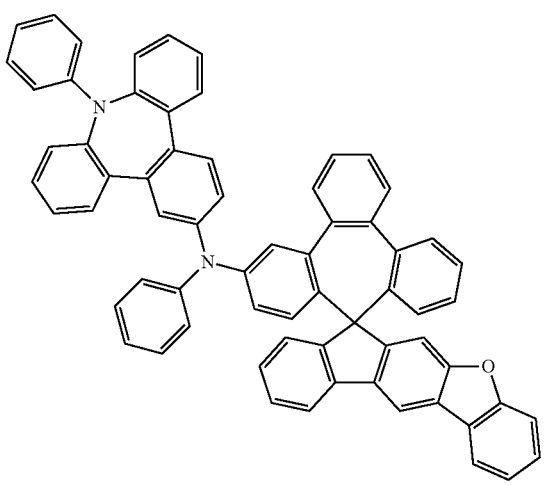
Compound 562
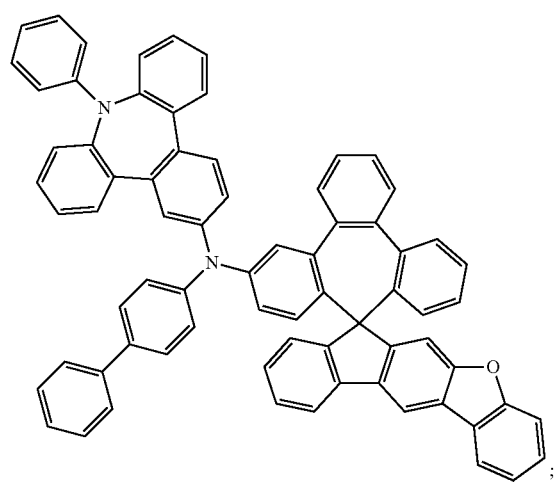
Compound 563
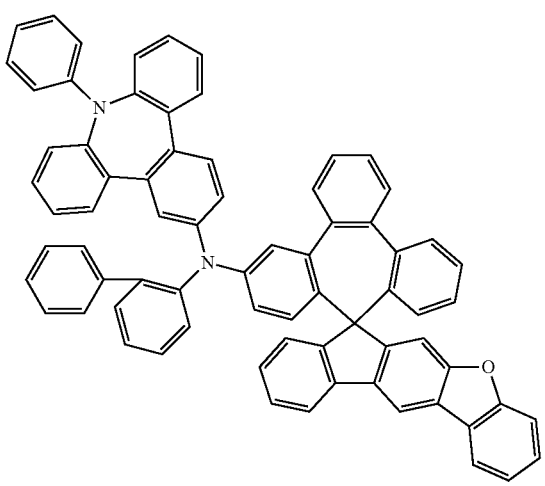

Compound 564
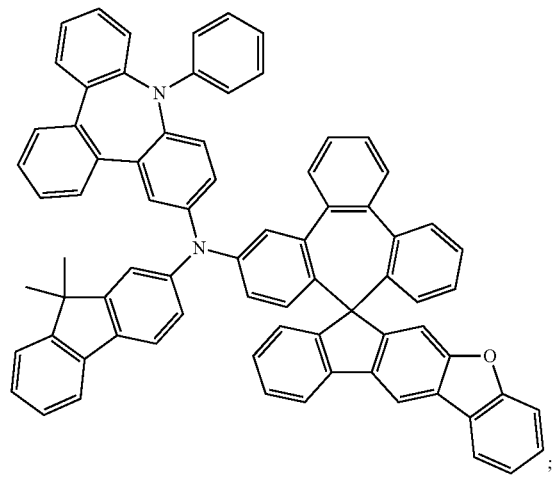
Compound 565
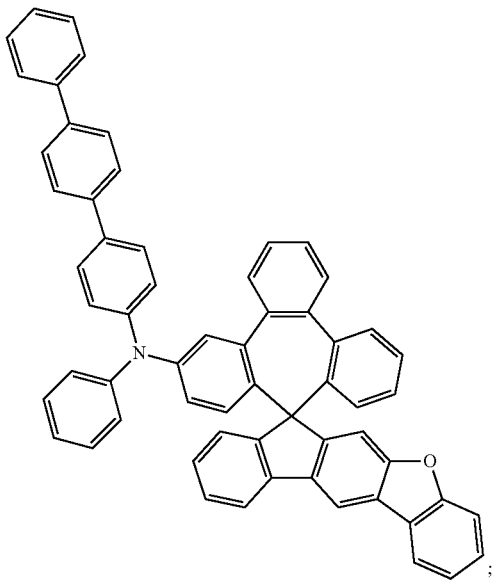
Compound 565
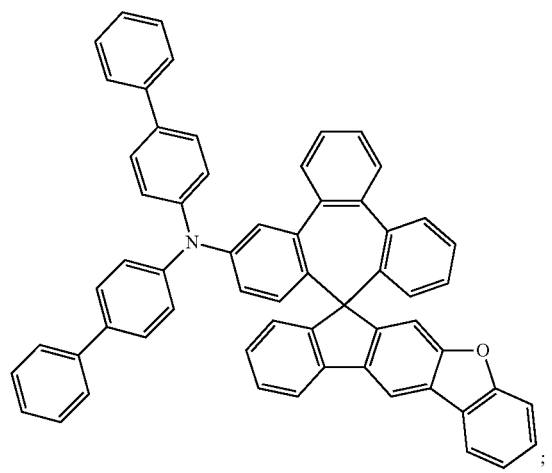
Compound 567
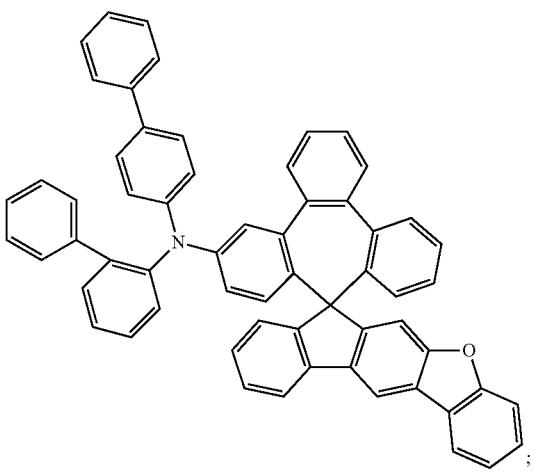

-continued
Compound 568
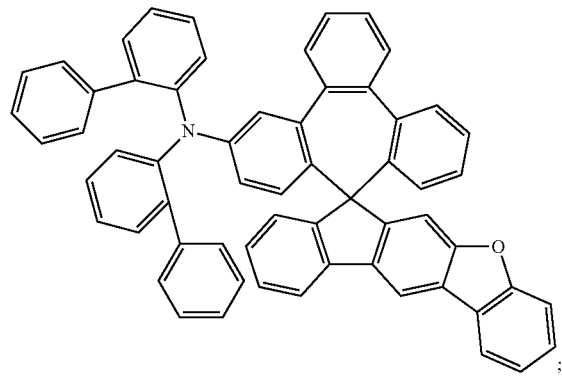
Compound 569
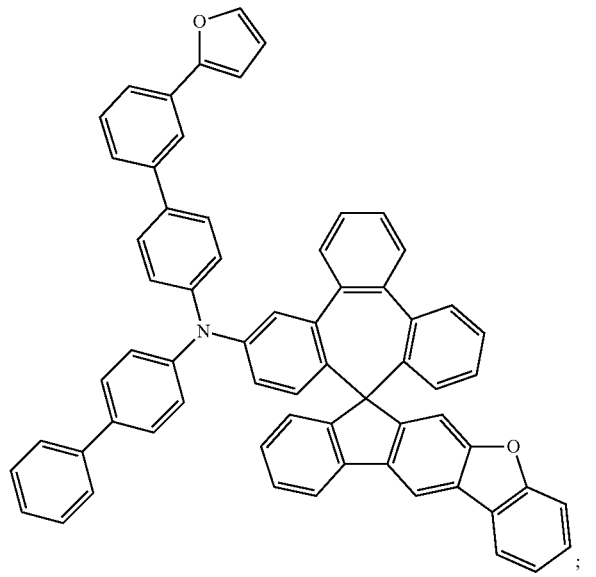
Compound 570
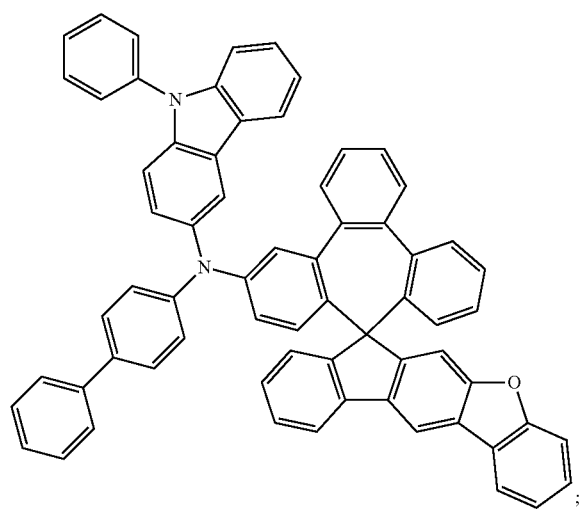
Compound 571
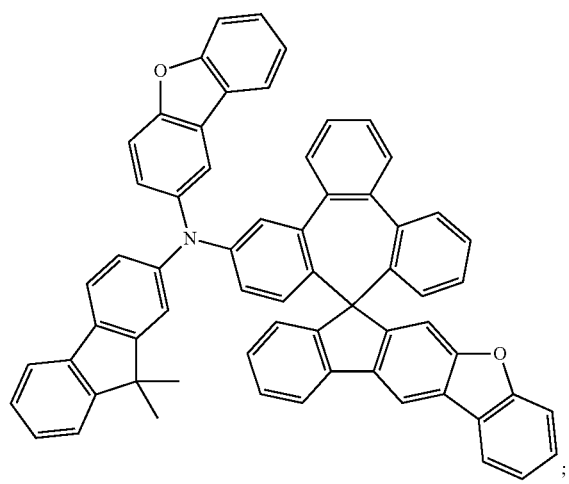
Compound 572
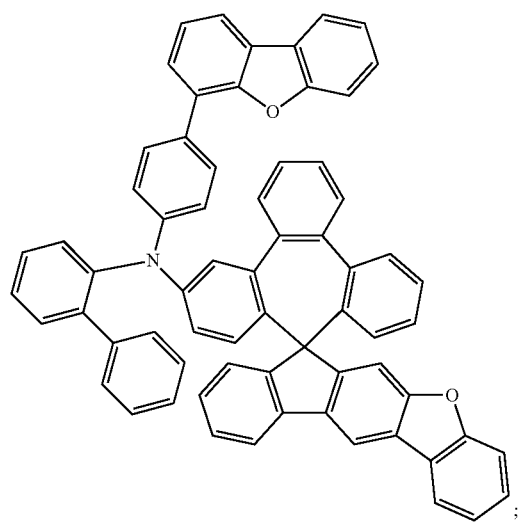
Compound 573
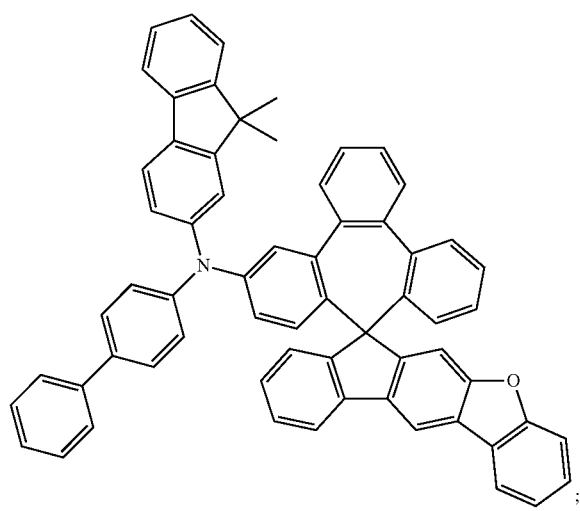

Compound 574
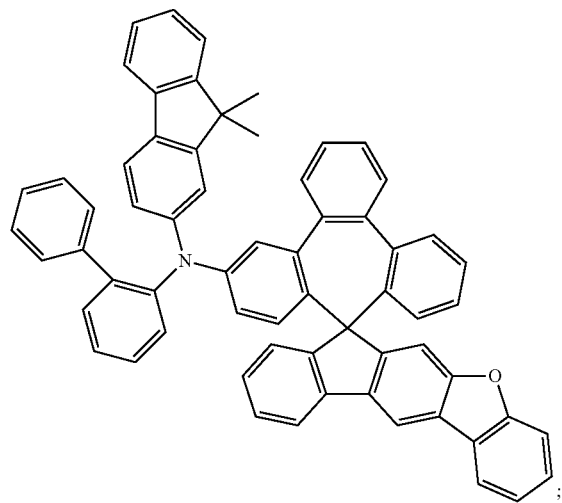
Compound 575
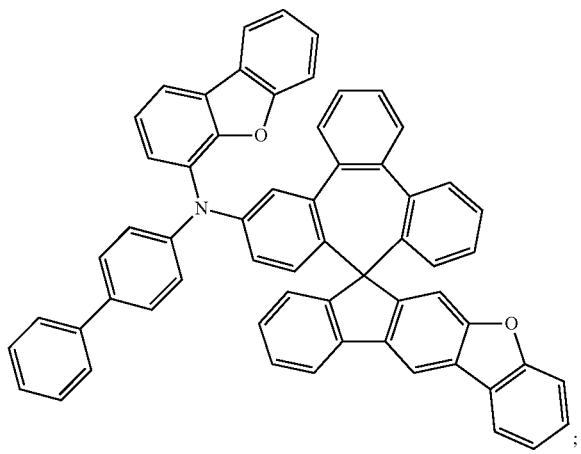
Compound 576
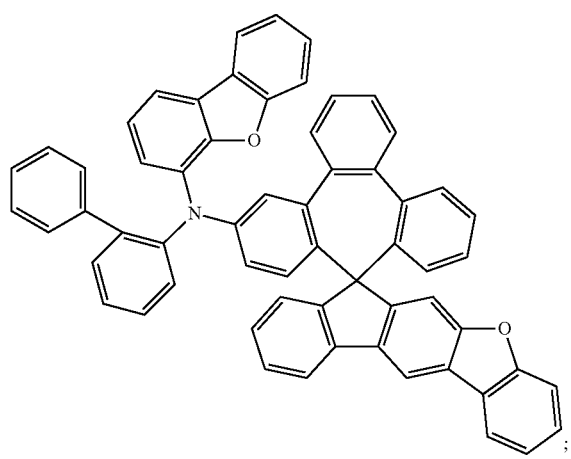
Compound 577
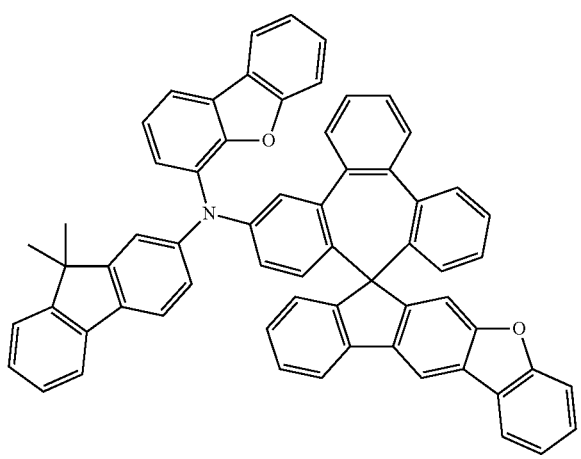
Compound 578
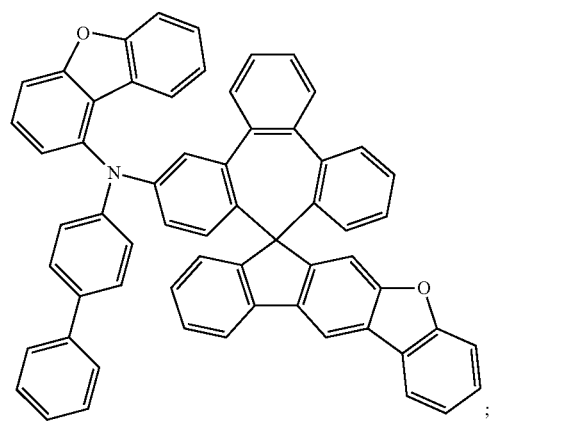
Compound 579
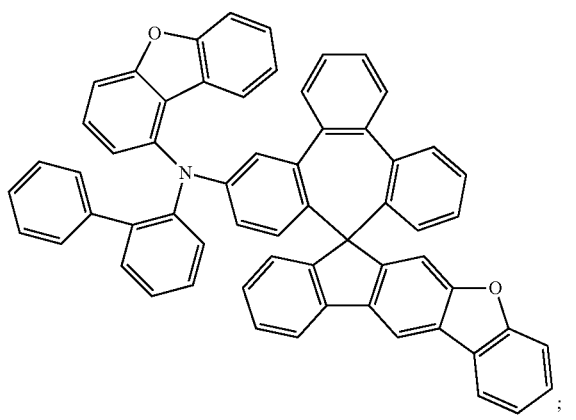

-continued
Compound 580
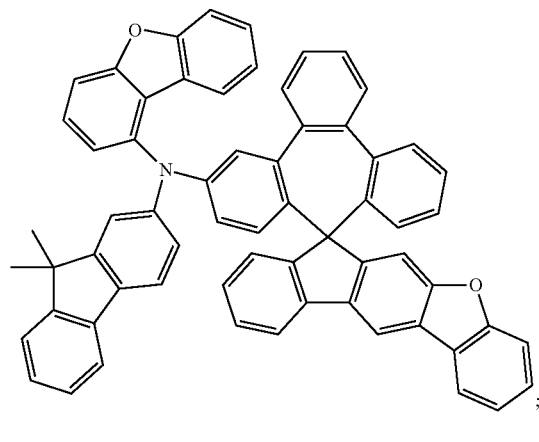
Compound 581
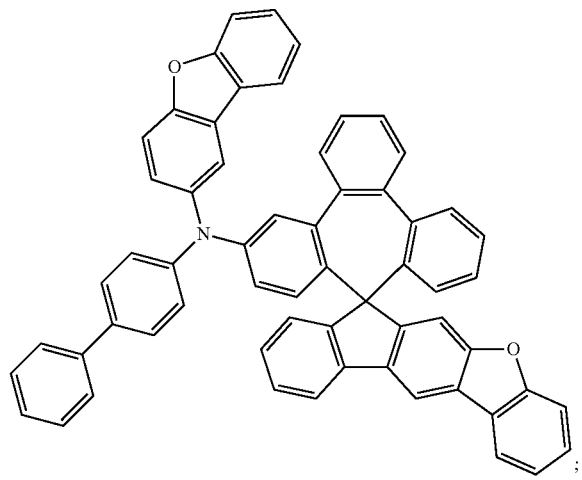
Compound 582
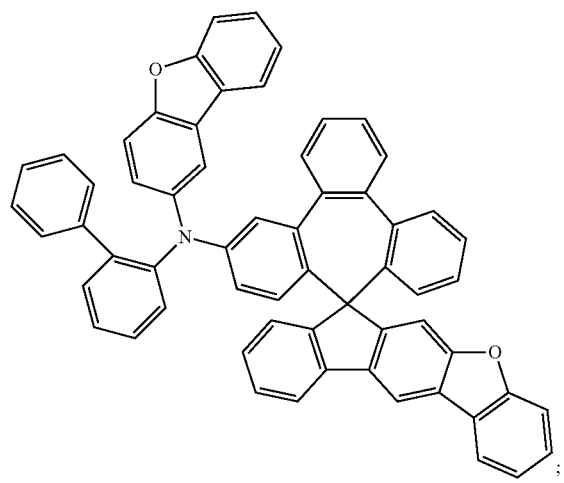
Compound 583
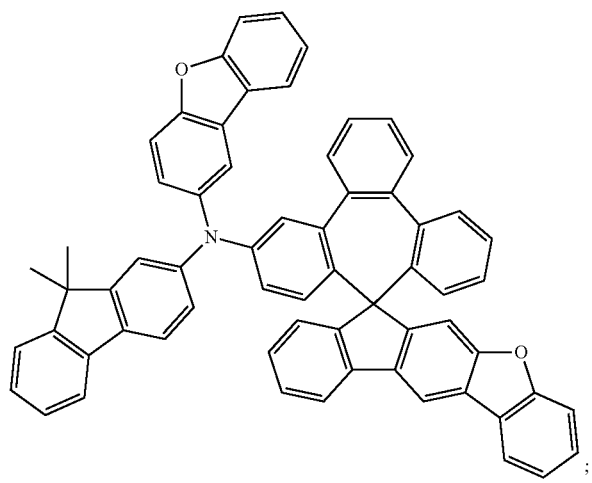
Compound 584
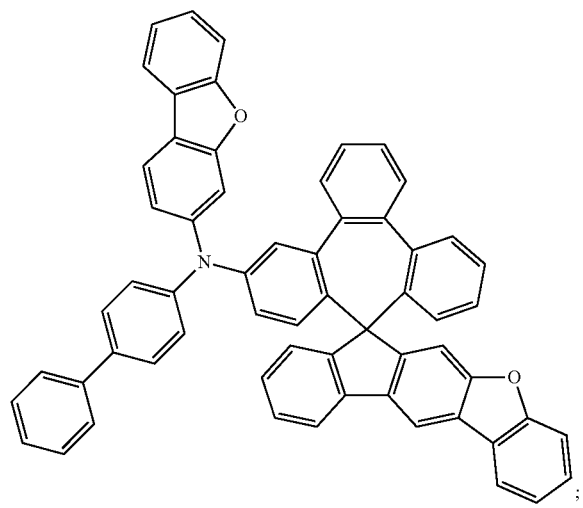
Compound 585
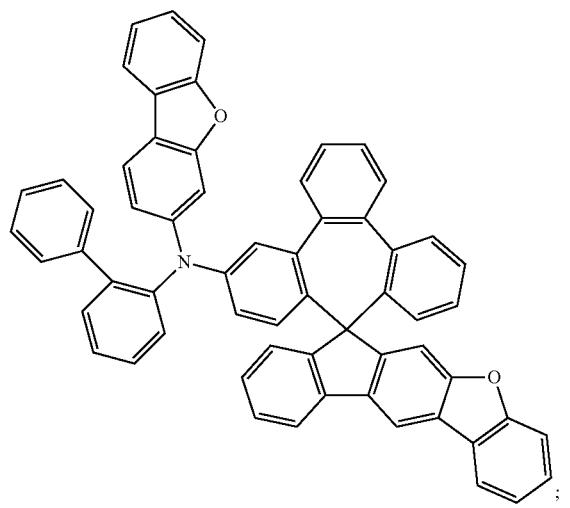

-continued
Compound 586
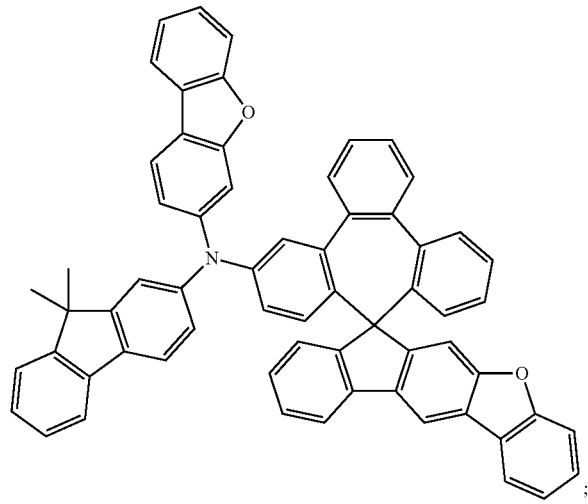
Compound 587
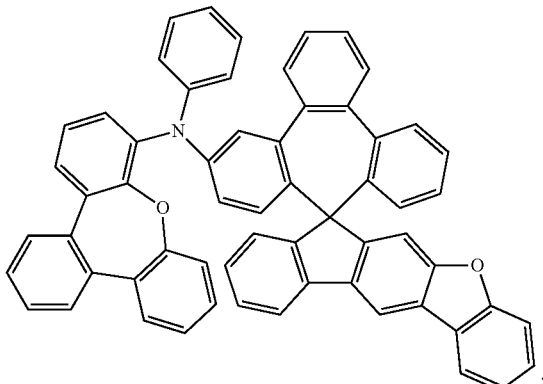
Compound 588
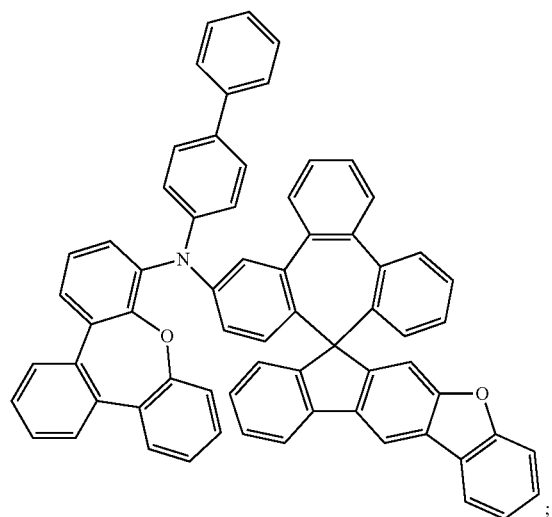
Compound 589
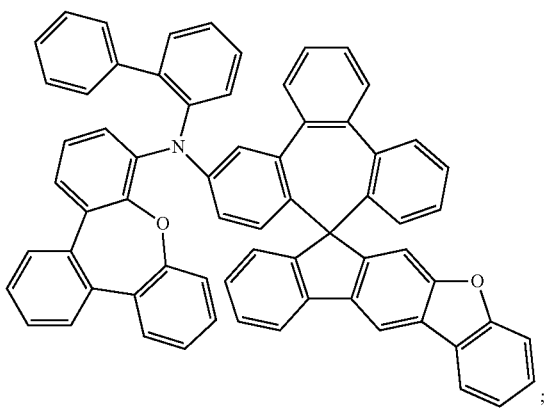
Compound 590
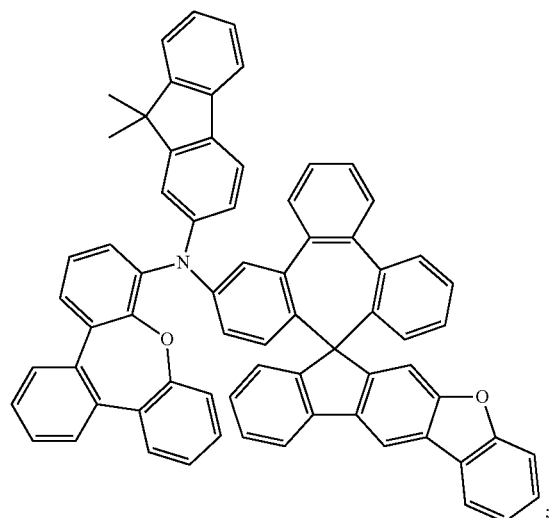
Compound 591
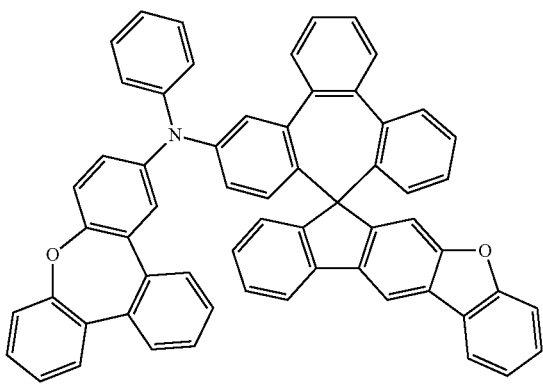

-continued
Compound 592
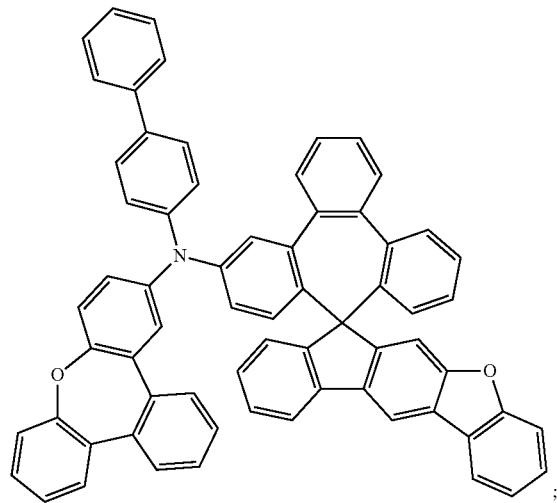
Compound 593
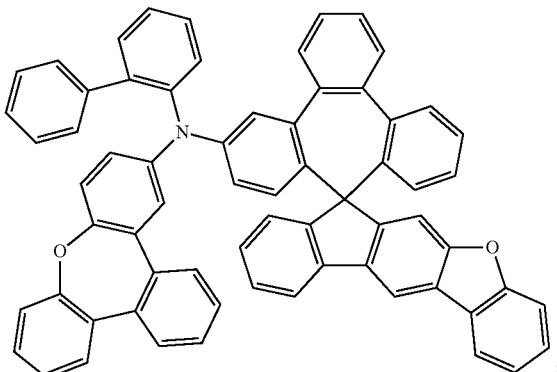
Compound 594
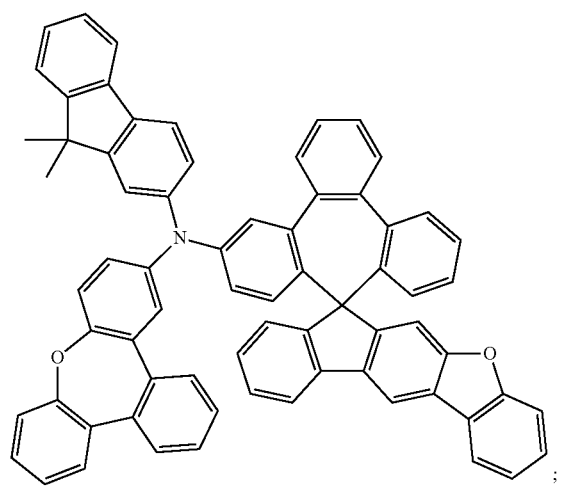
Compound 595
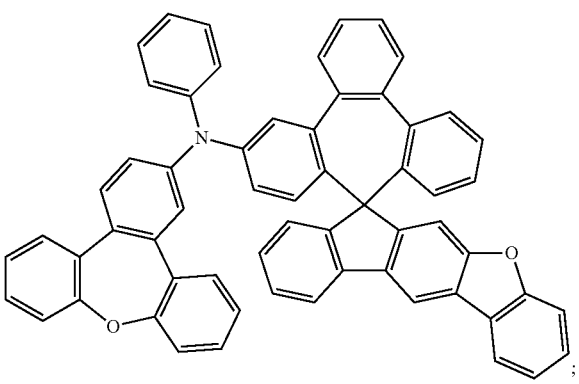
Compound 596
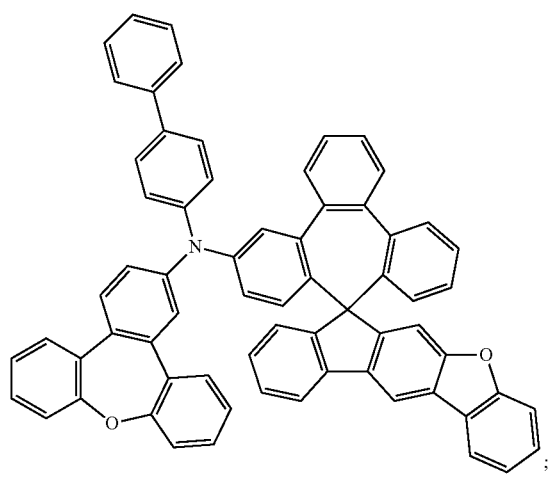
Compound 597
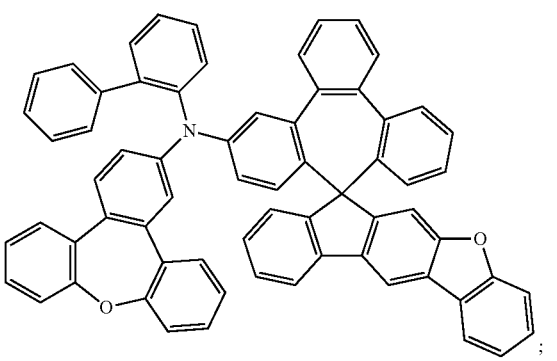

-continued
Compound 598
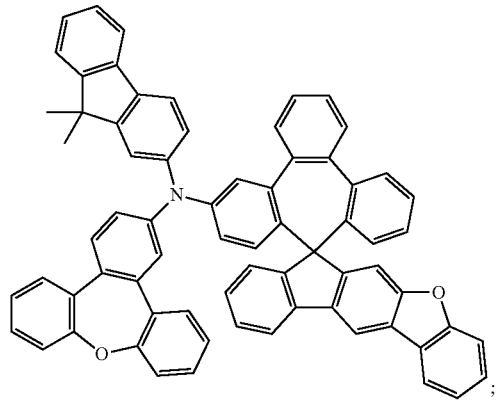
Compound 599
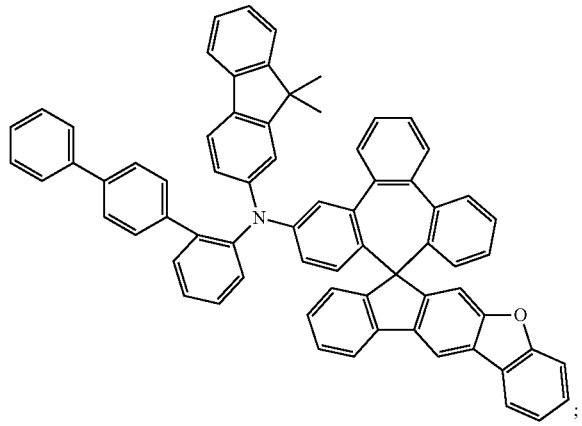
Compound 600
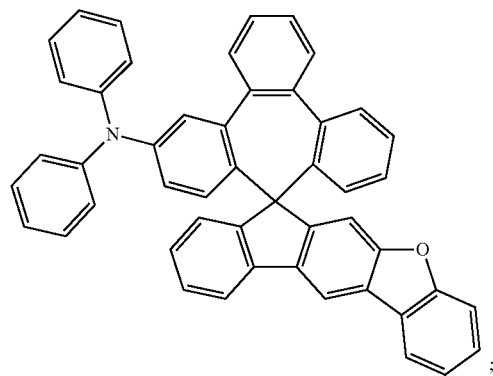
Compound 601
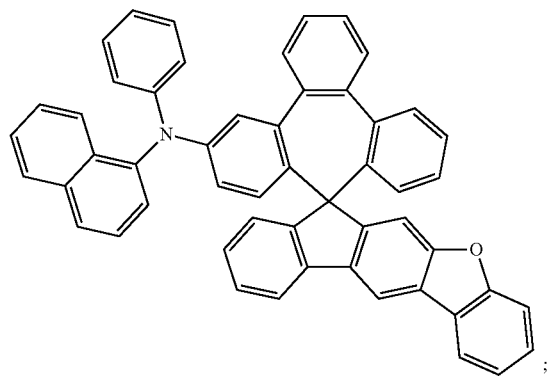
Compound 602
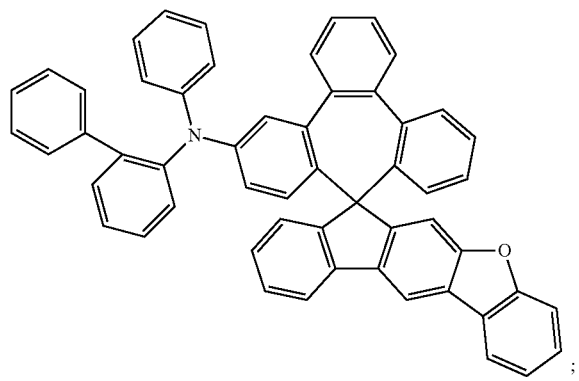
Compound 603
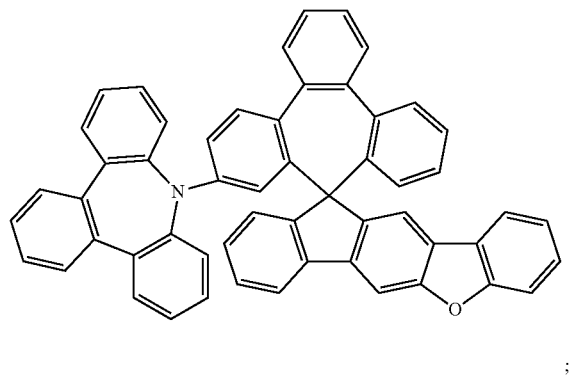

-continued
Compound 604
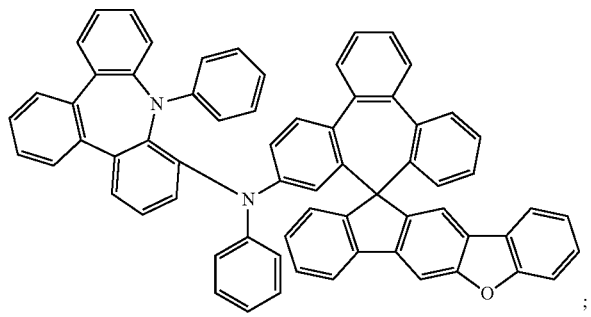
Compound 605
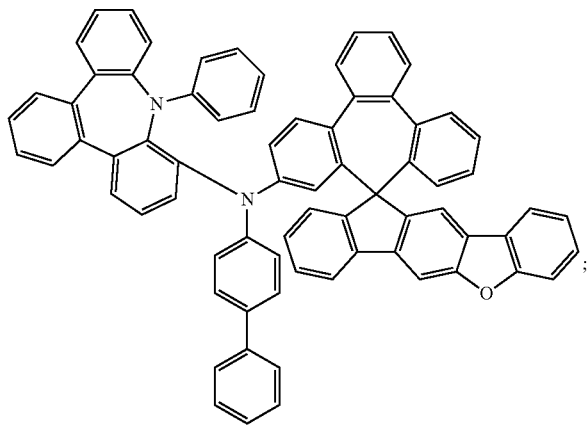
Compound 606
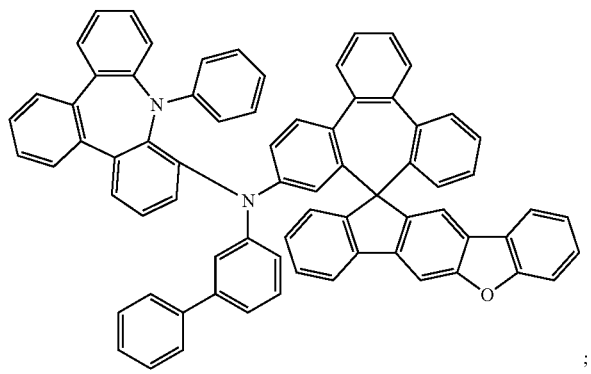
Compound 607
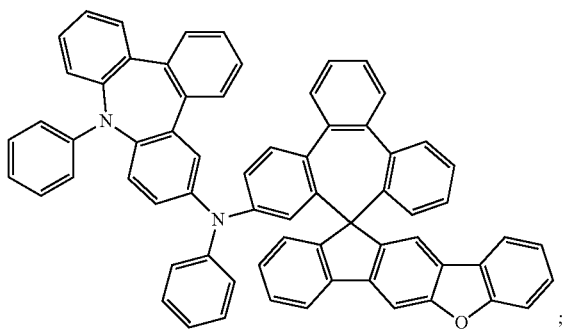
Compound 608
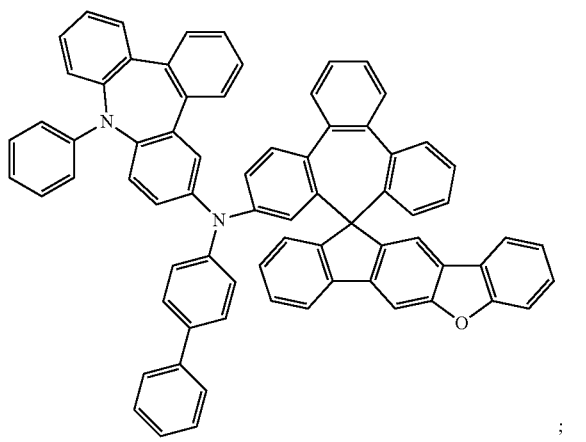
Compound 609
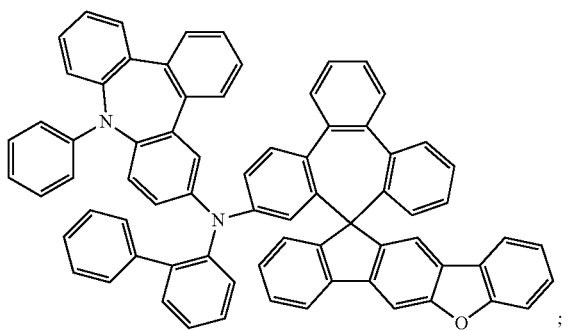

-continued
Compound 610
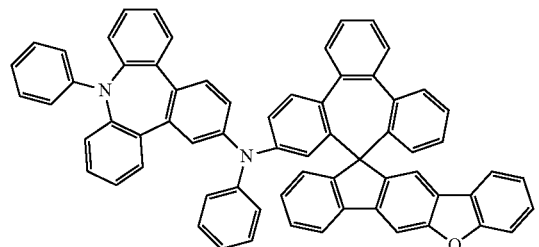
Compound 611
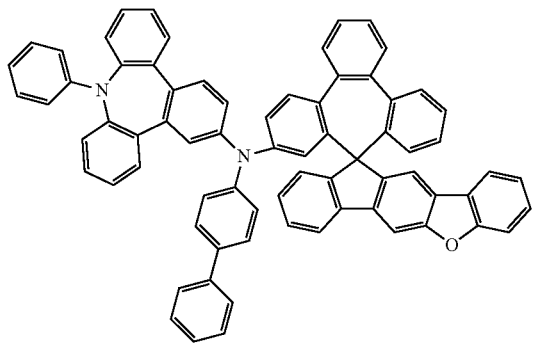
Compound 612
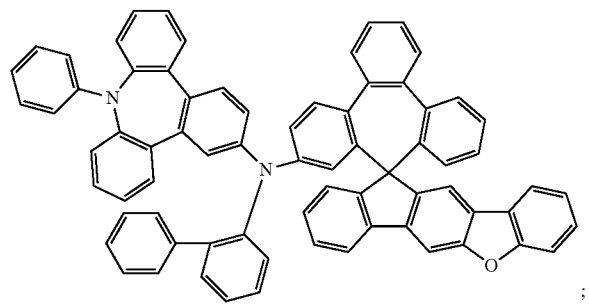
Compound 613
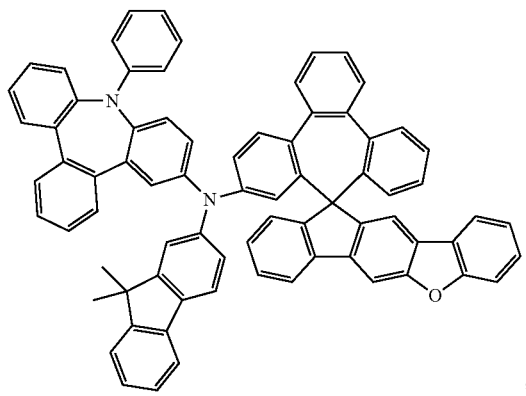
Compound 614
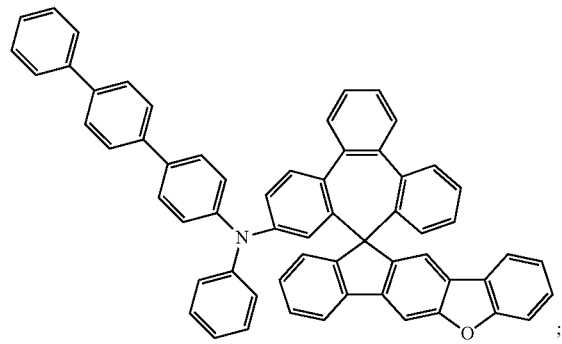
Compound 615
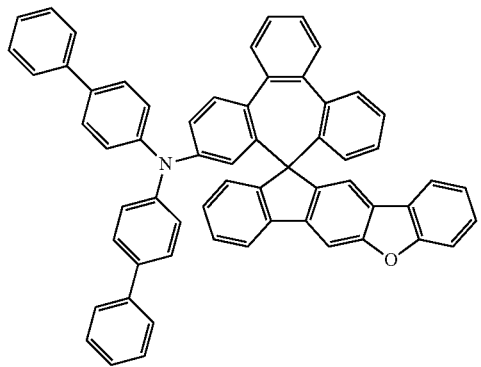
Compound 616
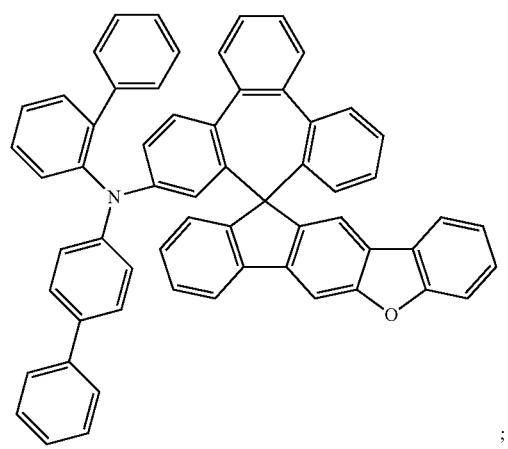
Compound 617
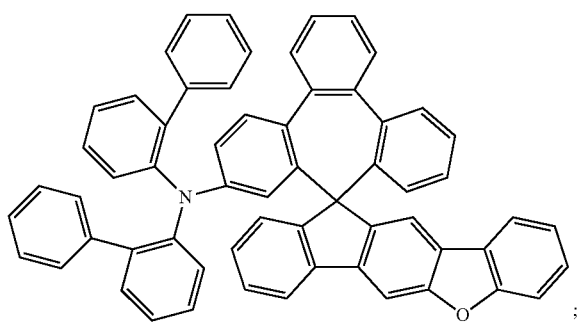

-continued
Compound 618
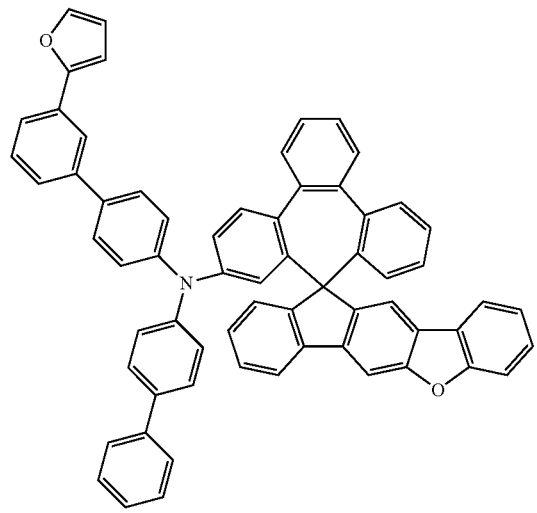
;
Compound 619
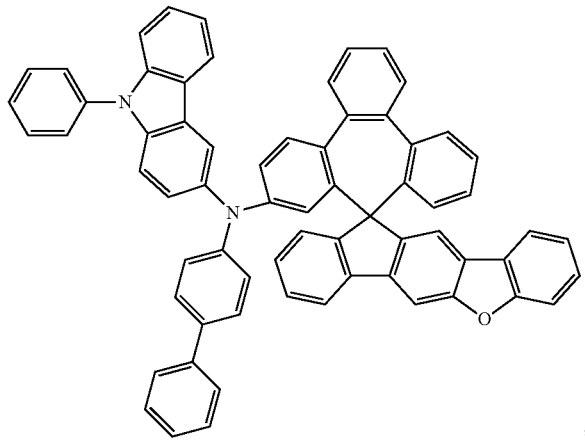
;
Compound 620
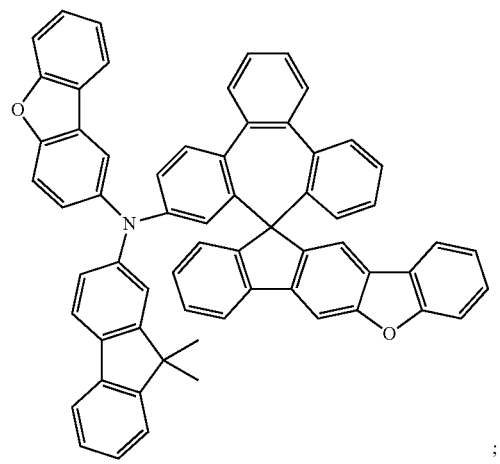
;
Compound 621
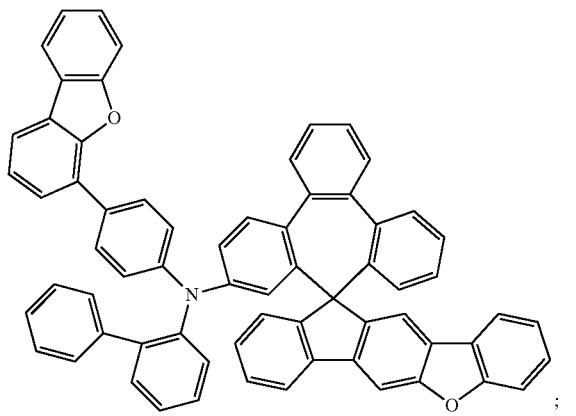
;
Compound 622
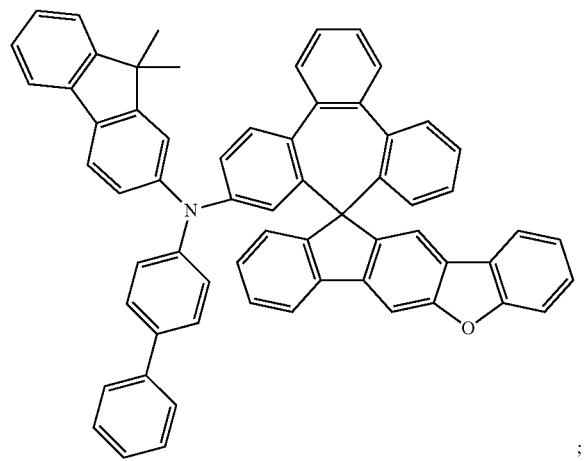
;
Compound 623
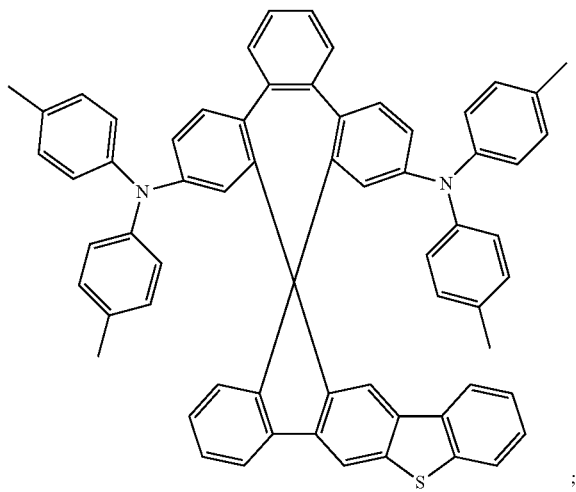
;

-continued
Compound 624
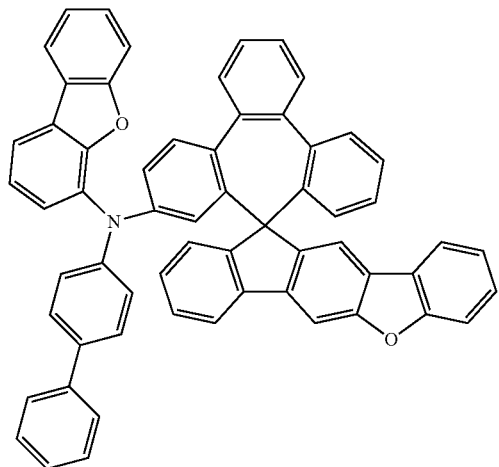
;
Compound 625
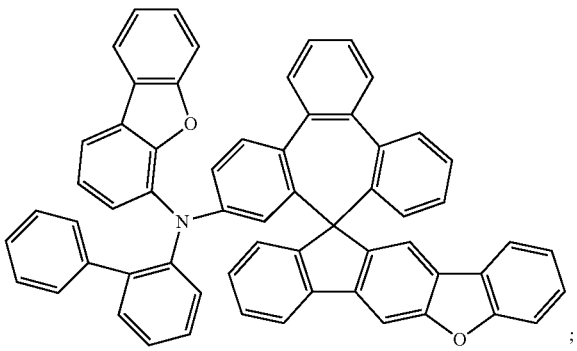
;
Compound 626
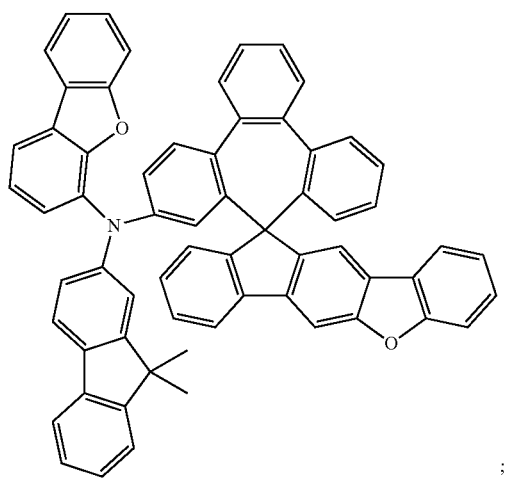
;
Compound 627
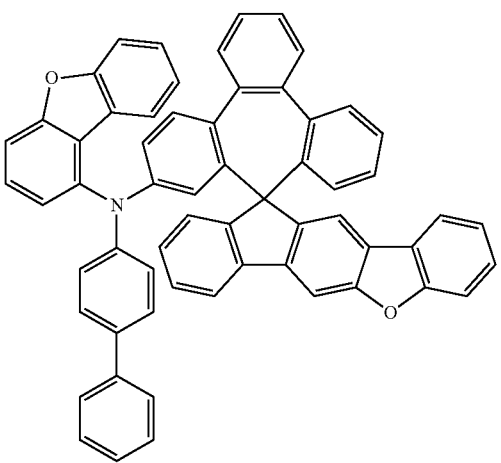
;
Compound 628
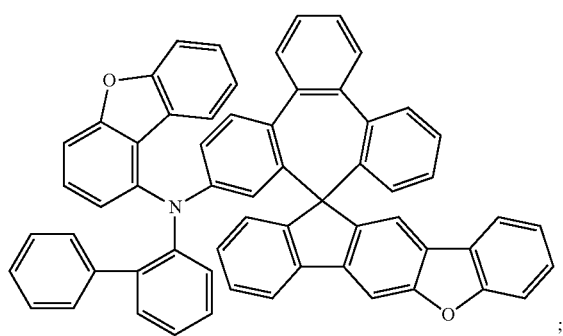
;
Compound 629
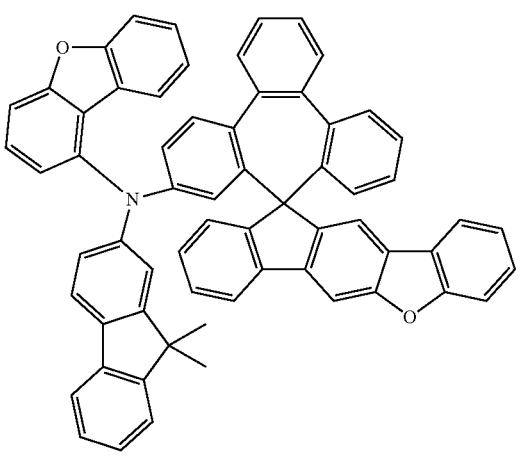
;

Compound 630
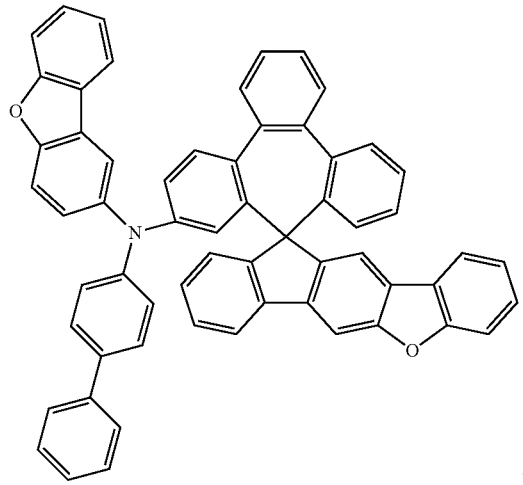
;
Compound 631
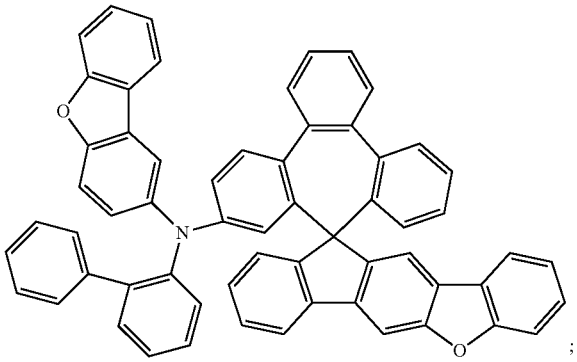
;
Compound 632
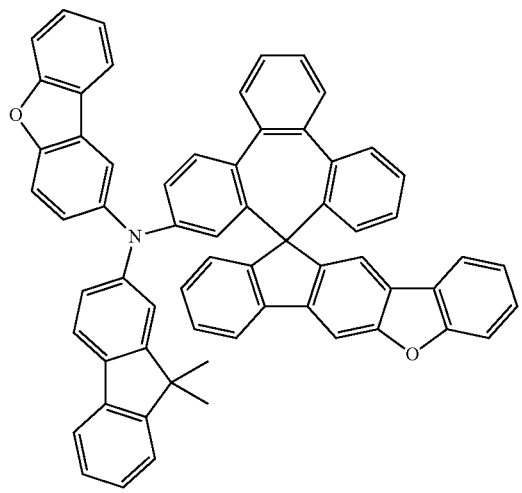
;
Compound 633
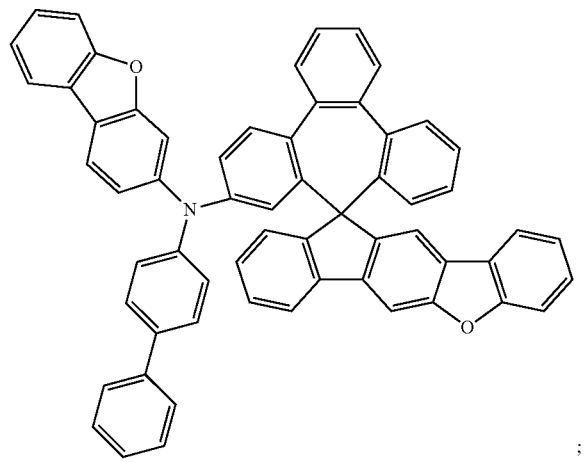
;
Compound 634
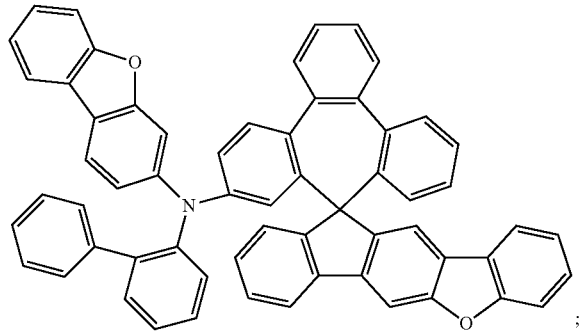
;
Compound 635
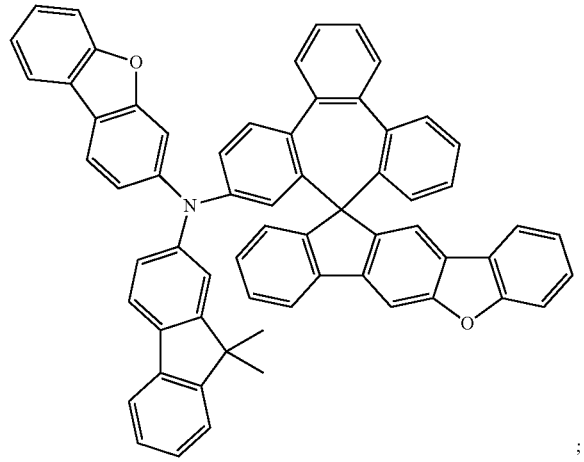
;

-continued
Compound 636
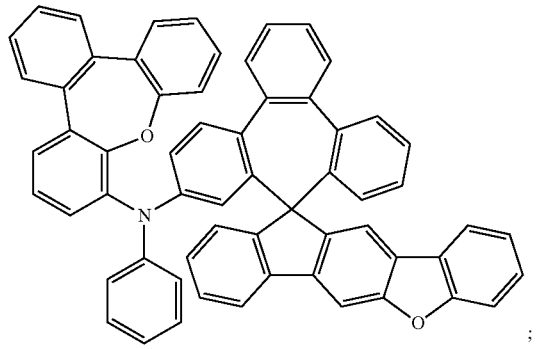
Compound 637
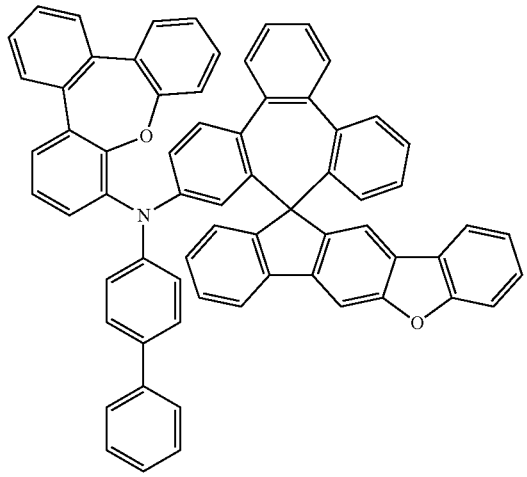
Compound 638
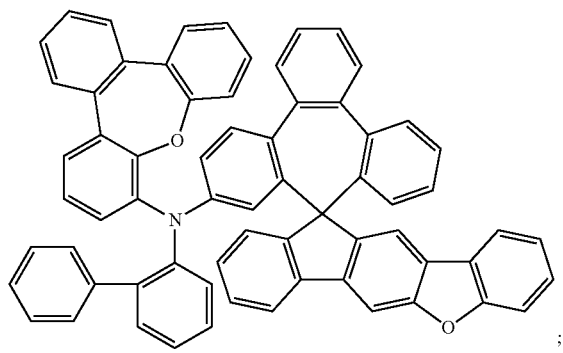
Compound 639
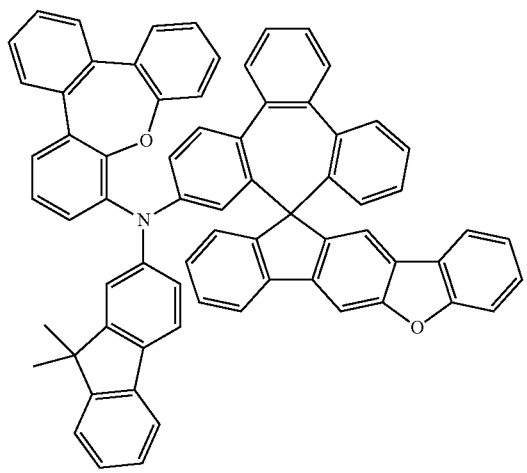
Compound 640
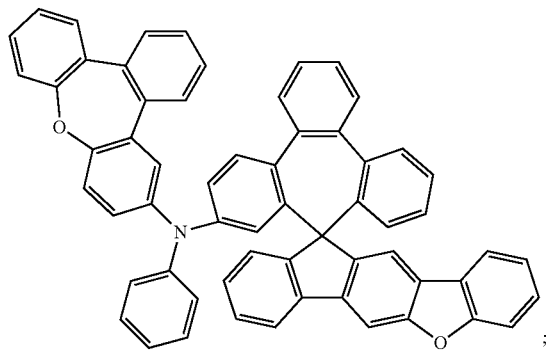
Compound 641
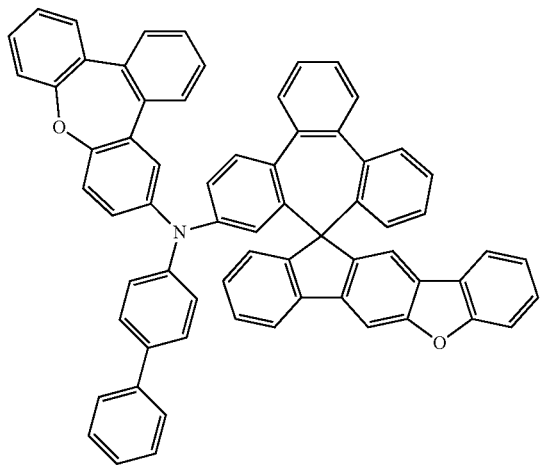

-continued
Compound 642
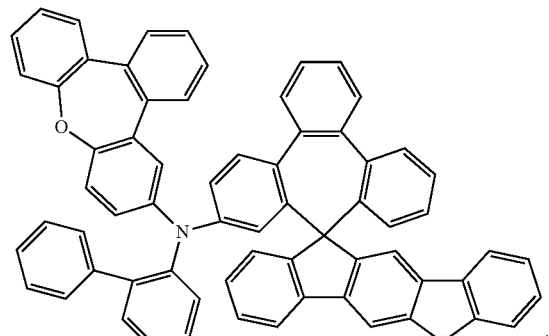
Compound 643
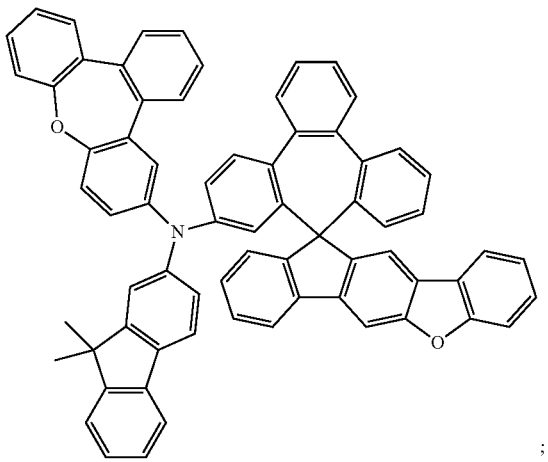
Compound 644
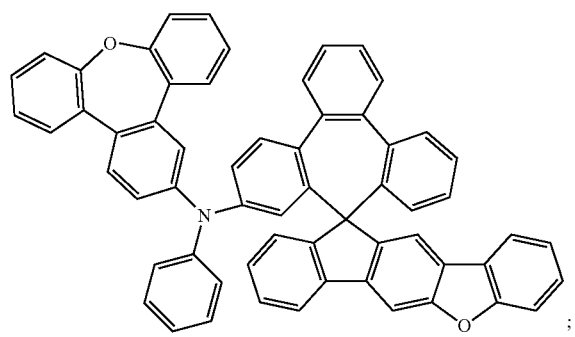
Compound 645
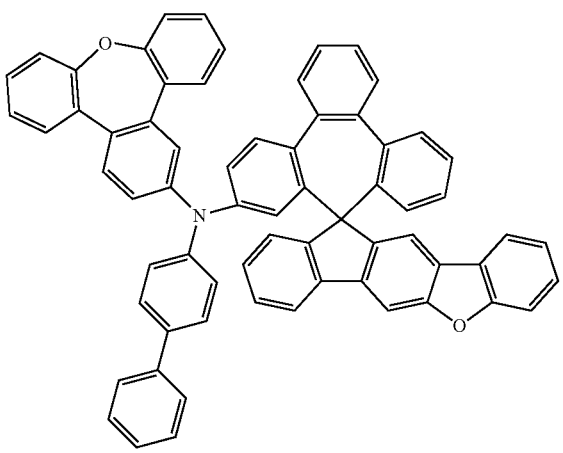
Compound 646
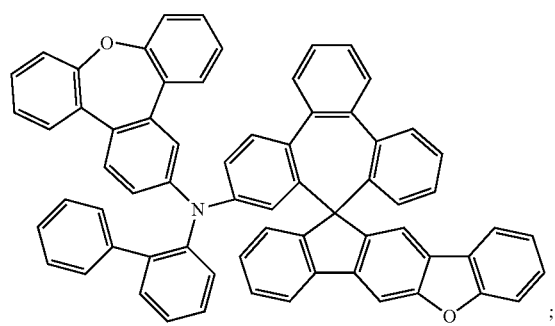
Compound 647
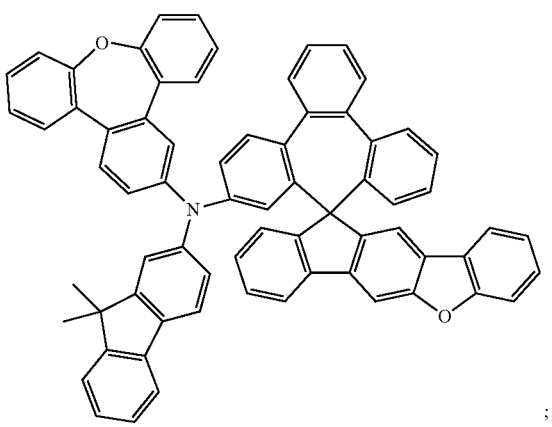

-continued
Compound 648
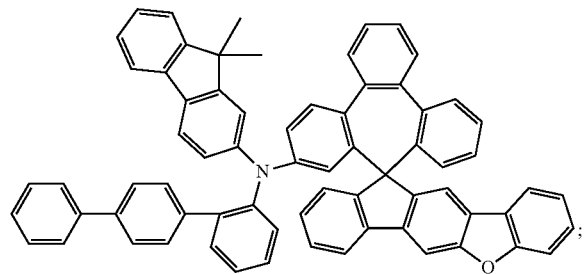
Compound 649
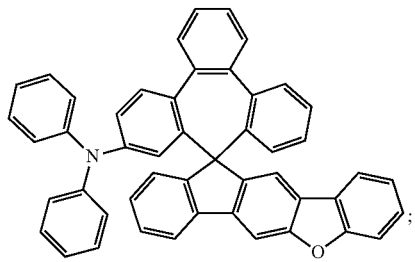
Compound 650
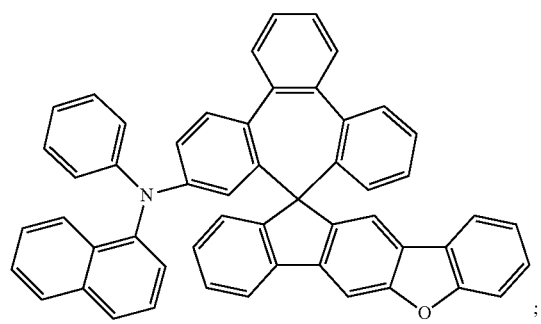
Compound 651
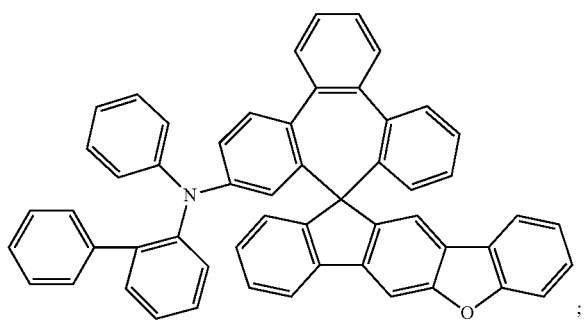
Compound 652
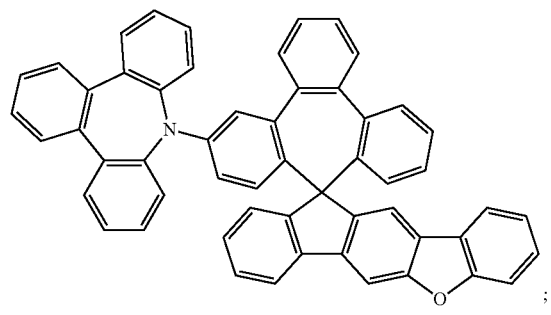
Compound 653
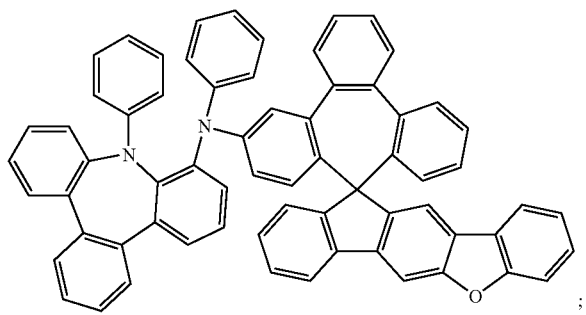
Compound 654
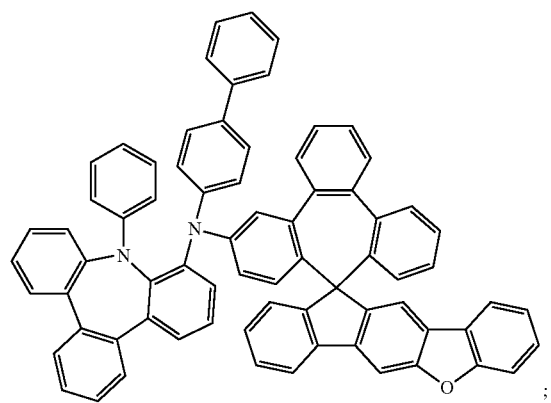
Compound 655
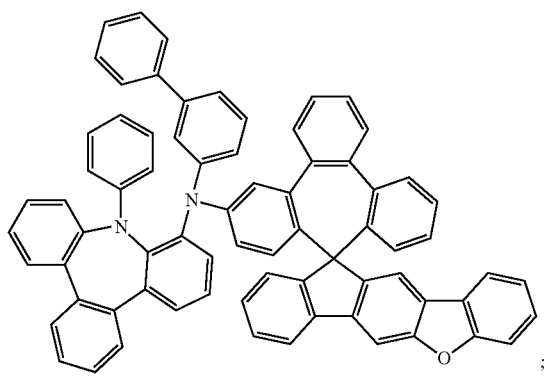

-continued
Compound 656
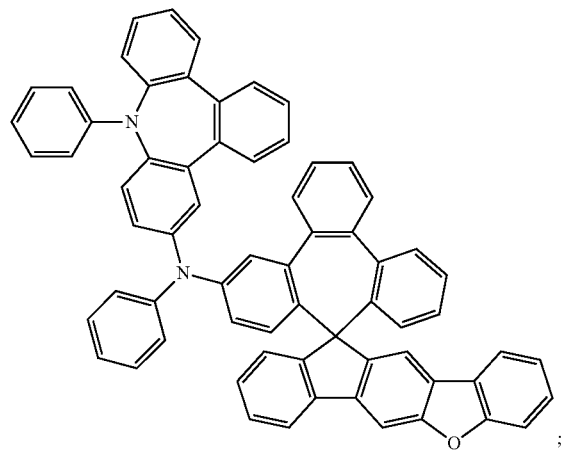
Compound 657
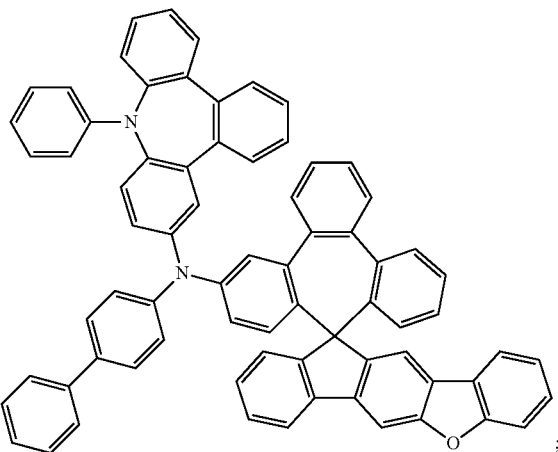
Compound 658
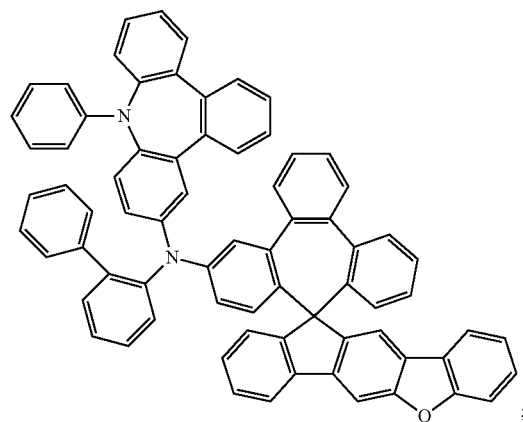
Compound 659
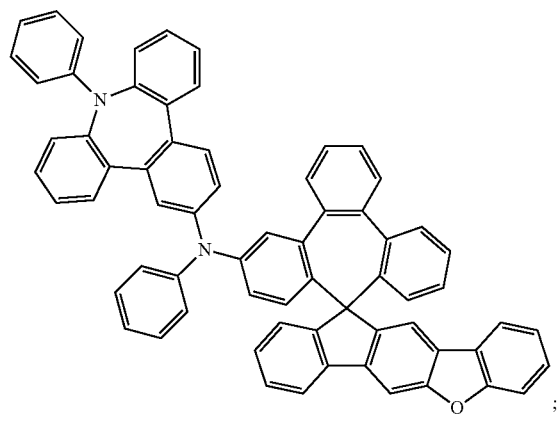
Compound 660
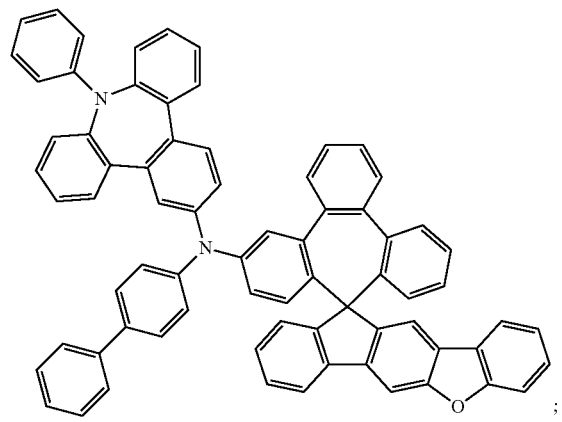
Compound 661
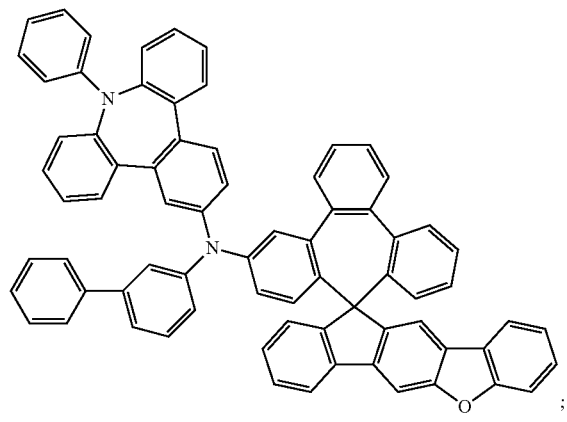

-continued
Compound 662
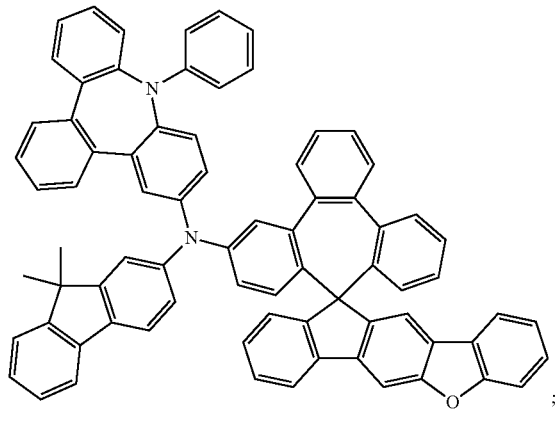
Compound 663
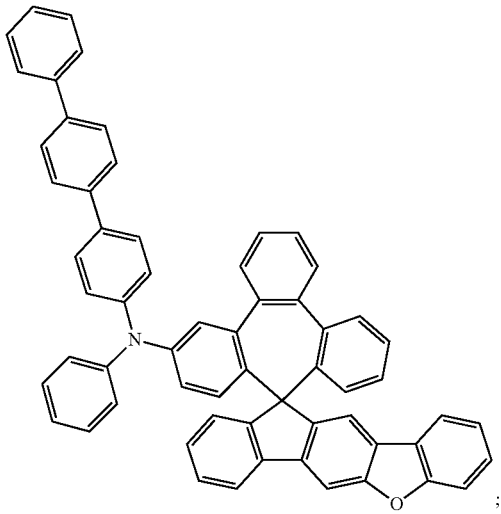
Compound 664
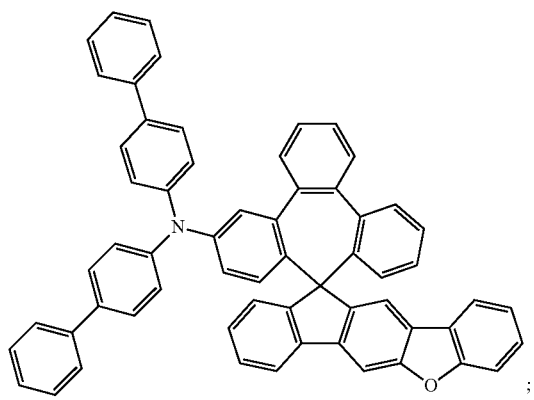
Compound 665
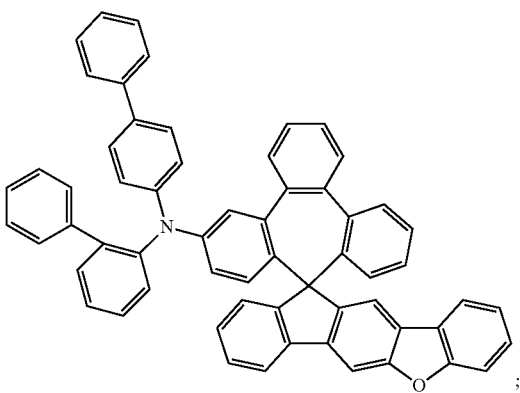
Compound 666
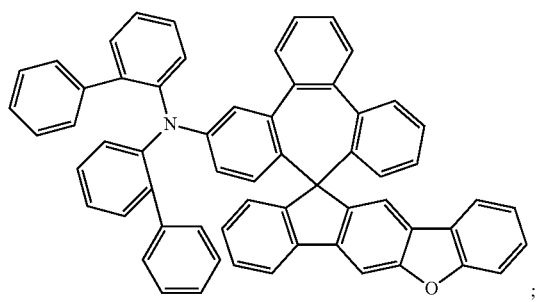
Compound 667
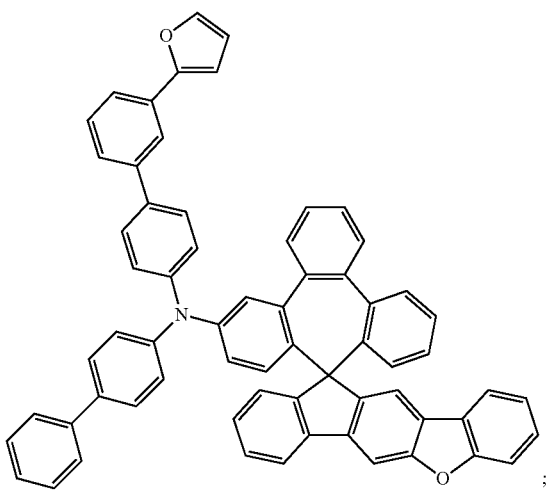

Compound 668
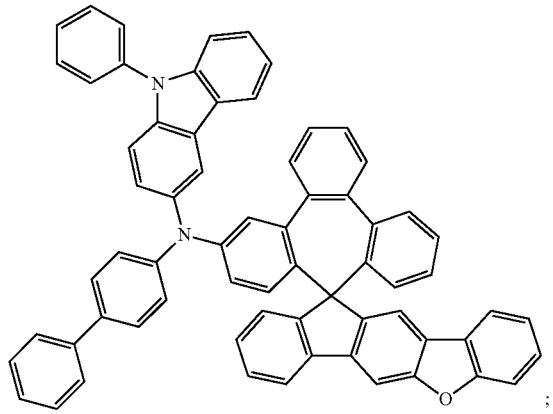
Compound 669
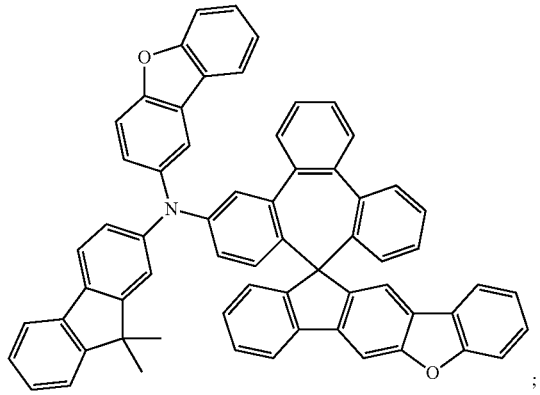
Compound 670
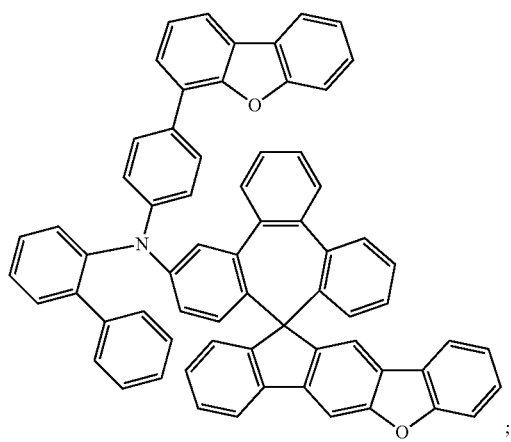
Compound 671
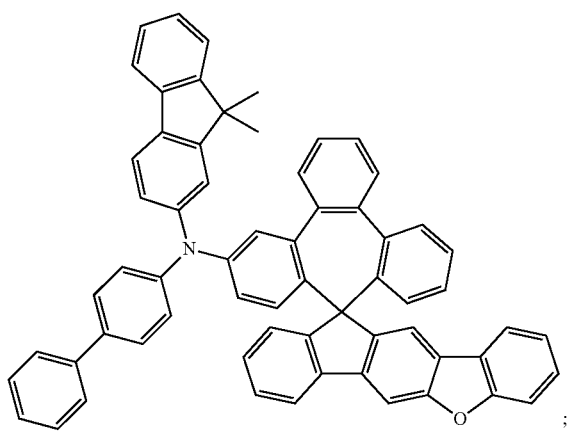
Compound 672
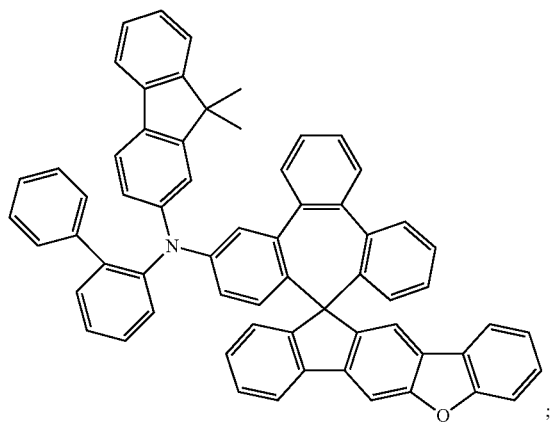
Compound 673
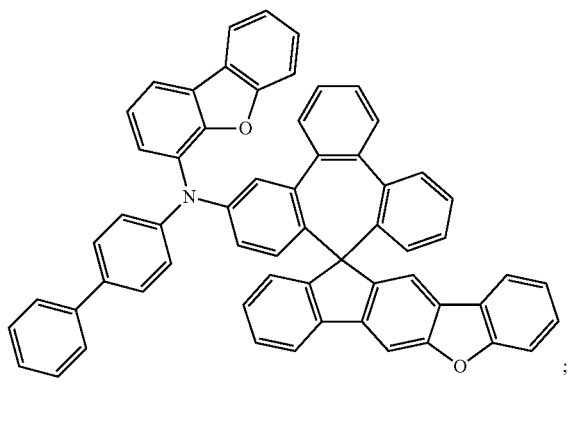

-continued
Compound 674
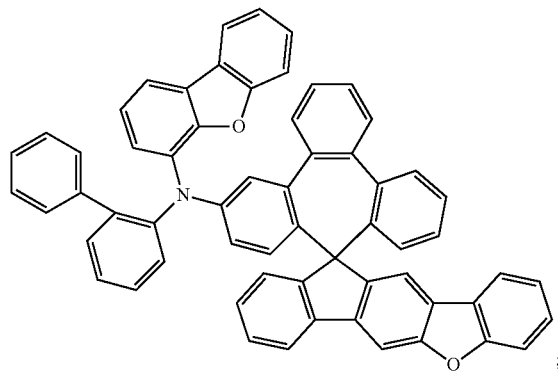
Compound 675
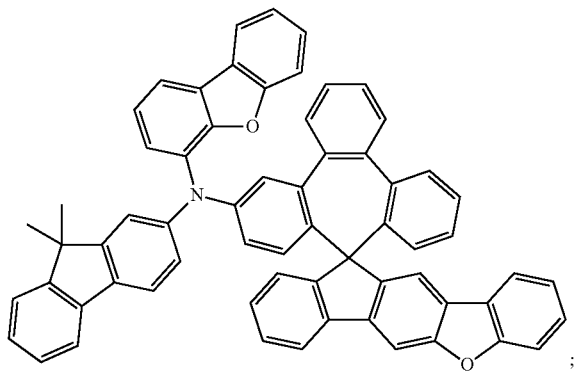
Compound 676
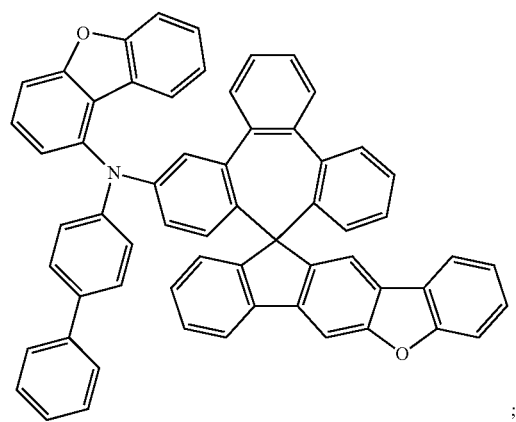
Compound 677
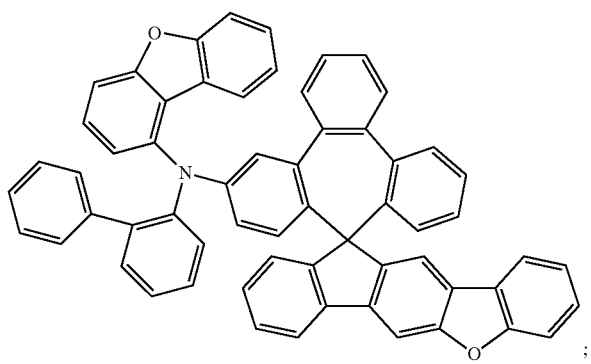
Compound 678
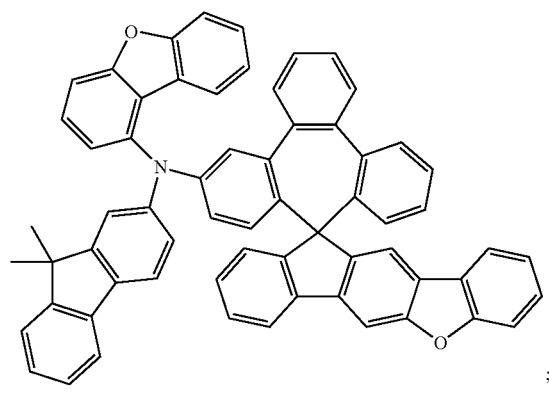
Compound 679
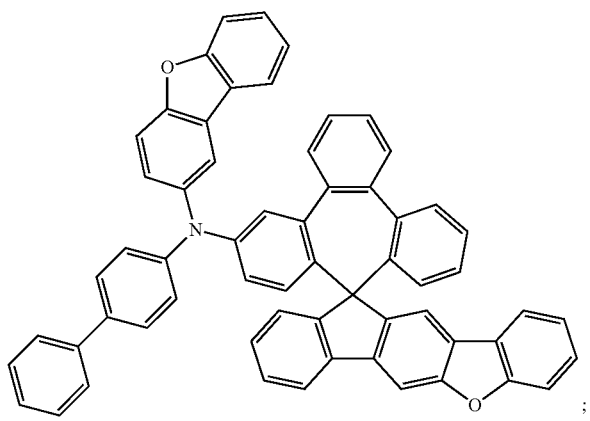

-continued
Compound 680
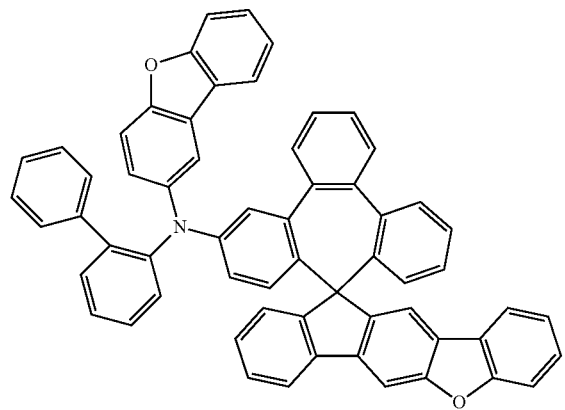
Compound 681
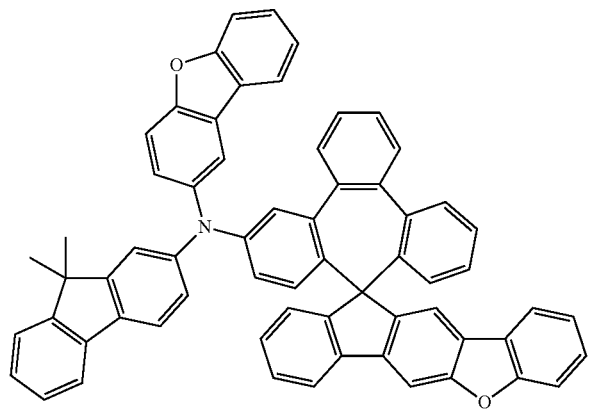
Compound 682
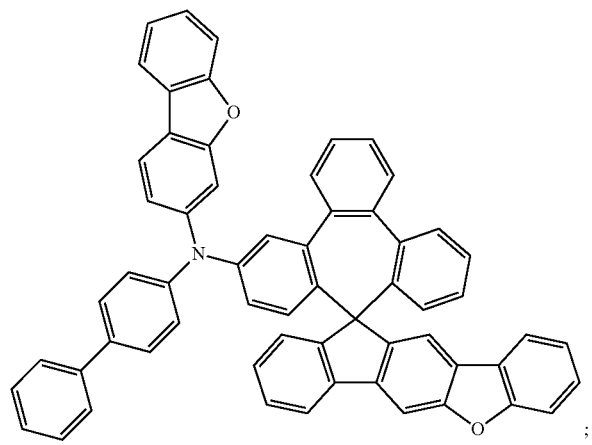
Compound 683
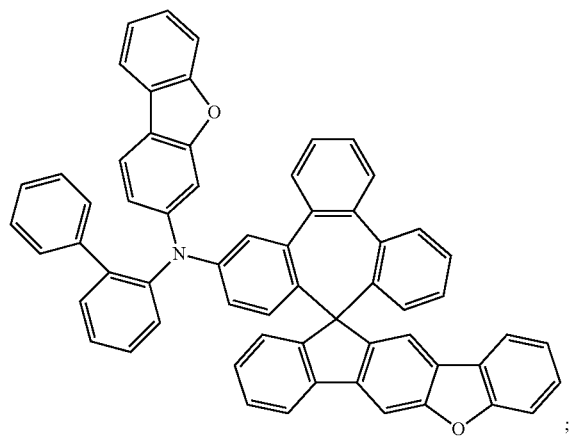
Compound 684
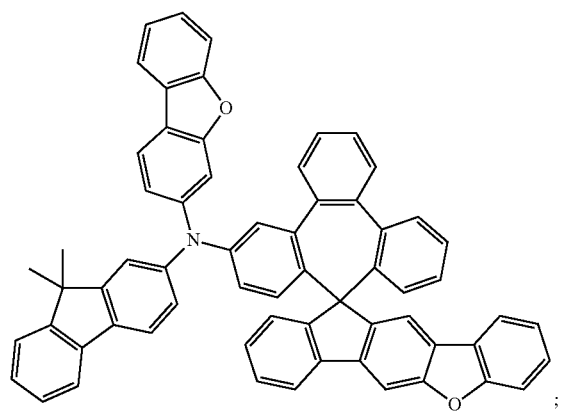
Compound 685
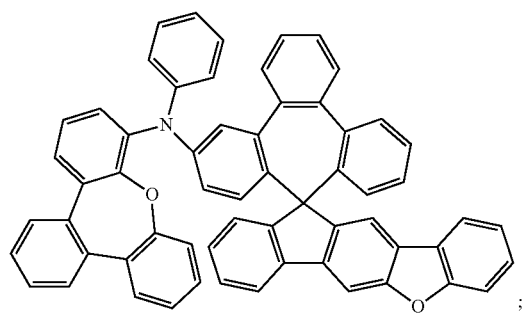

-continued
Compound 686
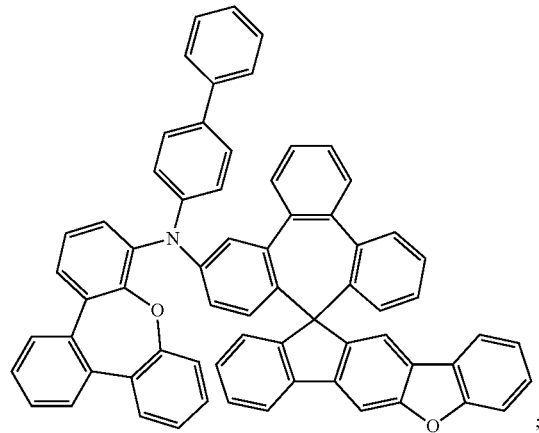
Compound 687
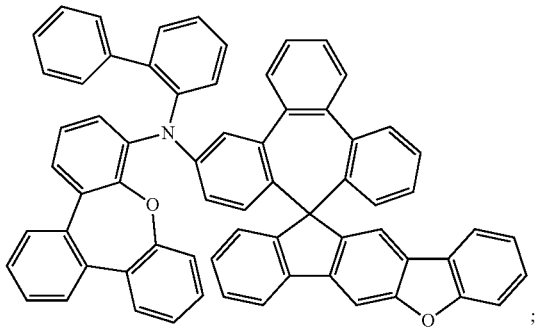
Compound 688
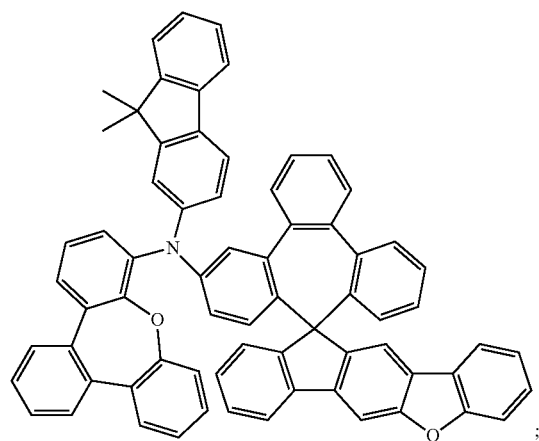
Compound 689
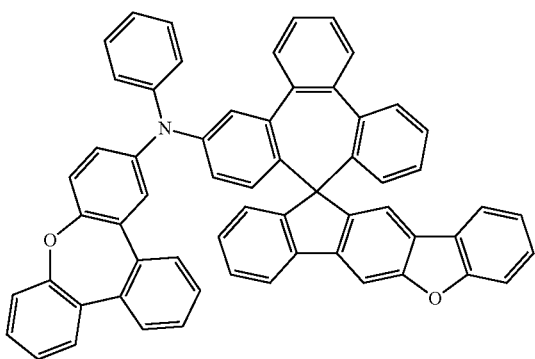
Compound 690
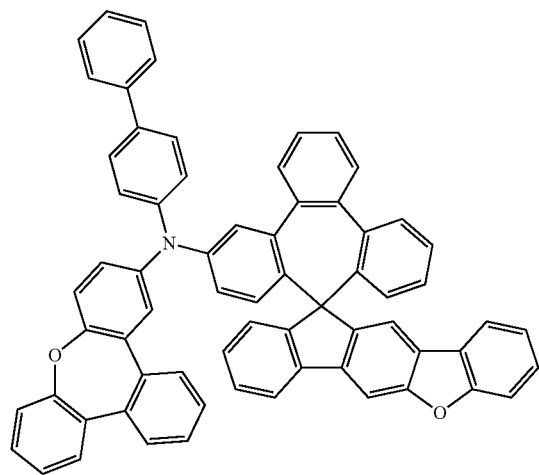
Compound 691
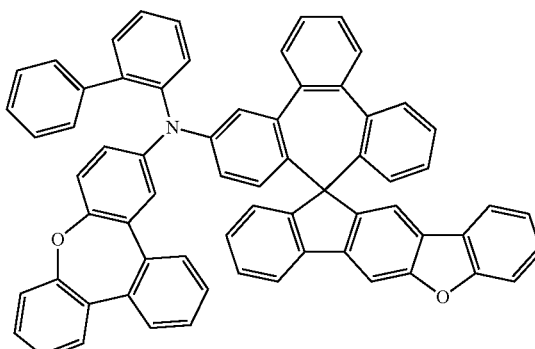

-continued
Compound 692
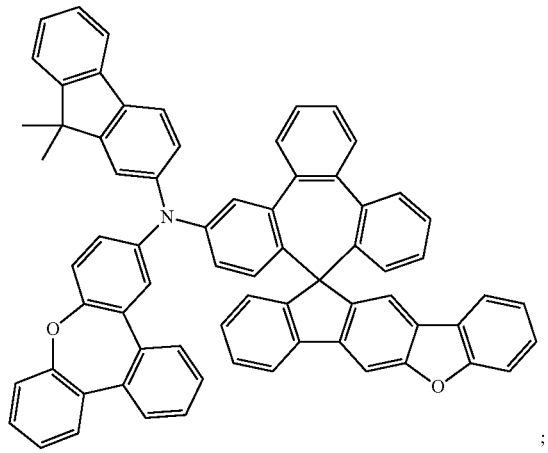
Compound 693
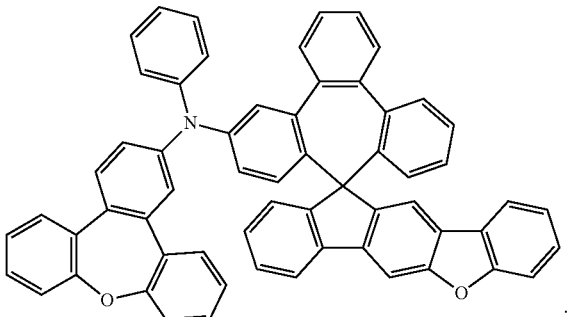
;
Compound 694
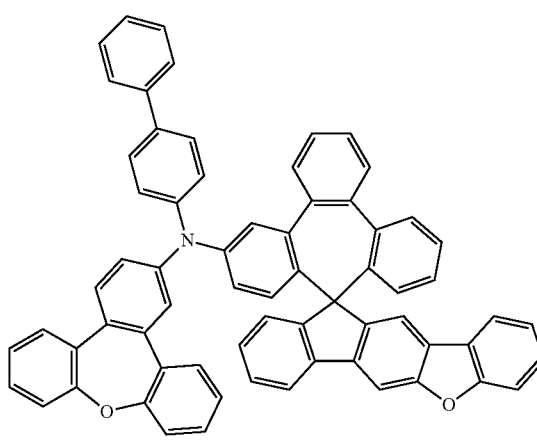
Compound 695
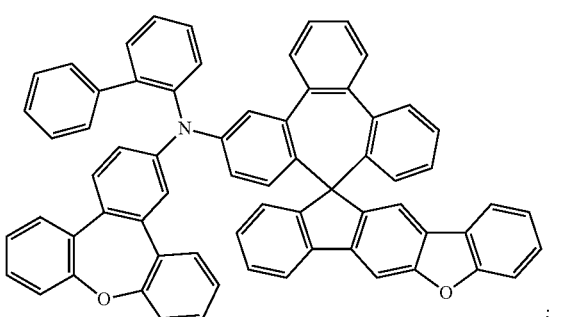
;
Compound 696
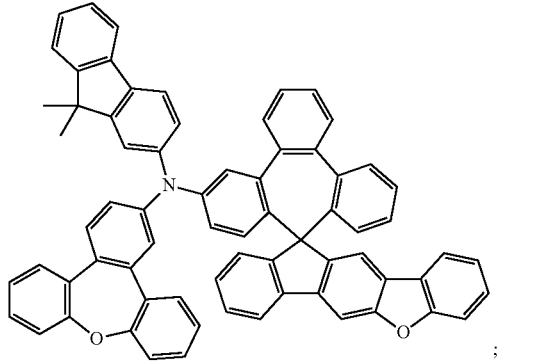
Compound 697
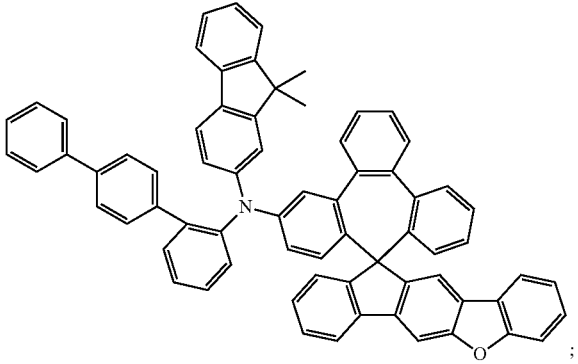
;
Compound 698
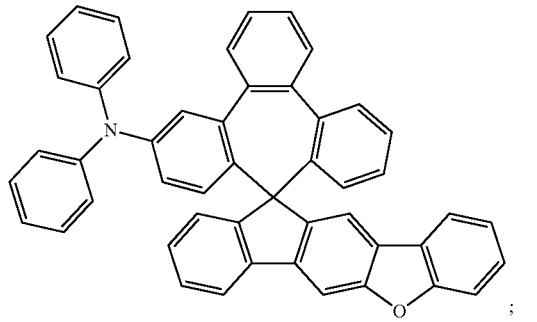
Compound 699
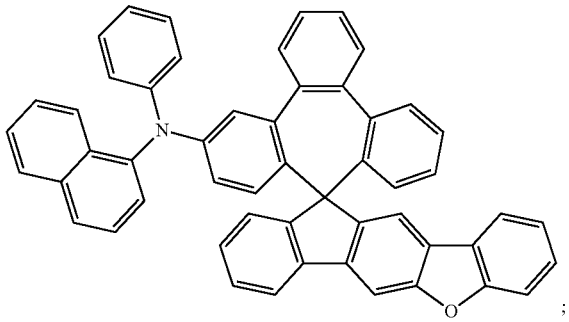
;

Compound 700
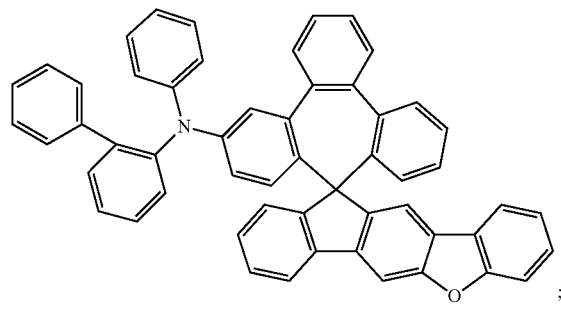
Compound 701
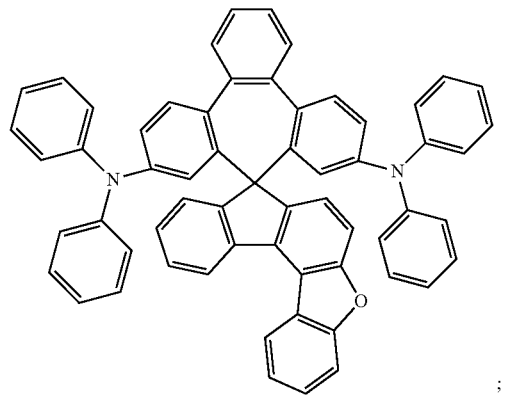
Compound 702
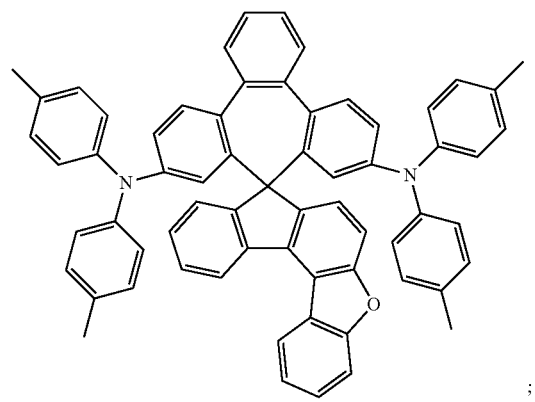
Compound 703
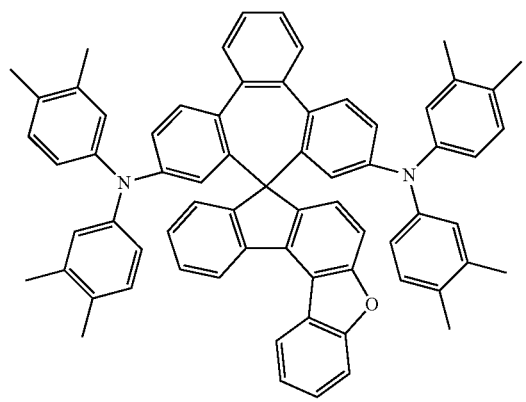
Compound 704
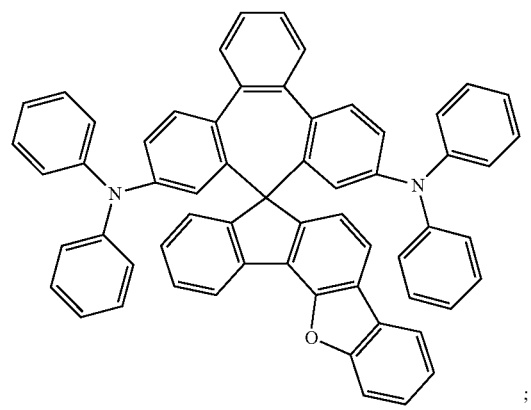
Compound 705
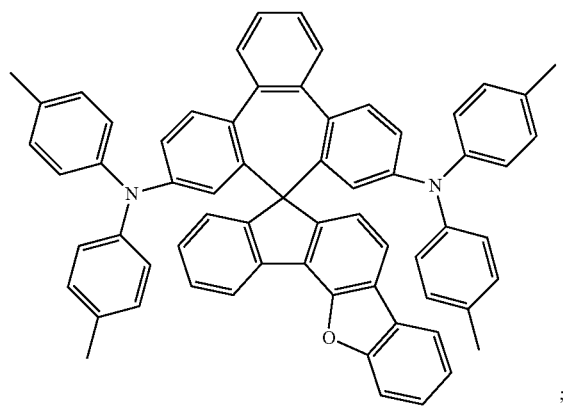

Compound 706
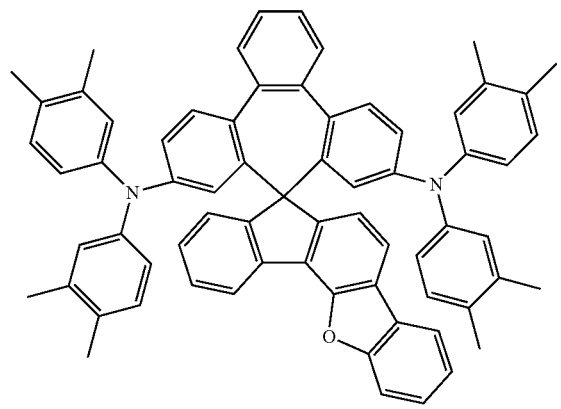
Compound 707
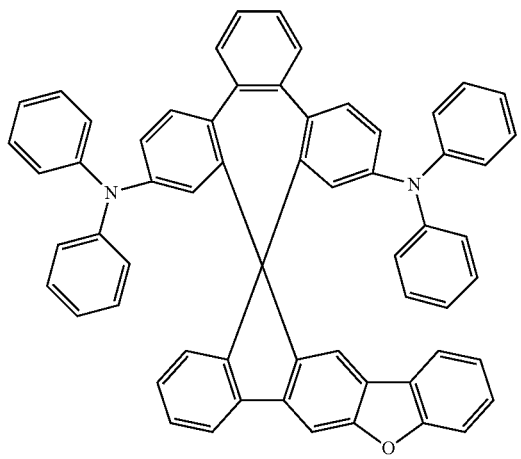
Compound 708
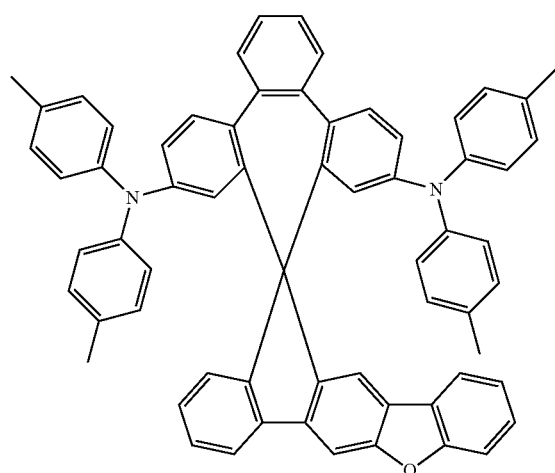
Compound 709
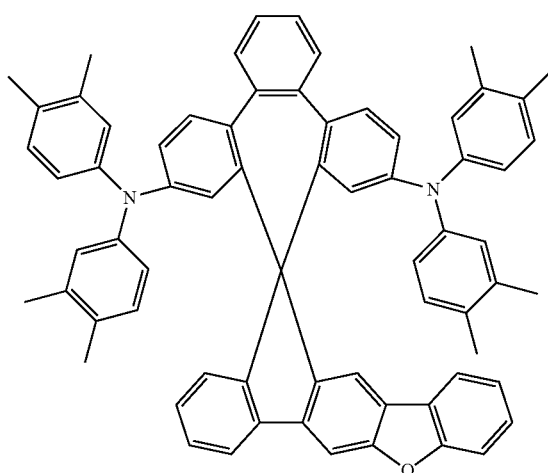
Compound 710
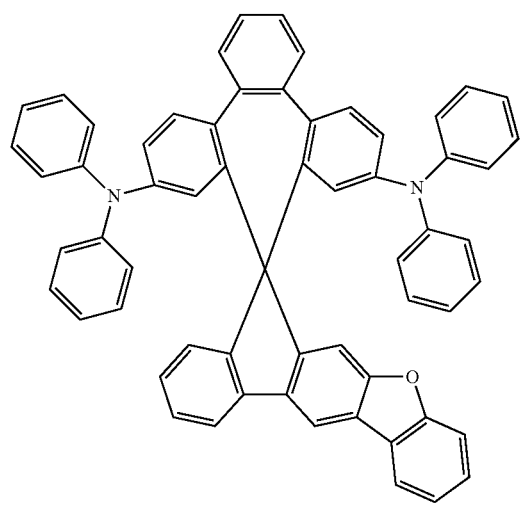
Compound 711
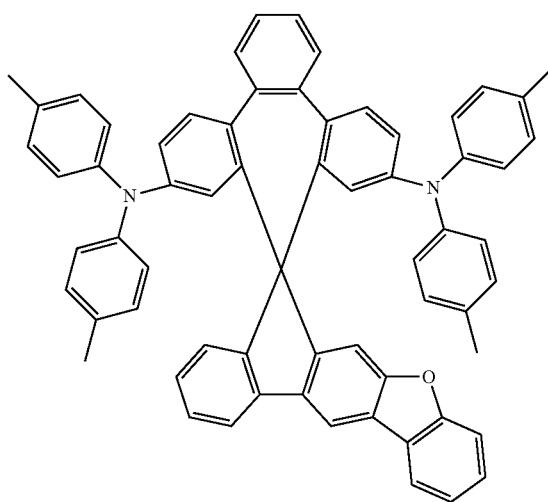

Compound 712
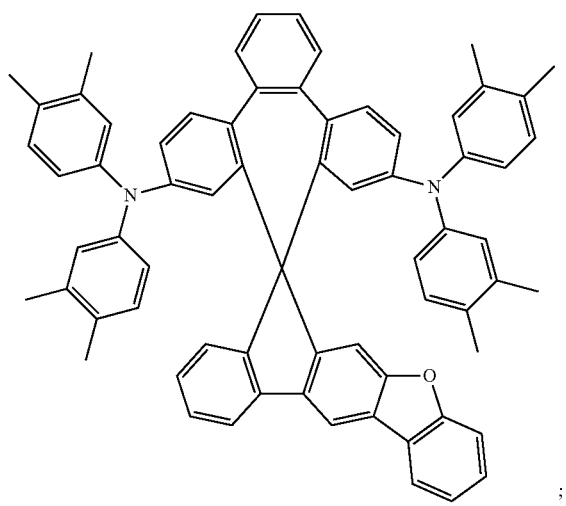
Compound 713
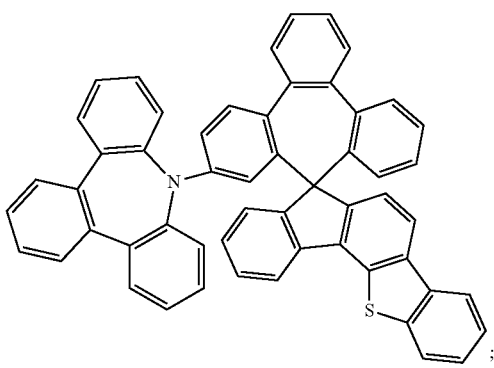
Compound 714
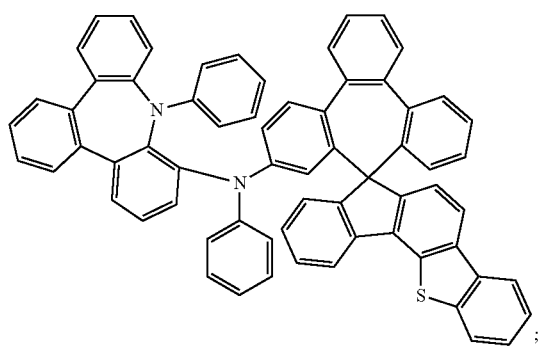
Compound 715
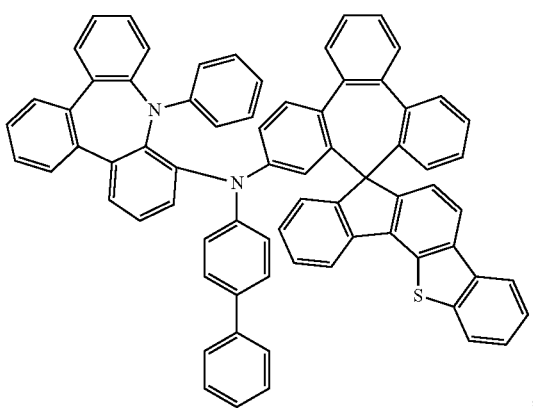
Compound 716
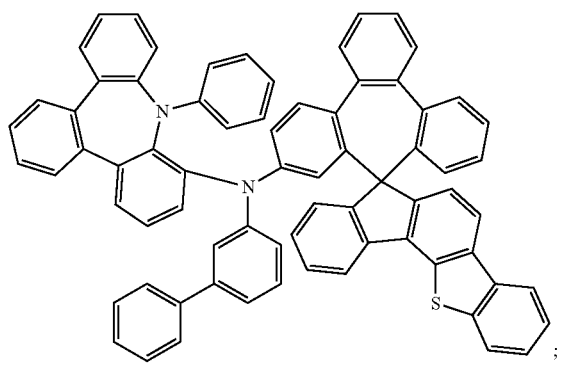
Compound 717
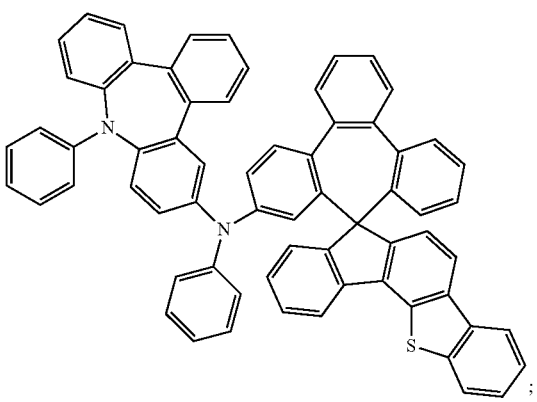

-continued
Compound 718
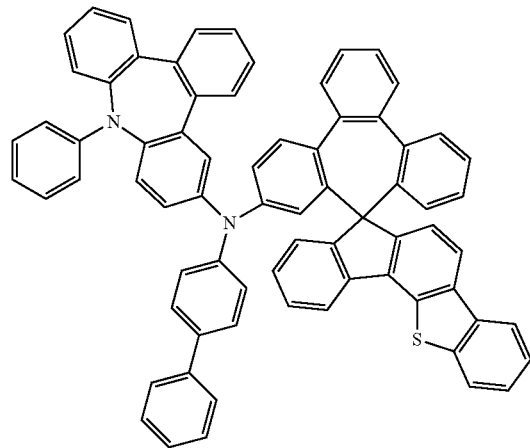
Compound 719
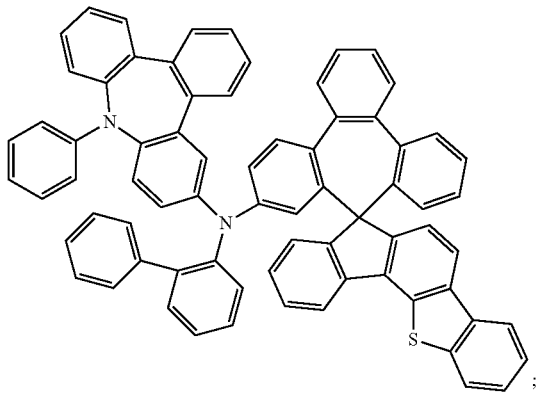
Compound 720
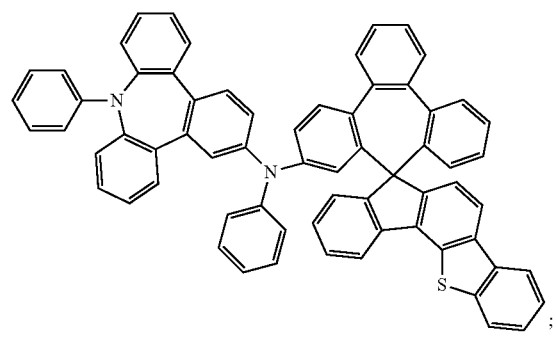
Compound 721
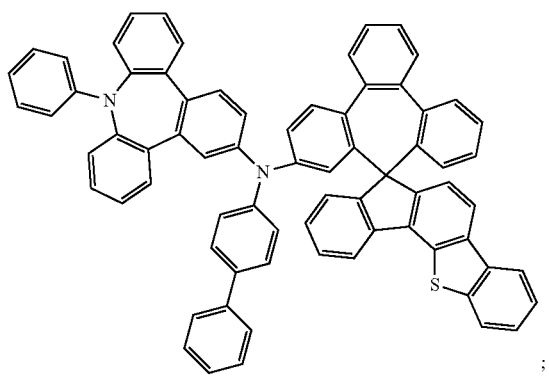
Compound 722
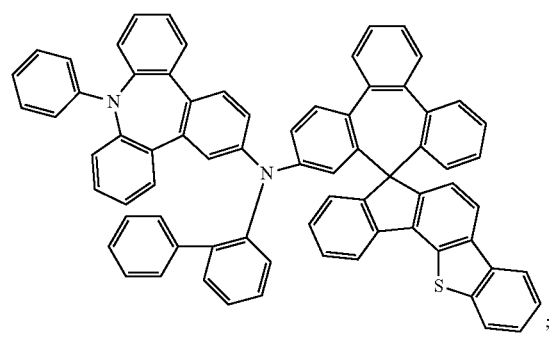
Compound 723
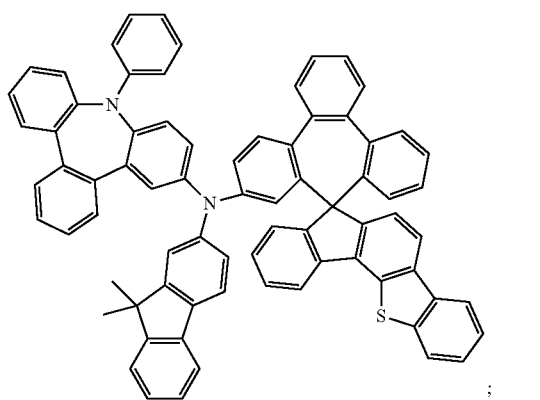

-continued
Compound 724
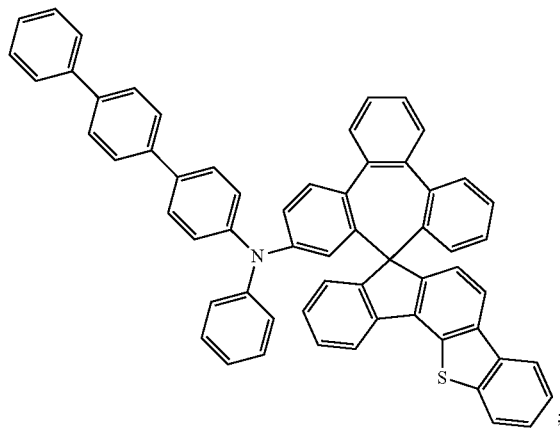
Compound 725
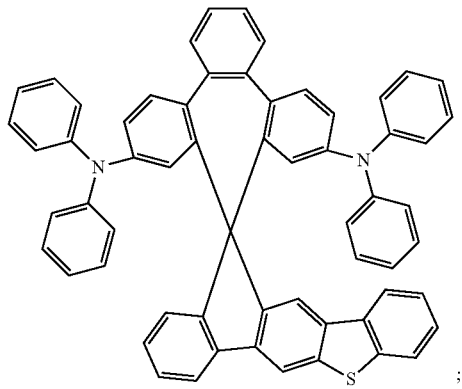
Compound 726
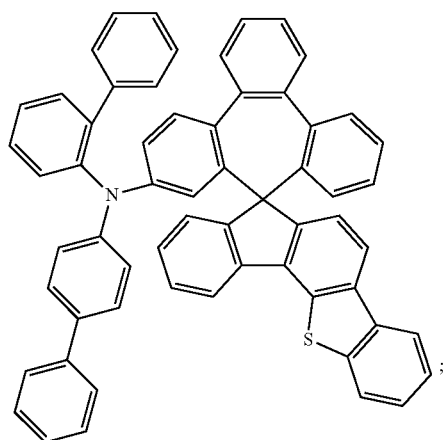
Compound 727
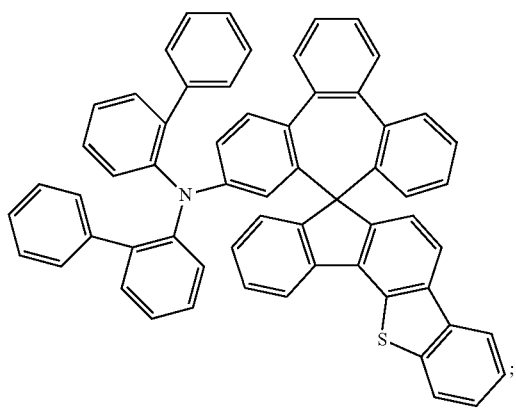
Compound 728
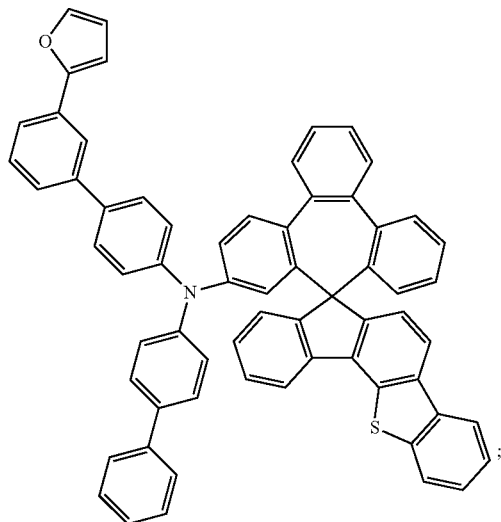
Compound 729
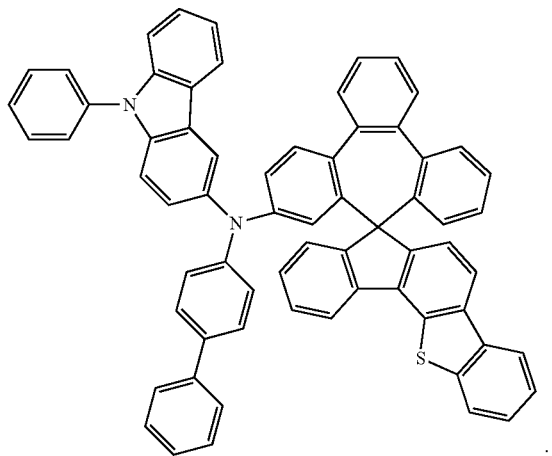

-continued
Compound 730
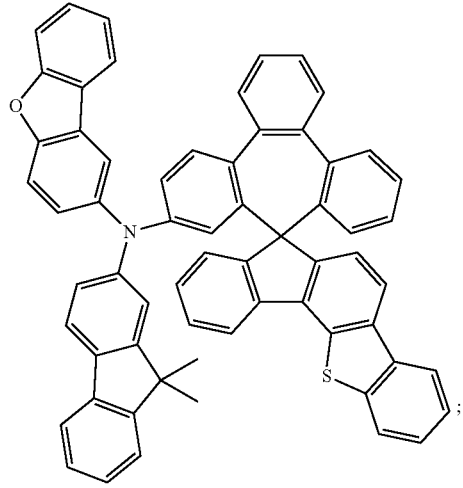
Compound 731
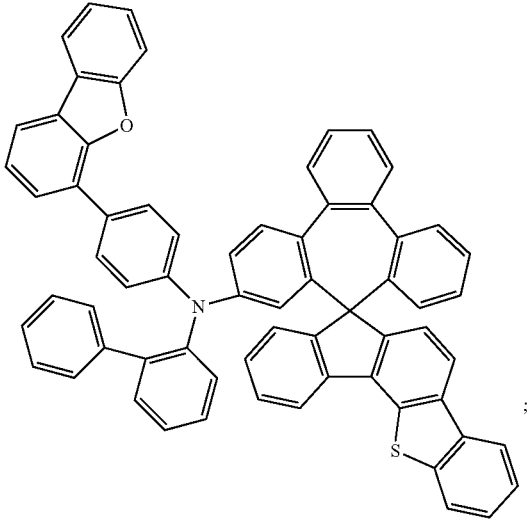
Compound 732
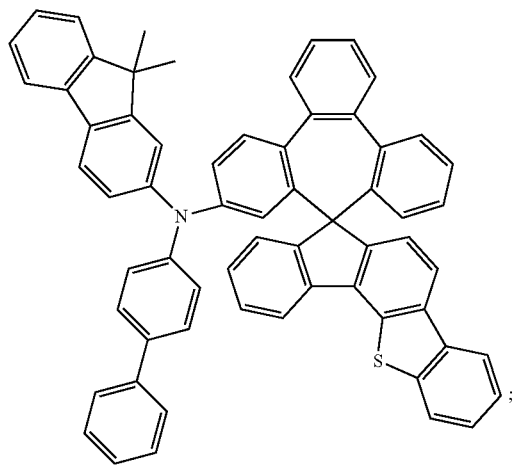
Compound 733
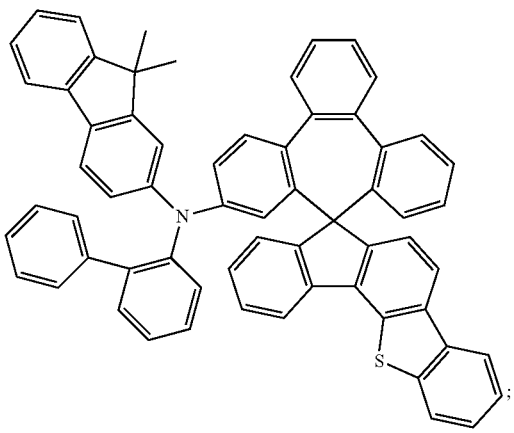
Compound 734
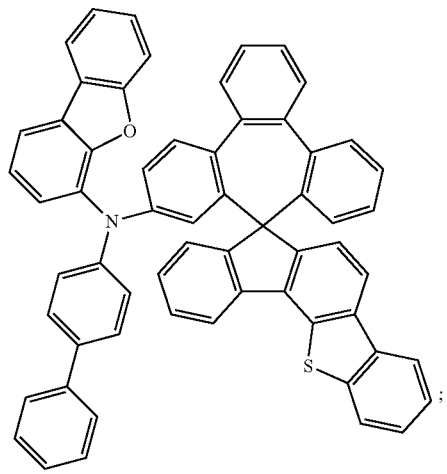
Compound 735
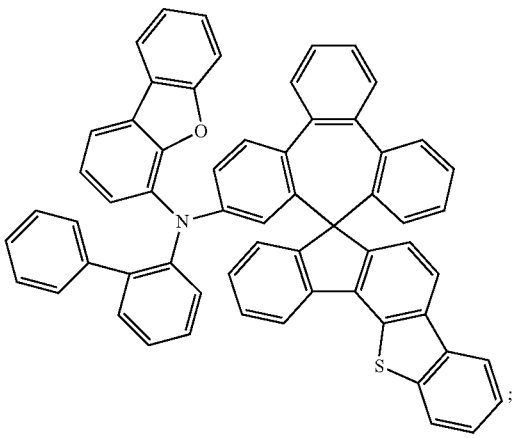

-continued
Compound 736
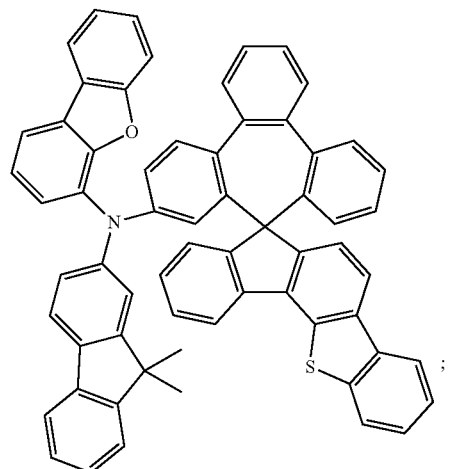
Compound 737
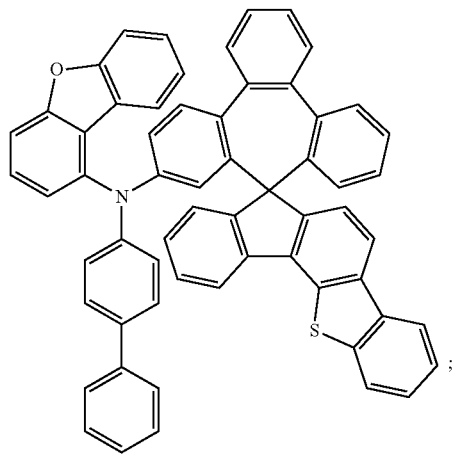
Compound 738
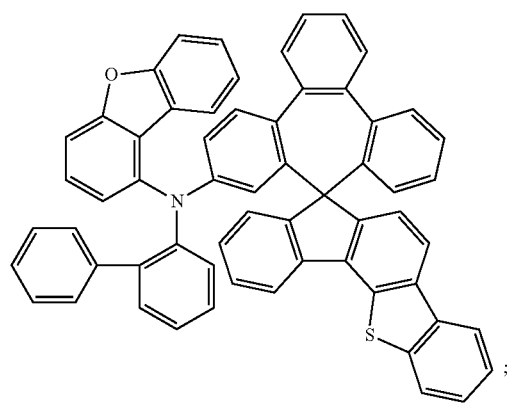
Compound 739
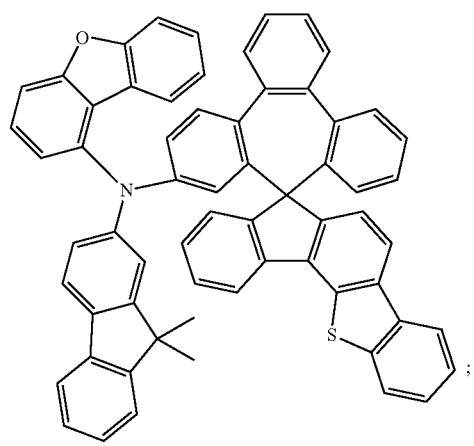
Compound 740
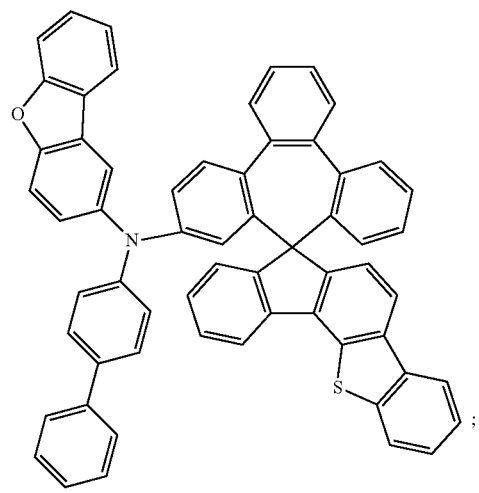
Compound 741
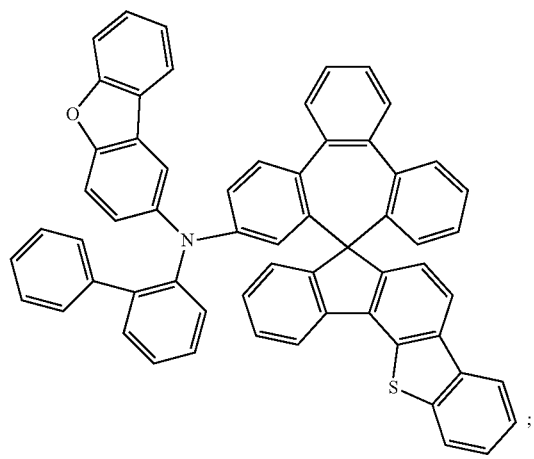

-continued
Compound 742
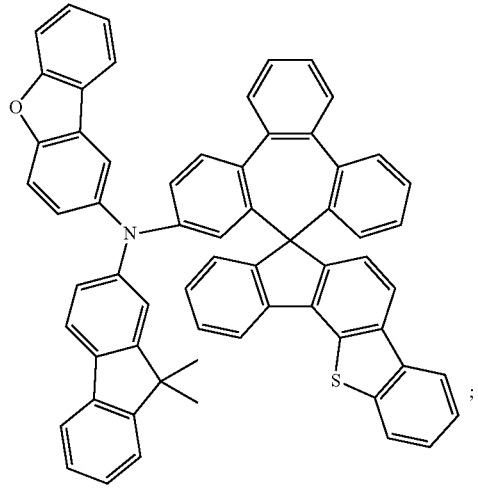
Compound 743
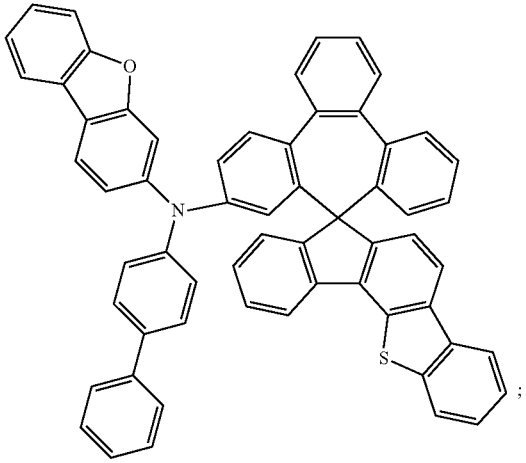
Compound 744
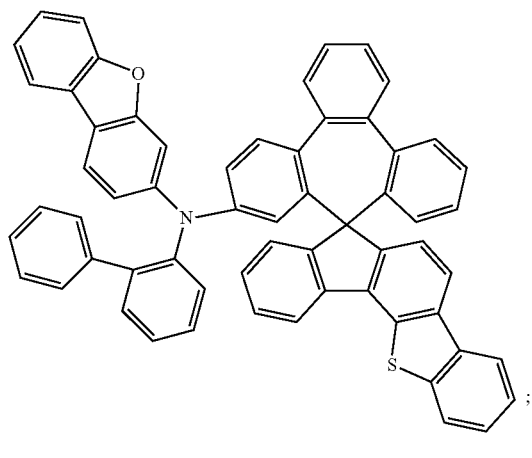
Compound 745
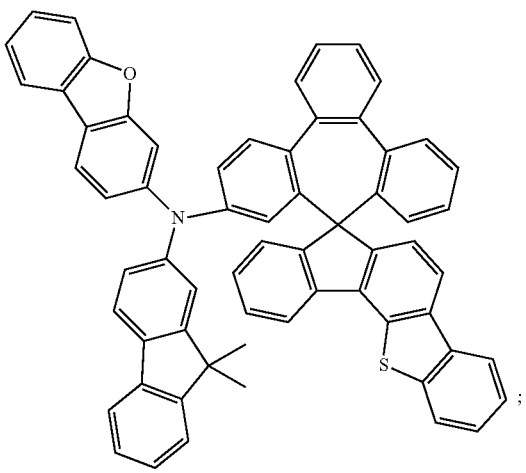
Compound 746
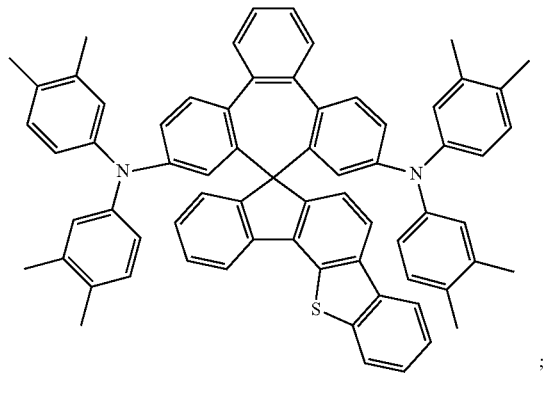
Compound 747
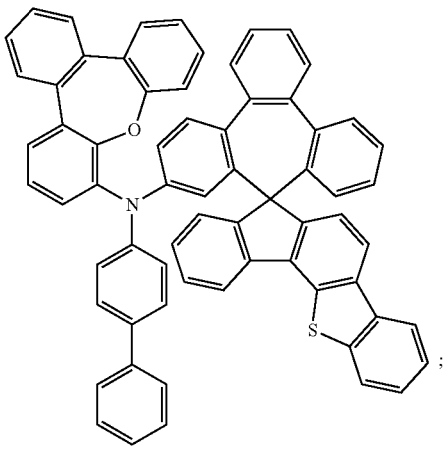

-continued
Compound 748
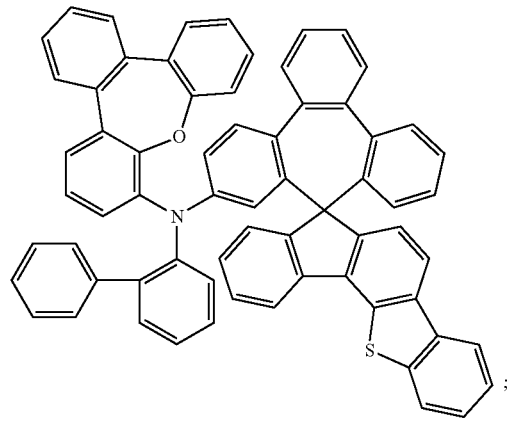
Compound 749
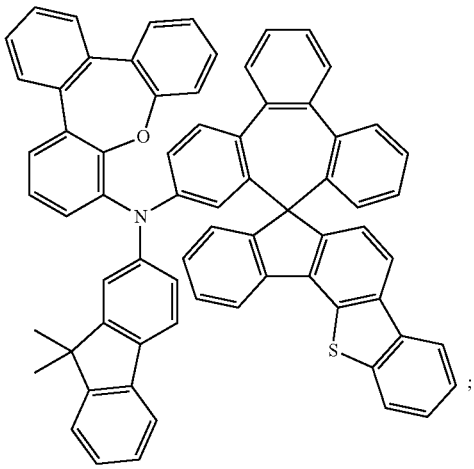
Compound 750
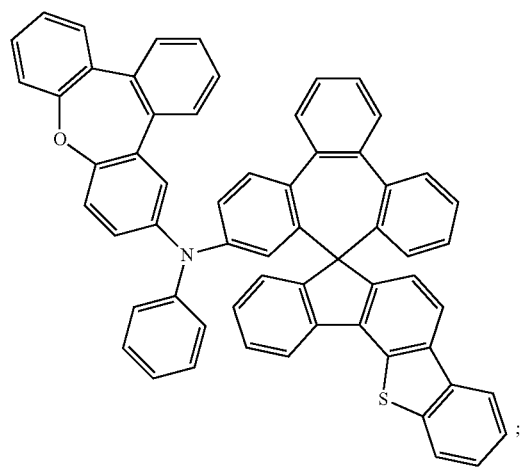
Compound 751
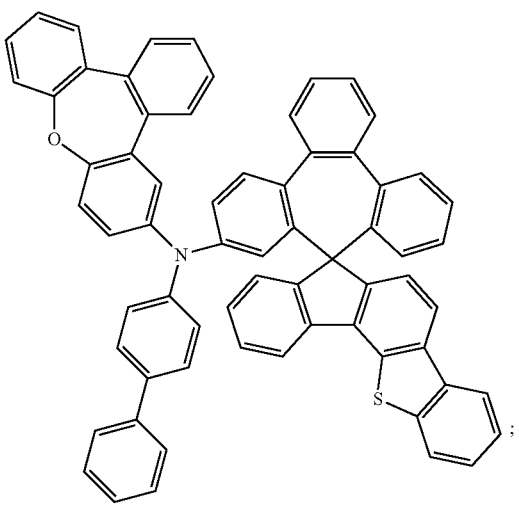
Compound 752
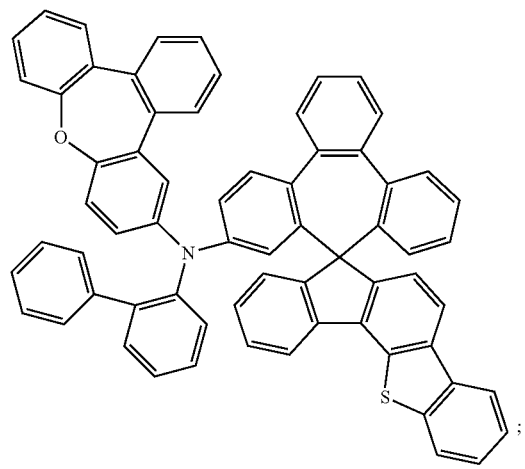
Compound 753
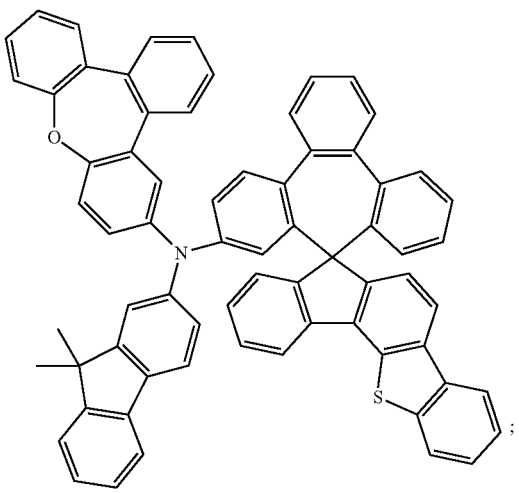

-continued
Compound 754
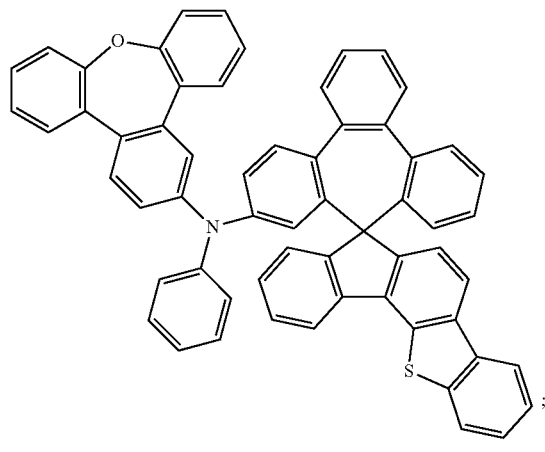
Compound 755
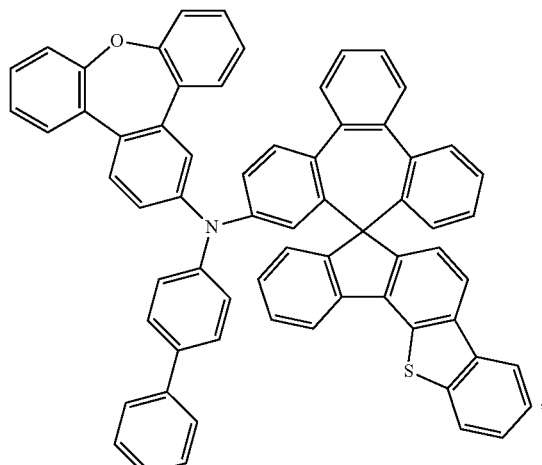
Compound 756
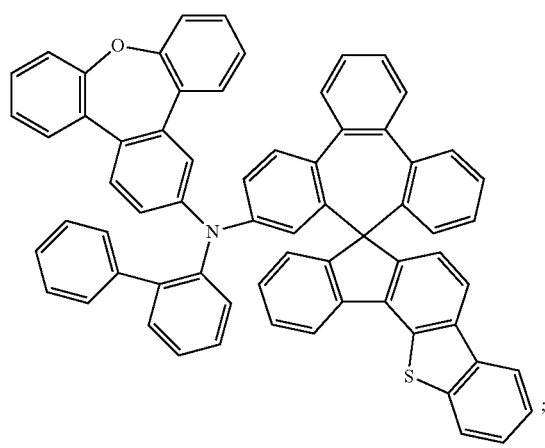
Compound 757
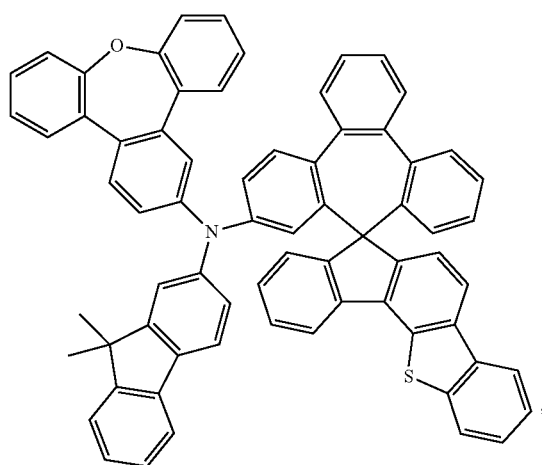
Compound 758
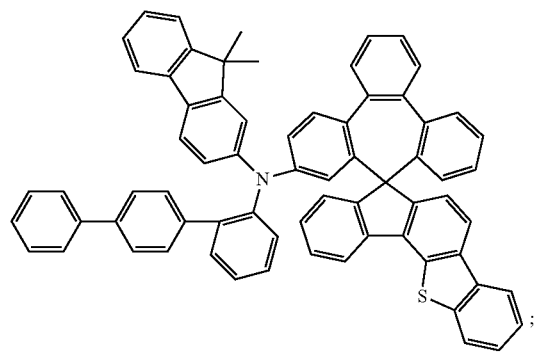
Compound 759
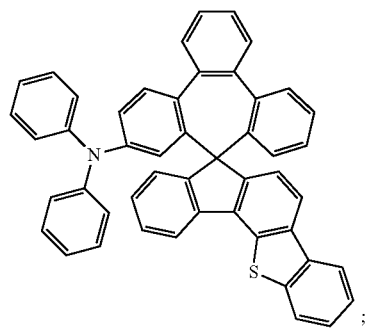

-continued
Compound 760
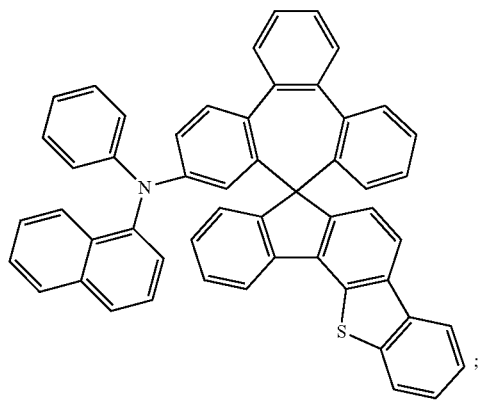
Compound 761
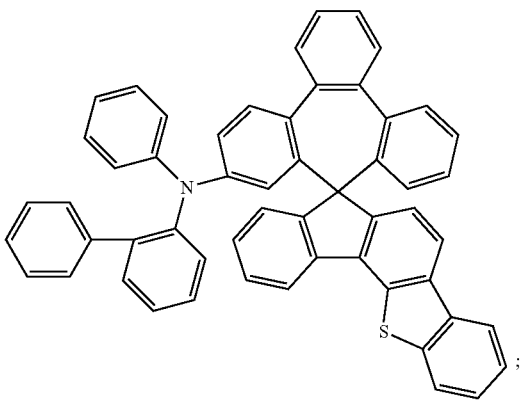
Compound 762
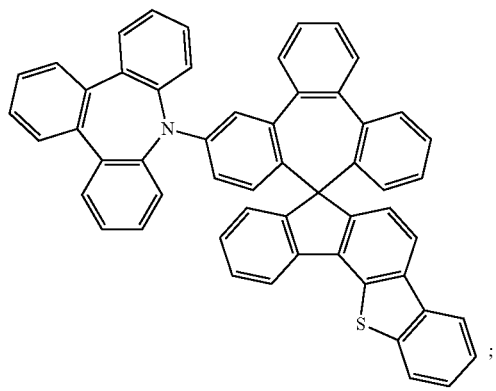
Compound 763
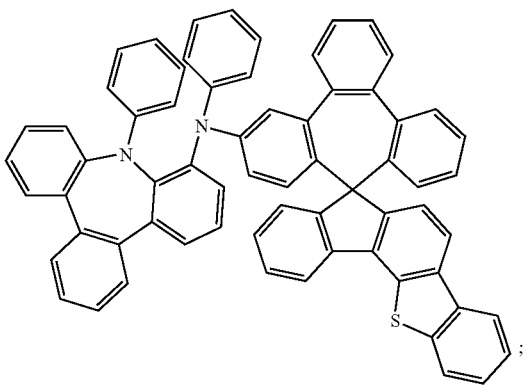
Compound 764
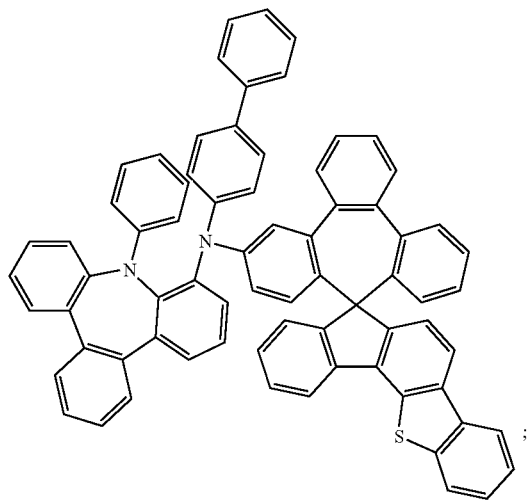
Compound 765
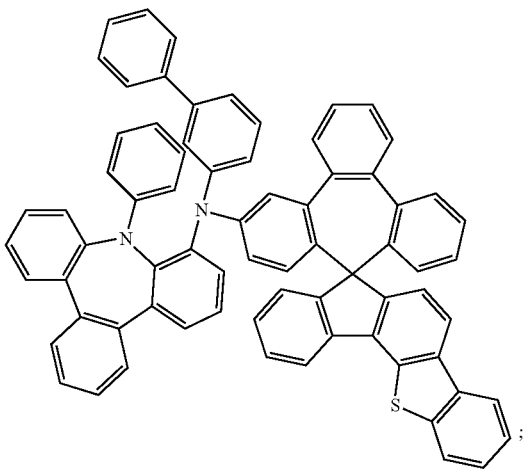

-continued
Compound 766
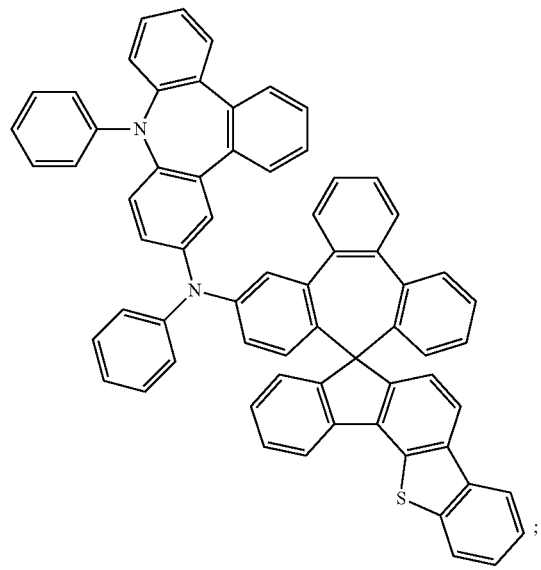
Compound 767
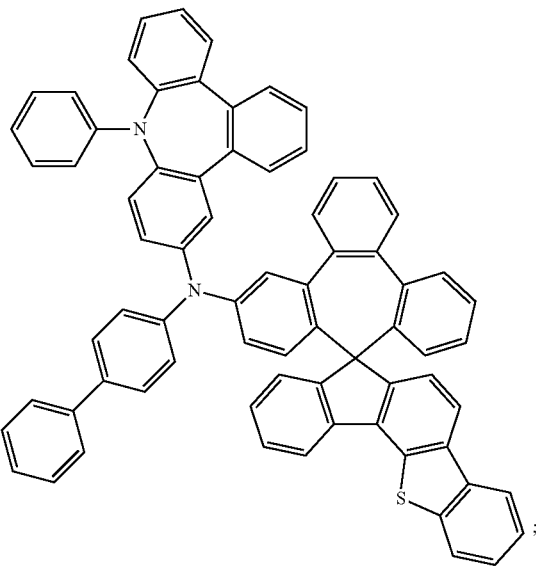
Compound 768
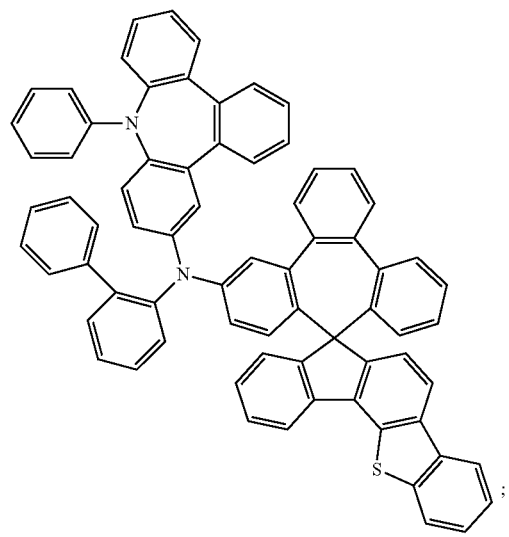
Compound 769
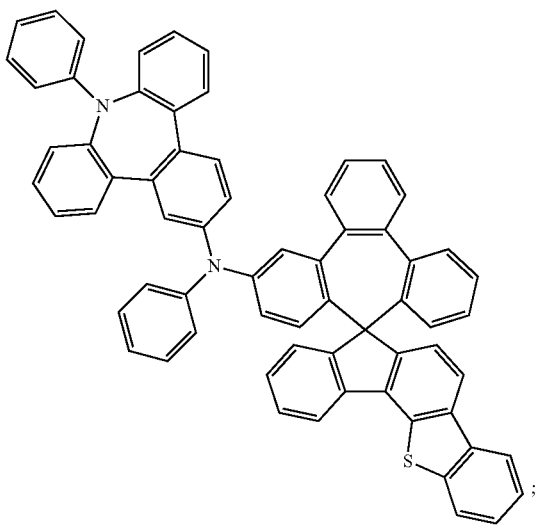

Compound 770
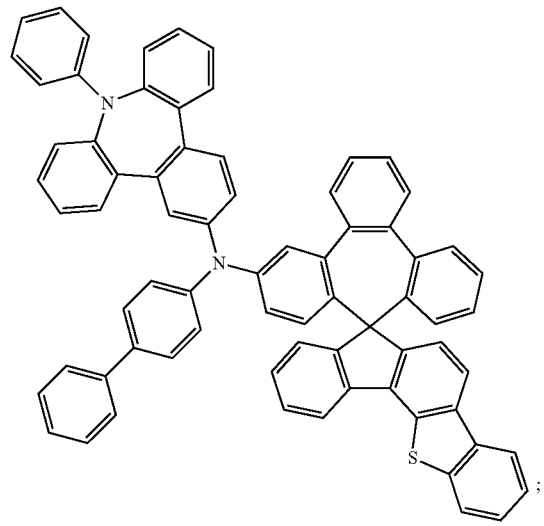
Compound 771
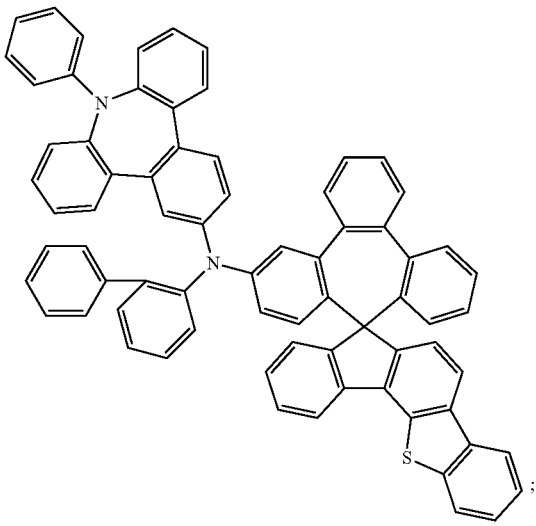
Compound 772
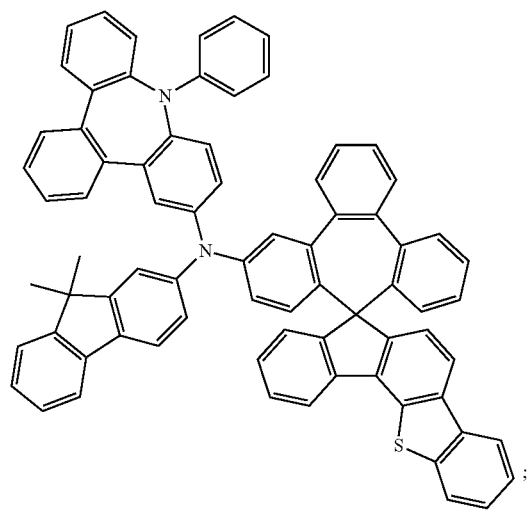
Compound 773
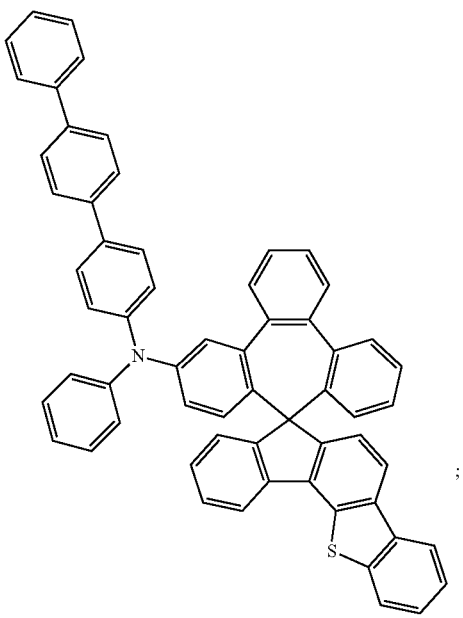

-continued
Compound 774
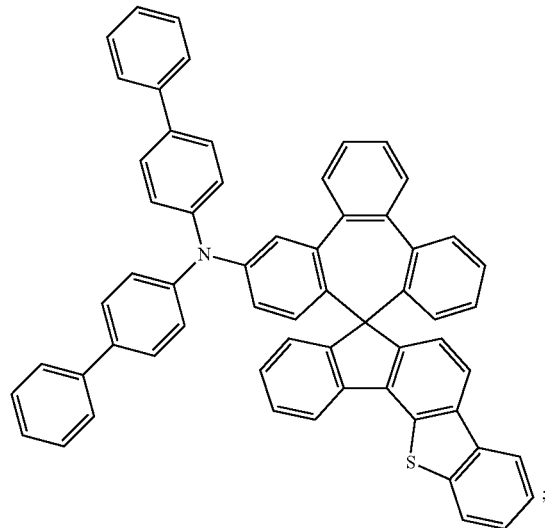
Compound 775
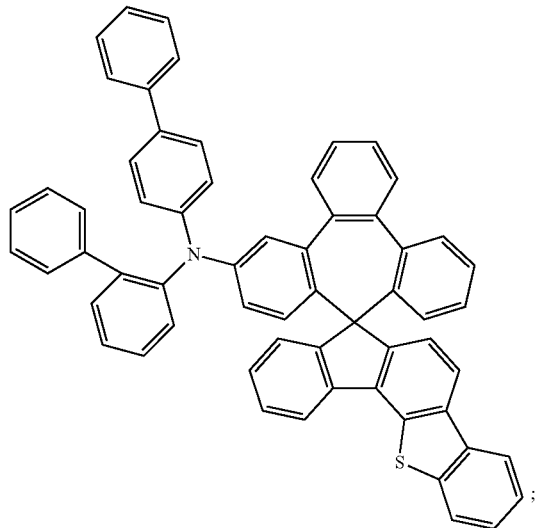
Compound 776
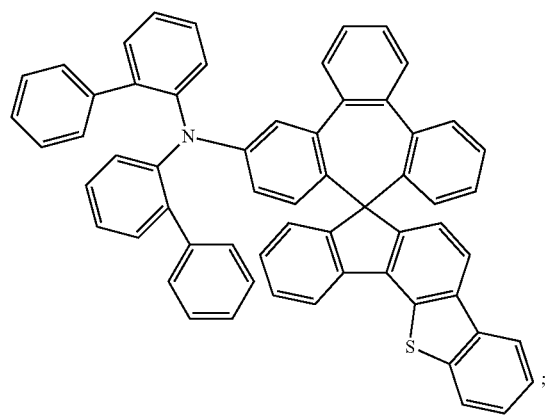
Compound 777
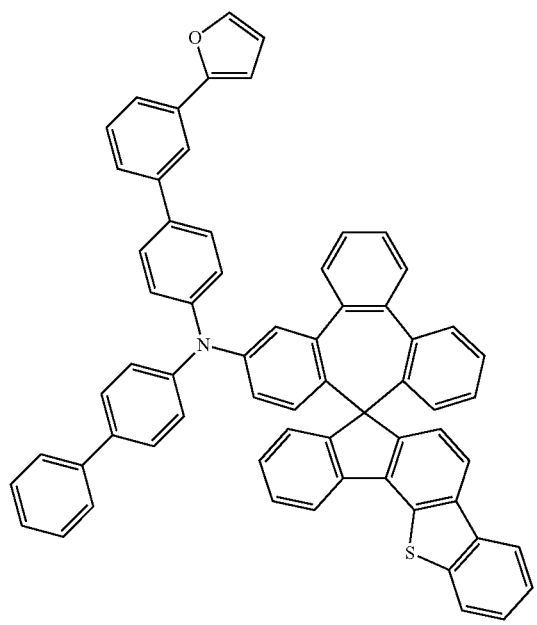

-continued
Compound 778
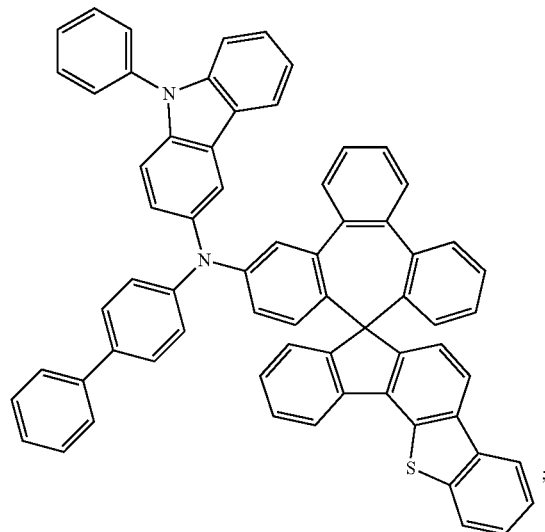
Compound 779
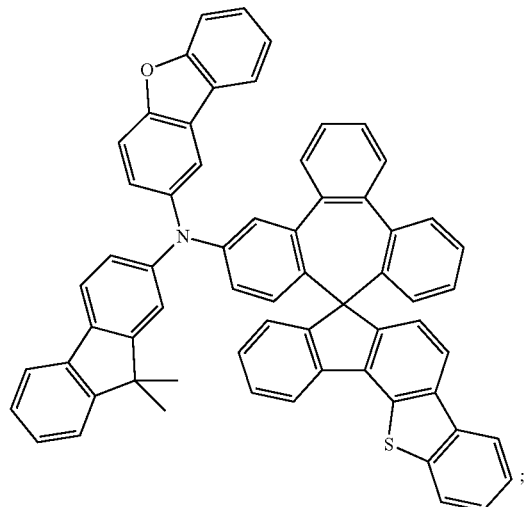
Compound 780
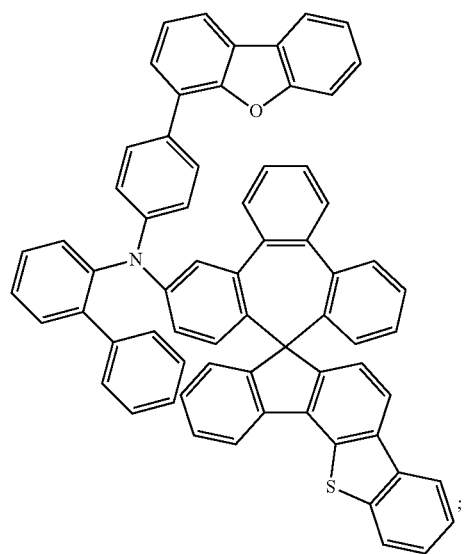
Compound 781
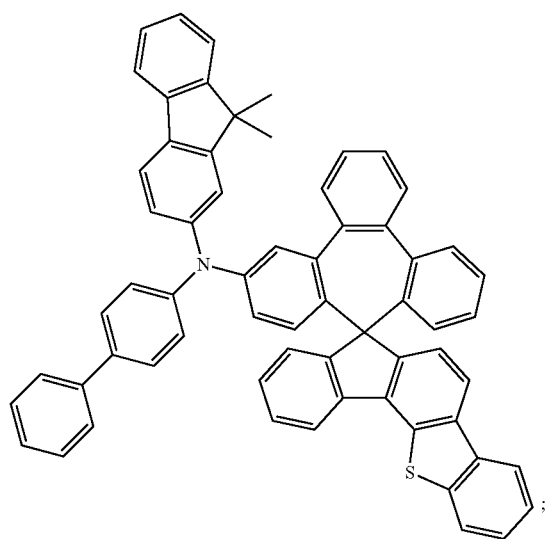

Compound 782
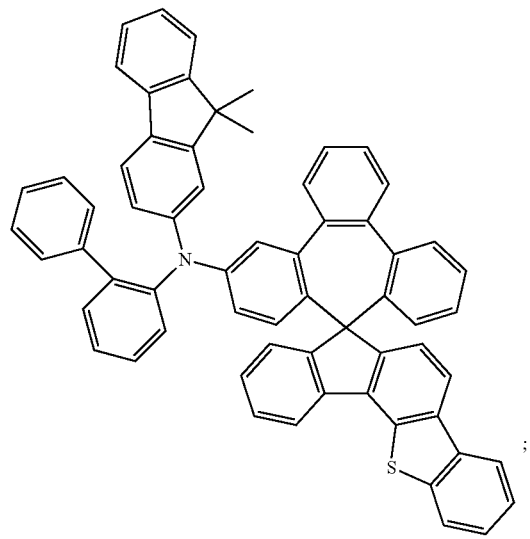
Compound 783
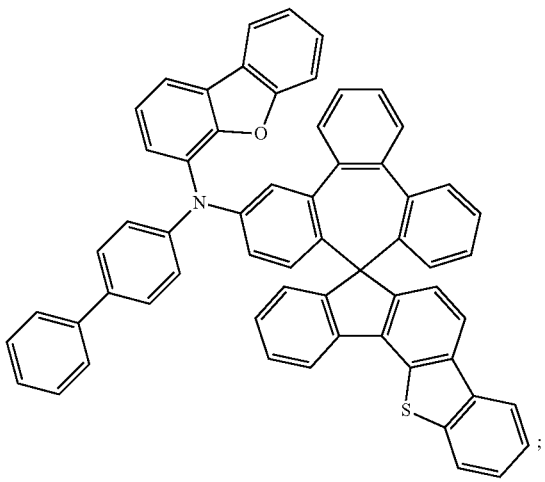
Compound 784
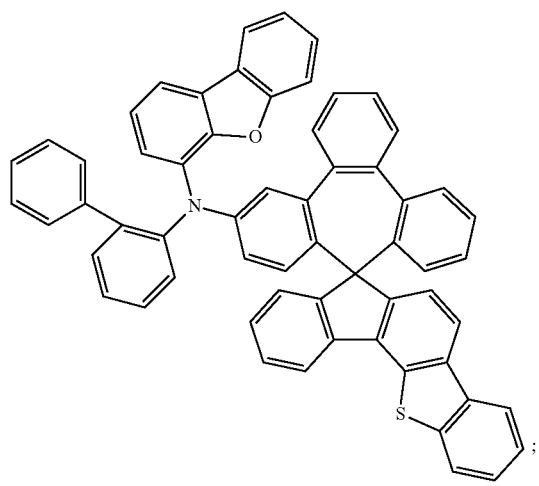
Compound 785
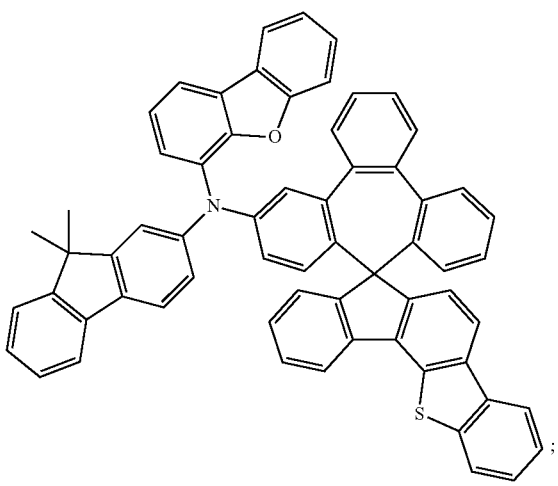
Compound 786
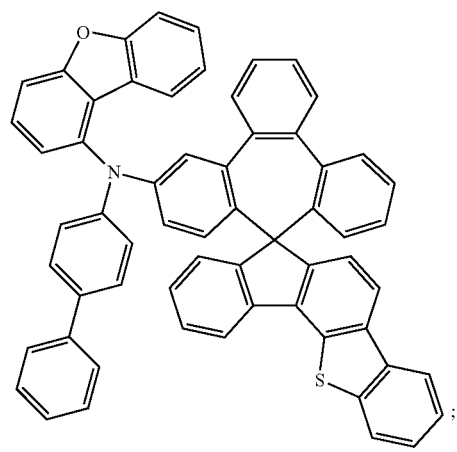
Compound 787
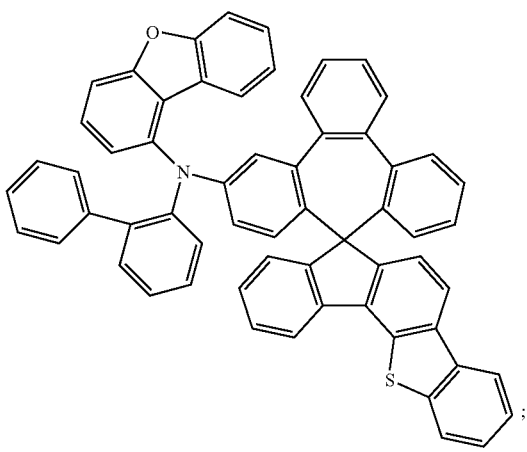

Compound 788
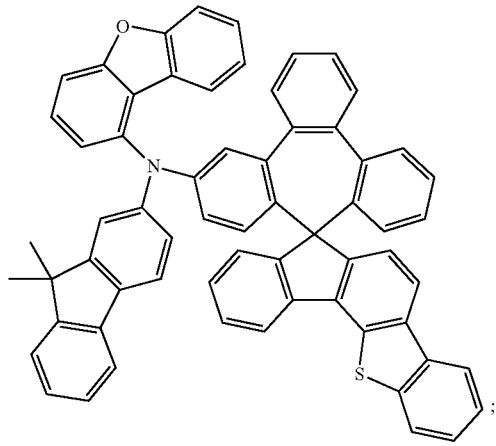
Compound 789
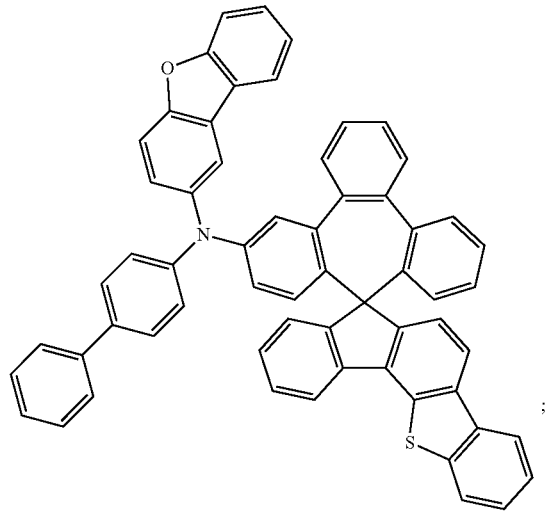
Compound 790
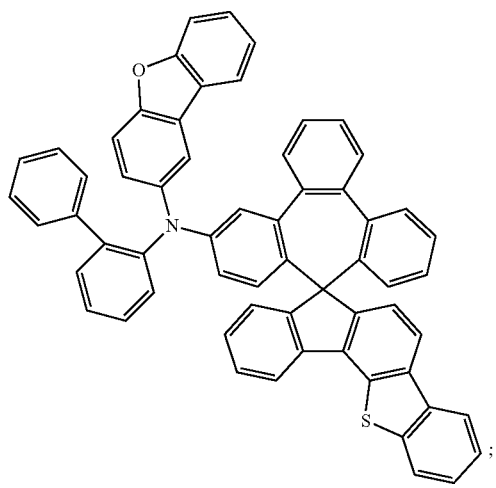
Compound 791
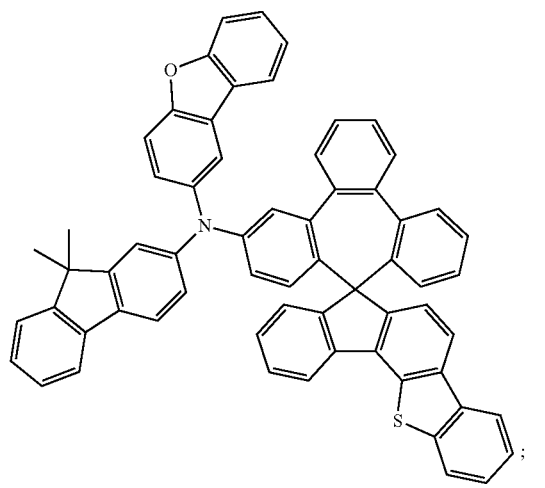
Compound 792
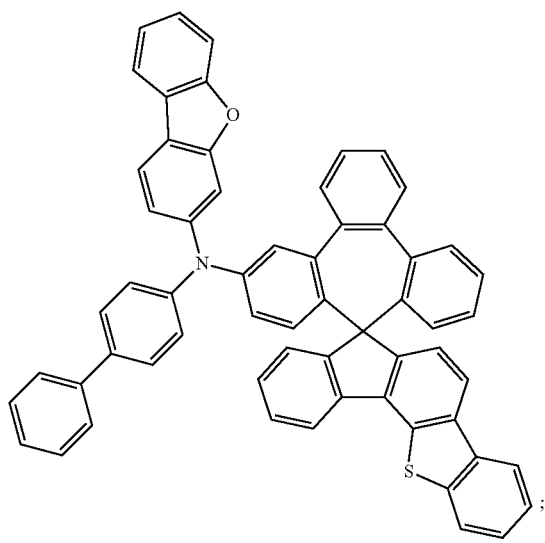
Compound 793
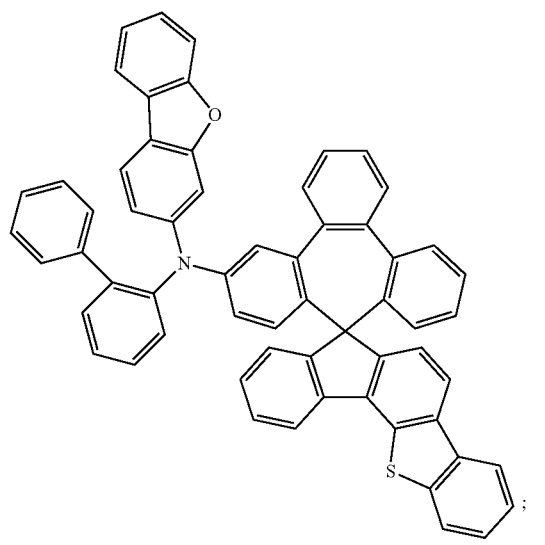

-continued
Compound 794
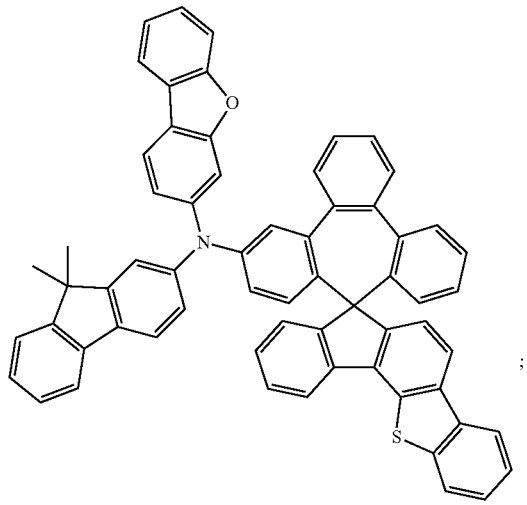
Compound 795
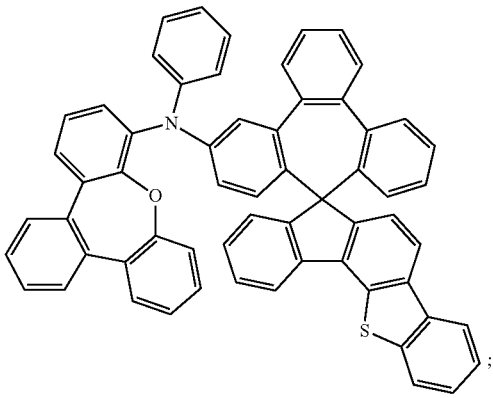
Compound 796
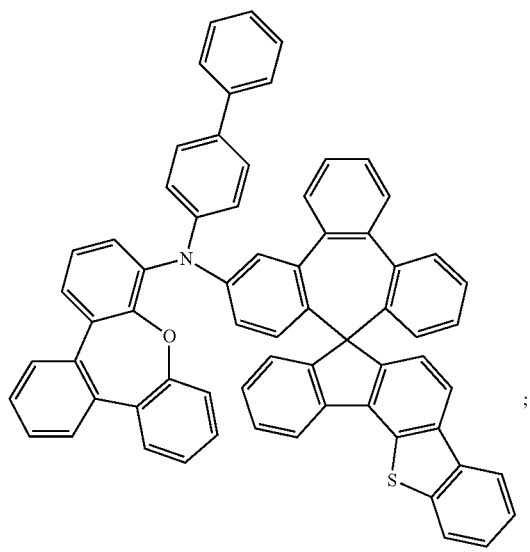
Compound 797
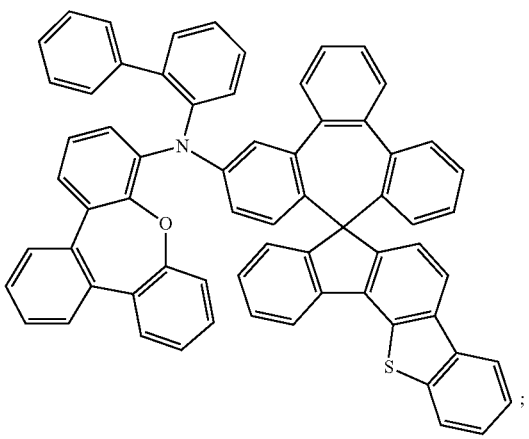
Compound 798
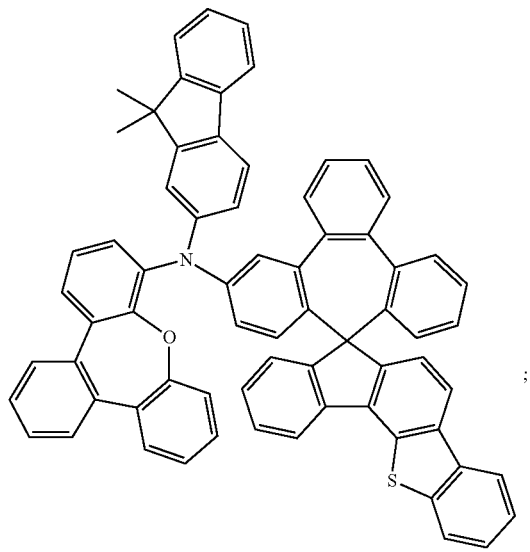
Compound 799
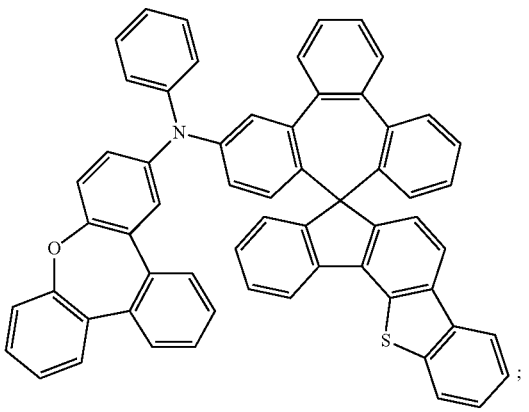

-continued
Compound 800
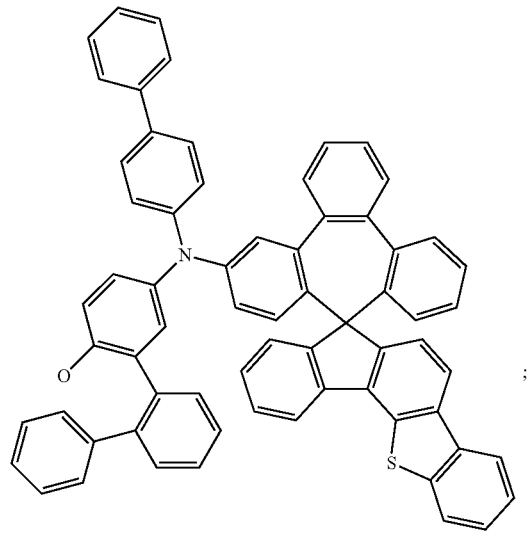
Compound 801
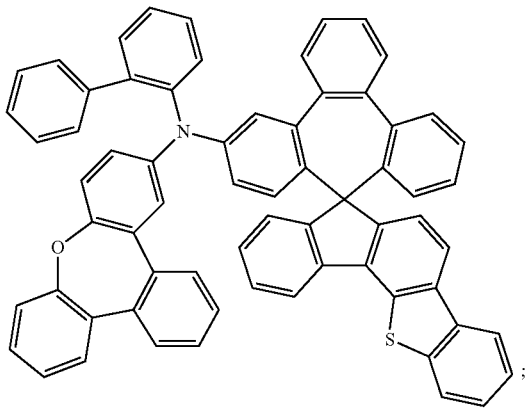
;
Compound 802
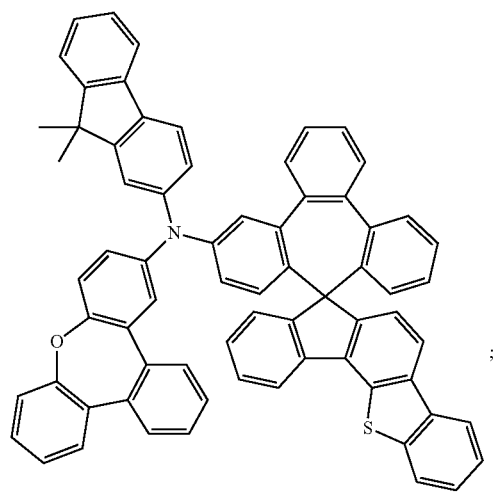
;
Compound 803
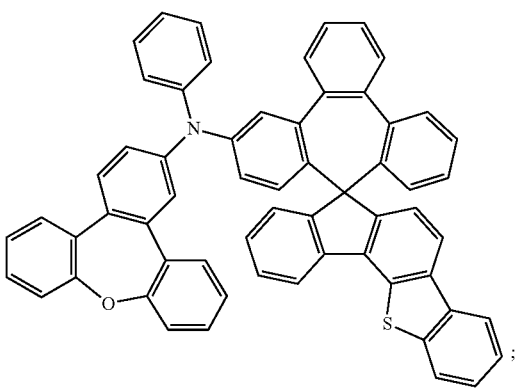
;
Compound 804
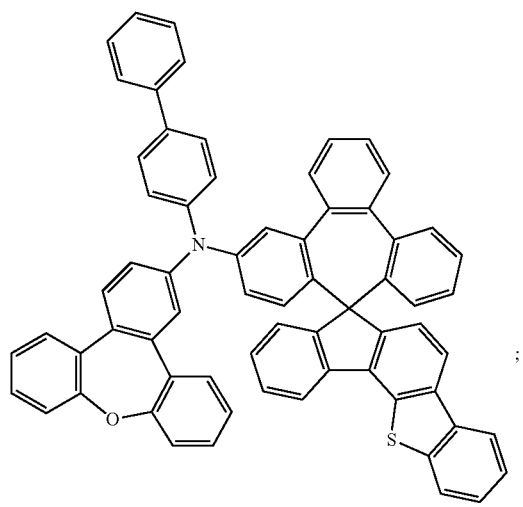
;
Compound 805
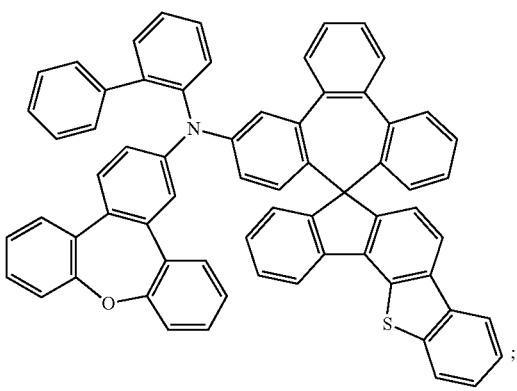
;

-continued
Compound 806
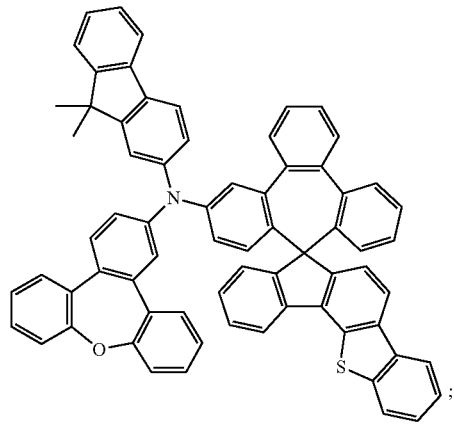
Compound 807
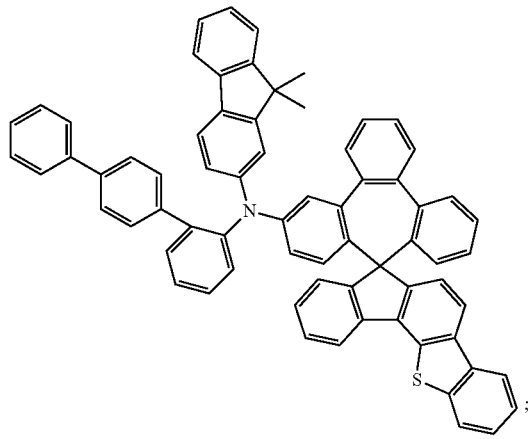
Compound 808
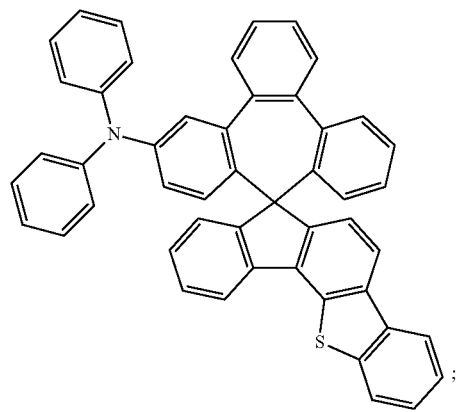
Compound 809
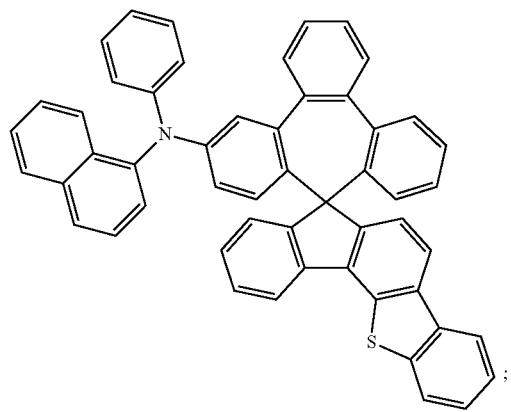
Compound 810
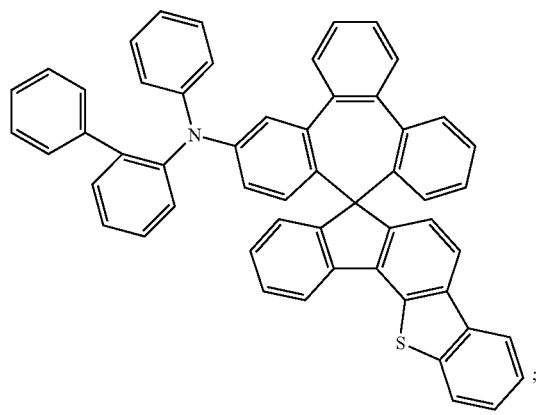
Compound 811
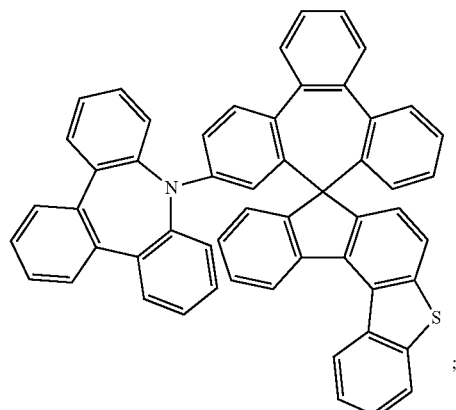

-continued
Compound 812
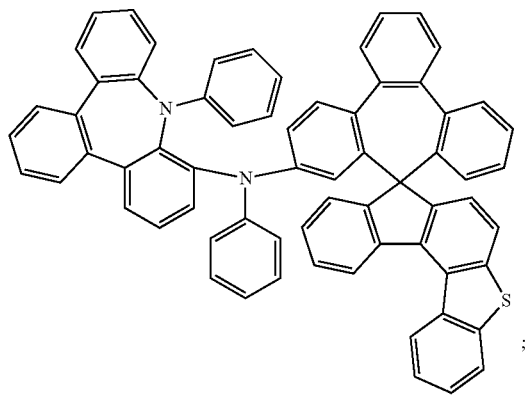
Compound 813
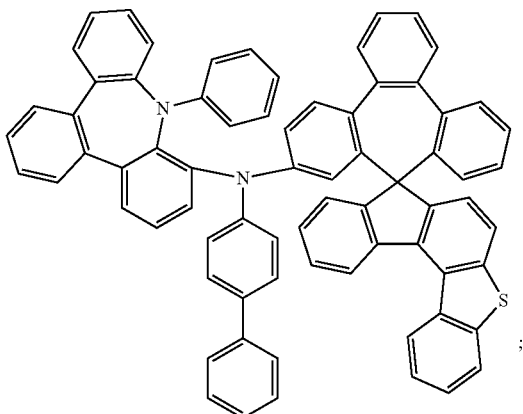
Compound 814
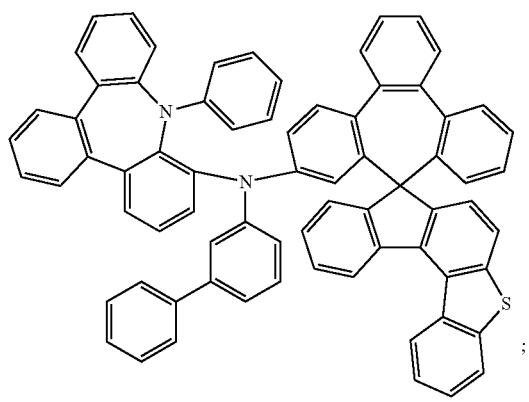
Compound 815
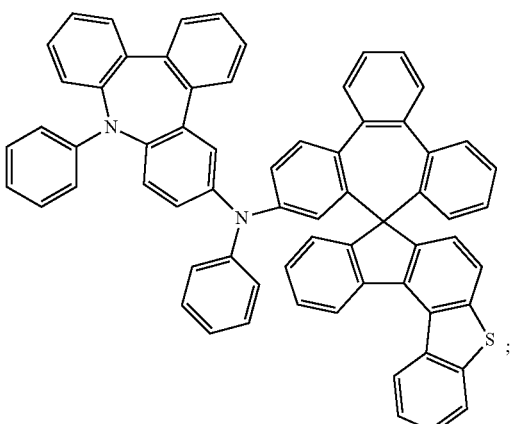
Compound 816
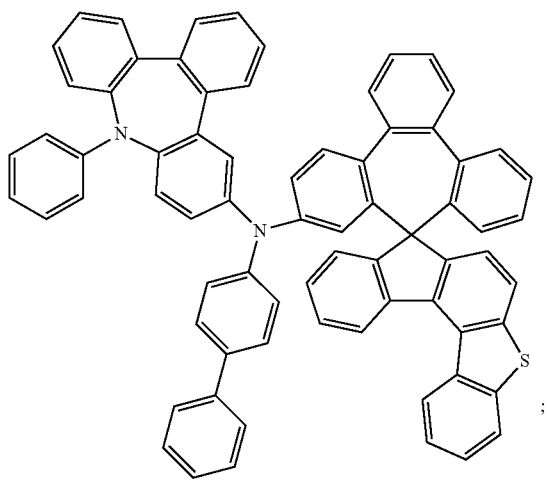
Compound 817
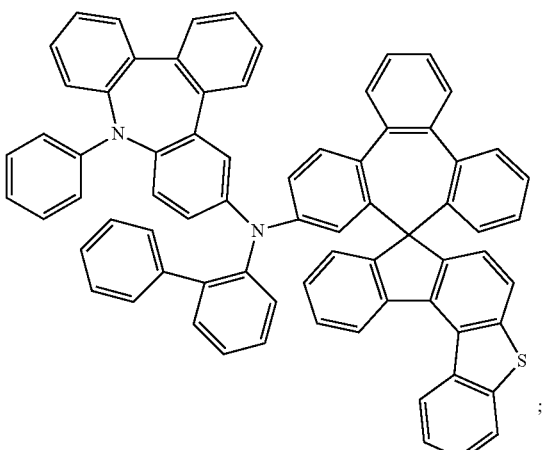

-continued
Compound 818
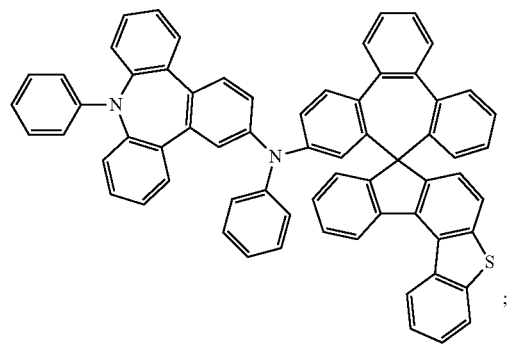
Compound 819
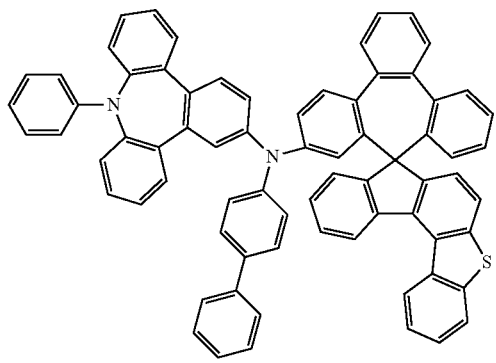
Compound 820
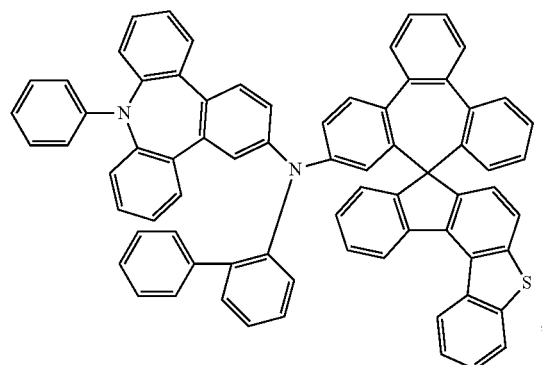
Compound 821
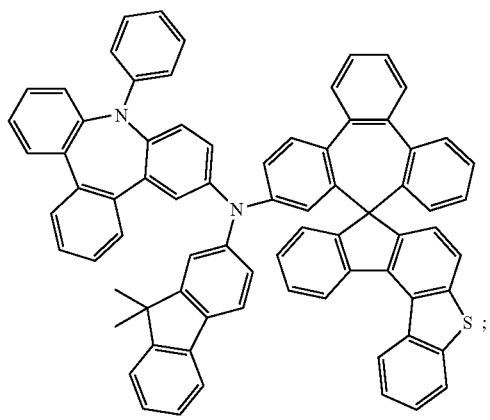
Compound 822
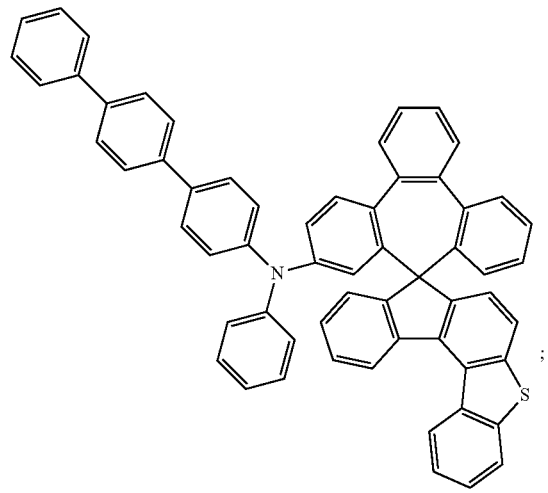
Compound 823
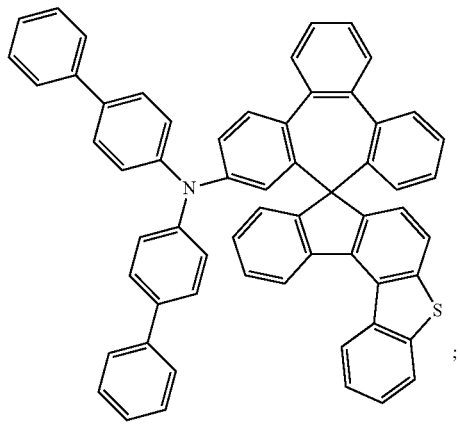

Compound 824
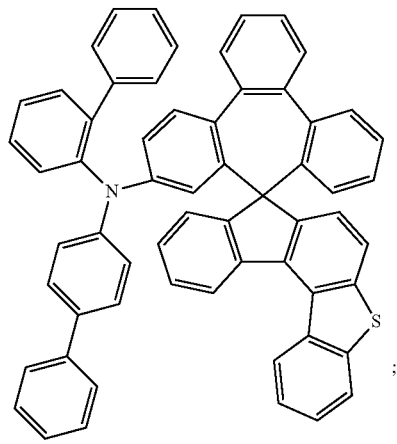
Compound 825
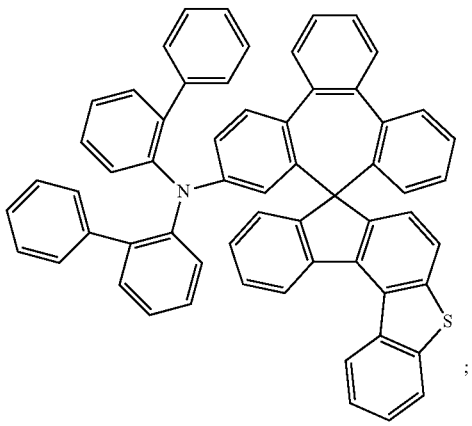
Compound 826
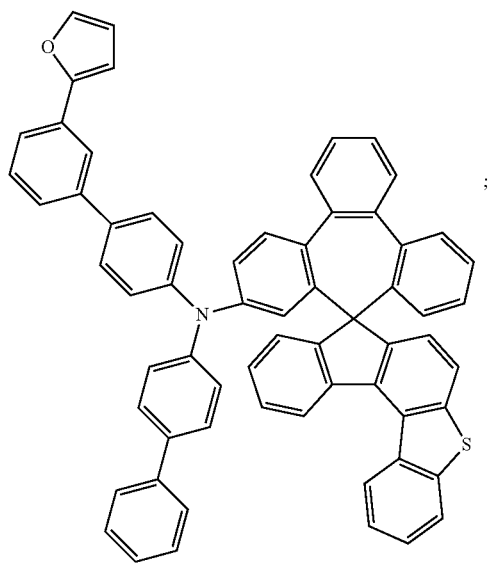
Compound 827
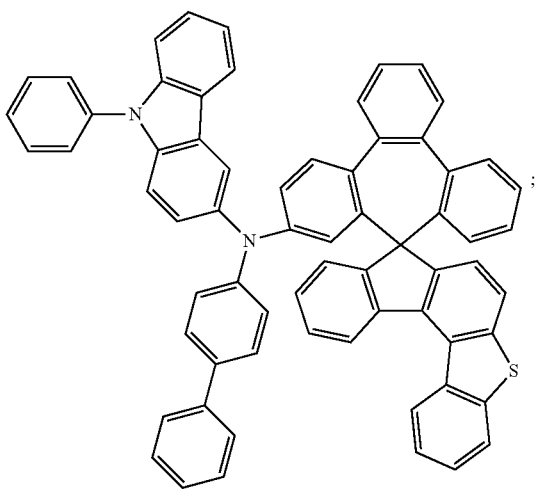
Compound 828
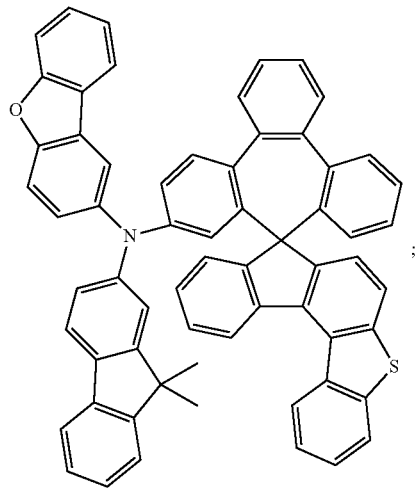
Compound 829
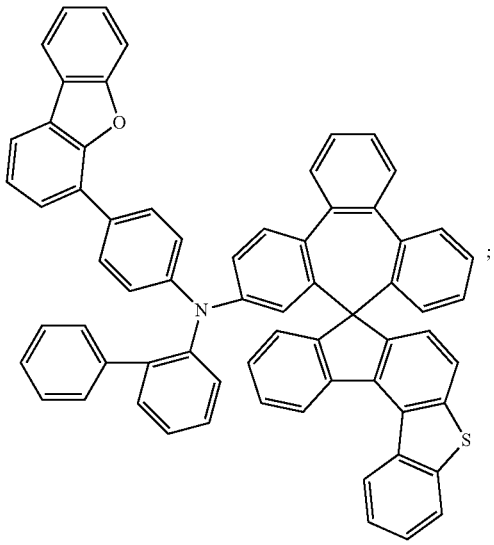

-continued
Compound 830
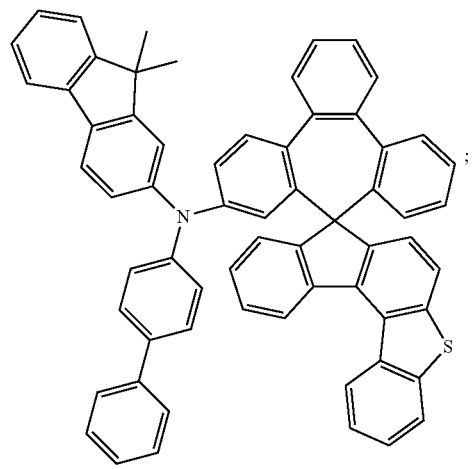
Compound 831
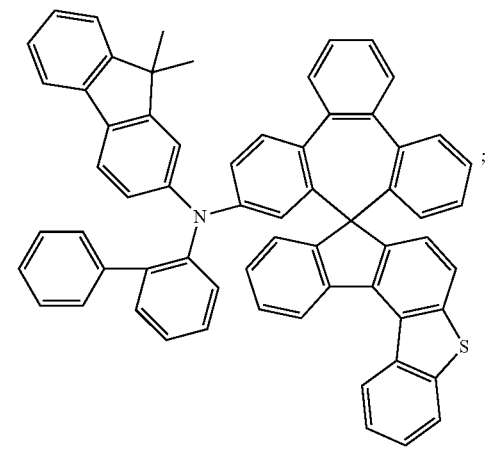
Compound 832
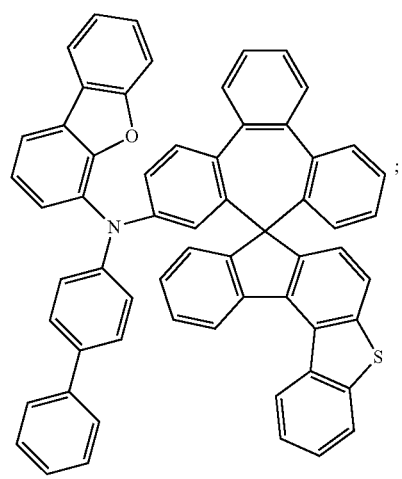
Compound 833
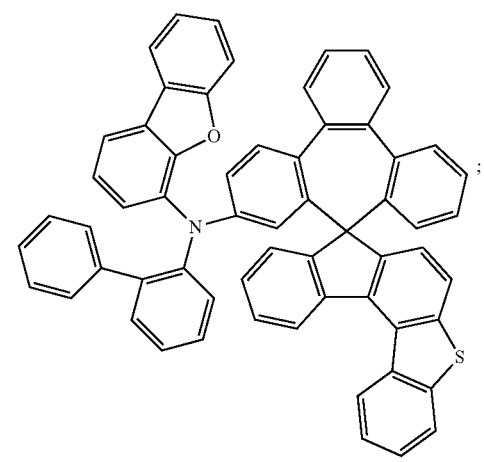
Compound 834
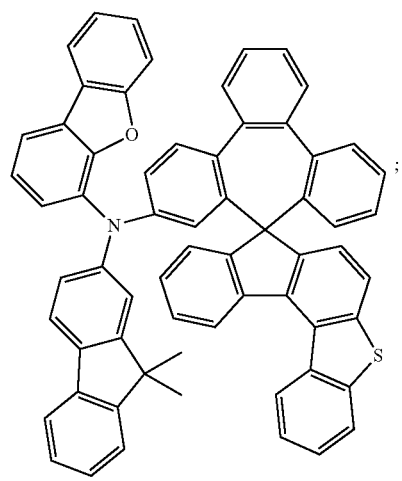
Compound 835
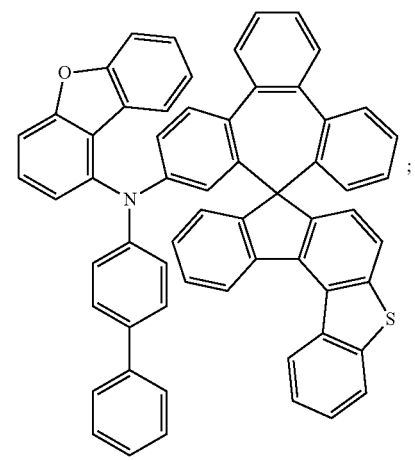

Compound 836
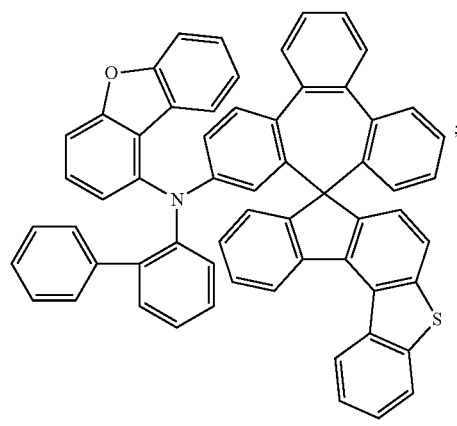
Compound 837
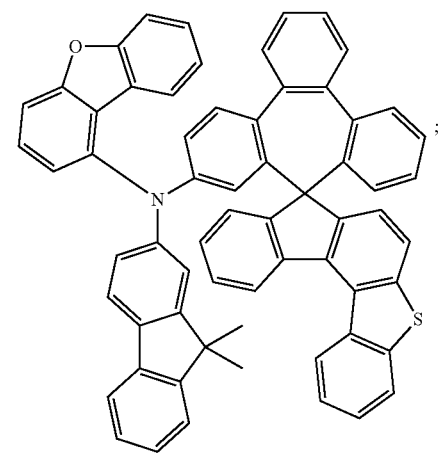
Compound 838
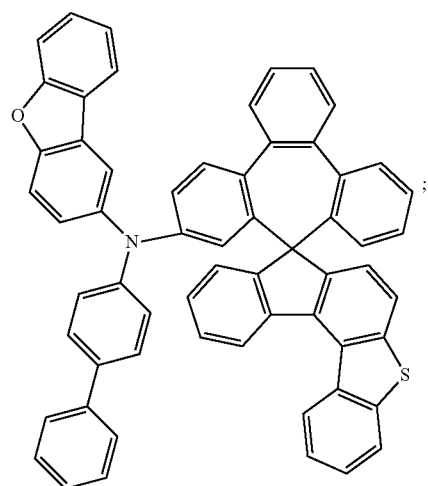
Compound 839
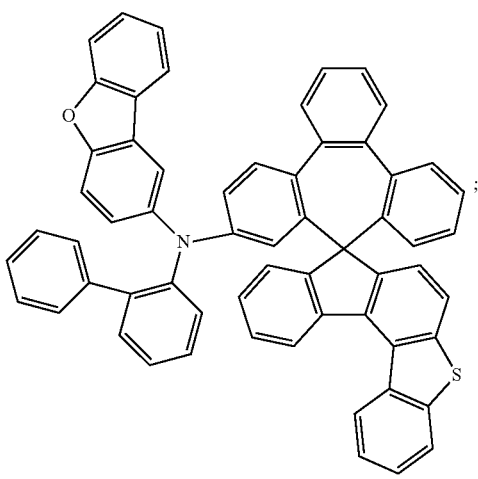
Compound 340
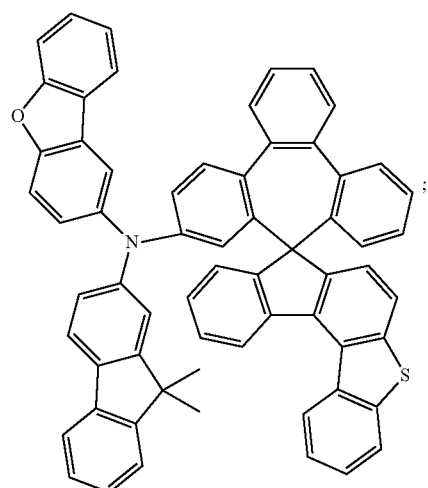
Compound 841
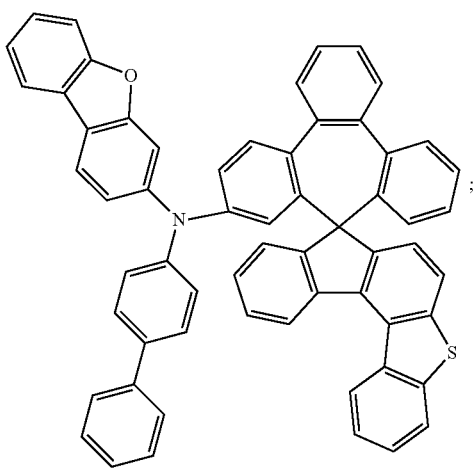

-continued
Compound 842
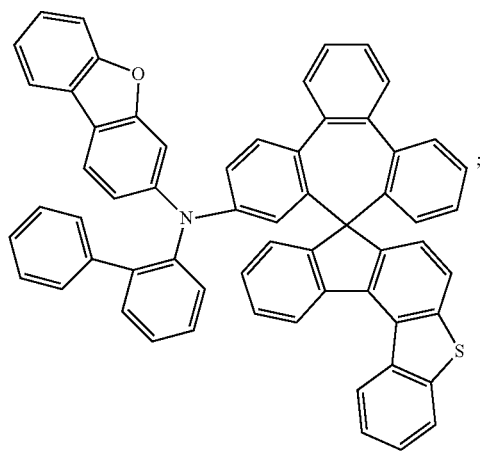
Compound 843
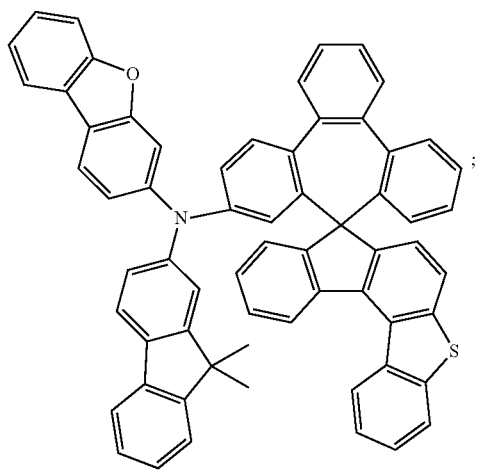
Compound 844
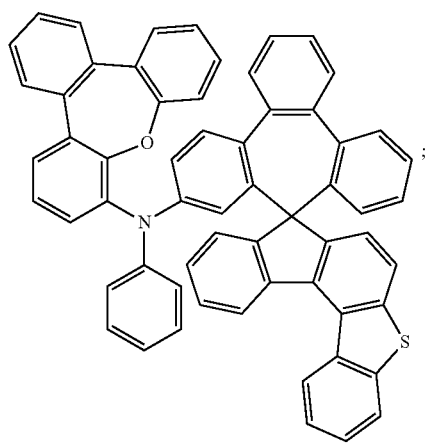
Compound 845
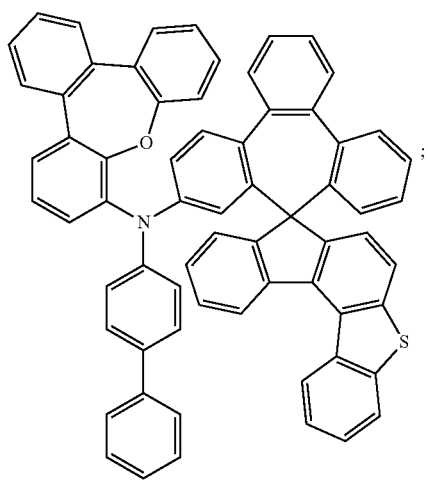
Compound 846
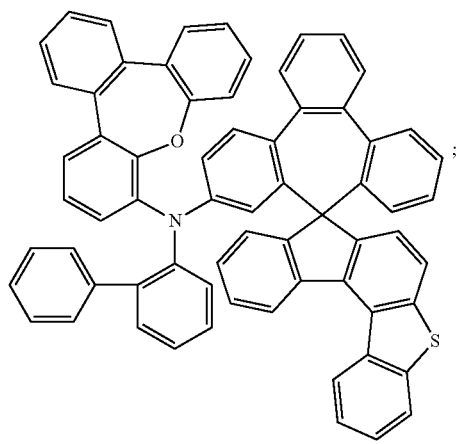
Compound 847
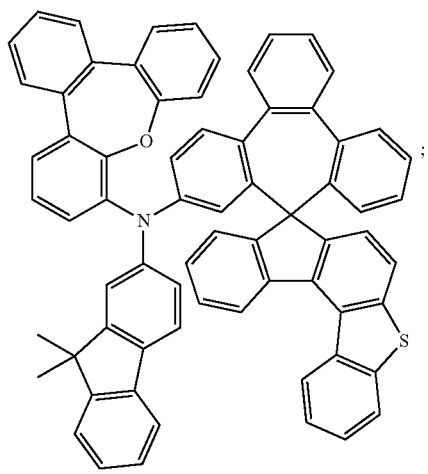

Compound 848
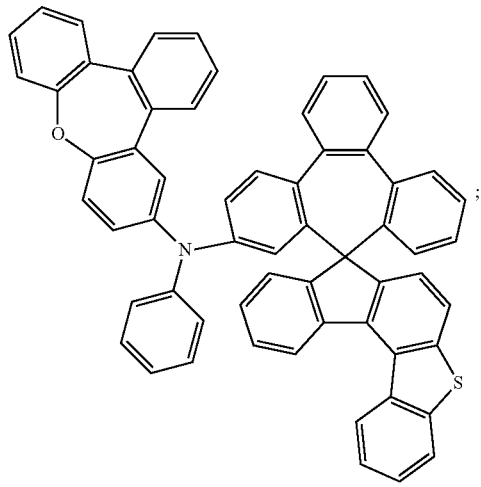
Compound 849
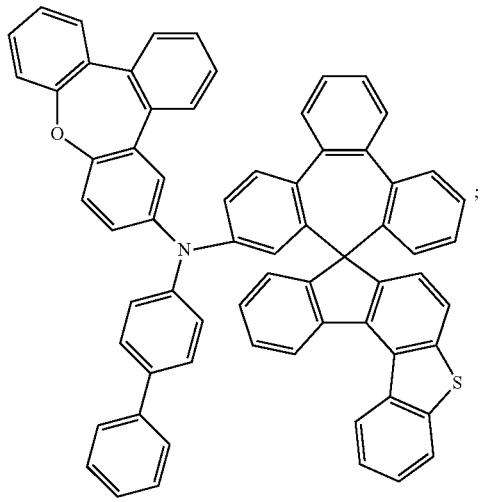
Compound 850
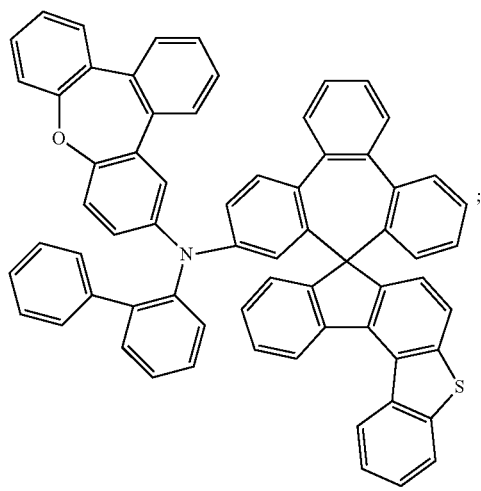
Compound 851
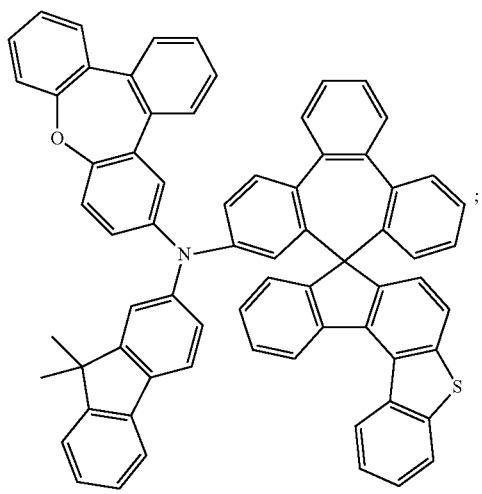
Compound 852
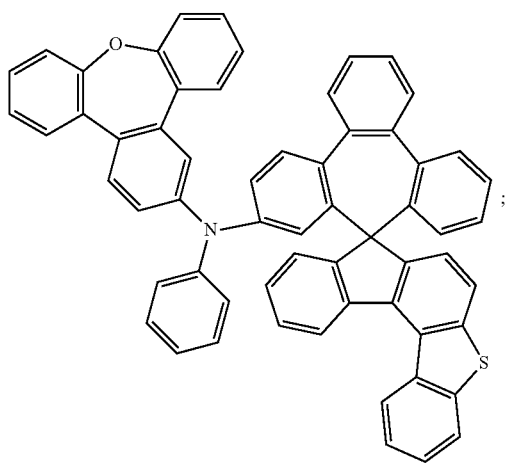

-continued
Compound 854
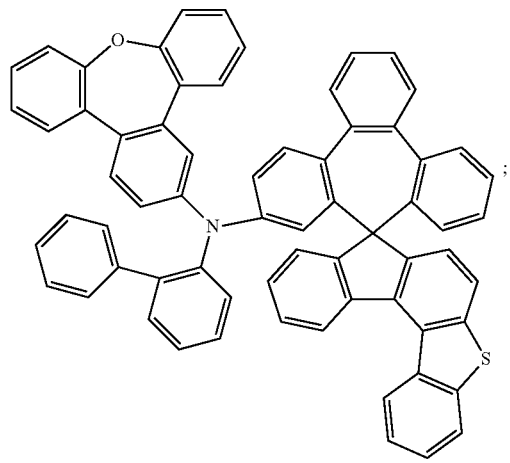
Compound 855
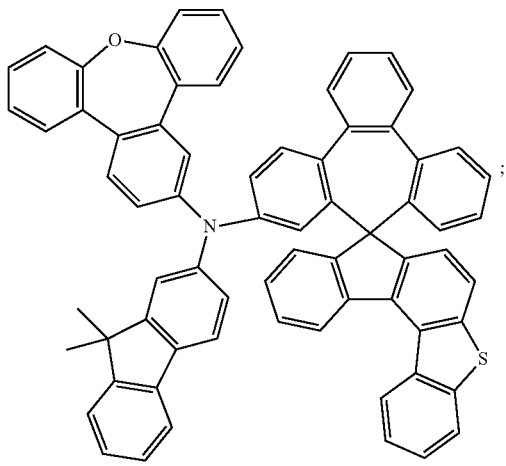
Compound 856
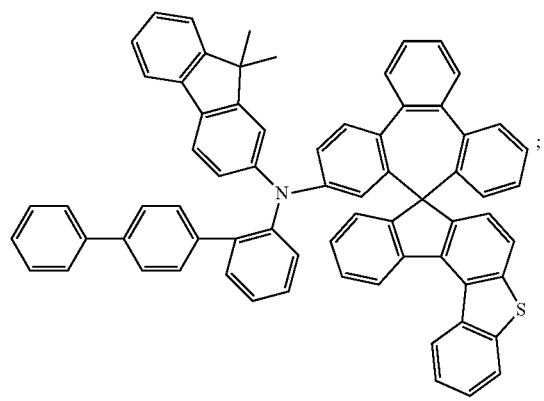
Compound 857
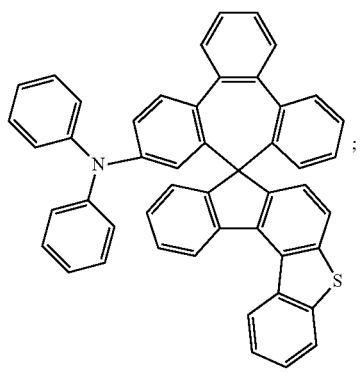
Compound 858
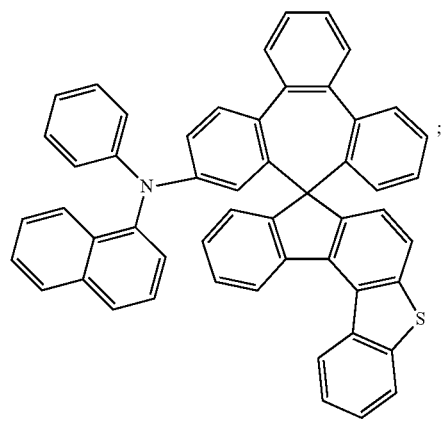
Compound 859
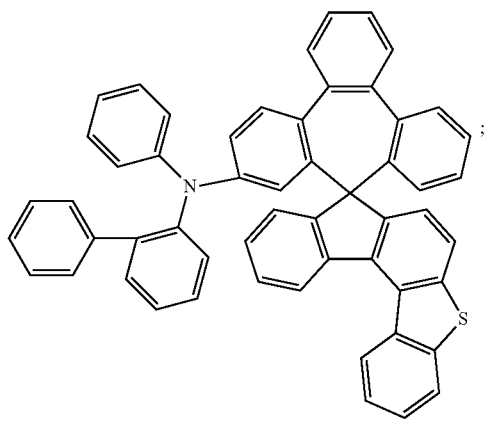

-continued
Compound 860
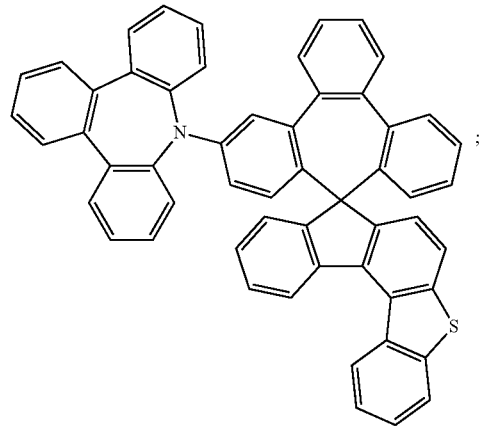
Compound 861
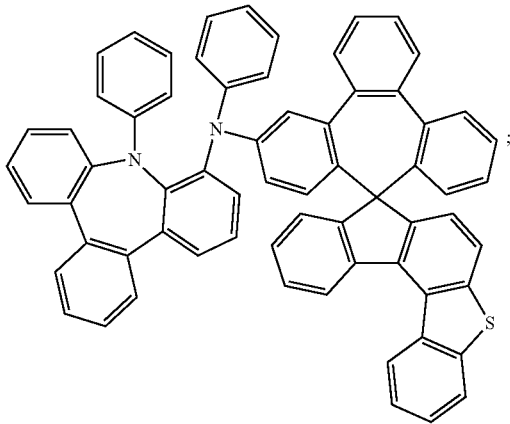
Compound 862
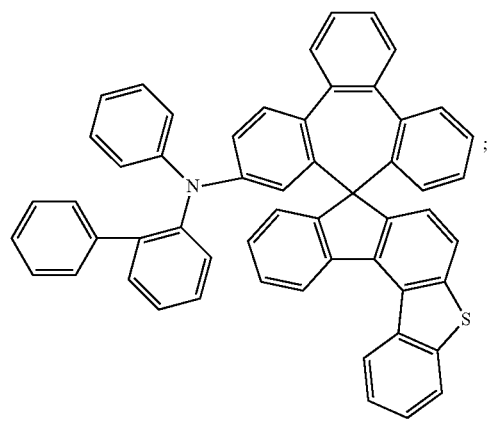
Compound 863
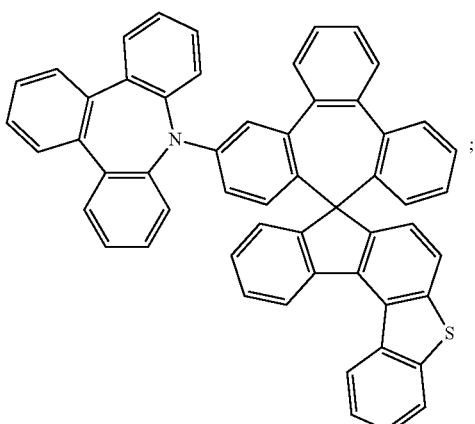
Compound 864
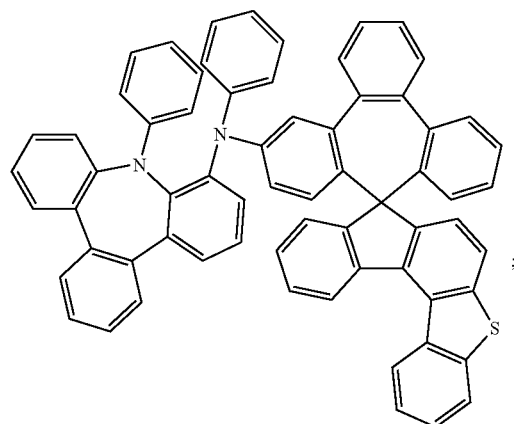
Compound 865
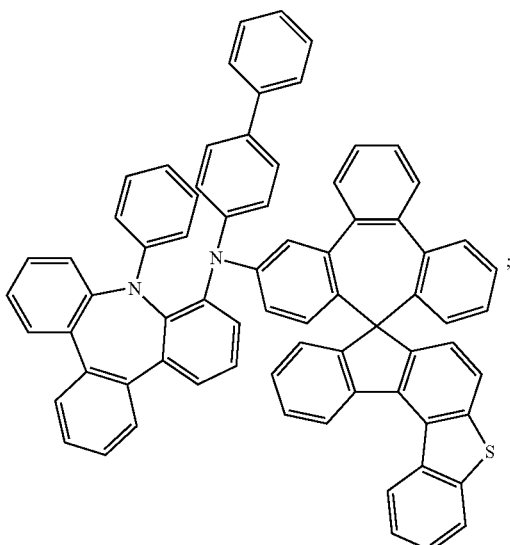

-continued
Compound 866
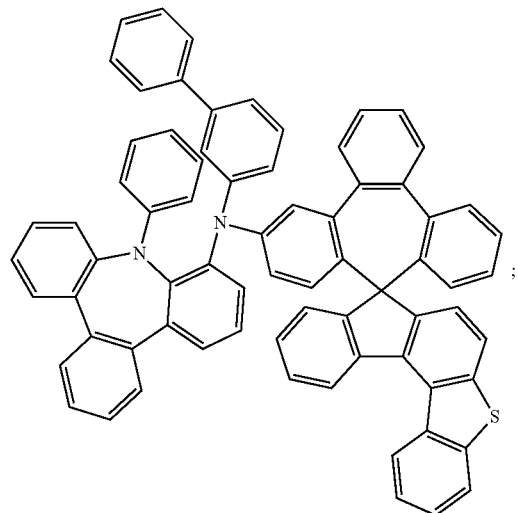
Compound 867
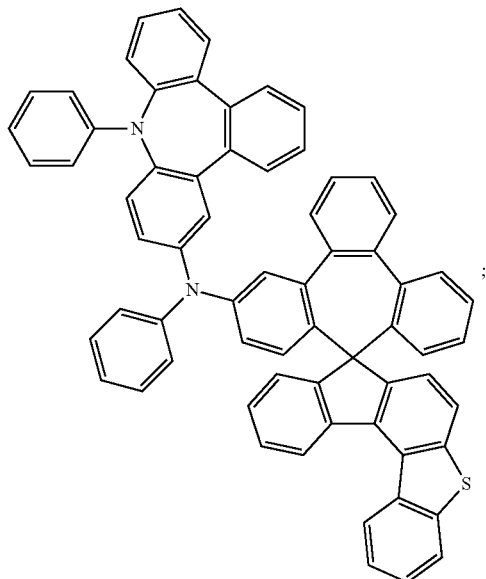
Compound 868
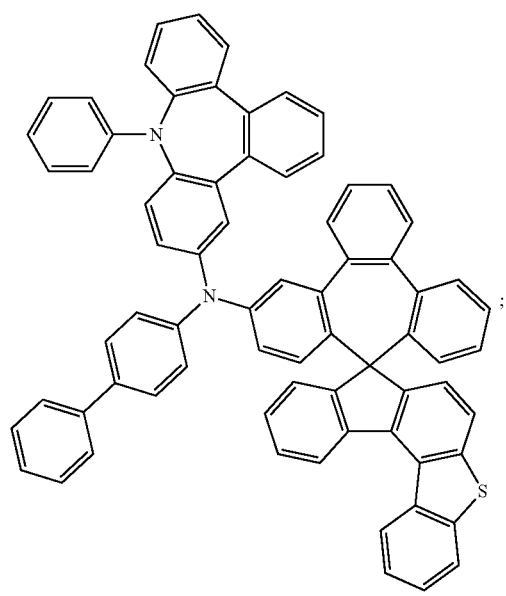
Compound 869
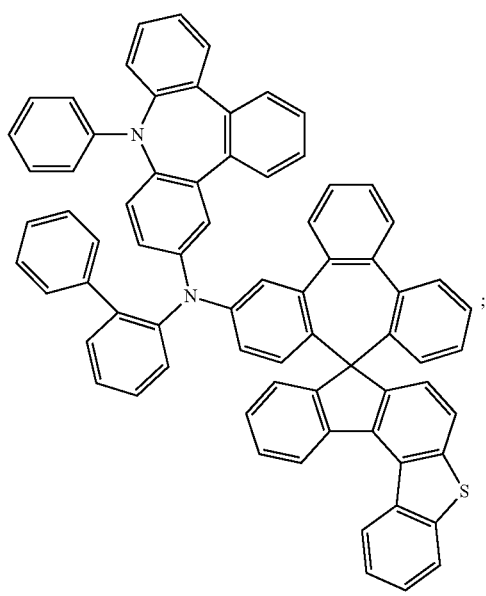

-continued
Compound 870
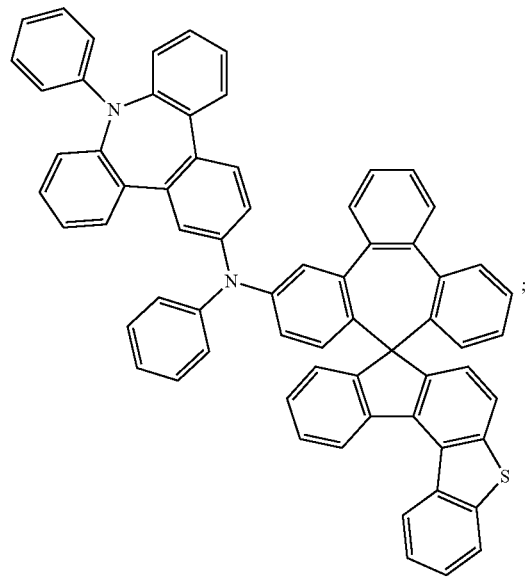
Compound 871
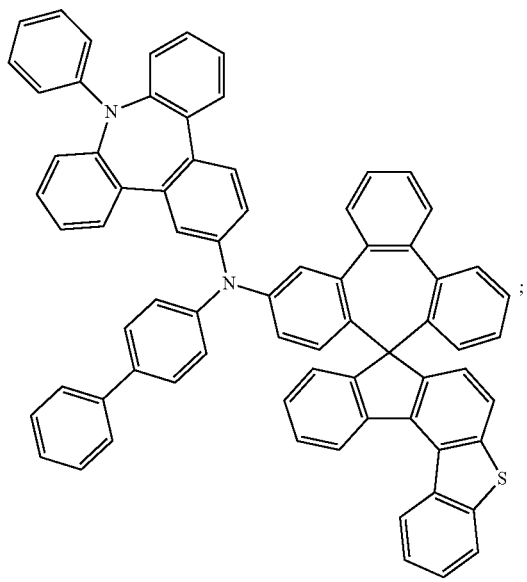
Compound 872
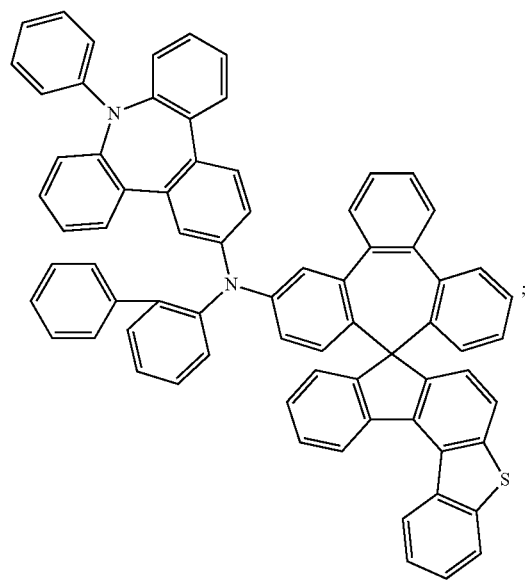
Compound 873
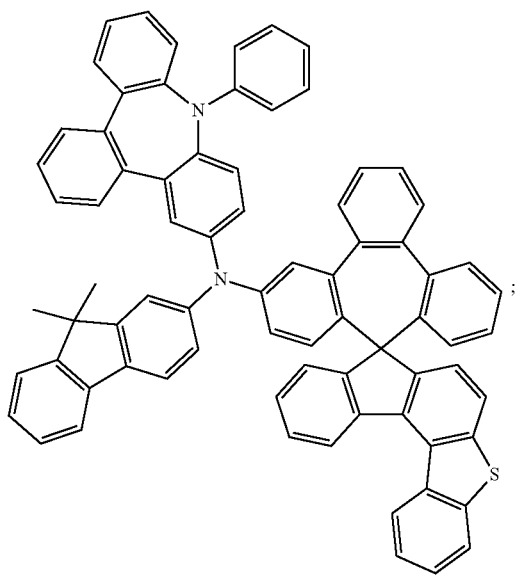

Compound 874
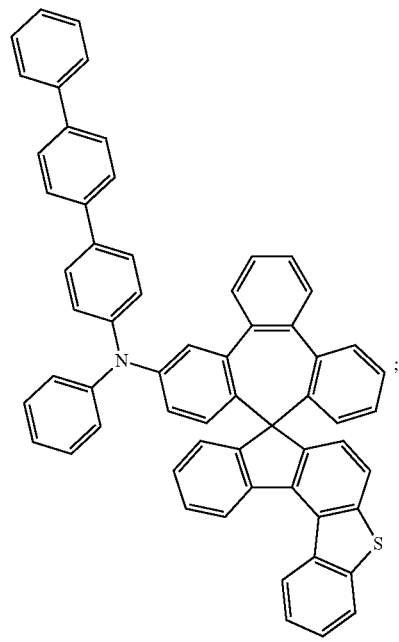
Compound 875
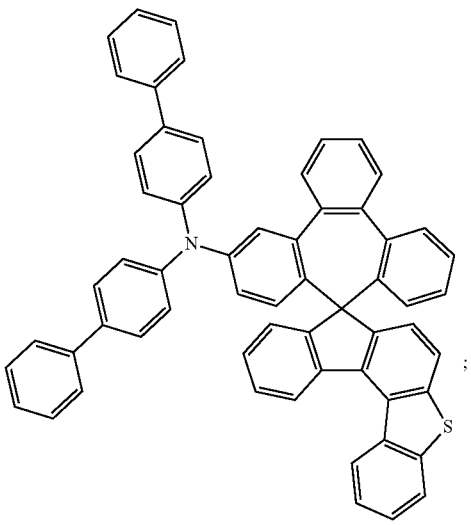
Compound 876
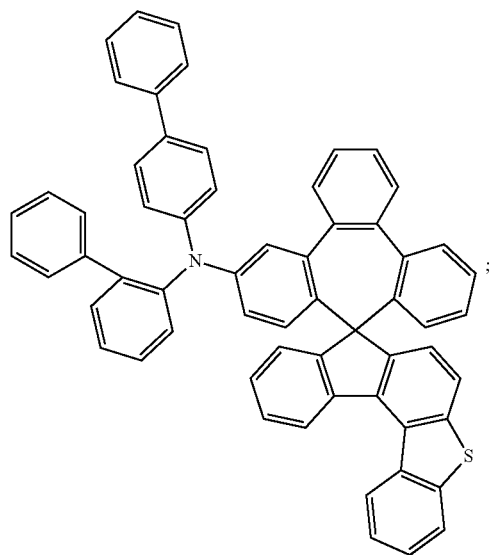
Compound 877
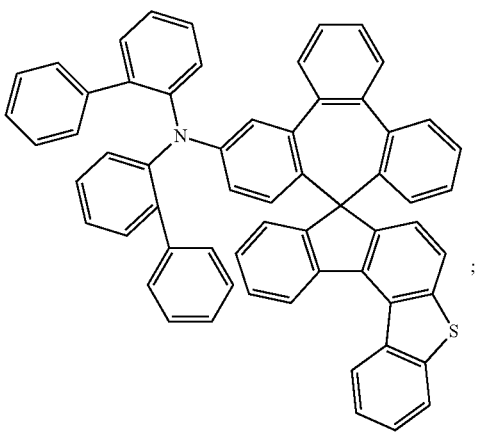

-continued
Compound 878
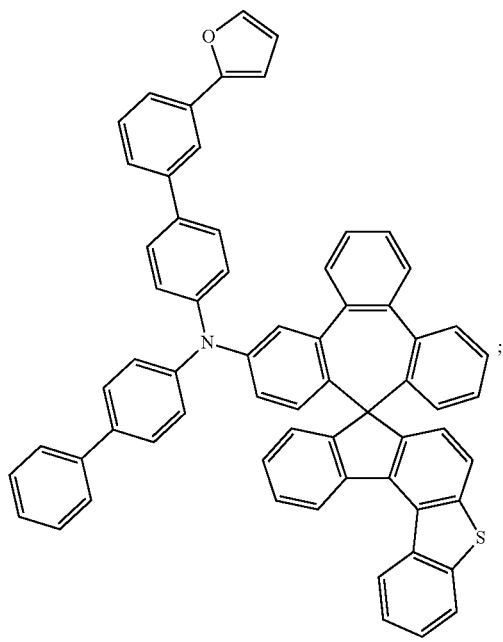
Compound 879
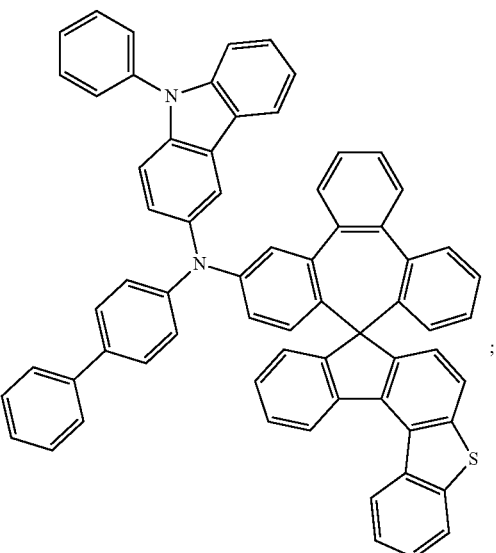
Compound 880
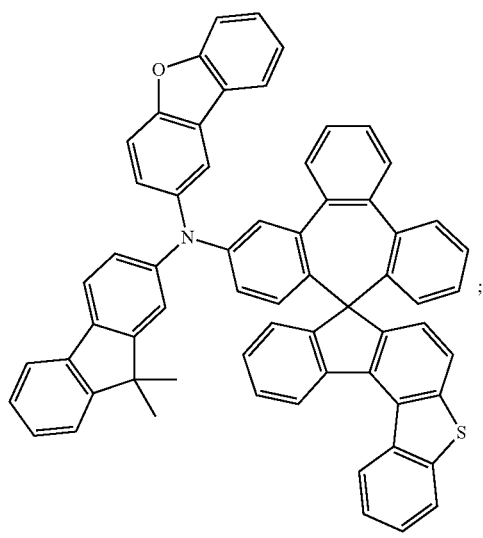
Compound 881
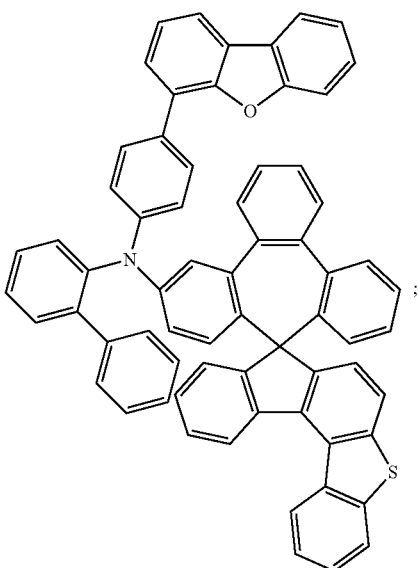

-continued
Compound 882
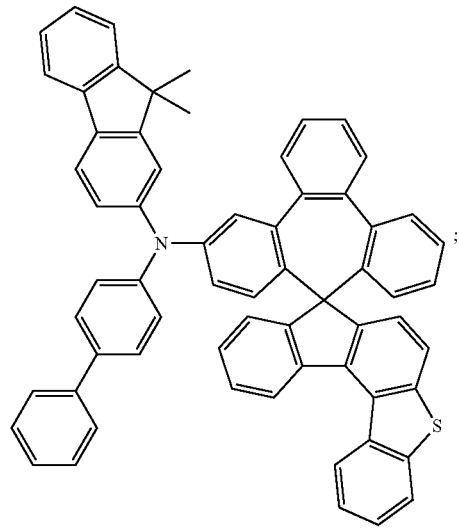
Compound 883
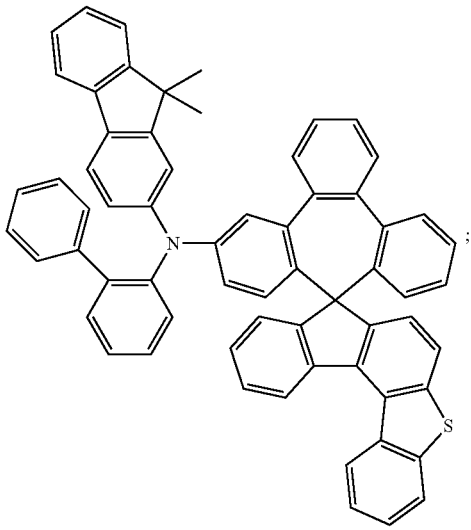
Compound 884
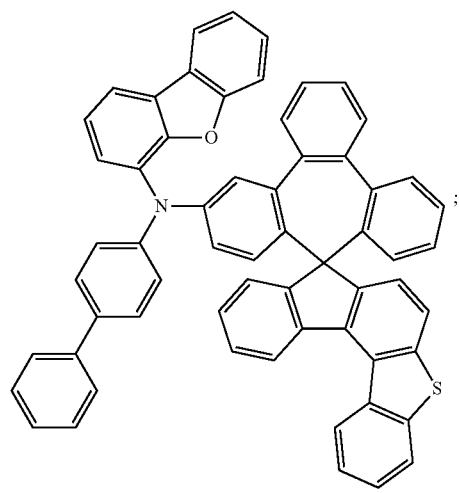
Compound 885
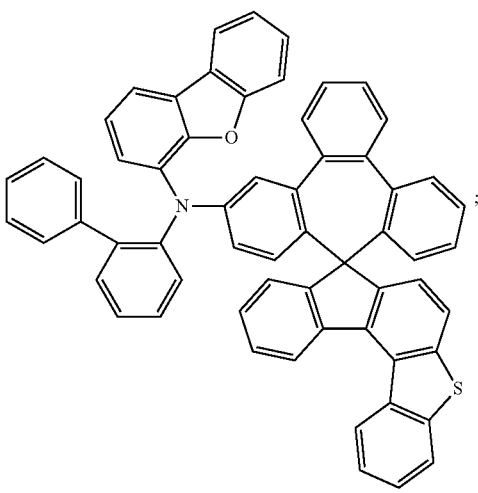
Compound 886
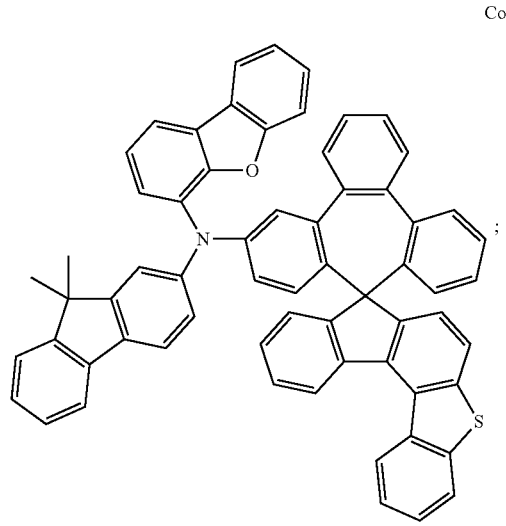
Compound 887
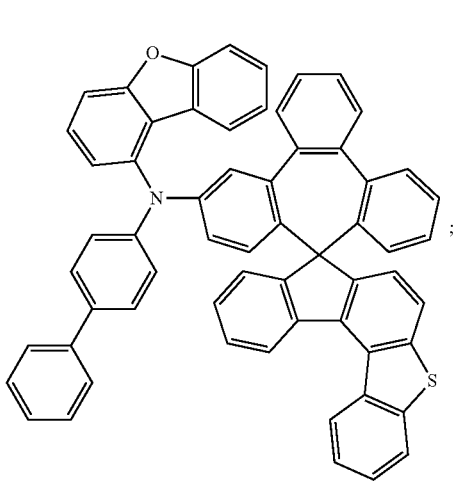

-continued
Compound 888
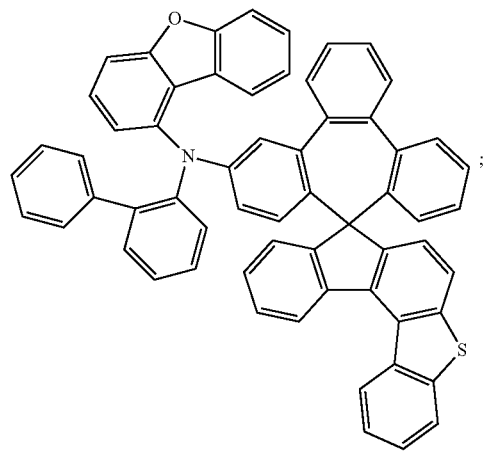
Compound 889
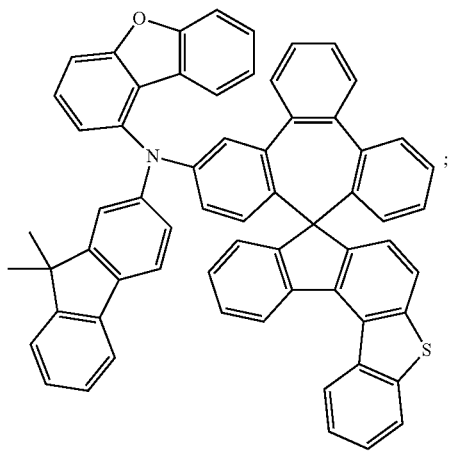
Compound 890
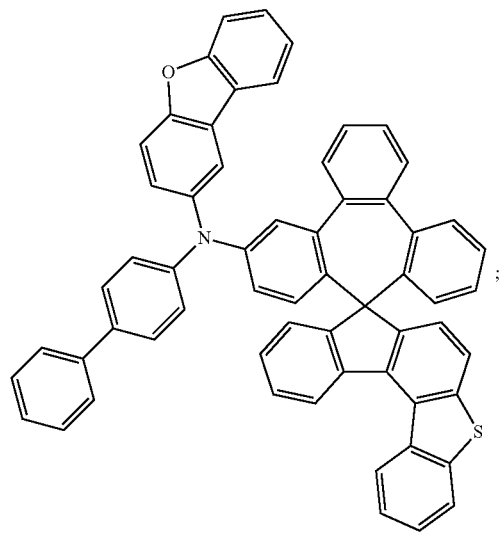
Compound 891
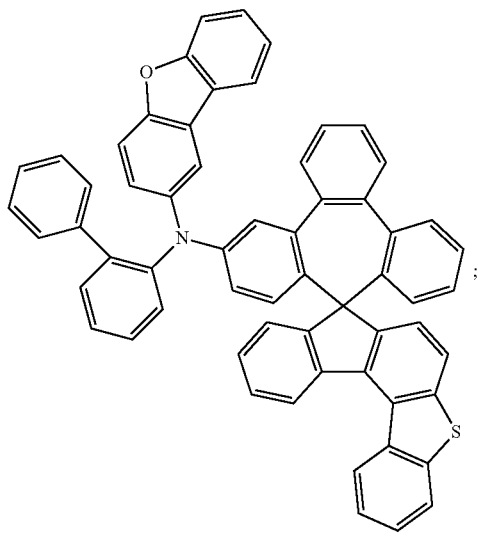
Compound 892
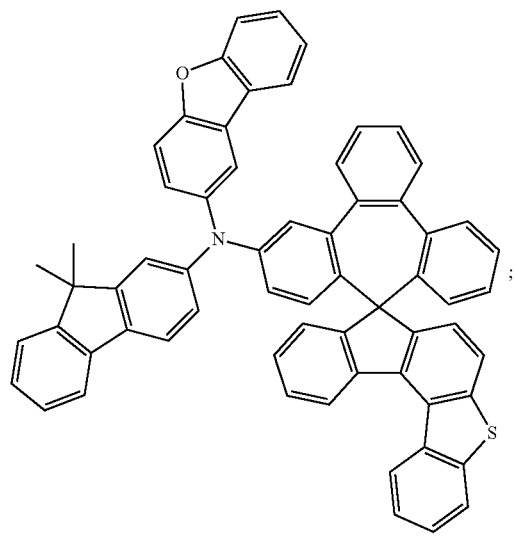
Compound 893
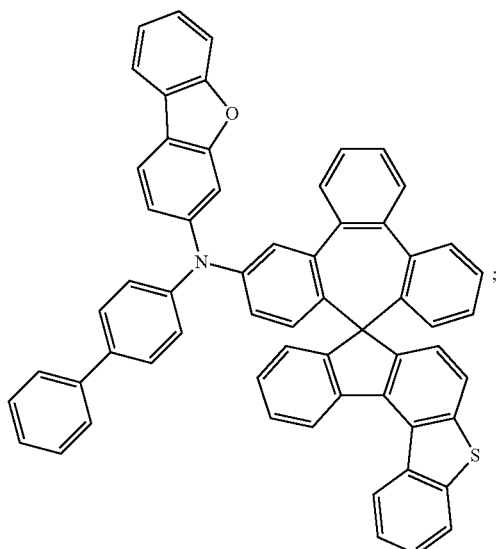

-continued
Compound 894
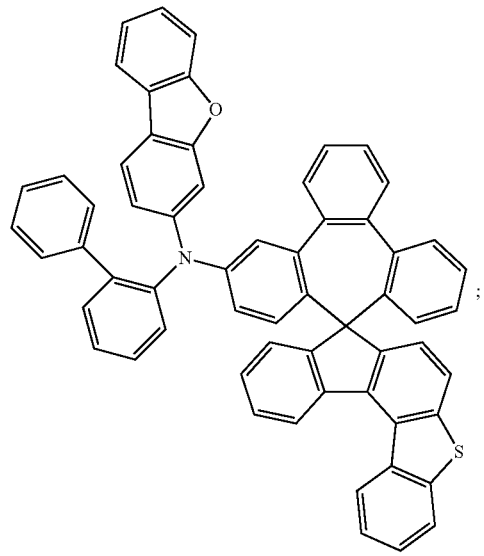
Compound 895
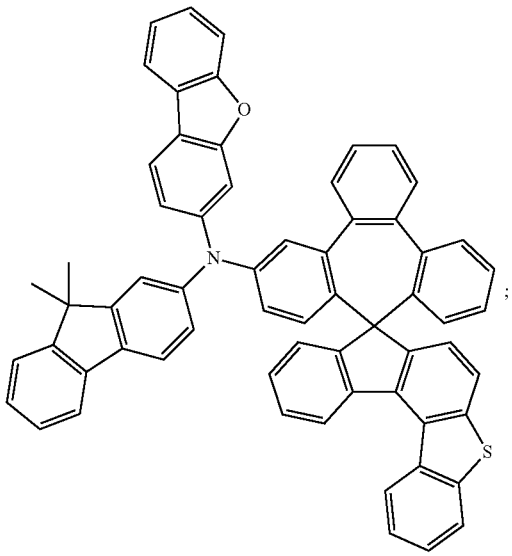
Compound 896
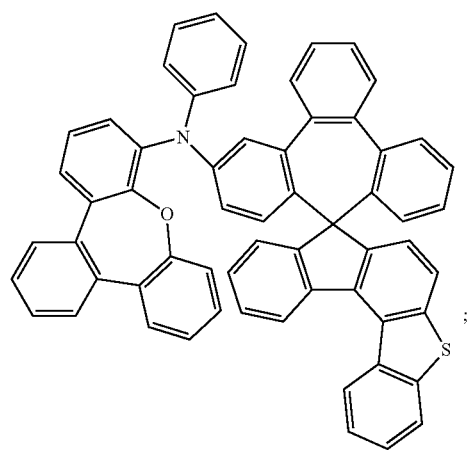
Compound 897
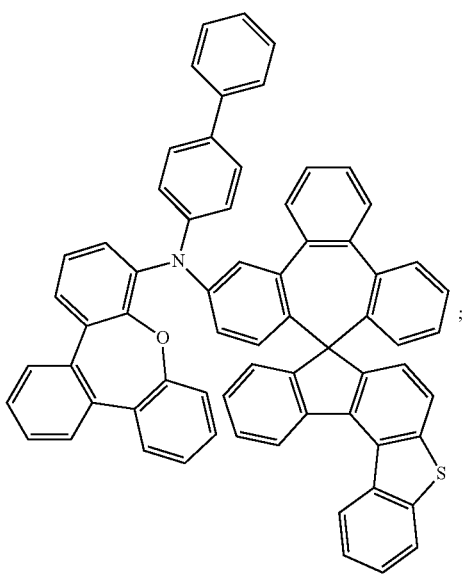

Compound 898
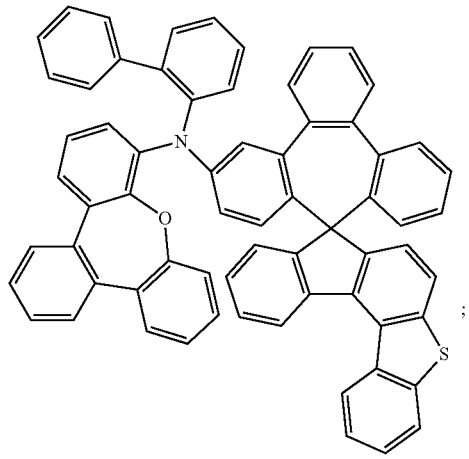
Compound 899
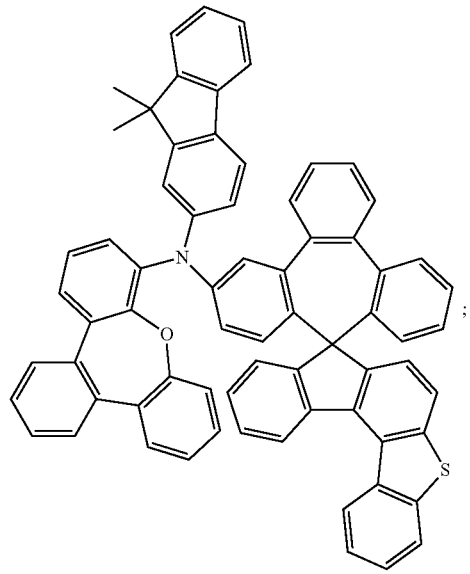
Compound 900
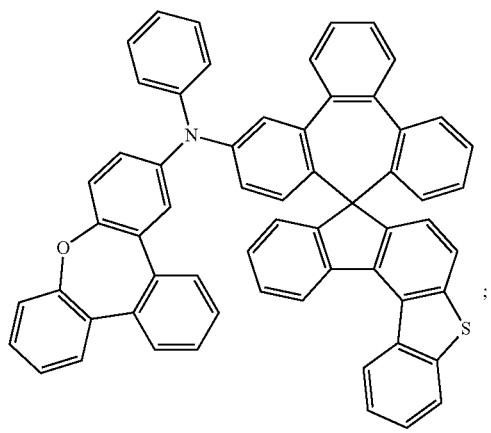
Compound 901
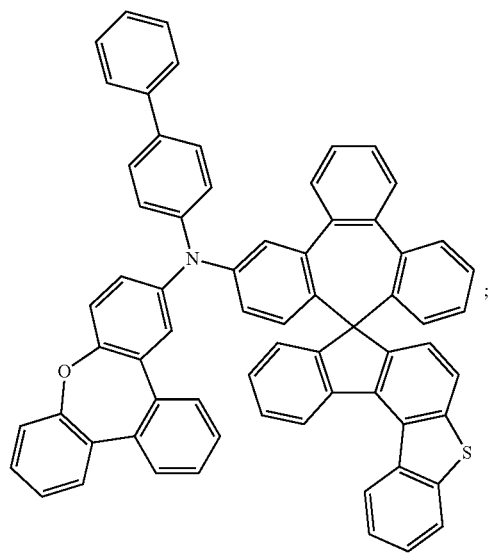

-continued
Compound 902
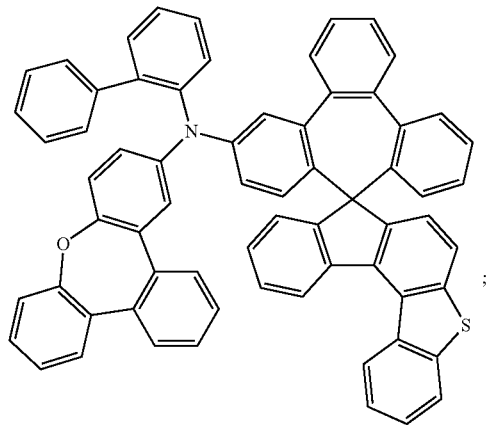
Compound 903
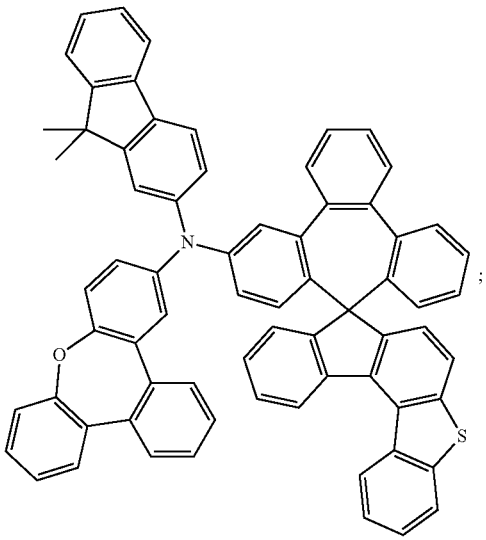
Compound 904
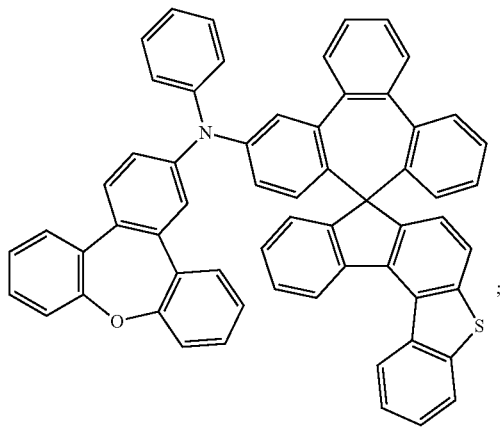
Compound 905
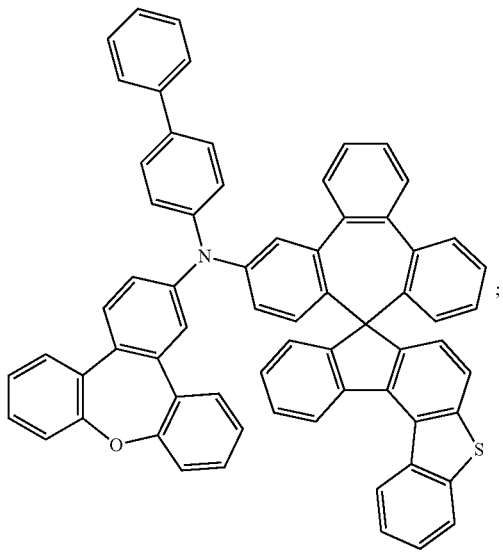

Compound 906
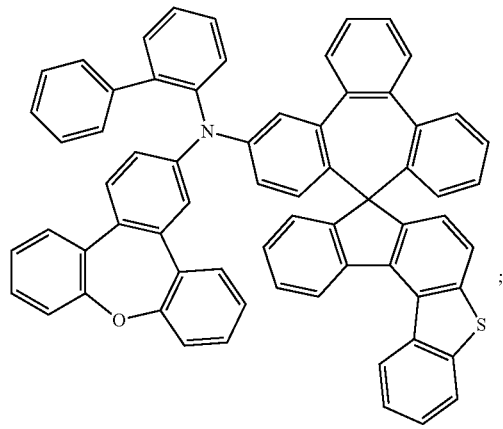
Compound 907
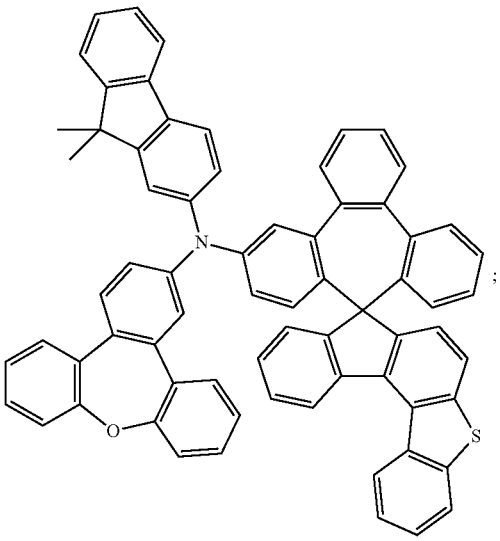
Compound 908
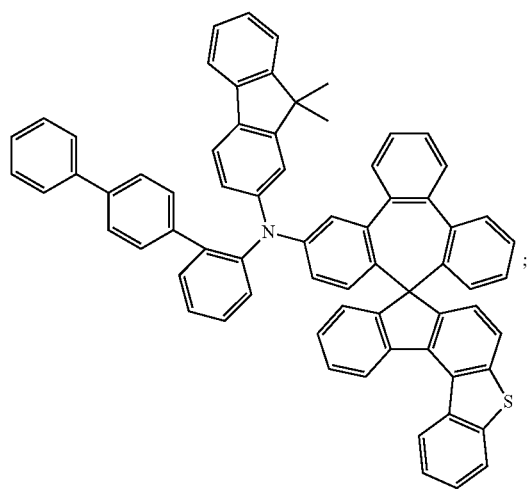
Compound 909
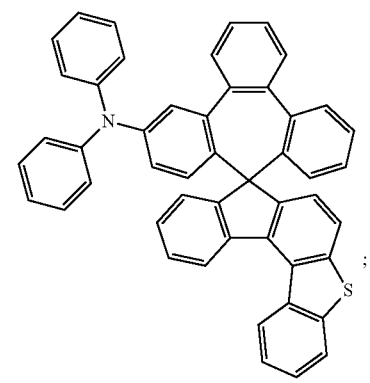
Compound 910
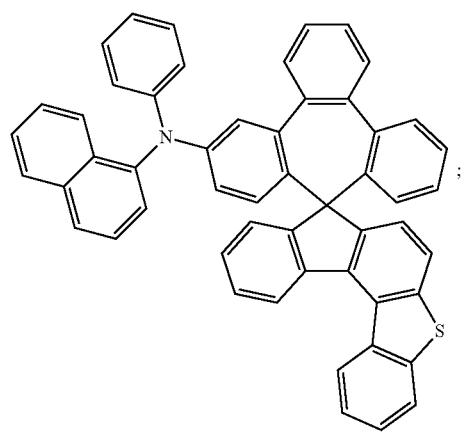
Compound 911
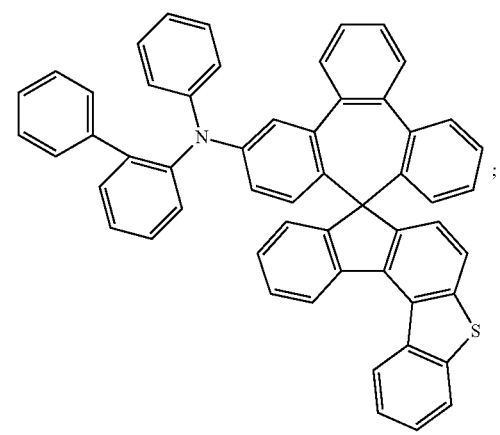

-continued
Compound 912
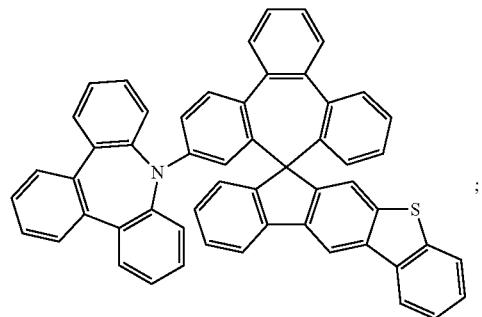
Compound 913
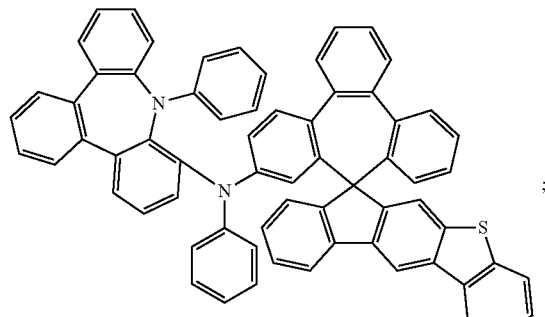
Compound 914
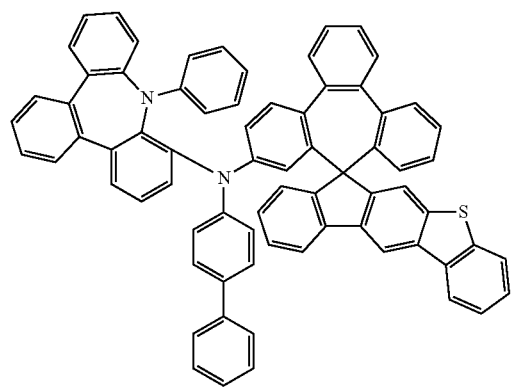
Compound 915
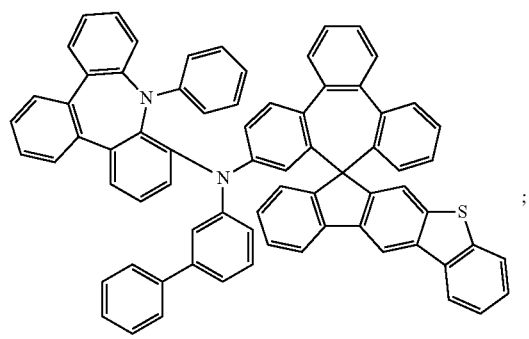
Compound 916
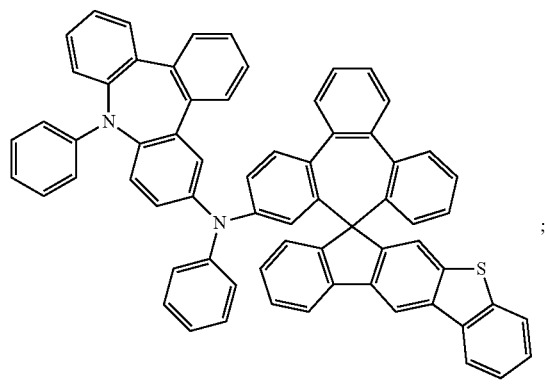
Compound 917
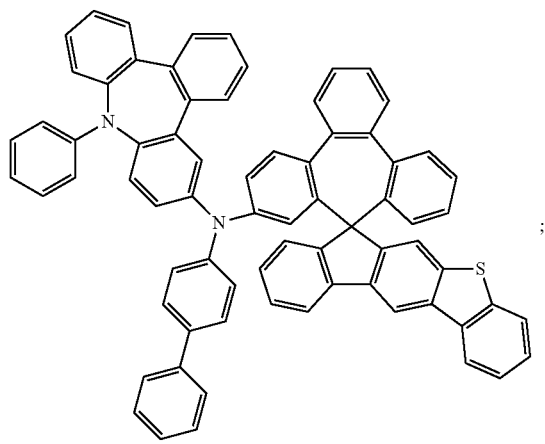
Compound 918
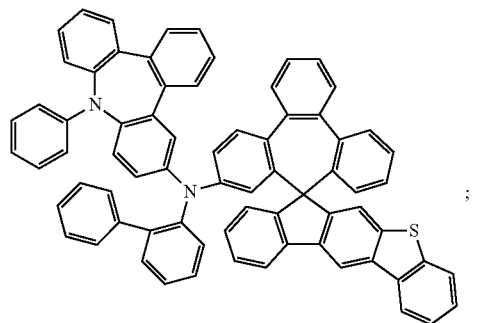
Compound 919
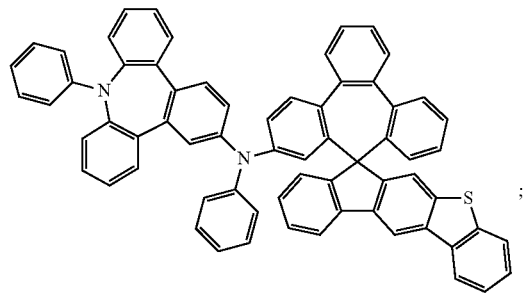

Compound 920
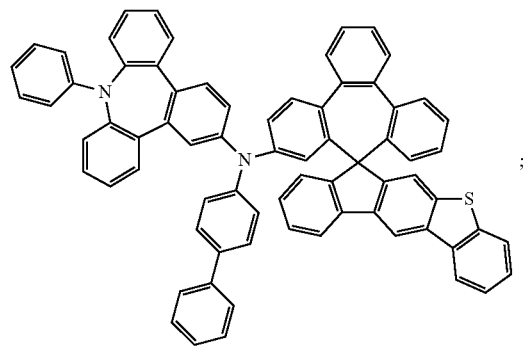
Compound 921
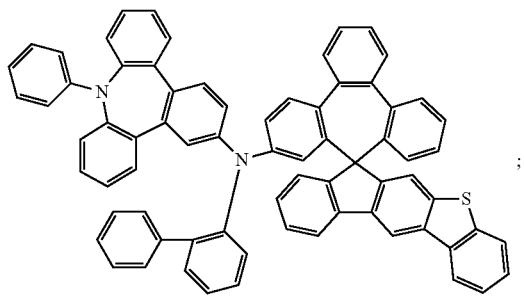
;
Compound 922
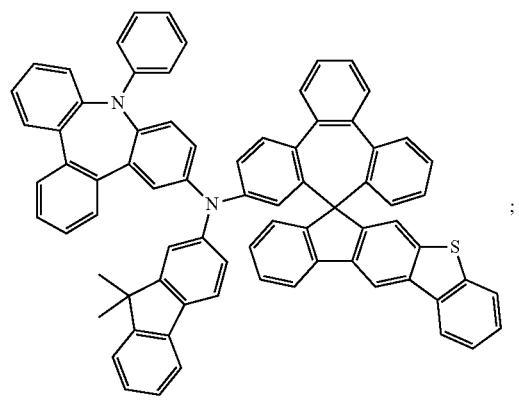
;
Compound 923
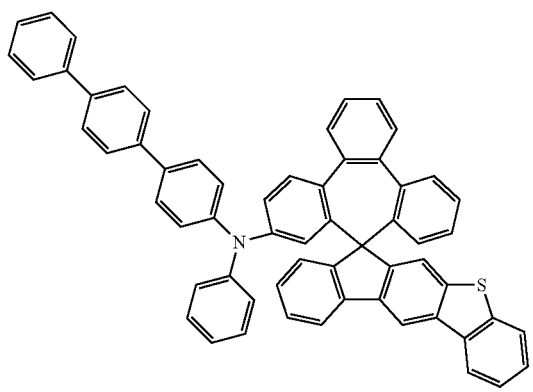
;
Compound 924
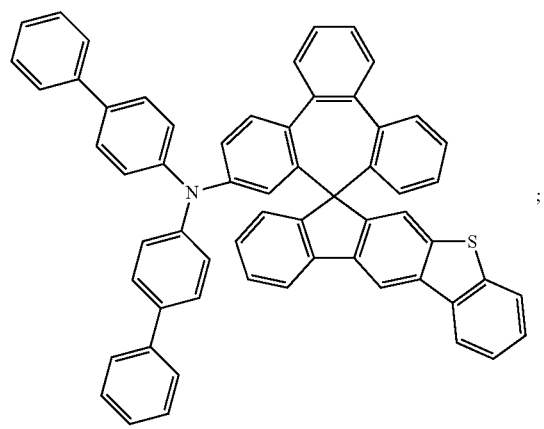
;
Compound 925
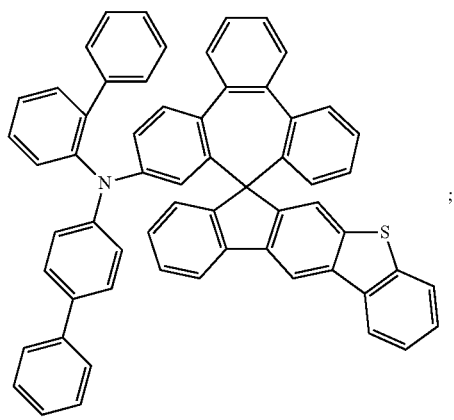
;

-continued
Compound 926
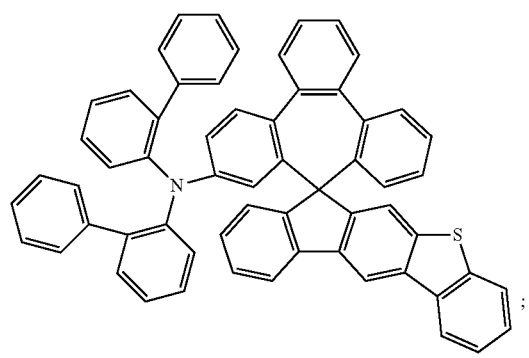
Compound 927
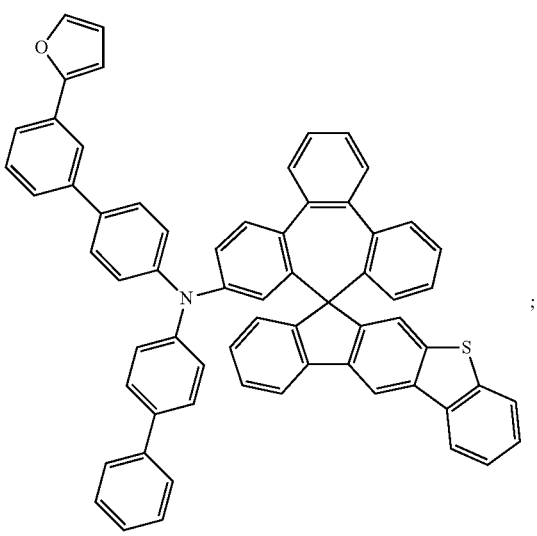
Compound 928
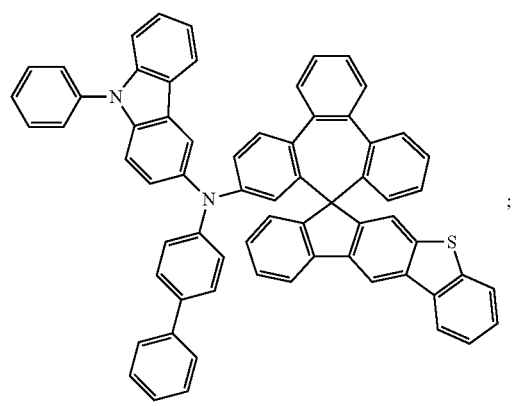
Compound 929
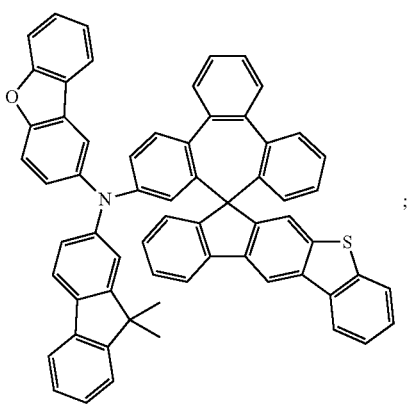
Compound 930
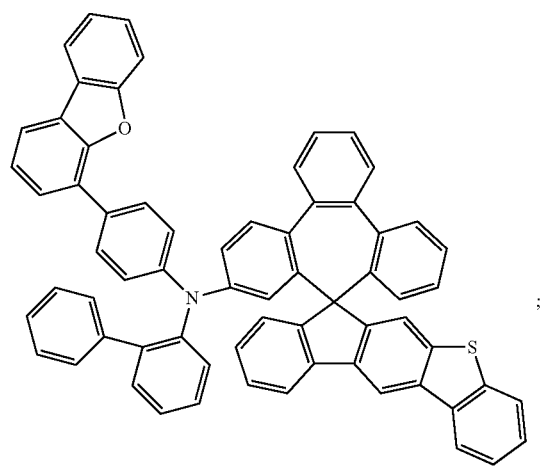
Compound 931
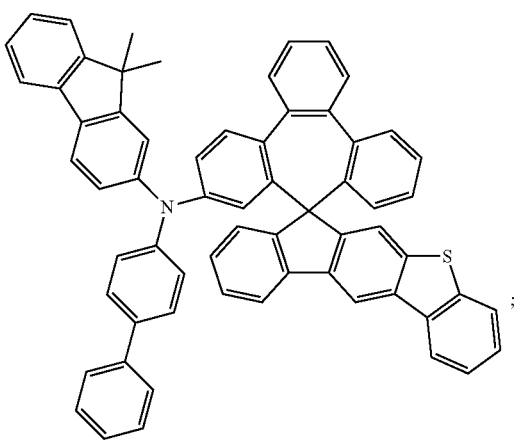

-continued
Compound 932
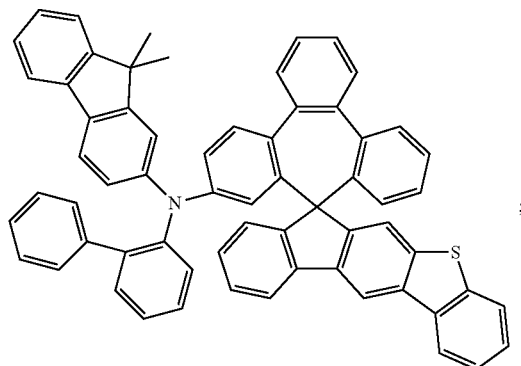
Compound 933
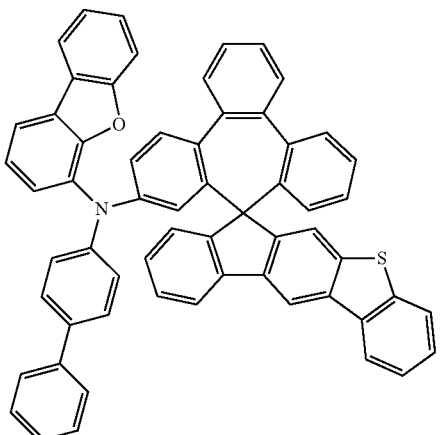
Compound 934
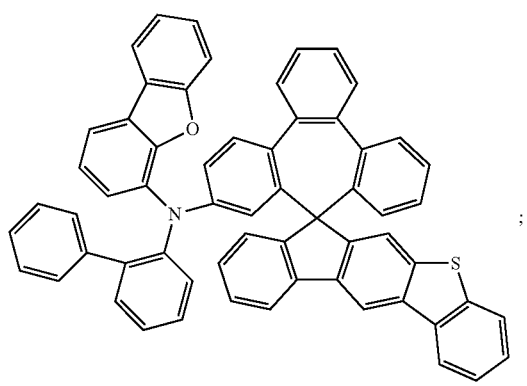
Compound 935
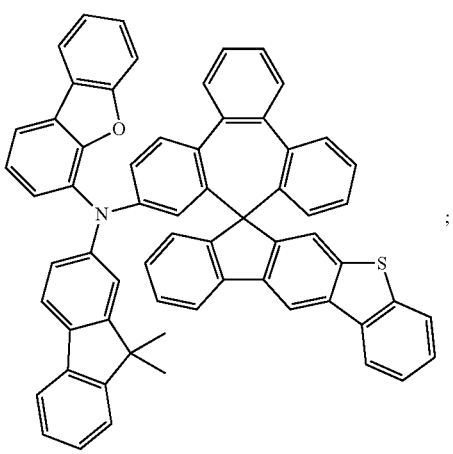
Compound 936
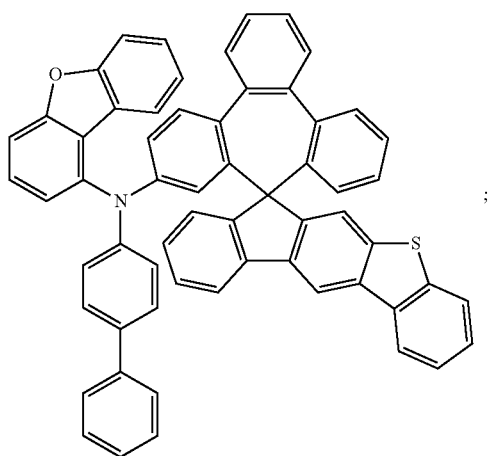
Compound 937
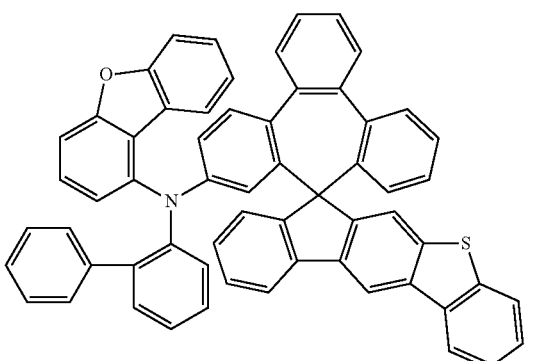

-continued
Compound 938
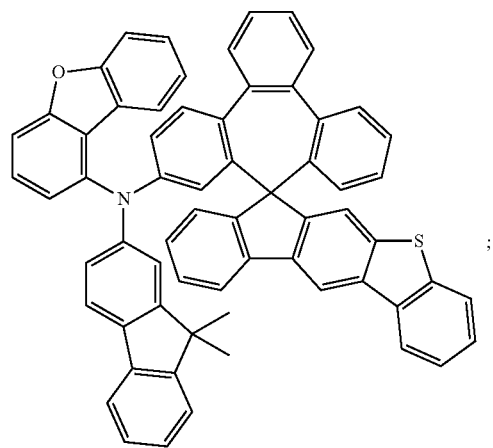
Compound 939
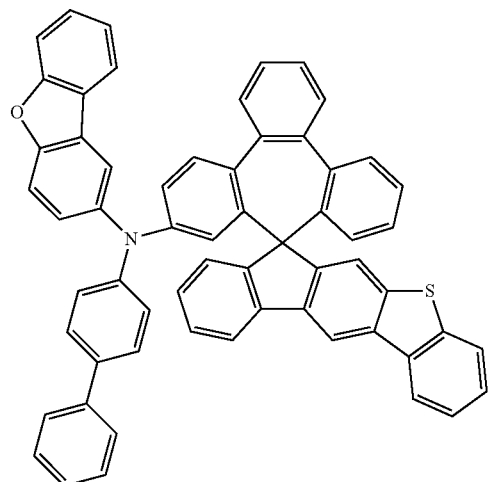
Compound 940
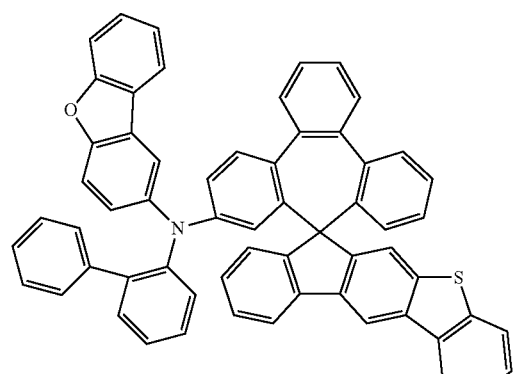
Compound 941
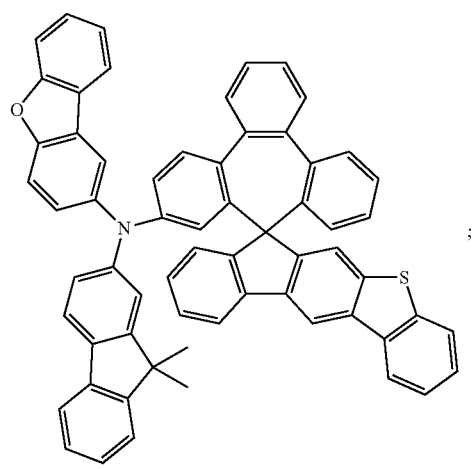
Compound 942
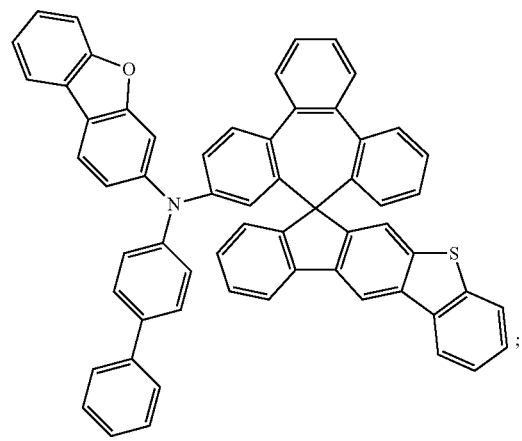
Compound 943
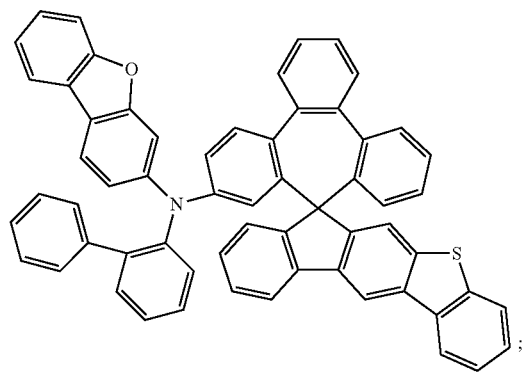

-continued
Compound 944
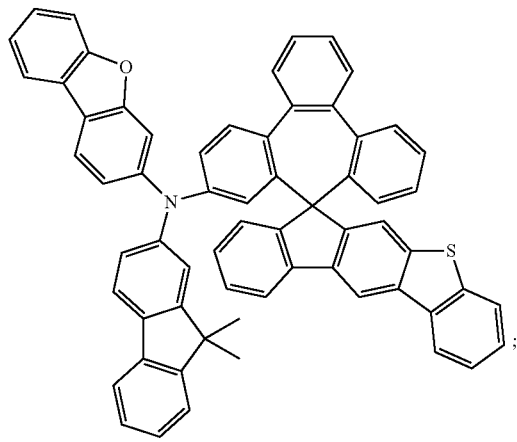
Compound 945
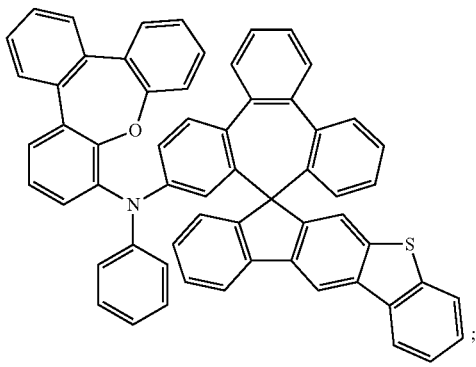
Compound 946
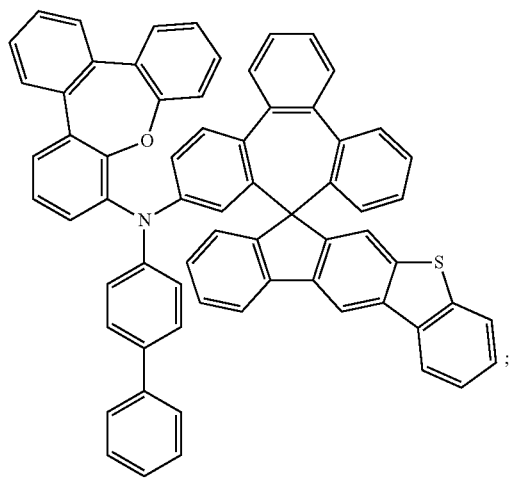
Compound 947
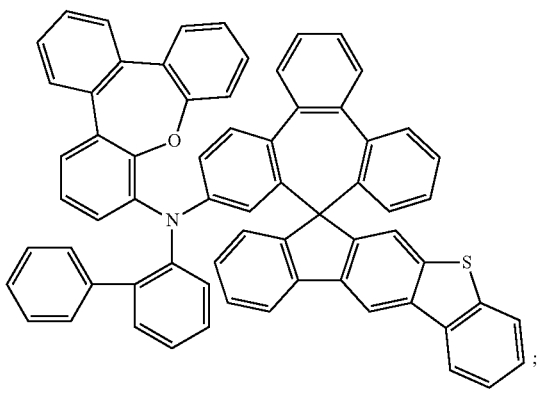
Compound 948
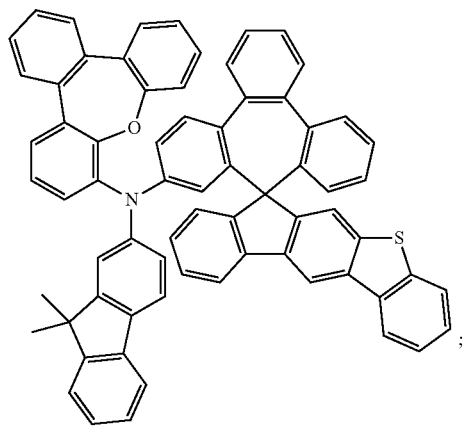
Compound 949
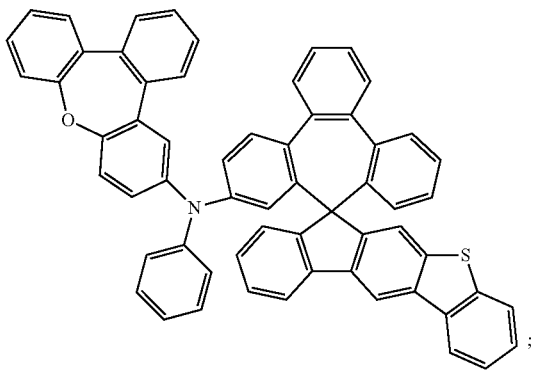

Compound 950
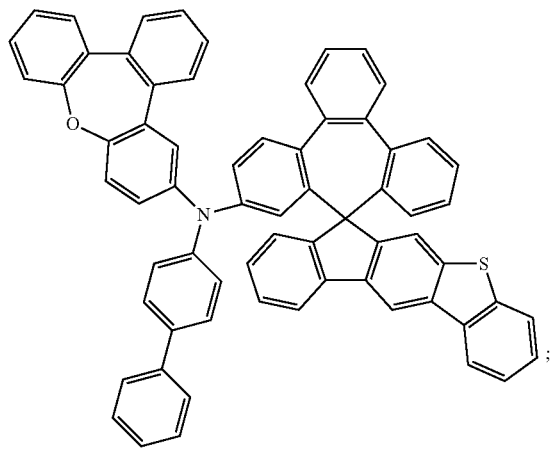
Compound 951
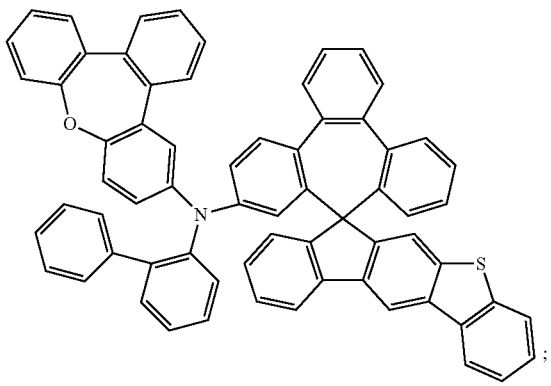
Compound 952
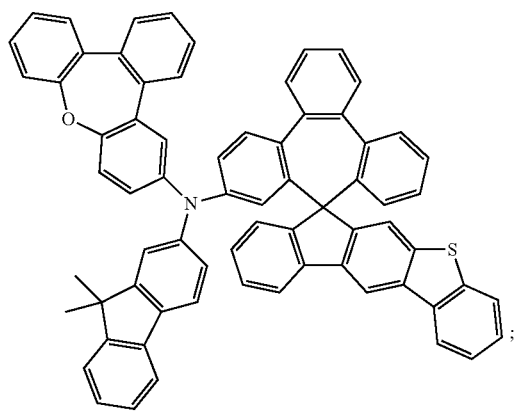
Compound 953
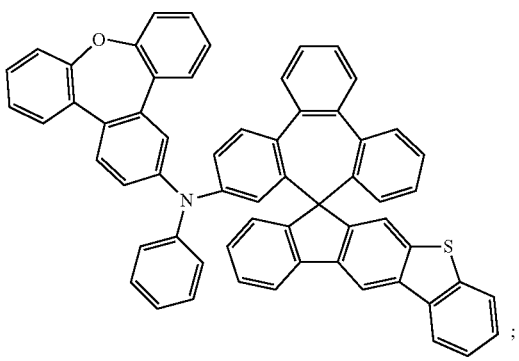
Compound 954
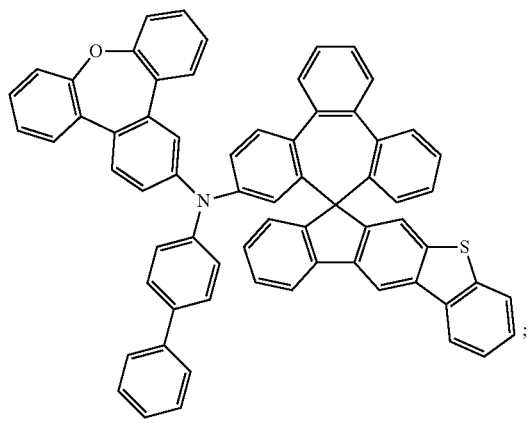
Compound 955
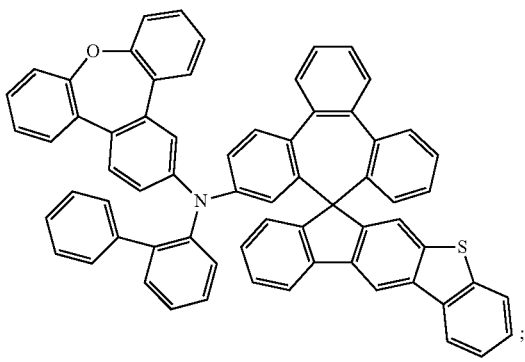

-continued
Compound 956
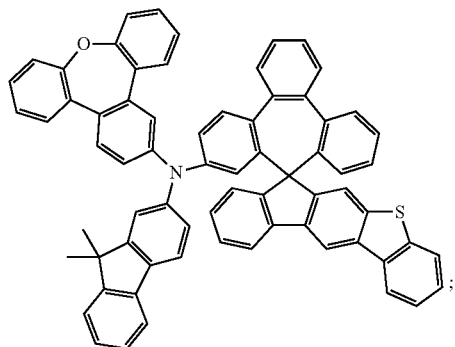
Compound 957
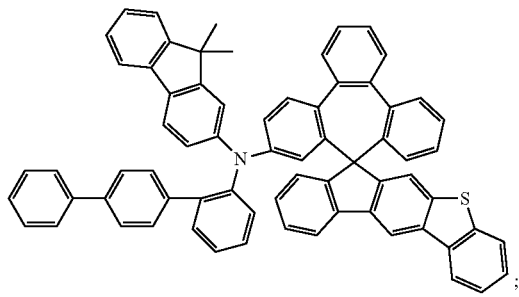
Compound 958
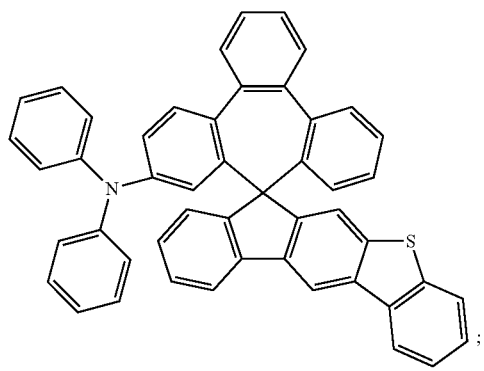
Compound 959
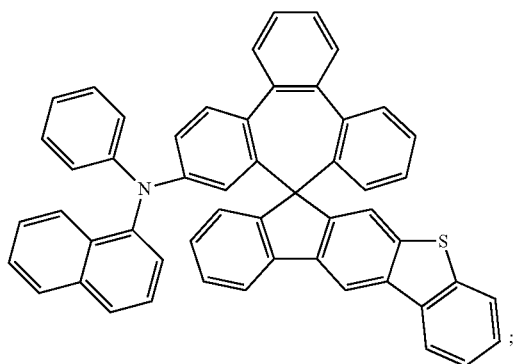
Compound 960
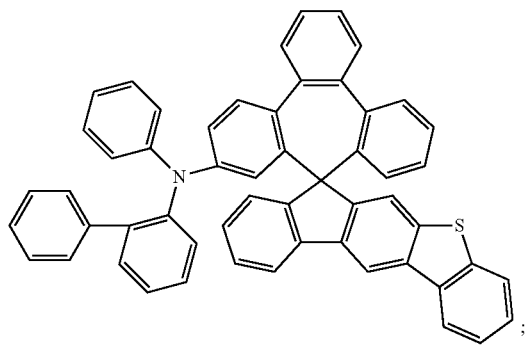
Compound 961
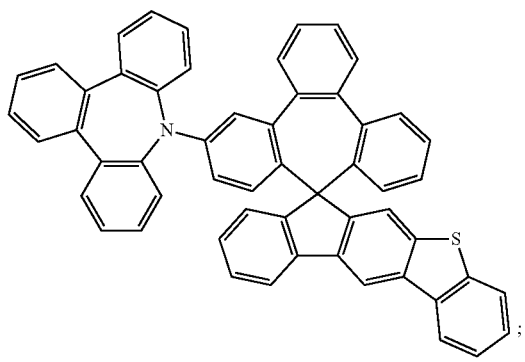
Compound 962
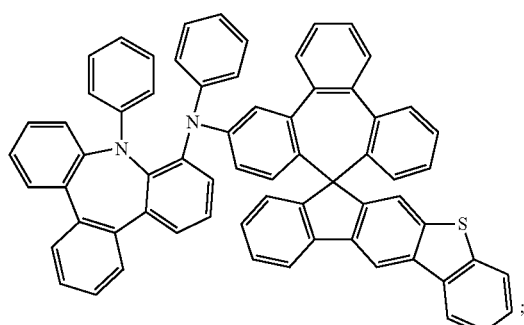
Compound 963
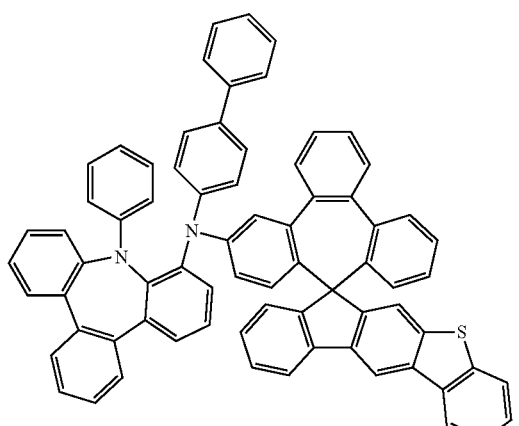

-continued
Compound 964
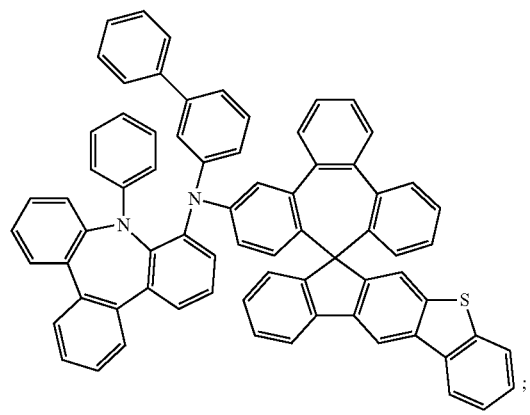
Compound 965
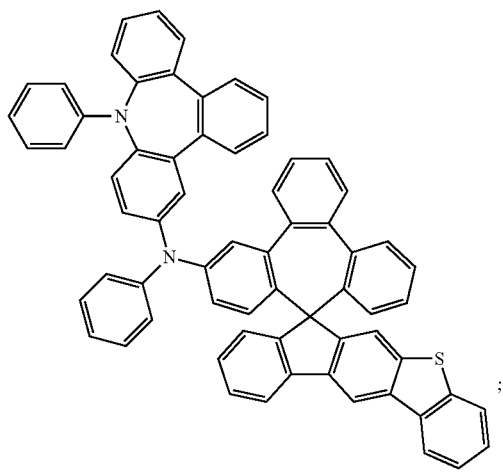
Compound 966
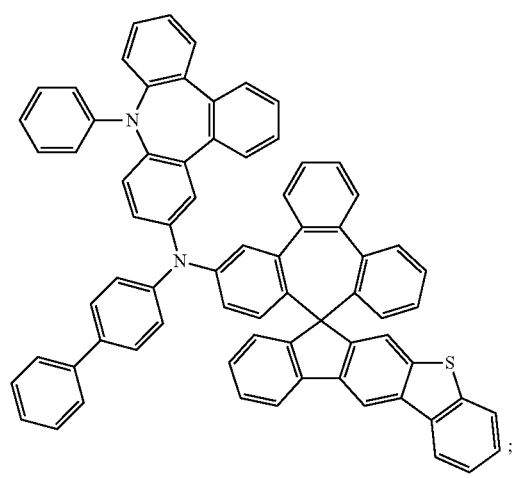
Compound 967
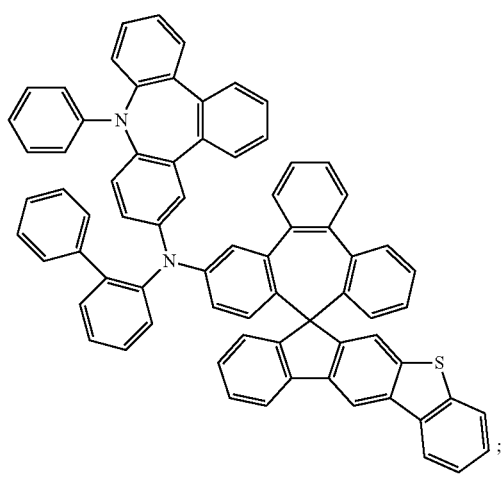
Compound 968
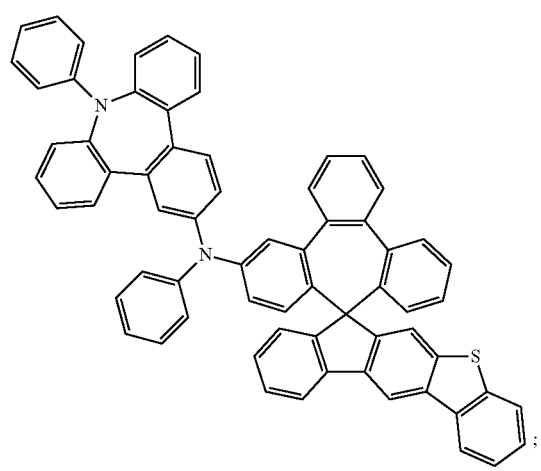
Compound 969
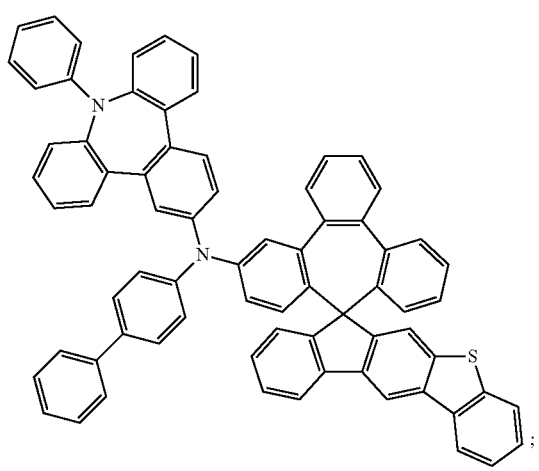

-continued
Compound 970
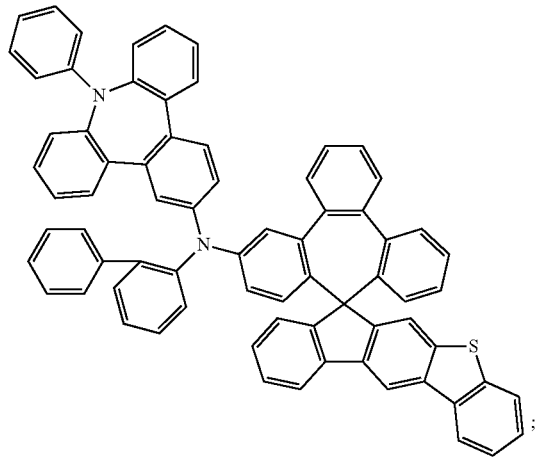
Compound 971
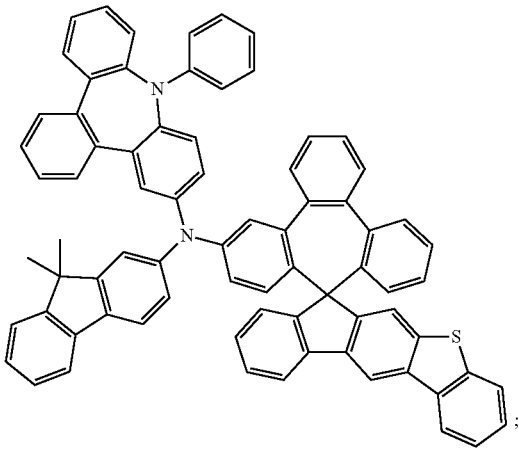
Compound 972
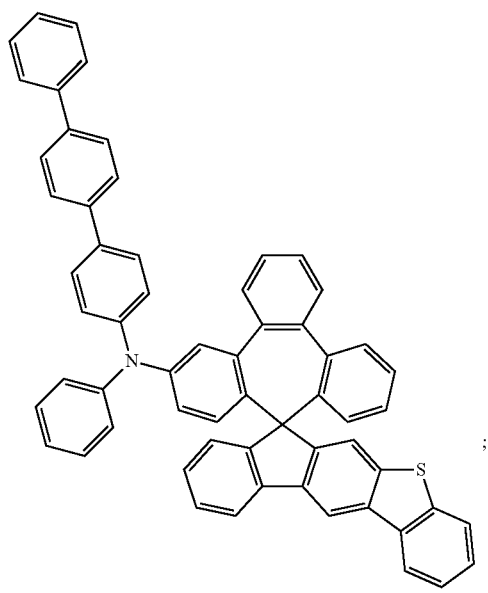
Compound 973
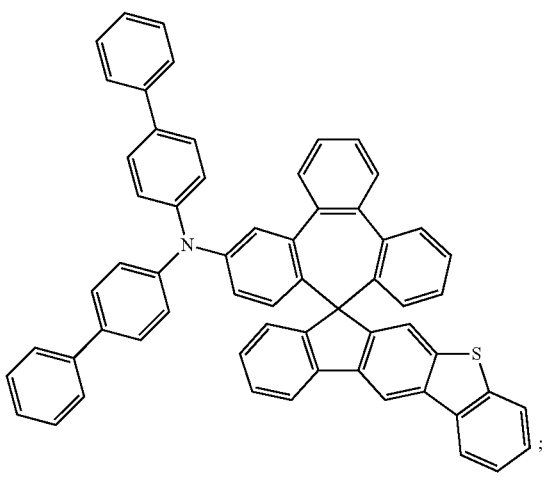
Compound 974
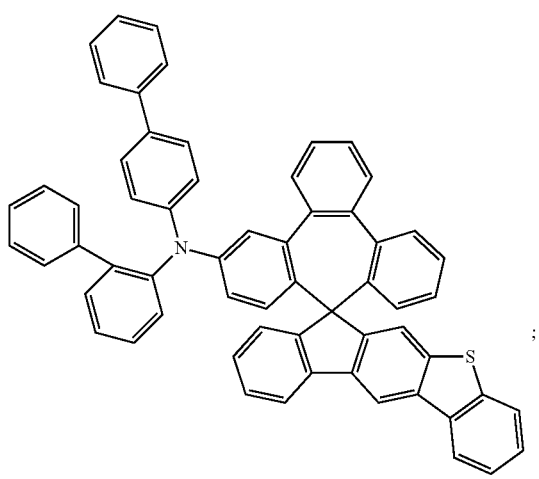
Compound 975
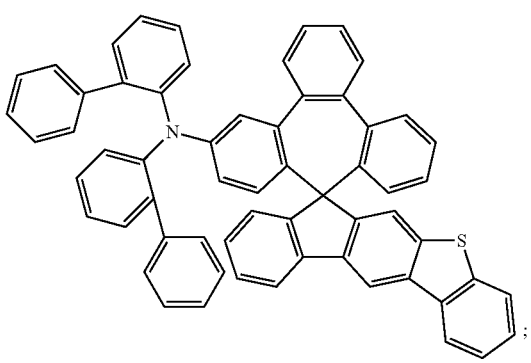

-continued
Compound 976
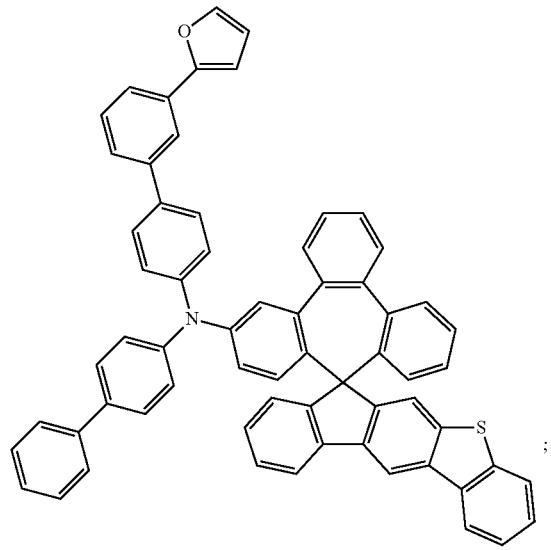
Compound 977
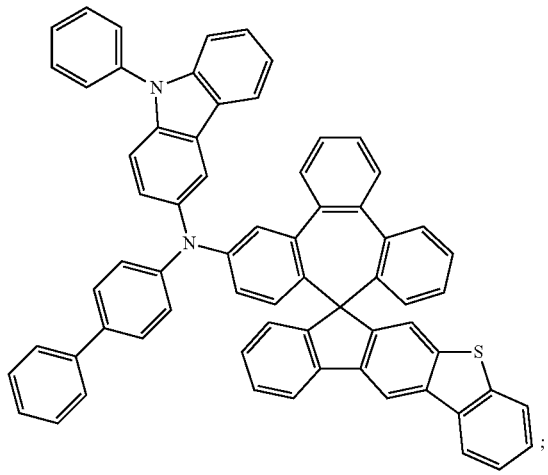
Compound 978
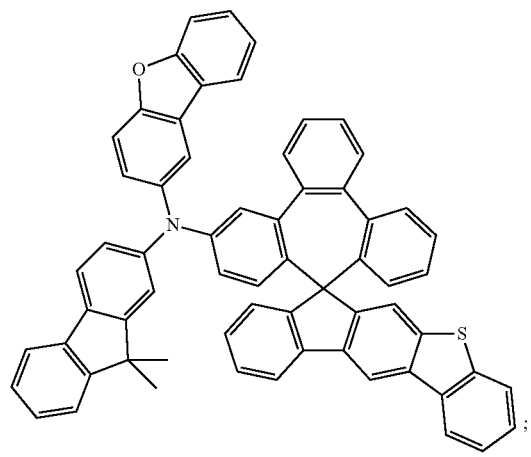
Compound 979
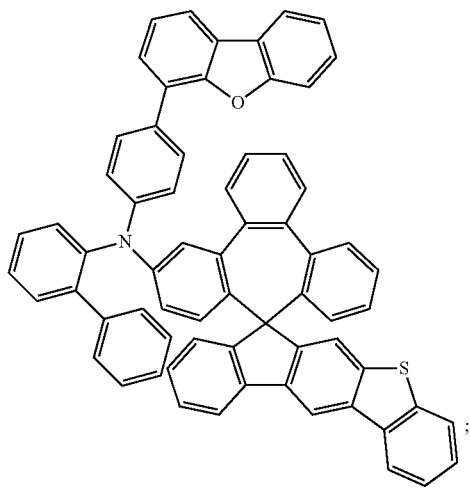
Compound 980
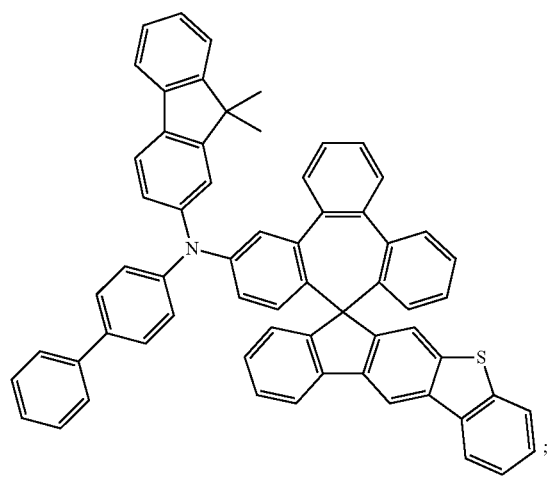
Compound 981
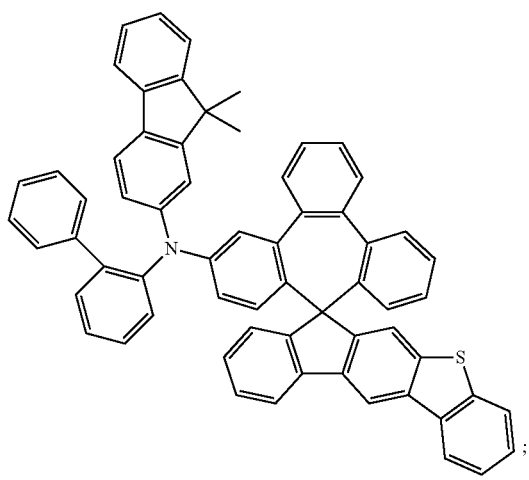

Compound 982
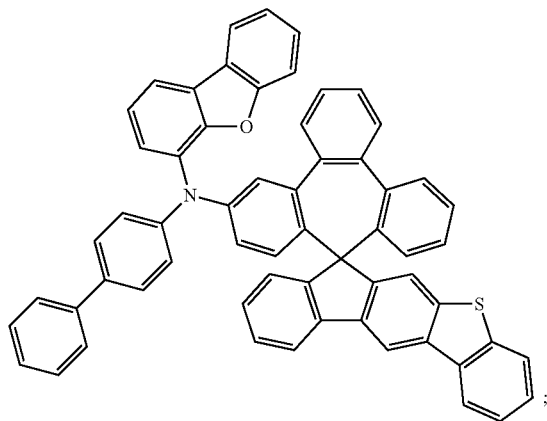
Compound 983
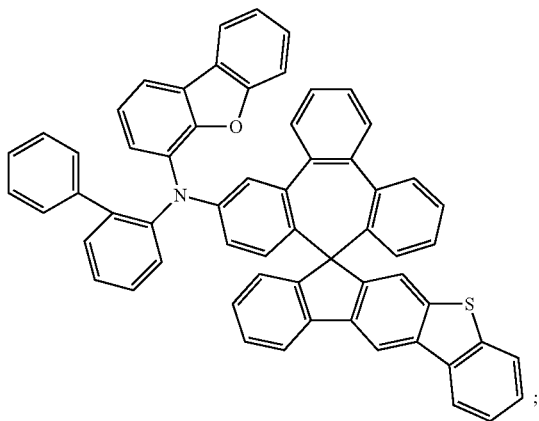
Compound 984
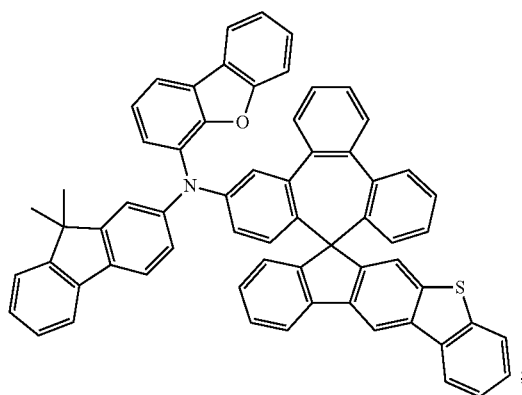
Compound 985
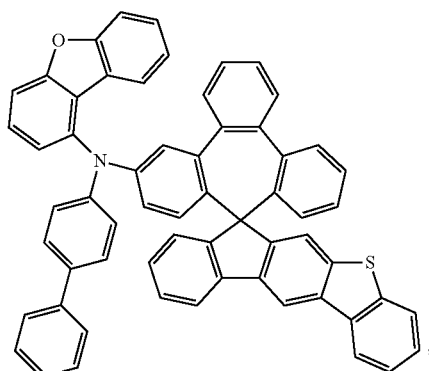
Compound 986
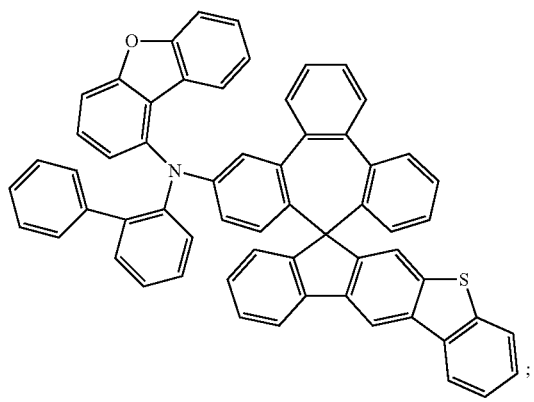
Compound 987
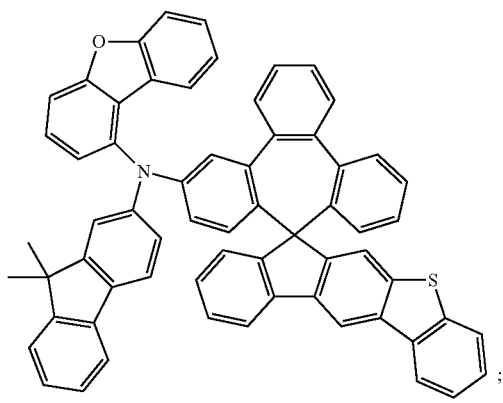

-continued
Compound 988
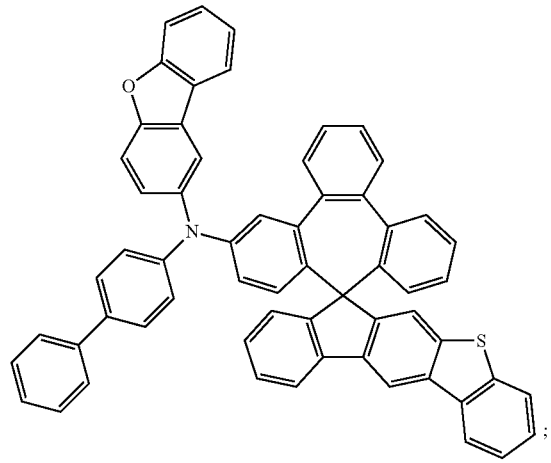
Compound 989
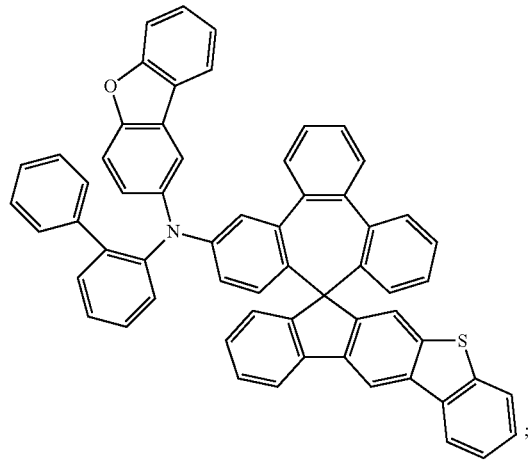
Compound 990
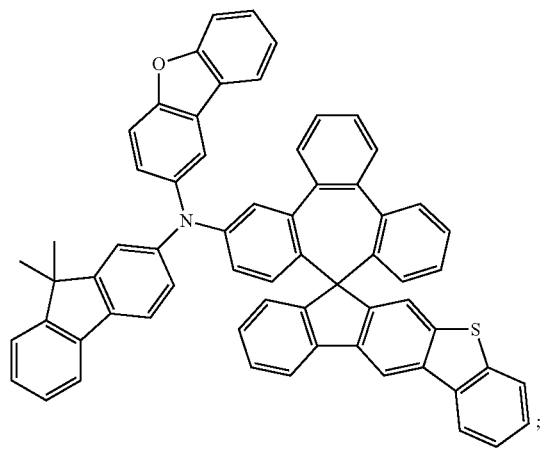
Compound 991
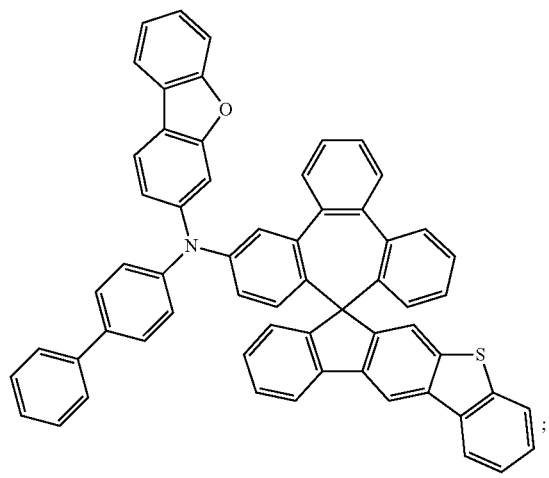
Compound 992
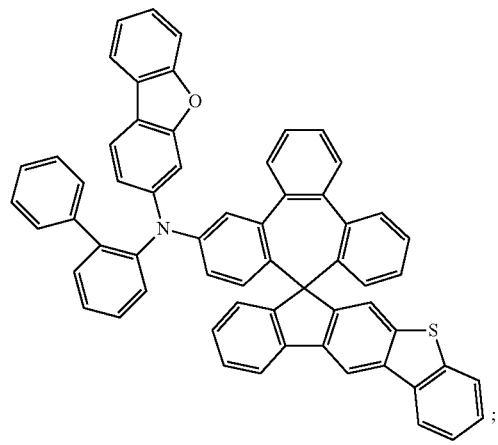
Compound 993
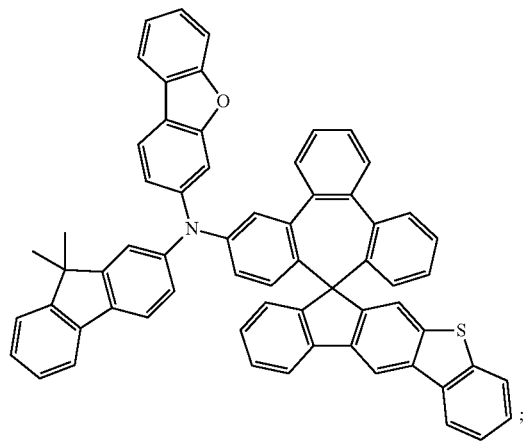

Compound 994
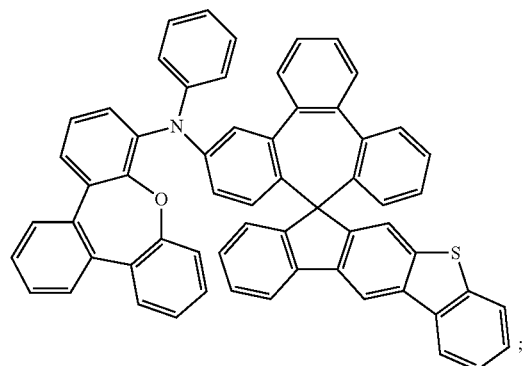
Compound 995
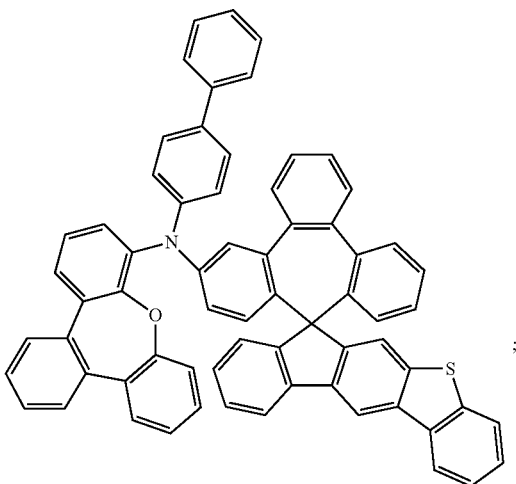
Compound 996
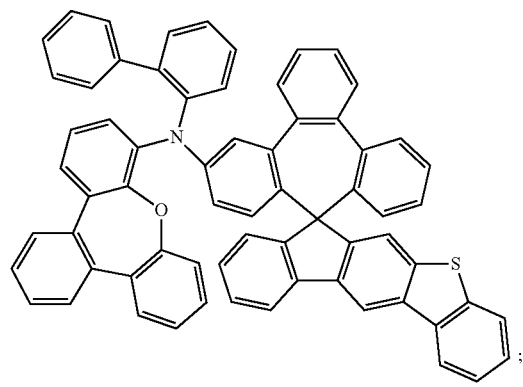
Compound 997
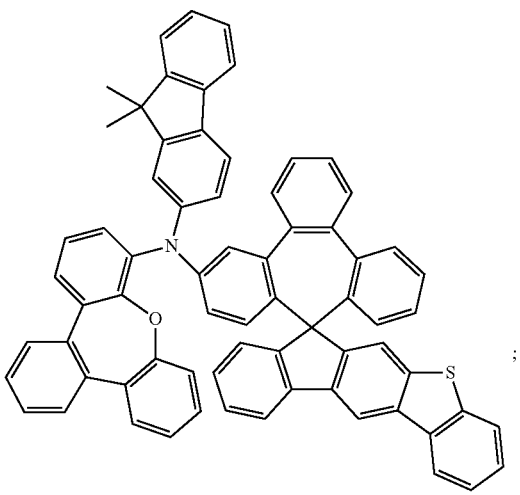
Compound 998
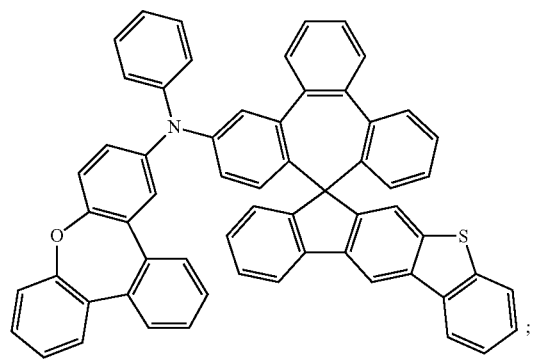
Compound 999
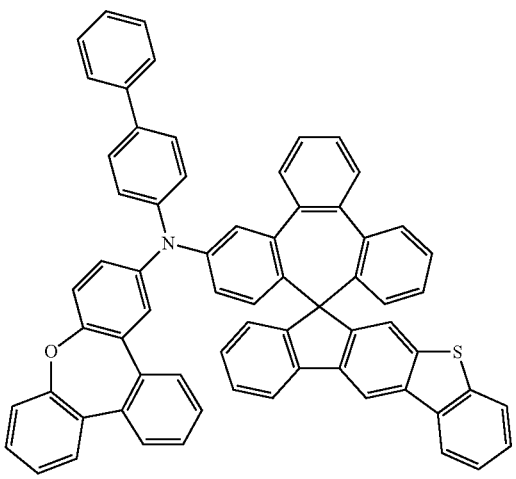

-continued
Compund 1000
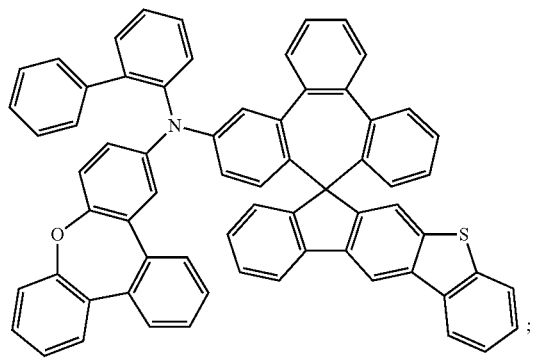
Compund 1001
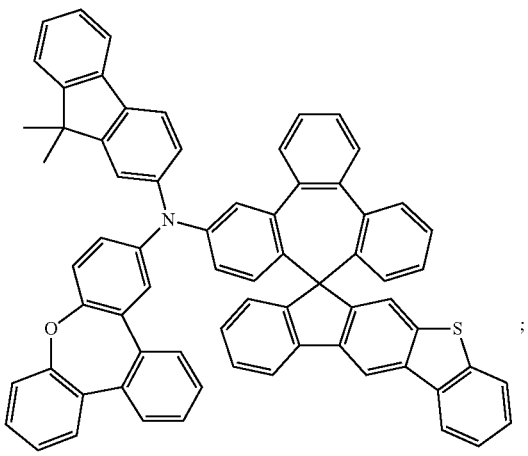
Compound 1002
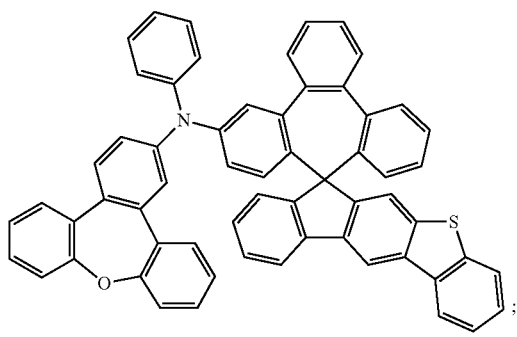
Compound 1003
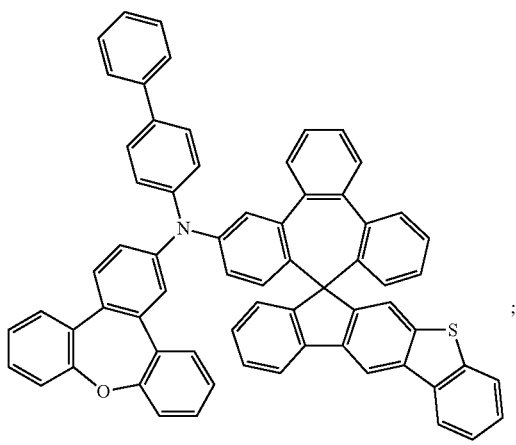
Compound 1004
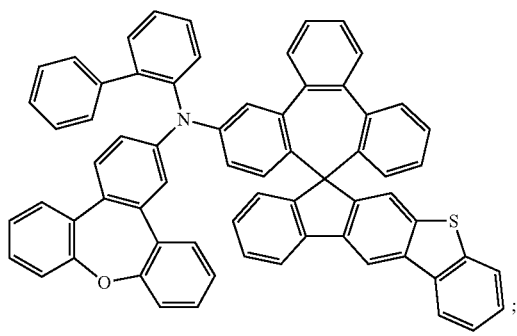
Compound 1005
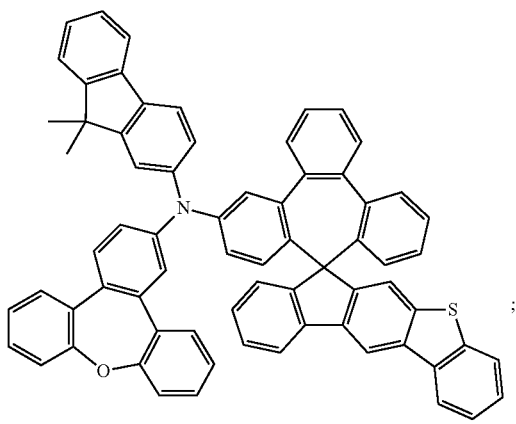

-continued
Compound 1006
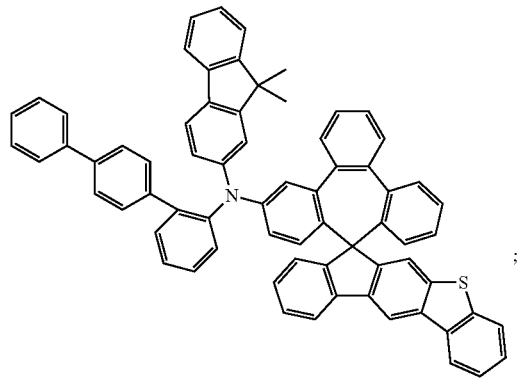
Compound 1007
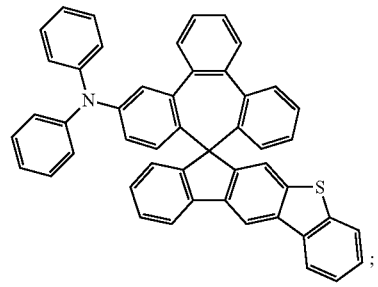
Compound 1008
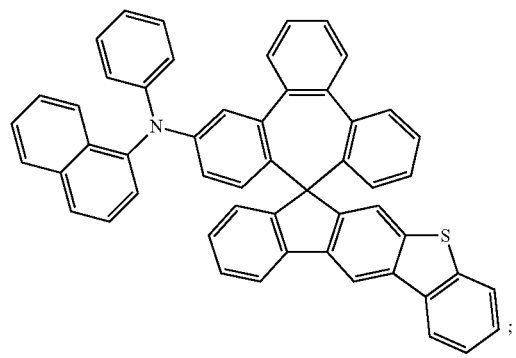
Compound 1009
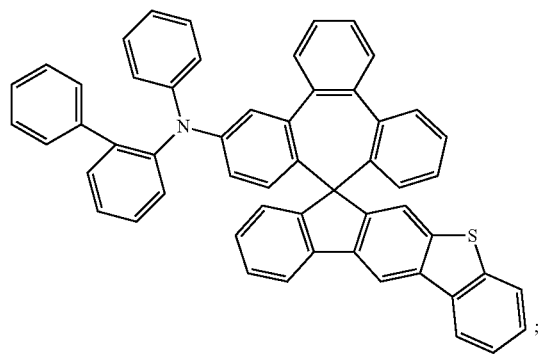
Compound 1010
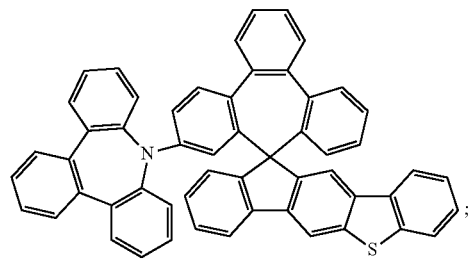
Compound 1011
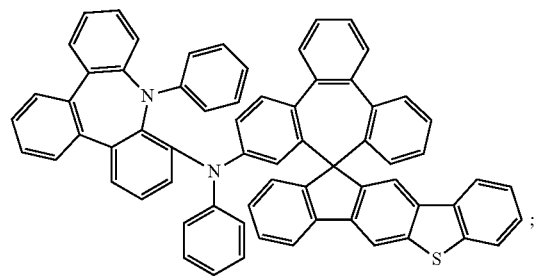
Compound 1012
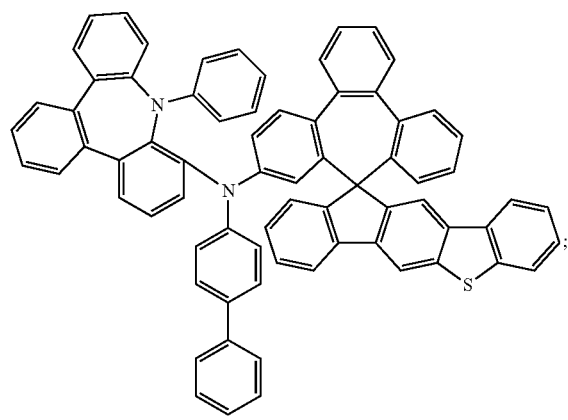
Compound 1013
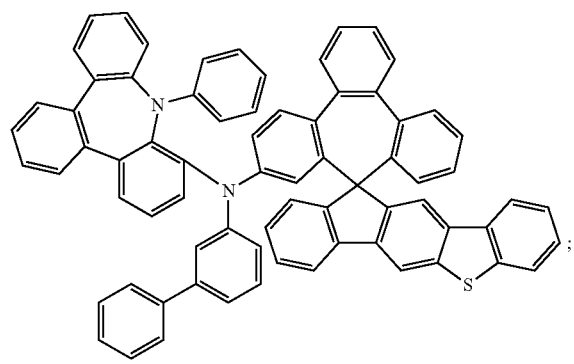

-continued
Compound 1014
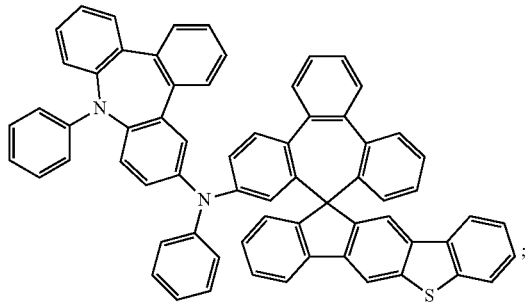
Compound 1015
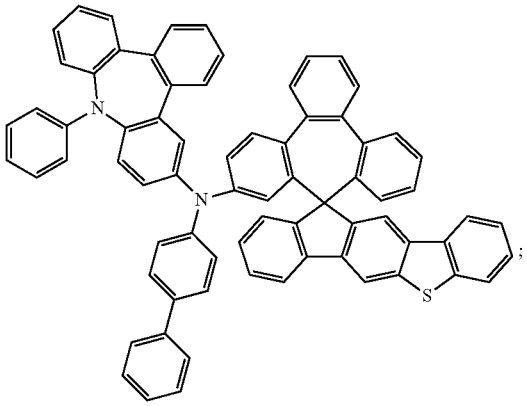
Compound 1016
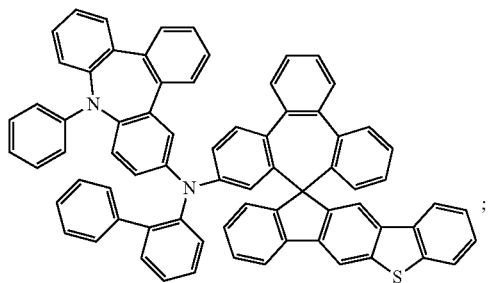
Compound 1017
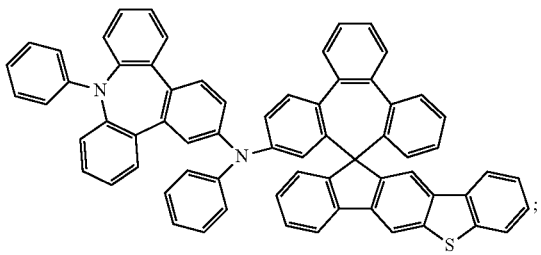
Compound 1018
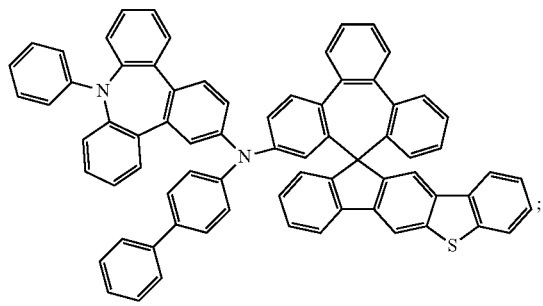
Compound 1019
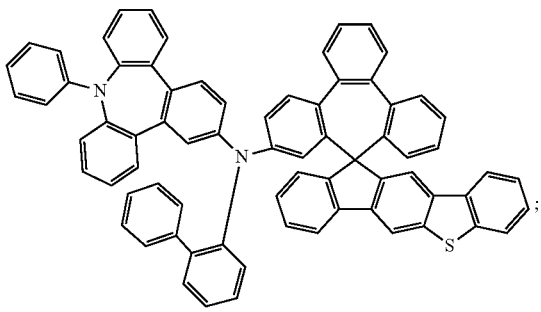
Compound 1020
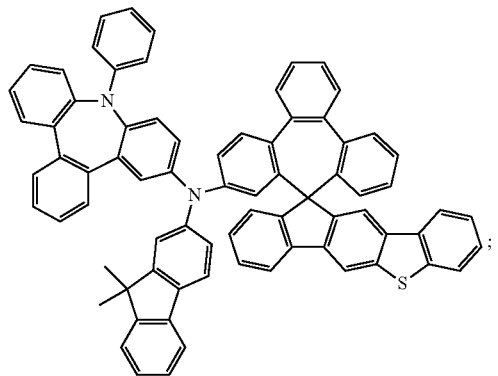
Compound 1021
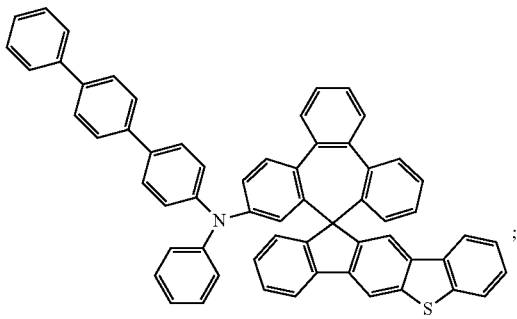

-continued
Compound 1022
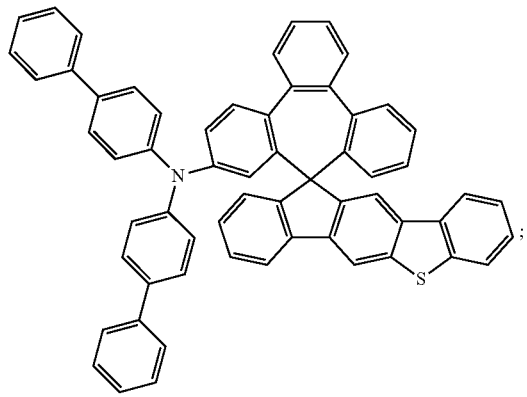
Compound 1023
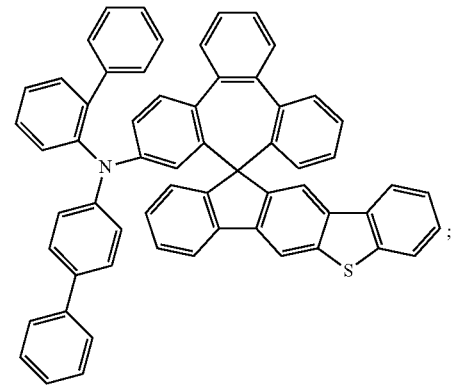
Compound 1024
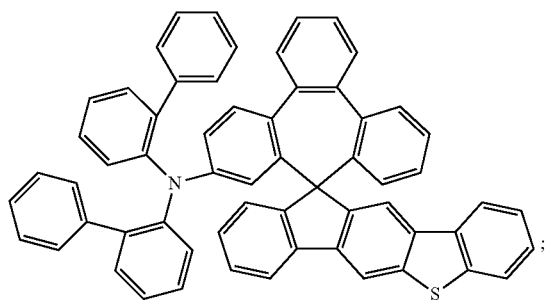
Compound 1025
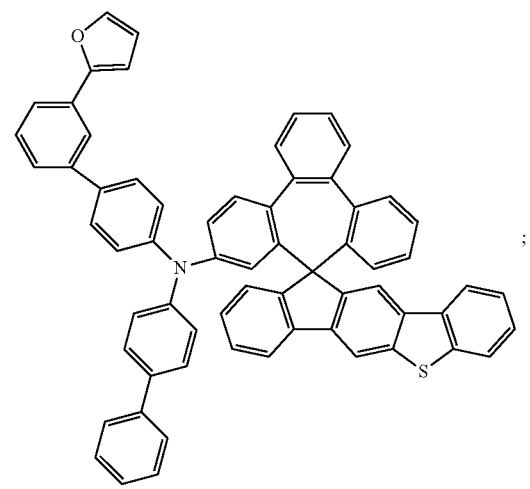
Compound 1026
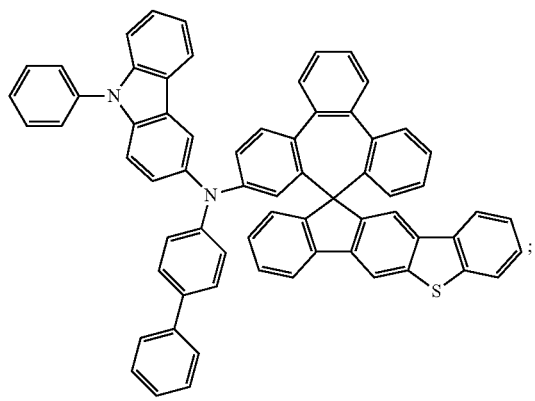
Compound 1027
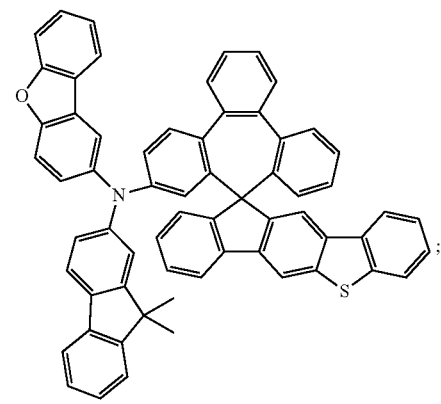

-continued
Compound 1028
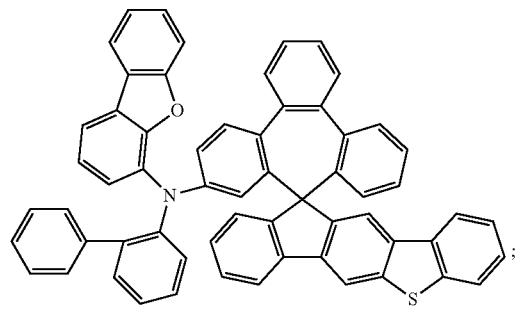
Compound 1029
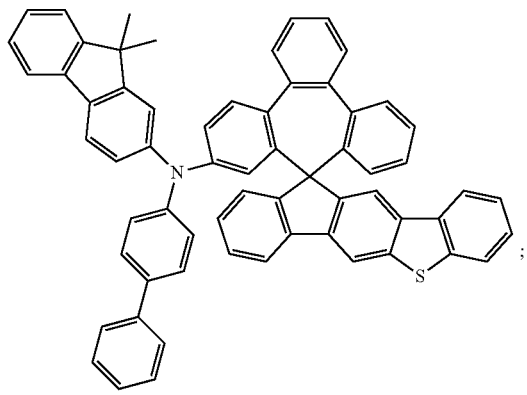
Compound 1030
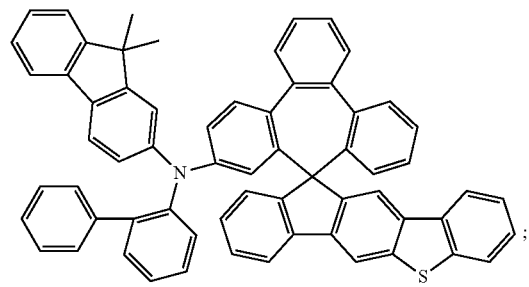
Compound 1031
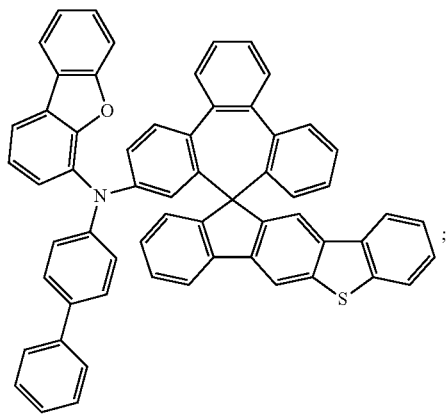
Compound 1032
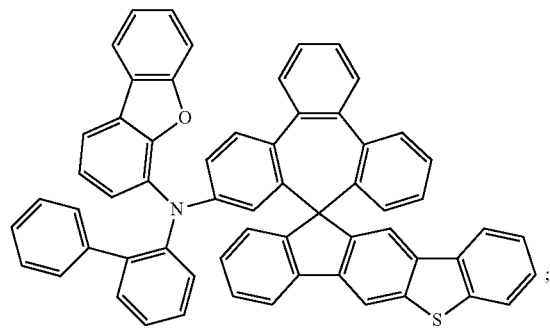
Compound 1033
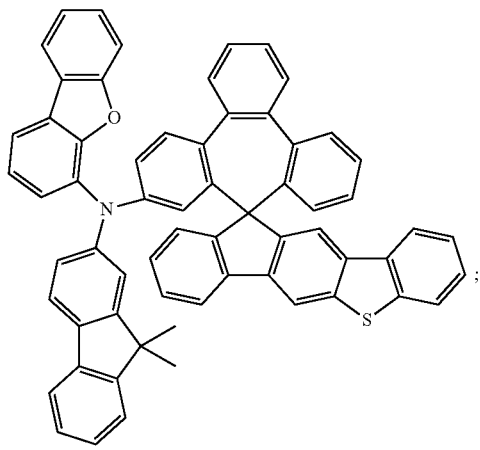

-continued
Compound 1034
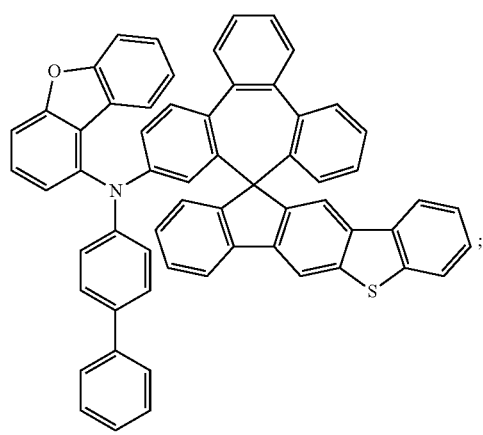
Compound 1035
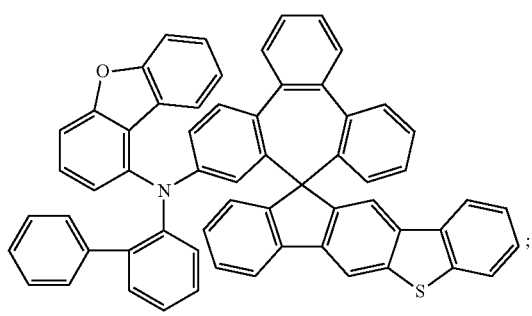
Compound 1036
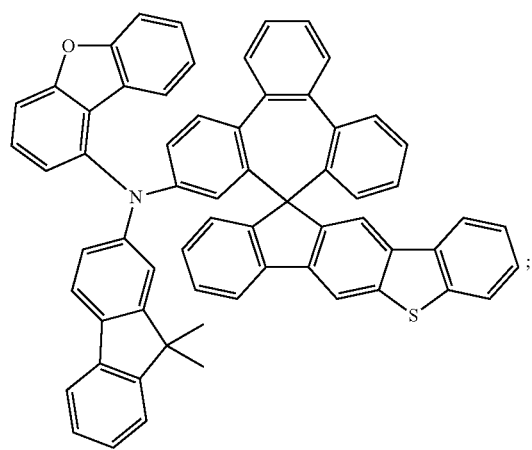
Compound 1037
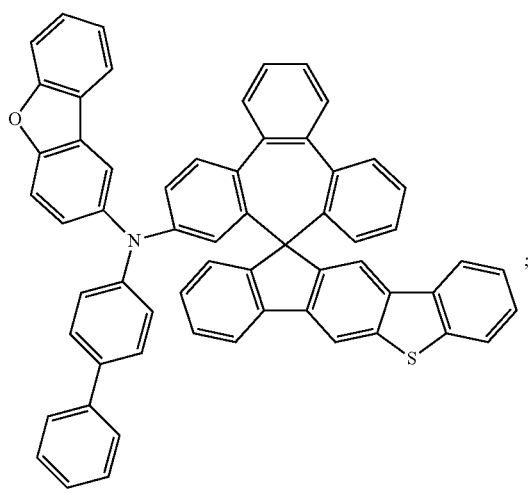
Compound 1038
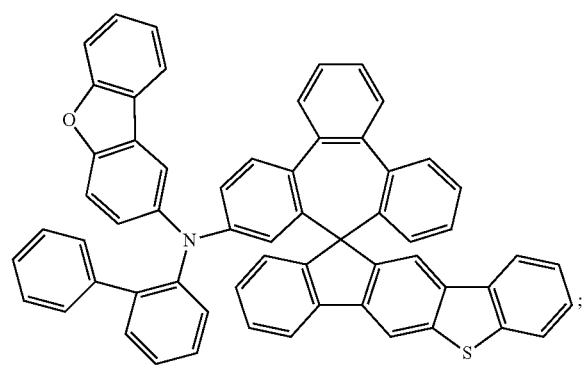
-continued
Compound 1039
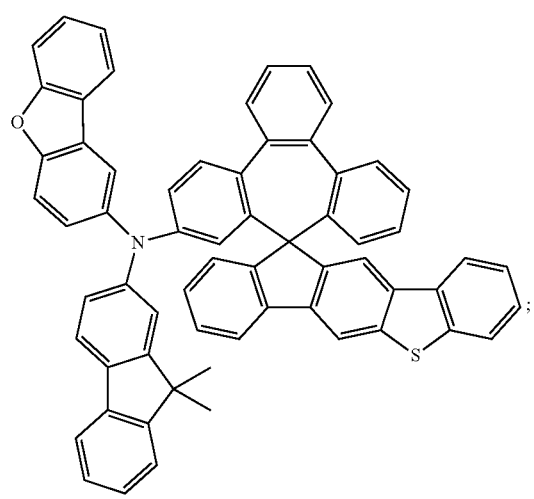

-continued
Compound 1040
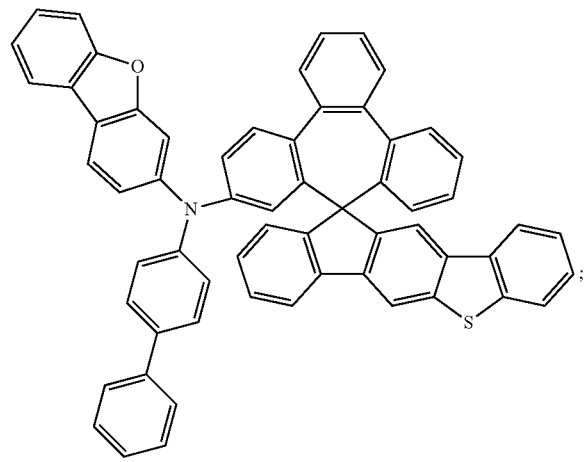
Compound 1041
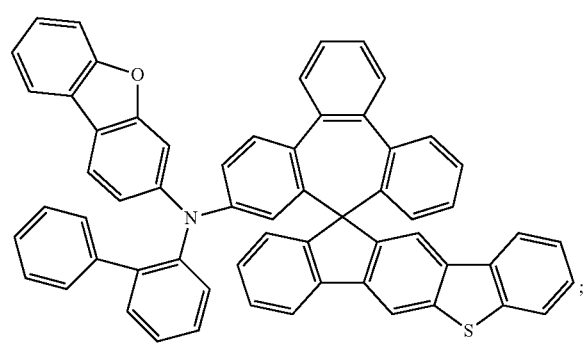
Compound 1042
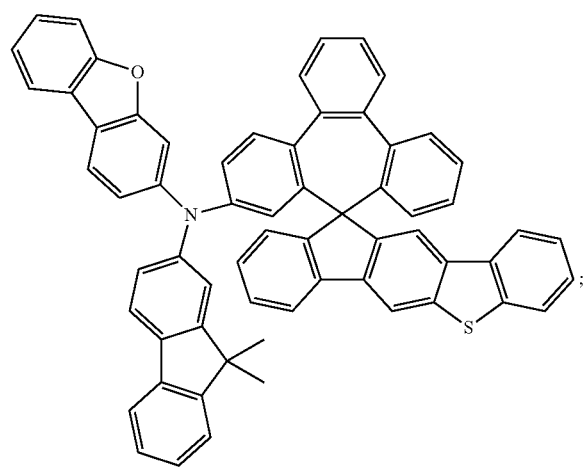
-continued
Compound 1043
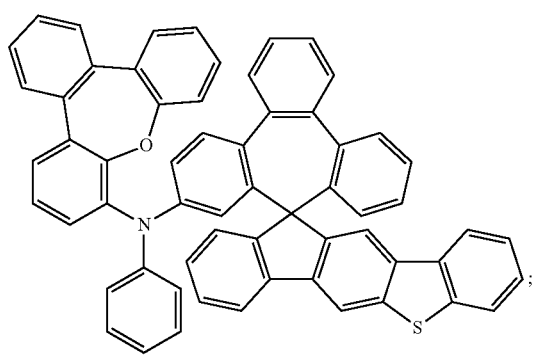
Compound 1044
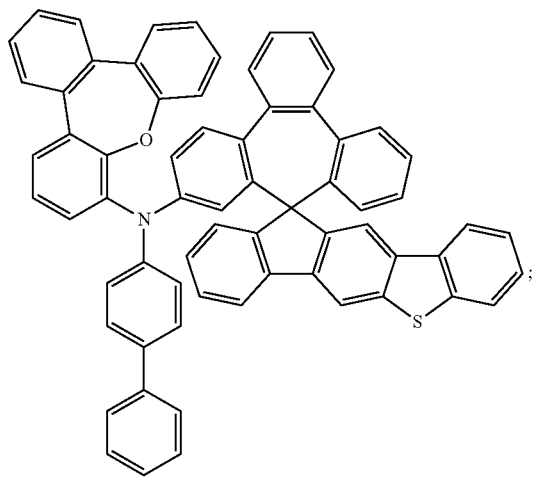
Compound 1045
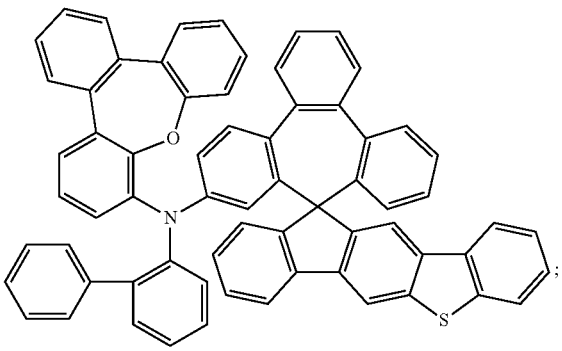

Compound 1046
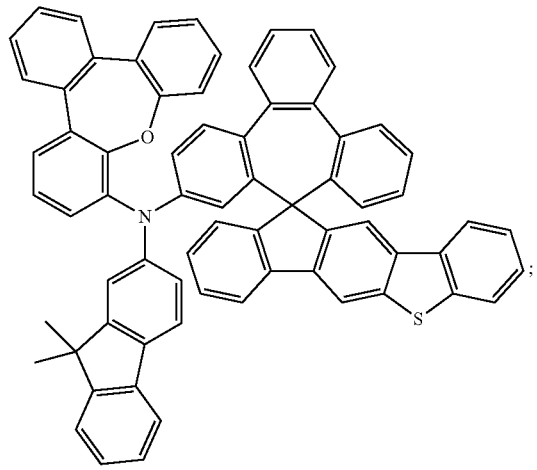
Compound 1047
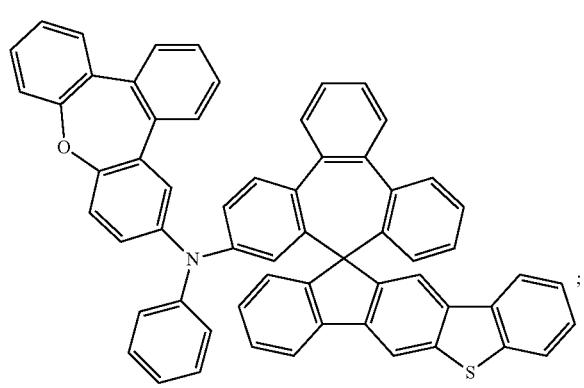
Compound 1048
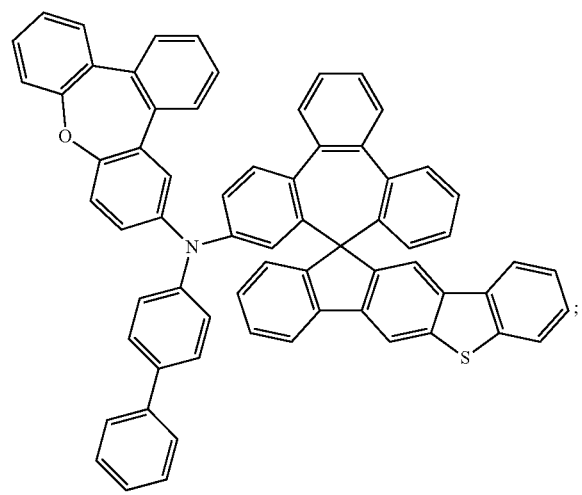
Compound 1049
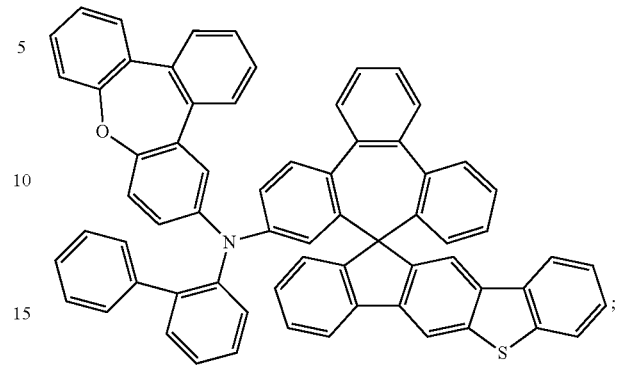
Compound 1050
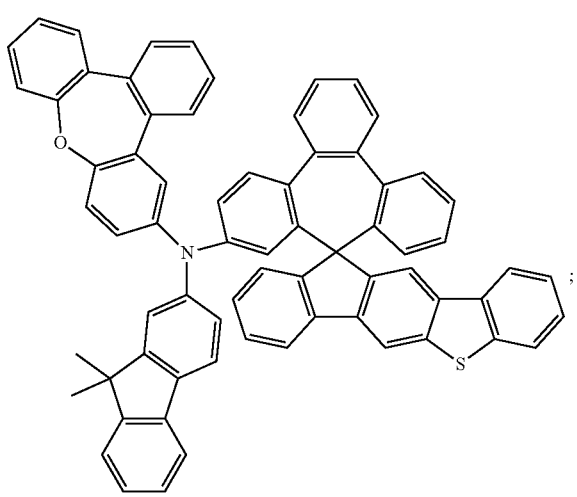
Compound 1051
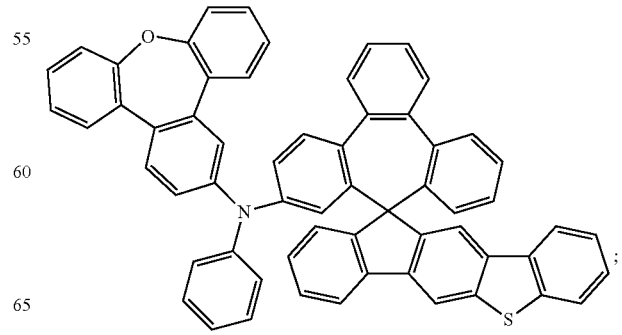

Compound 1052
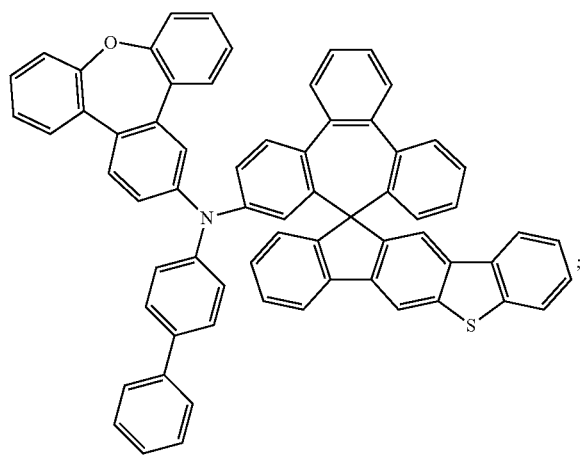
Compound 1053
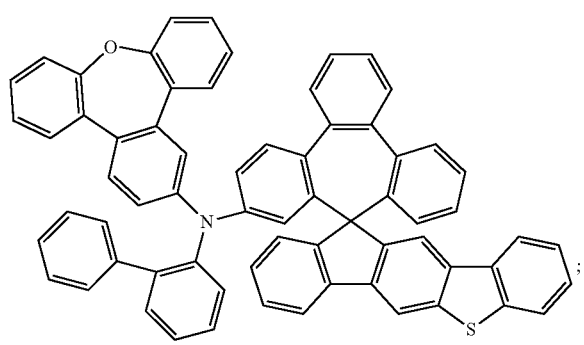
Compound 1054
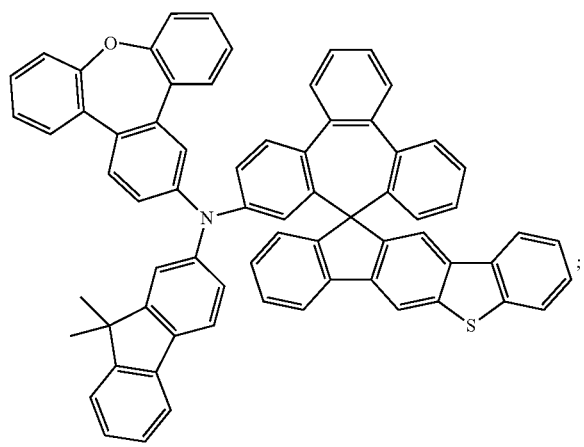
Compound 1055
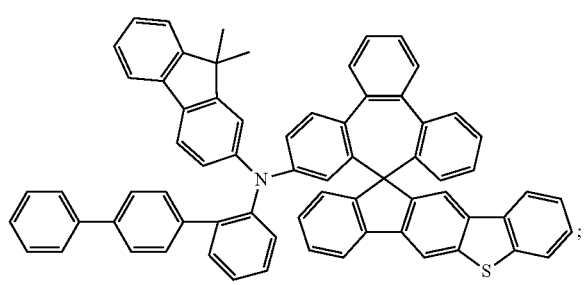
Compound 1056
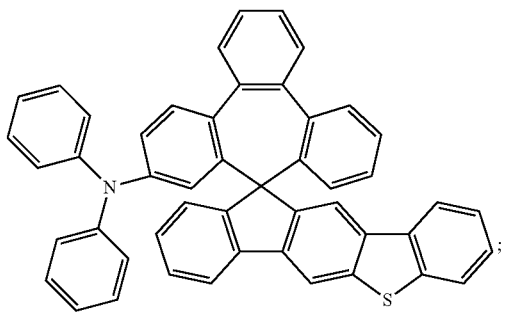
Compound 1057
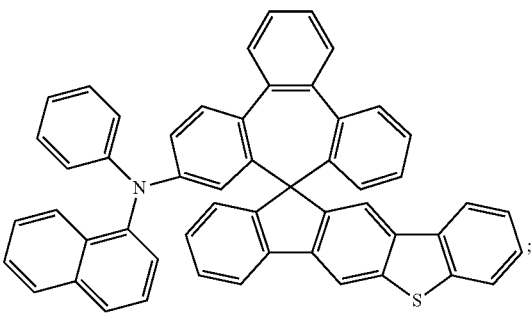
Compound 1058
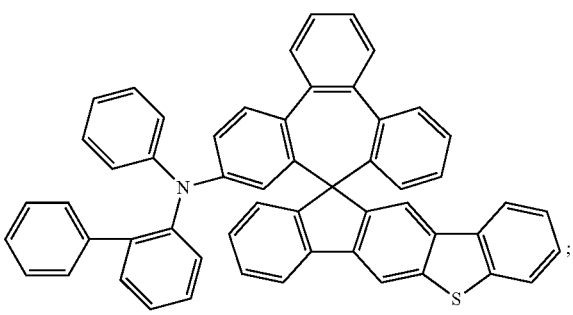
Compound 1059
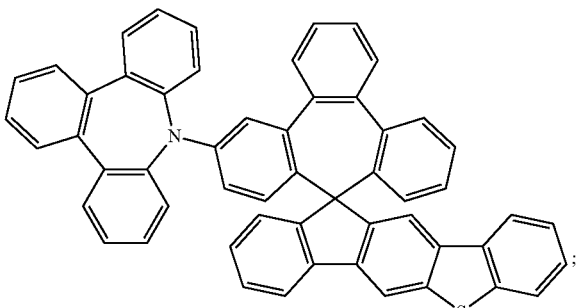

Compound 1060
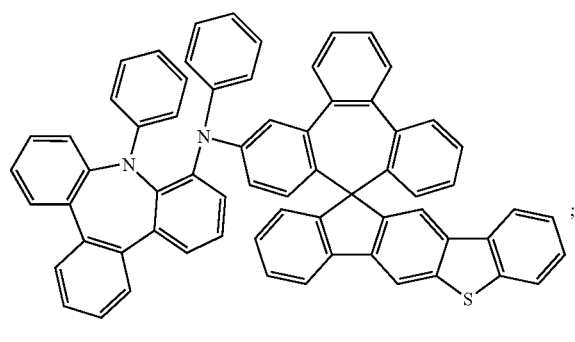
Compound 1061
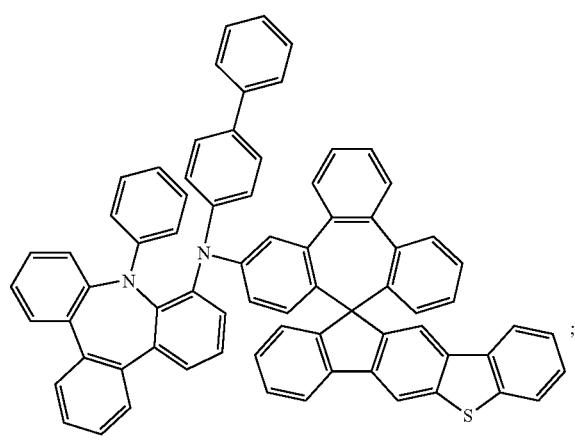
Compound 1062
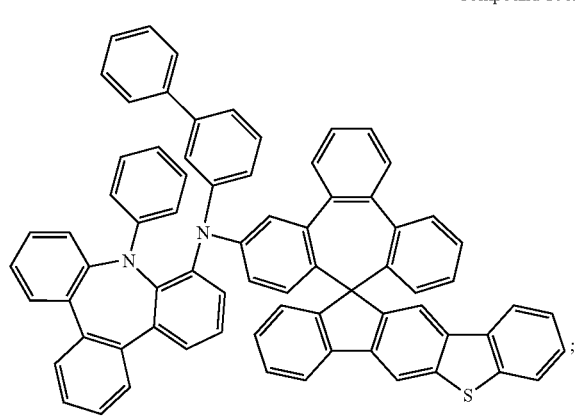
Compound 1063
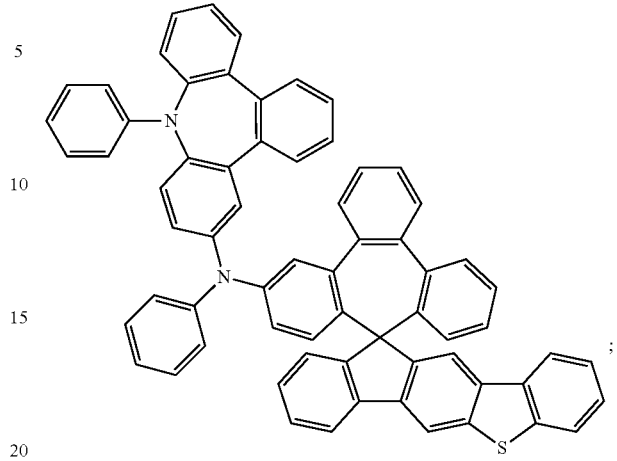
Compound 1064
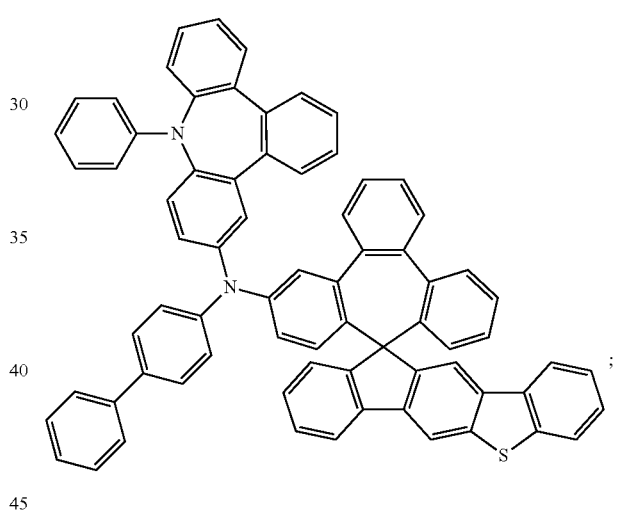
Compound 1065
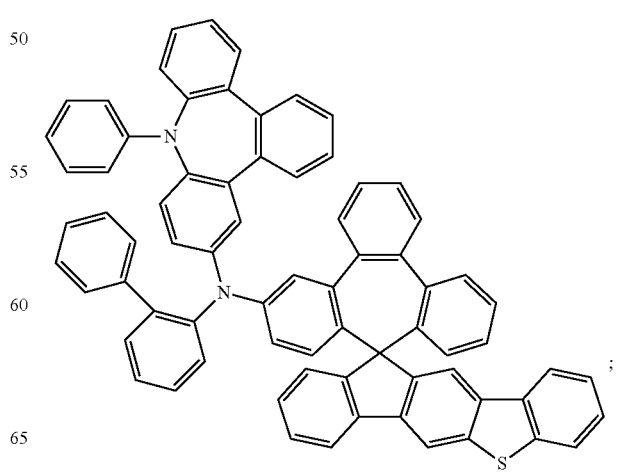

Compound 1066
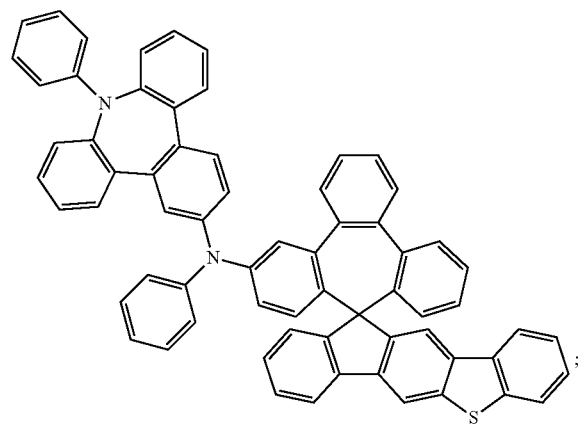
Compound 1067
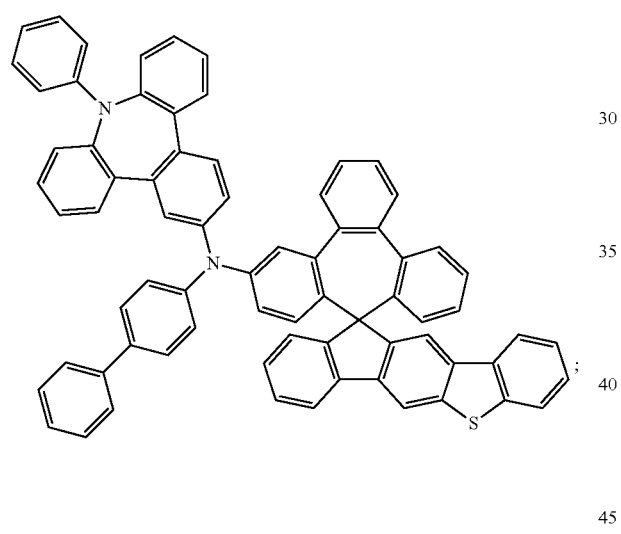
Compound 1068
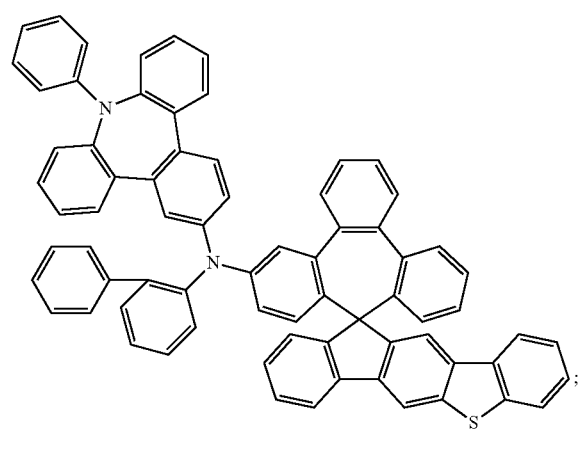
Compound 1069
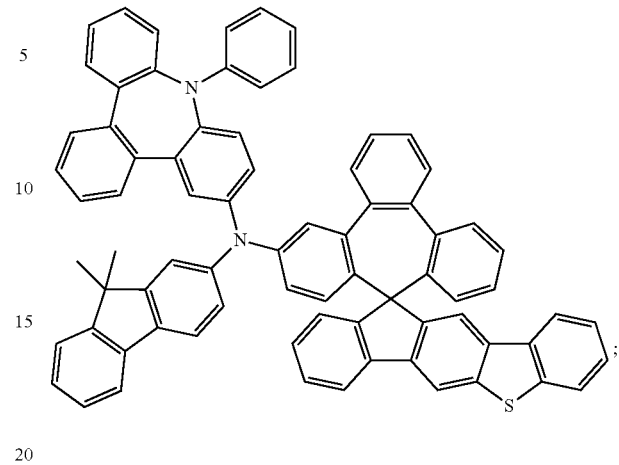
Compound 1070
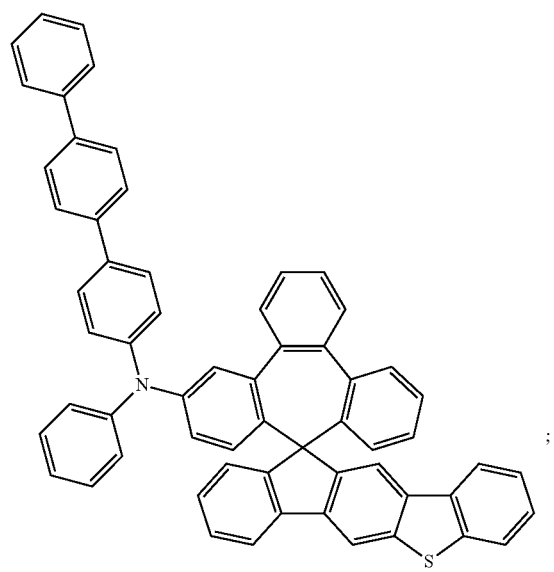
Compound 1071
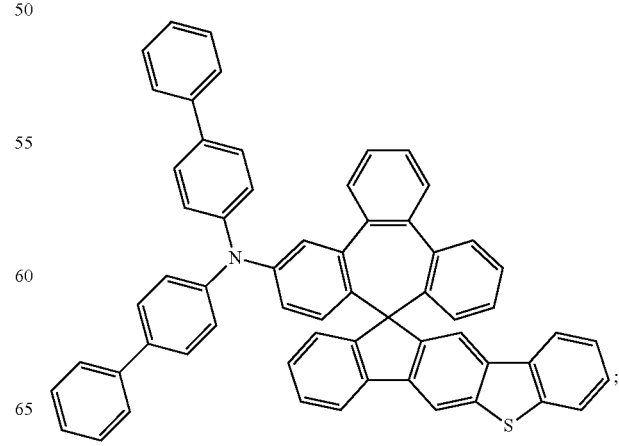

Compound 1072
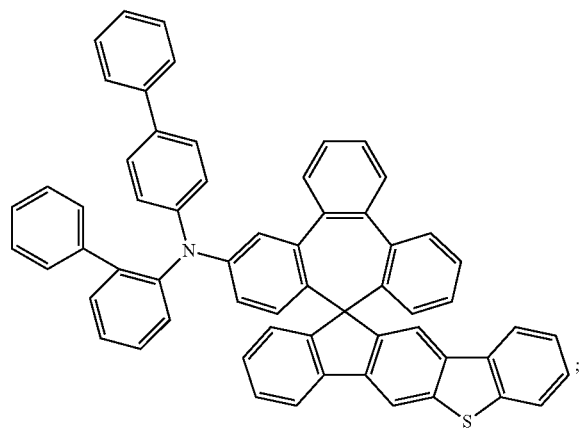
Compound 1073
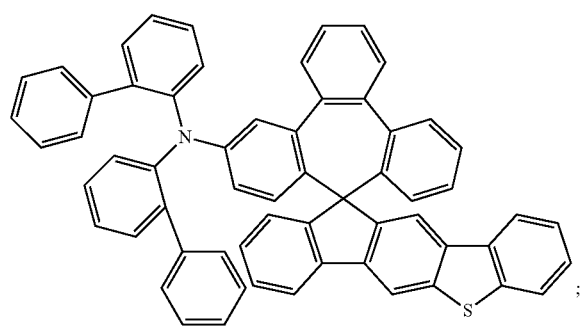
Compound 1074
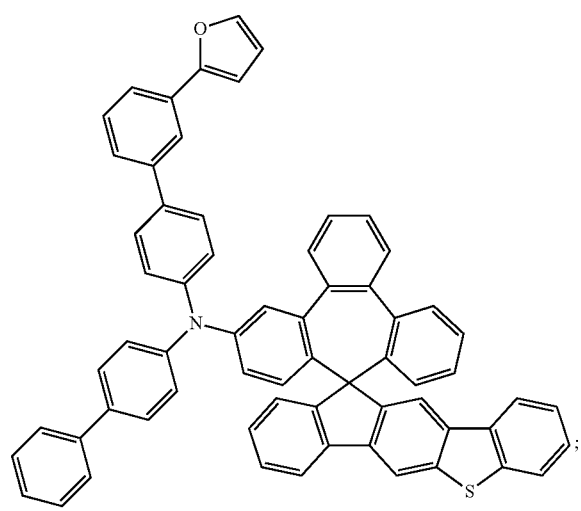
Compound 1075
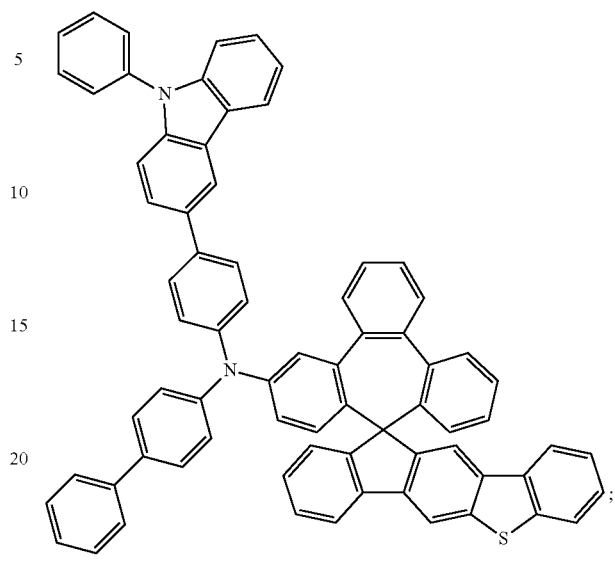
Compound 1076
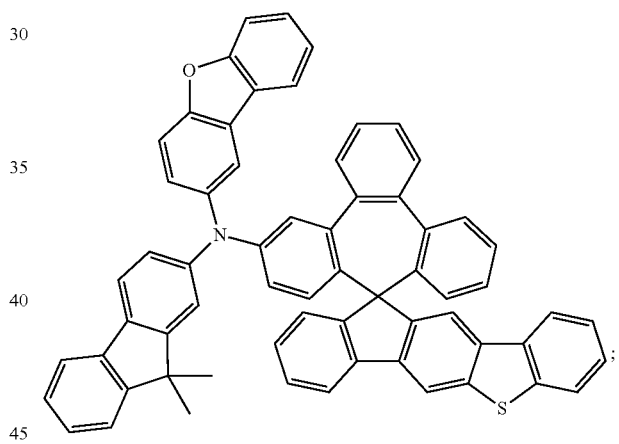
Compound 1077
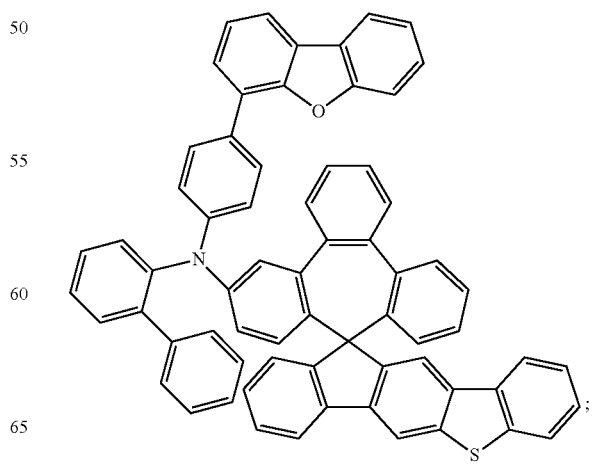

Compound 1078
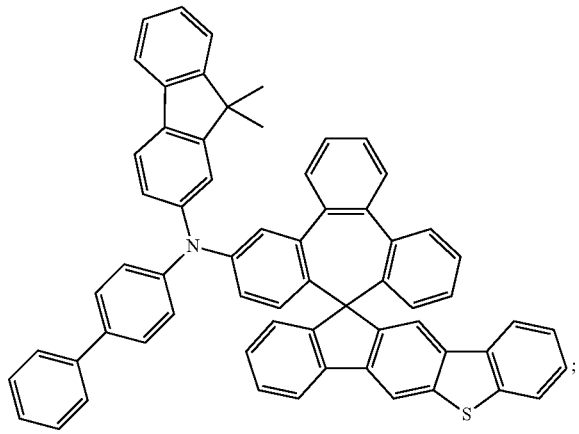
Compound 1079
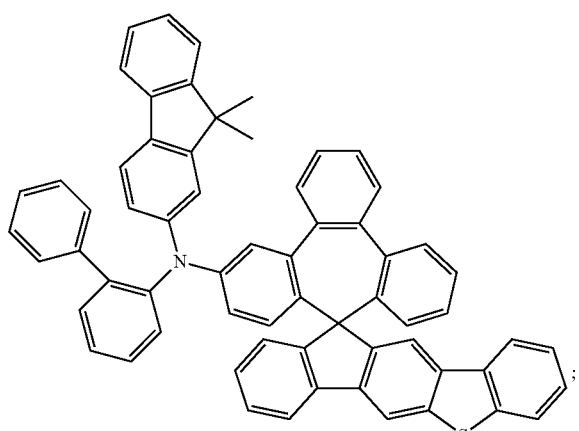
Compound 1080
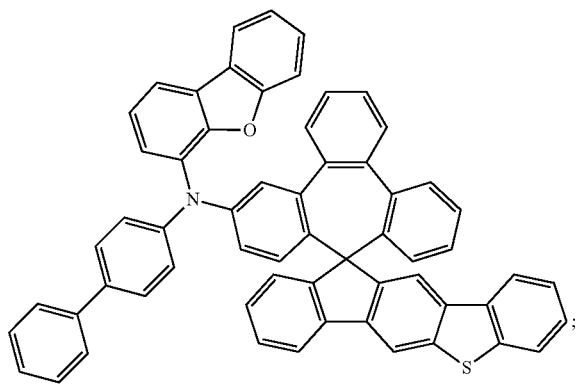
Compound 1081
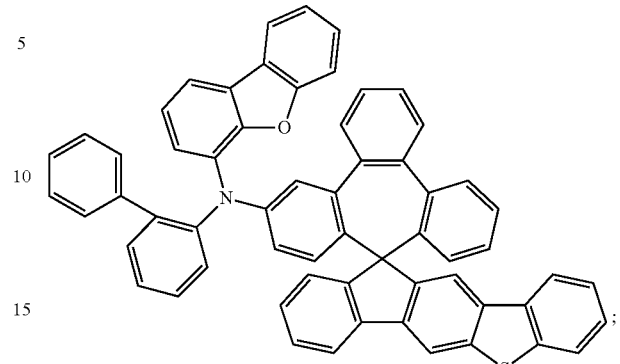
Compound 1082
Compound 1083
Compound 1084
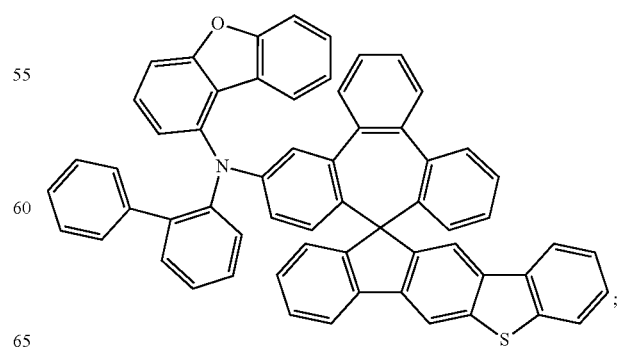

Compound 1085
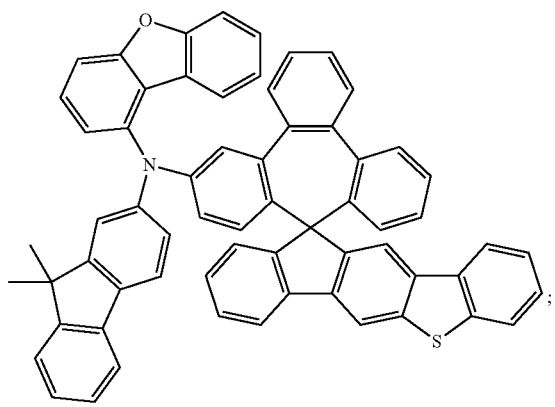
Compound 1086
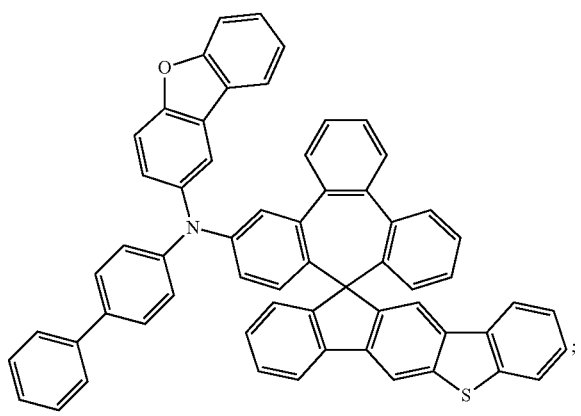
Compound 1087
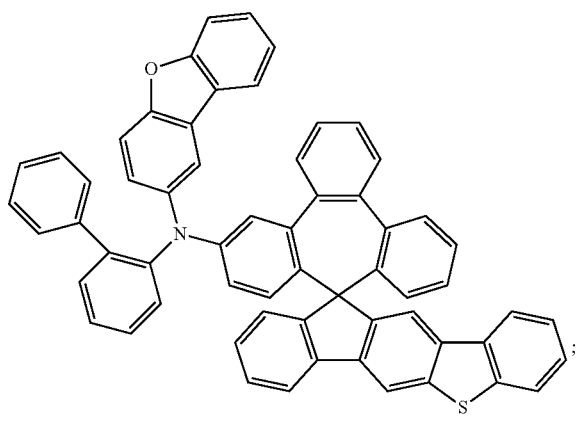
Compound 1088
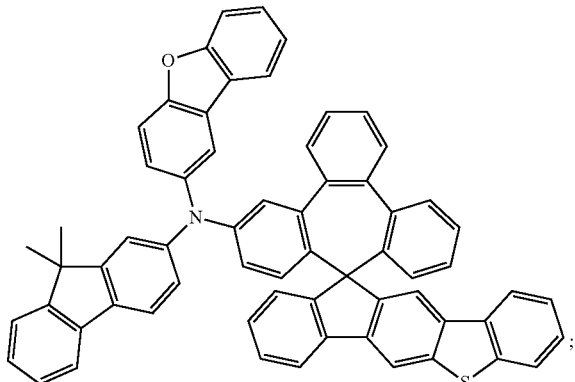
Compound 1089
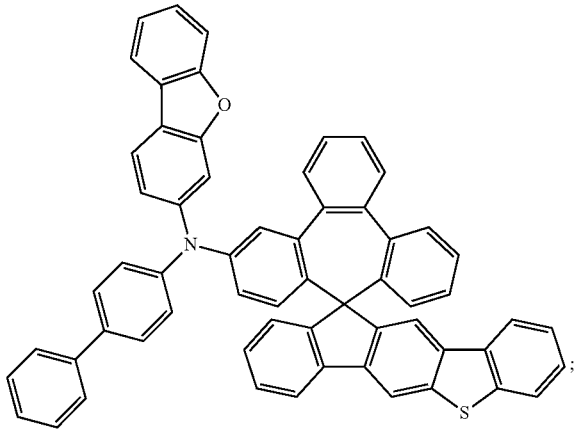
Compound 1090
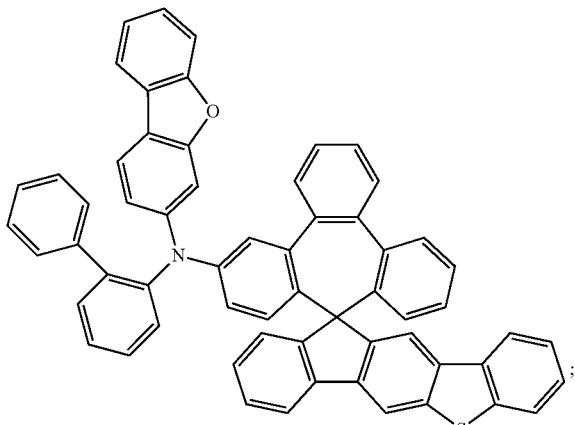

Compound 1091
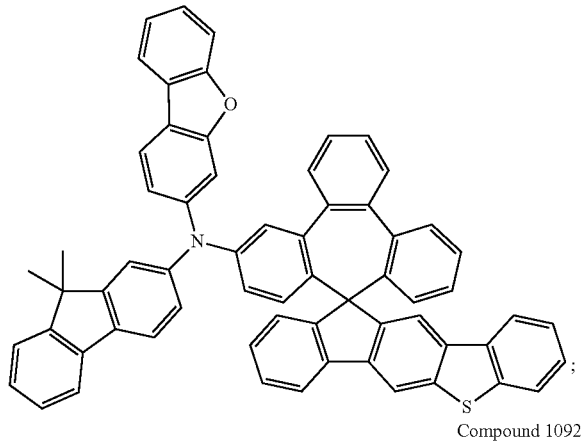
Compound 1092
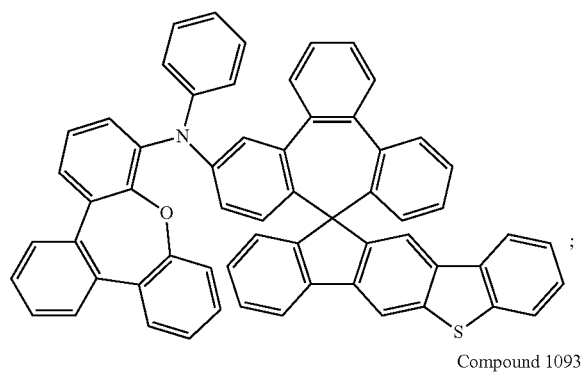
Compound 1093
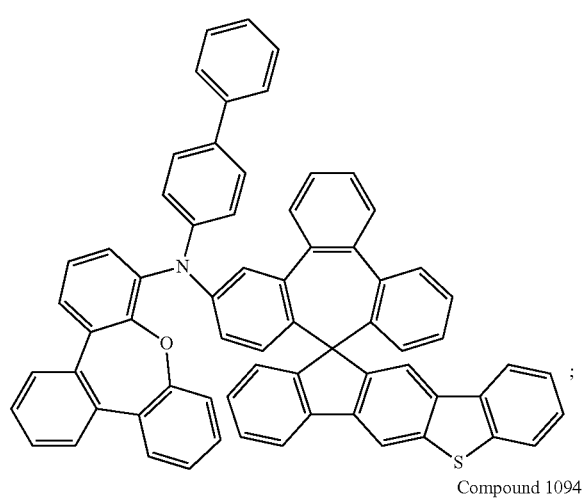
Compound 1094
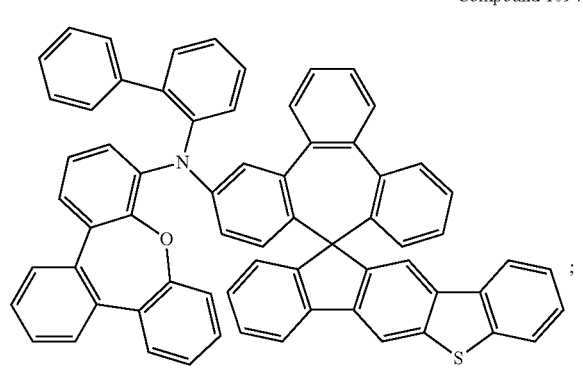
Compound 1095
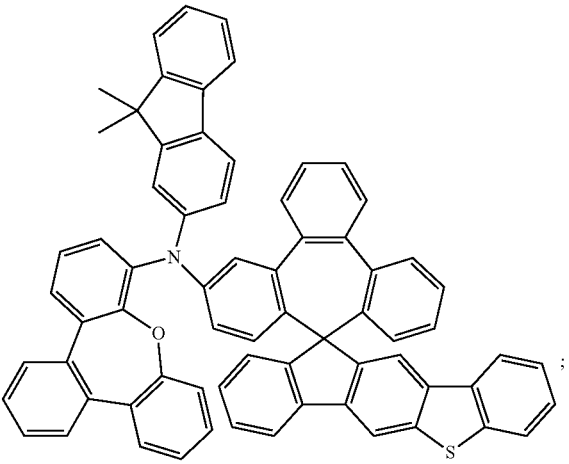
Compound 1096
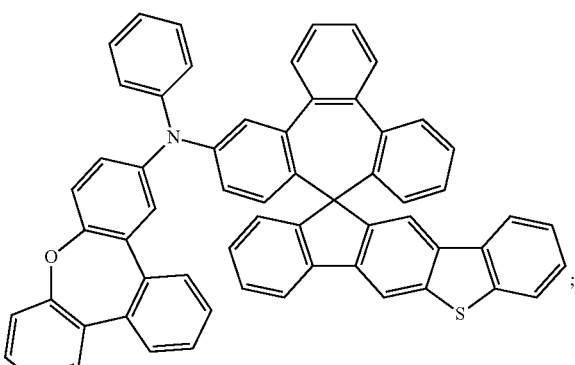
Compound 1097
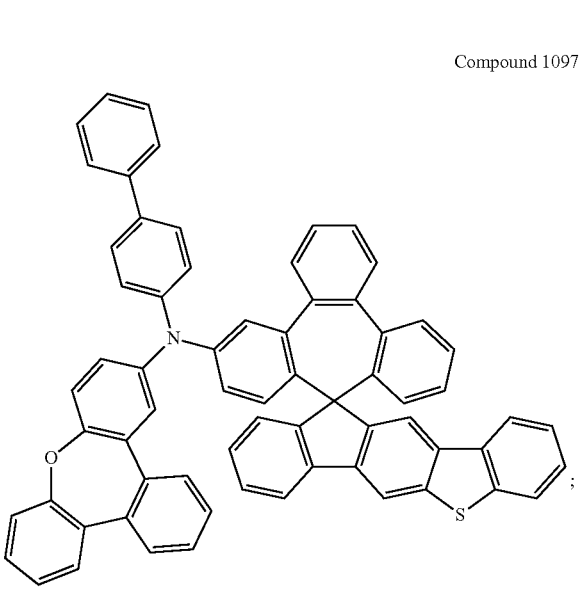

Compound 1098
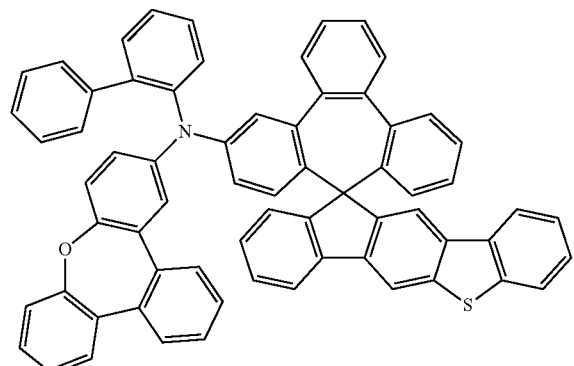
Compound 1099
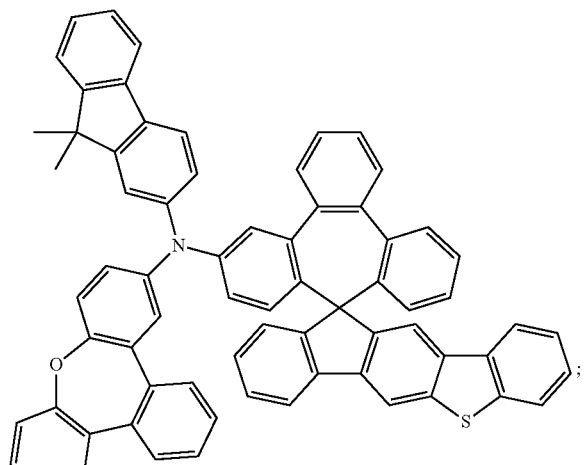
Compound 1100
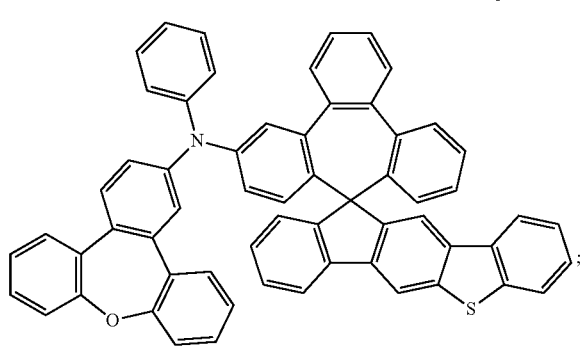
Compound 1101
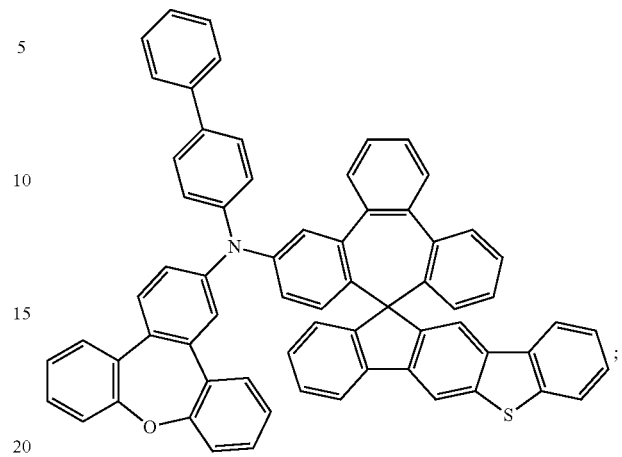
Compound 1102
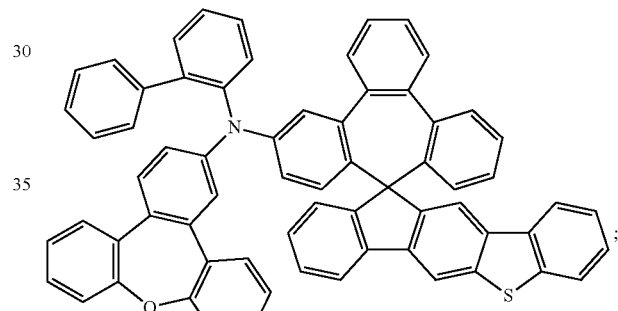
Compound 1103
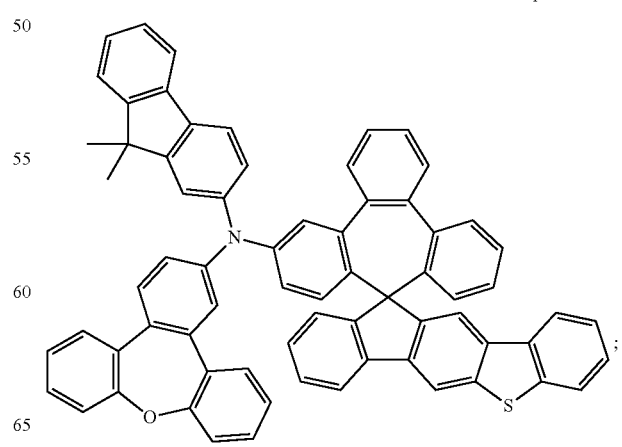

Compound 1104

Compound 1105

Compound 1106

Compound 1107

Compound 1108

Compound 1109

; and

Compound 1110

In accordance with the present invention, $Z^3$ in Formula (I) is selected from the group consisting of: a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as the material of a hole transport layer or of an electron blocking layer.

Specifically, the organic light emitting device may comprise:

a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

In one embodiment, the organic layer may be the hole transport layer, i.e., the hole transport layer comprises the novel compound as stated above.

Preferably, the hole injection layer may be a two-layered structure, i.e., the OLED comprises a first hole injection layer and a second hole injection layer disposed between the first electrode and the hole transport layer.

Preferably, the hole transport layer may be a two-layered structure, i.e., the OLED comprises a first hole transport layer and a second hole transport layer disposed between the two-layered hole injection layer and the emission layer.

Preferably, the electron transport layer can be made of, for example, but not limited to: 2-(4-(9,10-di(naphthalen-2-yl)anthracen-2-yl)phenyl)-1-phenyl-1H-benzo[d]imidazole; bis(2-methyl-8quinolinolato)(p-phenylphenolato) aluminum; and 2-(4-biphenylyl)-5-(4-tert-butylphenyl)-1,3,4-oxadiazole (PBD).

Preferably, the OLED comprises a hole blocking layer formed between the electron transport layer and the emission layer, to block holes overflow from the emission layer to the electron transport layer. Said hole blocking layer may be made of 2,9-dimethyl-4,7-diphenyl-1,10-phenanthroline (BCP) or 2,3,5,6-tetramethyl-phenyl-1,4-(bis-phthalimide) (TMPP), but not limited thereto.

Preferably, the OLED comprises an electron blocking layer formed between the hole transport layer and the emission layer, to block electrons overflow from the emission layer to the hole transport layer. Said electron blocking layer may be made of 9,9'[1,1'-biphenyl]-4,4'-diylbis-9H-carbazole (CBP) or 4,4',4"-tri(N-carbazolyl)-triphenylamine (TCTA), but not limited thereto. In further another embodiment, the organic layer may be the electron blocking layer, i.e., the electron blocking layer comprises the novel compound as stated above.

In the presence of such a hole blocking layer and/or an electron blocking layer in an OLED, the OLED has a higher luminous efficiency compared to a typical OLED.

Said first and second hole transport layers are made of the novel compound such as Compounds 1 to 17. The OLEDs using the novel compound as the hole transport material can have an improved efficiency compared to commercial OLEDs using known hole transport material, such as $N^1,N^{1'}$-(biphenyl-4,4'-diyl)bis($N^1$-(naphthalen-1-yl)-$N^4,N^{4'}$-diphenylbenzene-1,4-diamine); or $N^4,N^{4'}$-di(naphthalen-1-yl)-$N^4$, $N^{4'}$-diphenylbiphenyl-4,4'-diamine (NPB) as the hole transport material.

Said the hole injection layer may be made of, for example, but not limited to, polyaniline or polyethylenedioxythiophene.

Said emission layer can be made of an emission material including a host and a dopant. The host of the emission material is, for example, but not limited to, 9-(4-(naphthalen-1-yl)phenyl)-10-(naphthalen-2-yl)anthracene.

For red OLEDs, the dopant of the emission material is, for example, but not limited to: an organometallic compound of iridium (II) having quinoline ligands, isoquinoline ligands, or periflanthene ligands. For green OLEDs, the dopant of the emission material is, for example, but not limited to: diaminoflourenes; diaminoanthracenes; or organometallic compounds of iridium (II) having phenylpyridine ligands. For blue OLEDs, the dopant of the emission material is, for example, but not limited to: diaminoflourenes; diaminoanthracenes; diaminopyrenes; or organicmetallic compounds of iridium (II) having phenylpyridine ligands. With various host materials of the emission layer, the OLED can emit lights in red, green or blue.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
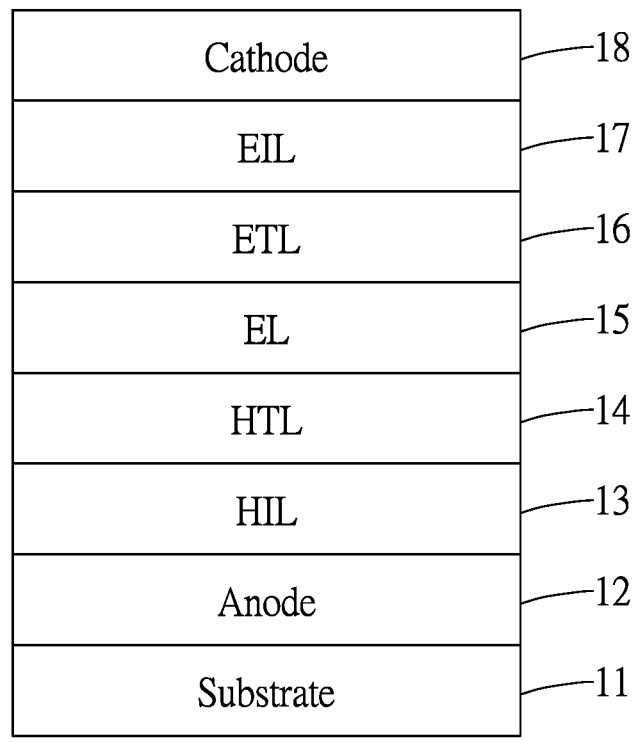
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of Intermediate A1

Intermediate A1 used for preparing a novel compound was synthesized by the following steps. The synthesis pathway of the Intermediate A1 was summarized in Scheme A1.

Scheme A1

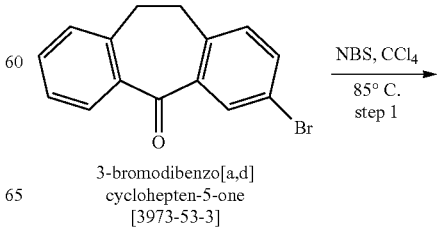

3-bromodibenzo[a,d]
cyclohepten-5-one
[3973-53-3]

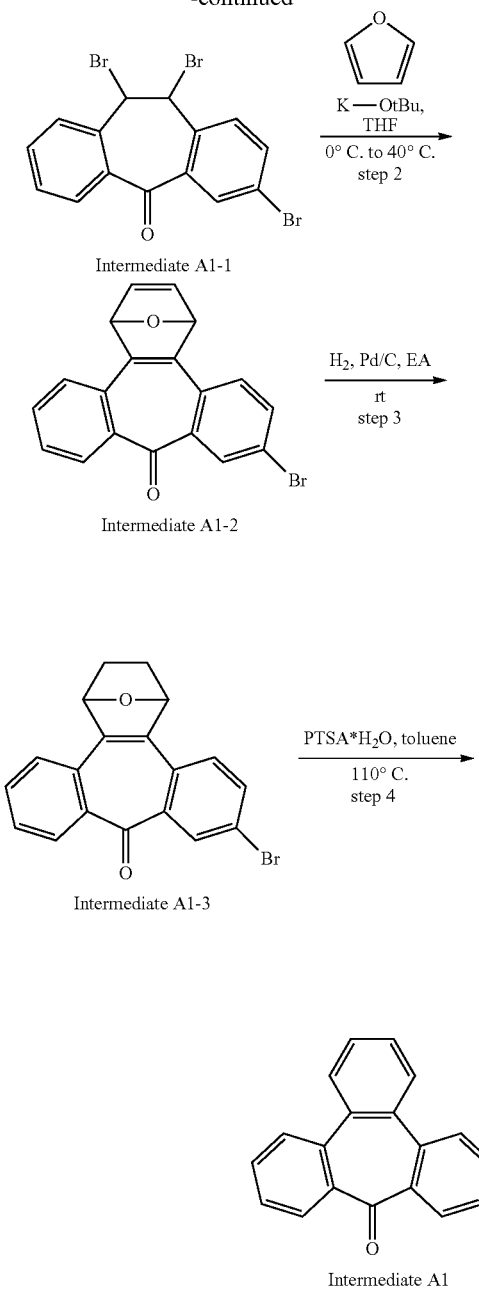

Intermediate A1-1

Intermediate A1-2

Intermediate A1-3

Intermediate A1

Step 1: Synthesis of Intermediate A1-1

A mixture of 3-bromodibenzo[a,d]cyclohepten-5-one (86 g, 1.0 eq), N-bromosuccinimide (NBS) (106 g, 2 eq), benzyl peroxide (0.7 g, 0.01 eq) in carbon tetrachloride ($CCl_4$) (430 ml) was heated to 85° C. The reaction was monitored by high performance liquid chromatography (HPLC). After completion of a reaction, the precipitate was separated by filtration and washed with $CH_3OH$ and then purified by recrystalization. The purified product was concentrated to dryness, whereby a white solid product was obtained in an amount of 123 g and a yield of 92.3%.

The solid product was identified as Intermediate A1-1 by a field desorption mass spectroscopy (FD-MS) analysis. FD-MS analysis: $C_{15}H_9Br_3O$: theoretical value of 444.94 and observed value of 444.94.

Step 2: Synthesis of Intermediate A1-2

The obtained Intermediate A1-1 (116.0 g, 1.0 eq) was dissolved in 960 ml of furan/THF (v/v=2/1), the reaction was cooled to 0° C. and then treated with potassium tert-butoxide (KO-t-Bu) (87.8 g, 3.0 eq). The reaction was allowed to stir at 0° C. for 1 hour, and then stirred at room temperature for another 12 hours. Quenched by DI water, the organic layer was recovered by solvent extraction operation and dried over sodium sulfate. The solvent was removed from the organic layer by distillation under reduced pressure, and the resulting residue was purified by silica gel column chromatography. The purified product was concentrated to dryness, whereby a light yellow solid product was obtained in an amount of 46.8 g and a yield of 51.1%.

The solid product was identified as Intermediate Al-2 by FD-MS analysis. FD-MS analysis $C_{19}H_{11}BrO_2$: theoretical value of 351.19 and observed value of 351.19.

Step 3: Synthesis of Intermediate A1-3

A suspension of Intermediate A1-2 (53.5 g, 1.0 eq) and 5% Pd/C (8.1 g, 0.025 eq) in 535 ml of ethyl acetate (EA) was stirred for 3 hours to 6 hours under a hydrogen atmosphere ($H_2$) provided by a balloon of hydrogen. The resulting mixture was filtered through a pad of celite and washed with EA, and the filtrate was concentrated under reduced pressure to obtain 100 g (100%) of yellow solid product.

The solid product was identified as Intermediate A1-3 by FD-MS analysis. FD-MS analysis $C_{19}H_{13}BrO_2$: theoretical value of 353.21 and observed value of 353.21. The intermediate A1-3 can be directly used in the following step without further purification.

Step 4: Synthesis of Intermediate A1-4

Intermediate A1-3 (53 g, 1.0 eq) and p-toluenesulfonic acid (PTSA) (57 g, 2.0 eq) in 530 ml of toluene was heated to reflux for 12 hours. The reaction mixture was cooled to room temperature and then quenched with a saturated aqueous solution of $NaHCO_3$ and extracted with $CH_2Cl_2$. The organic layer was washed with water, brine and dried with anhydrous $Na_2SO_4$ subsequently. Then the resulting solution was concentrated under reduced pressure and purified by column chromatography on silica gel with $CH_2Cl_2$/hexane (1:1 v/v) as an eluent, whereby a light yellow solid product was obtained in an amount of 46.0 g and a yield of 91.5%.

The solid product was identified as Intermediate A1 by FD-MS analysis. FD-MS analysis $C_{19}H_{11}BrO$: theoretical value of 335.19 and observed value of 335.19.

Synthesis of Intermediate A2

Intermediate A2 used for preparing a novel compound was synthesized in a similar manner as Intermediate A1 through steps 1 to 4, except that the starting material 3-bromodibenzo[a,d]cyclohepten-5-one was replaced by 2-bromodibenzo[a,d]cyclohepten-5-one (CAS No. 198707-82-3). The synthesis pathway of Intermediate A2 was summarized in Scheme A2. All intermediates were analyzed according to the methods as described above, and the results were listed in Table 1.

Scheme A2

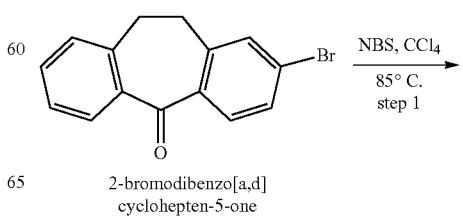

2-bromodibenzo[a,d]
cyclohepten-5-one

-continued

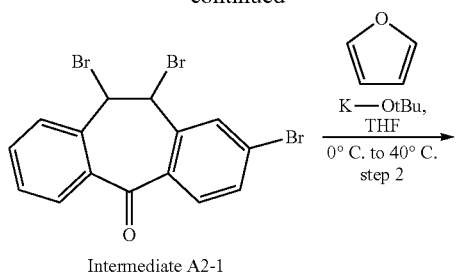

Intermediate A2-1

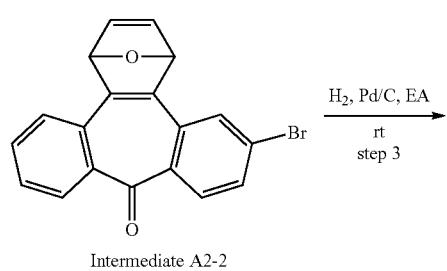

Intermediate A2-2

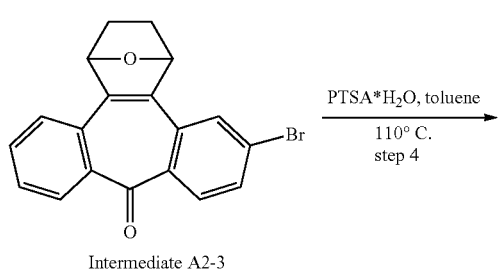

Intermediate A2-3

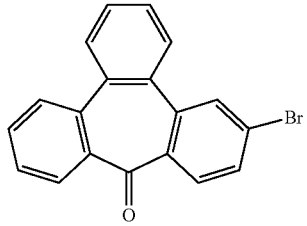 [SMILES: O=c1c2ccccc2c2ccccc2c2cc(Br)ccc12]

Intermediate A2

Scheme A3

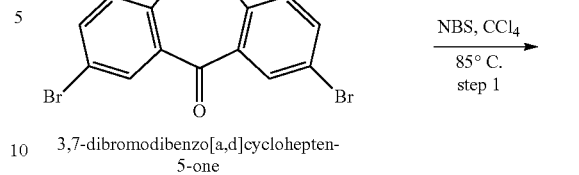

3,7-dibromodibenzo[a,d]cyclohepten-5-one

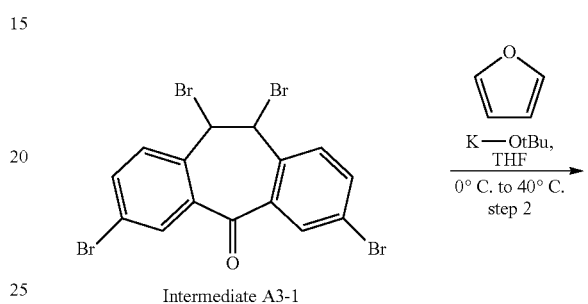

Intermediate A3-1

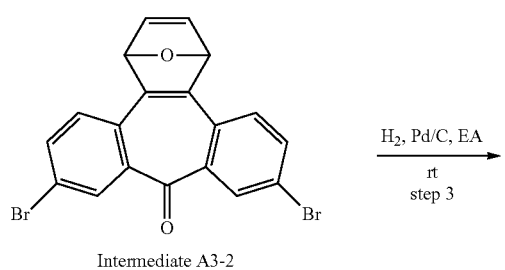

Intermediate A3-2

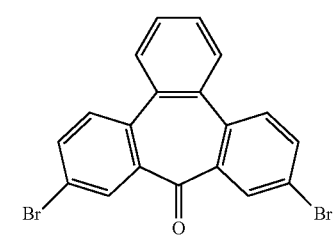 [SMILES: O=c1c2cc(Br)ccc2c2ccccc2c2ccc(Br)cc12]

Intermediate A3-3

Synthesis of Intermediate A3

Intermediate A3 used for preparing a novel compound was synthesized in a similar manner as Intermediate A1 through steps 1 to 4, except that the starting material 3-bromodibenzo[a,d]cyclohepten-5-one was replaced by 3,7-dibromodibenzo[a,d]cyclohepten-5-one (CAS No. 226946-20-9). The synthesis pathway of Intermediate A3 was summarized in Scheme A3. All intermediates were analyzed as described above, and the results were listed in Table 1.

Intermediate A3

TABLE 1 chemical structures, yields, formulae, and mass (M⁺) analyzed by FD-MS of intermediates.

| | Intermediate | |
|---|---|---|
| | A1-1 | A1-2 |
| Chemical Structure | (structure) | (structure) |
| Yield | 92.3% | 51.1% |
| Formula | $C_{15}H_9Br_3O$ | $C_{19}H_{11}BrO_2$ |
| Mass(M⁺) | 444.94 | 351.19 |
| | A2-1 | A2-2 |
| Chemical Structure | (structure) | (structure) |
| Yield | 91.5% | 58.2% |
| Formula | $C_{15}H_9Br_3O$ | $C_{19}H_{11}BrO_2$ |
| Mass(M⁺) | 444.94 | 351.19 |
| | A3-1 | A3-2 |
| Chemical Structure | (structure) | (structure) |
| Yield | 93.7% | 55.8% |
| Formula | $C_{15}H_8Br_4O$ | $C_{19}H_{10}Br_2O_2$ |
| Mass(M⁺) | 523.84 | 430.09 |
| | A1-3 | A1 |
| Chemical Structure | (structure) | (structure) |
| Yield | NA | 91.5% |
| Formula | $C_{19}H_{13}BrO_2$ | $C_{19}H_{11}BrO$ |
| Mass(M⁺) | 353.21 | 335.19 |

TABLE 1-continued chemical structures, yields, formulae, and mass (M+) analyzed by FD-MS of intermediates.

| Intermediate | A2-3 | A2 |
|---|---|---|
| Chemical Structure | | |
| Yield | NA | 93.5% |
| Formula | $C_{19}H_{13}BrO_2$ | $C_{19}H_{11}BrO$ |
| Mass(M+) | 353.21 | 335.19 |

| | A3-3 | A3 |
|---|---|---|
| Chemical Structure | | |
| Yield | NA | 93.0% |
| Formula | $C_{19}H_{12}Br_2O_2$ | $C_{19}H_{10}Br_2O$ |
| Mass(M+) | 432.11 | 414.09 |

Modifications of Intermediates A1 to A3

In addition to the Intermediates A1 to A3, one person skilled in the art can adopt other starting materials and successfully synthesize other desired intermediates through a reaction mechanism similar to Schemes A1 to A3. Applicable modifications of Intermediates A1 to A3 may be, for example, but not limited to, Intermediates A4 to A15 as follows.

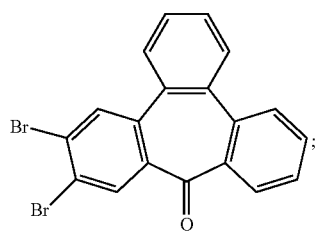

Intermediate A4

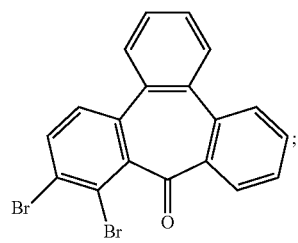

Intermediate A5

-continued

Intermediate A6

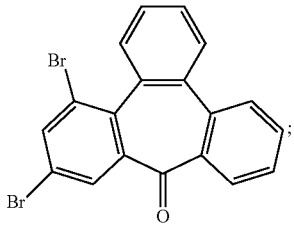

Intermediate A7

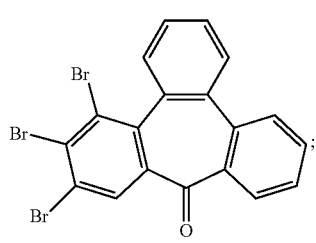

Intermediate A8

Intermediate A9

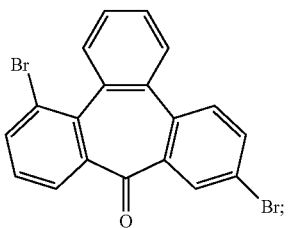

Intermediate A10

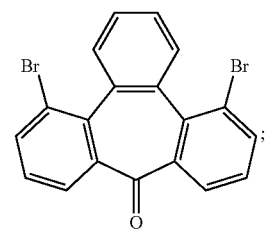

Intermediate A11

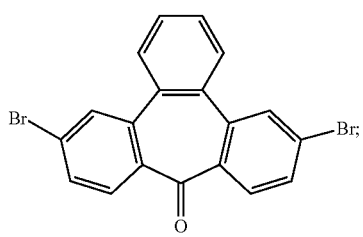

Intermediate A12

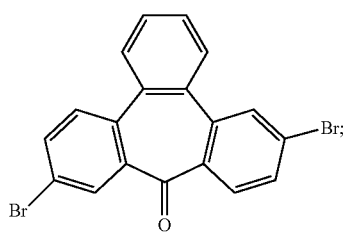

Intermediate A13

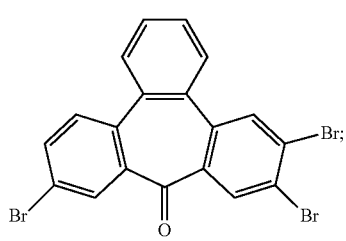

Intermediate A14

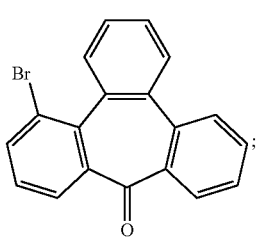

Intermediate A15

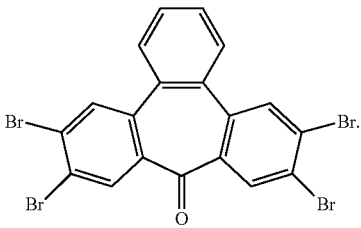

Synthesis of Intermediates B1 to B8

Intermediates B1 to B8 were synthesized by reacting 1-bromo-2-iodobenzene and aryl boronic acid (Reactant A). A general synthesis pathway for Intermediate B was summarized in Scheme B1. In the following Scheme B1, "Reactant A" may be any one of Reactants A1 to A8 as listed in Table 2 and the $R^{HR}$ in Reactant A is a heteroaryl ring containing furan group or thiofuran group. "Intermediate B" may be any one of Intermediates B1 to B8 as listed in Table 2.

Scheme B1

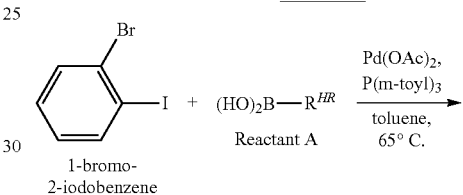

$R^{HR}$: heteroaryl ring containing furan group, or heteroaryl ring containing thiofuran group.

According to the Scheme B1, each of Intermediates B1 to B8 was synthesized by the steps as follows.

Water and toluene were poured into a round-bottomed flask, fitted with a condenser and argon flow, and bubbled through with argon. Potassium carbonate (1.5 eq), 1-bromo-2-iodobenzene (1.0 eq), Reactant A (1.05 eq), tri(m-tolyl)phosphine (P(m-tolyl)$_3$) (0.04 eq) and Pd(OAc)$_2$ (0.01 eq) were added to the mixture, which was heated at 65° C. for 5 hours in an oil bath. The reaction mixture was allowed to be cooled to room temperature, toluene was evaporated, and water and EA were added. The layers were separated and the aqueous layer was extracted with EA twice. The combined organic layers were washed with brine, dried over magnesium sulfate, filtered, and evaporated in vacuo to obtain a yellow oil. The yellow oil was further purified using column chromatography on silica gel (eluent: 30% EA in heptane) to give Intermediate B. All intermediates were analyzed according to the methods as described above, and the results were listed in Table 2.

Synthesis of Intermediates B9 to B12

Intermediates B9 to B12 were synthesized by reacting 1-bromo-2-iodobenzene and aryl boronic acid (Reactant A). A general synthesis pathway for Intermediates B9 to B12 was summarized in Scheme B2. In the following Scheme B2, "Reactant A" may be any one of Reactants A9 to A12 as listed in Table 2 and the $R^{PA}$ in Reactant A is a polycyclic aromatic group. "Intermediate B" may be any one of Intermediates B9 to B12 as listed in Table 2.

Scheme B2

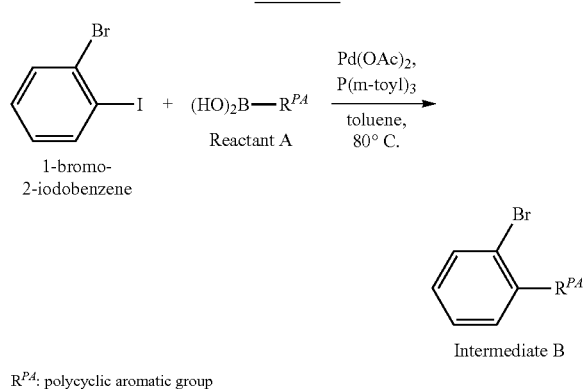

$R^{PA}$: polycyclic aromatic group

According to the Scheme B2, each of Intermediates B9 to B12 was synthesized by the steps as follows.

1-bromo-2-iodobenzene (1.0 eq), Reactant A (1.2 eq), potassium carbonate (3.0 eq), 200 ml of toluene, trim-tolyl) phosphine (P(m-toyl)$_3$) (0.06 eq) and Pd(OAc)$_2$ (0.015 eq) were mixed and stirred at 80° C. for 12 hours. The reaction mixture was then cooled to room temperature, and an organic layer was extracted with saturated aqueous solution of sodium chloride and EA and dried over magnesium sulfate, and then treated with activated charcoal, followed by filtering with silica gel. After a solid prepared by concentrating the filtrate under reduced pressure was suspended in hexane, the suspension was filtered again and washed with hexane to obtain Intermediate B. All intermediates were analyzed according to the methods as described above, and the results were listed in Table 2.

TABLE 2

Reactant A used for preparing Intermediates B1 to B12, and the chemical structures, yields, formulae, and mass analyzed by FD-MS of Intermediates B1 to B12.

| Reactant A Chemical Structure | Intermediate B Chemical Structure | Yield (%) | Formula/ Mass (M+) |
|---|---|---|---|
| Reactant A1 | Intermediate B1 | 80 | $C_{18}H_{11}BrO$/ (323.18) |
| Reactant A2 | Intermediate B2 | 63 | $C_{18}H_{11}BrO$/ (323.18) |
| Reactant A3 | Intermediate B3 | 85 | $C_{18}H_{11}BrO$/ (323.18) |
| Reactant A4 | Intermediate B4 | 87 | $C_{18}H_{11}BrO$/ (323.18) |

TABLE 2-continued

Reactant A used for preparing Intermediates B1 to B12, and the chemical structures, yields, formulae, and mass analyzed by FD-MS of Intermediates B1 to B12.

| Reactant A Chemical Structure | Intermediate B Chemical Structure | Yield (%) | Formula/ Mass (M+) |
|---|---|---|---|
| 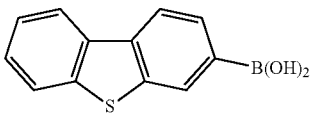<br>Reactant A5 | 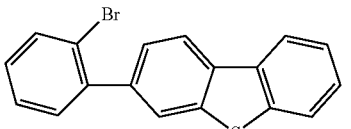<br>Intermediate B5 | 90 | $C_{18}H_{11}BrS/$ (339.25) |
| 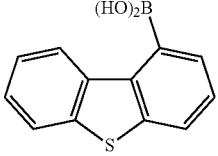<br>Reactant A6 | 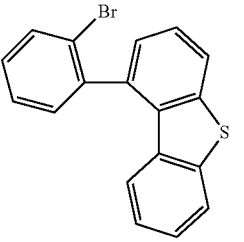<br>Intermediate B6 | 63 | $C_{18}H_{11}BrS/$ (339.25) |
| 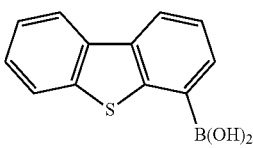<br>Reactant A7 | 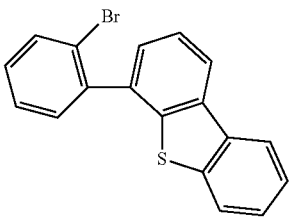<br>Intermediate B7 | 88 | $C_{18}H_{11}BrS/$ (339.25) |
| 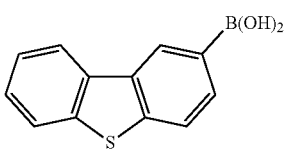<br>Reactant A8 | 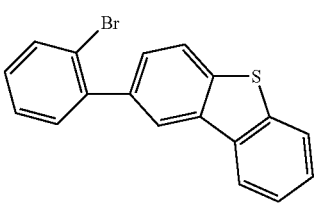<br>Intermediate B8 | 84 | $C_{18}H_{11}BrS/$ (339.25) |
| 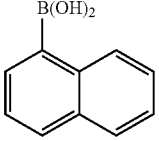<br>Reactant A9 | 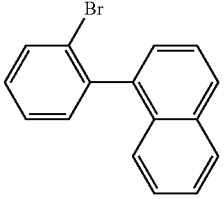<br>Intermediate B9 | 93 | $C_{16}H_{11}Br/$ (283.16) |

TABLE 2-continued

Reactant A used for preparing Intermediates B1 to B12, and the chemical structures, yields, formulae, and mass analyzed by FD-MS of Intermediates B1 to B12.

| Reactant A Chemical Structure | Intermediate B Chemical Structure | Yield (%) | Formula/ Mass (M+) |
|---|---|---|---|
| Reactant A10 | Intermediate B10 | 84 | $C_{22}H_{13}Br$/ (357.24) |
| Reactant A11 | Intermediate B11 | 62 | $C_{20}H_{13}Br$/ (333.22) |
| Reactant A12 | Intermediate B12 | 80 | $C_{22}H_{13}Br$/ (357.24) |

Synthesis of Intermediates B13

In addition to Schemes B1 and B2, another synthesis pathway for Intermediate B was summarized in Scheme B3.

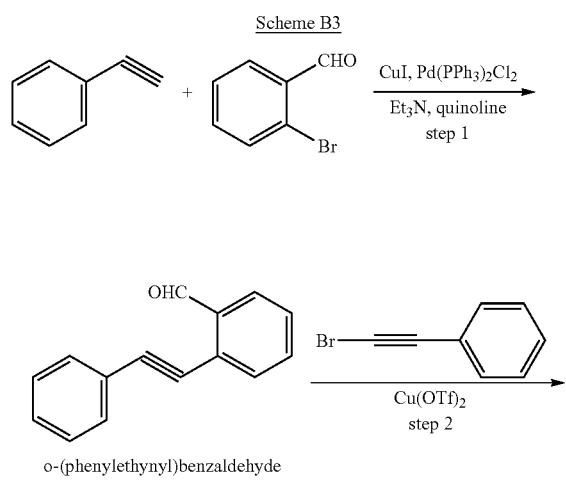

Scheme B3

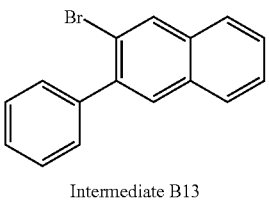

Intermediate B13

Step 1: Synthesis of o-(phenylethynyl)benzaldehyde

Referring to Chemistry—A European Journal, 2007, 13(19), 5632, 2-bromobenzaldehyde (1 eq, CAS No. 6630-33-7), CuI (0.025 eq), Pd(PPh$_3$)$_2$Cl$_2$ (0.05 eq), Et$_3$N (0.6 ml), and the ethynylbenzene (1.2 eq, CAS No. 536-74-3) were added under argon to a stirred solution of quinoline (1 mmol) in anhydrous DMF (1.0M to 2-bromobenzaldehyde). The mixture was stirred at room temperature and monitored by thin layer chromatography (TLC). After evaporation under vacuum, the crude mixture was purified by column chromatography on silica gel to give o-(phenylethynyl)benzaldehyde.

Step 2: Synthesis of Intermediate B13 (2-bromo-3-phenylnapthalene)

Referring to Journal of the American Chemical Society, 2003, 125(36), 10921, a mixture of o-(phenylethynyl)benzaldehyde (0.5 mmol, CAS No. 59046-72-9) and Cu(OTf)$_2$ (5 mol %) in 1,2-dichloroethane (2 ml) were added with (bromoethynyl)benzene (0.6 mmol, CAS No. 932-87-6) and CF$_2$HCO$_2$H (0.5 mmol) successively at room temperature under N$_2$ atmosphere. The resulting mixture was stirred at 100° C. for 15 min and then cooled to room temperature. A saturated aqueous solution of NaHCO$_3$ was added, and the mixture was extracted with ether three times. The combined extracts were washed with brine, dried over MgSO$_4$, and evaporated to leave the crude product, which was purified by silica gel column chromatography using hexane as eluent to give 2-bromo-3-phenylnaphthalene (0.43 mmol) in 86% yield.

Modifications of Intermediates B1 to B13

In addition to the Intermediates B1 to B12, one person skilled in the art can adopt any dihalobenzenes other than 1-bromo-2-iodobenzene and any aryl boronic acids other than Reactants A1 to A12 to successfully synthesize other desired Intermediates B through a reaction mechanism similar to Scheme B1 or Scheme B2. Similarly, one person skilled in the art can also synthesize other desired Intermediates B through a reaction mechanism similar to Scheme B3.

Synthesis of Intermediates C

The foresaid Intermediates B1 to B13 were further adopted to synthesize Intermediate C. A general synthesis pathway for Intermediate C was summarized in Scheme C. In the following Scheme C, "Intermediate A" may be any one of foresaid Intermediates A1 to A3, "Intermediate B" may be any one of foresaid Intermediates B1 to B13, and "Intermediate C" may be any one of Intermediates C1 to C29 as listed in Table 3. Intermediates C1 to C29 were each synthesized by the following steps.

Scheme C

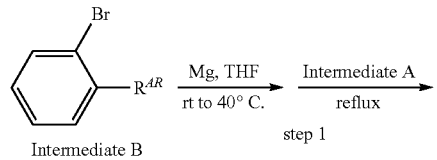

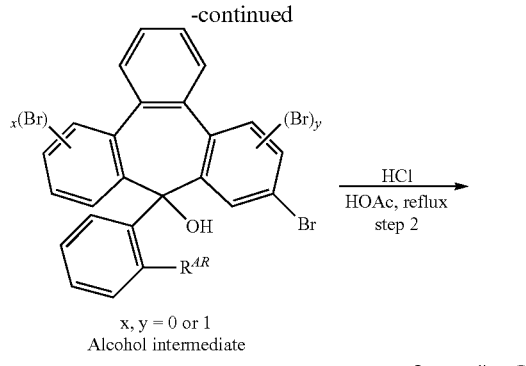

$R^{AR}$: heteroaryl ring containing furan group, heteroaryl ring containg thiofuran group, or polycyclic aromatic ring.

Step 1: Synthesis of Alcohol Intermediate 1.3 g (52 mmol) of magnesium was put into a 200 ml three-neck flask and stirred for 0.5 hours while reducing pressure with a rotary pump. Then 5.0 ml of diethyl ether and one drop of dibromoethane were added under a nitrogen gas stream. A solution in which Intermediate B (50 mmol) was dissolved in 15 ml of diethyl ether was dropped into this mixture at a pace that maintained reflux flow. After completion of dropping, the reaction mixture was heated at 40° C. for 3 hours so as to become a Grignard reagent. The foresaid Intermediate A (45 mmol) was put into a 200 ml three-neck flask, and after nitrogen substitution in the flask was carried out, 40 ml of diethyl ether was added into the flask. The synthesized Grignard reagent was dropped into this solution, and after completion of dropping, the solution was refluxed at 50° C. for 3 hours, and then stirred at room temperature for 24 hours. When the reaction was completed, the reaction solution was washed with water, and a water layer was extracted with ethyl acetate. The extracted solution and an organic layer were combined and washed with saturated saline, and then dried with MgSO$_4$. After drying, this mixture was subjected to suction filtration, and a filtrate was concentrated to give a light yellow, powdery solid of "alcohol intermediate".

The alcohol intermediate could be directly used in step 2 without further purification. Each alcohol intermediates synthesized by reacting different Intermediate A with Intermediate B was identified by FD-MS. The chemical structure of each alcohol intermediate was listed in Table 3.

Step 2: Synthesis of Intermediate C 93 mmol of alcohol intermediate obtained from step 1, 900 ml of acetic acid, and 0.5 ml of HCl were added, and the mixture was stirred at 110° C. for 6 hours. The solvent was then removed by a rotary evaporator, and the remaining substance was purified with column chromatography to obtain Intermediate C.

Intermediates C1 to C29 obtained from different alcohol intermediates were identified by FD-MS. The chemical structures of Intermediates C1 to C29 were listed in Table 3.

TABLE 3

Intermediates A and B used for preparing Intermediates C1 to C29, chemical structures of alcohol intermediates, and chemical structures, yields, formulae, and mass analyzed by FD-MS of Intermediates C1 to C29.

| Intermediate A | Intermediate B | Alcohol intermediate Chemical Structure | Intermediate C Chemical Structure | Yield (%) | Formula/ Mass (M+) |
|---|---|---|---|---|---|
| A1 | B1 | | Intermediate C1 | 65 | $C_{37}H_{21}BrO$/ (561.47) |
| A3 | B1 | | Intermediate C2 | 66 | $C_{37}H_{20}Br_2O$/ (640.36) |
| A1 | B2 | | Intermediate C3 | 78 | $C_{37}H_{21}BrO$/ (561.47) |

TABLE 3-continued

Intermediates A and B used for preparing Intermediates C1 to C29, chemical structures of alcohol intermediates, and chemical structures, yields, formulae, and mass analyzed by FD-MS of Intermediates C1 to C29.

| Intermediate A | Intermediate B | Alcohol intermediate Chemical Structure | Intermediate C Chemical Structure | Yield (%) | Formula/ Mass (M+) |
|---|---|---|---|---|---|
| A3 | B2 | | Intermediate C4 | 88 | $C_{37}H_{20}Br_2O$ / (640.36) |
| A1 | B3 | | Intermediate C5 | 84 | $C_{37}H_{21}BrO$ / (561.47) |
| A3 | B3 | | Intermediate C6 | 81 | $C_{37}H_{20}Br_2O$ / (640.36) |

TABLE 3-continued

Intermediates A and B used for preparing Intermediates C1 to C29, chemical structures of alcohol intermediates, and chemical structures, yields, formulae, and mass analyzed by FD-MS of Intermediates C1 to C29.

| Intermediate A | Intermediate B | Alcohol intermediate Chemical Structure | Intermediate C Chemical Structure | Yield (%) | Formula/ Mass (M$^{+}$) |
|---|---|---|---|---|---|
| A1 | B4 | | Intermediate C7 | 86 | $C_{37}H_{21}BrO$/ (561.47) |
| A3 | B4 | | Intermediate C8 | 86 | $C_{37}H_{20}Br_2O$/ (640.36) |
| A2 | B3 | | Intermediate C9 | 73 | $C_{37}H_{21}BrO$/ (561.47) |

TABLE 3-continued

Intermediates A and B used for preparing Intermediates C1 to C29, chemical structures of alcohol intermediates, and chemical structures, yields, formulae, and mass analyzed by FD-MS of Intermediates C1 to C29.

| Intermediate A | Intermediate B | Alcohol intermediate Chemical Structure | Intermediate C Chemical Structure | Yield (%) | Formula/ Mass (M+) |
|---|---|---|---|---|---|
| A1 | B7 | 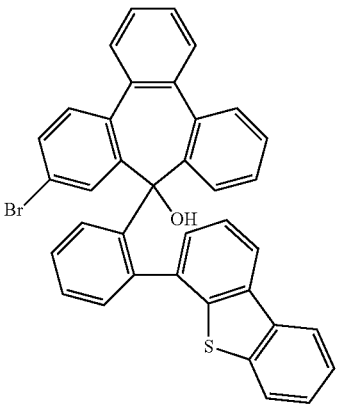 [SMILES: OC1(c2ccccc2-c2cccc3c2oc2ccccc23)c2ccccc2-c2ccccc2-c2ccc(Br)cc21] | 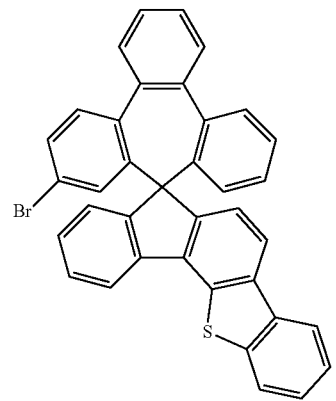 Intermediate C10 | 82 | $C_{37}H_{21}BrS$/ (577.53) |
| A2 | B7 | 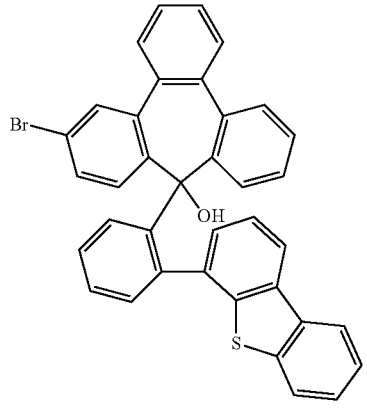 [SMILES: OC1(c2ccccc2-c2cccc3c2sc2ccccc23)c2ccccc2-c2ccccc2-c2cc(Br)ccc21] | 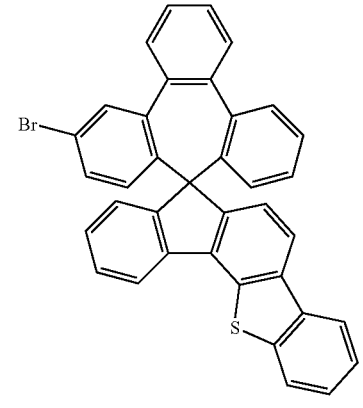 Intermediate C11 | 84 | $C_{37}H_{21}BrS$/ (577.53) |
| A3 | B7 | 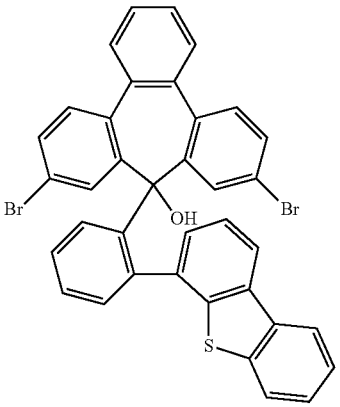 [SMILES: OC1(c2ccccc2-c2cccc3c2sc2ccccc23)c2cc(Br)ccc2-c2ccccc2-c2ccc(Br)cc21] | 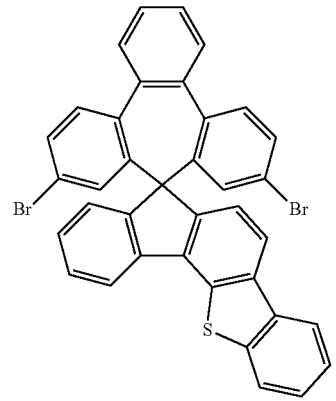 Intermediate C12 | 84 | $C_{37}H_{20}Br_2S$/ (656.43) |

TABLE 3-continued

Intermediates A and B used for preparing Intermediates C1 to C29, chemical structures of alcohol intermediates, and chemical structures, yields, formulae, and mass analyzed by FD-MS of Intermediates C1 to C29.

| Intermediate A | Intermediate B | Alcohol intermediate Chemical Structure | Intermediate C Chemical Structure | Yield (%) | Formula/ Mass (M+) |
|---|---|---|---|---|---|
| A1 | B6 | | Intermediate C13 | 71 | $C_{37}H_{21}BrS$/ (577.53) |
| A3 | B6 | | Intermediate C14 | 72 | $C_{37}H_{20}Br_2S$/ (656.43) |
| A1 | B5 | | Intermediate C15 | 68 | $C_{37}H_{21}BrS$/ (577.53) |

TABLE 3-continued

Intermediates A and B used for preparing Intermediates C1 to C29, chemical structures of alcohol intermediates, and chemical structures, yields, formulae, and mass analyzed by FD-MS of Intermediates C1 to C29.

| Intermediate A | Intermediate B | Alcohol intermediate Chemical Structure | Intermediate C Chemical Structure | Yield (%) | Formula/ Mass (M+) |
|---|---|---|---|---|---|
| A3 | B5 | 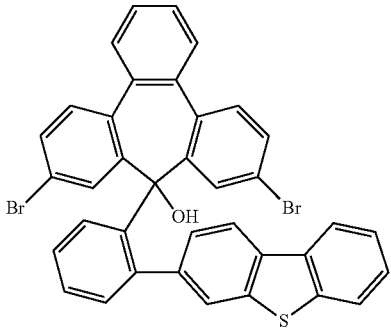 [SMILES: OC1(c2ccccc2-c2ccc3c(c2)sc2ccccc23)c2cc(Br)ccc2-c2ccccc2-c2ccc(Br)cc21] | 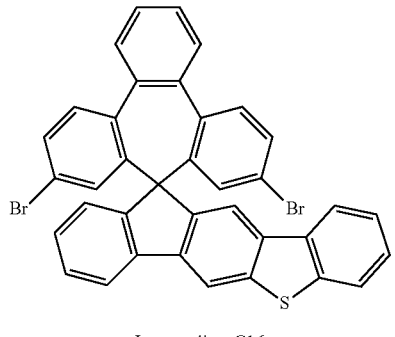<br>Intermediate C16 | 58 | $C_{37}H_{20}Br_2S$ / (656.43) |
| A1 | B8 | 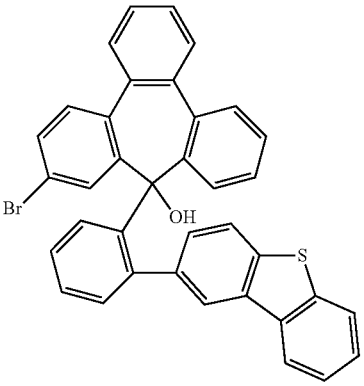 [SMILES: OC1(c2ccccc2-c2ccc3sc4ccccc4c3c2)c2ccccc2-c2ccccc2-c2ccc(Br)cc21] | 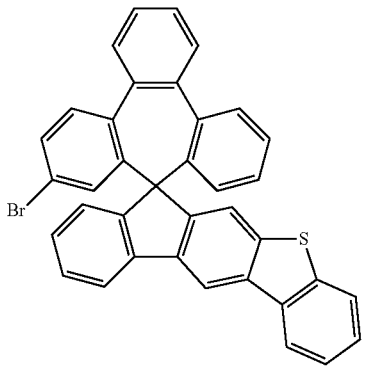<br>Intermediate C17 | 67 | $C_{37}H_{21}BrS$ / (577.53) |
| A3 | B8 | 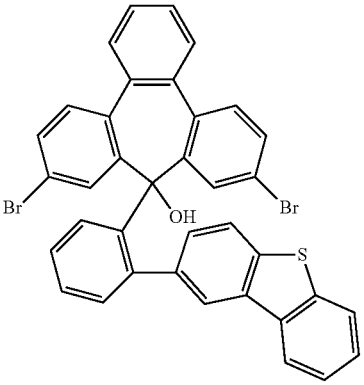 [SMILES: OC1(c2ccccc2-c2ccc3sc4ccccc4c3c2)c2cc(Br)ccc2-c2ccccc2-c2ccc(Br)cc21] | 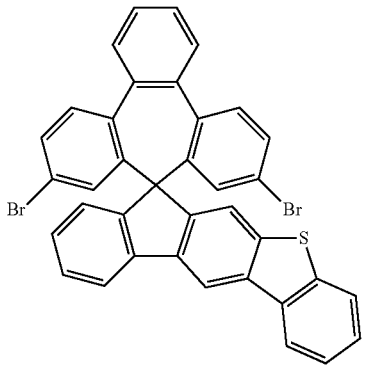<br>Intermediate C18 | 71 | $C_{37}H_{20}Br_2S$ / (656.43) |

TABLE 3-continued

Intermediates A and B used for preparing Intermediates C1 to C29, chemical structures of alcohol intermediates, and chemical structures, yields, formulae, and mass analyzed by FD-MS of Intermediates C1 to C29.

| Intermediate A | Intermediate B | Alcohol intermediate Chemical Structure | Intermediate C Chemical Structure | Yield (%) | Formula/ Mass (M+) |
|---|---|---|---|---|---|
| A1 | B9 | | Intermediate C19 | 83 | $C_{35}H_{21}Br$/ (521.45) |
| A2 | B9 | | Intermediate C20 | 79 | $C_{35}H_{21}Br$/ (521.45) |
| A3 | B9 | | Intermediate C21 | 76 | $C_{35}H_{20}Br_2$/ (600.34) |

TABLE 3-continued

Intermediates A and B used for preparing Intermediates C1 to C29, chemical structures of alcohol intermediates, and chemical structures, yields, formulae, and mass analyzed by FD-MS of Intermediates C1 to C29.

| Inter-mediate A | Inter-mediate B | Alcohol intermediate Chemical Structure | Intermediate C Chemical Structure | Yield (%) | Formula/ Mass (M$^+$) |
|---|---|---|---|---|---|
| A1 | B13 | | Intermediate C22 | 63 | $C_{35}H_{21}Br$/ (521.45) |
| A3 | B13 | | Intermediate C23 | 68 | $C_{35}H_{20}Br_2$/ (600.34) |
| A1 | B11 | | Intermediate C24 | 71 | $C_{39}H_{23}Br$/ (571.5) |

TABLE 3-continued

Intermediates A and B used for preparing Intermediates C1 to C29, chemical structures of alcohol intermediates, and chemical structures, yields, formulae, and mass analyzed by FD-MS of Intermediates C1 to C29.

| Intermediate A | Intermediate B | Alcohol intermediate Chemical Structure | Intermediate C Chemical Structure | Yield (%) | Formula/ Mass (M+) |
|---|---|---|---|---|---|
| A3 | B11 | 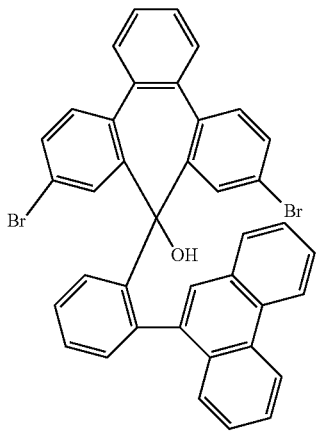 [SMILES: OC1(c2ccccc2-c2cc3ccccc3c3ccccc23)c2cc(Br)ccc2-c2ccccc2-c2ccc(Br)cc21] | 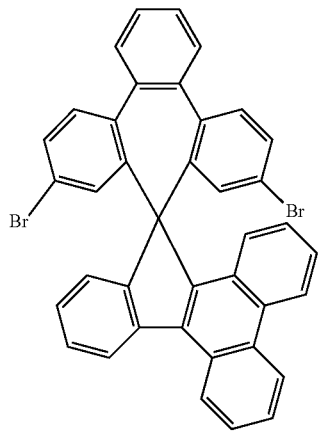<br>Intermediate C25 | 77 | C₃₉H₂₂Br₂/ (650.4) |
| A1 | B12 | 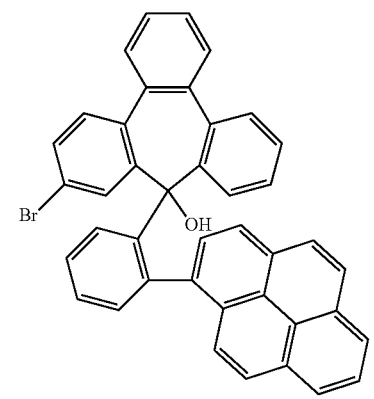 [SMILES: OC1(c2ccccc2-c2ccc3ccc4cccc5ccc2c3c45)c2ccccc2-c2ccccc2-c2ccc(Br)cc21] | 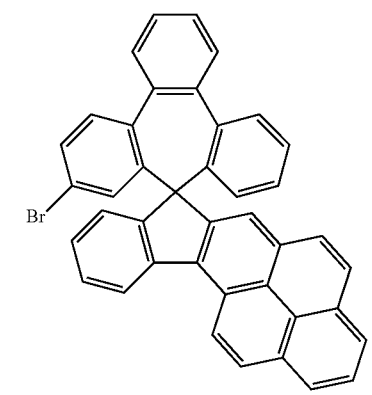<br>Intermediate C26 | 58 | C₄₁H₂₃Br/ (595.53) |
| A3 | B12 | 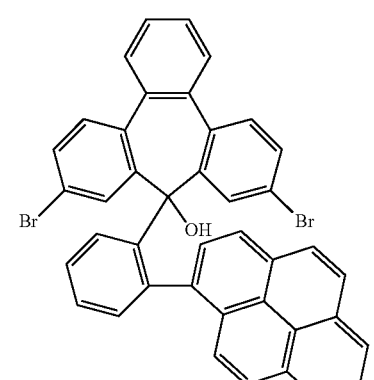 | 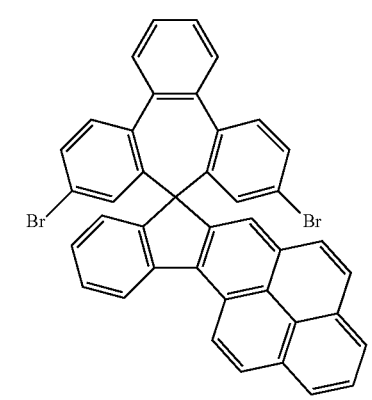<br>Intermediate C27 | 73 | C₄₁H₂₂Br₂/ (674.42) |

TABLE 3-continued

Intermediates A and B used for preparing Intermediates C1 to C29, chemical structures of alcohol intermediates, and
chemical structures, yields, formulae, and mass analyzed by FD-MS of Intermediates C1 to C29.

| Intermediate A | Intermediate B | Alcohol intermediate Chemical Structure | Intermediate C Chemical Structure | Yield (%) | Formula/ Mass (M+) |
|---|---|---|---|---|---|
| A1 | B10 | | Intermediate C28 | 63 | $C_{41}H_{23}Br$/ (595.53) |
| A3 | B10 | | Intermediate C29 | 84 | $C_{41}H_{23}Br_2$/ (674.42) |

Modifications of Intermediates C1 to C29

In addition to the Intermediates C1 to C29, one person skilled in the art can adopt any intermediate A other than Intermediates A1 to A3 and any Intermediate B other than Intermediates B1 to B13 to successfully synthesize other desired Intermediates C through a reaction mechanism similar to Scheme C.

Synthesis of Novel Compounds

Each of Intermediates C1 to C29 could be reacted with various reactants to synthesize various claimed novel compounds. The general synthesis pathway of the claimed novel compound was summarized in Scheme I. In the following Scheme I, "Reactant B" may be any one of Reactants B1 to B5 as listed in Table 4, and "Intermediate C" may be any one of foresaid Intermediates C1 to C29. The compounds were each synthesized by the following steps.

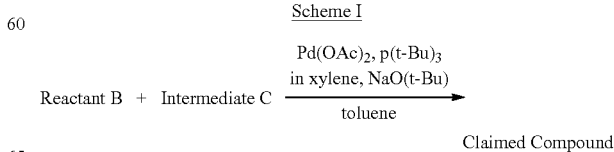

Scheme I

Reactant B + Intermediate C $\xrightarrow[\text{toluene}]{\text{Pd(OAc)}_2, \text{p(t-Bu)}_3 \text{ in xylene, NaO(t-Bu)}}$ Claimed Compound

TABLE 4 chemical structure and CAS No. of Reactants B1 to B5.

| | Reactant B1 | Reactant B2 | Reactant B3 |
|---|---|---|---|
| Chemical Structure | 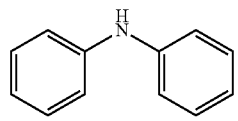 [SMILES: c1ccc(Nc2ccccc2)cc1] | 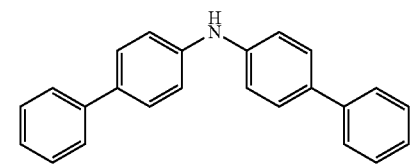 [SMILES: c1ccc(-c2ccc(Nc3ccc(-c4ccccc4)cc3)cc2)cc1] | 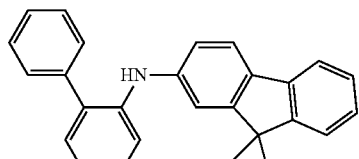 |
| CAS No. | 122-39-4 | 102113-98-4 | NA |

| | Reactant B4 | Reactant B5 |
|---|---|---|
| Chemical Structure | 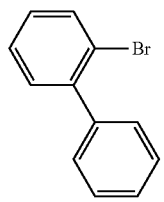 [SMILES: Brc1ccccc1-c1ccccc1] | 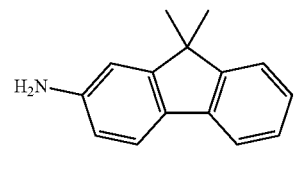 [SMILES: CC1(C)c2ccccc2-c2ccc(N)cc21] |
| CAS No. | NA | NA |

Reactants B1 to B5 were used to prepare the novel compounds. Among them, Reactants B1 to B2 were purchased from Aldrich or Alfa, and CAS numbers were listed in Table 4. In addition, Reactants B3 to B5 were synthesized by the Scheme I-I below.

Synthesis of Reactants B3 to B5

Reactants B3 to B5 were synthesized by the Scheme I-I. The Reactants B3 to B5 can be prepared according to the above Scheme I-I. The starting materials $Ar_1$—$NH_2$ (arylamine) and Br—$Ar_2$ (arylbromide) to prepare the Reactants B3 to B5 are listed in the following Table 5.

Scheme I-I $$Ar_1\text{—}NH_2 \; + \; Br\text{—}Ar_2 \xrightarrow[\text{NaO-t-Bu, toluene}]{\text{Pd(OAc)}_2,\,\text{dppf}} H\text{—}N\begin{smallmatrix}Ar_1\\ \\Ar_2\end{smallmatrix}$$

A mixture of arylbromide (1.0 eq), arylamine (1.05 eq), $Pd(OAc)_2$ (0.01 eq), 1,1'-Bis(diphenylphosphino)ferrocene (DPPF) (0.04 eq), sodium tert-butoxide (1.5 eq), and toluene was taken in a pressure tube and heated at 80° C. for 12 h under $N_2$ atmosphere. After completion of the reaction, the volatiles were removed under vacuum, and the resulting solution extracted with 60 mL dichloromethane for 3 times. The combined organic extract was washed with brine solution, dried over $Na_2SO_4$, and concentrated to leave a yellow solid. Further, the crude product was purified by column chromatography on silica gel by using hexane/dichloromethane mixture (2:1 v/v) as an eluent. The analysis data of the obtained products, i.e. Reactants B3 to B5, are listed in the following Table 5.

TABLE 5 the arylbromide and the arylamine used to prepare the Reactants B3 to B5 and the yield and the chemical structures, yields, formulae, and mass analyzed by FD-MS of Reactants B3 to B5.

| Arylbromide | Arylamine | Reactant | Yield (%) | Formula/Mass (M+) |
|---|---|---|---|---|
| 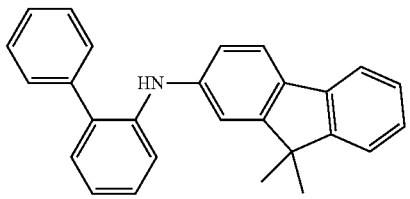 | | | 83 | $C_{27}H_{23}N$/ (361.48) |

Reactant B3

TABLE 5-continued the arylbromide and the arylamine used to prepare the Reactants B3 to B5 and the yield and the chemical structures, yields, formulae, and mass analyzed by FD-MS of Reactants B3 to B5.

| Arylbromide | Arylamine | Reactant | Yield (%) | Formula/ Mass (M+) |
|---|---|---|---|---|
| (structure) | (structure) | Reactant B4 | 80 | $C_{21}H_{19}NO$/ (301.38) |
| (structure) | (structure) | Reactant B5 | 82 | $C_{24}H_{17}NO$/ (335.4) |

Intermediate C (1.0 eq) and Reactant B (2.1 eq) were dissolved in toluene (105 ml) and saturated with $N_2$. Pd(OAc)$_2$ (0.02 g, 0.005 eq), 10% (w/w) P(t-Bu)$_3$ in xylene and NaO-t-Bu (5.24 g, 3.0 eq) were added in the solution in succession and heated at 80° C. for 12 hours. DI water (20 ml) was poured into the resulting suspension and the mixed solution was stirred for 30 min. After that, the mixed solution was filtered with suction to obtain solid. Then, the solid was washed by $H_2O$ and methanol and recrystallized (3 times) with toluene to obtain the white solid of the claimed novel compound.

Figure 2:
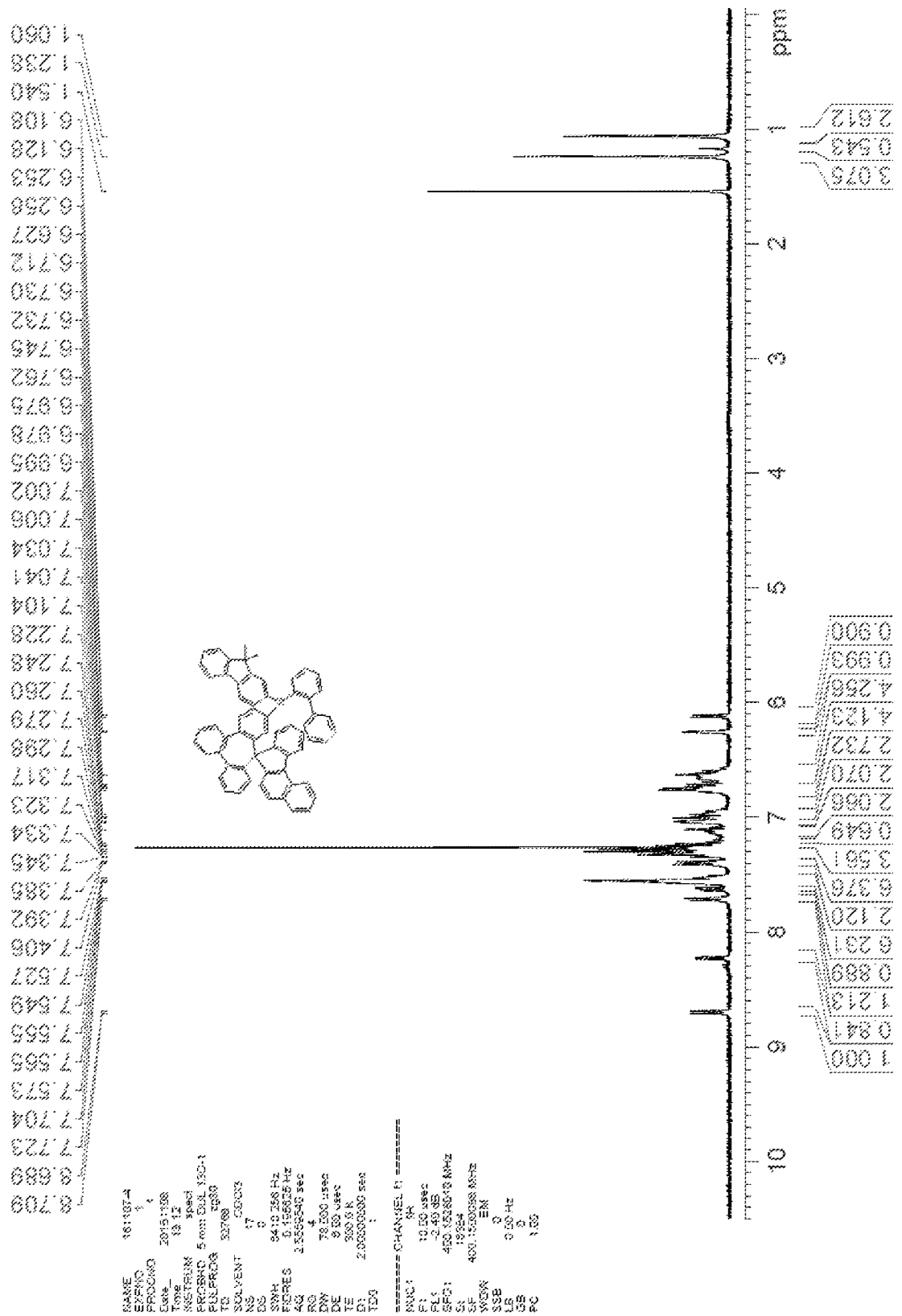
FIGS. 2 to 18 respectively are $^1$H nuclear magnetic resonance (NMR) spectra of Compounds 1 to 17.
Figure 3:
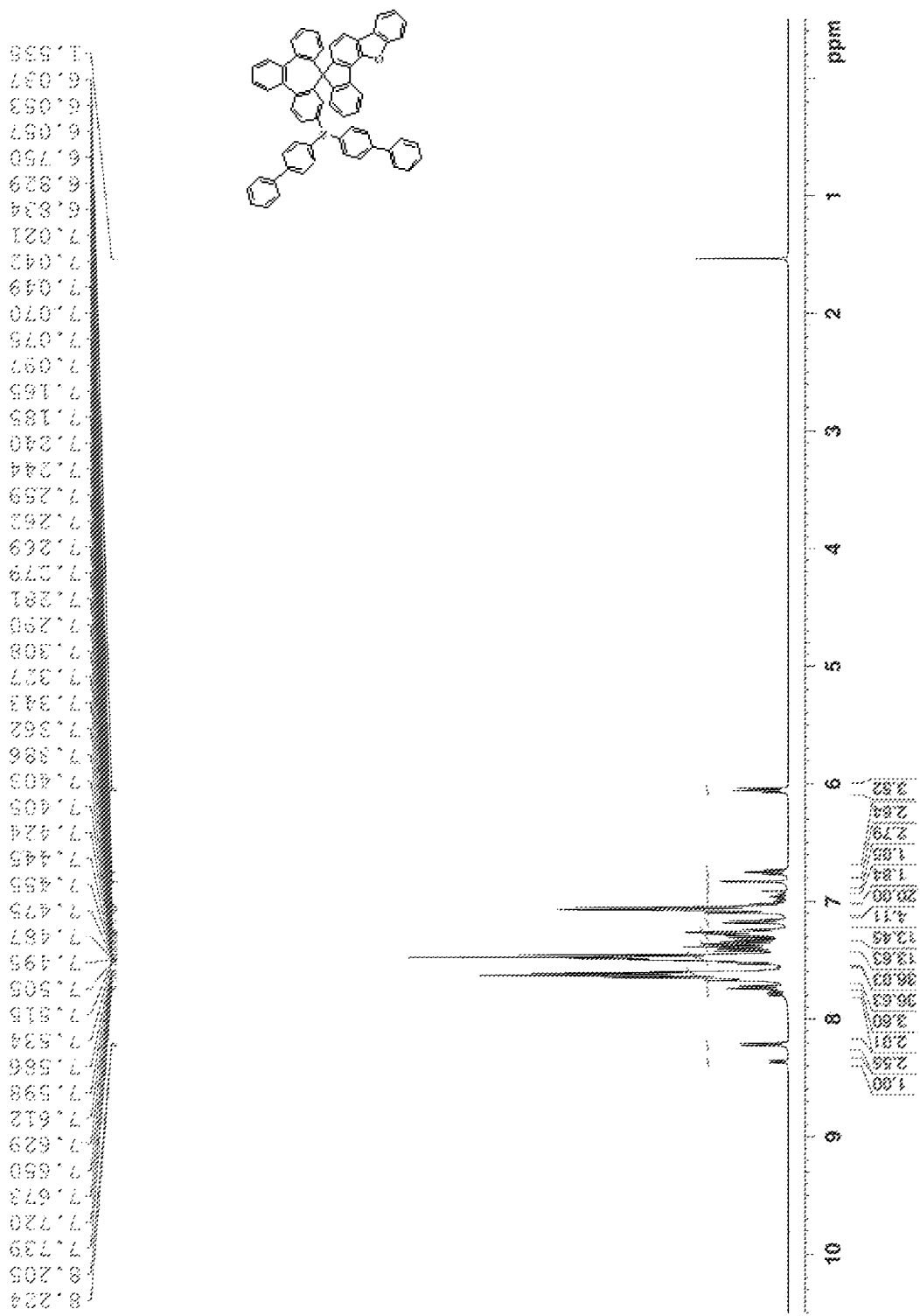
Figure 4:
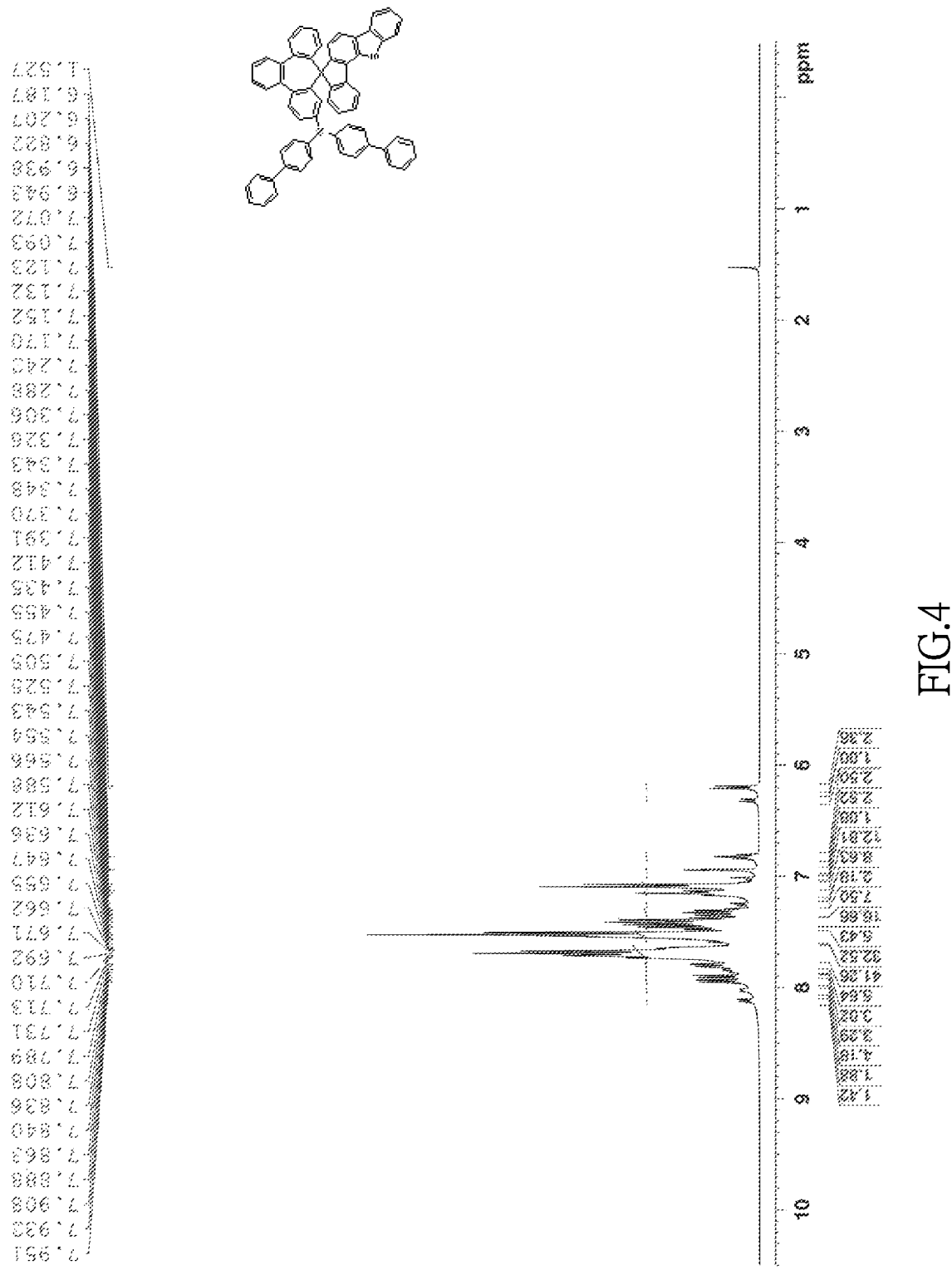
Figure 5:
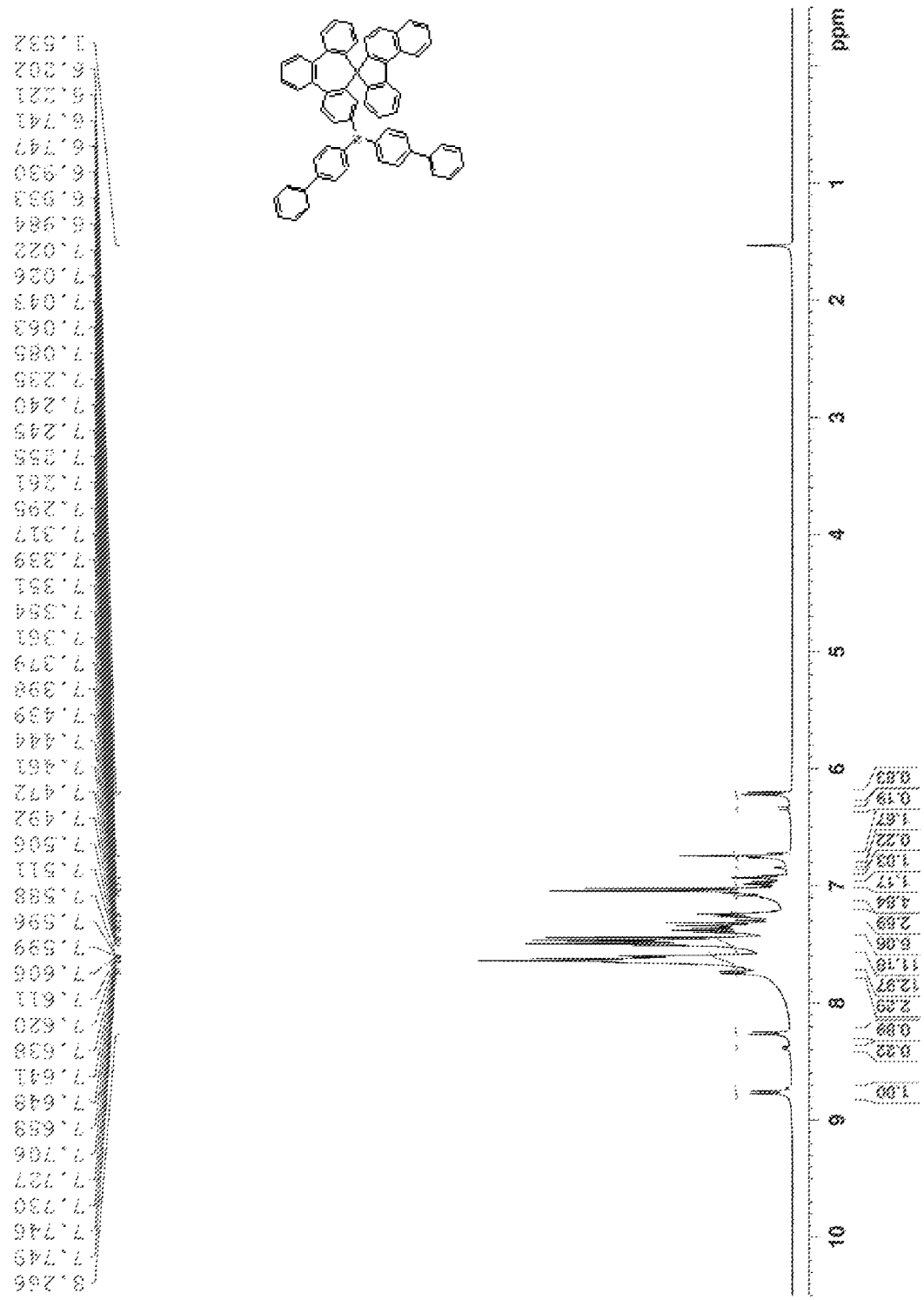
Figure 6:
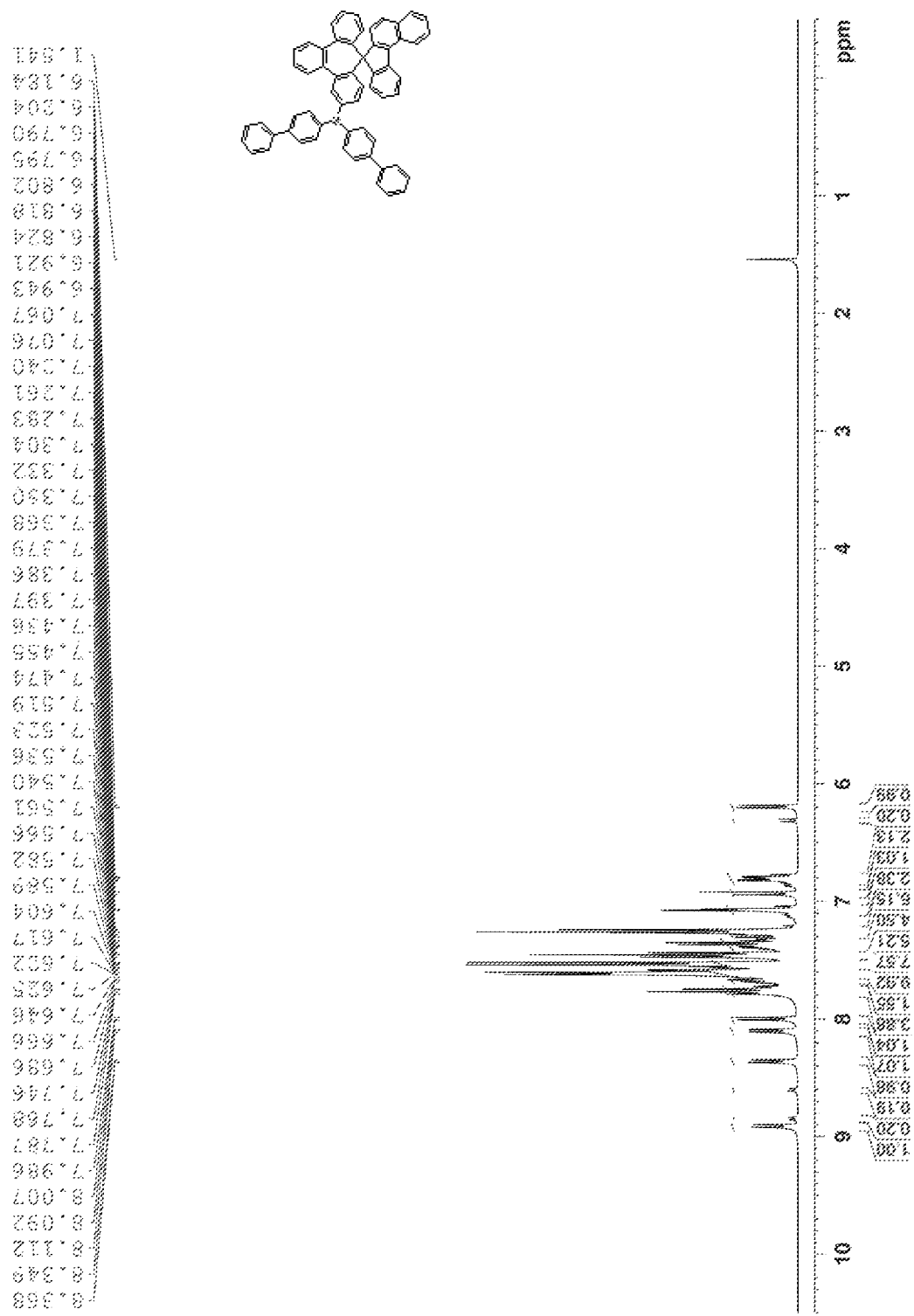
Figure 7:
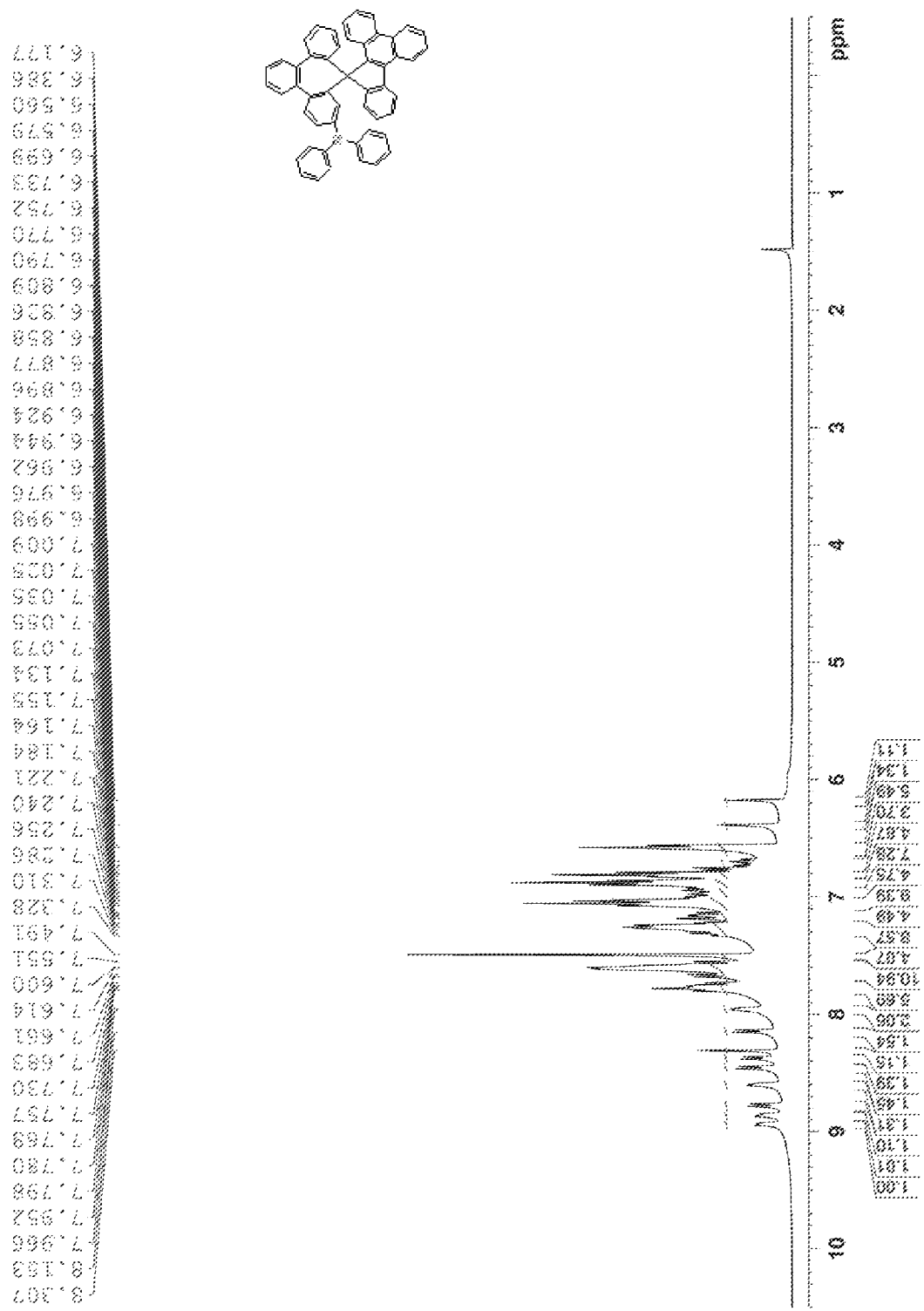
Figure 8:
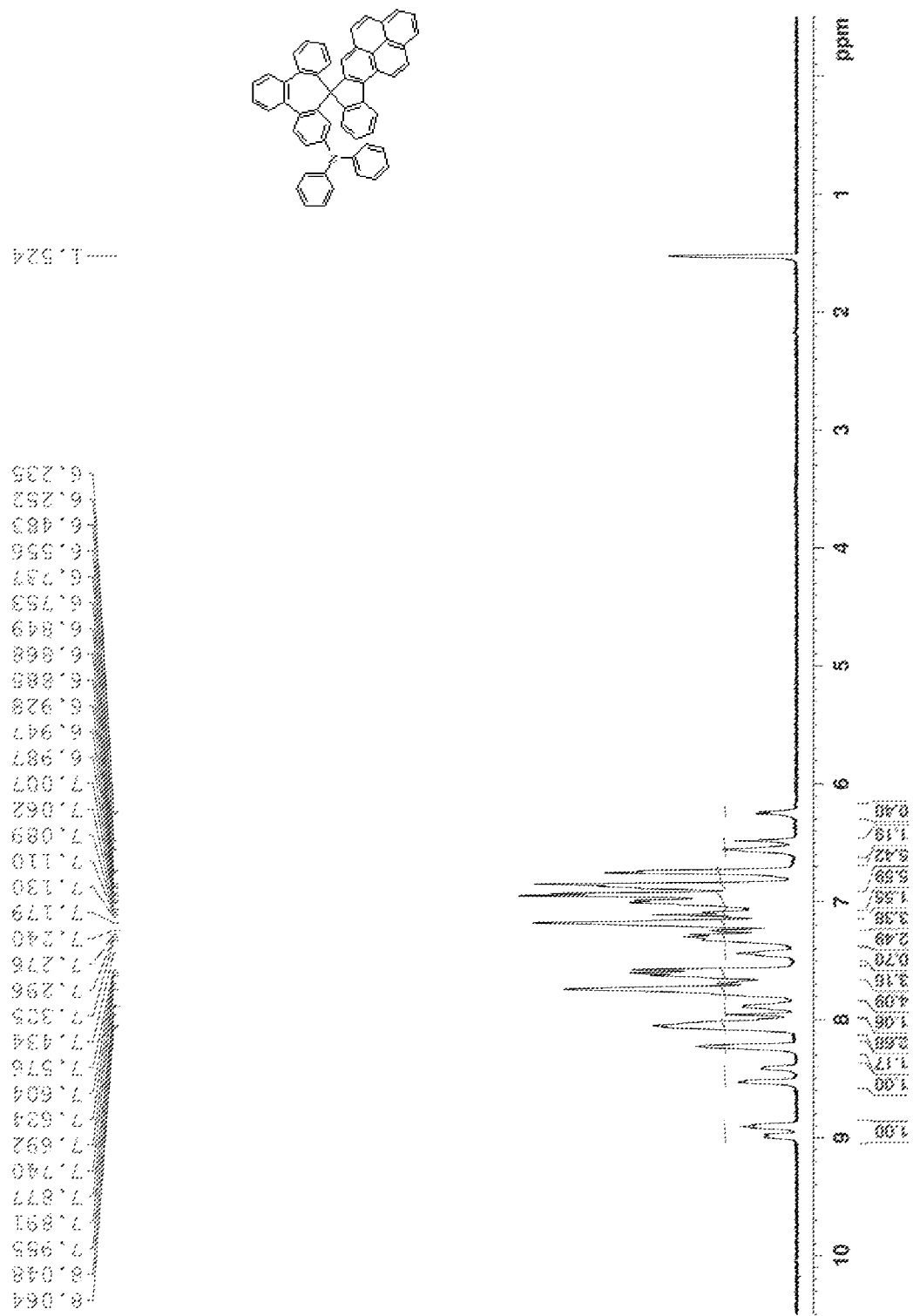
Figure 9:
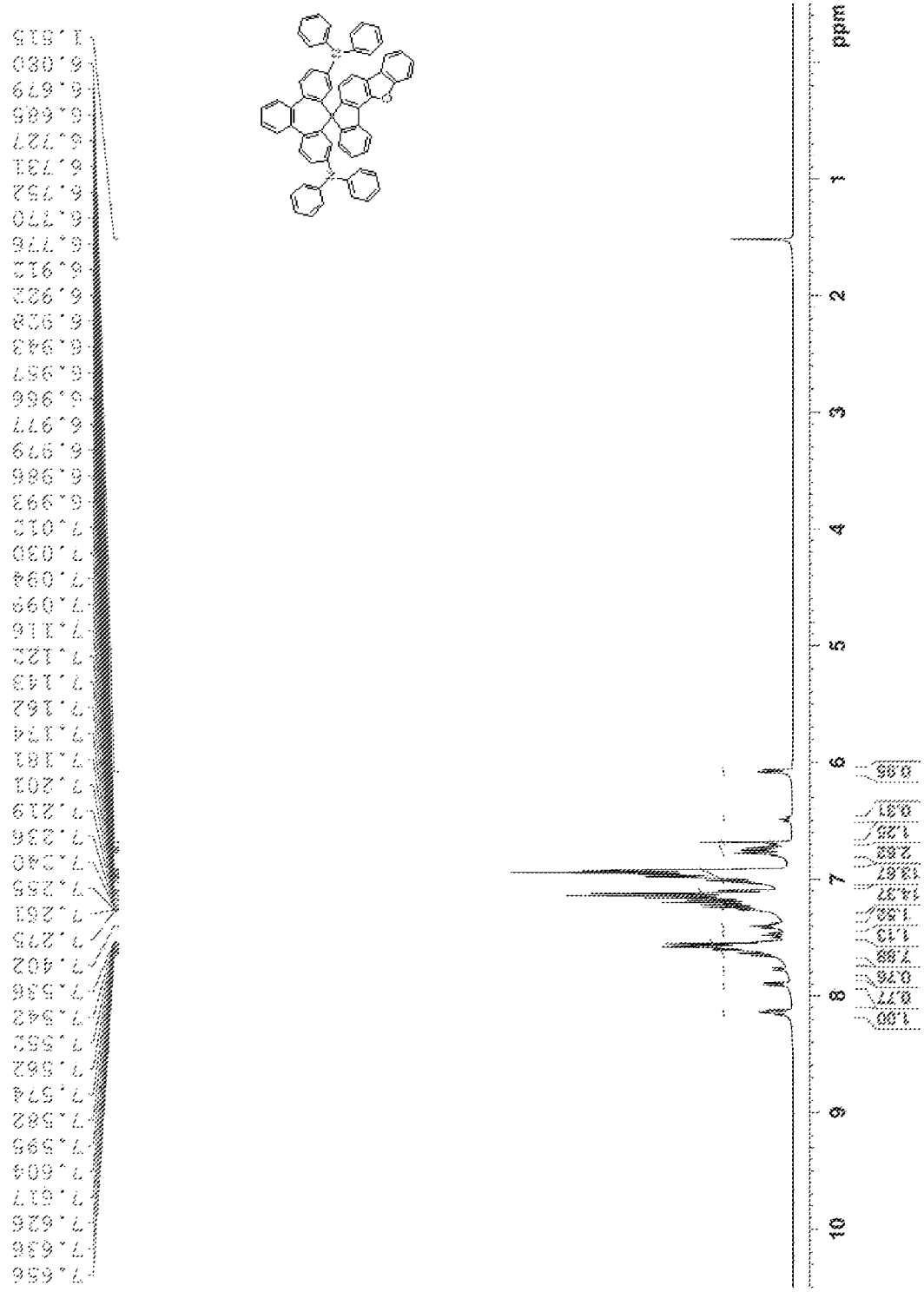
Figure 10:
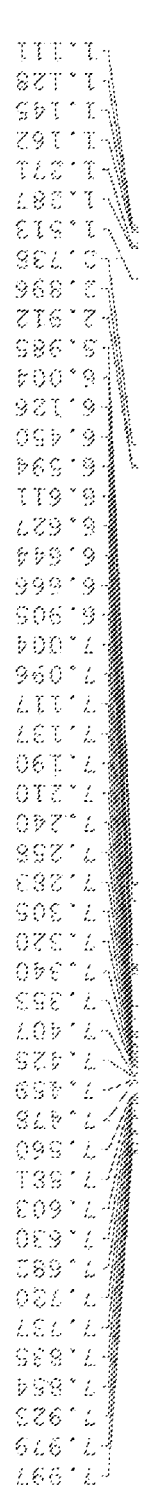
Figure 10:
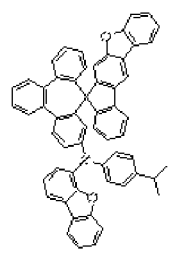
Figure 10:
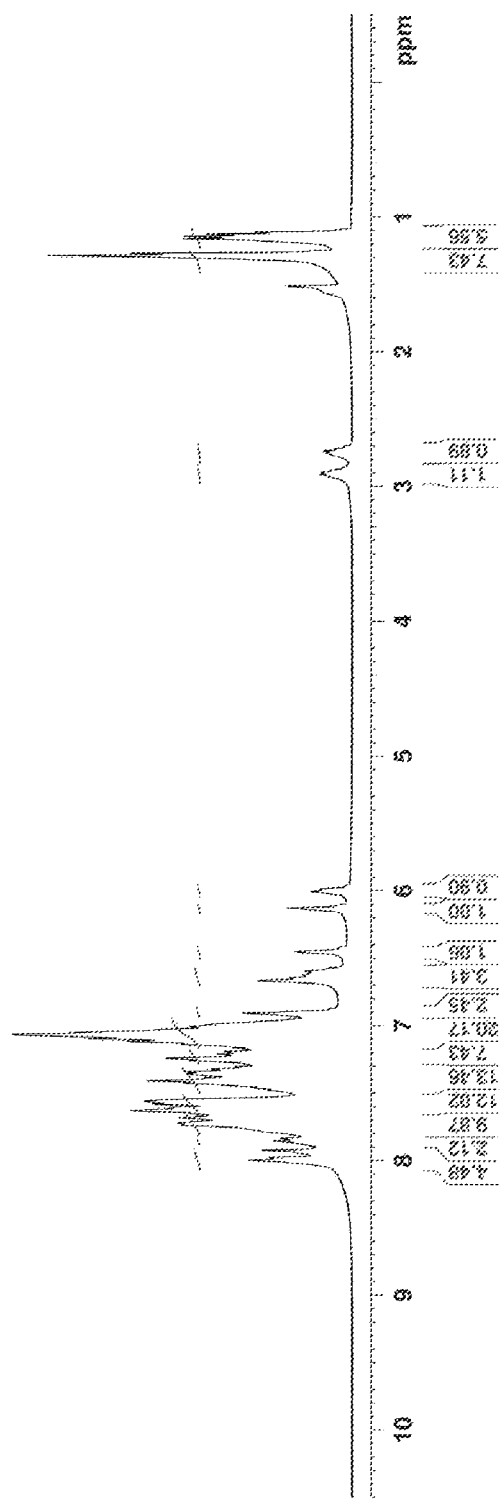
Figure 11:
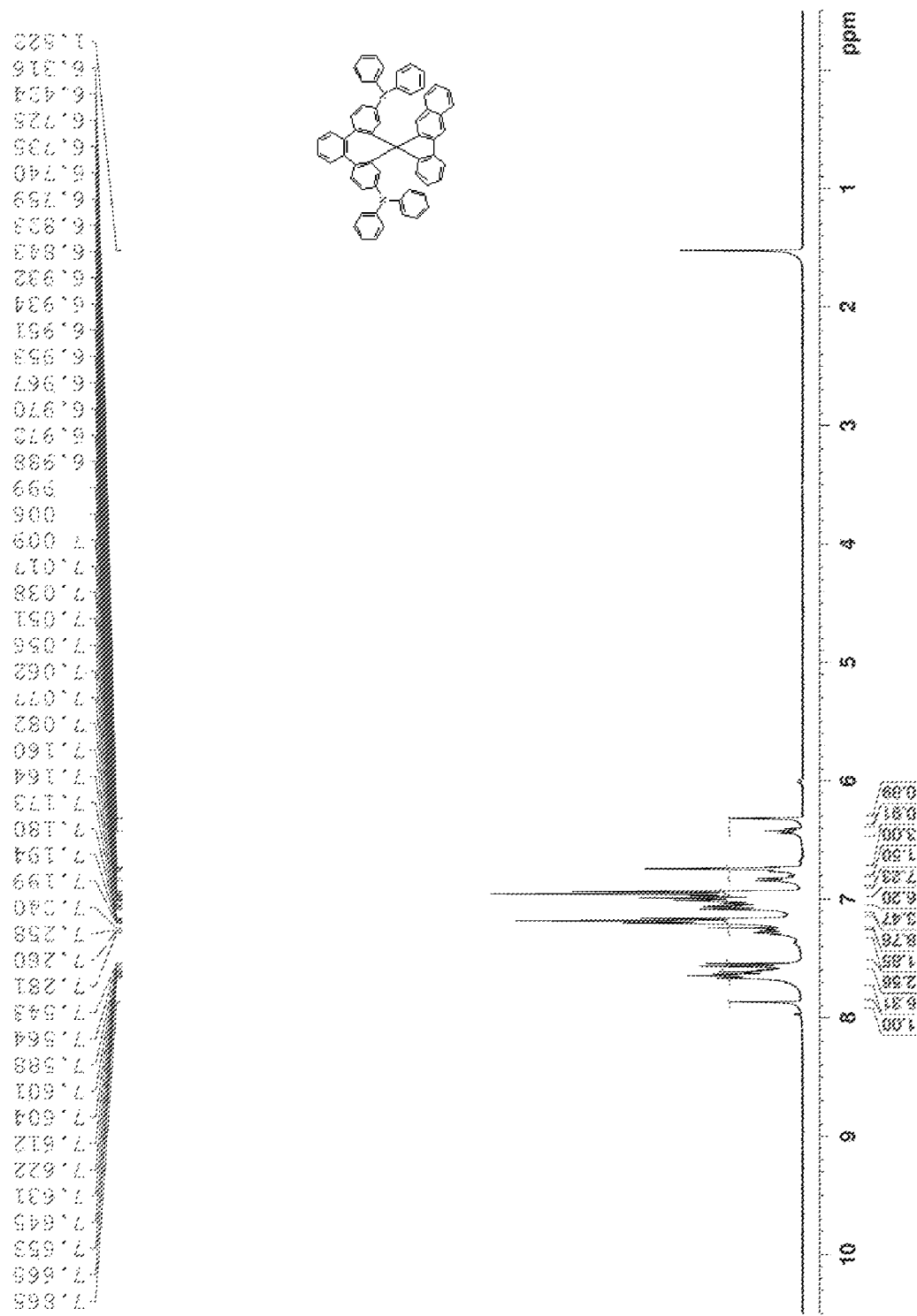
Figure 12:
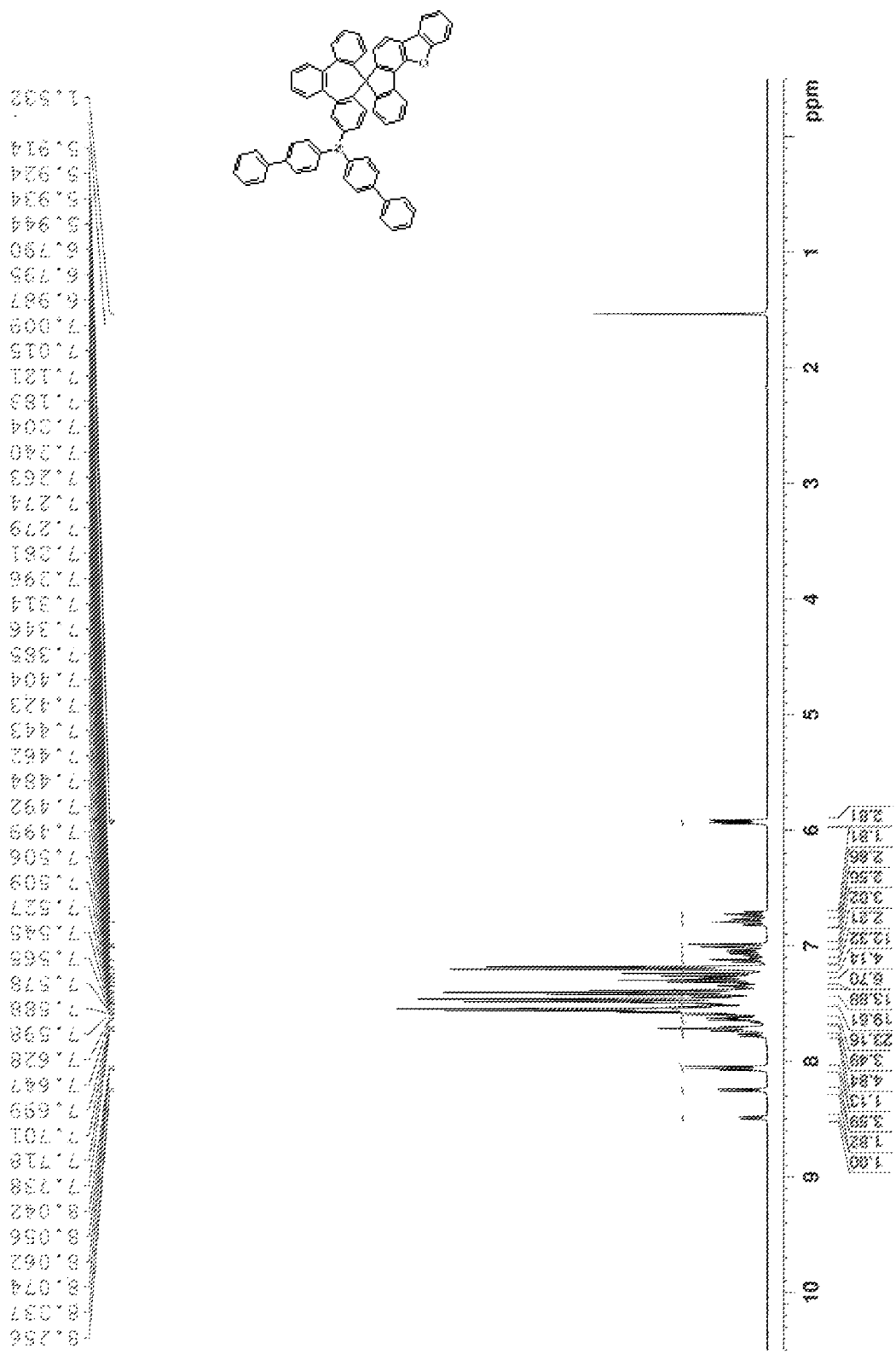
Figure 13:
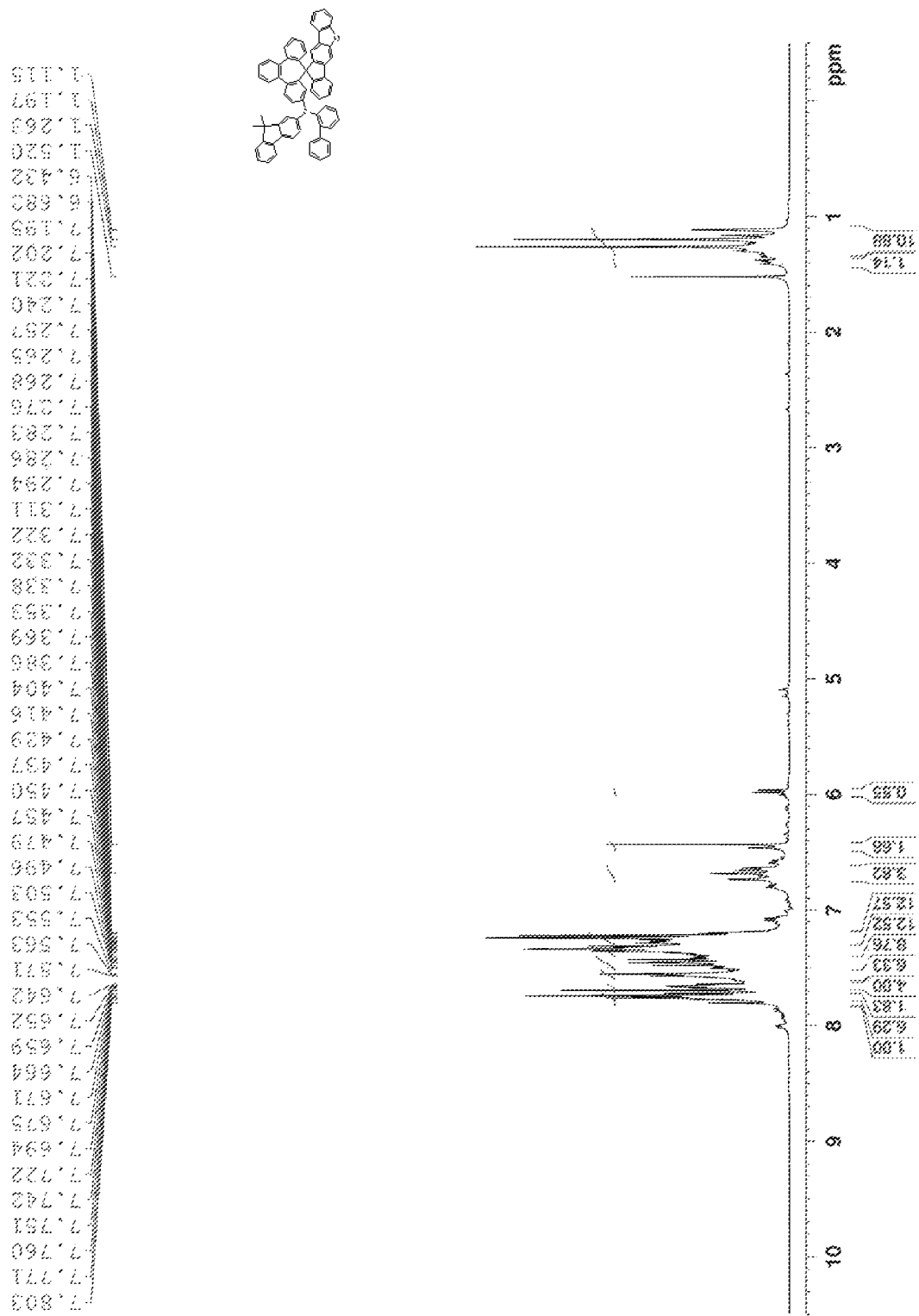
Figure 14:
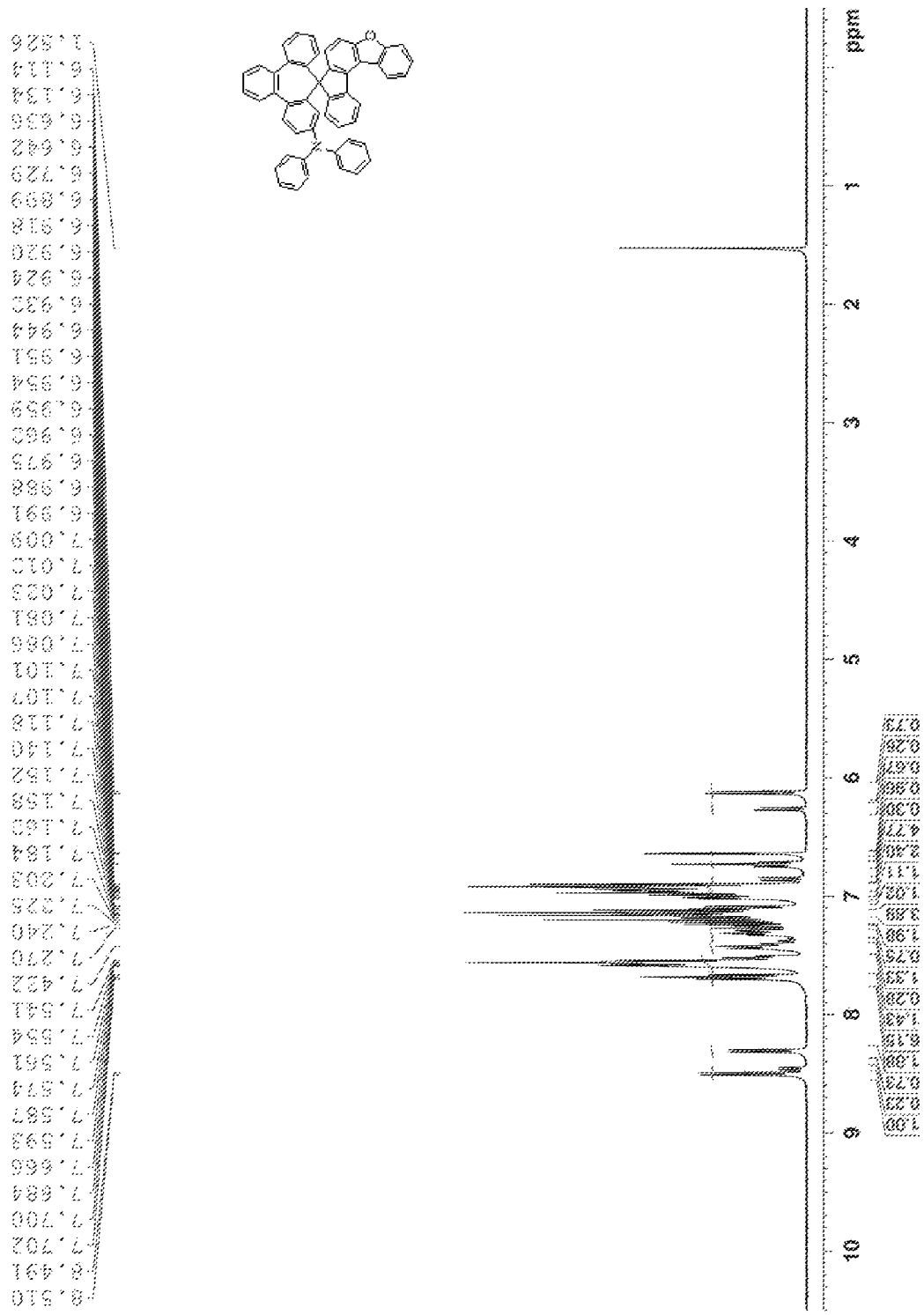
Figure 15:
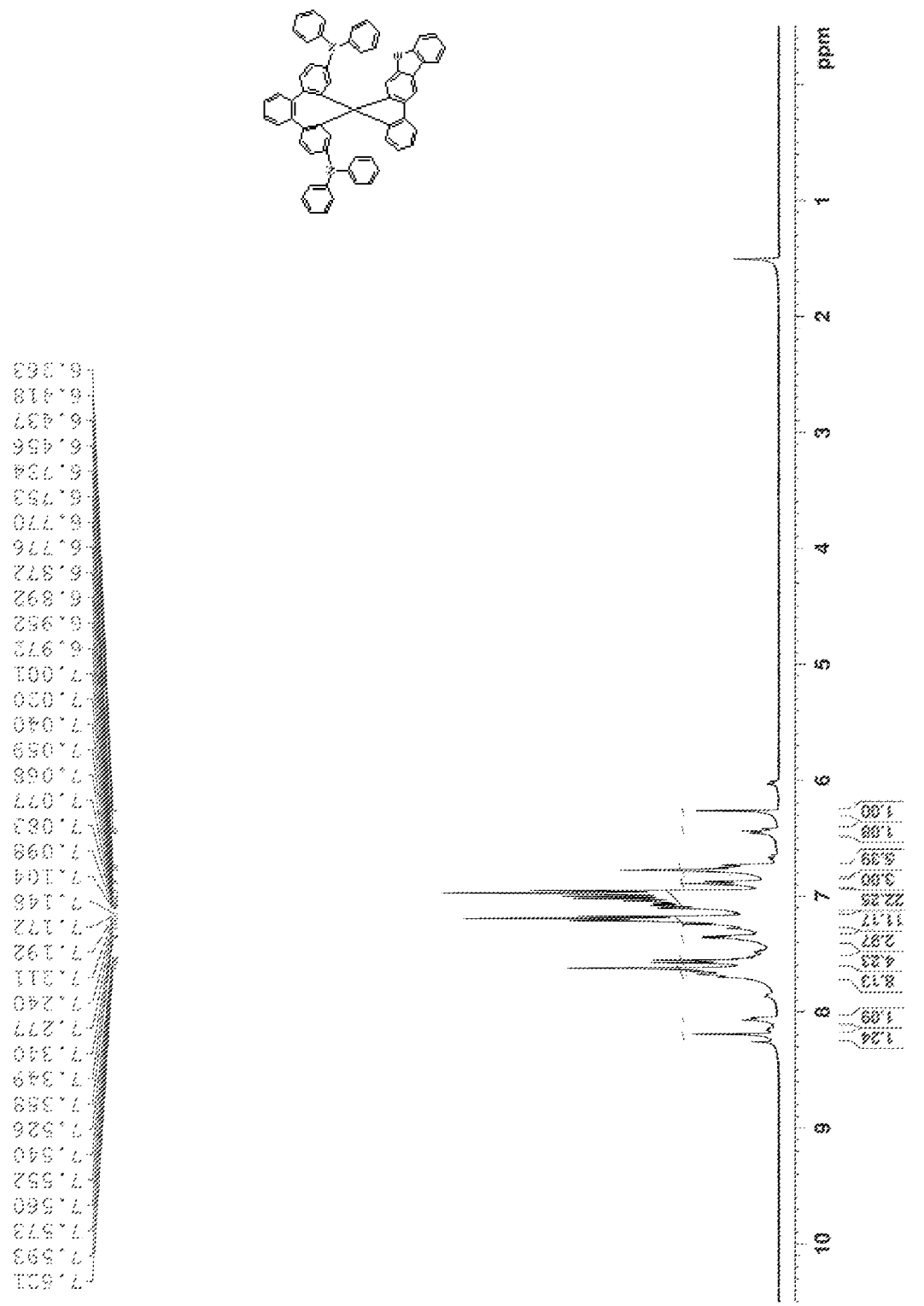
Figure 16:
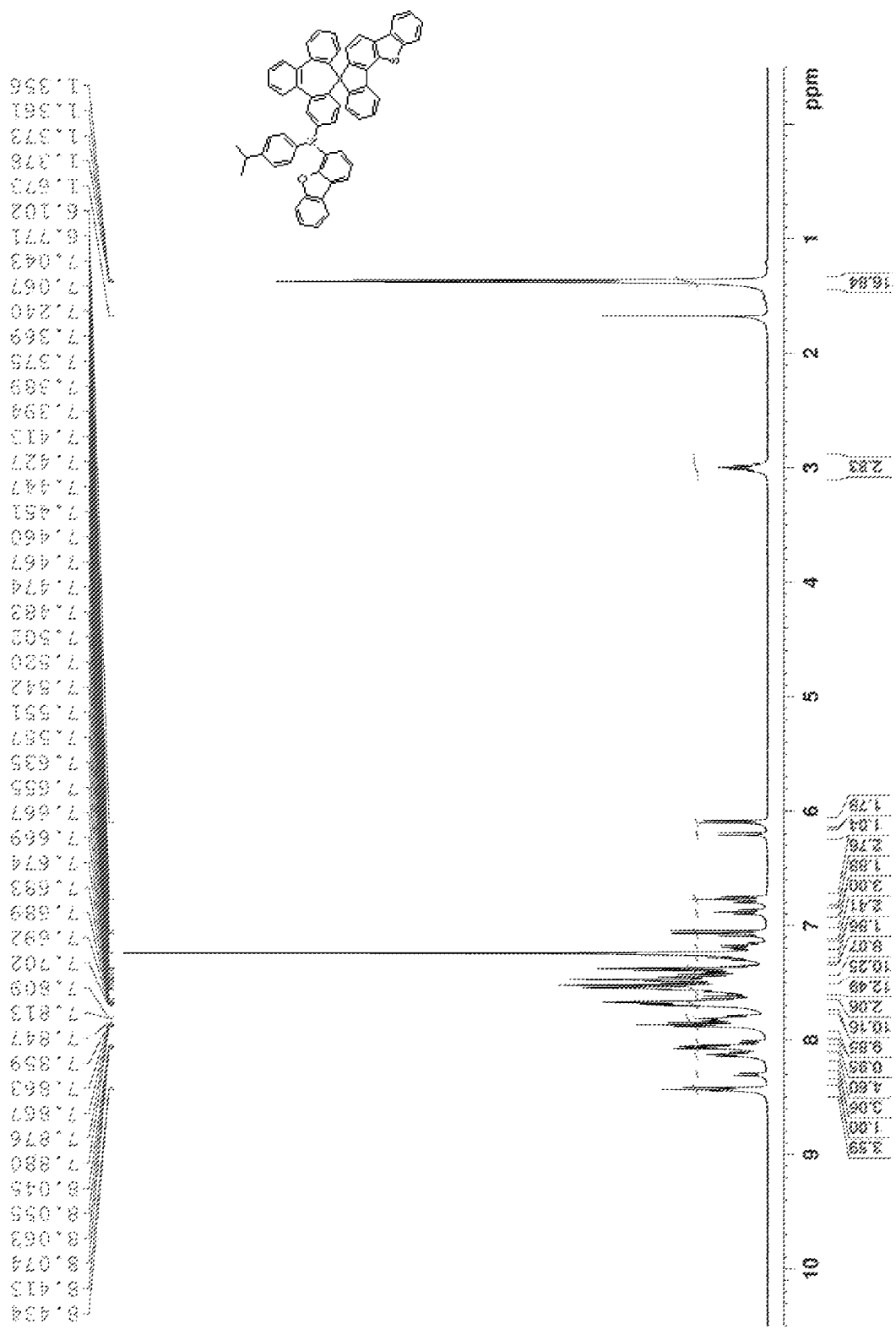
Figure 17:
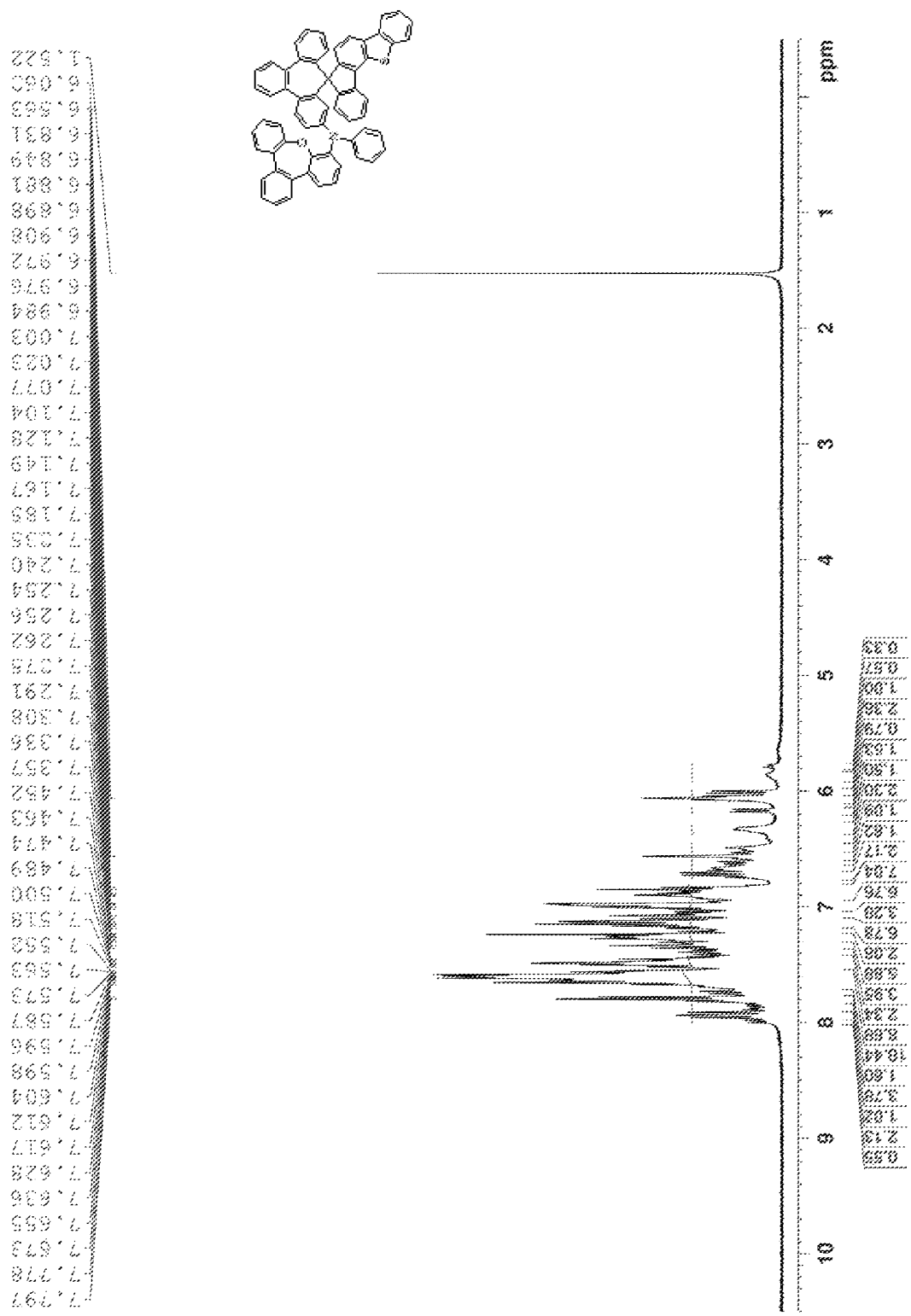
Figure 18:
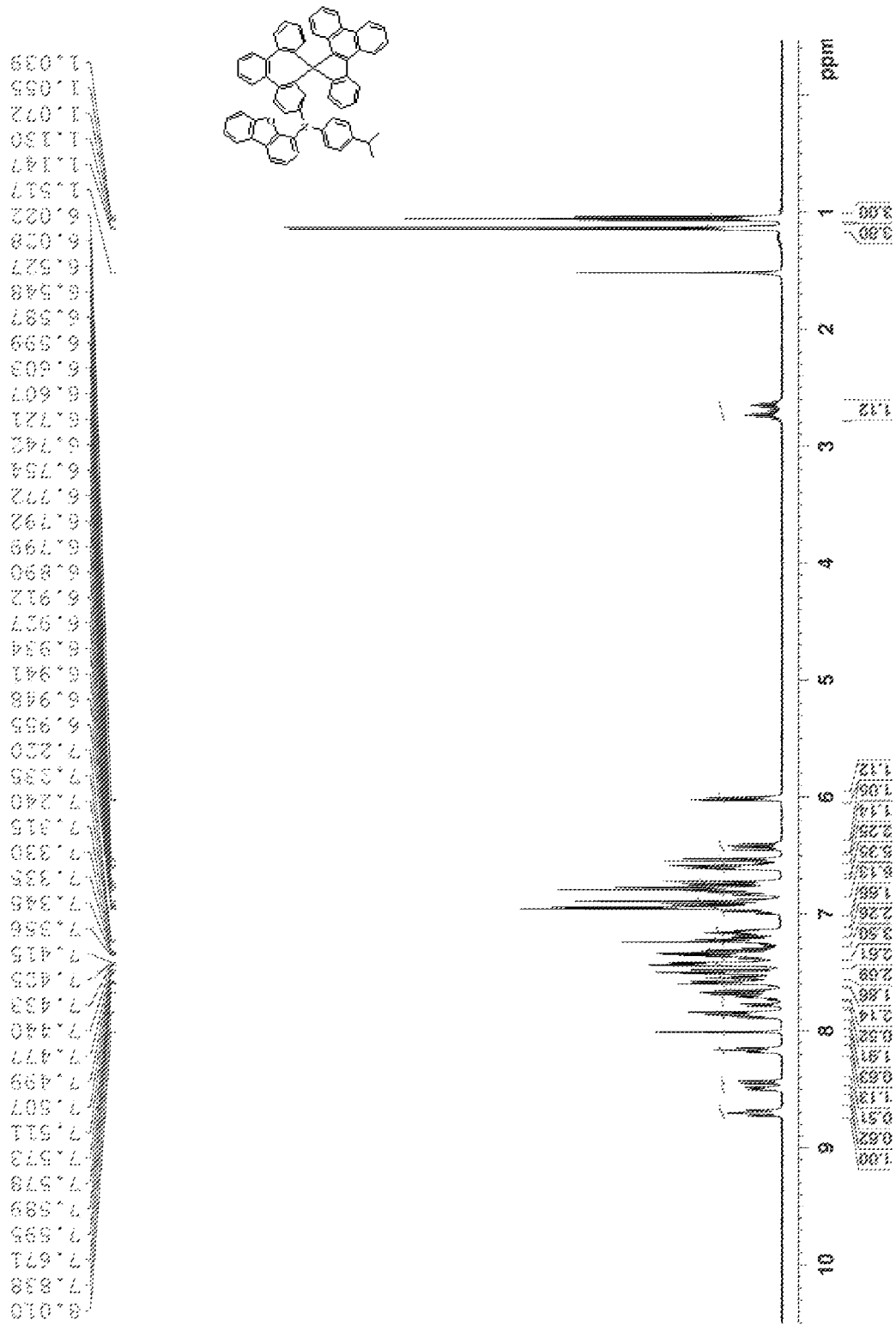

The reactants B and intermediates C adopted to synthesize Compounds 1 to 17 were listed in Table 6. Compounds 1 to 17 were identified by $H^1$-NMR and FD-MS, and the chemical structure, yield, formulae and mass of each of Compounds 1 to 17 were also listed in Table 6. Take Compounds 1 to 17 as examples, the $^1$H-NMR spectra were shown in FIGS. 2 to 18.

TABLE 6 reactants and intermediates adopted to prepare Compounds 1 to 17 and their yields, formulae, and FD-MS data.

| Reactant No. | Intermediate No. | Claimed Compound Chemical Structure | Yield | Formula/ Mass (M+) |
|---|---|---|---|---|
| B3 | C19 | Compound 1 | 82 | $C_{62}H_{43}N$/ (802.01) |
| B2 | C5 | Compound 2 | 87 | $C_{61}H_{39}NO$/ (801.97) |
| B2 | C10 | Compound 3 | 91 | $C_{61}H_{39}NS$/ (818.03) |

TABLE 6-continued
reactants and intermediates adopted to prepare Compounds 1 to 17 and their yields, formulae, and FD-MS data.
| | | Claimed Compound | | |
|---|---|---|---|---|
| Reactant No. | Intermediate No. | Chemical Structure | Yield | Formula/ Mass (M+) |
| B2 | C19 | 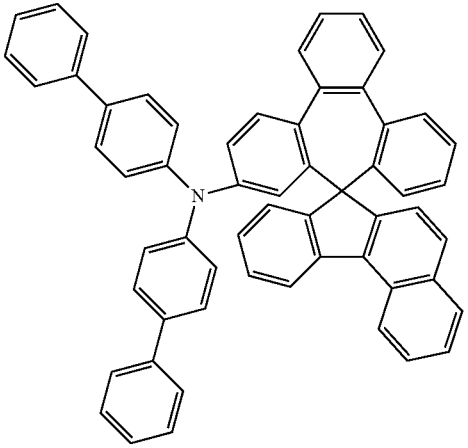<br>Compound 4 | 89 | $C_{59}H_{39}N$/ (761.95) |
| B2 | C20 | 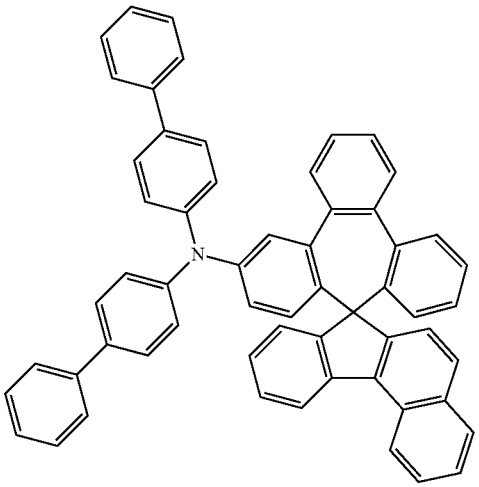<br>Compound 5 | 92 | $C_{59}H_{39}N$/ (761.95) |
| B1 | C24 | 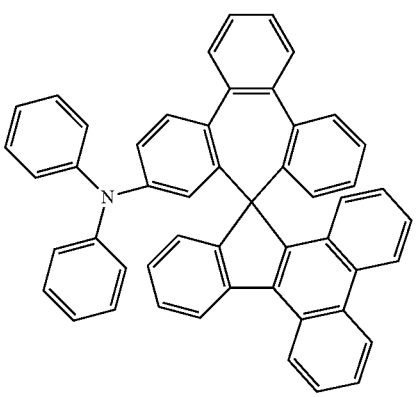<br>Compound 6 | 78 | $C_{51}H_{33}N$/ (659.81) |

TABLE 6-continued
reactants and intermediates adopted to prepare Compounds 1 to 17 and their yields, formulae, and FD-MS data.
| Reactant No. | Intermediate No. | Chemical Structure | Yield | Formula/ Mass (M+) |
|---|---|---|---|---|
| B1 | C26 | 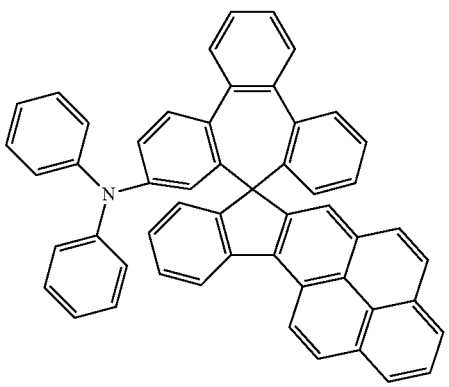 Compound 7 | 75 | $C_{53}H_{33}N$/ (683.84) |
| B1 | C6 | 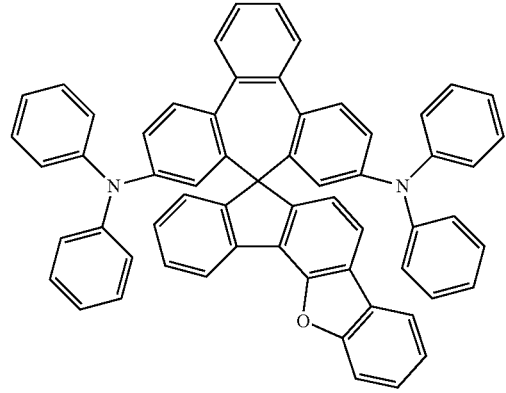 Compound 8 | 81 | $C_{61}H_{10}N_2O$/ (816.98) |
| B4 | C7 | 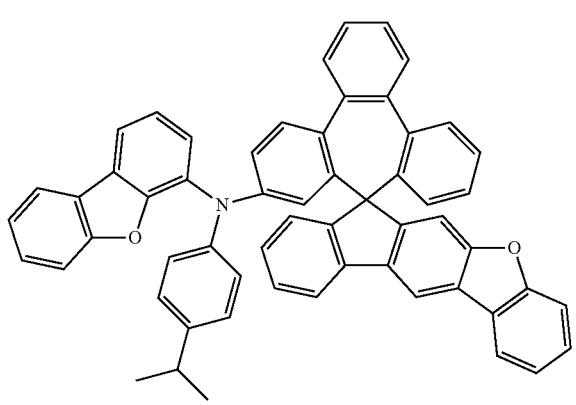 Compound 9 | 93 | $C_{58}H_{39}NO_2$/ (781.94) |

TABLE 6-continued reactants and intermediates adopted to prepare Compounds 1 to 17 and their yields, formulae, and FD-MS data.

| Reactant No. | Intermediate No. | Claimed Compound Chemical Structure | Yield | Formula/ Mass (M+) |
|---|---|---|---|---|
| B1 | C23 | Compound 10 | 68 | $C_{59}H_{40}N_2$/ (776.96) |
| B2 | C9 | Compound 11 | 94 | $C_{61}H_{39}NO$/ (801.97) |
| B3 | C1 | Compound 12 | 68 | $C_{64}H_{43}NO$/ (842.03) |

TABLE 6-continued
reactants and intermediates adopted to prepare Compounds 1 to 17 and their yields, formulae, and FD-MS data.
| | | Claimed Compound | | |
|---|---|---|---|---|
| Reactant No. | Intermediate No. | Chemical Structure | Yield | Formula/ Mass (M+) |
| B1 | C3 | 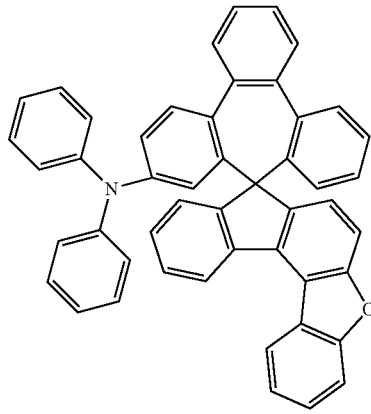<br>Compound 13 | 76 | $C_{49}H_{31}NO/$ (649.78) |
| B1 | C18 | 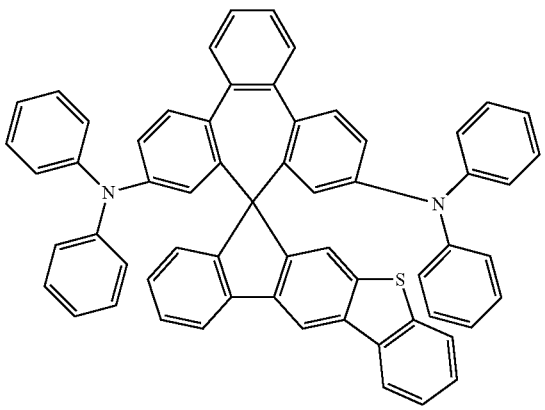<br>Compound 14 | 95 | $C_{61}H_{40}N_2S/$ (833.05) |
| B4 | C11 | 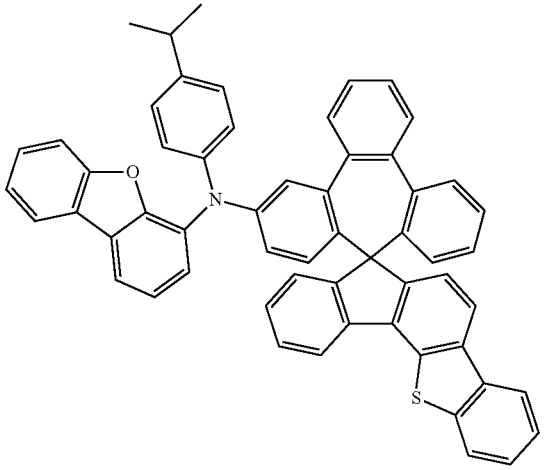<br>Compound 15 | 80 | $C_{58}H_{39}NOS/$ (798.01) |

TABLE 6-continued reactants and intermediates adopted to prepare Compounds 1 to 17 and their yields, formulae, and FD-MS data.

| Reactant No. | Intermediate No. | Chemical Structure | Yield | Formula/ Mass (M+) |
|---|---|---|---|---|
| B5 | C10 | Compound 16 | 85 | $C_{61}H_{37}NOS$/ (832.02) |
| B4 | C24 | Compound 17 | 82 | $C_{60}H_{41}NO$/ (791.97) |

Modifications of Compounds 1 to 17

In addition to the Compounds 1 to 17, one person skilled in the art can react any Intermediate C with any Reactant B through a reaction mechanism similar to Scheme I to synthesize other desired claimed novel compounds.

Preparation of OLED Devices

A glass substrate coated with ITO layer in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples 1 to 43. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a first hole transporting layer (HTL-1), a second hole transporting layer (HTL-2), a blue/green/red emission layer (BEL/GEL/REL), an electron transporting layer (ETL), an electron injection layer (EIL), and a cathode (Cthd).

Herein, HAT was a material for forming HIL-1 and HID; HI-2 was a material for forming HIL-2; HT-1, HT-1', and the novel compounds of the present invention were a material for forming HTL-1; HT-2, HT-2', and the novel compounds of the present invention were materials for forming HTL-2; conventional ET was materials for forming ETL; Liq was a material for forming ETD and EIL. RH/GH/BH were host material for forming REL/GEL/BEL, and RD/GD/BD were dopant for forming REL/GEL/BEL. The detailed chemical structures of foresaid commercial materials were listed in Table 7, and the novel compounds of the present invention were listed in Table 6.

TABLE 7
chemical structures of commercial materials for OLED devices.
HAT
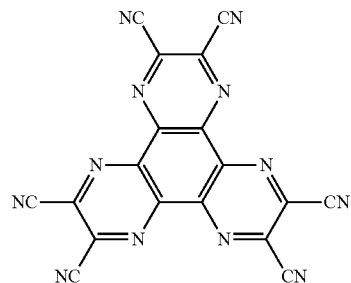 [SMILES: N#Cc1nc2c3nc(C#N)c(C#N)nc3c3nc(C#N)c(C#N)nc3c2nc1C#N]
HI-2
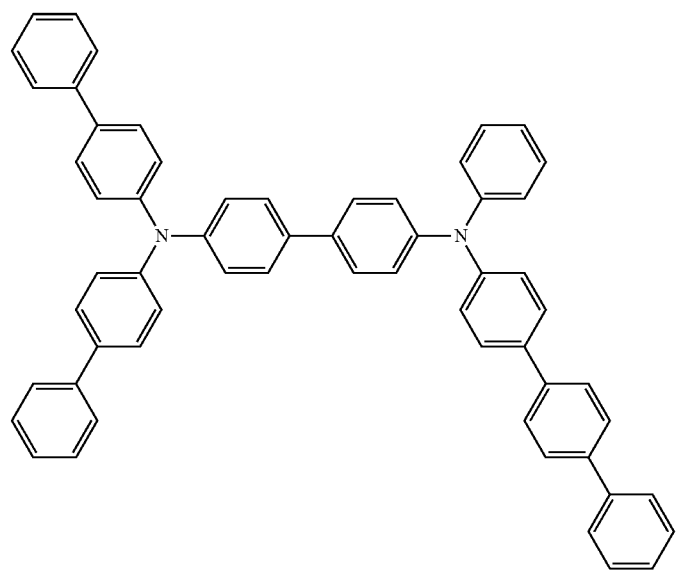 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]
HT-1
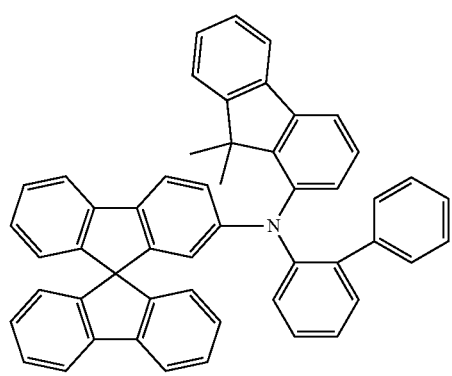 [SMILES: CC1(C)c2ccccc2-c2cccc(N(c3ccc4c(c3)C3(c5ccccc5-c5ccccc53)c3ccccc3-4)c3ccccc3-c3ccccc3)c21]
HT-2

TABLE 7-continued
chemical structures of commercial materials for OLED devices.
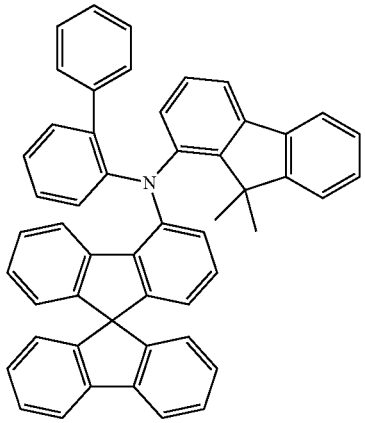 [SMILES: CC1(C)c2ccccc2-c2cccc(N(c3ccccc3-c3ccccc3)c3cccc4c3-c3ccccc3C43c4ccccc4-c4ccccc43)c21]
ET
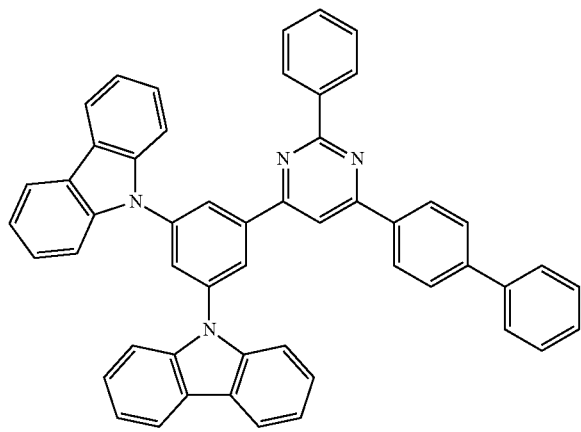 [SMILES: c1ccc(-c2ccc(-c3cc(-c4cc(-n5c6ccccc6c6ccccc65)cc(-n5c6ccccc6c6ccccc65)c4)nc(-c4ccccc4)n3)cc2)cc1]
Liq
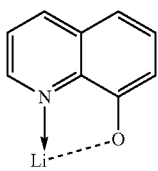
RH
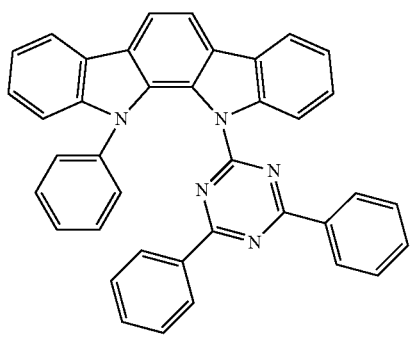 [SMILES: c1ccc(-c2nc(-c3ccccc3)nc(-n3c4ccccc4c4ccc5c6ccccc6n(-c6ccccc6)c5c43)n2)cc1]
GH TABLE 7-continued
chemical structures of commercial materials for OLED devices.
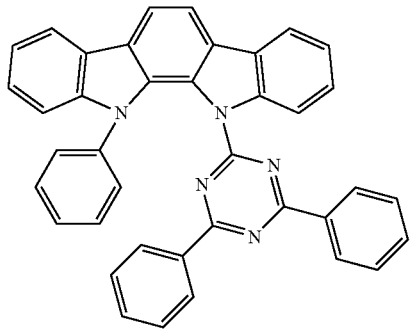 [SMILES: c1ccc(-c2nc(-c3ccccc3)nc(-n3c4ccccc4c4ccc5c6ccccc6n(-c6ccccc6)c5c43)n2)cc1]
BH
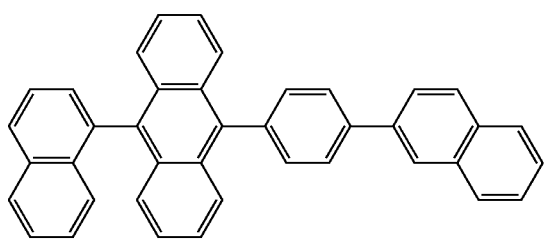 [SMILES: c1ccc2cc(-c3ccc(-c4c5ccccc5c(-c5cccc6ccccc56)c5ccccc45)cc3)ccc2c1]
RD
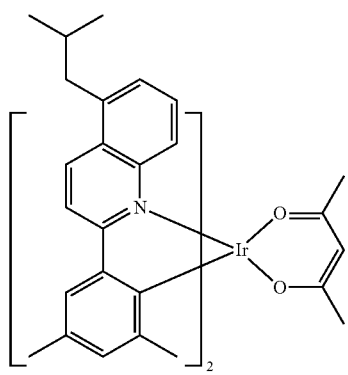
GD
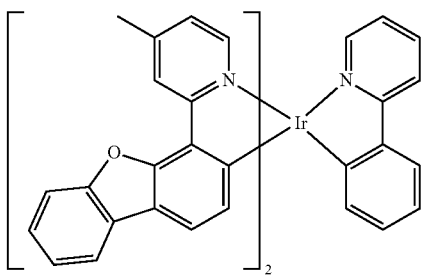
BD TABLE 7-continued chemical structures of commercial materials for OLED devices.

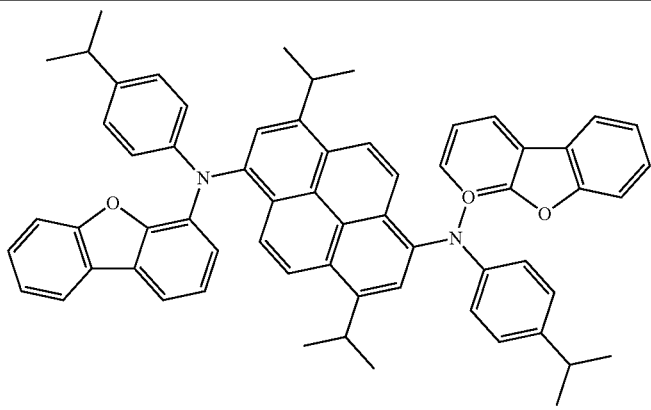

HT-1'

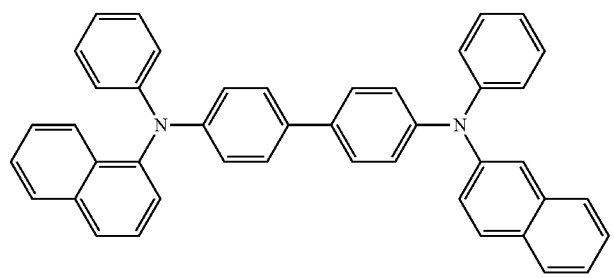 [SMILES: c1ccc(N(c2ccc(-c3ccc(N(c4ccccc4)c4cccc5ccccc45)cc3)cc2)c2ccc3ccccc3c2)cc1]

HT-2'

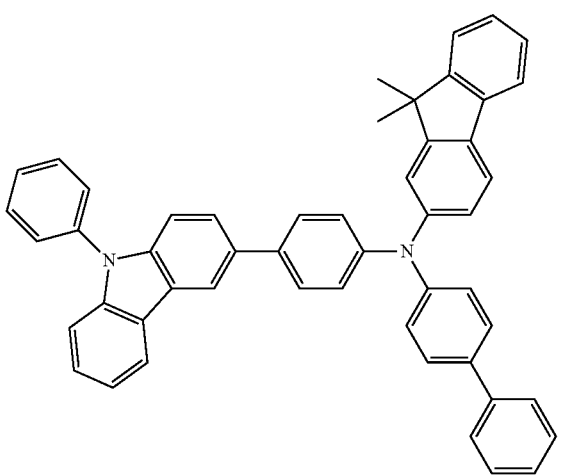 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

Preparation of Red OLED Devices

To prepare the red OLED device, multiple organic layers were respectively deposited on the ITO substrate according to the sequence as listed in Table 8, and the materials and the thicknesses of the organic layers in red OLED devices were also listed in Table 8.

TABLE 8 coating sequence, materials and thickness of the organic layers in red OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 2100 Å |

TABLE 8-continued coating sequence, materials and thickness of the organic layers in red OLED device.

| Coating Sequence | Layer | Material | Thickness |
|---|---|---|---|
| 3 | HTL-1 | Commercial HT-1/HT-1'/Novel compound | 100 Å |
| 4 | HTL-2 | Commercial HT-2/HT-2'/Novel compound | 100 Å |
| 5 | REL | RH doped with 3.5 wt of RD | 300 Å |
| 6 | ETL | ET doped with 35.0 wt of Liq | 350 Å |
| 7 | EIL | Liq | 15 Å |
| 8 | Cthd | Al | 1500 Å |

Preparation of Green OLED Devices

To prepare the green OLED device, multiple organic layers were respectively deposited on the ITO substrate according to the sequence as listed in Table 9, and the materials and the thicknesses of the organic layers in green OLED devices were also listed in Table 9.

TABLE 9 coating sequence, materials and thickness of the layers in green OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 1300 Å |
| 3 | HTL-1 | Commercial HT-1/HT-1'/Novel compound | 100 Å |
| 4 | HTL-2 | Commercial HT-2/HT-2'/Novel compound | 100 Å |
| 5 | GEL | GH doped with 10.0 wt % of GD | 400 Å |
| 6 | ETL | ET doped with 35.0 wt % of Liq | 350 Å |
| 7 | EIL | Liq | 1.5 Å |
| 8 | Cthd | Al | 1500 Å |

Preparation of Blue OLED Devices

To prepare the blue OLED device, multiple organic layers were respectively deposited on the ITO substrate according to the sequence as listed in Table 10, and the materials and the thicknesses of the organic layers in green OLED devices were also listed in Table 10.

TABLE 10 coating sequence, materials and thickness of the layers in blue OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 750 Å |
| 3 | HTL-1 | Commercial HT-1/HT-1'/Novel compound | 100 Å |
| 4 | HTL-2 | Commercial HT-2/HT-2'/Novel compound | 100 Å |
| 5 | BEL | BH doped with 3.5 wt % of BD | 250 Å |
| 6 | ETL | ET doped with 35.0 wt % of Liq | 250 Å |
| 7 | EIL | Liq | 15 Å |
| 8 | Cthd | Al | 1500 Å |

Performance of OLED Device

To evaluate the performance of OLED devices, red, green, and blue OLED devices were measured by PR650 as photometer and Keithley 2400 as power supply. Color coordinates (x,y) were determined according to the CIE chromaticity scale (Commission Internationale de L'Eclairage, 1931). The results were shown in Table 11. For the blue and red OLED devices, the data were collected at 1000 nits. For the green OLED devices, the data were collected at 3000 nits. The materials of HTL, color and data of CIE, driving voltage, and current efficiency of Examples 1 to 43 and Comparative Examples 1 to 4 were listed in Table 11.

TABLE 11 materials of HTL-1, materials of HTL-2, characteristics and performance of OLED devices of Examples 1 to 43 (E1 to E43) and Comparative Examples 1 to 4(C1 to C4).

| | Material of HTL-1 (novel compound or commercial materials) | Material of HTL-2 | Color, CIE(x, y) | Voltage (V) | Current Efficiency (cd/A) |
|---|---|---|---|---|---|
| | | | Red OLED devices | | |
| E1 | Compound 2 | HT-2 | R(0.659, 0.339) | 3.64 | 24.0 |
| E2 | Compound 3 | HT-2 | R(0.660, 0.339) | 3.64 | 26.1 |
| E3 | Compound 4 | HT-2 | R(0.661, 0.338) | 3.62 | 25.2 |
| E4 | Compound 5 | HT-2 | R(0.658, 0.340) | 3.68 | 23.6 |
| E5 | Compound 6 | HT-2 | R(0.659, 0.339) | 3.61 | 26.9 |
| E6 | Compound 7 | HT-2 | R(0.660, 0.338) | 3.61 | 25.5 |
| E7 | Compound 8 | HT-2 | R(0.661, 0.337) | 3.62 | 27.2 |
| E8 | Compound 9 | HT-2 | R(0.659, 0.339) | 3.71 | 30.4 |
| E9 | Compound 14 | HT-2 | R(0.659, 0.340) | 3.48 | 26.8 |
| E10 | Compound 17 | HT-2 | R(0.658, 0.340) | 3.52 | 24.3 |
| E11 | HT-1 | Compound 10 | R(0.657, 0.340) | 3.57 | 19.2 |
| E12 | HT-1 | Compound 11 | R(0.659, 0.339) | 3.46 | 23.1 |
| E13 | HT-1 | Compound 13 | R(0.659, 0.339) | 3.56 | 24.6 |
| E14 | HT-1 | Compound 15 | R(0.660, 0.338) | 3.44 | 26 |
| E15 | HT-1 | Compound 6 | R(0.661, 0.338) | 3.58 | 25.3 |
| | | | Green OLED devices | | |
| E16 | Compound 2 | HT-2 | G(0.316, 0.637) | 3.06 | 77.0 |
| E17 | Compound 3 | HT-2 | G(0.318, 0.636) | 3.09 | 70.8 |
| E18 | Compound 4 | HT-2 | G(0.316, 0.637) | 2.95 | 77.7 |
| E19 | Compound 5 | HT-2 | G(0.316, 0.638) | 3.08 | 81.0 |

TABLE 11-continued materials of HTL-1, materials of HTL-2, characteristics and performance of OLED devices of Examples 1 to 43 (E1 to E43) and Comparative Examples 1 to 4(C1 to C4).

| | Material of HTL-1 (novel compound or commercial materials) | Material of HTL-2 | Color, CIE(x, y) | Voltage (V) | Current Efficiency (cd/A) |
|---|---|---|---|---|---|
| E20 | Compound 6 | HT-2 | G(0.317, 0.637) | 3.03 | 77.3 |
| E21 | Compound 7 | HT-2 | G(0.316, 0.637) | 3.02 | 74.3 |
| E22 | Compound 8 | HT-2 | G(0.322, 0.634) | 3.08 | 80.7 |
| E23 | Compound 9 | HT-2 | G(0.313, 0.639) | 3.09 | 82.5 |
| E24 | Compound 16 | HT-2 | G(0.319, 0.637) | 3.05 | 79.5 |
| E25 | Compound 17 | HT-2 | G(0.312, 0.639) | 3.05 | 75.4 |
| E26 | HT-1 | Compound 11 | G(0.314, 0.638) | 2.91 | 73.6 |
| E27 | HT-1 | Compound 13 | G(0.317, 0.637) | 2.94 | 75.2 |
| E28 | HT-1 | Compound 15 | G(0.318, 0.636) | 3.02 | 76.8 |
| E29 | HT-1 | Compound 6 | G(0.314, 0.639) | 3.03 | 74.4 |
| C1 | HT-1' | HT-2 | G(0.318, 0.637) | 3.10 | 70.1 |
| C2 | HT-1 | HT-2' | G(0.314, 0.639) | 3.12 | 42.7 |
| | | Blue OLED devices | | | |
| E30 | Compound 2 | HT-2 | B(0.130, 0.146) | 4.55 | 9.83 |
| E31 | Compound 3 | HT-2 | B(0.130, 0.151) | 4.71 | 10.1 |
| E32 | Compound 4 | HT-2 | B(0.129, 0.151) | 4.66 | 10.2 |
| E33 | Compound 5 | HT-2 | B(0.130, 0.149) | 4.68 | 10.2 |
| E34 | Compound 6 | HT-2 | B(0.129, 0.154) | 4.54 | 10.7 |
| E35 | Compound 7 | HT-2 | B(0.128, 0.161) | 4.54 | 11.2 |
| E36 | Compound 8 | HT-2 | B(0.129, 0.149) | 4.54 | 11.4 |
| E37 | Compound 14 | HT-2 | B(0.129, 0.153) | 4.63 | 11.6 |
| E38 | Compound 17 | HT-2 | B(0.129, 0.152) | 4.63 | 11.5 |
| E39 | HT-1 | Compound 10 | B(0.130, 0.154) | 4.30 | 10.9 |
| E40 | HT-1 | Compound 11 | B(0.129, 0.157) | 4.47 | 11.0 |
| E41 | HT-1 | Compound 13 | B(0.130, 0.151) | 4.45 | 11.1 |
| E42 | HT-1 | Compound 15 | B(0.129, 0.150) | 4.25 | 11.5 |
| E43 | HT-1 | Compound 6 | B(0.129, 0.158) | 4.30 | 11.7 |
| C3 | HT-1' | HT-2 | B(0.129, 0.160) | 4.77 | 9.5 |
| C4 | HT-1 | HT-2' | B(0.129, 0.159) | 4.49 | 9.1 |

Based on the results, in comparison with the commercial electron transport material, adopting Compounds 1 to 17 as the hole transport material can reduce the driving voltage and improve the current efficiency of the red, green, or blue OLEDs. It demonstrates that the novel compound of the present invention is suitable as a hole transport material for any color OLEDs, and allows the OLEDs using the same to have low driving voltage and improved current efficiency.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the Willis in which the appended claims are expressed.

What is claimed is:

1. A compound represented by the following Formula (I):

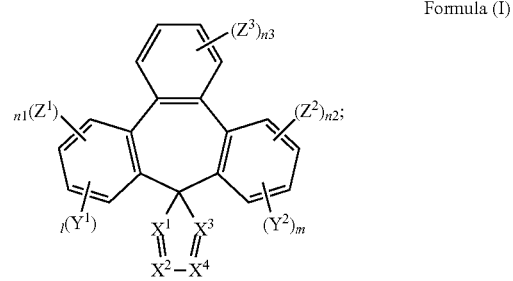

Formula (I)

wherein $X^1$ and $X^2$ are each independently $C(R^a)$ and the two $(R^a)$s are the same or different; $X^3$ and $X^4$ are each independently $C(R^b)$ and the two $(R^b)$s are the same or different; the two $(R^a)$s are joined together to form an aryl ring and the two $(R^b)$s are joined together to form an oxygen-containing heteroaryl ring, a sulfur-containing heteroaryl ring, or a polycyclic aromatic ring;

wherein $Y^1$ and $Y^2$ are the same or different; $Y^1$ and $Y^2$ are each represented by NR'R"; R' and R" are the same or different; at least one of R' and R" is an aryl group;

wherein $Z^1$ to $Z^3$ are each independently selected from the group consisting of: a deuterium atom, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 carbon atoms, a heterocycloalkyl group having 3 to 60 carbon atoms, an aryl group having 6 to 60 carbon atoms, a heteroaryl group having 3 to 60 carbon atoms, an alkoxy group having 1 to 40 carbon atoms, an aryloxy group having 6 to 60 carbon atoms, an alkylsilyl group having 1 to 40 carbon atoms, an arylsilyl group having 6 to 60 carbon atoms, an alkylboron group having 1 to 40 carbon atoms, an arylboron group having 6 to 60 carbon atoms, a phosphine group having 1 to 40 carbon atoms, and a phosphine oxide group having 1 to 40 carbon atoms;

wherein l is an integer from 1 to 4; m is an integer from 0 to 4; n1 is an integer from 0 to 3; n2 is an integer from 0 to 4; n3 is an integer from 0 to 4; the total of n1 and l is not more than 4; the total of n2 and m is not more than 4.

2. The compound as claimed in claim 1, wherein the oxygen-containing heteroaryl ring contains at least one furan group.

3. The compound as claimed in claim 2, wherein the compound is represented by the following Formulae (I-I) to (I-VI):

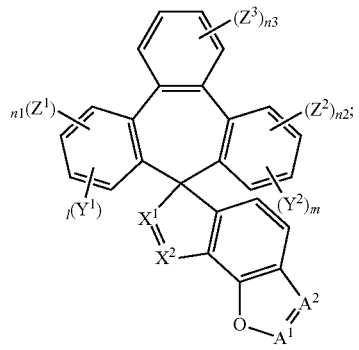

Formula (I-I)

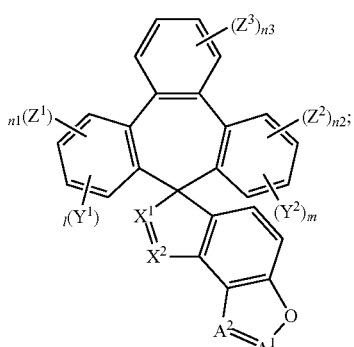

Formula (I-II)

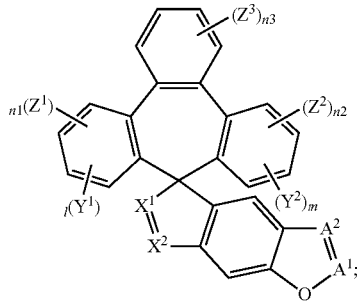

Formula (I-III)

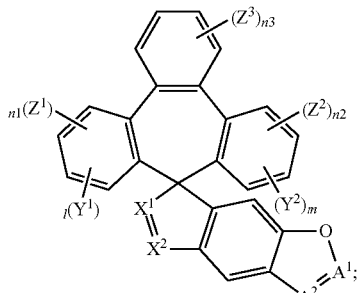

Formula (I-IV)

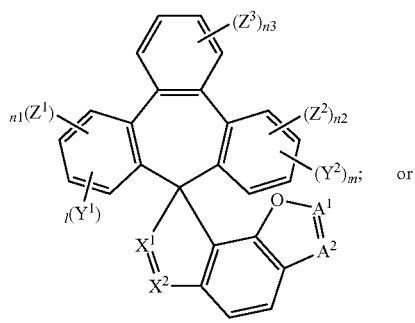

Formula (I-V)

or

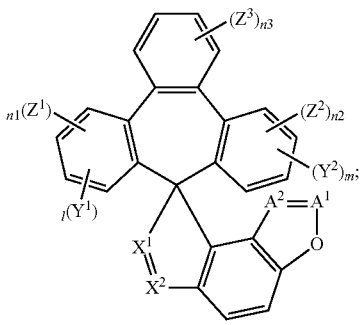

Formula (I-VI)

wherein $A^1$ and $A^2$ are each independently $C(R^c)$, the two $(R^c)$s are the same or different, and the two $(R^c)$s are joined together to form an aromatic structure contained in the oxygen-containing heteroaryl ring.

4. The compound as claimed in claim 3, wherein the aromatic structure contained in the oxygen-containing heteroaryl ring is a substituted or unsubstituted 6 to 20-membered carbon cyclic structure.

5. The compound as claimed in claim 1, wherein the sulfur-containing heteroaryl ring contains at least one thio-furan group.

6. The compound as claimed in claim 5, wherein the compound is represented by the following Formulae (II-I) to (II-VI):

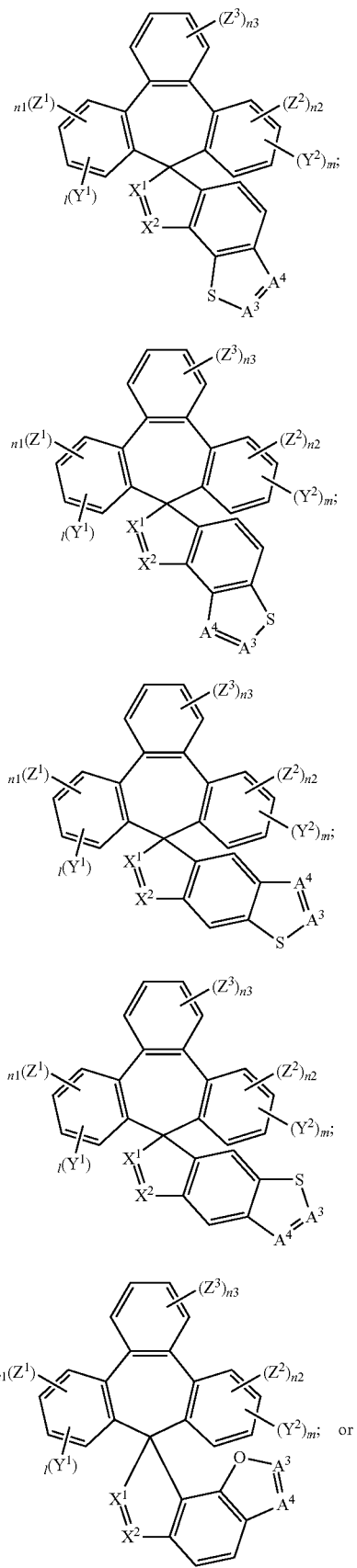

Formula (II-I)

Formula (II-II)

Formula (II-III)

Formula (II-IV)

Formula (II-V) or

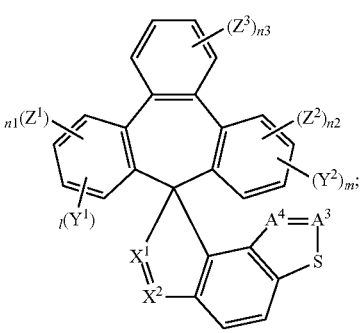

Formula (II-VI)

wherein $A^3$ and $A^4$ are each independently $C(R^d)$, the two $(R^d)$s are the same or different, and the two $(R^d)$s are joined together to form an aromatic structure contained in the sulfur-containing heteroaryl ring.

7. The compound as claimed in claim 6, wherein the aromatic structure contained in the sulfur-containing heteroaryl ring is a substituted or unsubstituted 6 to 20-membered carbon cyclic structure.

8. The compound as claimed in claim 1, wherein the polycyclic aromatic ring is selected from the group consisting of: a benzene ring, a dimethylfluorene, a naphthalene ring, an anthracene ring, a phenanthrene ring, a tetracene ring, a chrysene ring, a triphenylene ring, a pyrene ring, a perylene ring, a pentacene ring, a benzopyrene ring, a corannulene ring, a benzoperylene ring, a coronene ring, an ovalene ring, a benzofluorine ring, an indene ring, a fluoranthene ring, and a benzofluoranthene ring.

9. The compound as claimed in claim 8, wherein the compound is represented by the following Formulae (III-I) to (III-XVIII):

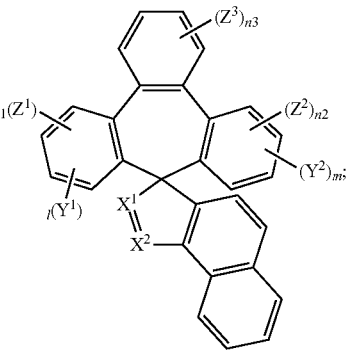

Formula (III-I)

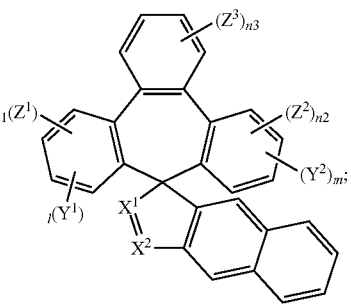

Formula (III-II)

Formula (III-III)
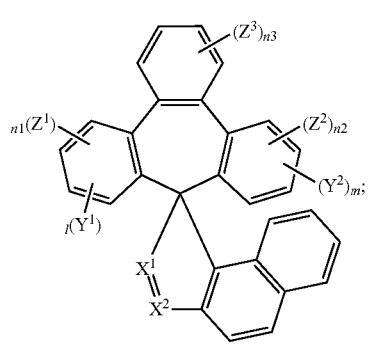
Formula (III-IV)
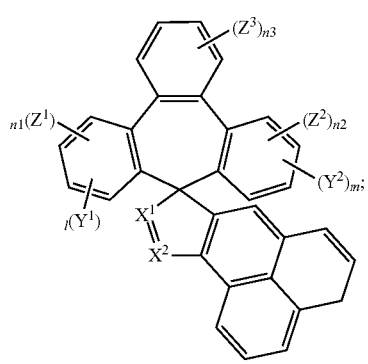
Formula (III-V)
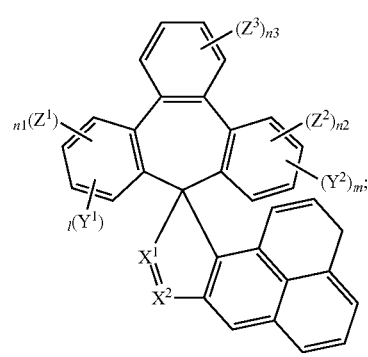
Formula (III-VI)
Formula (III-VII)
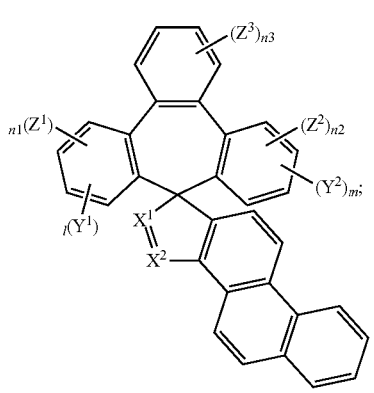
Formula (III-VIII)
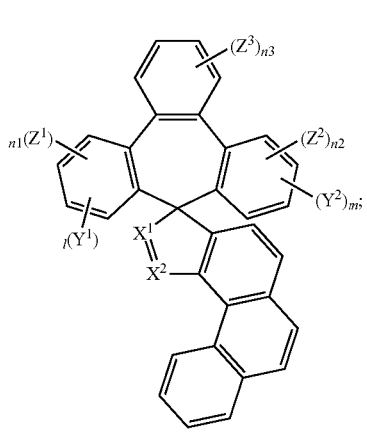
Formula (III-IX)
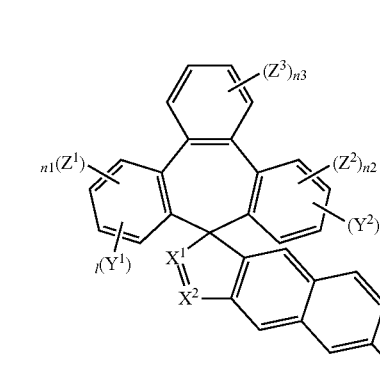
Formula (III-X)
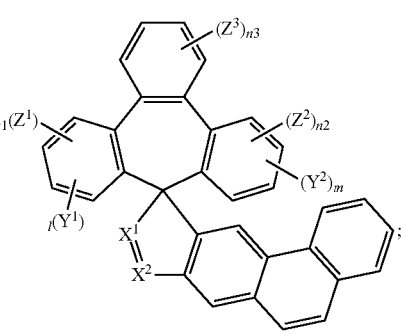

Formula (III-XI)
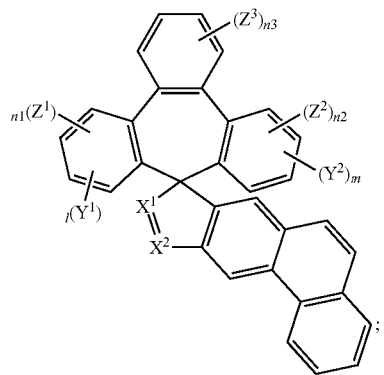
Formula (III-XII)
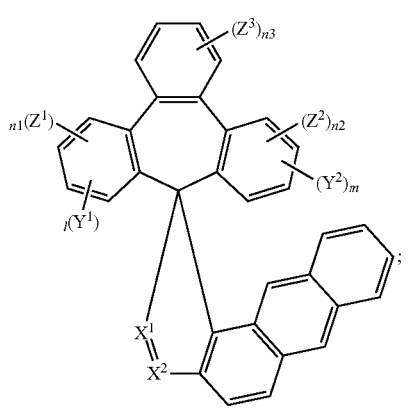
Formula (III-XIII)
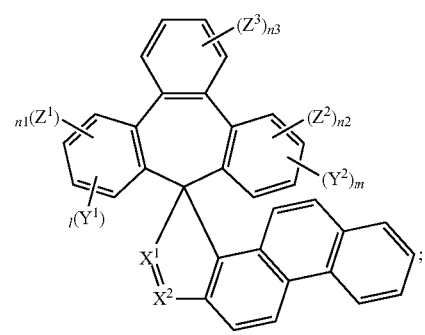
Formula (III-XIV)
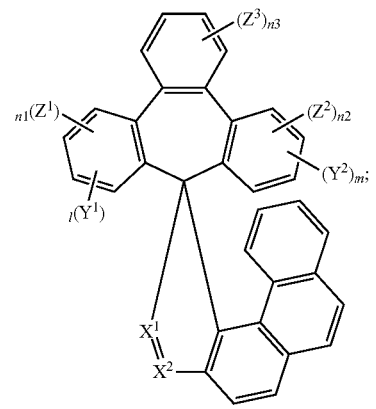
Formula (III-XV)
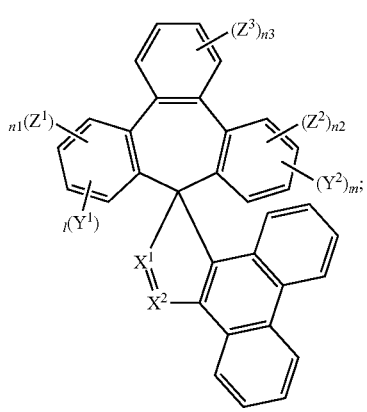
Formula (III-XVI)
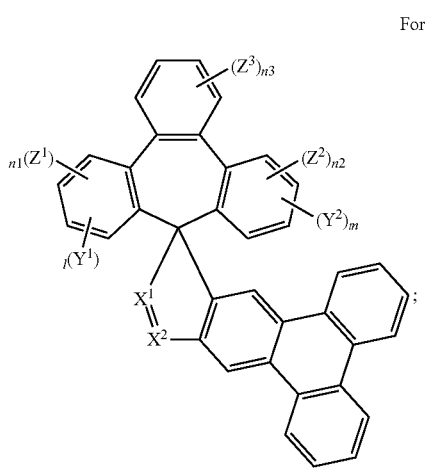
Formula (III-XVII)
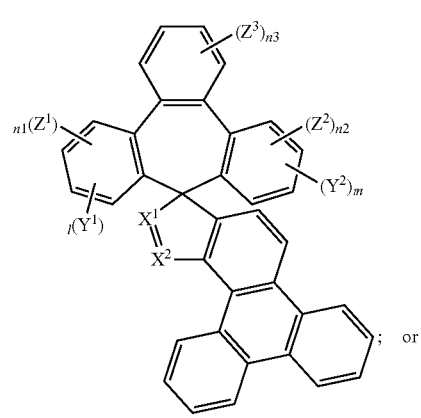
; or Formula (III-XVIII)

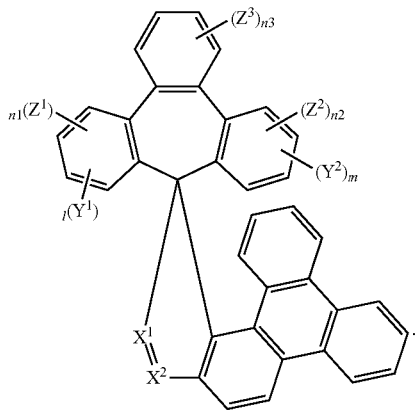

10. The compound as claimed in claim 1, wherein the aryl ring formed by the two (R$^a$)s is selected from the group consisting of: a substituted or unsubstituted benzene ring, a substituted or unsubstituted dimethylfluorene, a substituted or unsubstituted naphthalene ring, a substituted or unsubstituted anthracene ring, a substituted or unsubstituted phenanthrene ring, a substituted or unsubstituted tetracene ring, a substituted or unsubstituted chrysene ring, a substituted or unsubstituted triphenylene ring, a substituted or unsubstituted pyrene ring, a substituted or unsubstituted perylene ring, a substituted or unsubstituted pentacene ring, a substituted or unsubstituted benzopyrene ring, a substituted or unsubstituted corannulene ring, a substituted or unsubstituted benzoperylene ring, a substituted or unsubstituted coronene ring, a substituted or unsubstituted ovalene ring, a substituted or unsubstituted benzofluorine ring, a substituted or unsubstituted indene ring, a substituted or unsubstituted fluoranthene ring, and a substituted or unsubstituted benzofluoranthene ring.

11. The compound as claimed in claim 1, wherein the aryl ring formed by the two (R$^a$)s is a substituted or unsubstituted 6 to 60-membered aryl ring.

12. The compound as claimed in claim 1, wherein R' contained in Y$^1$ and Y$^2$ is the aryl group and R" contained in Y$^1$ and Y$^2$ is selected from the group consisting of: an alkyl group having 1 to 40 carbon atoms, an alkenyl group having 2 to 40 carbon atoms, an alkynyl group having 2 to 40 carbon atoms, a cycloalkyl group having 3 to 60 carbon atoms, and an aryl group having 6 to 60 carbon atoms.

13. The compound as claimed in claim 1, wherein Y$^1$ and Y$^2$ in Formula (I) are each independently selected from the group consisting of:

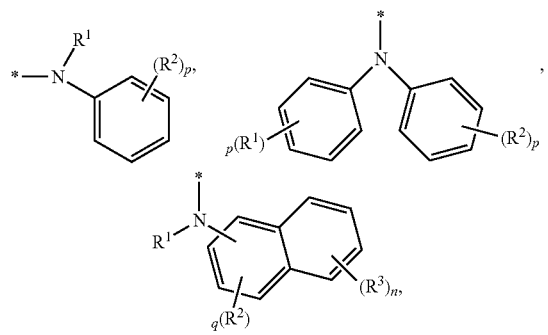

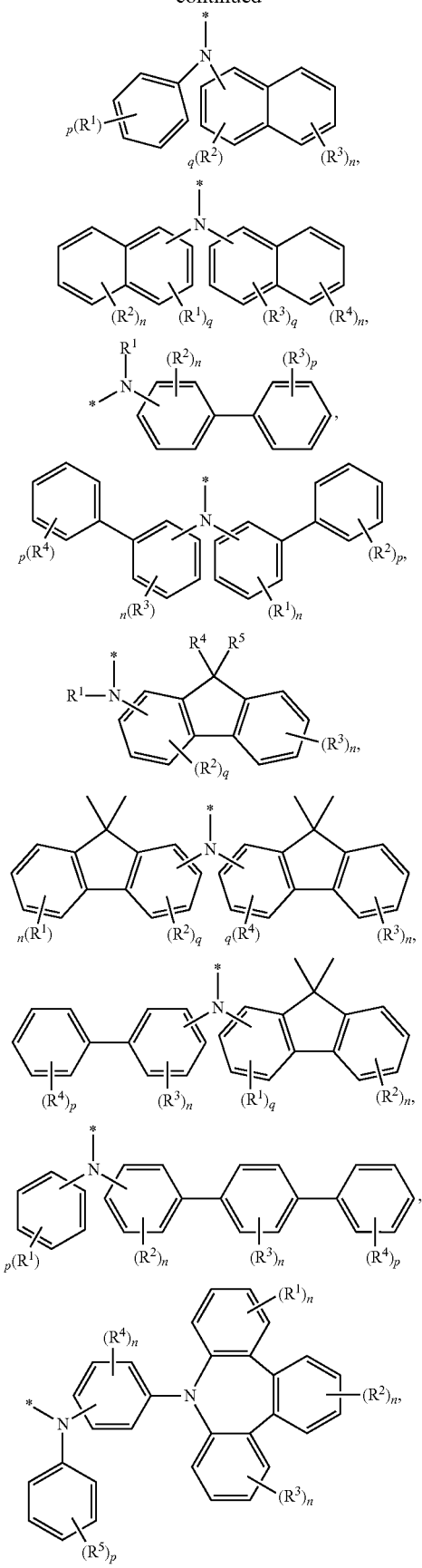

471
-continued
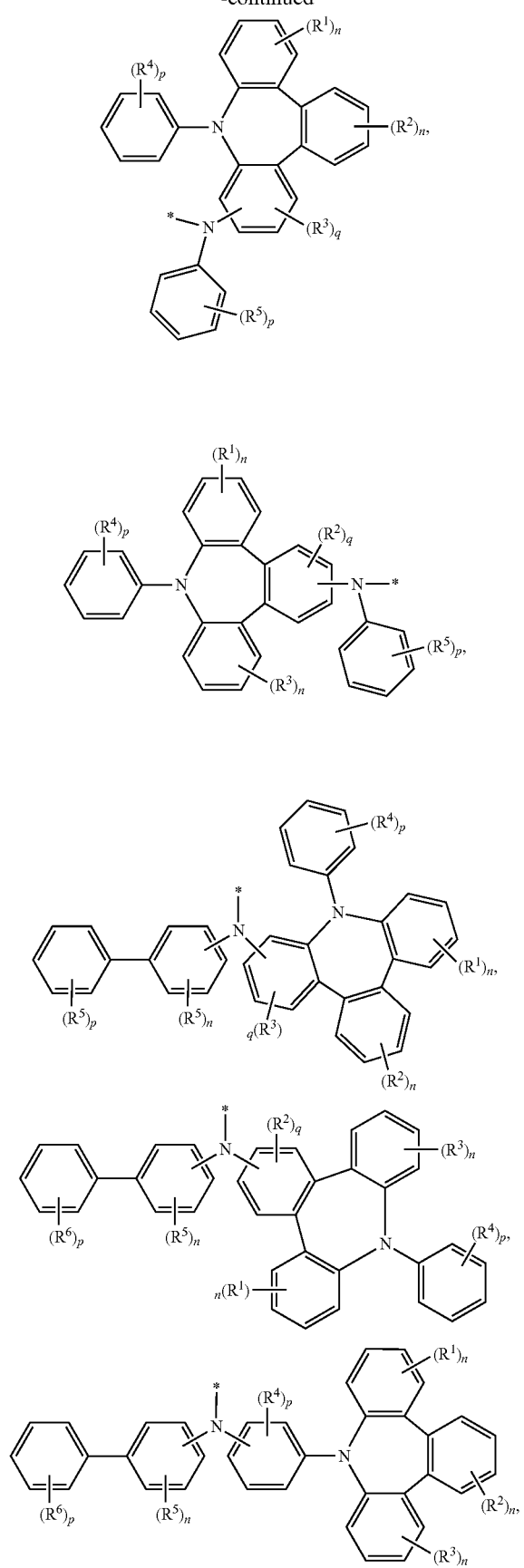
472
-continued
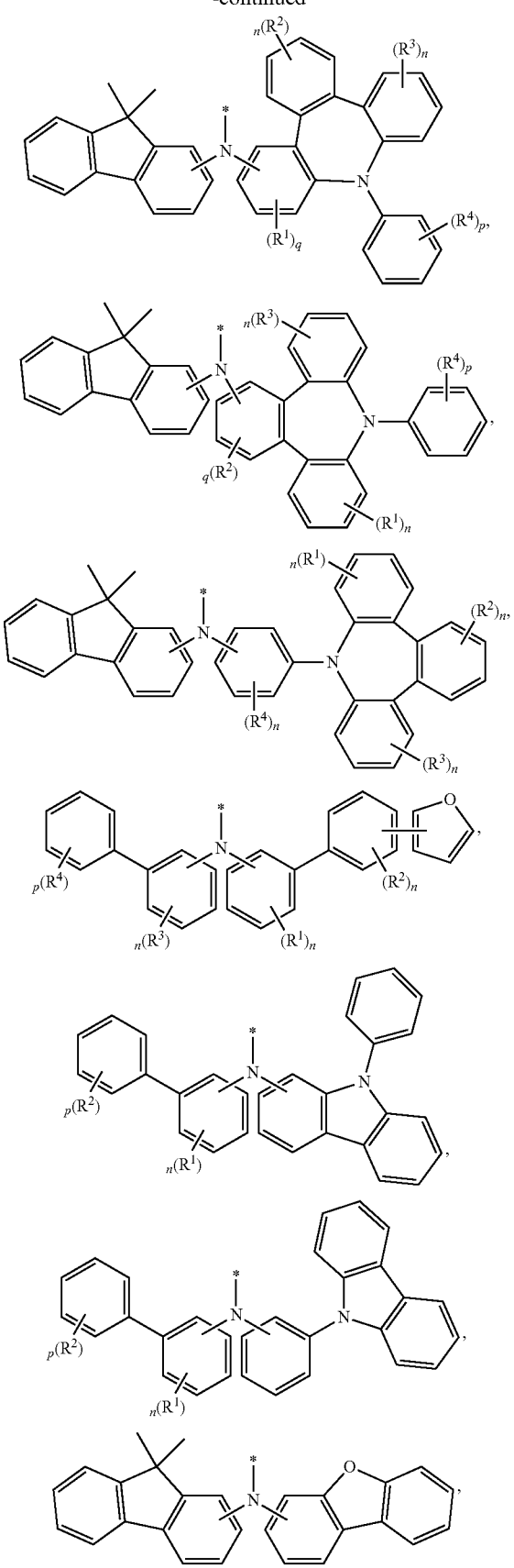

473
-continued
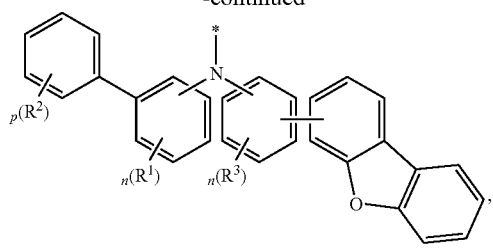
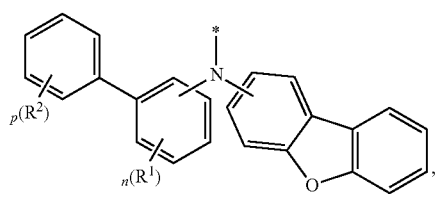
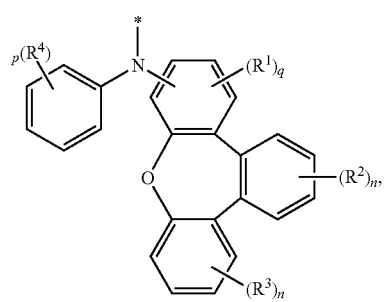
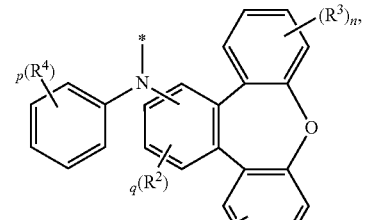
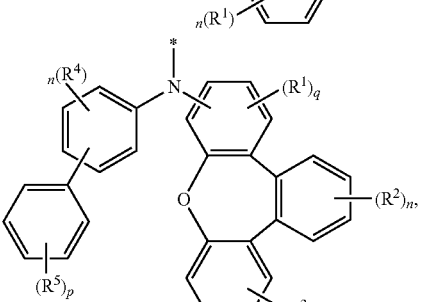
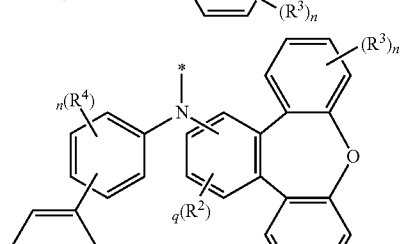
474
-continued
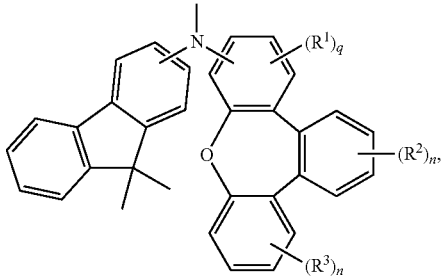
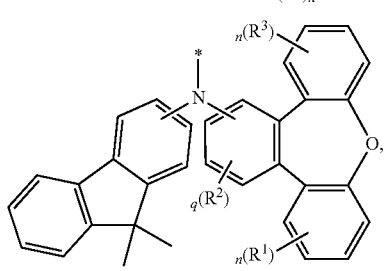
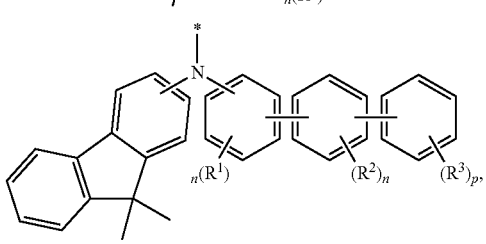
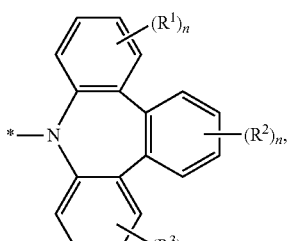
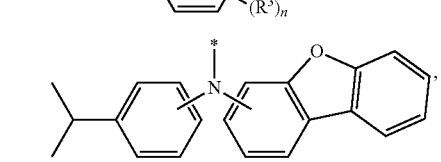

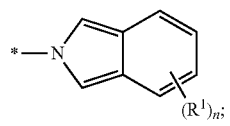

wherein $R^1$ to $R^5$ are each independently selected from the group consisting of: a deuterium atom, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 carbon atoms, a heterocycloalkyl group having 3 to 30 carbon atoms, an aryl group having 6 to 30 carbon atoms, a heteroaryl group having 3 to 20 carbon atoms, an alkoxy group having 1 to 40 carbon atoms, an aryloxy group having 6 to 30 carbon atoms, an alkylsilyl group having 1 to 40 carbon atoms, an arylsilyl group having 6 to 30 carbon atoms, an alkylboron group having 1 to 40 carbon atoms, an arylboron group having 6 to 30 carbon atoms, a phosphine group having 1 to 30 carbon atoms, and a phosphine oxide group having 1 to 30 carbon atoms;

wherein p is an integer from 0 to 5; n is an integer from 0 to 4; q is an integer from 0 to 3.

14. The compound as claimed in claim 1, wherein the compound is selected from the group consisting of:

Compound 1

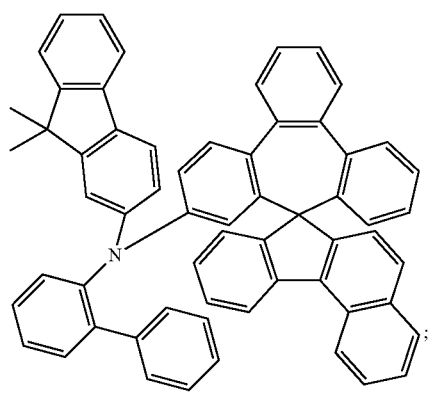

Compound 2

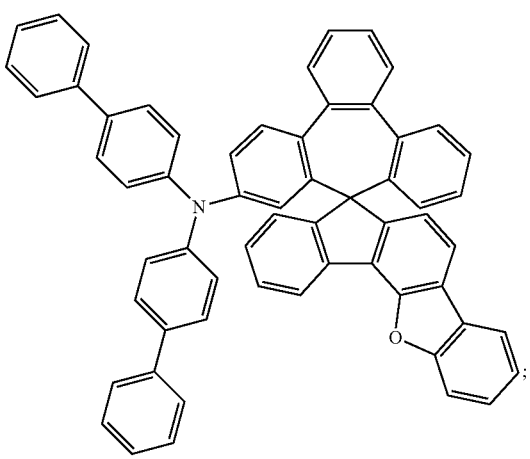

Compound 3

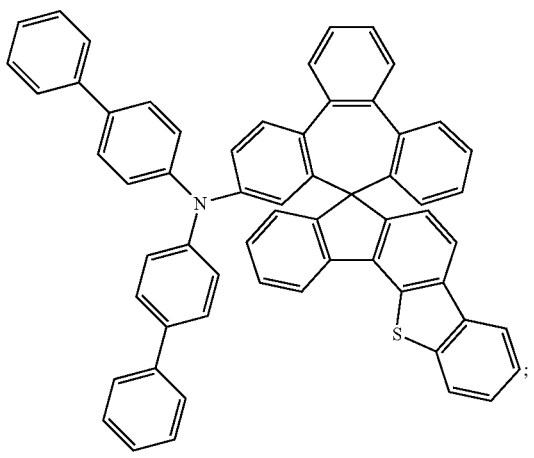

Compound 4

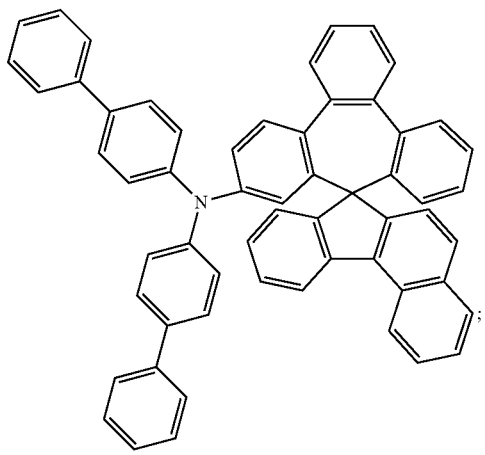

Compound 5

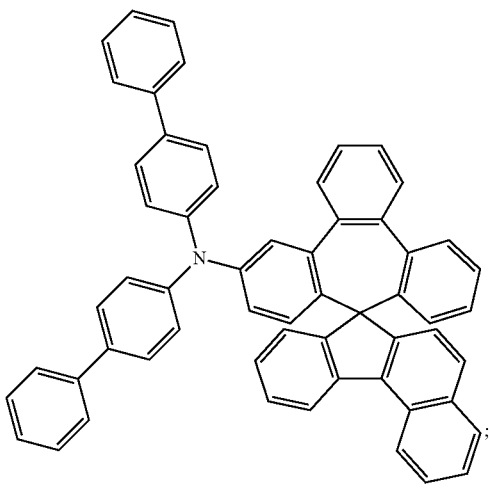

Compound 6
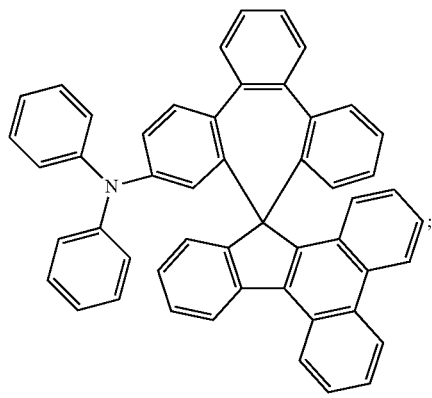
Compound 7
Compound 8
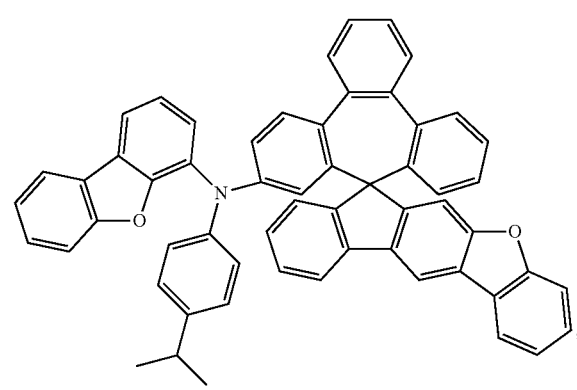
Compound 9
Compound 10
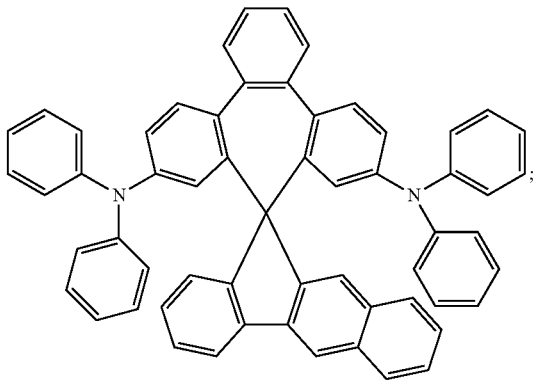
Compound 11
Compound 12
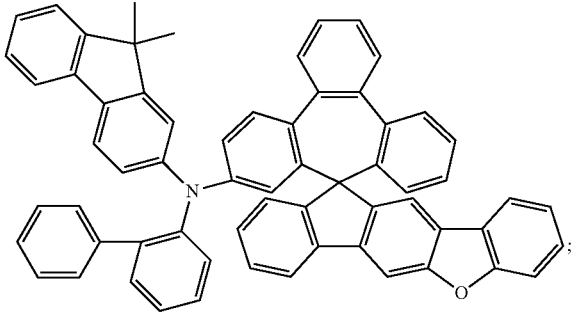

-continued
Compound 13
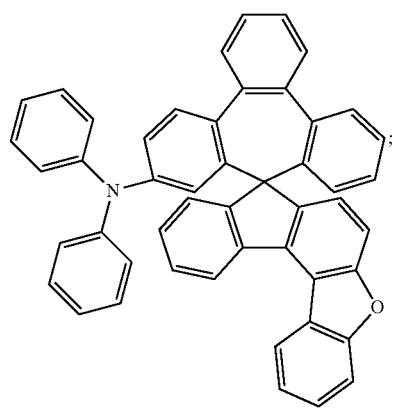
Compound 14
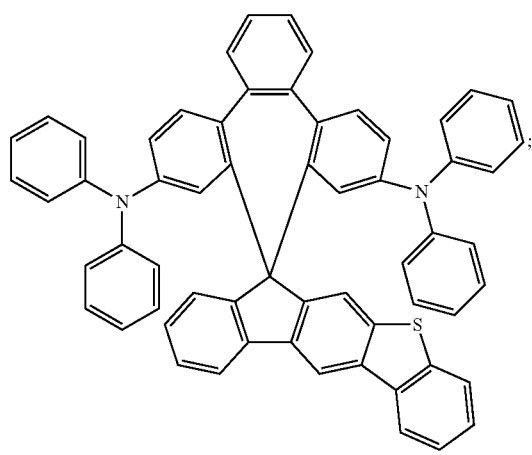
Compound 15
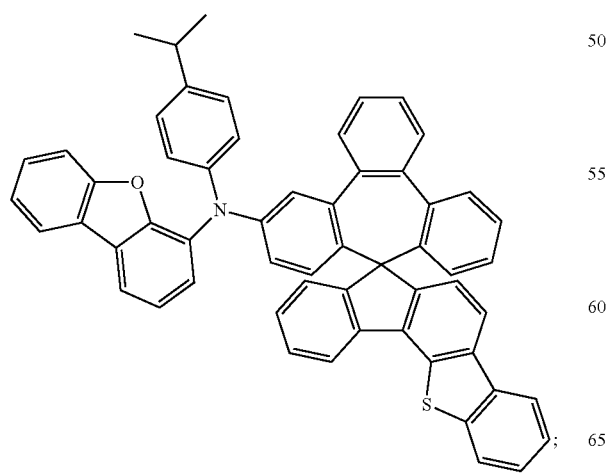
-continued
Compound 16
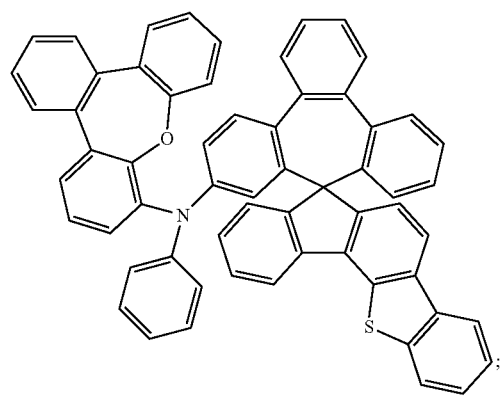
Compound 17
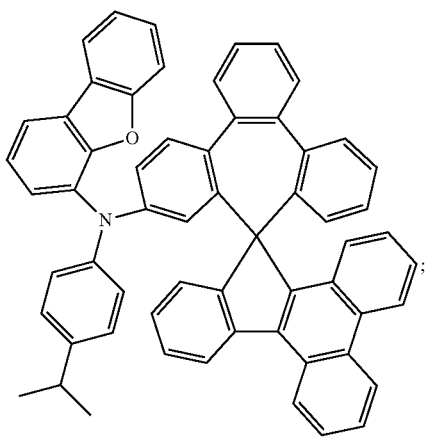
Compound 18
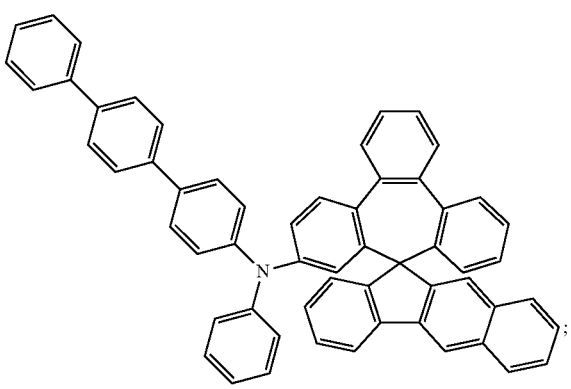

Compound 19
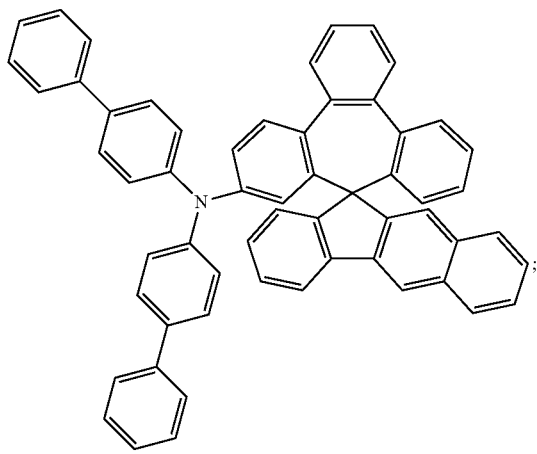
Compound 22
Compound 20
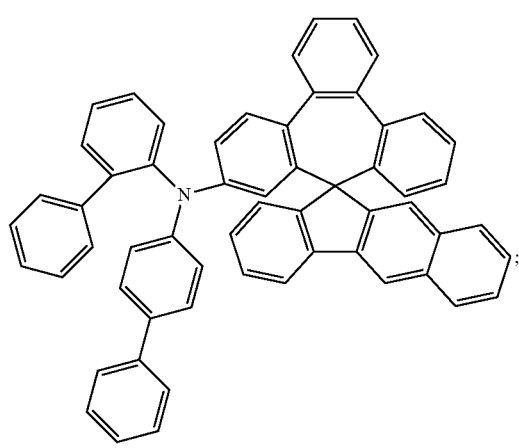
Compound 23
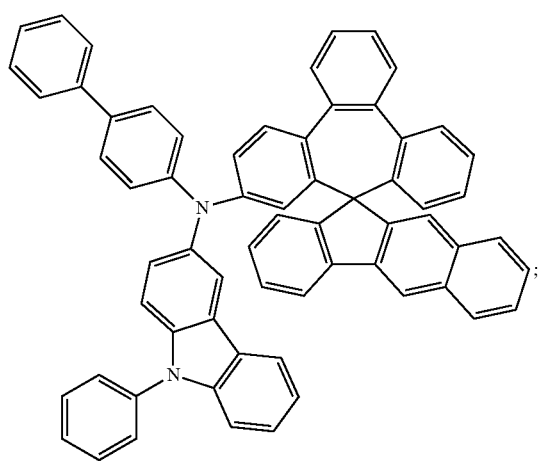
Compound 21
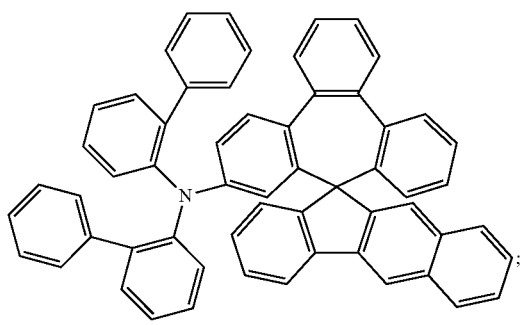
Compound 24
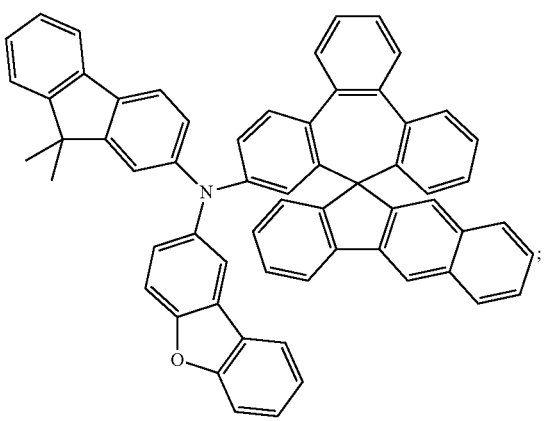

Compound 25
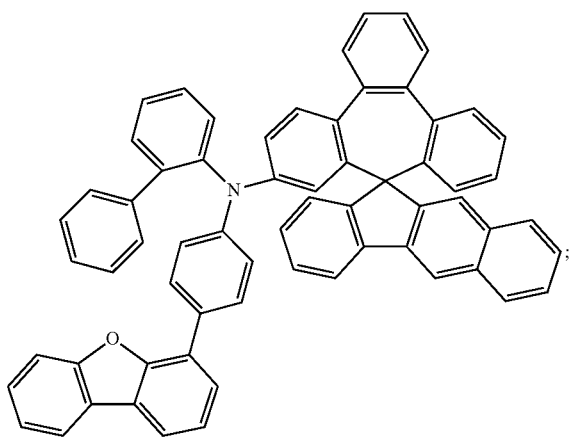
Compound 26
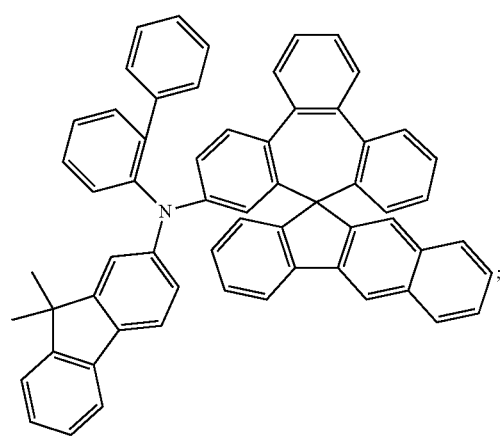
Compound 27
Compound 28
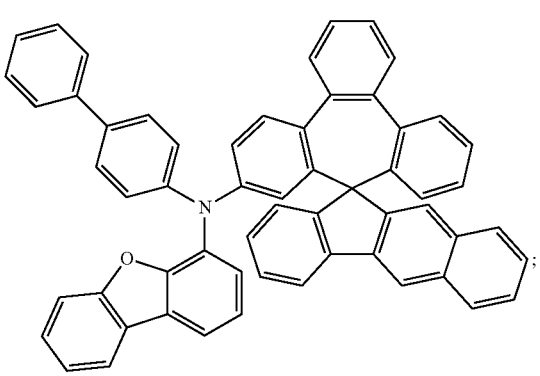
Compound 29
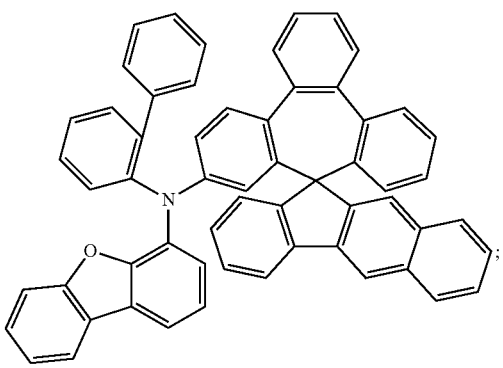
Compound 30
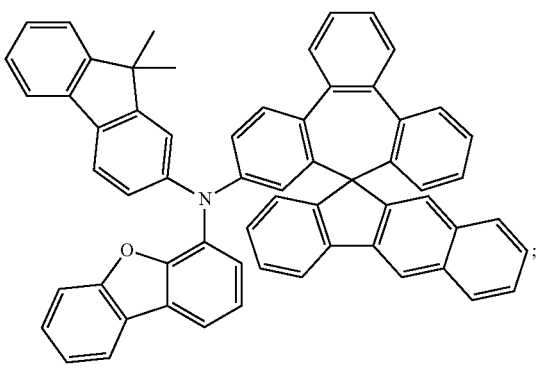
Compound 31
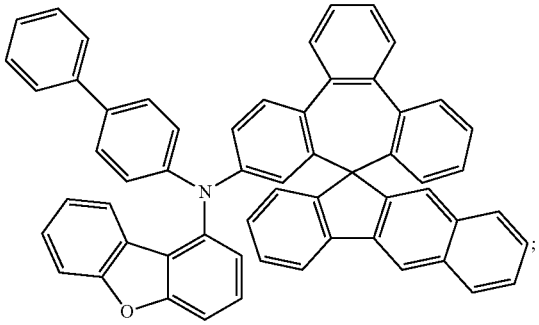

Compound 32
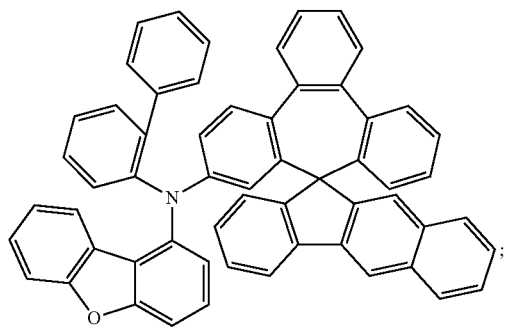
Compound 33
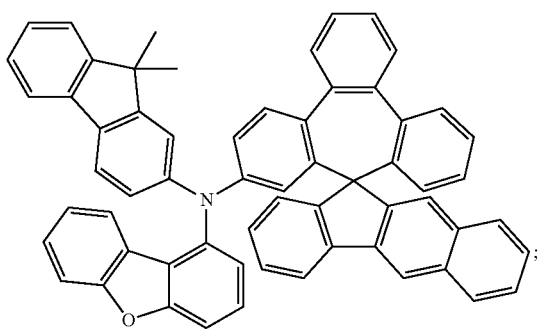
Compound 34
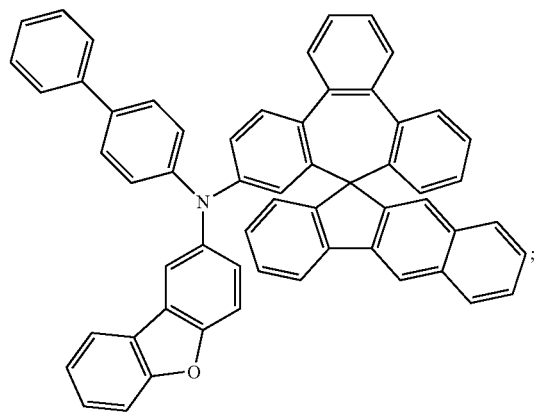
Compound 35
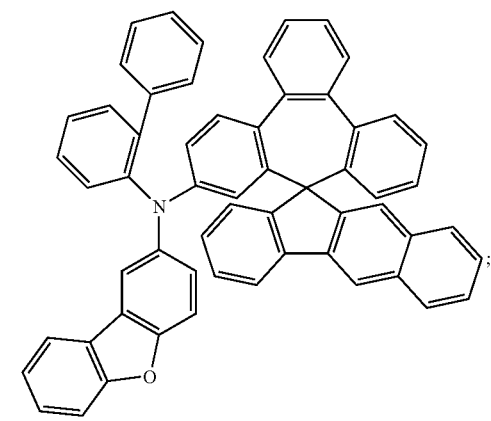
Compound 36
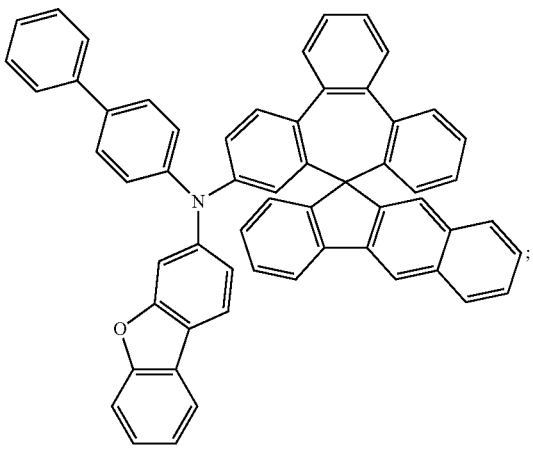
Compound 37
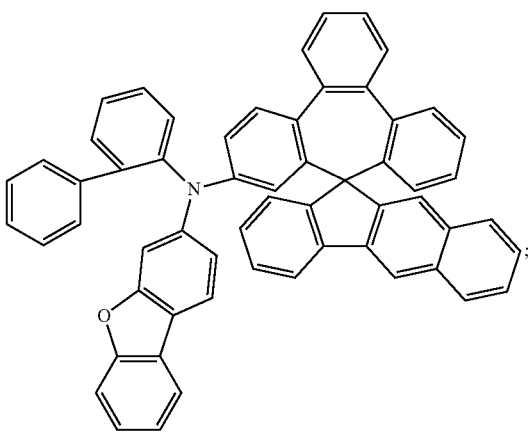
Compound 38
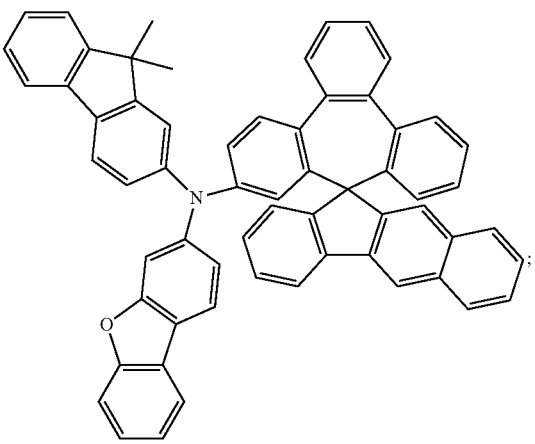

Compound 39
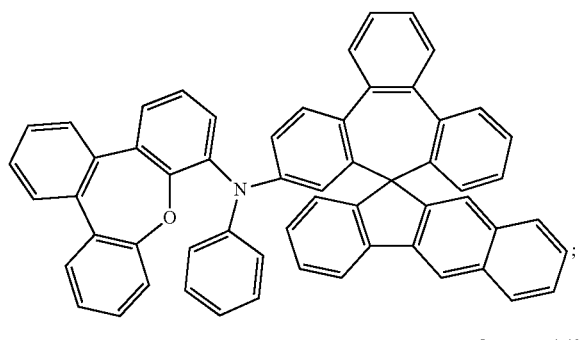
Compound 40
Compound 41
Compound 42
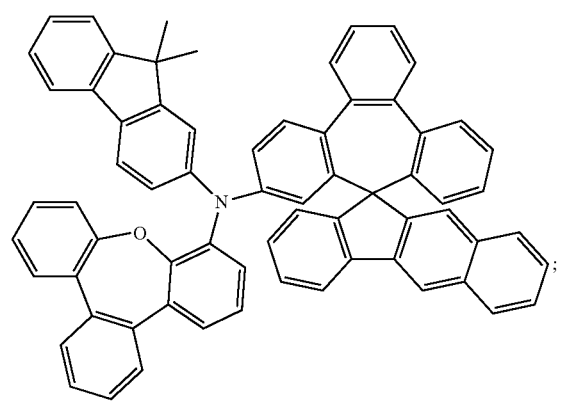
Compound 43
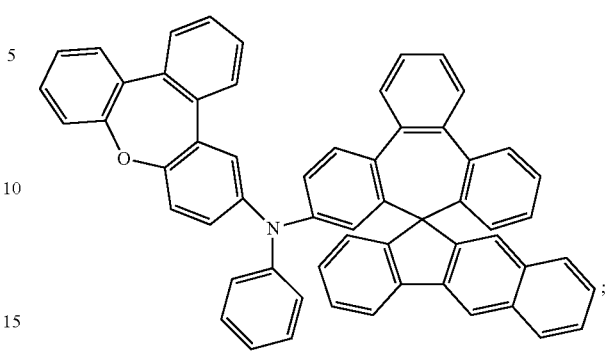
Compound 44
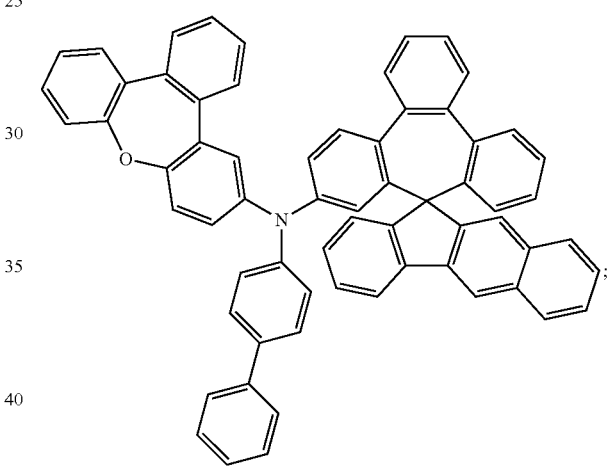
Compound 45
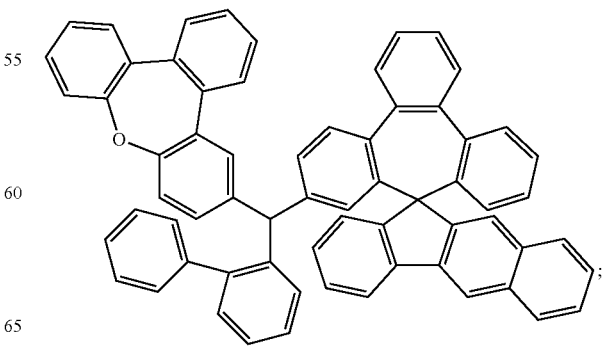

Compound 46
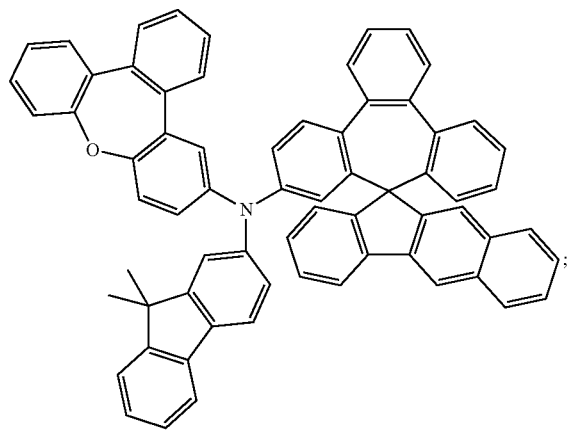
Compound 47
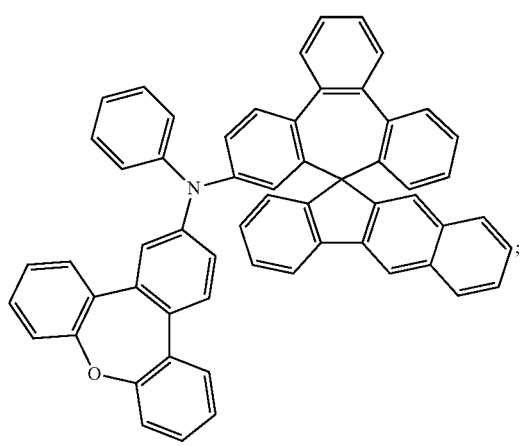
Compound 48
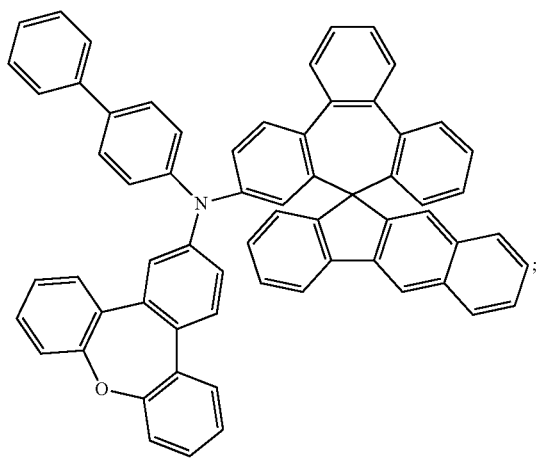
Compound 49
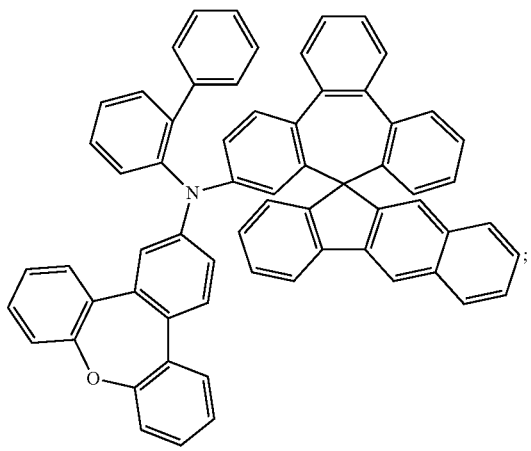
Compound 50
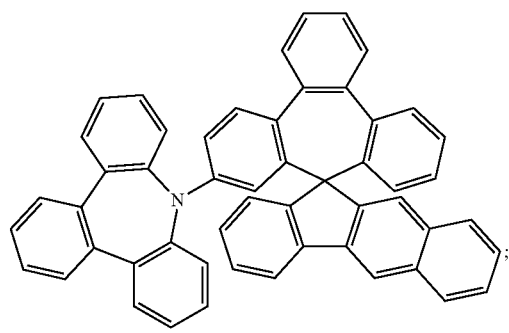
Compound 51
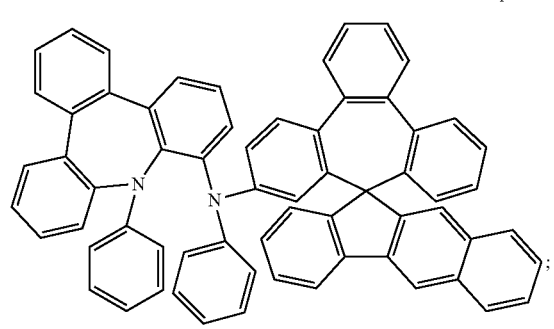
Compound 52
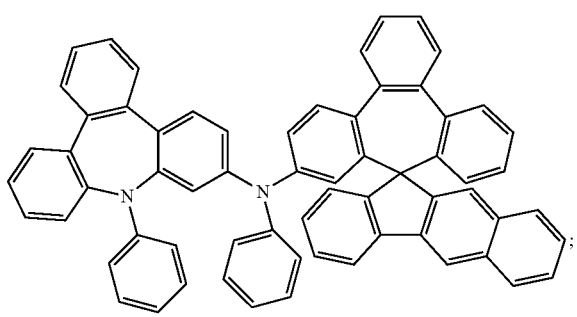

-continued
Compound 53
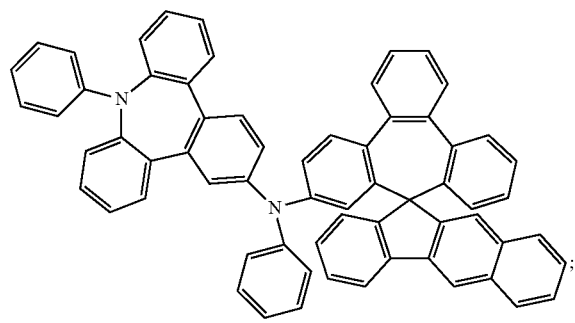
Compound 54
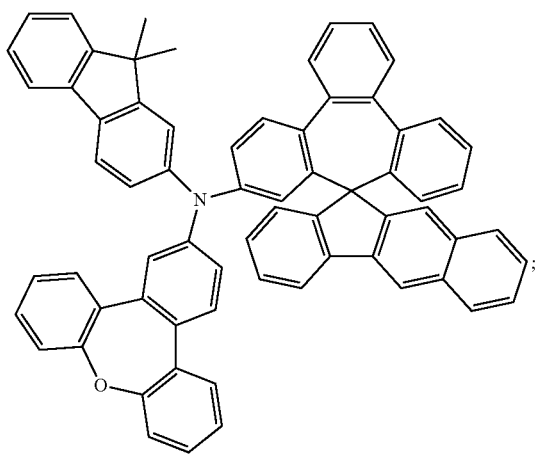
Compound 55
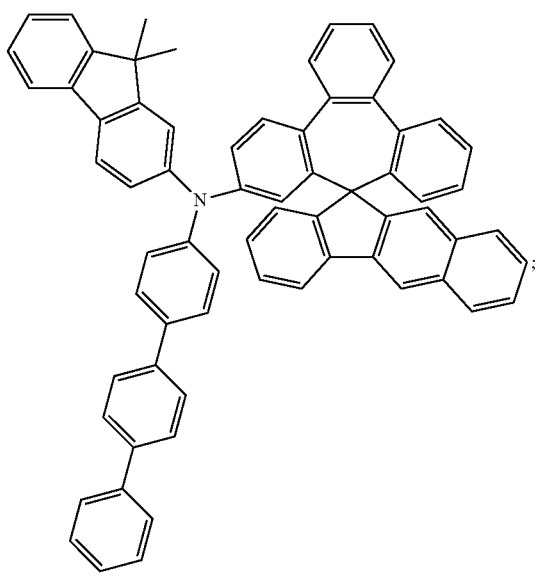
-continued
Compound 56
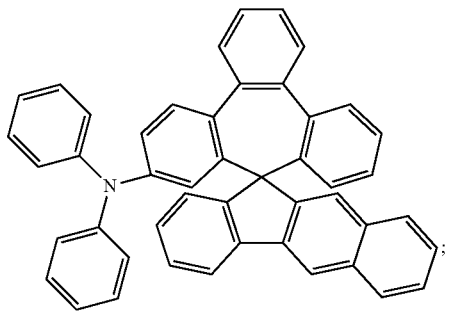
Compound 57
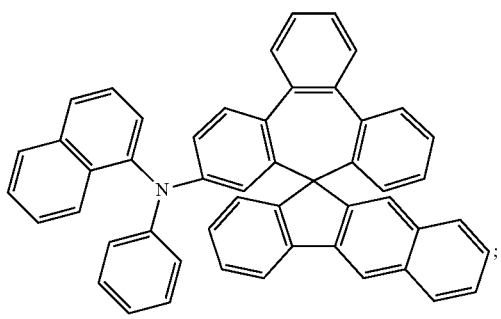
Compound 58
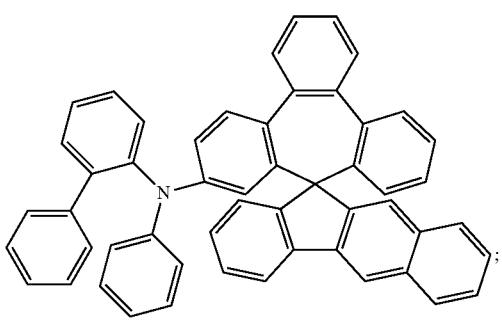
Compound 59
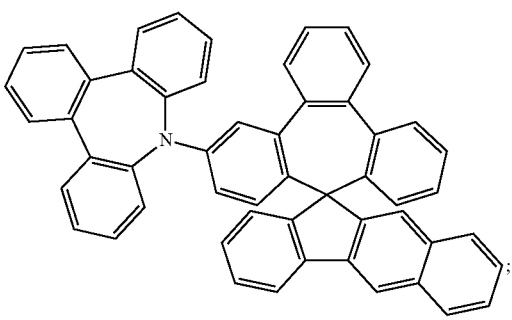

Compound 60
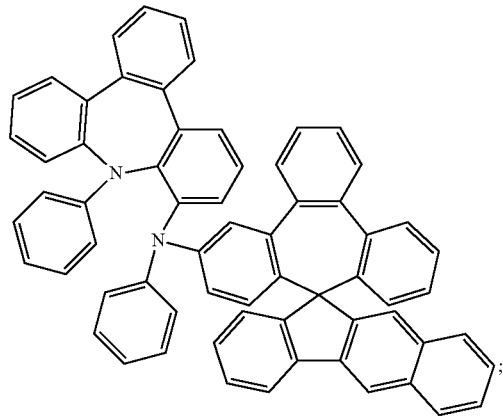
Compound 61
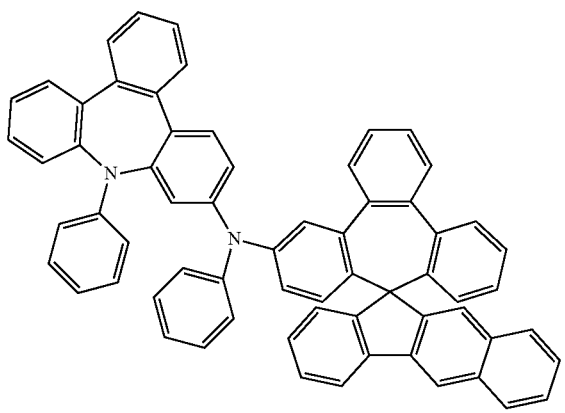
Compound 62
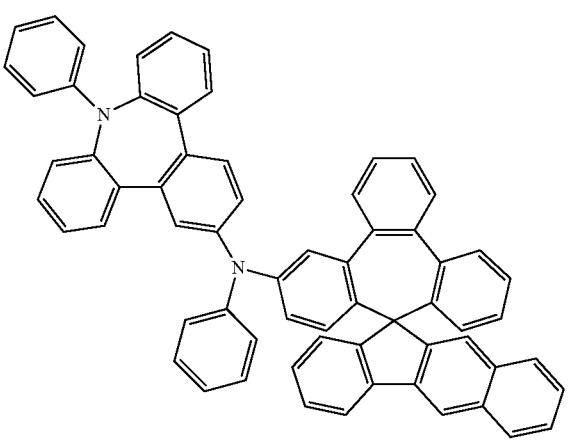
Compound 63
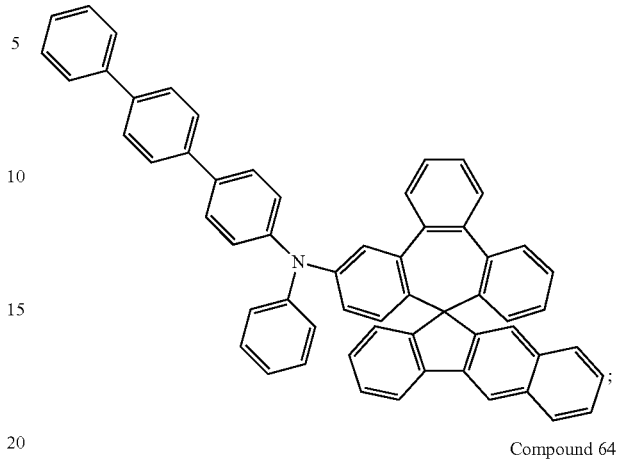
Compound 64
Compound 65
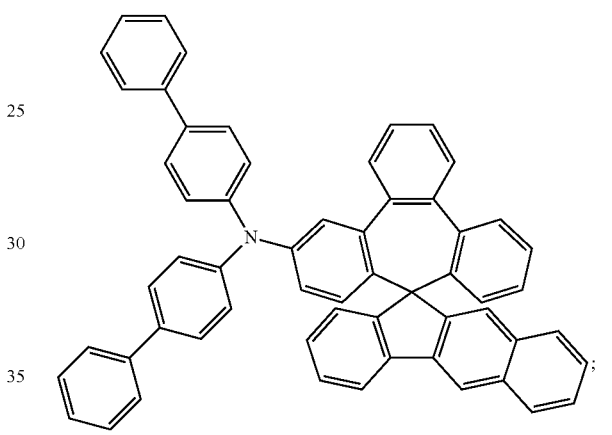
Compound 66
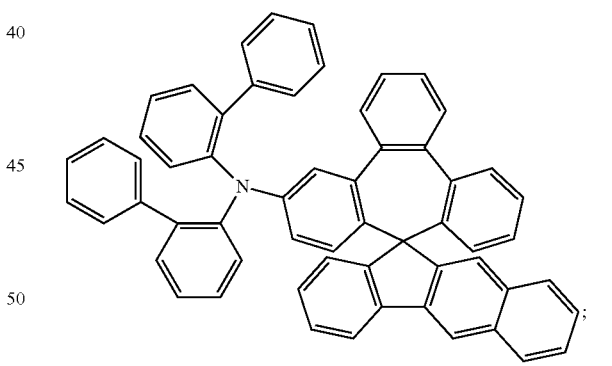

-continued
Compound 67
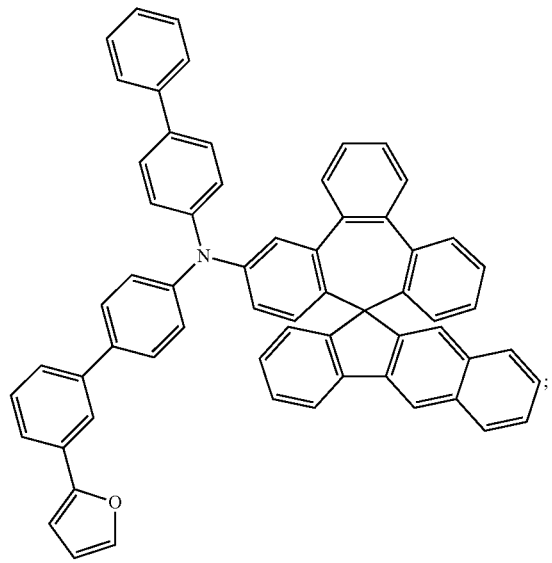
Compound 68
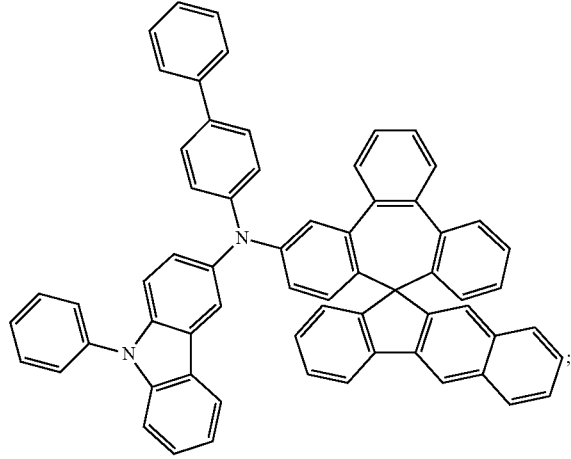
Compound 69
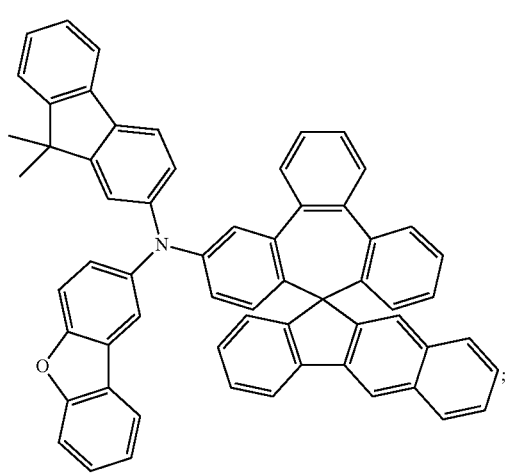
-continued
Compound 70
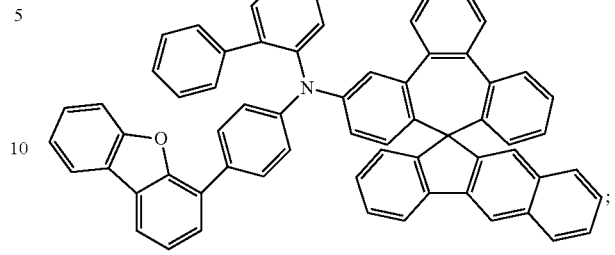
Compound 71
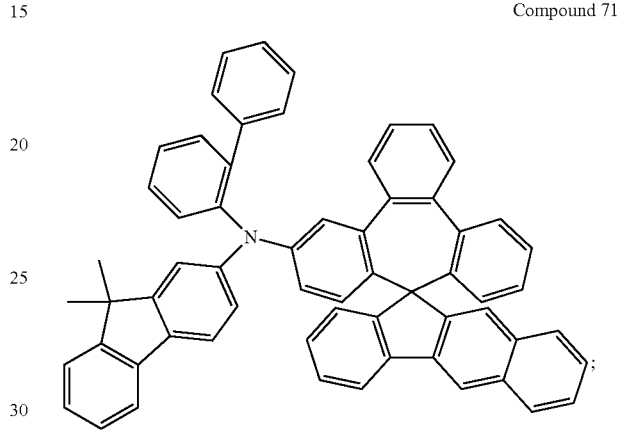
Compound 72
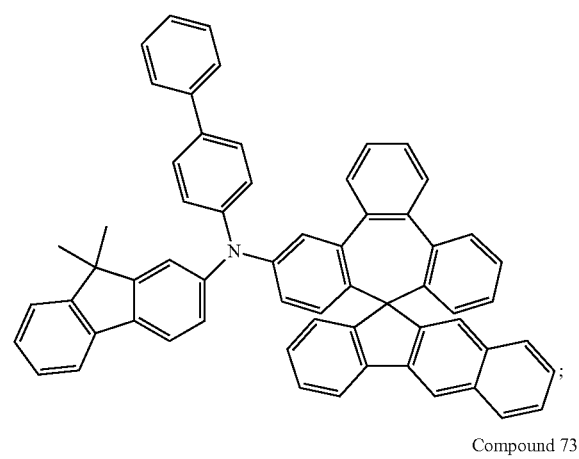
Compound 73

Compound 74
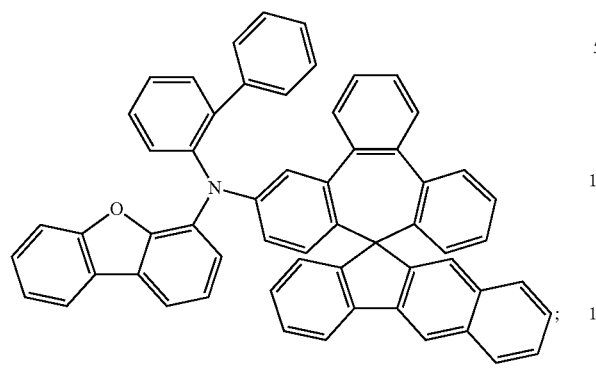
Compound 77
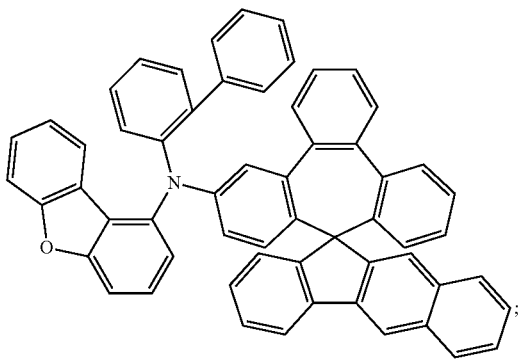
Compound 75
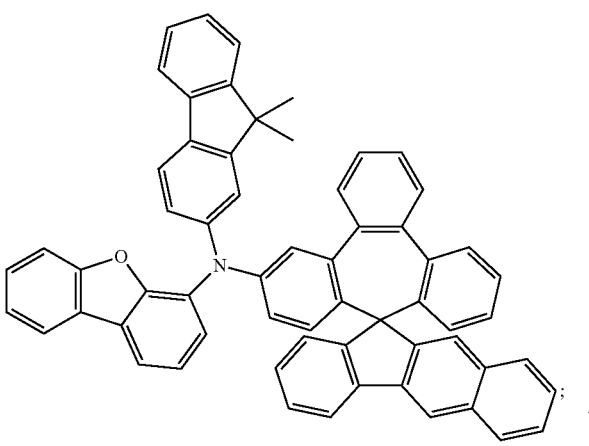
Compound 78
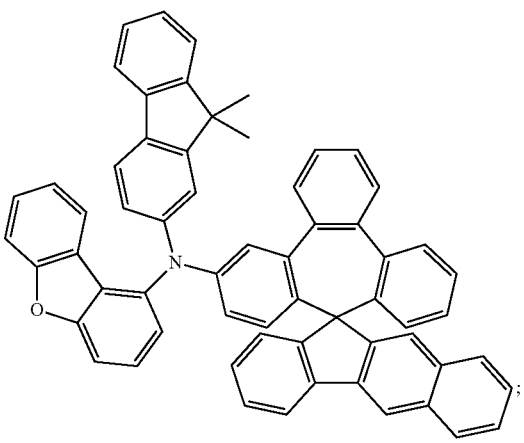
Compound 76
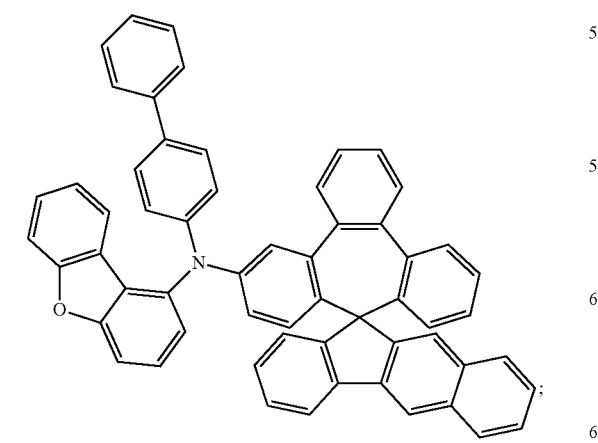
Compound 79
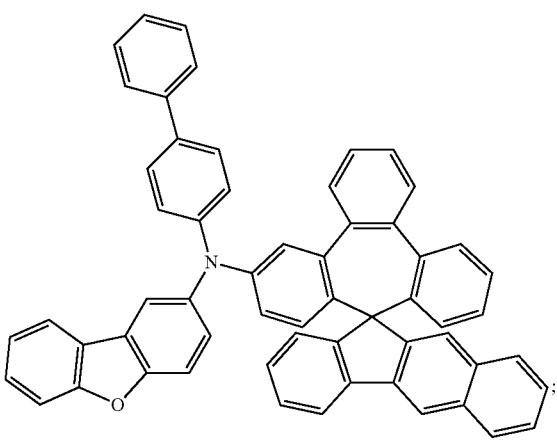

Compound 80
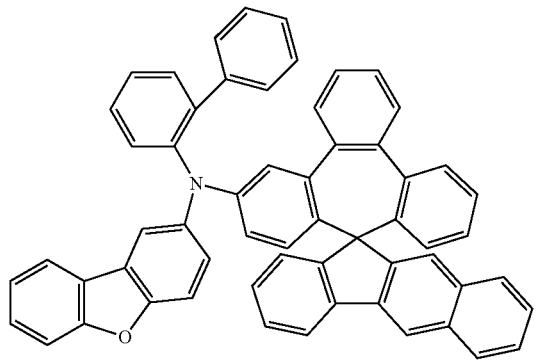
Compound 84
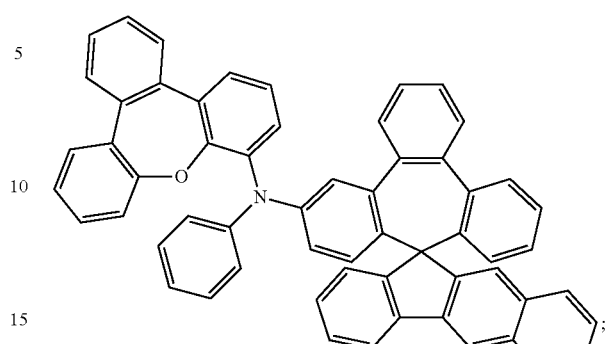
Compound 81
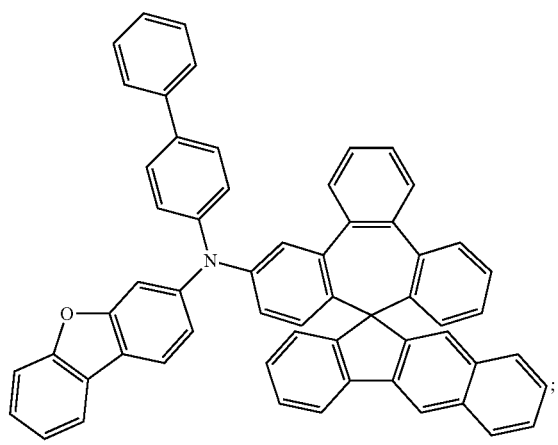
Compound 85
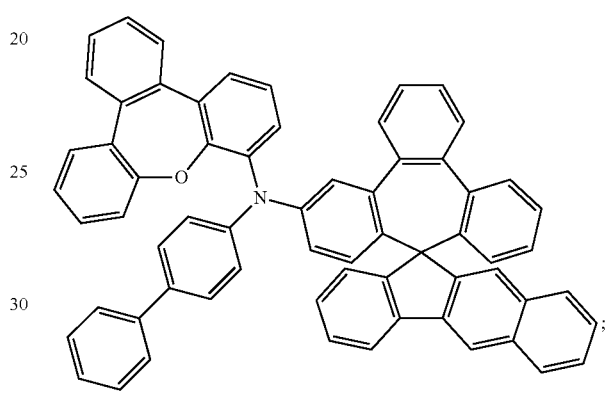
Compound 82
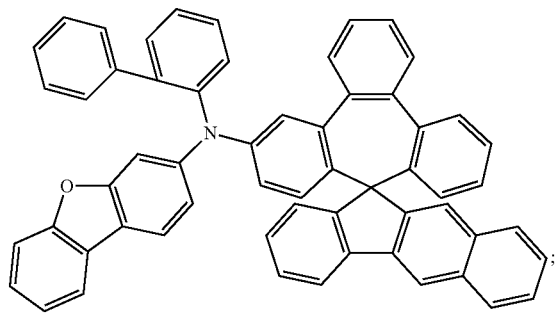
Compound 86
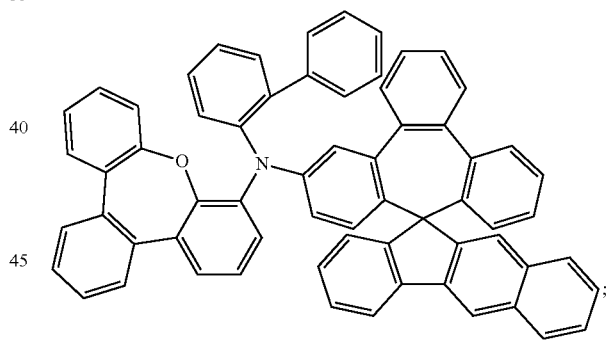
Compound 83
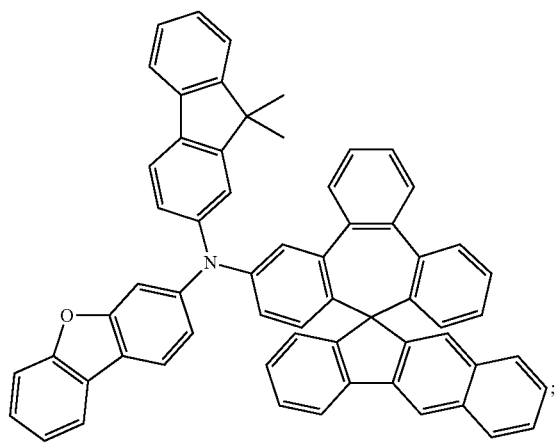
Compound 87
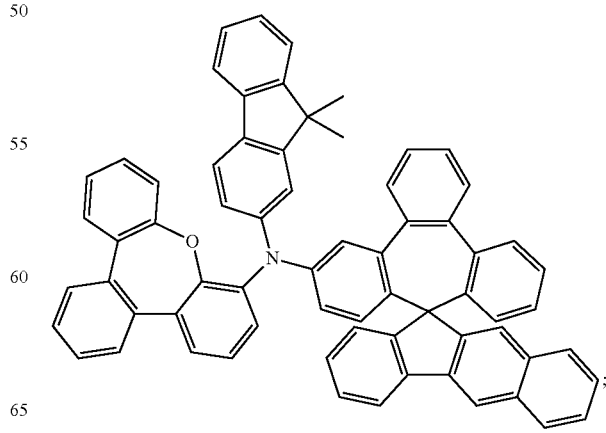

Compound 88
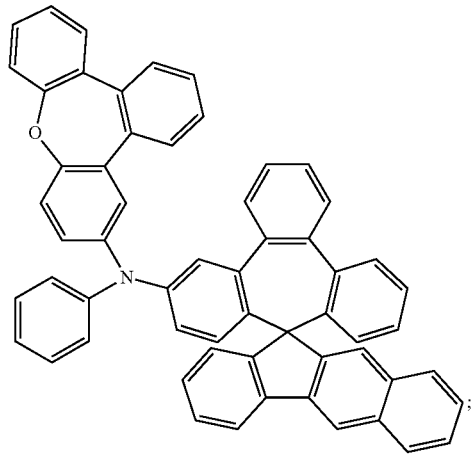
Compound 89
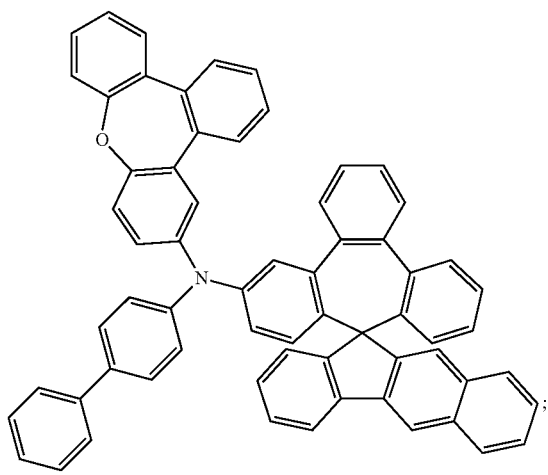
Compound 90
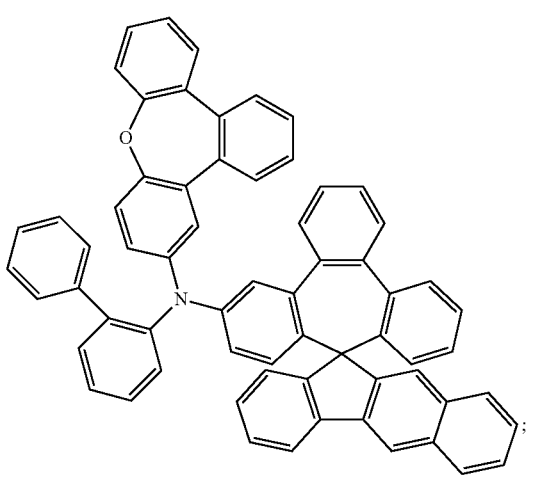
Compound 91
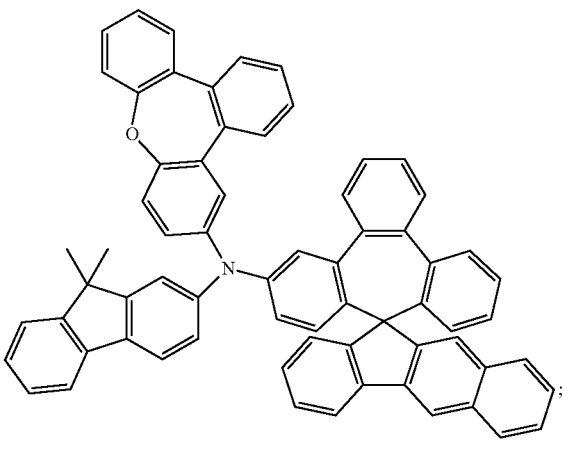
Compound 92
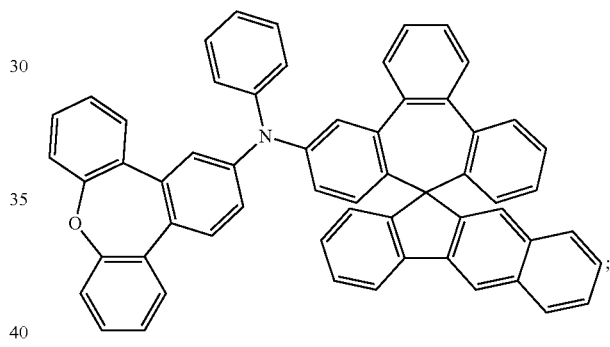
Compound 93
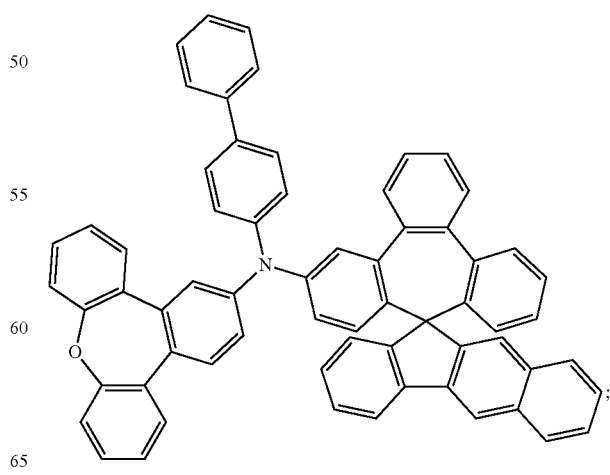

Compound 94
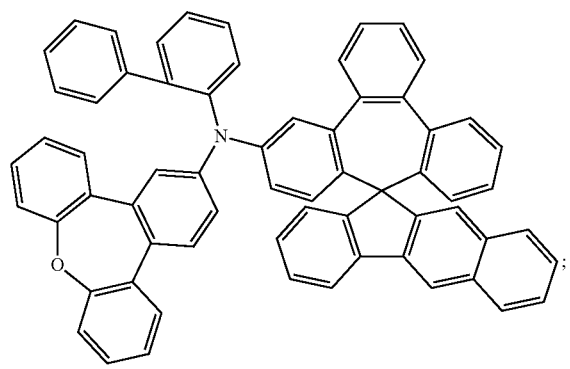
Compound 95
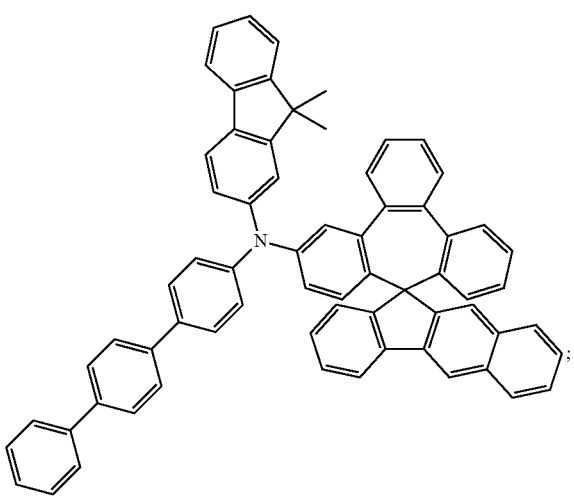
Compound 96
Compound 97
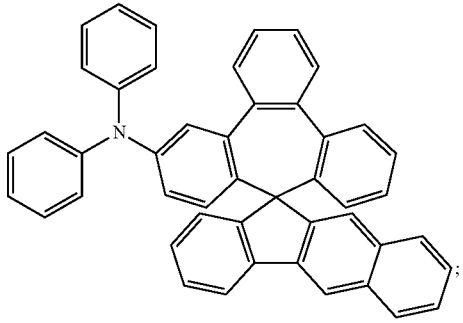
Compound 98
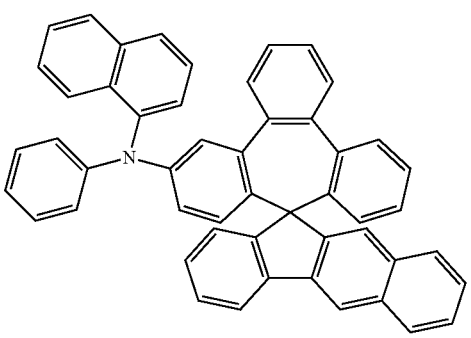
Compound 99
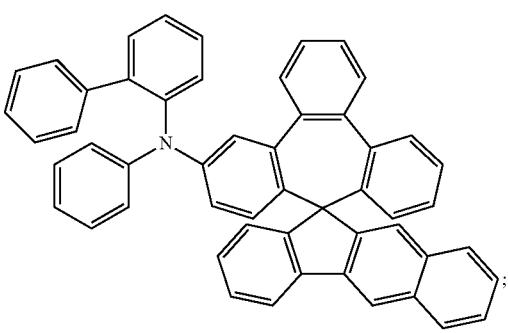
Compound 100
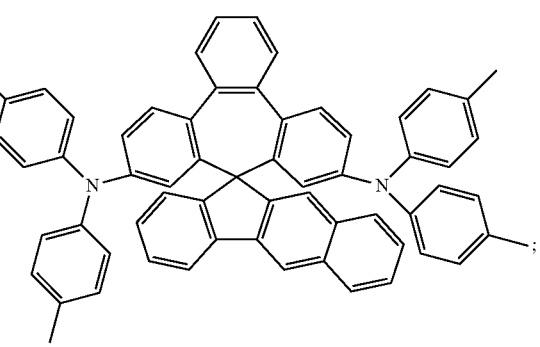

-continued
Compound 101
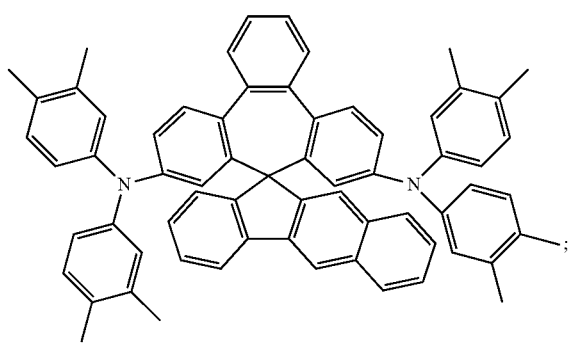
Compound 102
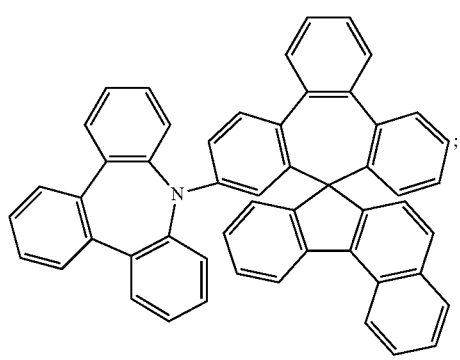
Compound 103
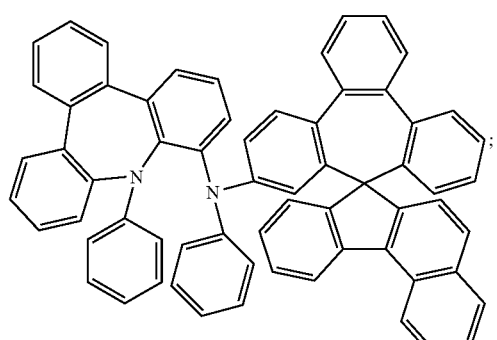
Compound 104
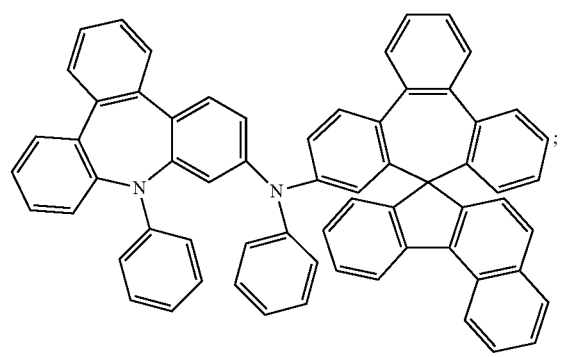
-continued
Compound 105
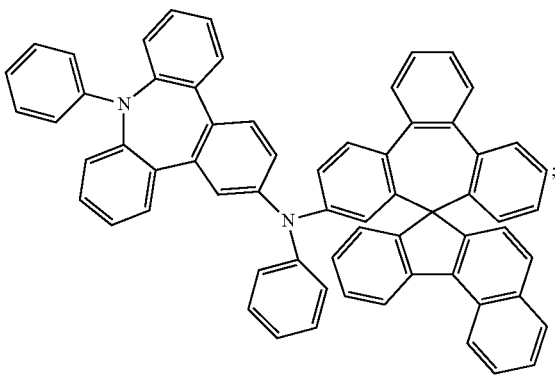
Compound 106
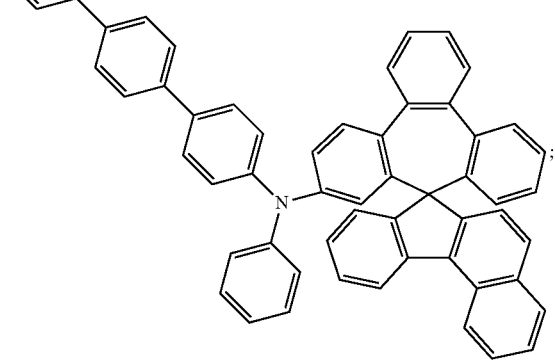
Compound 107
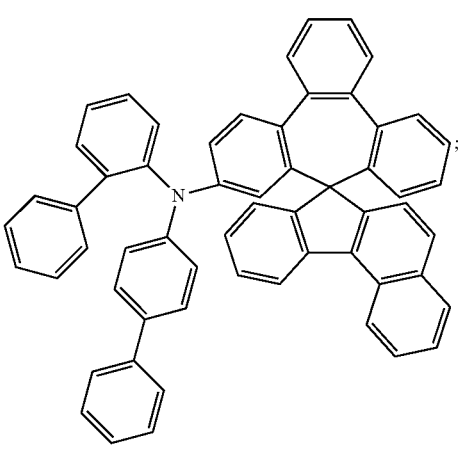

-continued
Compound 108
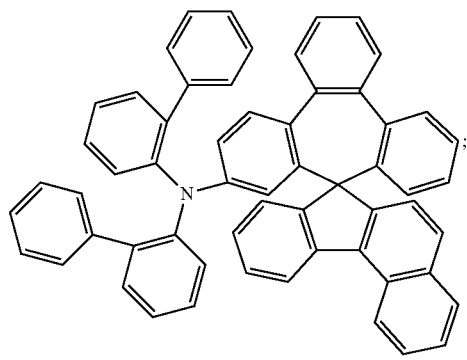
Compound 109
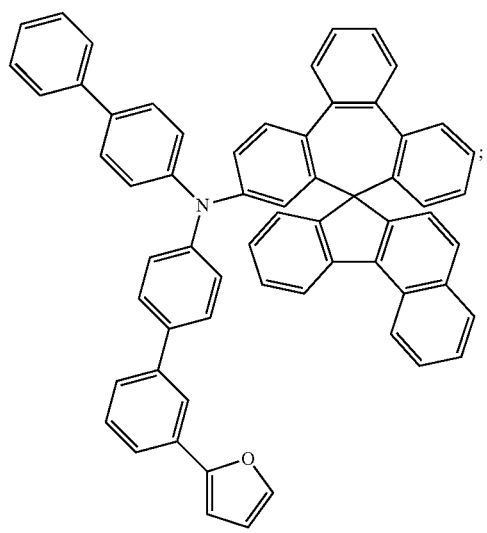
Compound 110
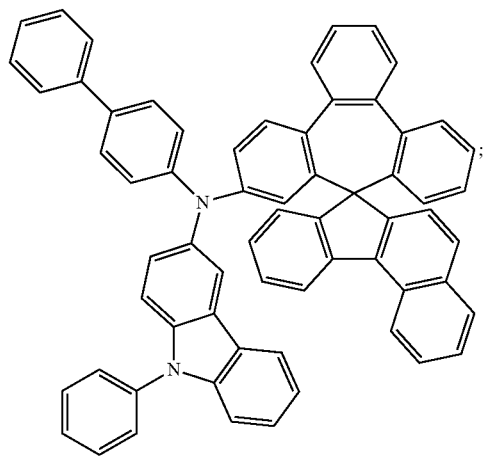
-continued
Compound 111
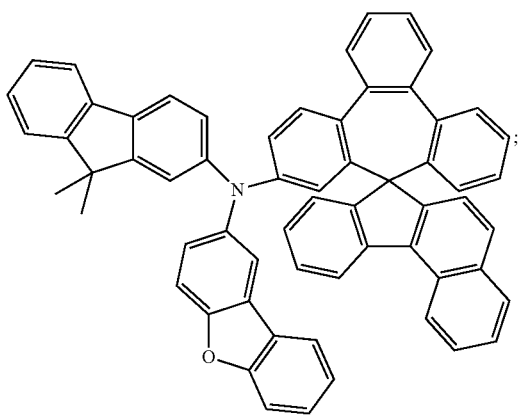
Compound 112
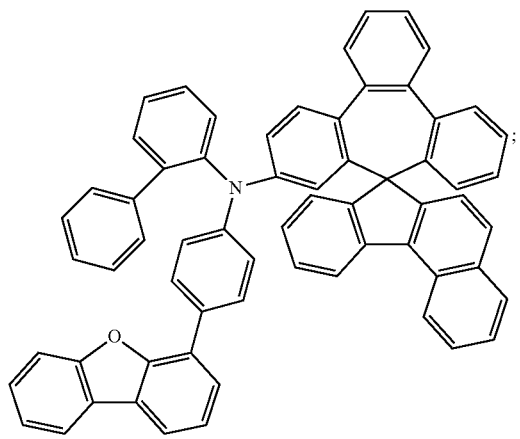
Compound 113
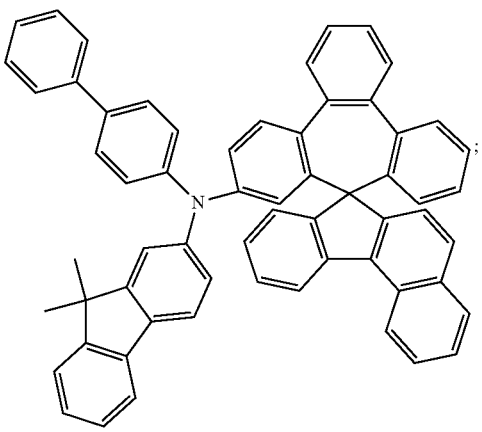

-continued
Compound 114
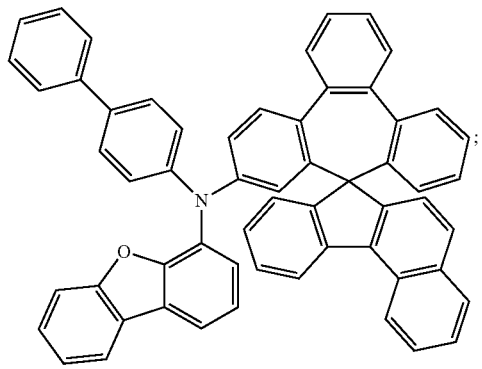
Compound 115
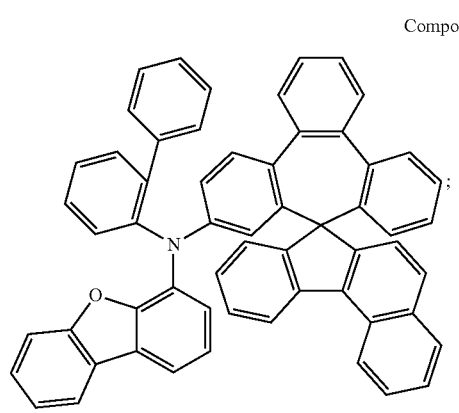
Compound 116
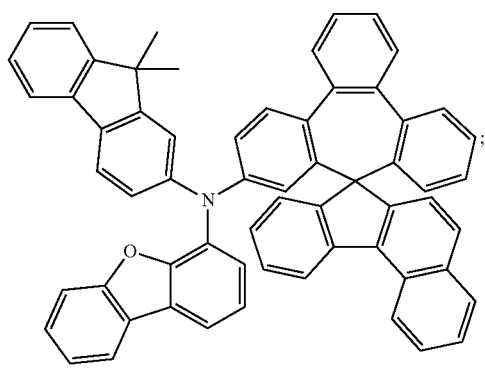
Compound 117
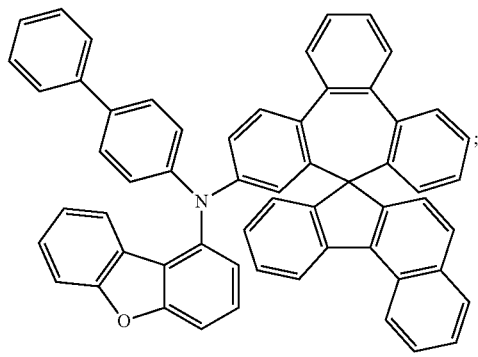
-continued
Compound 118
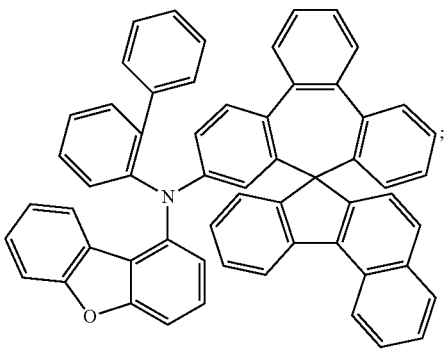
Compound 119
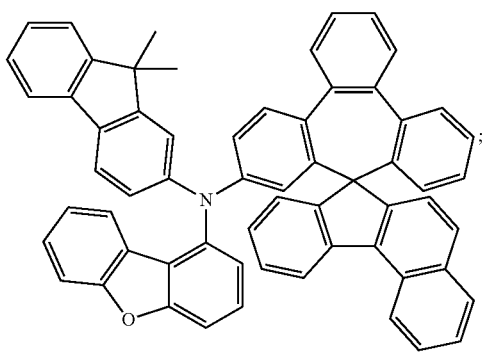
Compound 120
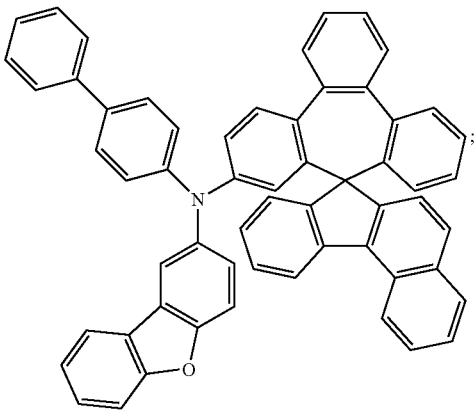
Compound 121
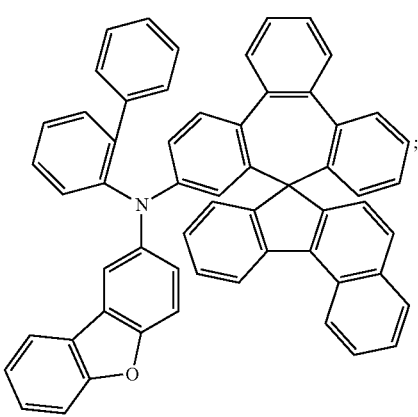

Compound 122
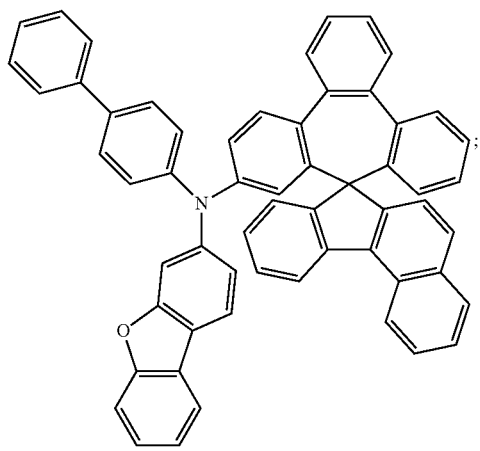
Compound 123
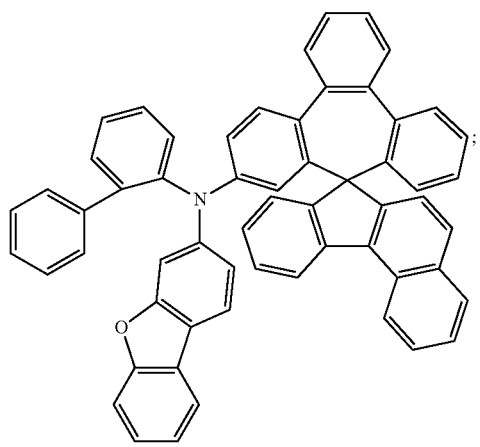
Compound 124
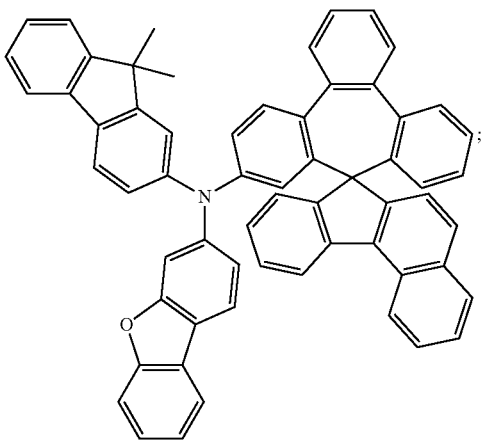
Compound 125
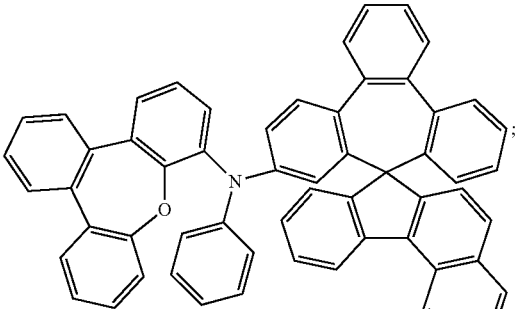
Compound 126
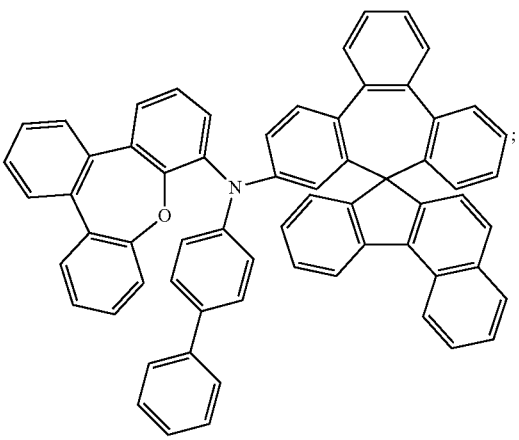
Compound 127
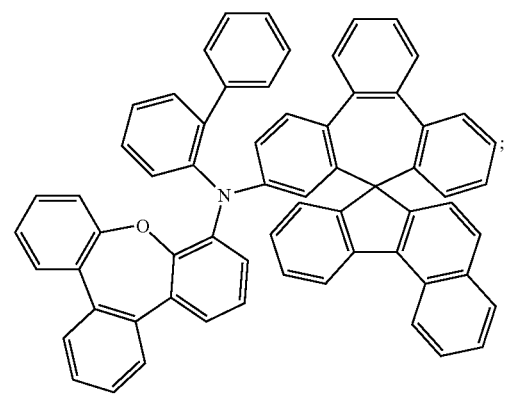
Compound 128
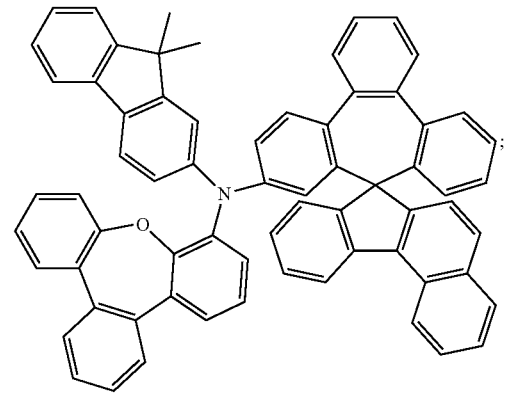

Compound 129
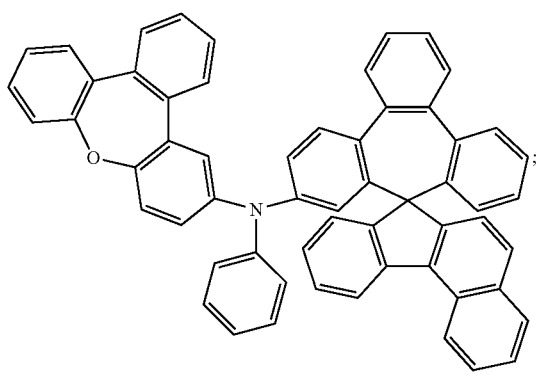
Compound 130
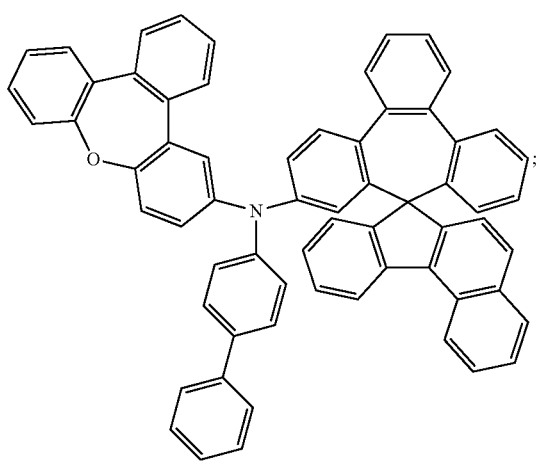
Compound 131
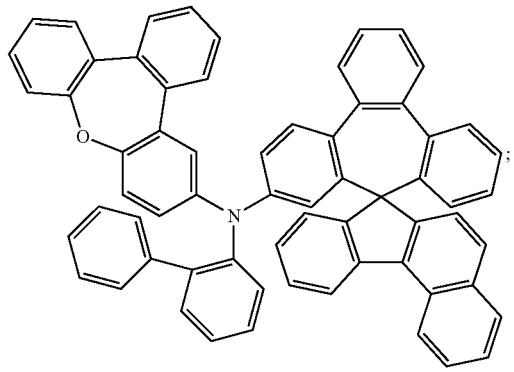
Compound 132
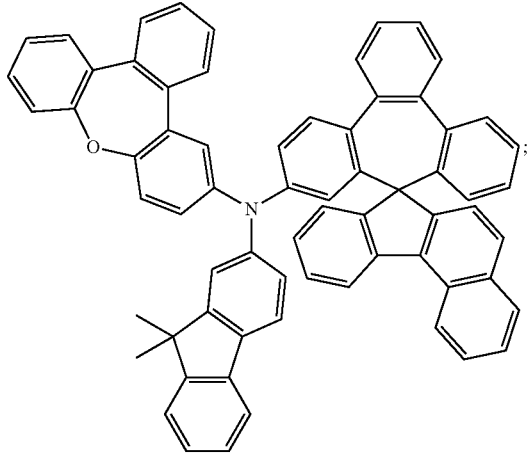
Compound 133
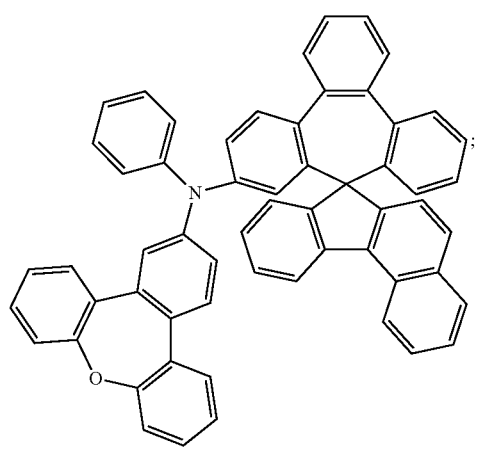
Compound 134
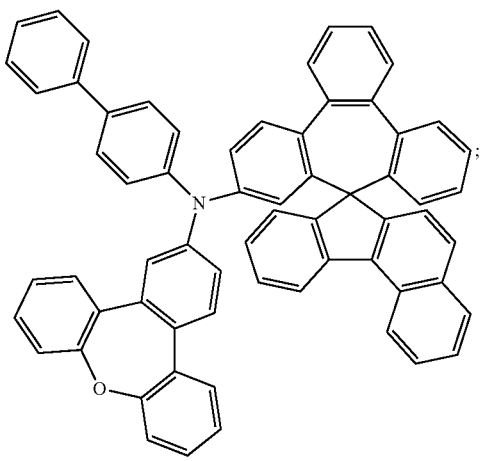

Compound 135
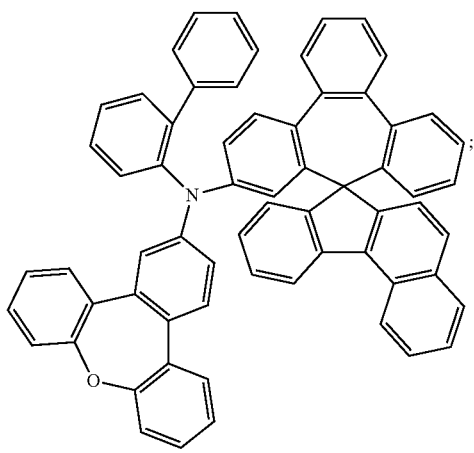
Compound 136
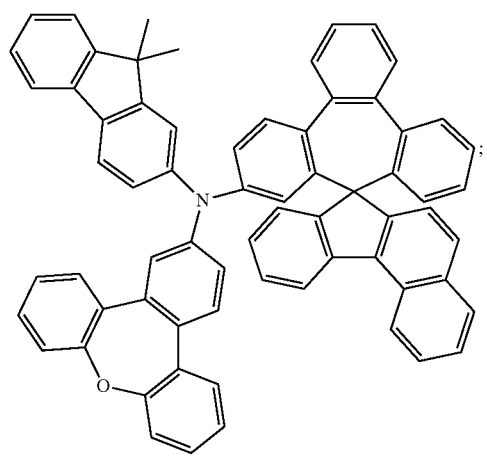
Compound 137
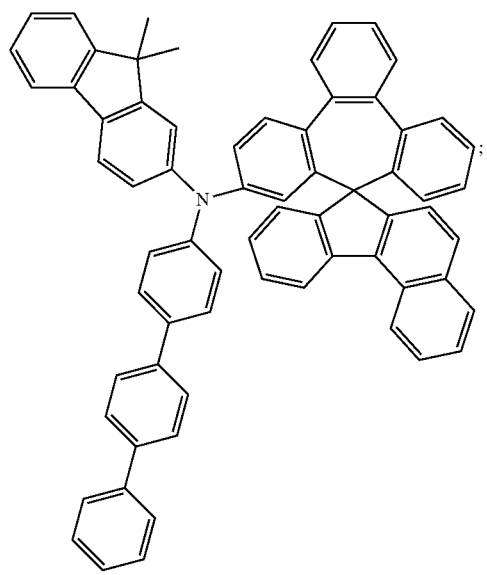
Compound 138
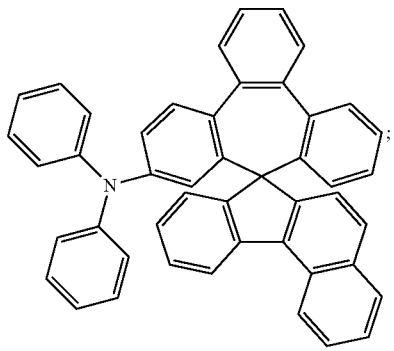
Compound 139
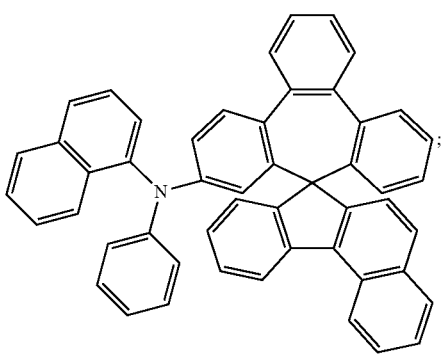
Compound 140
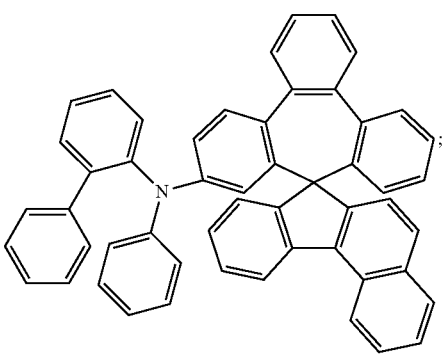
Compound 141
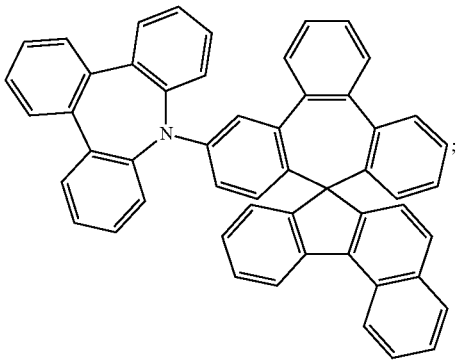

Compound 142
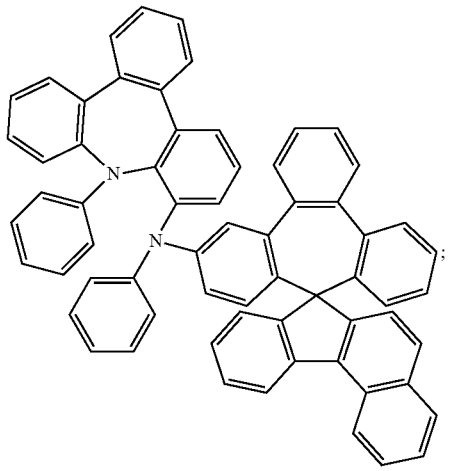
Compound 143
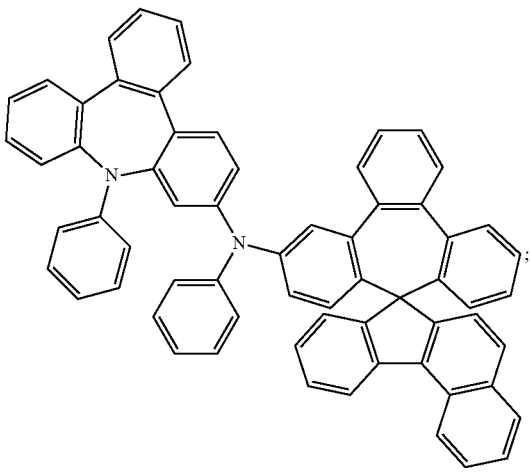
Compound 144
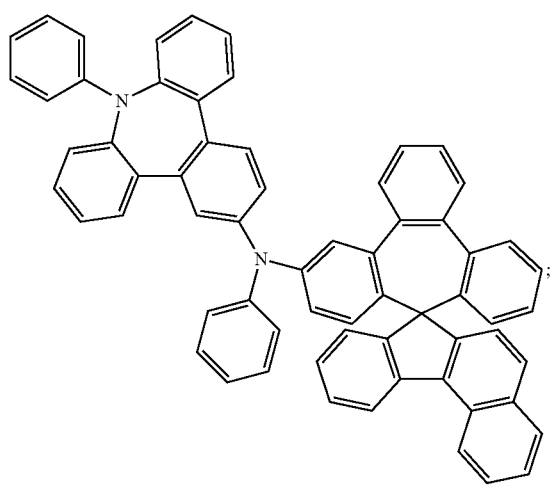
Compound 145
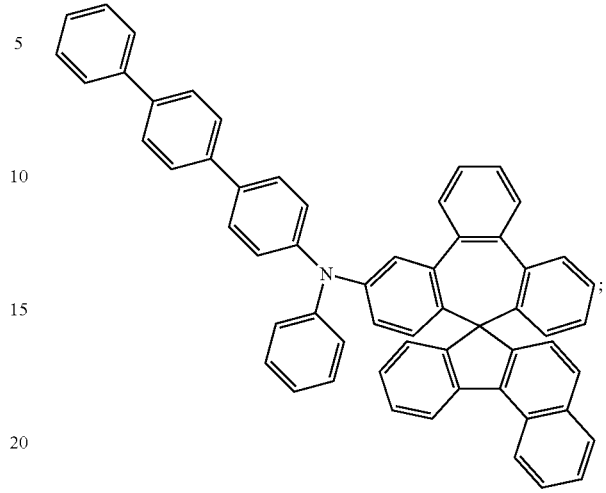
Compound 146
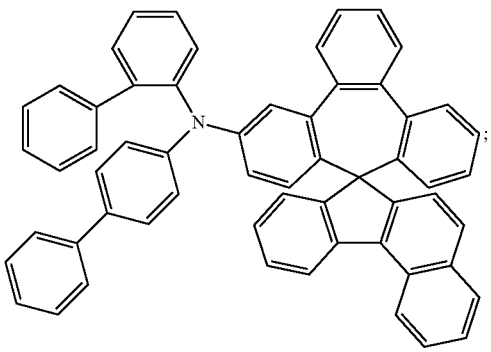
Compound 147
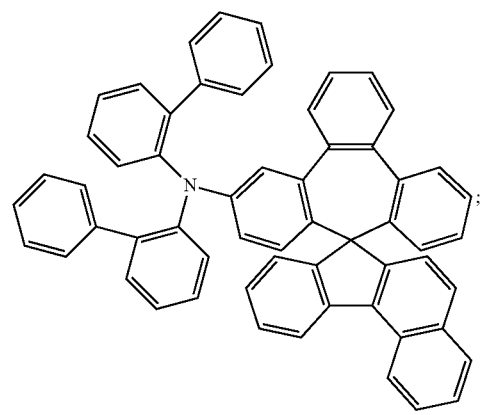

Compound 148
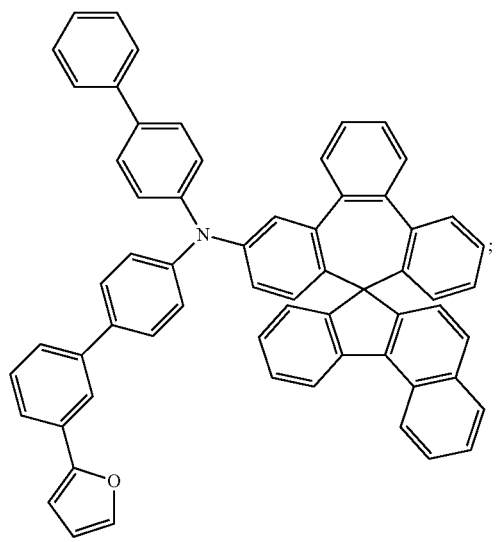
Compound 149
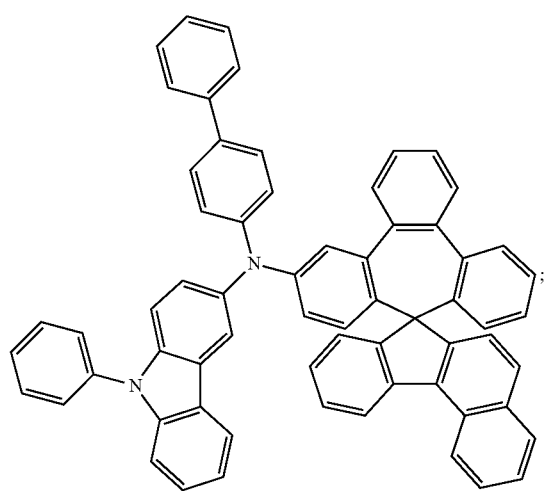
Compound 150
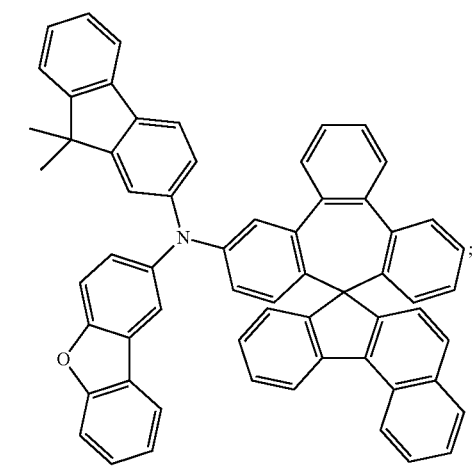
Compound 151
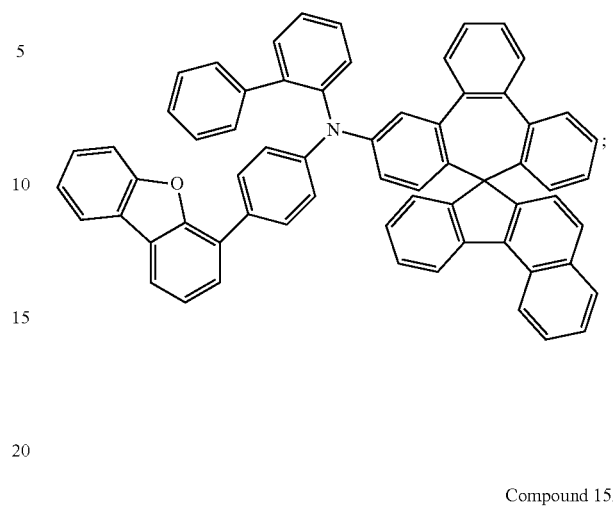
Compound 152
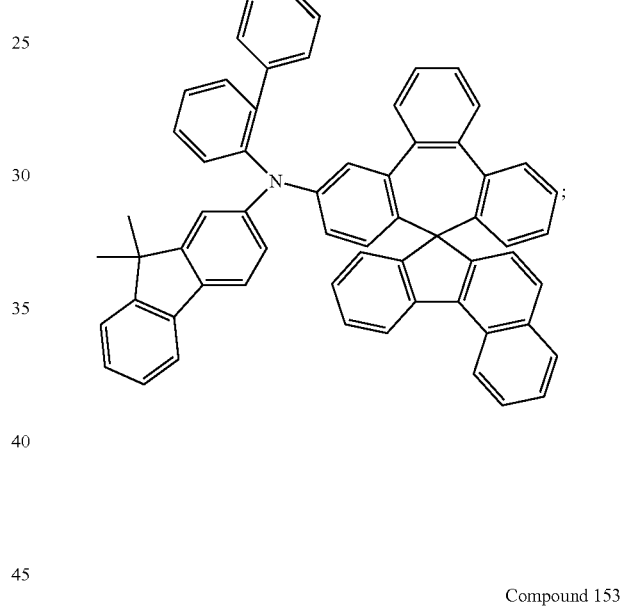
Compound 153
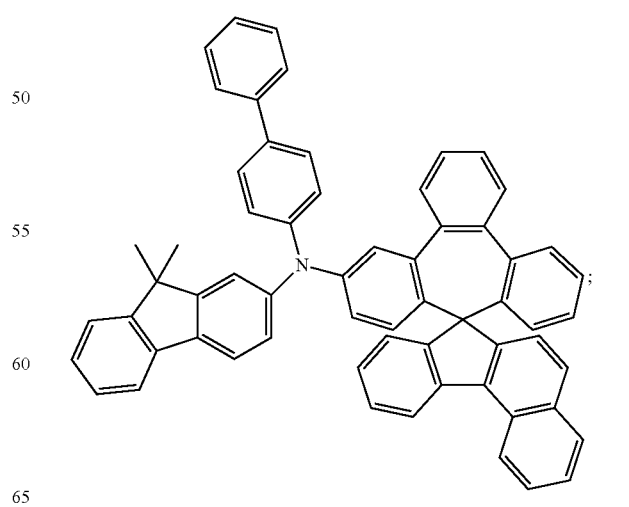

Compound 154
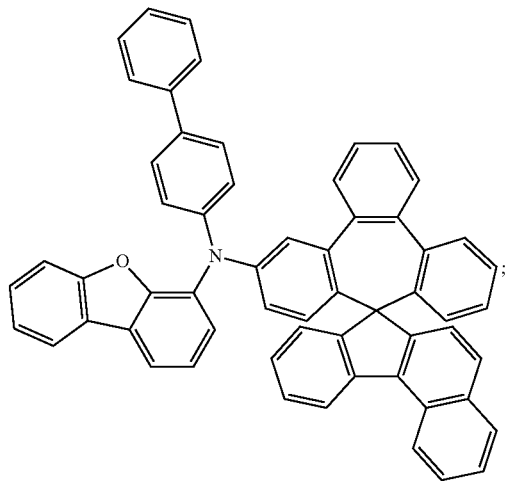
Compound 155
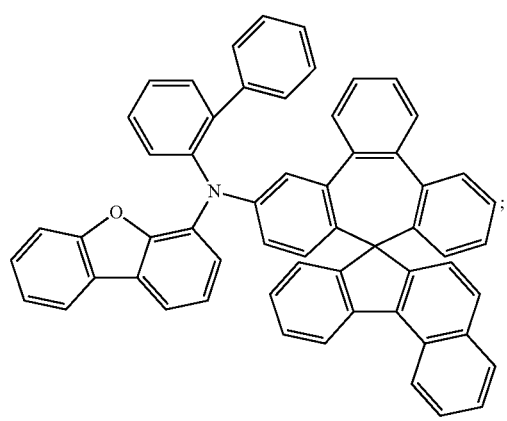
Compound 156
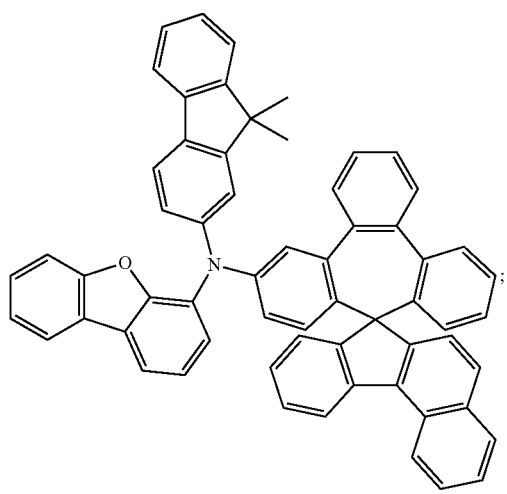
Compound 157
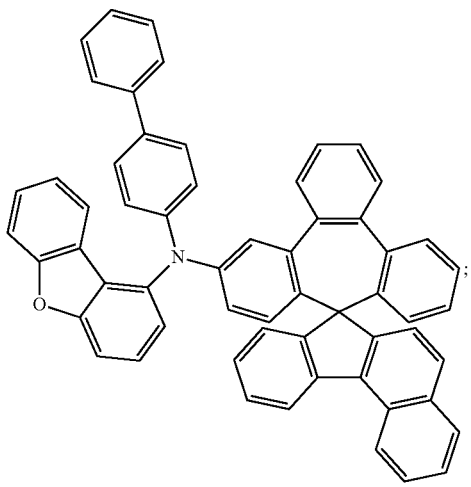
Compound 158
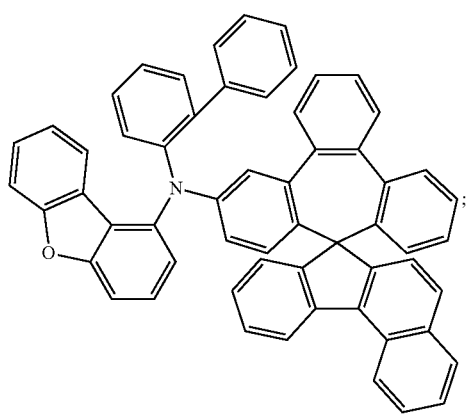
Compound 159
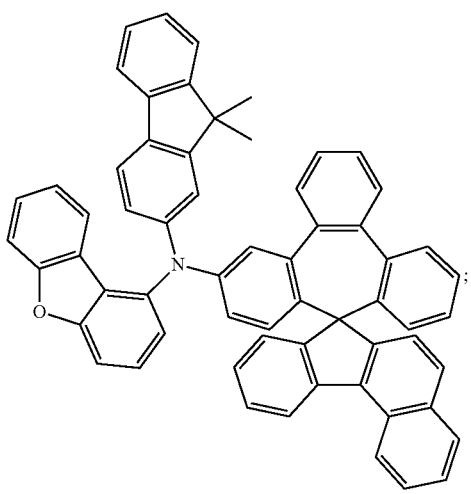

Compound 160
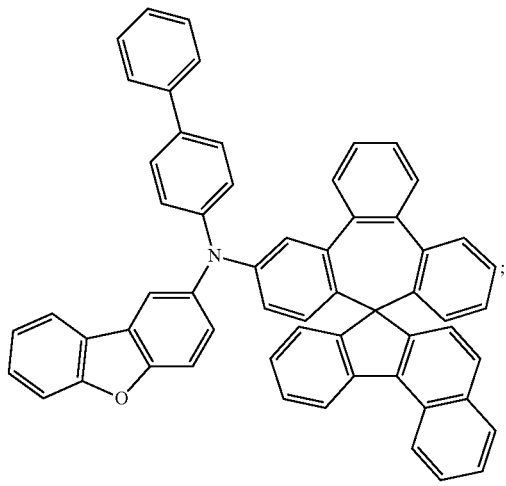
Compound 161
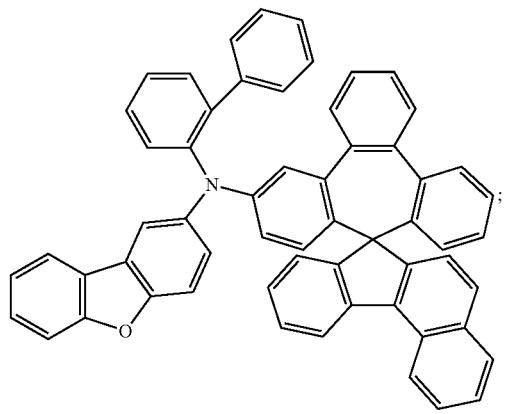
Compound 162
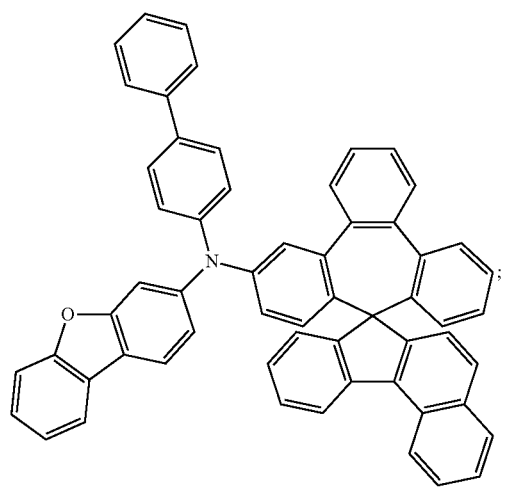
Compound 163
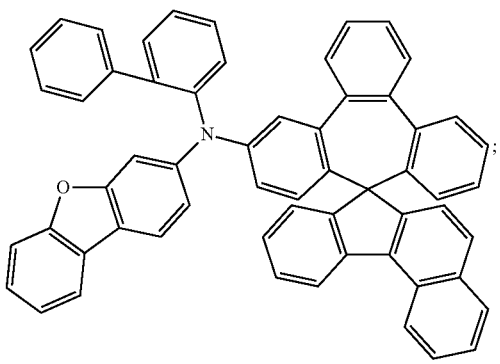
Compound 164
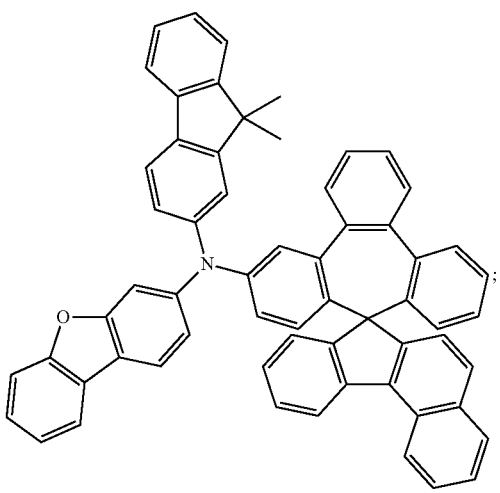
Compound 165
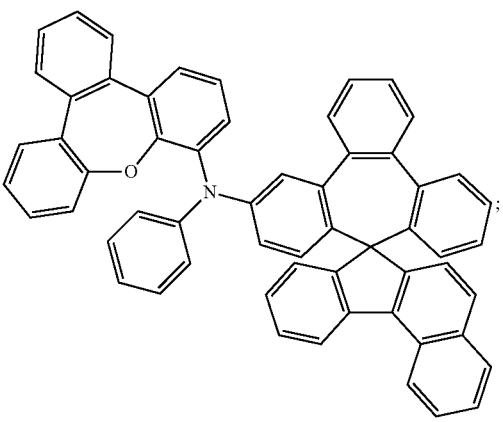

Compound 166
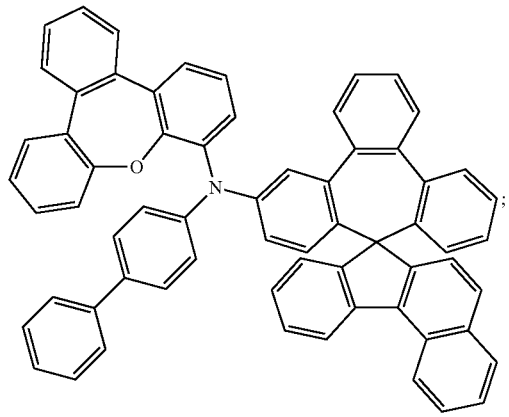
Compound 169
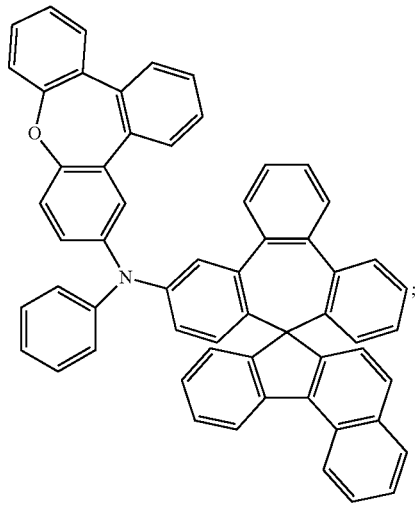
Compound 167
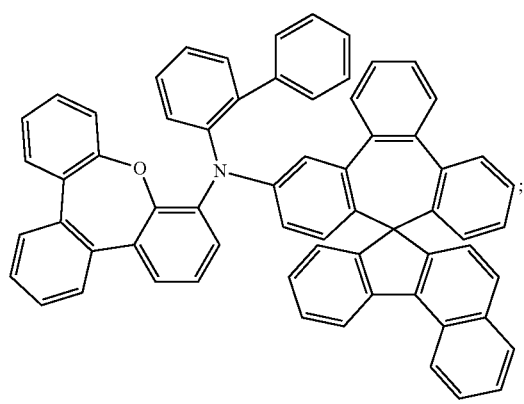
Compound 170
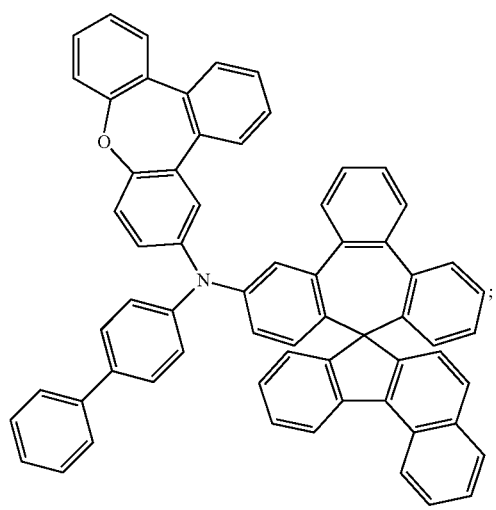
Compound 168
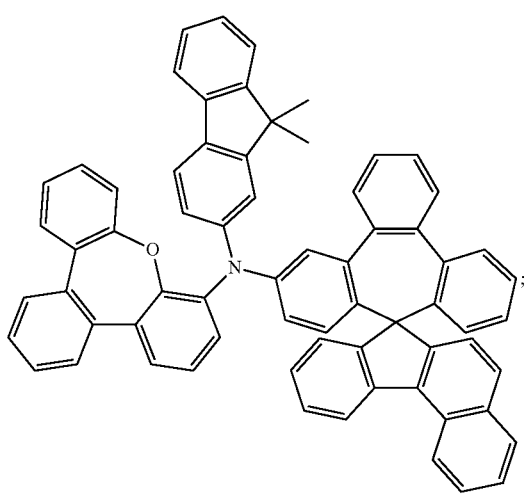
Compound 171
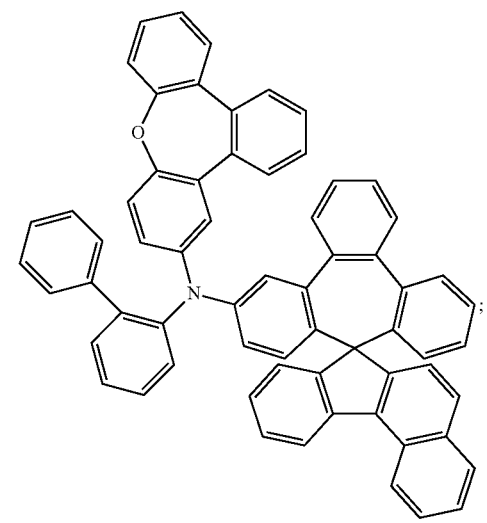

Compound 172
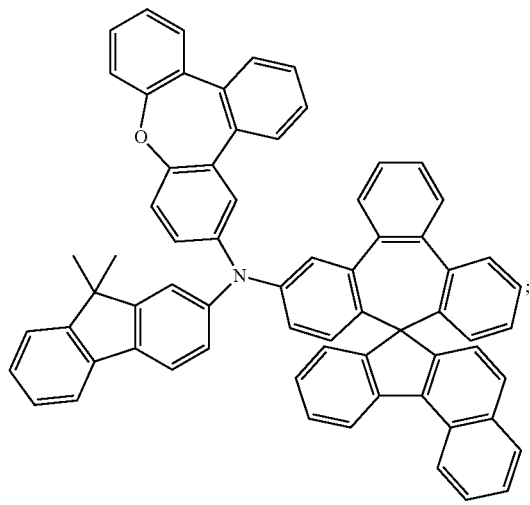
Compound 173
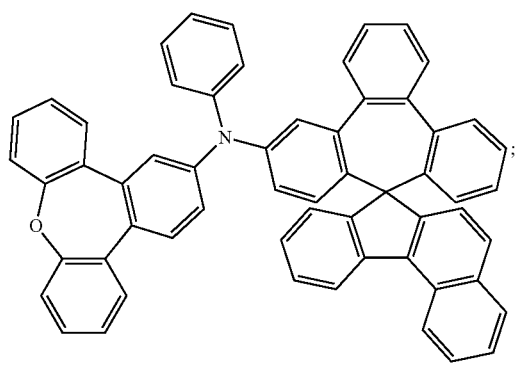
Compound 174
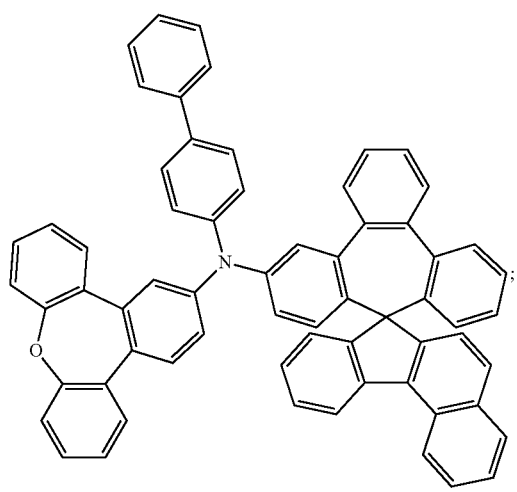
Compound 175
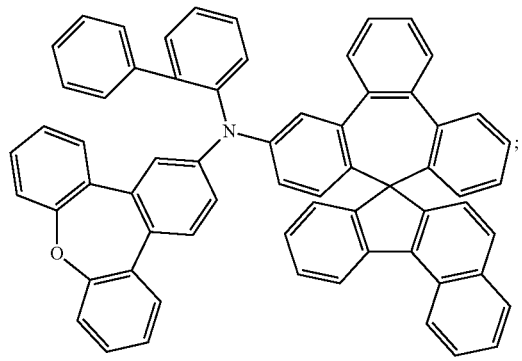
Compound 176
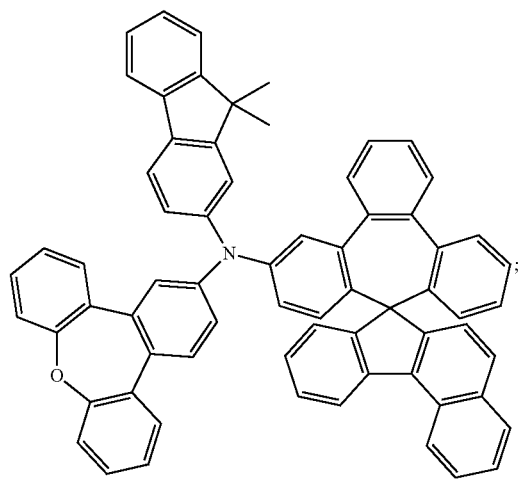
Compound 177
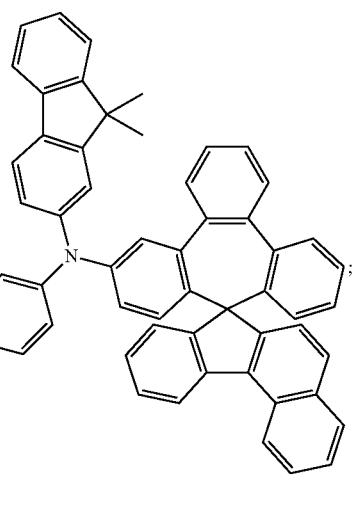

Compound 178
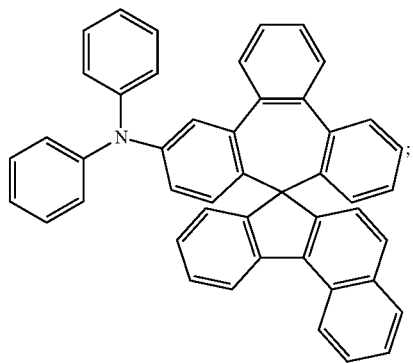
Compound 182
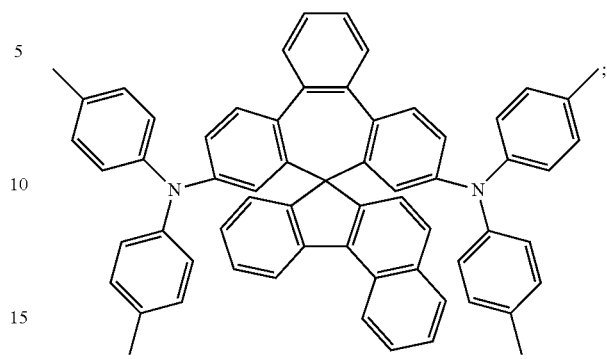
Compound 179
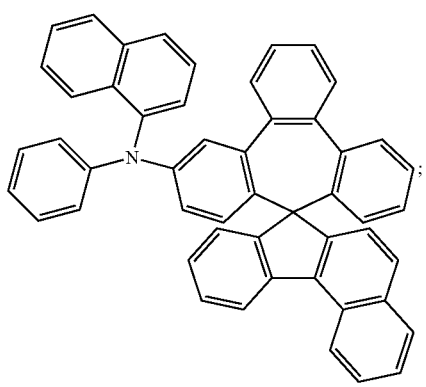
Compound 183
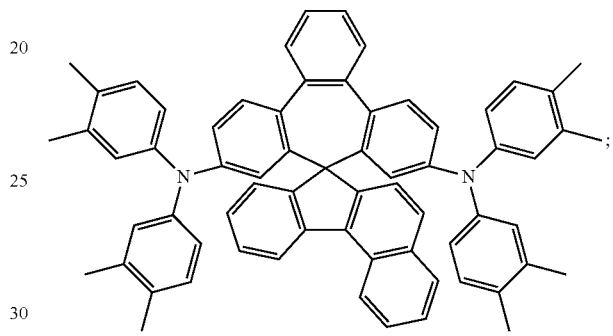
Compound 180
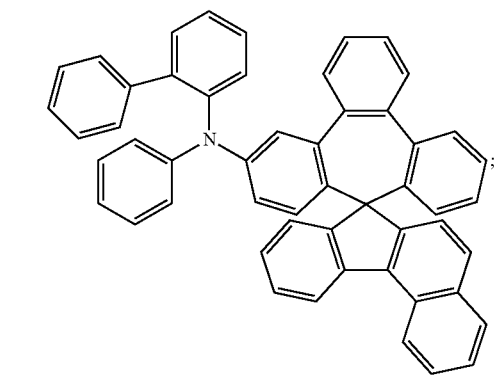
Compound 184
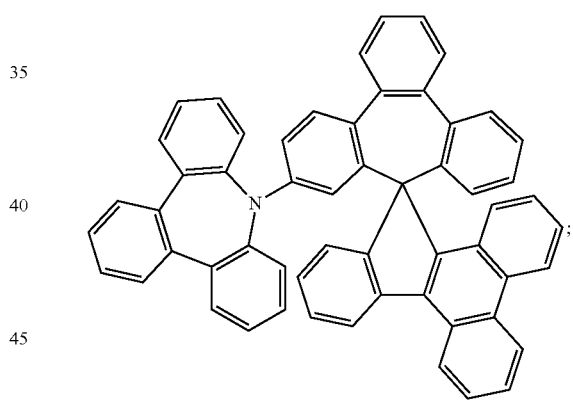
Compound 181
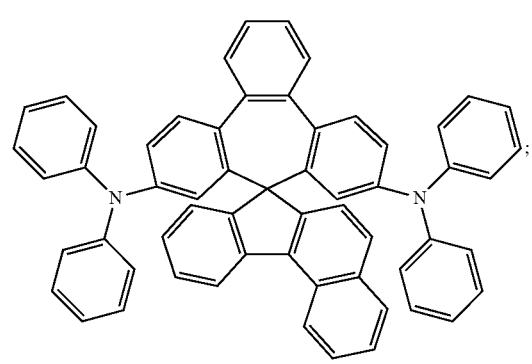
Compound 185
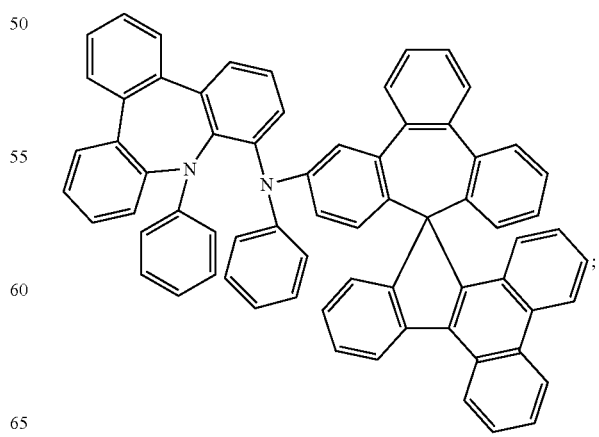

Compound 186
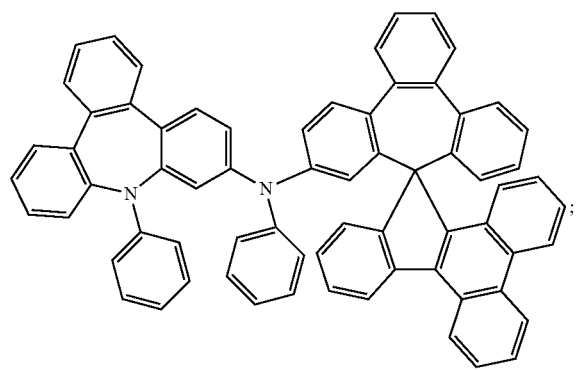
Compound 187
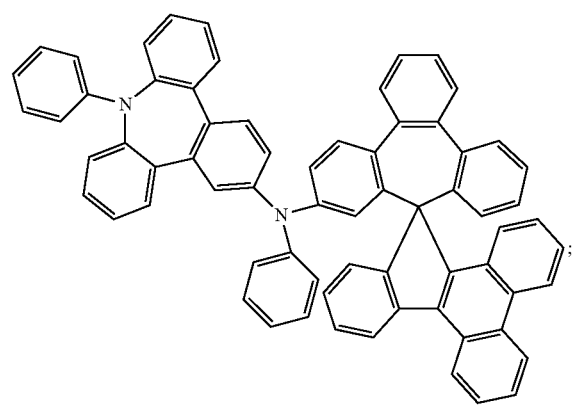
Compound 188
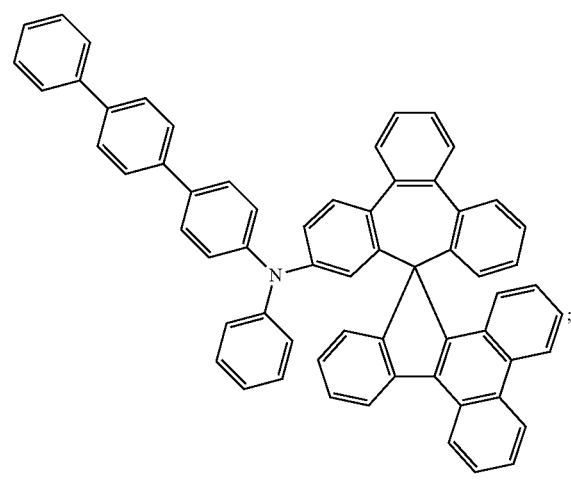
Compound 189
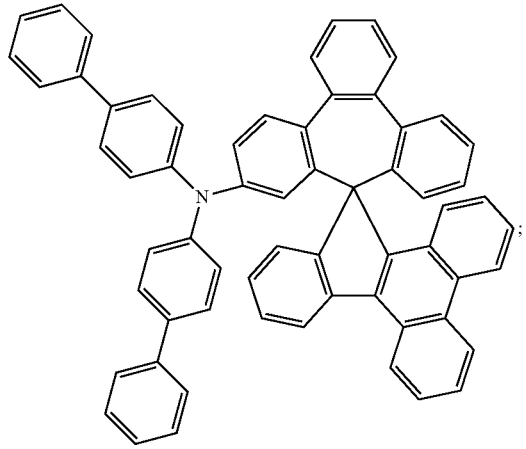
Compound 190
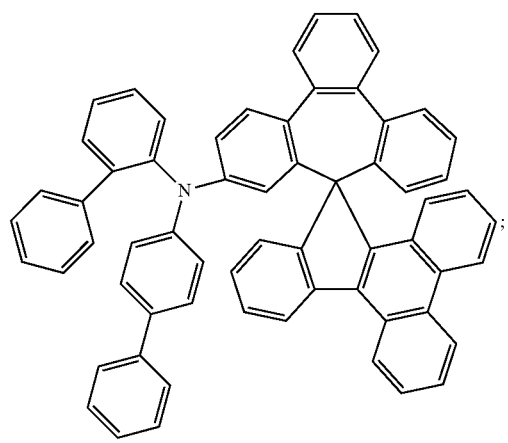
Compound 191
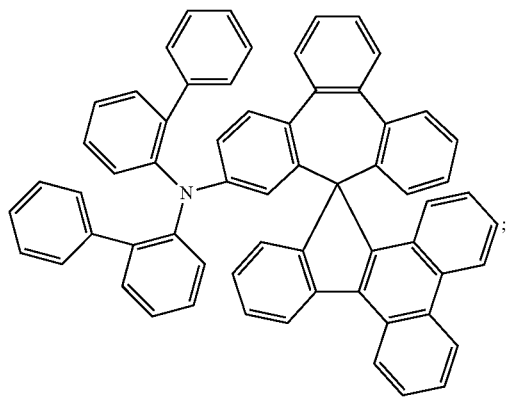

Compound 192
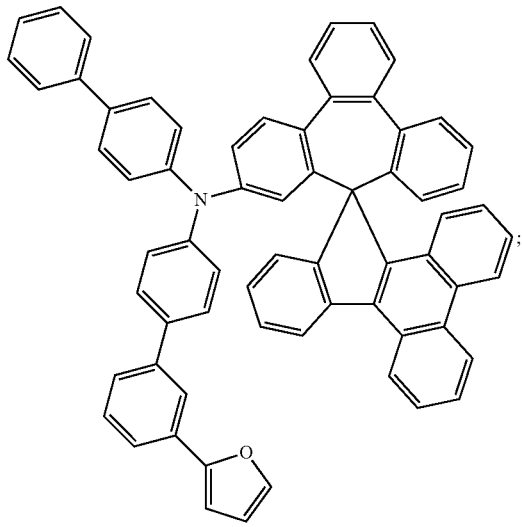
Compound 193
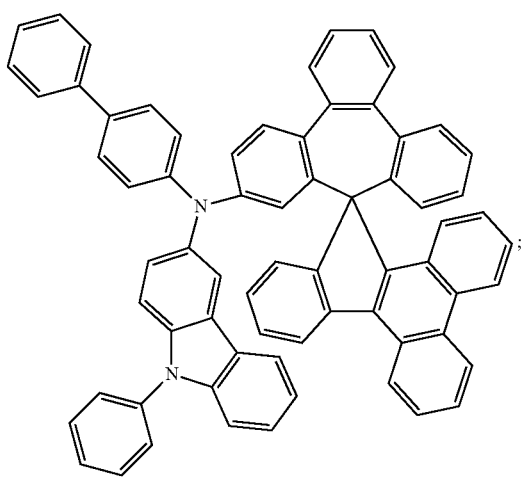
Compound 194
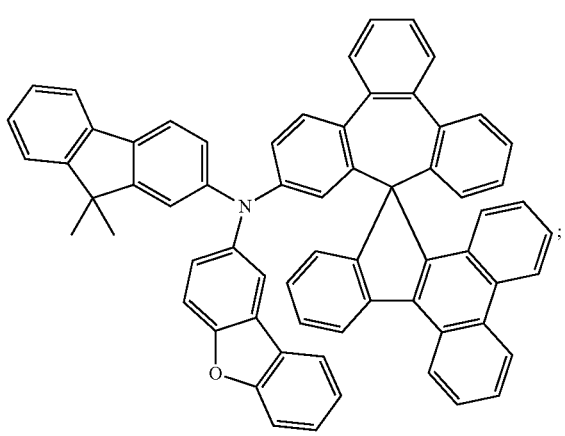
Compound 195
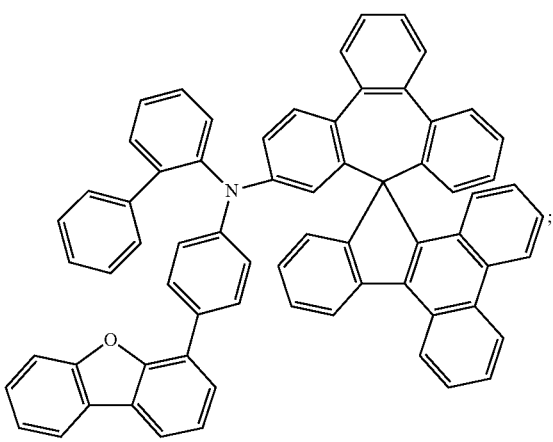
Compound 196
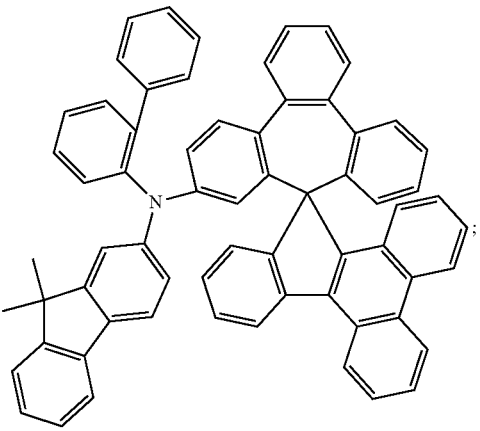
Compound 197
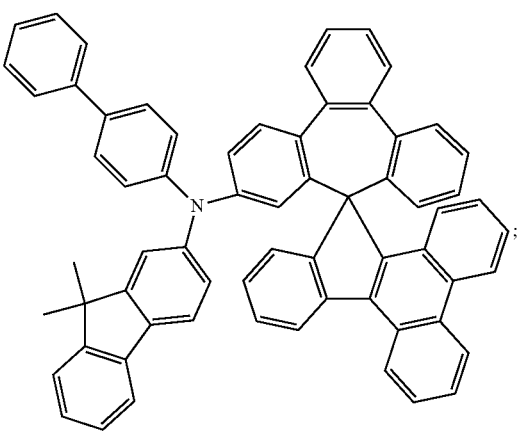

Compound 198
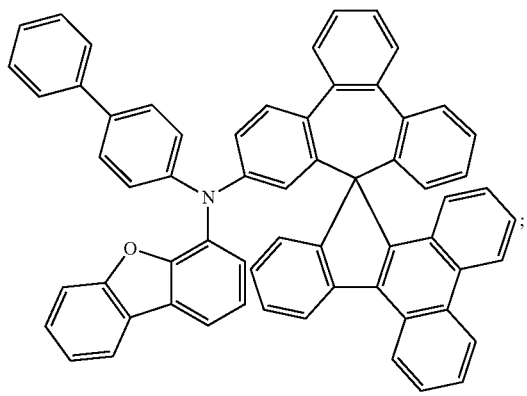
Compound 199
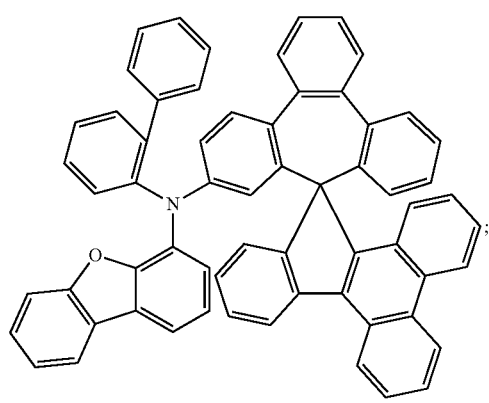
Compound 200
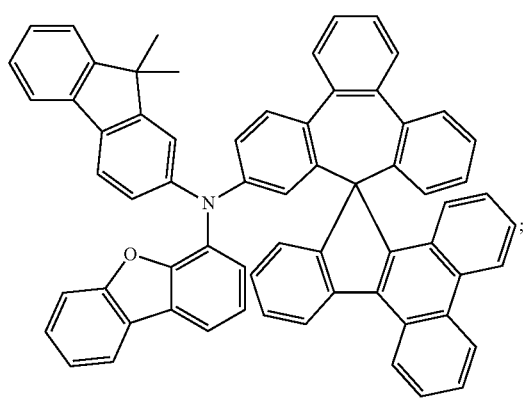
Compound 201
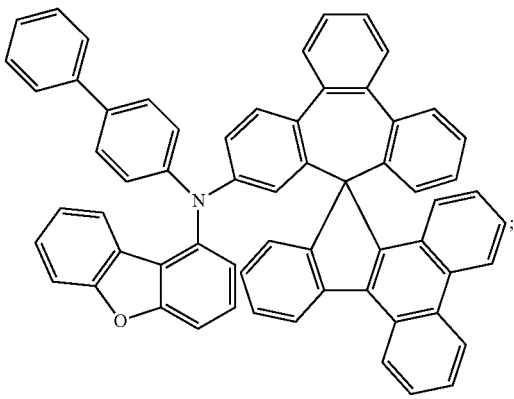
Compound 202
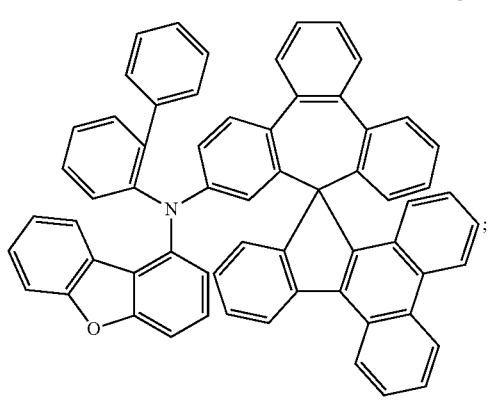
Compound 203
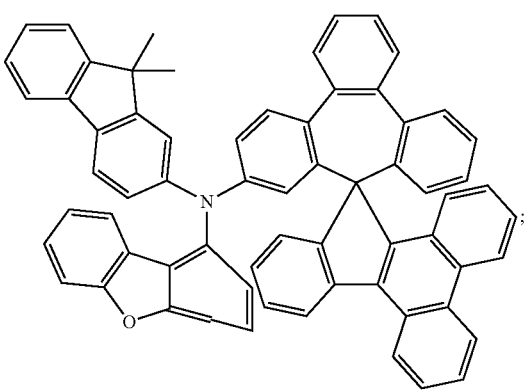

Compound 204
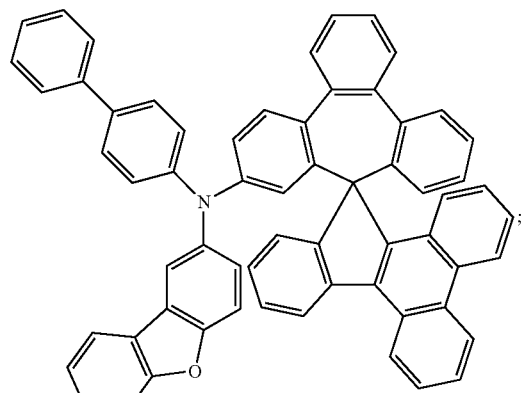
Compound 205
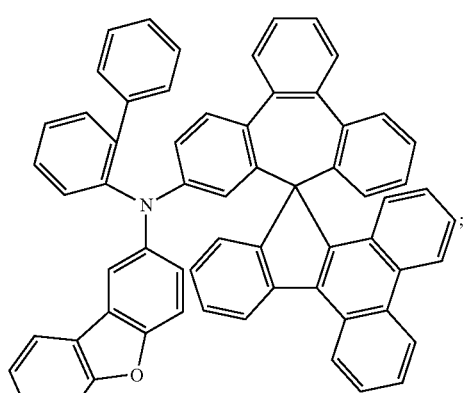
Compound 206
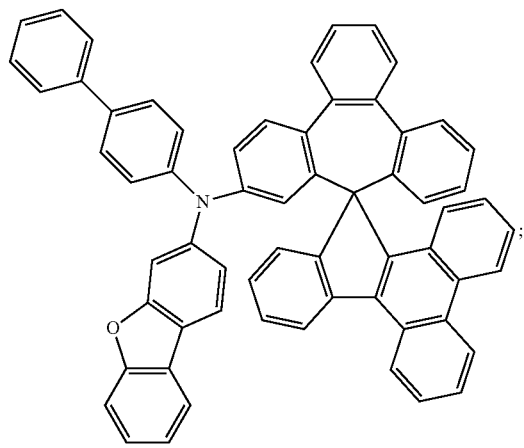
Compound 207
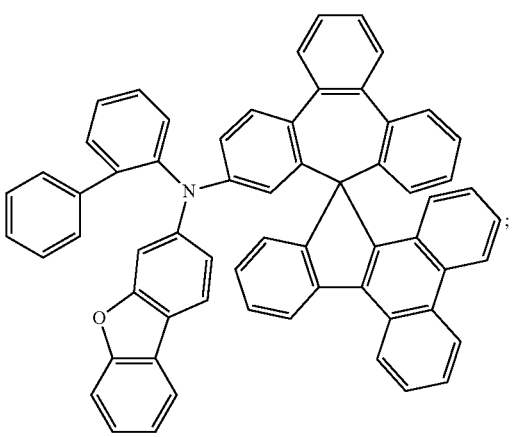
Compound 208
Compound 209

Compound 210
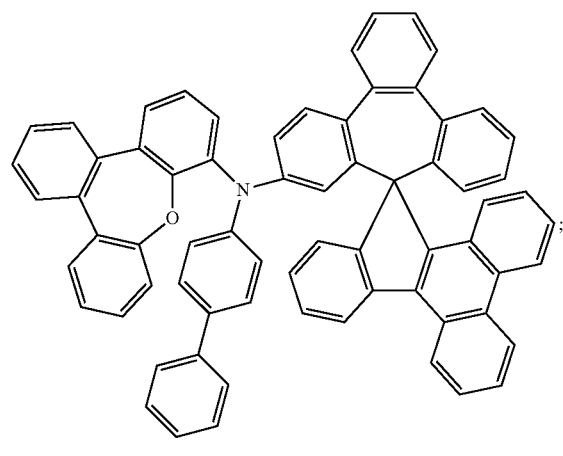
Compound 211
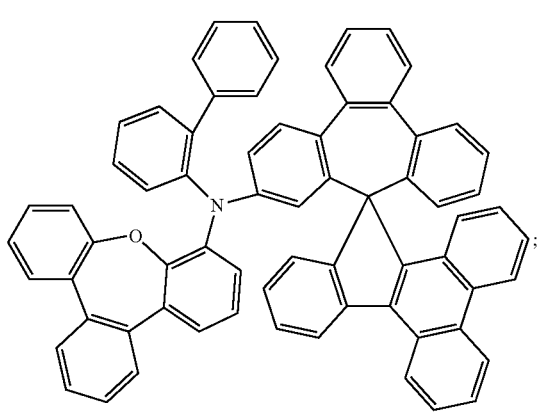
Compound 212
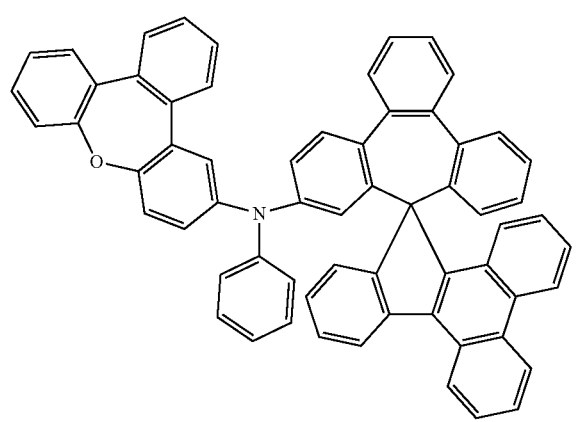
Compound 213
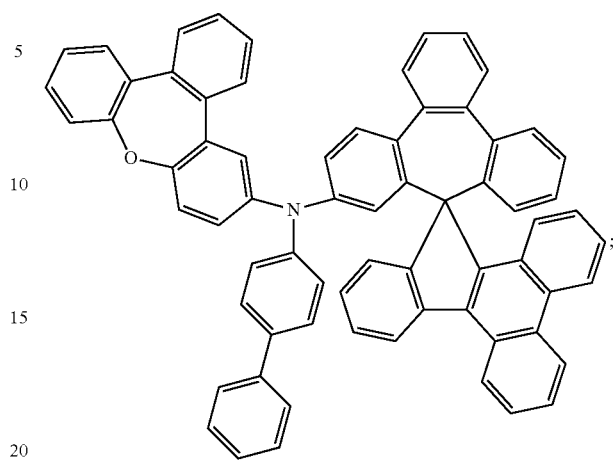
Compound 214
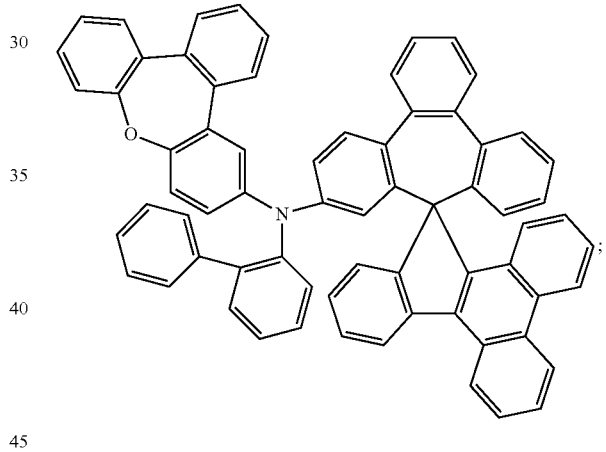
Compound 215
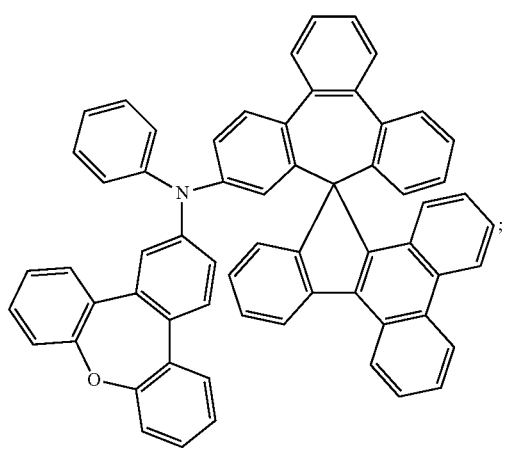

Compound 216
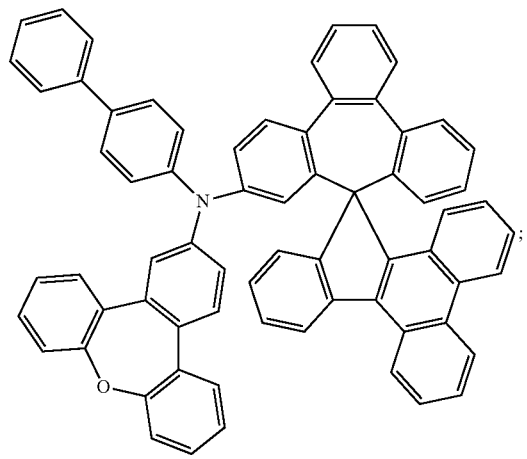
Compound 217
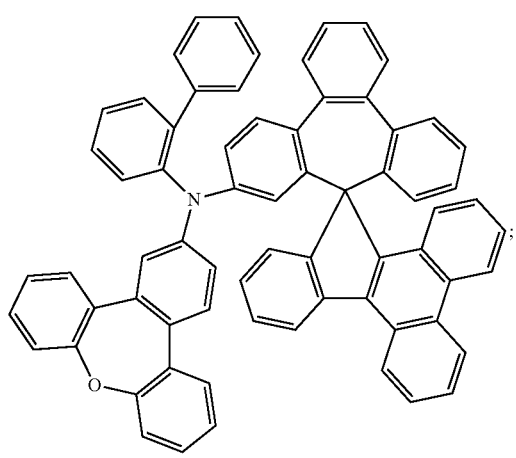
Compound 218
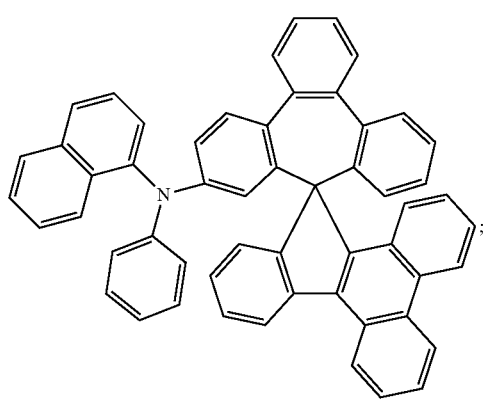
Compound 219
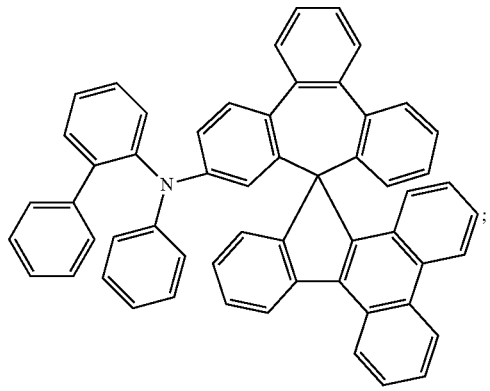
Compound 220
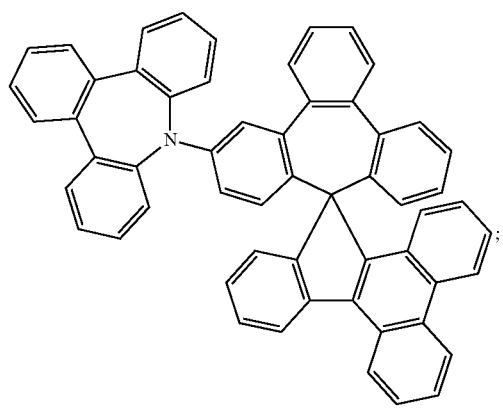
Compound 221
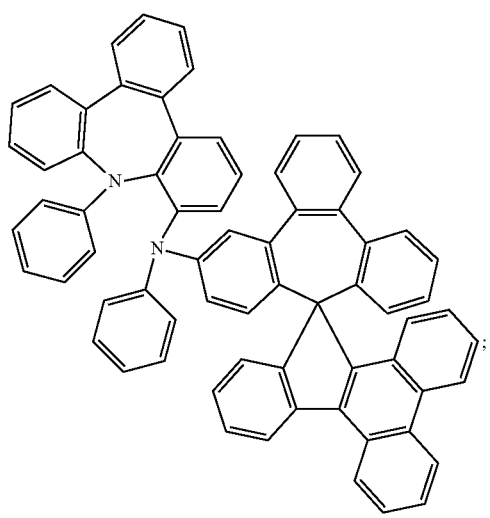

-continued
Compound 222
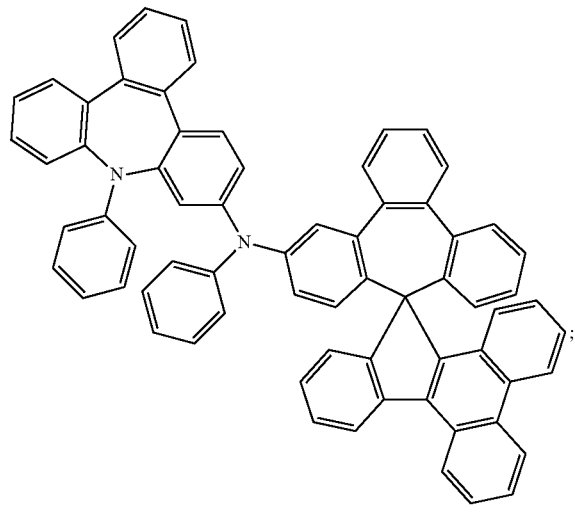
Compound 223
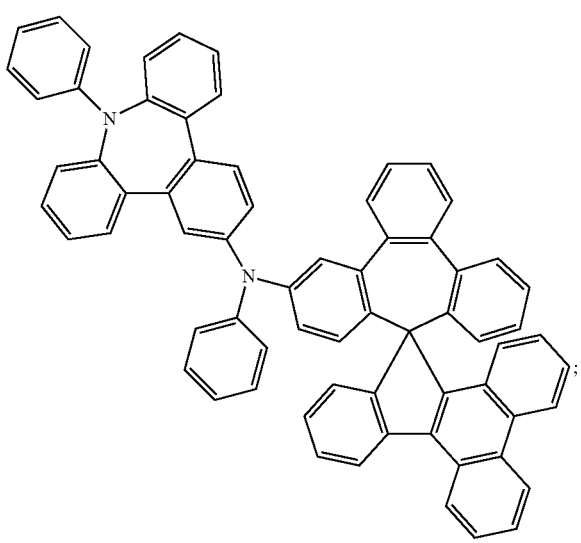
Compound 224
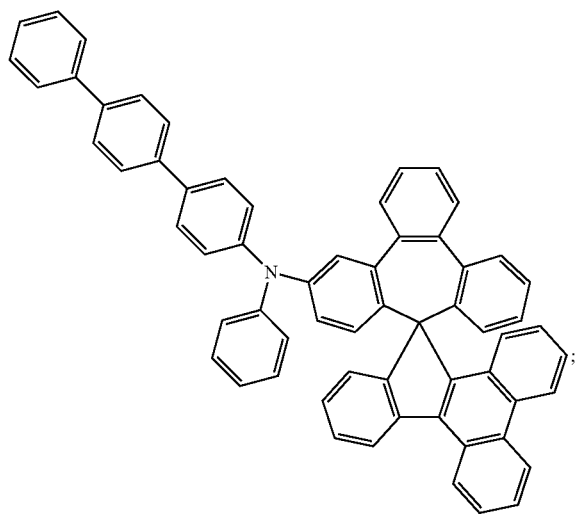
-continued
Compound 225
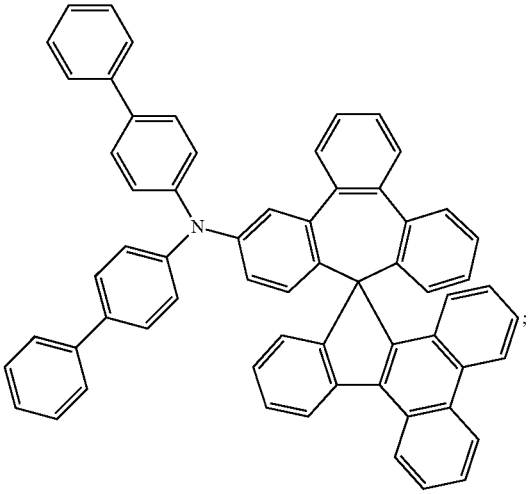
Compound 226
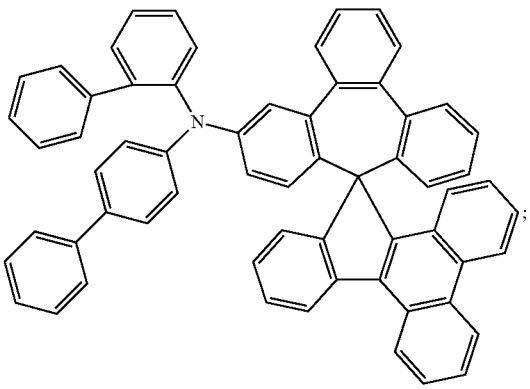
Compound 227
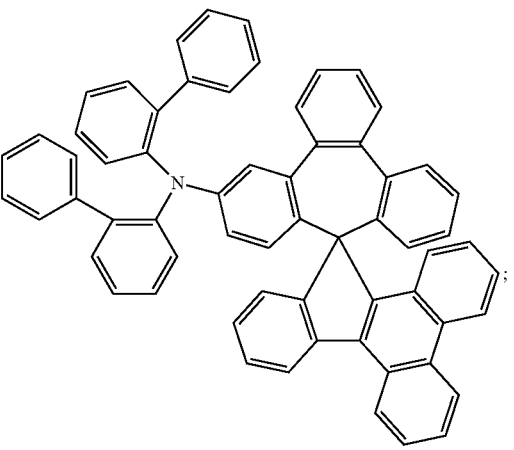

-continued
Compound 228
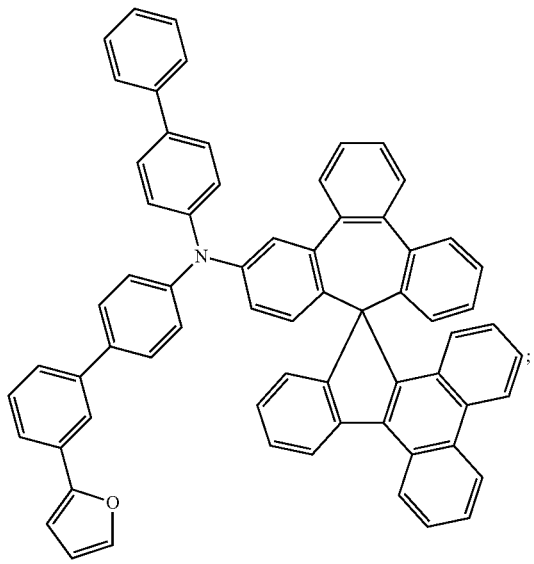
Compound 229
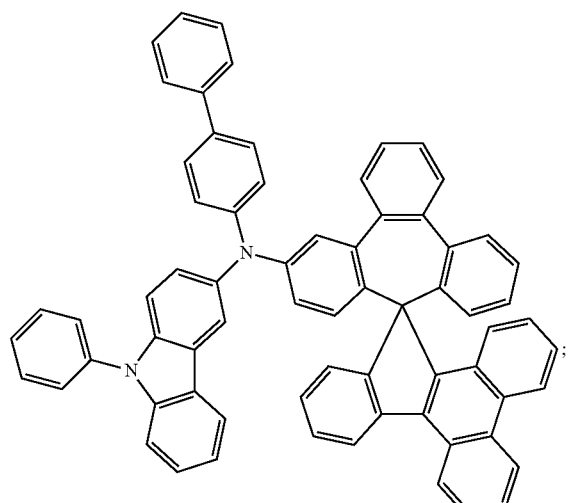
Compound 230
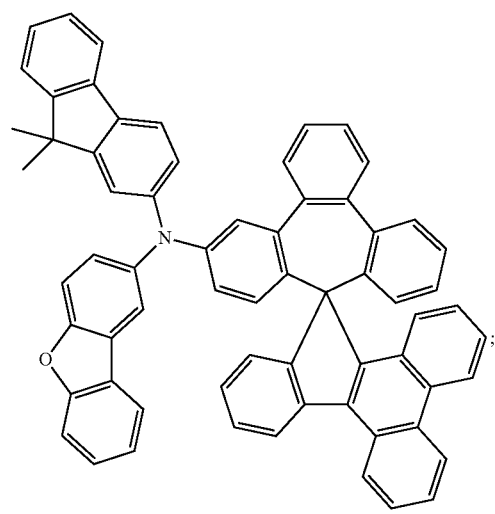
-continued
Compound 231
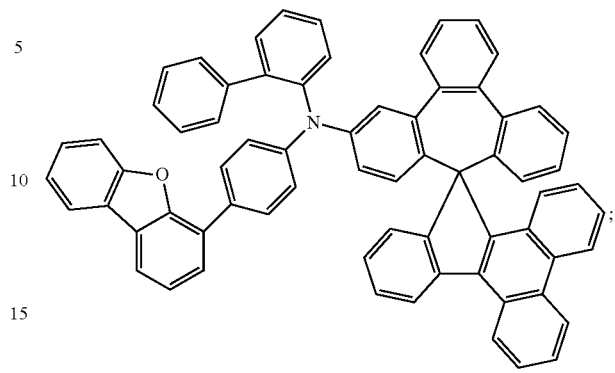
Compound 232
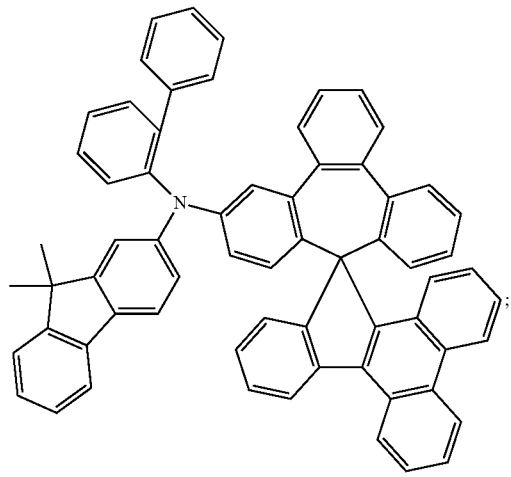
Compound 233
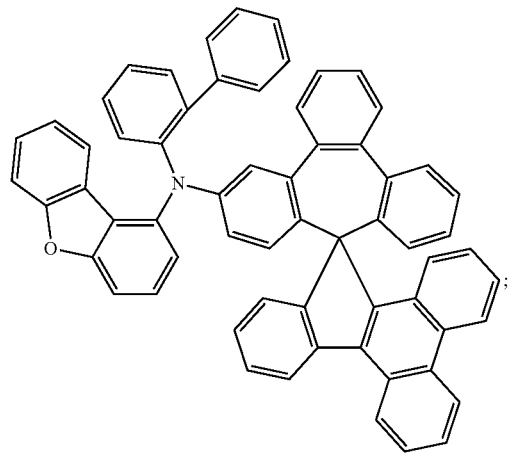

Compound 234
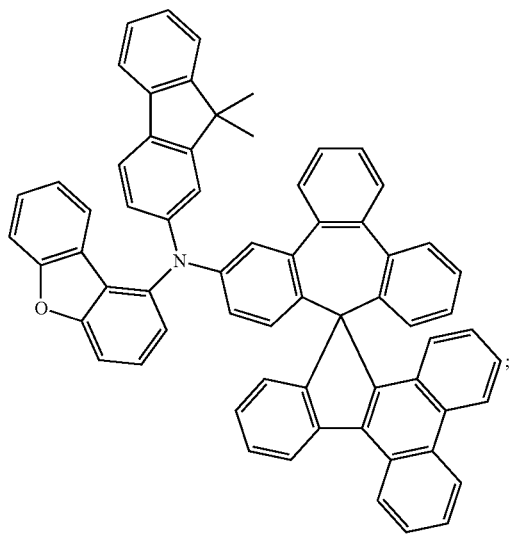
Compound 235
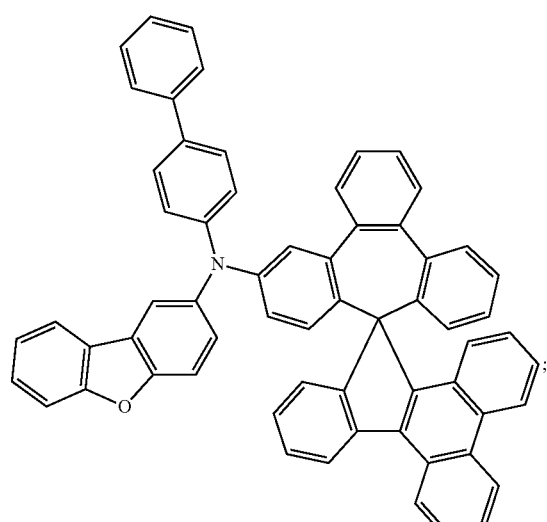
Compound 236
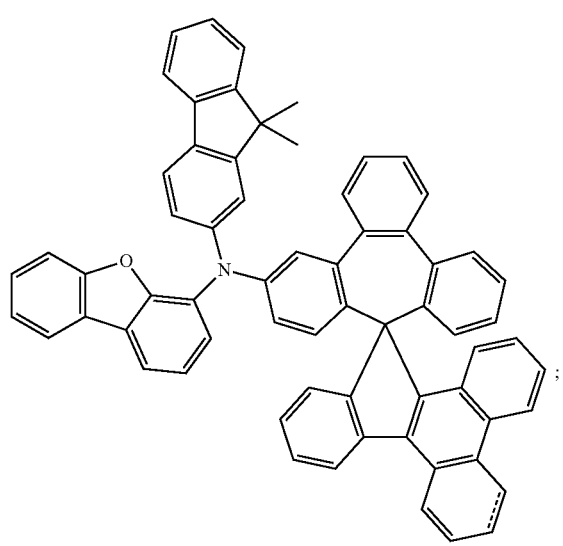
Compound 237
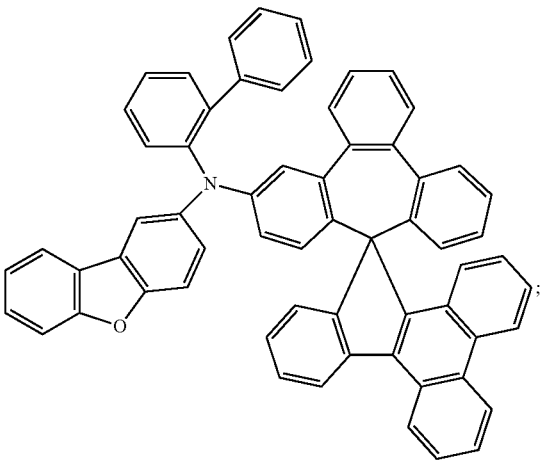
Compound 238
Compound 239
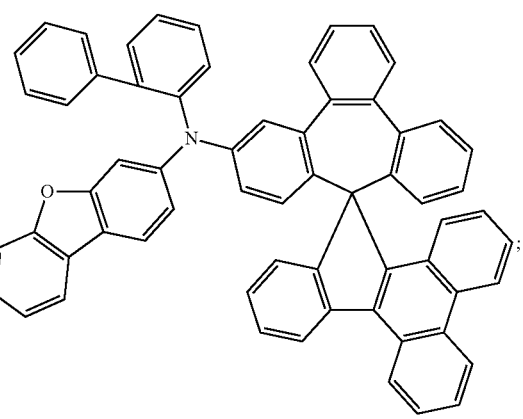

-continued
Compound 240
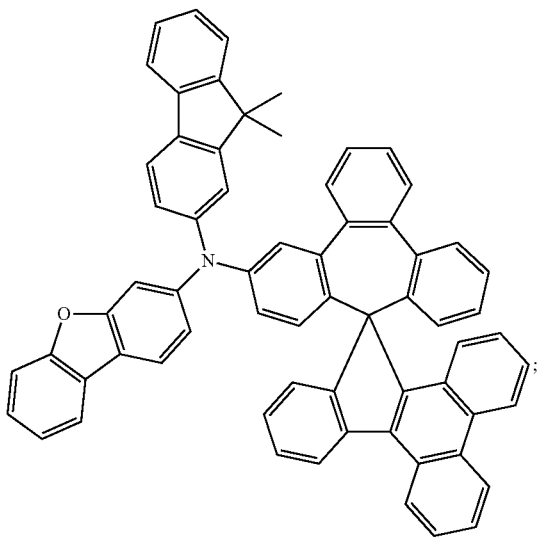
Compound 241
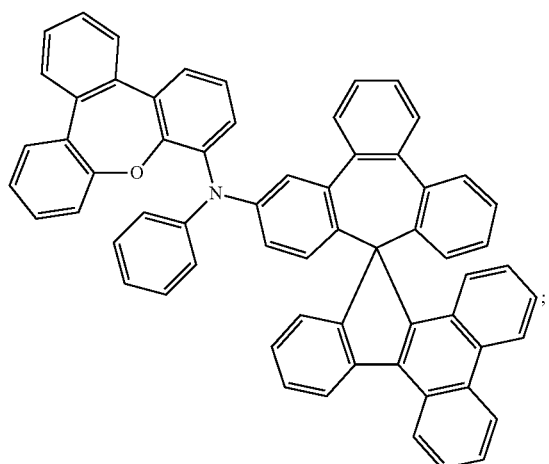
Compound 242
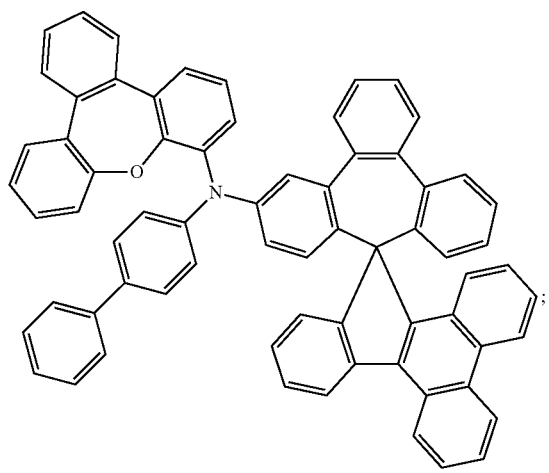
-continued
Compound 243
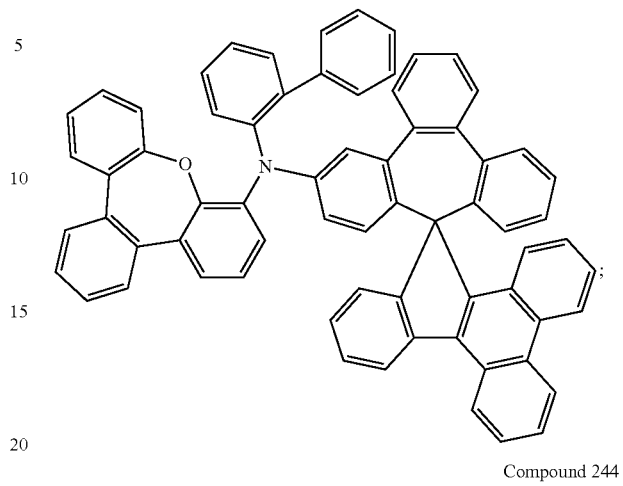
Compound 244
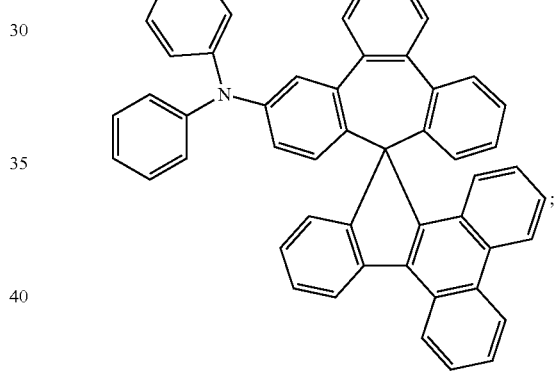
Compound 245
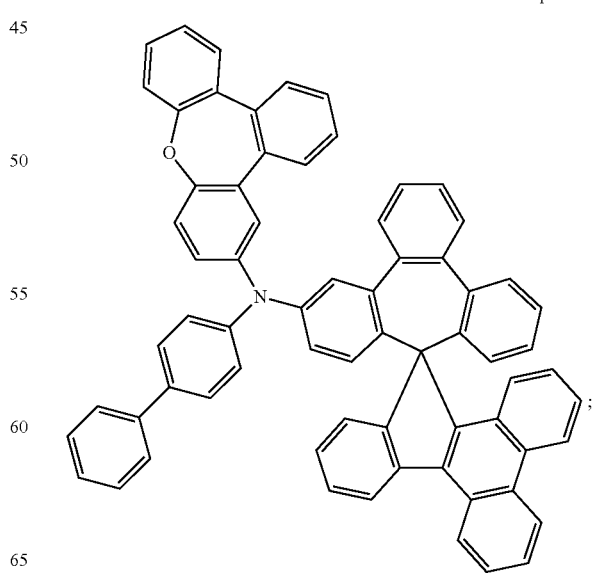

Compound 246
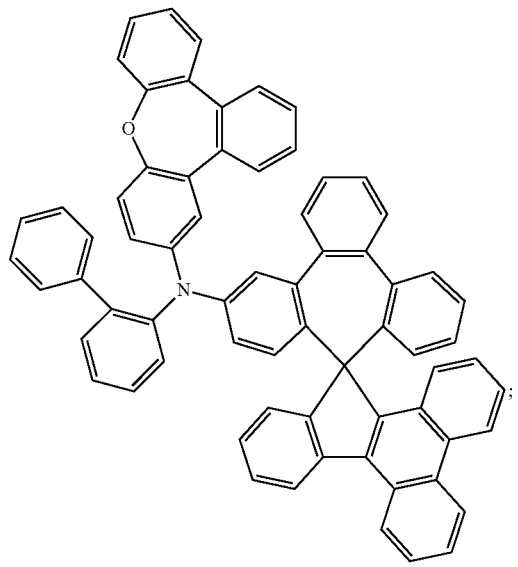
Compound 247
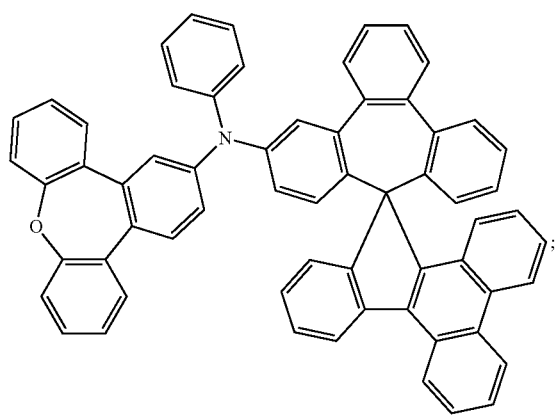
Compound 248
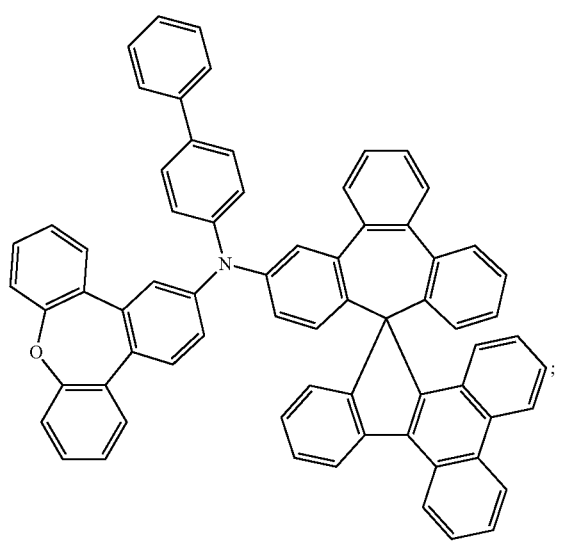
Compound 249
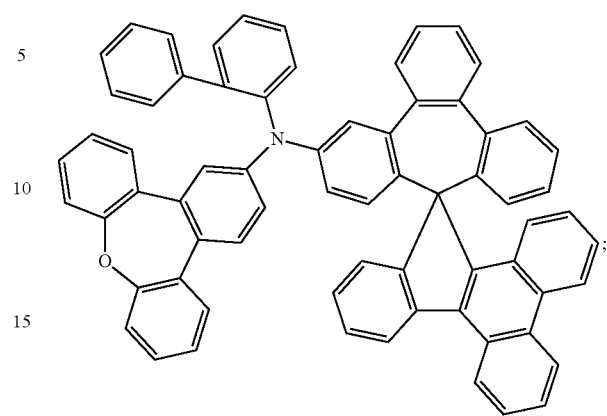
Compound 250
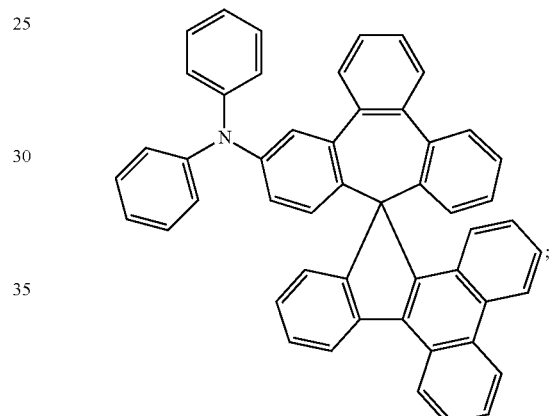
Compound 251
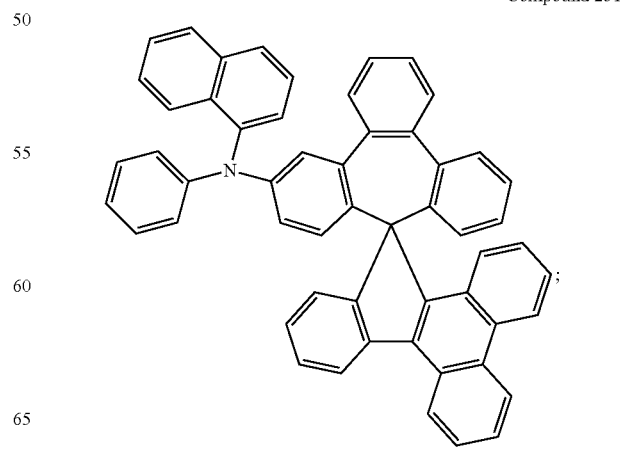

Compound 252
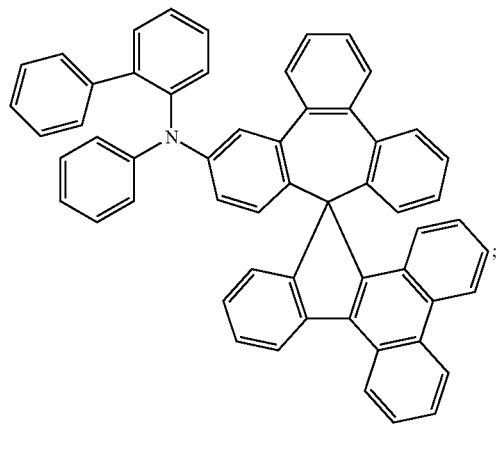
Compound 253
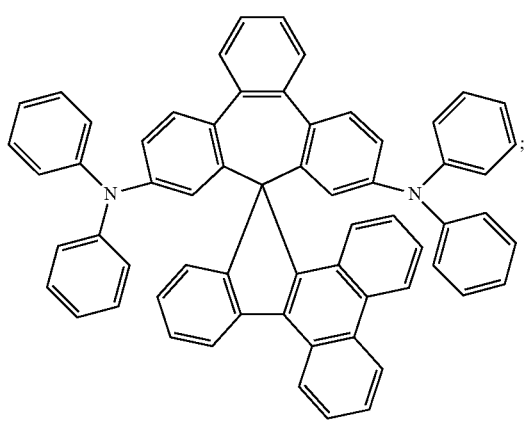
Compound 254
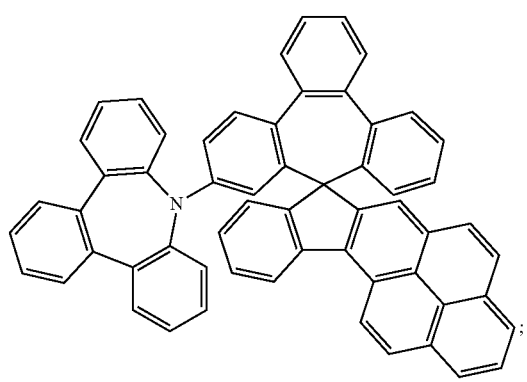
Compound 255
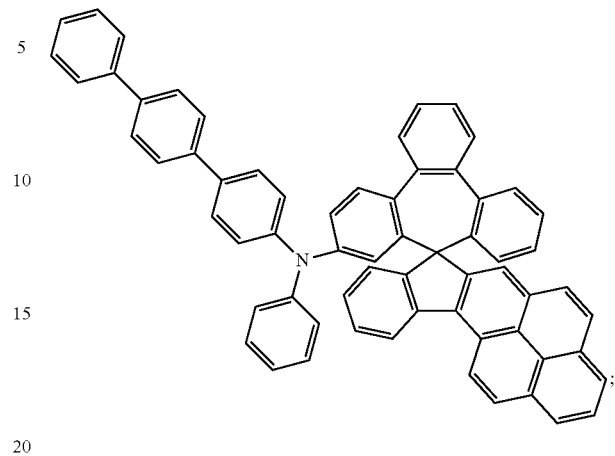
Compound 256
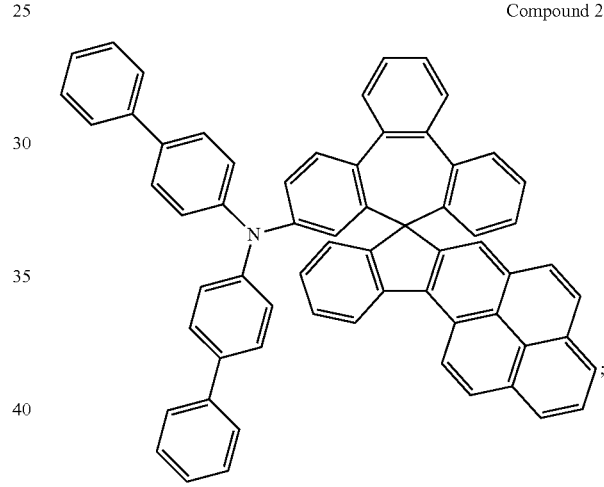
Compound 257
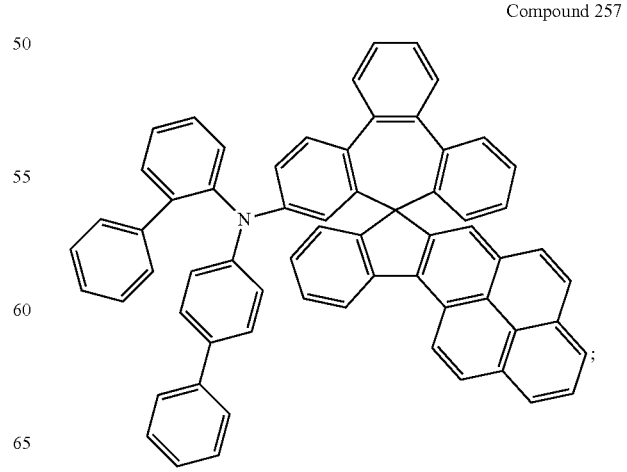

Compound 258
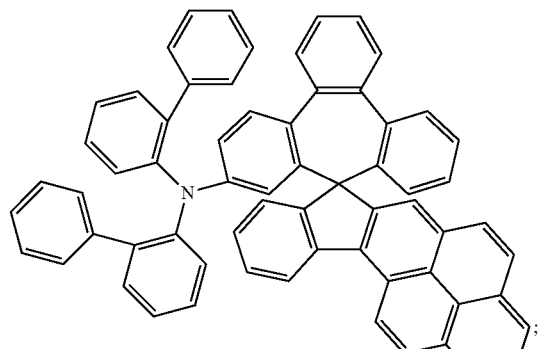
Compound 259
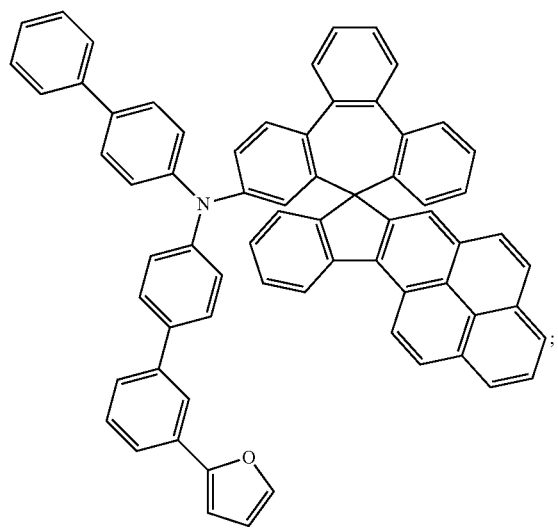
Compound 260
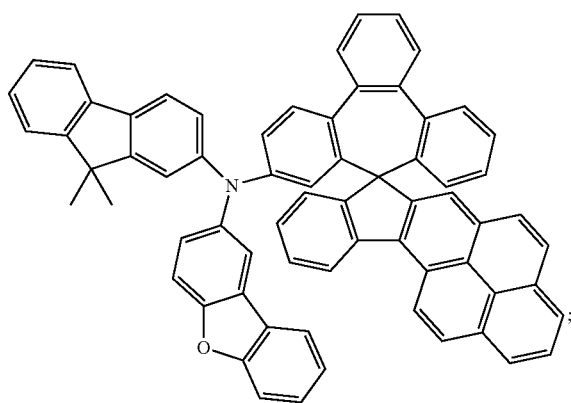
Compound 261
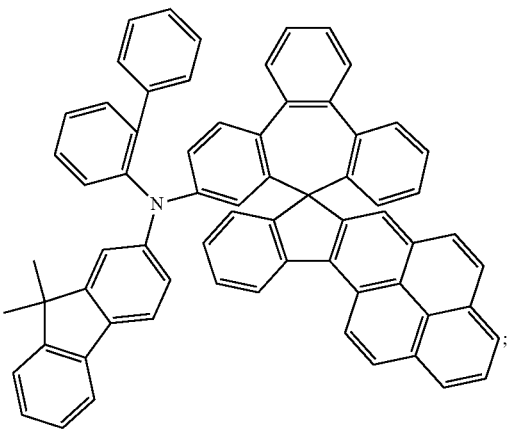
Compound 262
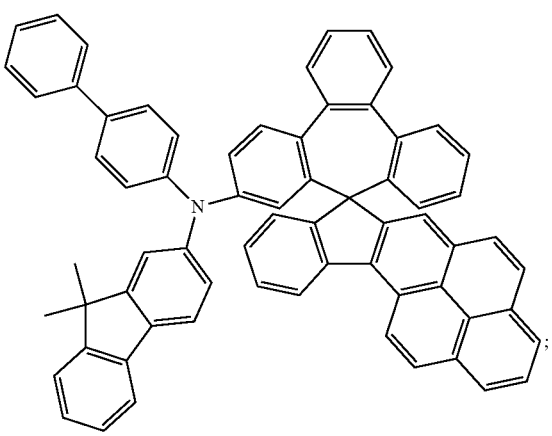
Compound 263
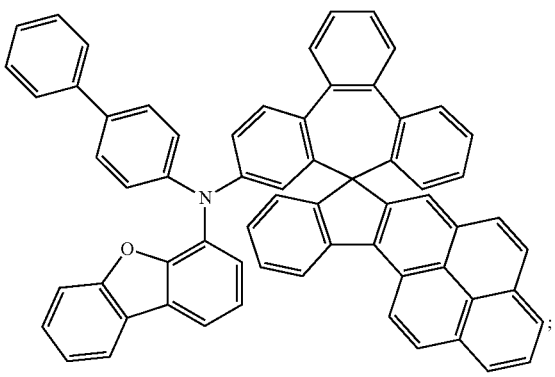

Compound 264
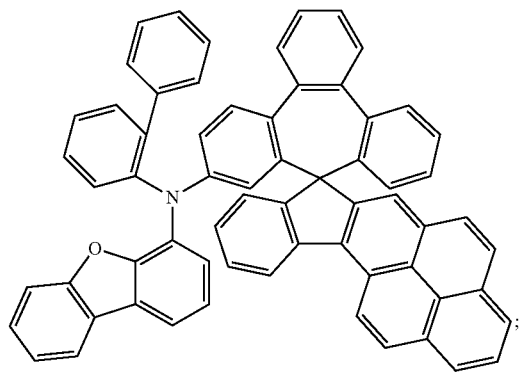
Compound 265
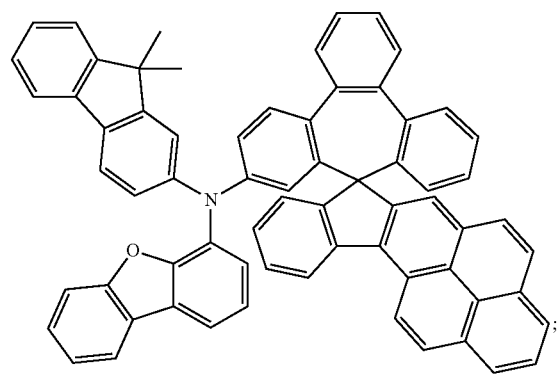
Compound 266
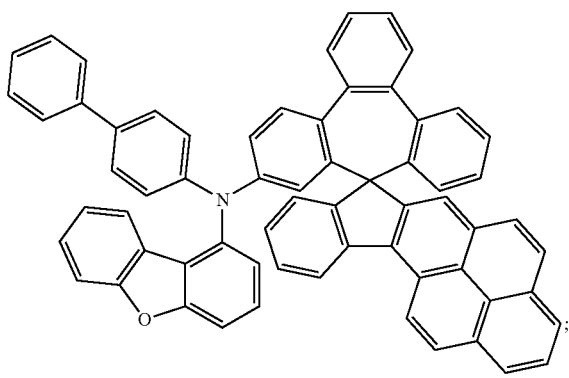
Compound 267
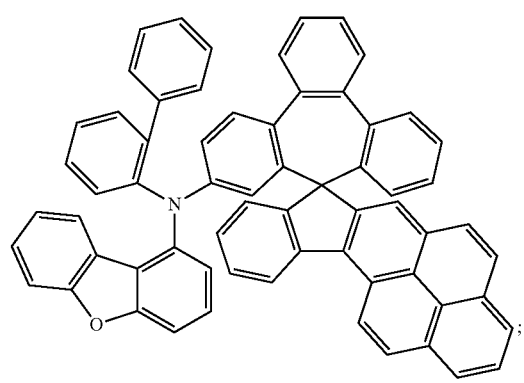
Compound 268
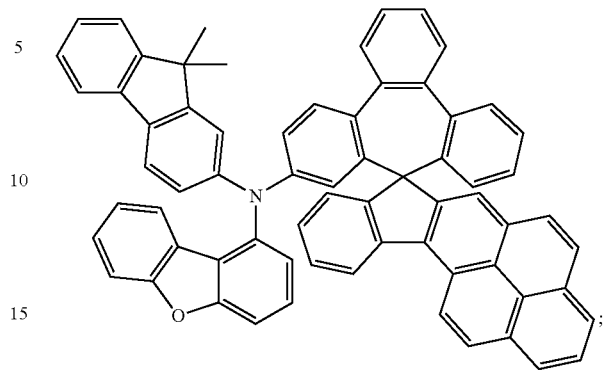
Compound 269
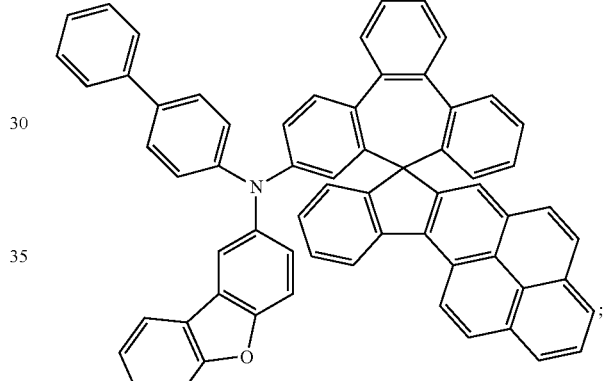
Compound 270
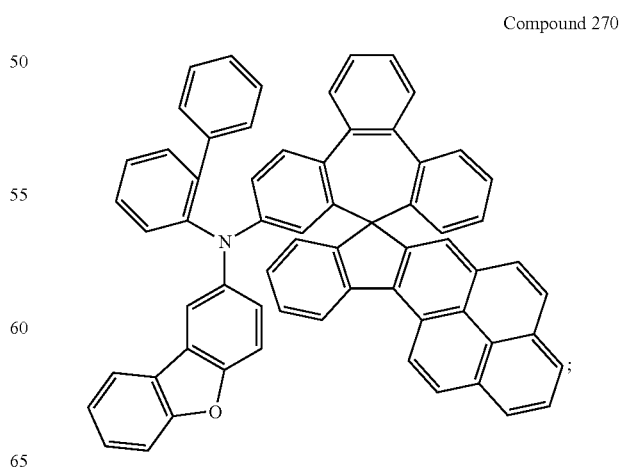

-continued
Compound 271
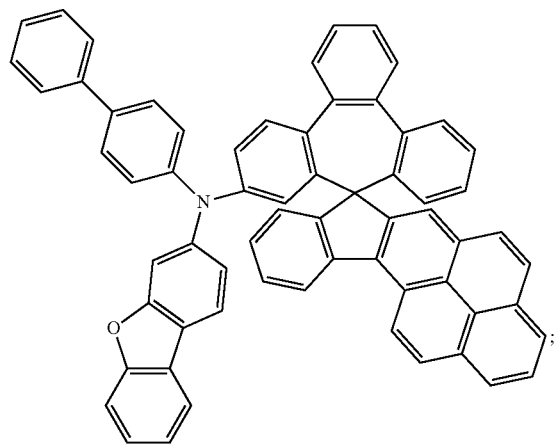
Compound 272
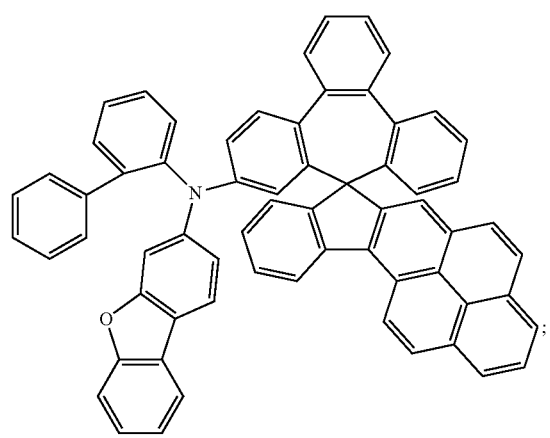
Compound 273
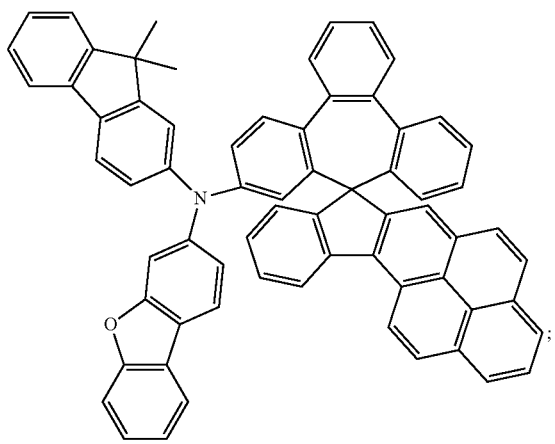
-continued
Compound 274
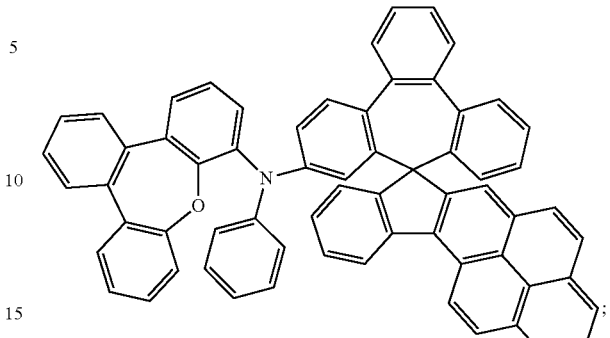
Compound 275
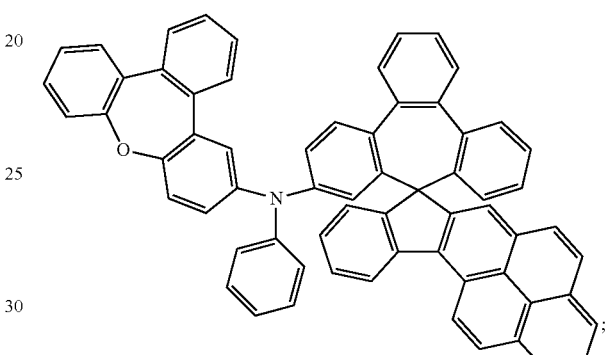
Compound 276
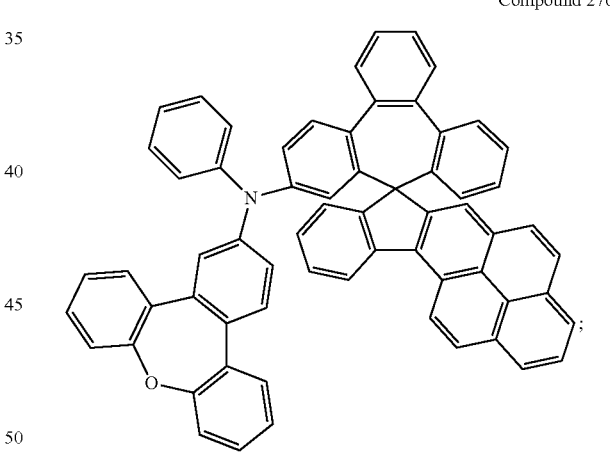
Compound 277

Compound 278
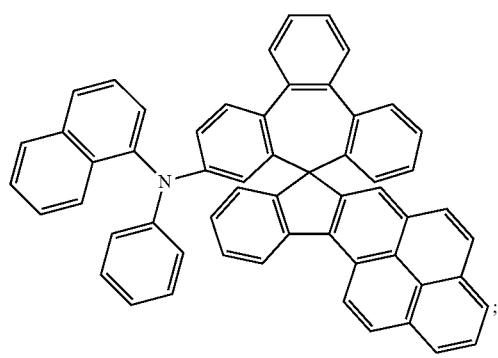
Compound 279
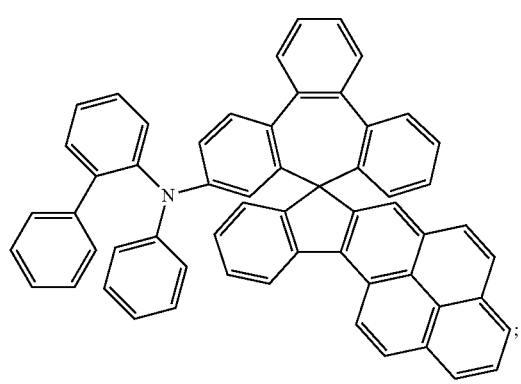
Compound 280
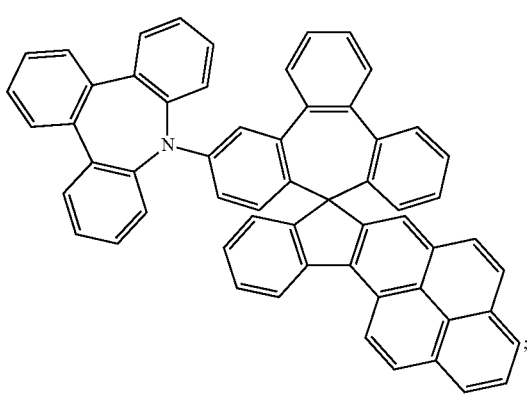
Compound 281
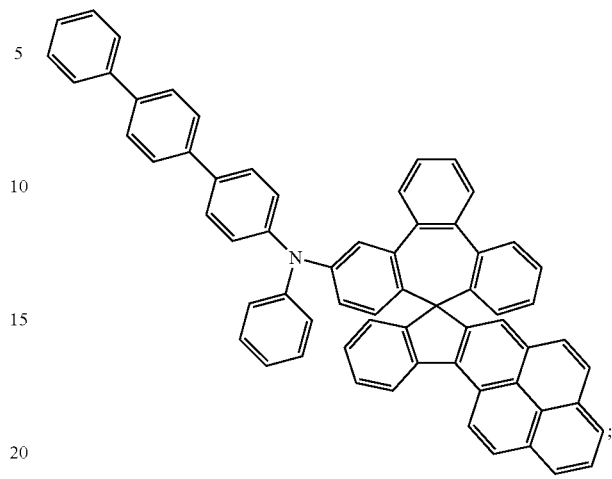
Compound 282
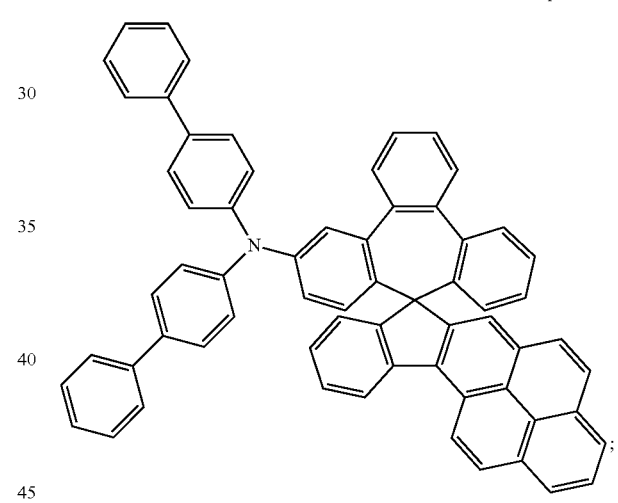
Compound 283
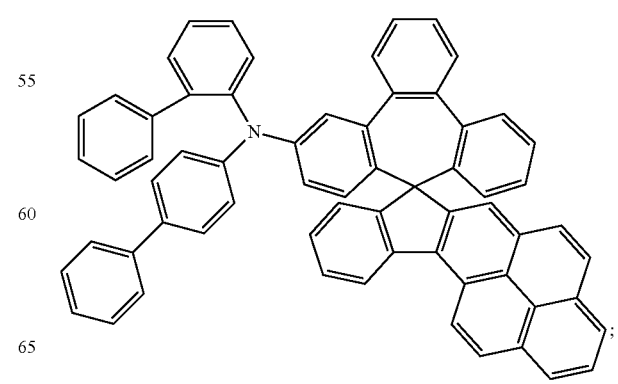

Compound 284
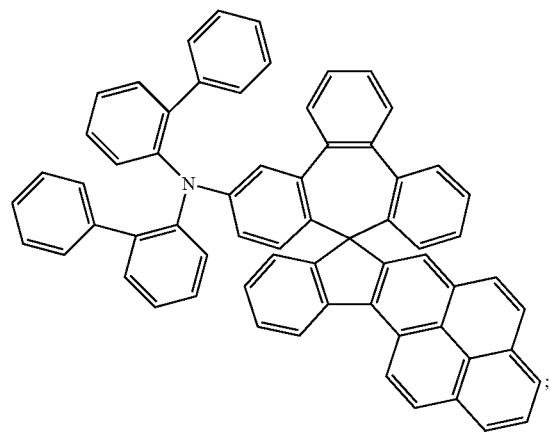
Compound 285
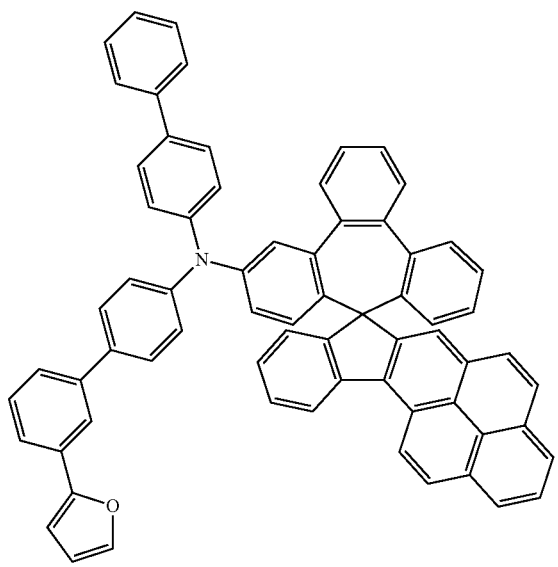
Compound 286
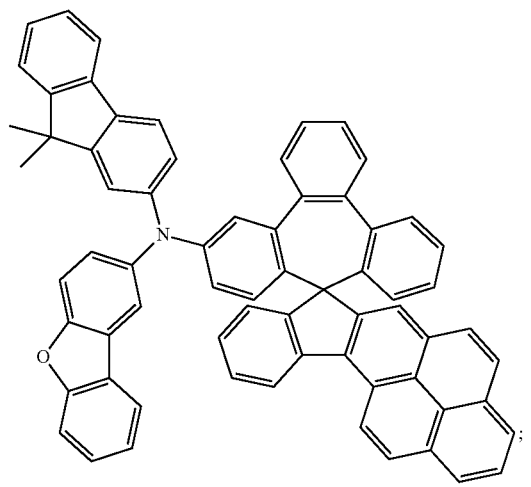
Compound 287
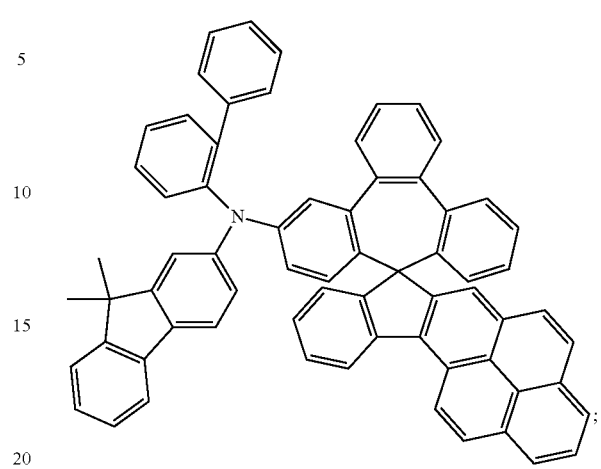
Compound 288
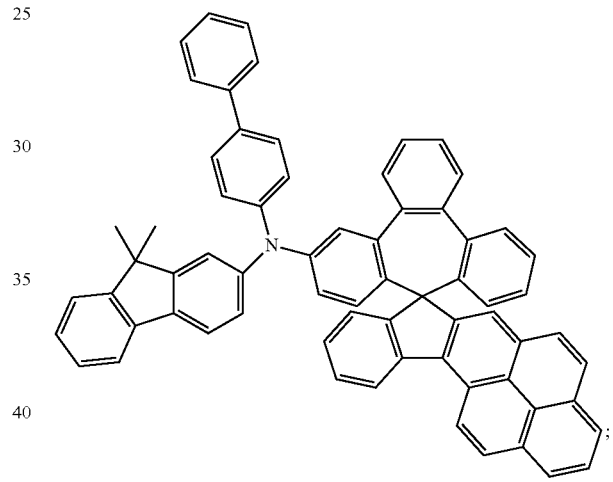
Compound 289
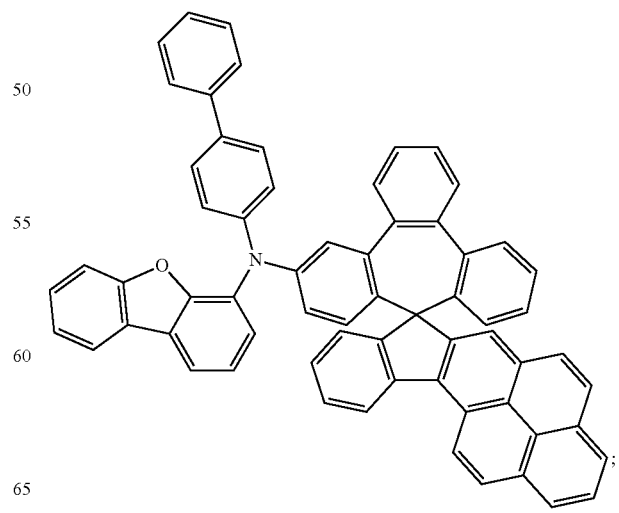

Compound 290
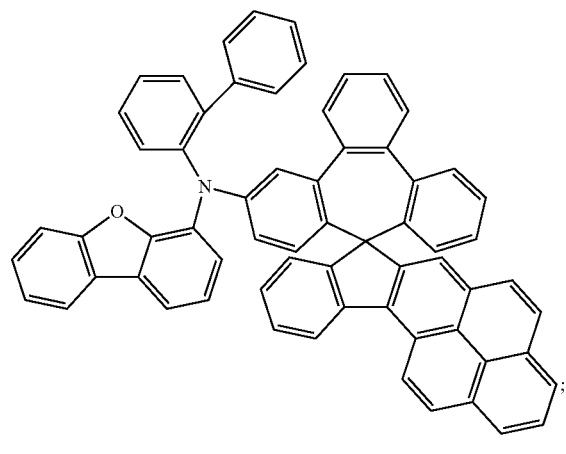
Compound 293
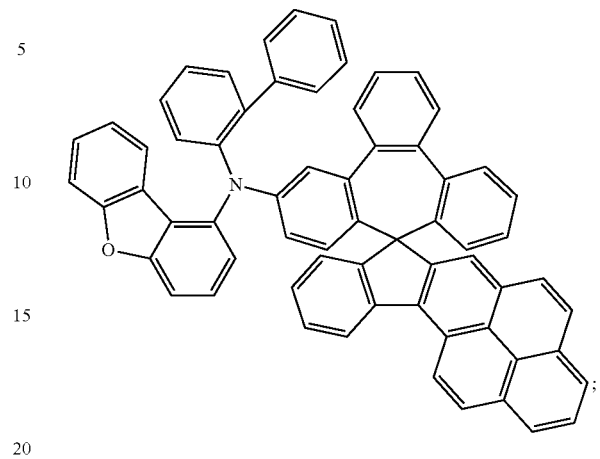
Compound 291
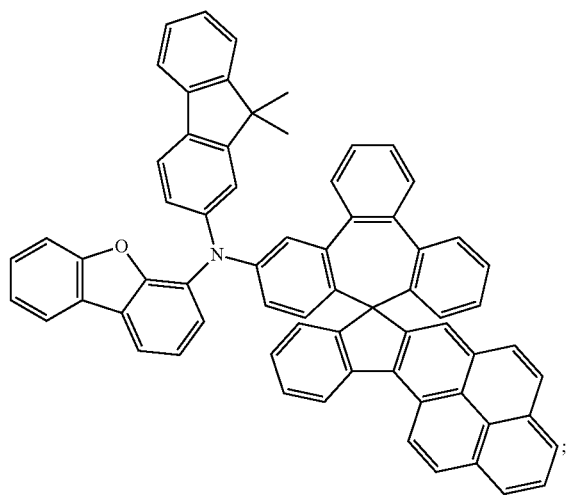
Compound 294
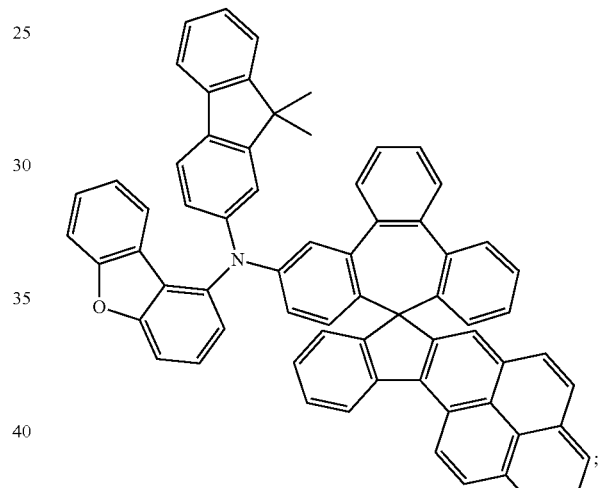
Compound 292
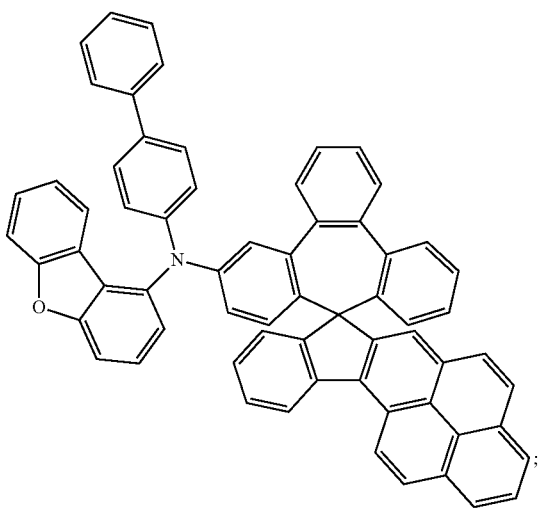
Compound 295
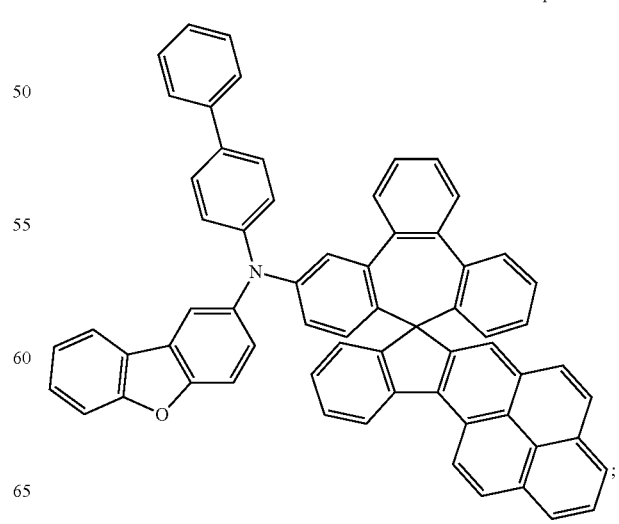

Compound 296
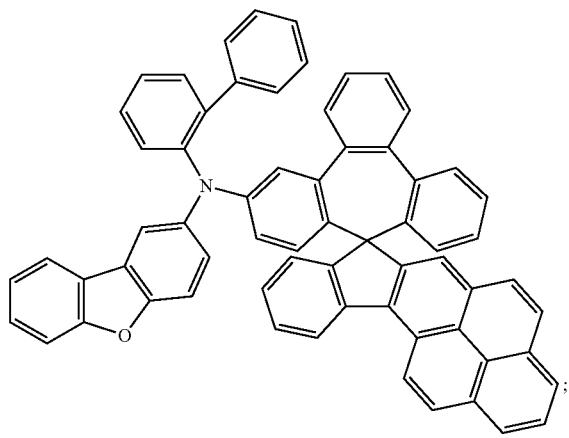
Compound 297
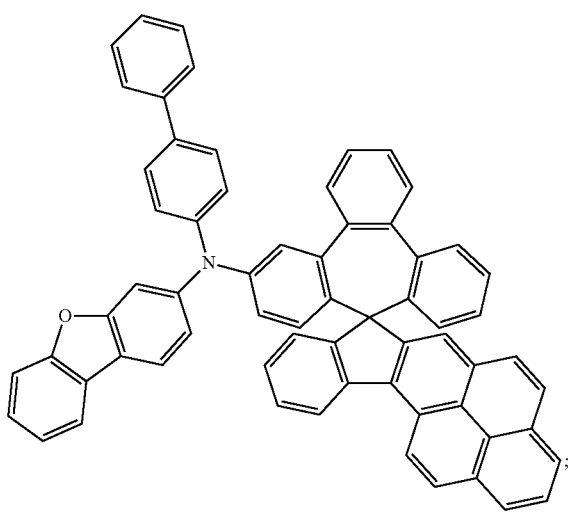
Compound 298
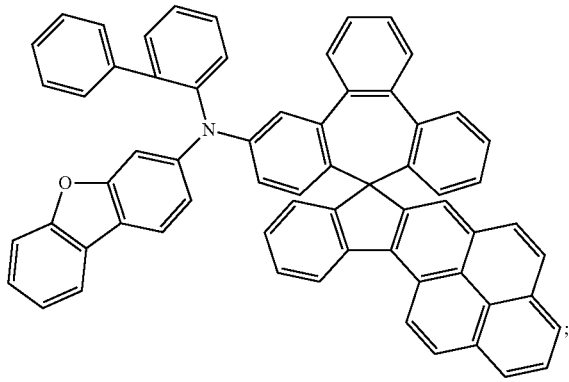
Compound 299
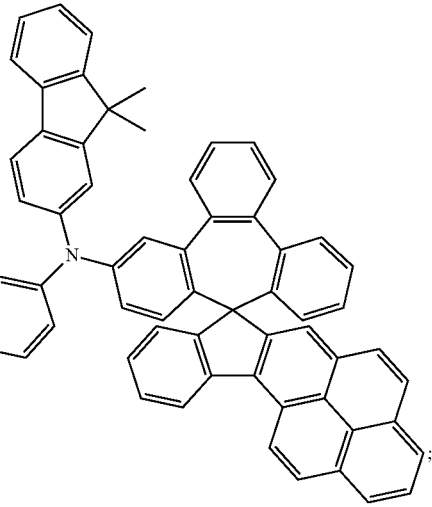
Compound 300
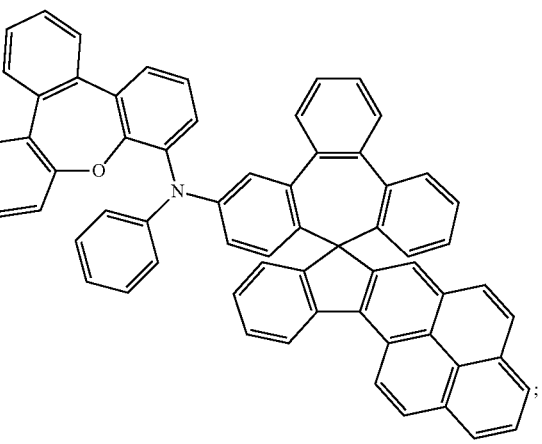
Compound 301
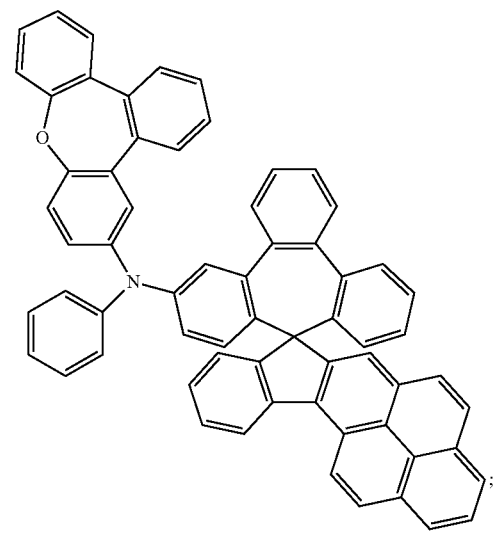

-continued
Compound 302
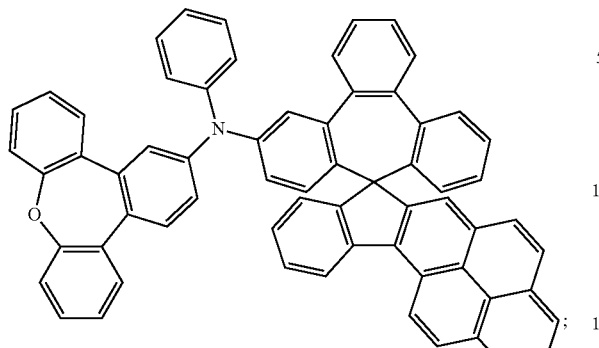
Compound 303
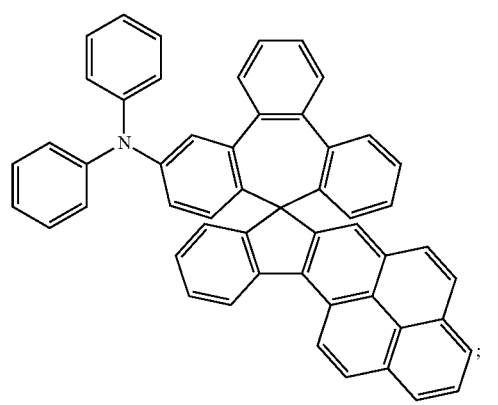
Compound 304
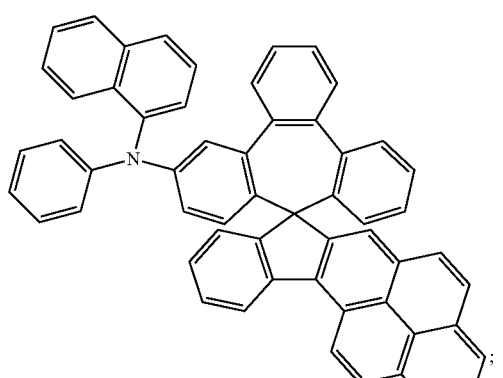
Compound 305
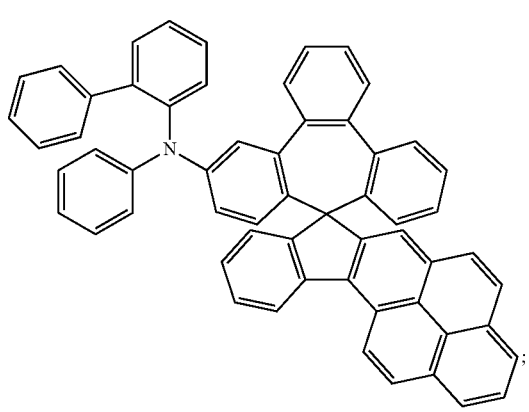
-continued
Compound 306
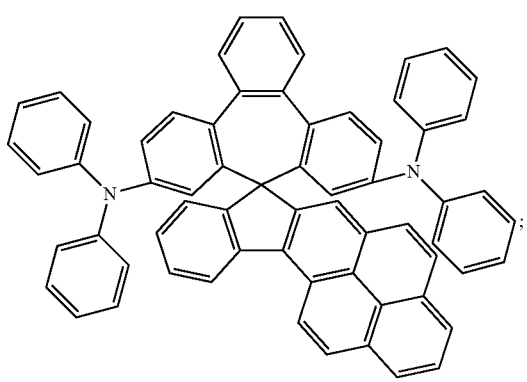
Compound 307
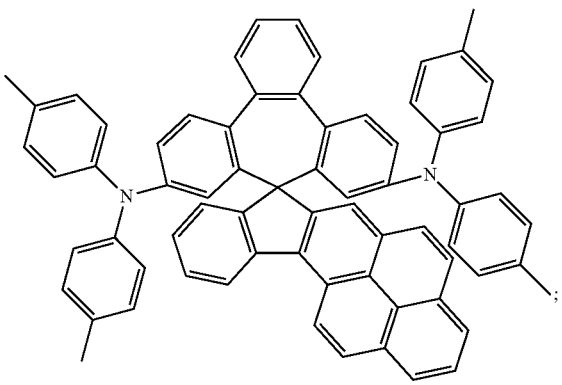
Compound 308
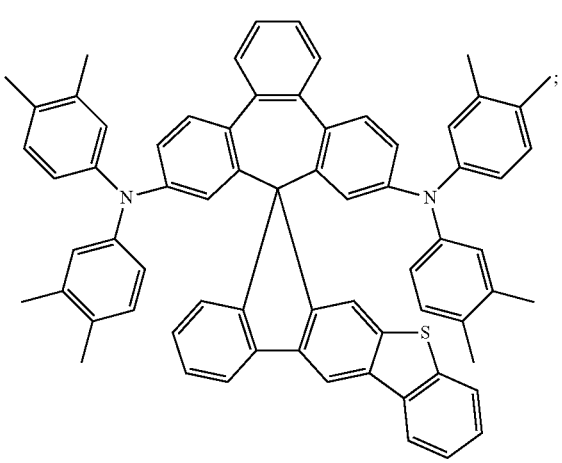

Compound 309
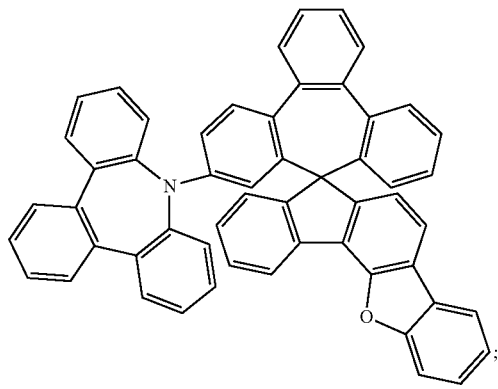
Compound 310
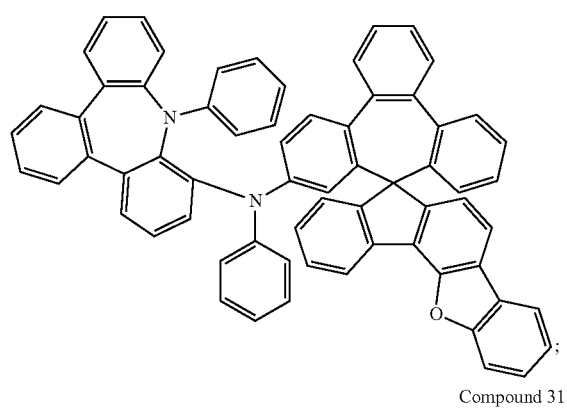
Compound 311
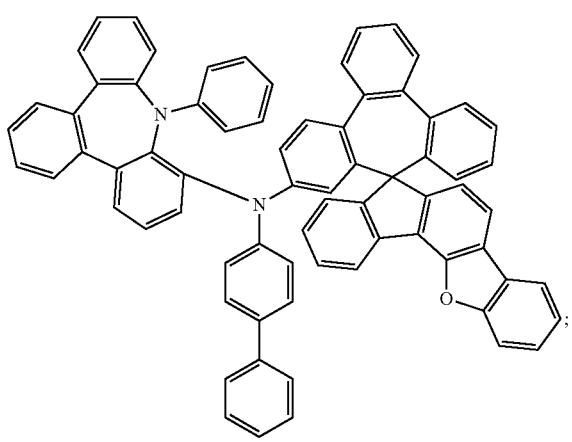
Compound 312
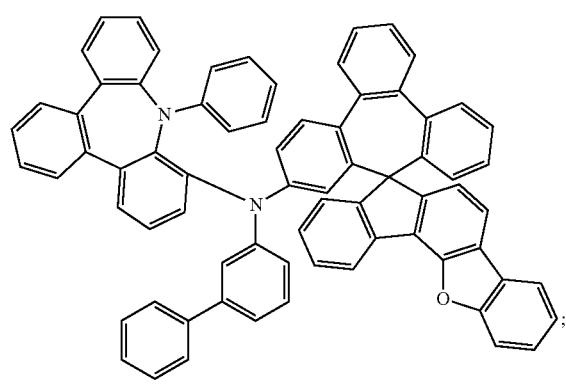
Compound 313
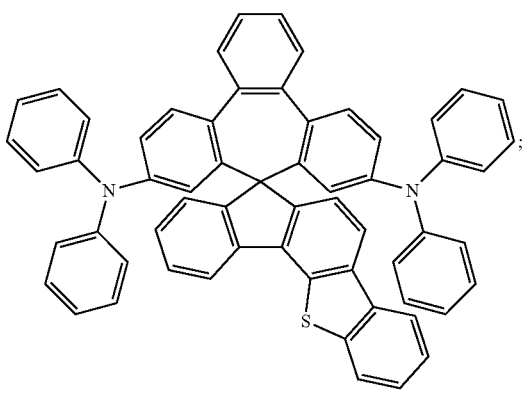
Compound 314
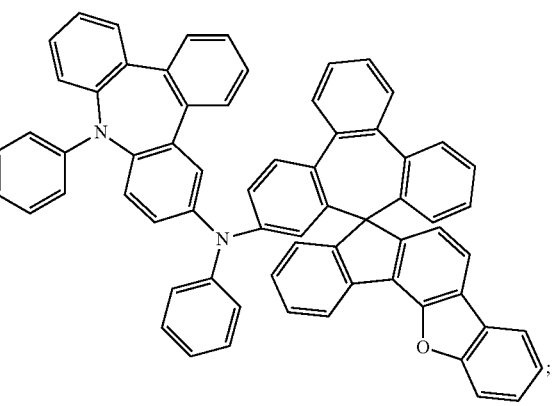
Compound 315
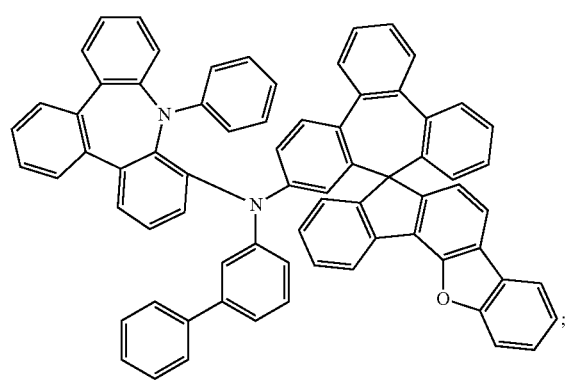

Compound 316
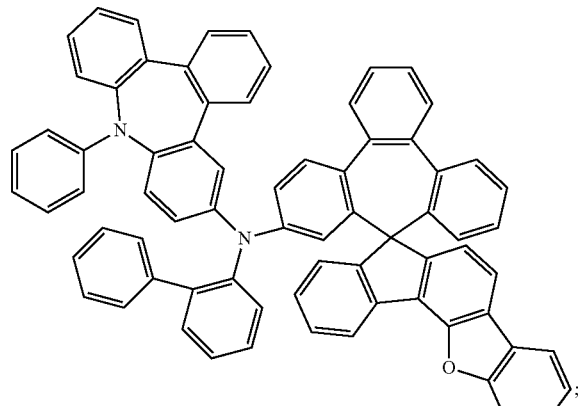
Compound 317
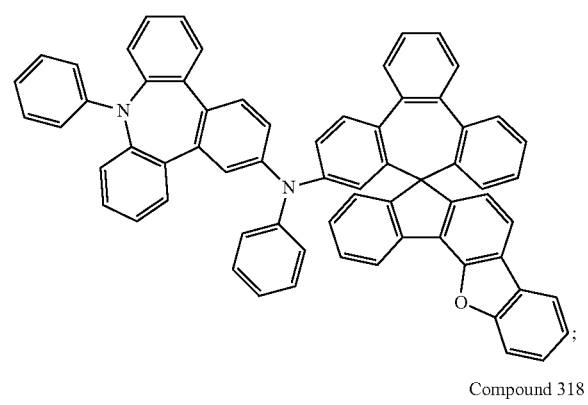
Compound 318
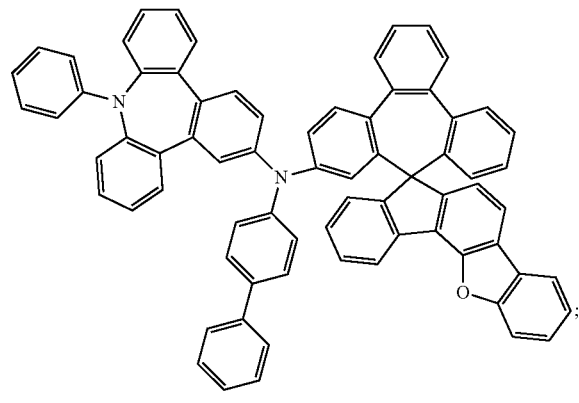
Compound 319
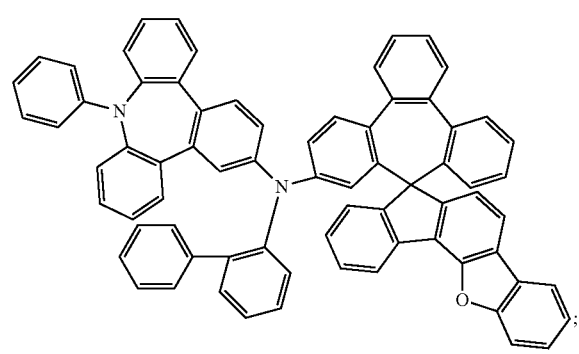
Compound 320
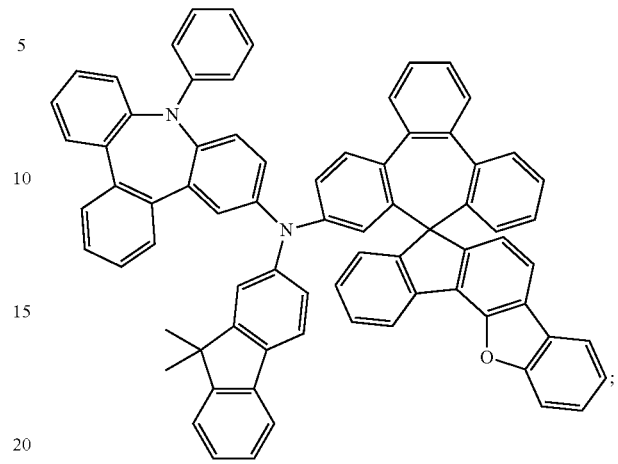
Compound 321
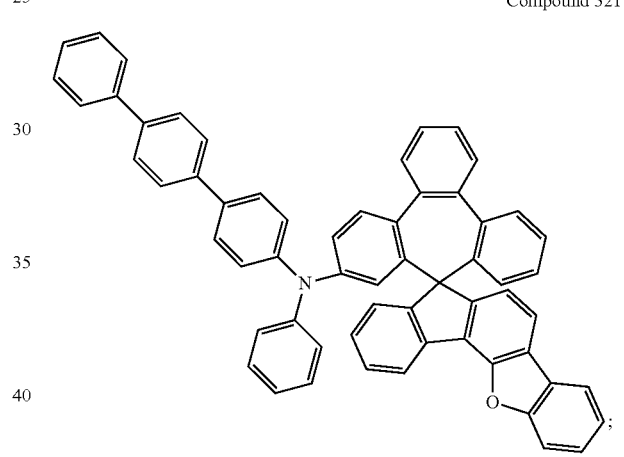
Compound 322
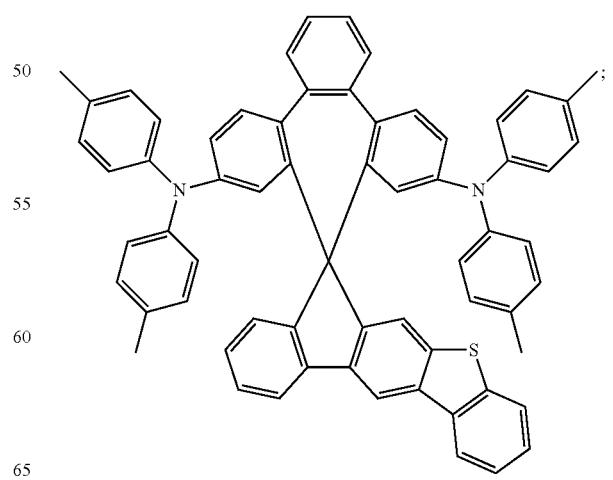

Compound 323
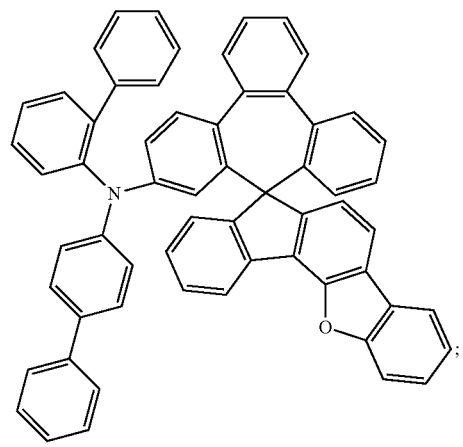
Compound 326
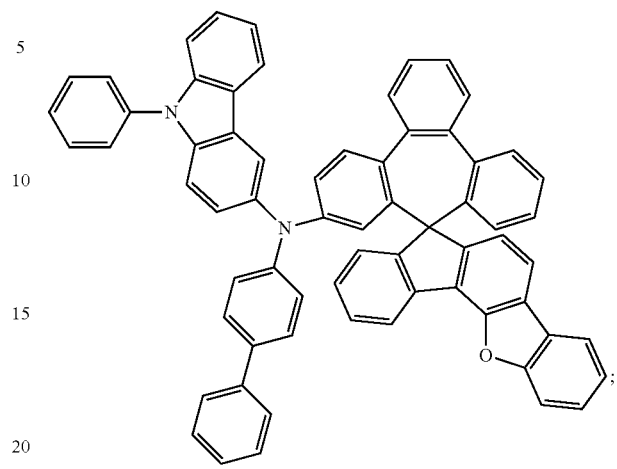
Compound 324
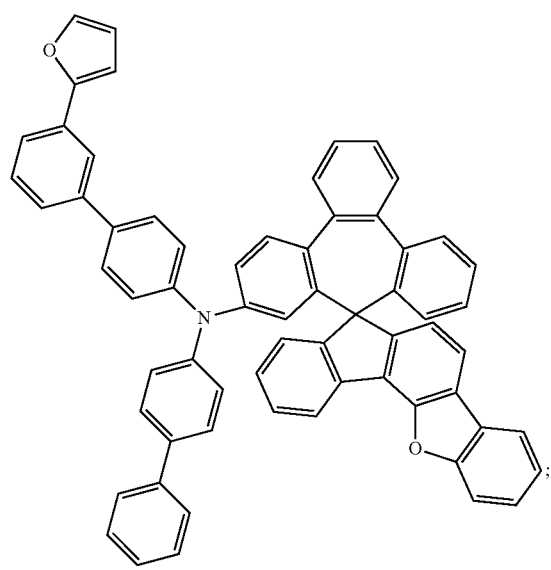
Compound 327

Compound 325
Compound 328

Compound 329
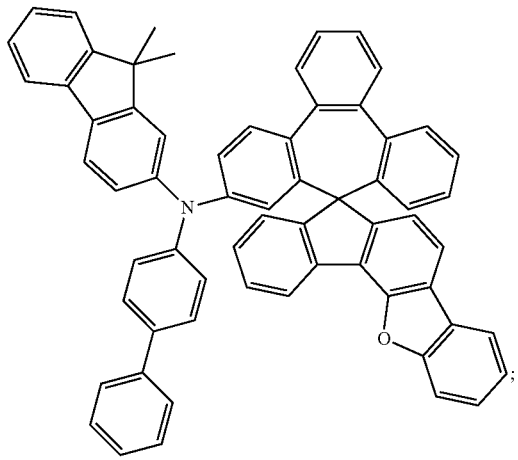
Compound 330
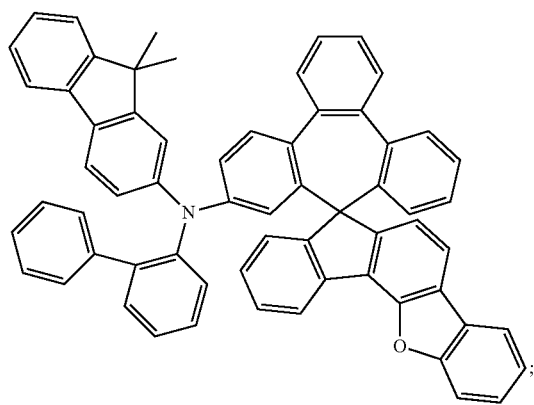
Compound 331
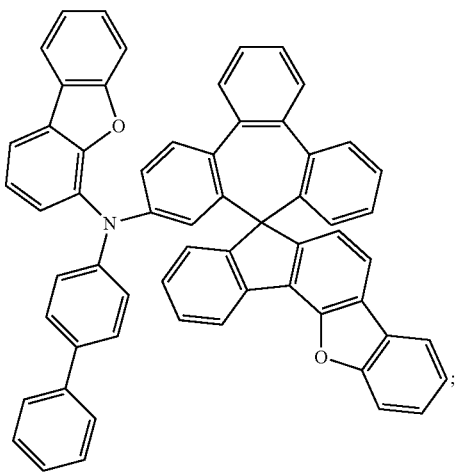
Compound 332
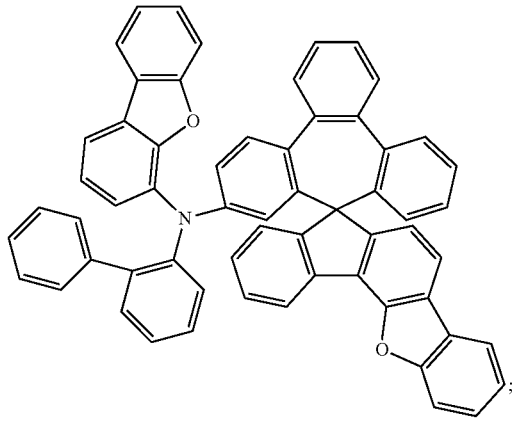
Compound 333
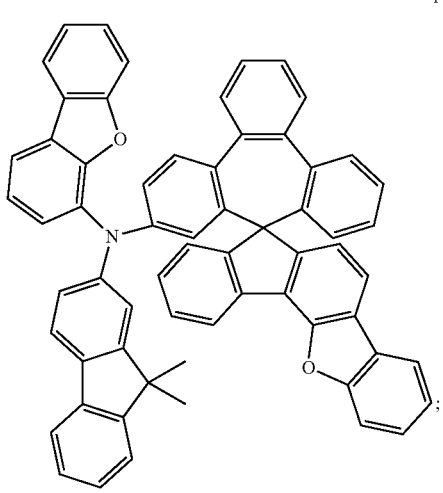
Compound 334
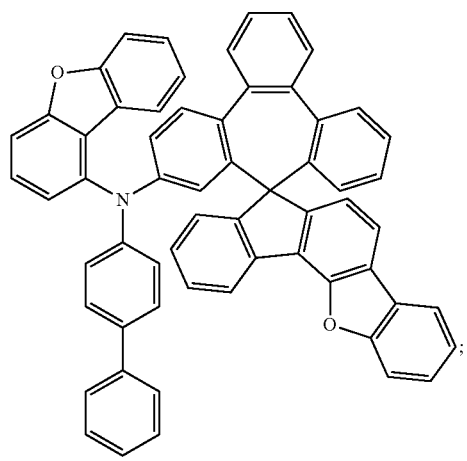

Compound 335
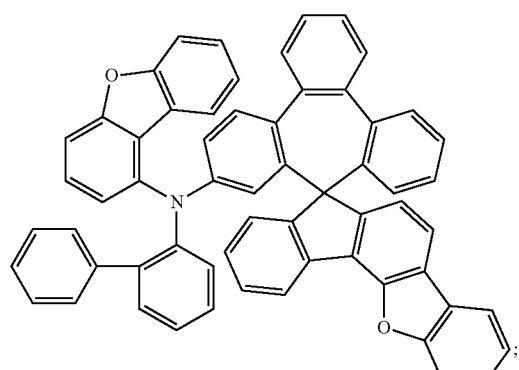
Compound 336
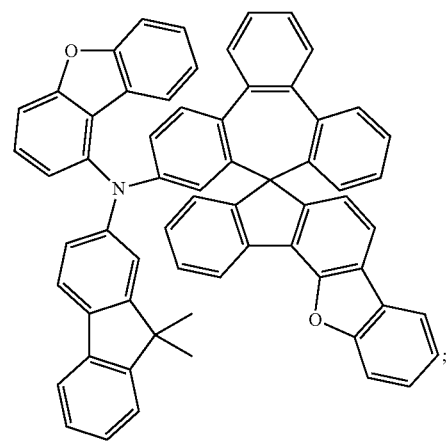
Compound 337
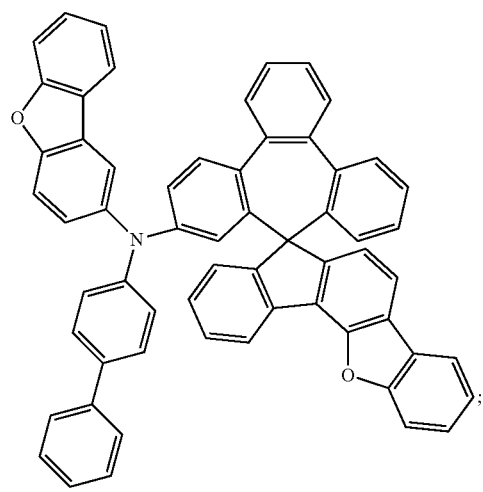
Compound 338
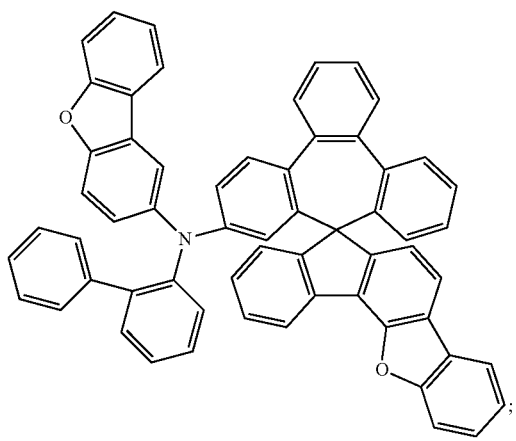
Compound 339
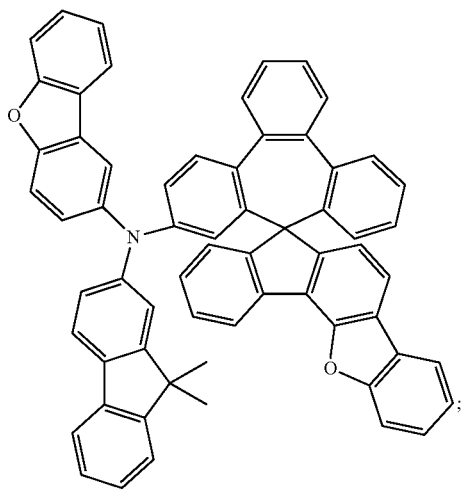
Compound 340
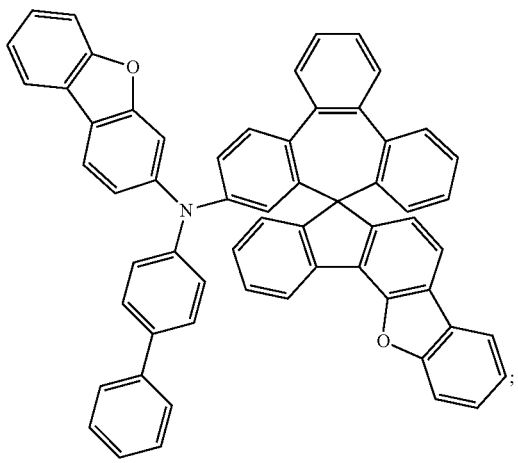

Compound 341
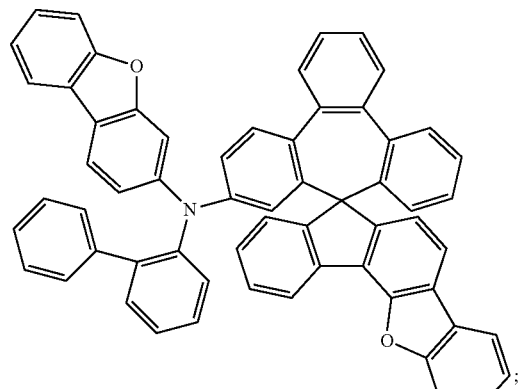
Compound 344
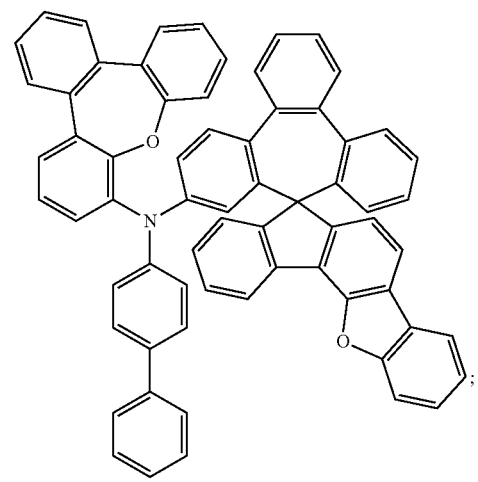
Compound 342
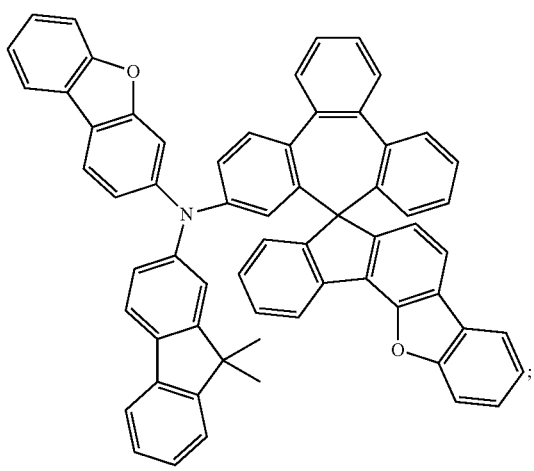
Compound 345
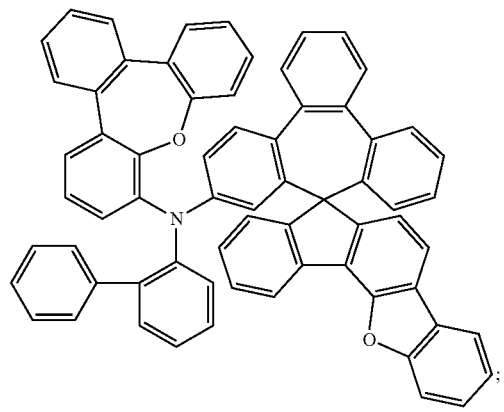
Compound 343
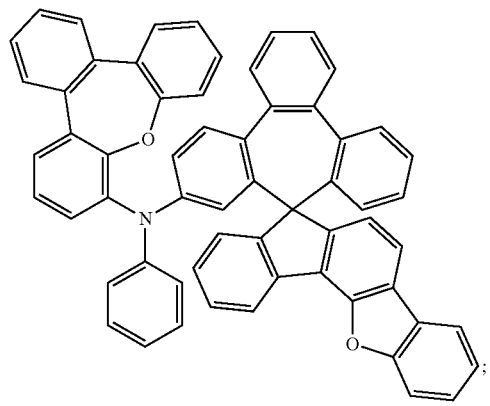
Compound 346
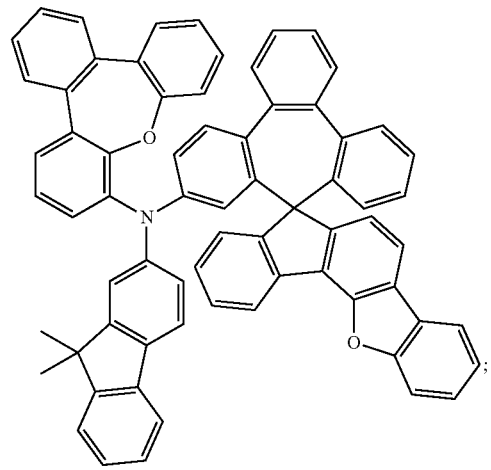

Compound 347
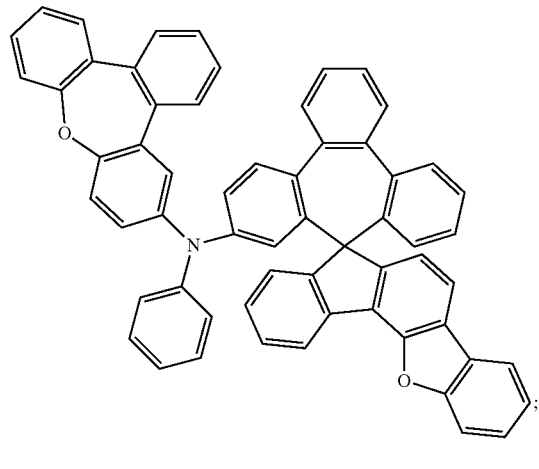
Compound 348
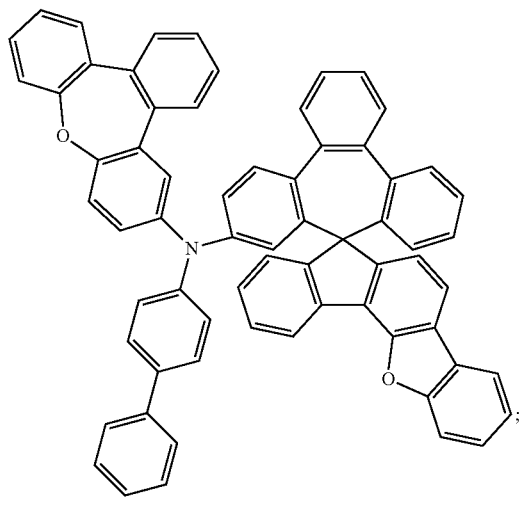
Compound 349
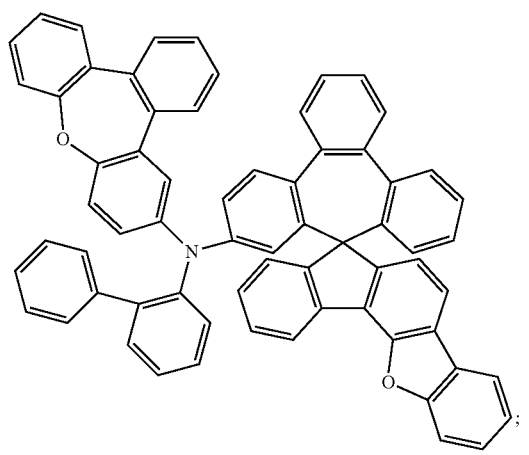
Compound 350
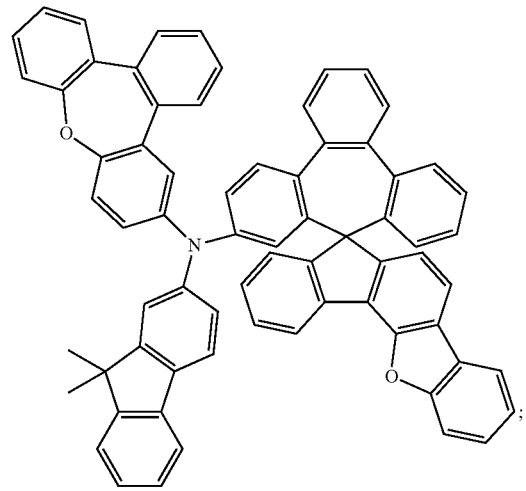
Compound 351
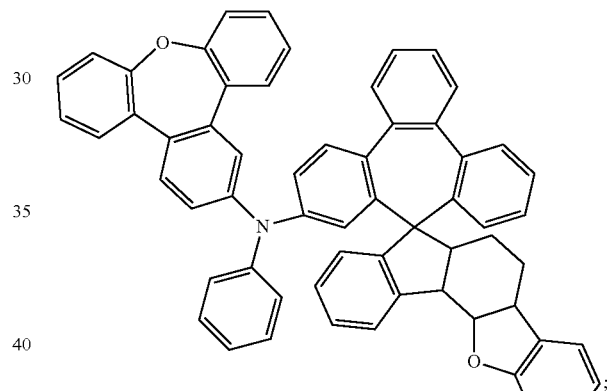
Compound 352
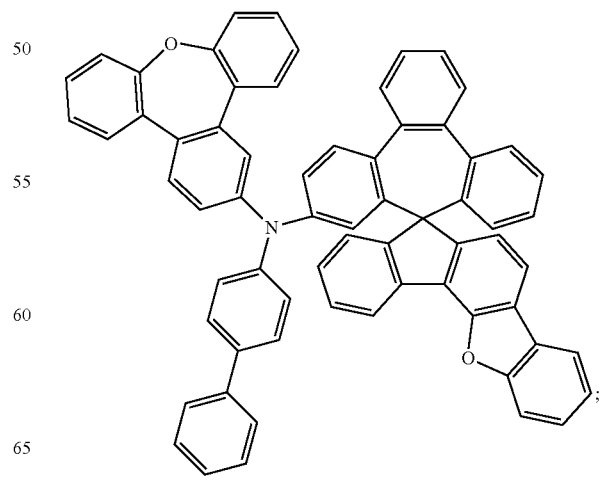

Compound 353
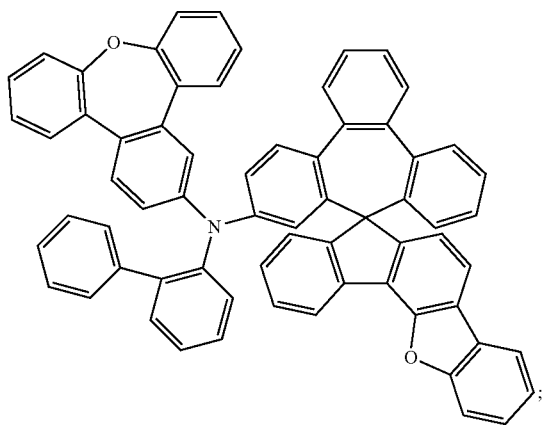
Compound 354
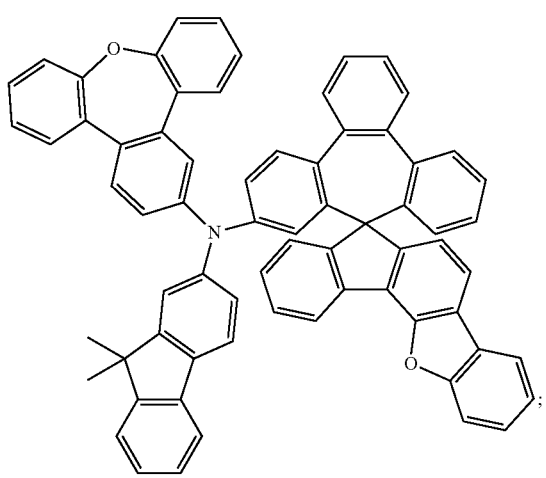
Compound 355
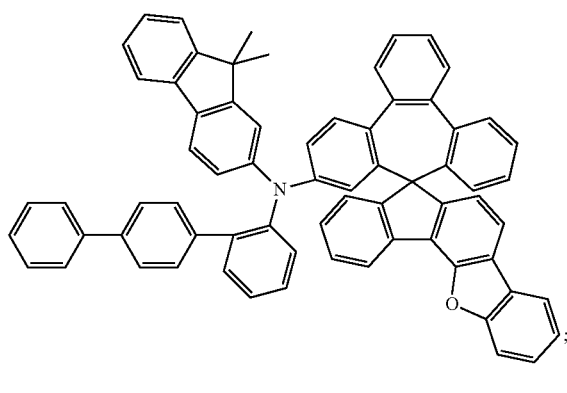
Compound 356
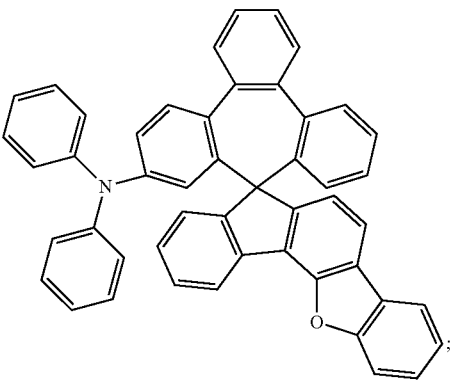
Compound 357
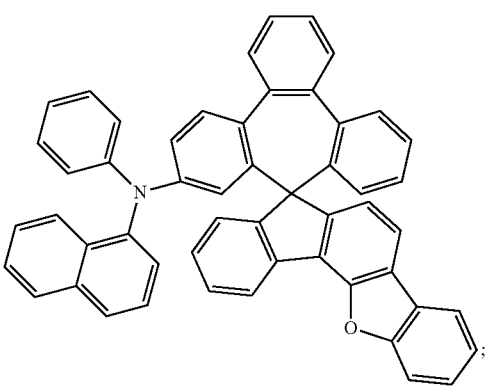
Compound 358
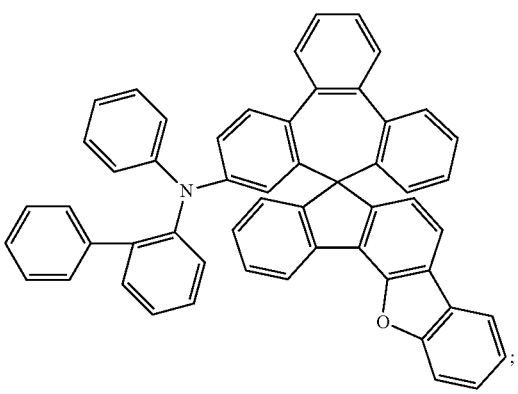
Compound 359
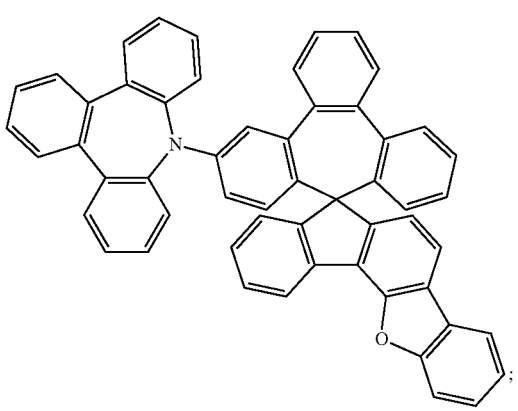

Compound 360
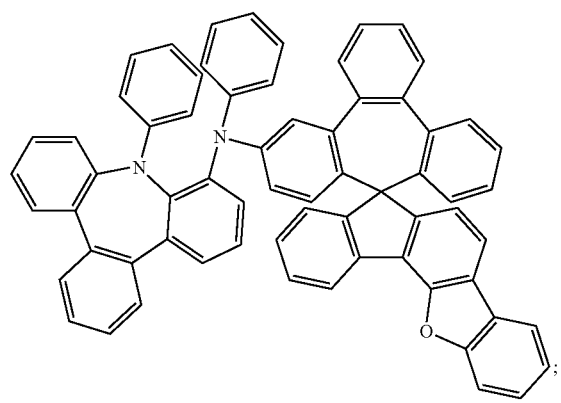
Compound 361
Compound 362
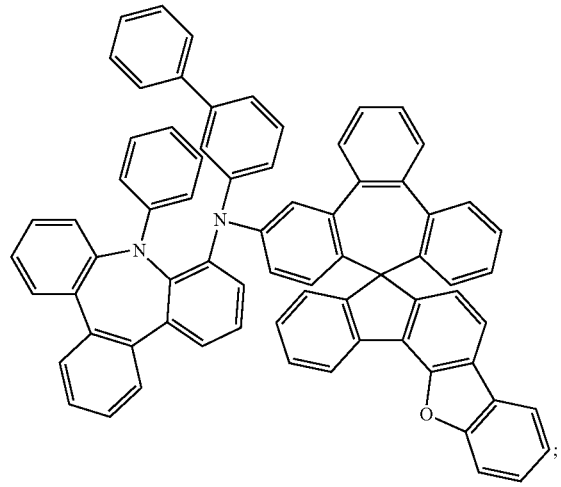
Compound 363
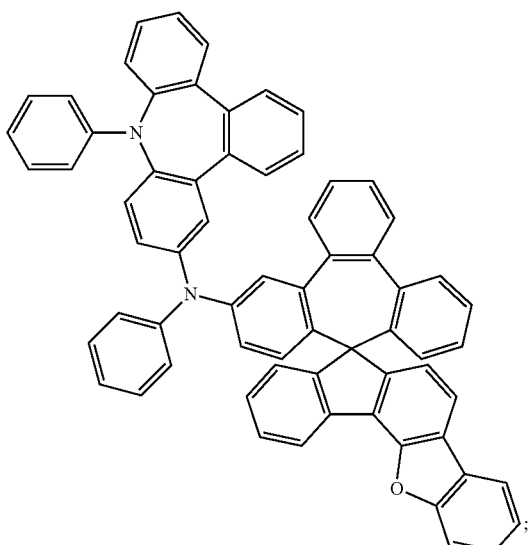
Compound 364
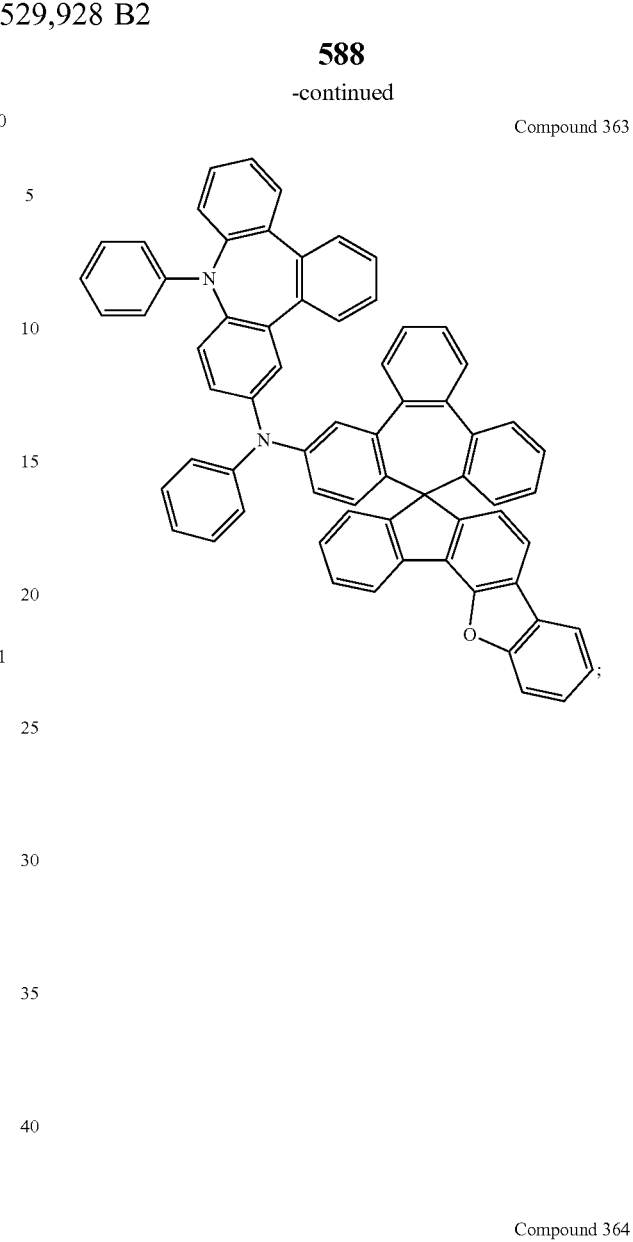

Compound 365
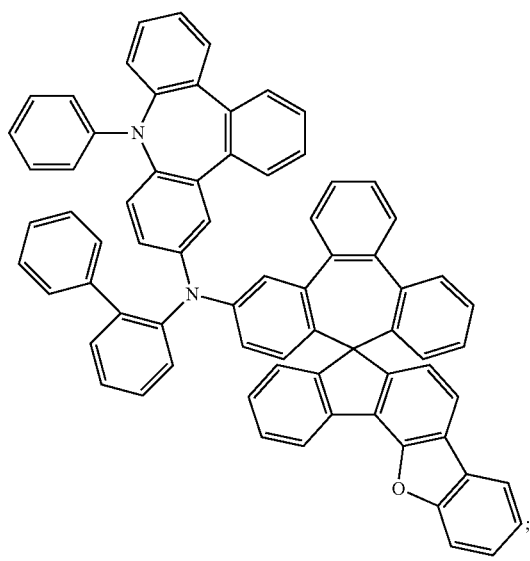
Compound 367
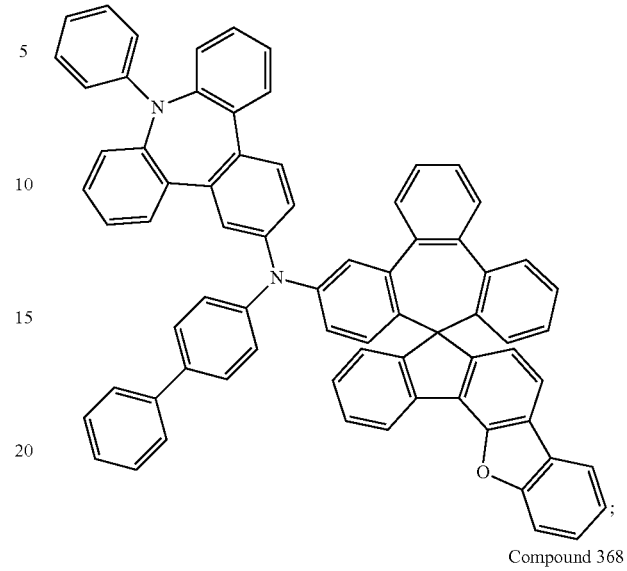
Compound 368
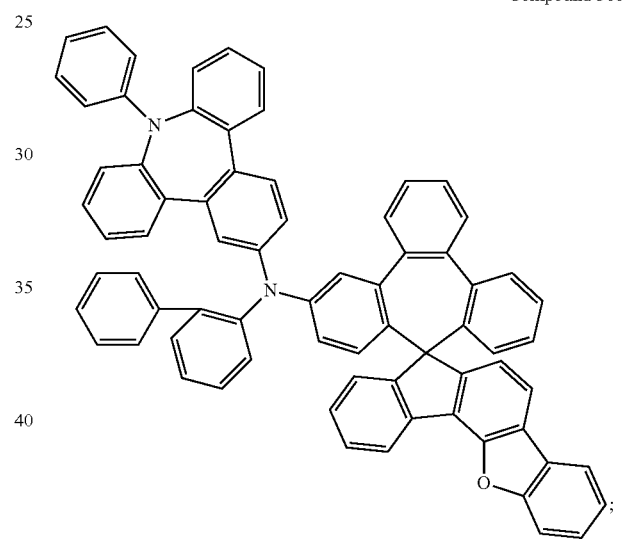
Compound 366
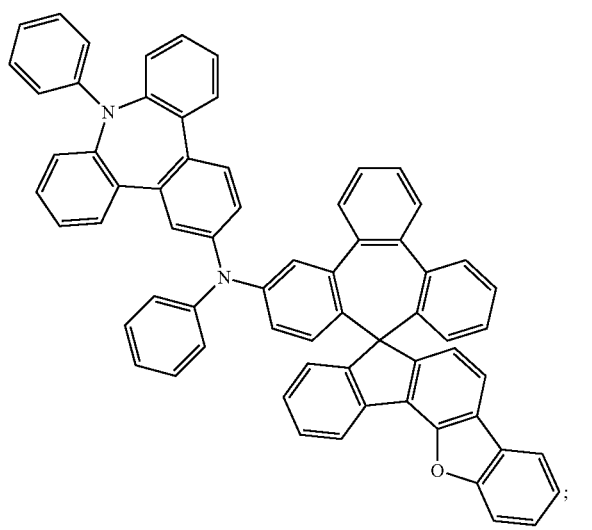
Compound 369
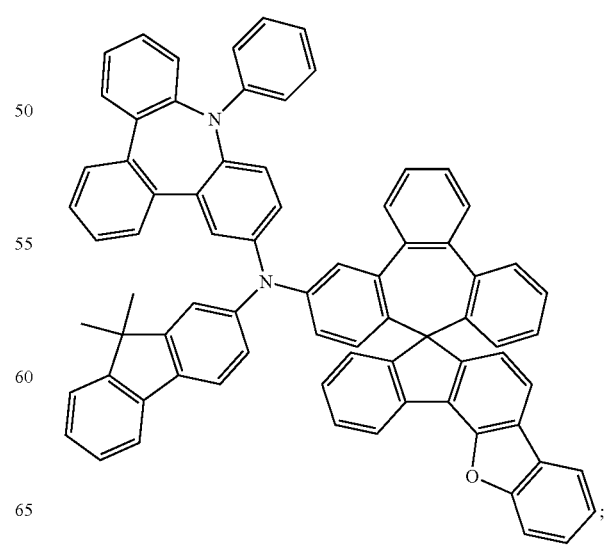

Compound 370
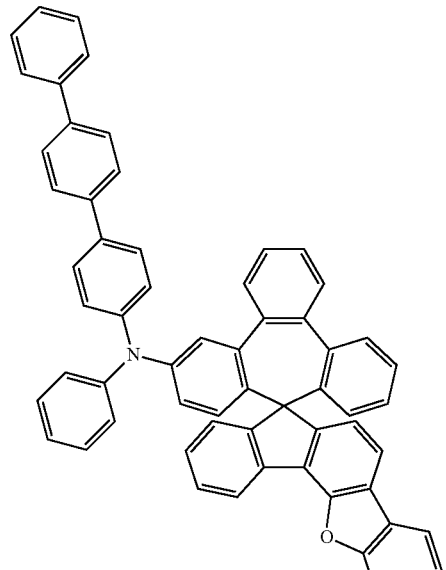
Compound 371
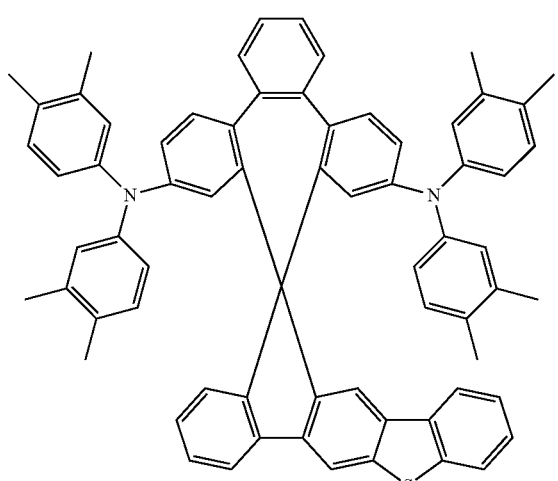
Compound 372
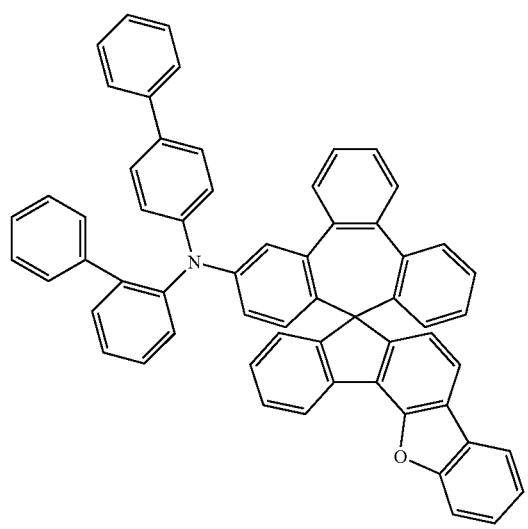
Compound 373
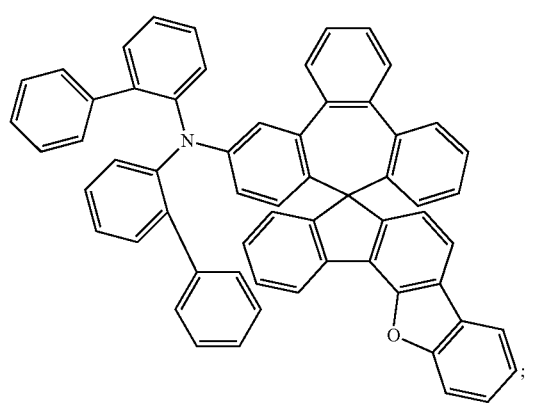
Compound 374
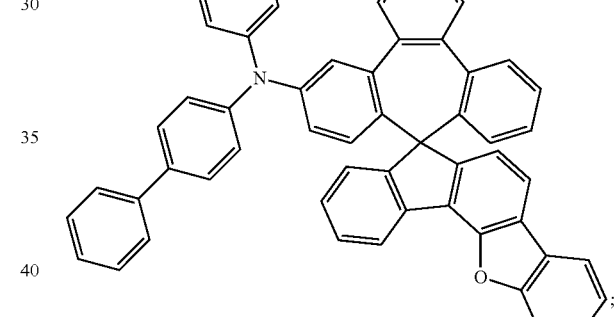
Compound 375
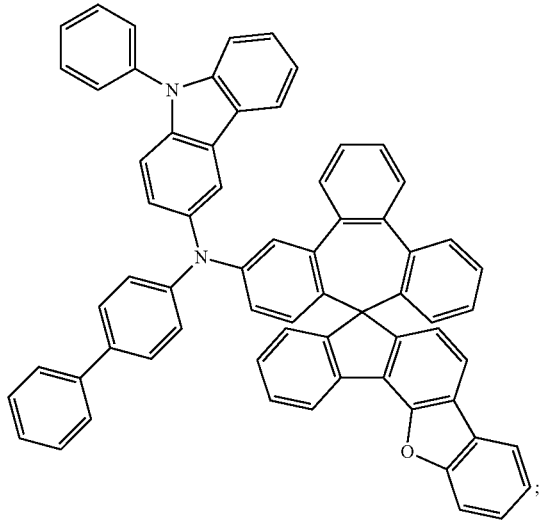

Compound 376
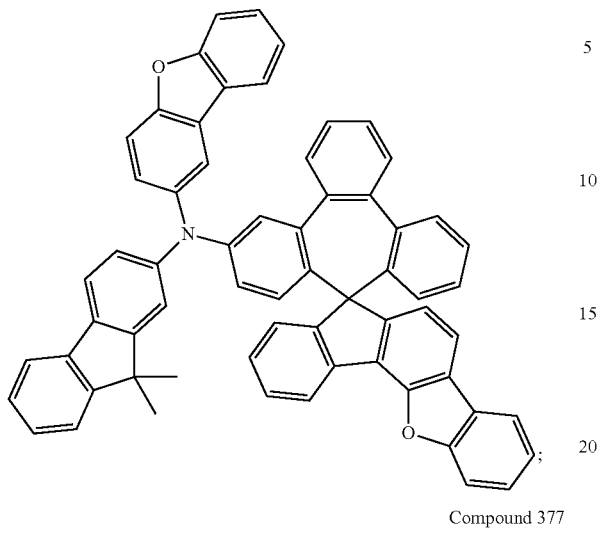
Compound 377
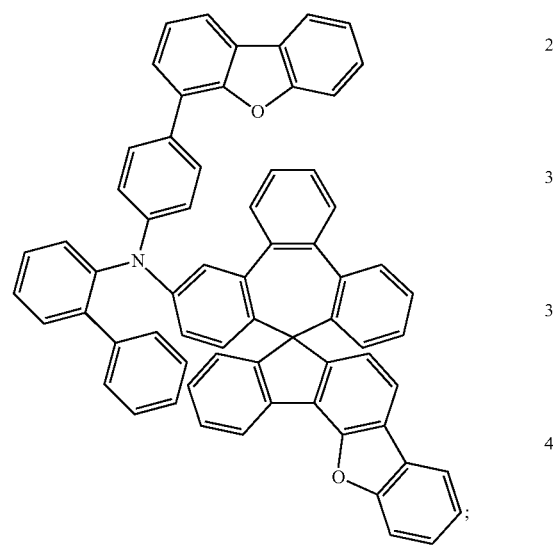
Compound 378
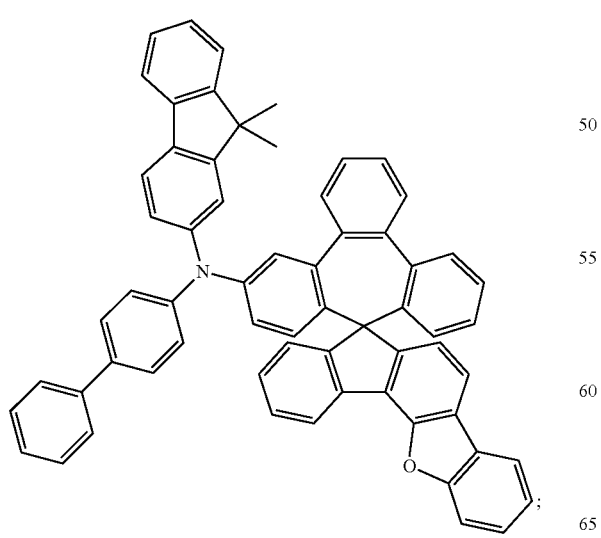
Compound 379
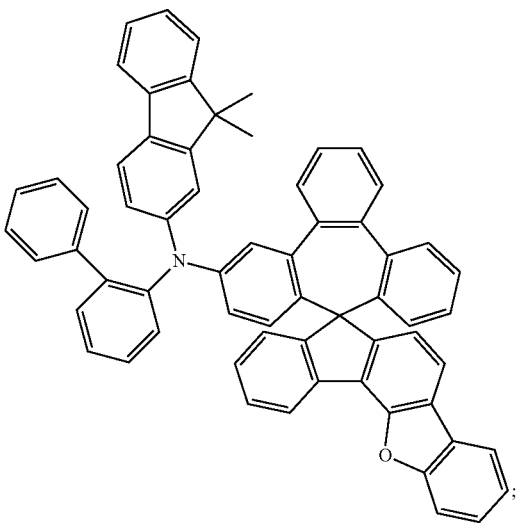
Compound 380
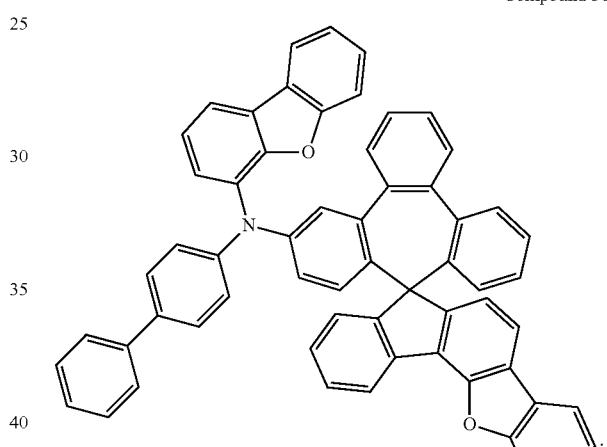
Compound 381
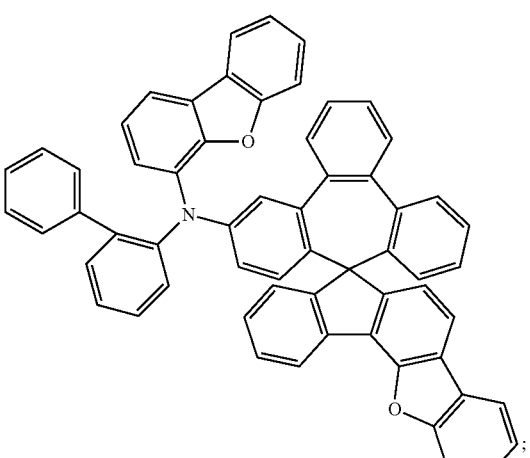

Compound 382
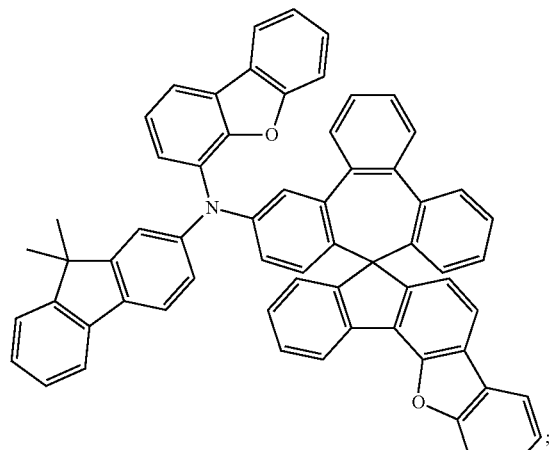
Compound 383
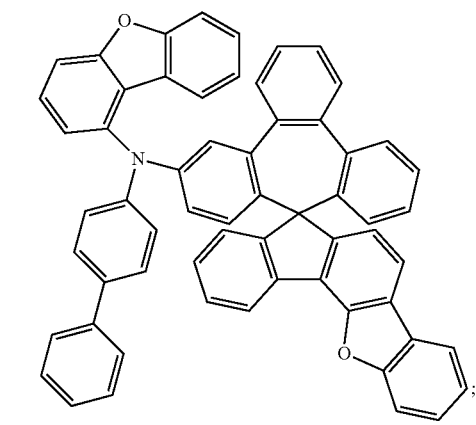
Compound 384
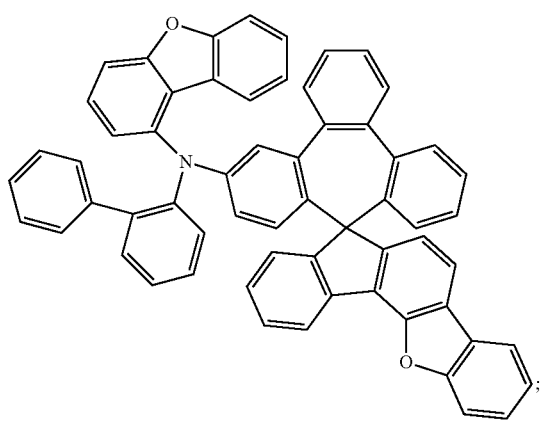
Compound 385
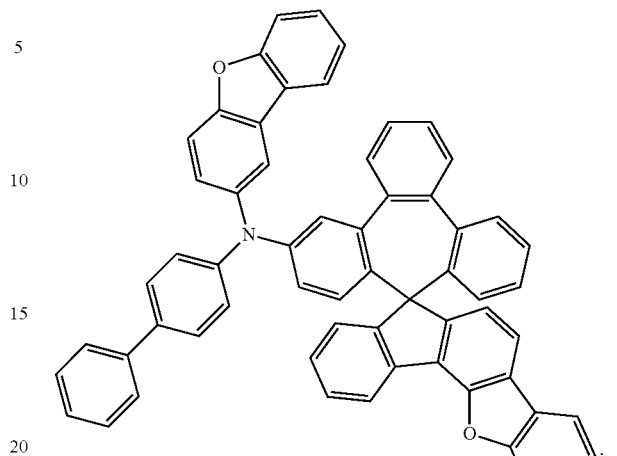
Compound 386
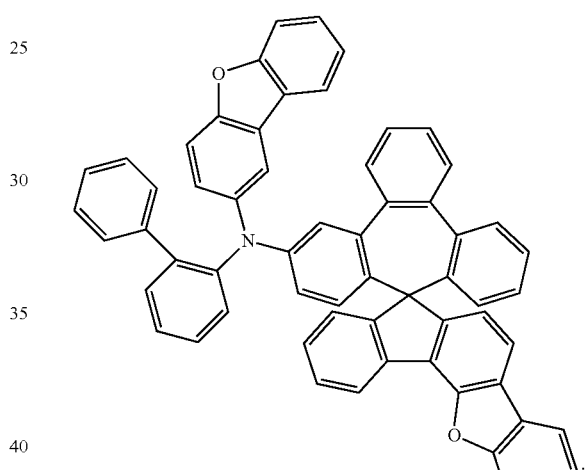
Compound 387
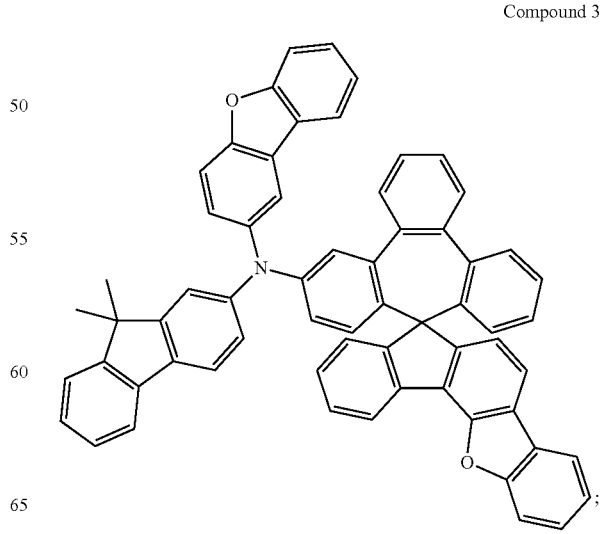

Compound 388
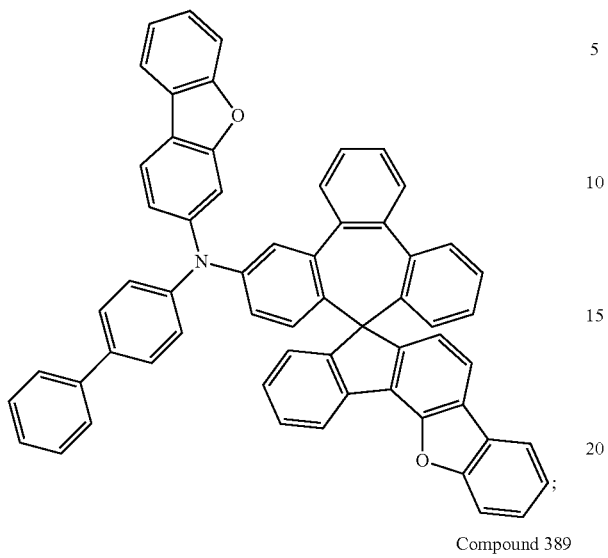
Compound 389
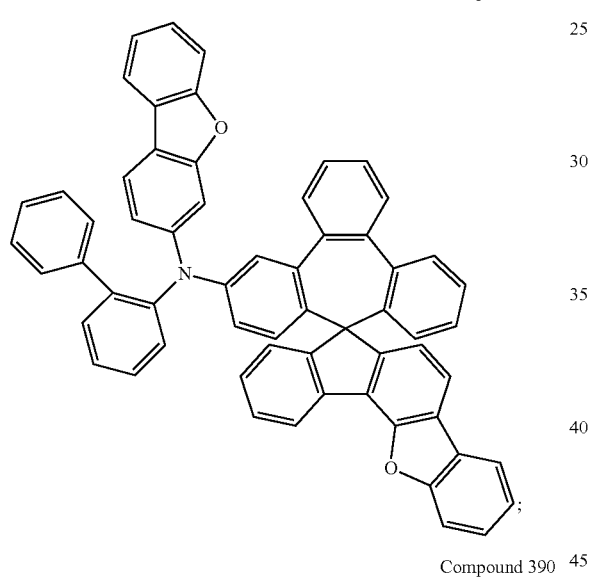
Compound 390
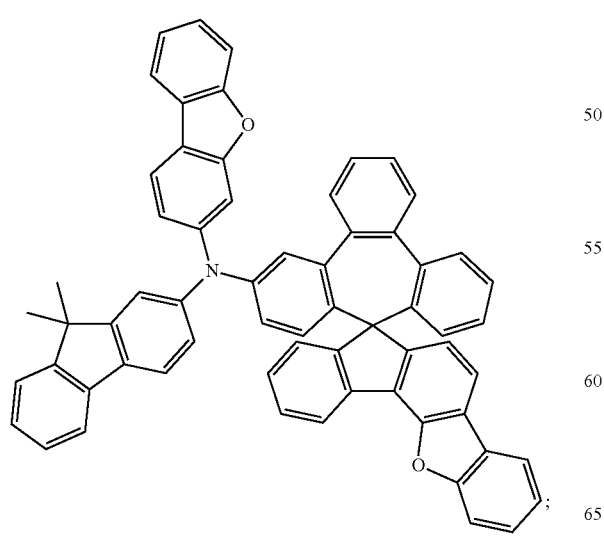
Compound 391
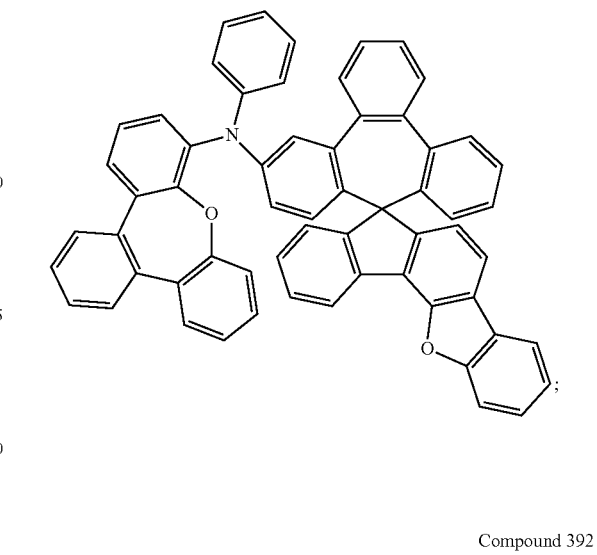
Compound 392
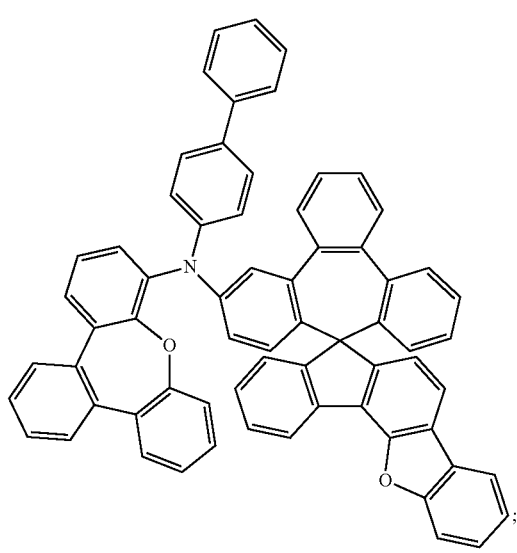
Compound 393
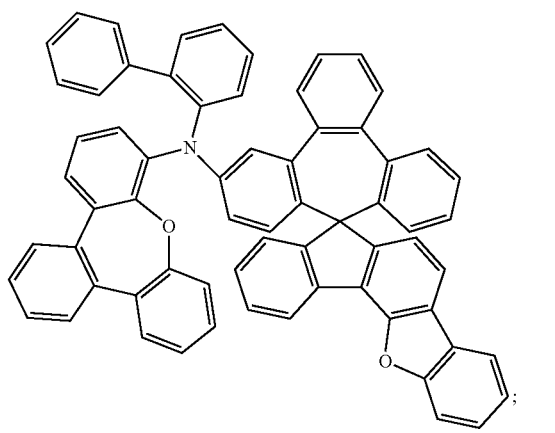

Compound 394
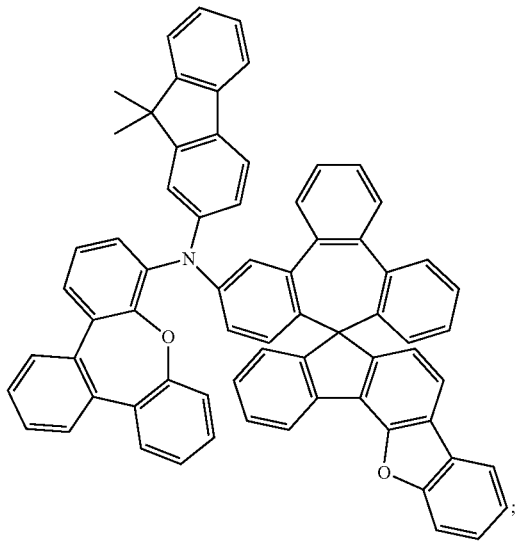
Compound 395
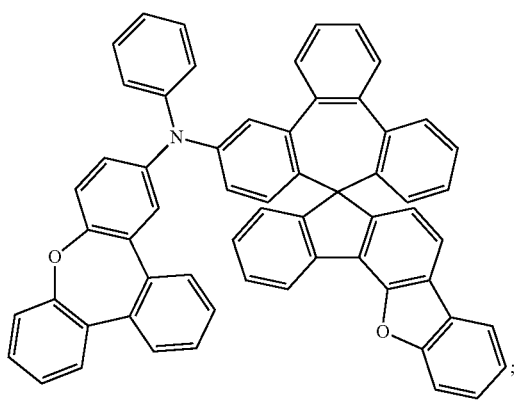
Compound 396
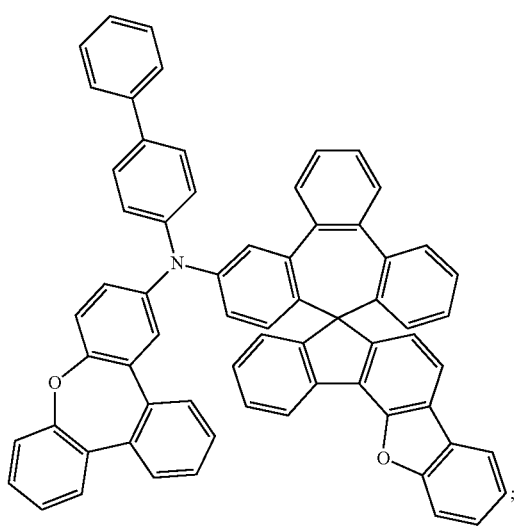
Compound 397
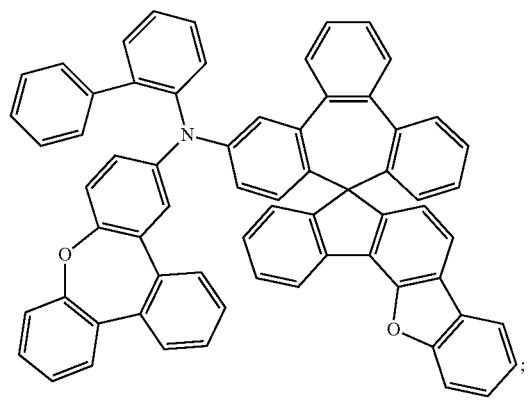
Compound 398
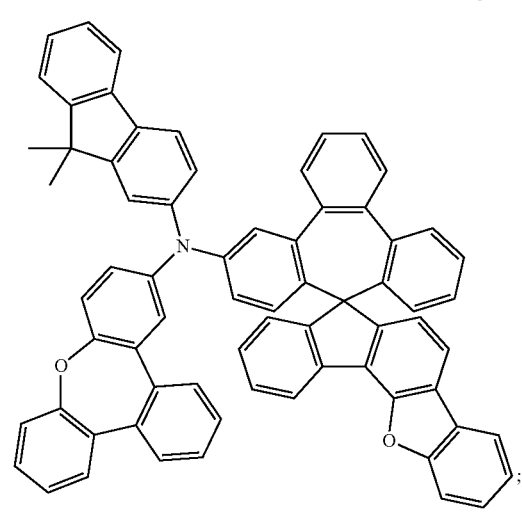
Compound 399
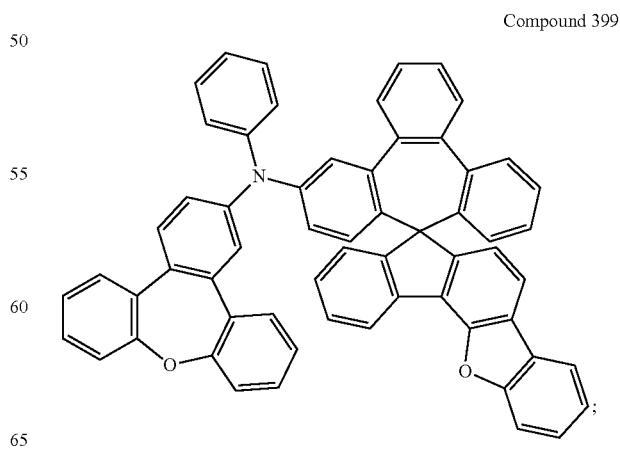

Compound 400
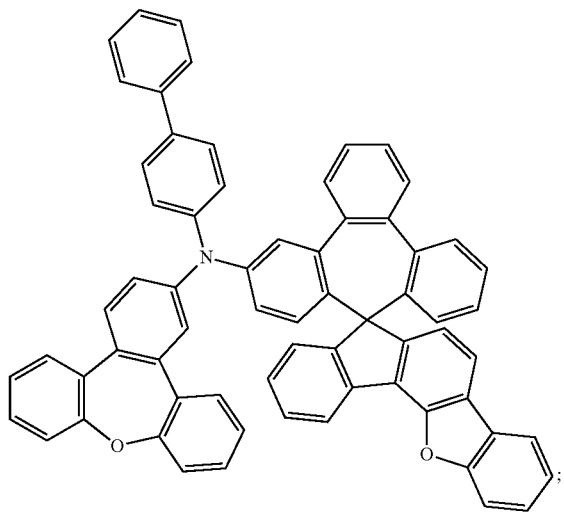
Compound 401
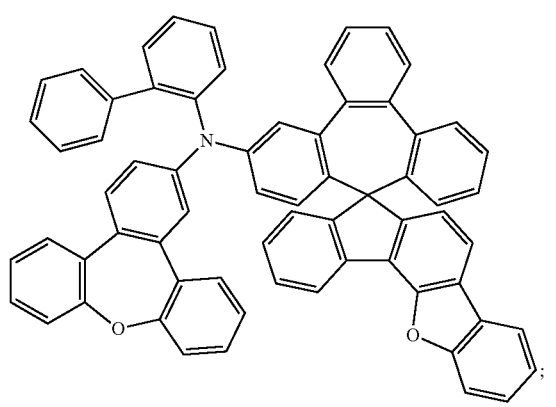
Compound 402
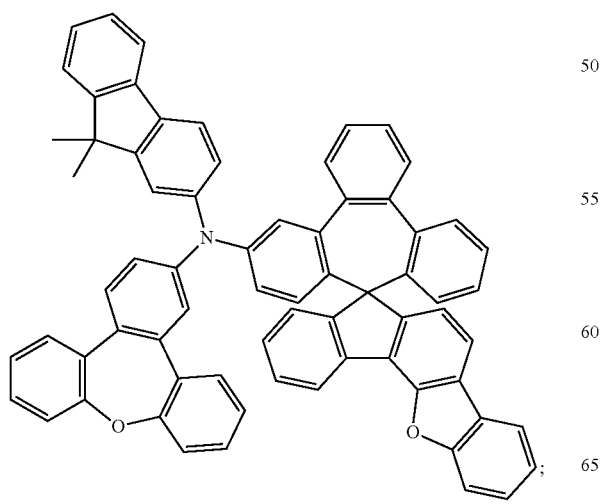
Compound 403
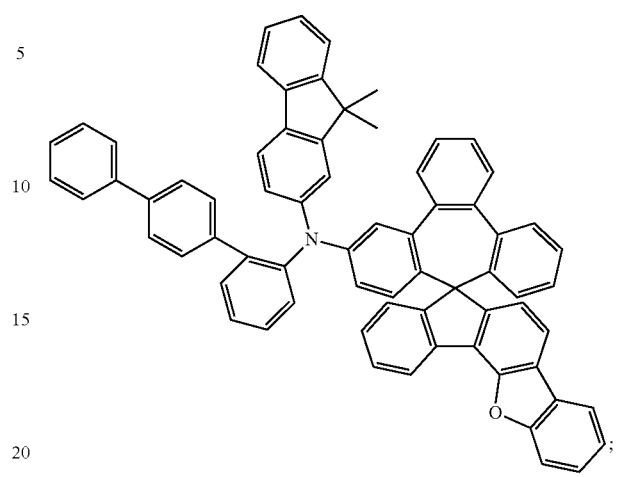
Compound 404
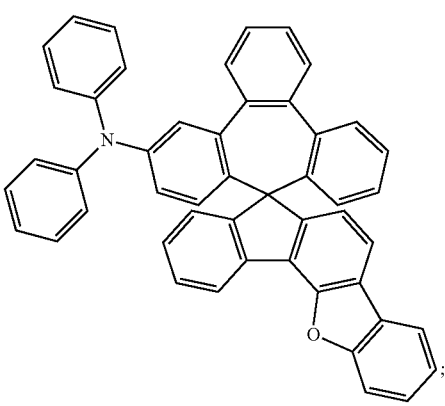
Compound 405
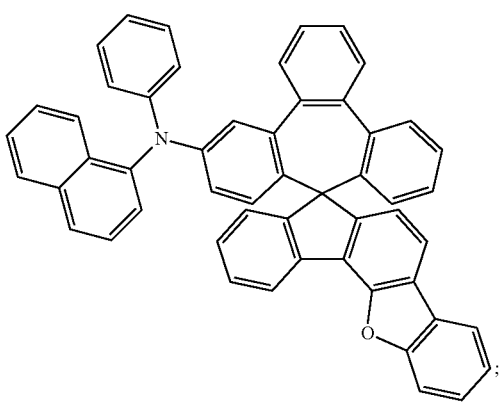

Compound 406
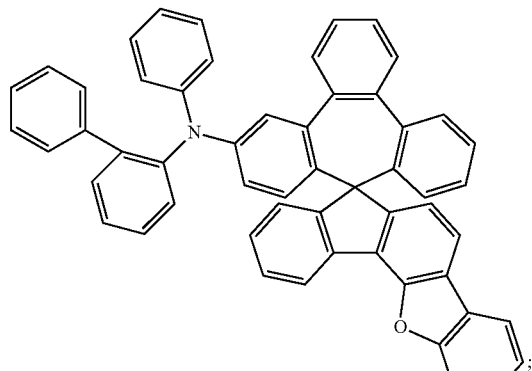
Compound 407
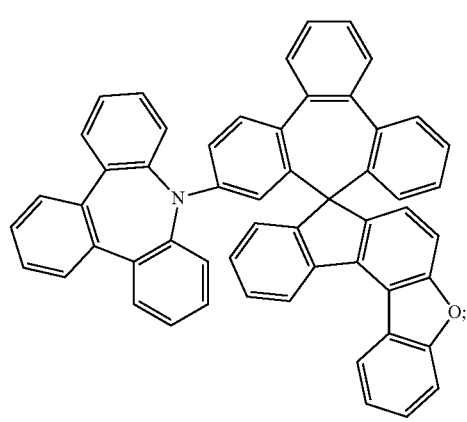
Compound 408
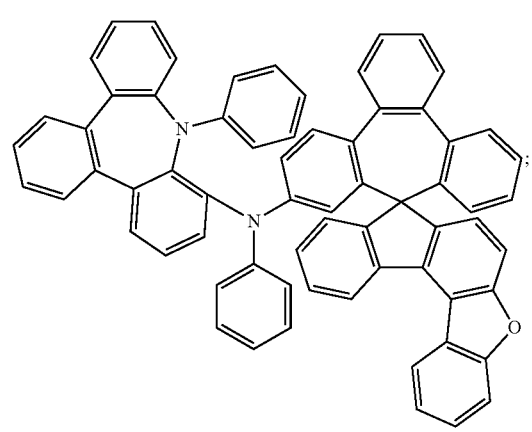
Compound 409
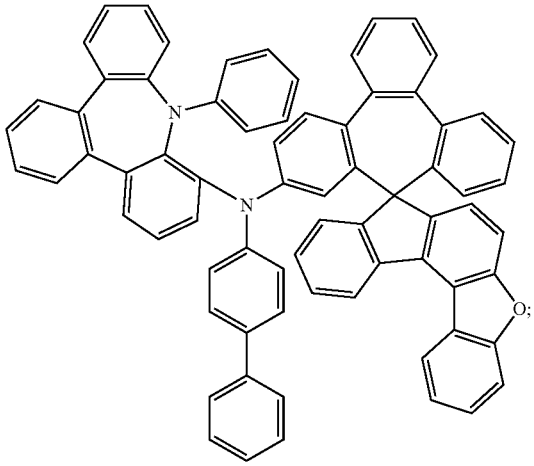
Compound 410
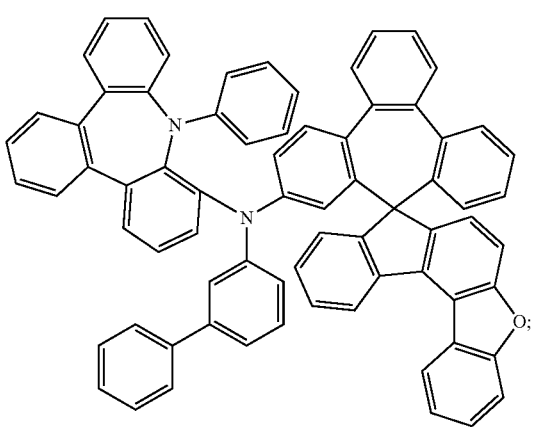
Compound 411
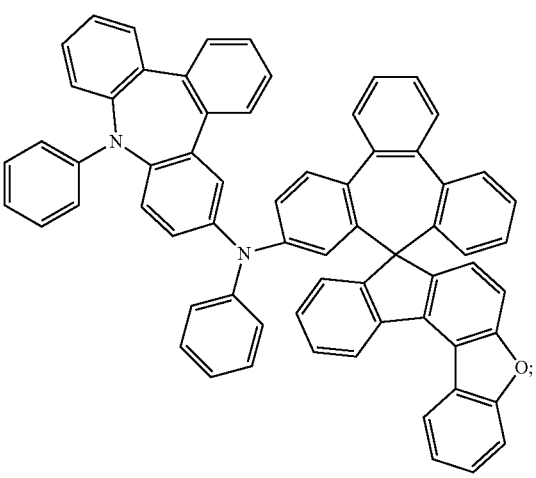

Compound 412
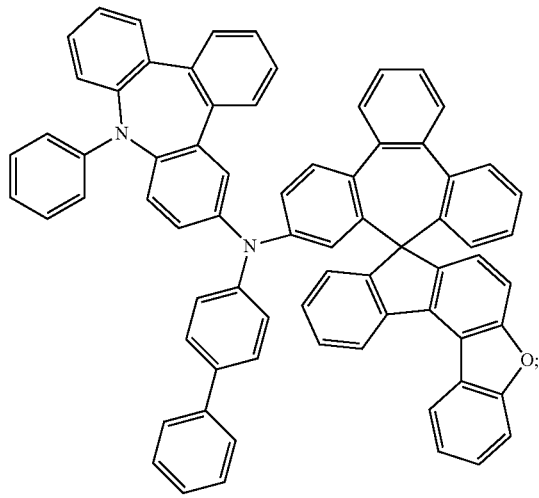
Compound 413
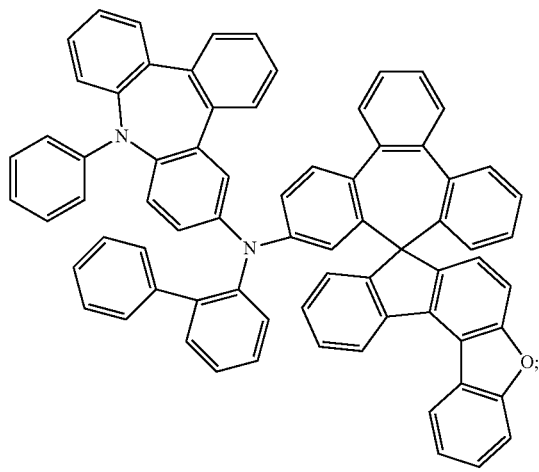
Compound 414
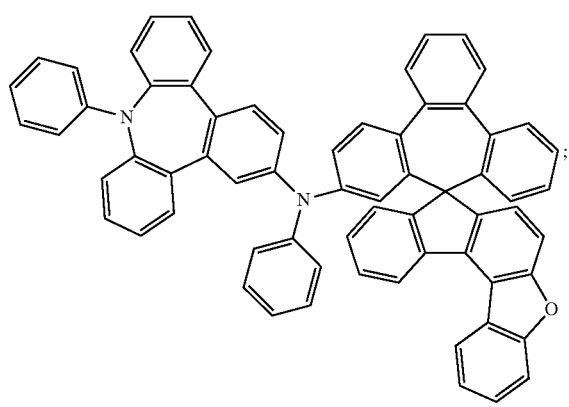
Compound 415
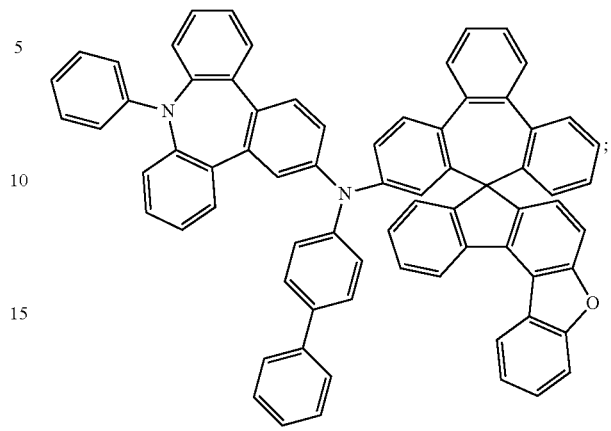
Compound 416
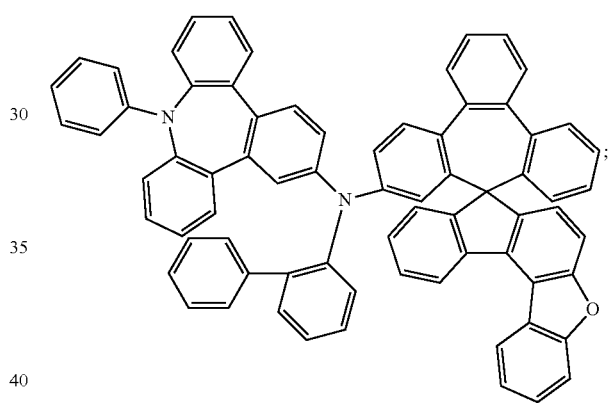
Compound 417
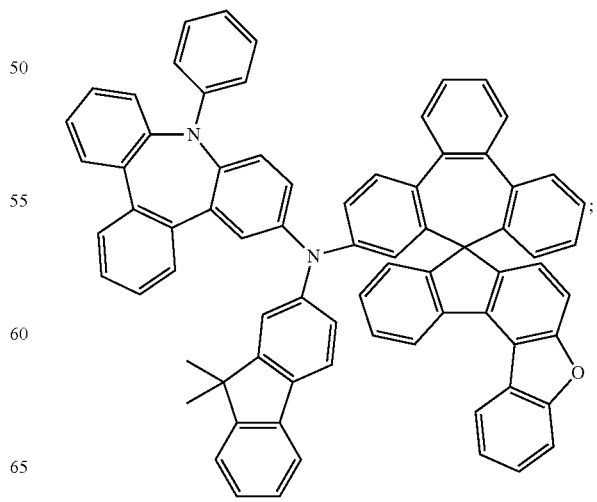

-continued
Compound 418
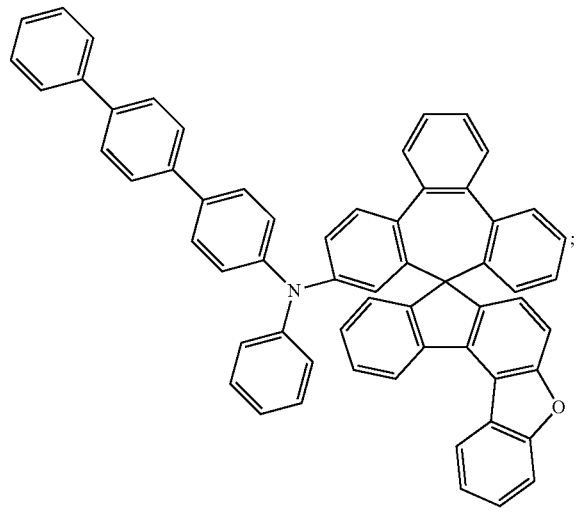
Compound 419
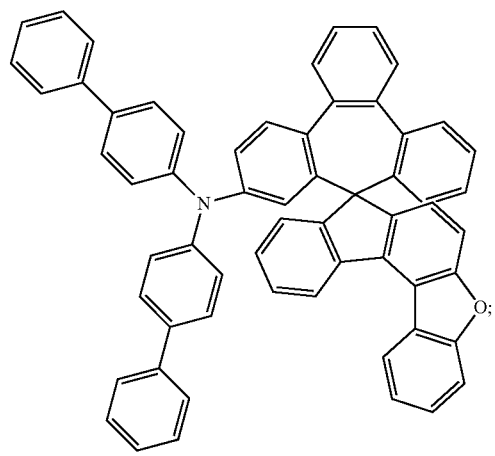
Compound 420
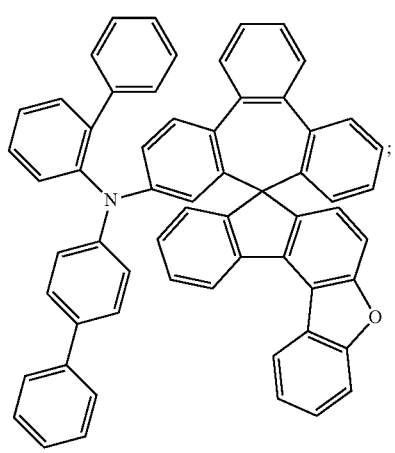
-continued
Compound 421
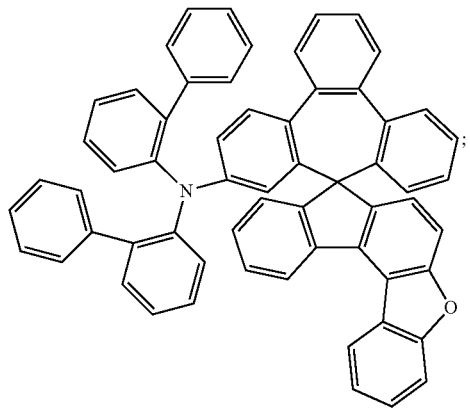
Compound 422
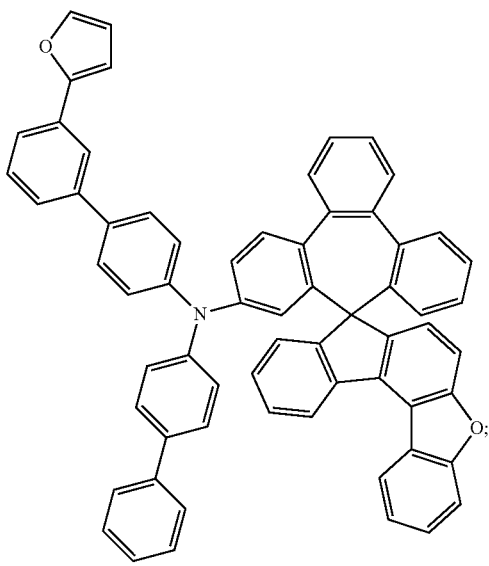
Compound 423
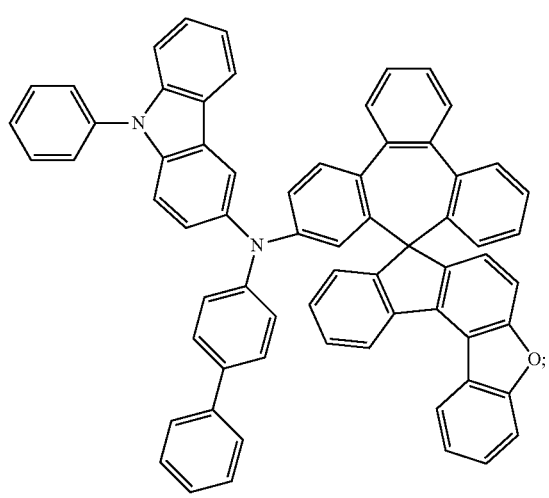

Compound 424
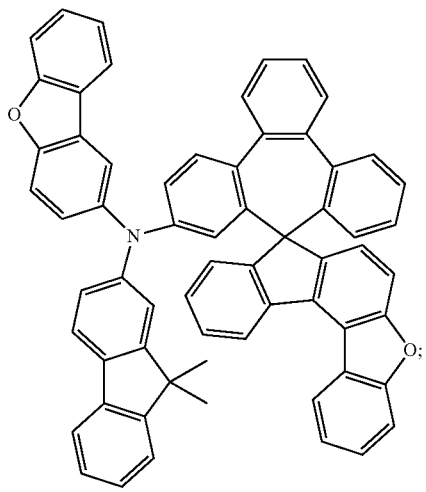
Compound 425
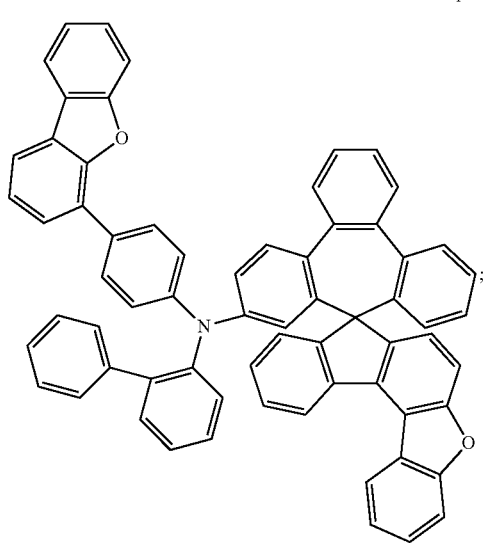
Compound 426
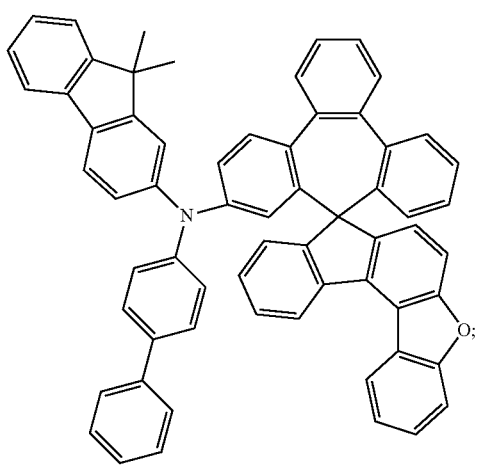
Compound 427
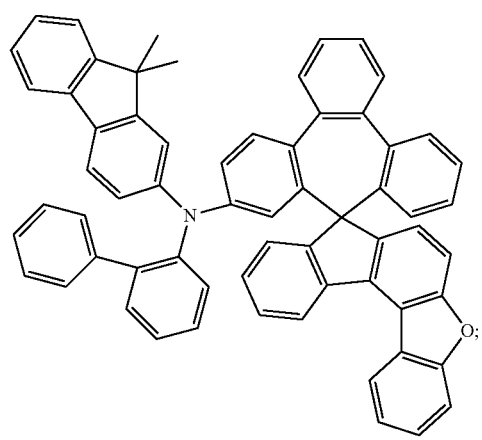
Compound 428
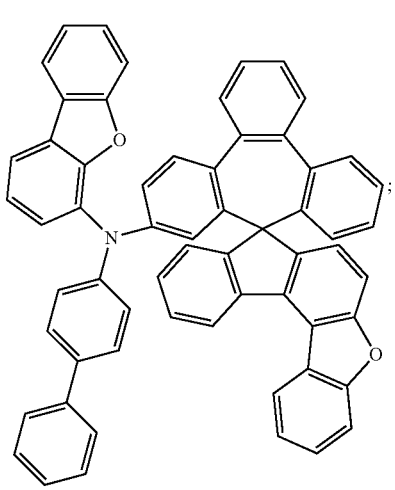
Compound 429
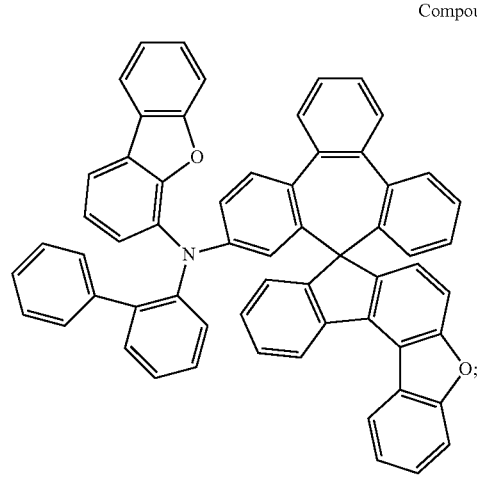

Compound 430
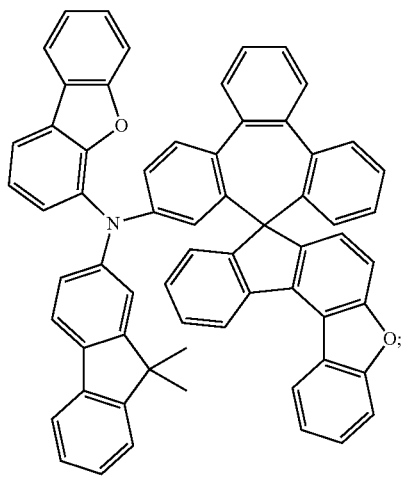
Compound 431
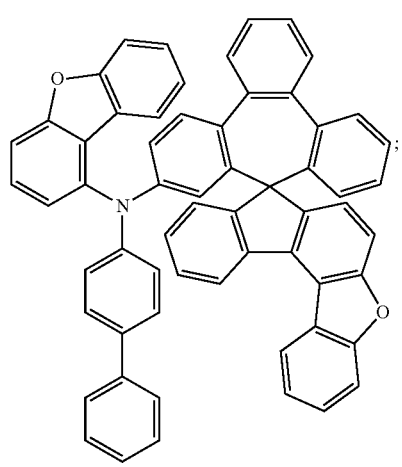
Compound 432
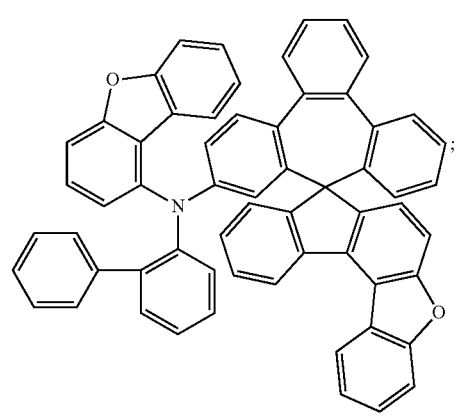
Compound 433
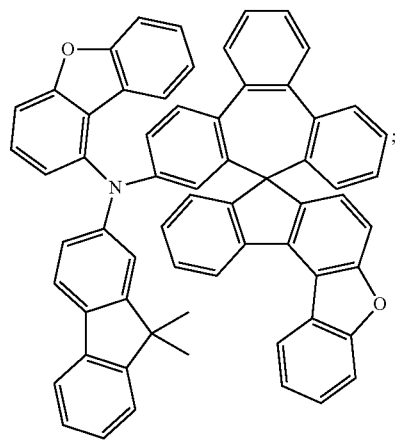
Compound 434
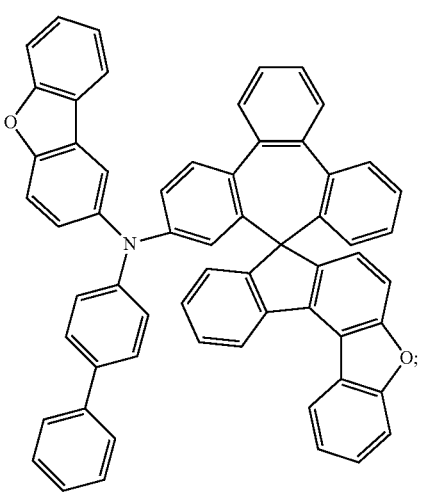
Compound 435
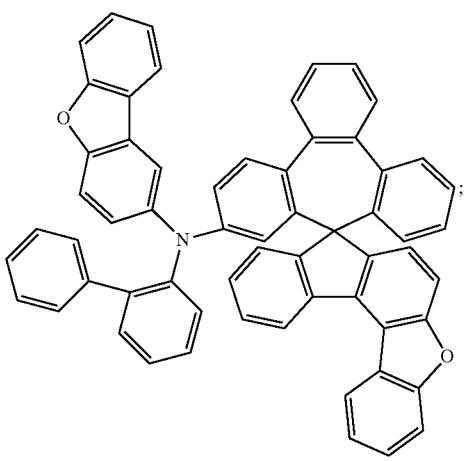

Compound 436
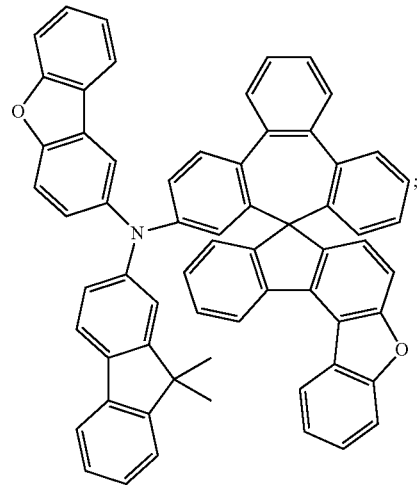
Compound 339
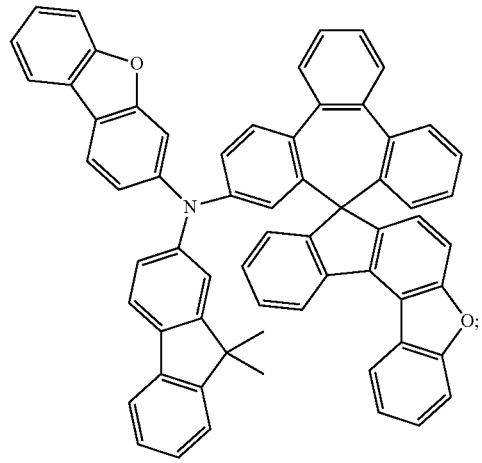
Compound 437
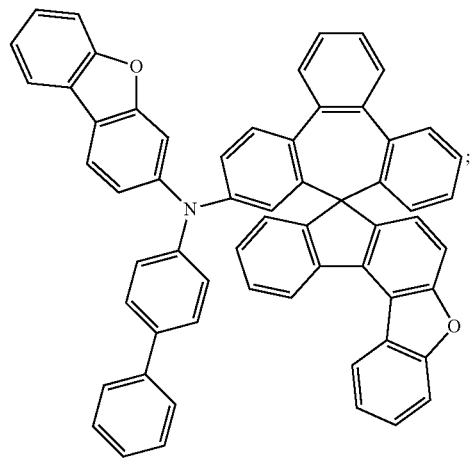
Compound 440
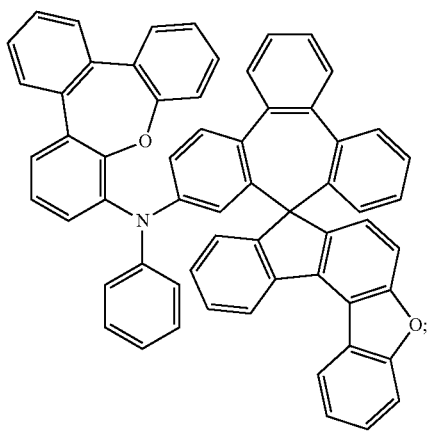
Compound 438
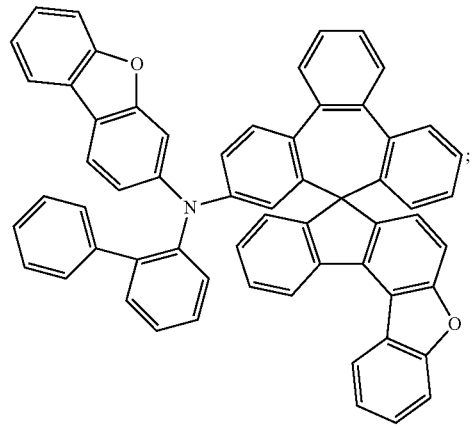
Compound 441
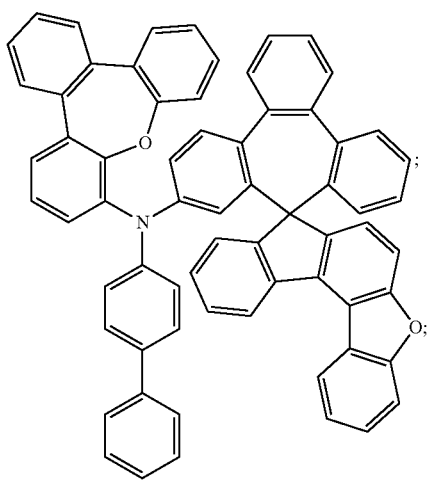

-continued
Compound 442
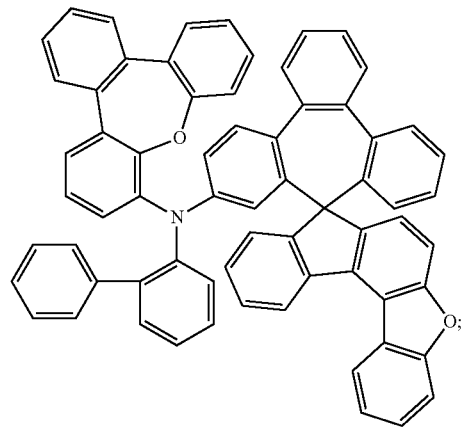
Compound 443
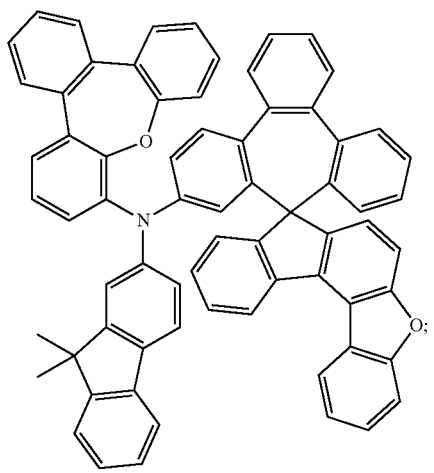
Compound 444
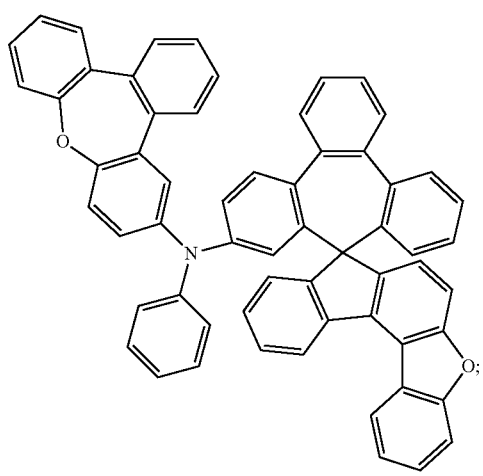
-continued
Compound 445
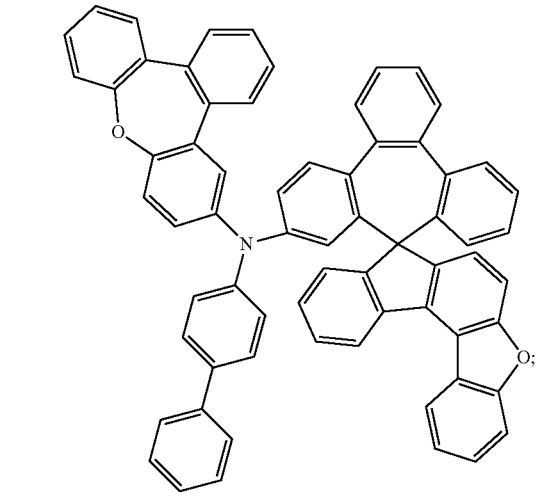
Compound 446
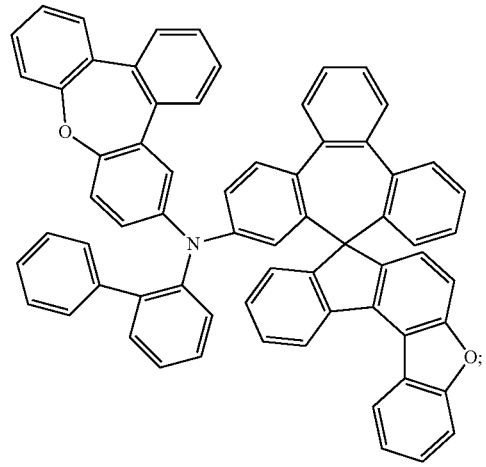
Compound 447
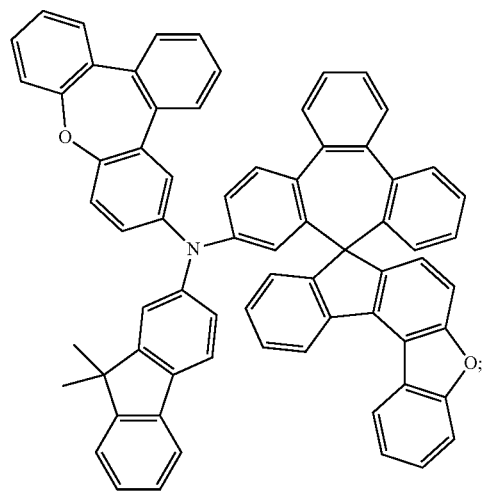

Compound 448
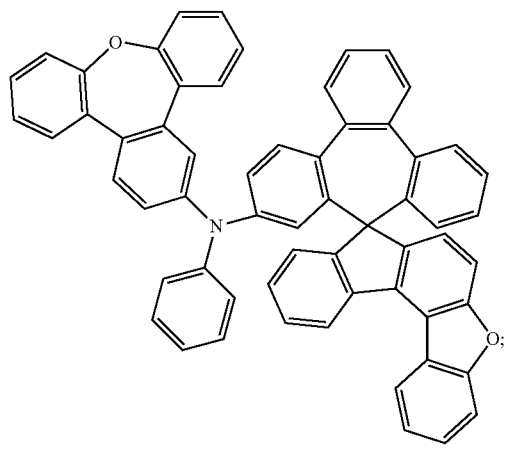
Compound 451
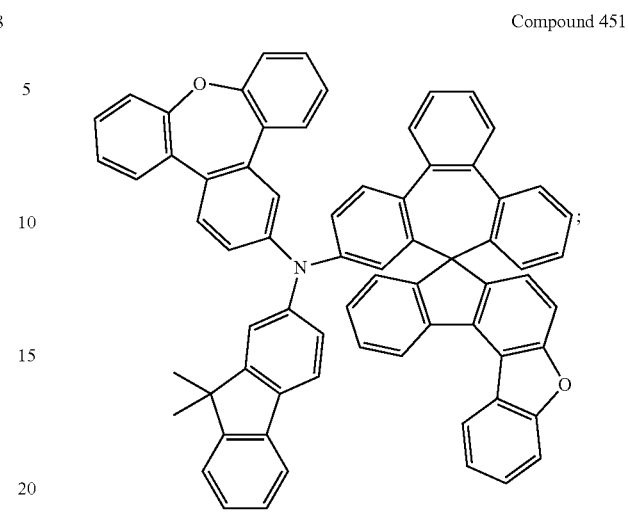
Compound 449
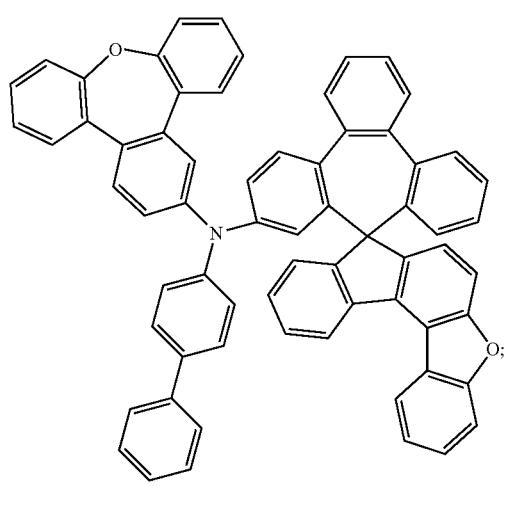
Compound 452
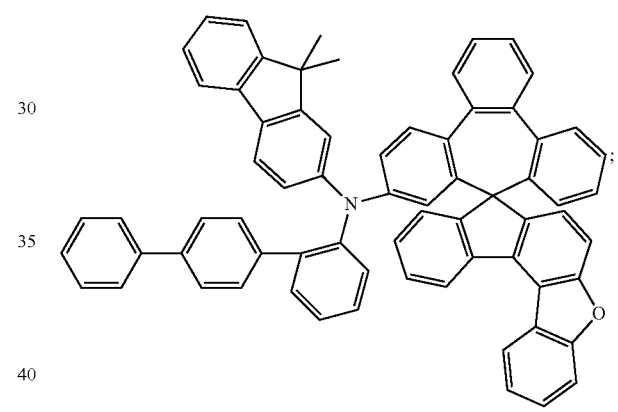
Compound 450
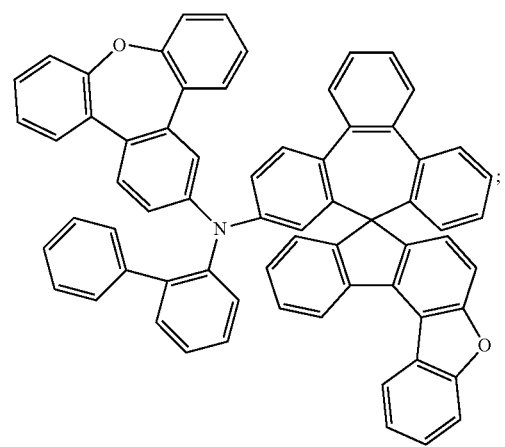
Compound 453
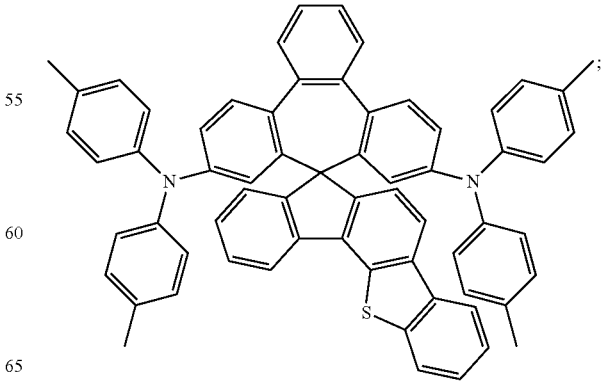

-continued
Compound 454
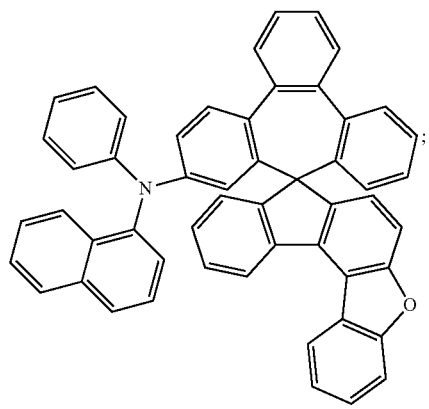
Compound 455
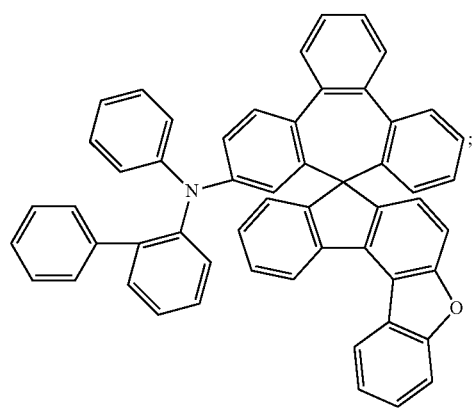
Compound 456
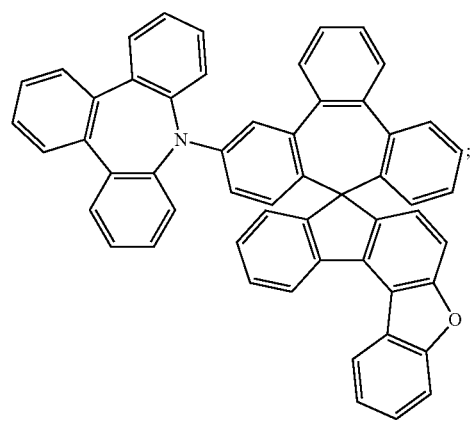
-continued
Compound 457
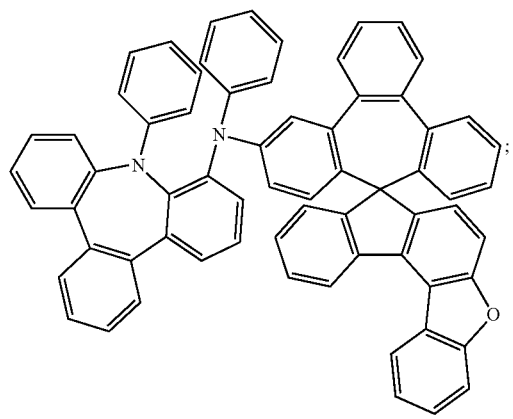
Compound 458
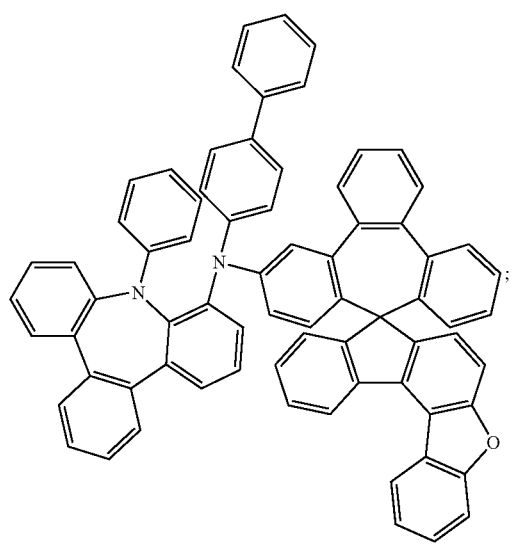
Compound 459
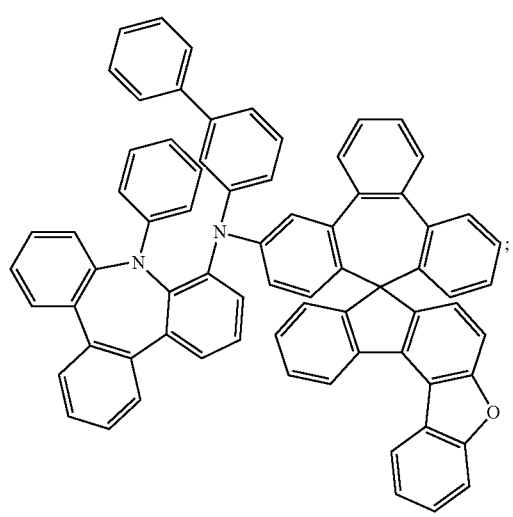

Compound 460
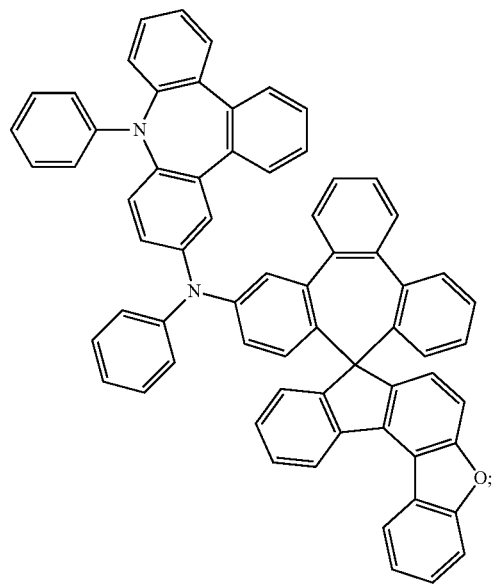
Compound 461
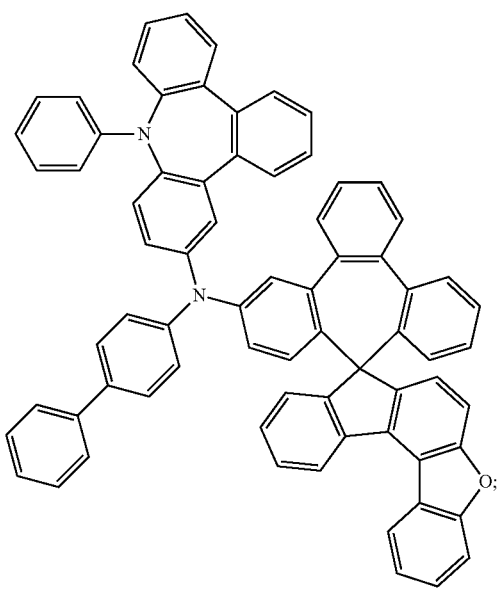
Compound 462
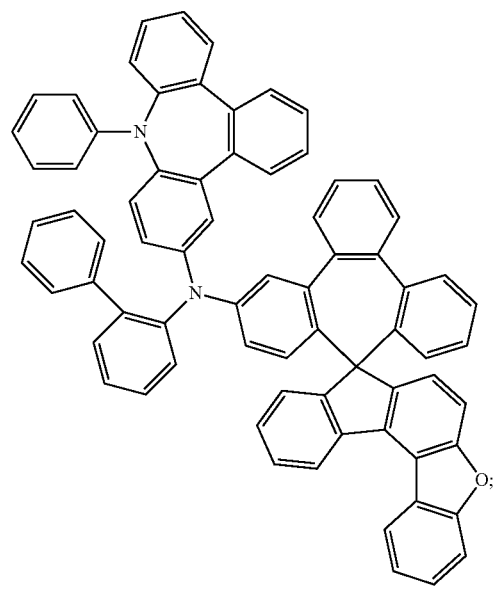
Compound 463
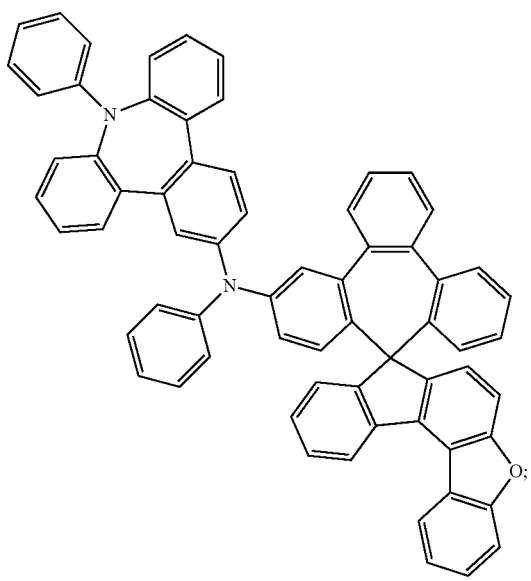

Compound 464
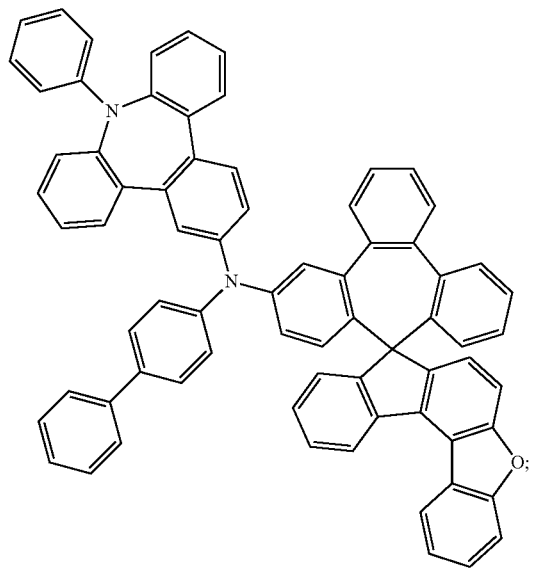
Compound 466
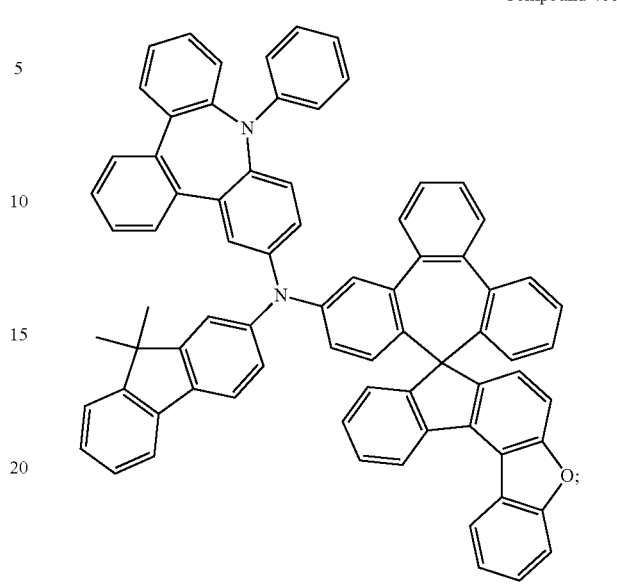
Compound 465
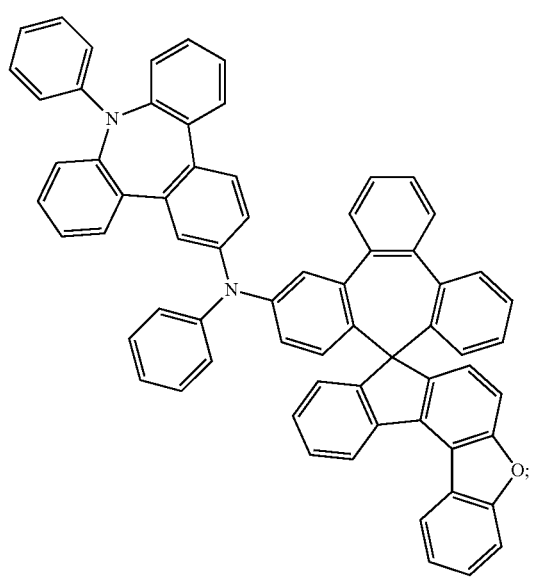
Compound 467
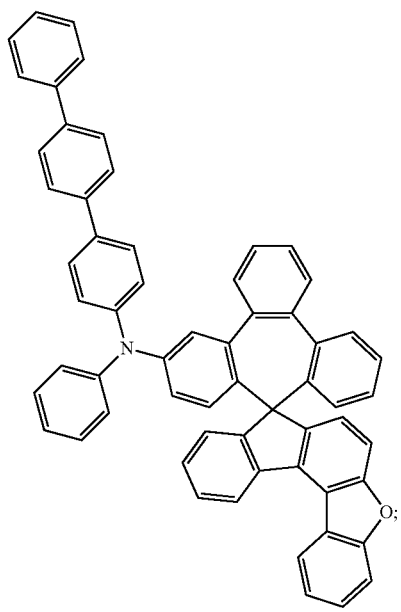

Compound 468
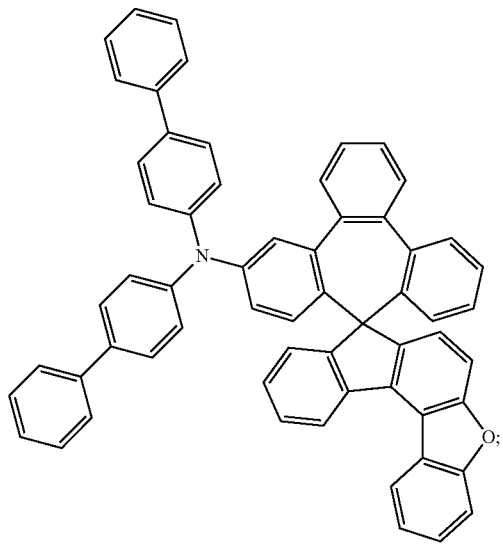
Compound 469
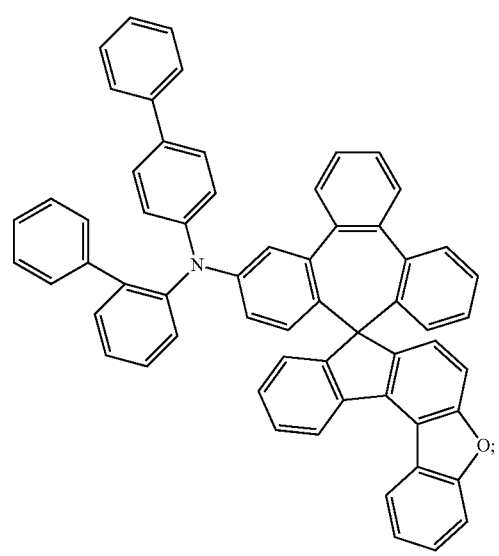
Compound 470
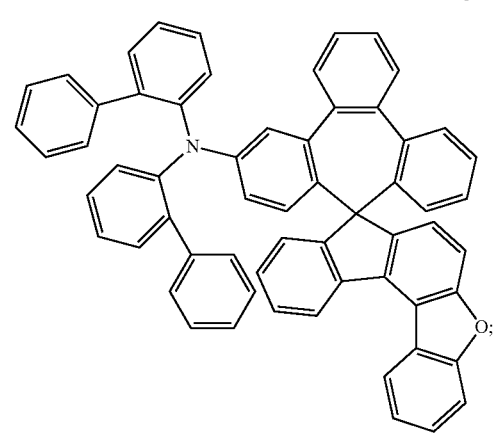
Compound 471
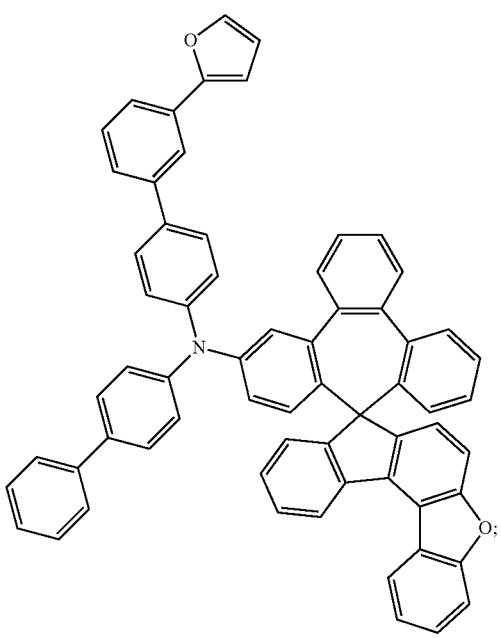
Compound 472

Compound 473
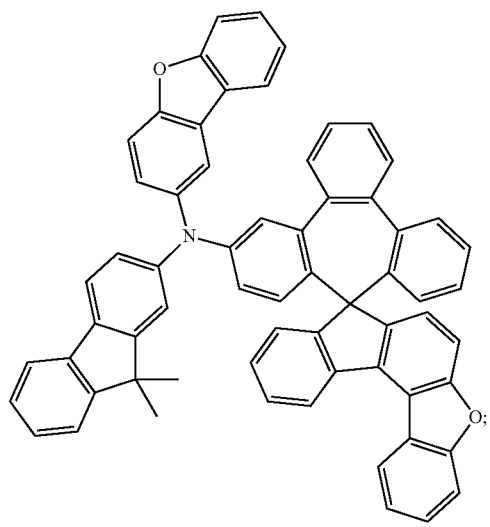
Compound 474
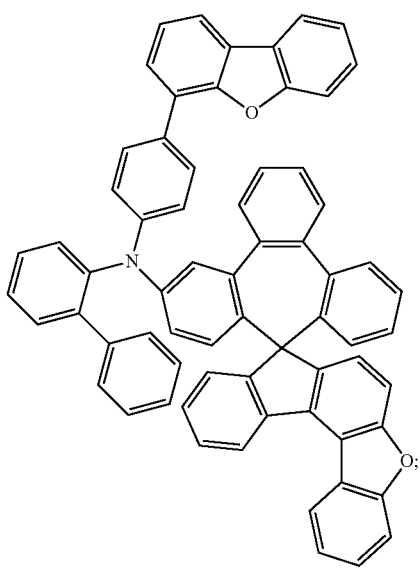
Compound 475
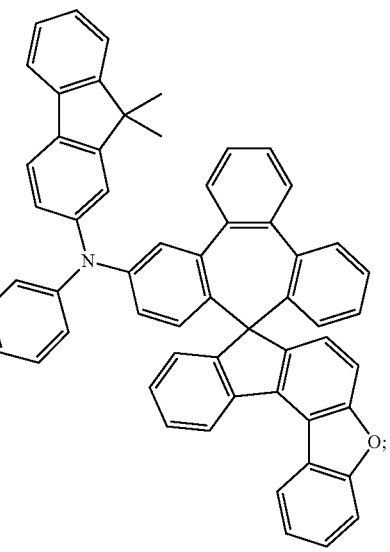
Compound 476
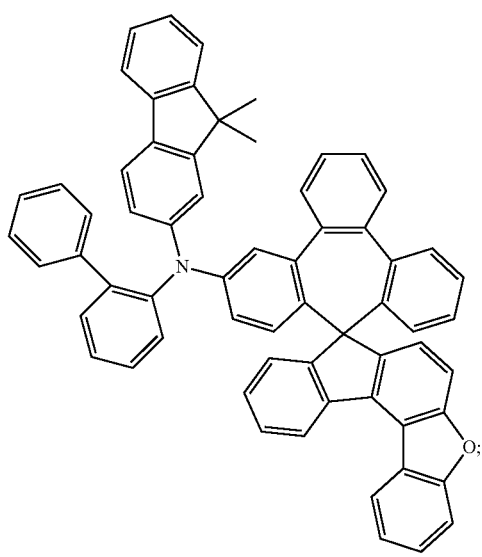
Compound 477
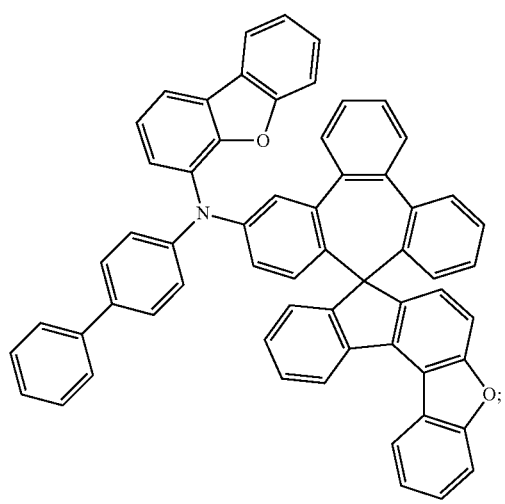

Compound 478
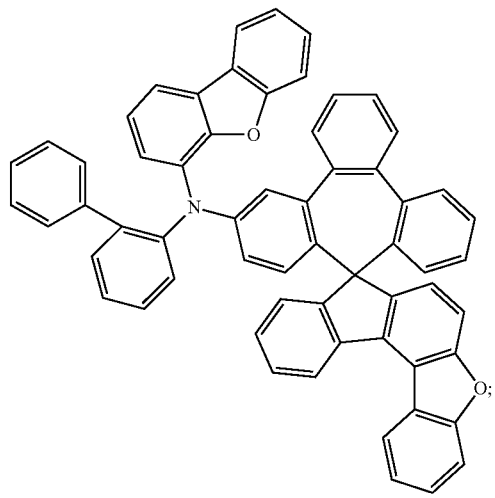
Compound 479
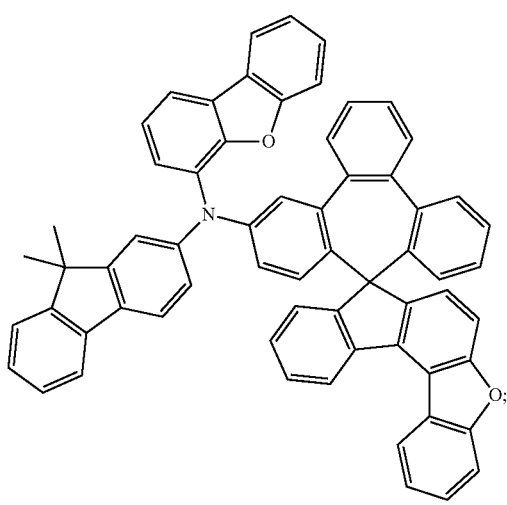
Compound 480
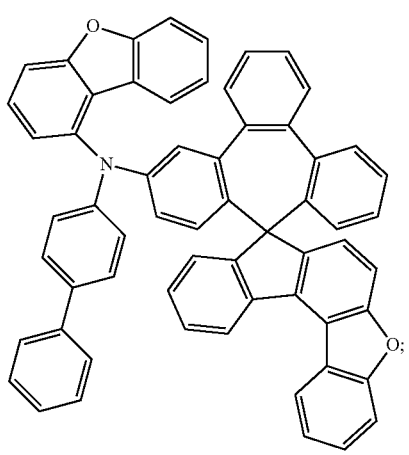
Compound 481
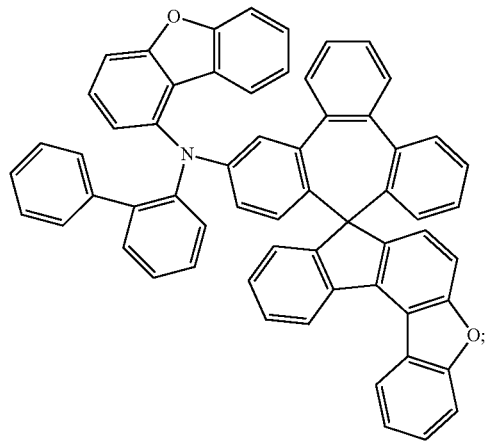
Compound 482
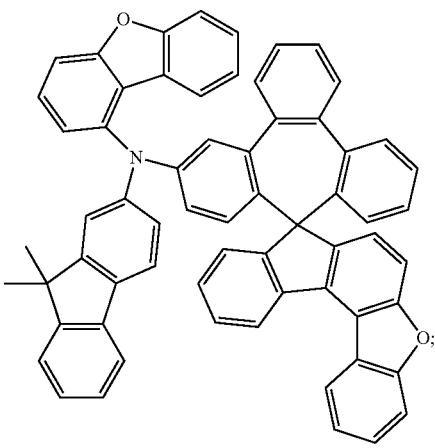
Compound 483
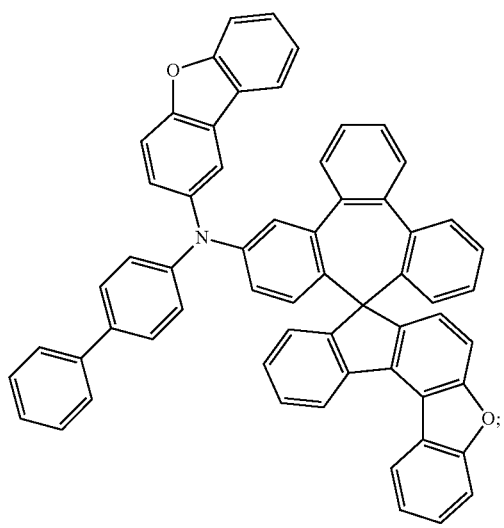

Compound 484
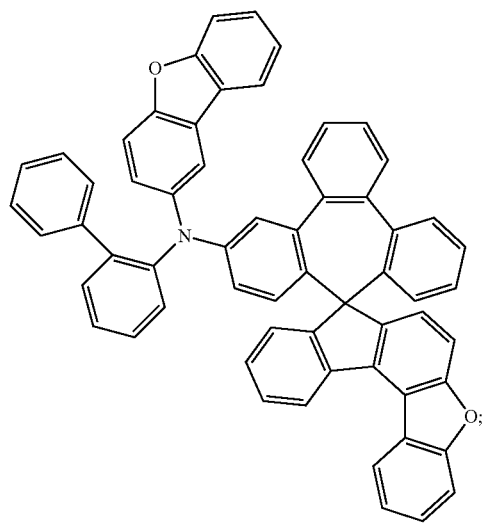
Compound 485
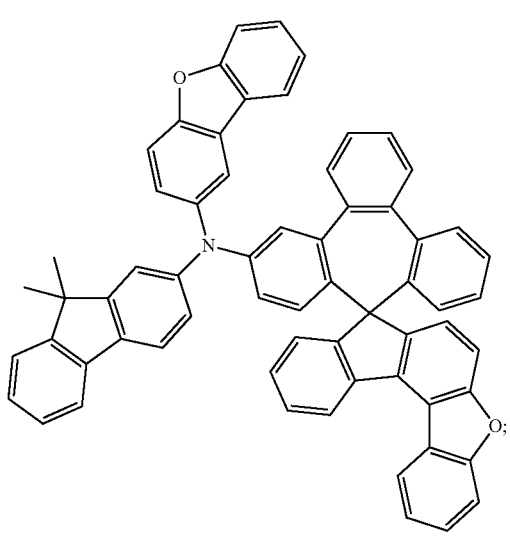
Compound 486
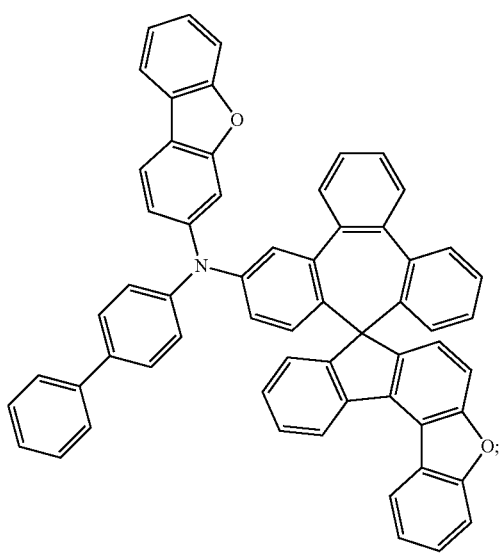
Compound 487
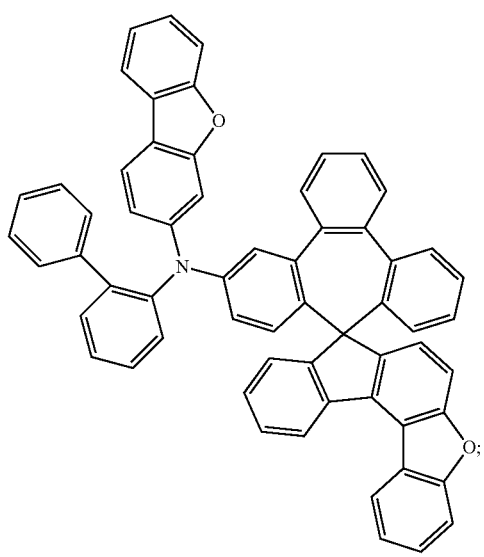
Compound 488
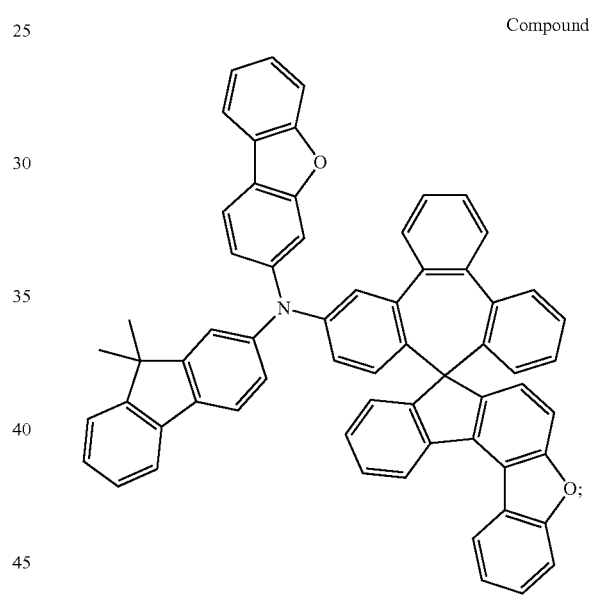
Compound 489
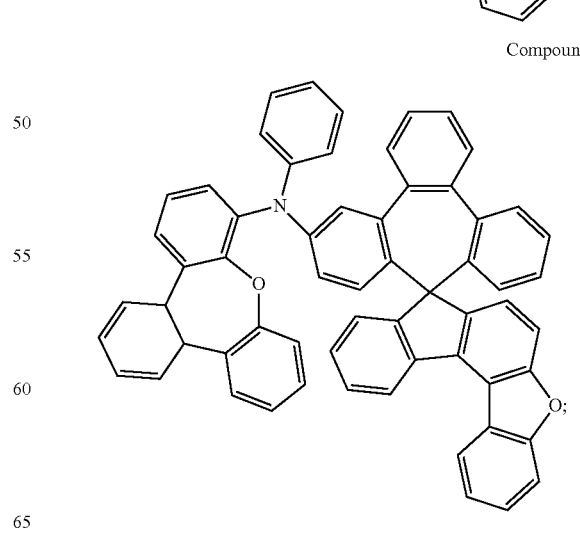

Compound 490
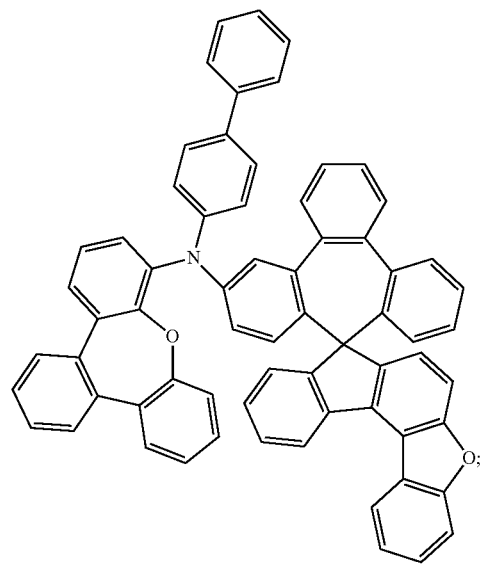
Compound 491
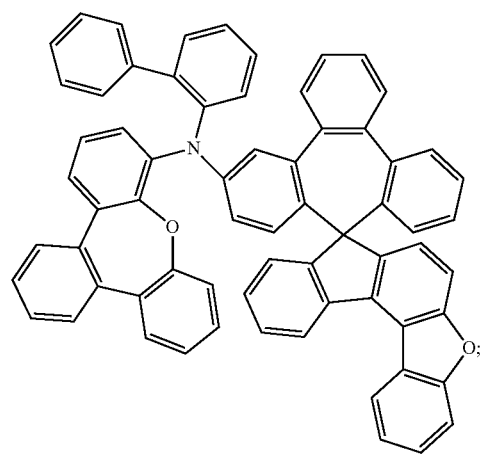
Compound 492
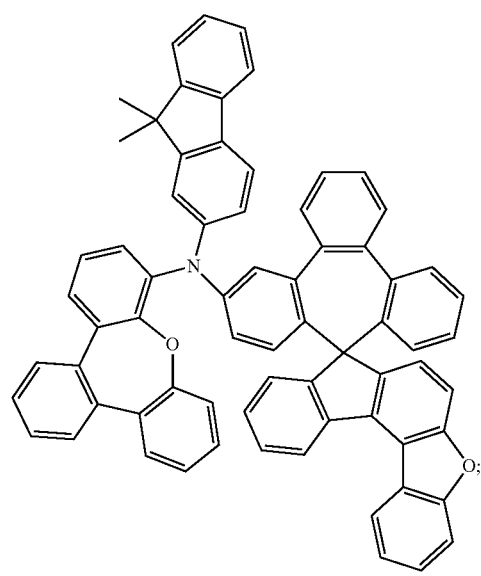
Compound 493
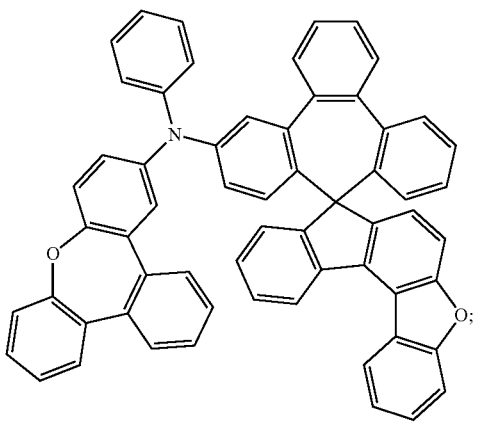
Compound 494
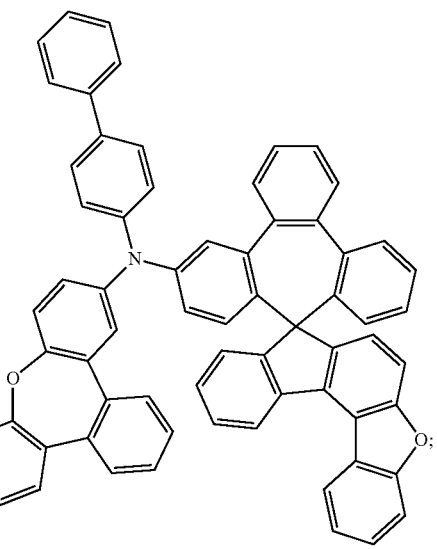
Compound 495
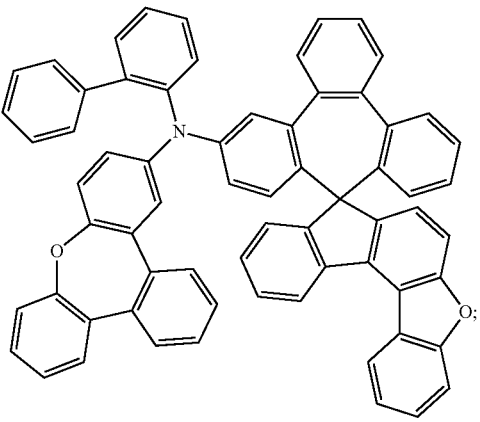

Compound 496
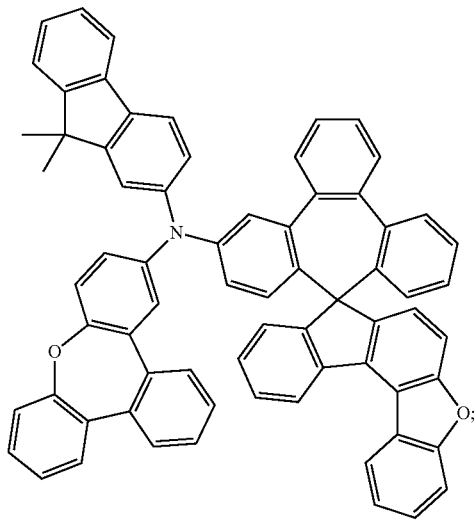
Compound 497
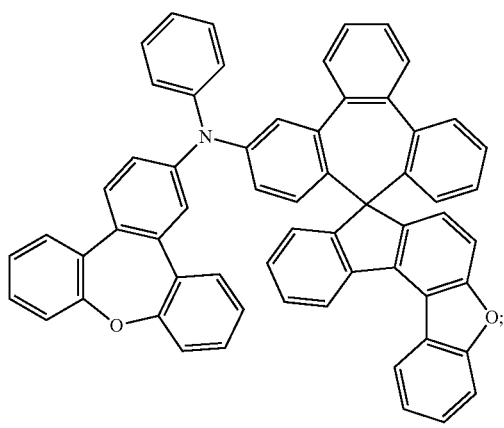
Compound 498
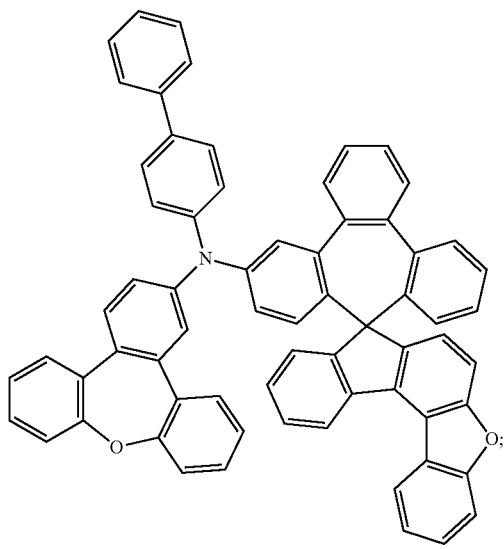
Compound 499
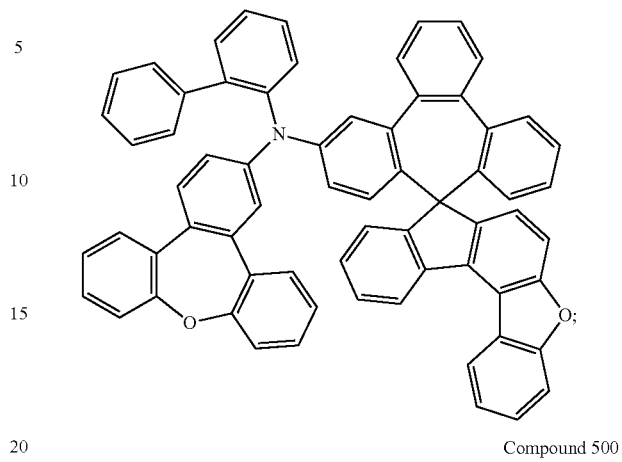
Compound 500
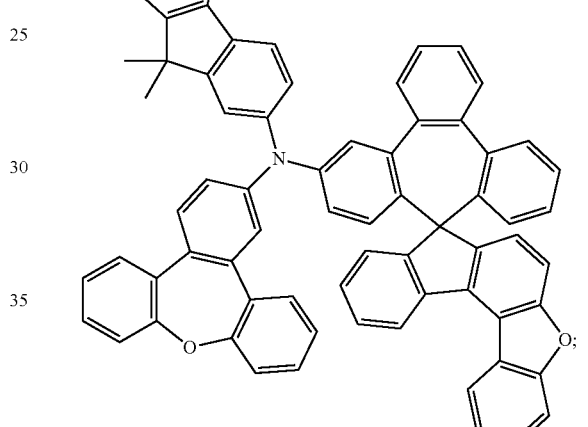
Compound 501
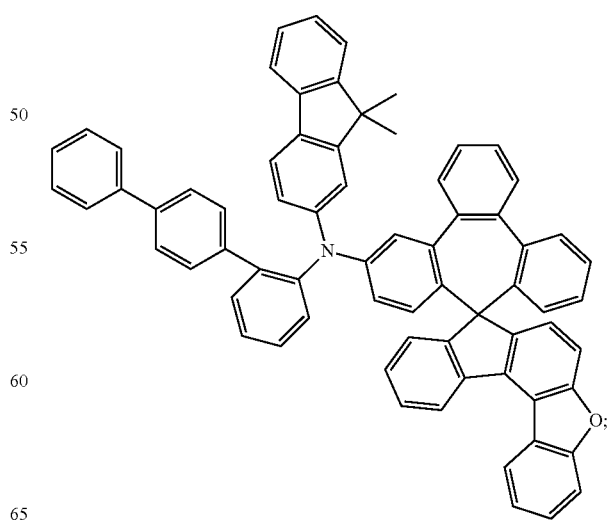

Compound 502
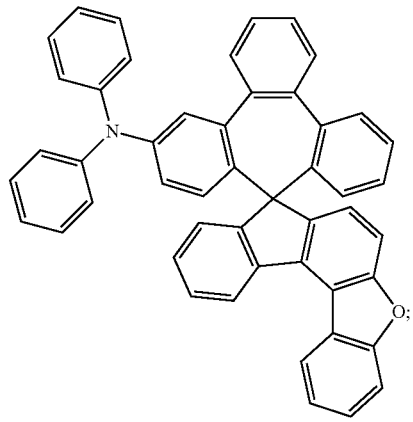
Compound 505
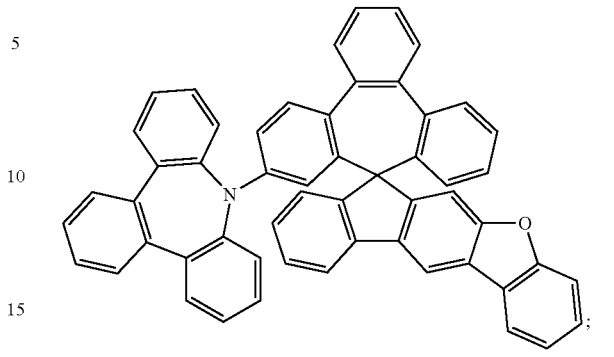
Compound 506
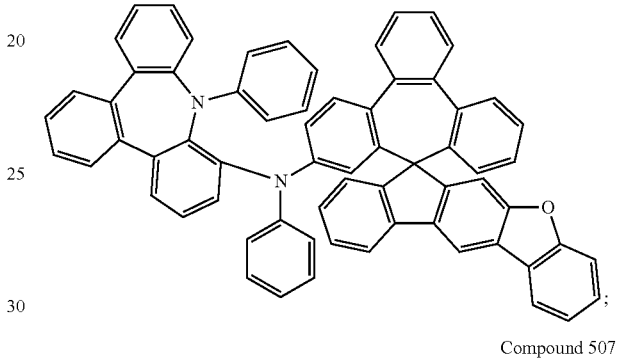
Compound 503
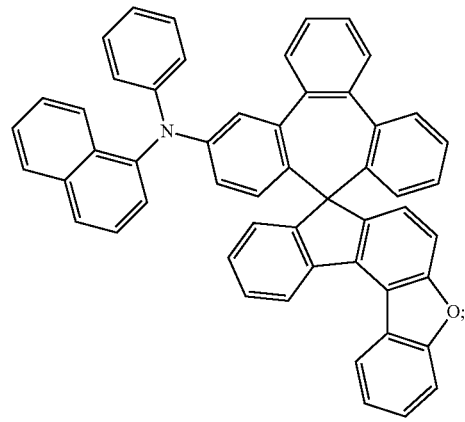
Compound 507
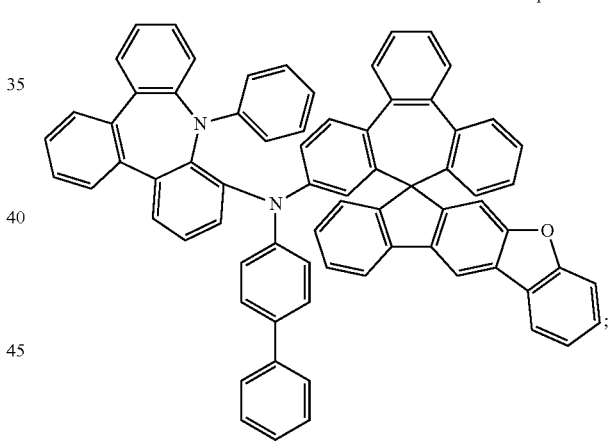
Compound 504
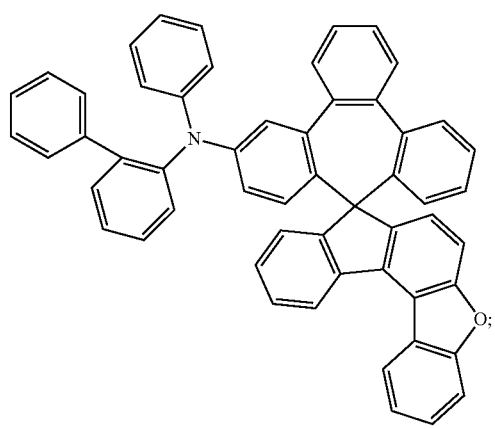
Compound 508
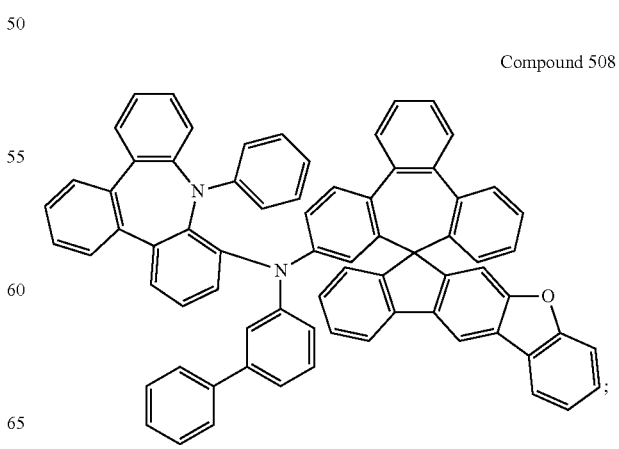

Compound 509
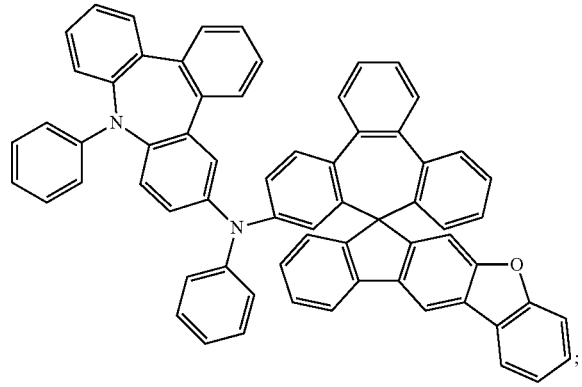
Compound 513
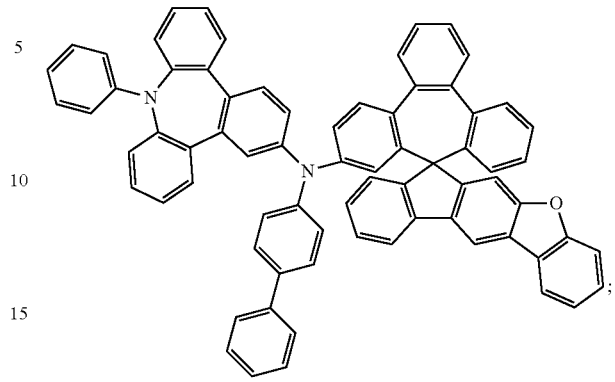
Compound 510
Compound 514
Compound 511
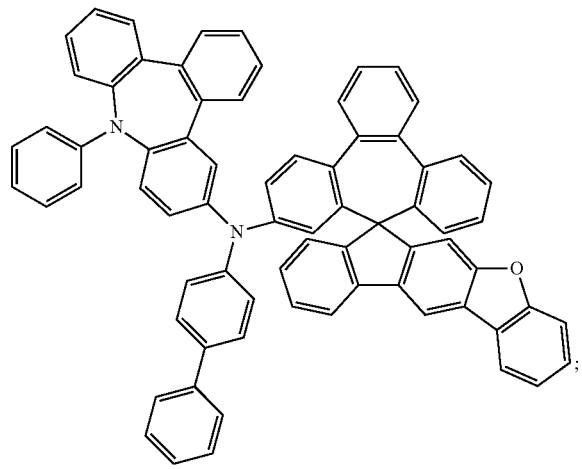
Compound 515
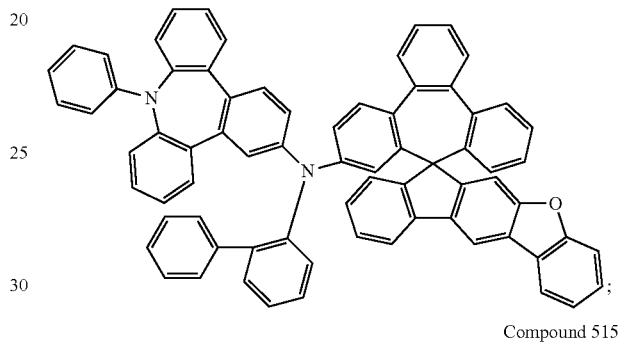
Compound 512
Compound 516
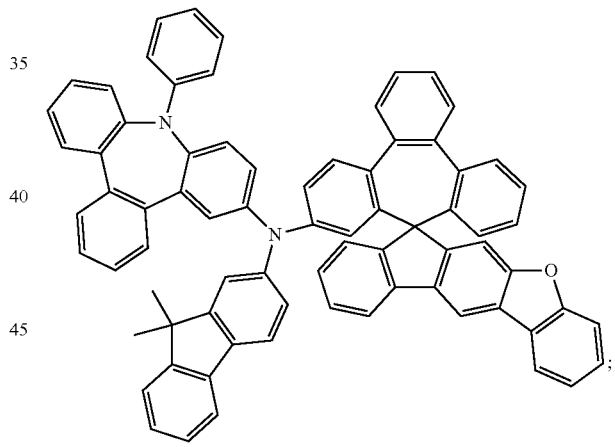
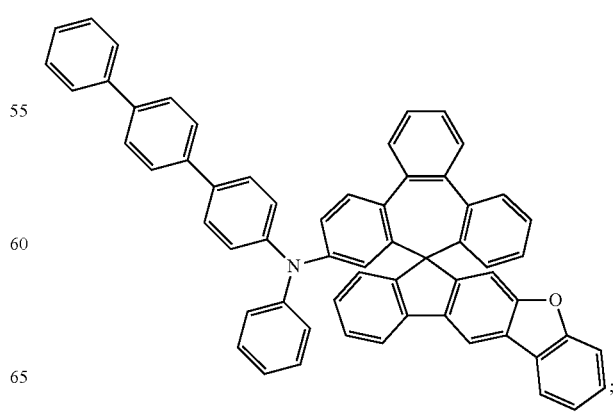

Compound 517
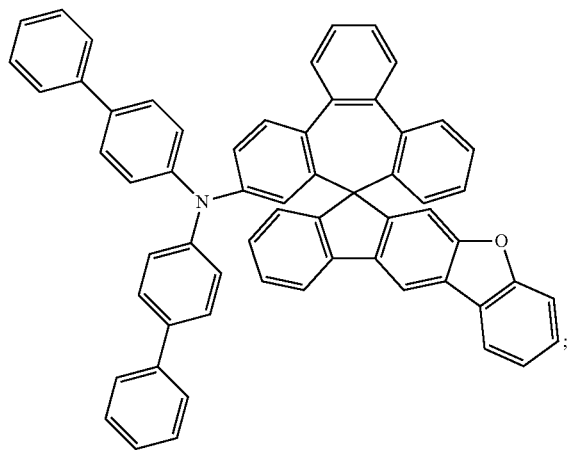
Compound 518
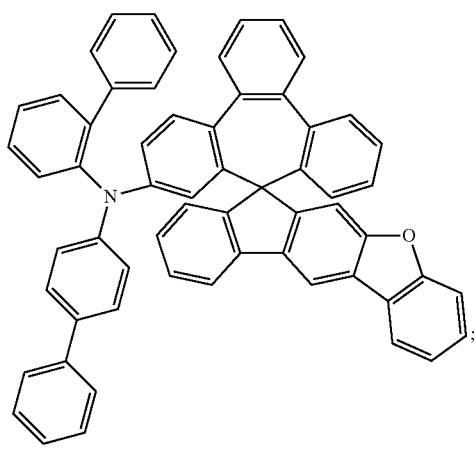
Compound 519
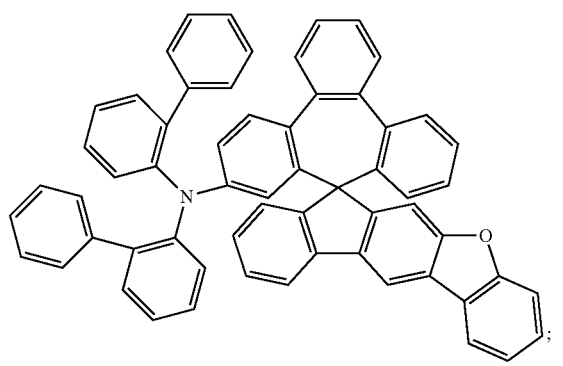
Compound 520
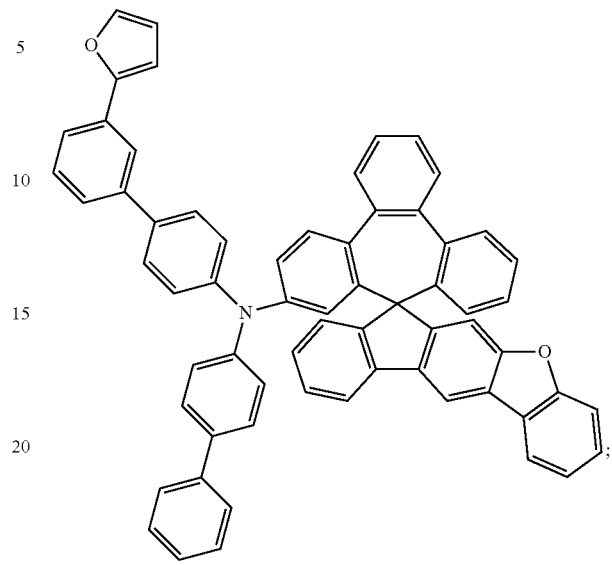
Compound 521
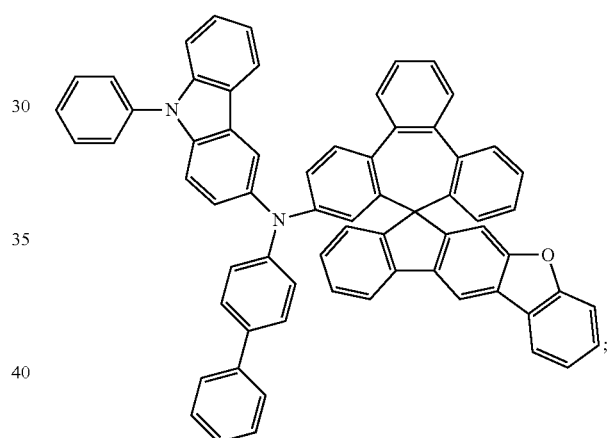
Compound 522
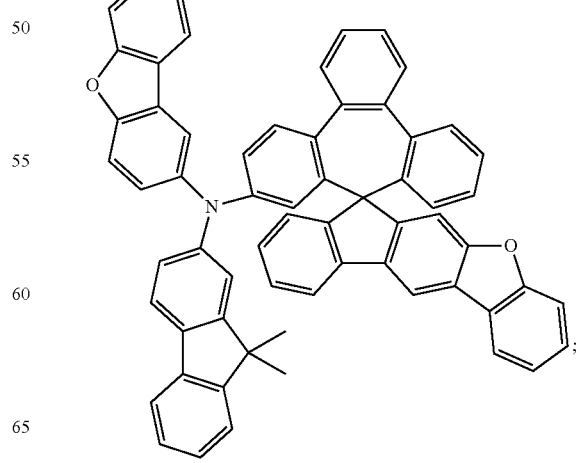

Compound 523
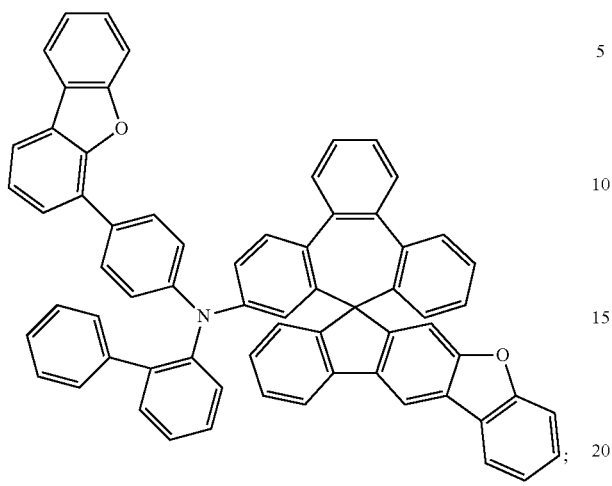
Compound 526
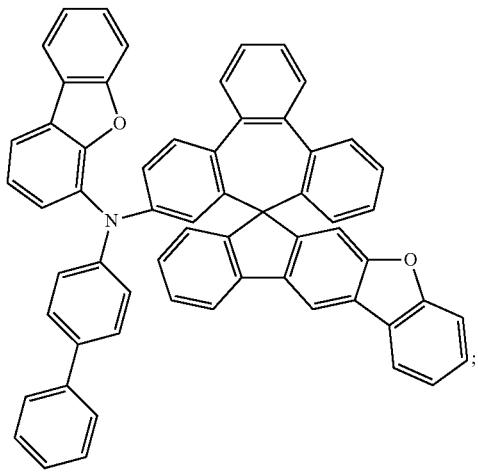
Compound 524
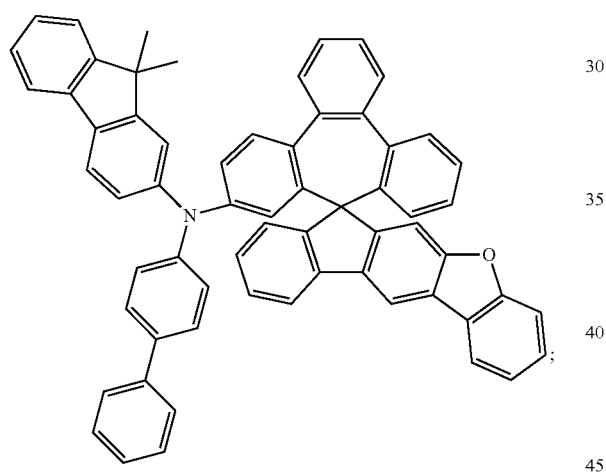
Compound 527
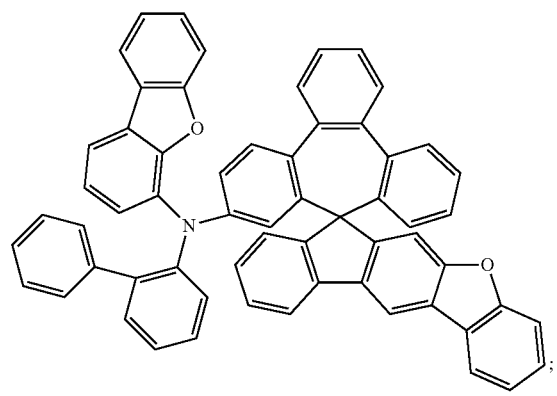
Compound 525
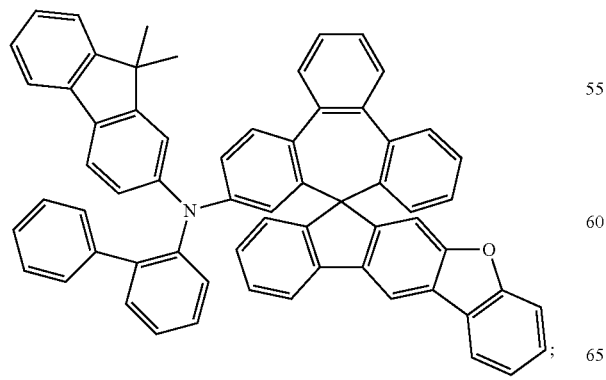
Compound 528
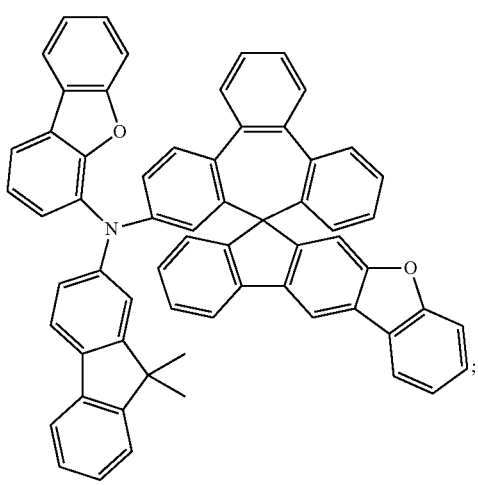

-continued
Compound 529
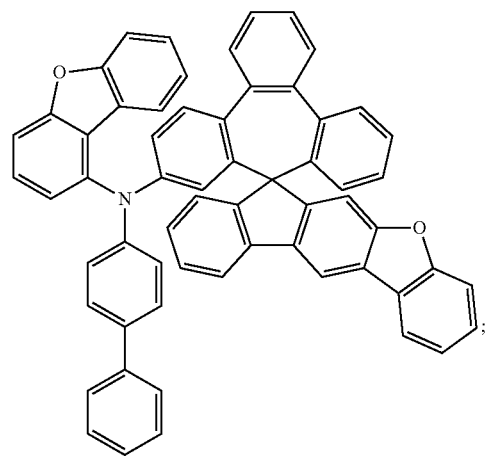
Compound 530
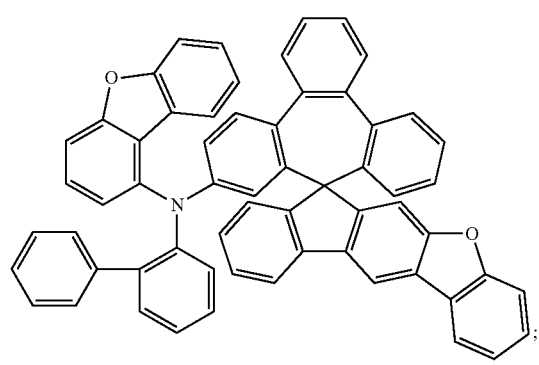
Compound 531
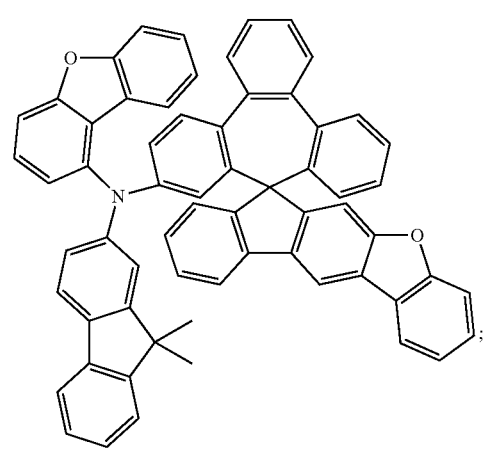
-continued
Compound 532
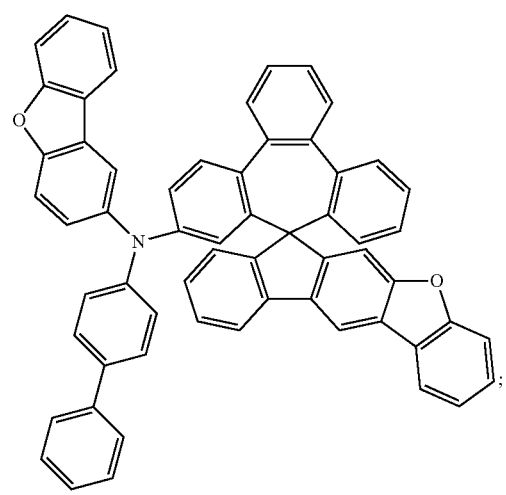
Compound 533
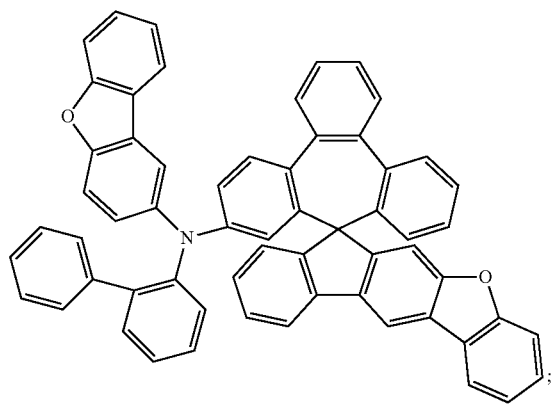
Compound 534
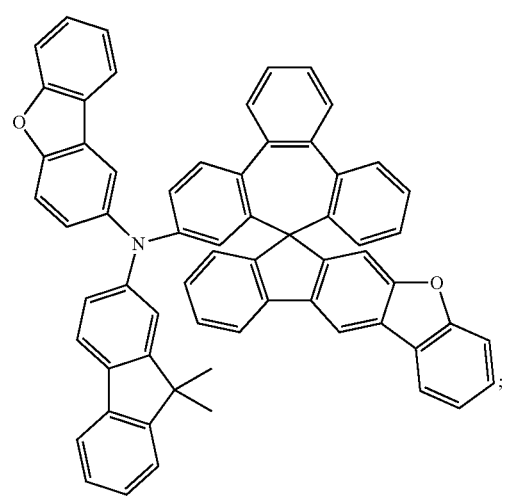

-continued
Compound 535
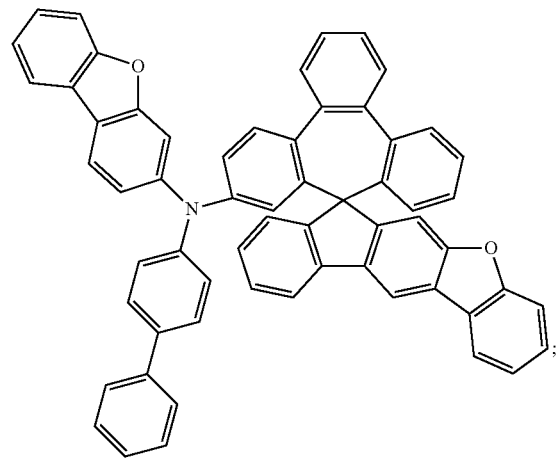
Compound 536
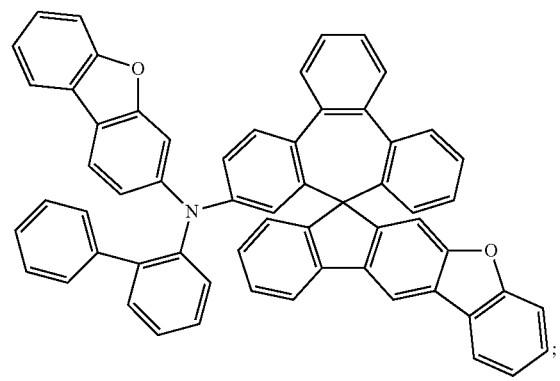
Compound 537
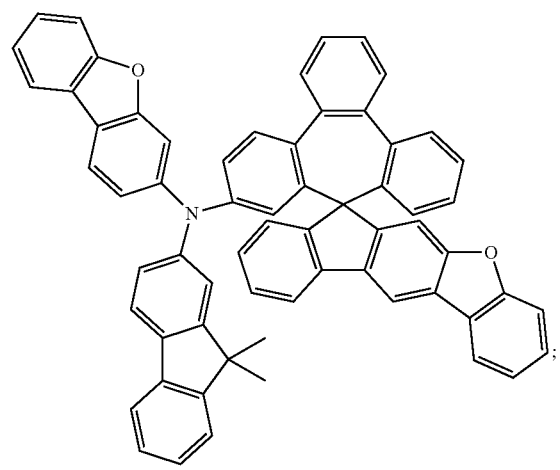
-continued
Compound 538
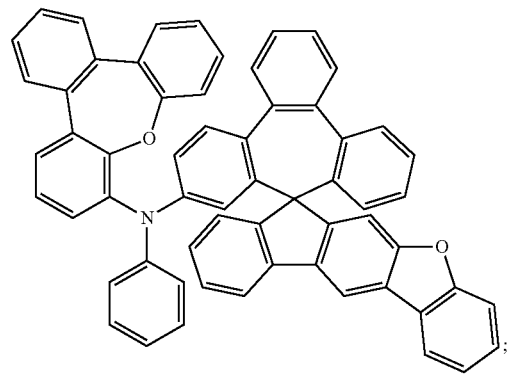
Compound 539
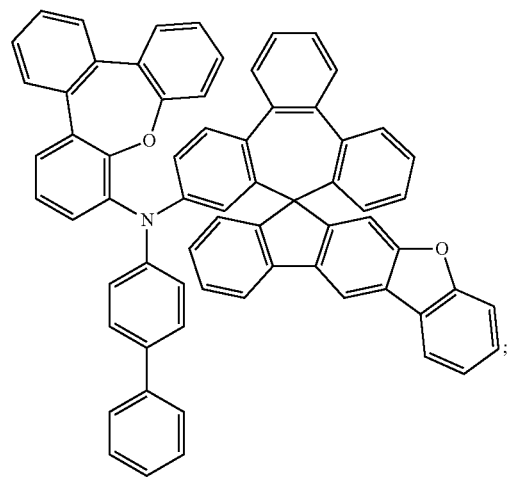
Compound 540
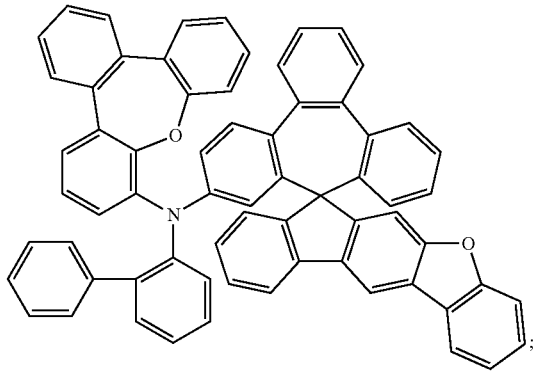

Compound 541
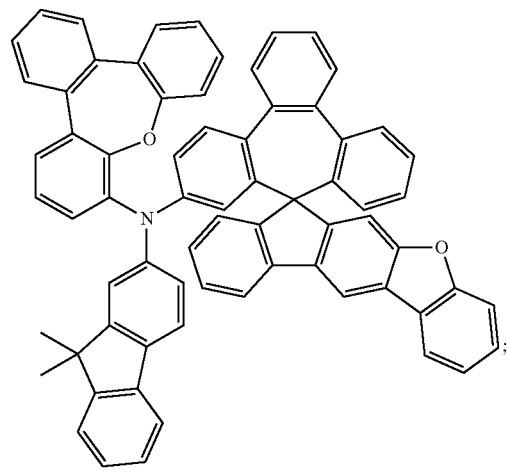
Compound 544
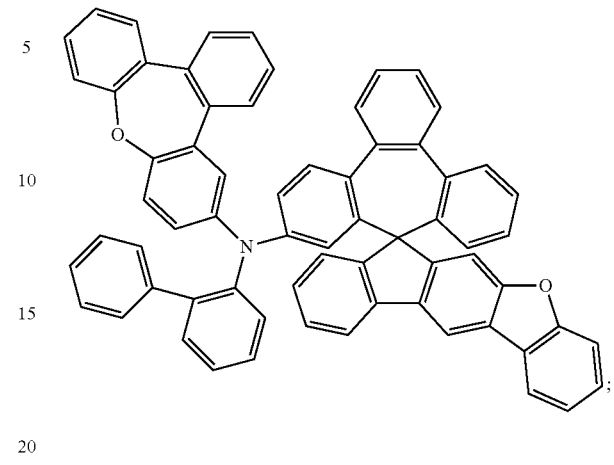
Compound 542
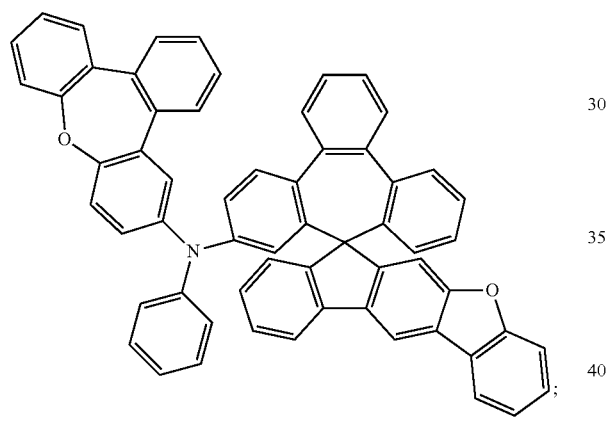
Compound 545
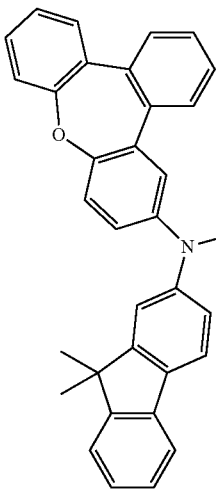
Compound 543
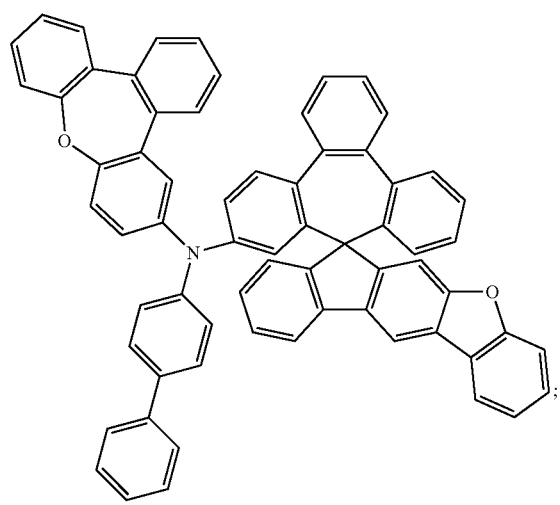
Compound 546
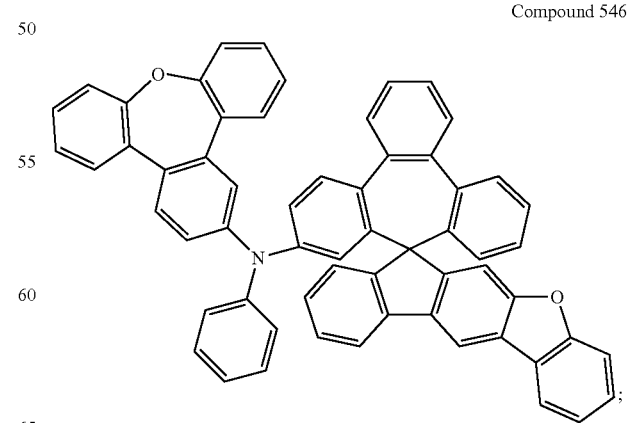

-continued
Compound 547
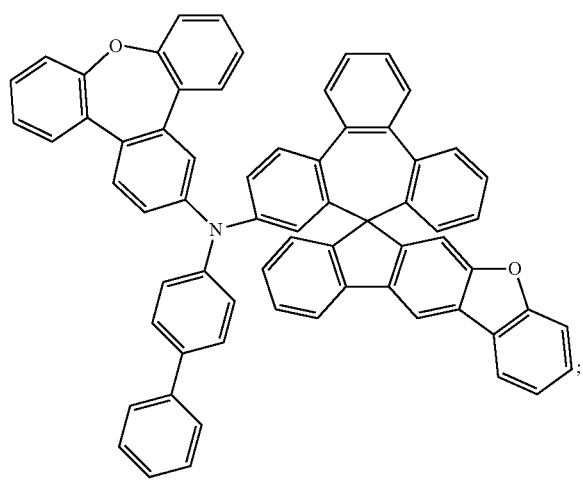
Compound 548
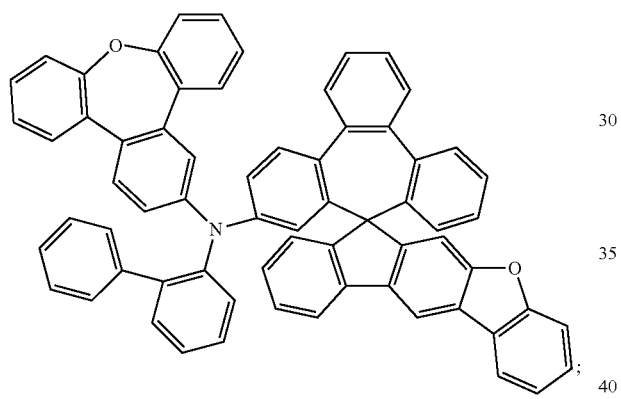
Compound 549
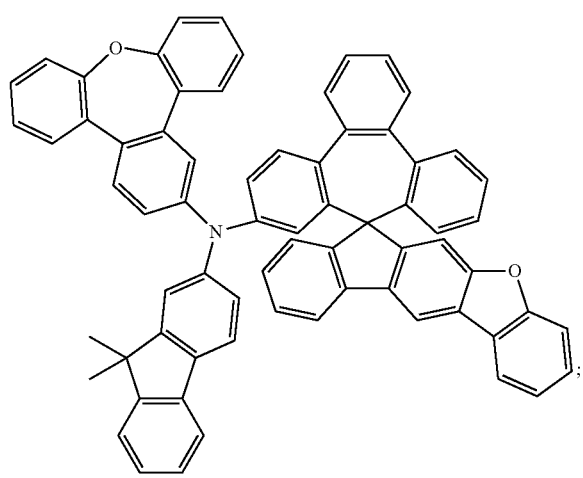
-continued
Compound 550
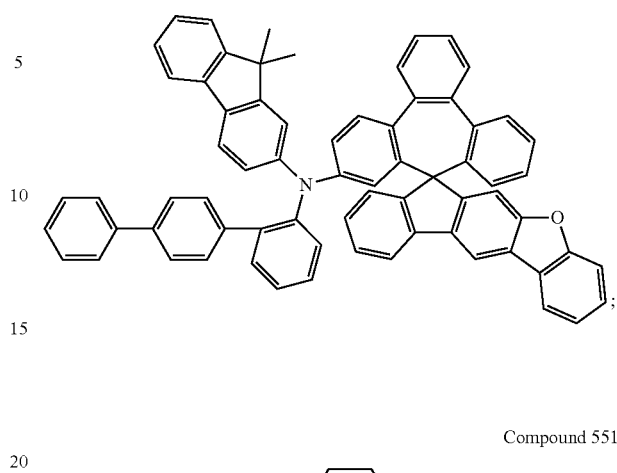
Compound 551
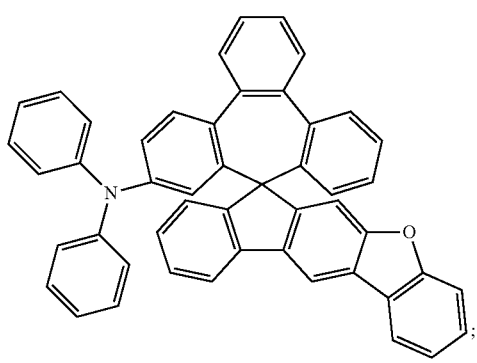
Compound 552
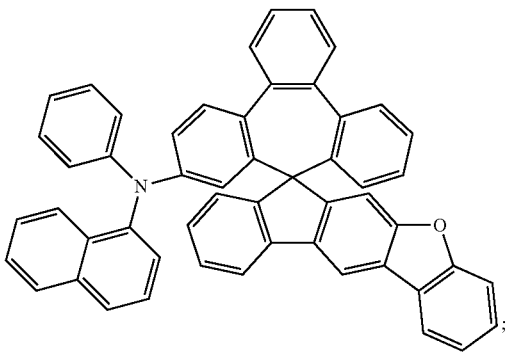
Compound 553
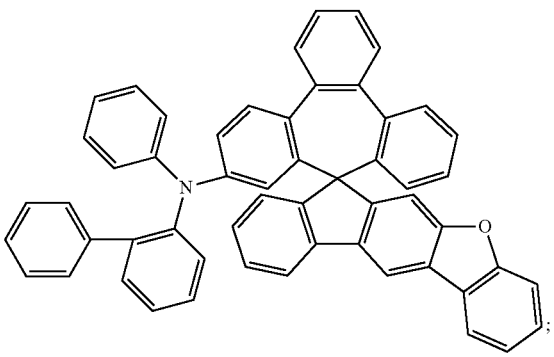

Compound 554
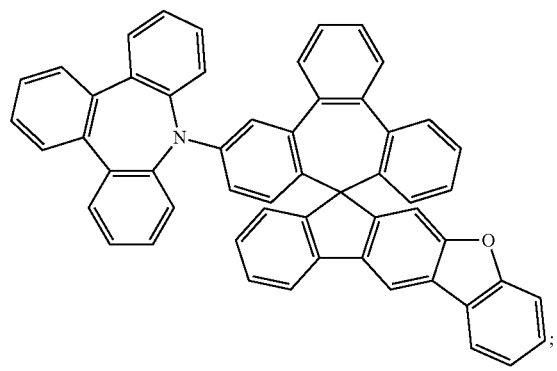
Compound 555
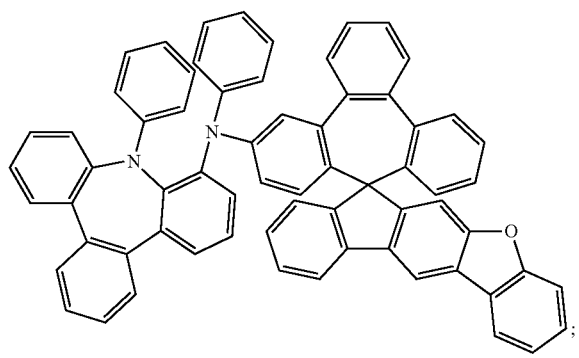
Compound 556
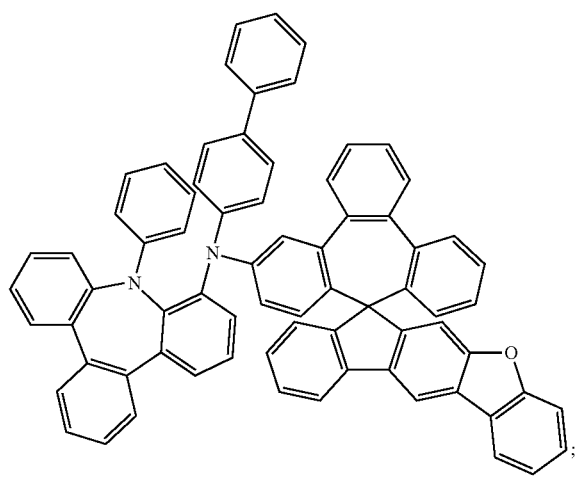
Compound 557
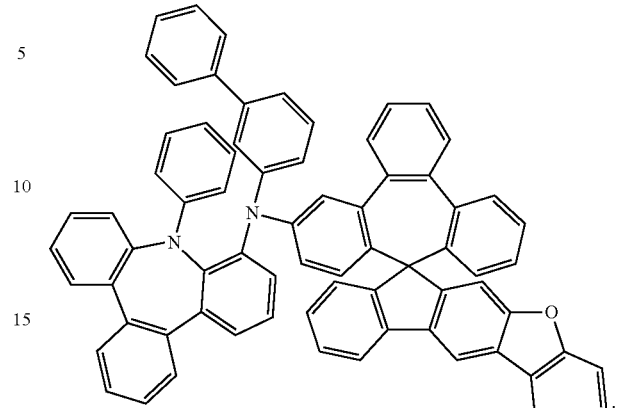
Compound 558
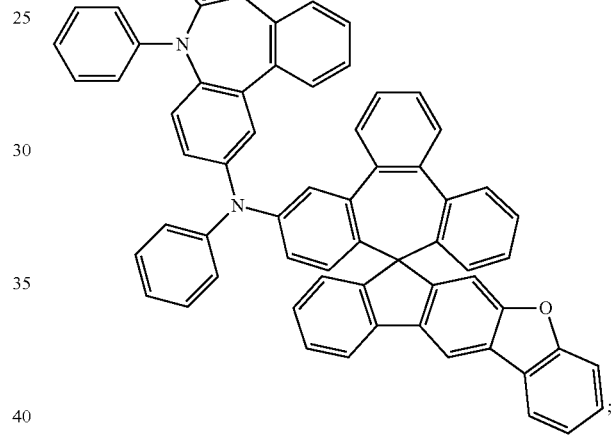
Compound 559
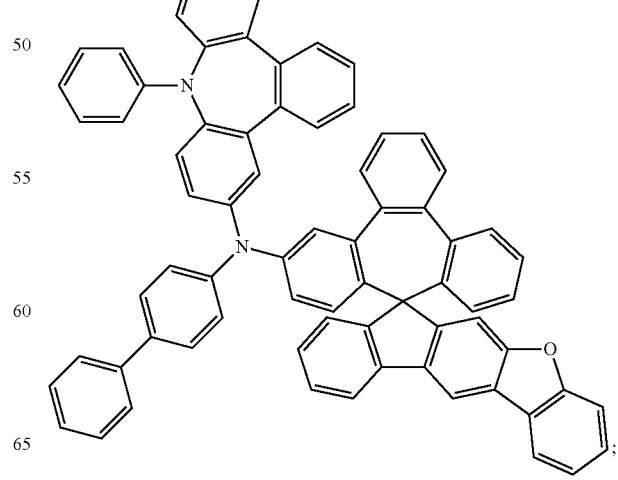

Compound 560
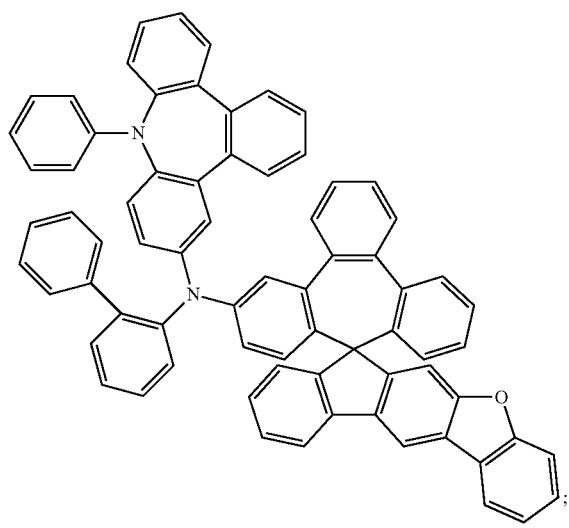
Compound 563
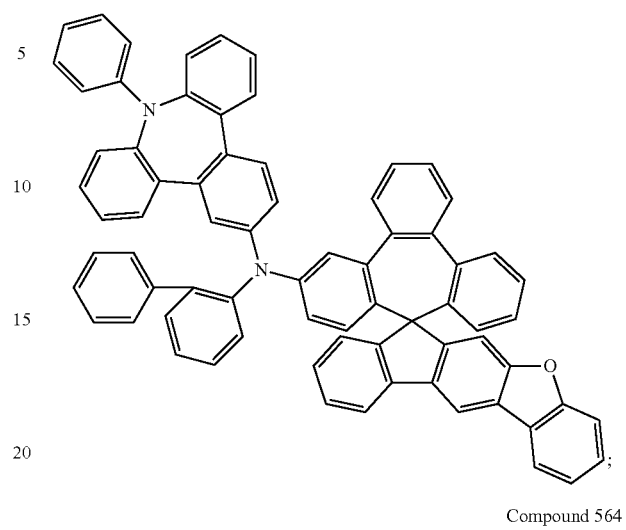
Compound 561
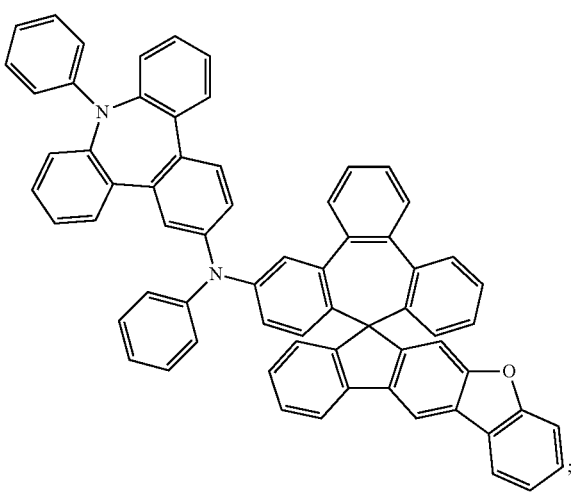
Compound 564
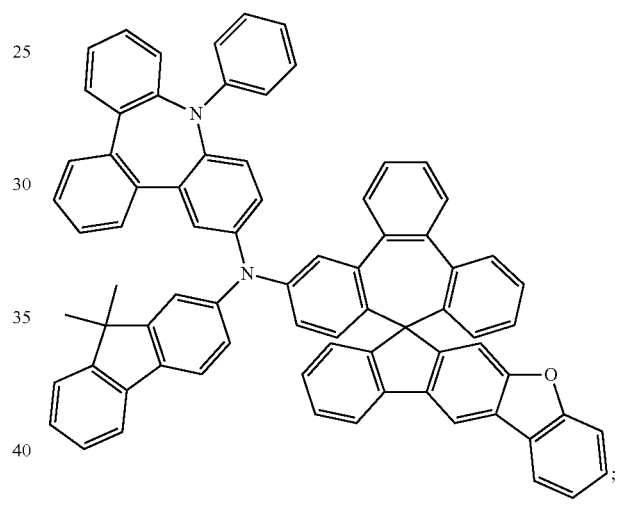
Compound 562
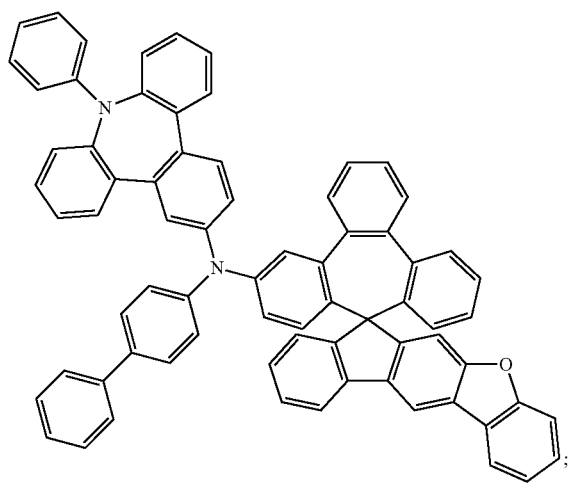
Compound 565
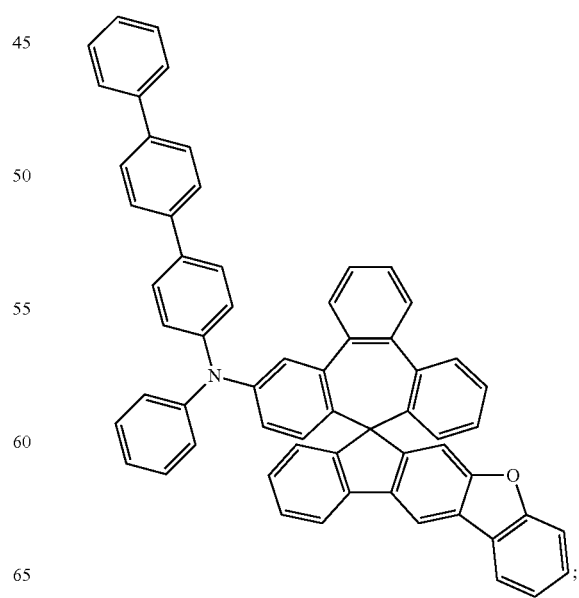

Compound 566
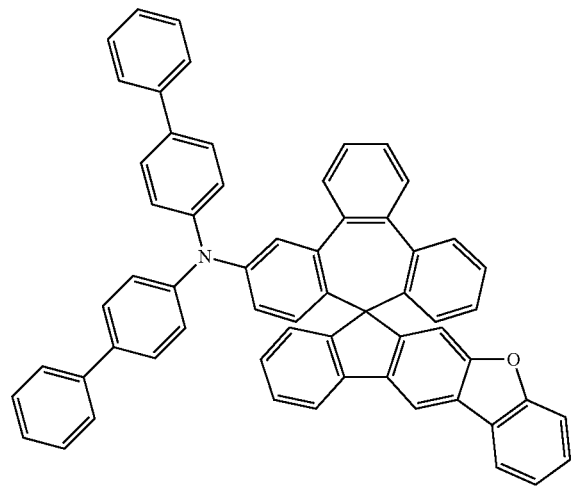
Compound 567
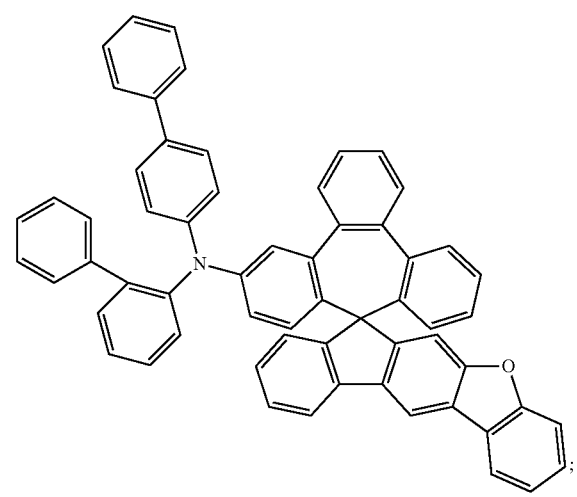
Compound 568
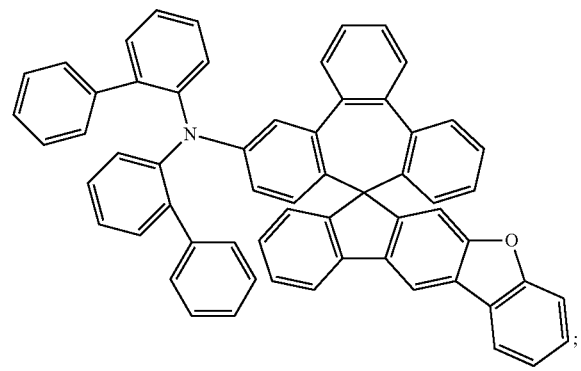
Compound 569
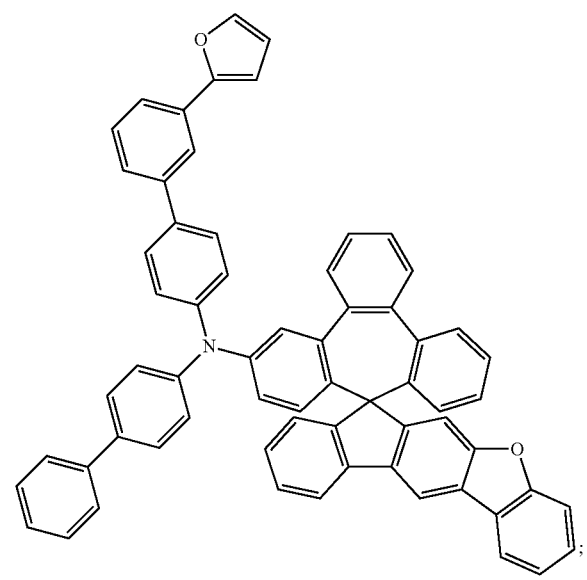
Compound 570
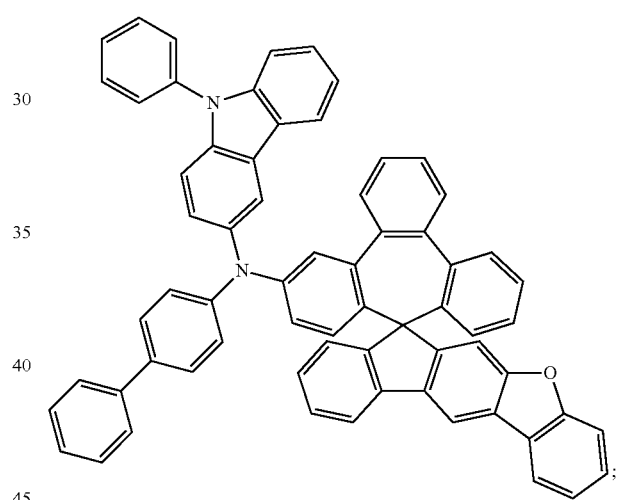
Compound 571
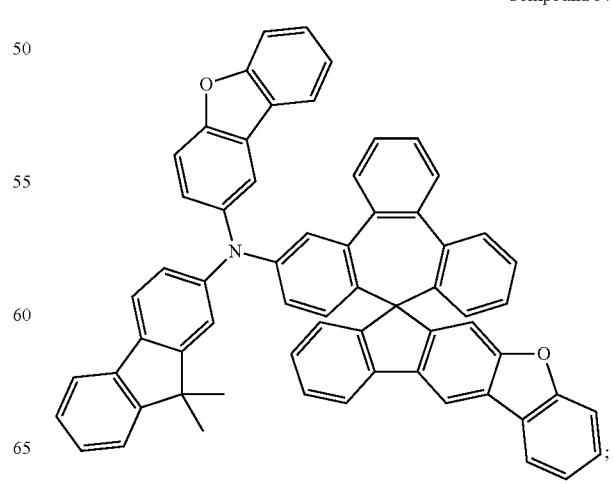

-continued
Compound 572
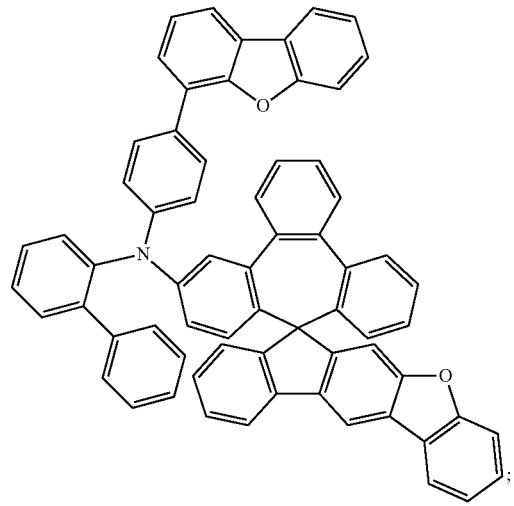
Compound 573
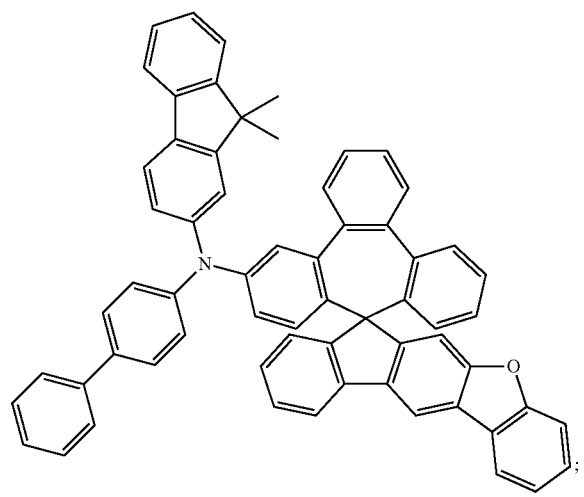
Compound 574
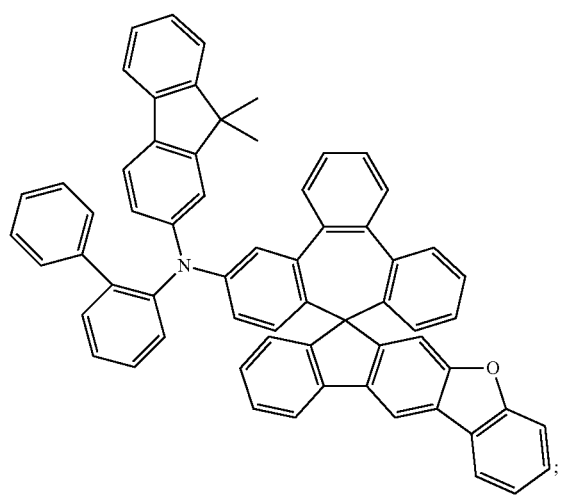
-continued
Compound 575
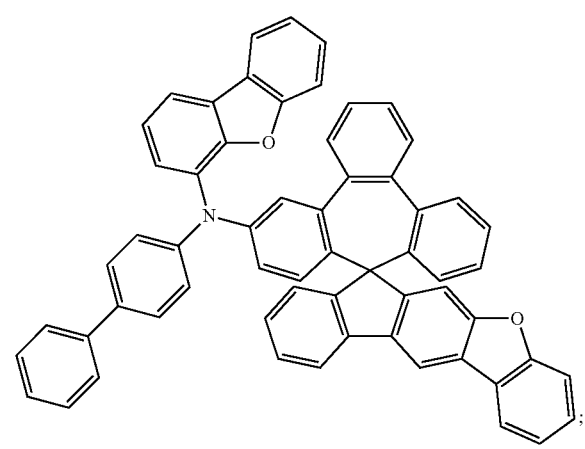
Compound 576
Compound 577

Compound 578
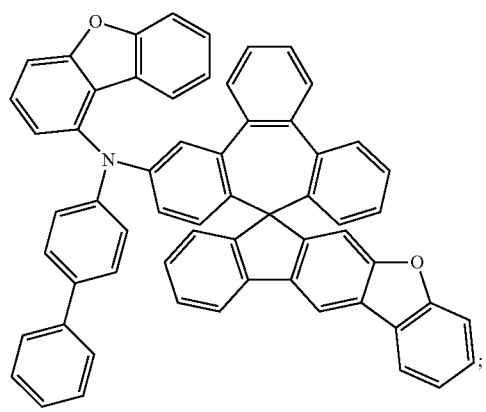
Compound 579
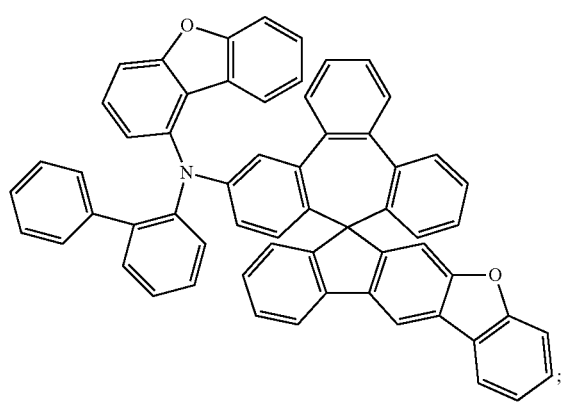
Compound 580
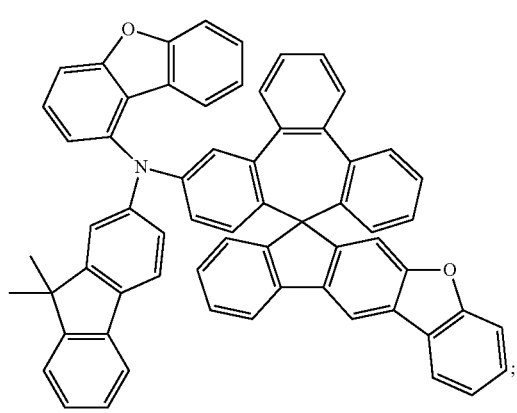
Compound 581
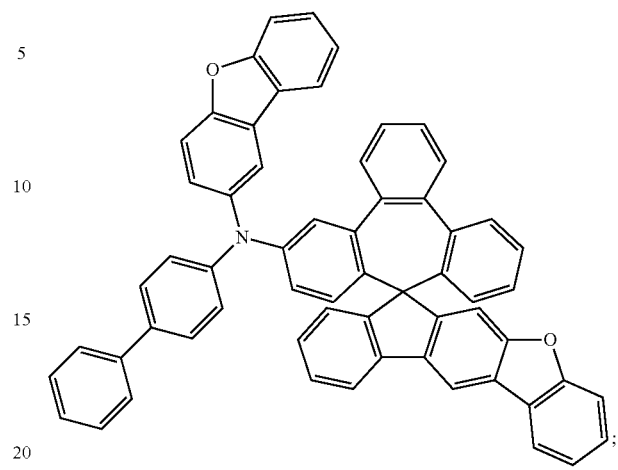
Compound 582
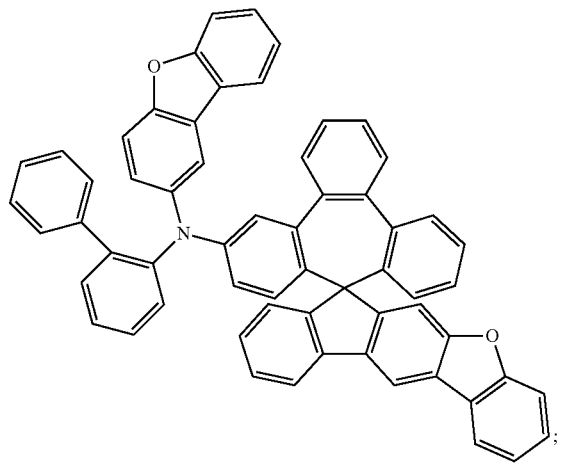
Compound 583
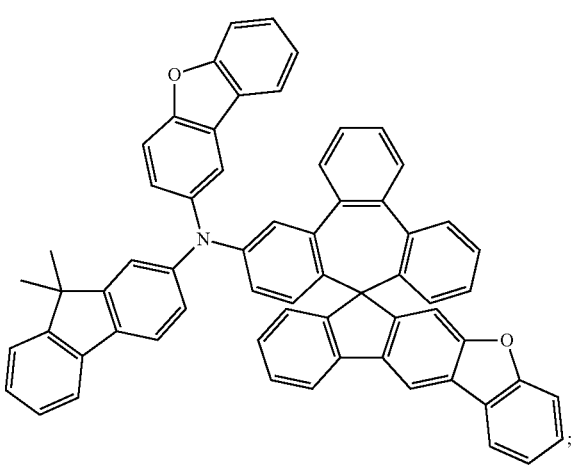

Compound 584
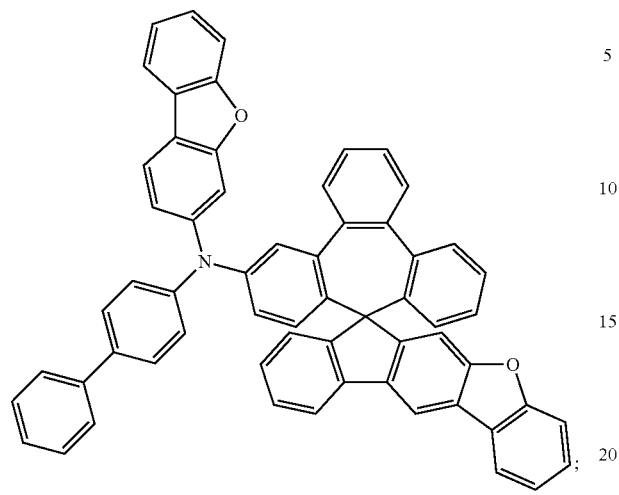
Compound 585
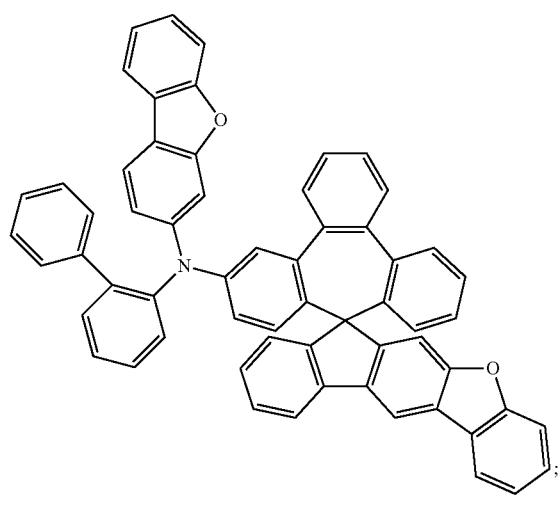
Compound 586
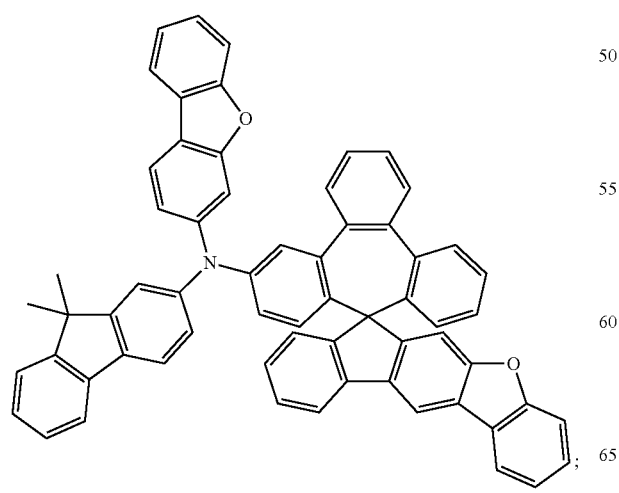
Compound 587
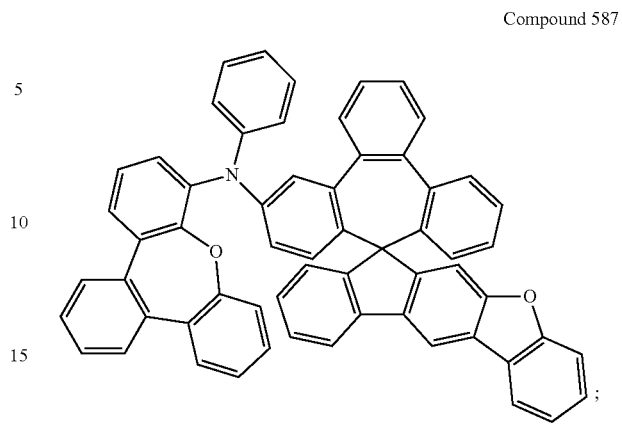
Compound 588
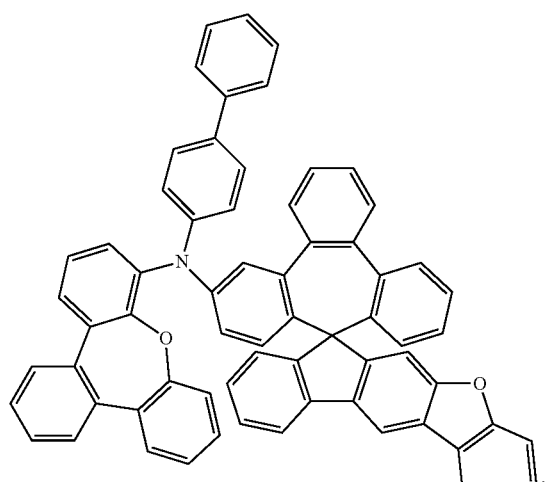
Compound 589
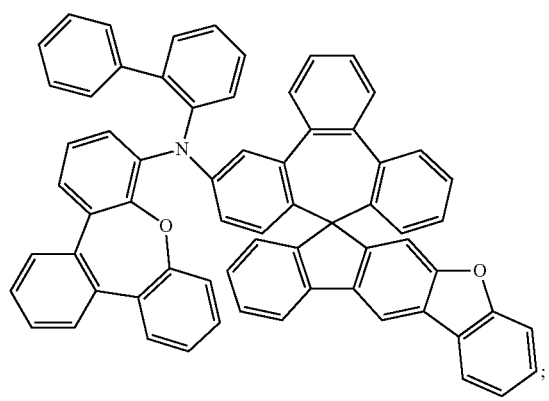

Compound 590
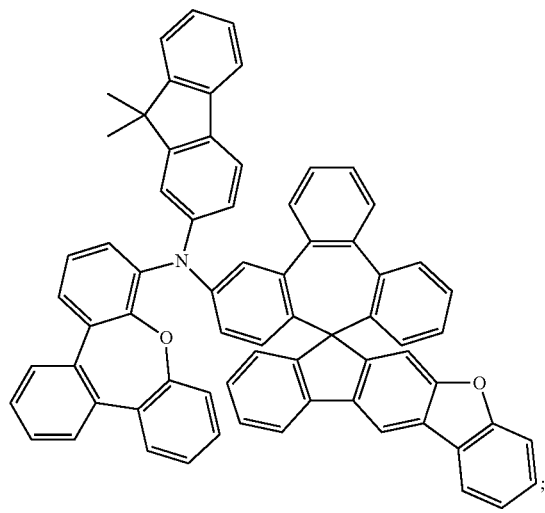
Compound 591
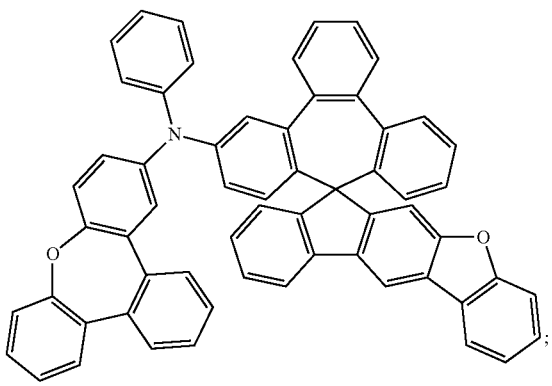
Compound 592
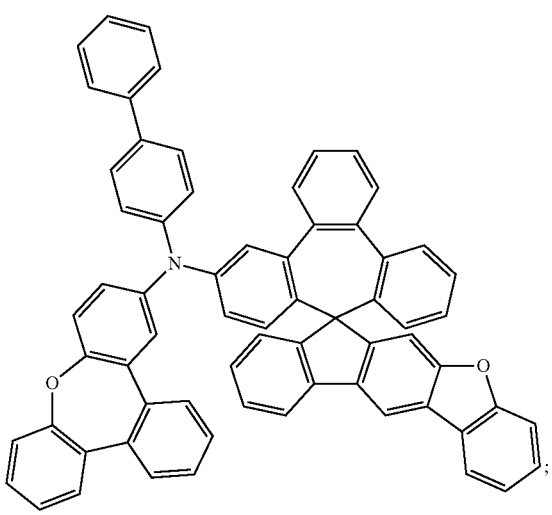
Compound 593
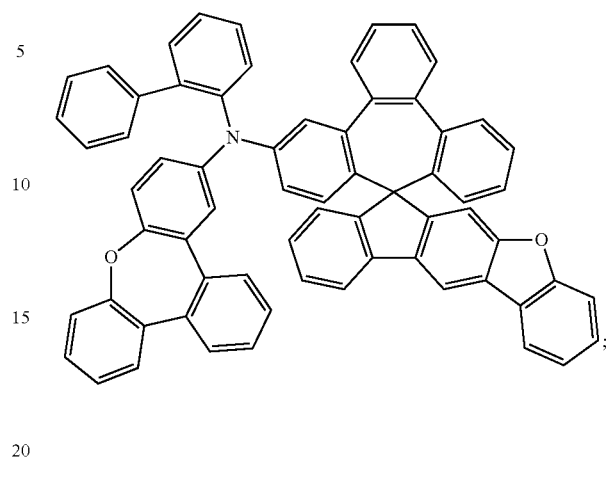
Compound 594
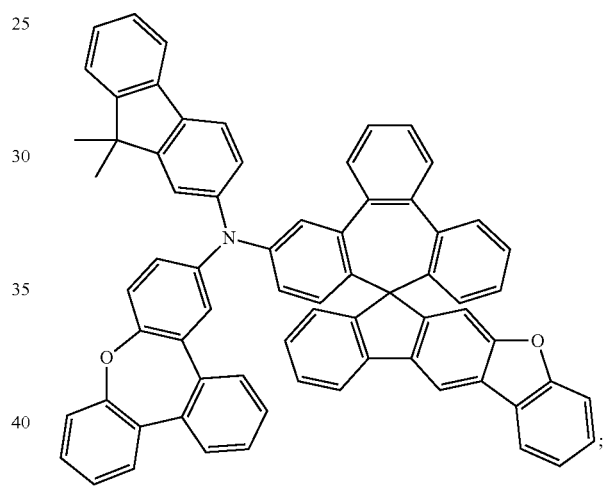
Compound 595
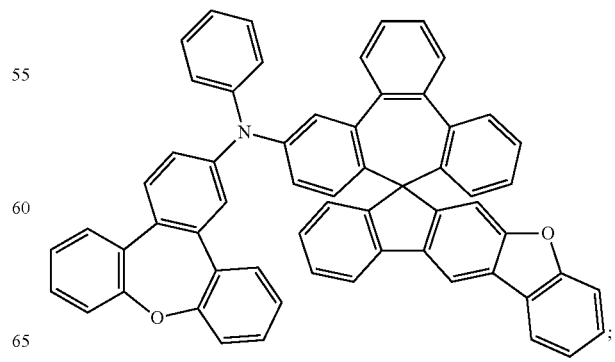

Compound 596
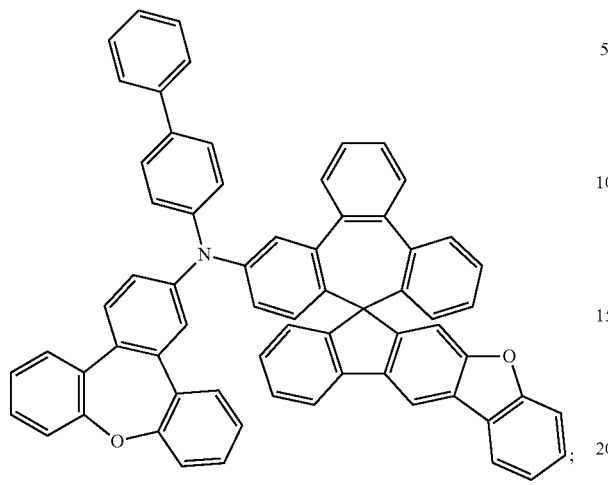
Compound 597
Compound 598
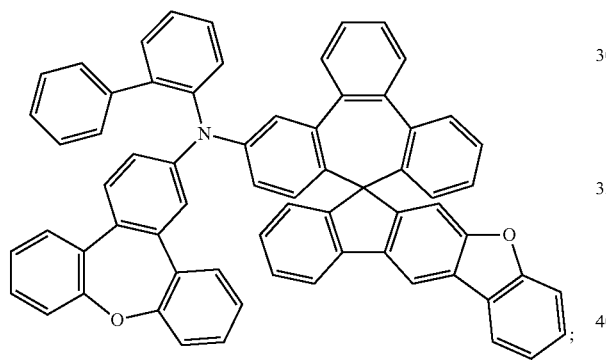
Compound 599
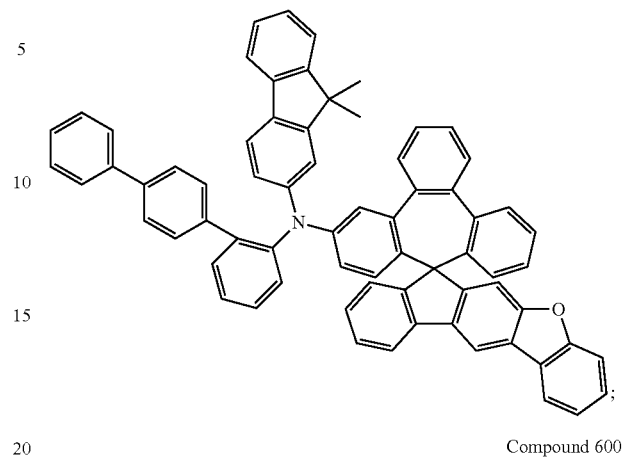
Compound 600
Compound 601
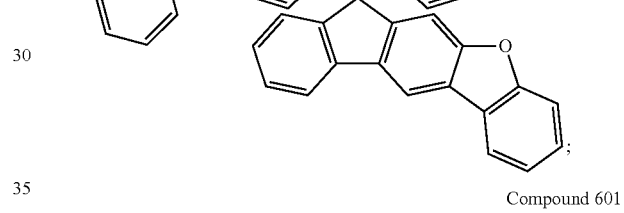
Compound 602
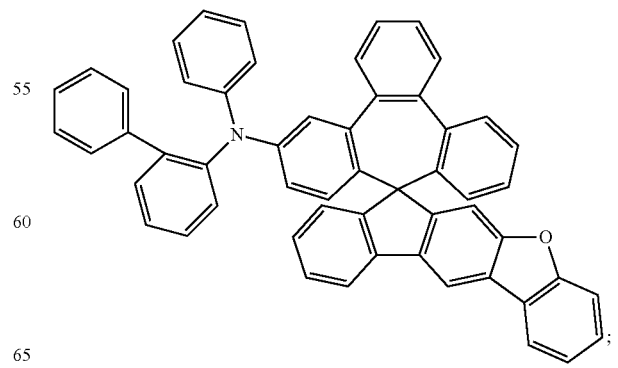

Compound 603
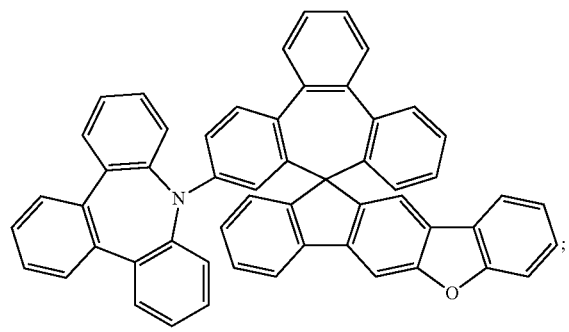
Compound 604
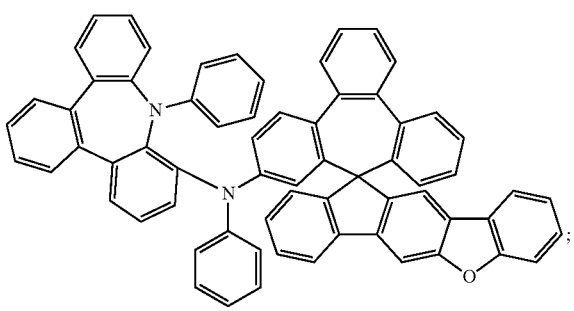
Compound 605
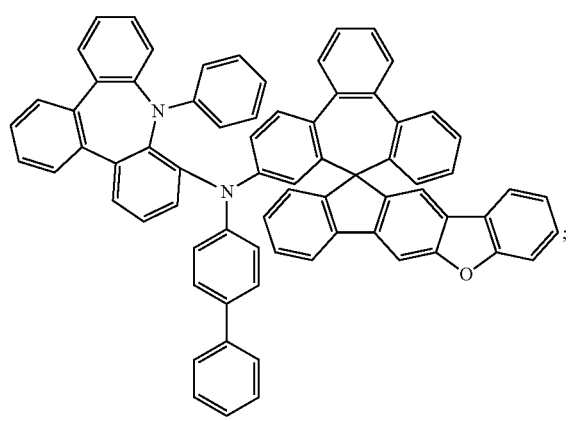
Compound 606
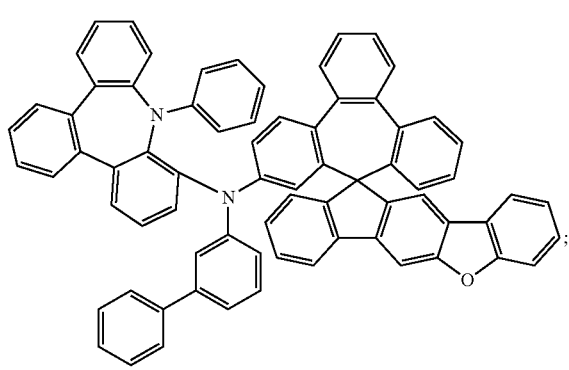
Compound 607
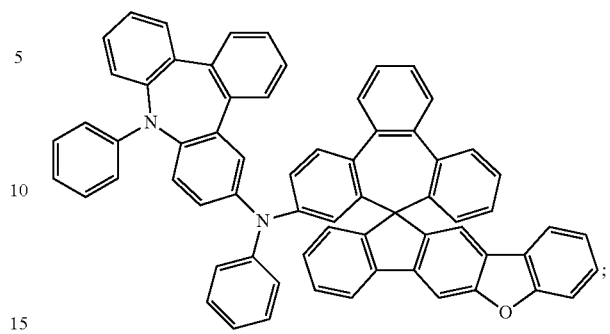
Compound 608
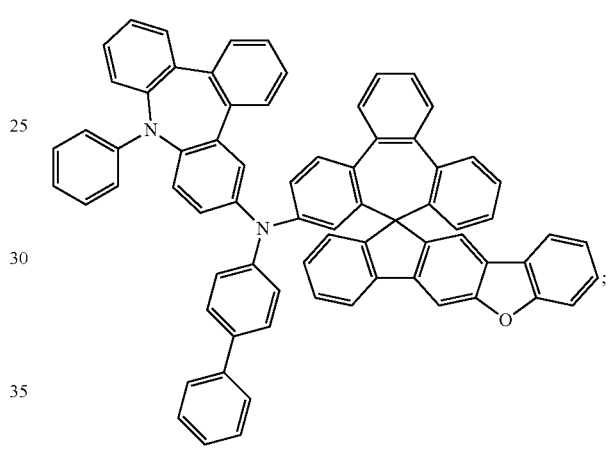
Compound 609
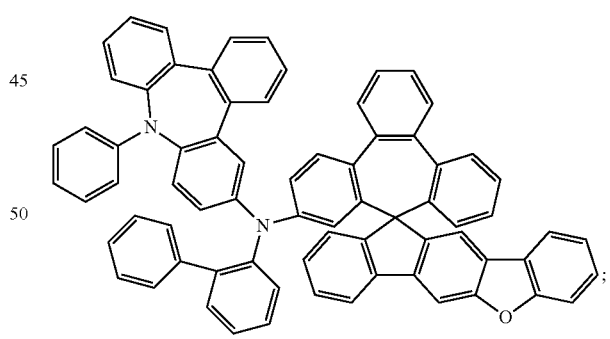
Compound 610
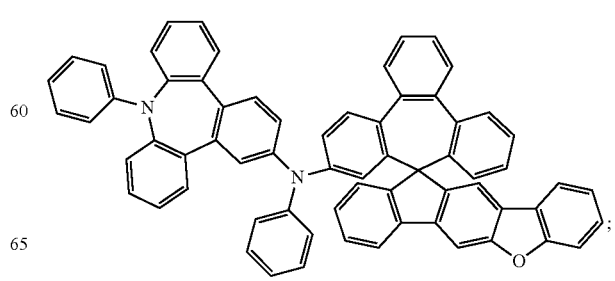

-continued
Compound 611
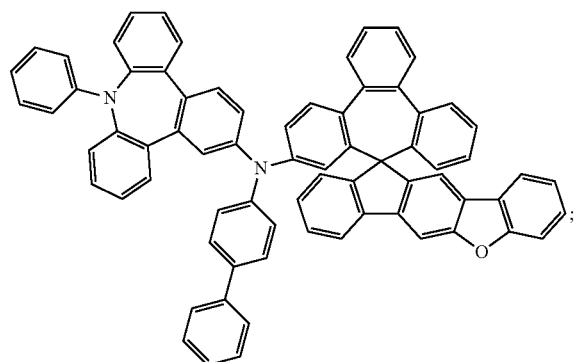
Compound 612
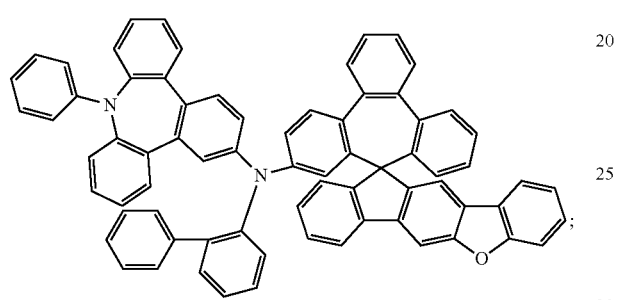
Compound 613
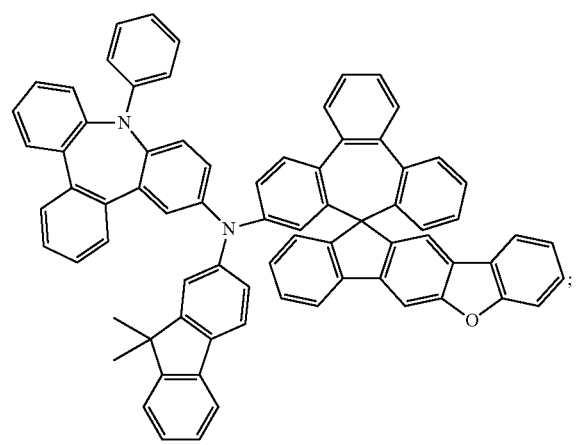
Compound 614
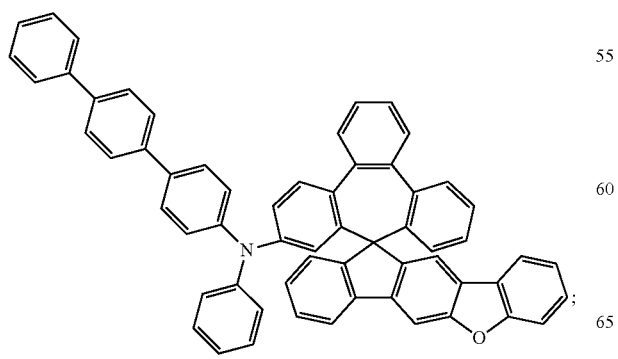
-continued
Compound 615
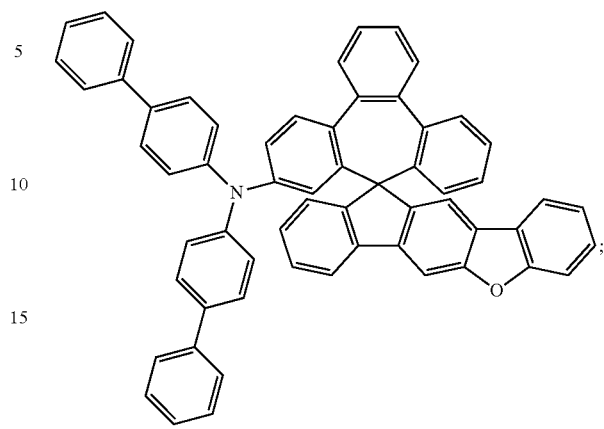
Compound 616
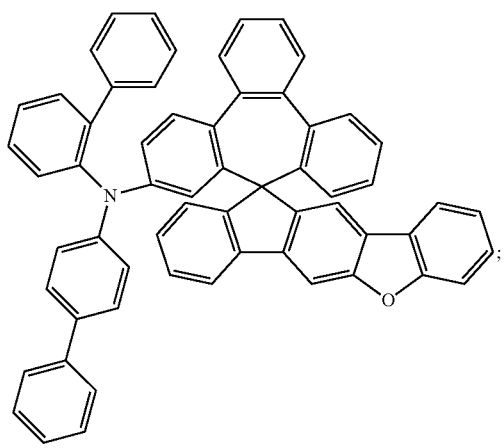
Compound 617
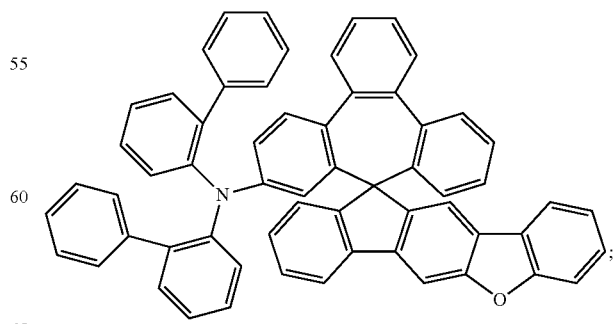

Compound 618
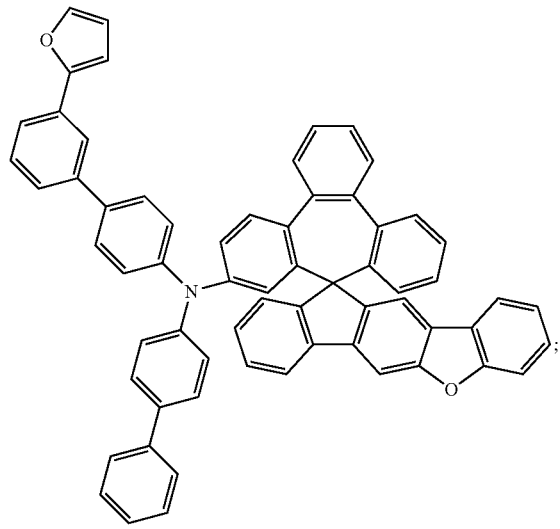
Compound 619
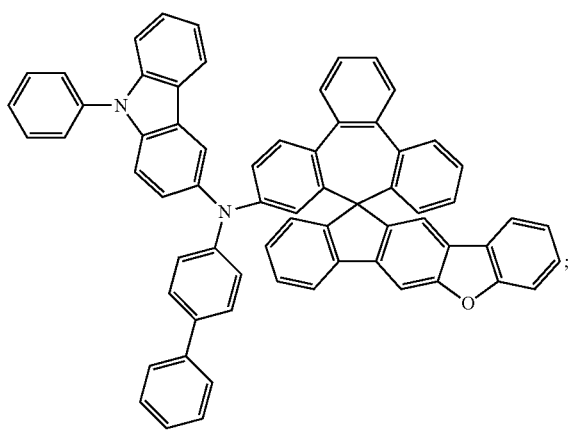
Compound 620
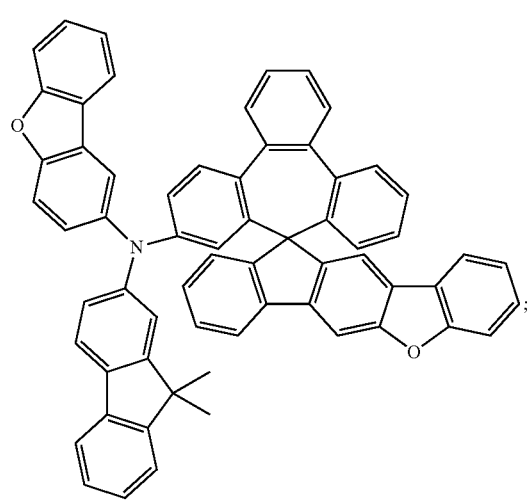
Compound 621
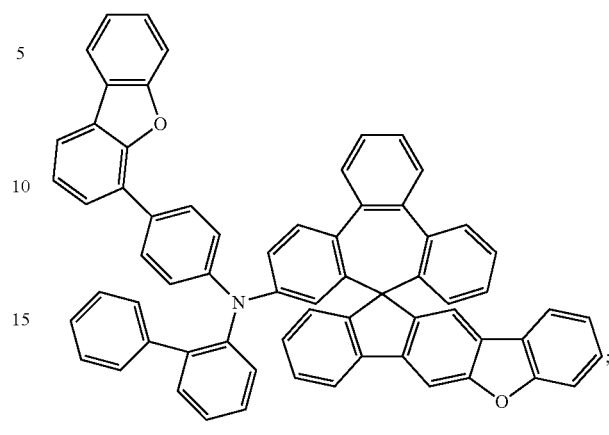
Compound 622
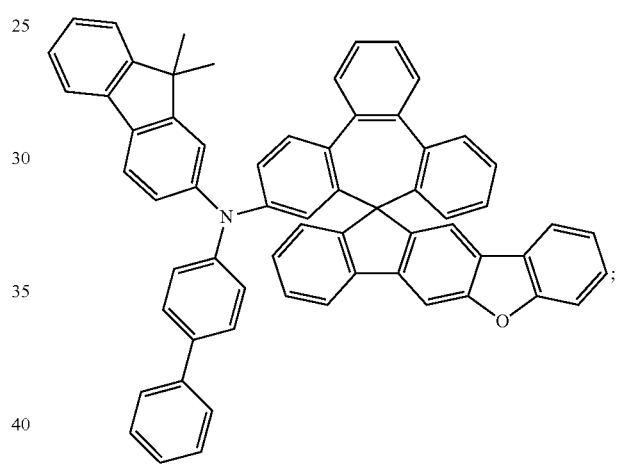
Compound 623
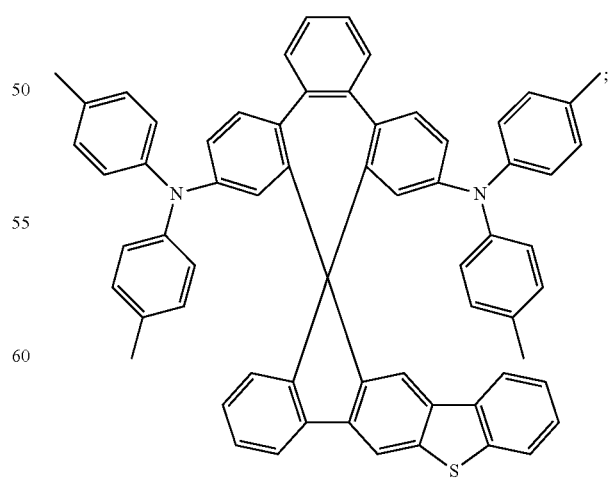

Compound 624
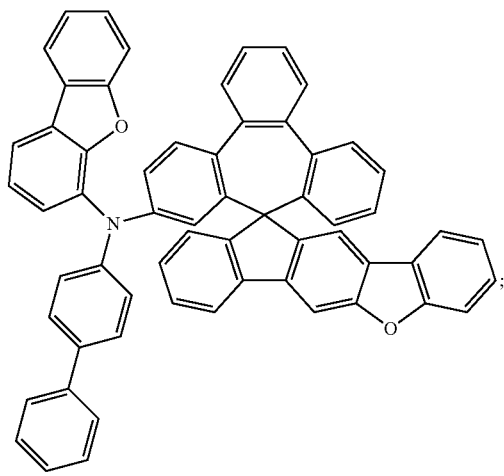
Compound 625
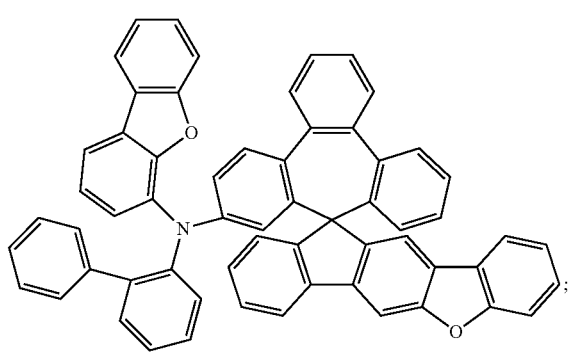
Compound 626
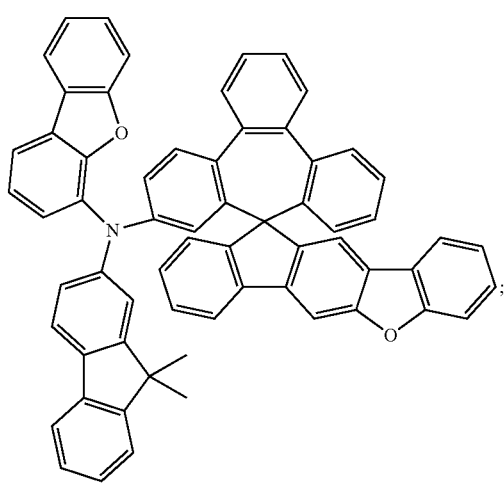
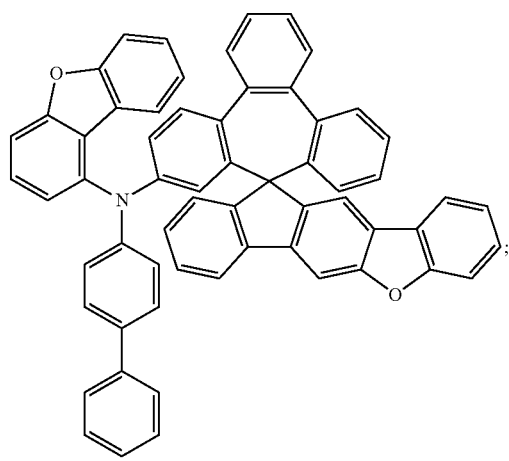
Compound 627
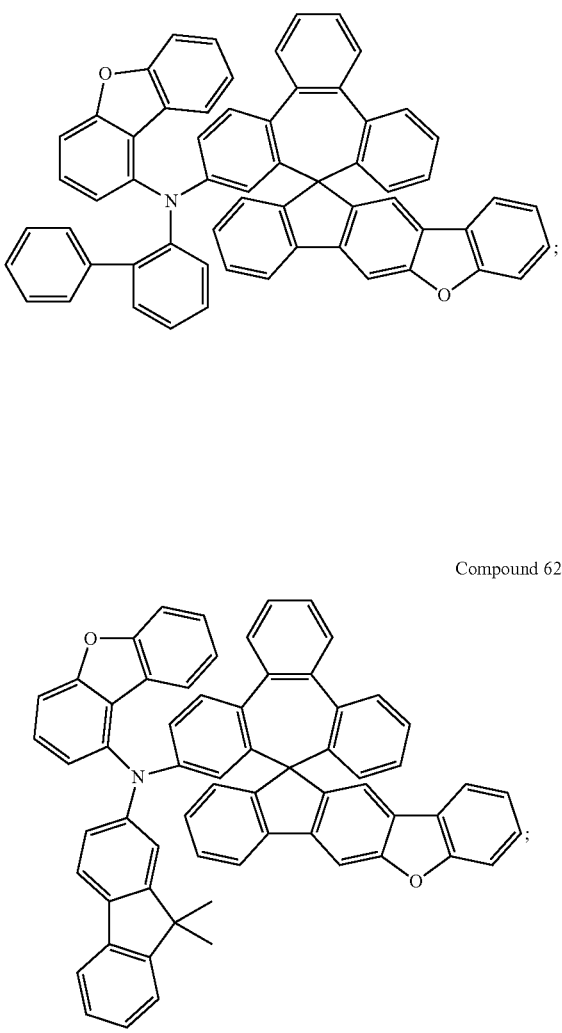

Compound 630
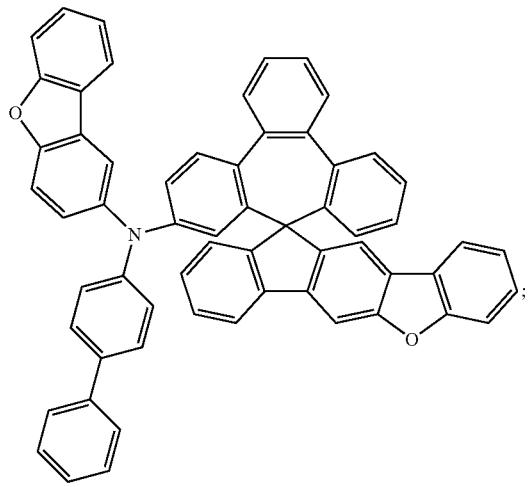
Compound 633
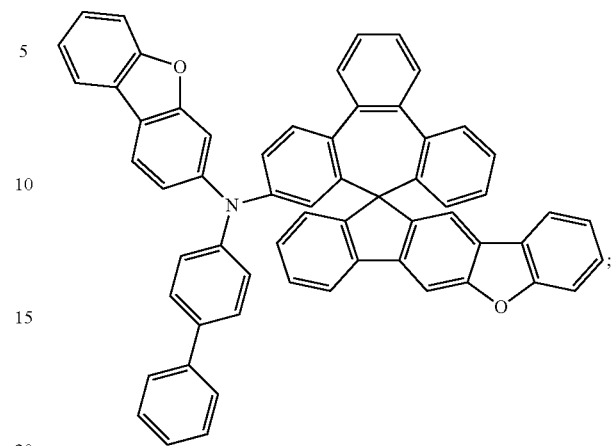
Compound 631
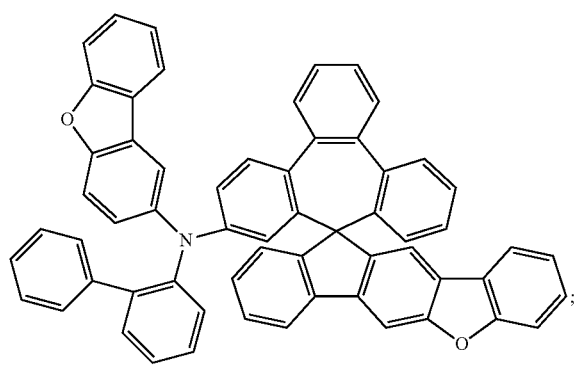
Compound 634
Compound 632
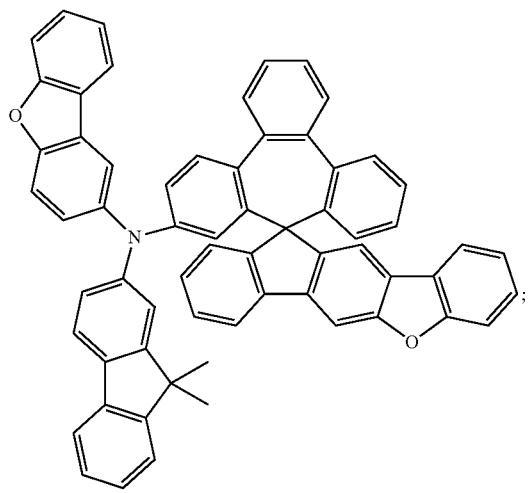
Compound 635
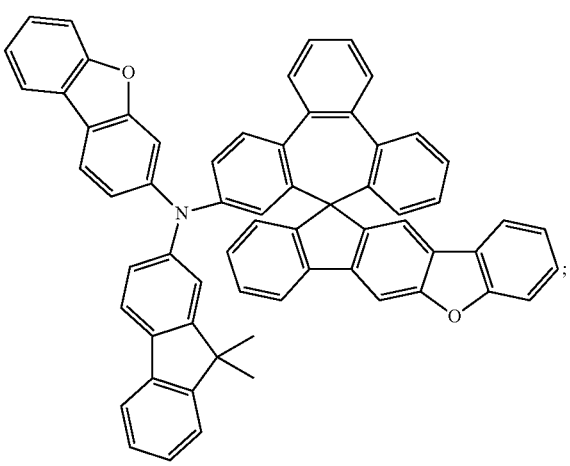

-continued
Compound 636
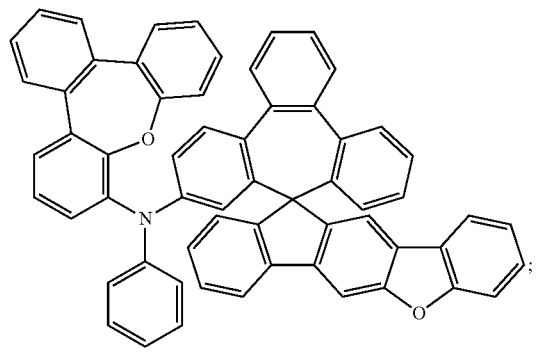
Compound 637
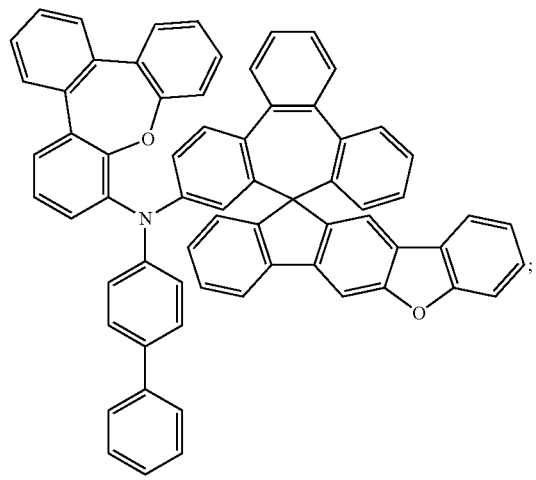
Compound 638
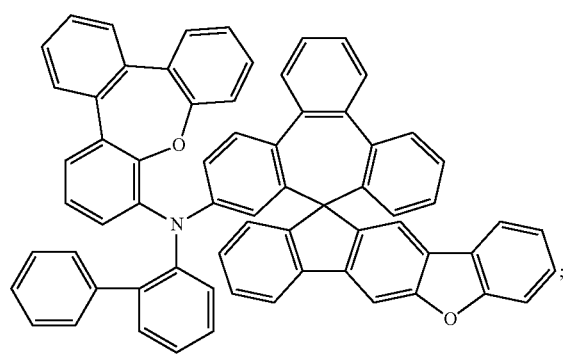
-continued
Compound 639
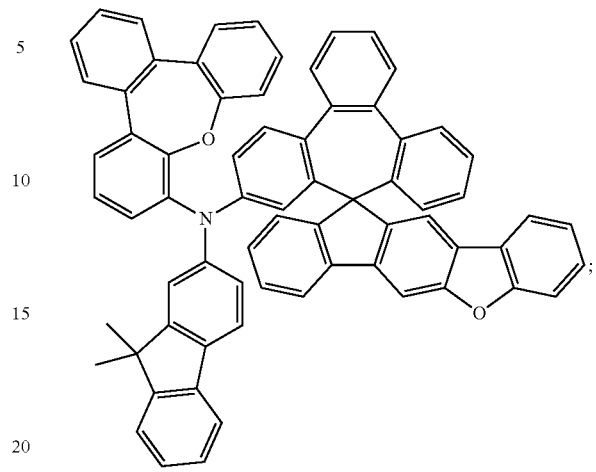
Compound 640
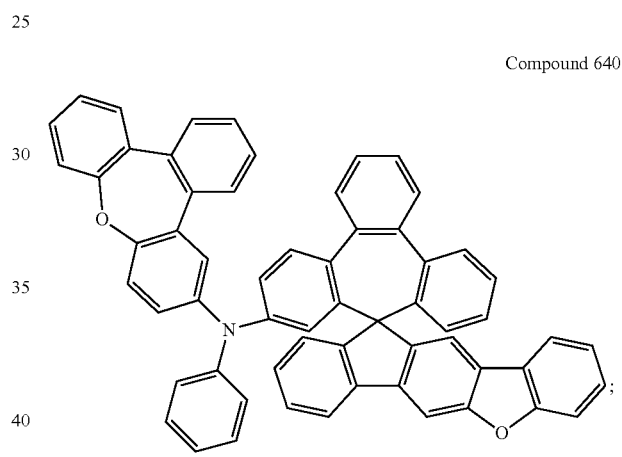
Compound 641
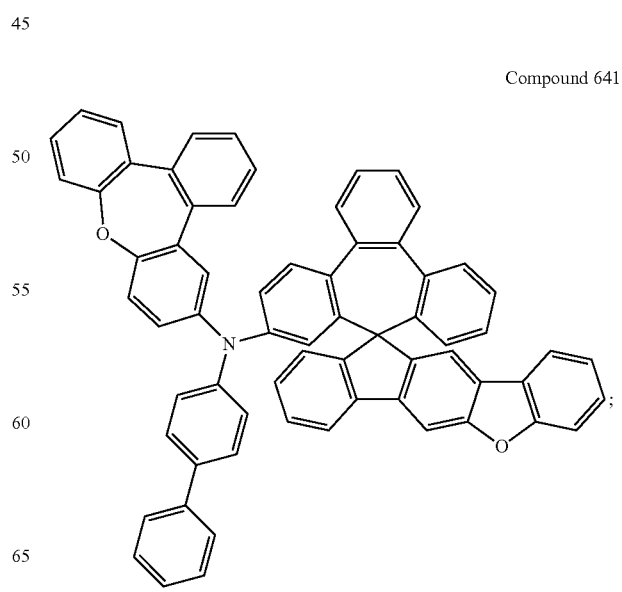

Compound 642
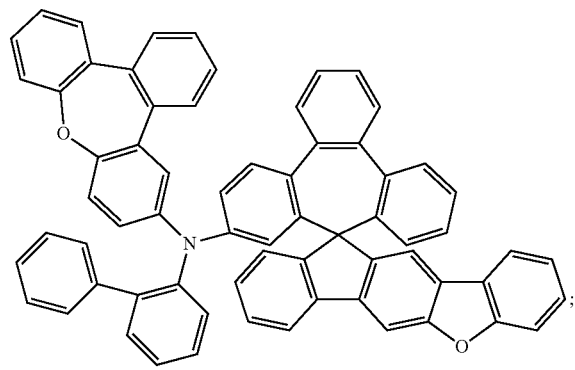
Compound 643
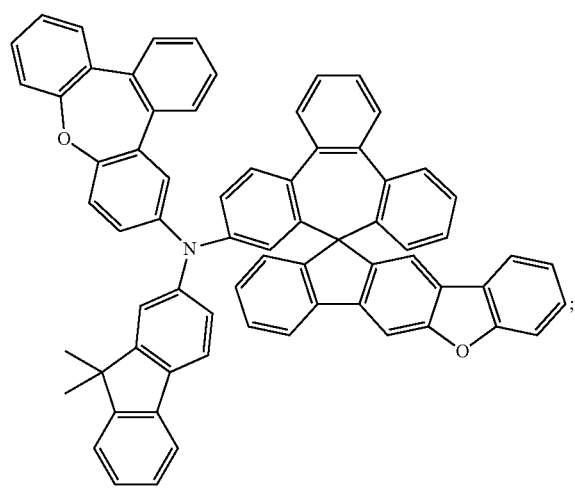
Compound 644
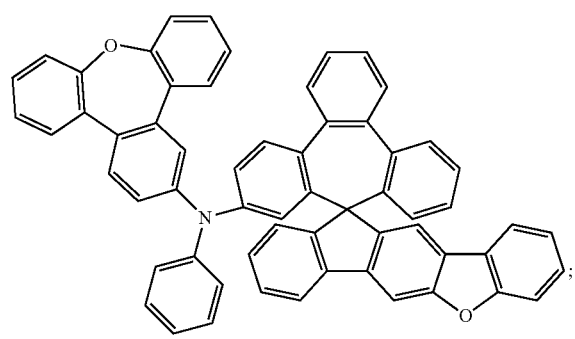
Compound 645
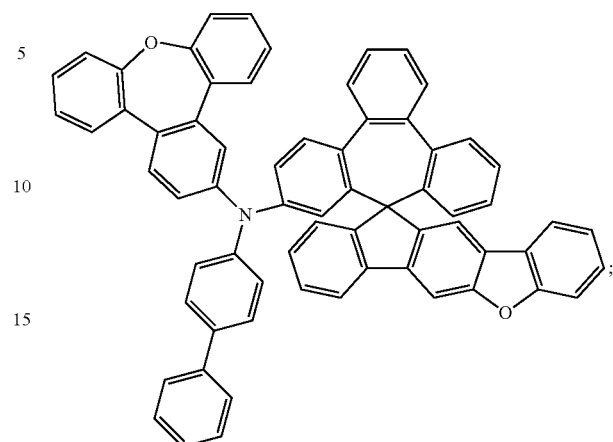
Compound 646
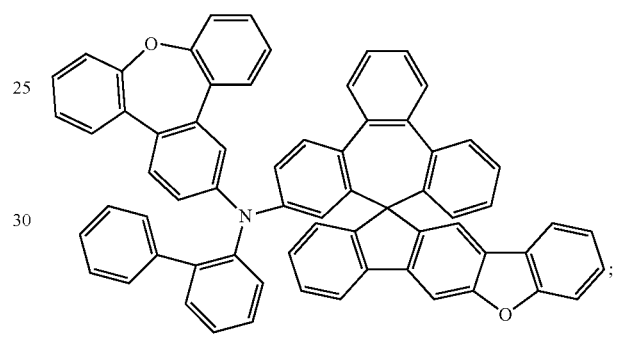
Compound 647
Compound 648
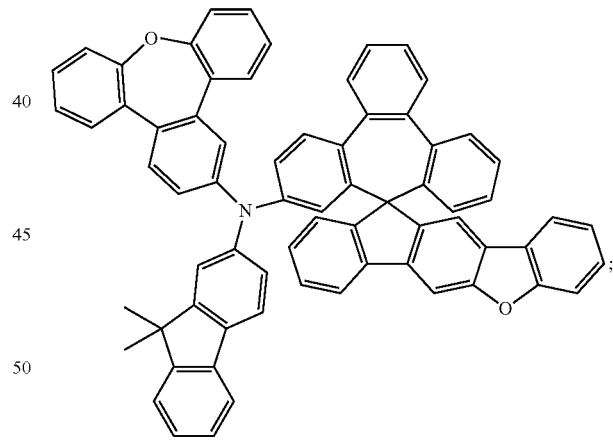

Compound 649
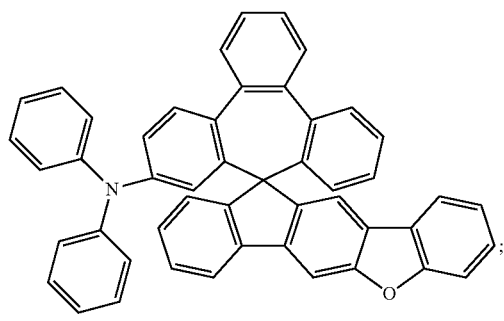
Compound 650
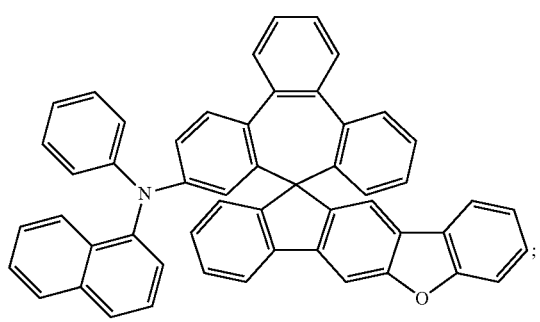
Compound 651
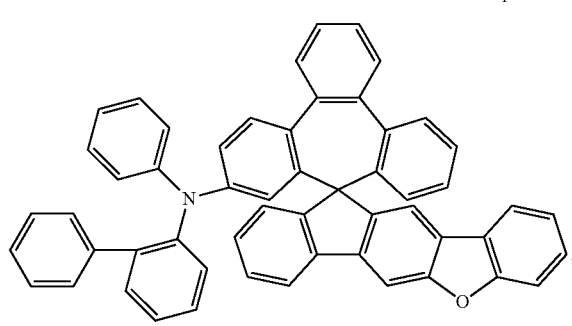
Compound 652
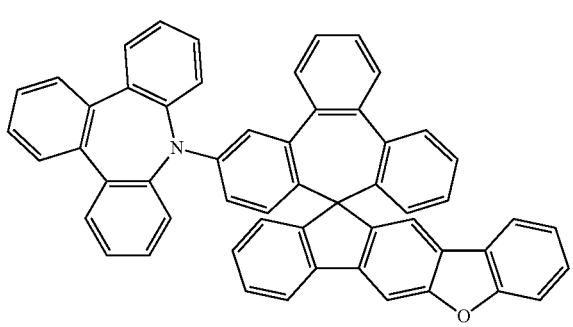
Compound 653
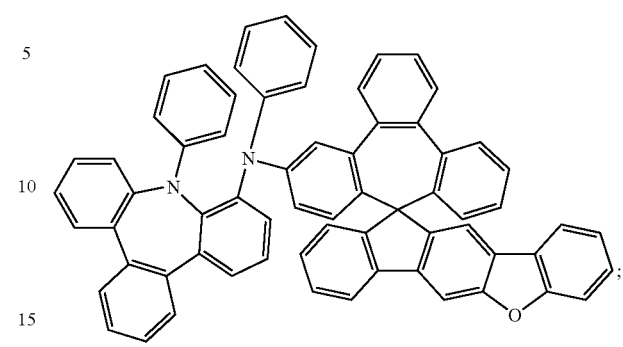
Compound 654
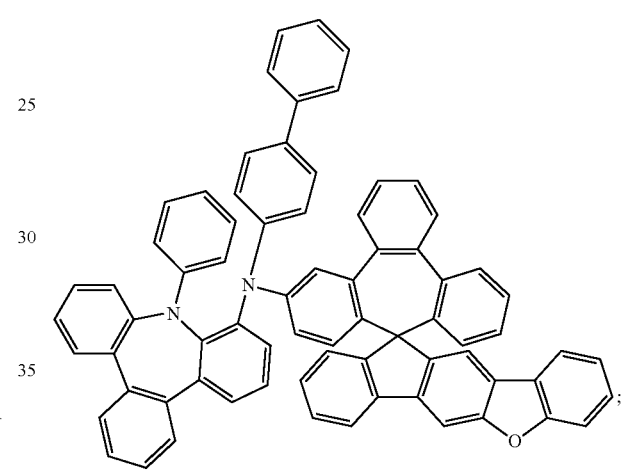
Compound 655
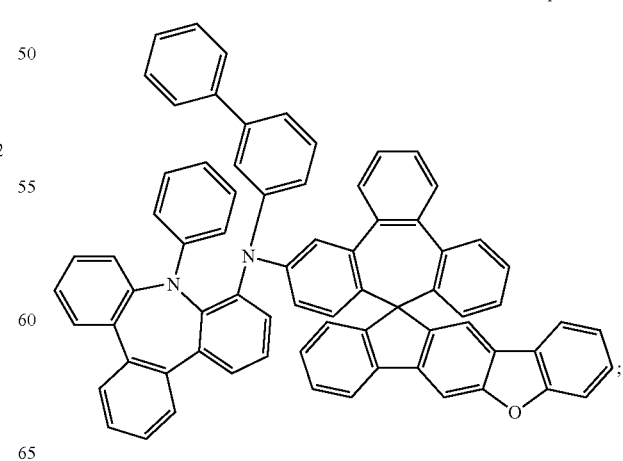

Compound 656
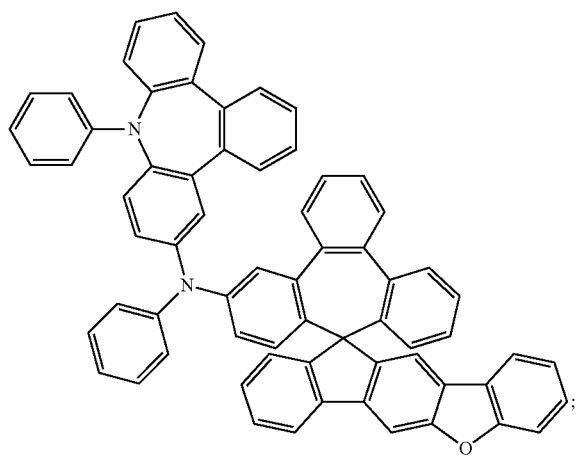
Compound 657
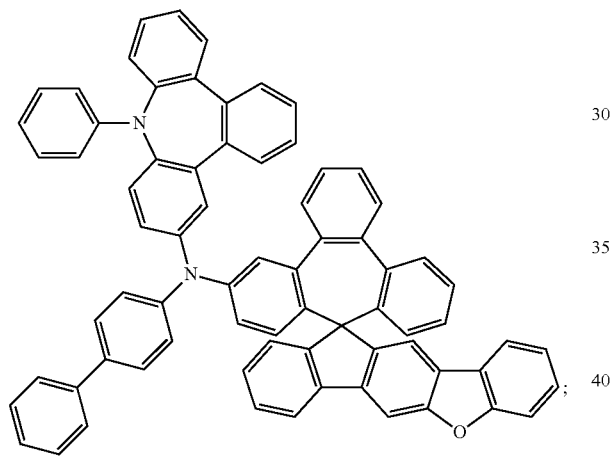
Compound 658
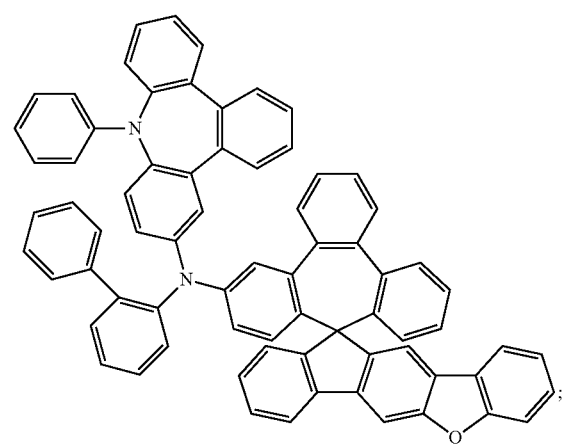
Compound 659
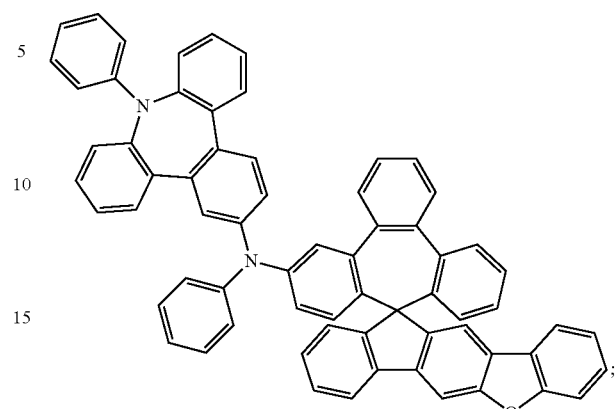
Compound 660
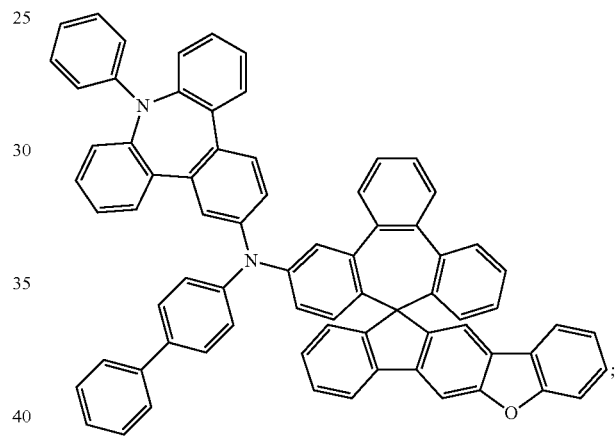
Compound 661
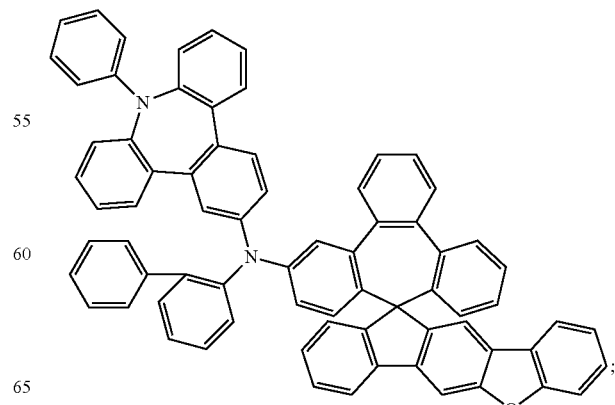

Compound 662
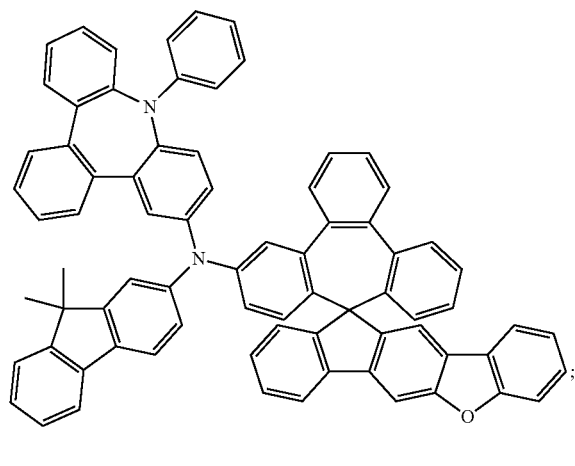
Compound 665
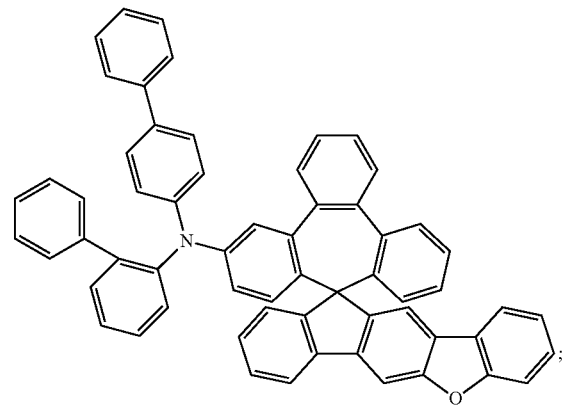
Compound 663
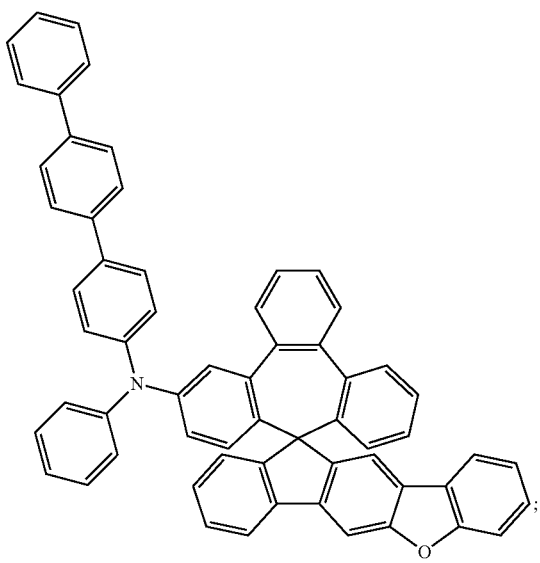
Compound 666
Compound 664
Compound 667
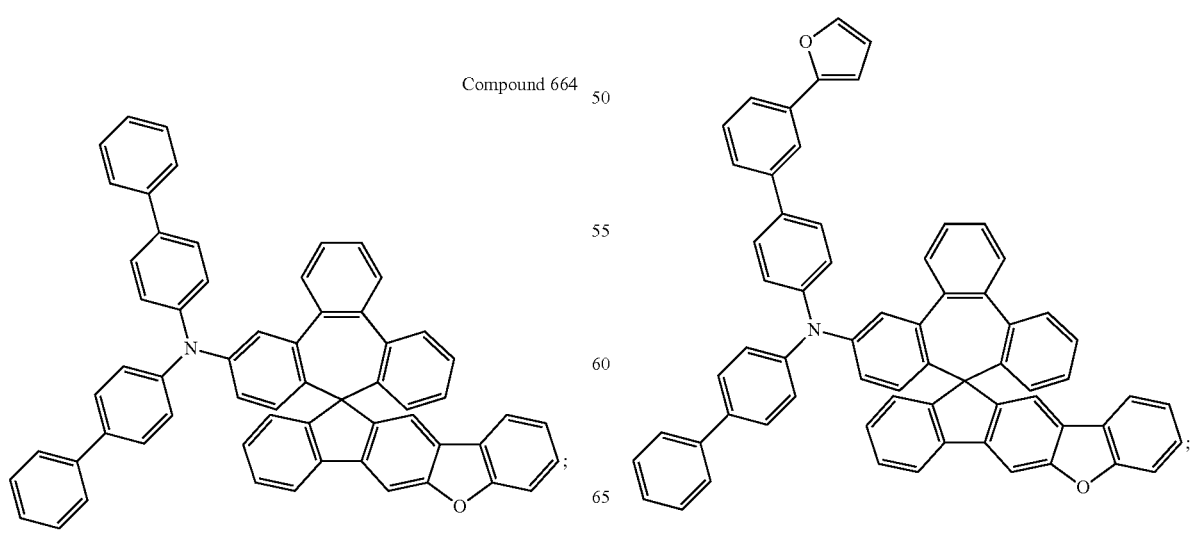

Compound 668
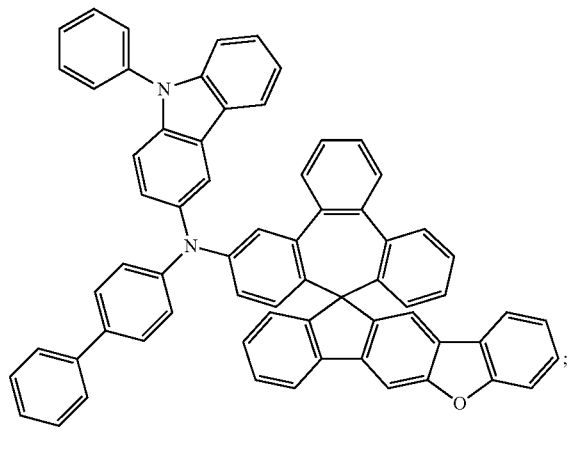
Compound 671
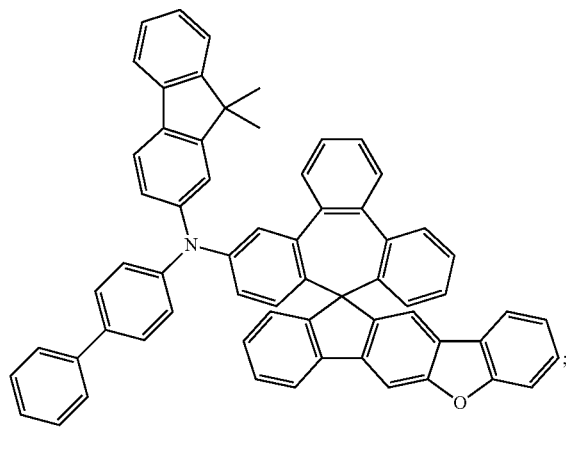
Compound 669
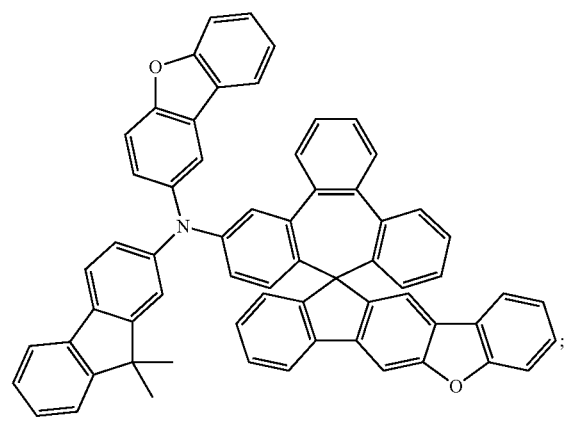
Compound 672
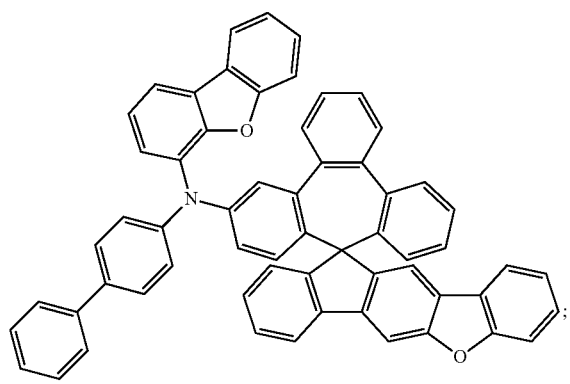
Compound 670
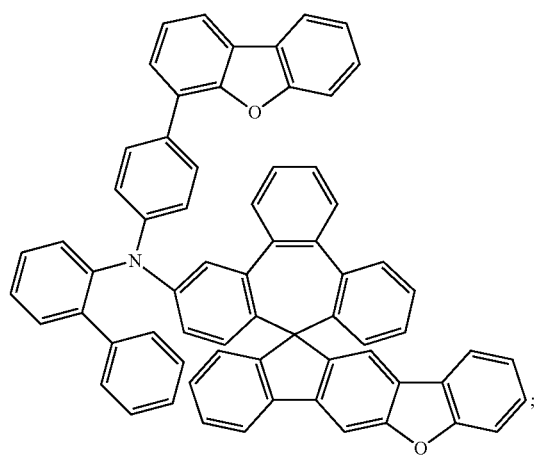
Compound 673

Compound 674
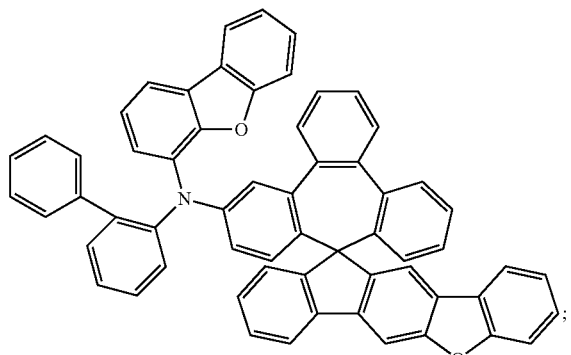
Compound 675
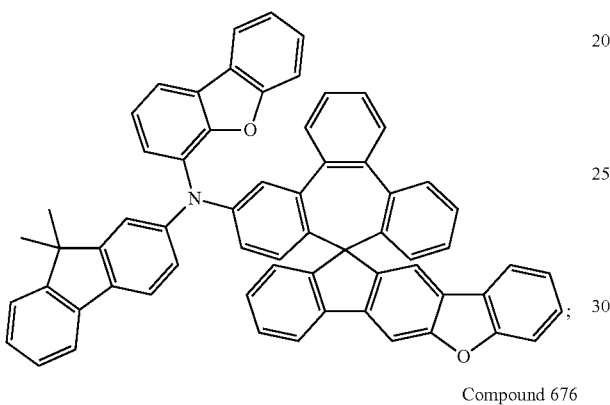
Compound 676
Compound 677
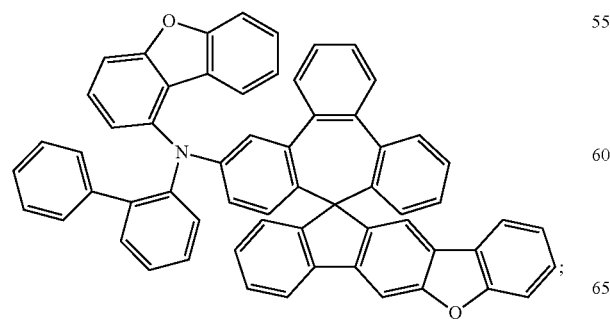
Compound 678
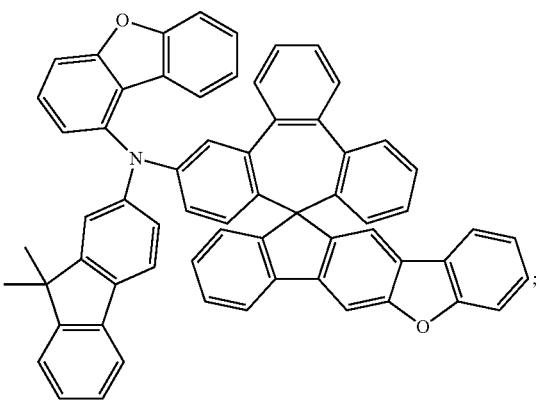
Compound 679
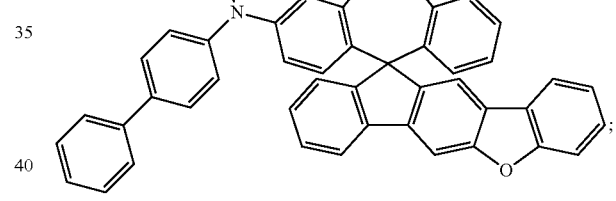
Compound 680
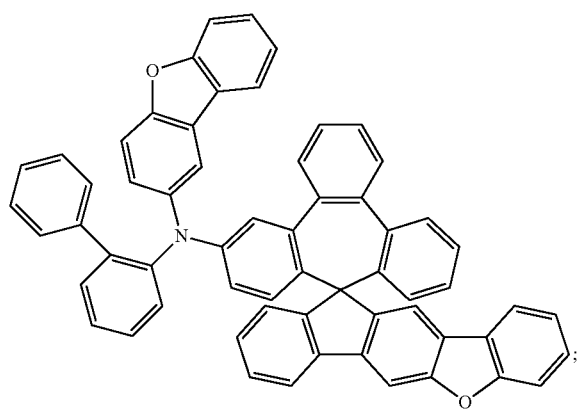

Compound 681
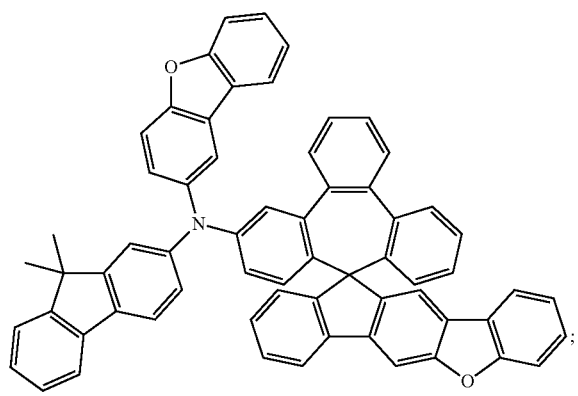
Compound 682
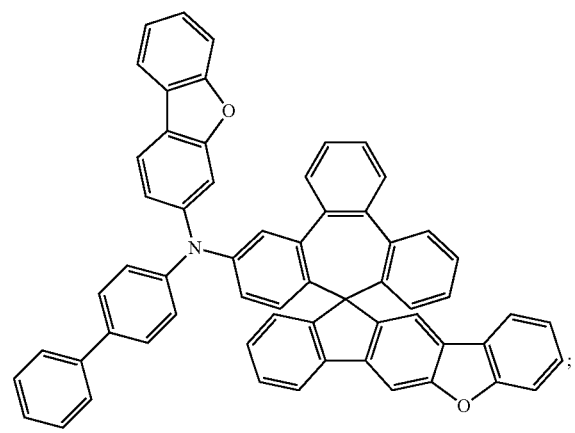
Compound 683
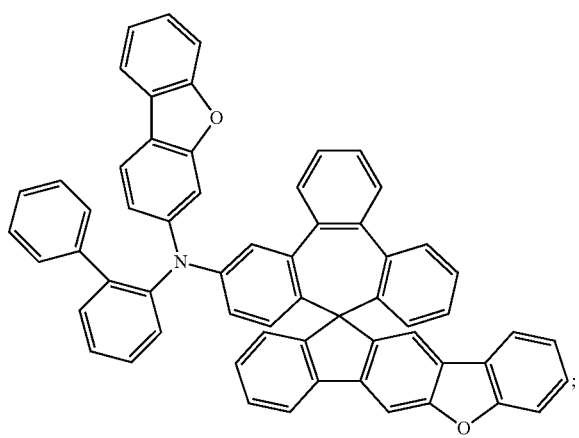
Compound 684
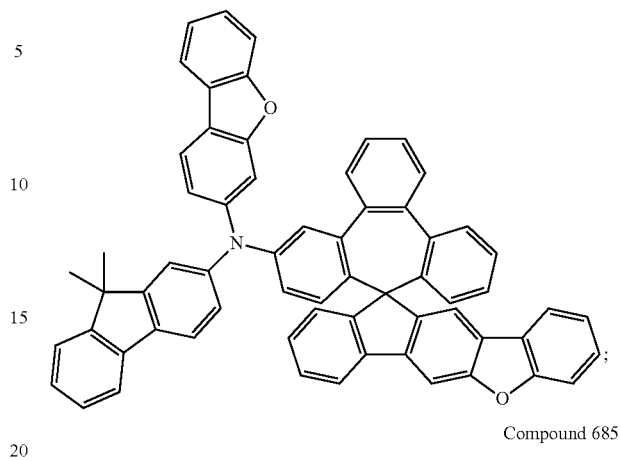
Compound 685
Compound 686
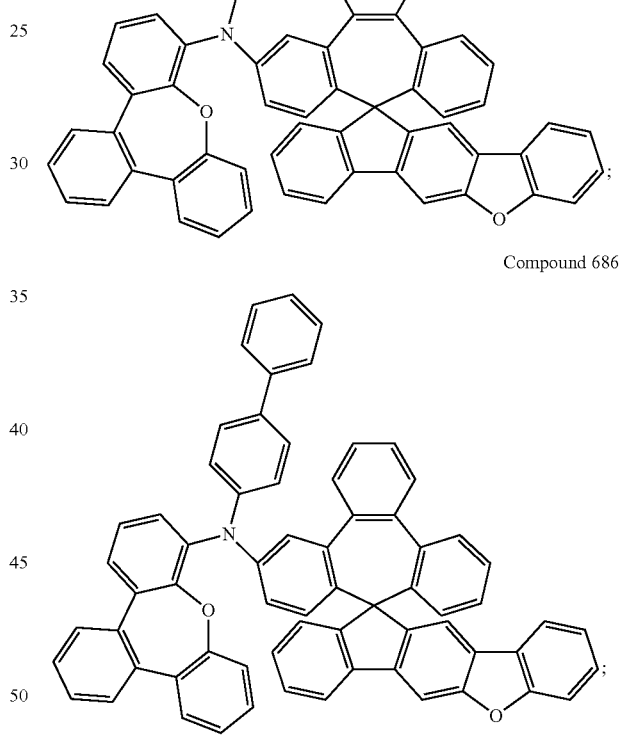
Compound 687
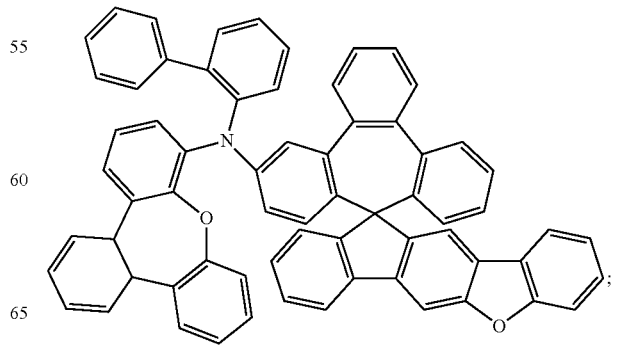

Compound 688
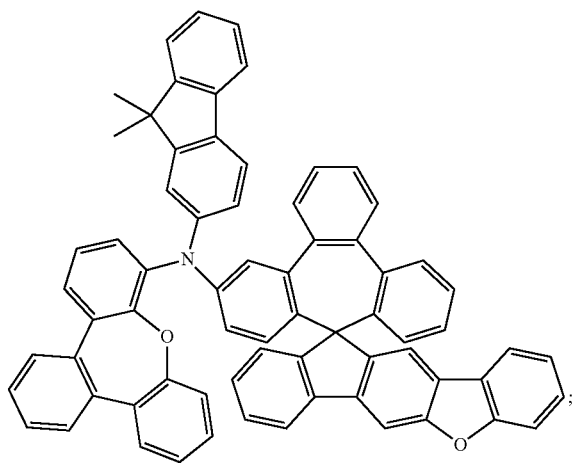
Compound 689
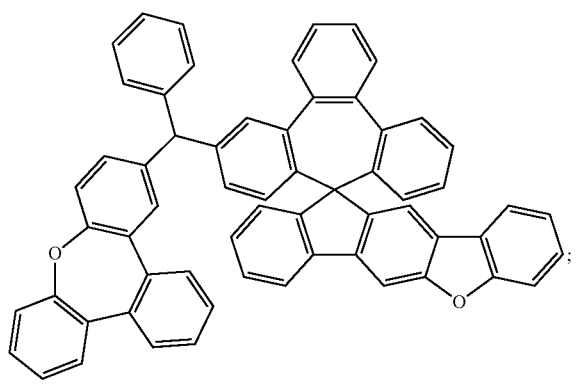
Compound 690
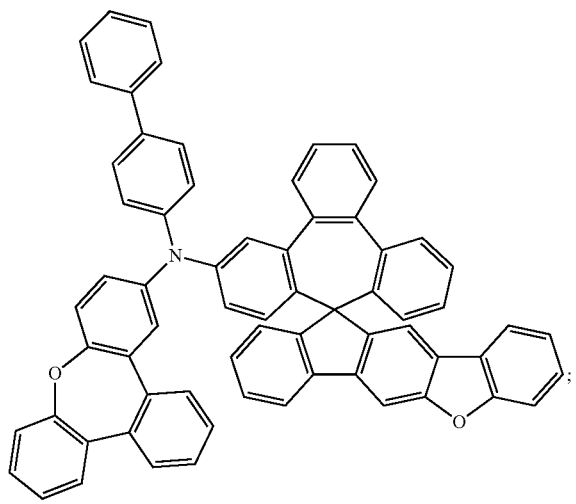
Compound 691
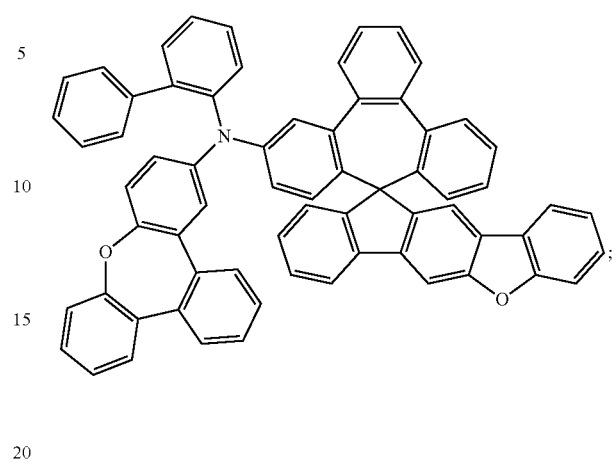
Compound 692
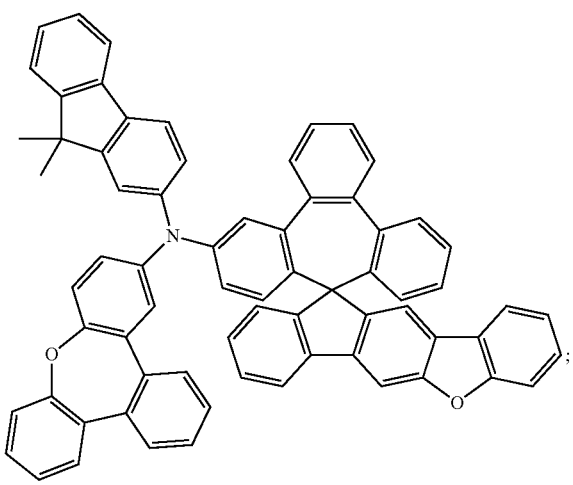
Compound 693
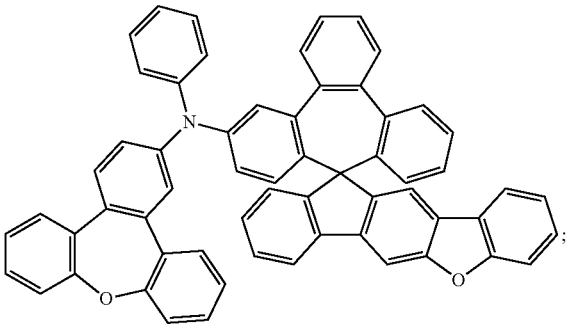

Compound 694
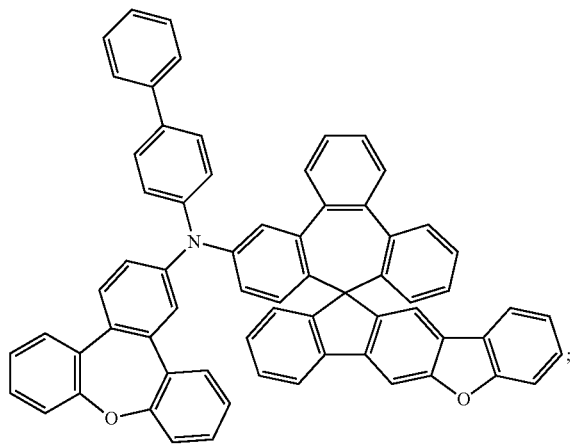
Compound 695
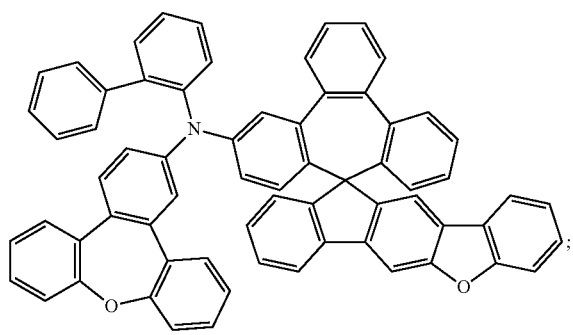
Compound 696
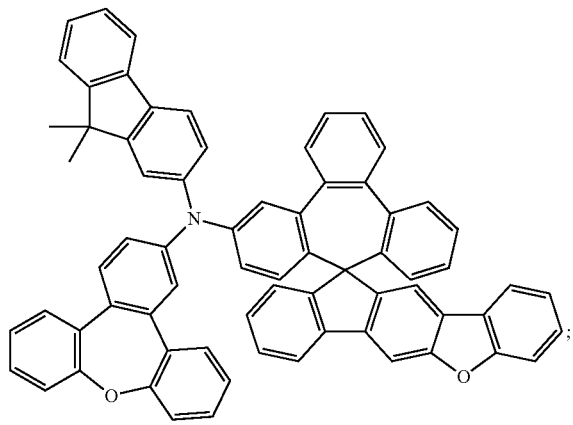
Compound 697
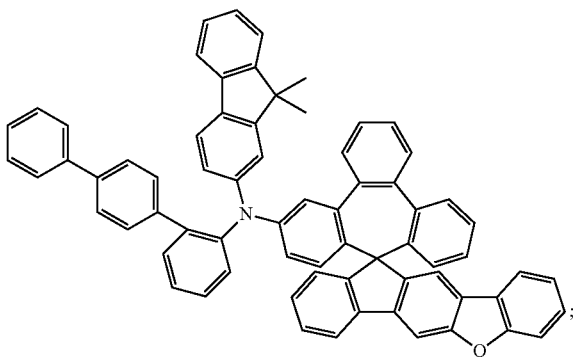
Compound 698
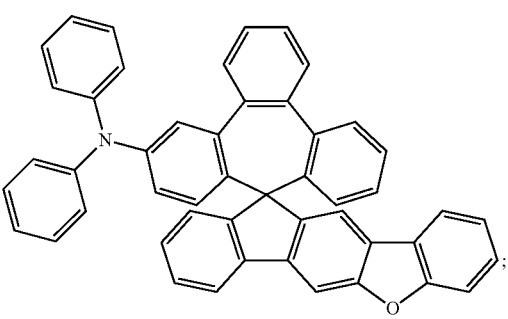
Compound 699
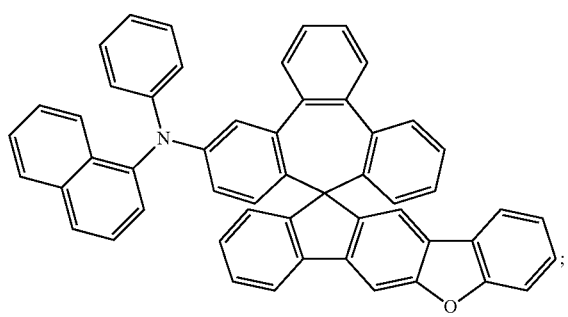
Compound 700
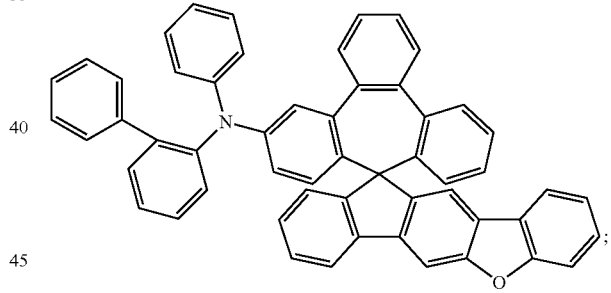
Compound 701
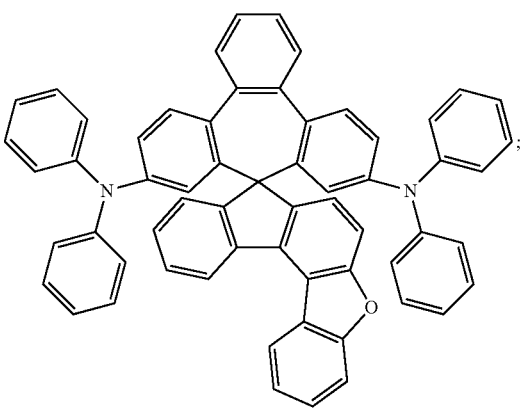

Compound 702
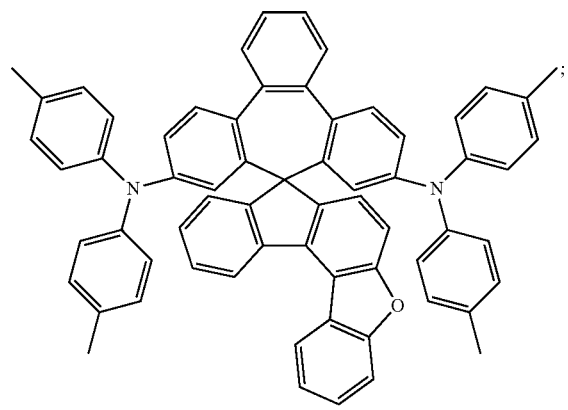
Compound 703
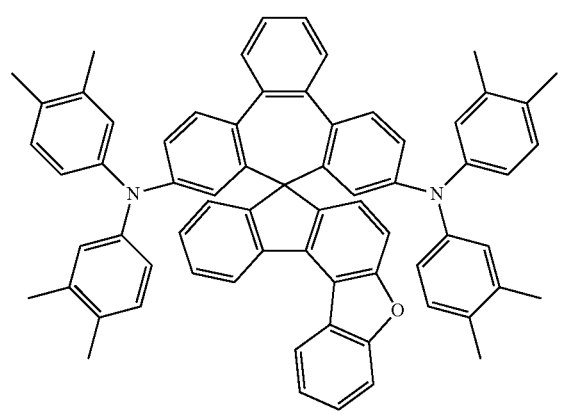
Compound 704
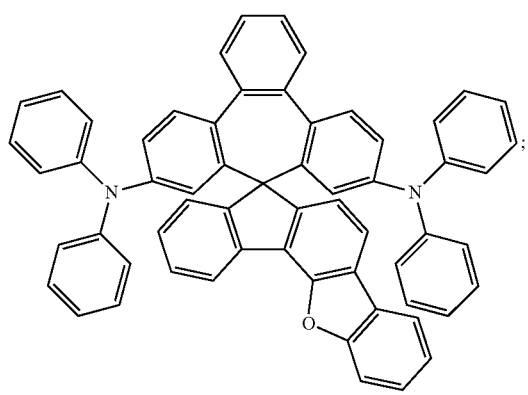
Compound 705
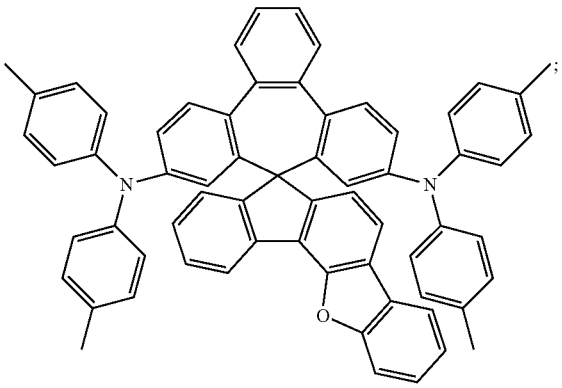
Compound 706
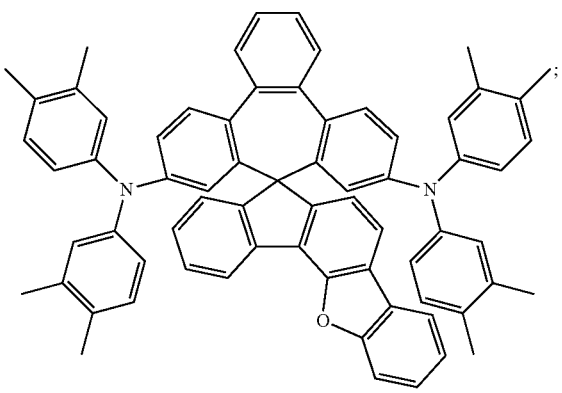
Compound 707
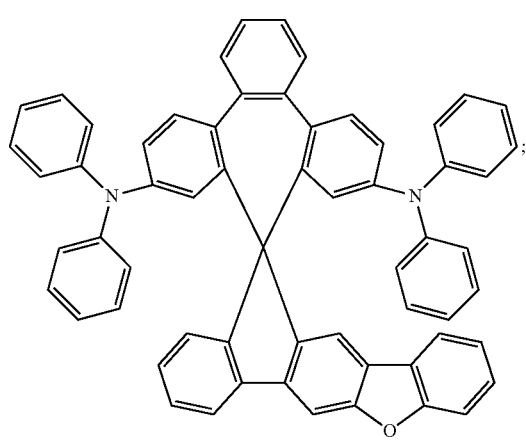

Compound 708
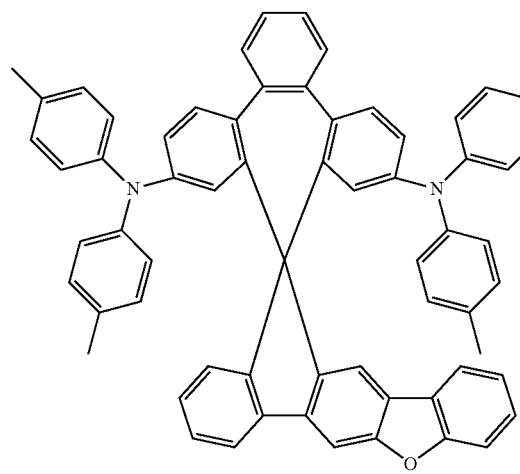
Compound 711
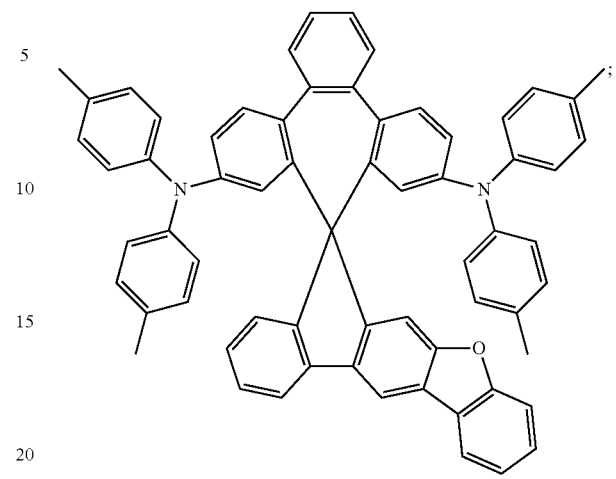
Compound 709
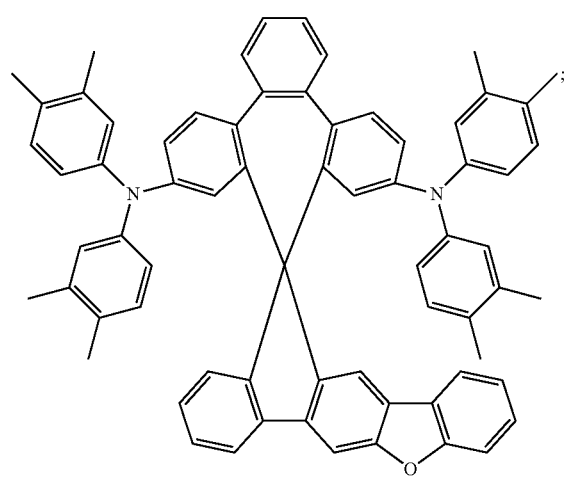
Compound 712
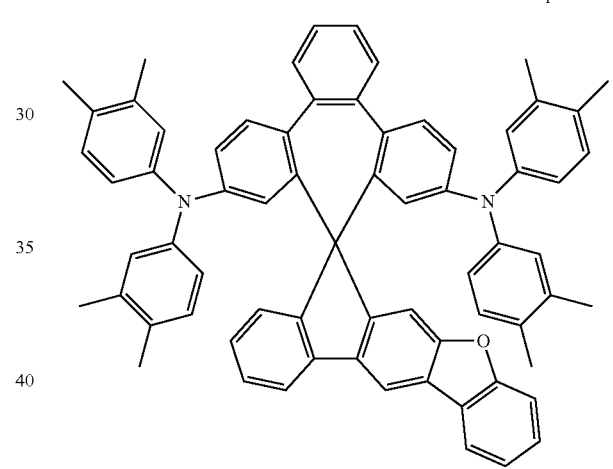
Compound 710
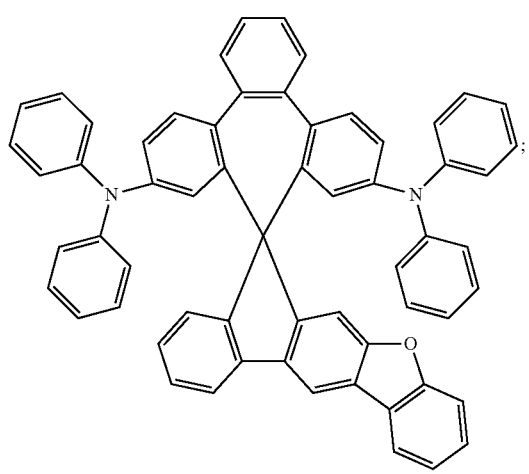
Compound 713
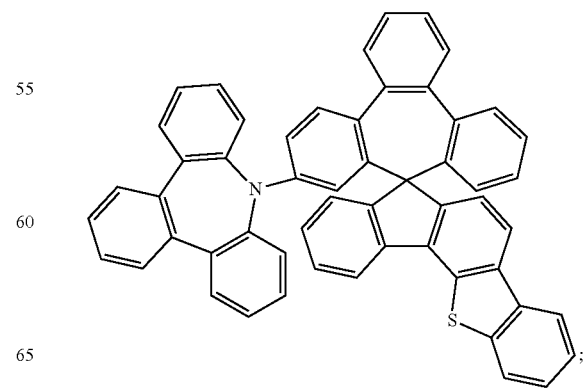

Compound 714
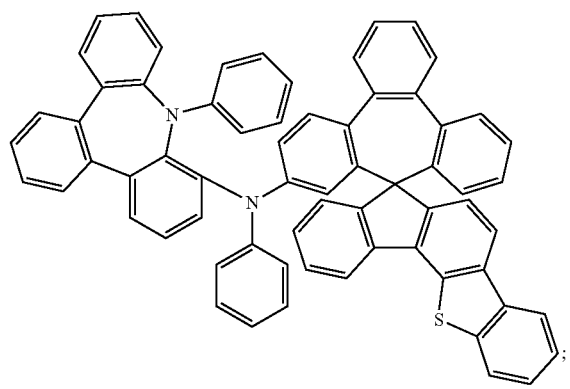
Compound 715
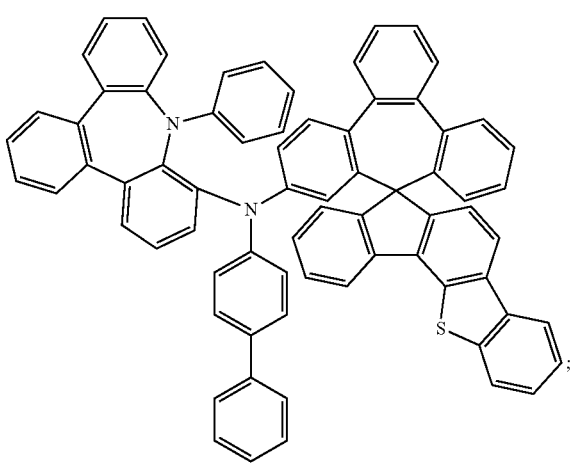
Compound 716
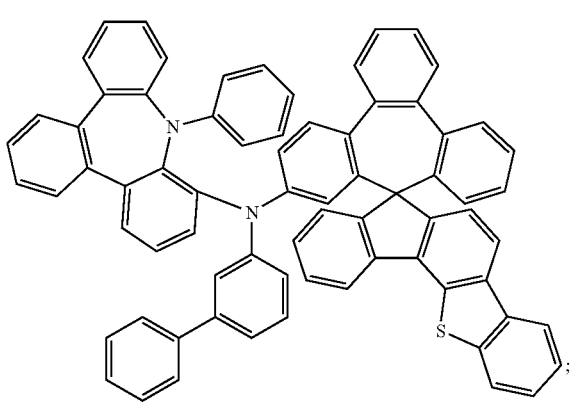
Compound 717
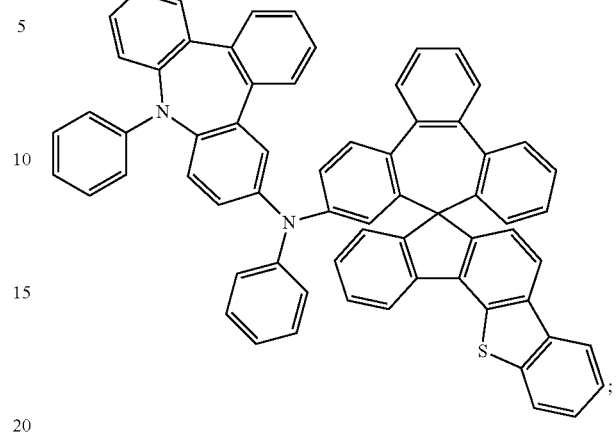
Compound 718
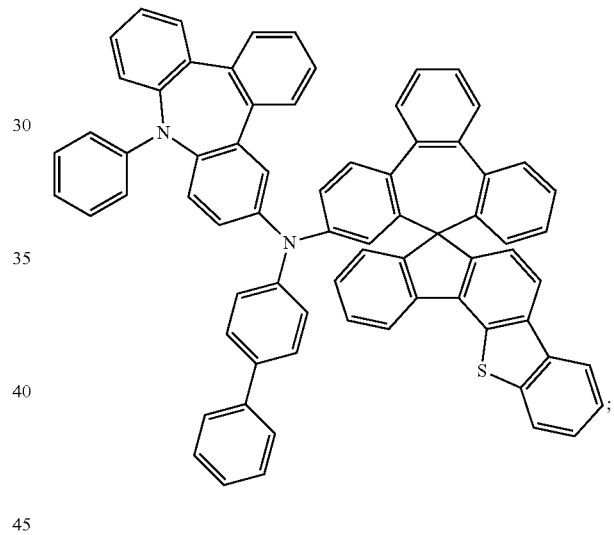
Compound 719
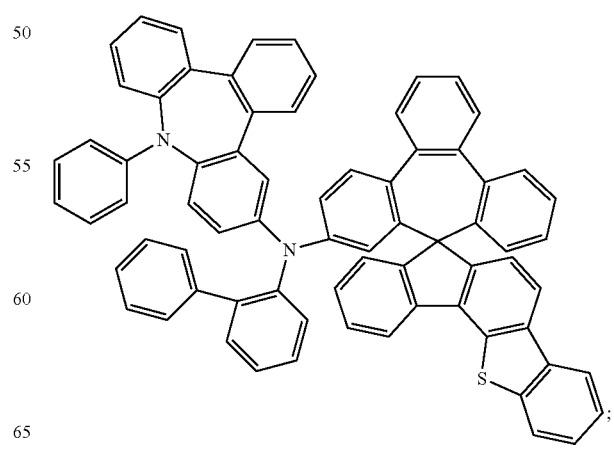

Compound 720
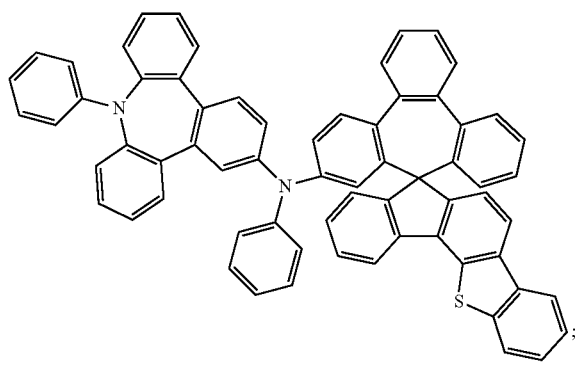
Compound 723
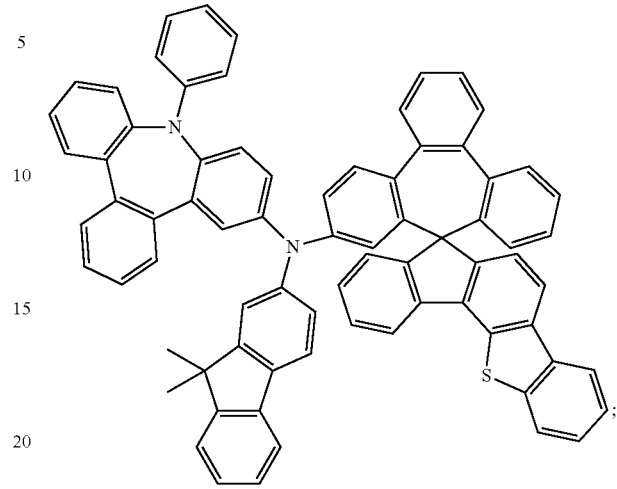
Compound 721
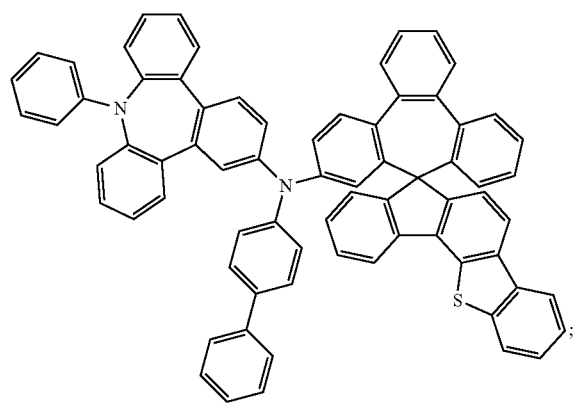
Compound 724
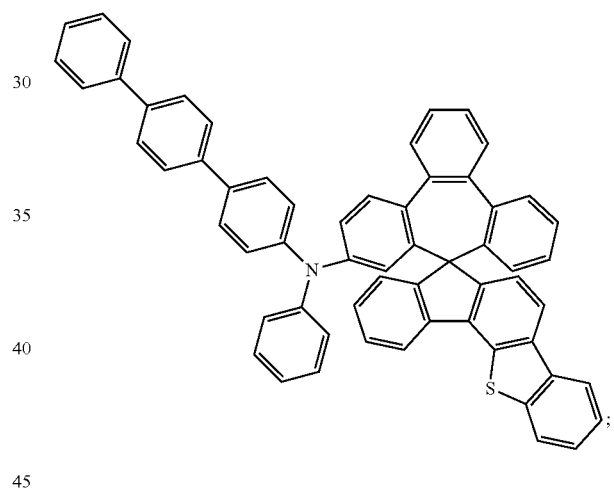
Compound 722
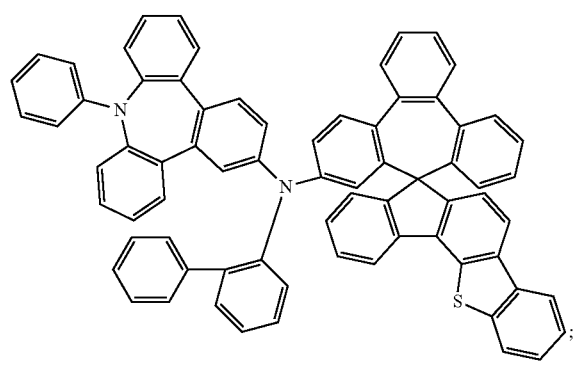
Compound 725
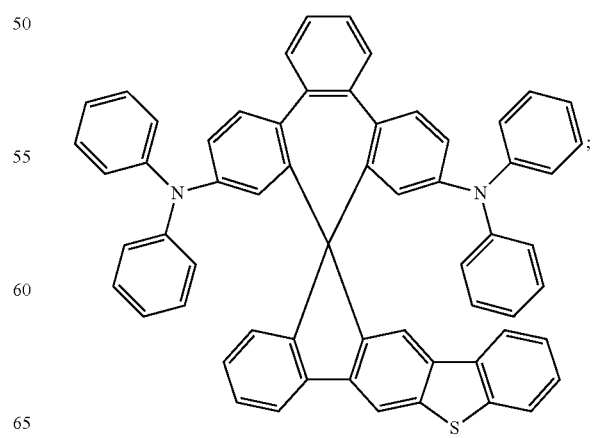

Compound 726
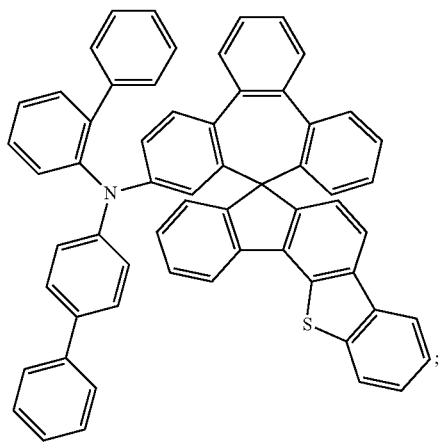
Compound 727
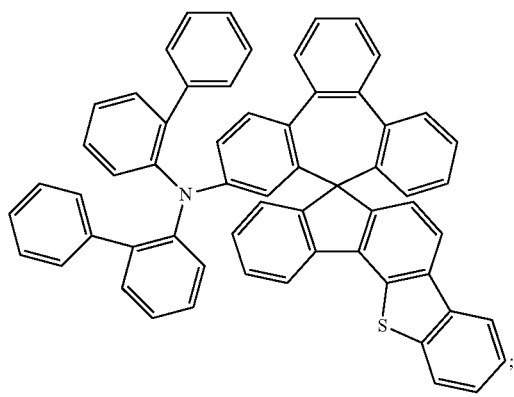
Compound 728
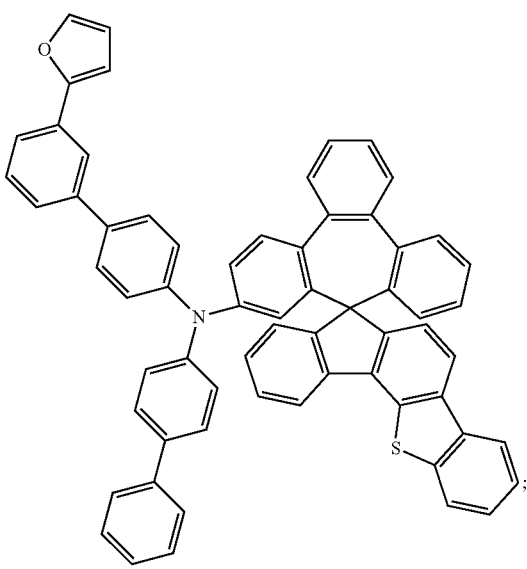
Compound 729
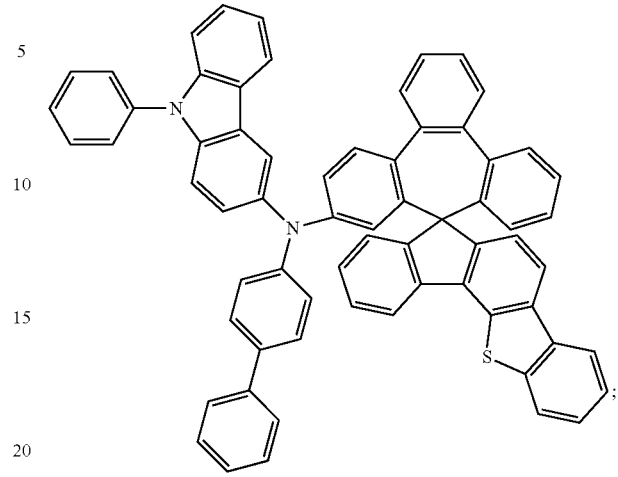
Compound 730
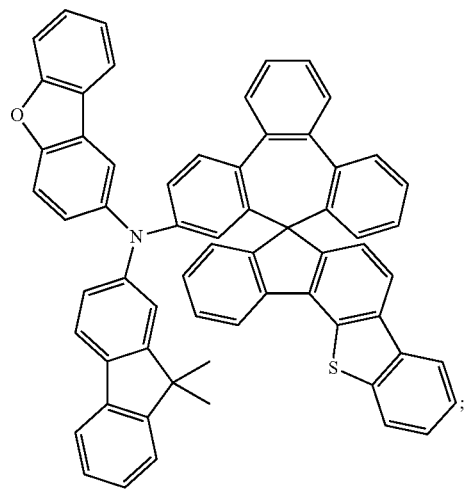
Compound 731
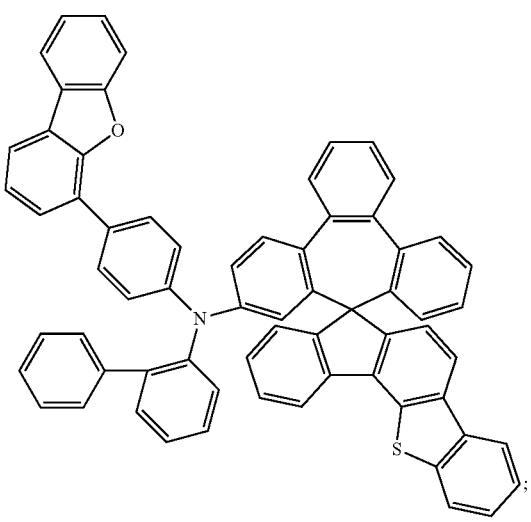

Compound 732
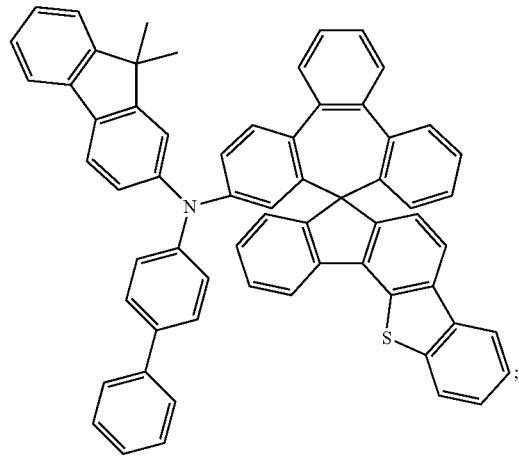
Compound 733
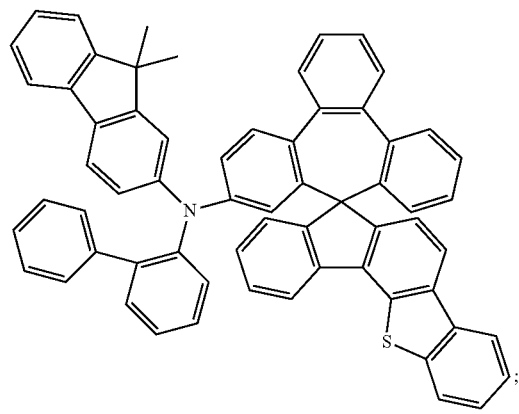
Compound 734
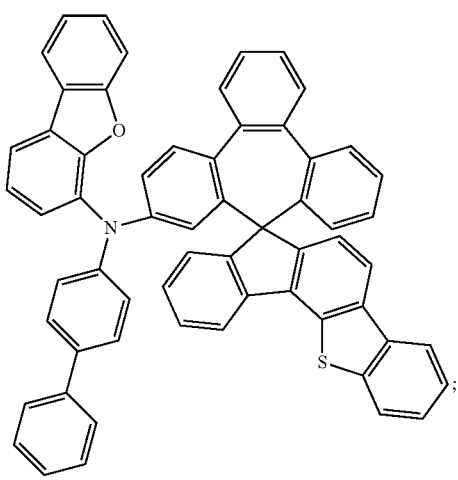
Compound 735
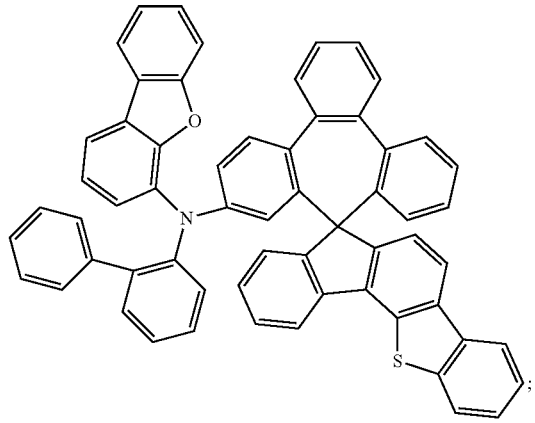
Compound 736
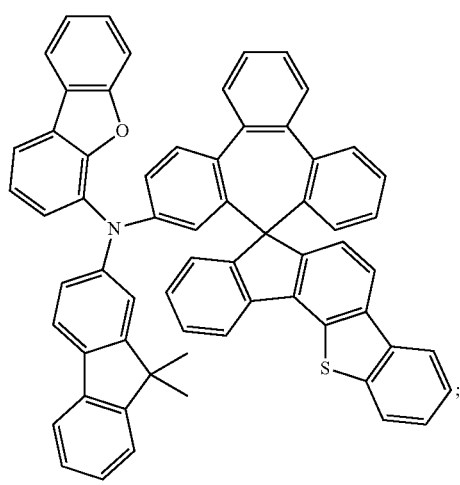
Compound 737
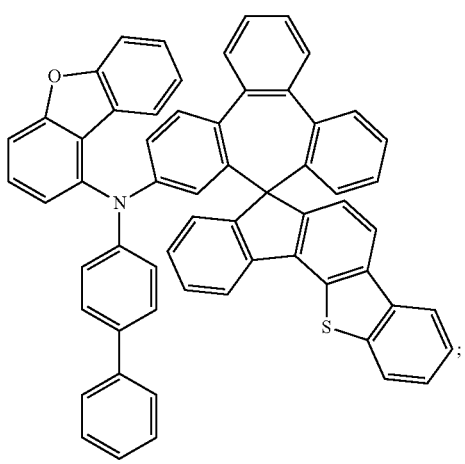

Compound 738
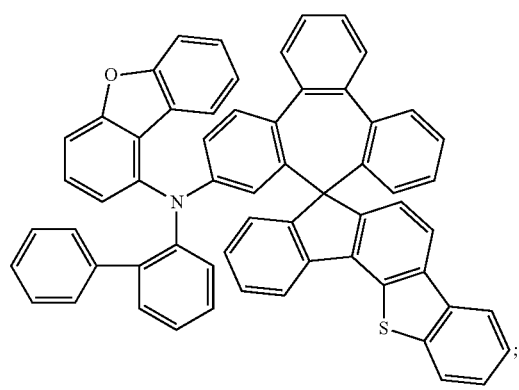
Compound 739
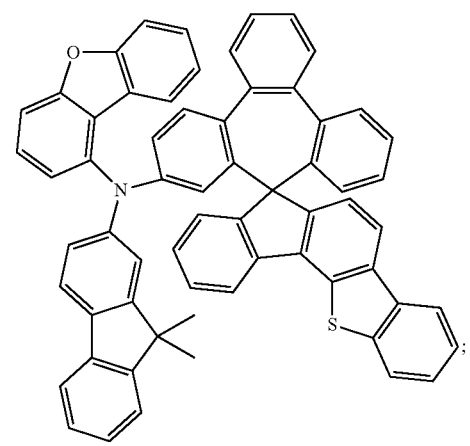
Compound 740
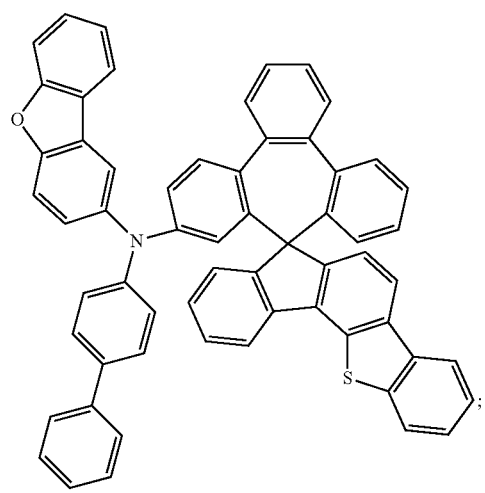
Compound 741
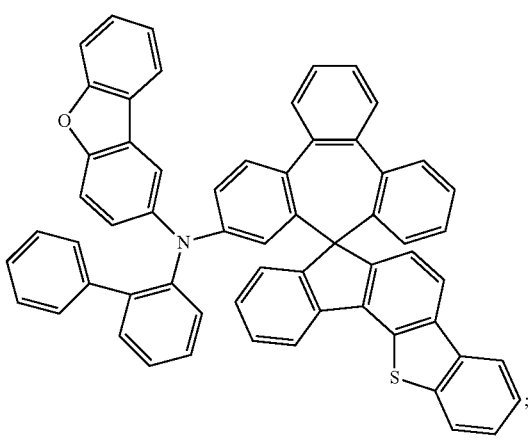
Compound 742
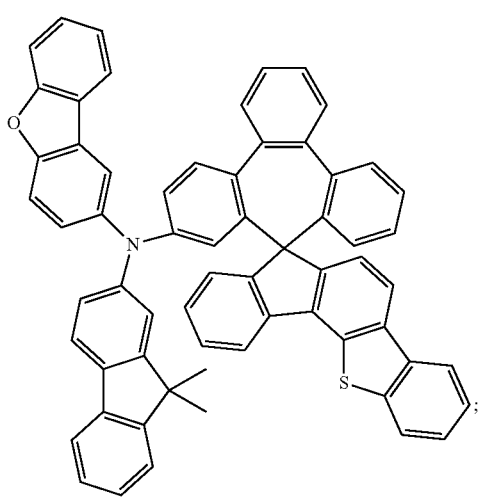
Compound 743
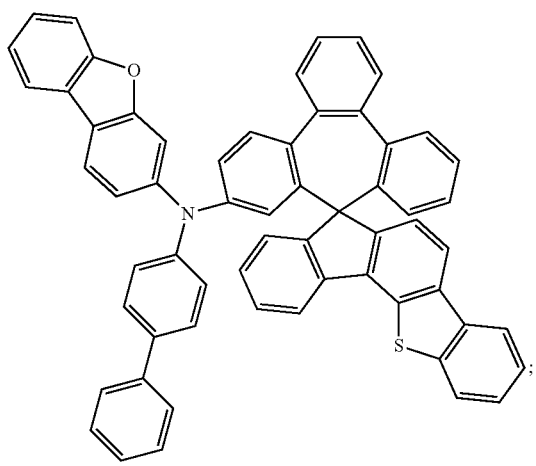

Compound 744
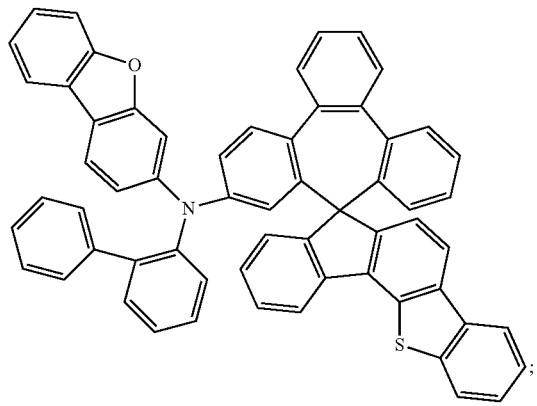
Compound 745
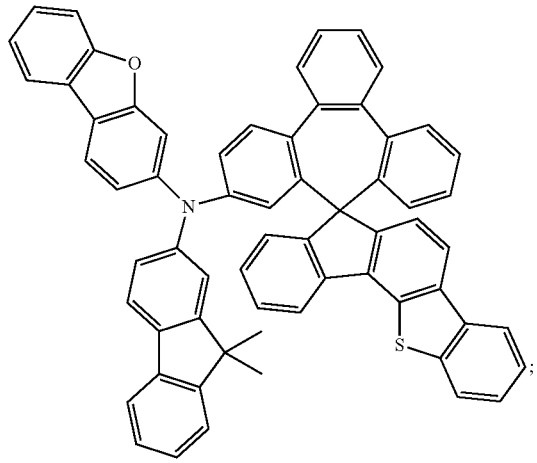
Compound 746
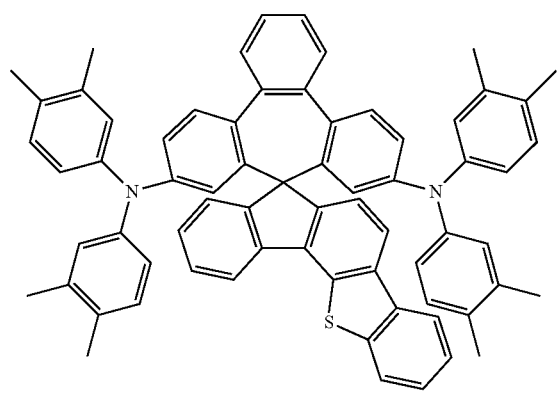
Compound 747
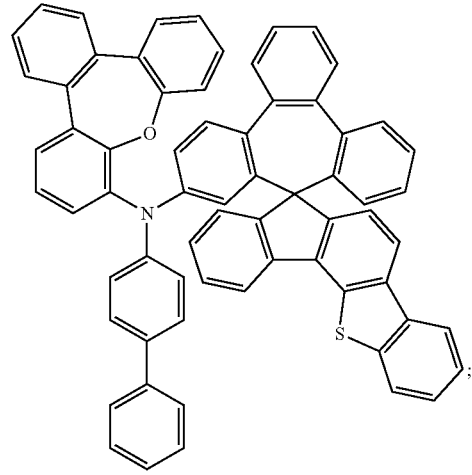
Compound 748
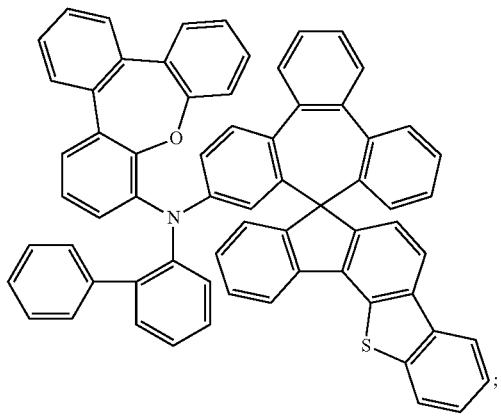
Compound 749
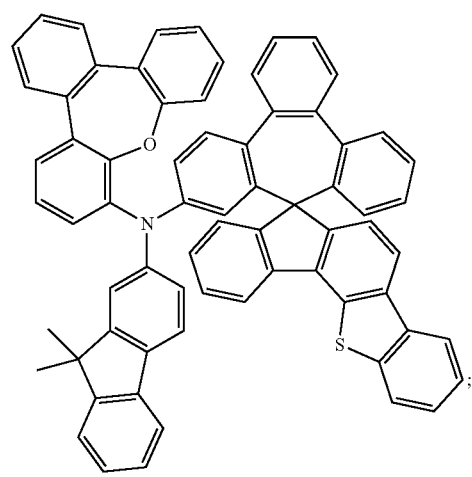

Compound 750
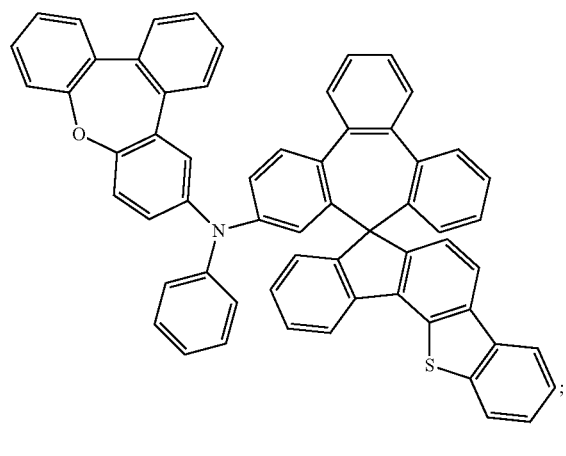
Compound 751
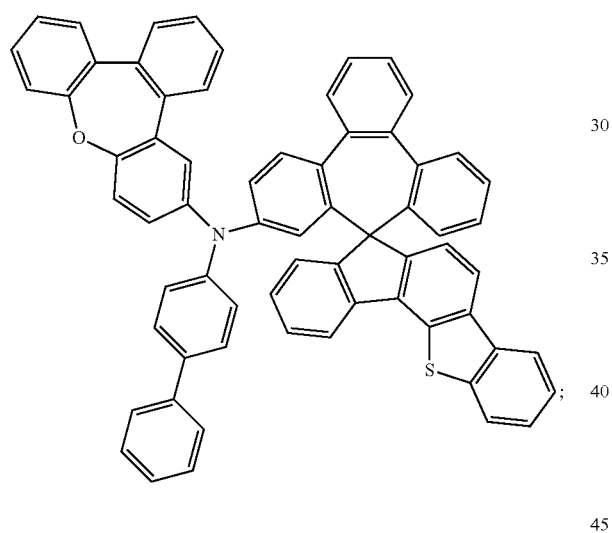
Compound 752
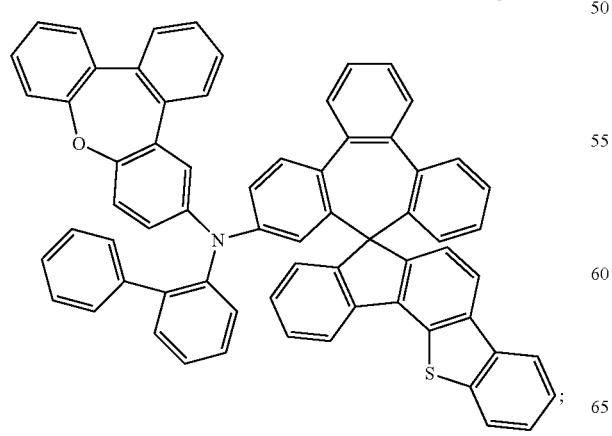
Compound 753
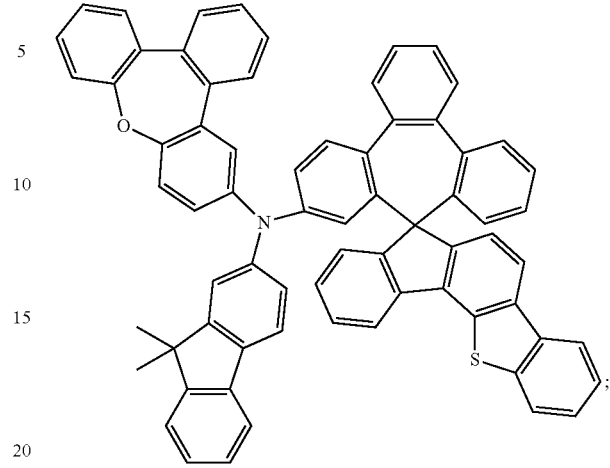
Compound 754
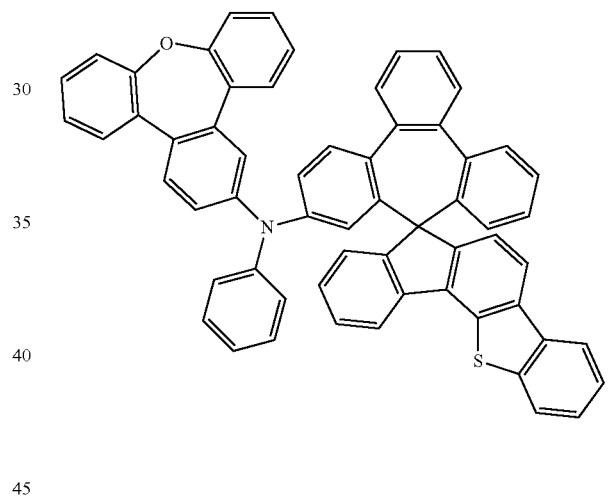
Compound 755
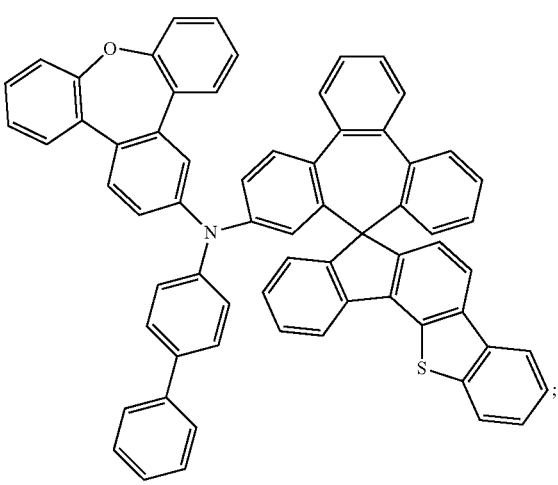

Compound 756
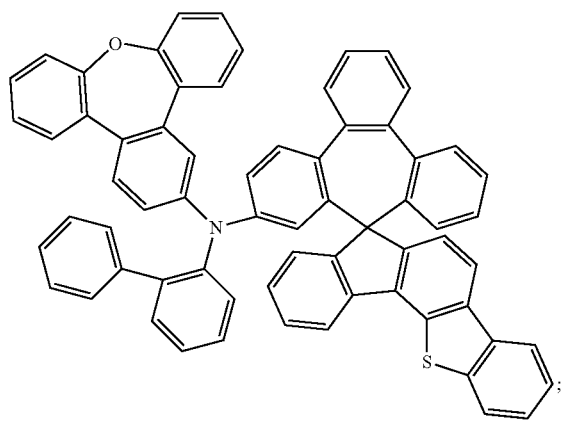
Compound 757
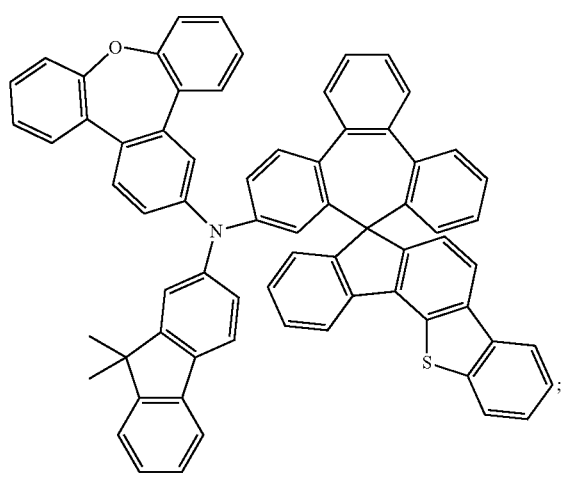
Compound 758
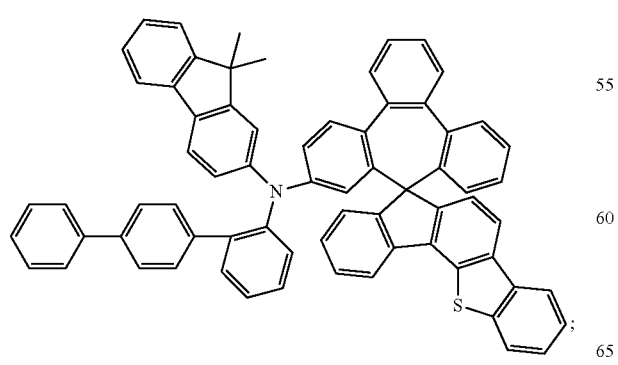
Compound 759
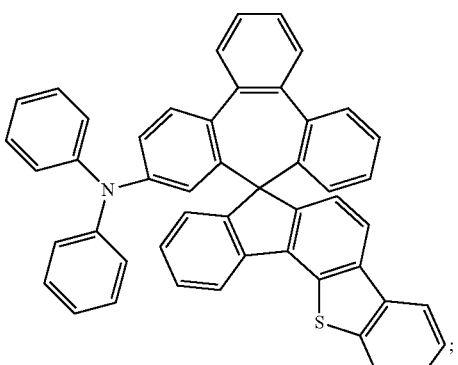
Compound 760
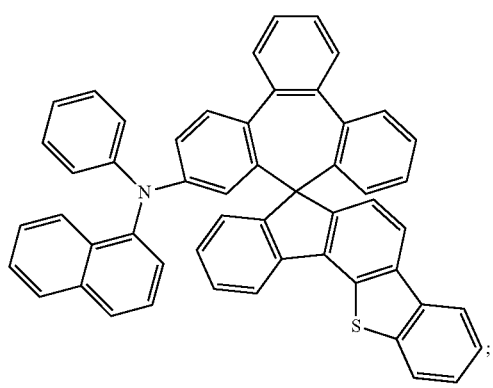
Compound 761
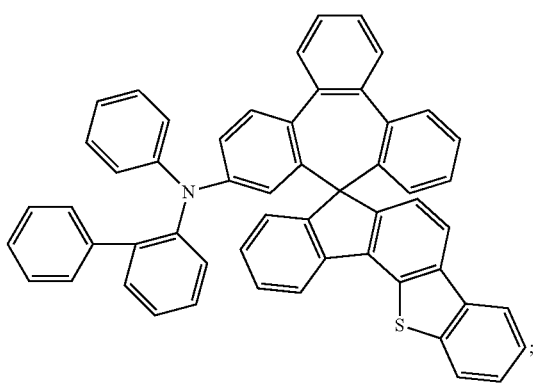
Compound 762
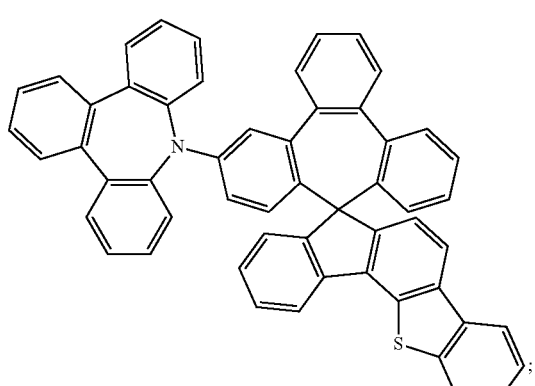

Compound 763
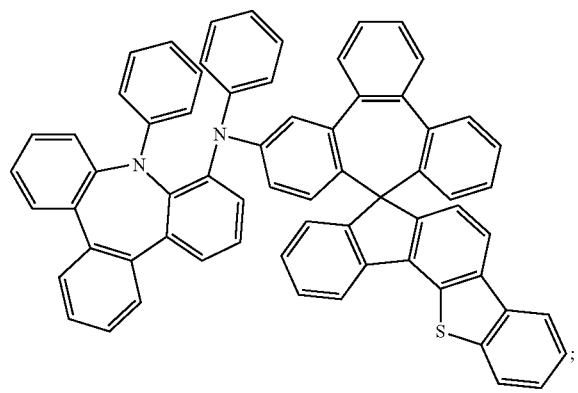
Compound 764
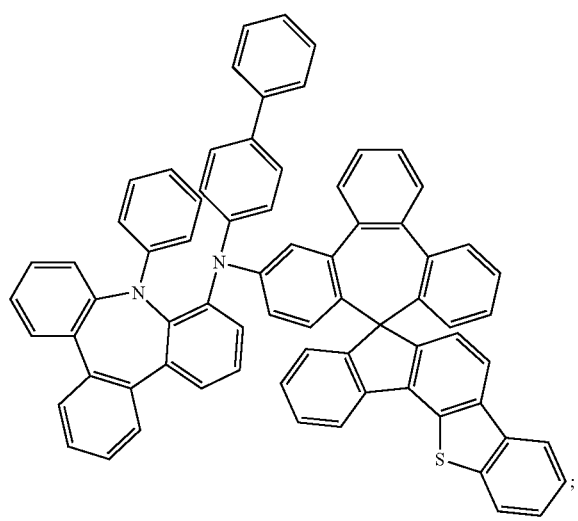
Compound 765
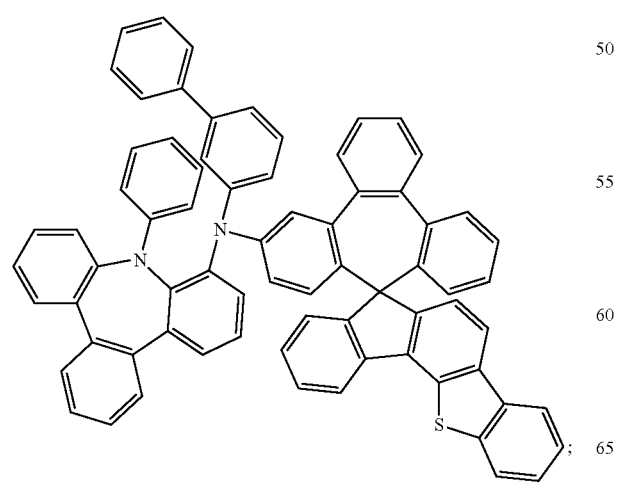
Compound 766
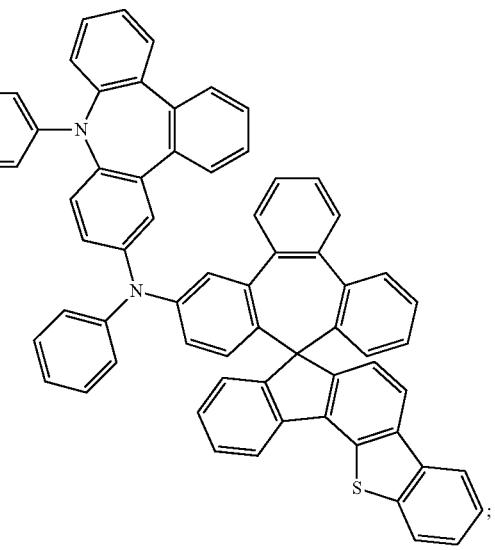
Compound 767
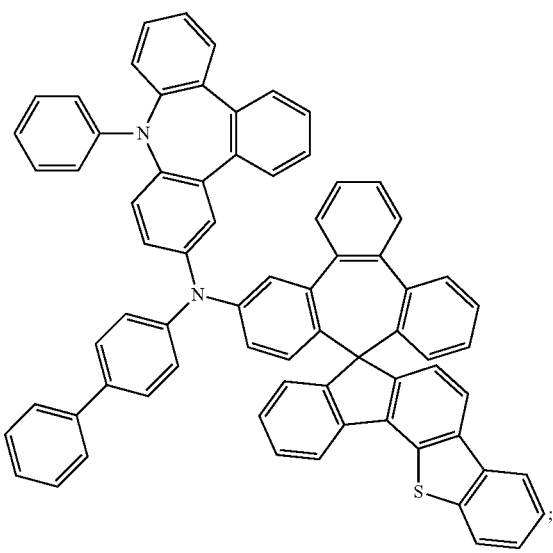

Compound 768
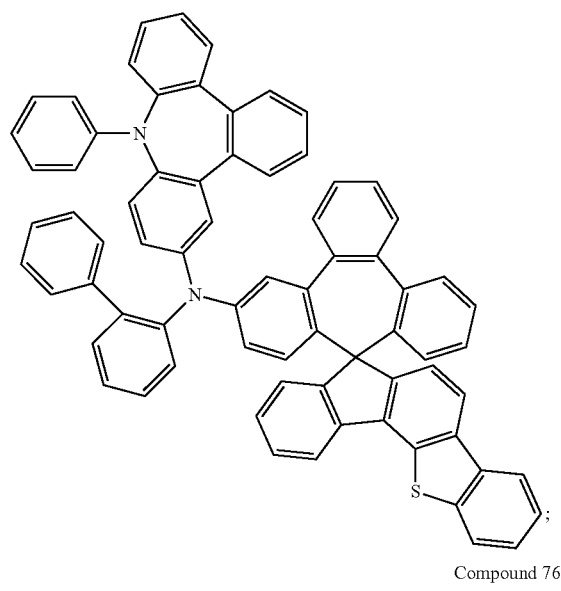
Compound 771
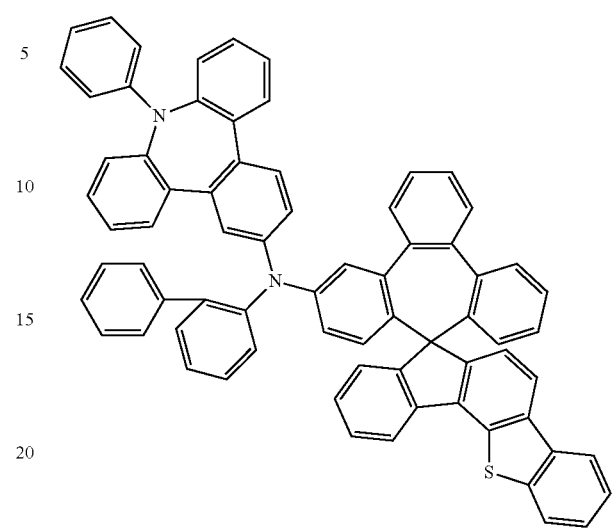
Compound 769
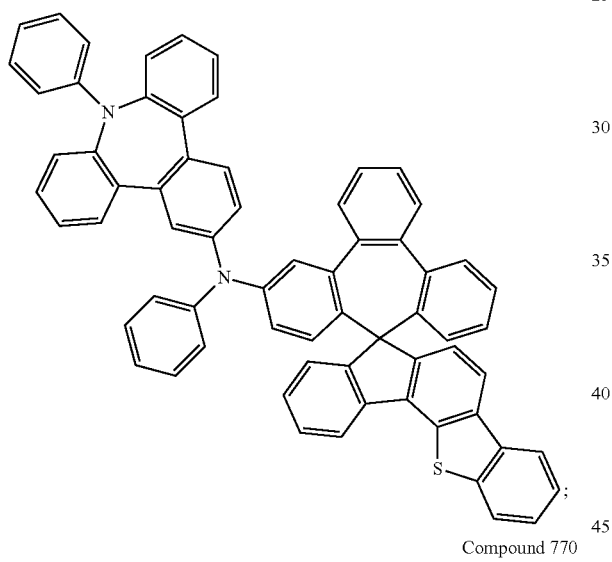
Compound 770
Compound 772
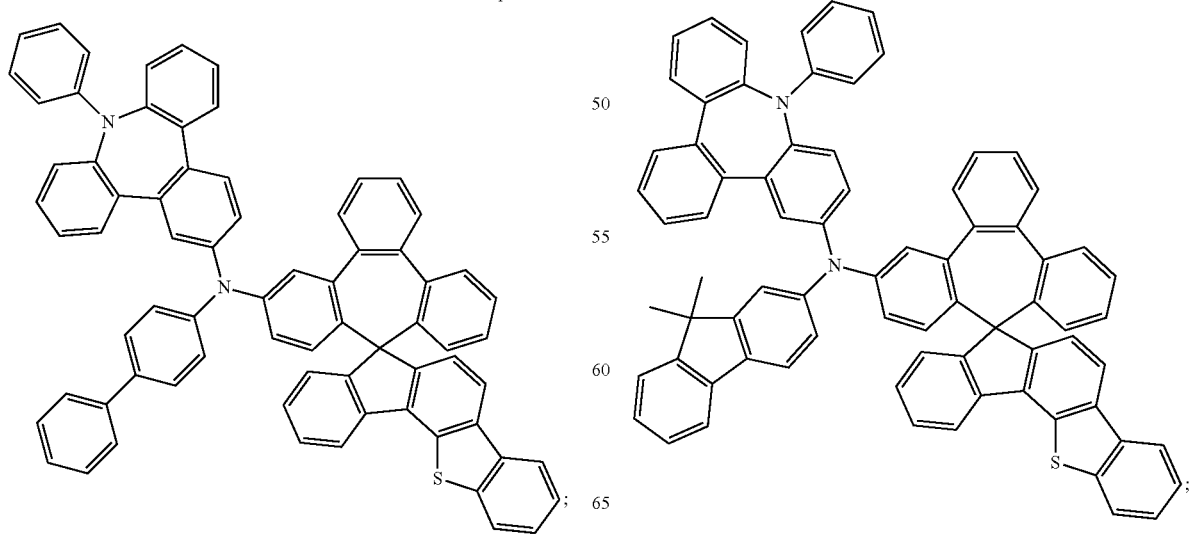

Compound 773
Compound 774
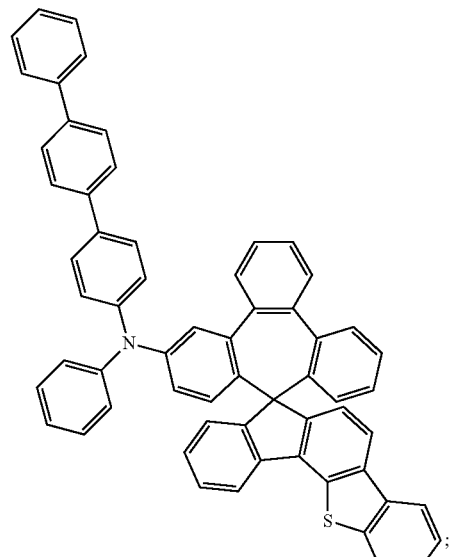
Compound 775
Compound 776
Compound 777
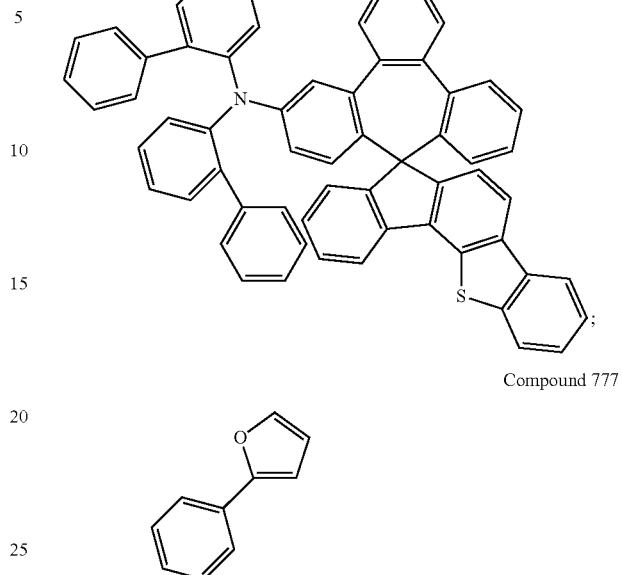
Compound 778

Compound 779
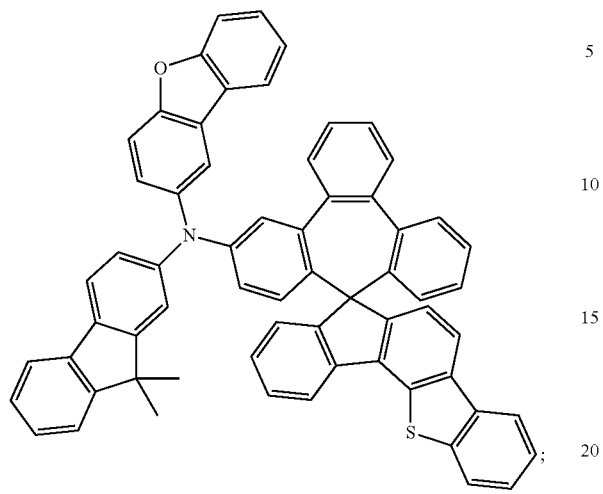
Compound 782
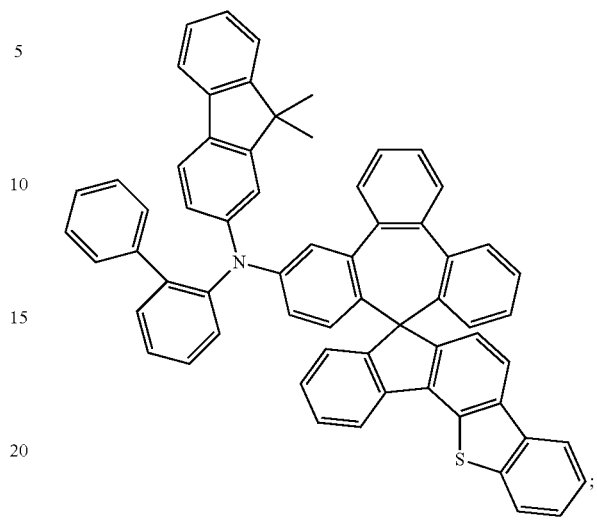
Compound 780
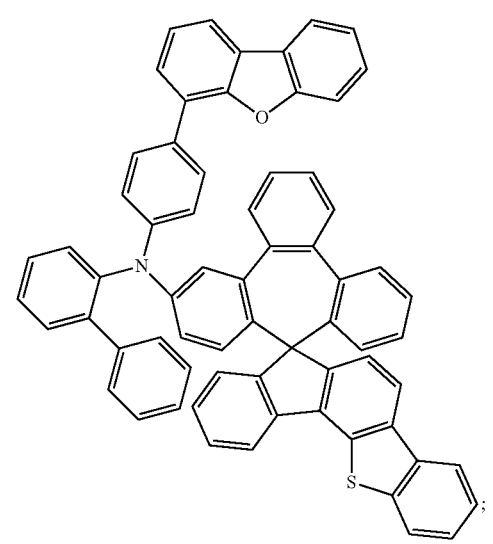
Compound 783
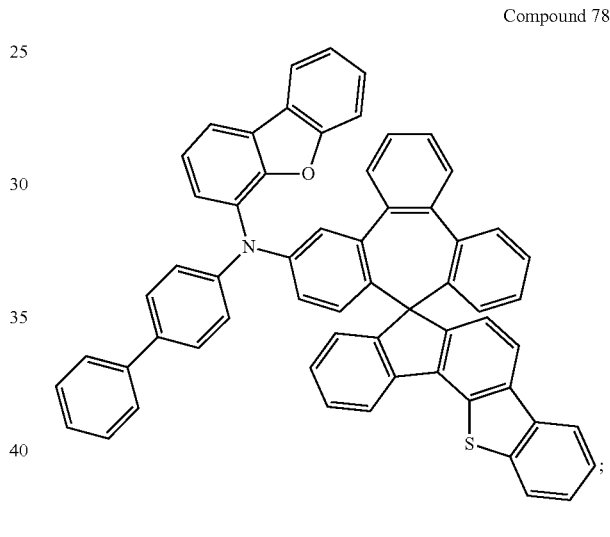
Compound 781
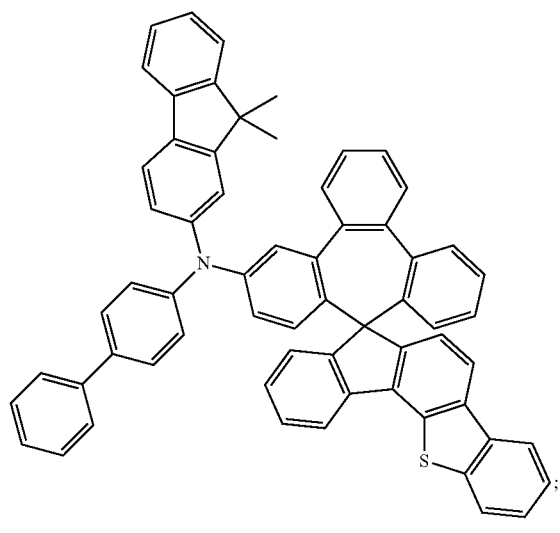
Compound 784
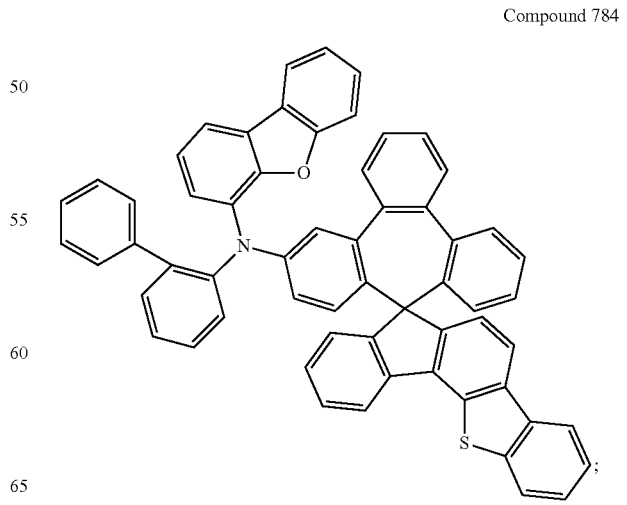

727
-continued
Compound 785
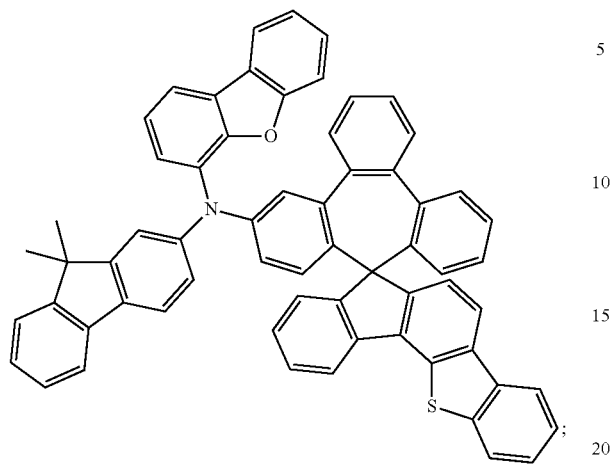
Compound 786
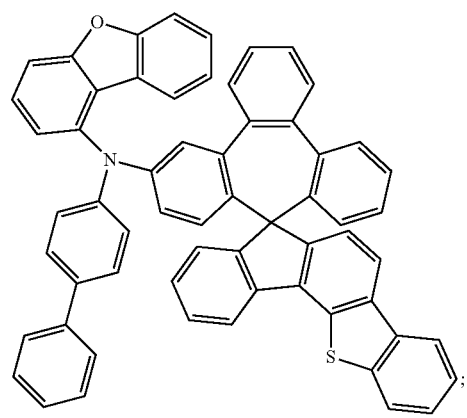
Compound 787
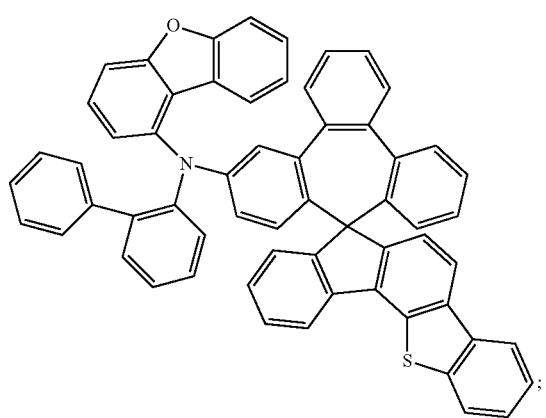
728
-continued
Compound 788
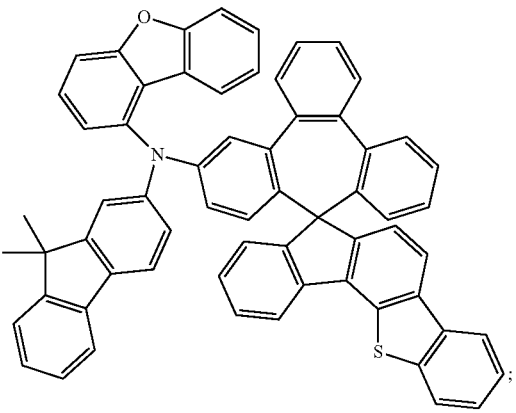
Compound 789
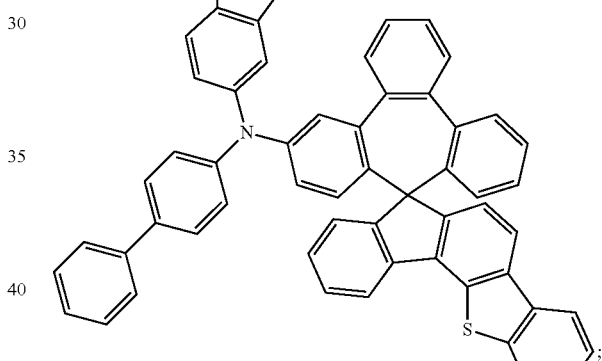
Compound 790
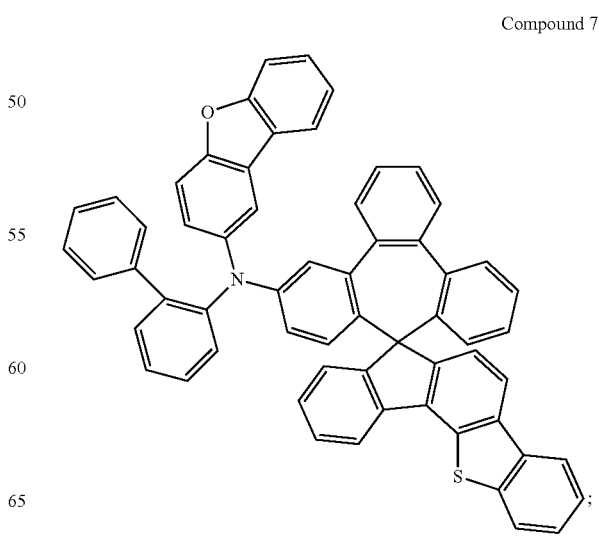

Compound 791
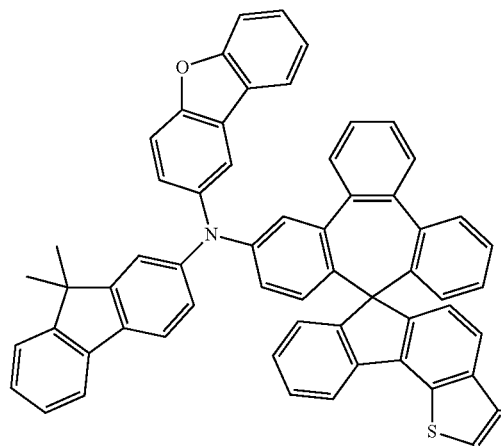
Compound 792
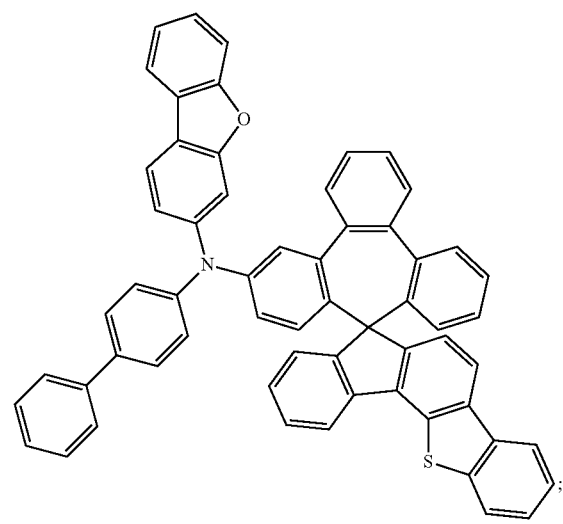
Compound 793
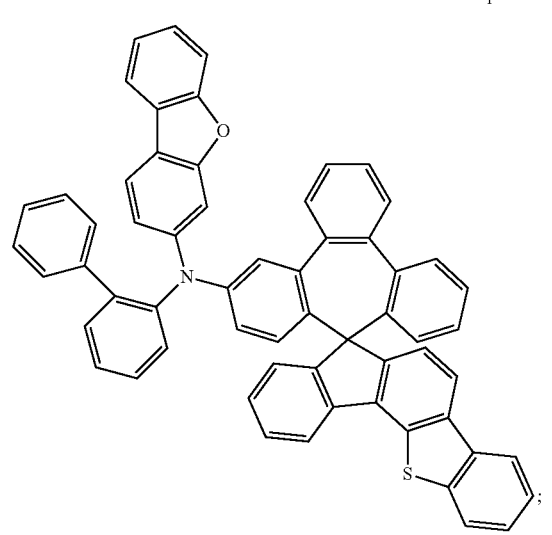
Compound 794
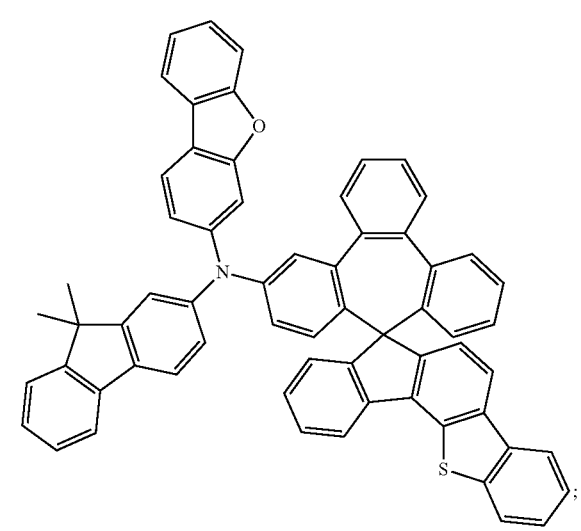
Compound 795
Compound 796
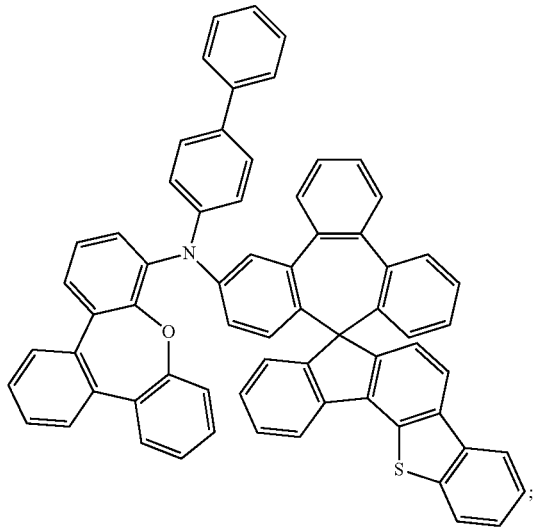

Compound 797
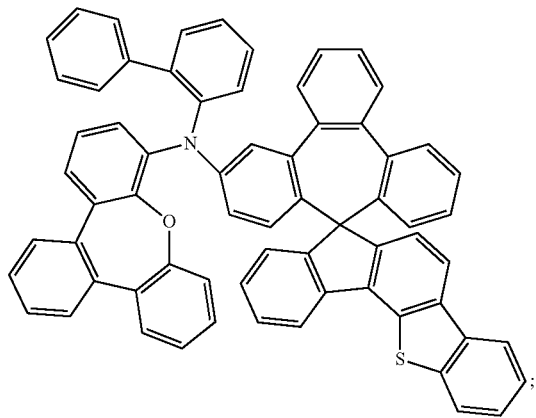
Compound 798
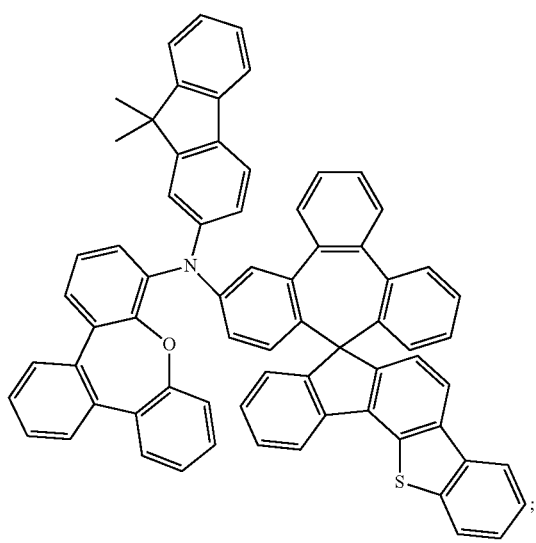
Compound 799
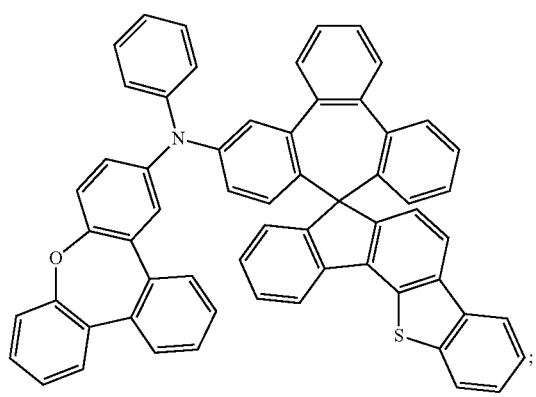
Compound 800
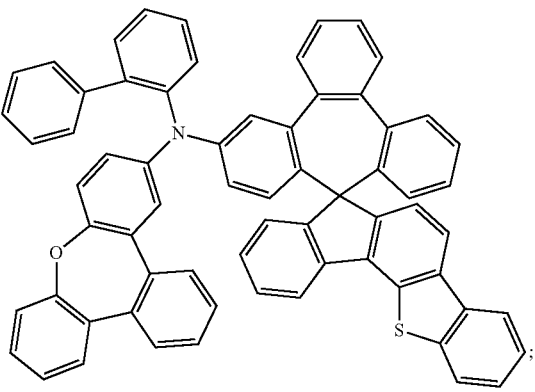
Compound 801
Compound 802
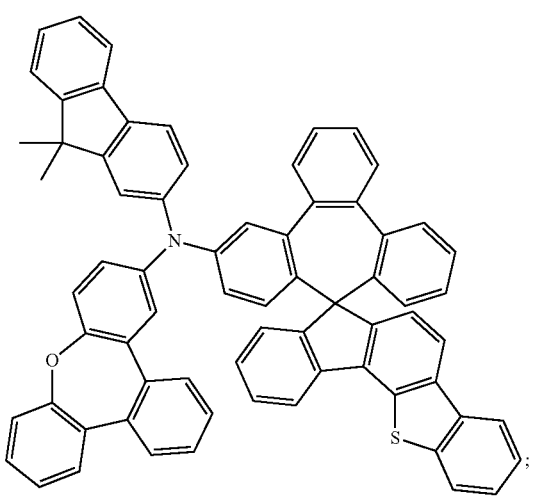

Compound 803
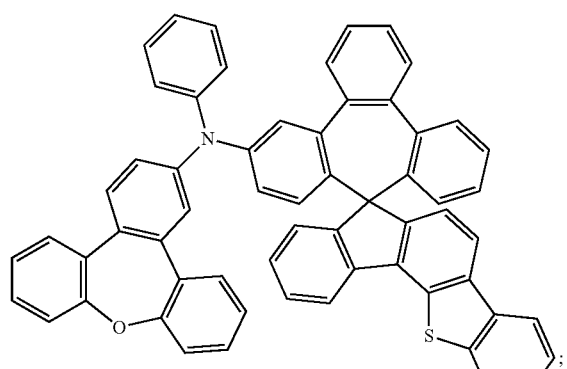
Compound 804
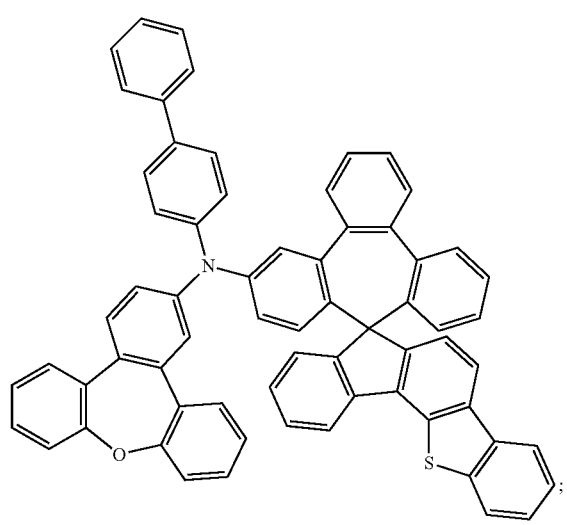
Compound 805
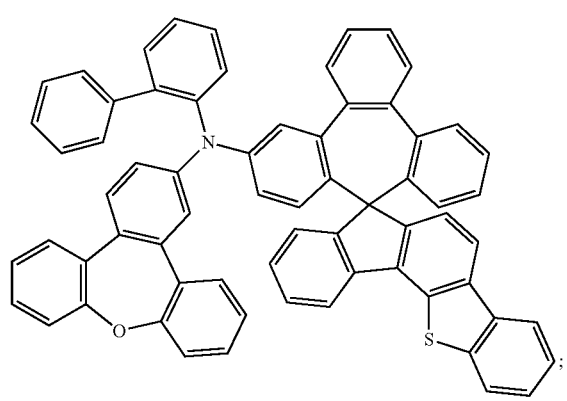
Compound 806
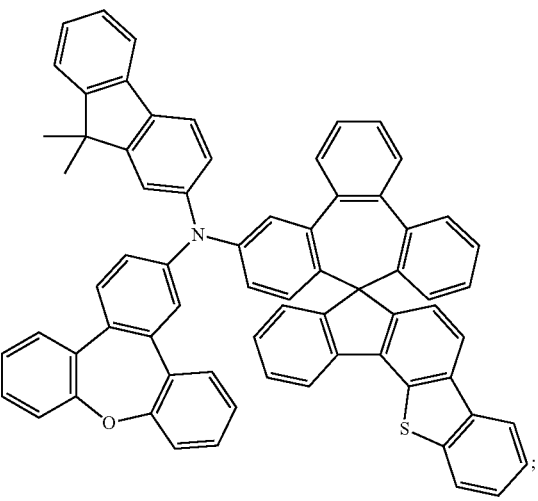
Compound 807
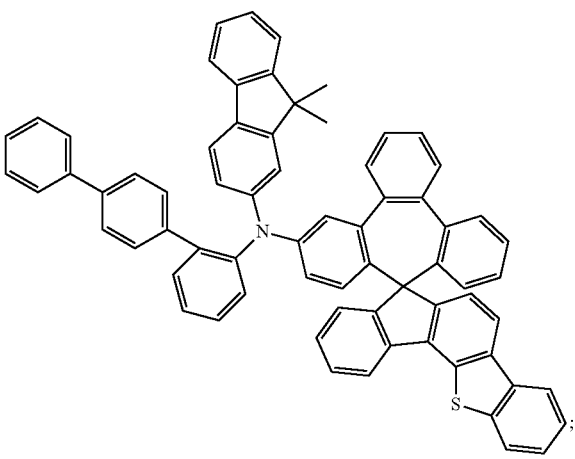
Compound 808
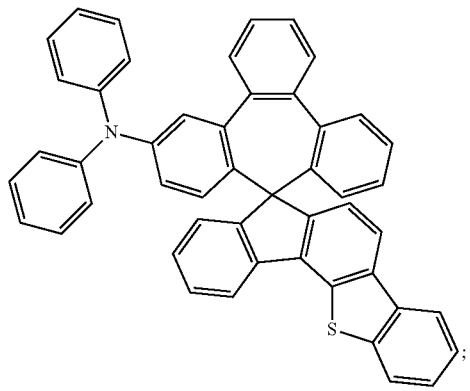

Compound 809
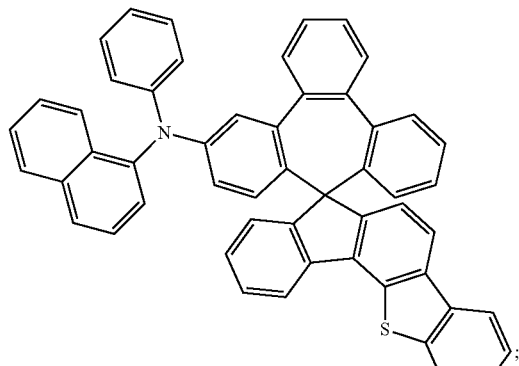
Compound 812
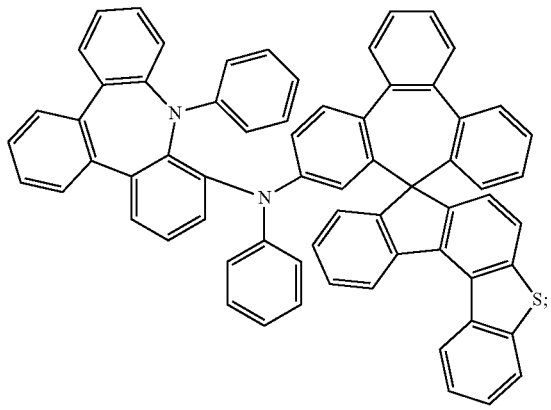
Compound 810
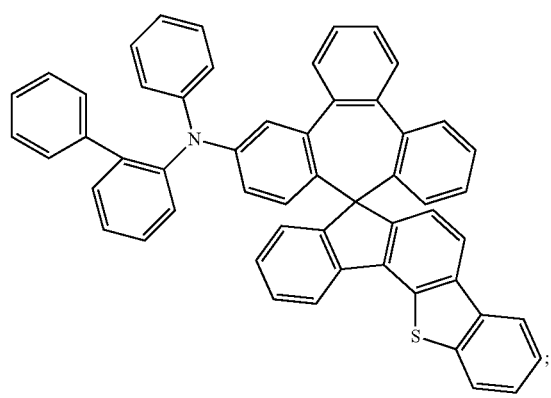
Compound 813
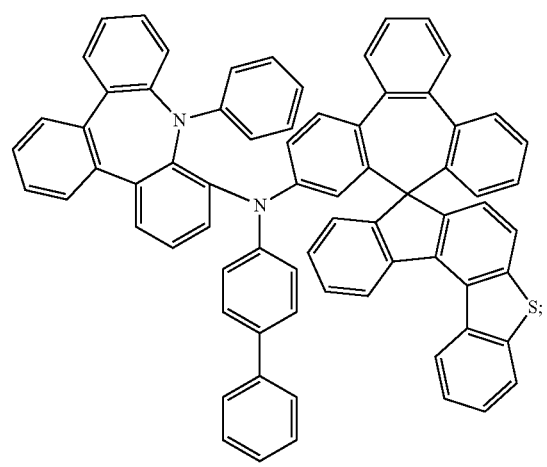
Compound 811
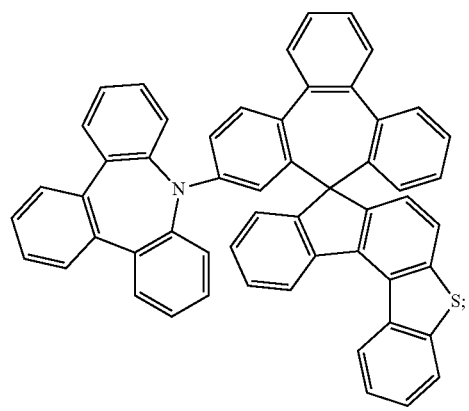
Compound 814
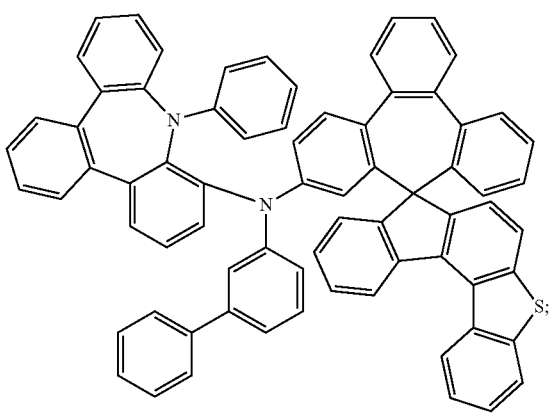

Compound 815
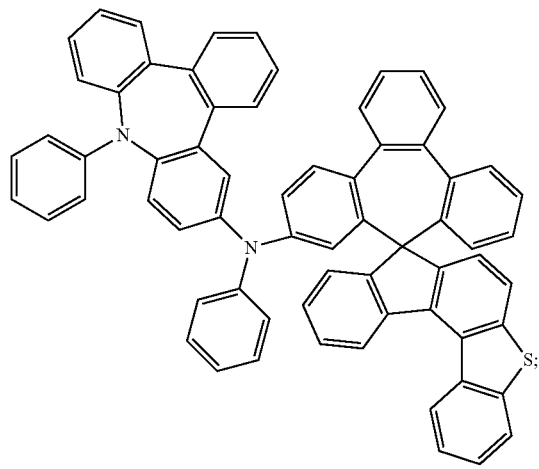
Compound 818
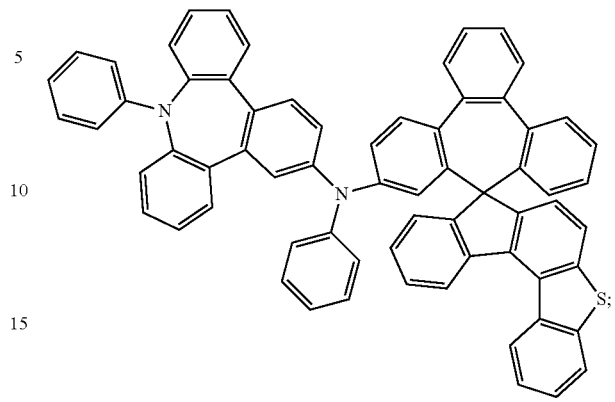
Compound 816
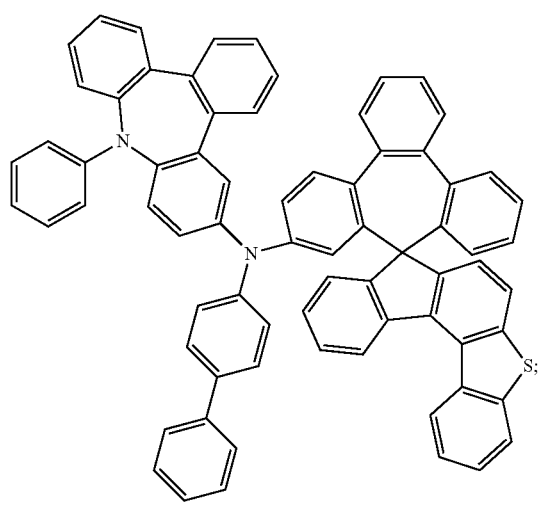
Compound 819
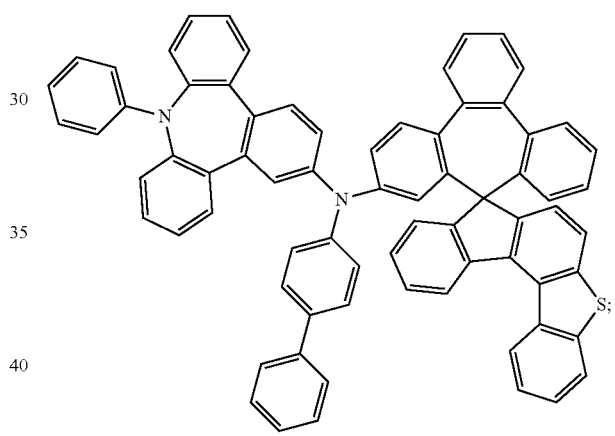
Compound 817
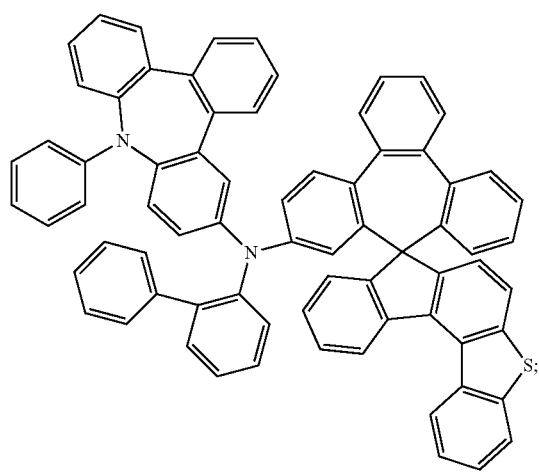
Compound 820
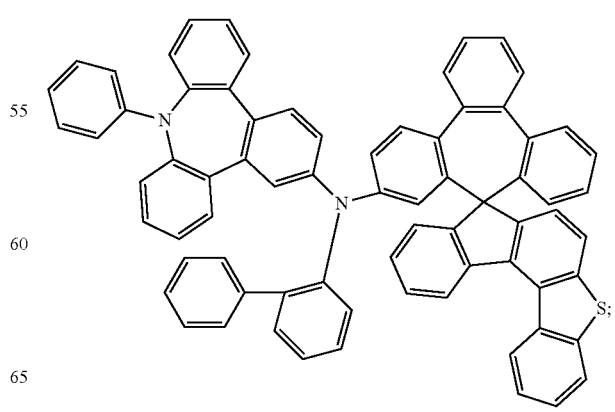

Compound 821
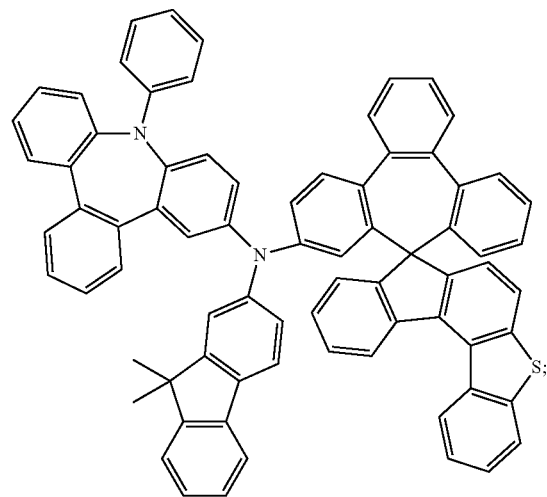
Compound 822
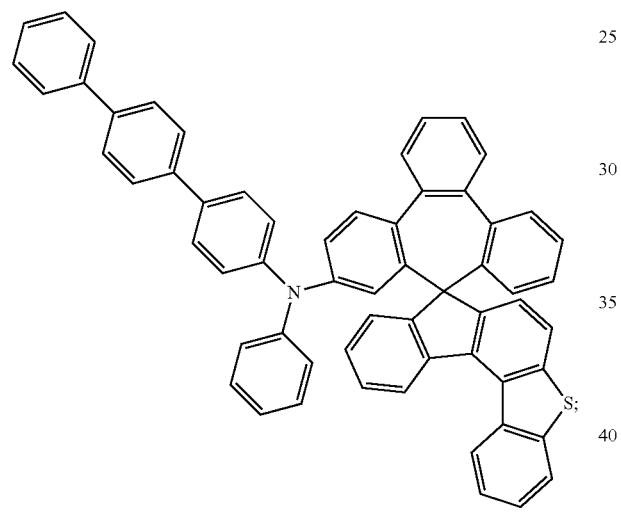
Compound 823
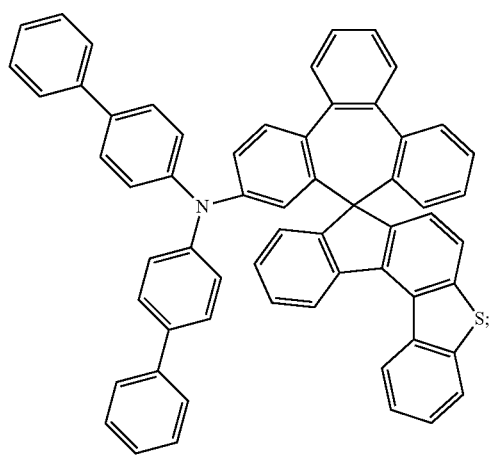
Compound 824
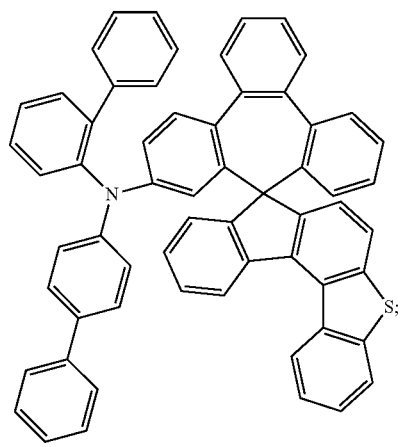
Compound 825
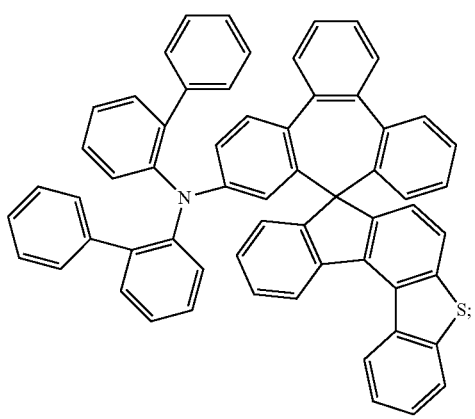
Compound 826
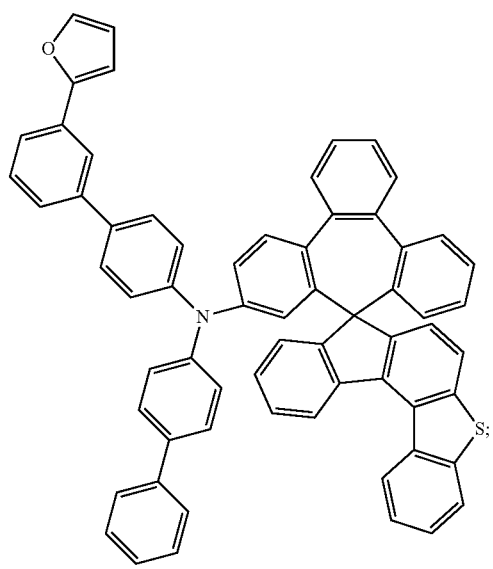

Compound 827
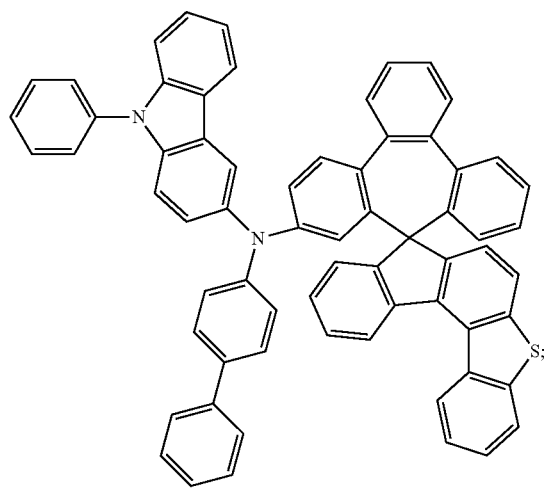
Compound 828
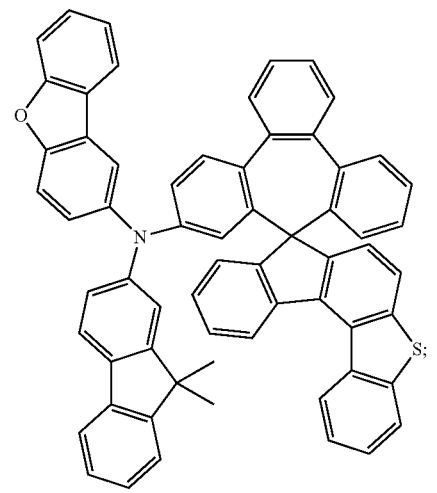
Compound 829
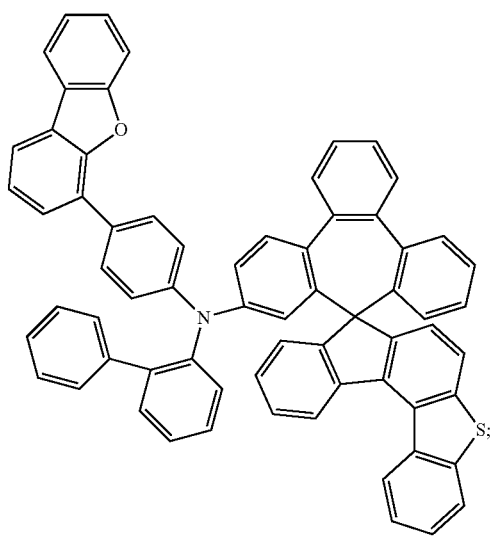
Compound 830
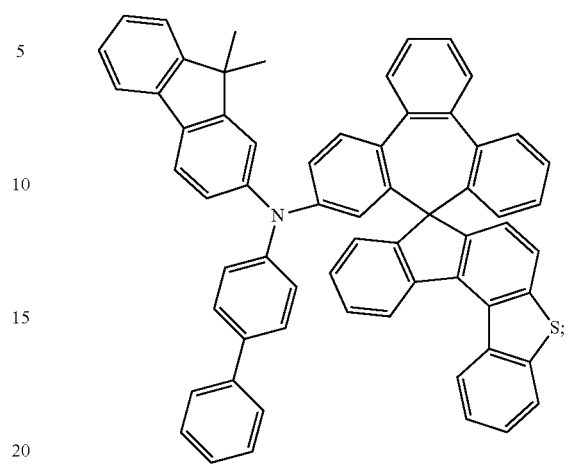
Compound 831
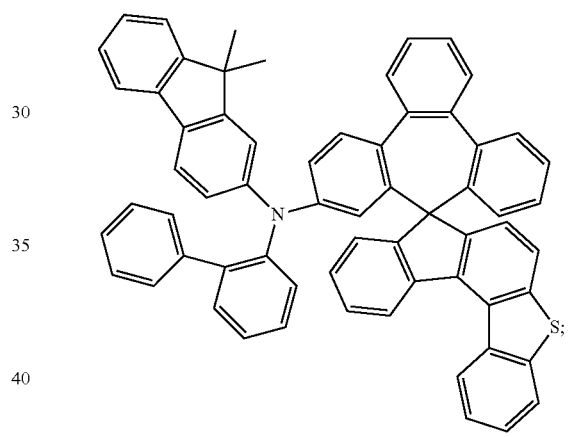
Compound 832
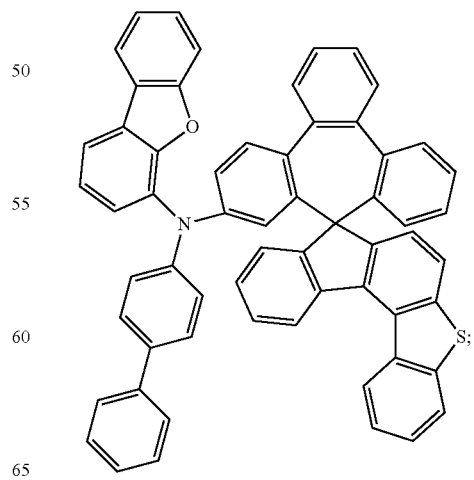

Compound 833
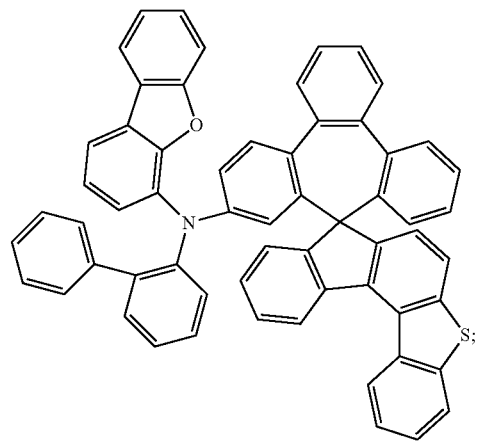
Compound 836
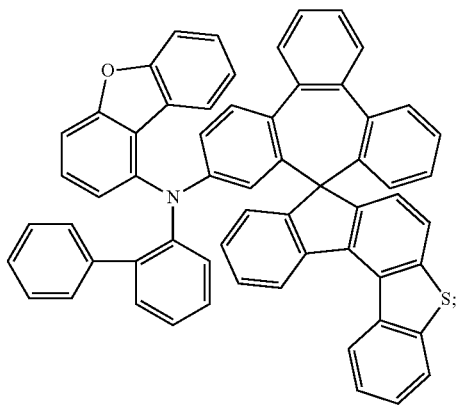
Compound 834
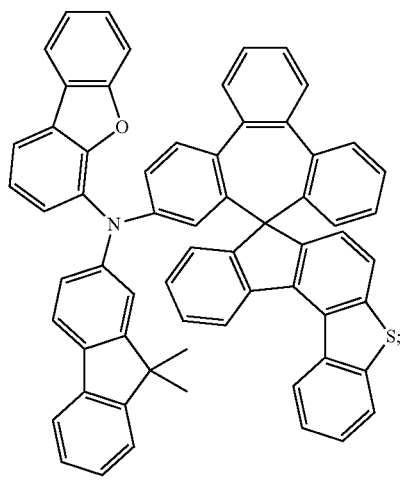
Compound 837
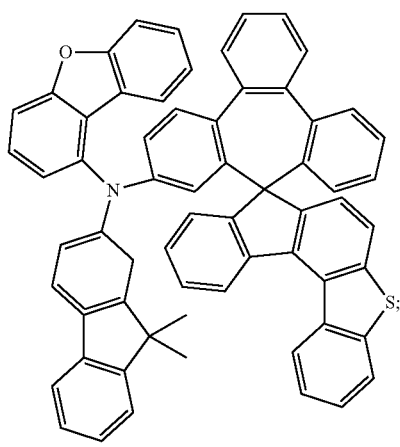
Compound 835
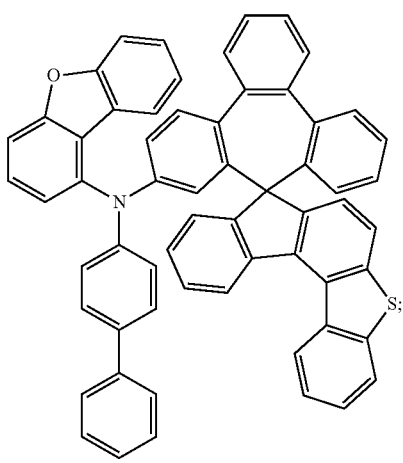
Compound 838
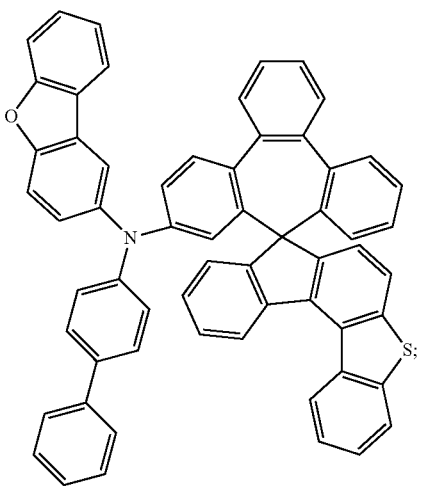

Compound 839
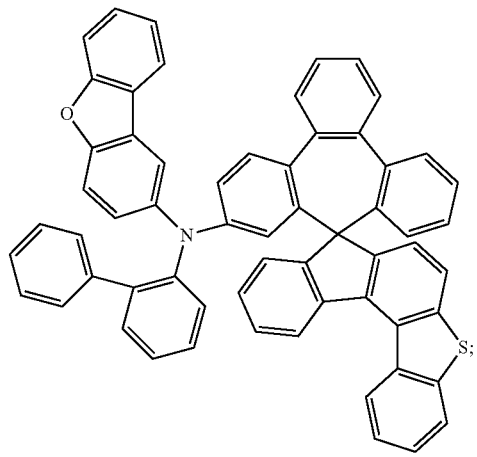
Compound 842
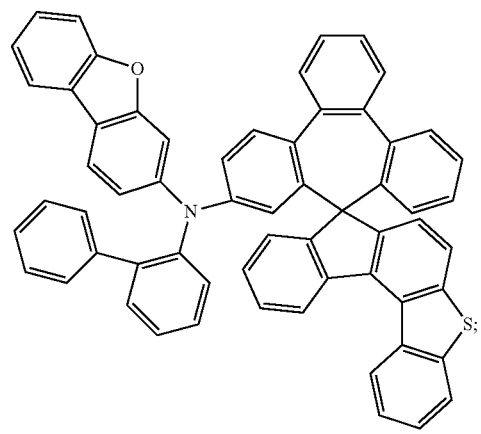
Compound 840
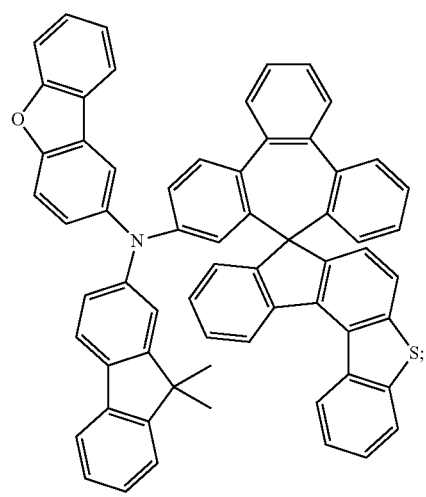
Compound 843
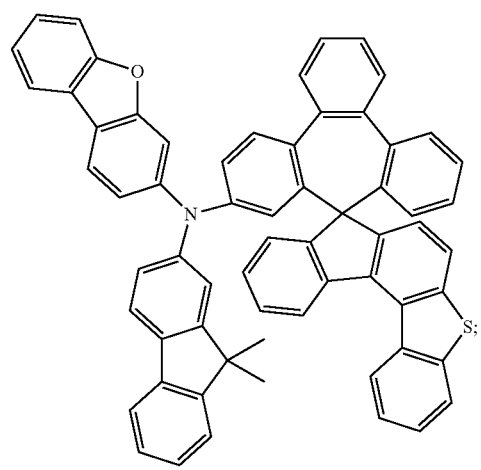
Compound 841
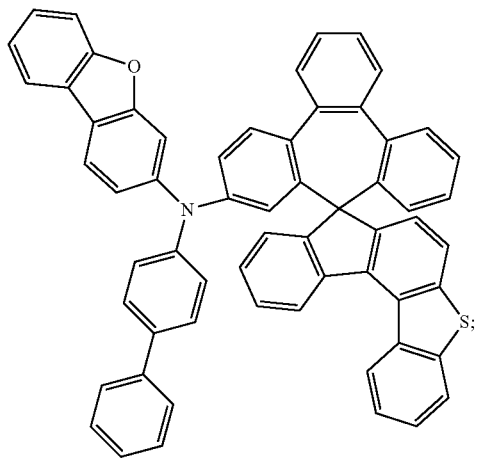
Compound 844
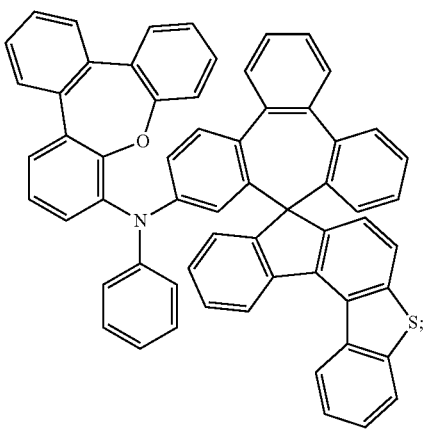

Compound 845
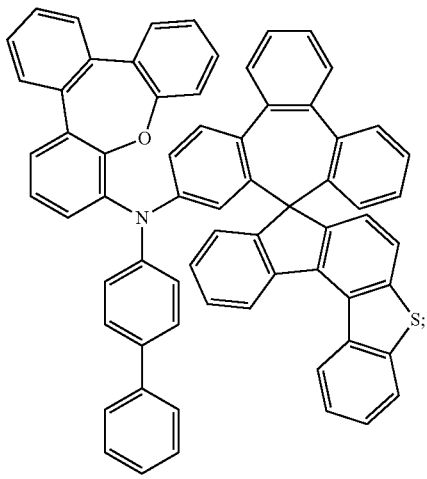
Compound 846
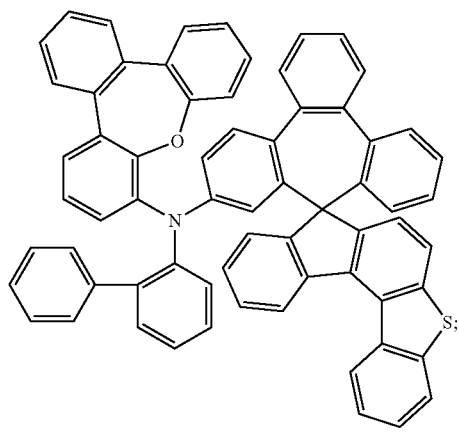
Compound 847
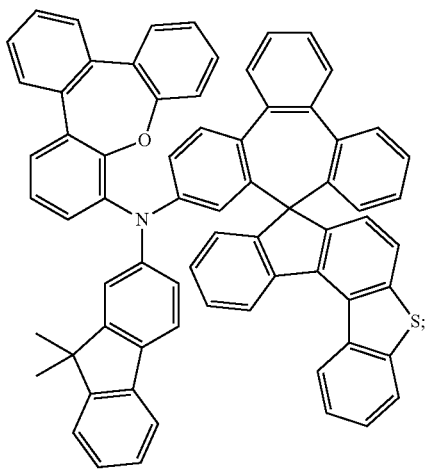
Compound 848
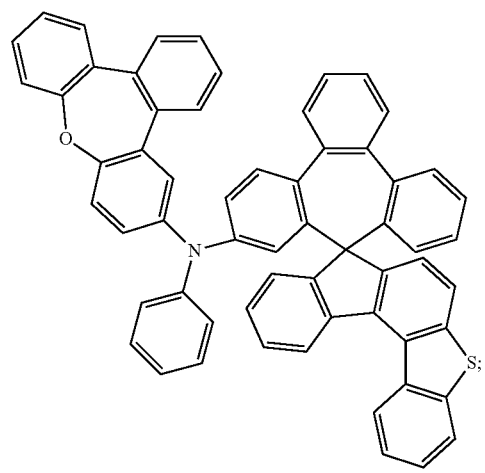
Compound 849
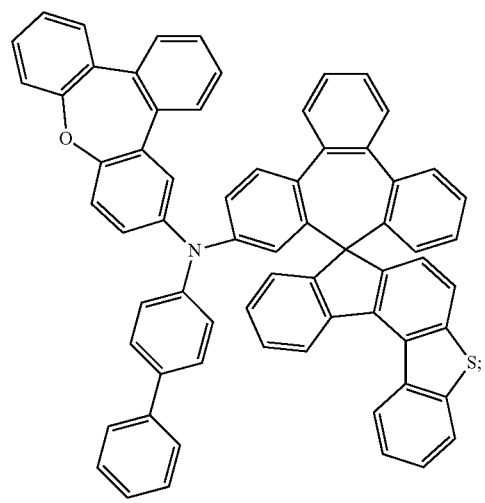
Compound 850
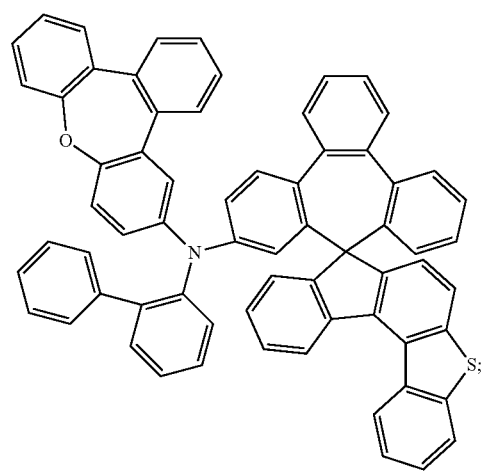

Compound 851
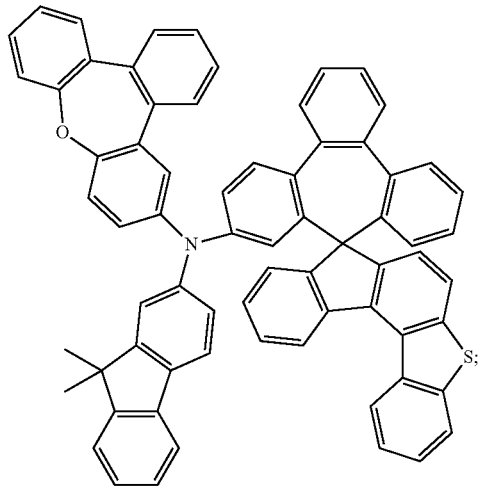
Compound 852
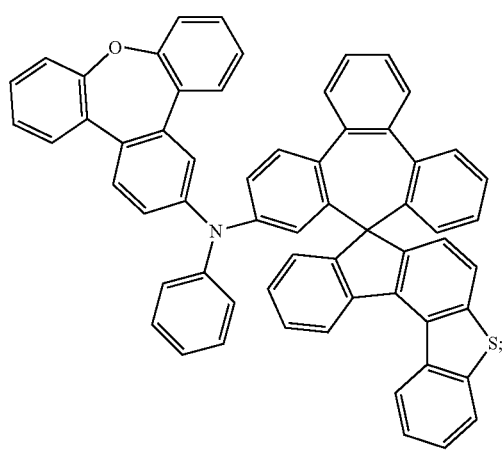
Compound 853
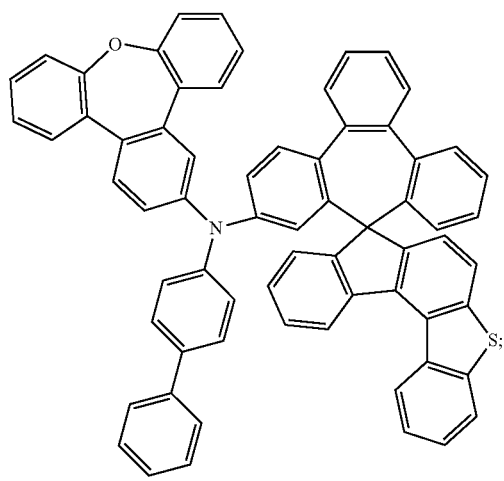
Compound 854
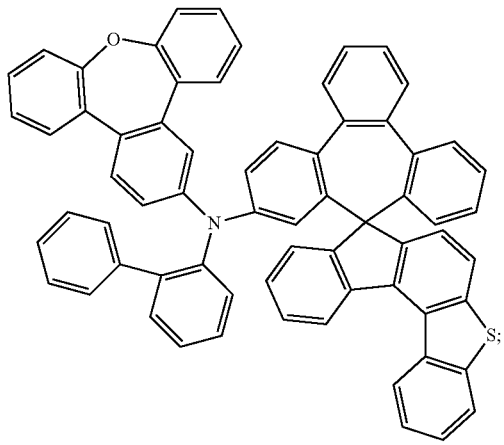
Compound 855
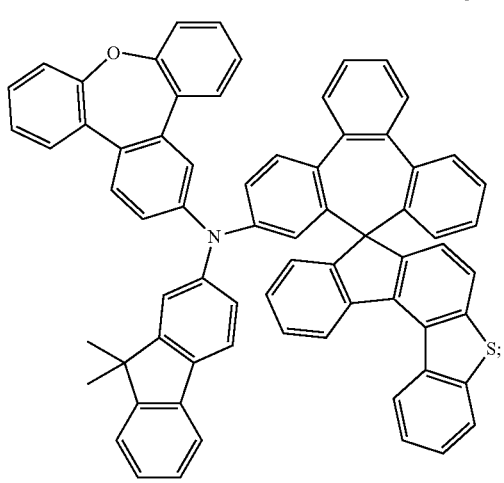
Compound 856
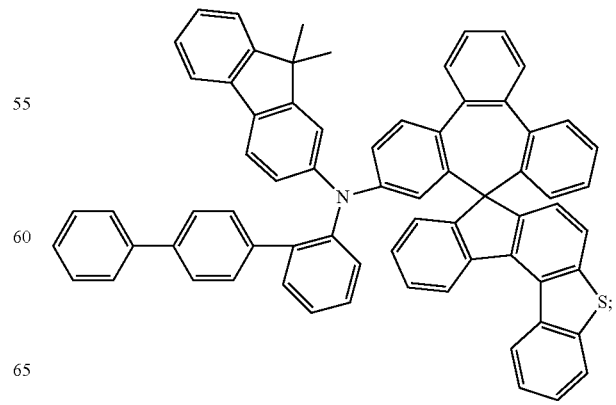

Compound 857
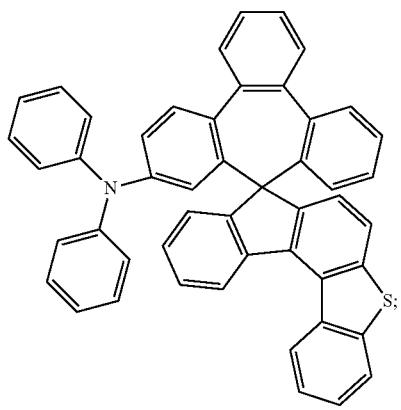
Compound 860
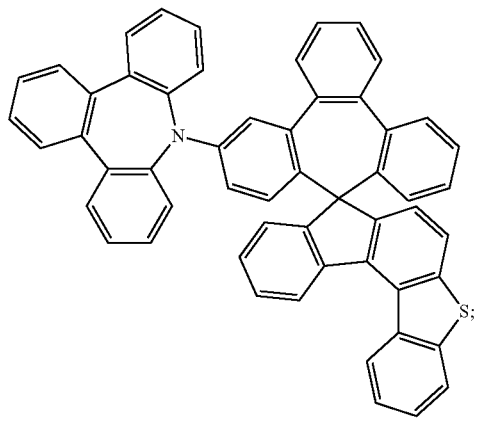
Compound 858
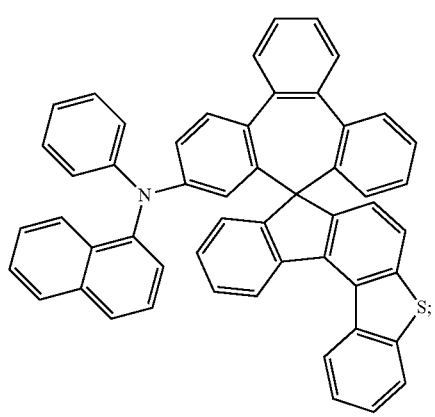
Compound 861
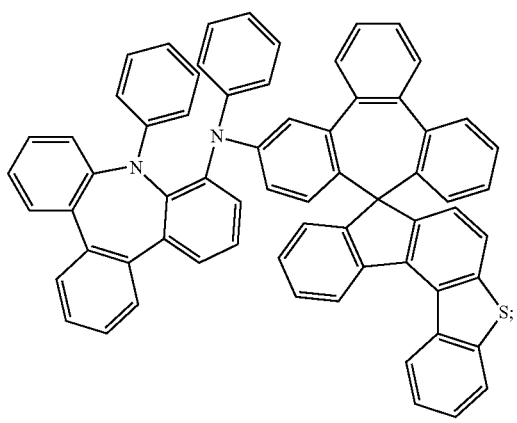
Compound 859
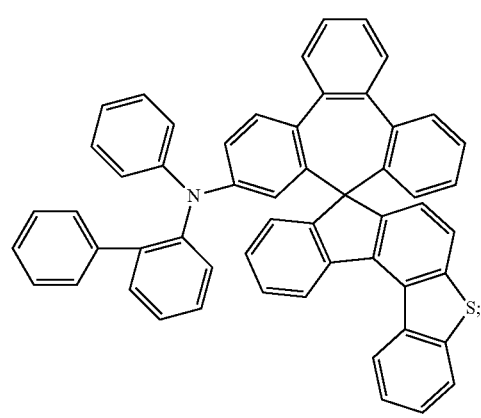
Compound 862
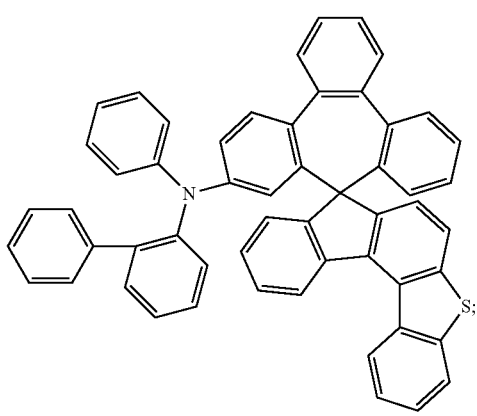

Compound 863
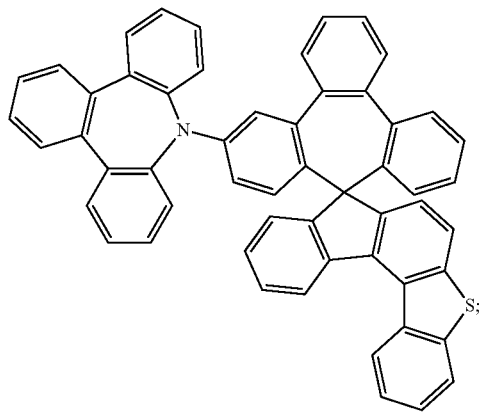
Compound 864
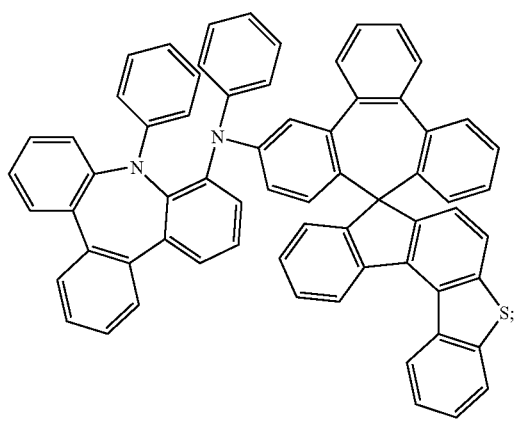
Compound 865
Compound 866
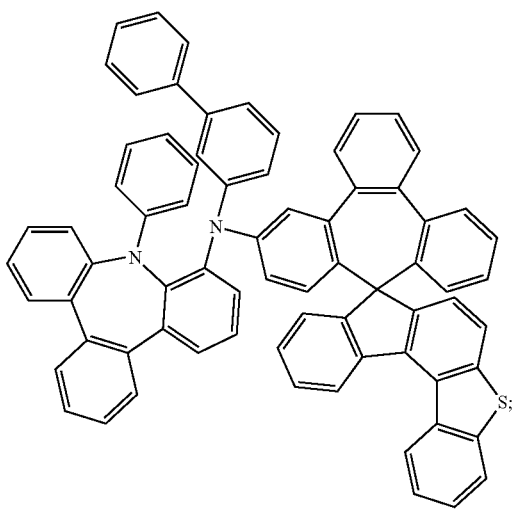
Compound 867
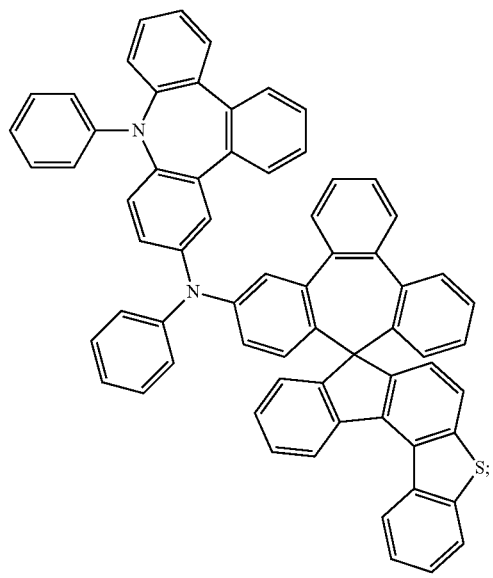

Compound 868
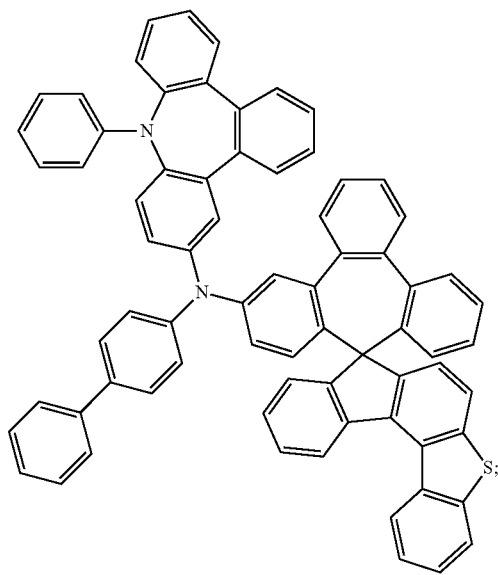
Compound 869
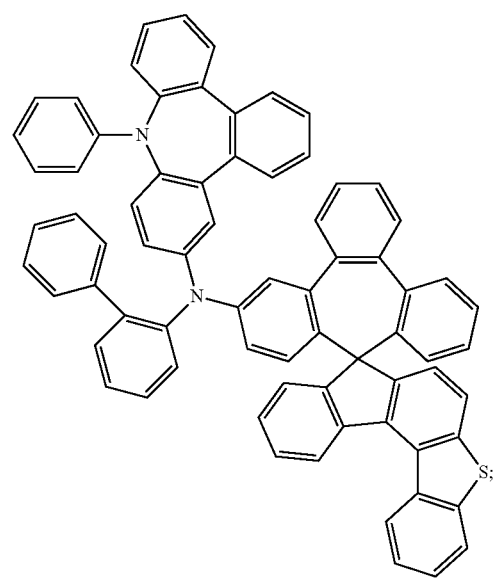
Compound 870
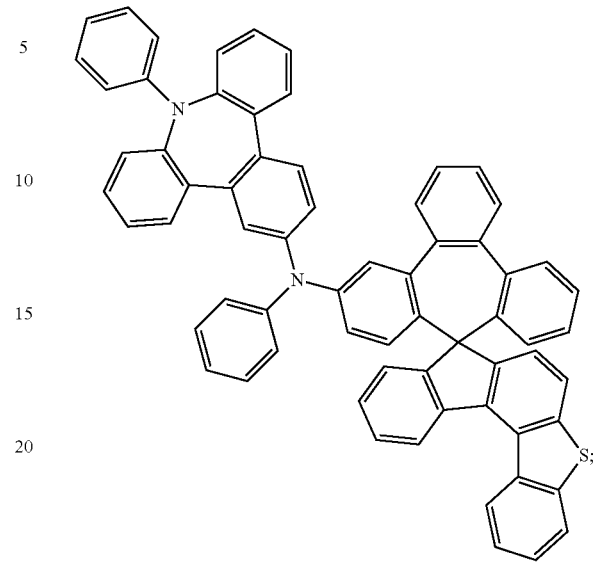
Compound 871
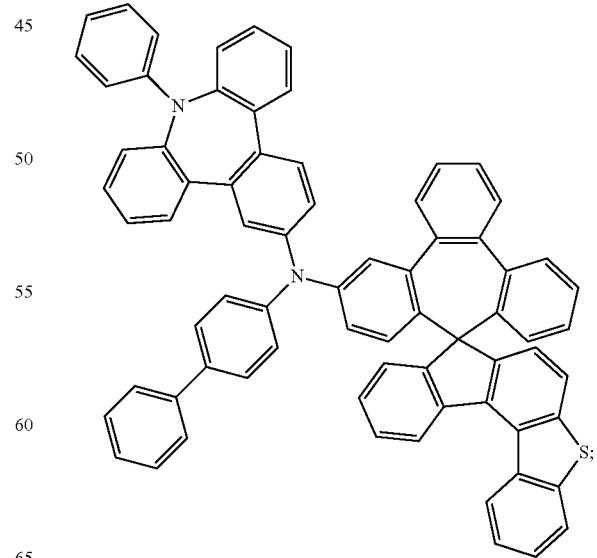

Compound 872
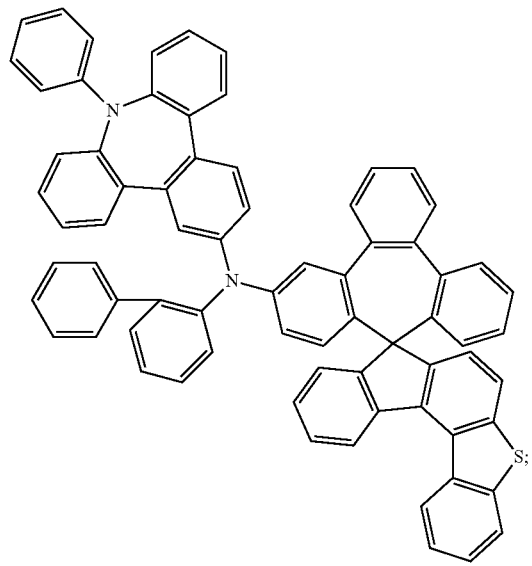
Compound 874
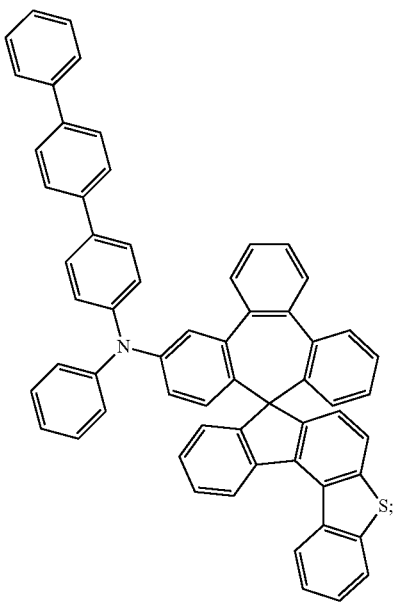
Compound 873
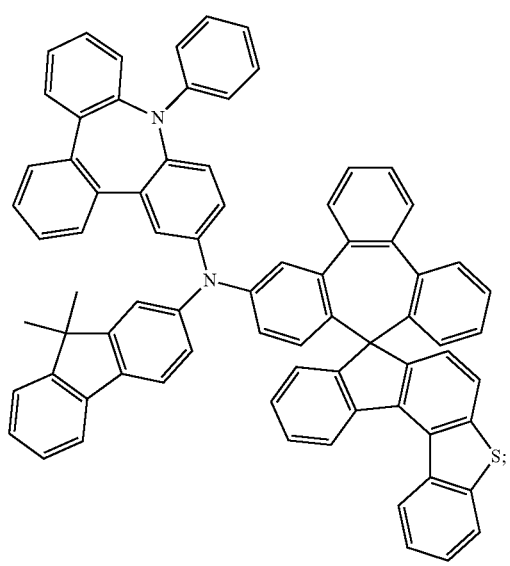
Compound 875
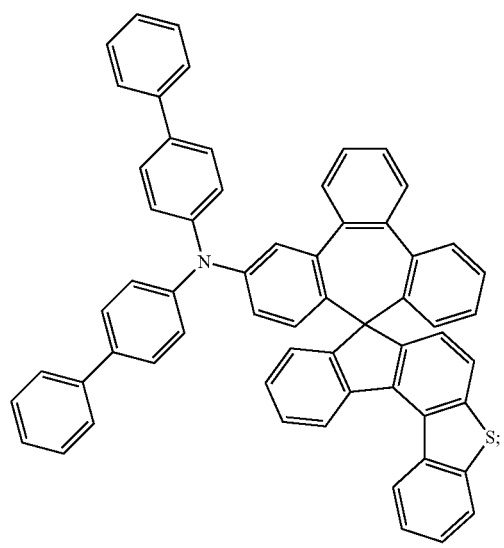

Compound 876
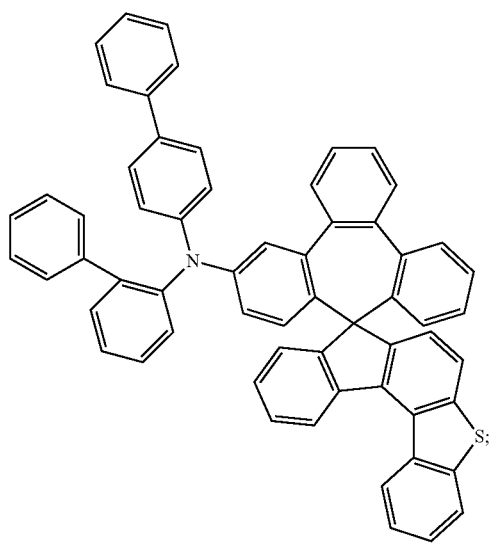
Compound 877
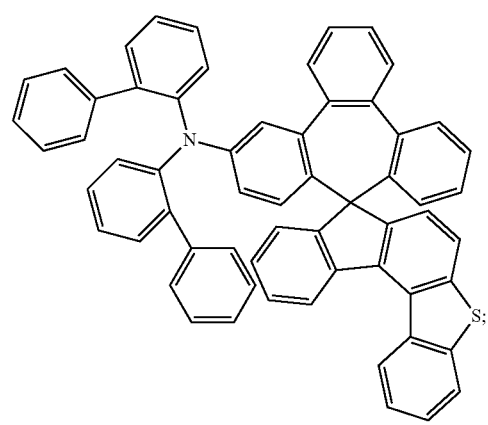
Compound 878
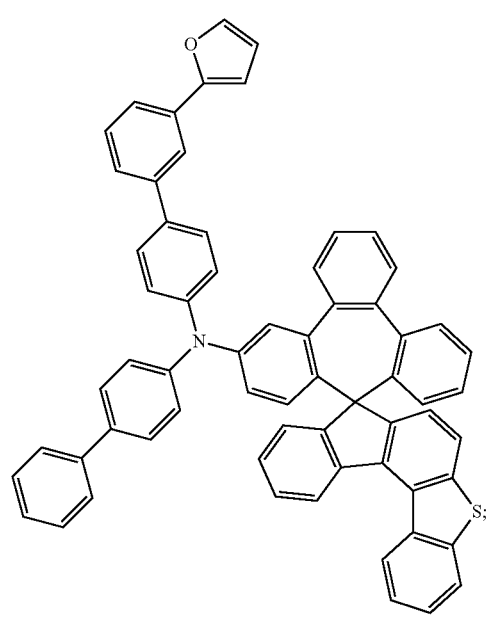
Compound 879
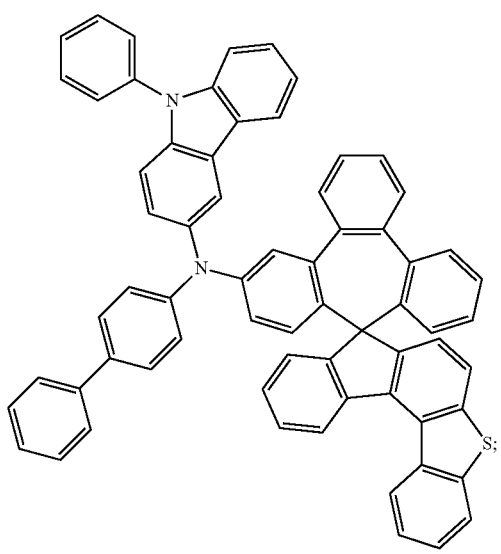
Compound 880
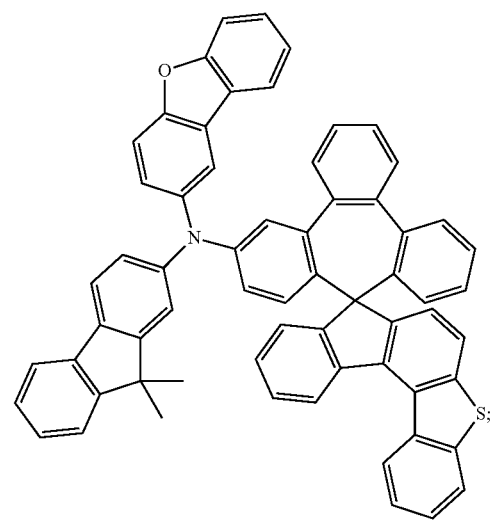

Compound 881
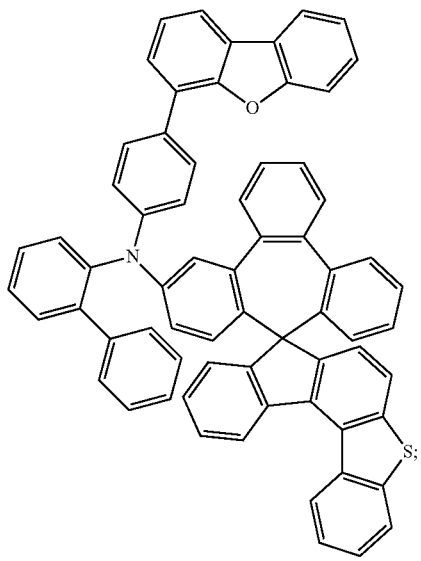
Compound 882
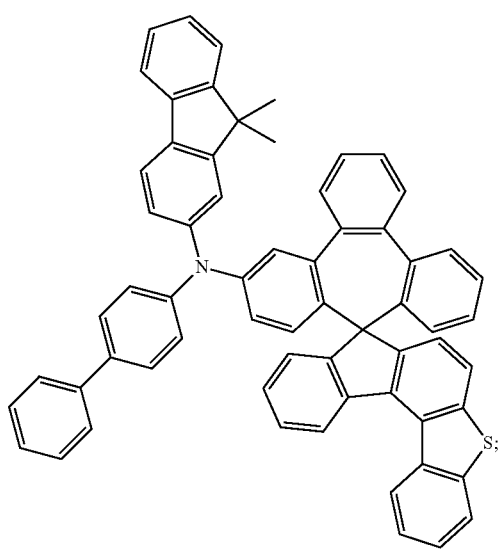
Compound 883
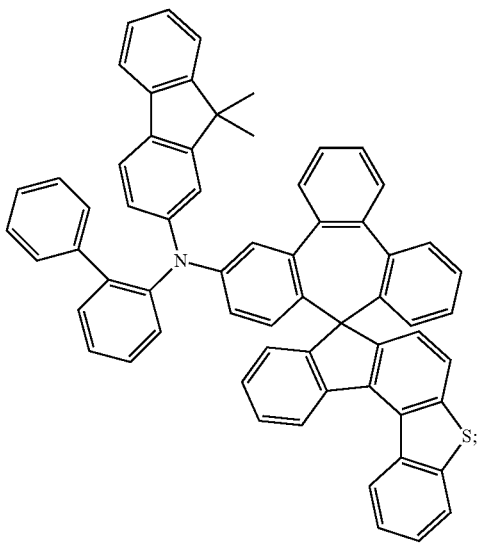
Compound 884
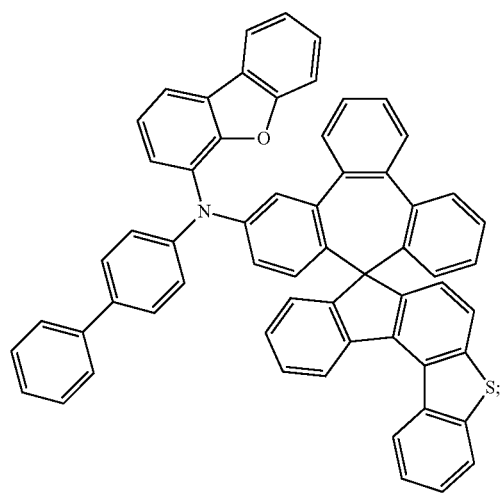
Compound 885
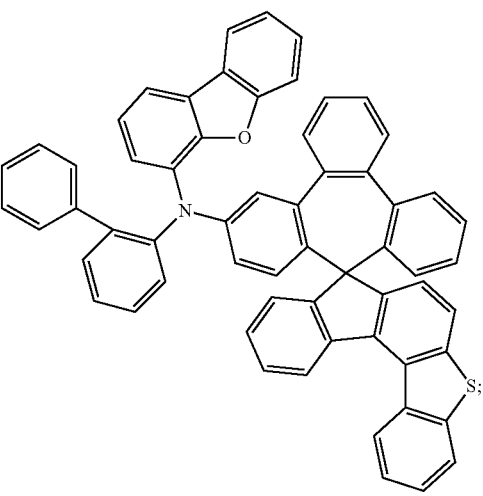

Compound 886
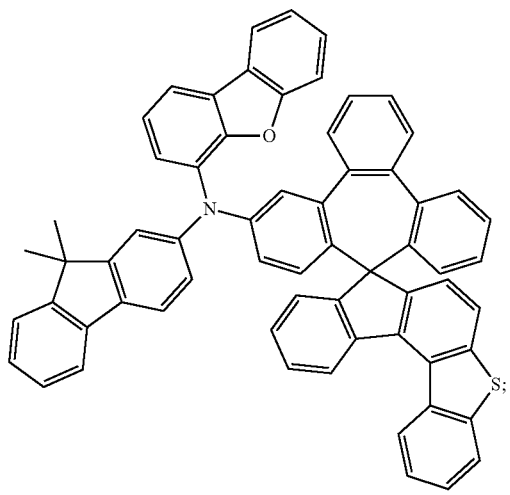
Compound 887
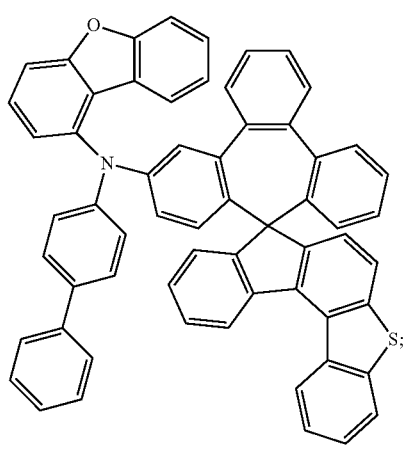
Compound 888
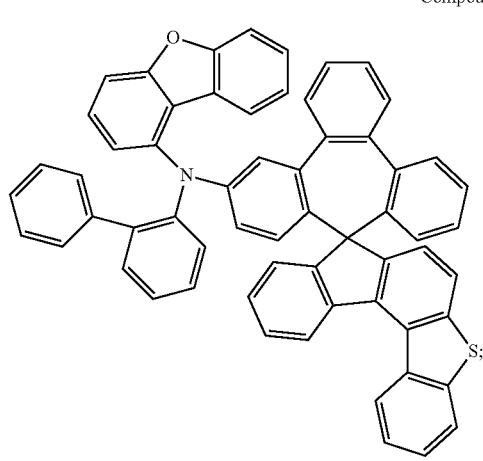
Compound 899
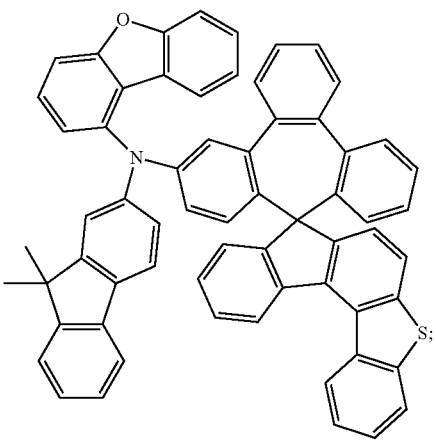
Compound 890
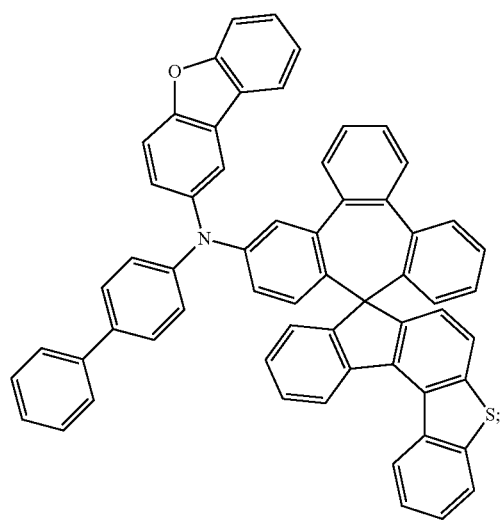
Compound 891
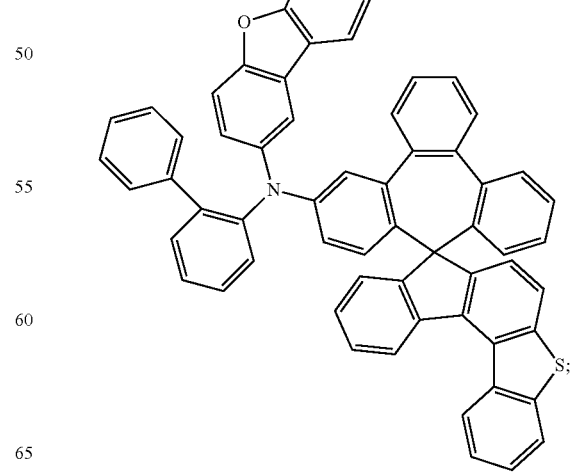

Compound 892
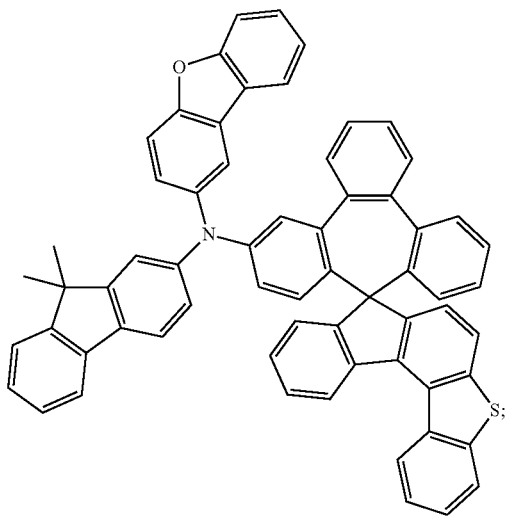
Compound 893
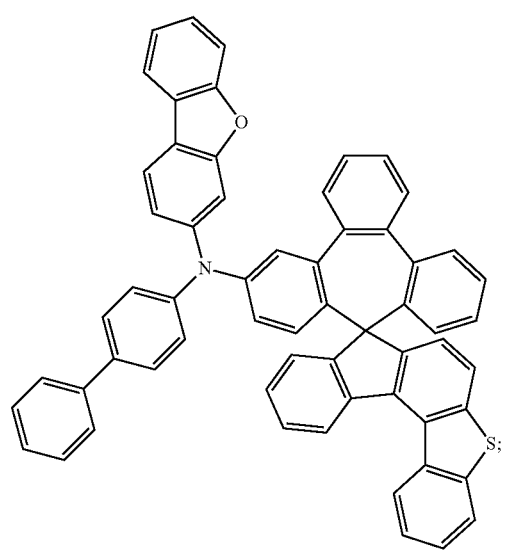
Compound 894
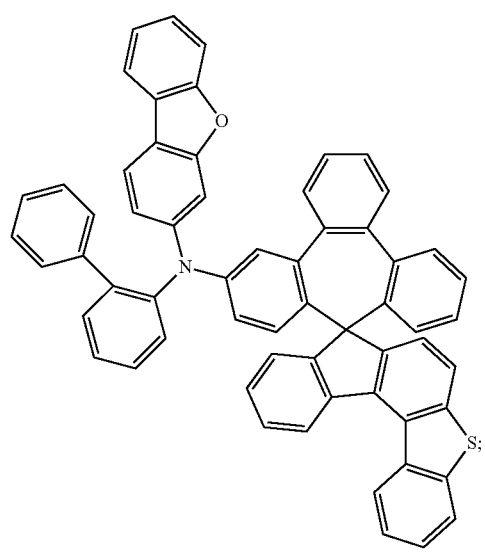
Compound 895
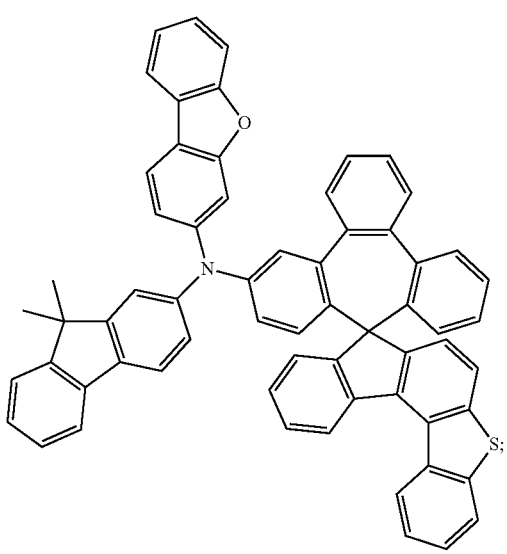
Compound 896
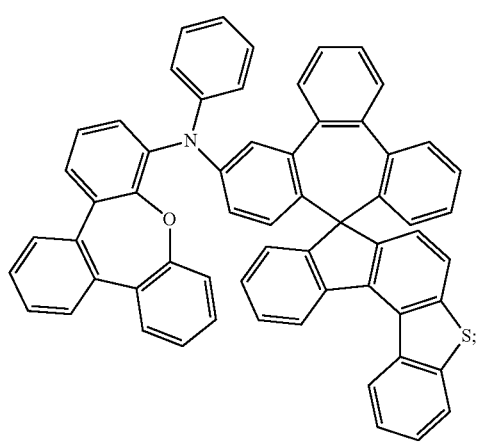
Compound 897
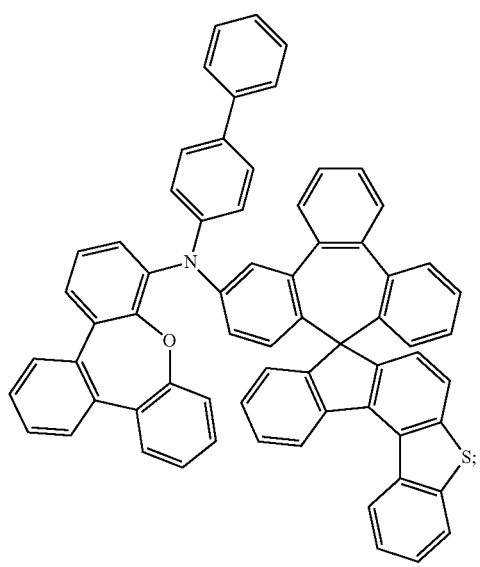

Compound 898
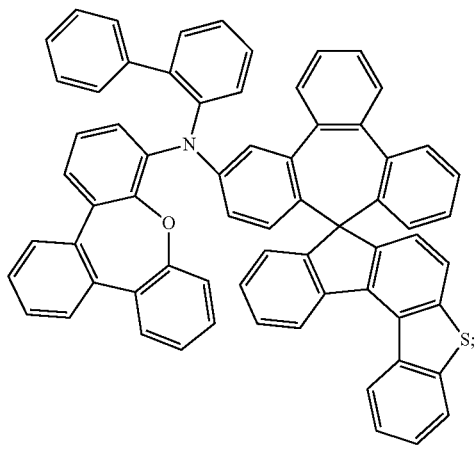
Compound 899
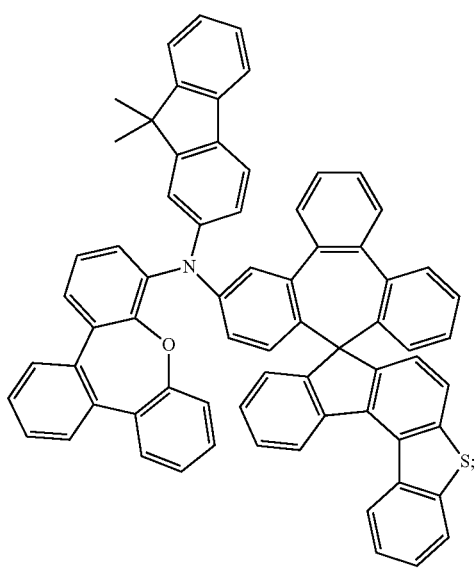
Compound 900
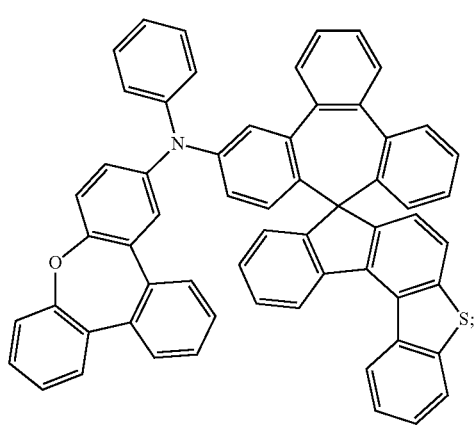
Compound 901
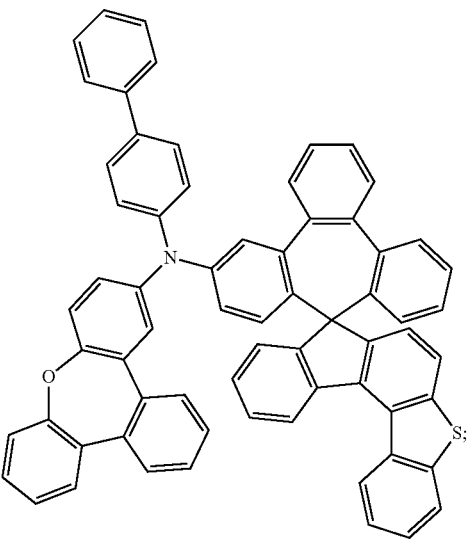
Compound 902
Compound 903
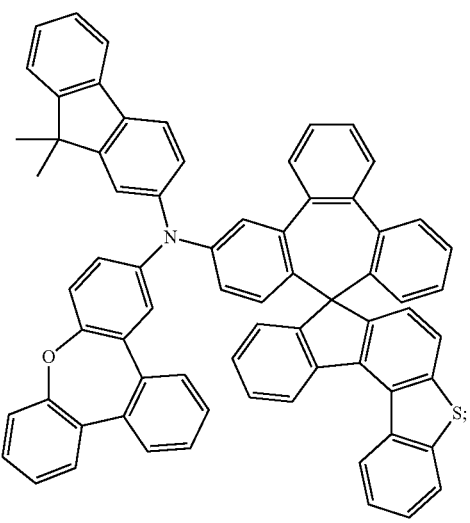

Compound 904
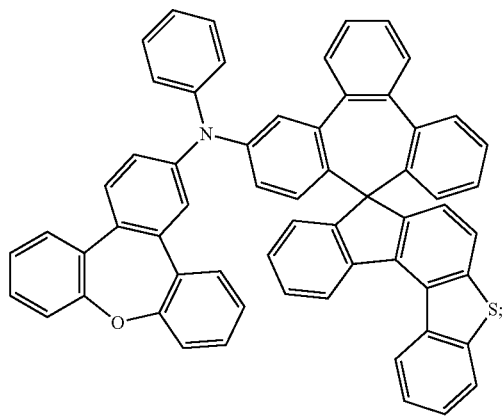
Compound 905
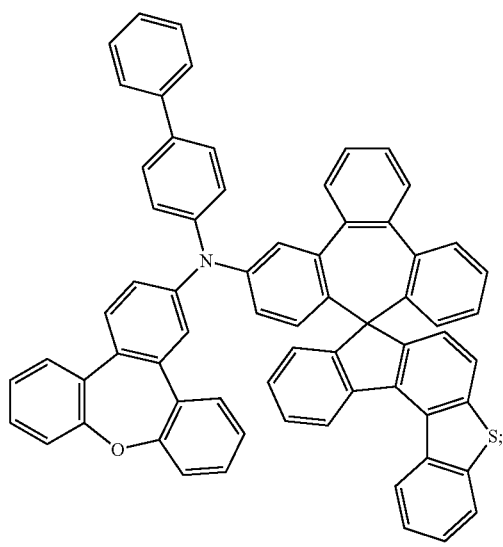
Compound 906
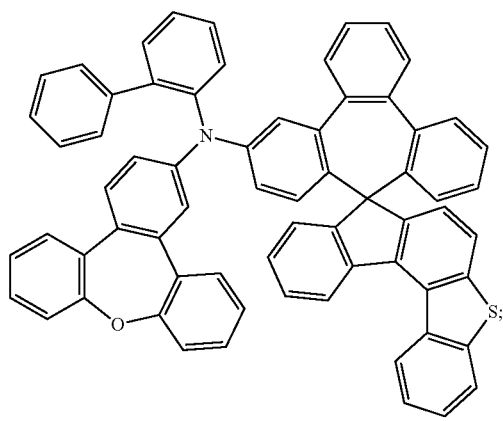
Compound 907
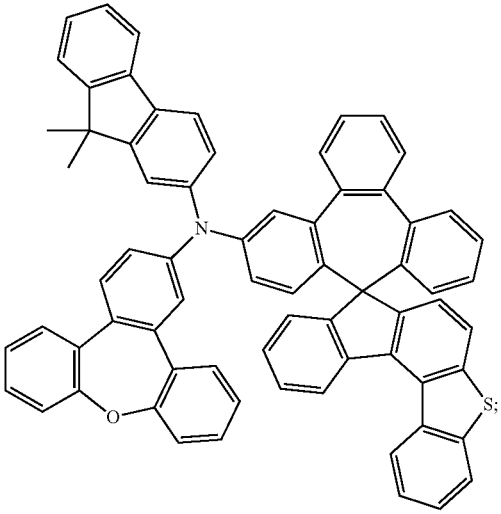
Compound 908
Compound 909
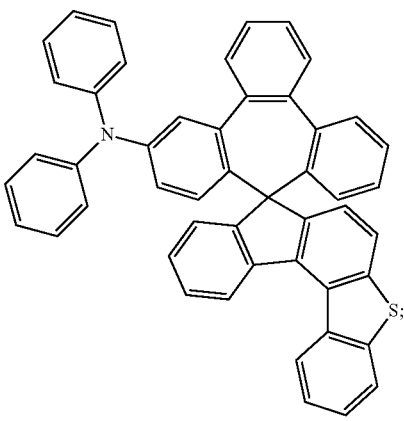

-continued
Compound 910
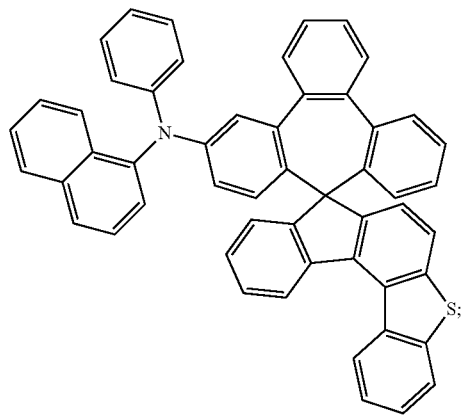
Compound 911
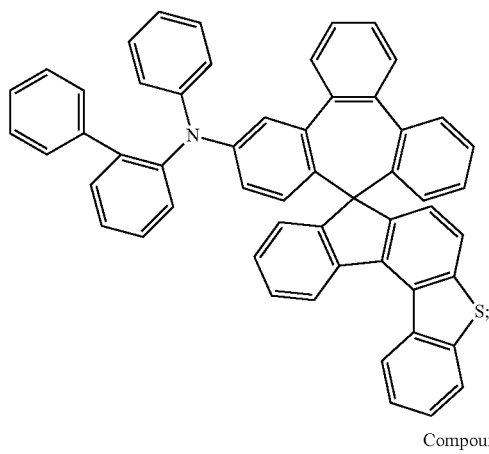
Compound 912
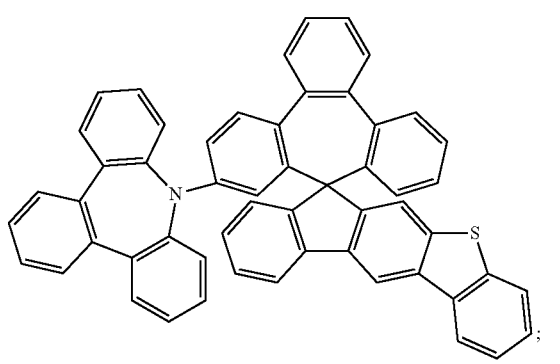
-continued
Compound 914
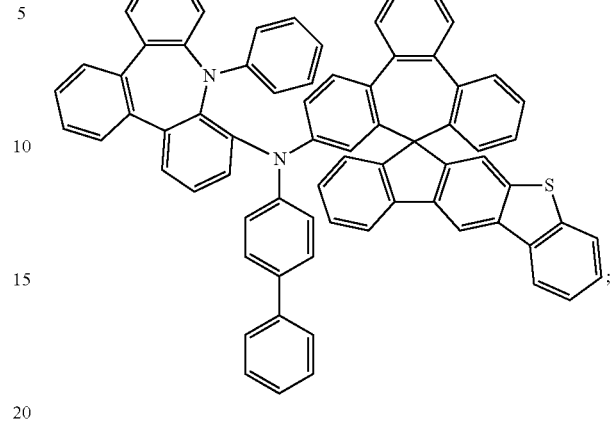
Compound 915
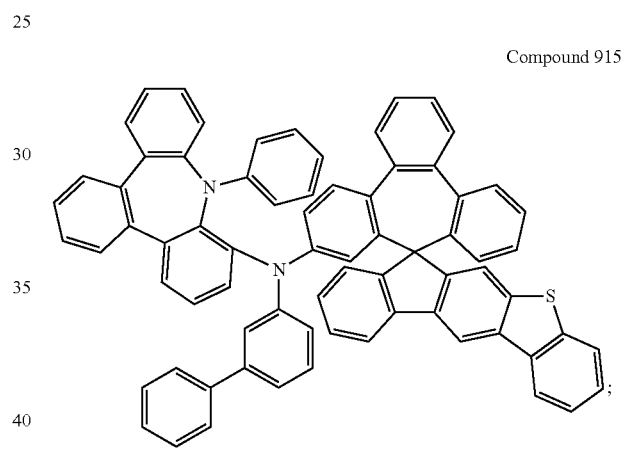
Compound 916
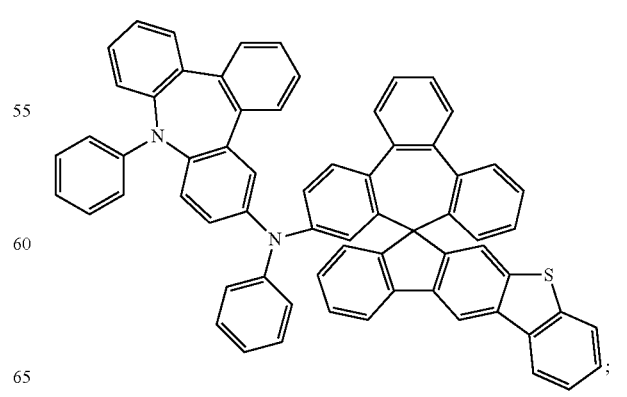

Compound 917
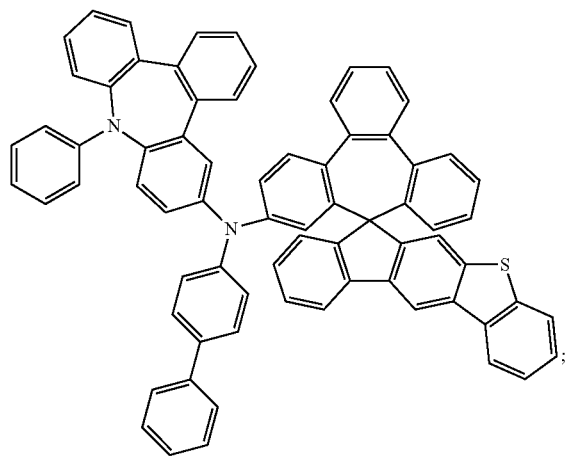
Compound 918
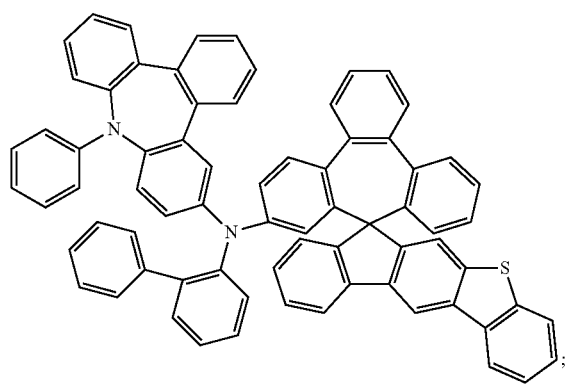
Compound 919
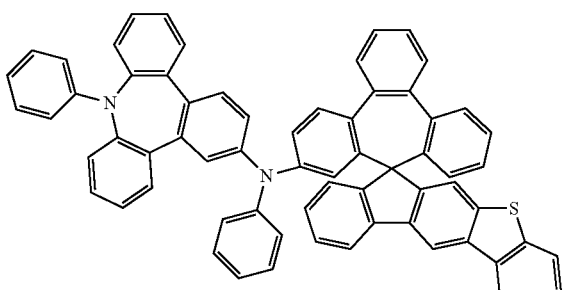
Compound 920
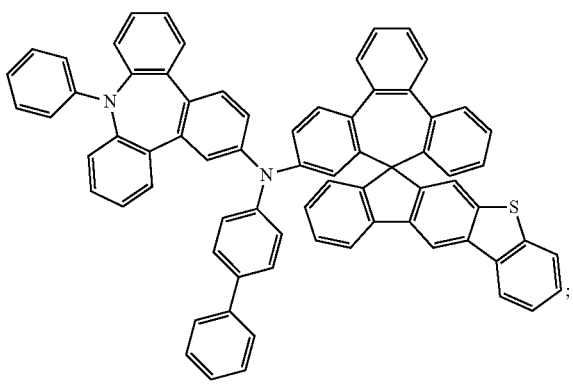
Compound 921
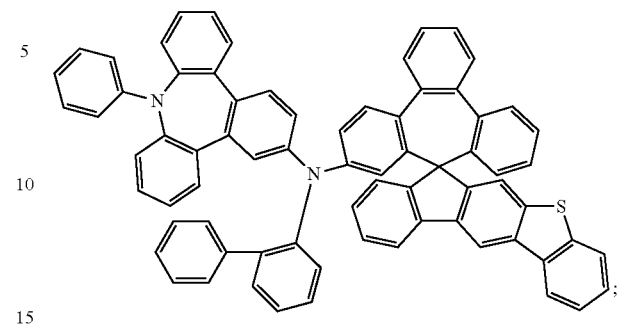
Compound 922
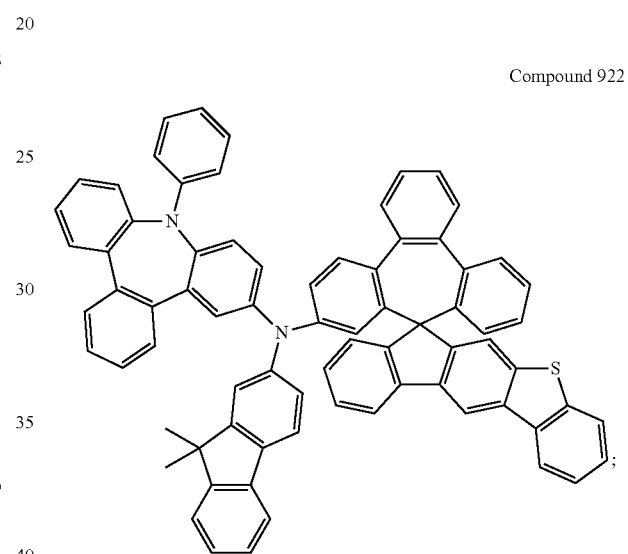
Compound 923
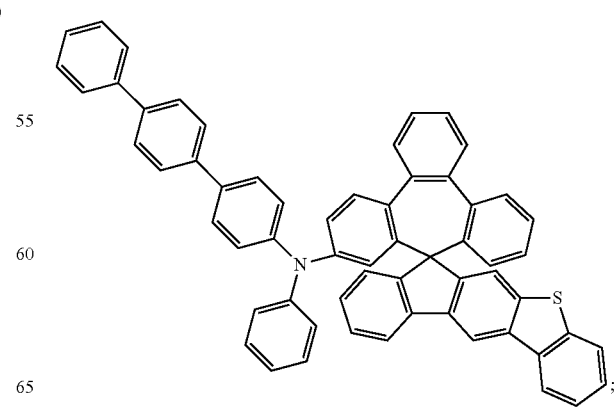

Compound 924
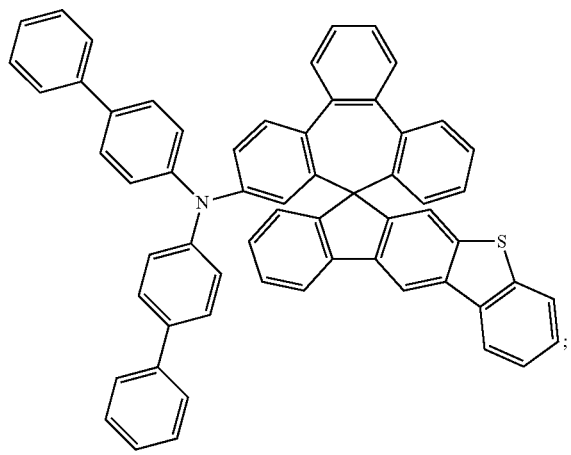
Compound 925
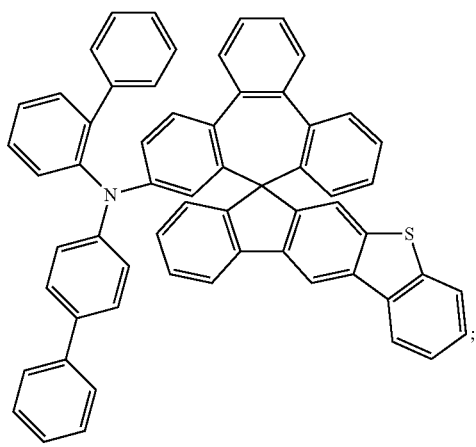
Compound 926
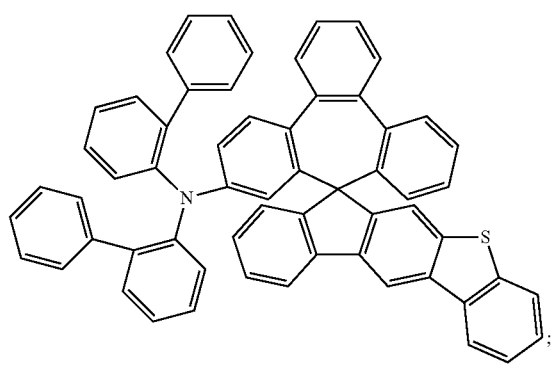
Compound 927
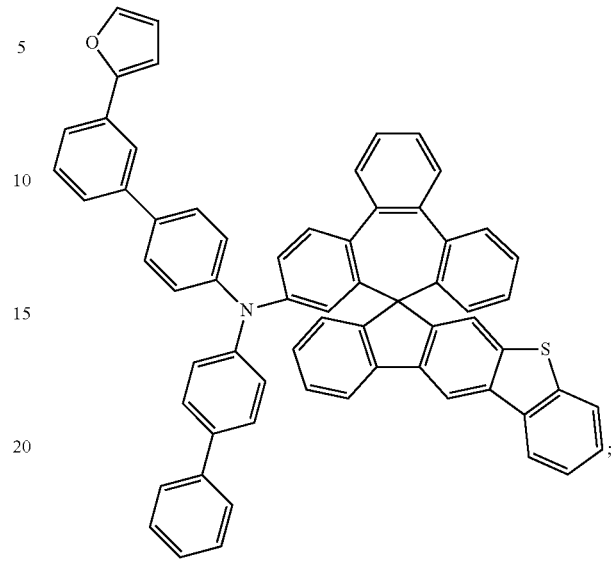
Compound 928
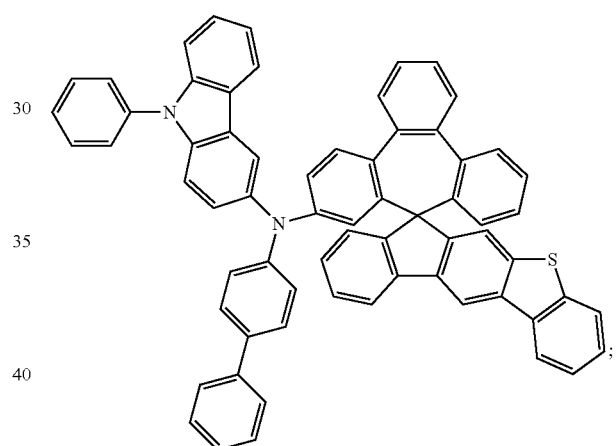
Compound 929
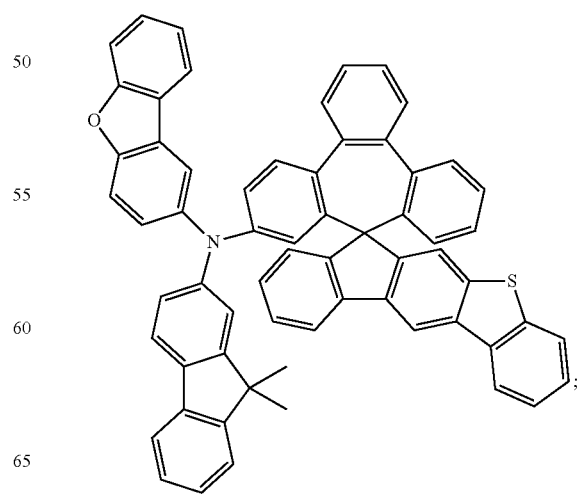

Compound 930
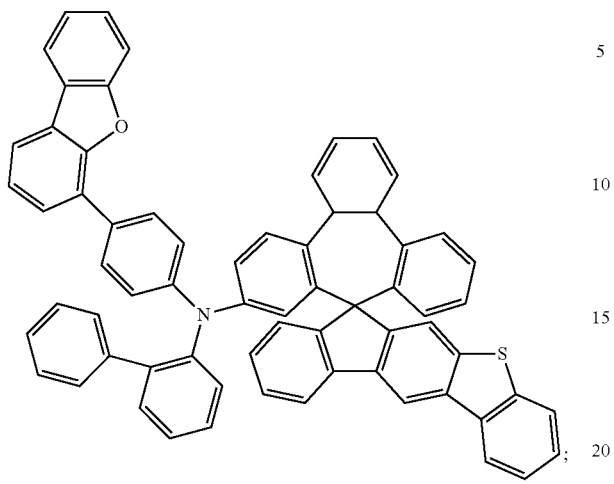
Compound 931
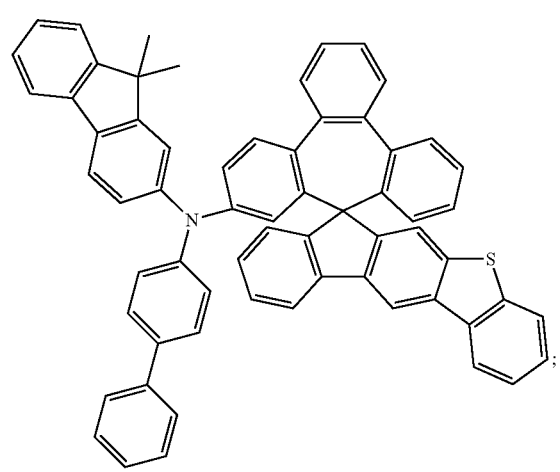
Compound 932
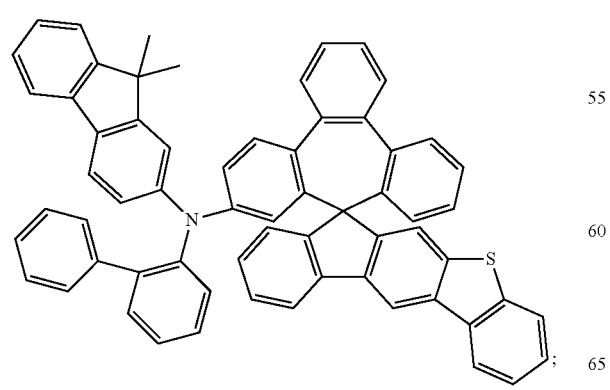
Compound 933
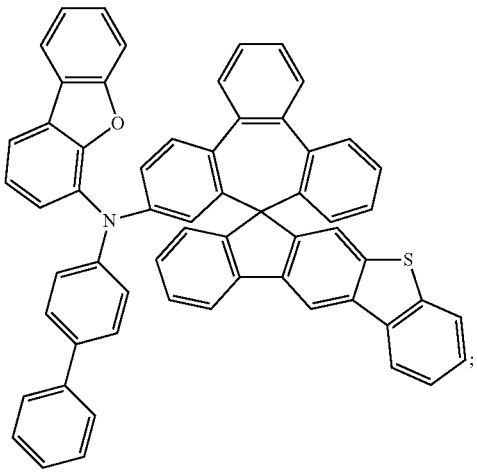
Compound 934
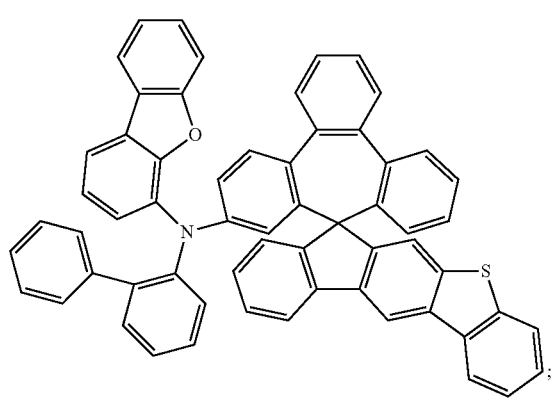
Compound 935
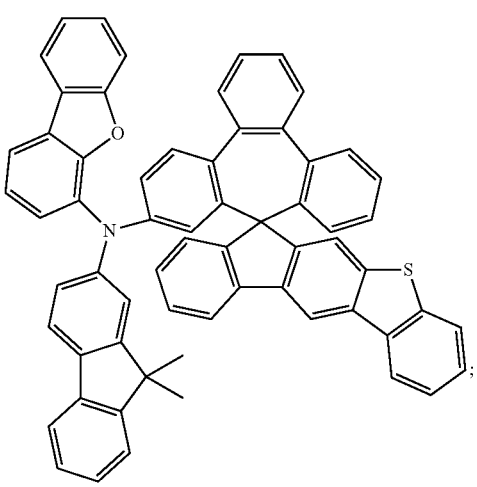

Compound 936
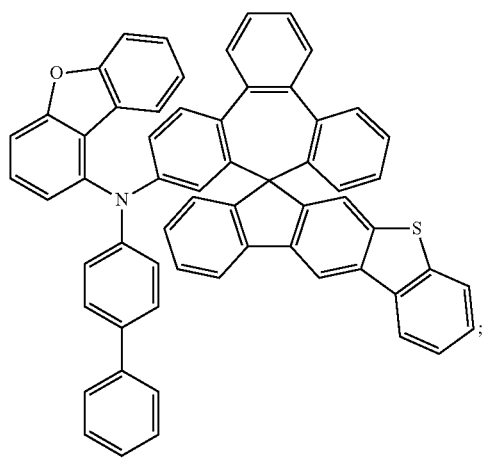
Compound 937
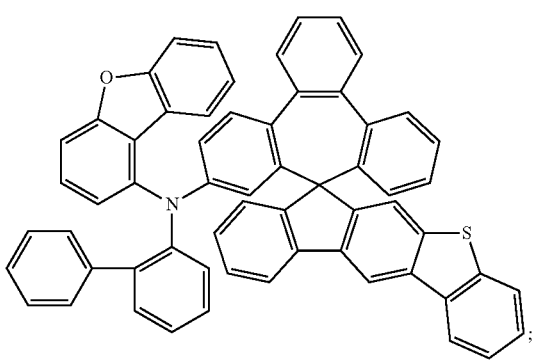
Compound 938
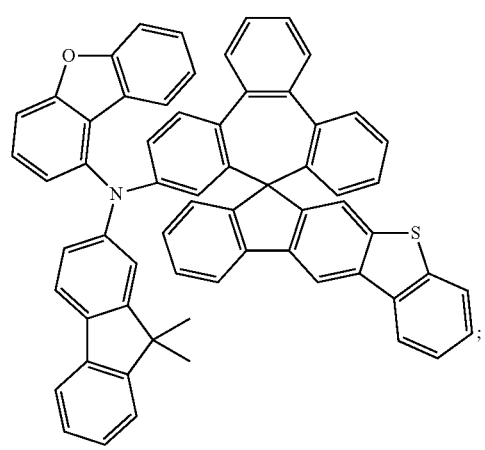
Compound 939
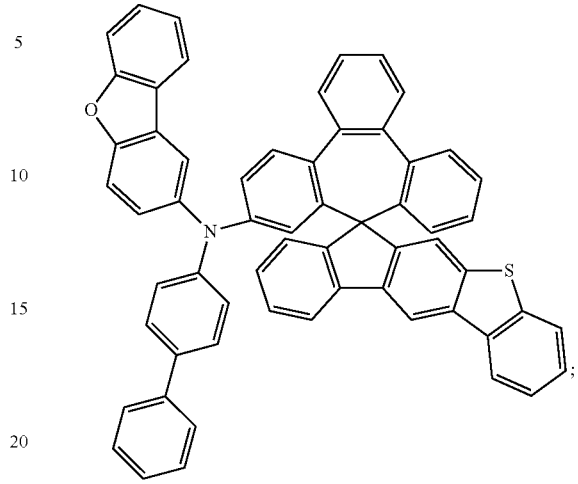
Compound 940
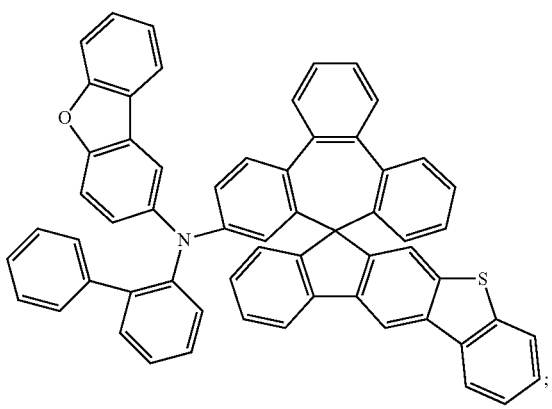
Compound 941
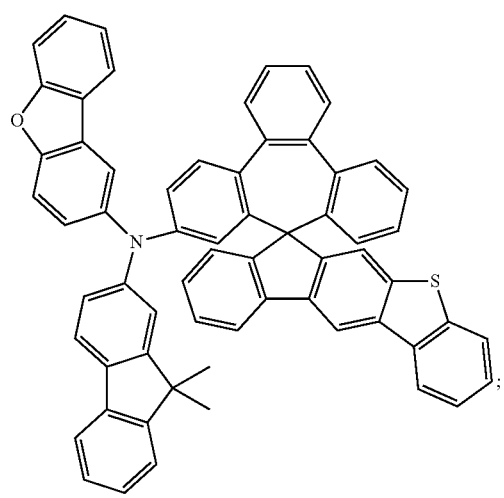

Compound 942
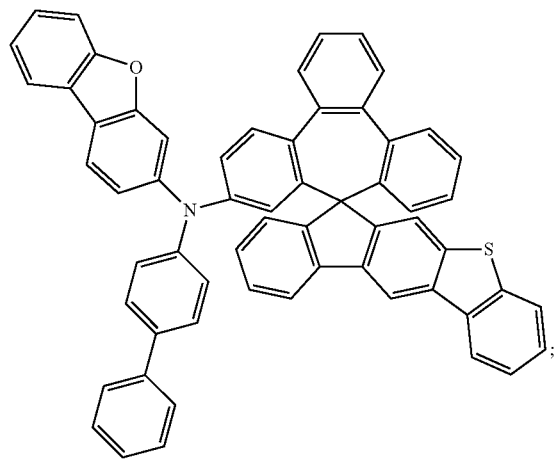
Compound 943
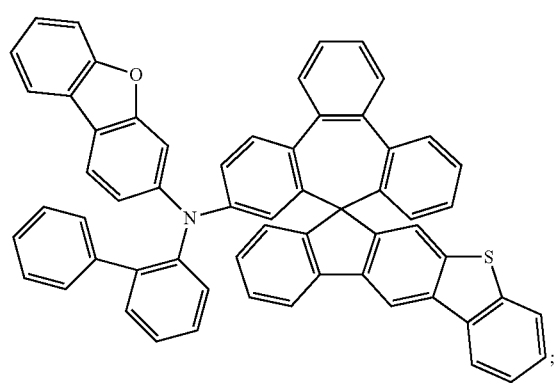
Compound 944
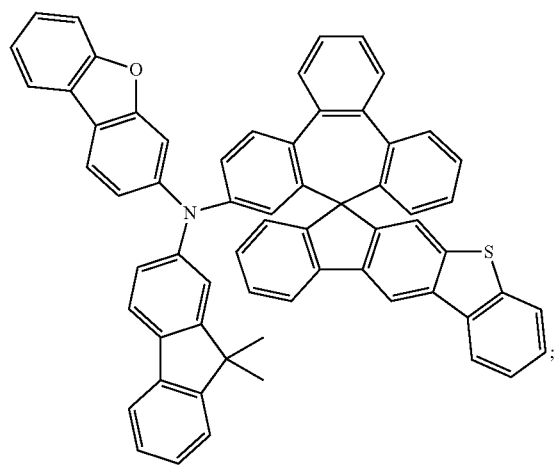
Compound 945
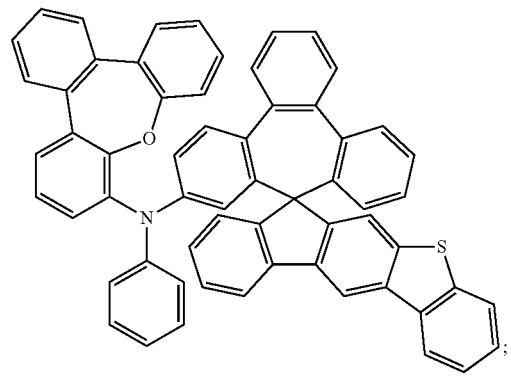
Compound 946
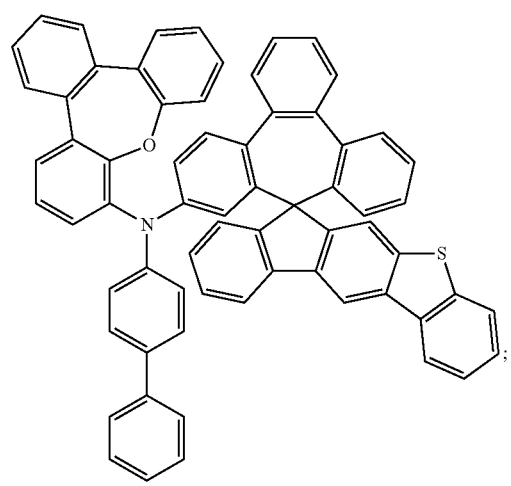
Compound 947
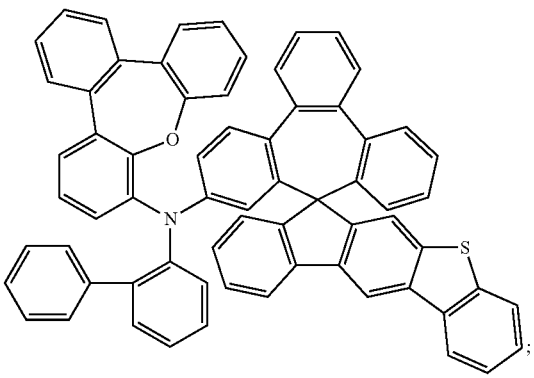

Compound 948

Compound 949

Compound 950

Compound 951

Compound 952

Compound 953

Compound 954
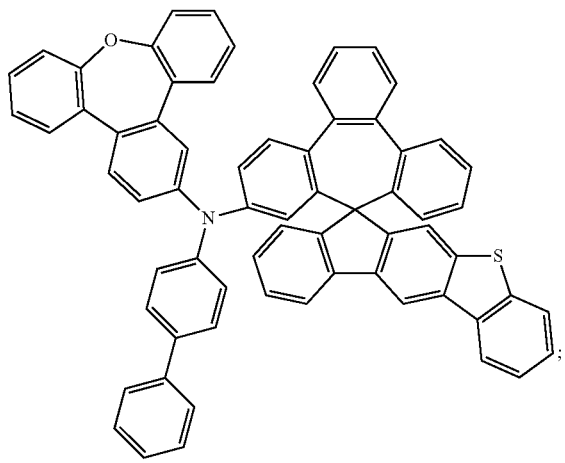
Compound 955
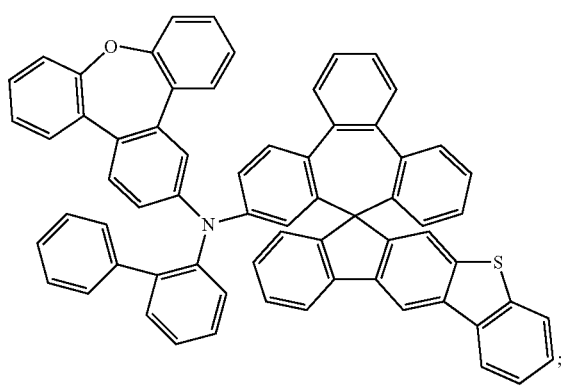
Compound 956
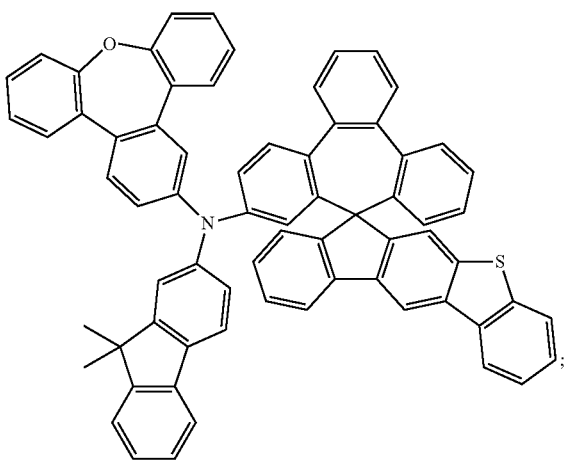
Compound 957
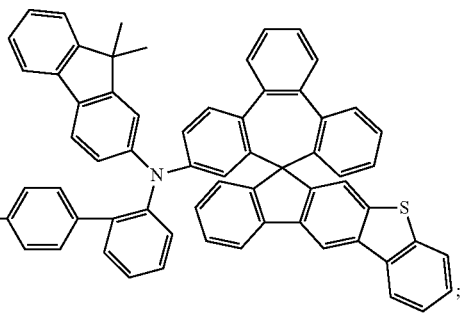
Compound 958
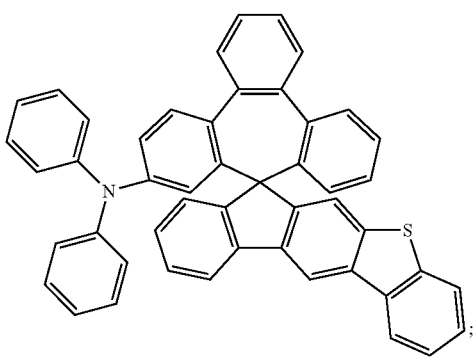
Compound 959
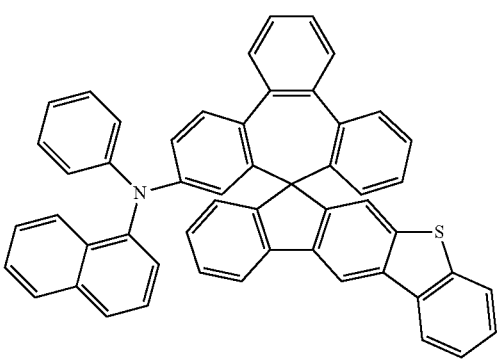
Compound 960
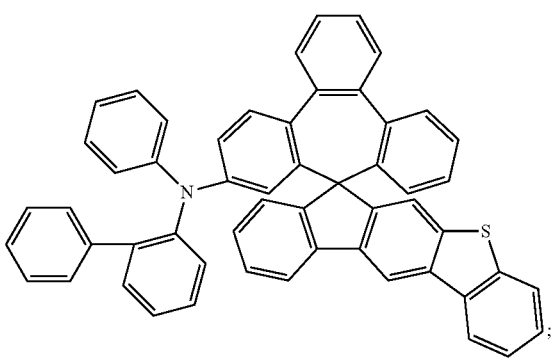

Compound 961
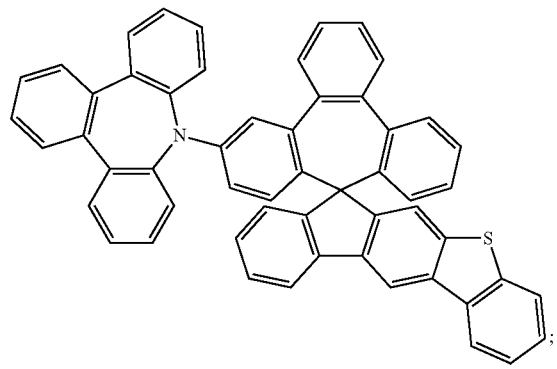
Compound 962
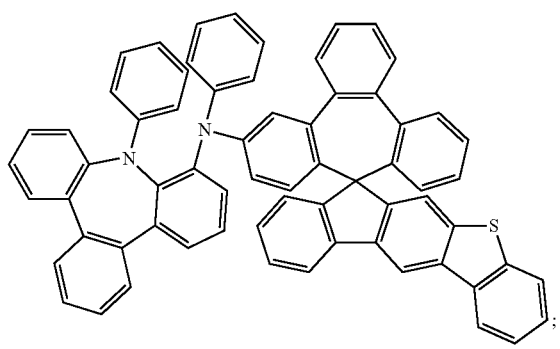
Compound 963
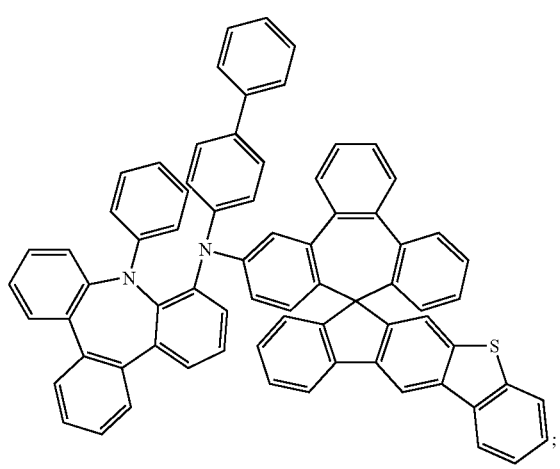
Compound 964
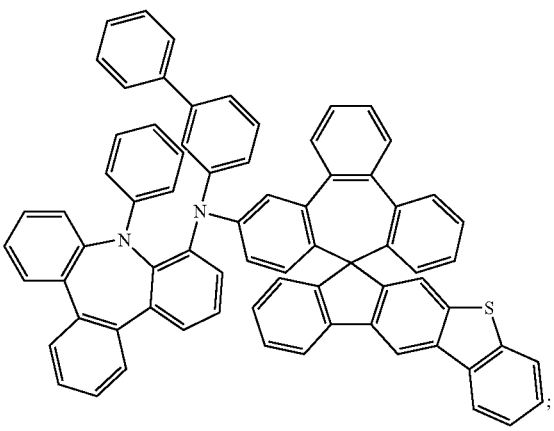
Compound 965
Compound 966
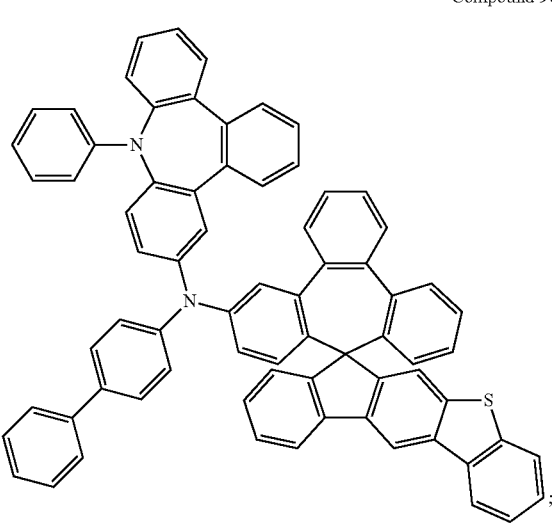

Compound 967
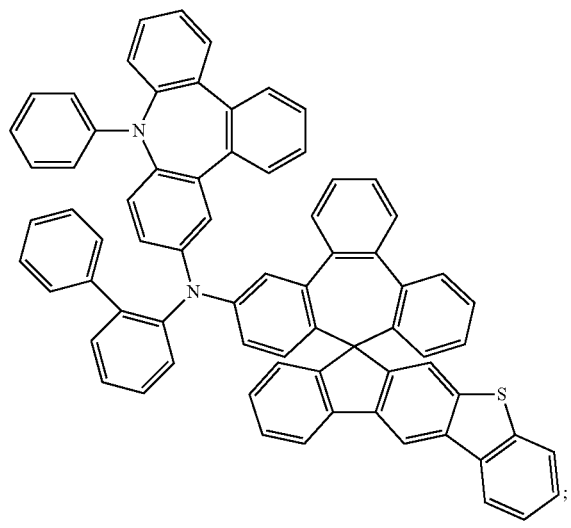
Compound 968
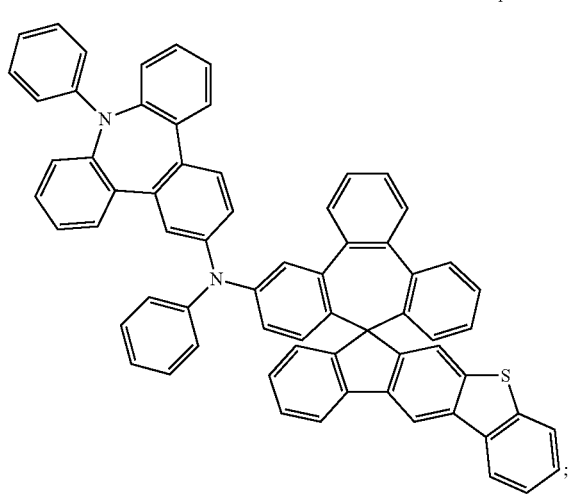
Compound 969
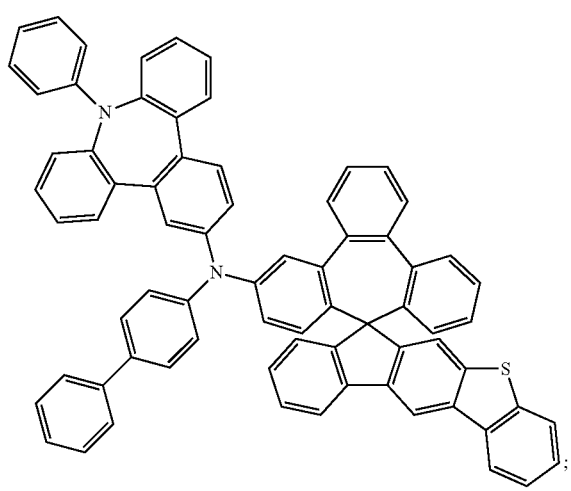
Compound 970
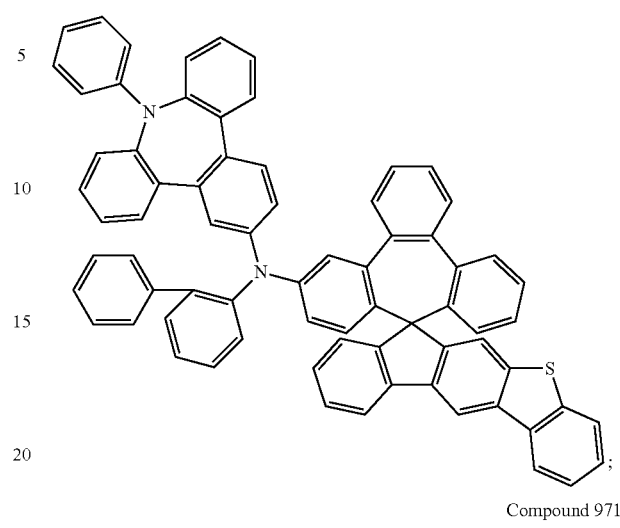
Compound 971
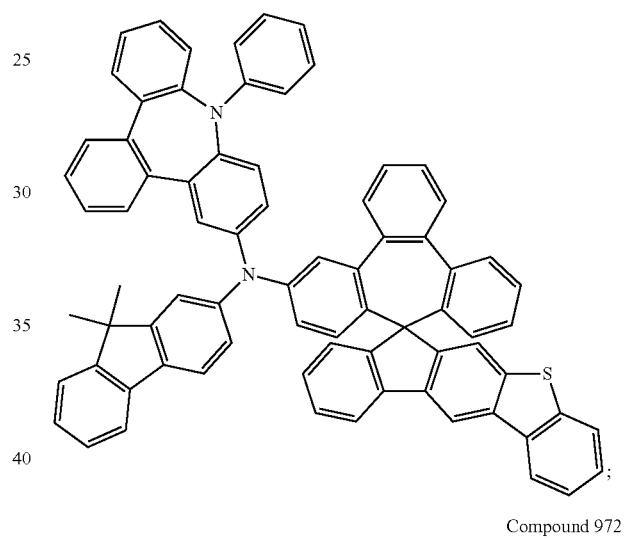
Compound 972
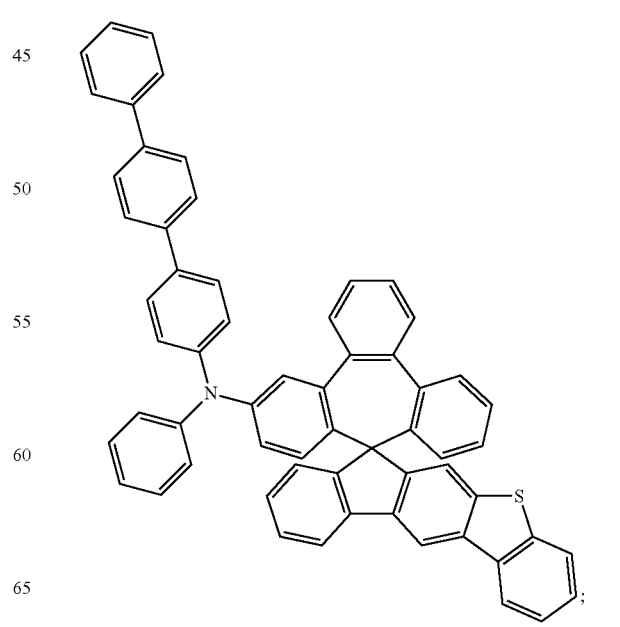

Compound 973
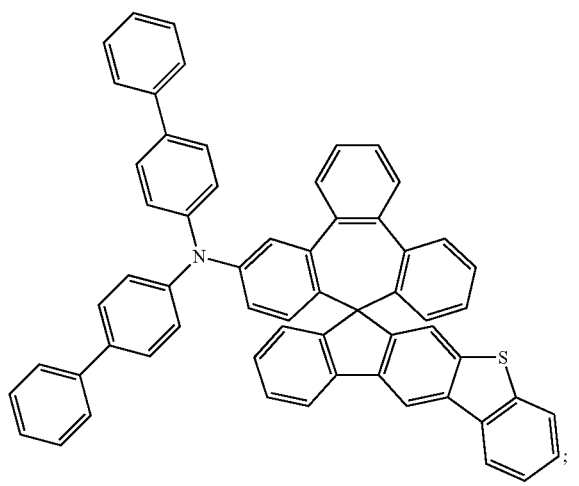
Compound 974
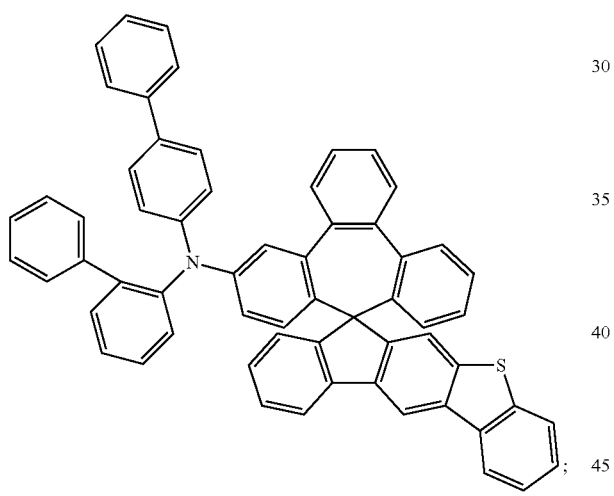
Compound 975
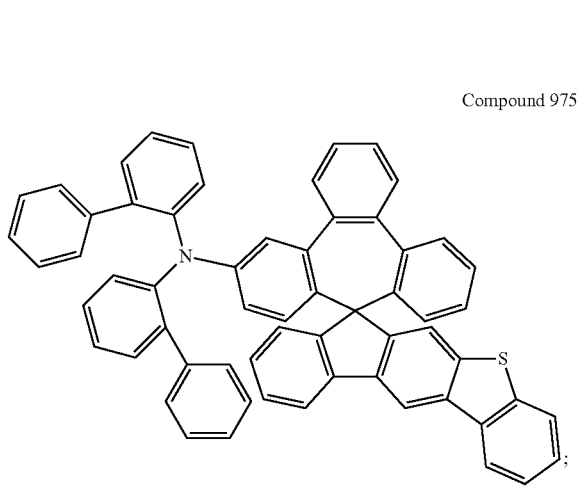
Compound 976
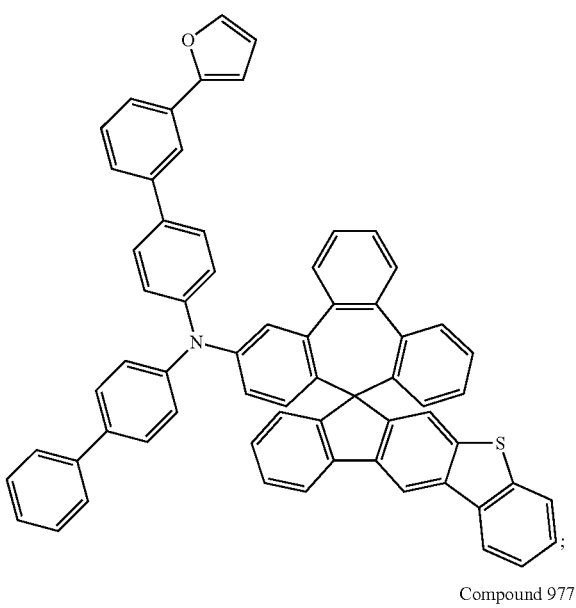
Compound 977
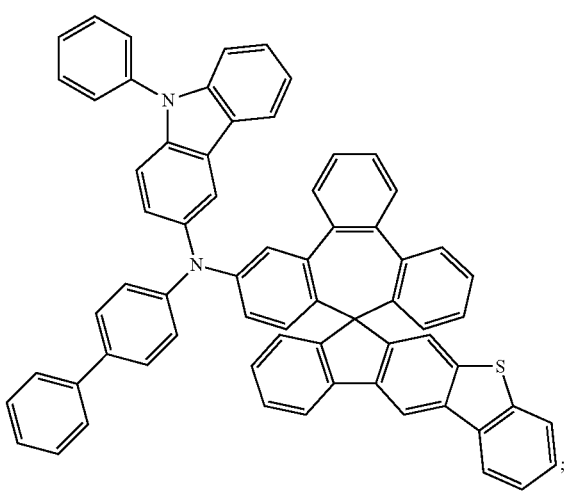
Compound 978
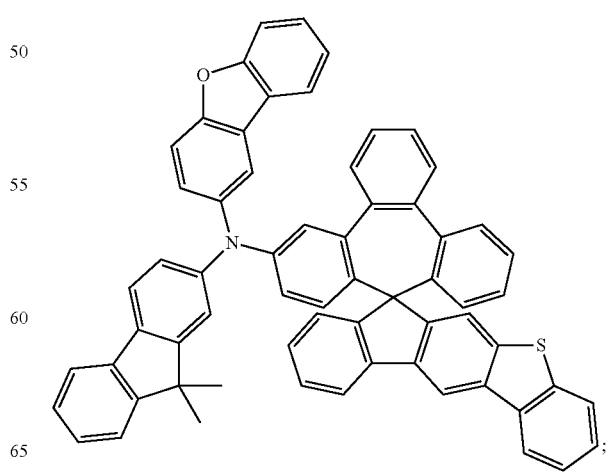

-continued
Compound 979
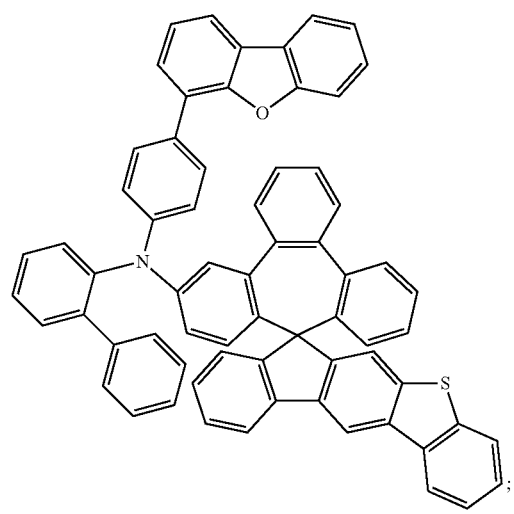
Compound 980
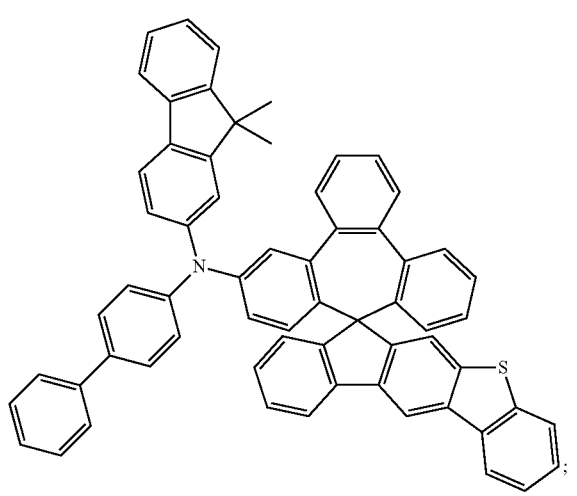
Compound 981
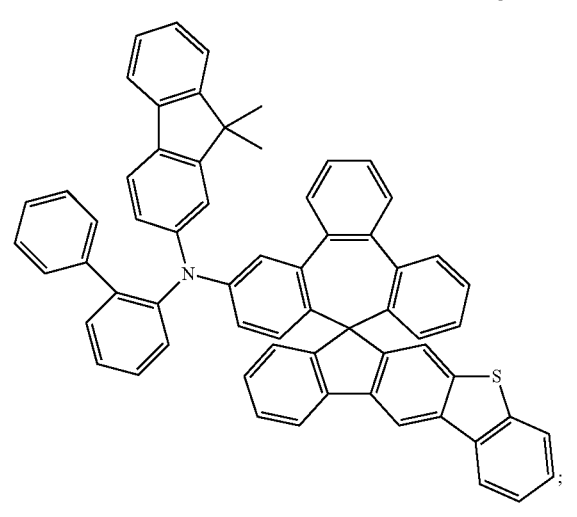
-continued
Compound 982
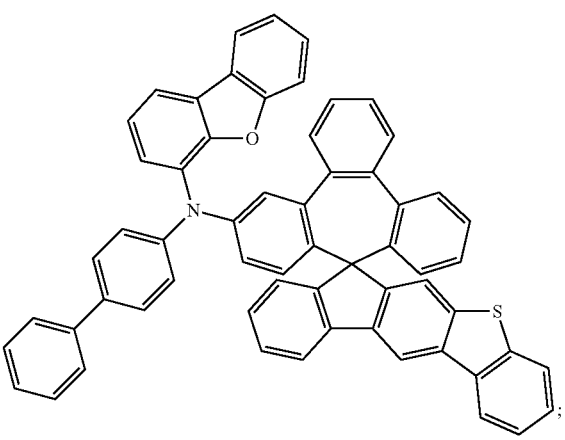
Compound 983
Compound 984
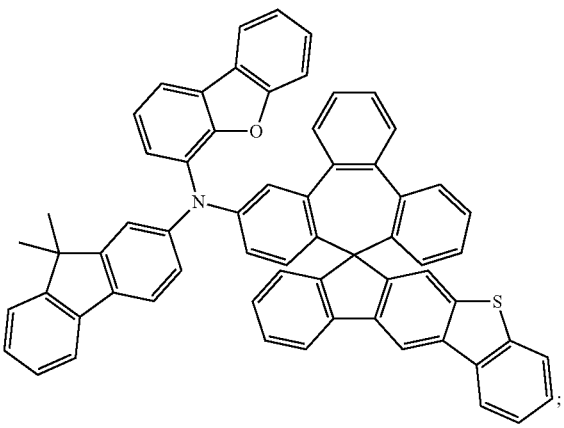

Compound 985
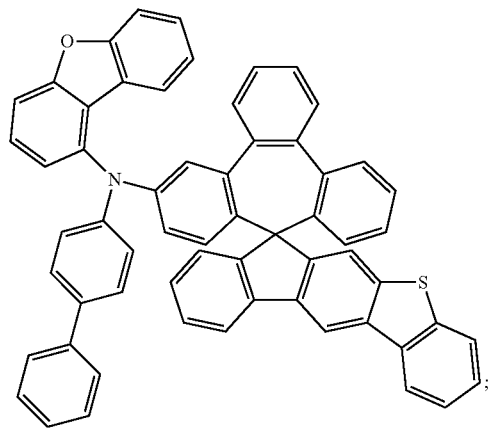
Compound 988
Compound 986
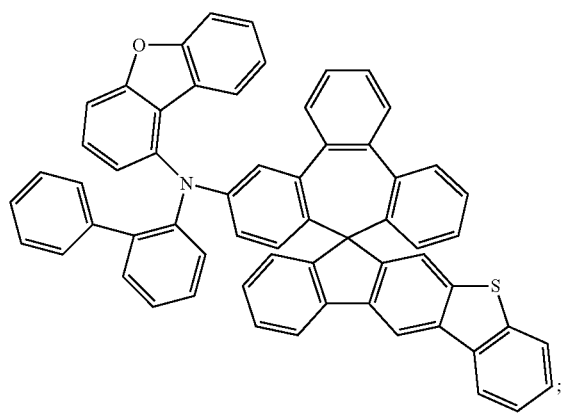
Compound 989
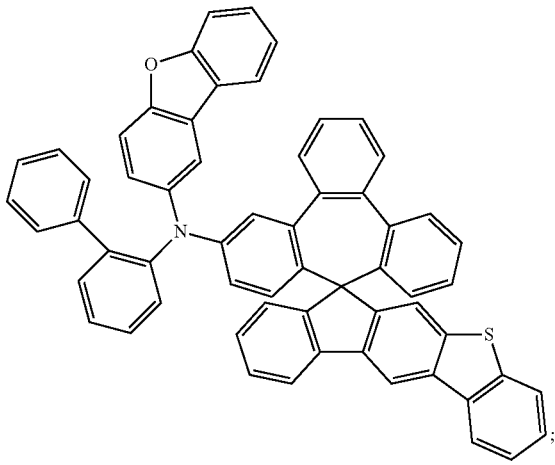
Compound 987
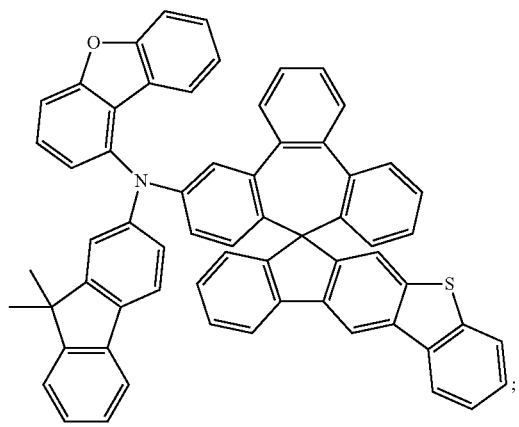
Compound 990
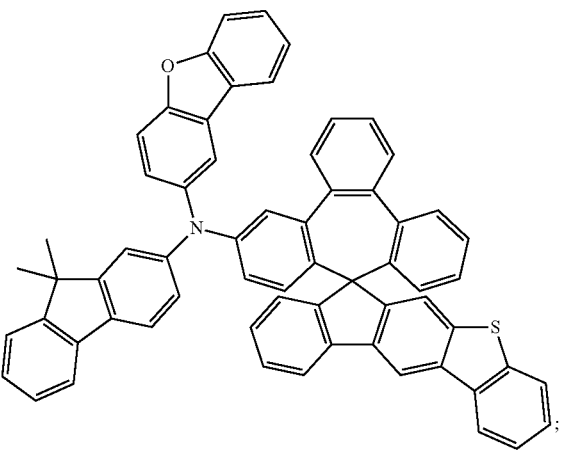

Compound 991
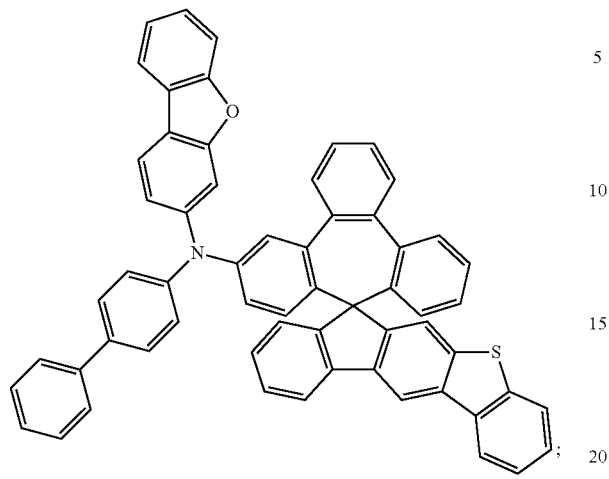
Compound 992
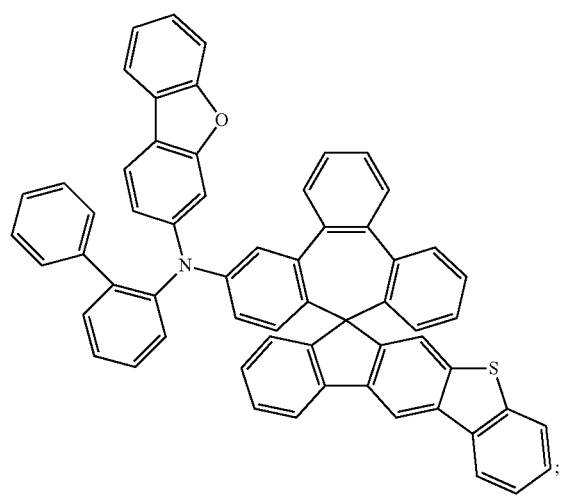
Compound 993
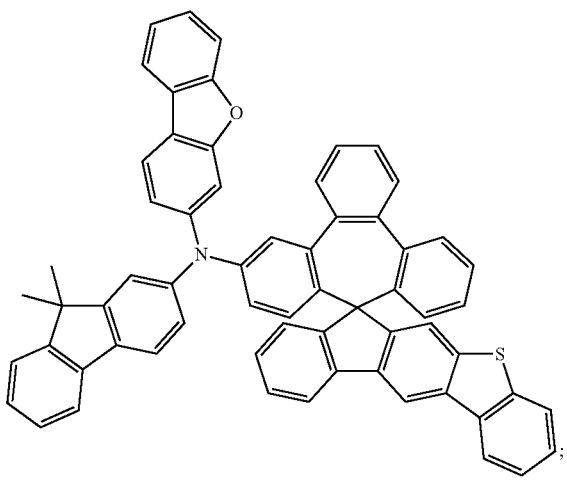
Compound 994
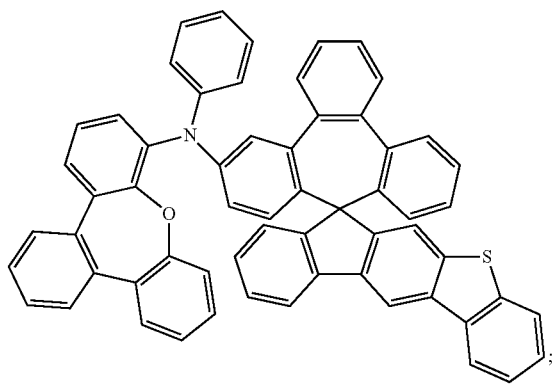
Compound 995
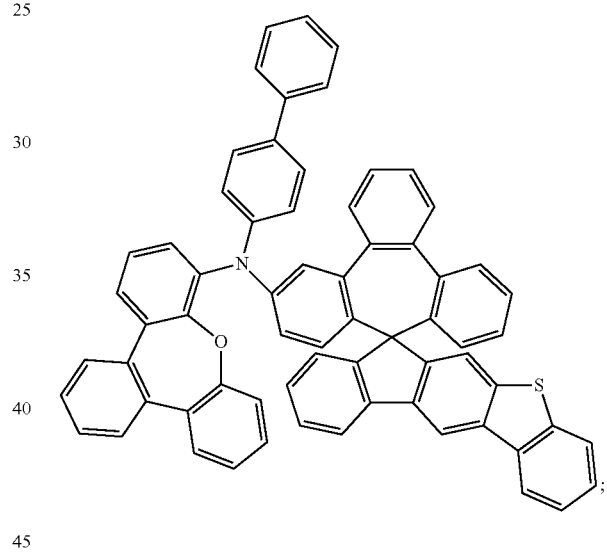
Compound 996
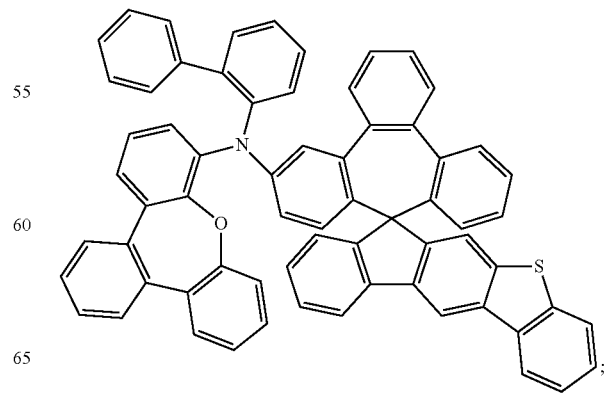

Compound 997
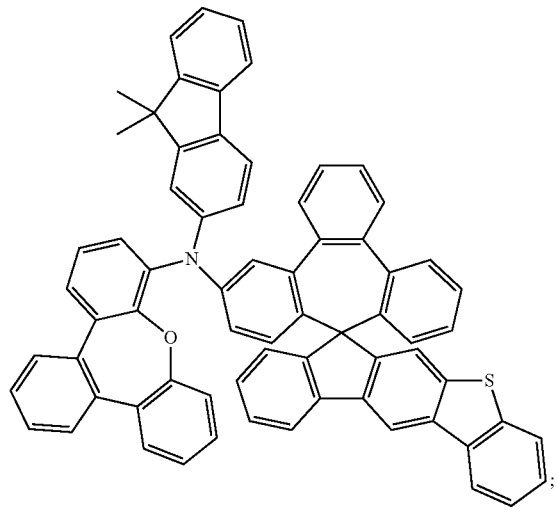
Compound 998
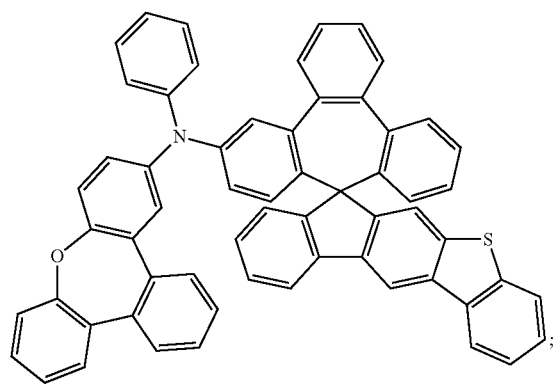
Compound 999
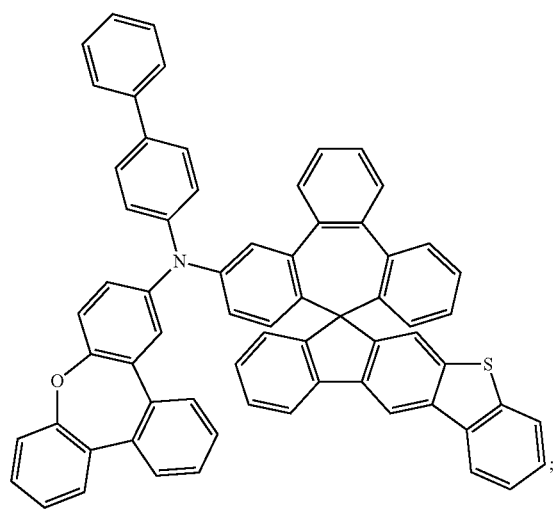
Compound 1000
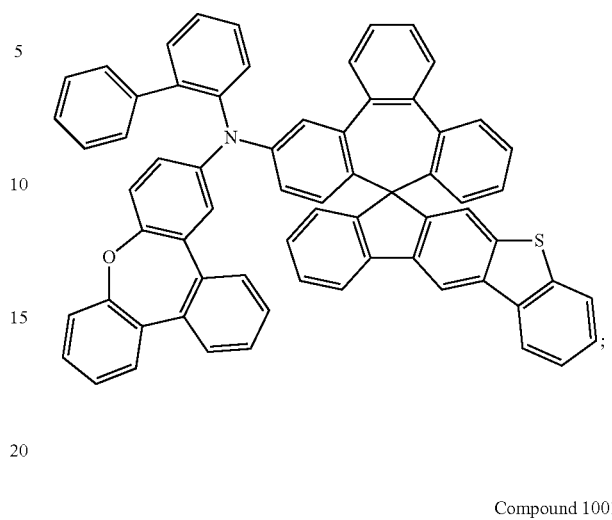
Compound 1001
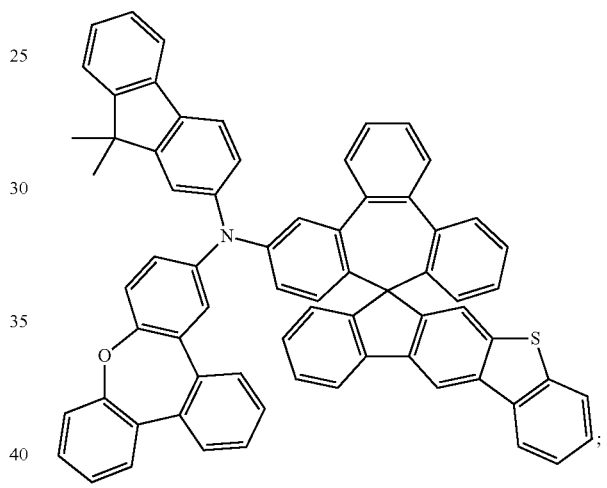
Compound 1002
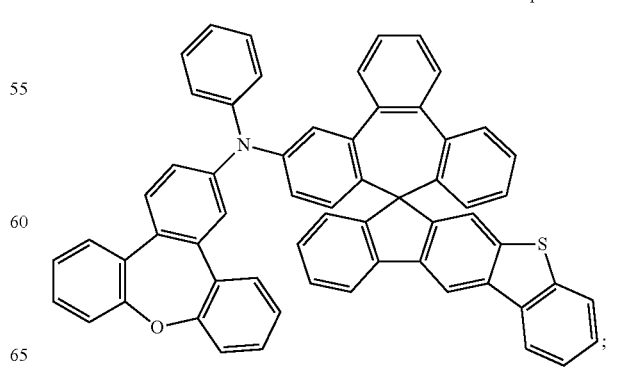

Compound 1003
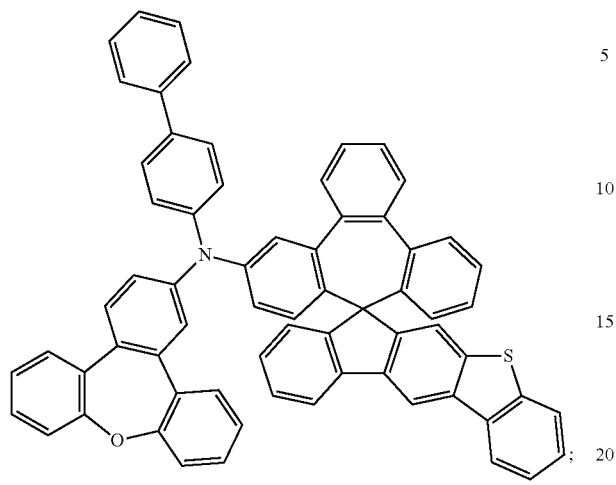
Compound 1004
Compound 1005
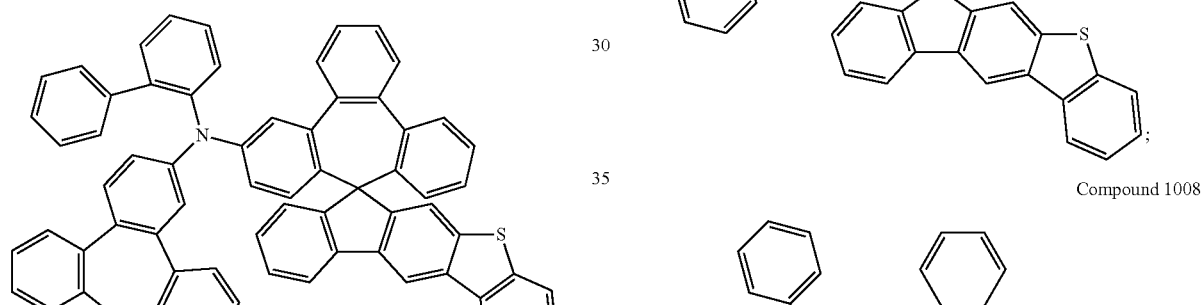
Compound 1006
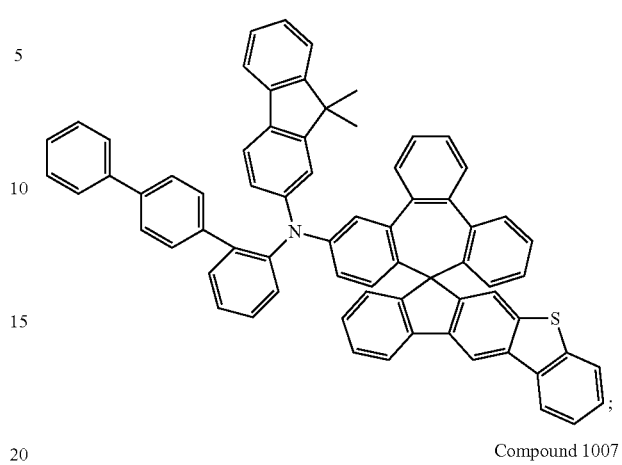
Compound 1007
Compound 1008
Compound 1009
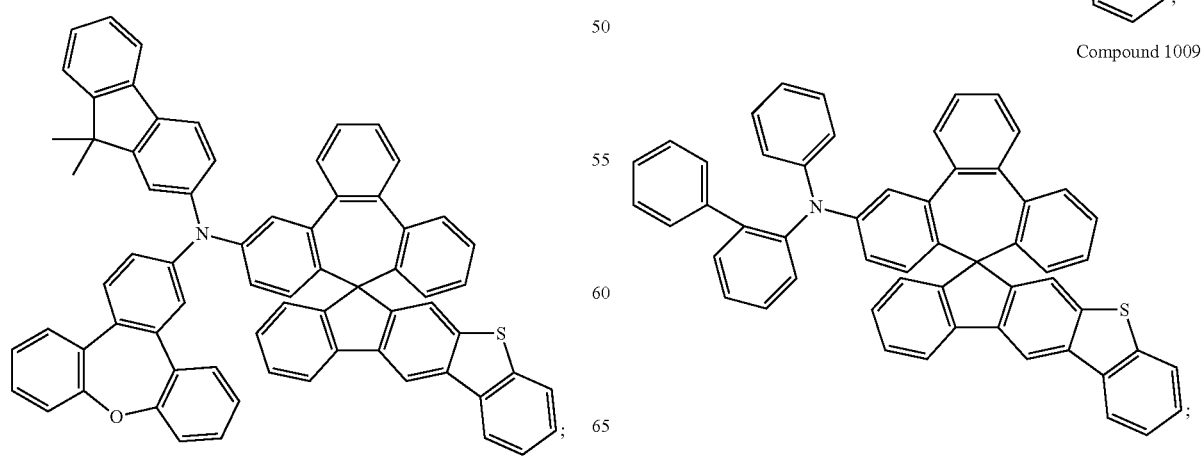

Compound 1010
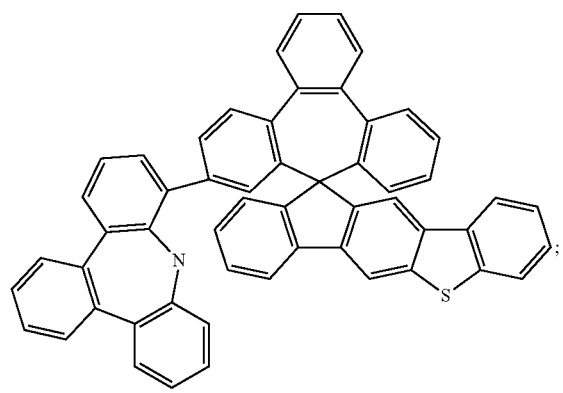
Compound 1011
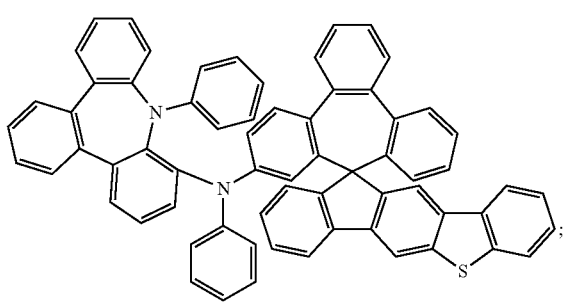
Compound 1012
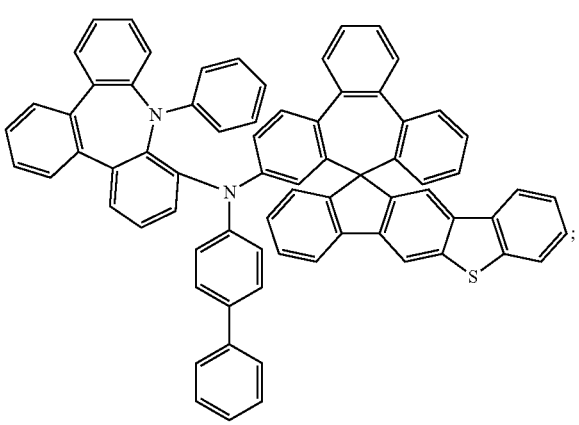
Compound 1013
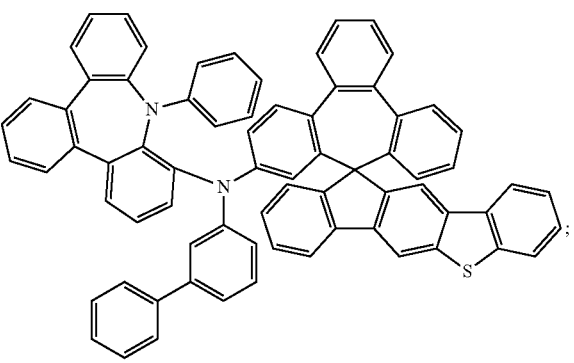
Compound 1014
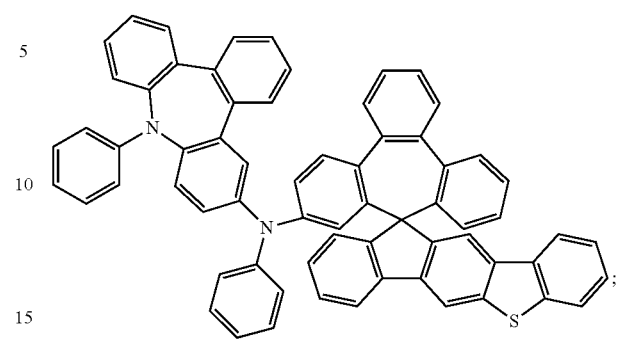
Compound 1015
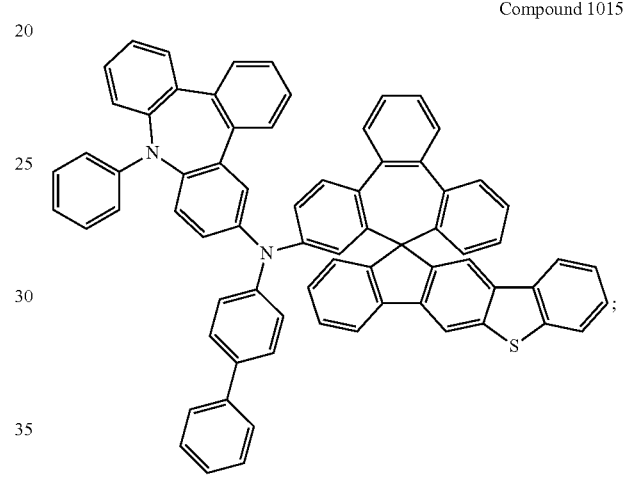
Compound 1016
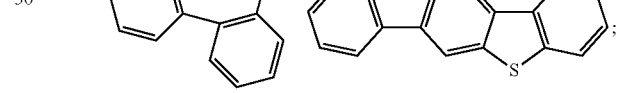
Compound 1017
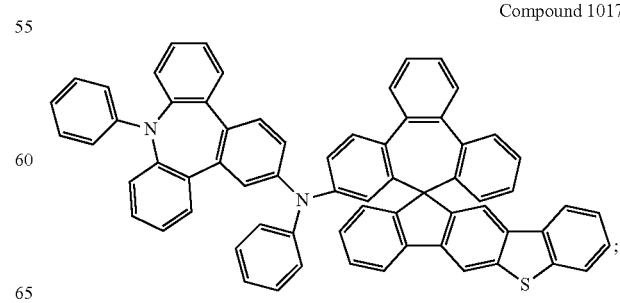

Compound 1018
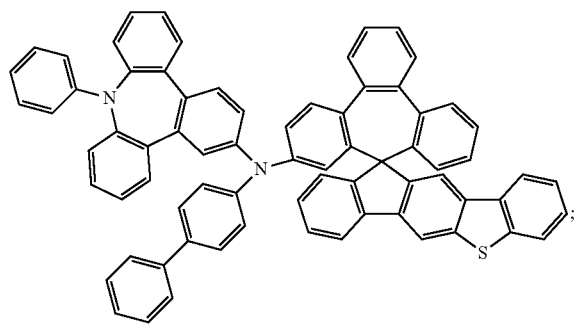
Compound 1019
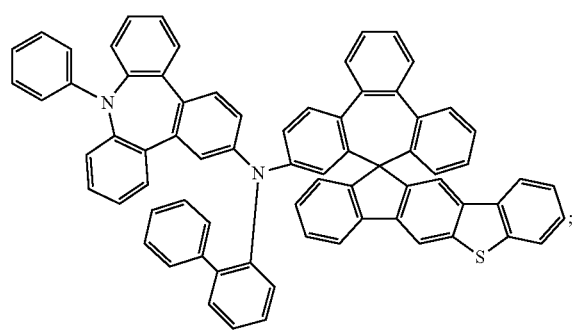
Compound 1020
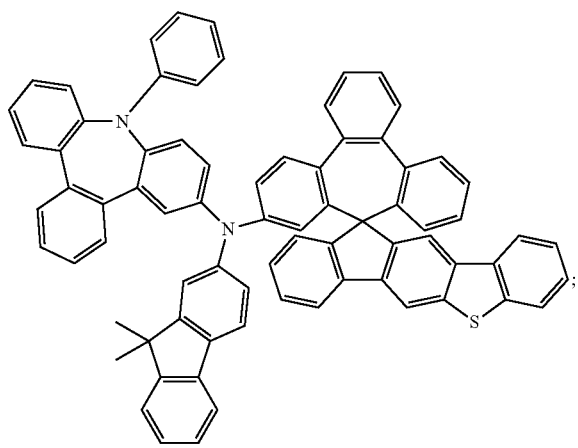
Compound 1021
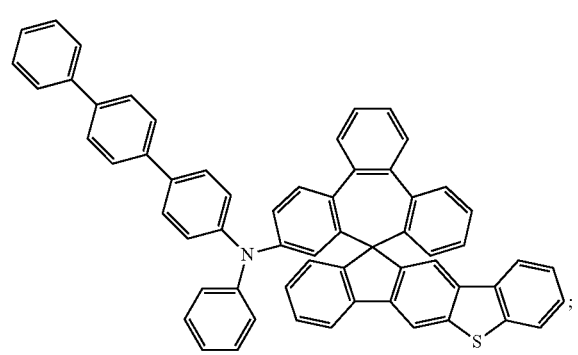
Compound 1022
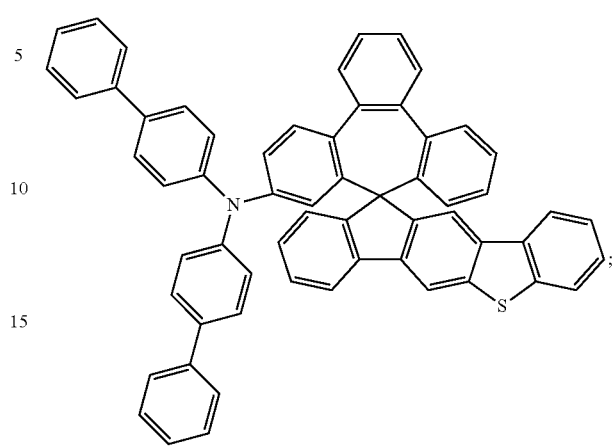
Compound 1023
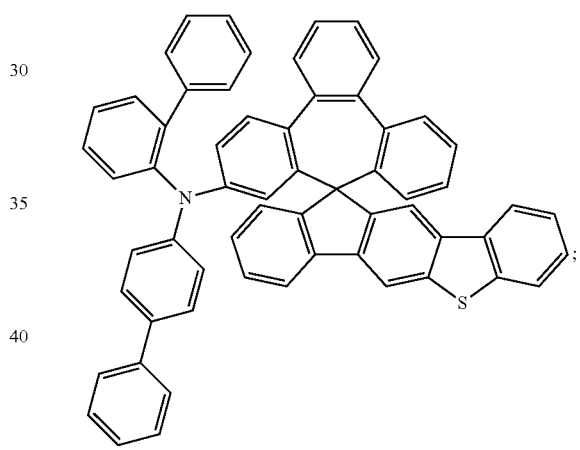
Compound 1024
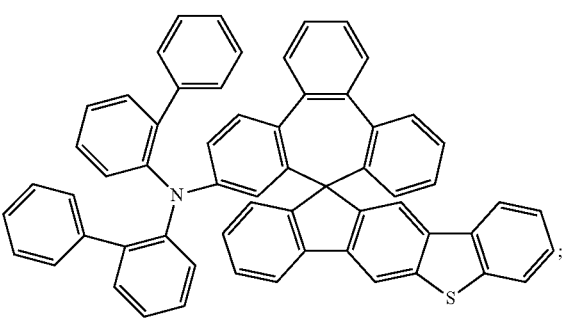

Compound 1025
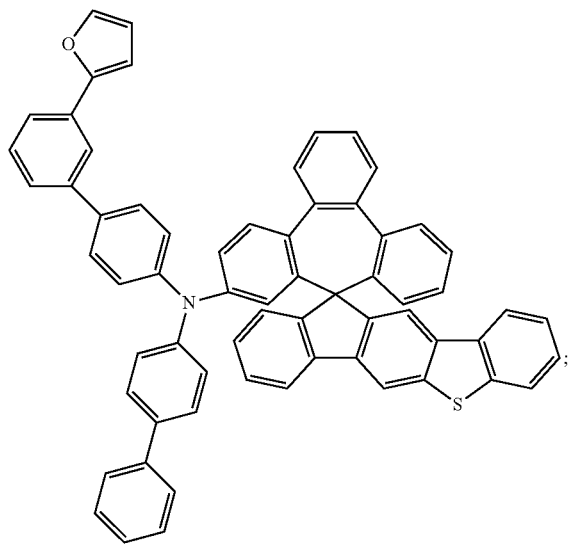
Compound 1026
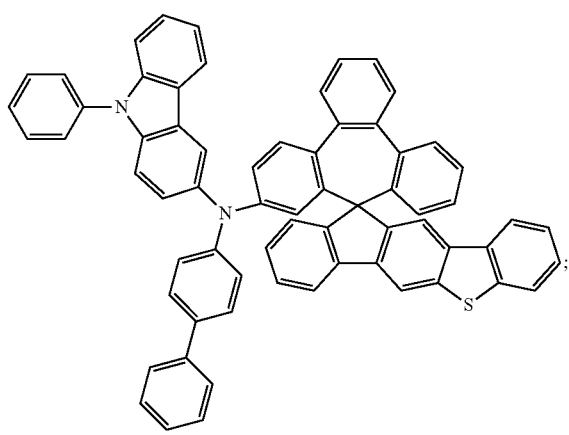
Compound 1027
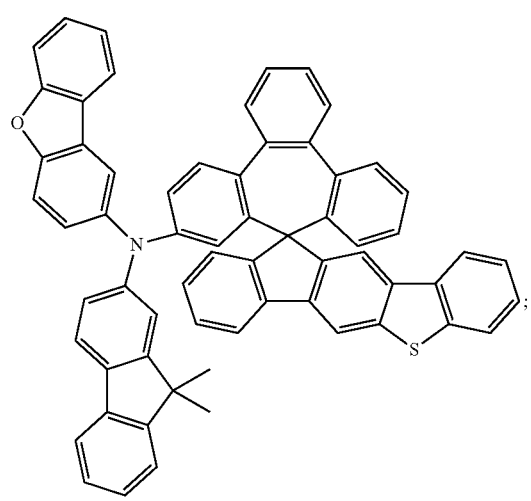
Compound 1028
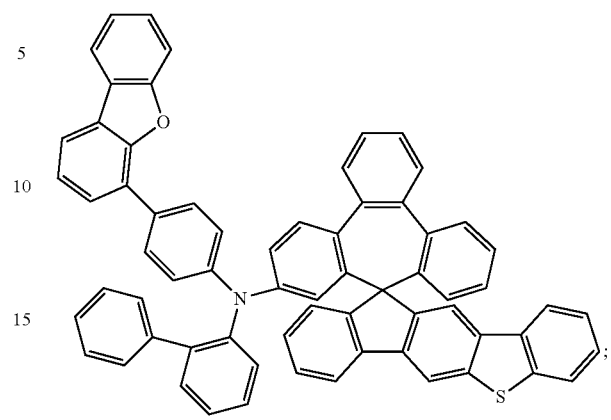
Compound 1029
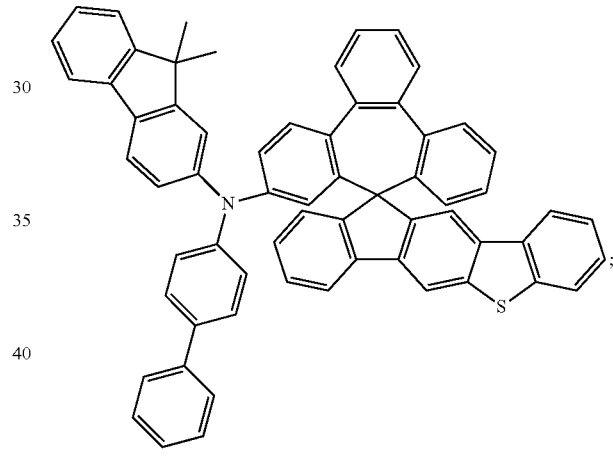
Compound 1030
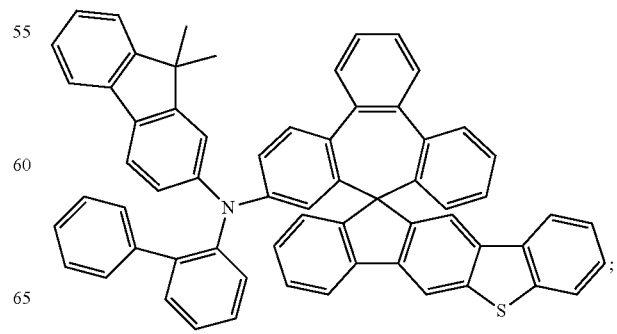

Compound 1031
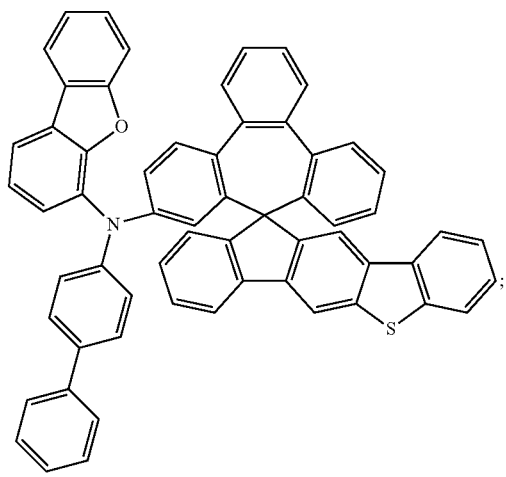
Compound 1032
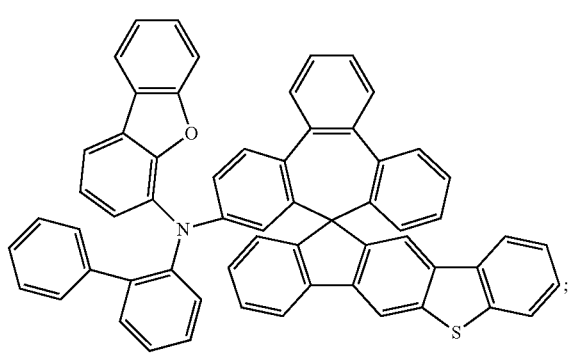
Compound 1033
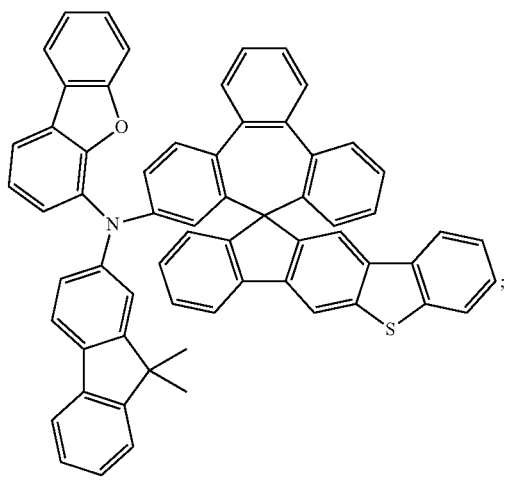
Compound 1034
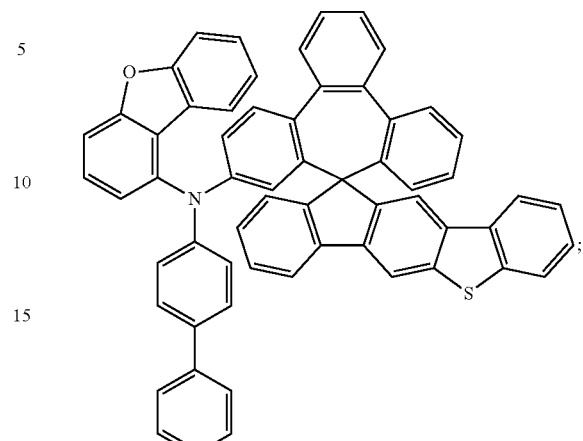
Compound 1035
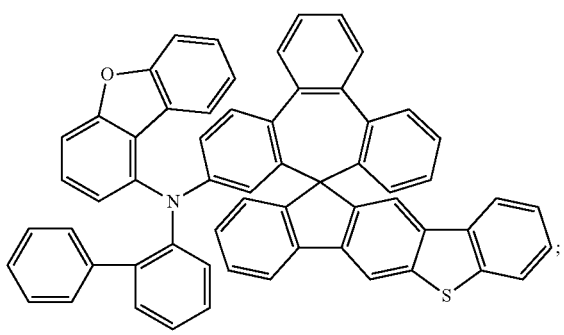
Compound 1036
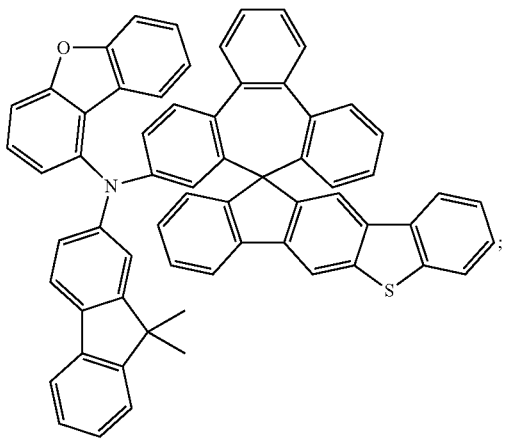

-continued
Compound 1037
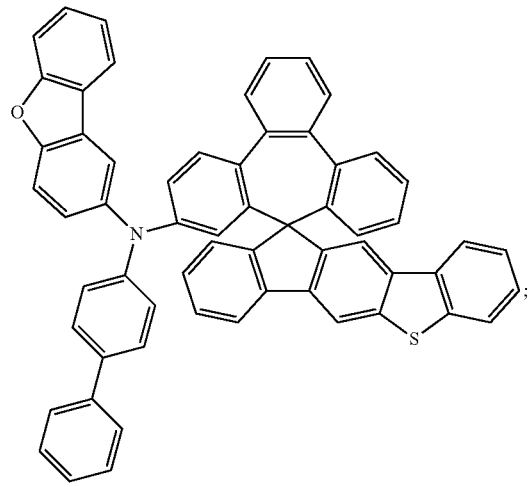
Compound 1038
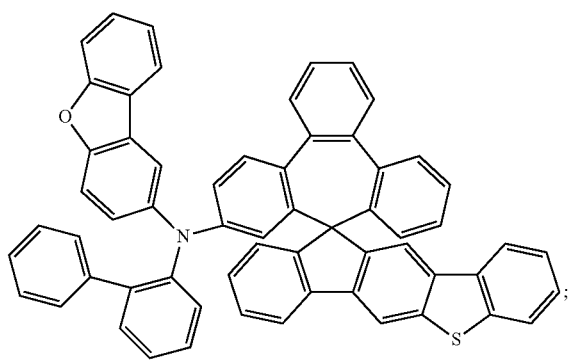
Compound 1039
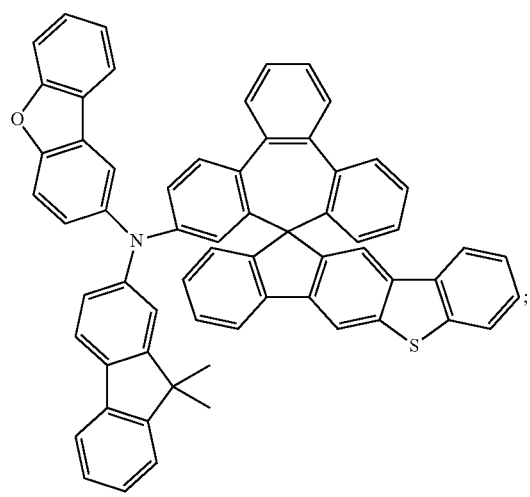
-continued
Compound 1040
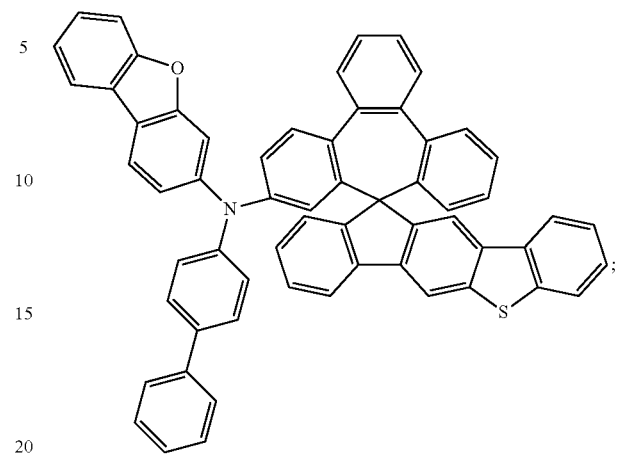
Compound 1041
Compound 1042
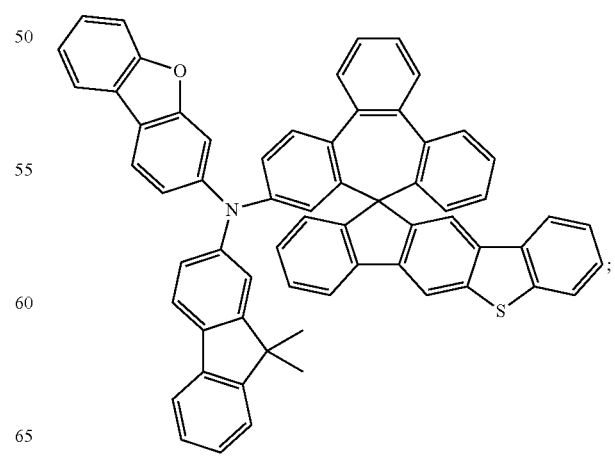

Compound 1043
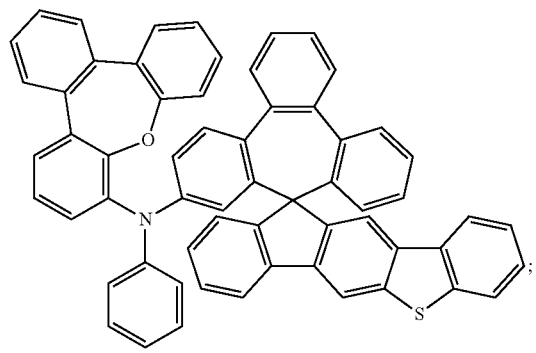
Compound 1044
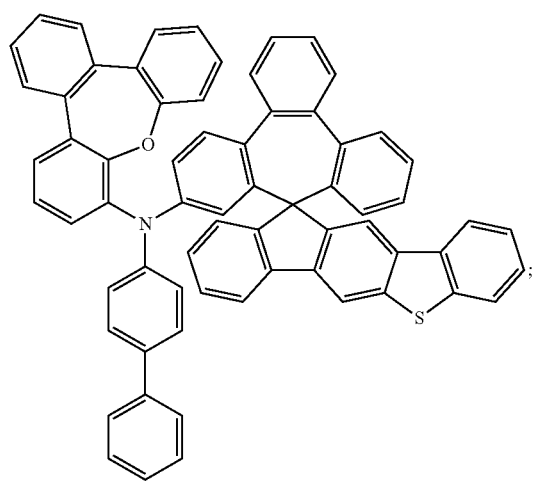
Compound 1045
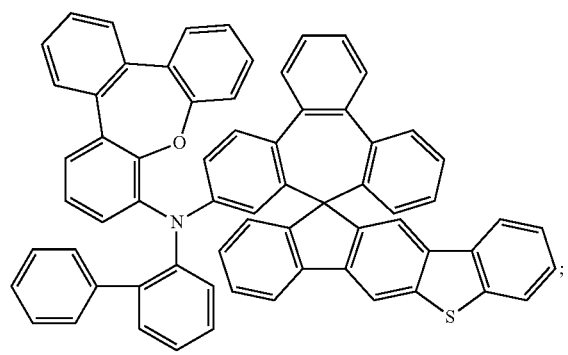
Compound 1046
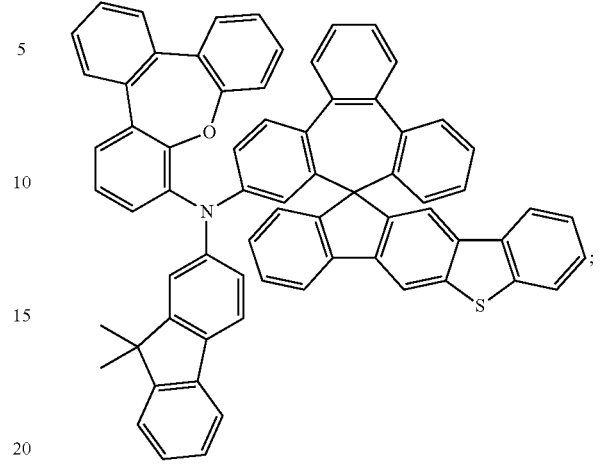
Compound 1047
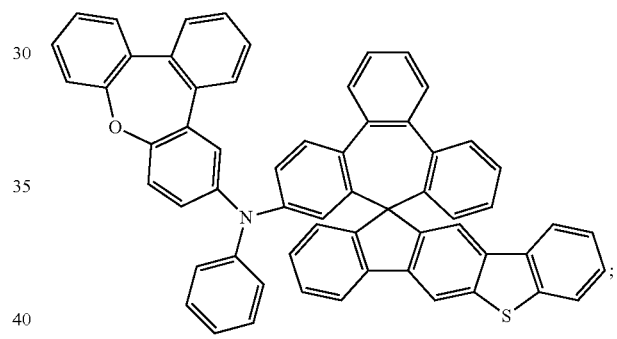
Compound 1048
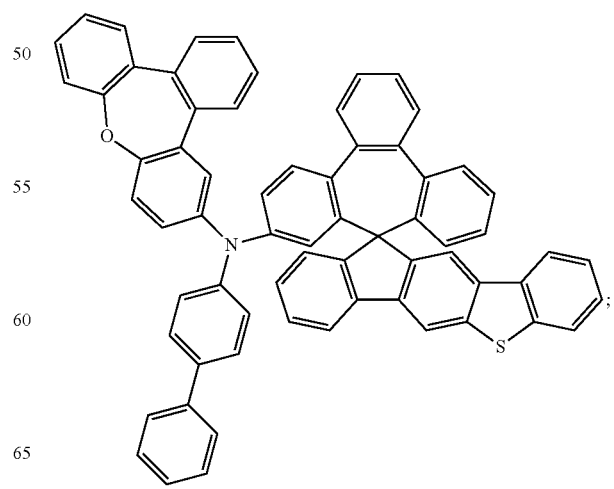

Compound 1049
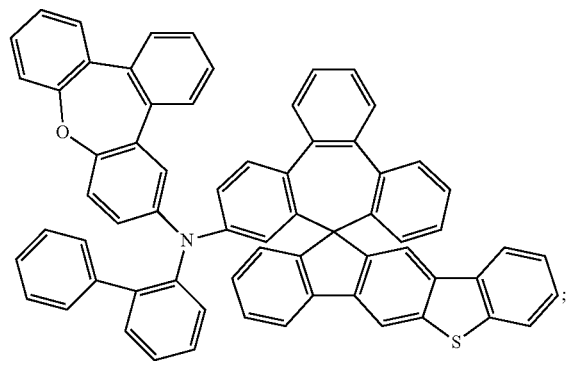
Compound 1050
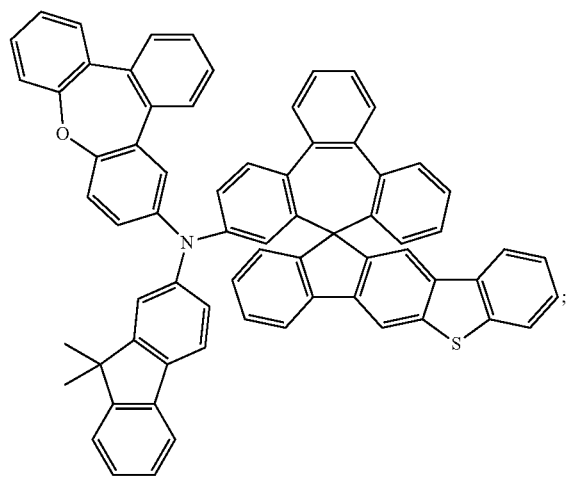
Compound 1051
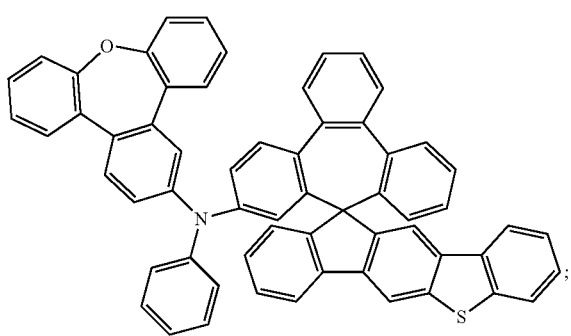
Compound 1052
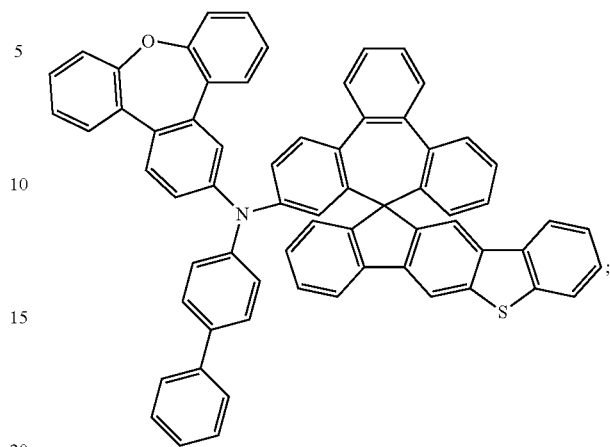
Compound 1053
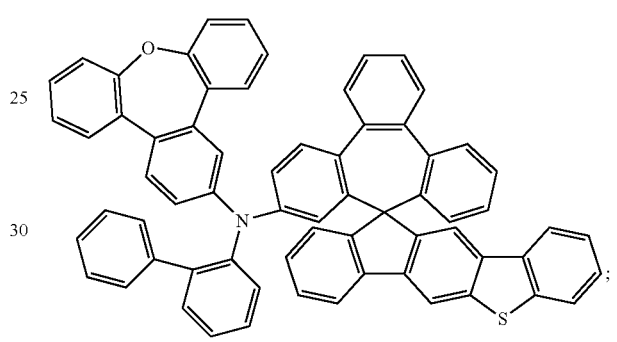
Compound 1054
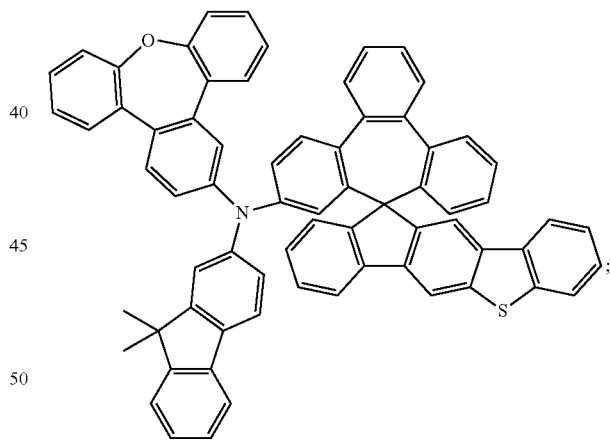
Compound 1055
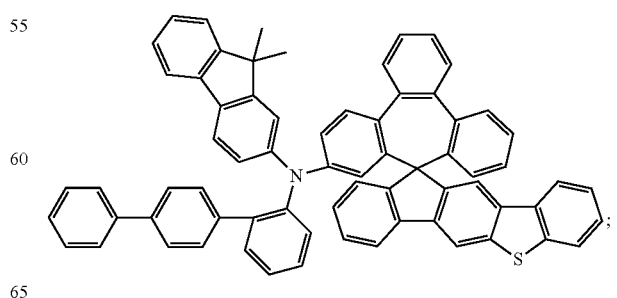

Compound 1056
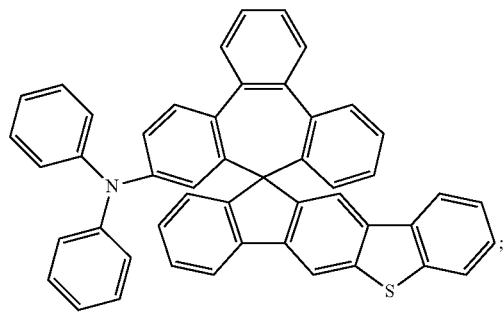
Compound 1060
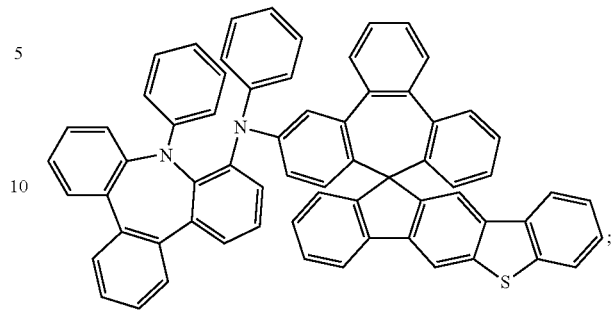
Compound 1057
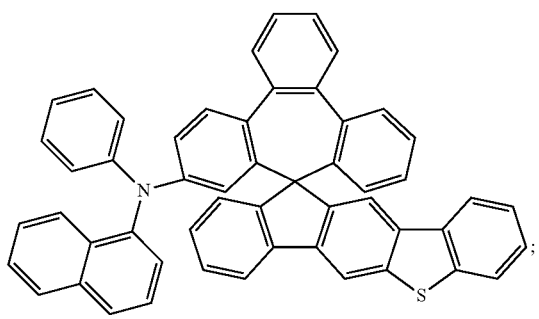
Compound 1061
Compound 1058
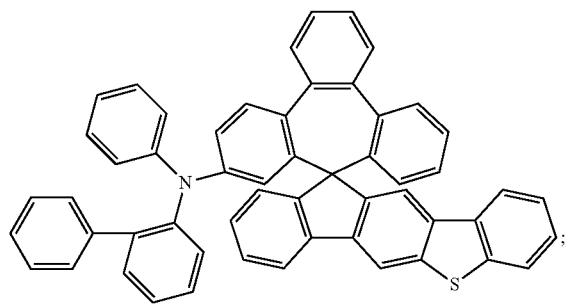
Compound 1062
Compound 1059
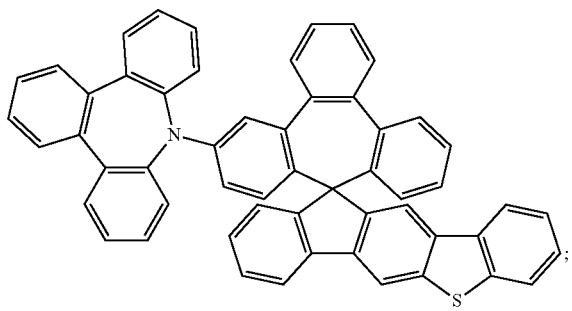
Compound 1063
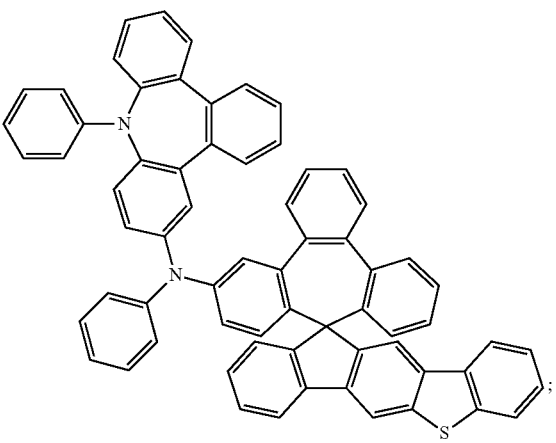

Compound 1064
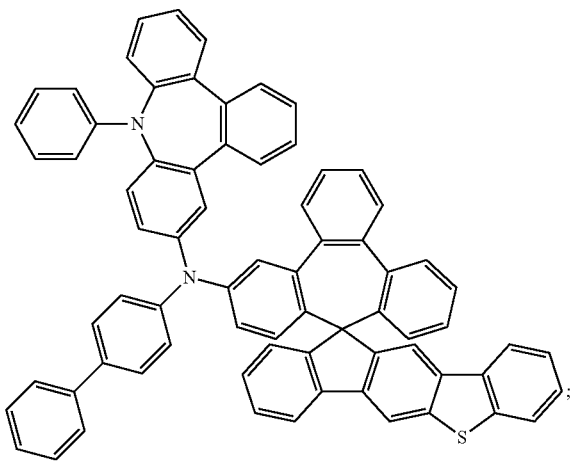
Compound 1065
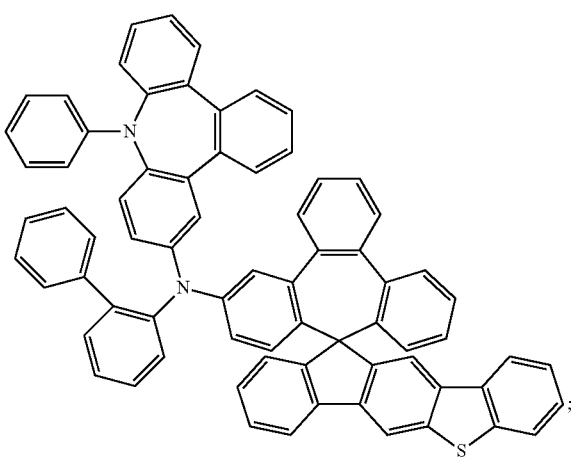
Compound 1066
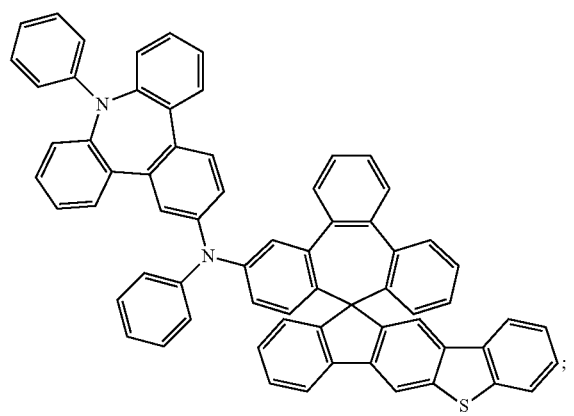
Compound 1067
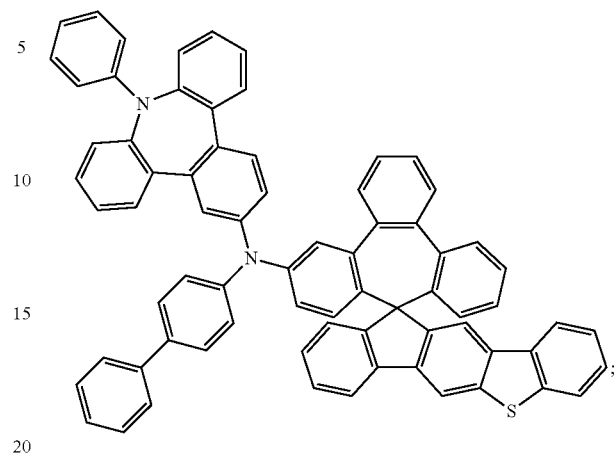
Compound 1068
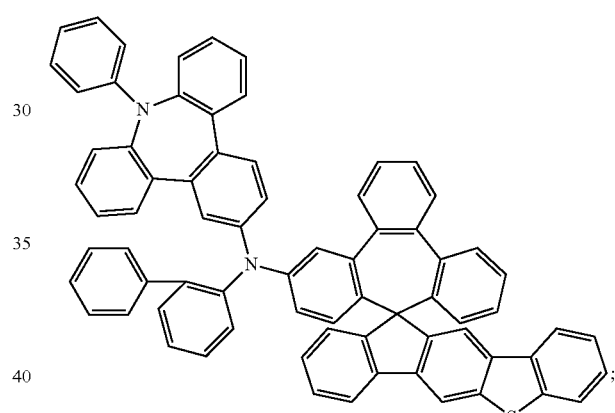
Compound 1069
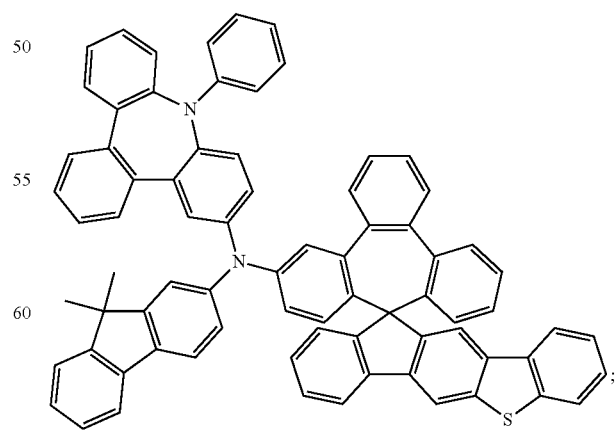

Compound 1070
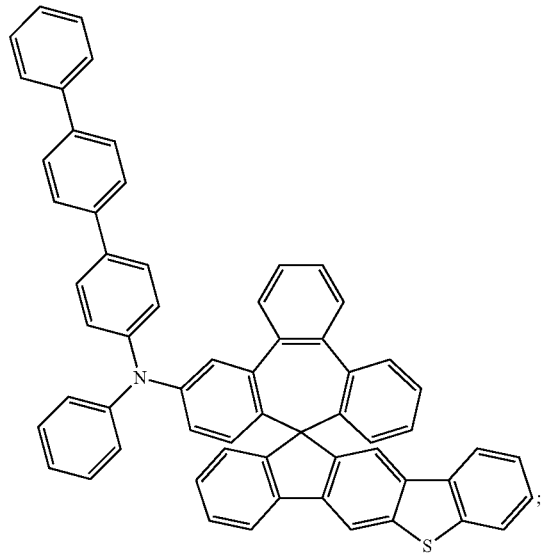
Compound 1071
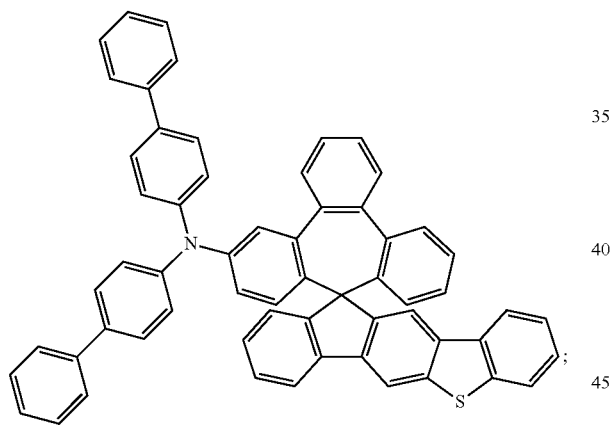
Compound 1072
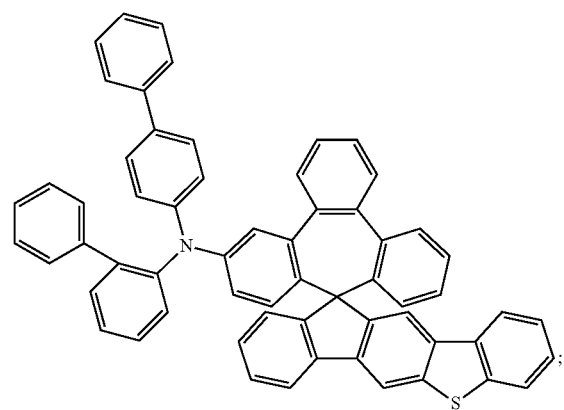
Compound 1073
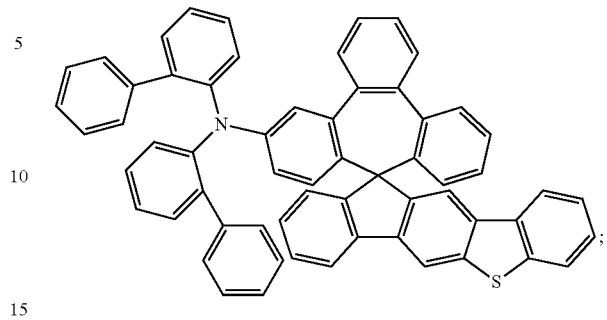
Compound 1074
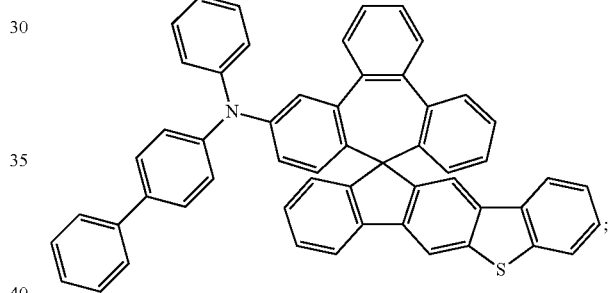
Compound 1075
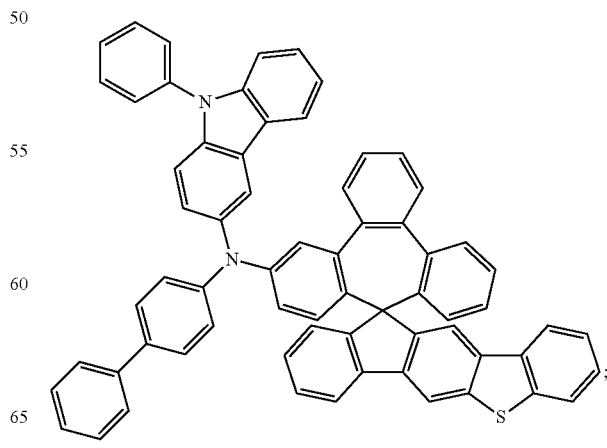

Compound 1076
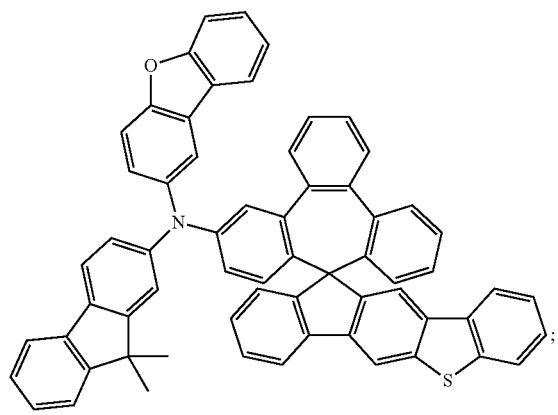
Compound 1077
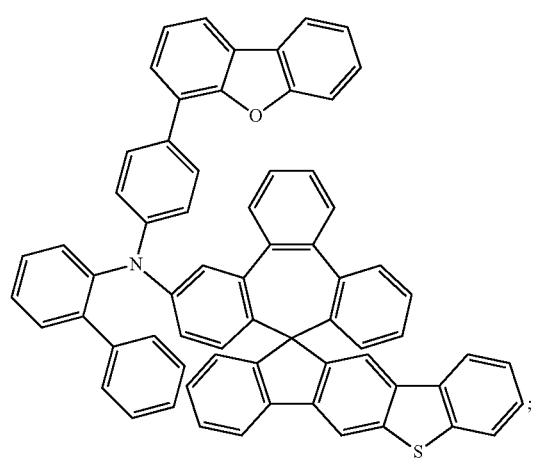
Compound 1078
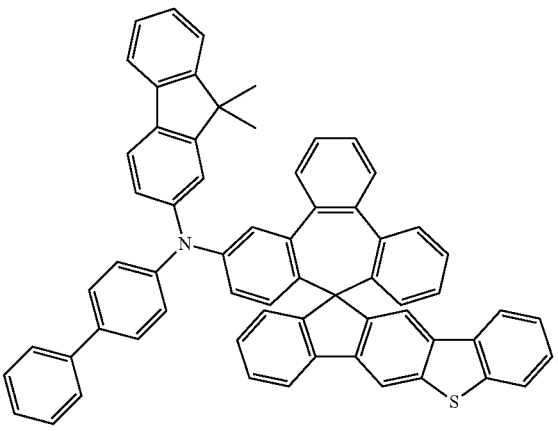
Compound 1079
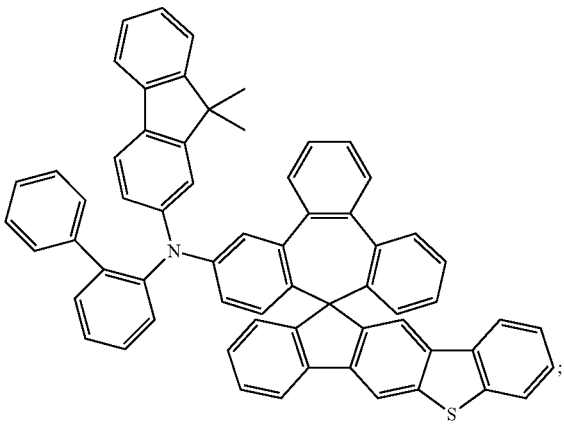
Compound 1080
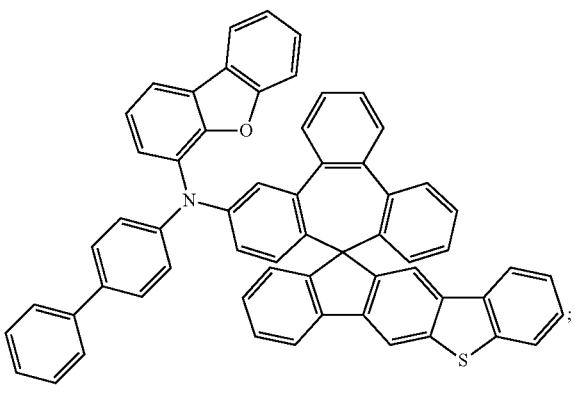
Compound 1081
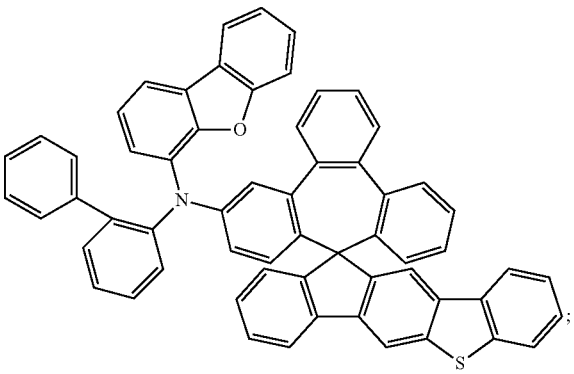
Compound 1082
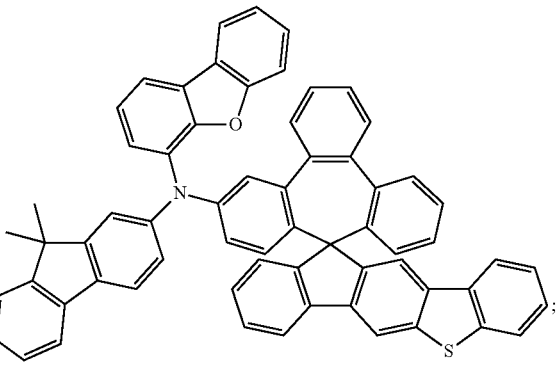

Compound 1083
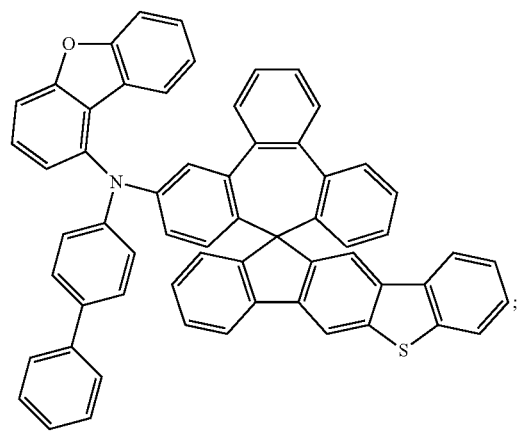
Compound 1084
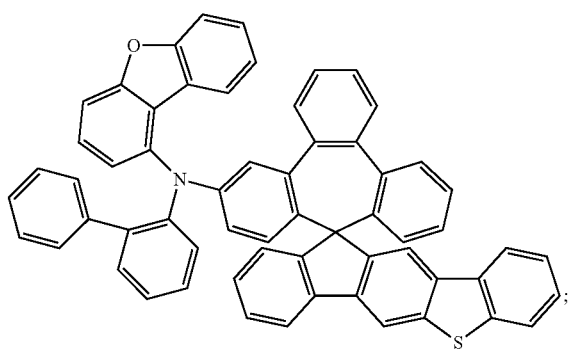
Compound 1085
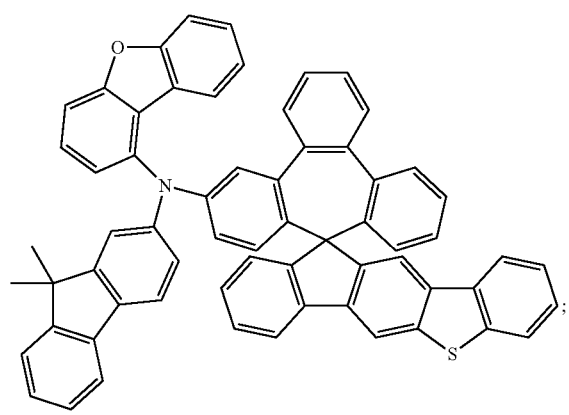
Compound 1086
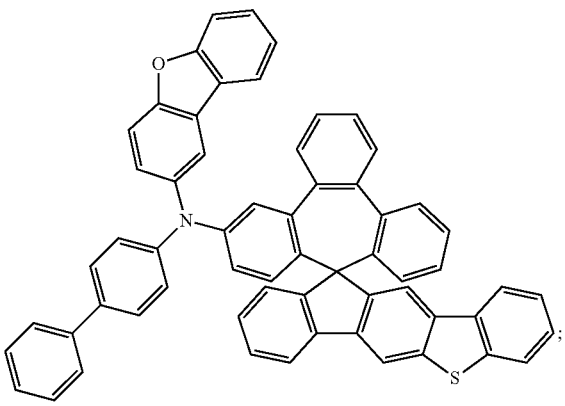
Compound 1087
Compound 1088
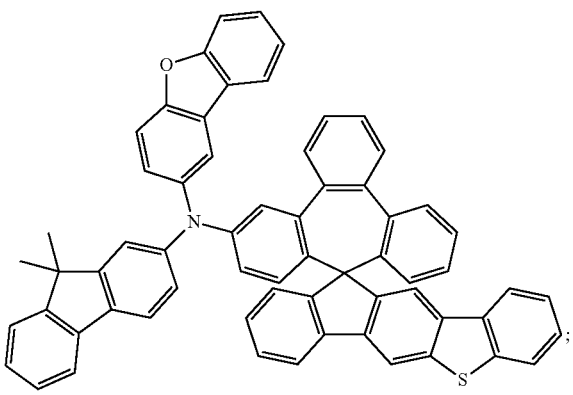

Compound 1089
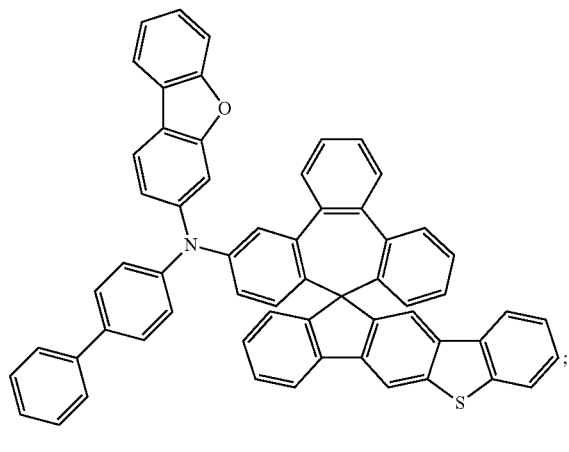
Compound 1090
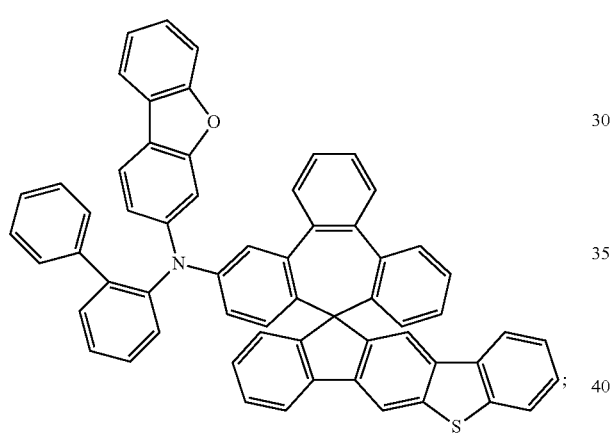
Compound 1091
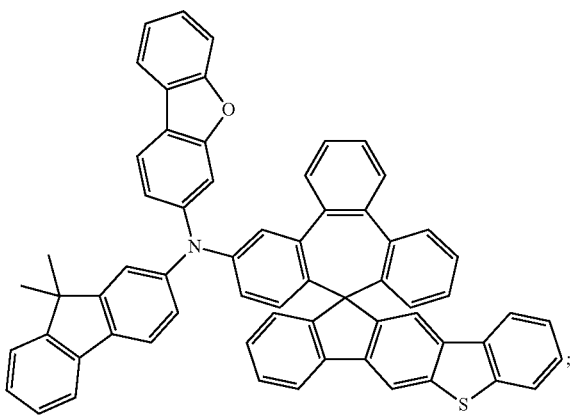
Compound 1092
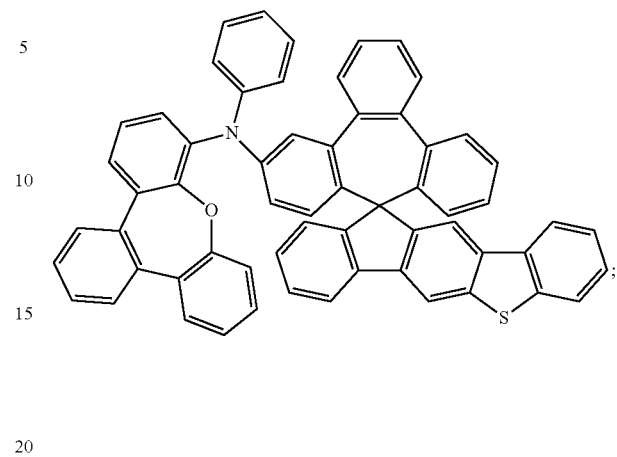
Compound 1093
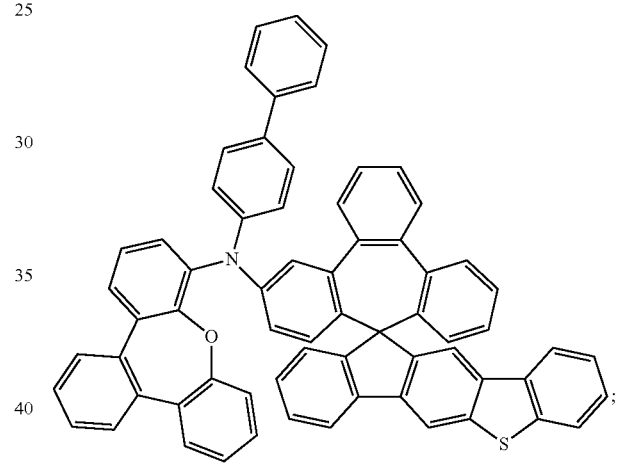
Compound 1094
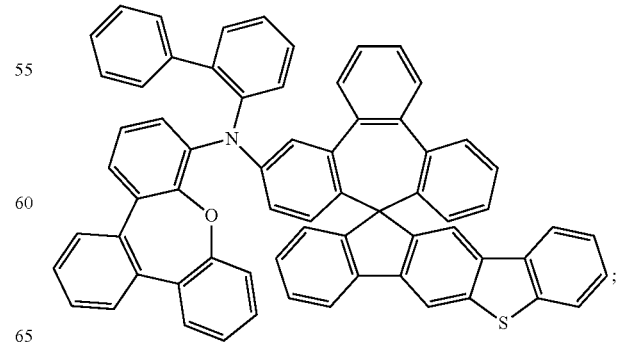

-continued
Compound 1095
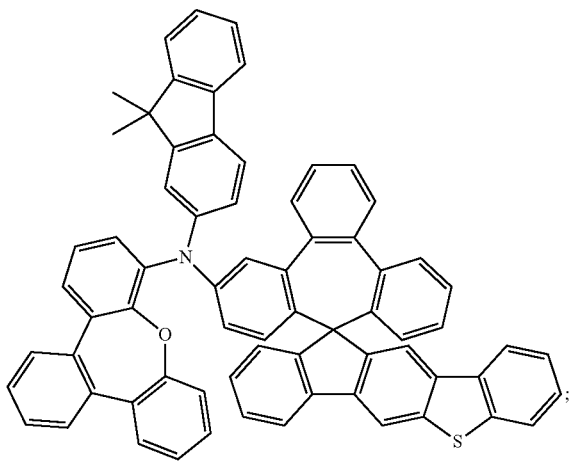
Compound 1096
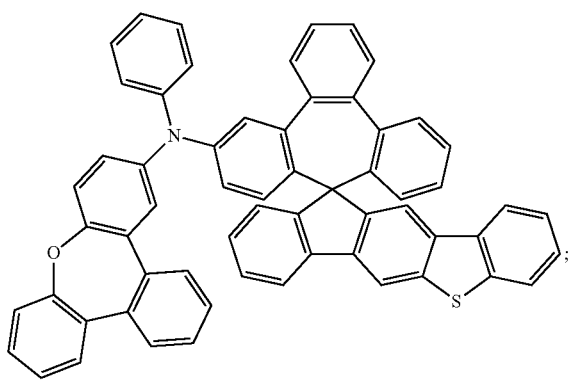
Compound 1097
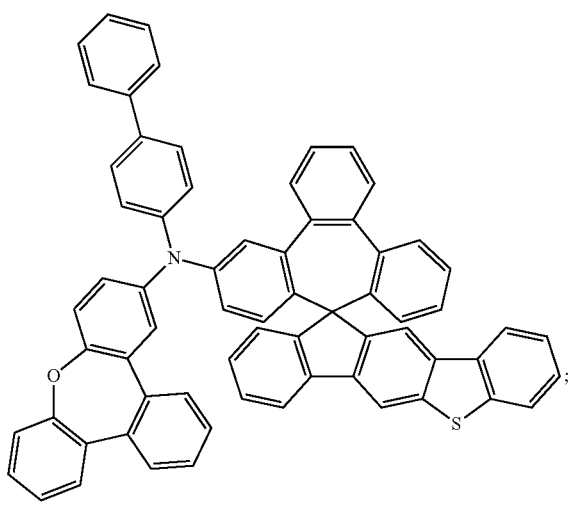
-continued
Compound 1098
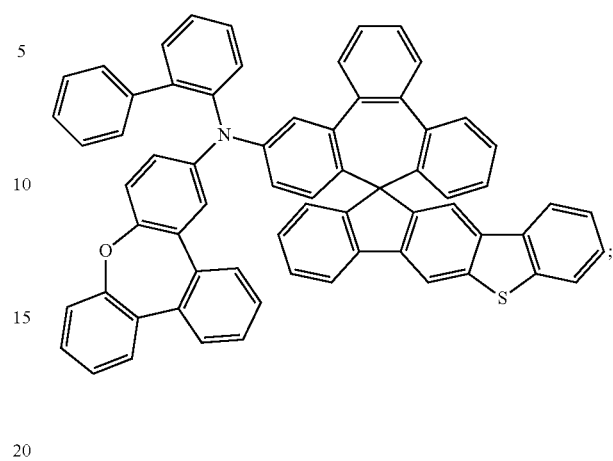
Compound 1099
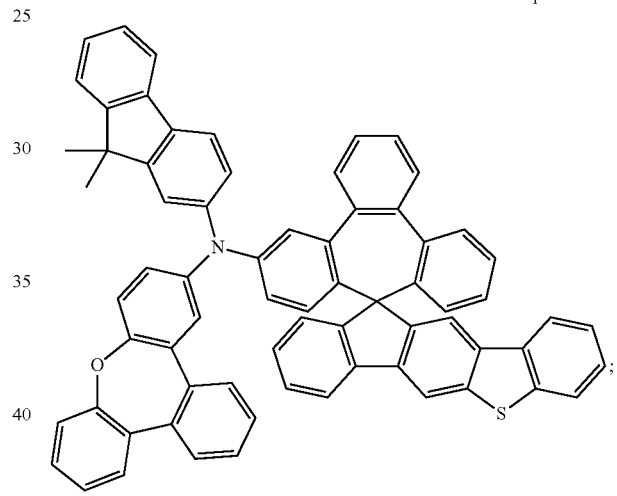
Compound 1100
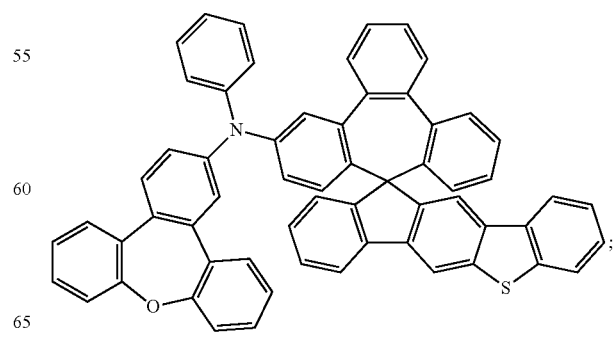

Compound 1101
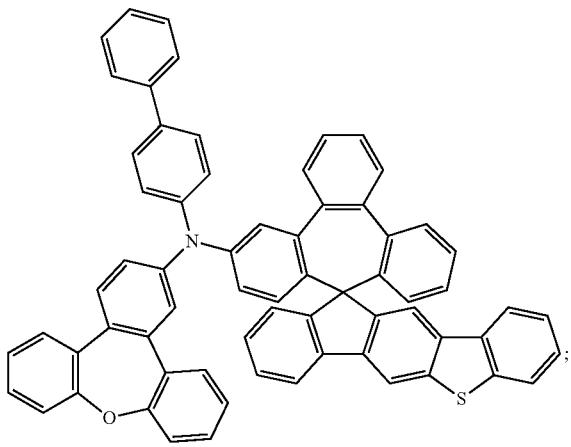
Compound 1102
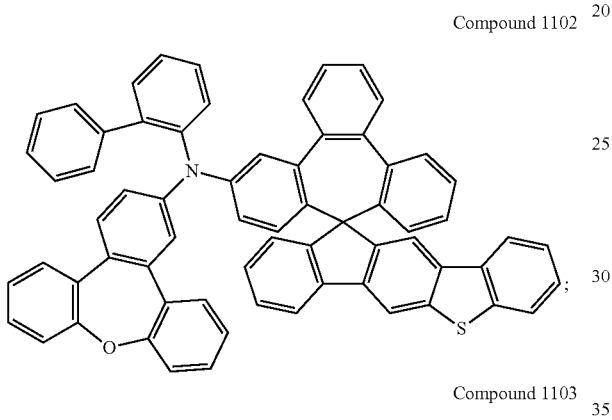
Compound 1103
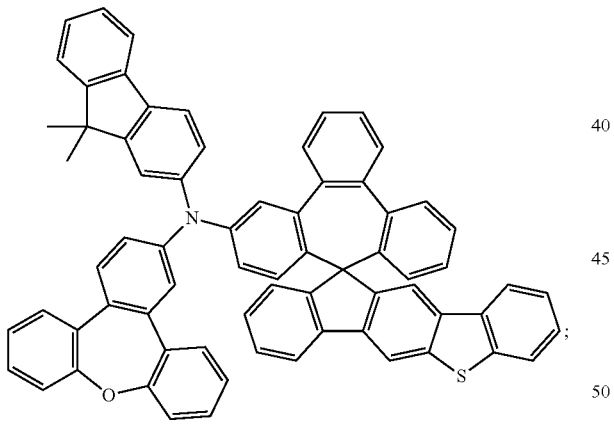
Compound 1104
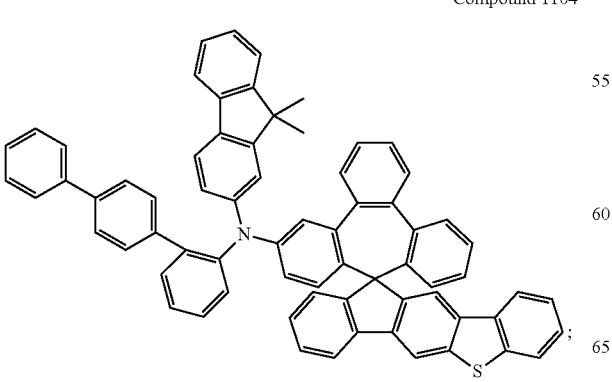
Compound 1105
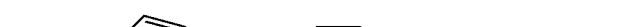
Compound 1106
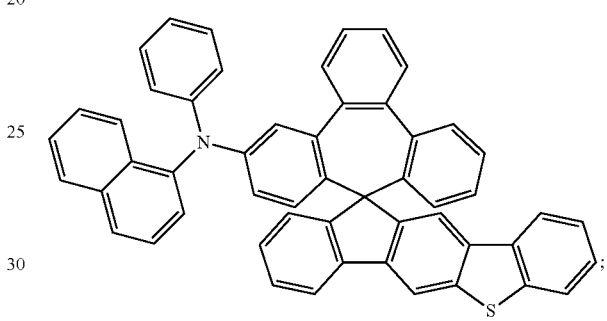
Compound 1107
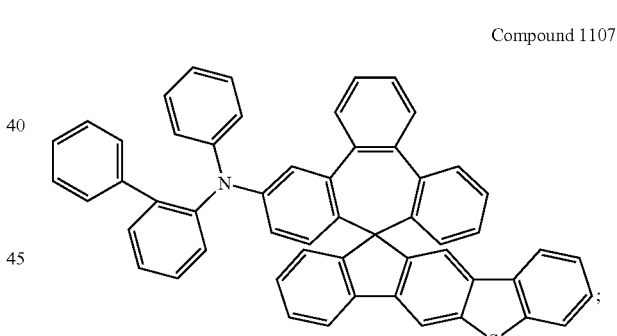
Compound 1108
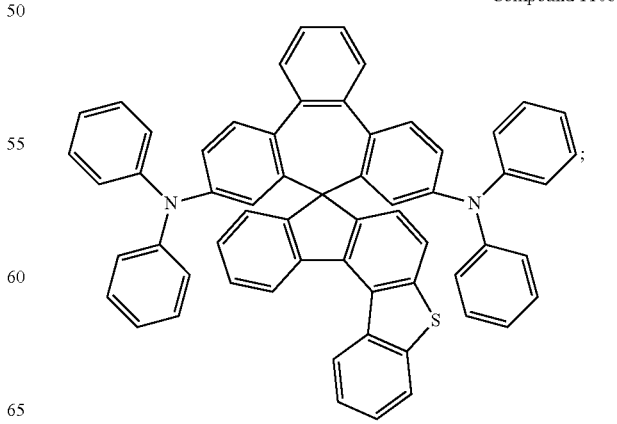

-continued

Compound 1109

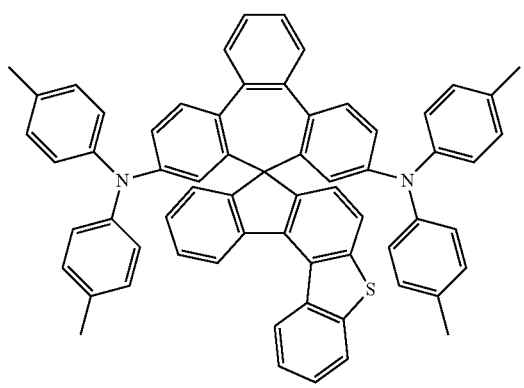

; and

Compound 1110

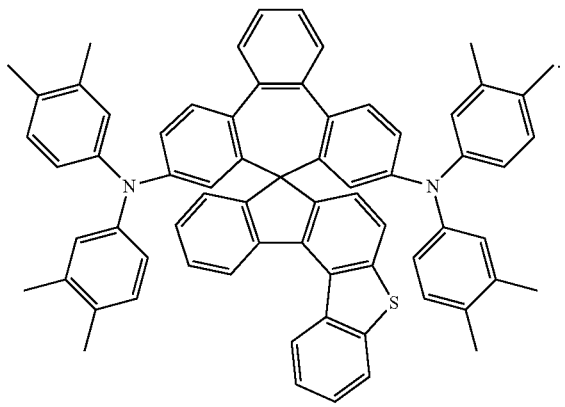

15. The compound as claimed in claim 1, wherein $Z^3$ in Formula (I) is selected from the group consisting of: a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

16. An organic electronic device, comprising a first electrode, a second electrode, and an organic layer disposed between the first electrode and the second electrode, wherein the organic layer comprises the compound as claimed in claim 1.

17. The organic electronic device as claimed in claim 16, wherein the organic electronic device is an organic light emitting device.

18. The organic electronic device as claimed in claim 17, wherein the organic light emitting device comprises:
   a hole injection layer formed on the first electrode;
   a hole transport layer formed on the hole injection layer, wherein the organic layer is the hole transport layer;
   an emission layer formed on the hole transport layer;
   an electron transport layer formed on the emission layer; and
   an electron injection layer formed between the electron transport layer and the second electrode.

19. The organic electronic device as claimed in claim 17, wherein the organic light emitting device comprises:
   a hole injection layer formed on the first electrode;
   a hole transport layer formed on the hole injection layer;
   an electron blocking layer formed on the hole injection layer, wherein the organic layer is the electron blocking layer;
   an emission layer formed on the electron blocking layer;
   an electron transport layer formed on the emission layer; and
   an electron injection layer formed between the electron transport layer and the second electrode.

20. The organic electronic device as claimed in claim 17, wherein the compound is selected from the group consisting of:

Compound 1

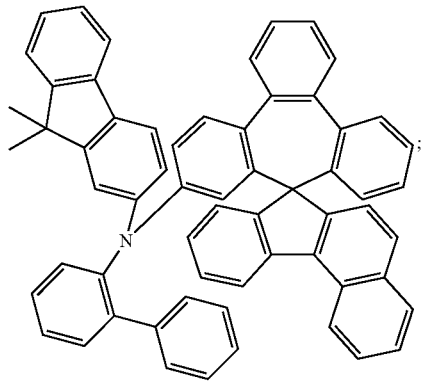

;

Compound 2

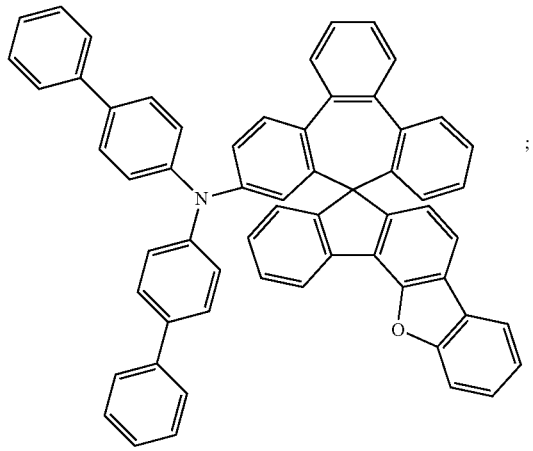

;

-continued
Compound 3
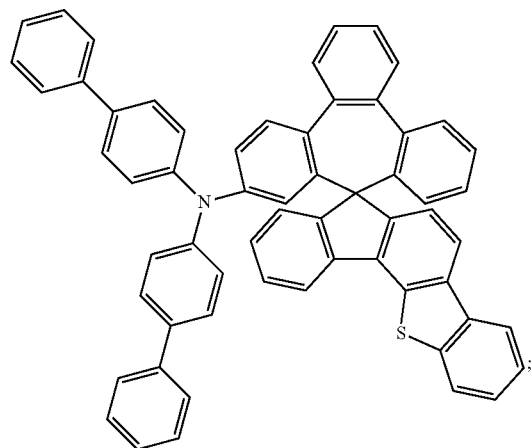
Compound 4
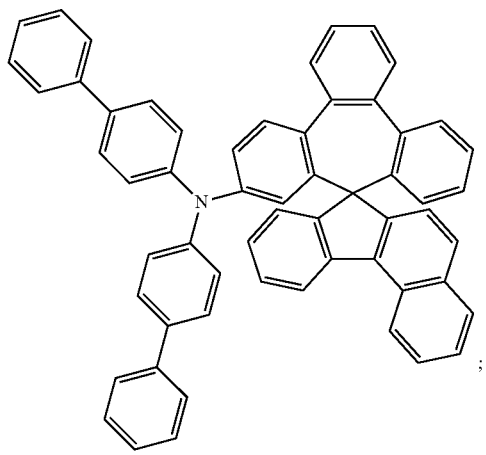
Compound 5
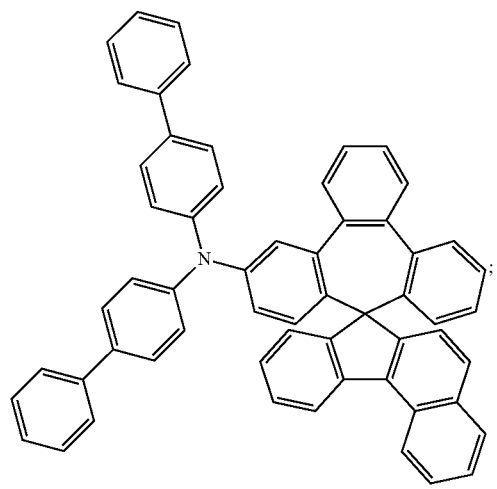
Compound 6
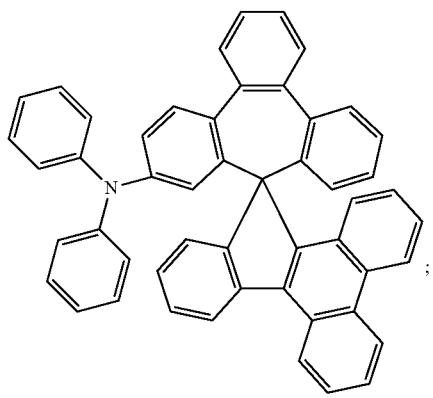
Compound 7
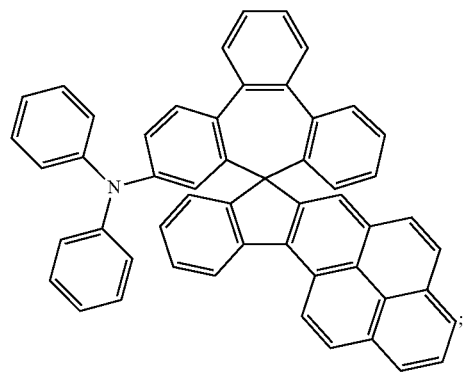
Compound 8
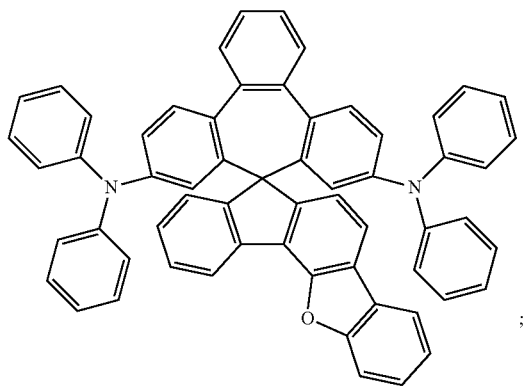

-continued
Compound 9
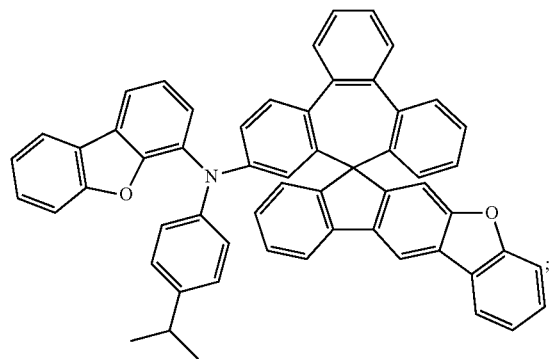
Compound 10
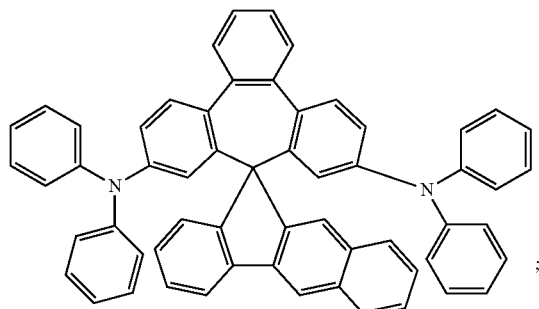
Compound 11
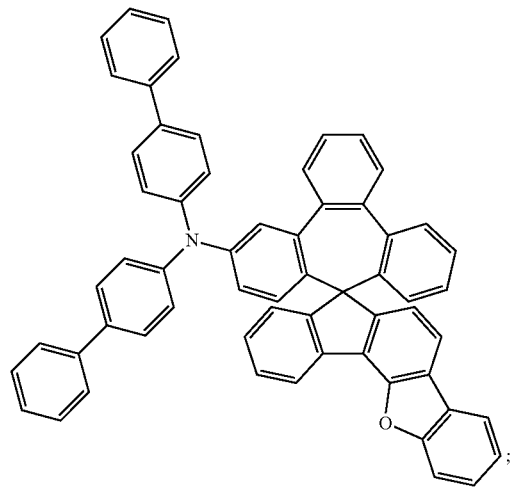
Compound 12
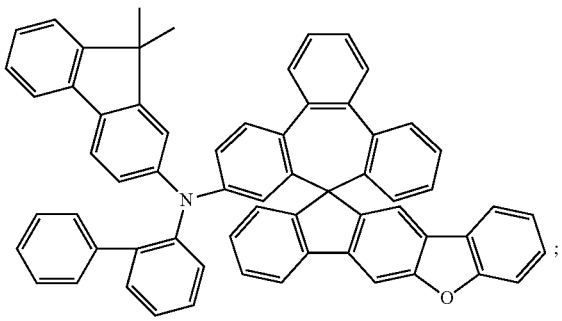
Compound 13
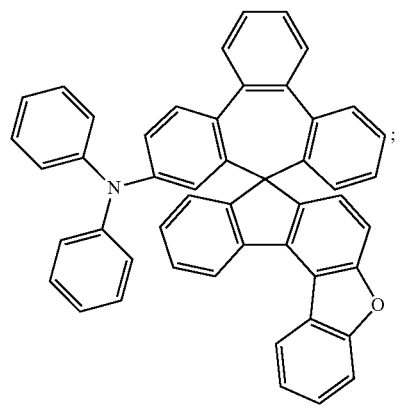
Compound 14
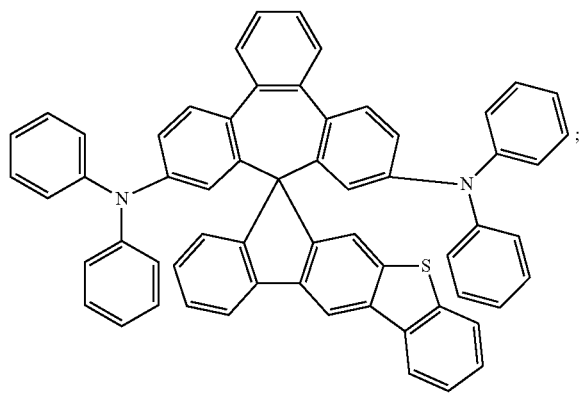

-continued
Compound 15
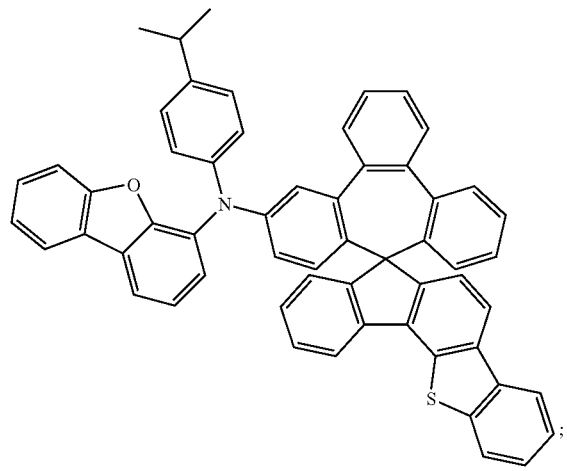
Compound 16
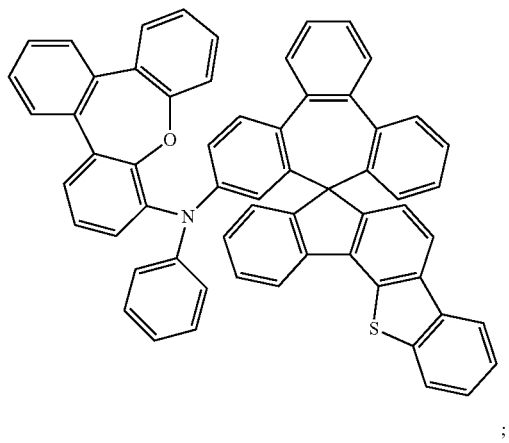
Compound 17
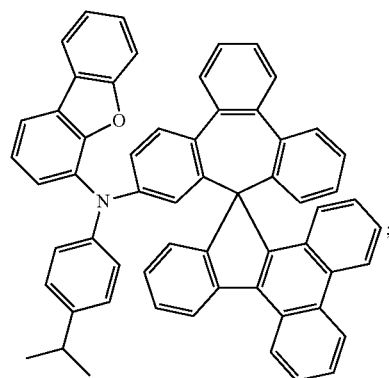
Compound 18
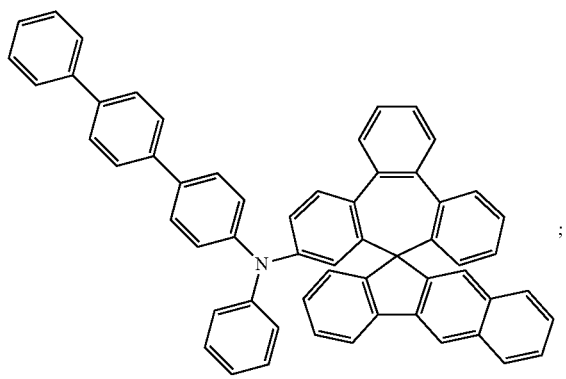
Compound 19
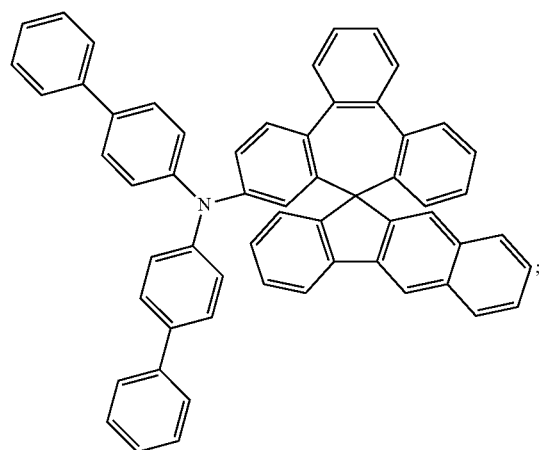
Compound 20
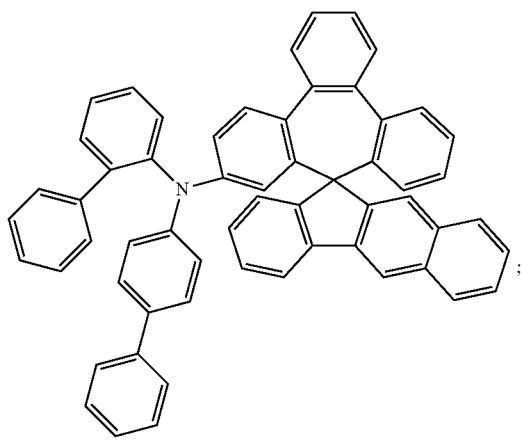

-continued
Compound 21
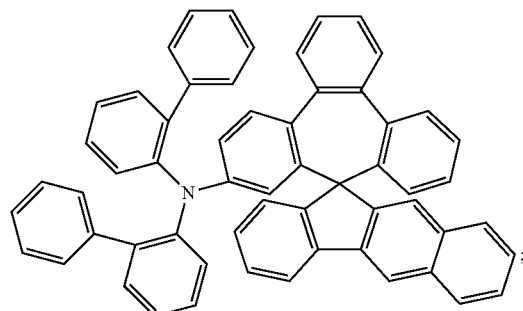
Compound 22
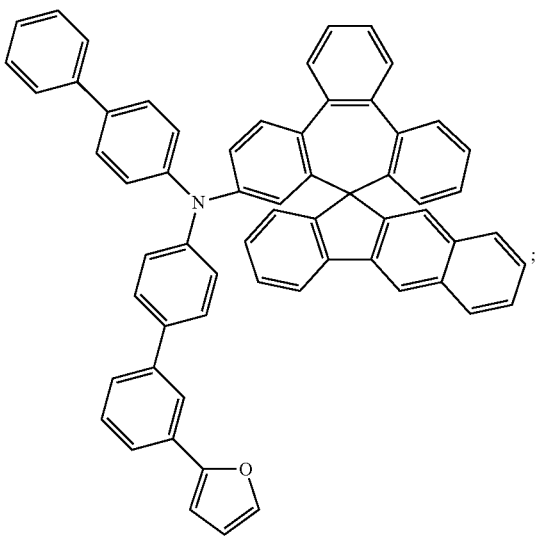
Compound 23
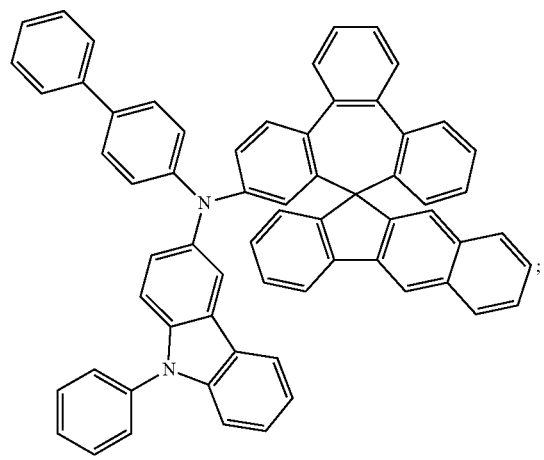
Compound 24
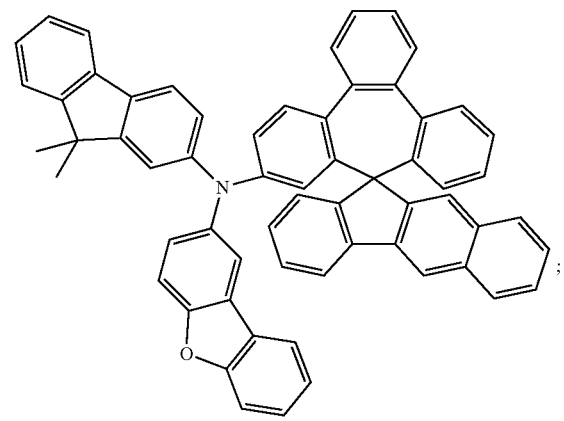
Compound 25
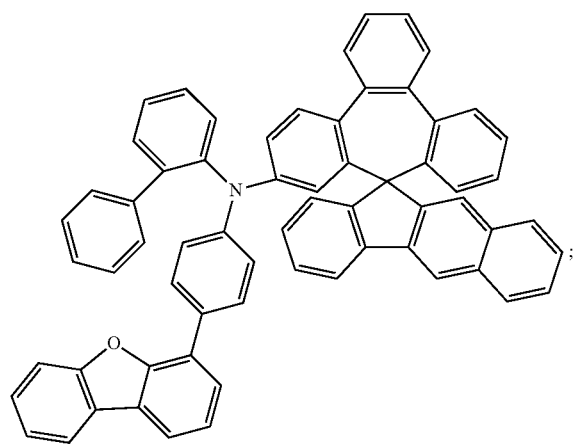
Compound 26
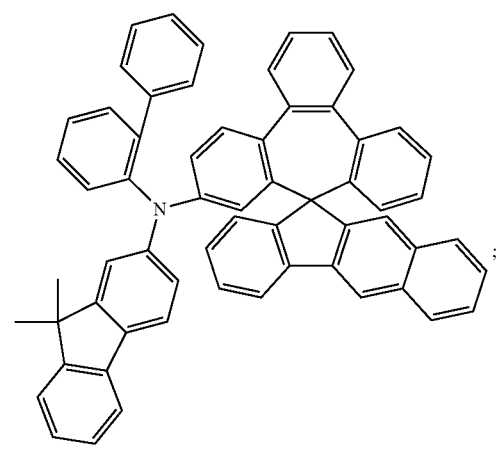

Compound 27
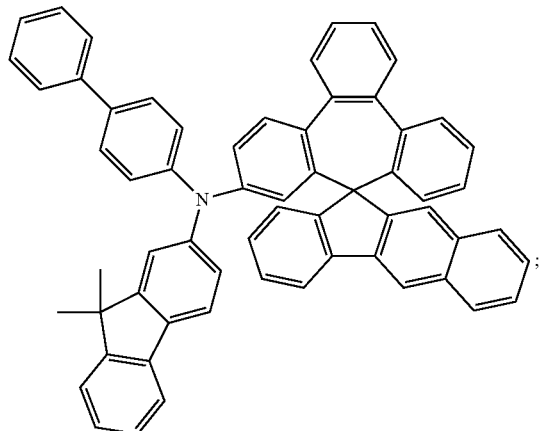
Compound 28
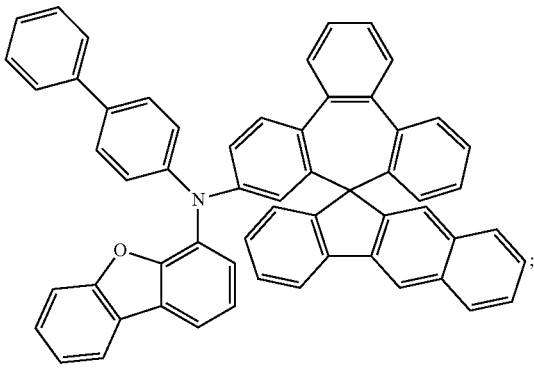
Compound 29
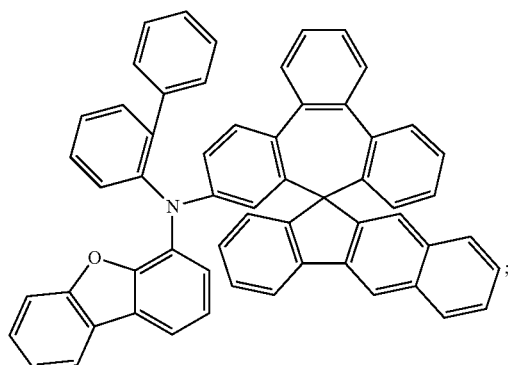
Compound 30
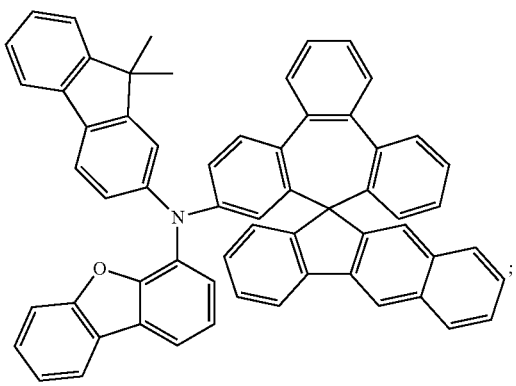
Compound 31
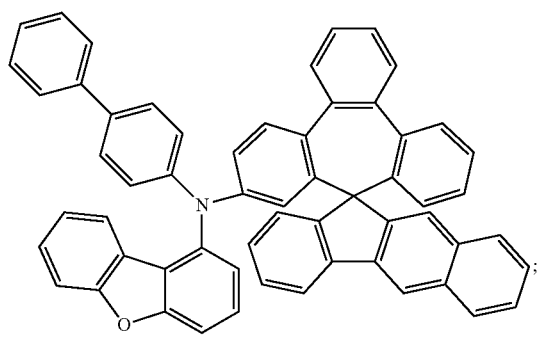
Compound 32
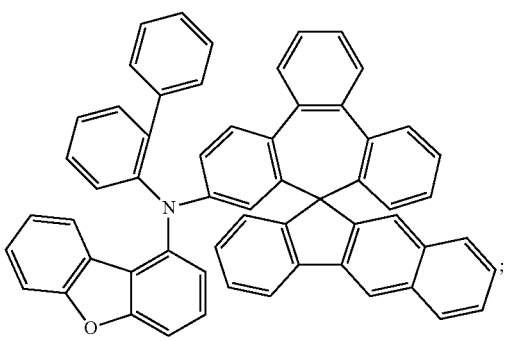
Compound 33
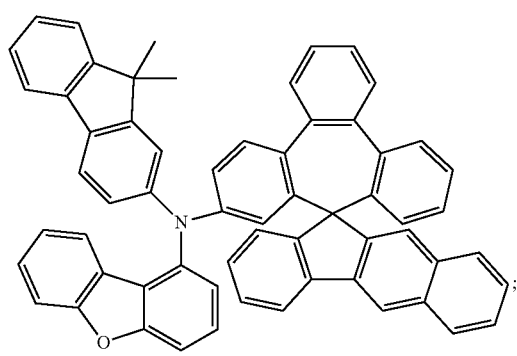
Compound 34
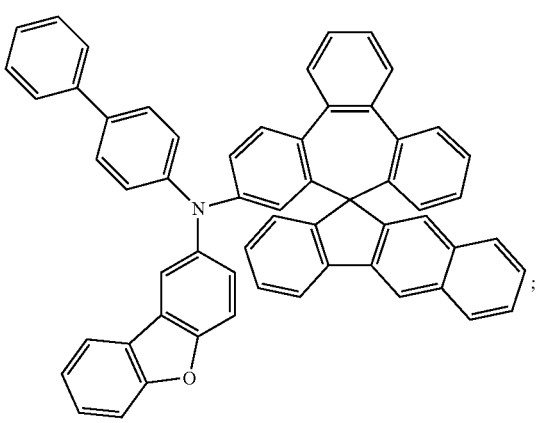

-continued
Compound 35
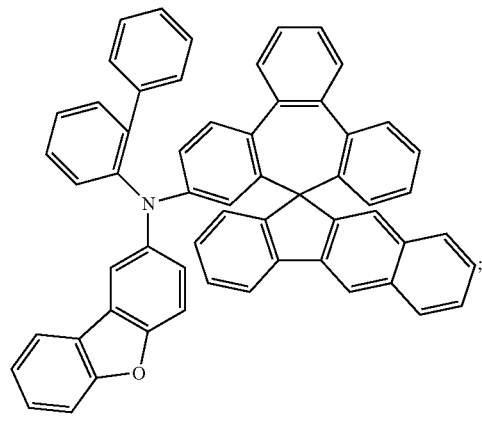
Compound 36
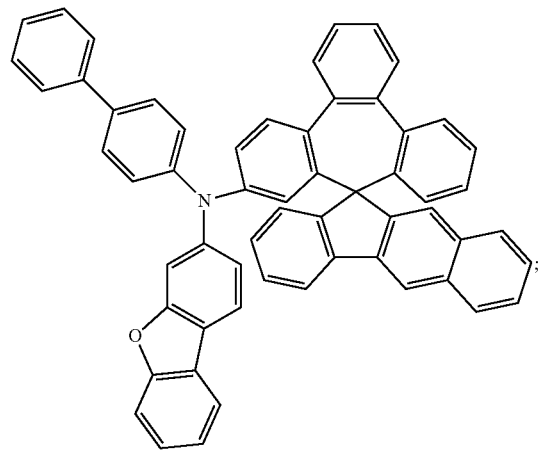
Compound 37
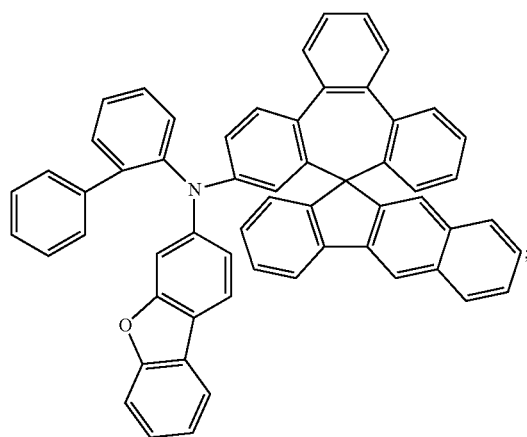
Compound 38
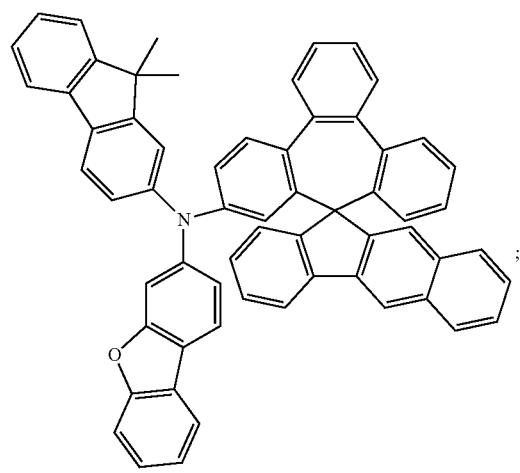
Compound 39
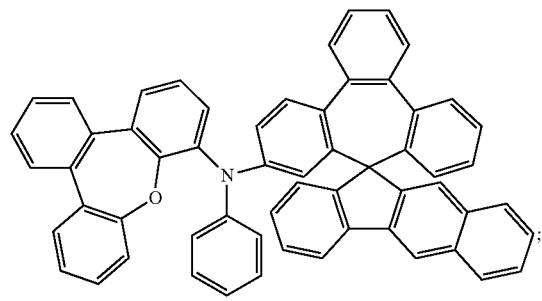
Compound 40
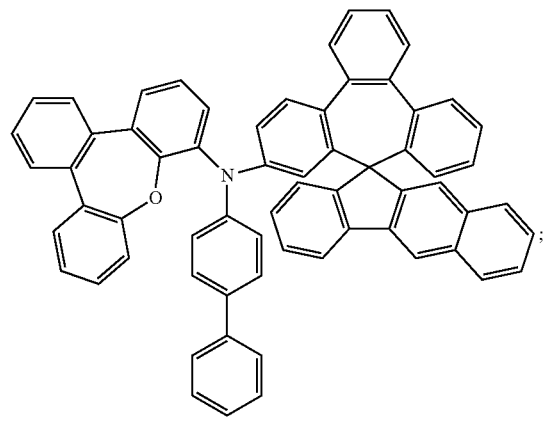

-continued
Compound 41
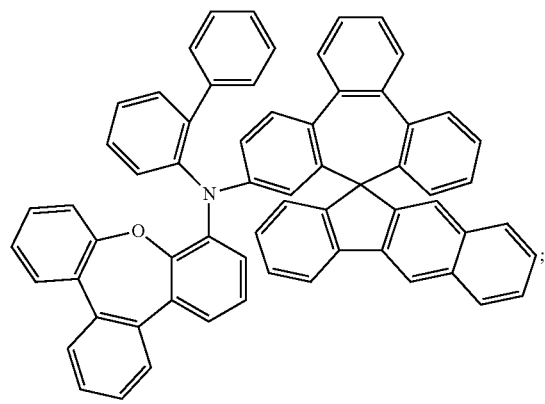
Compound 42
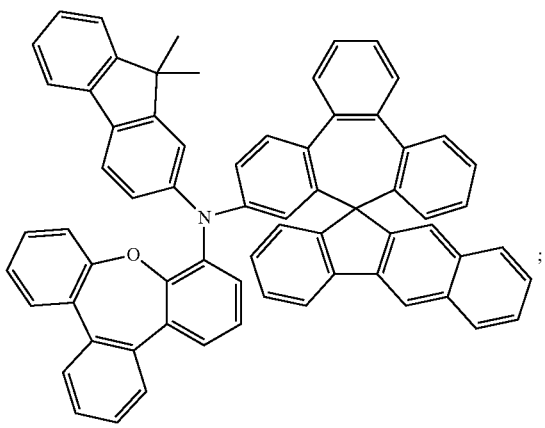
Compound 43
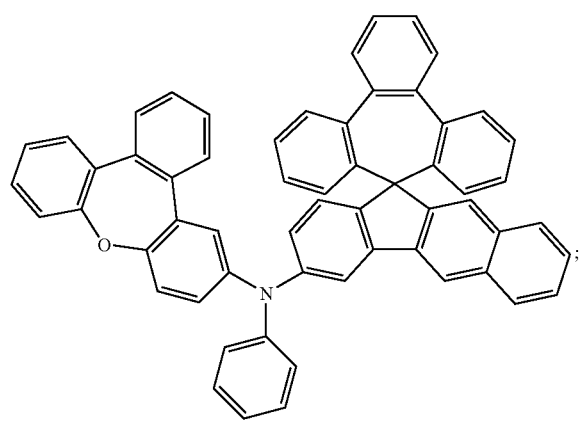
Compound 44
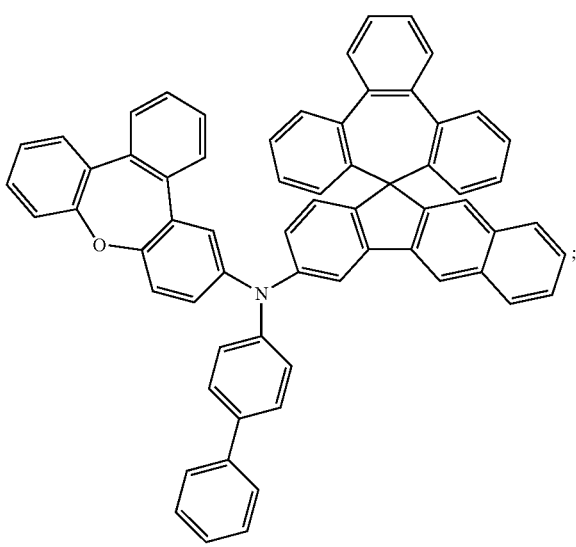
Compound 45
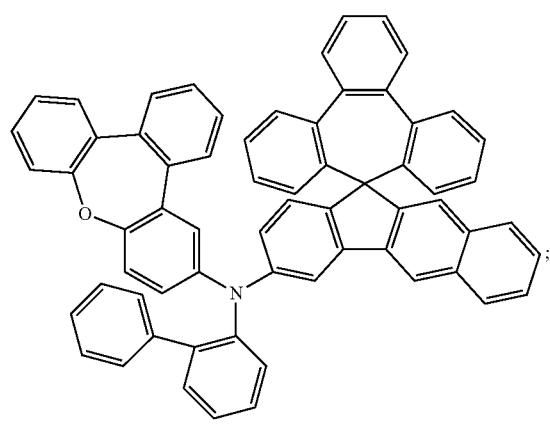
Compound 46
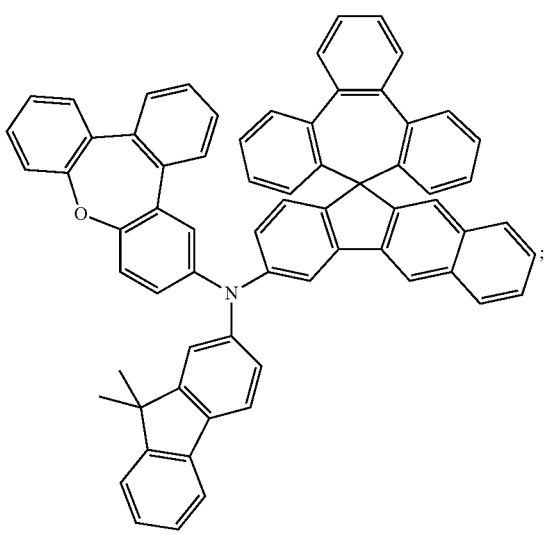

-continued
Compound 47
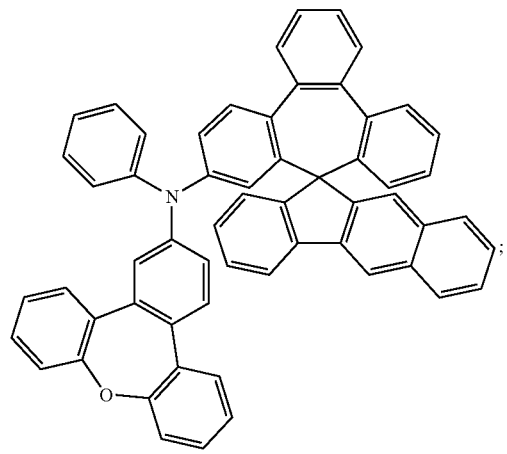
Compound 48
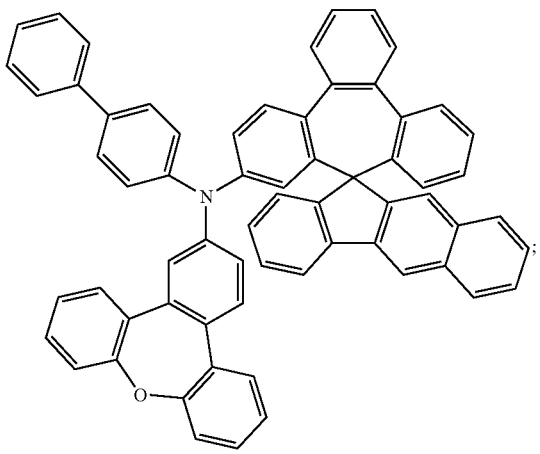
Compound 49
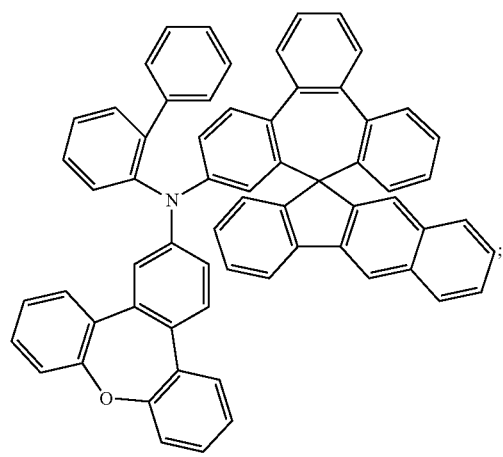
Compound 50
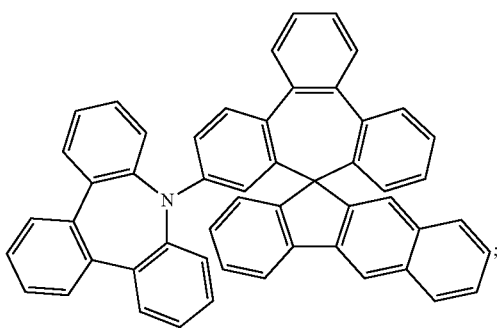
Compound 51
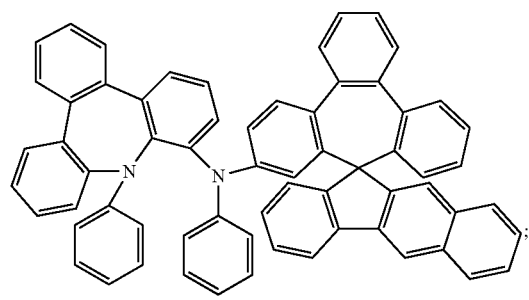
Compound 52
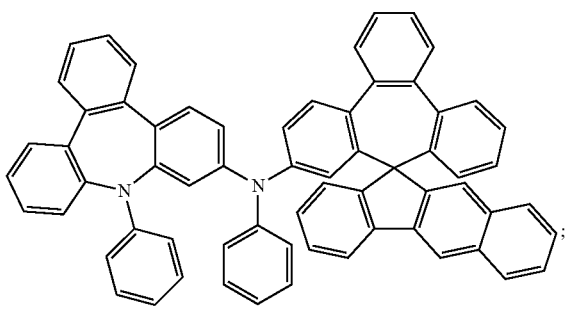

-continued
Compound 53
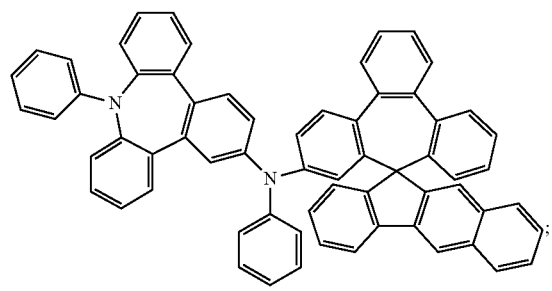
Compound 54
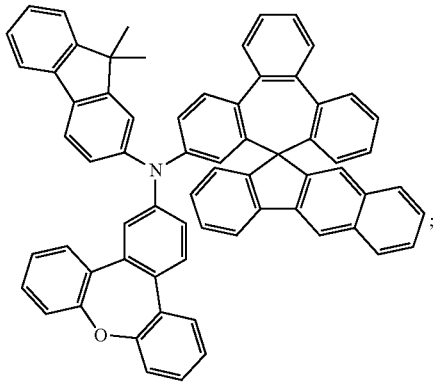
Compound 55
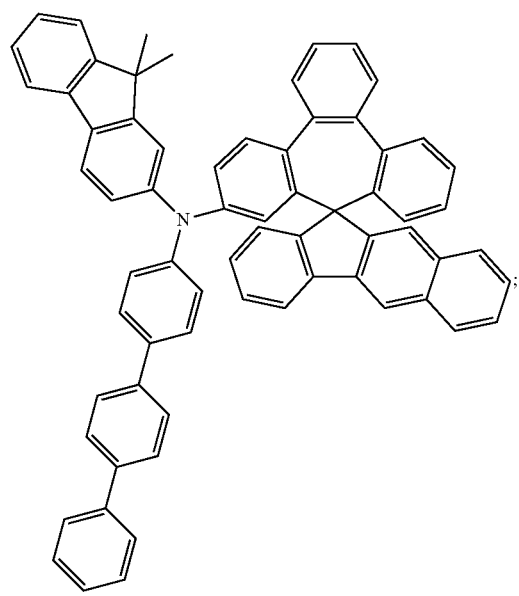
Compound 56
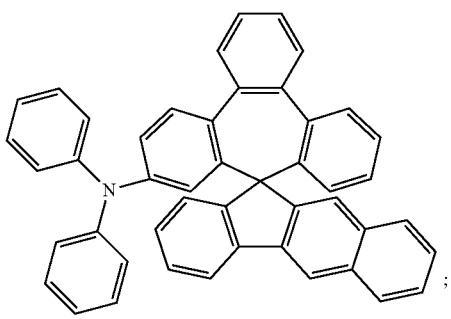
Compound 57
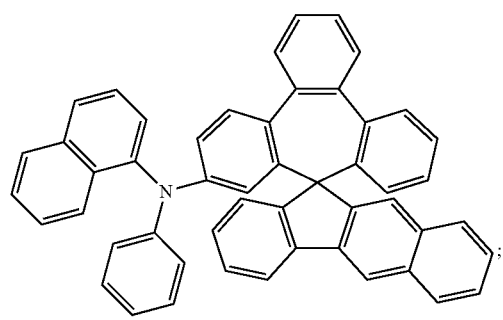
Compound 58
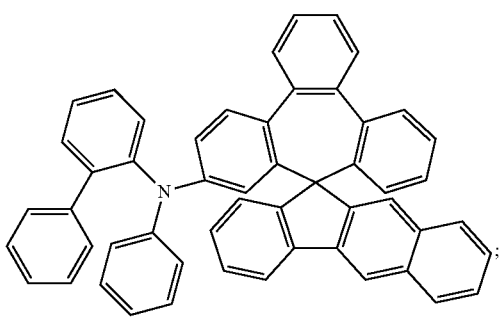

Compound 59
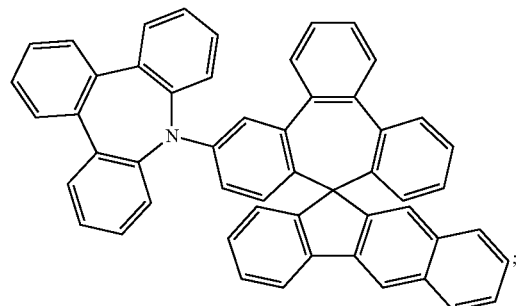
Compound 60
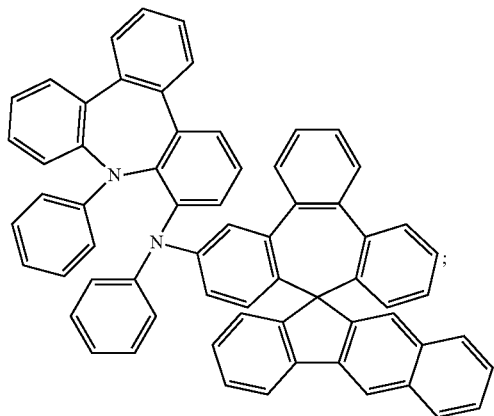
Compound 61
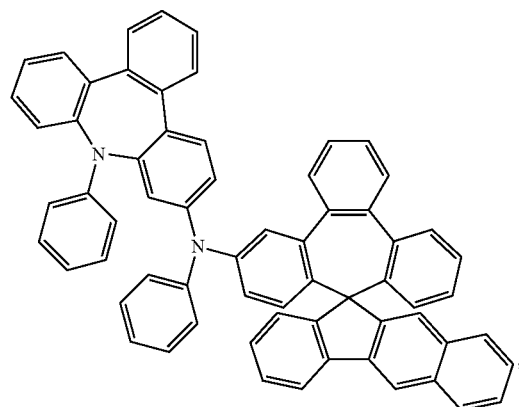
Compound 62
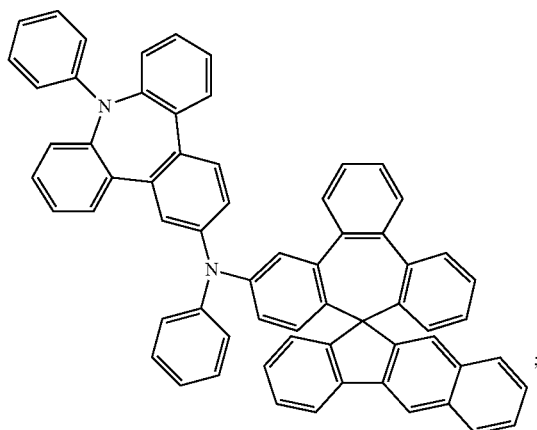
Compound 63
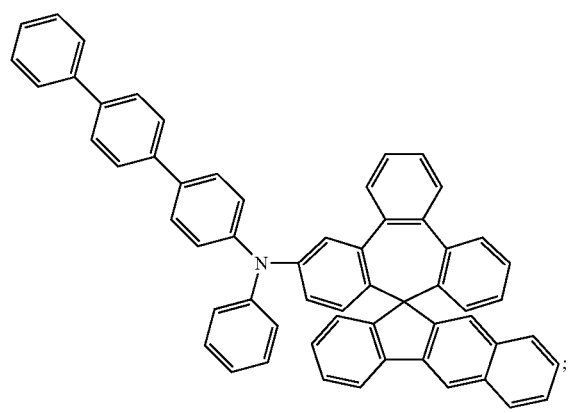
Compound 64
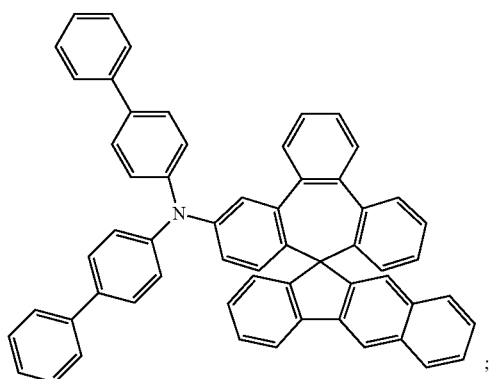

-continued
Compound 65
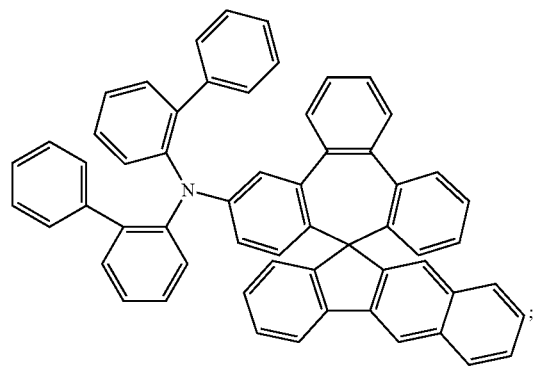
Compound 66
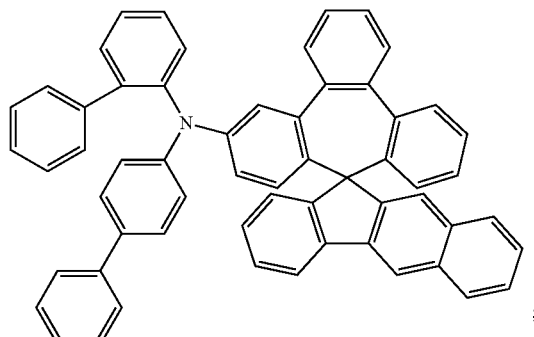
Compound 67
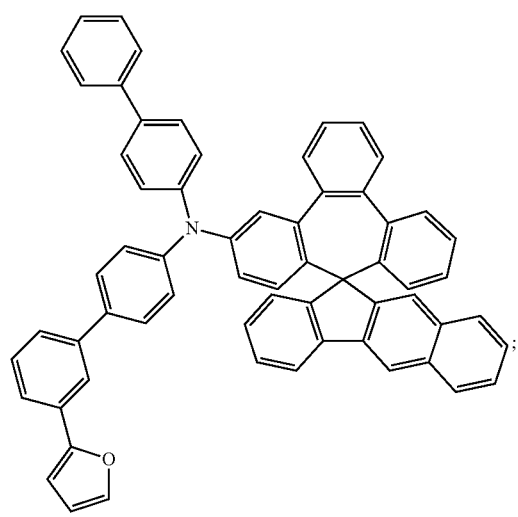
Compound 68
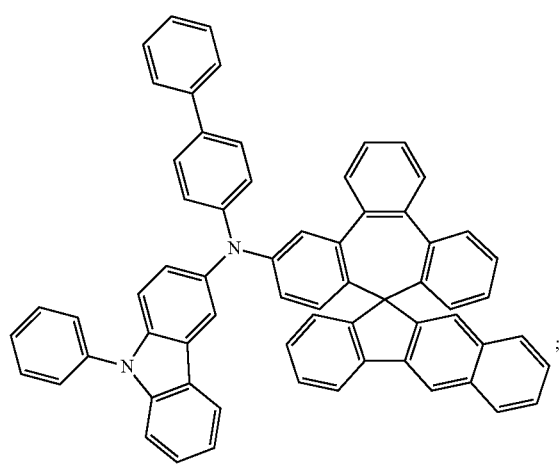
Compound 69
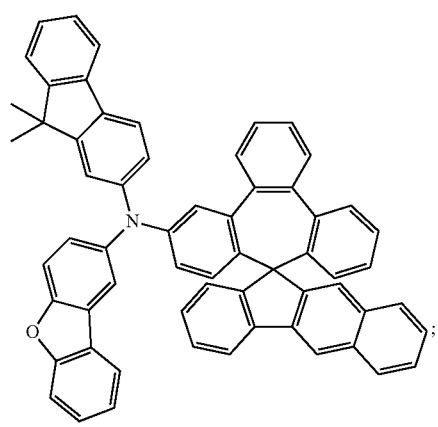
Compound 70
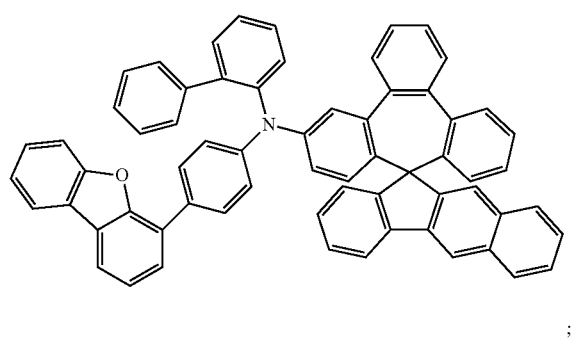

-continued
Compound 71
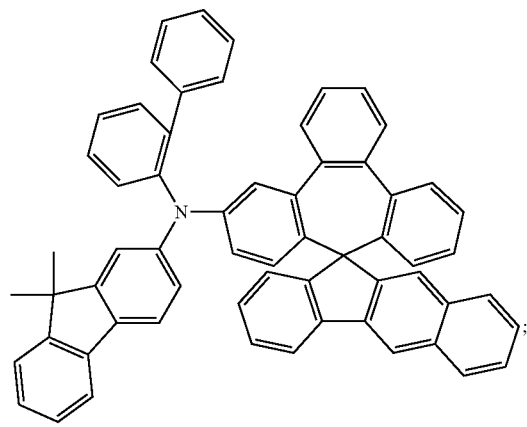
Compound 72
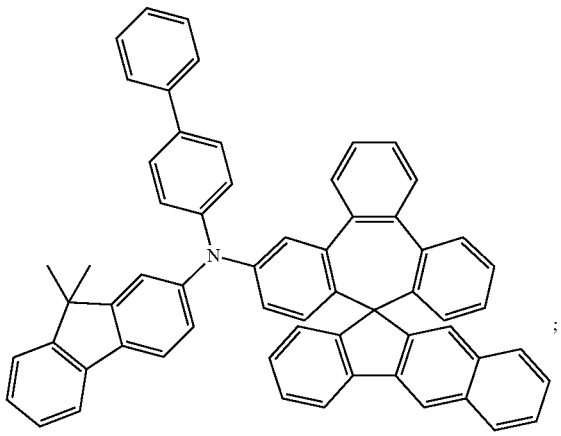
Compound 73
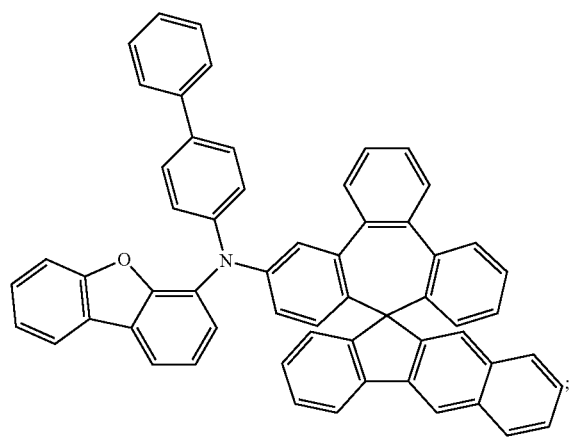
Compound 74
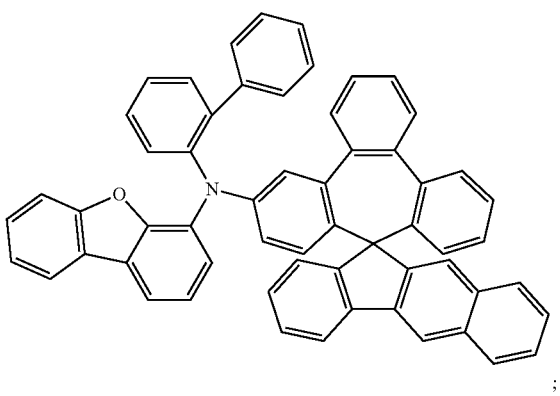
Compound 75
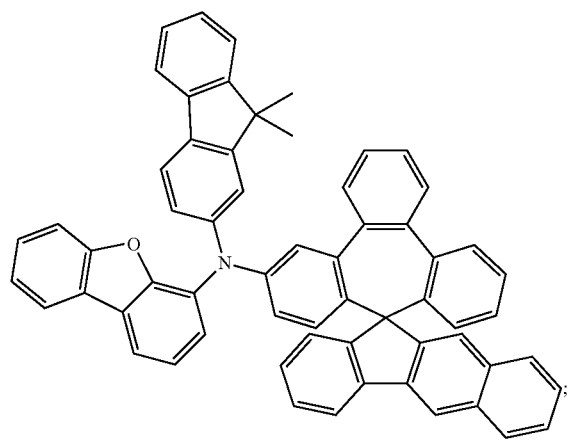
Compound 76
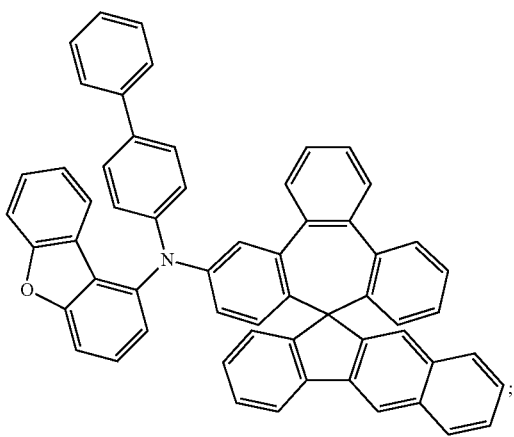

-continued
Compound 77
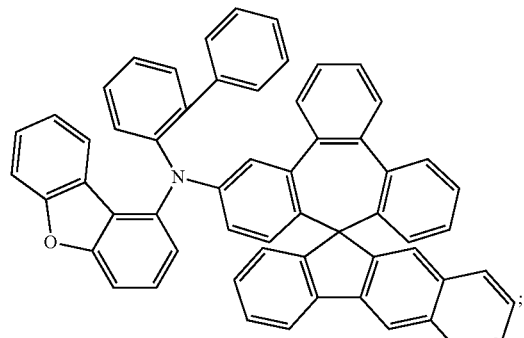
Compound 78
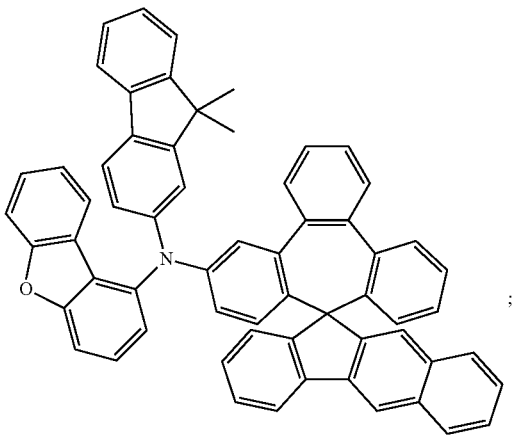
Compound 79
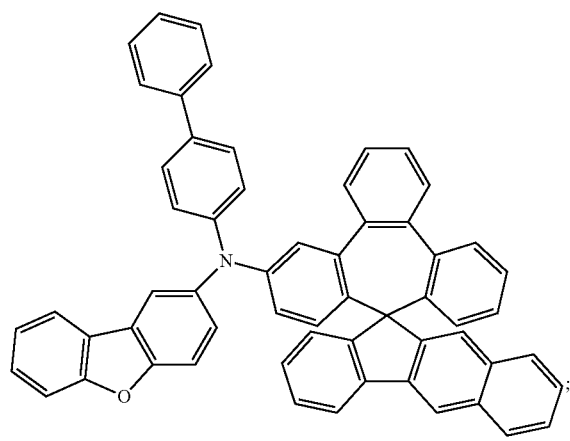
Compound 80
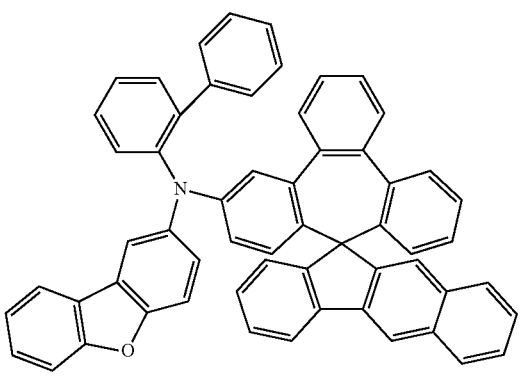
Compound 81
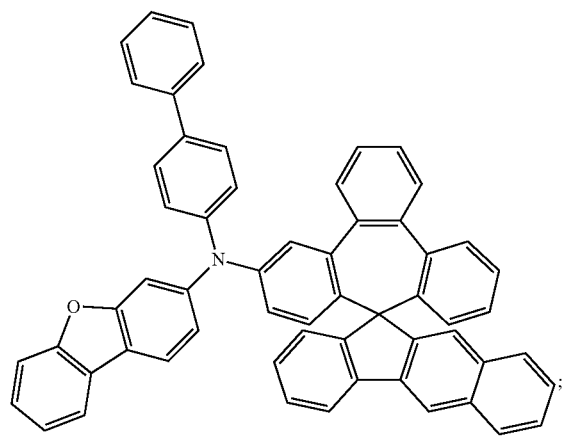
Compound 82
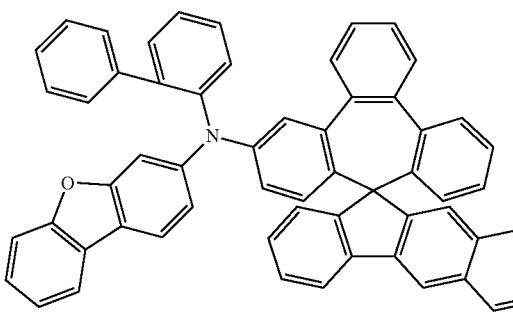

Compound 83
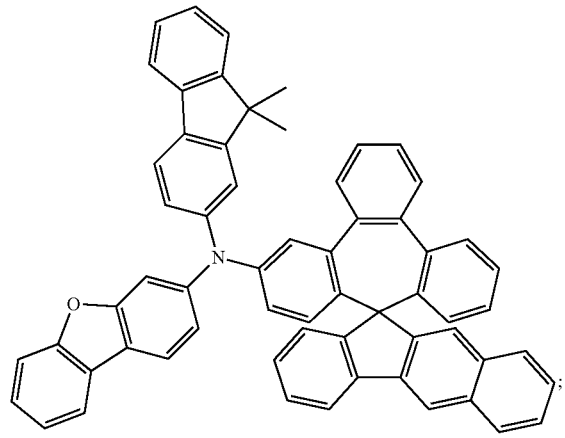
Compound 84
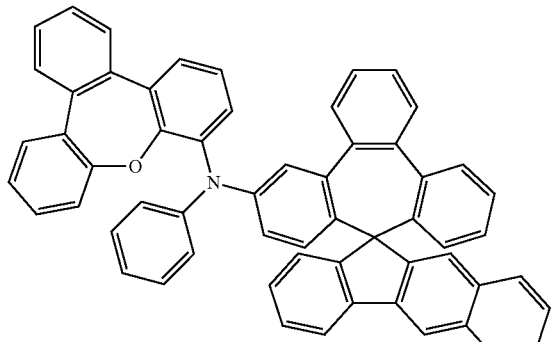
Compound 85
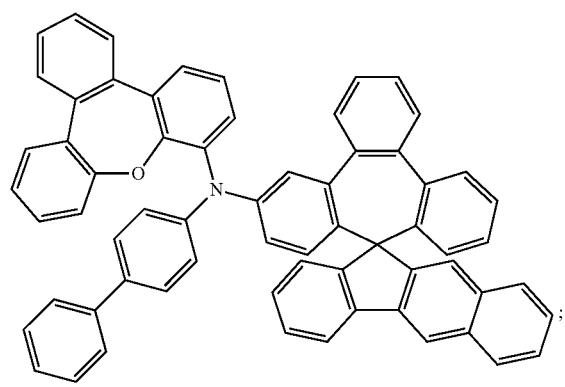
Compound 86
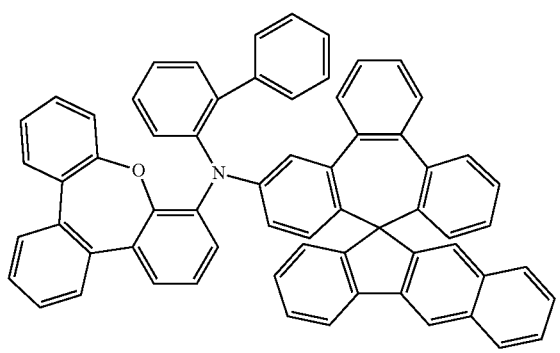
Compound 87
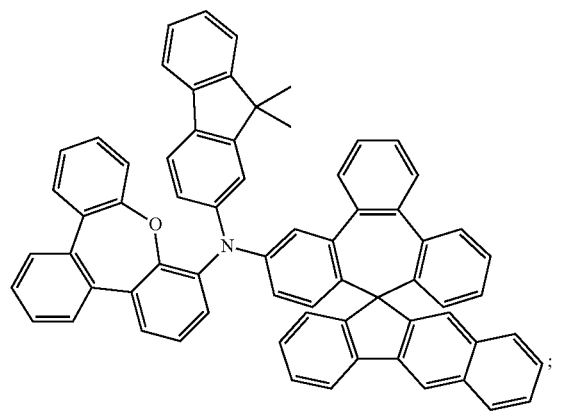
Compound 88
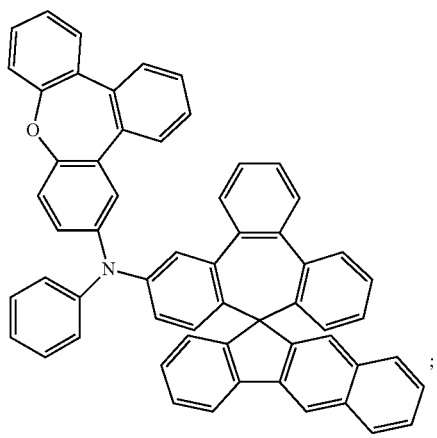

-continued
Compound 89
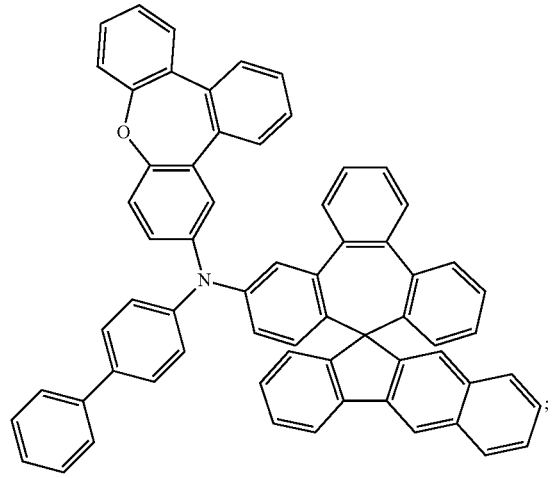
Compound 90
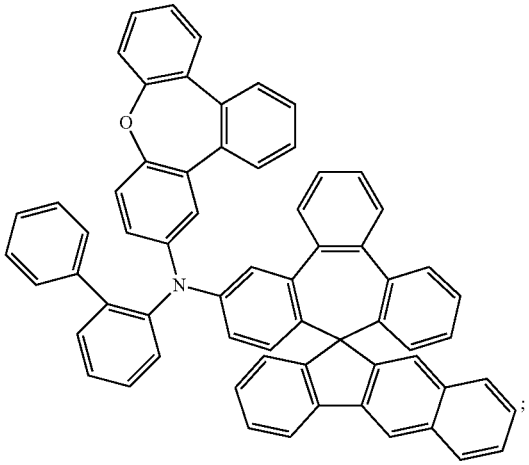
Compound 91
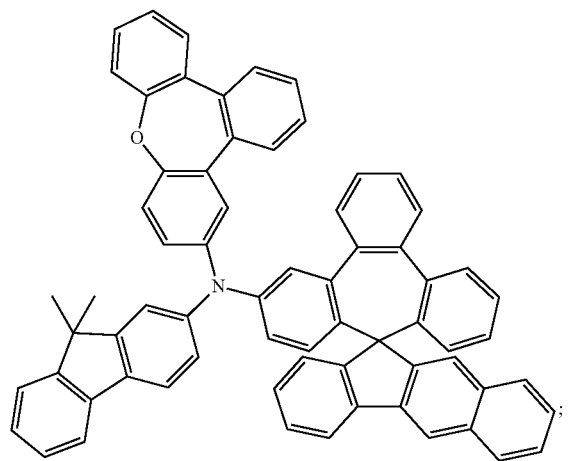
Compound 92
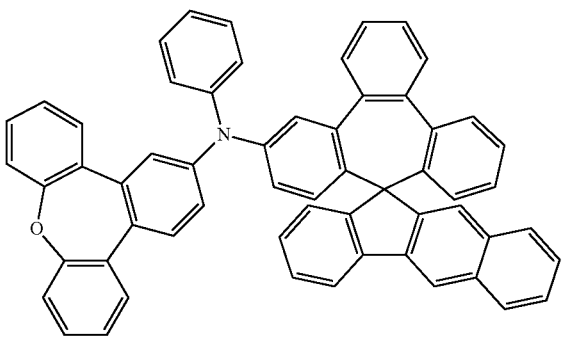
Compound 93
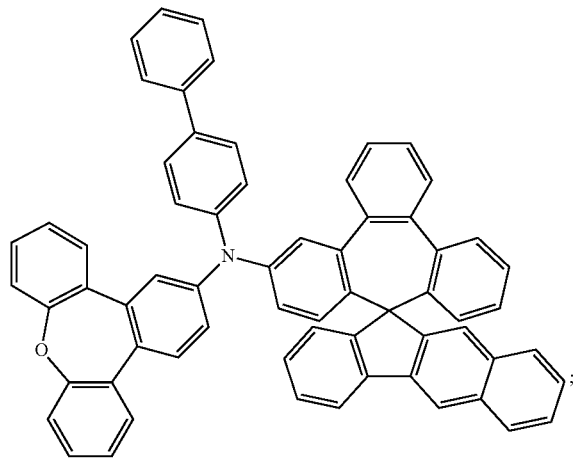
Compound 94
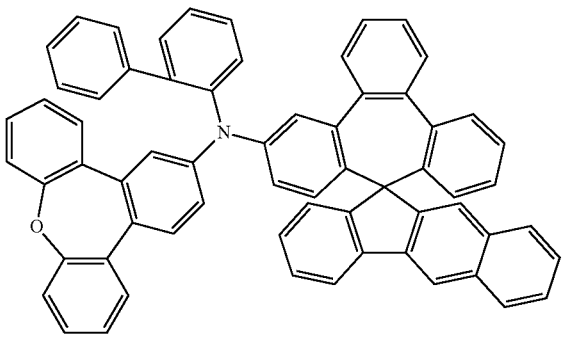

-continued
Compound 95
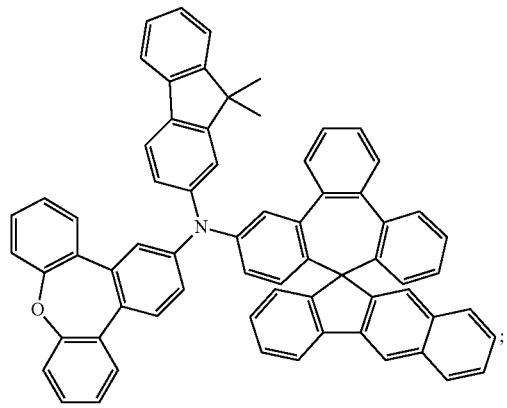
Compound 96
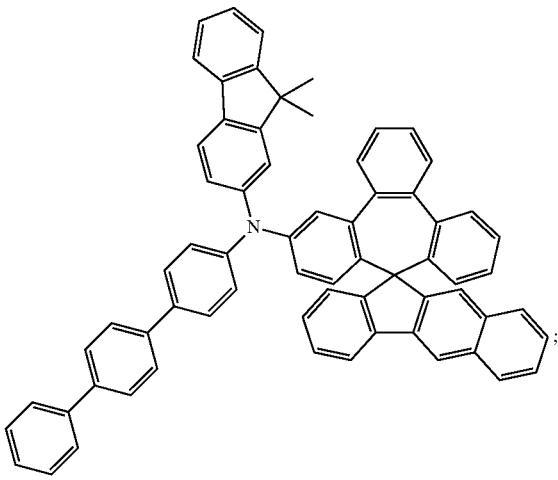
Compound 97
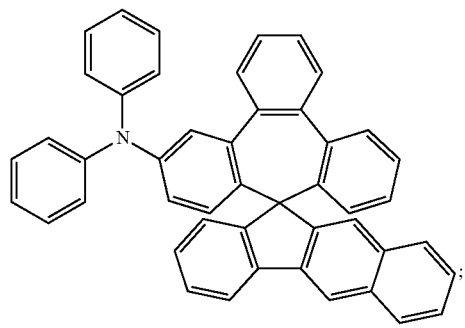
Compound 98
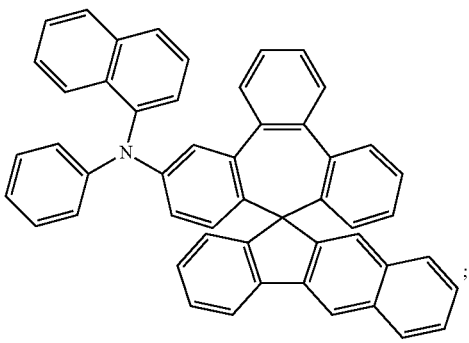
Compound 99
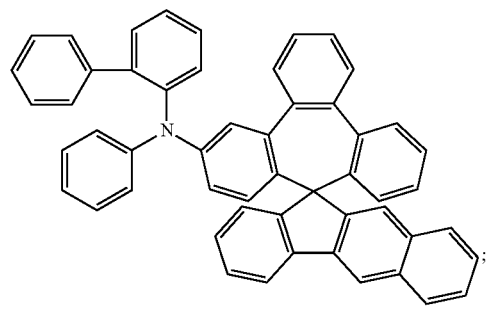
Compound 100
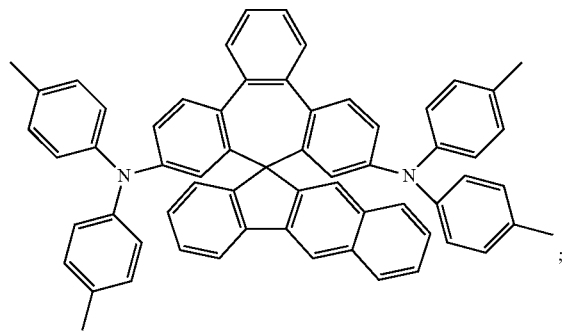
Compound 101
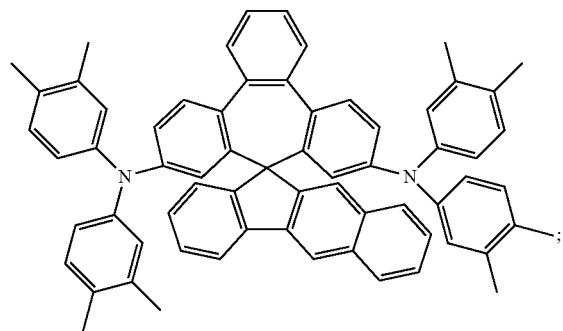
Compound 102
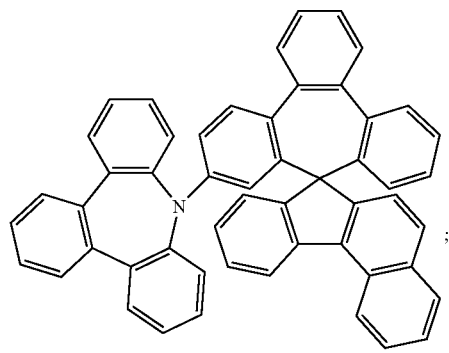

-continued
Compound 103
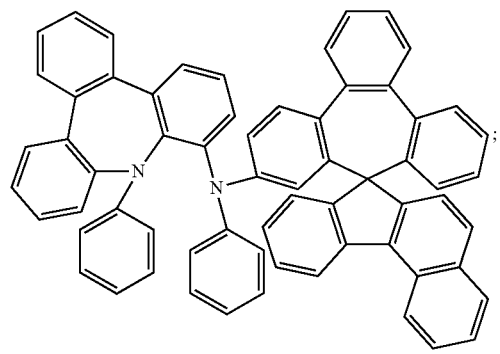
Compound 104
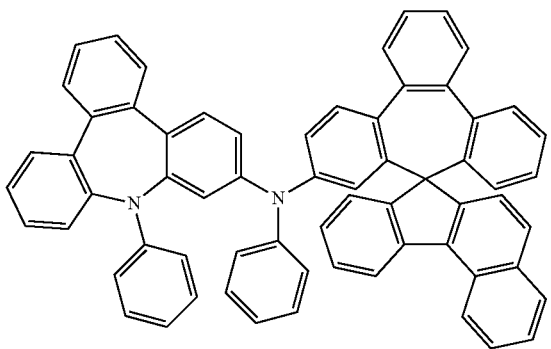
Compound 105
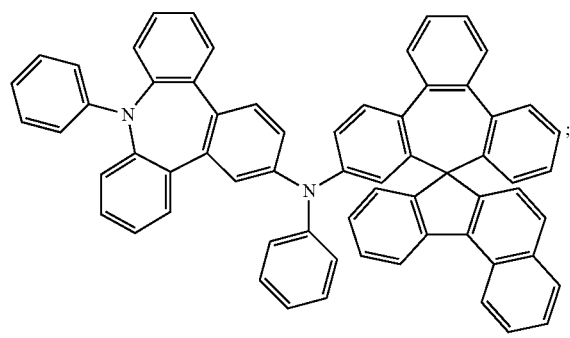
Compound 106
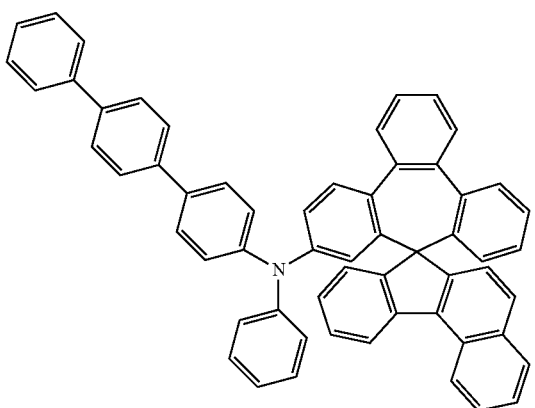
Compound 107
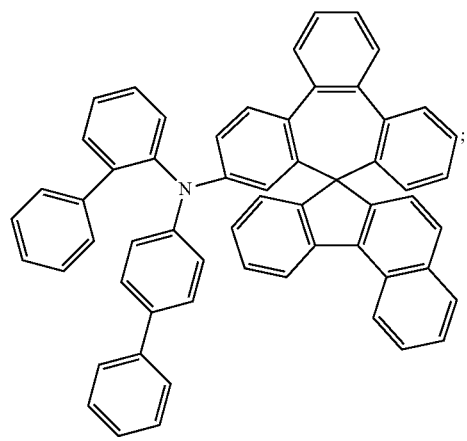
Compound 108
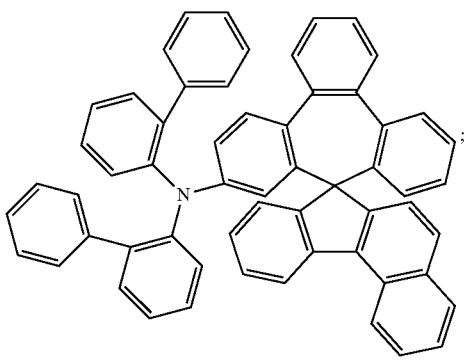

-continued
Compound 109
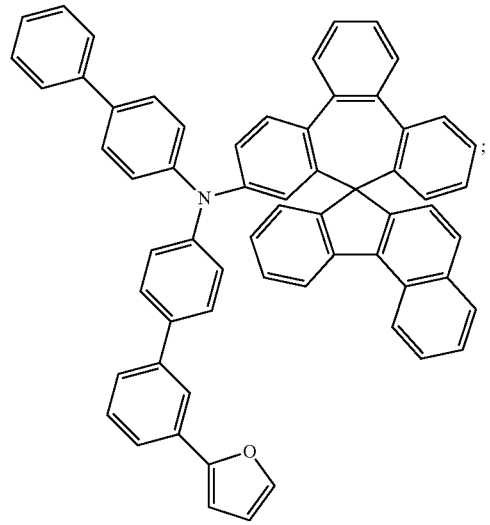
Compound 110
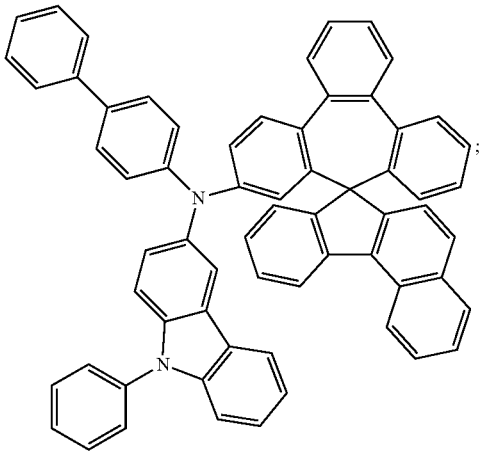
Compound 111
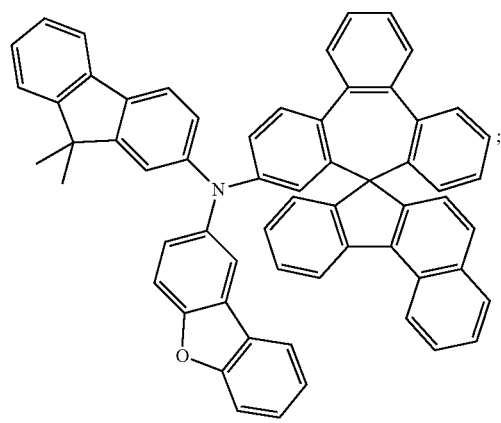
Compound 112
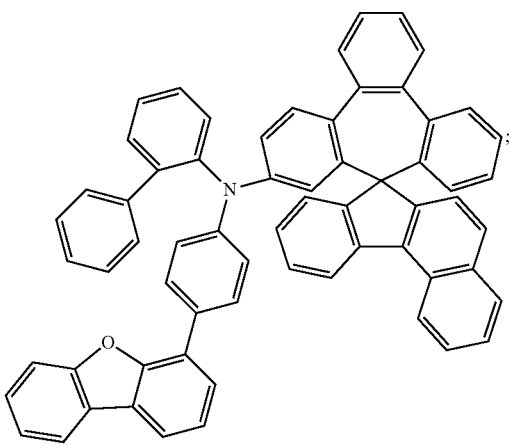
Compound 113
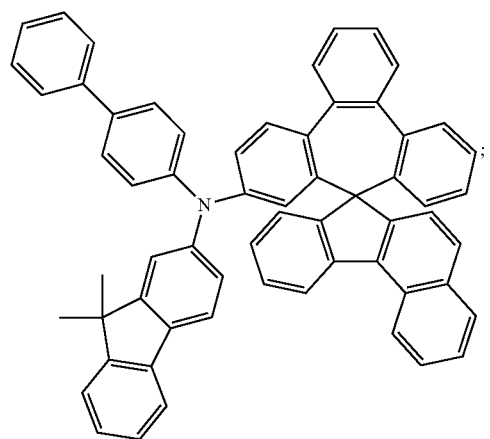
Compound 114
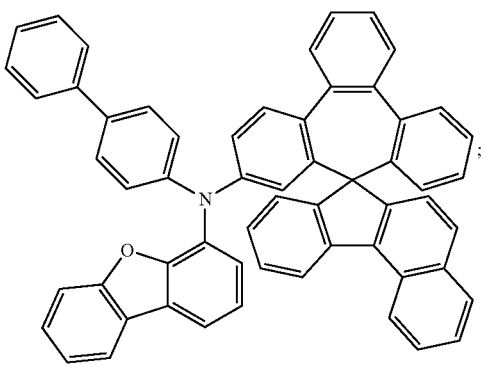

-continued
Compound 115
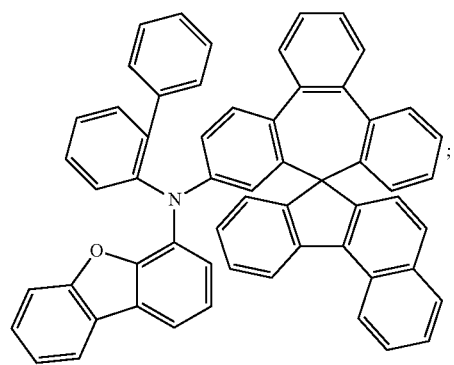
Compound 116
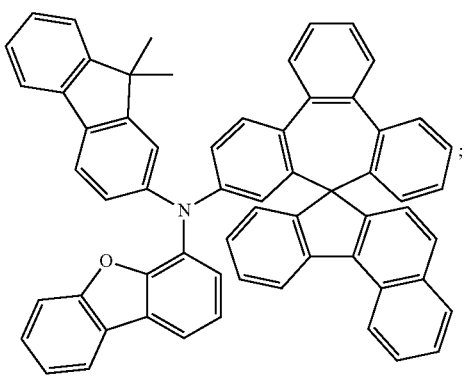
Compound 117
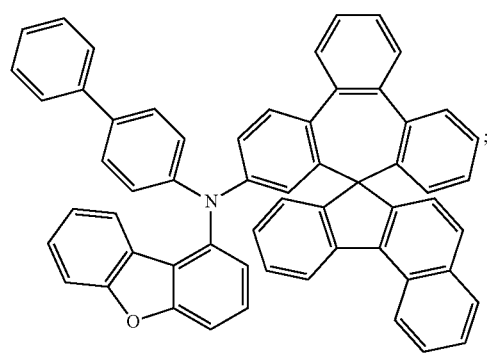
Compound 118
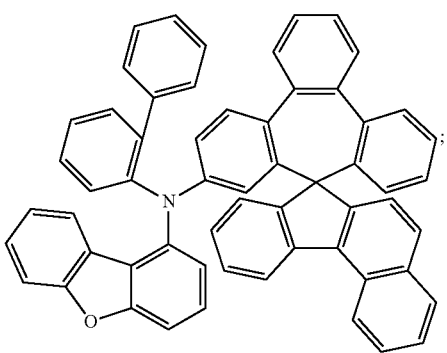
Compound 119
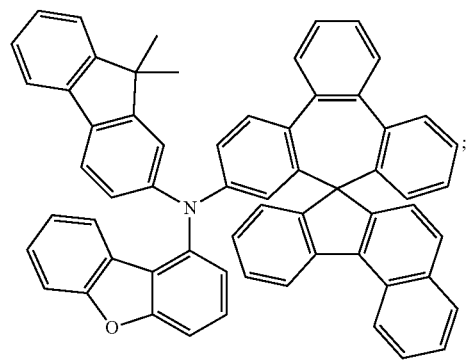
Compound 120
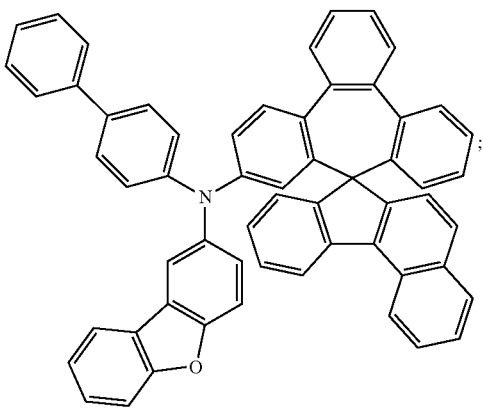

-continued
Compound 121
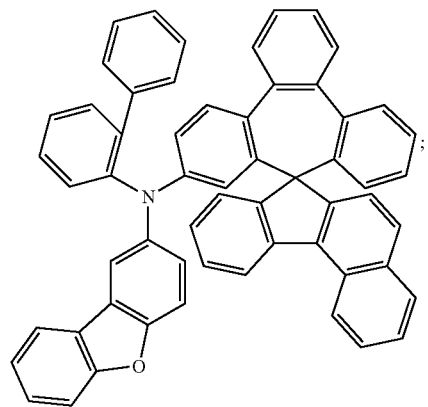
Compound 122
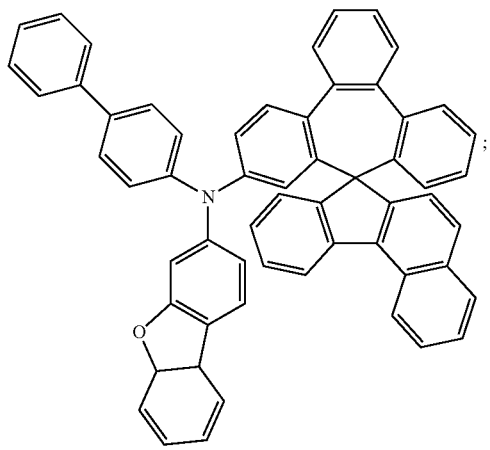
Compound 123
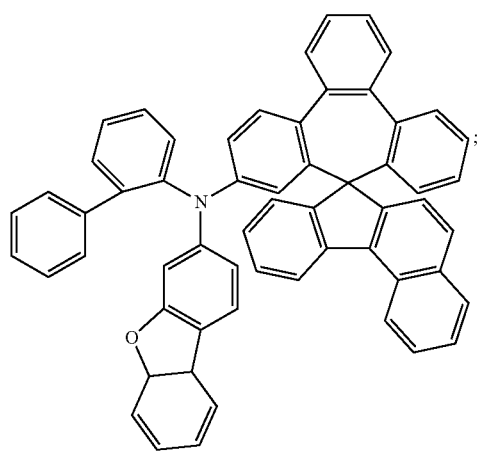
Compound 124
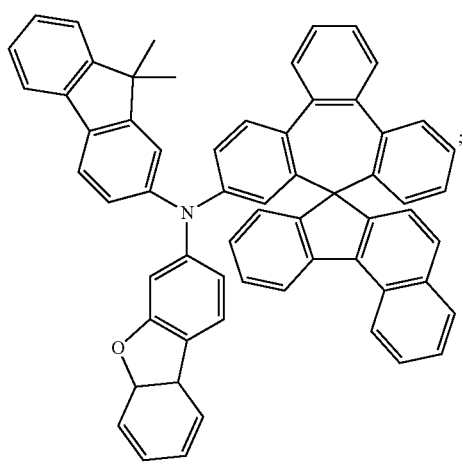
Compound 125
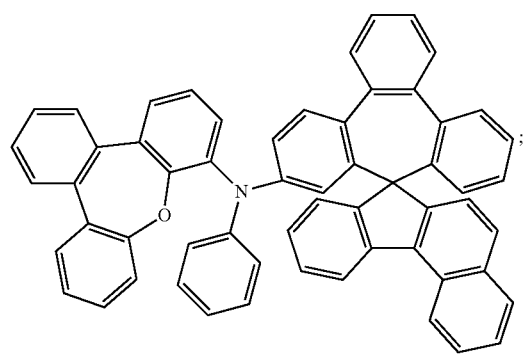
Compound 126
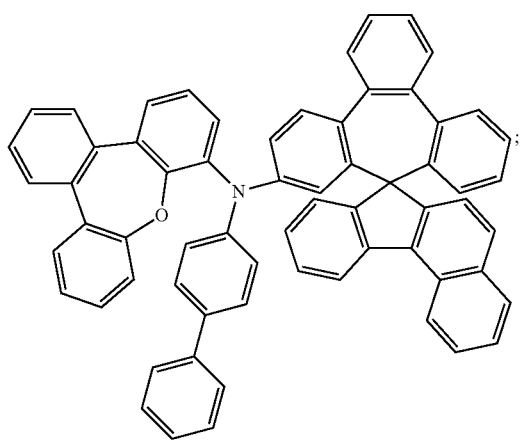

Compound 127
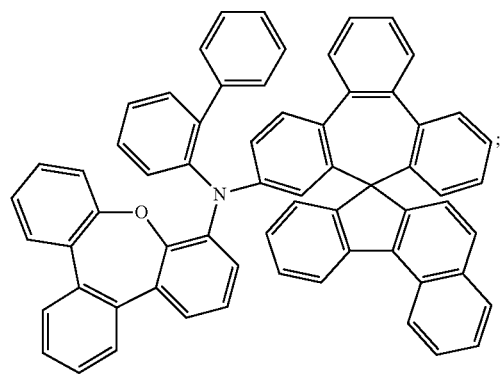
Compound 128
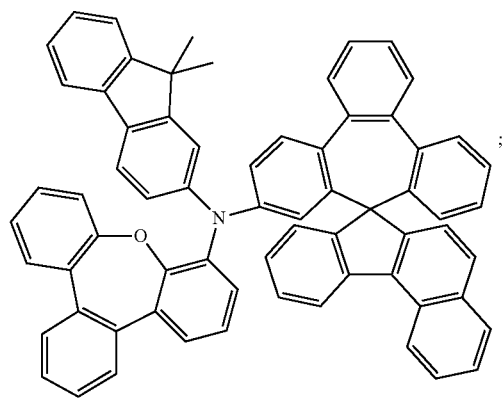
Compound 129
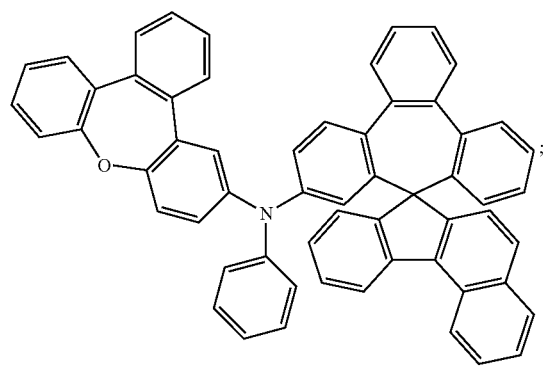
Compound 130
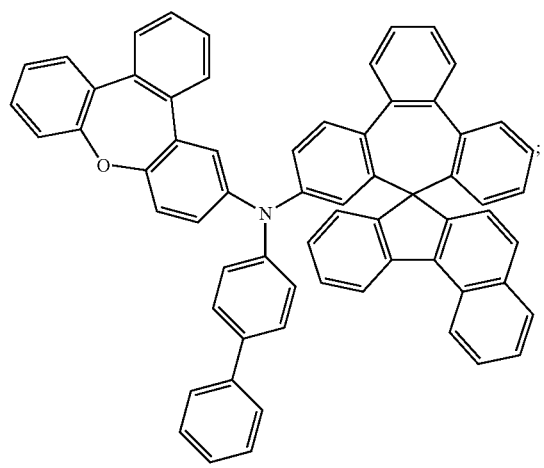
Compound 131
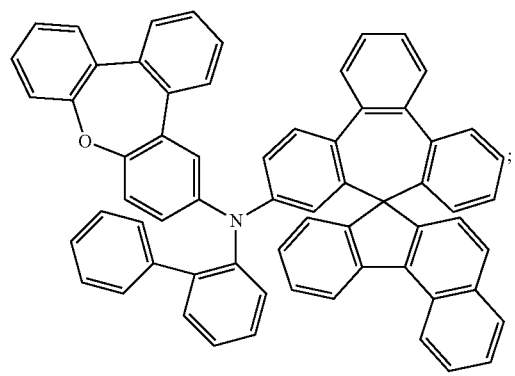
Compound 132
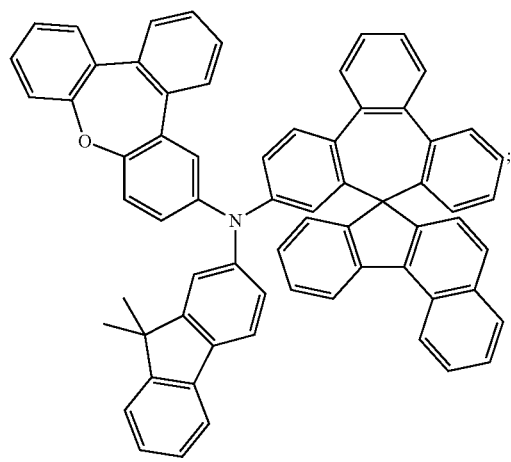

-continued
Compound 133
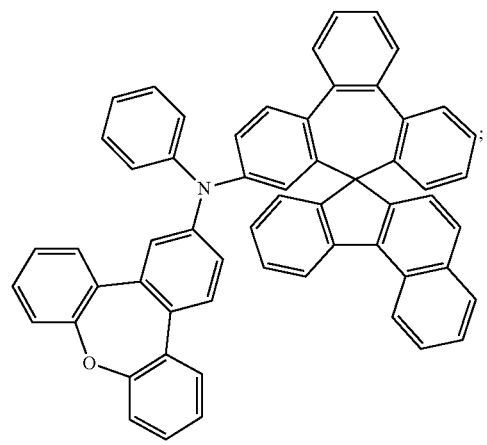
Compound 134
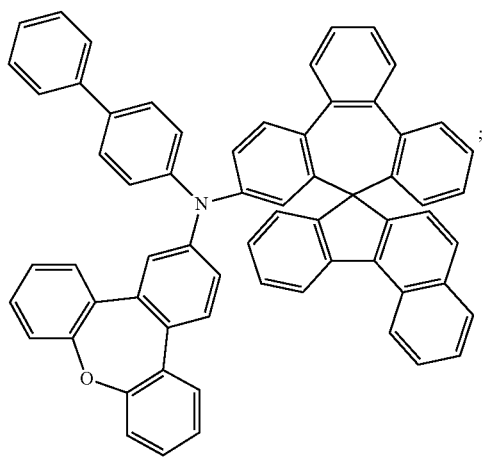
Compound 135
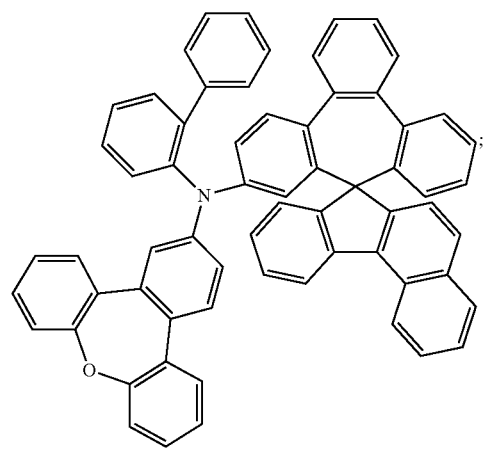
Compound 136
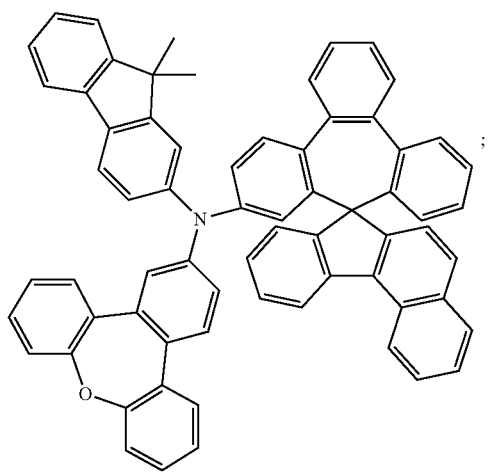
Compound 137
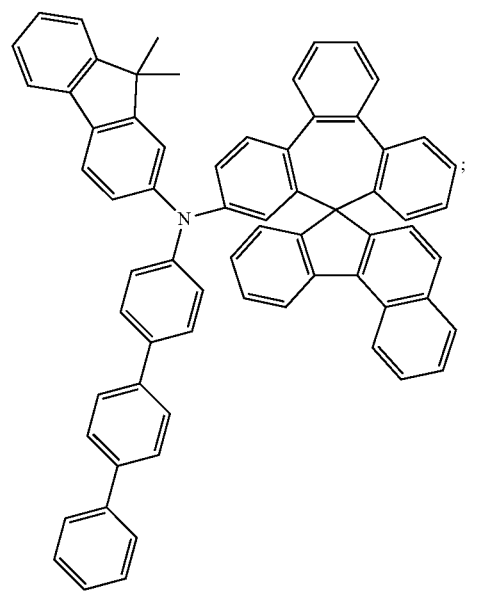
Compound 138
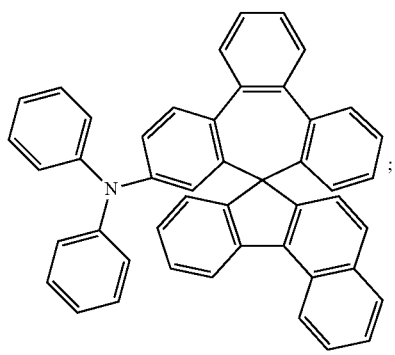

-continued
Compound 139
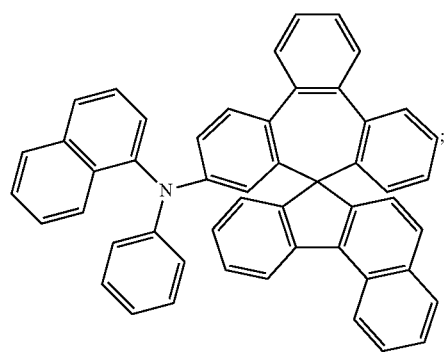
Compound 140
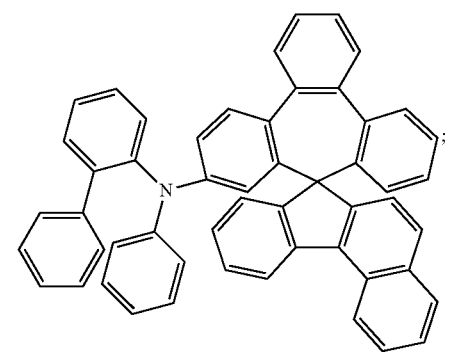
Compound 141
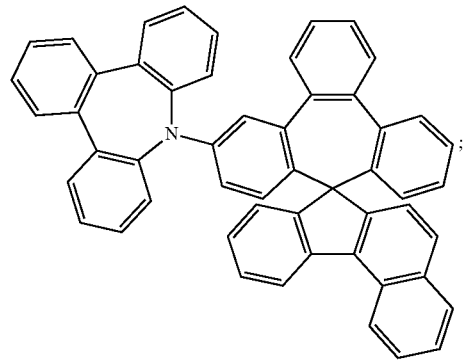
Compound 142
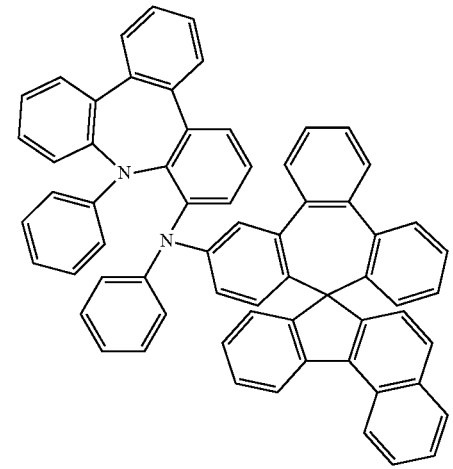
Compound 143
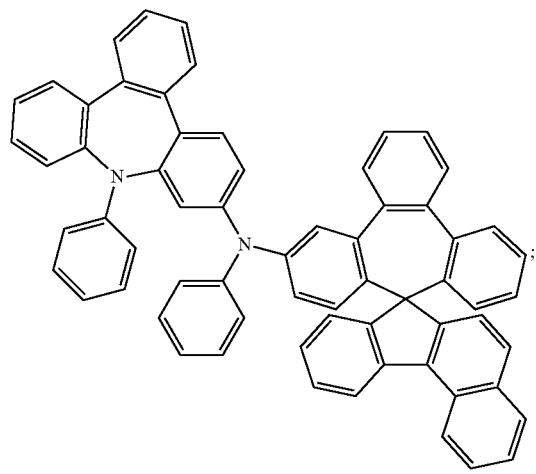
Compound 144
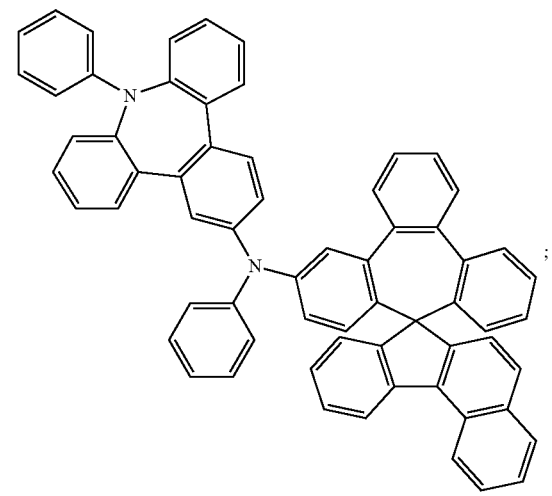

-continued
Compound 145
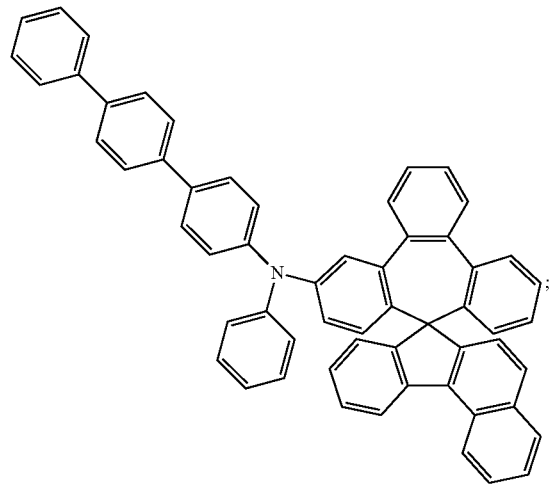
Compound 146
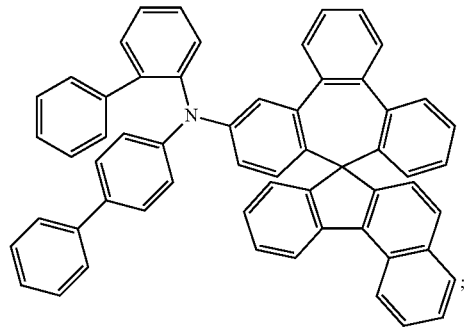
Compound 147
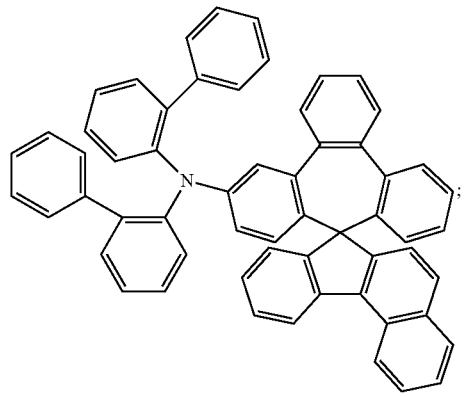
Compound 148
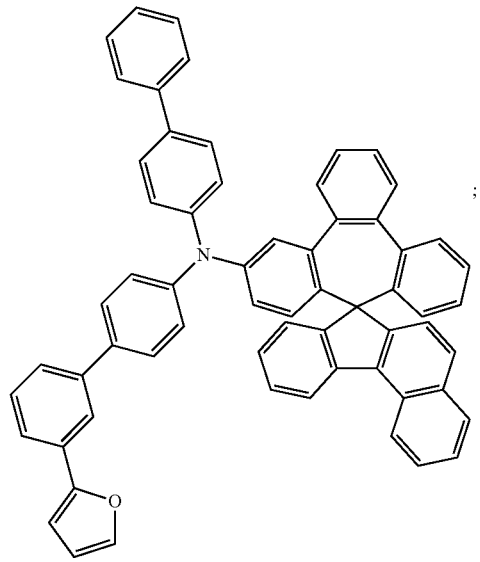
Compound 149
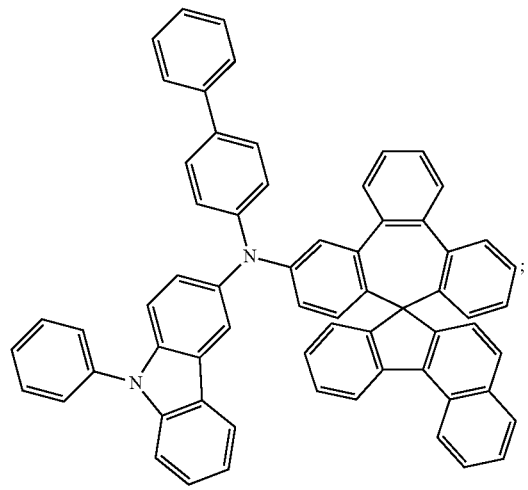
Compound 150
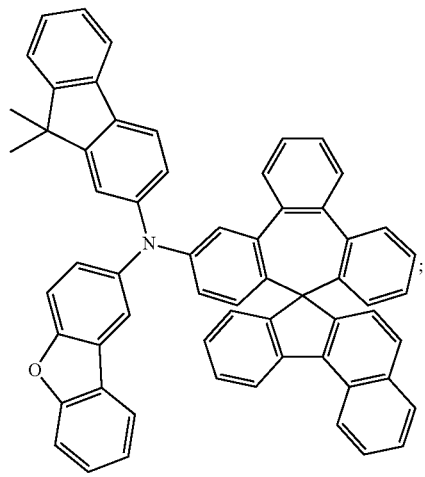

-continued
Compound 151
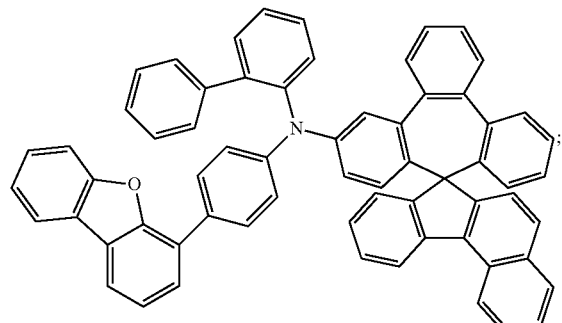
Compound 152
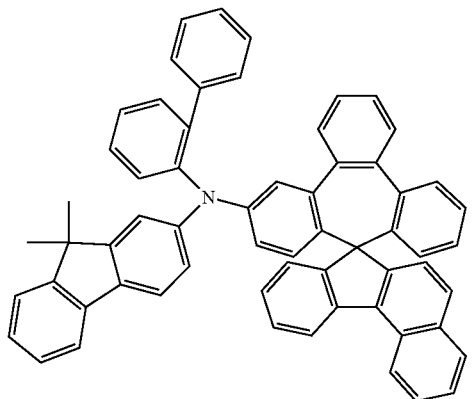
Compound 153
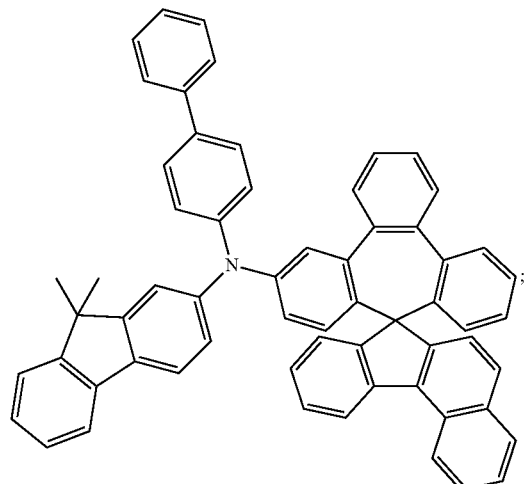
Compound 154
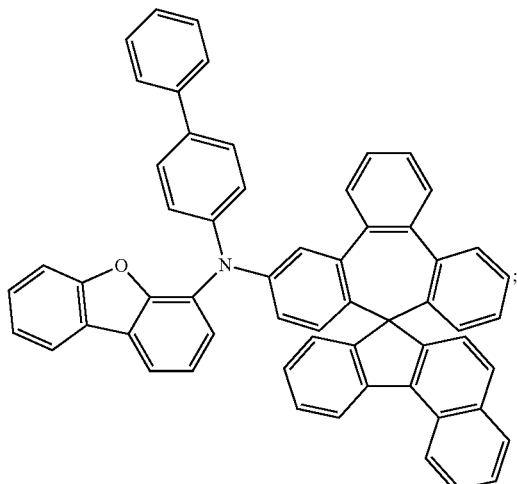
Compound 155
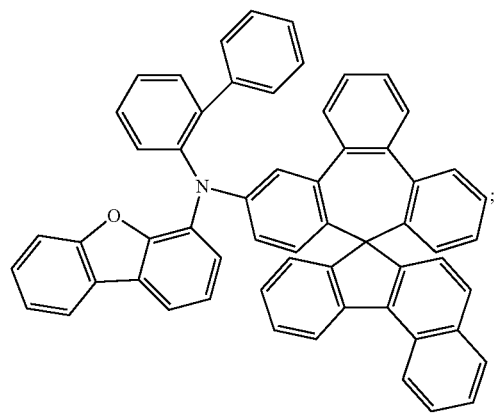
Compound 156
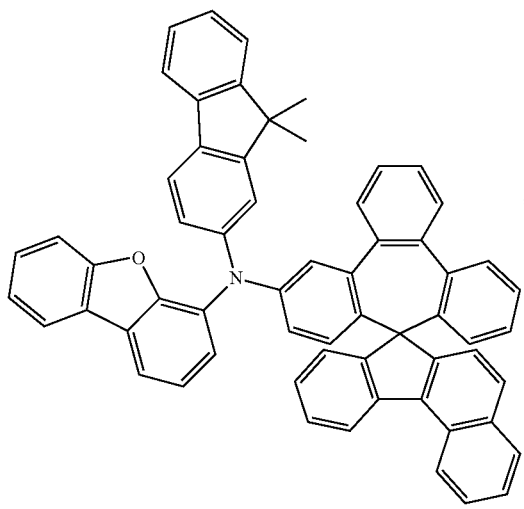

-continued
Compound 157
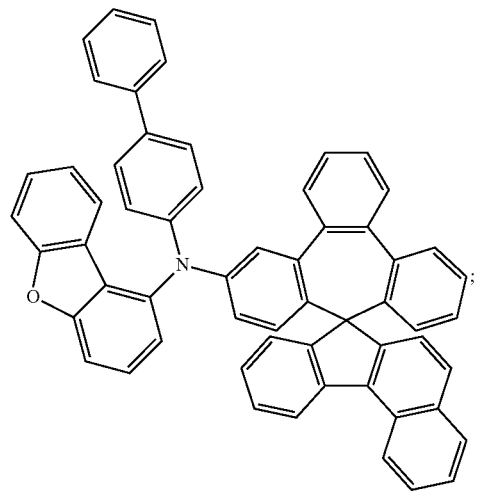
Compound 158
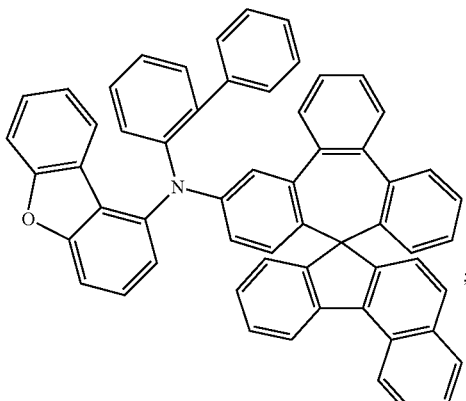
Compound 159
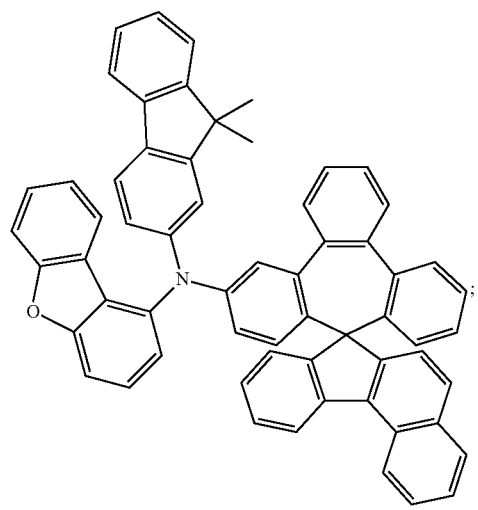
Compound 160
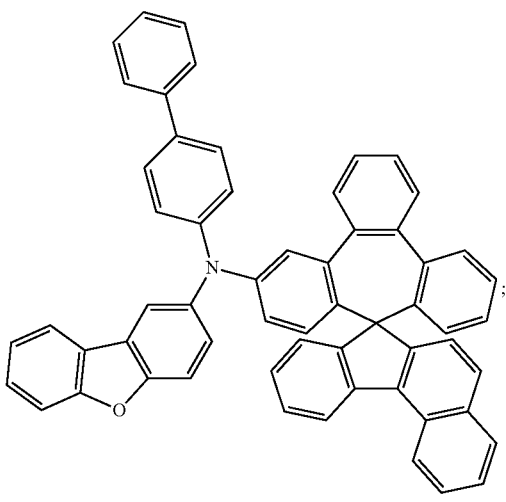
Compound 161
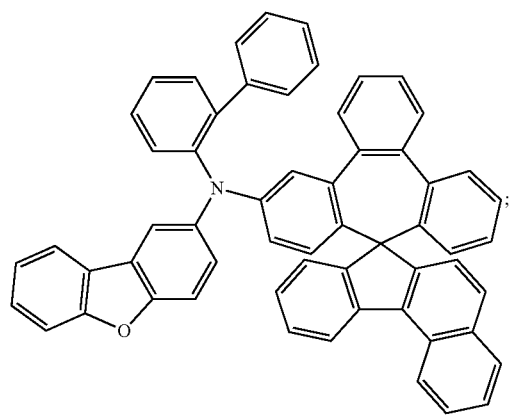
Compound 162
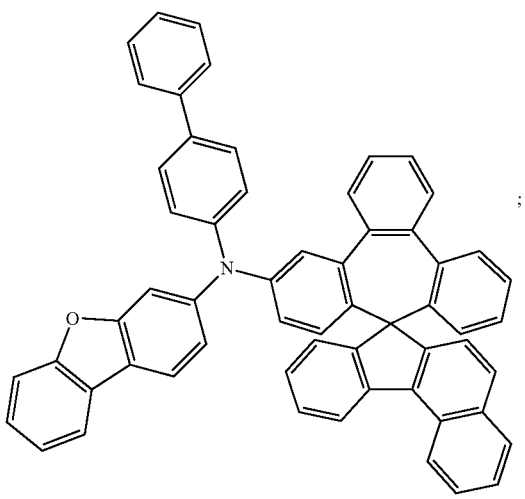

-continued
Compound 163
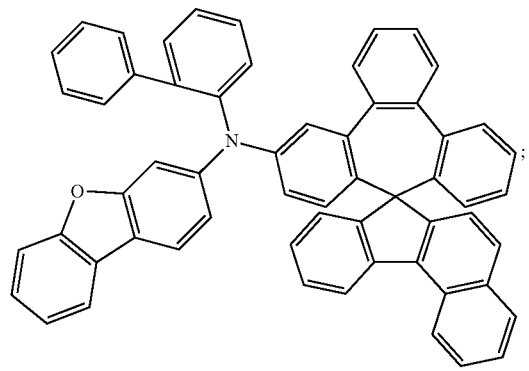
Compound 164
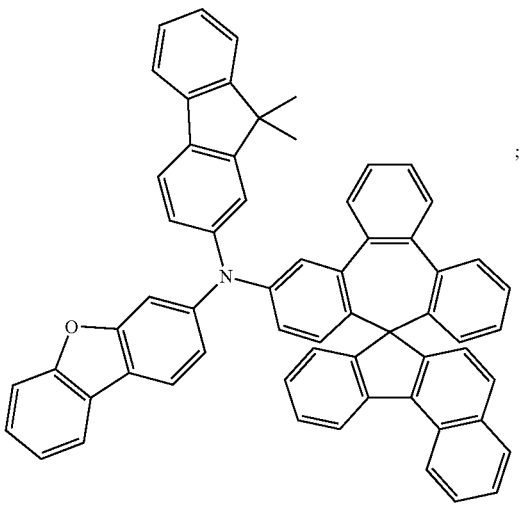
Compound 165
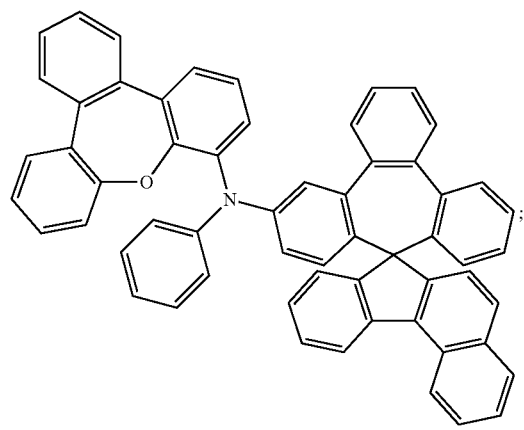
Compound 166
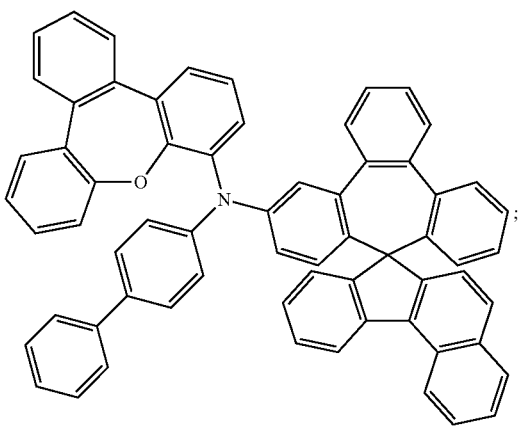
Compound 167
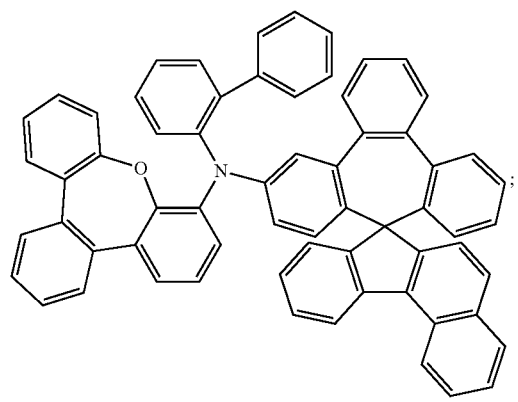
Compound 168
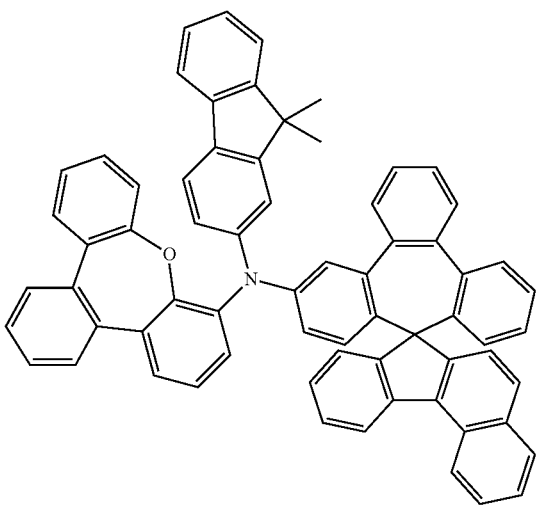

-continued
Compound 169
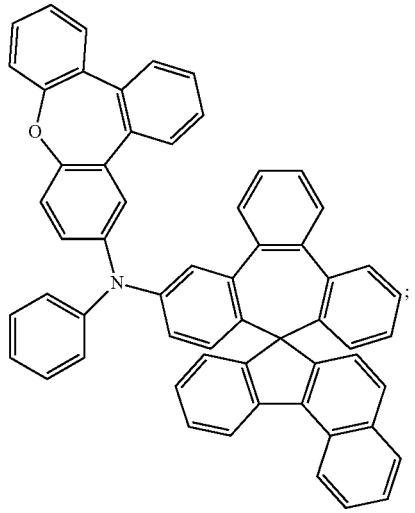
Compound 170
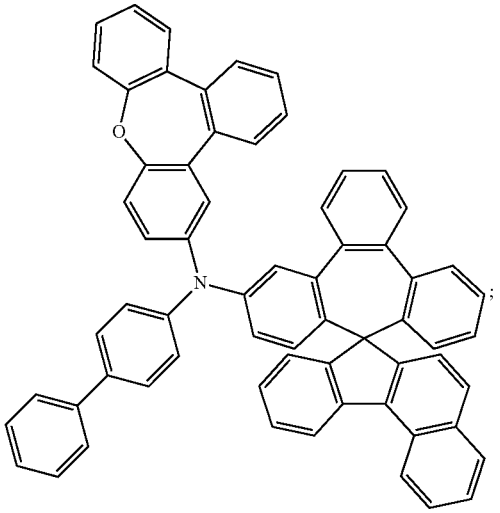
Compound 171
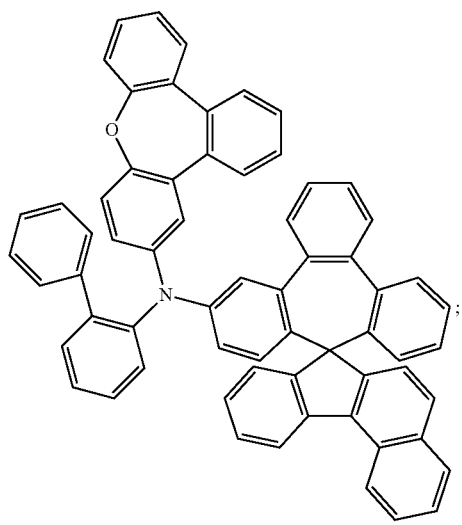
Compound 172
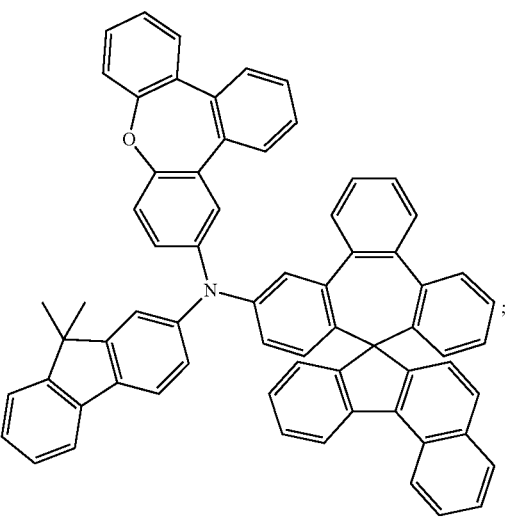
Compound 173
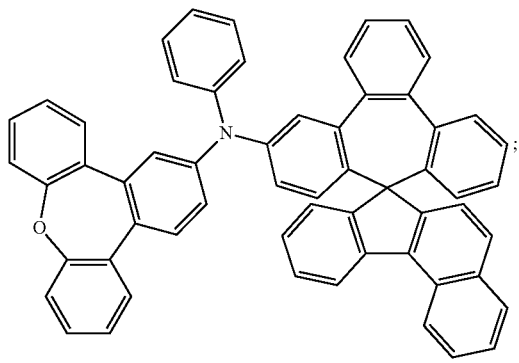
Compound 174
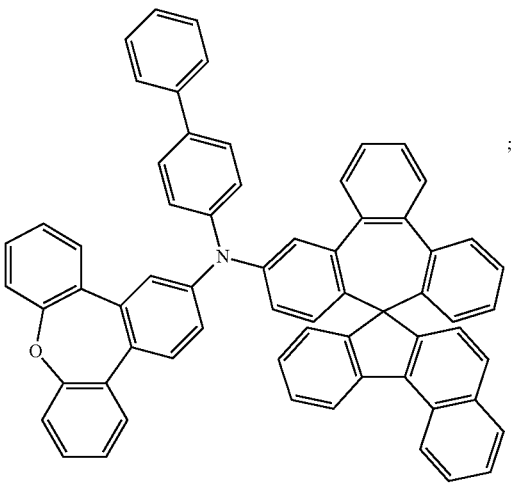

Compound 175
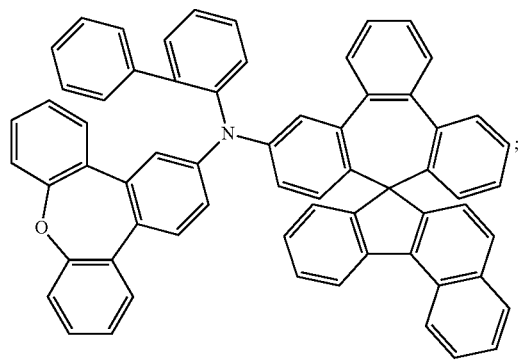
Compound 176
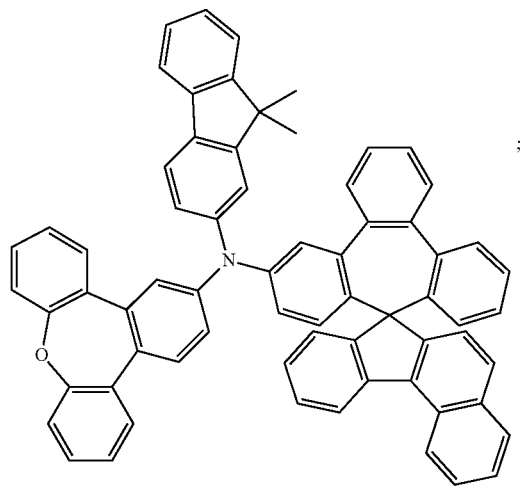
Compound 177
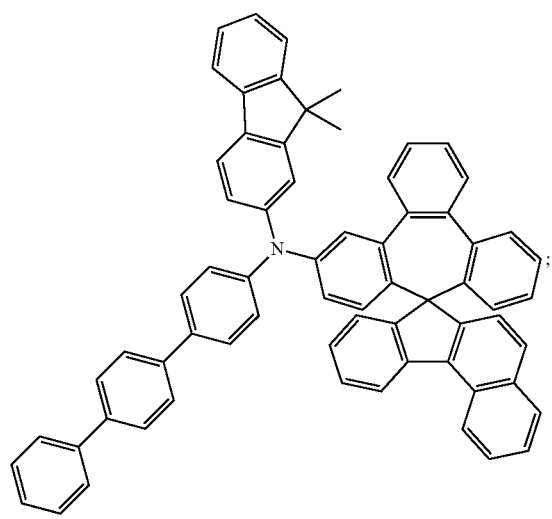
Compound 178
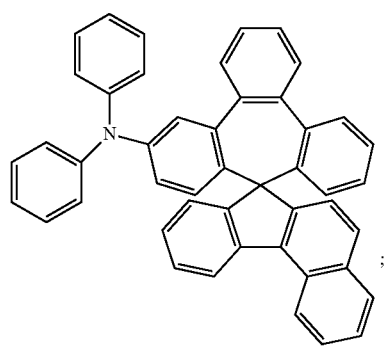
Compound 179
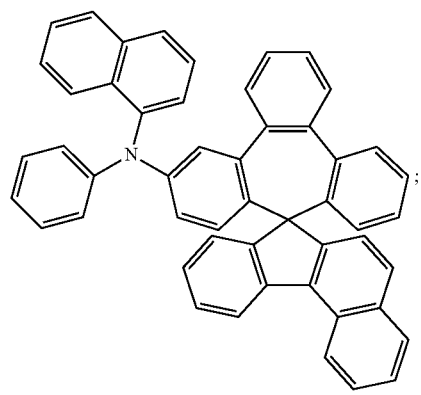
Compound 180
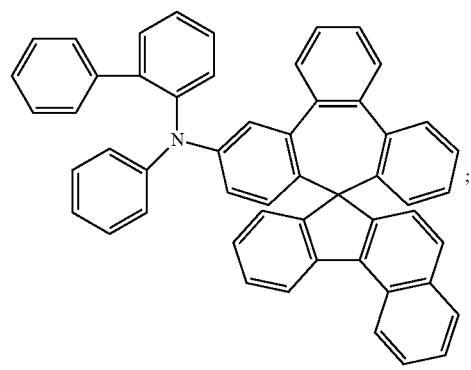

-continued
Compound 181
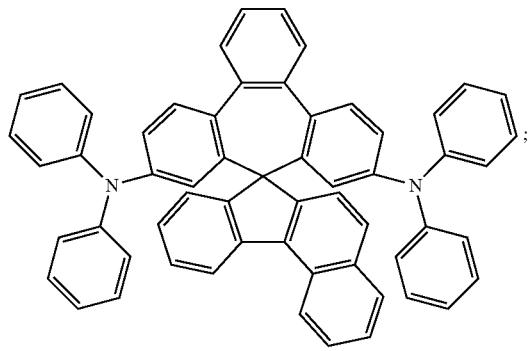
Compound 182
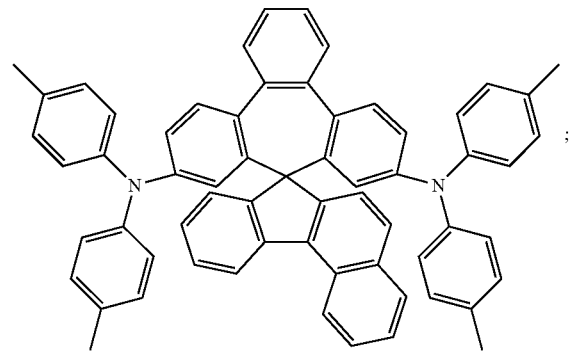
Compound 183
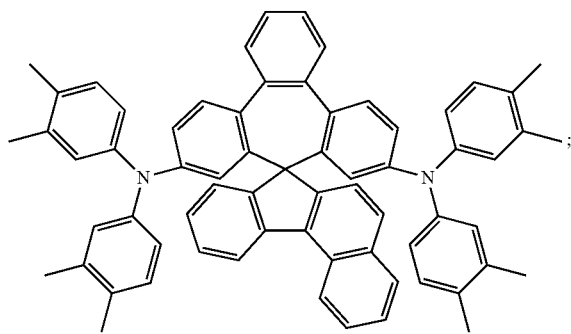
Compound 184
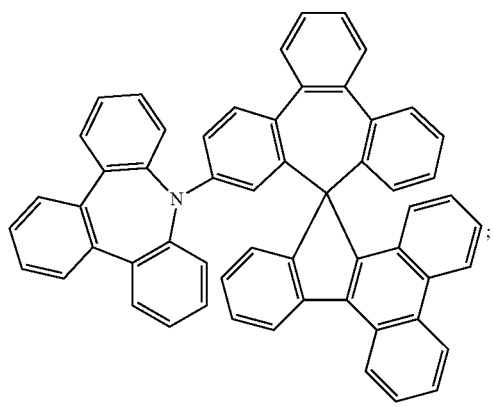
Compound 185
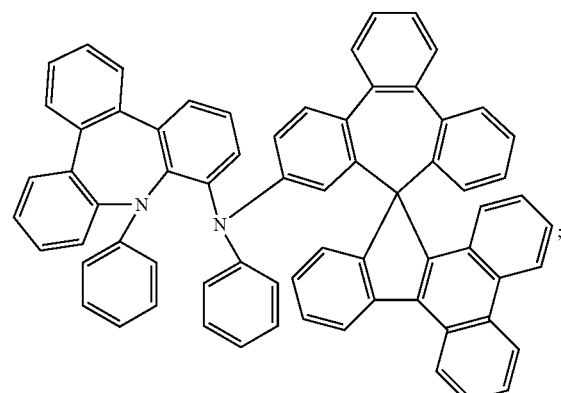
Compound 186
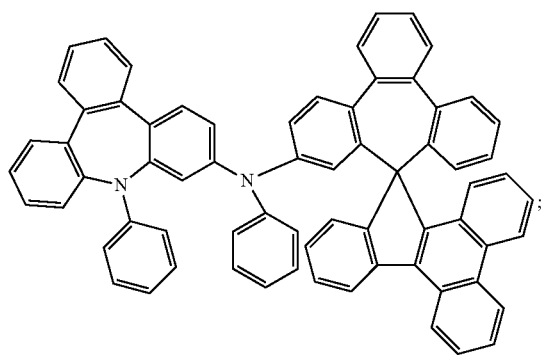
Compound 187
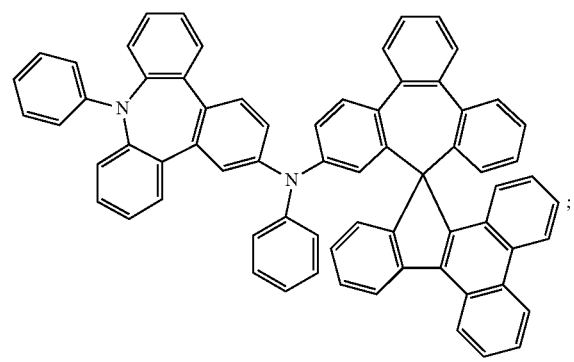

-continued
Compound 188
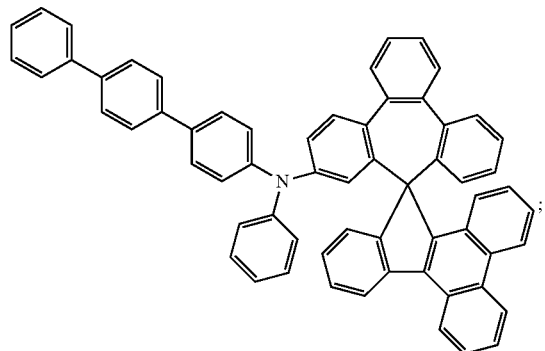
Compound 189
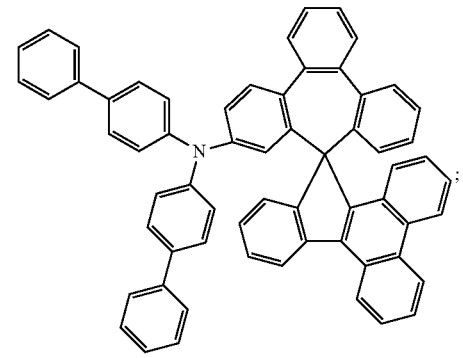
Compound 190
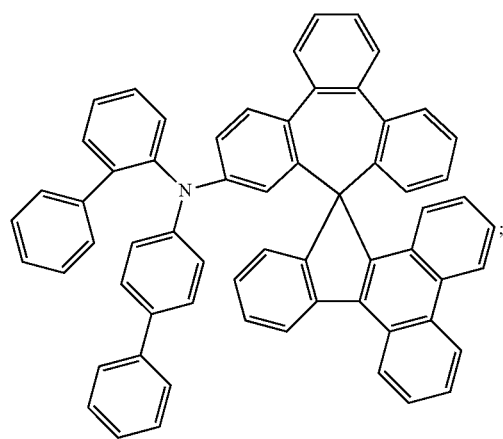
Compound 191
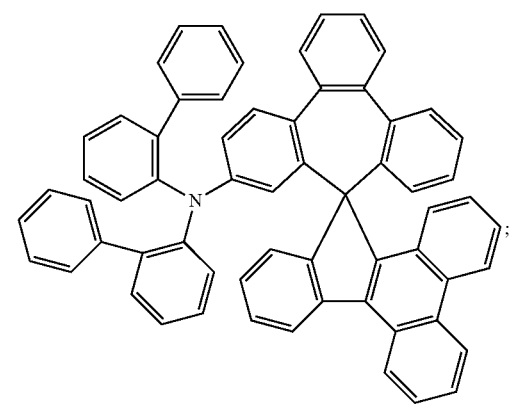
Compound 192
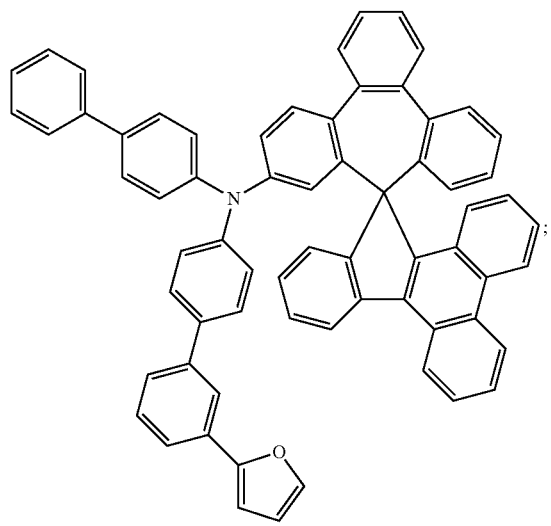
Compound 193
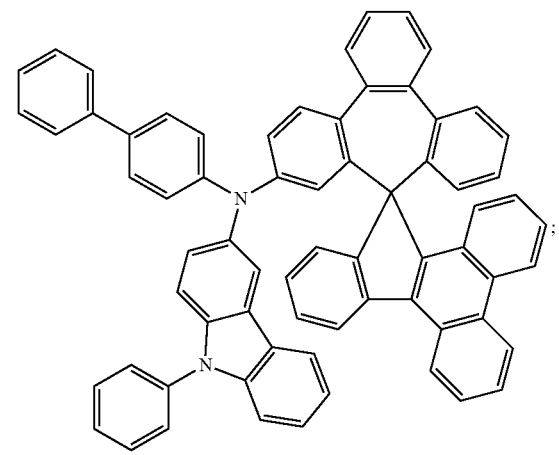

Compound 194
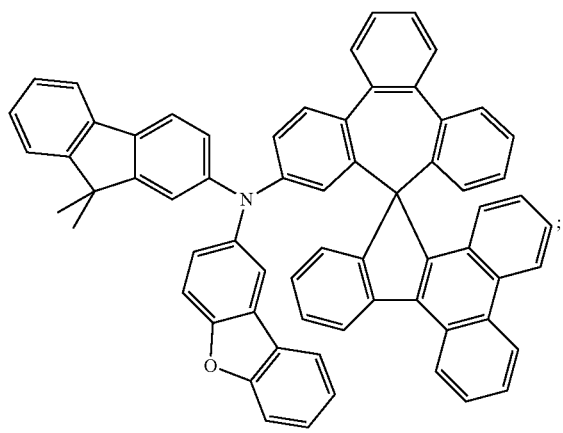
Compound 195
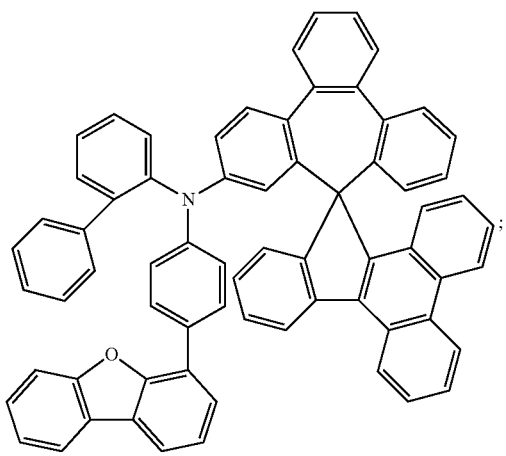
Compound 196
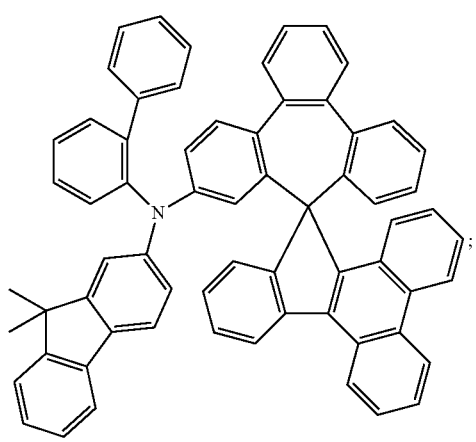
Compound 197
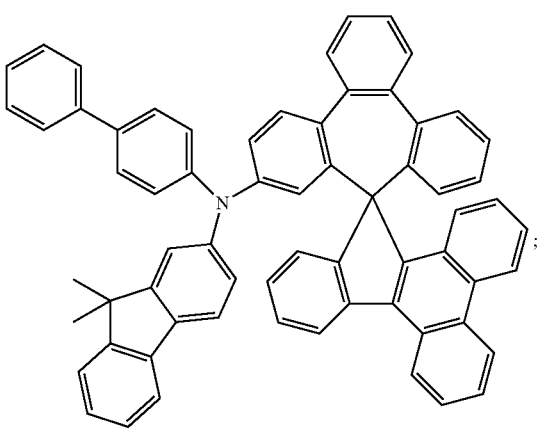
Compound 198
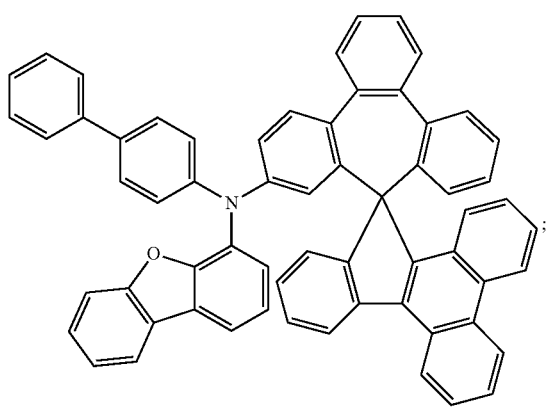
Compound 199
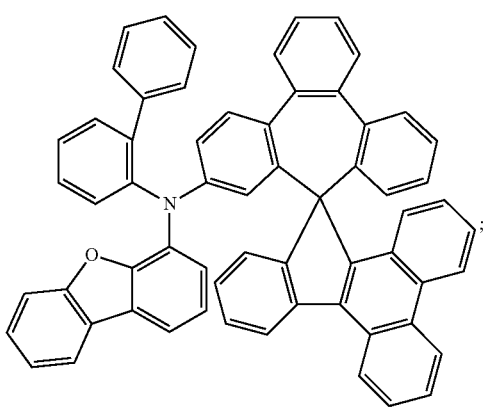

Compound 200 Compound 201
Compound 202 Compound 203
Comopund 204 Compound 205
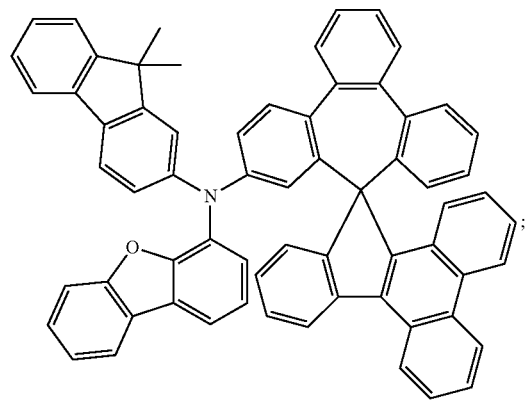

-continued
Compound 206
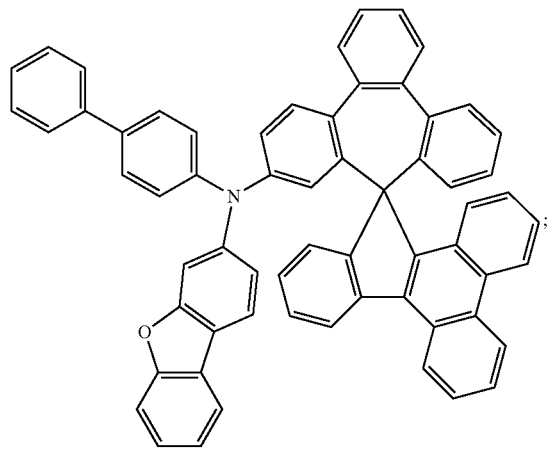
Compound 207
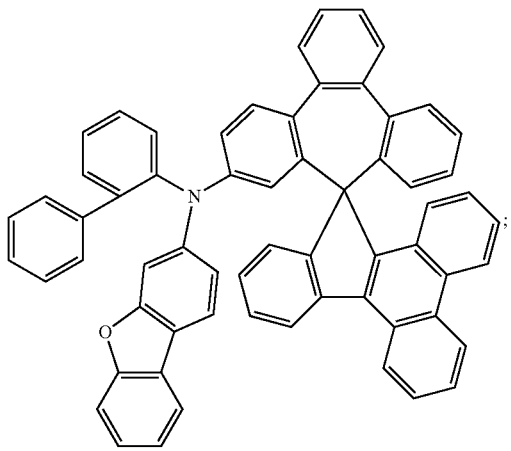
Compound 208
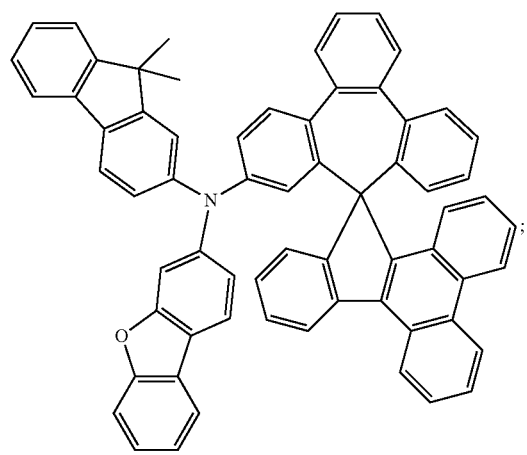
Compound 209
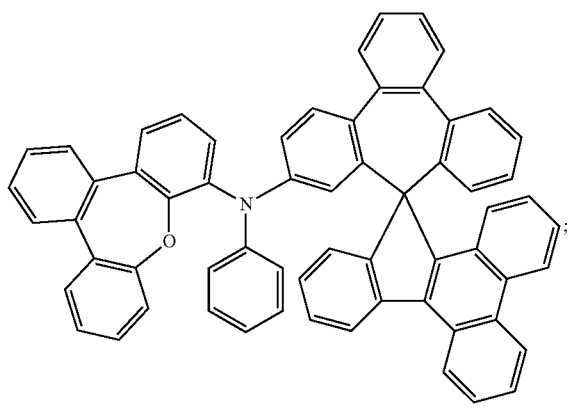
Compound 210
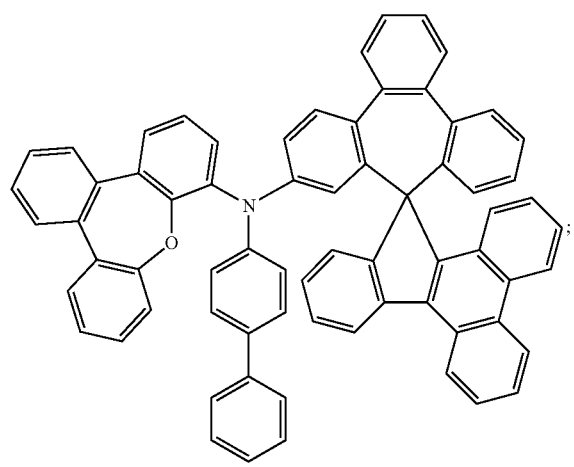
Compound 211
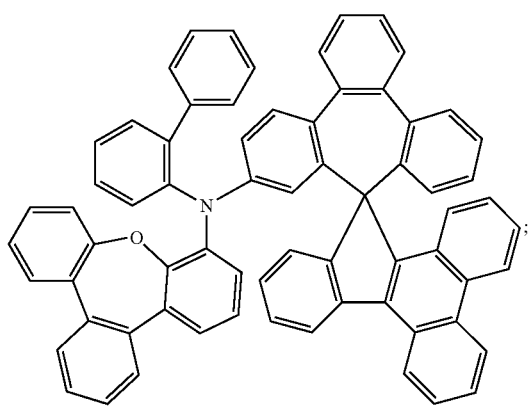

Compound 212
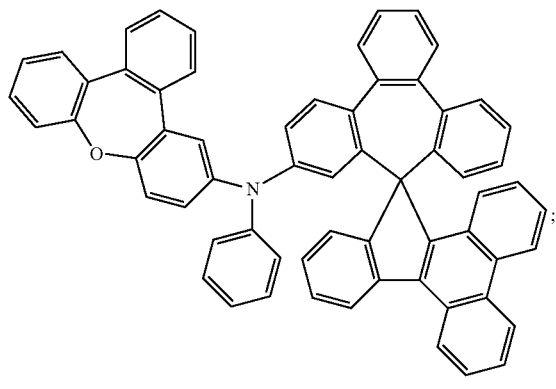
Compound 213
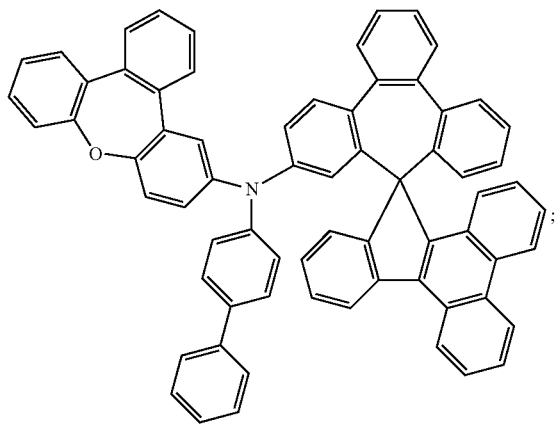
Compound 214
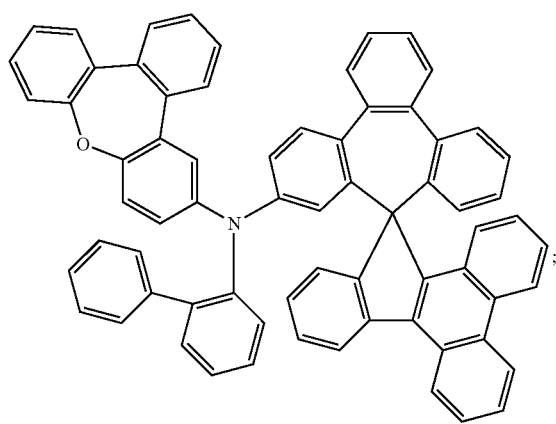
Compound 215
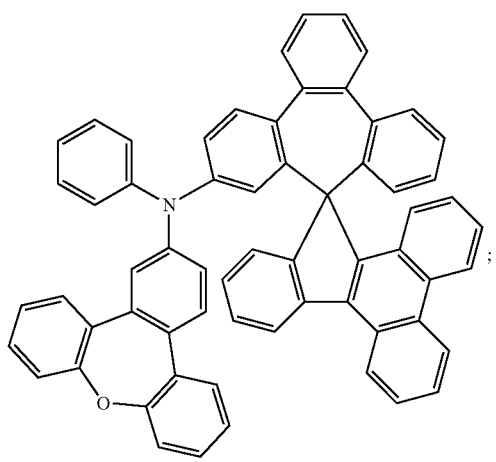
Compound 216
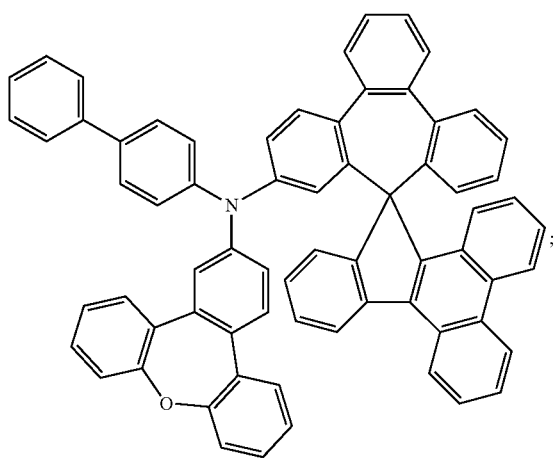
Compound 217
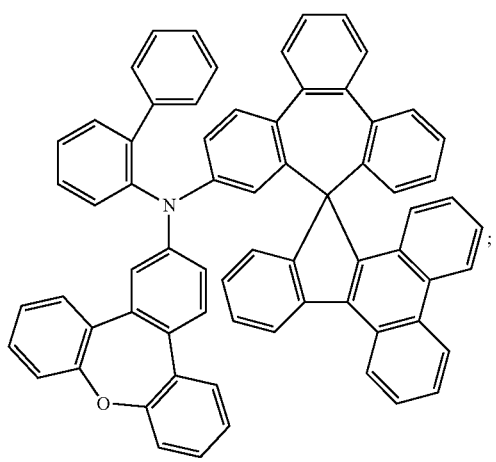

-continued
Compound 218
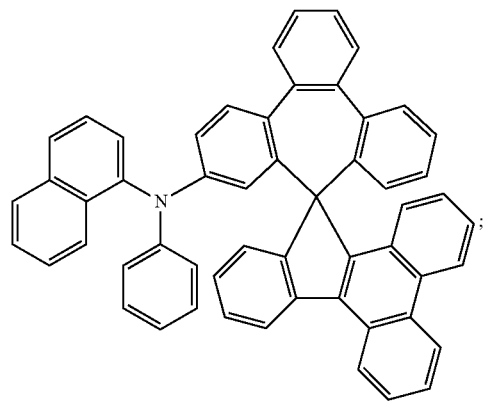
Compound 219
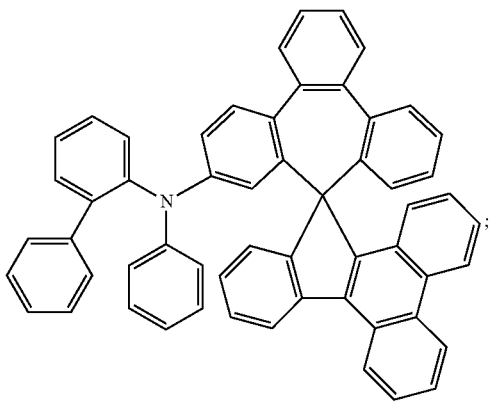
Compound 220
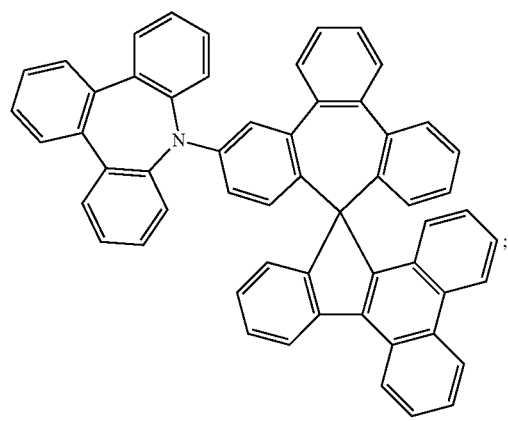
Compound 221
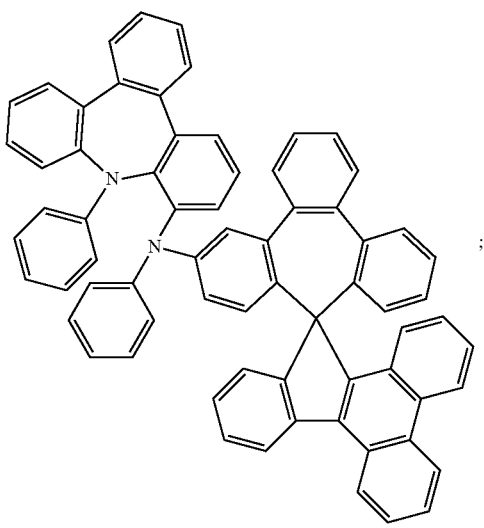
Compound 222
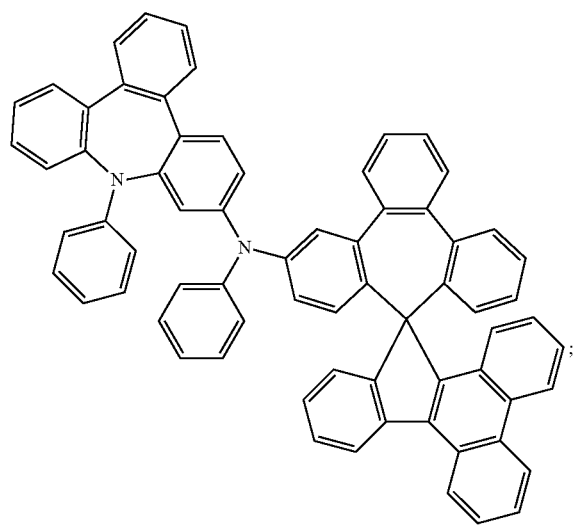
Compound 223
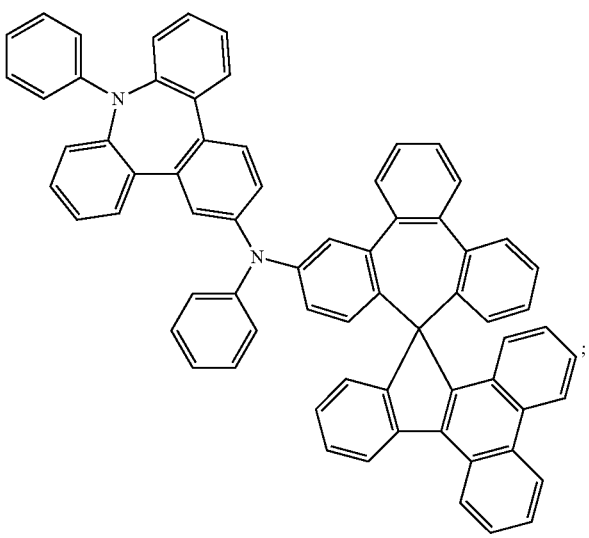

Compound 224
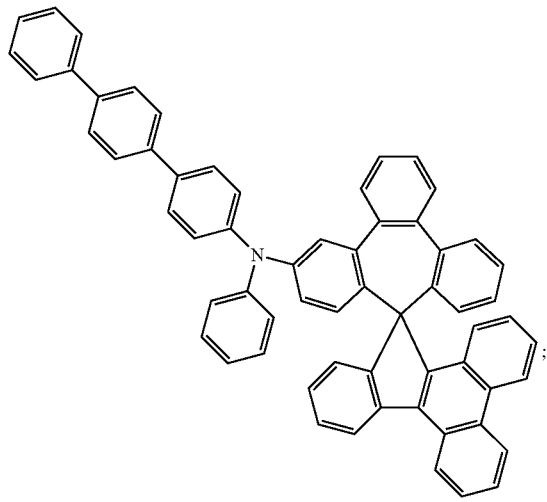
Compound 225
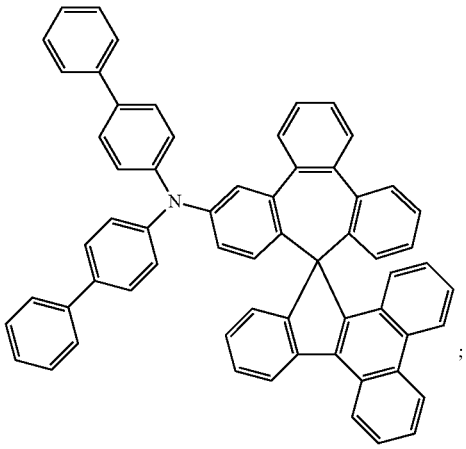
Compound 226
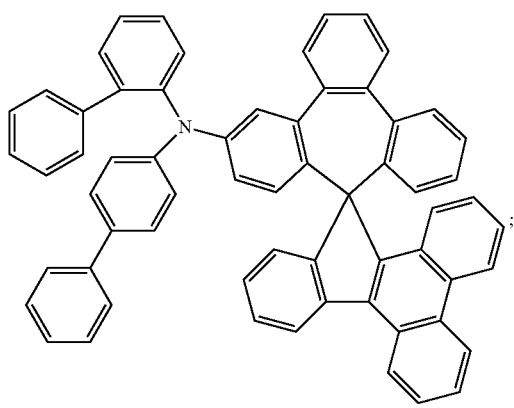
Compound 227
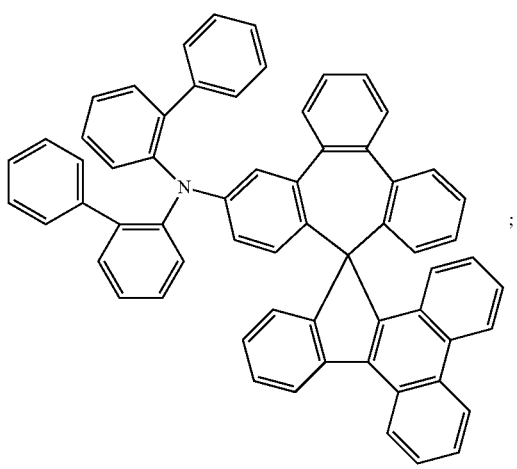
Compound 228
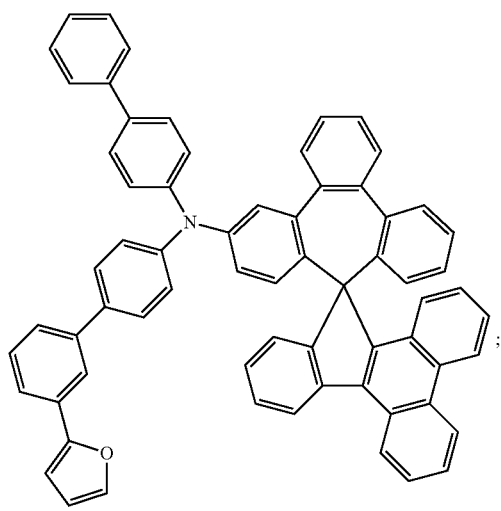
Compound 229
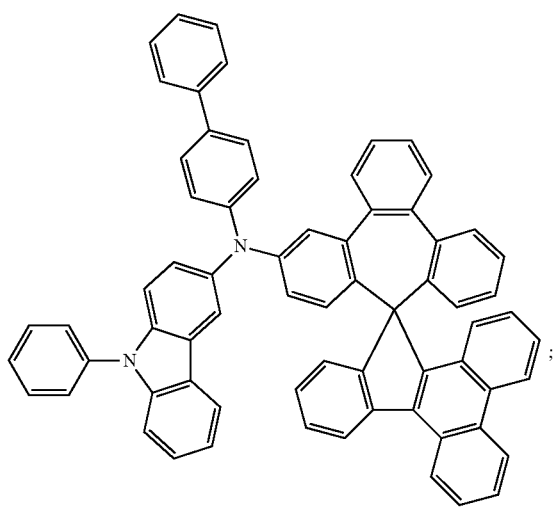

-continued
Compound 230
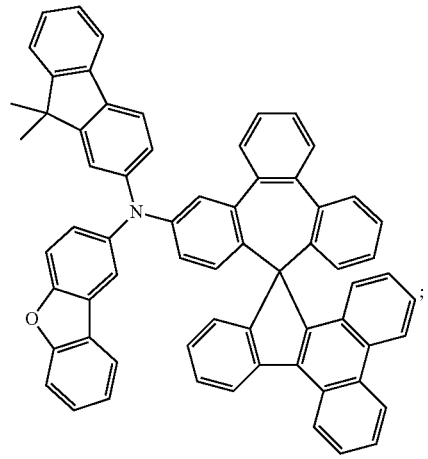
Compound 231
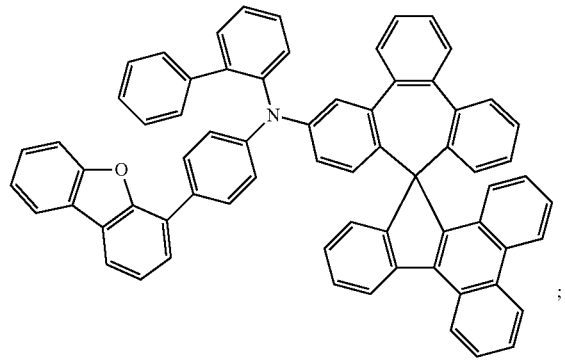
Compound 232
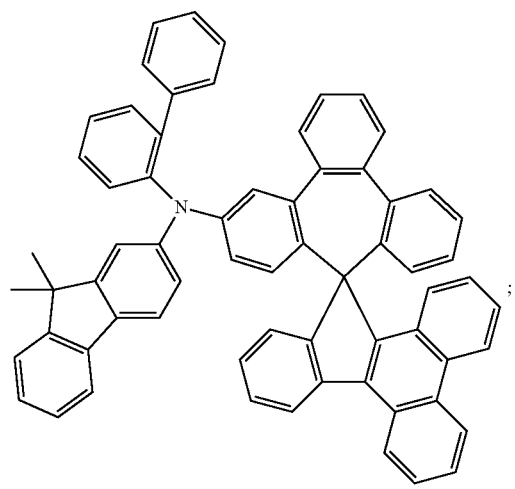
Compound 233
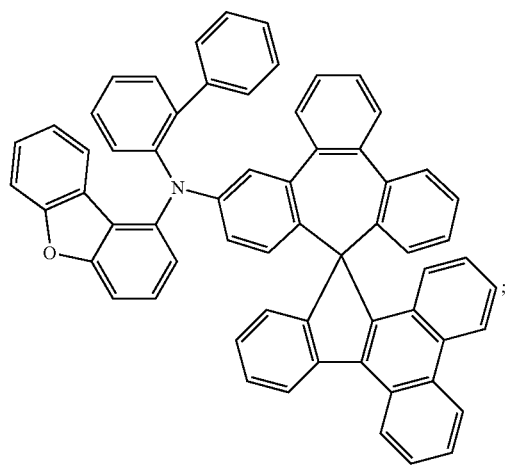
Compound 234
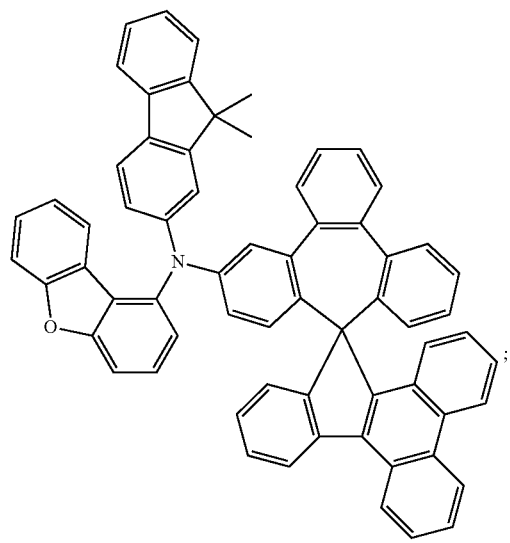
Compound 235
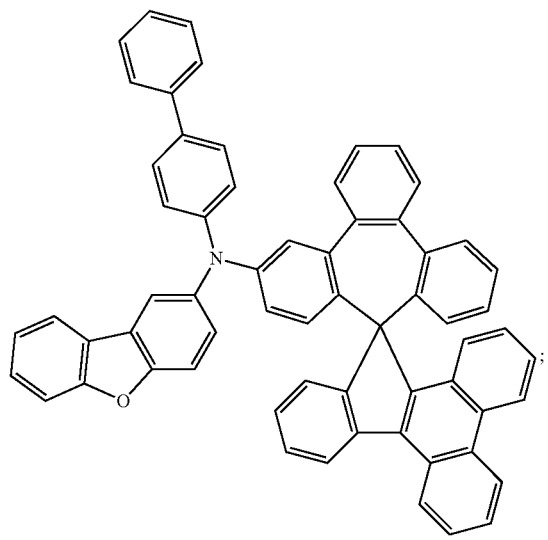

-continued
Compound 236
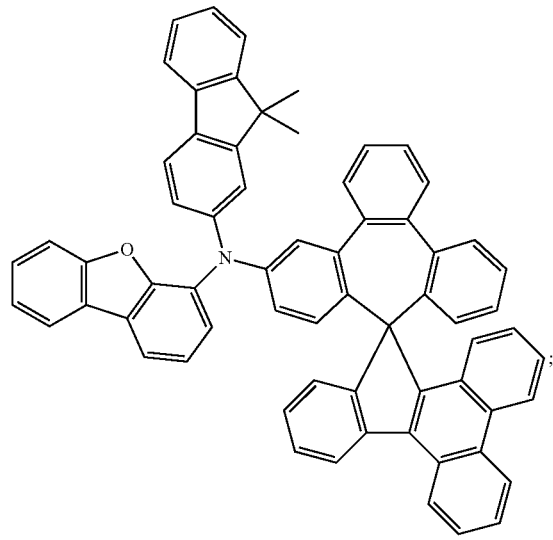
Compound 237
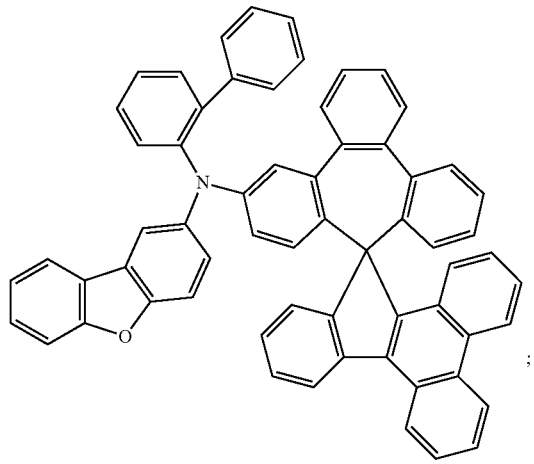
Compound 238
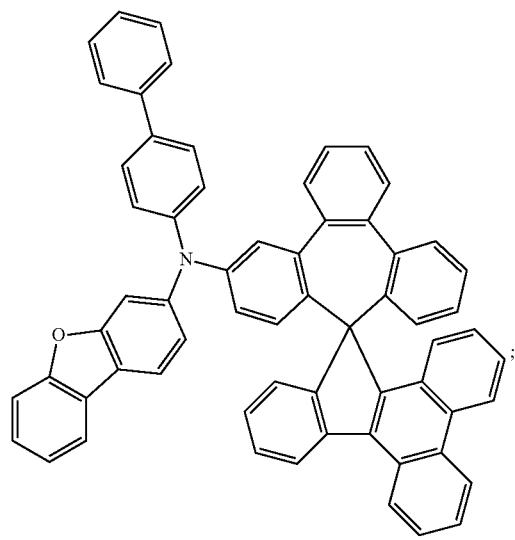
Compound 239
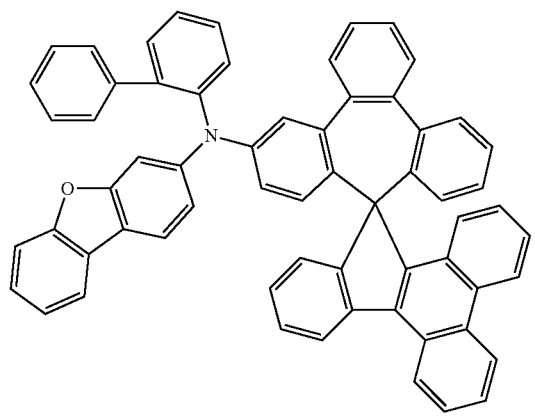
Compound 240
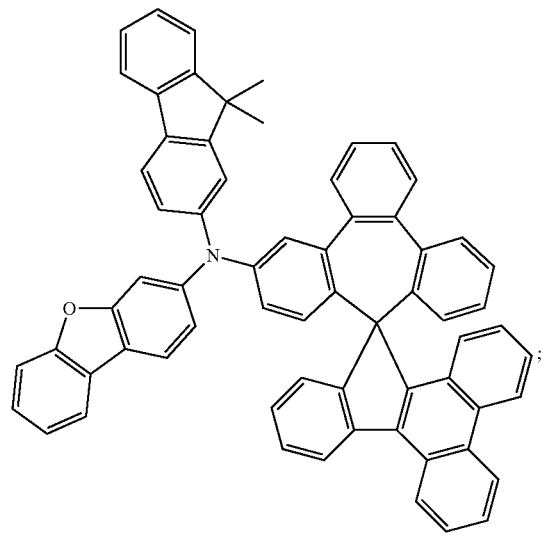
Compound 241
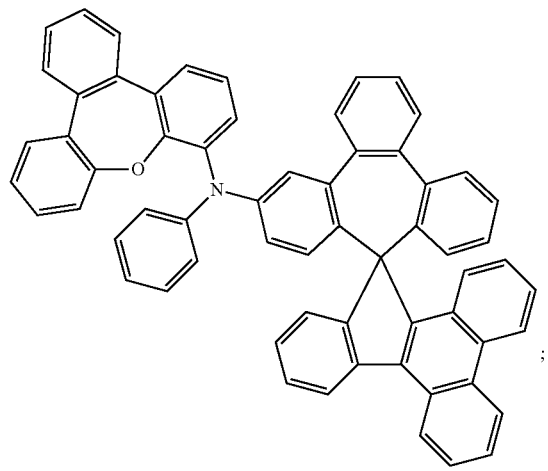

-continued
Compound 242
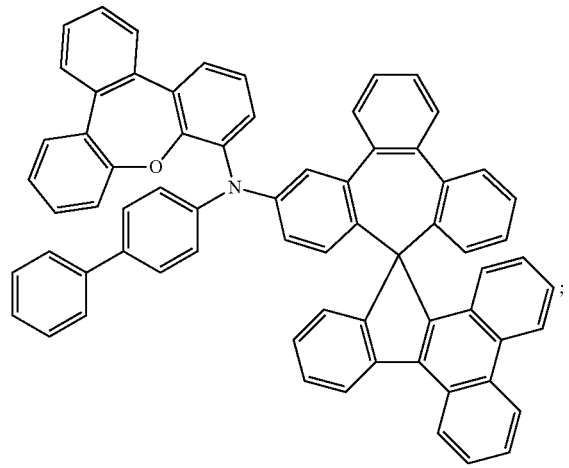
Compound 243
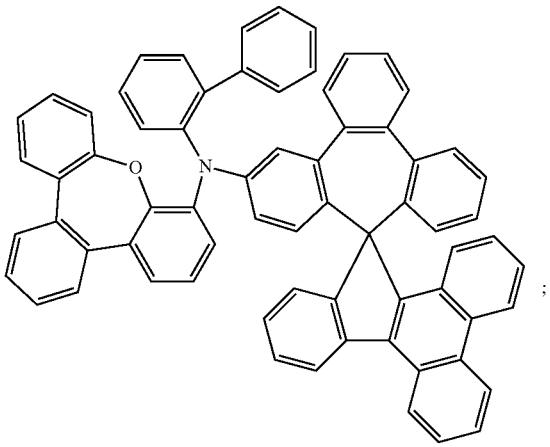
Compound 244
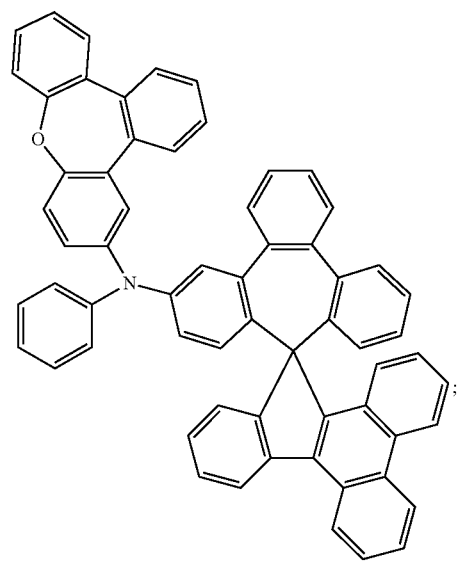
Compound 245
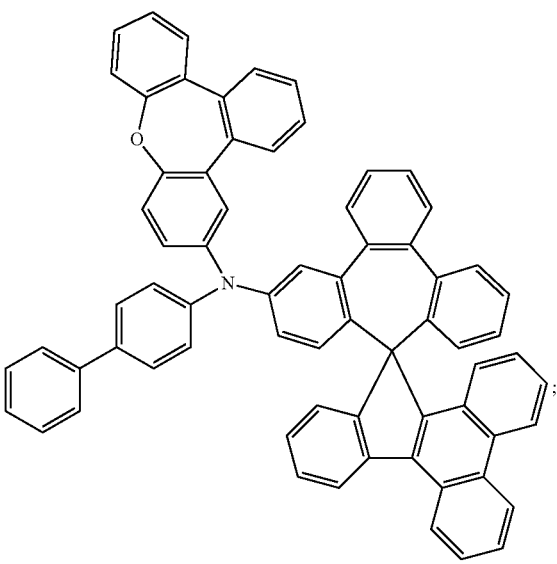
Compound 246
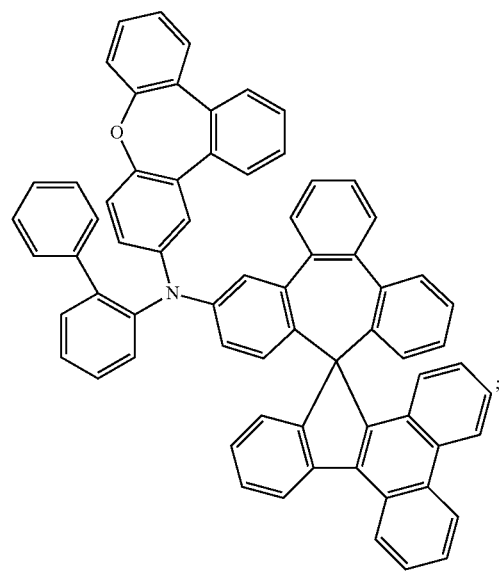
Compound 247
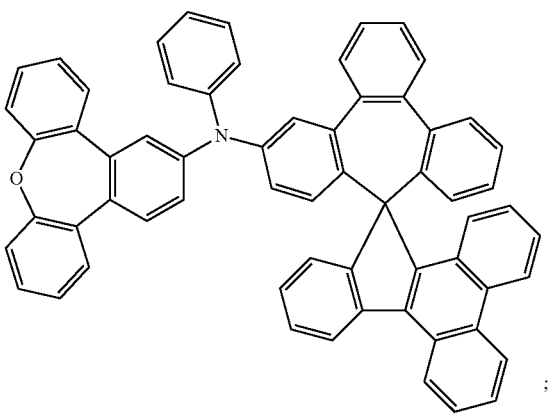

-continued
Compound 248
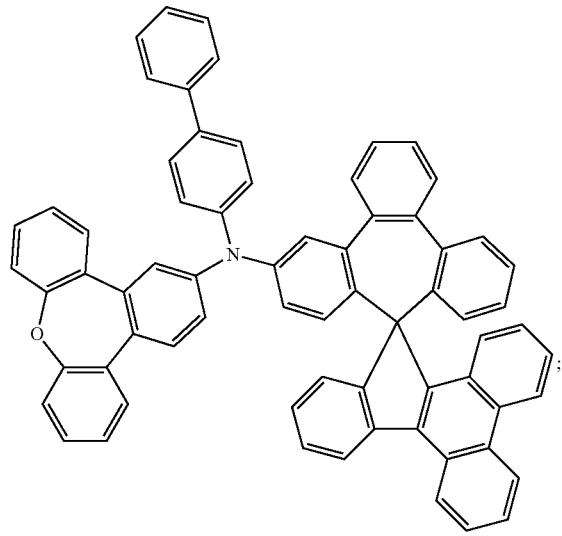
Compound 249
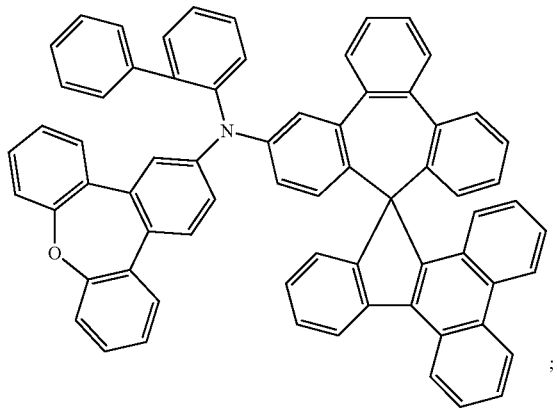
Compound 250
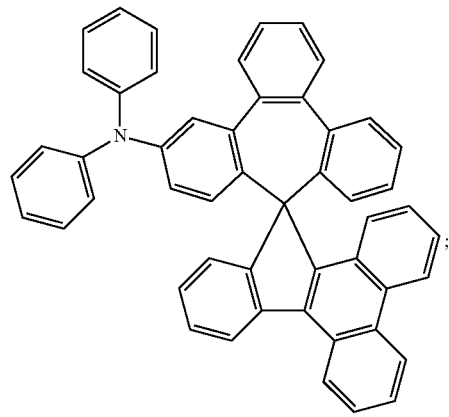
Compound 251
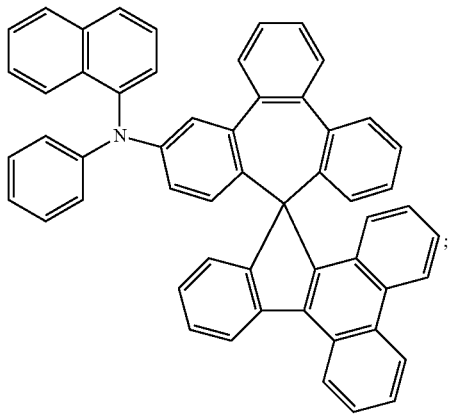
Compound 252
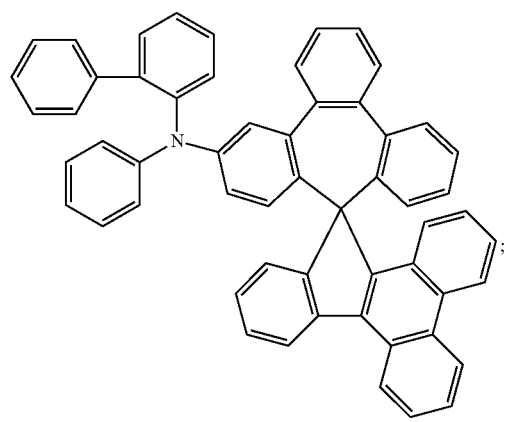
Compound 253
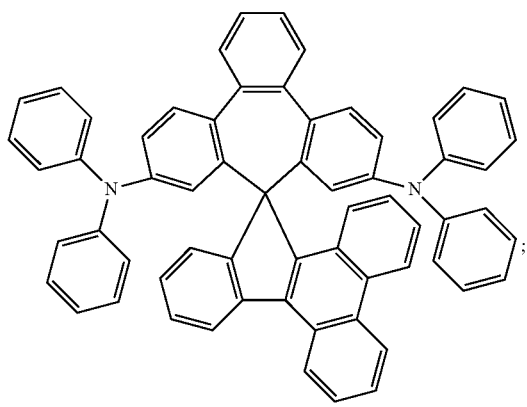

-continued
Compound 254
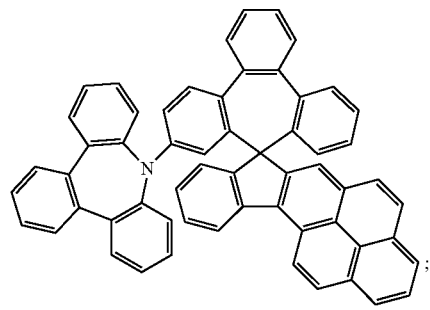
Compound 255
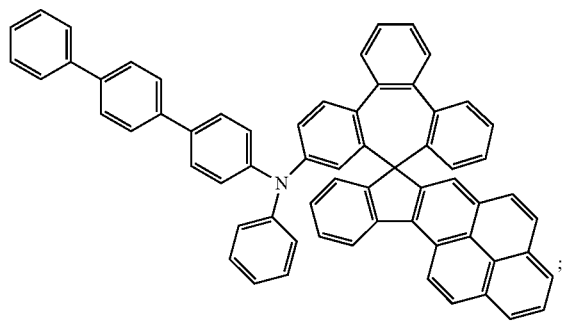
Compound 256
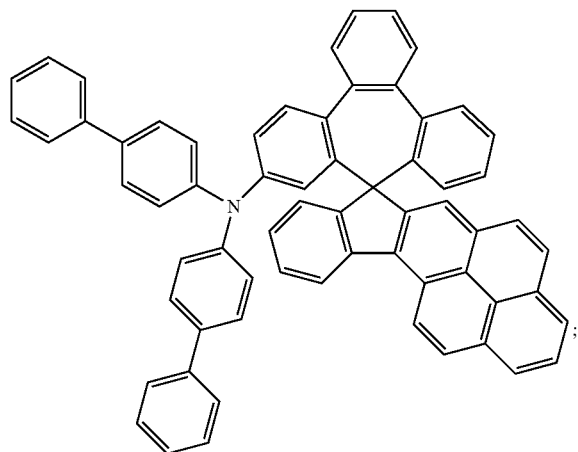
Compound 257
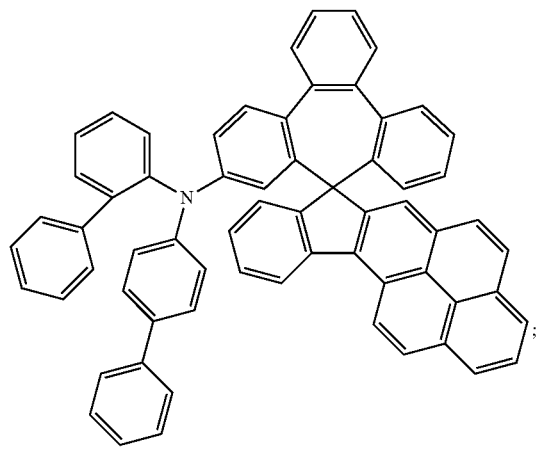
Compound 258
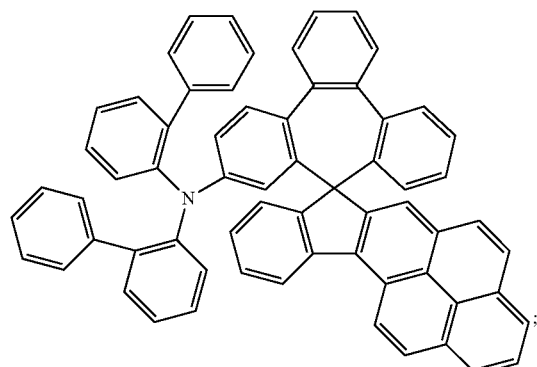
Compound 259
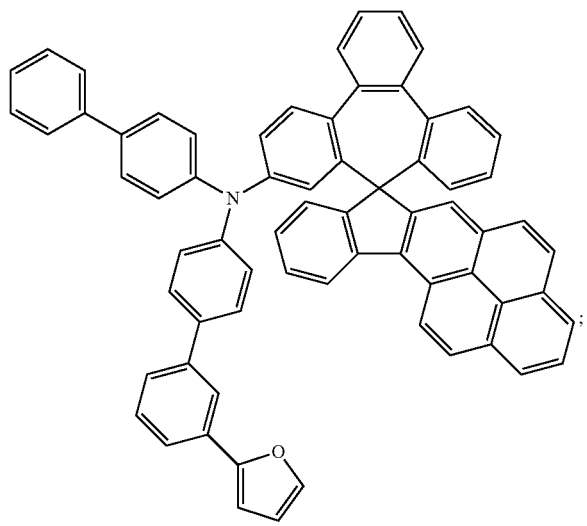

-continued
Compound 260
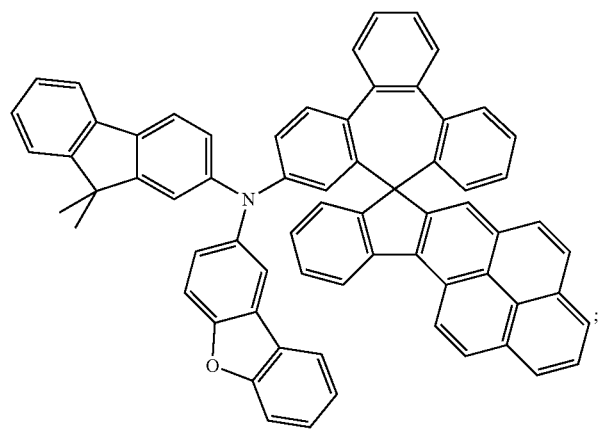
Compound 261
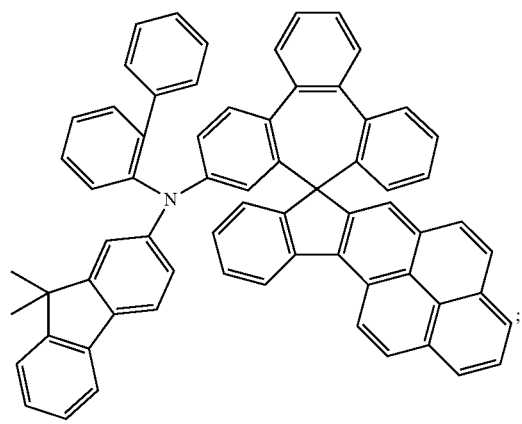
Compound 262
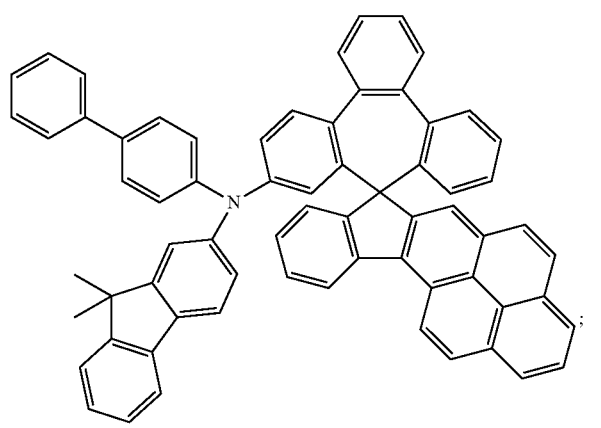
Compound 263
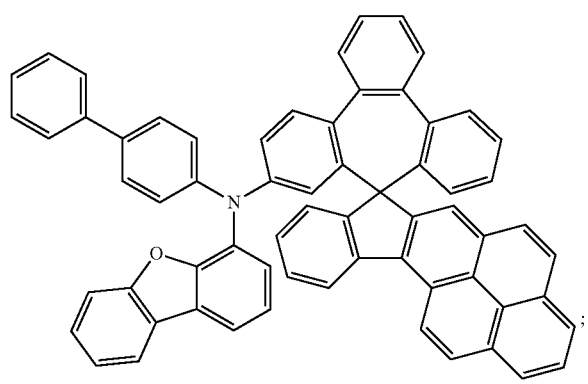
Compound 264
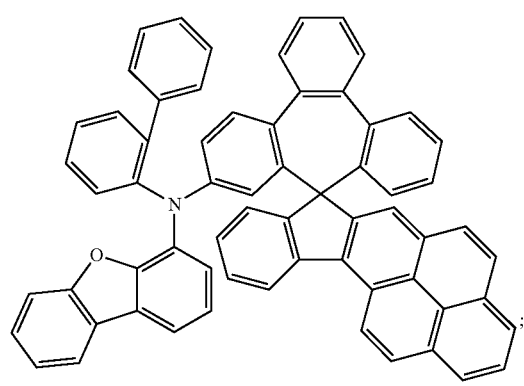
Compound 265
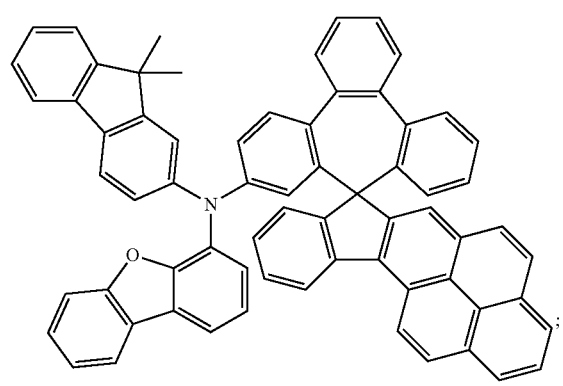

-continued
Compound 266
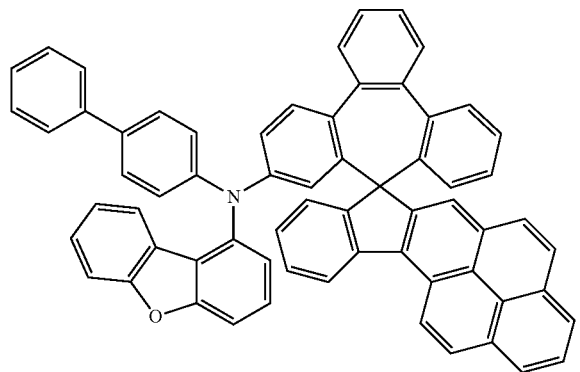
Compound 267
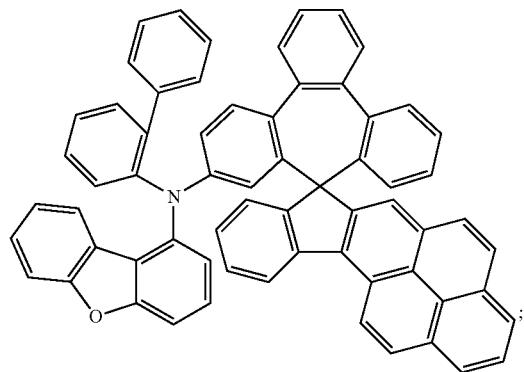
Compound 268
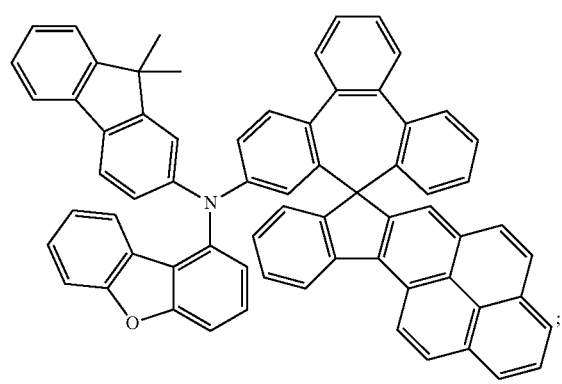
Compound 269
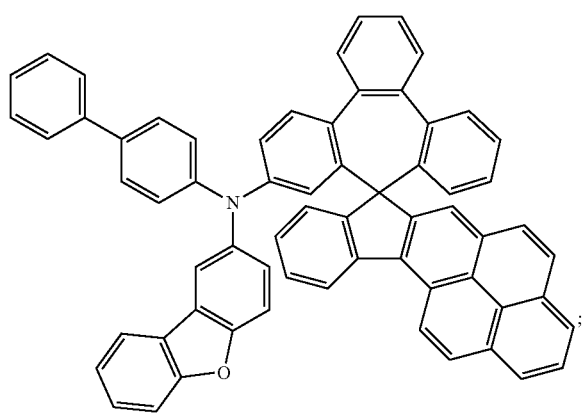
Compound 270
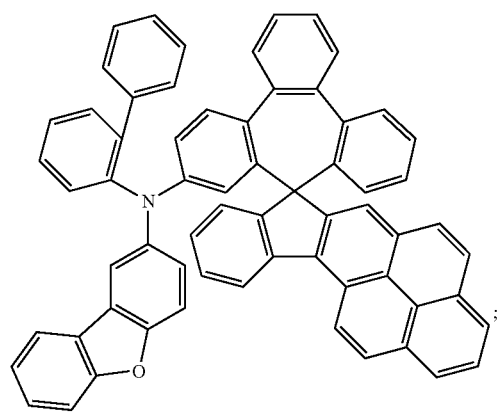
Compound 271
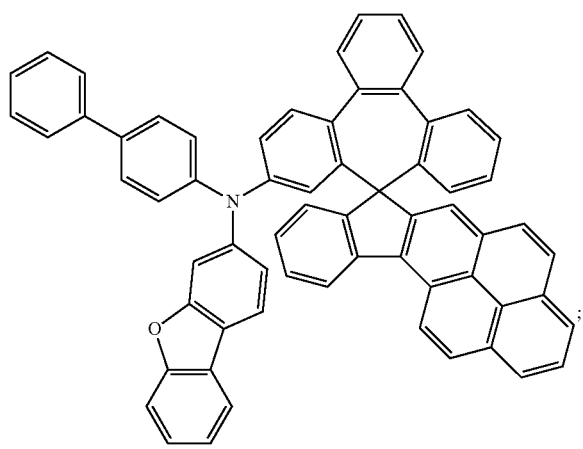

-continued
Compound 272
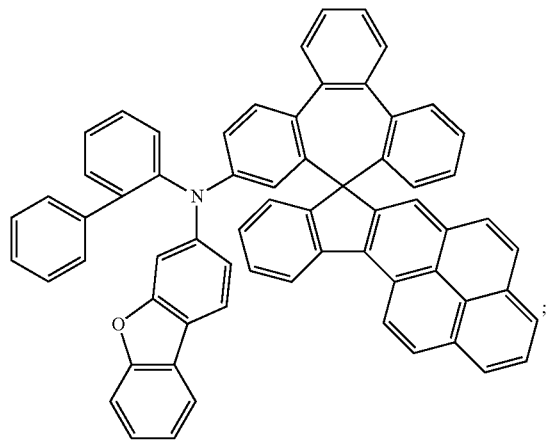
Compound 273
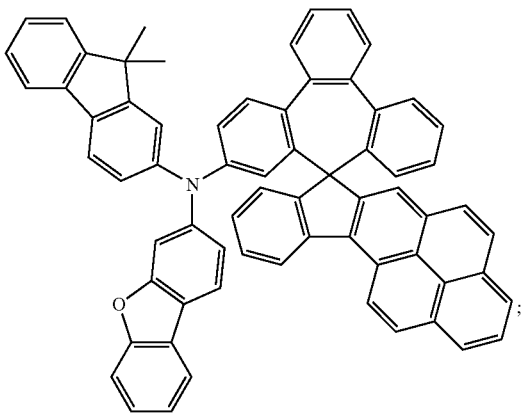
Comopund 274
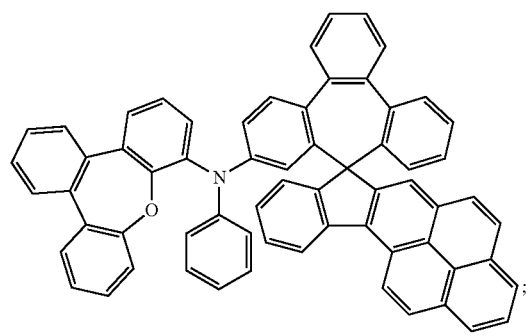
Compound 275
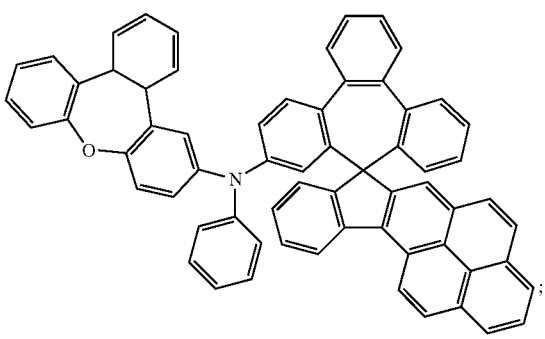
Compound 276
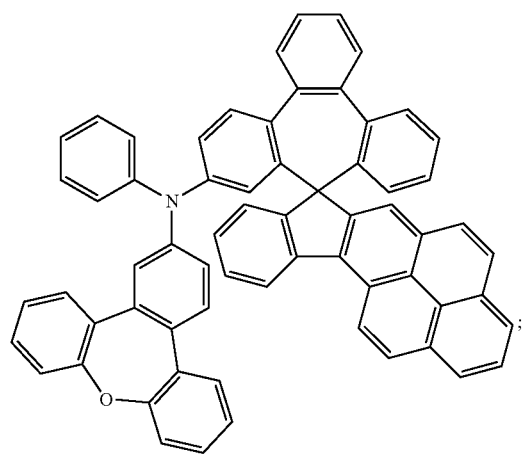
Compound 277
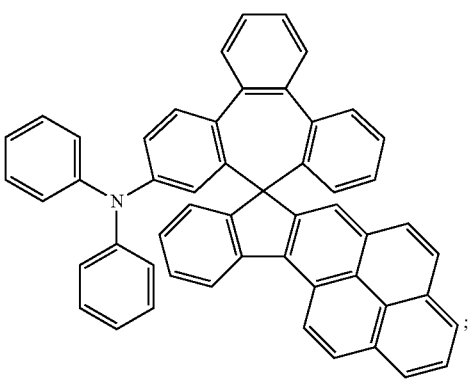

-continued
Compound 278
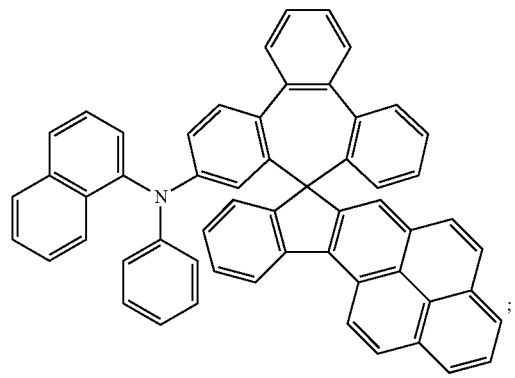
Compound 279
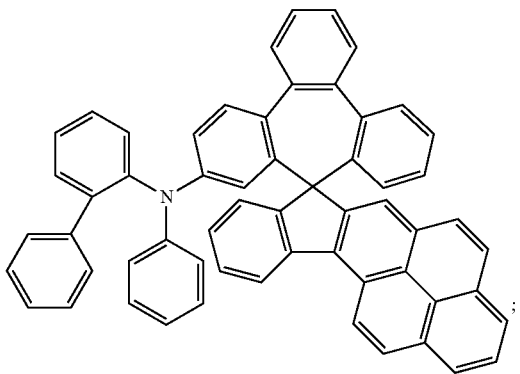
Compound 280
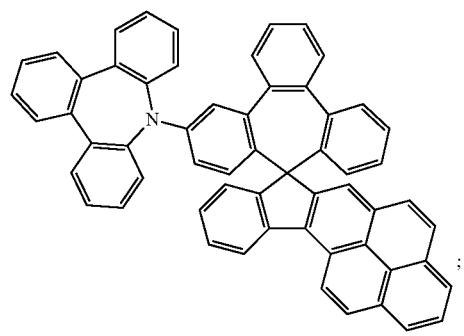
Compound 281
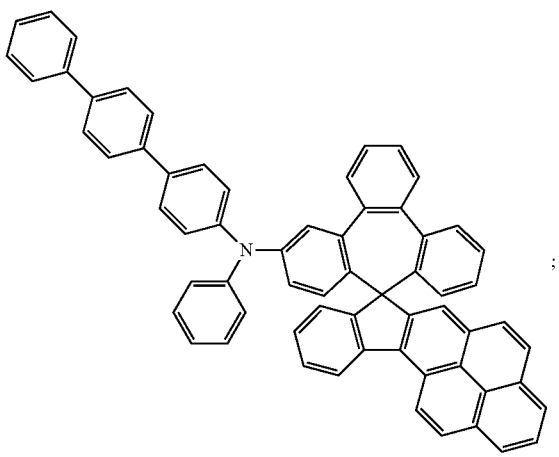
Compound 282
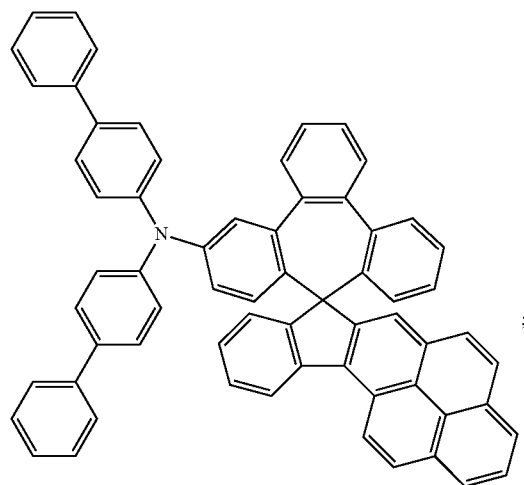
Compound 283
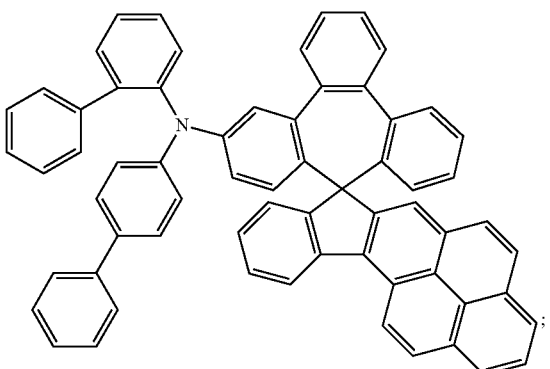

-continued
Compound 284
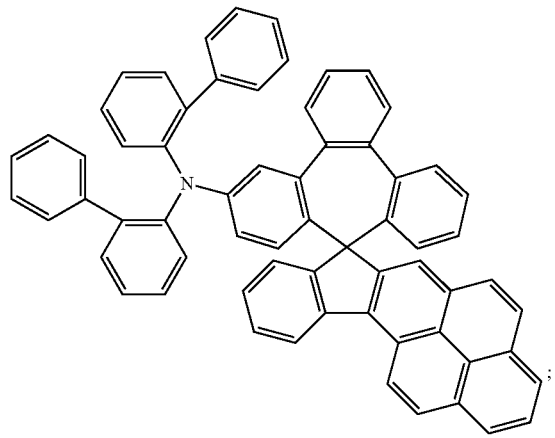
Compound 285
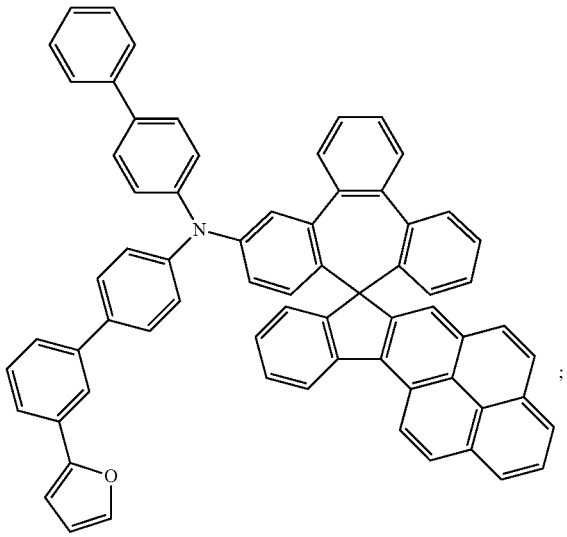
Compound 286
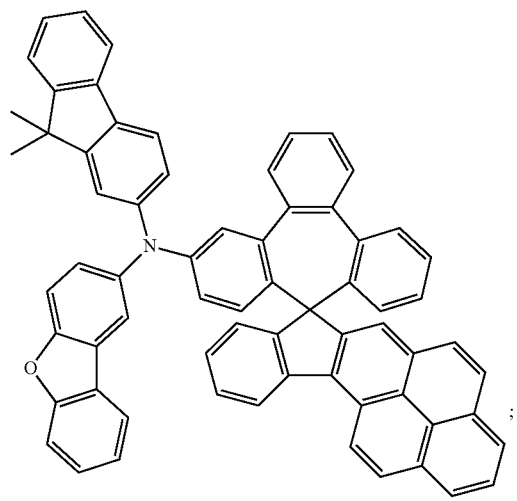
Compound 287
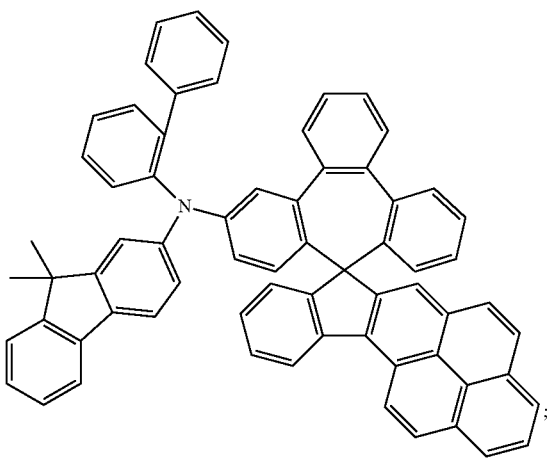
Compound 288
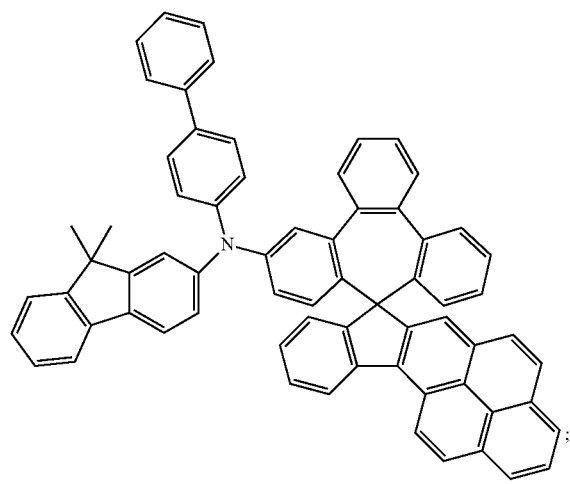
Compound 289
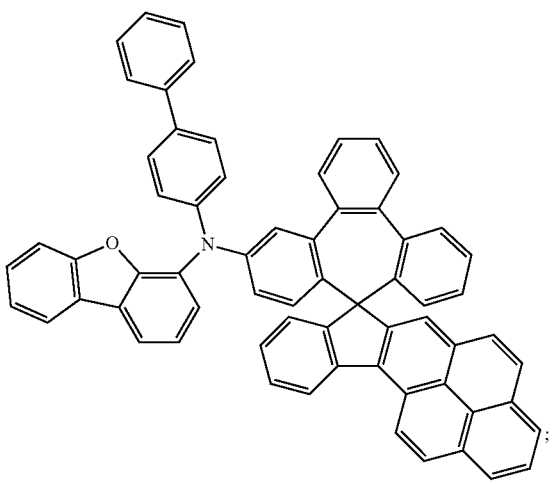

-continued
Compound 290
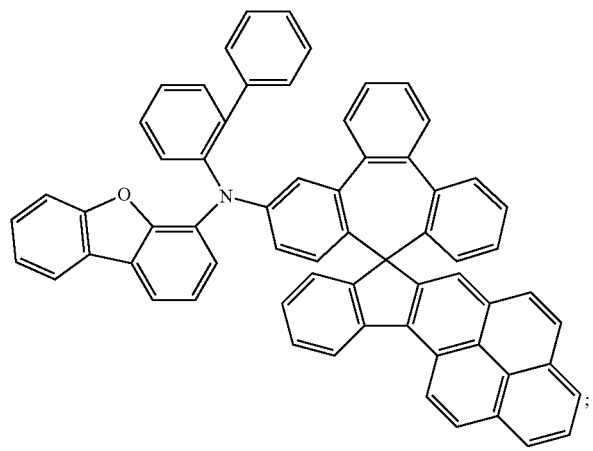
Compound 291
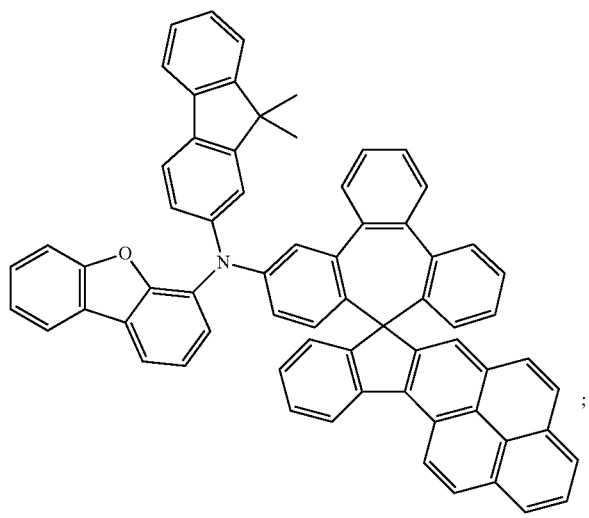
Compound 292
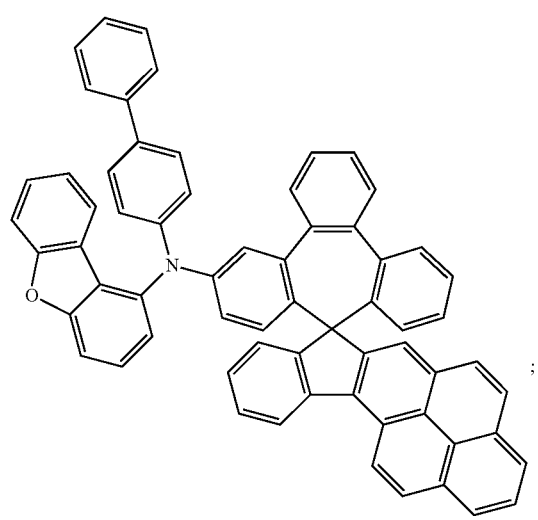
Compound 293
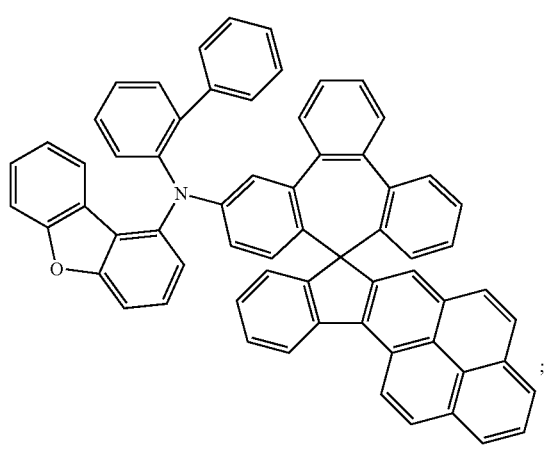
Compound 294
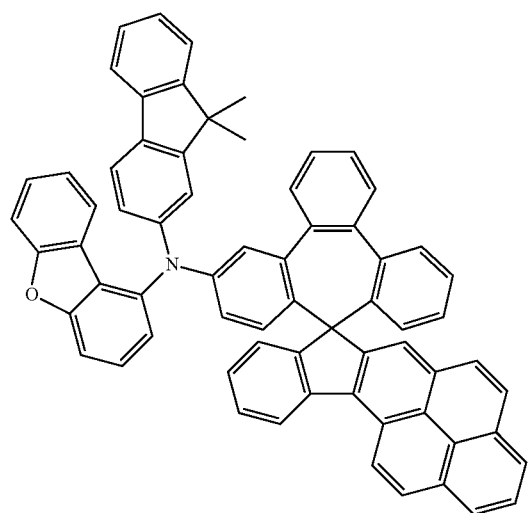
Compound 295
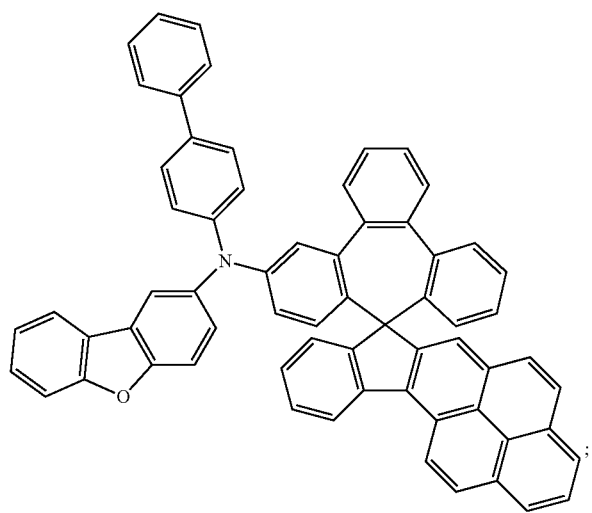

-continued
Compound 296
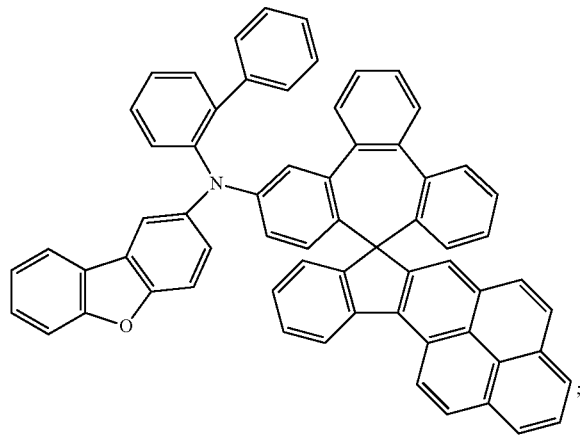
Compound 297
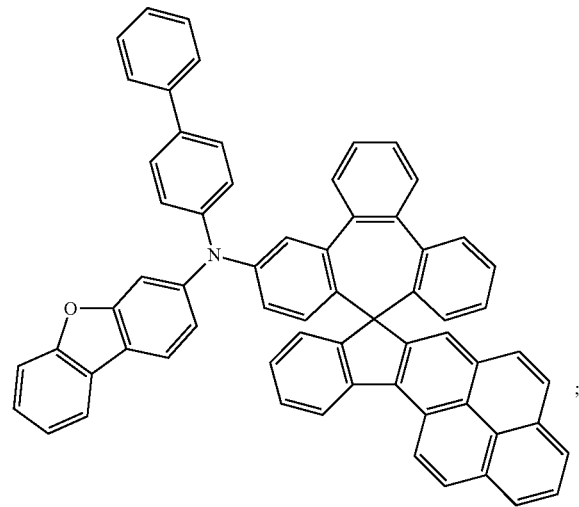
Compound 298
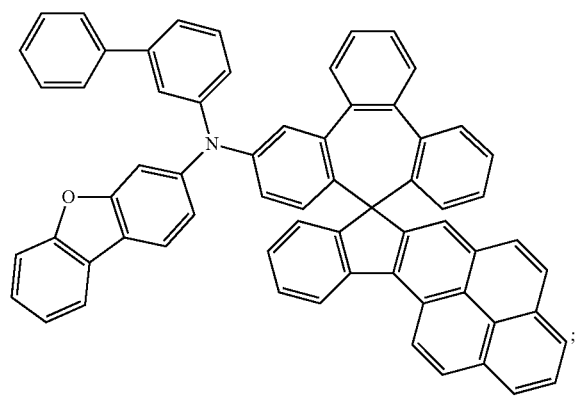
Compound 299
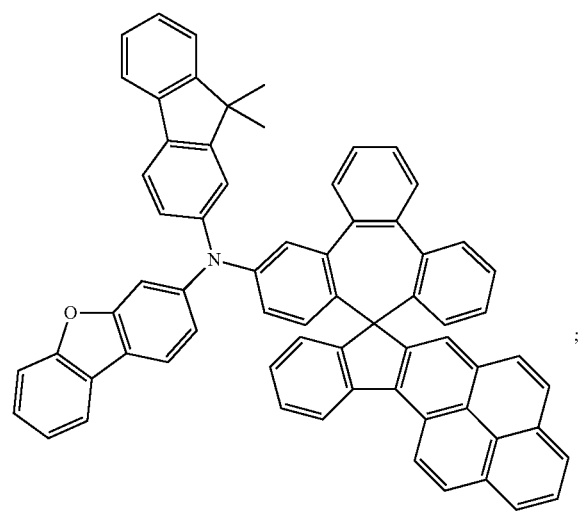
Compound 300
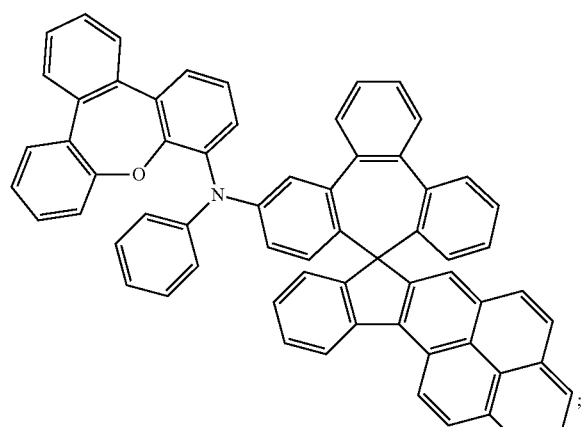
Compound 301
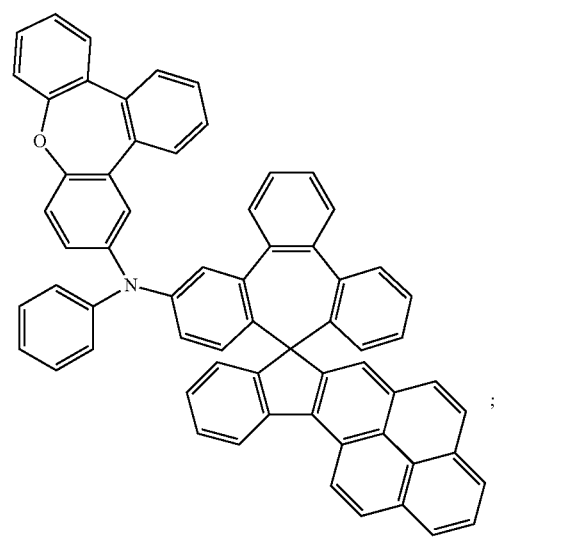

-continued
Compound 302
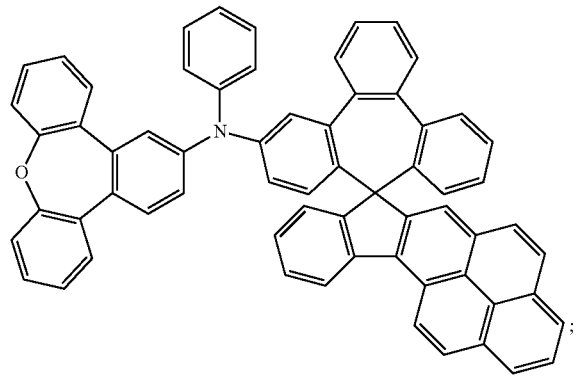
Compound 303
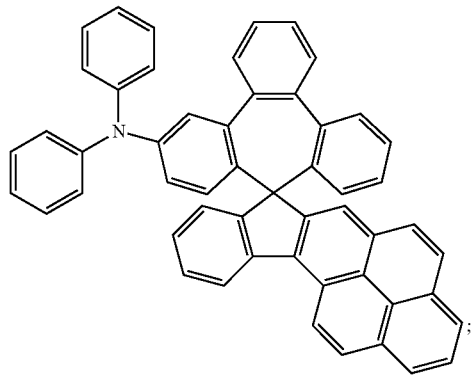
Compound 304
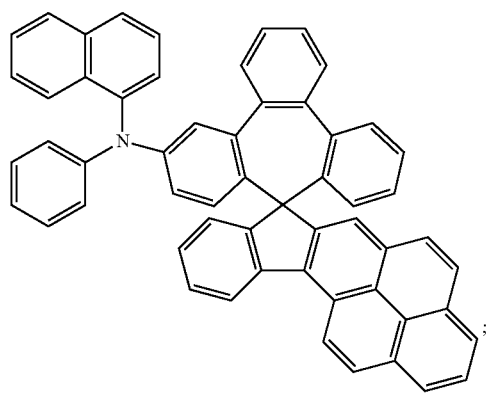
Compound 305
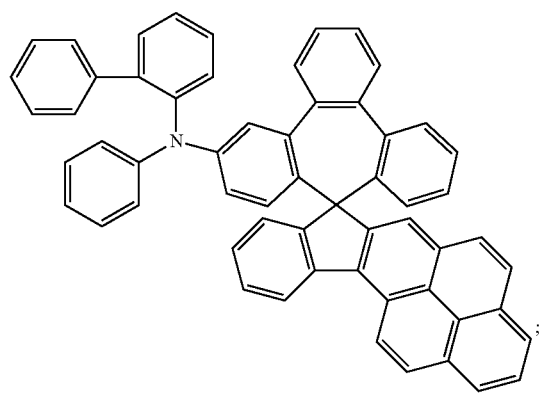
Compound 306
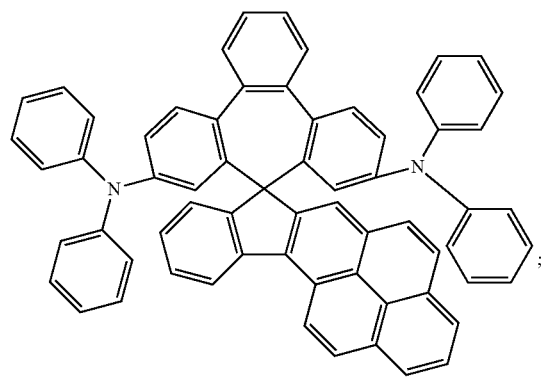
Compound 307
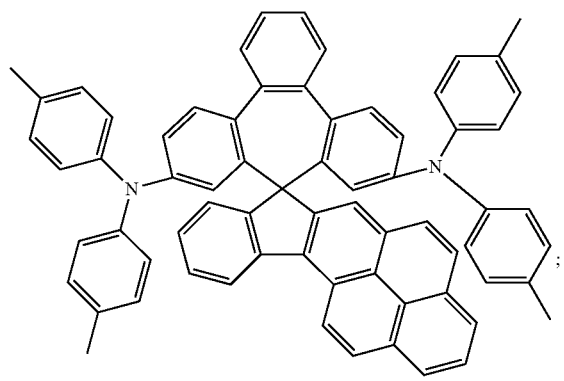

-continued
Compound 308
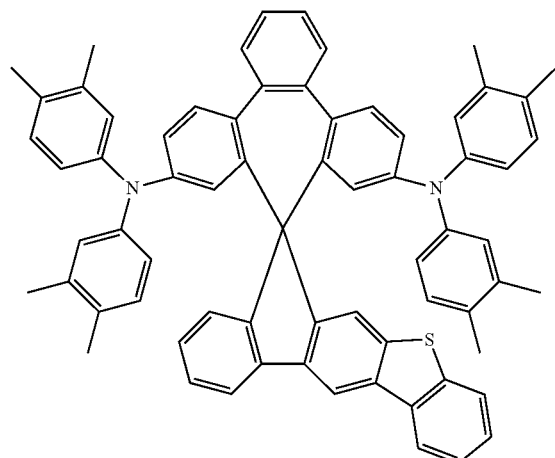
Compound 309
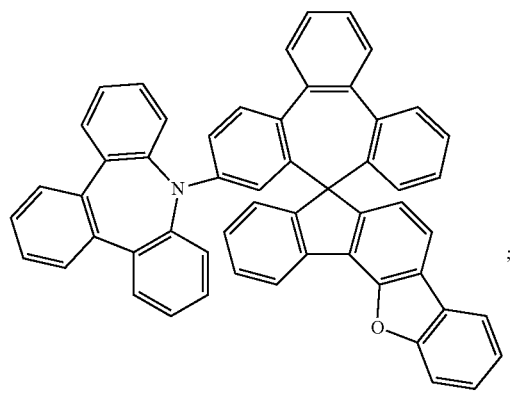
Compound 310
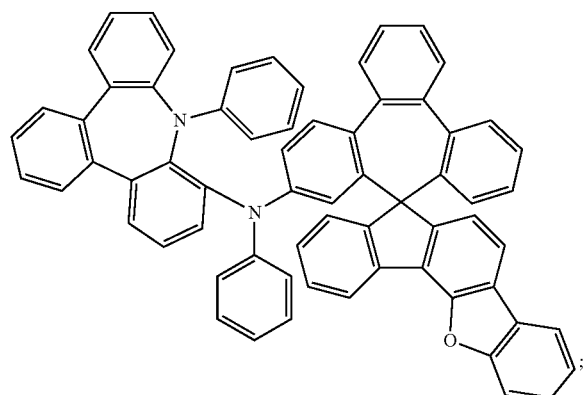
Compound 311
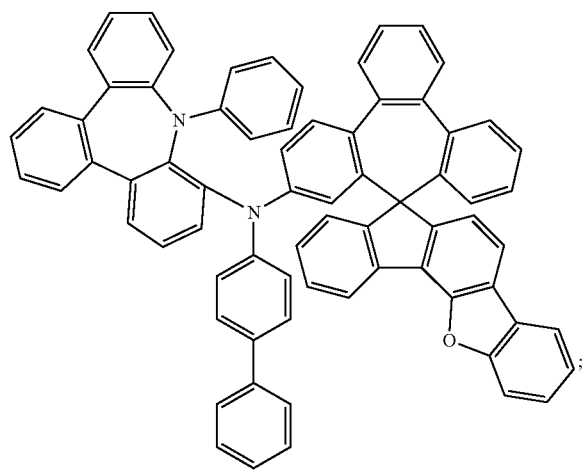
Compound 312
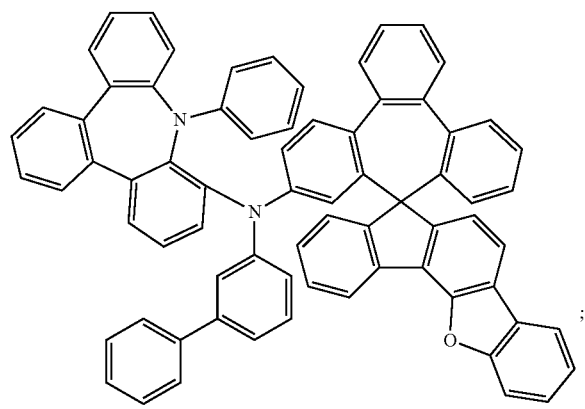
Compound 313
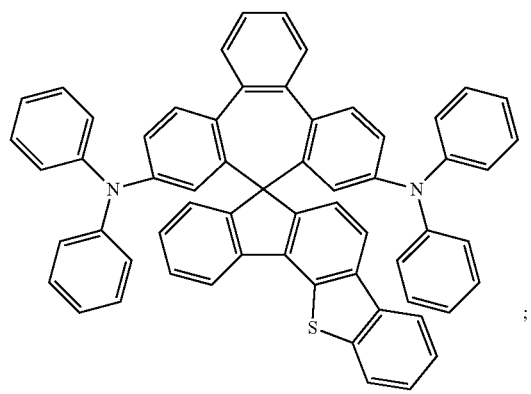

-continued
Compound 314
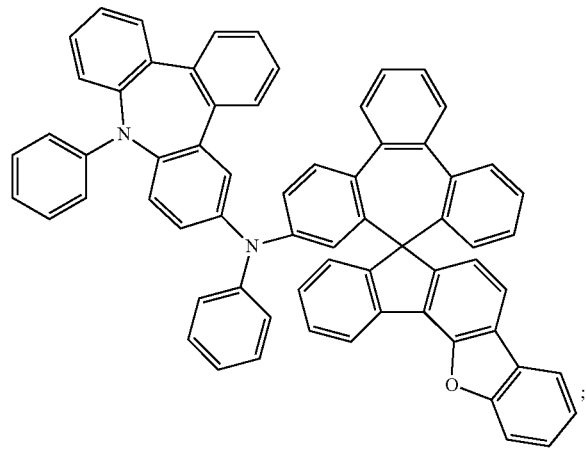
Compound 315
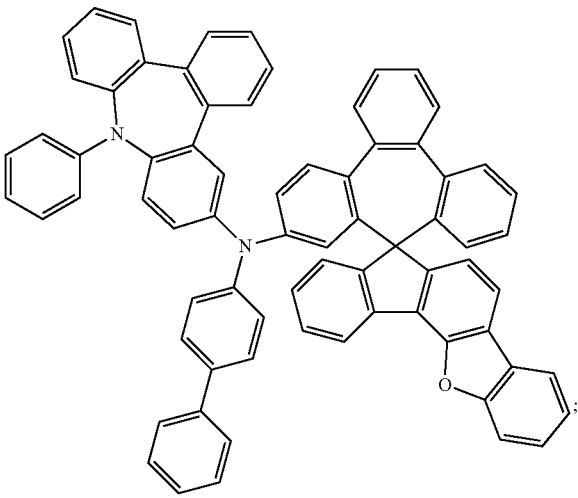
Compound 316
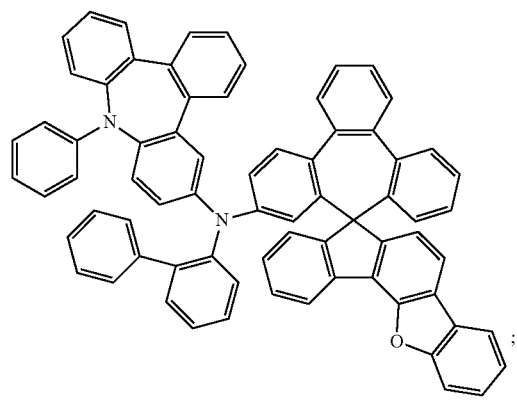
Compound 317
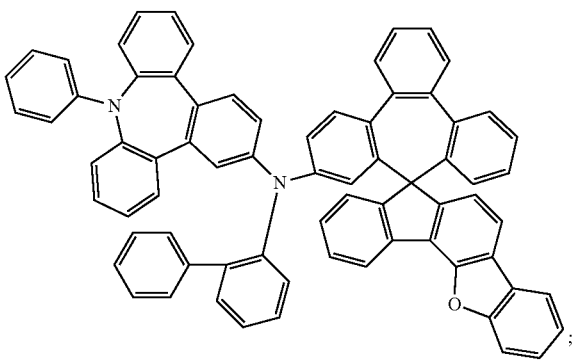
Compound 318
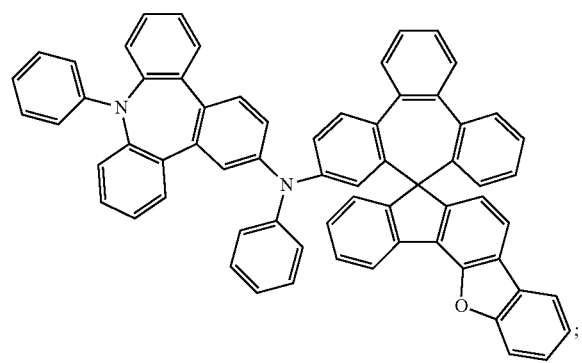
Compound 319
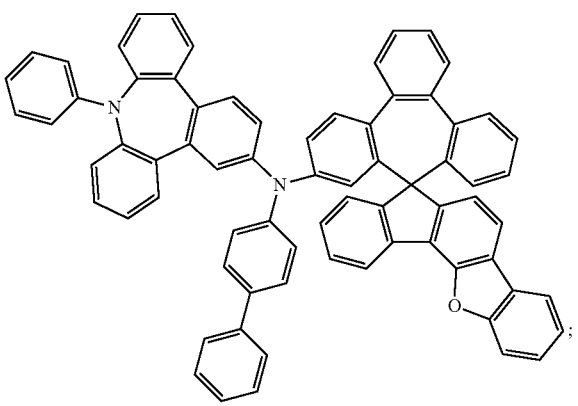

-continued
Compound 320 Compound 321
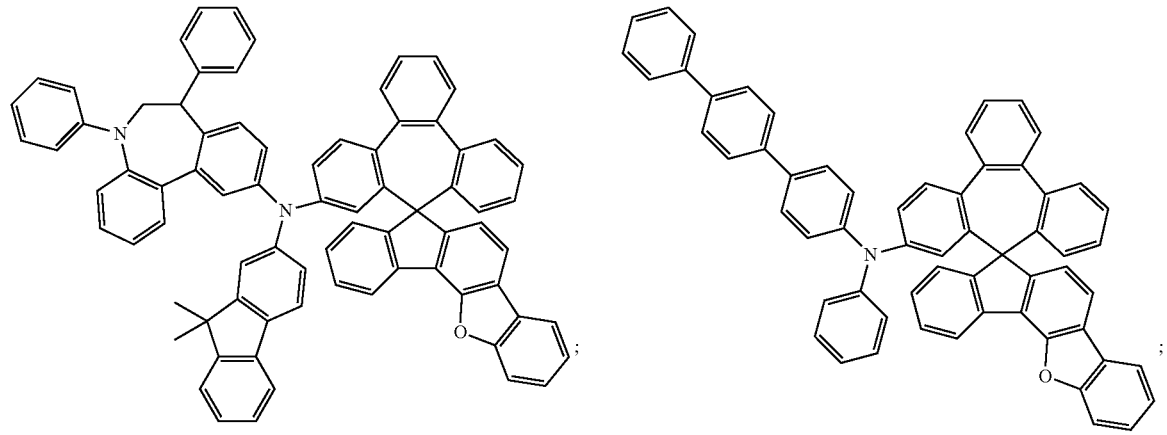
Compound 322 Compound 323
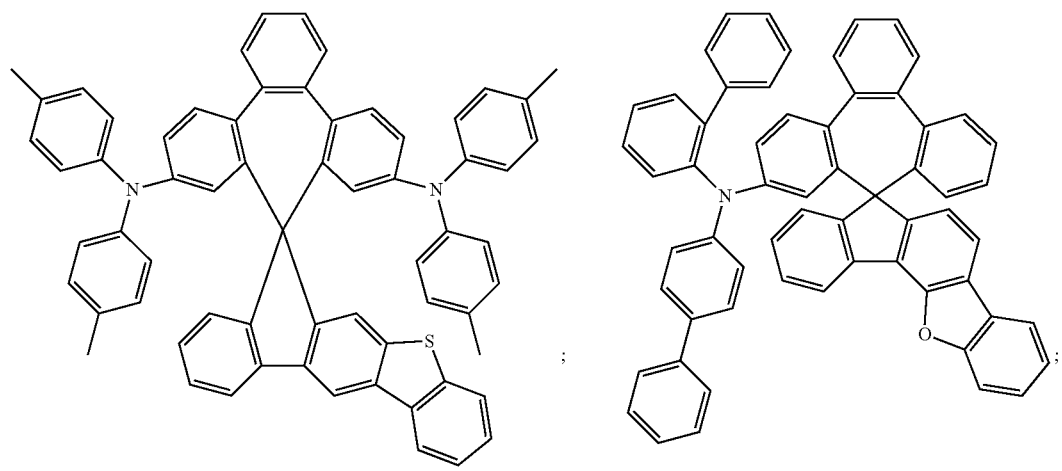
Compound 324 Compound 325
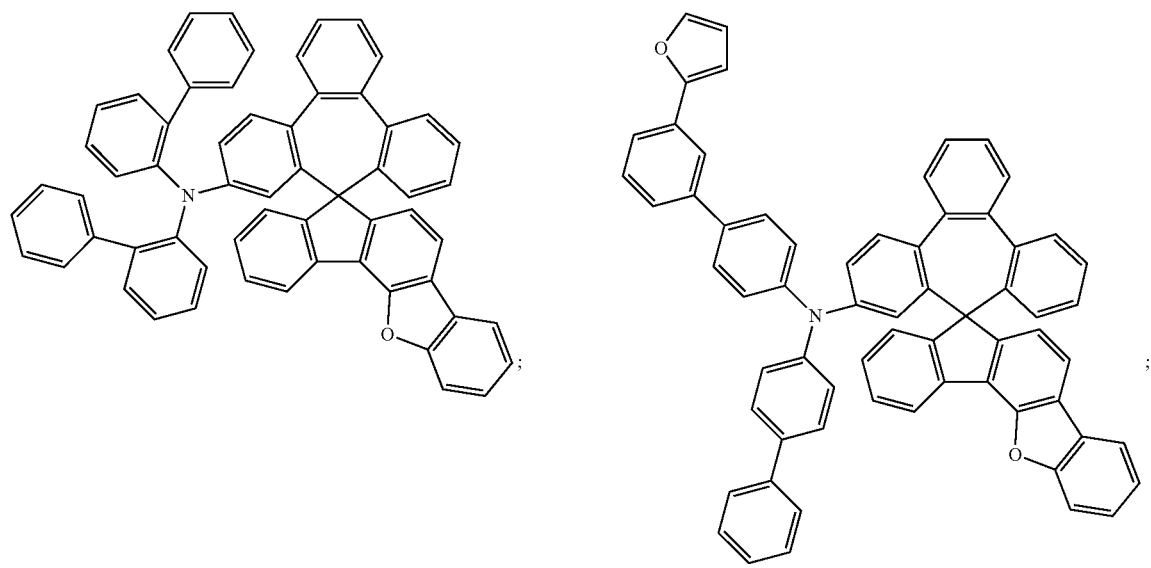

-continued
Compound 326
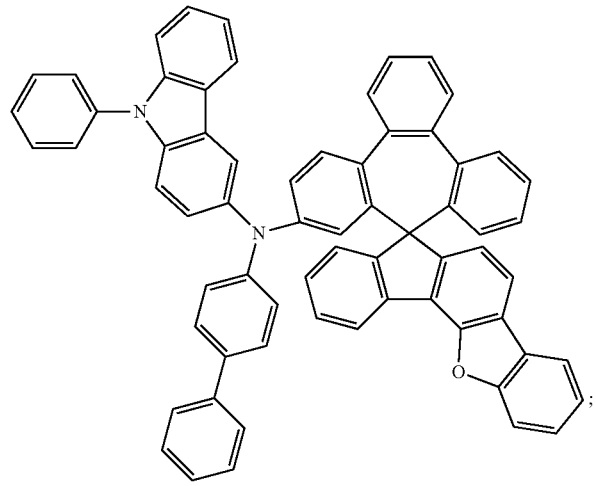
Compound 327
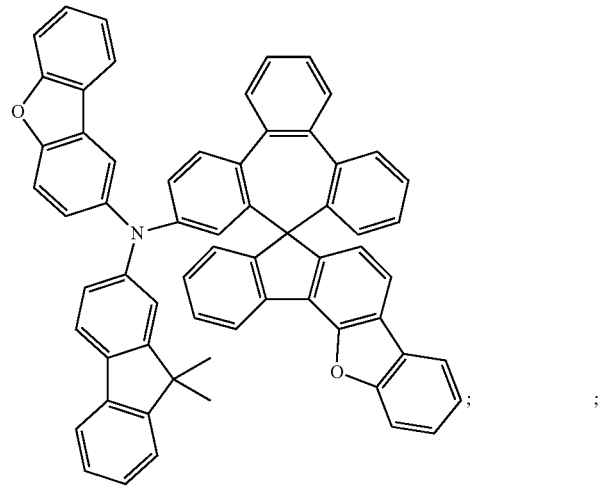
Compound 328
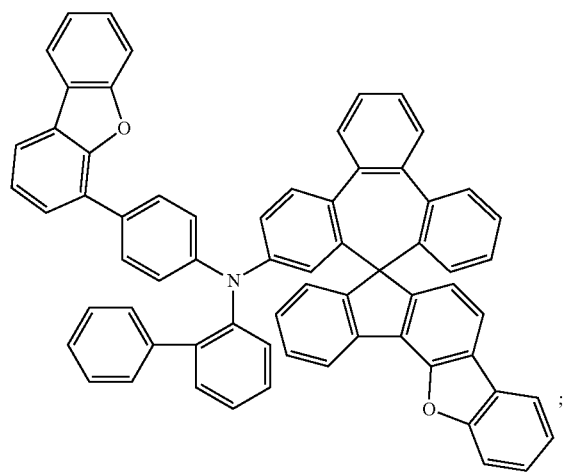
Compound 329
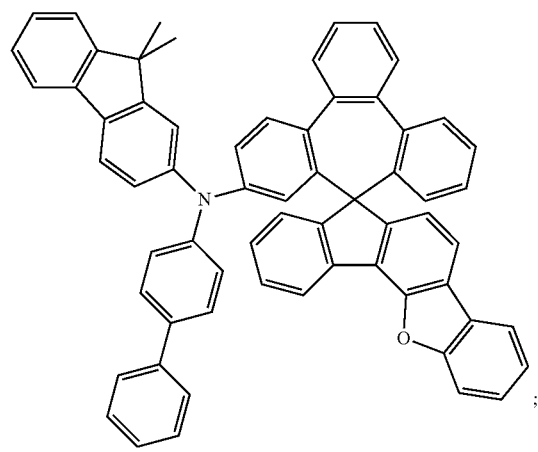
Compound 330
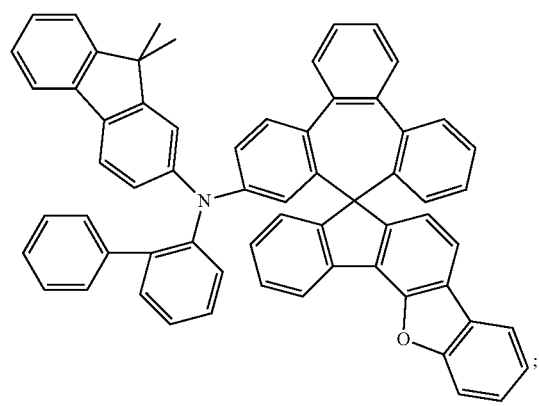
Compound 331
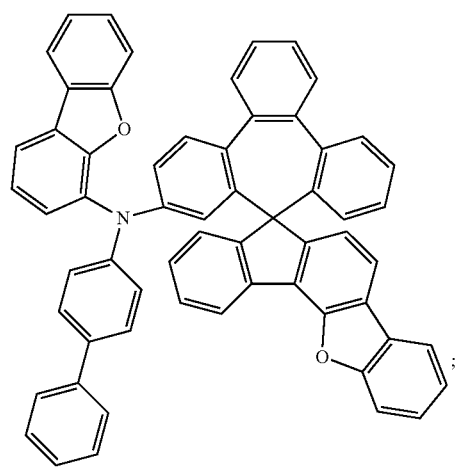

Compound 332
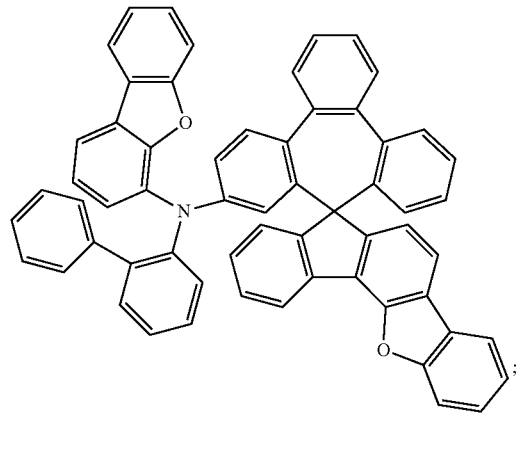
Compount 333
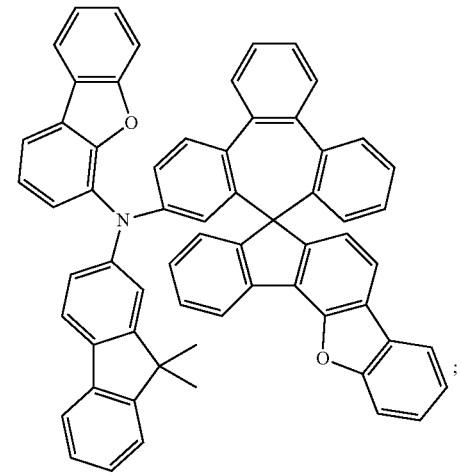
Compound 334
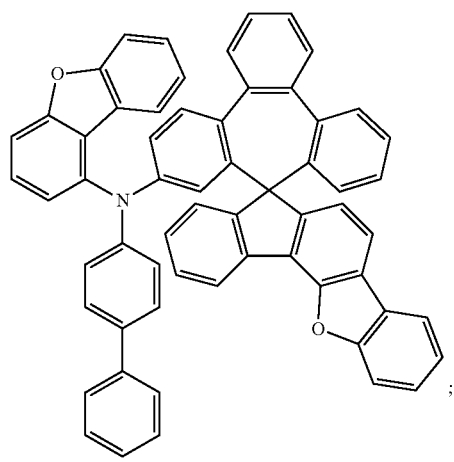
Compound 335
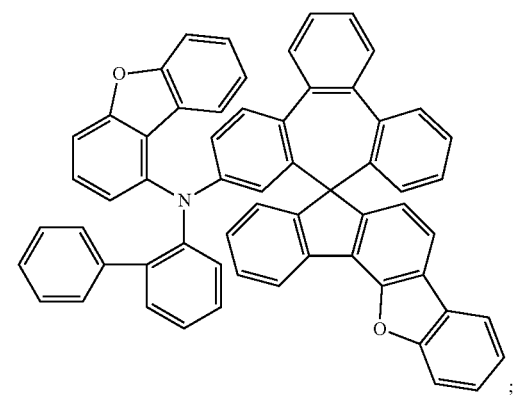
Compound 336
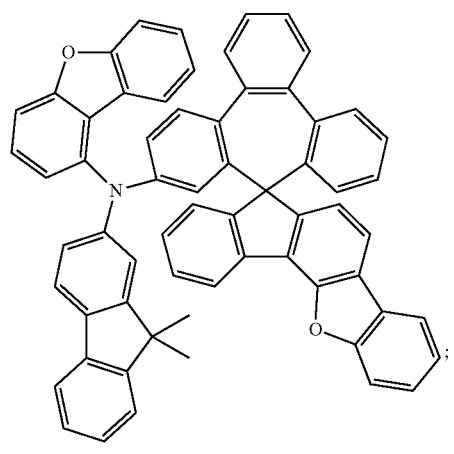
Compound 337
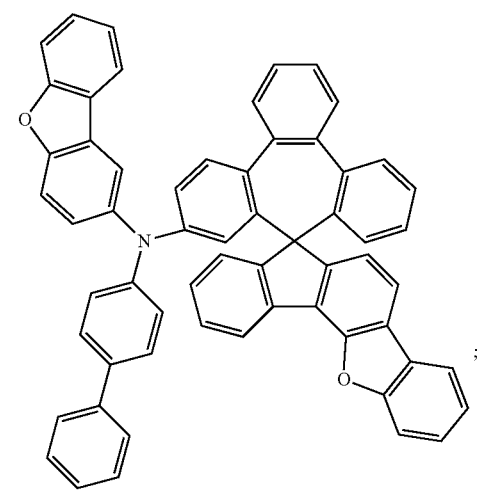

-continued
Compound 338
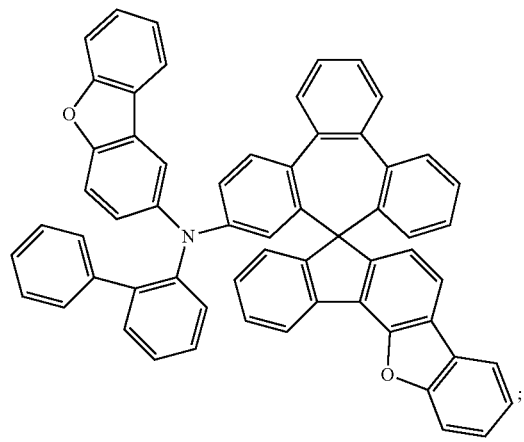
Compound 339
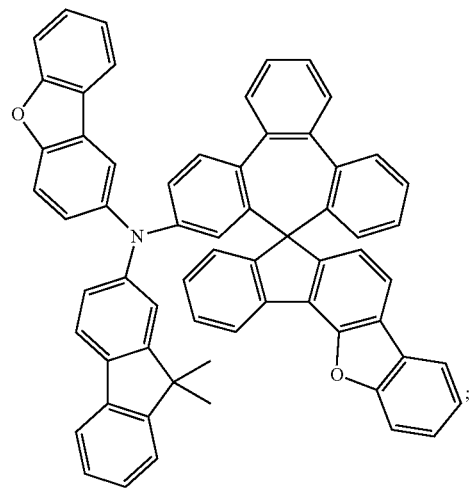
Compound 340
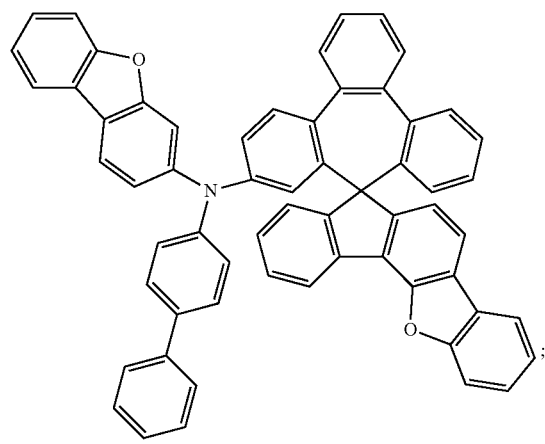
Compound 341
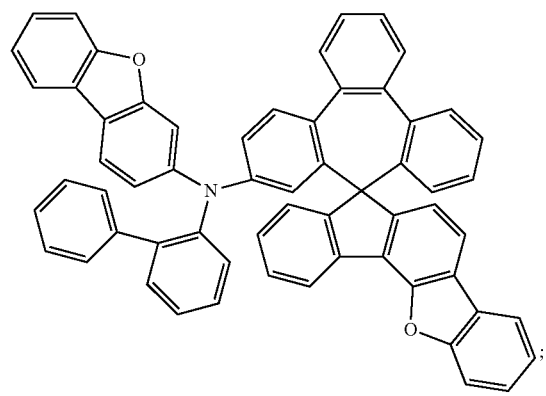
Compound 342
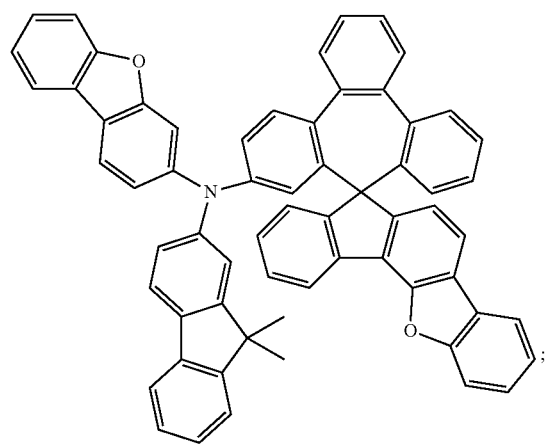
Compound 343
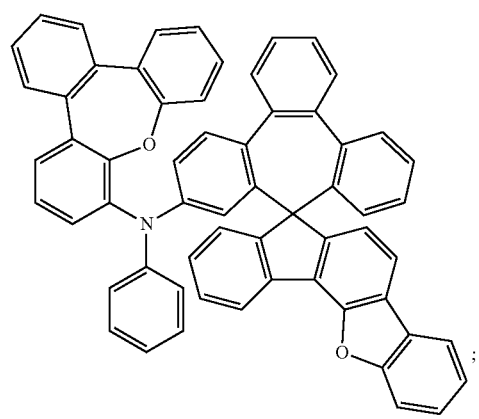

Compound 344
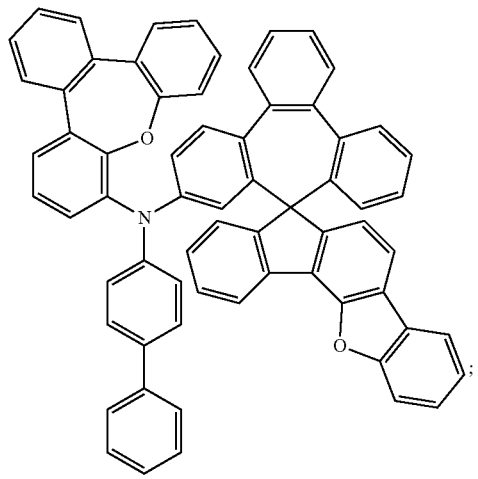
Compound 345
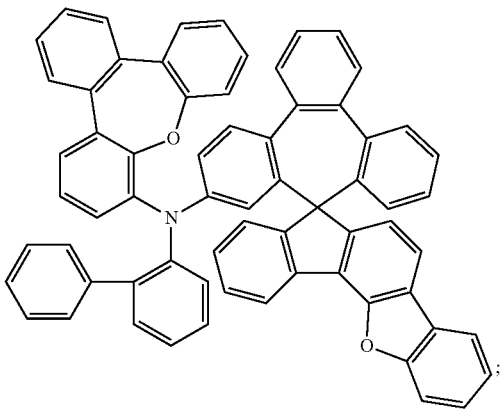
Compound 346
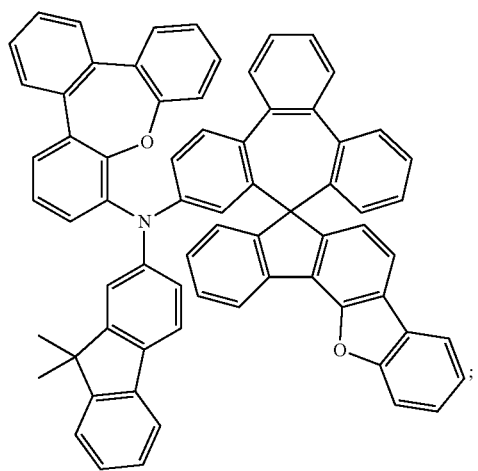
Compound 347
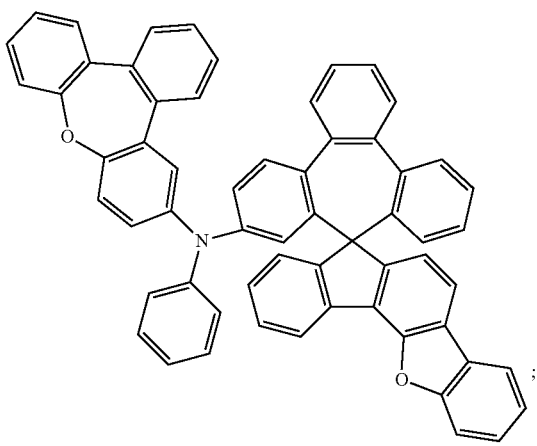
Compound 348
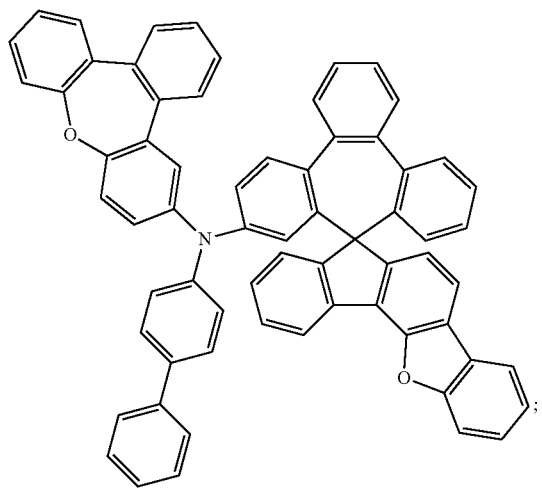
Compound 349
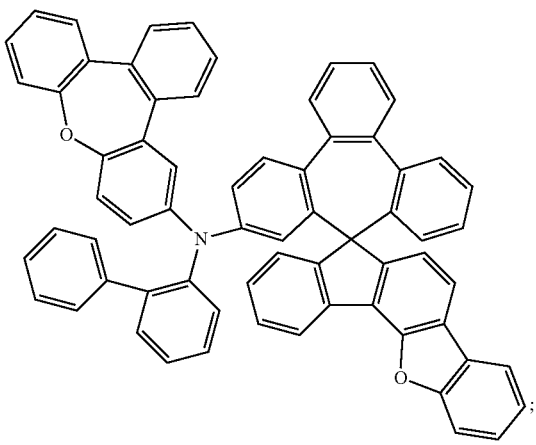

-continued
Compound 350
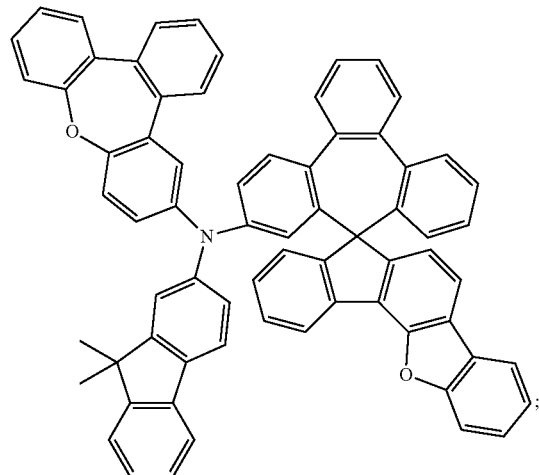
Compound 351
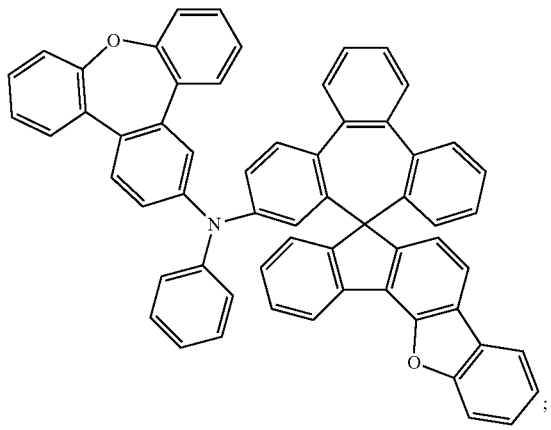
Compound 352
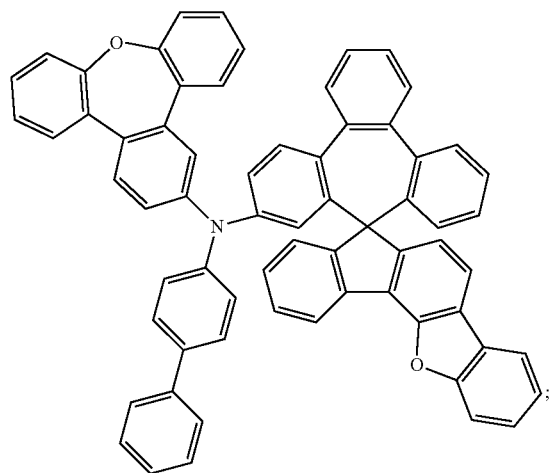
Compound 353
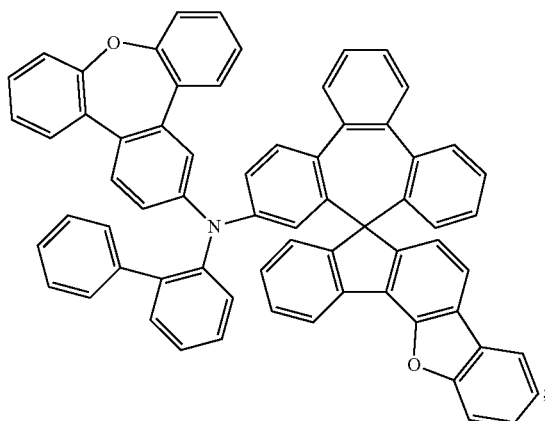
Compound 354
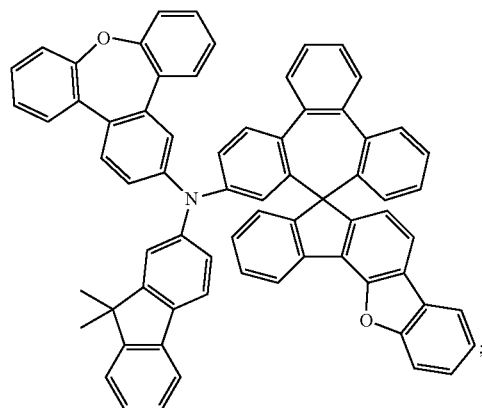
Compound 355
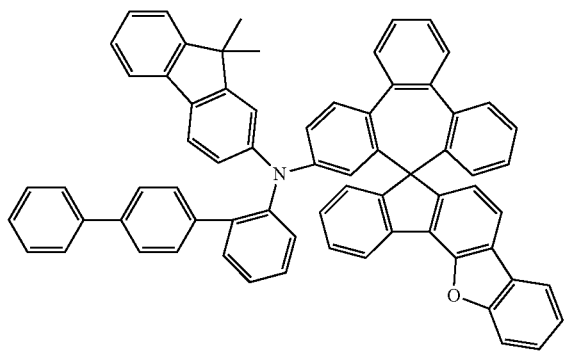

-continued
Compound 356
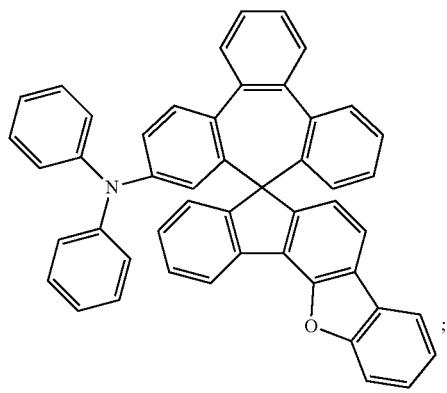
Compound 357
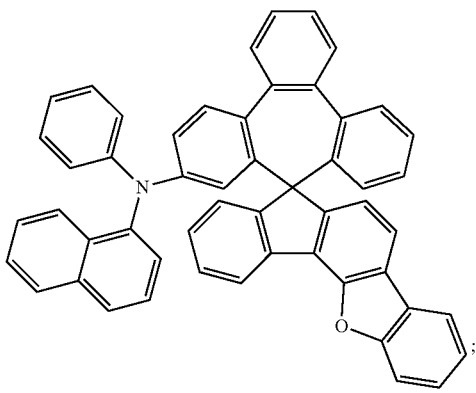
Compound 358
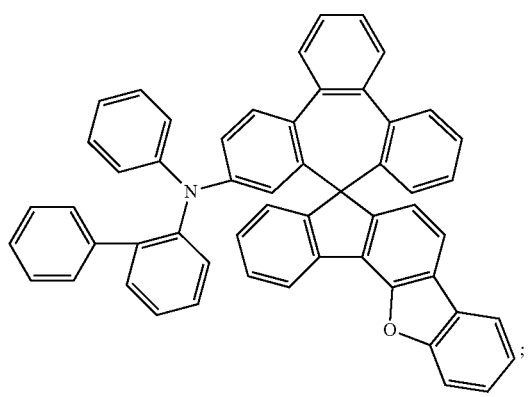
Compound 359
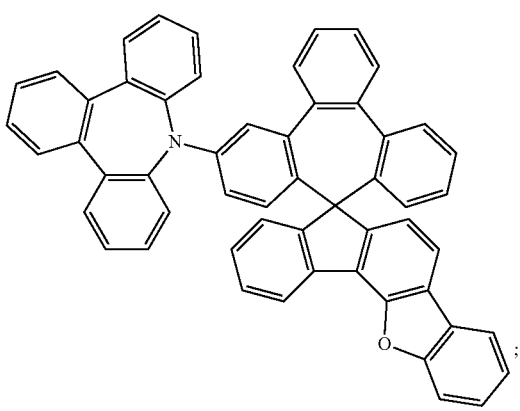
Compound 360
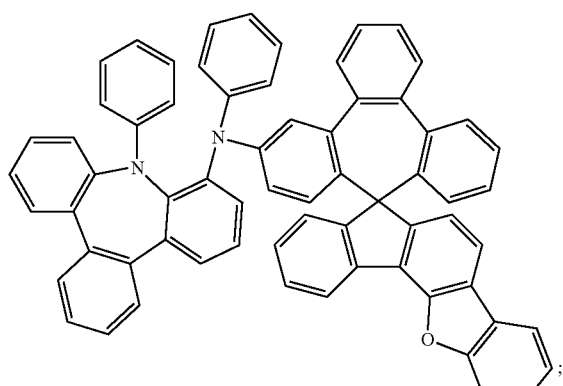
Compound 361
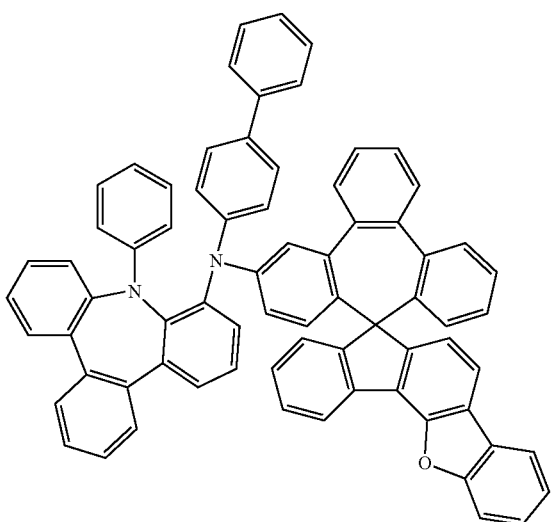

-continued
Compound 362
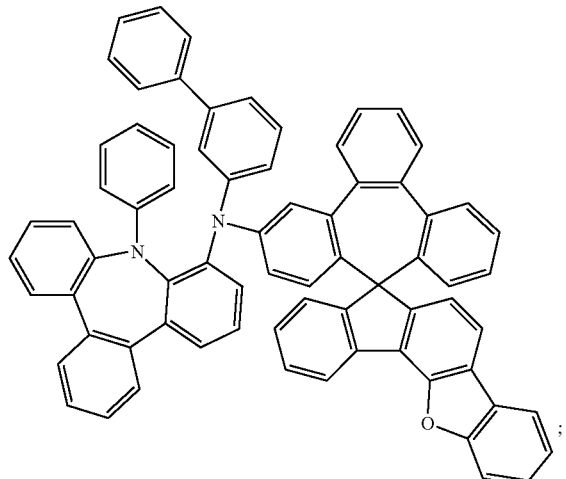
Compound 363
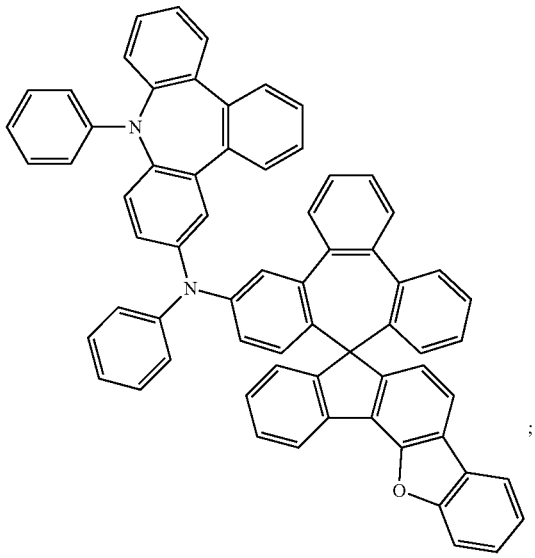
Compound 364
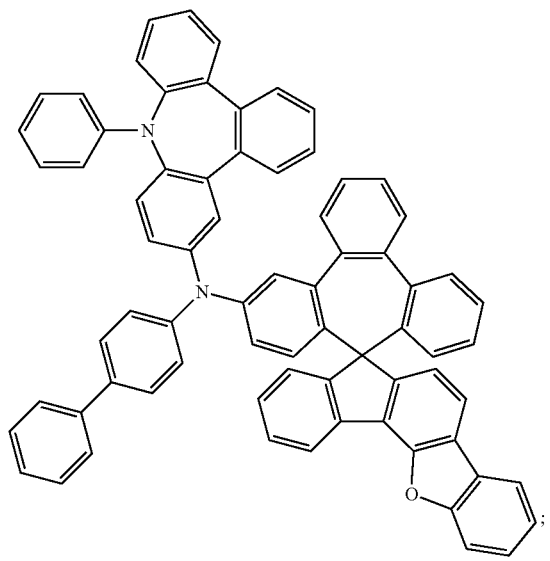
Compound 365
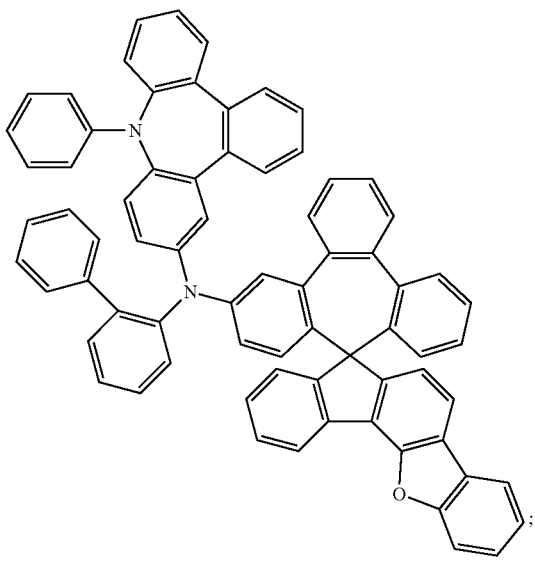

-continued
Compound 366
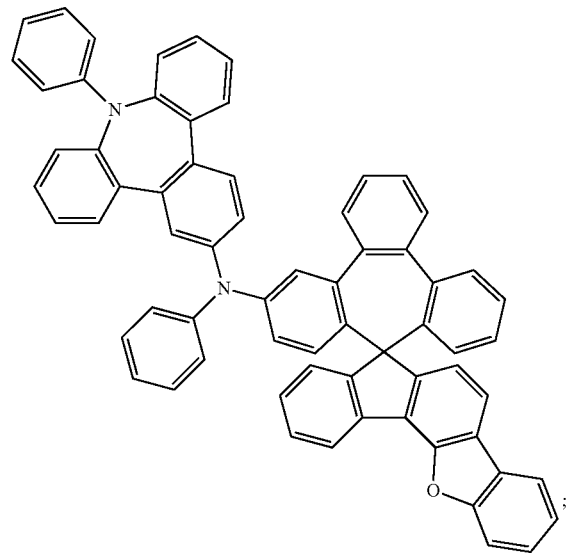
Compound 367
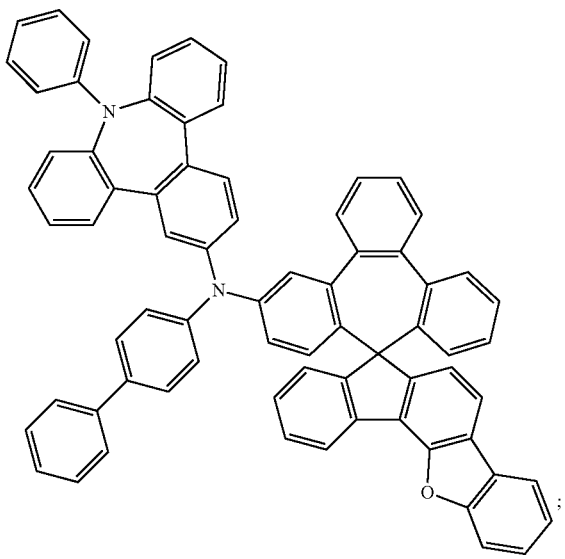
Compound 368
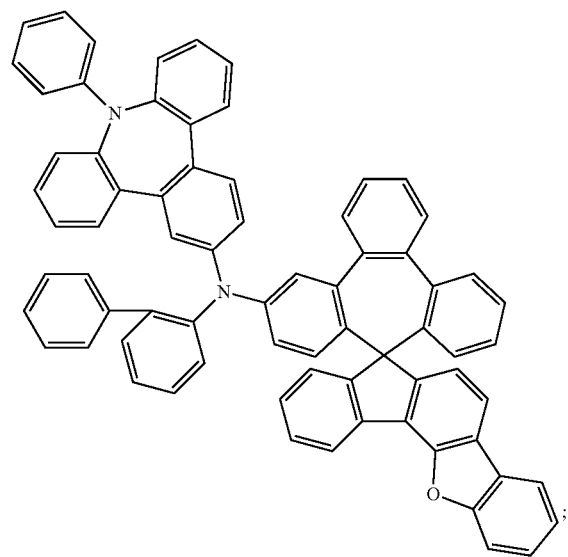
Compound 369
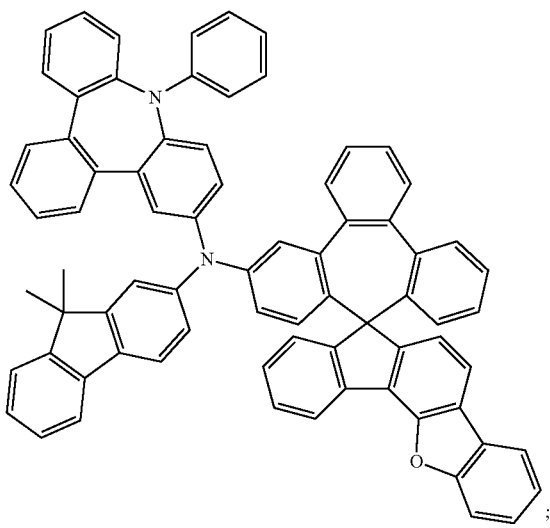

Comopund 370
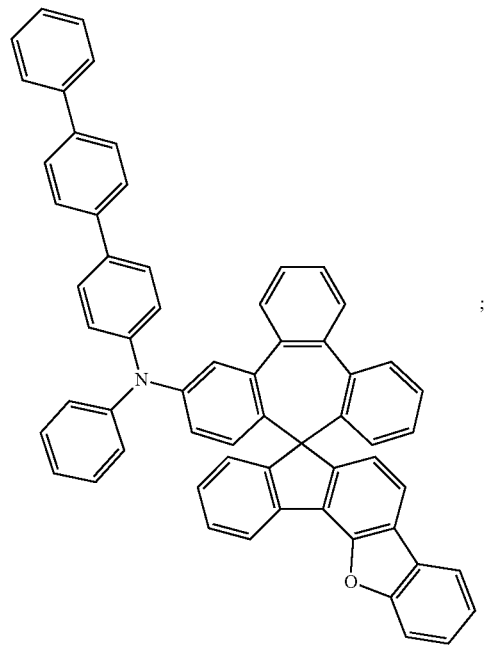
Compound 371
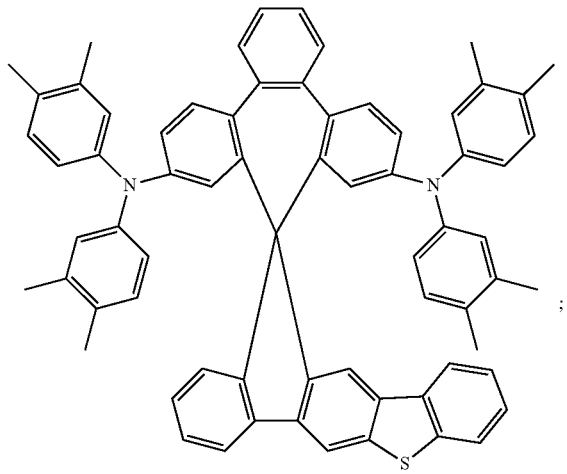
Compound 372
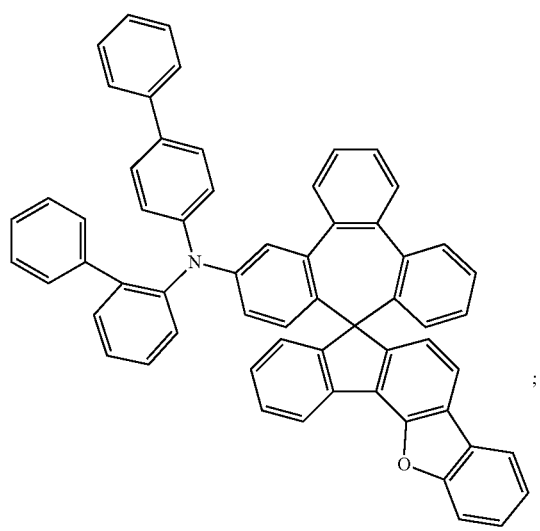
Compound 373
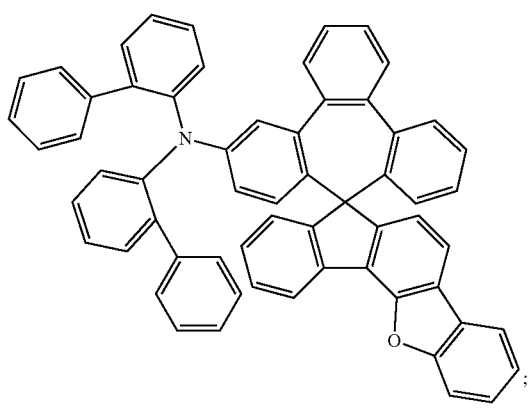

-continued
Compound 374
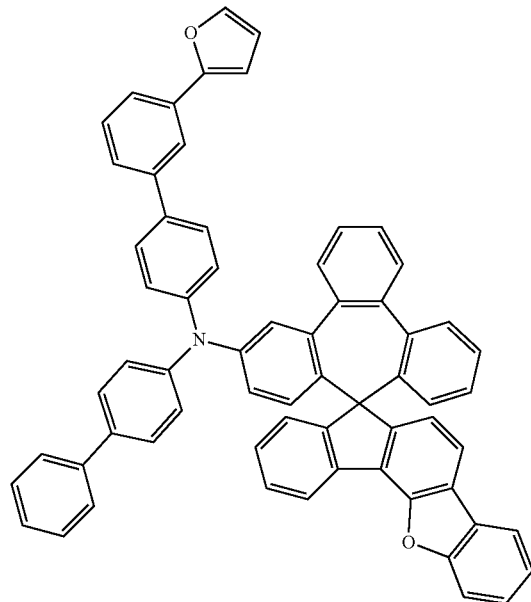
Compound 375
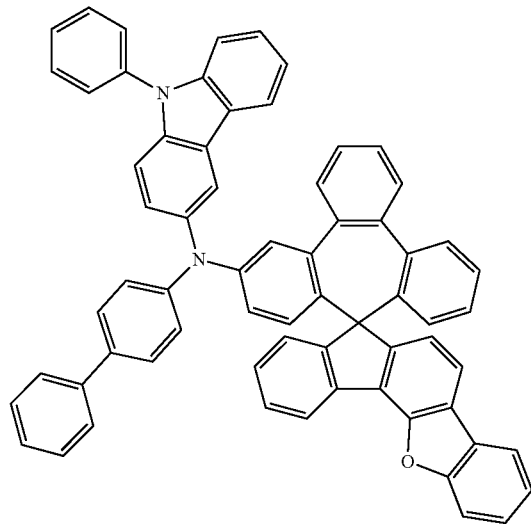
Compound 376
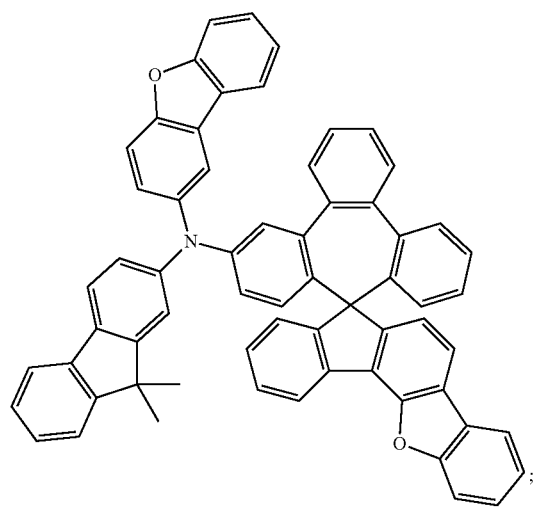
Compound 377
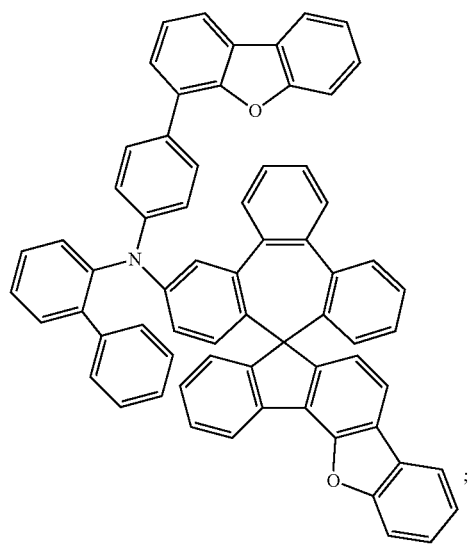

-continued
Compound 378
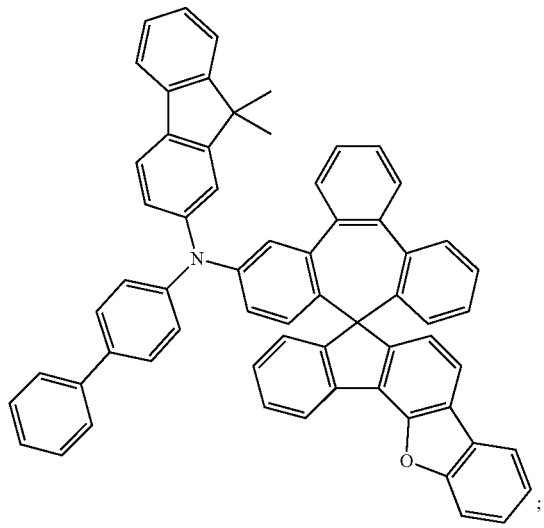
Compound 379
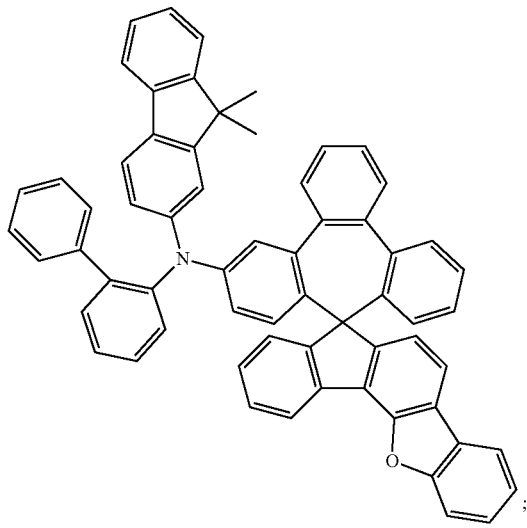
Compound 380
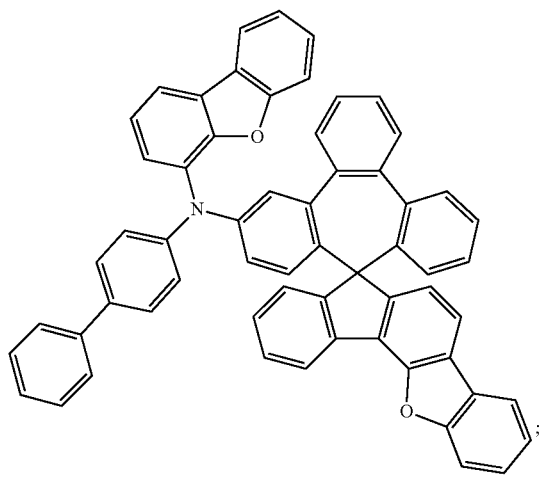
Compound 381
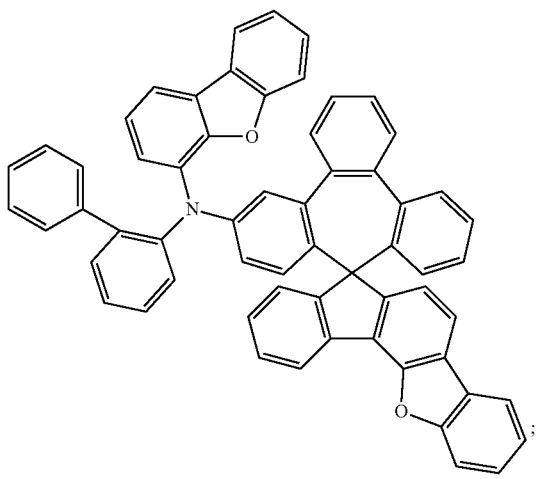
Compound 382
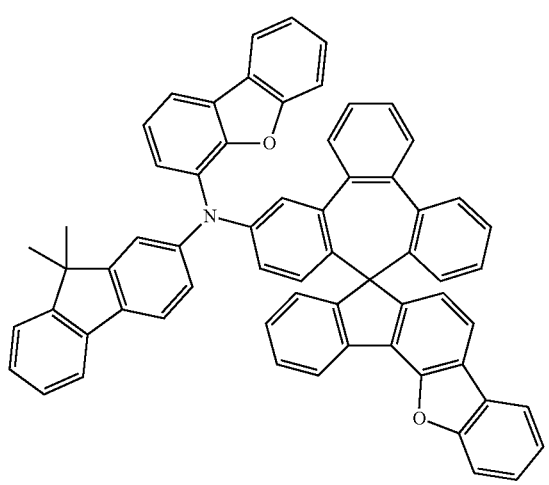
Compound 383
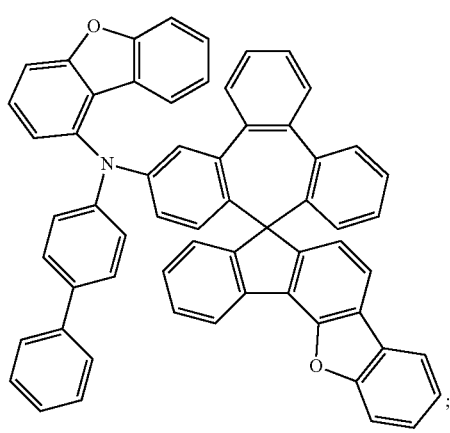

-continued
Compound 384
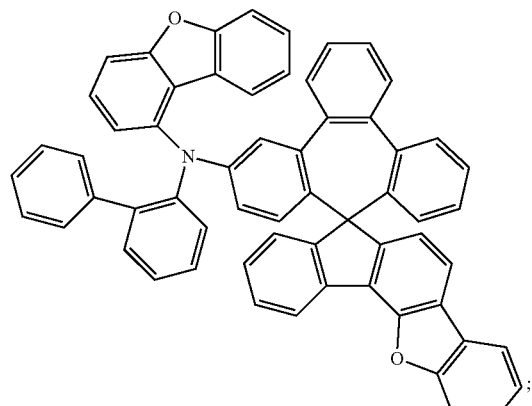
Compound 385
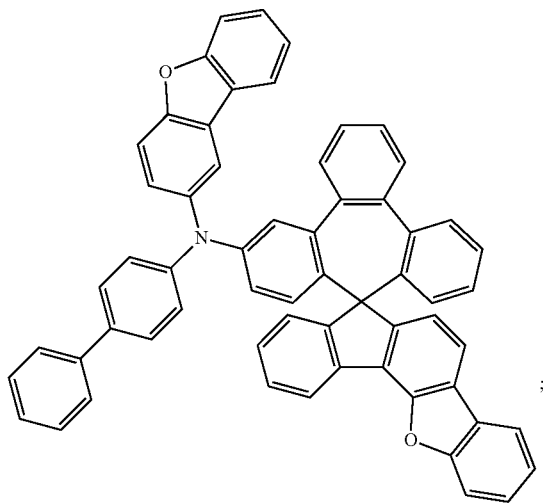
Compound 386
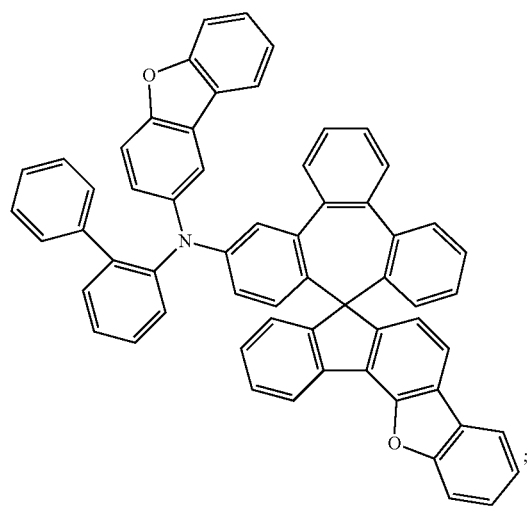
Compound 387
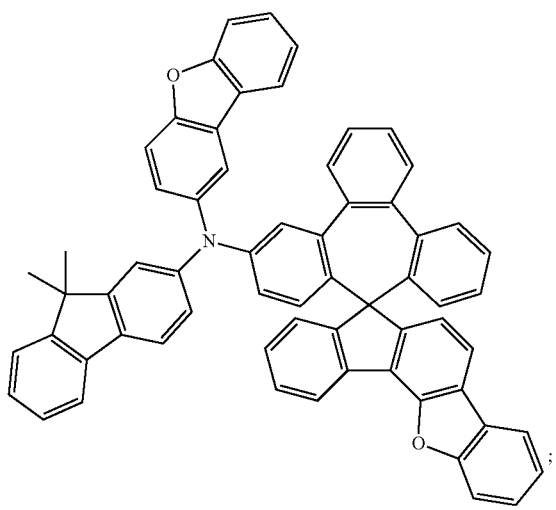
Compound 388
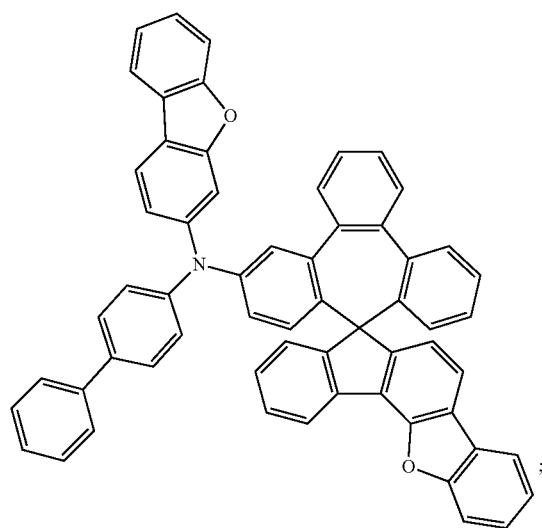
Compound 389
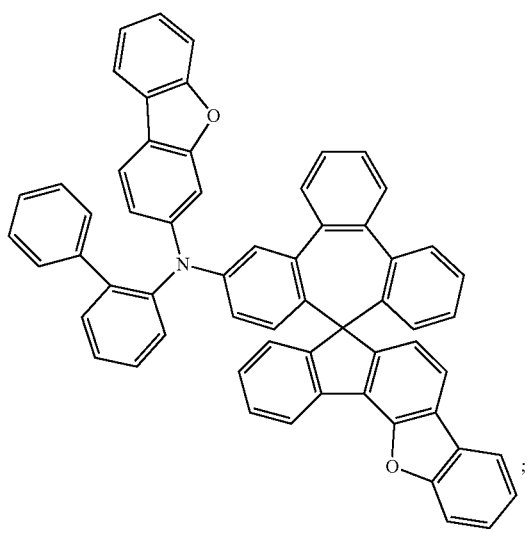

-continued
Compound 390
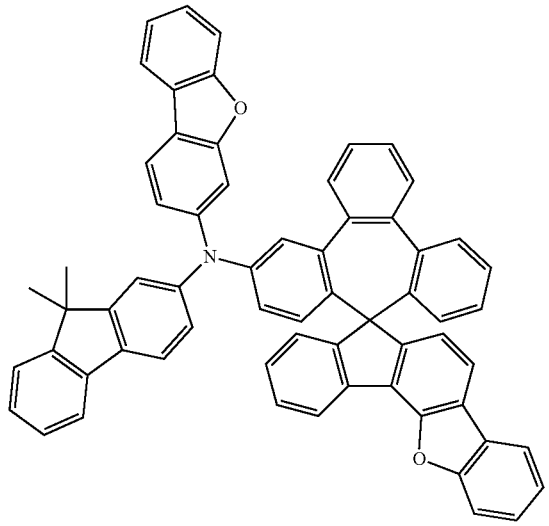
Compound 391
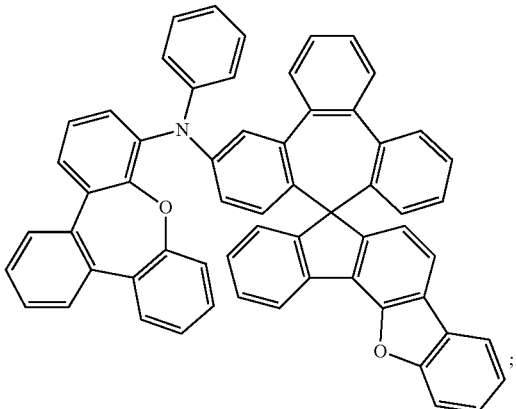
Compound 392
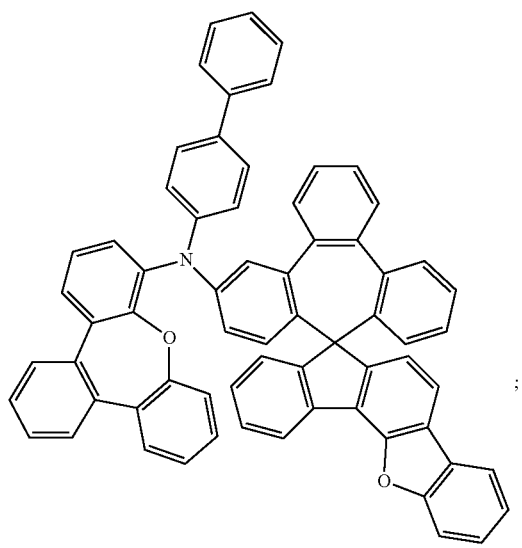
Compound 393
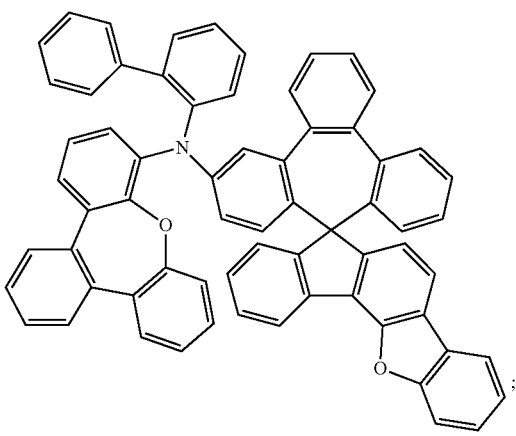
Compound 394
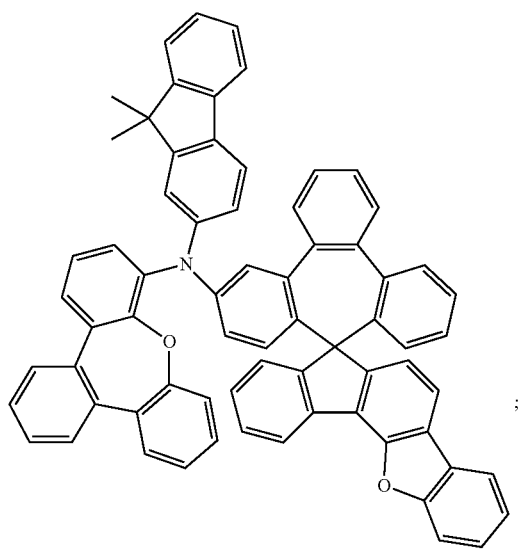
Compound 395
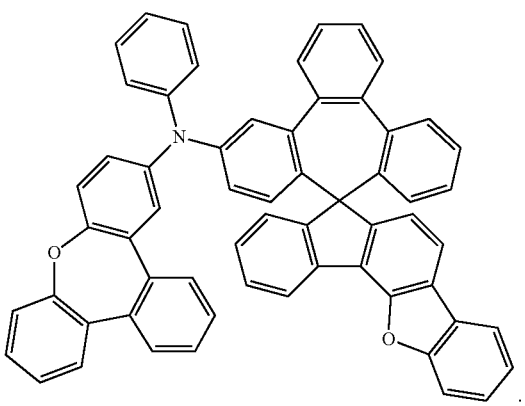

-continued
Compound 396
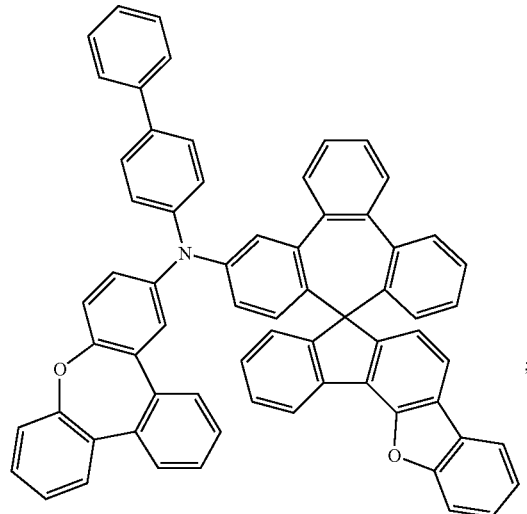
Compound 397
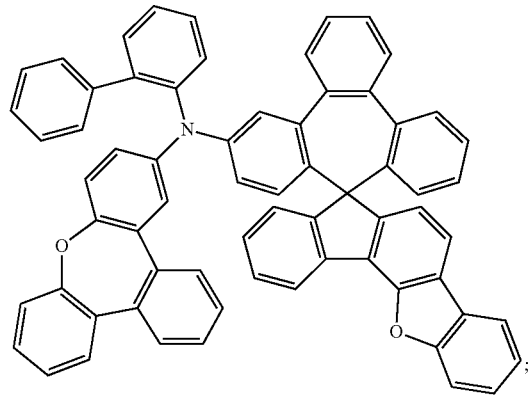
Compound 398
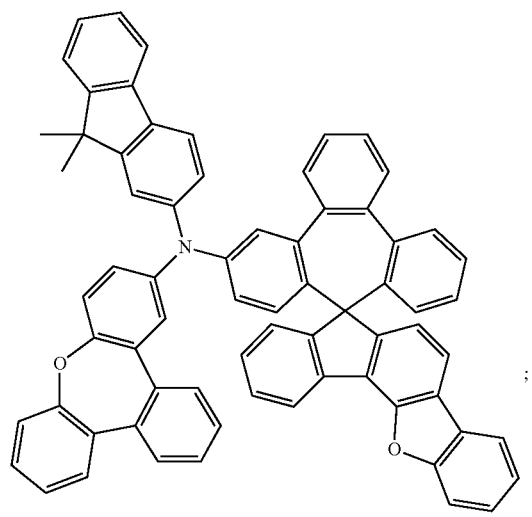
Compound 399
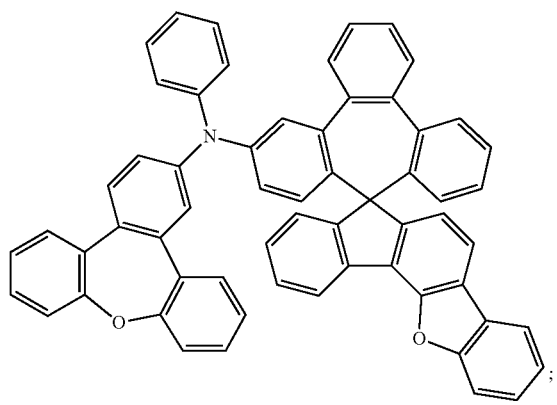
Compound 400
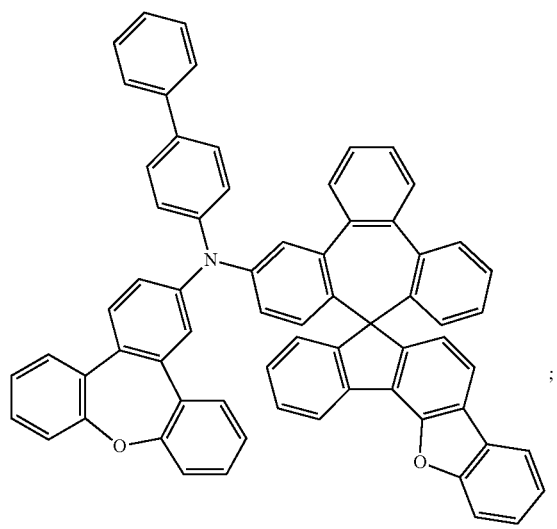
Compound 401
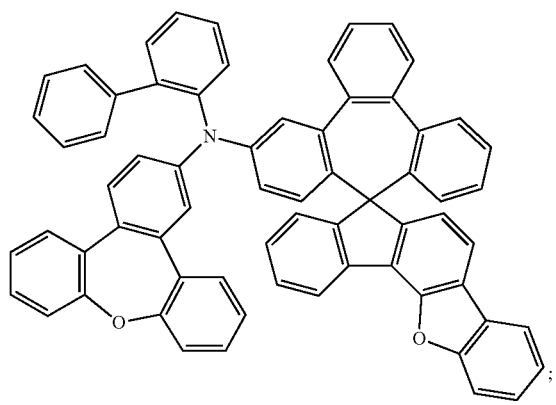

-continued
Compound 402
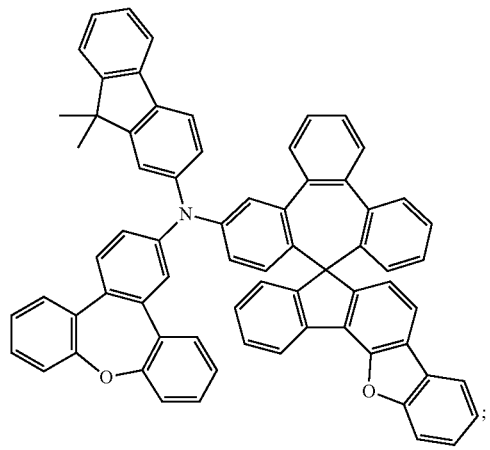
Compound 403
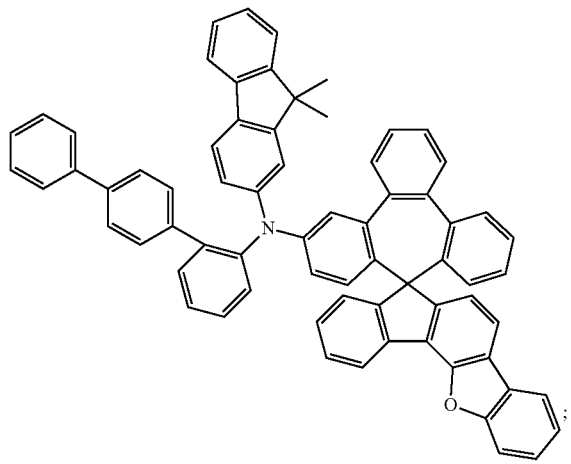
Compound 404
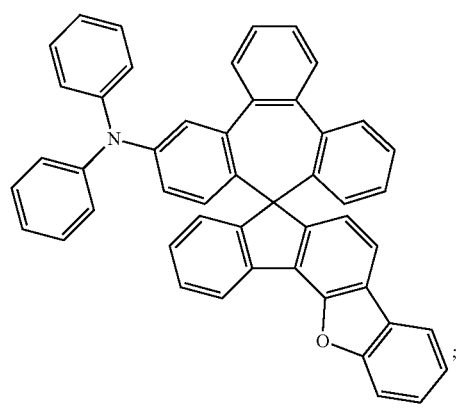
Compound 405
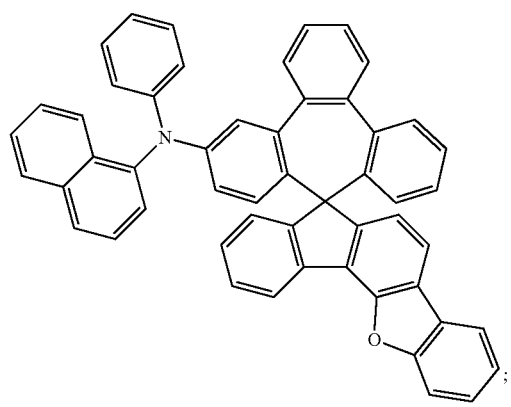
Compound 406
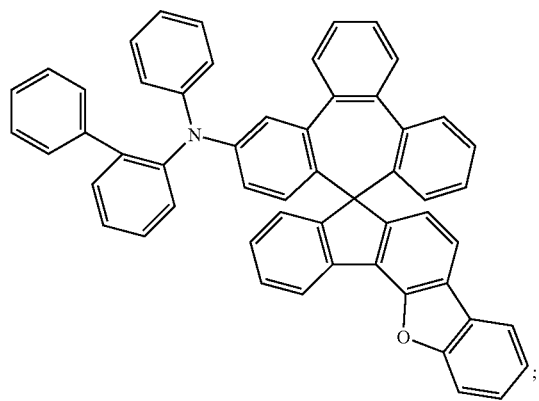
Compound 407
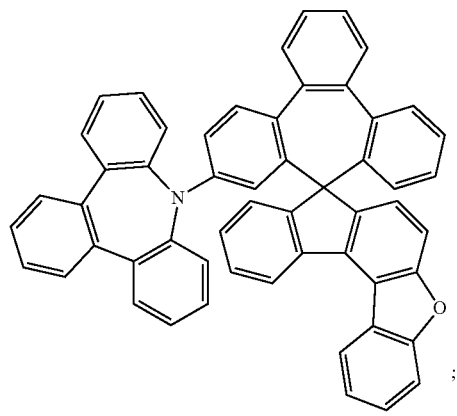

-continued
Compound 408
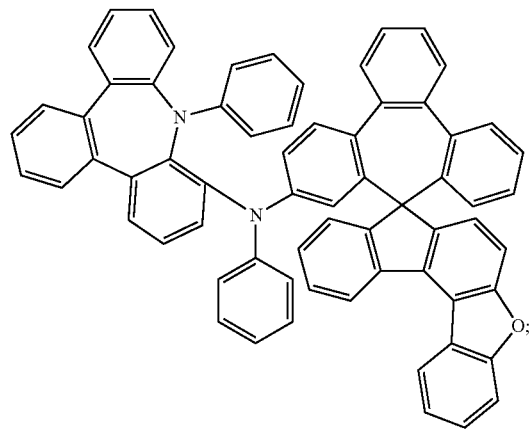
Compound 409
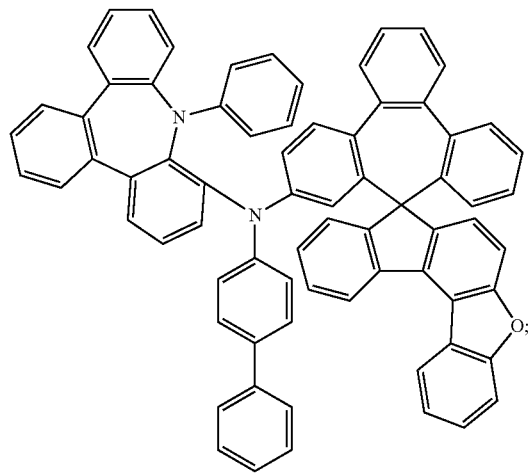
Compound 410
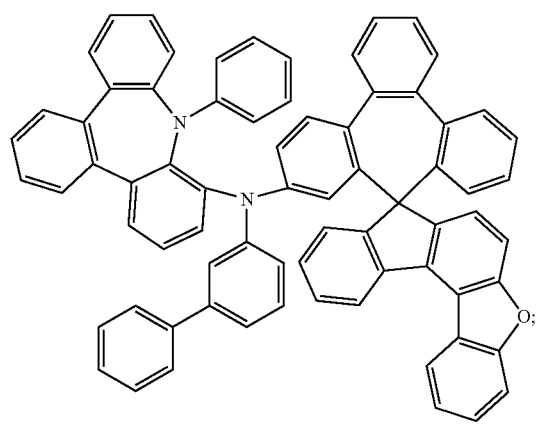
Compound 411
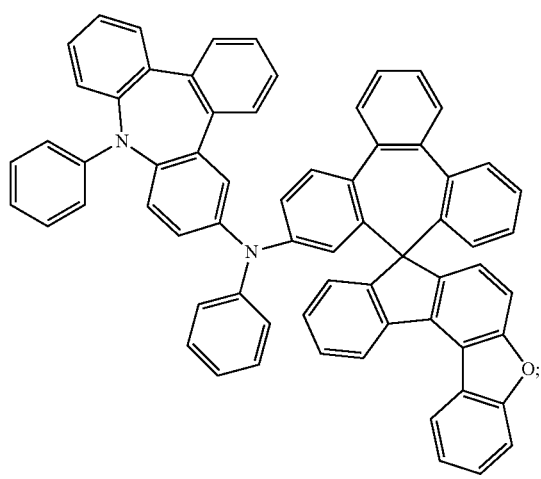
Compound 412
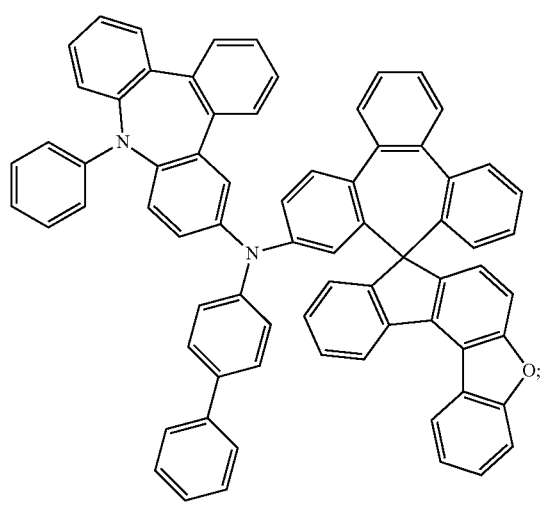
Compound 413
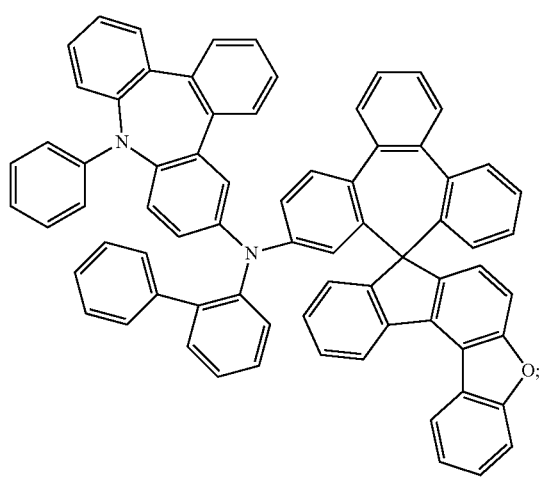

-continued
Compound 414
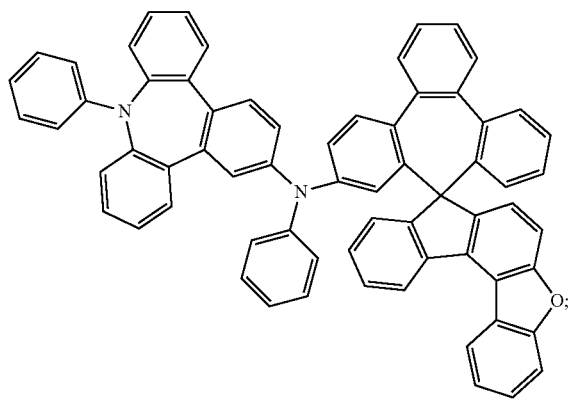
Compound 415
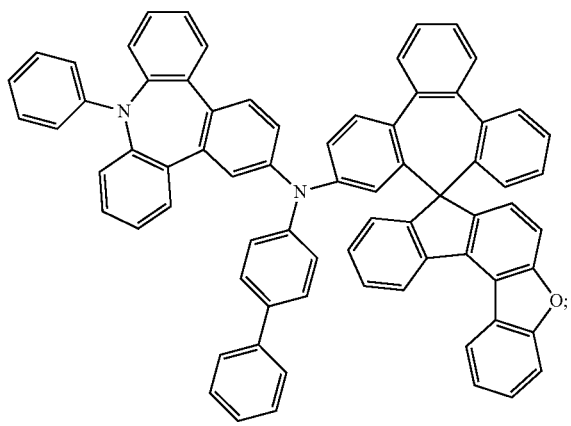
Compound 416
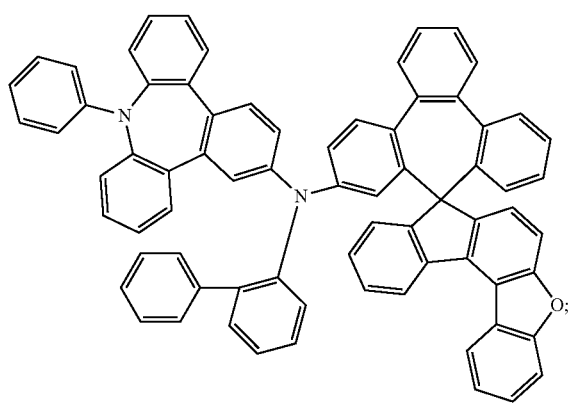
Compound 417
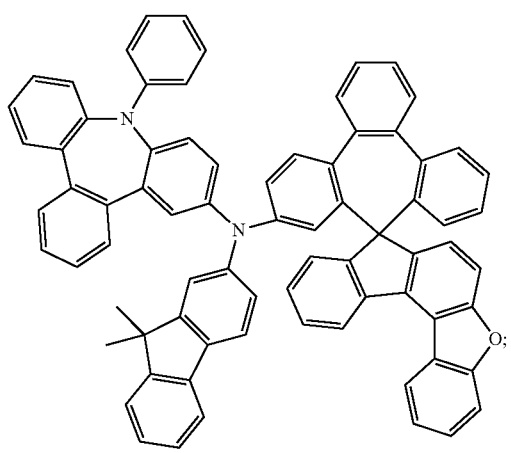
Compound 418
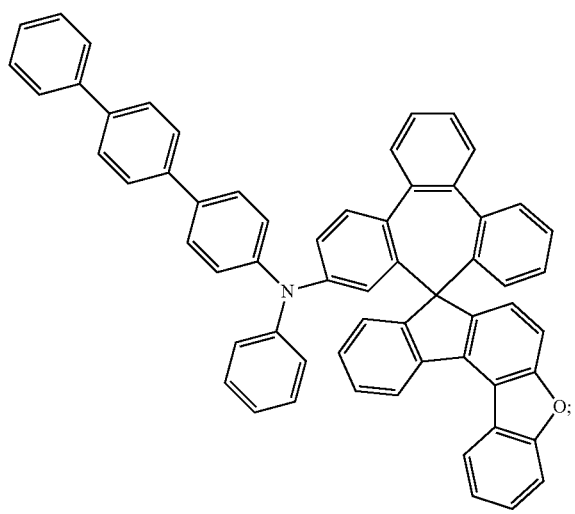
Compound 419
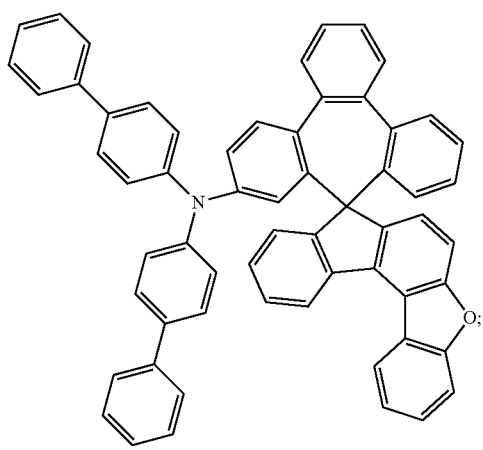

-continued
Compound 420
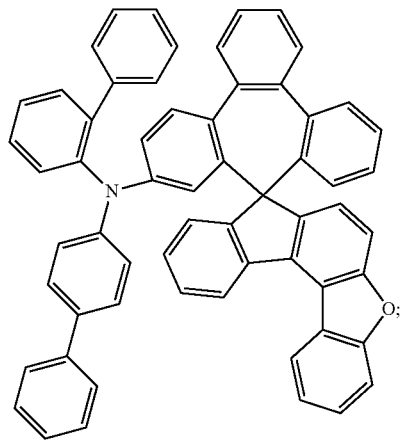
Compound 421
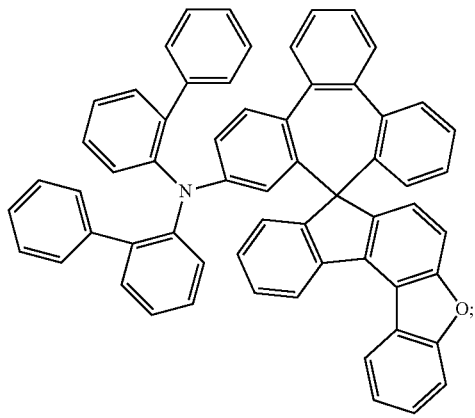
Compound 422
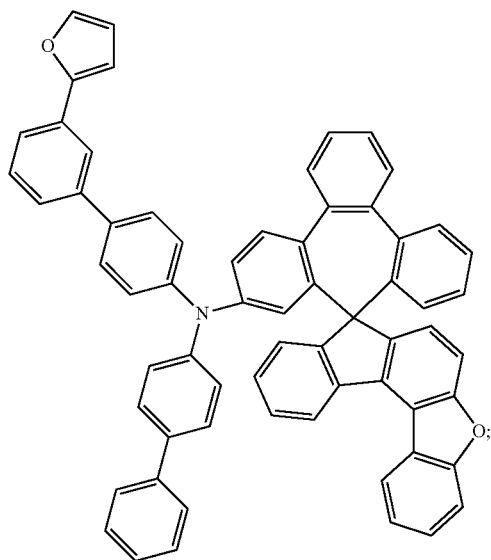
Compound 423
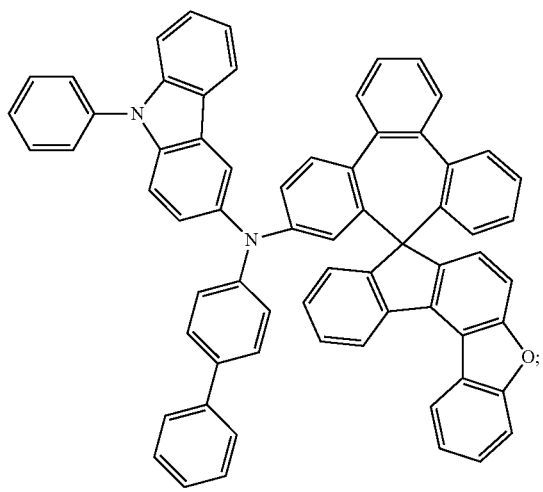
Compound 424
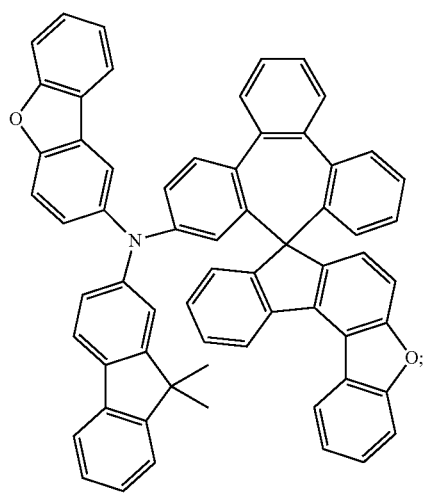
Compound 425
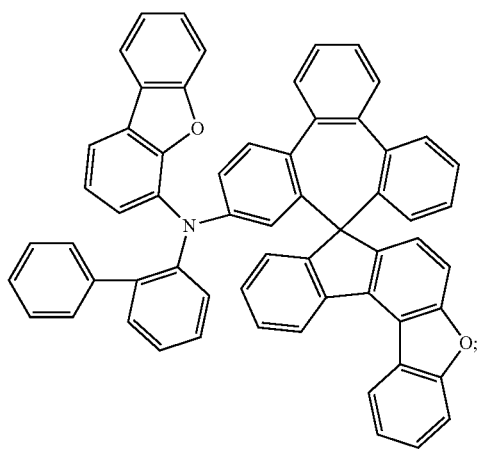

-continued
Compound 426
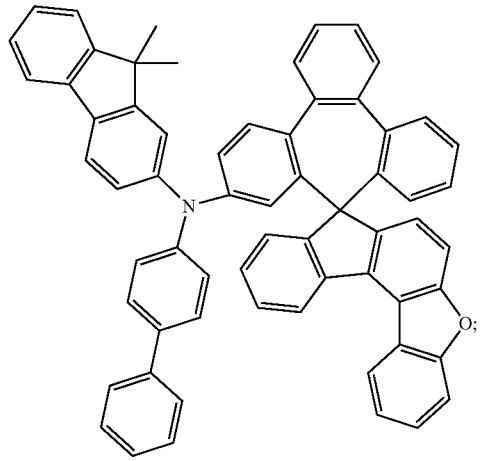
Compound 427
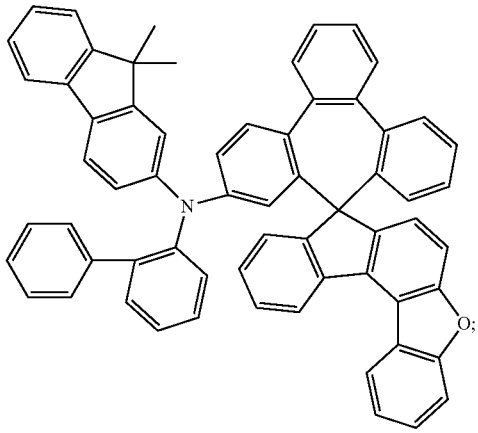
Compound 428
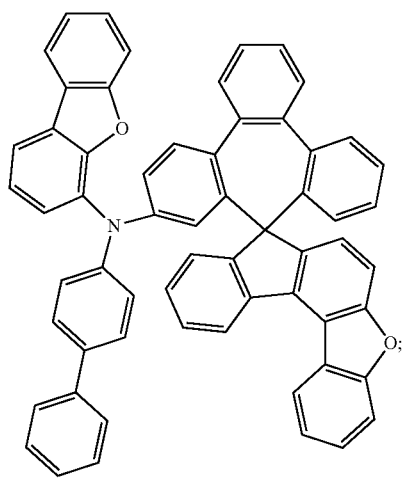
Compound 429
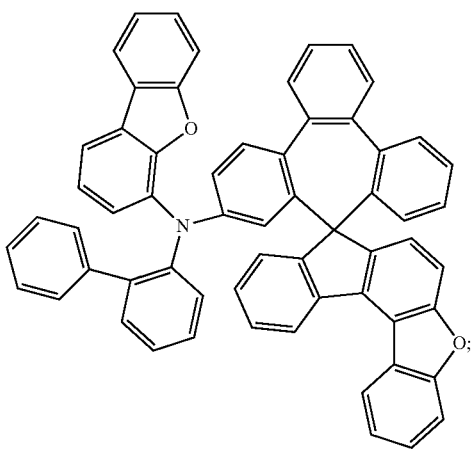
Compound 430
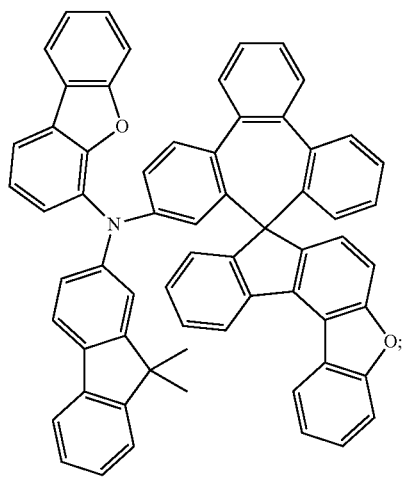
Compound 431
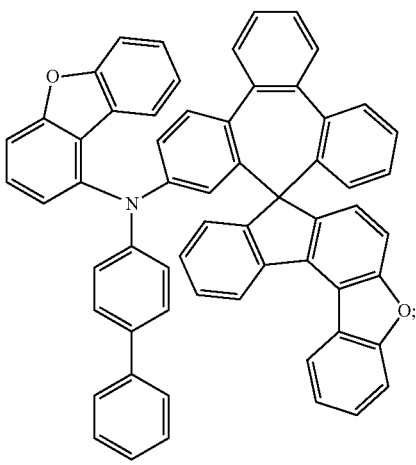

-continued
Compound 432
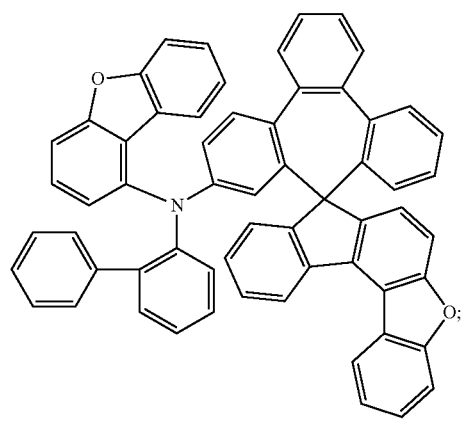
Compound 433
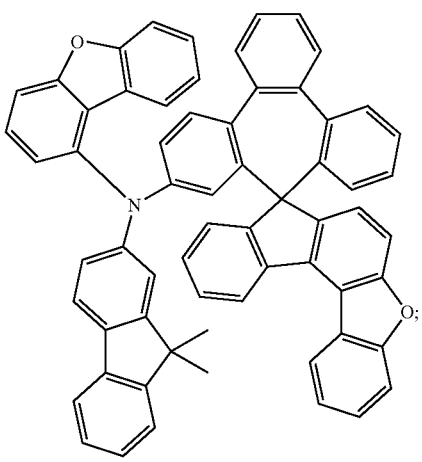
Compound 434
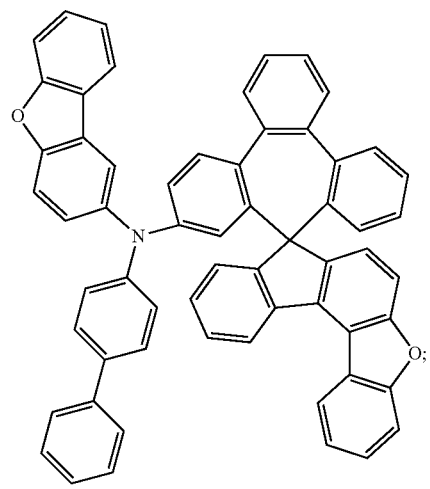
Compound 435
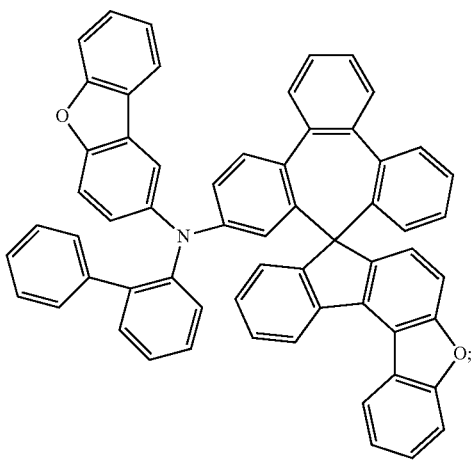
Compound 436
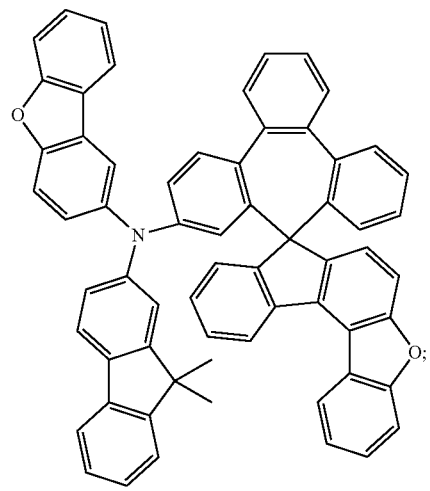
Compound 437
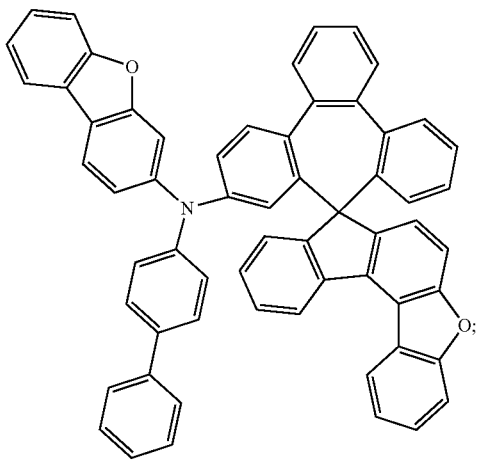

-continued
Compound 438
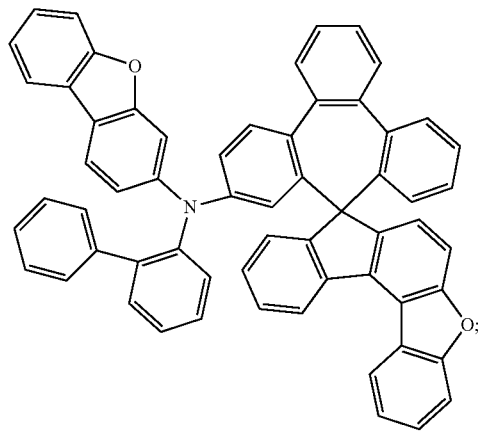
Compound 439
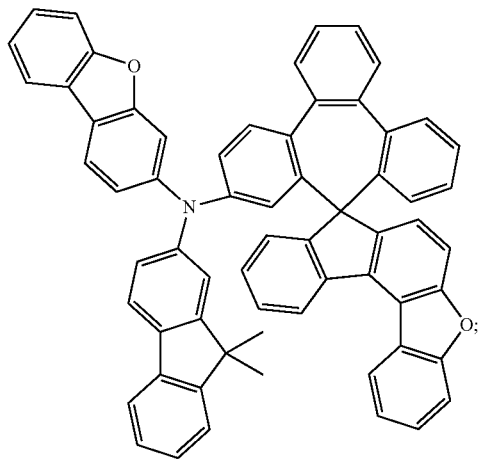
Compound 440
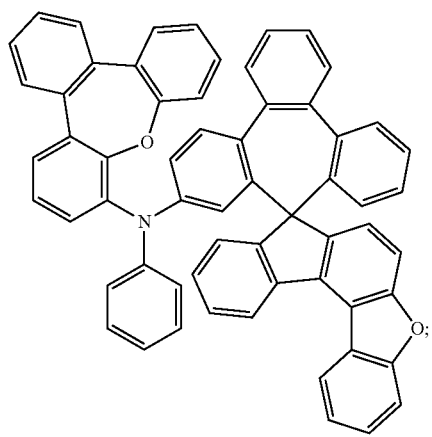
Compound 441
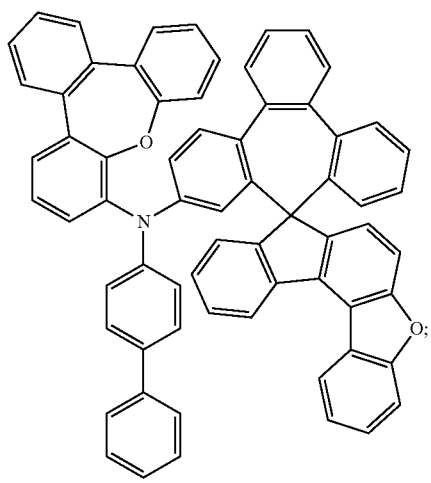
Compound 442
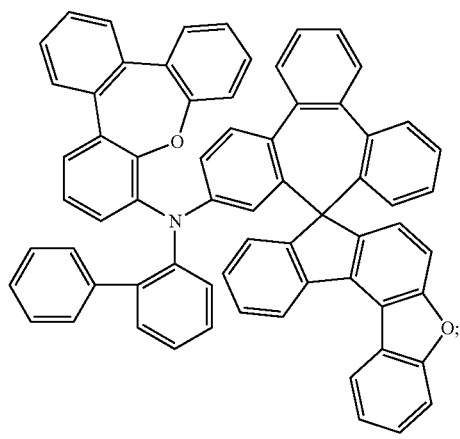
Compound 443
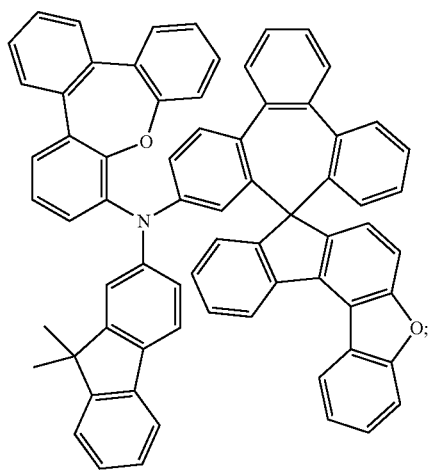

Compound 444
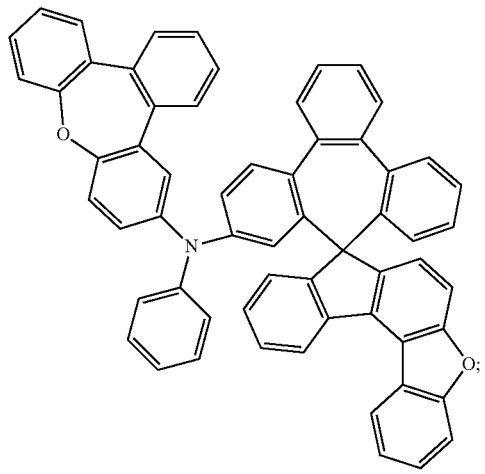
Compound 445
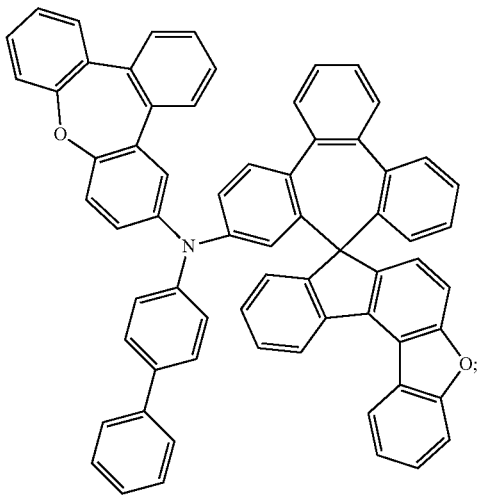
Compound 446
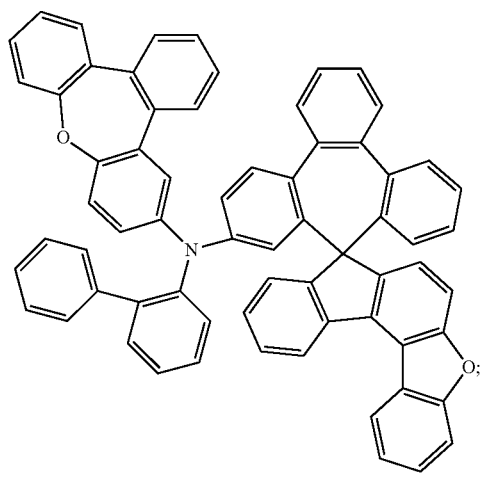
Compound 447
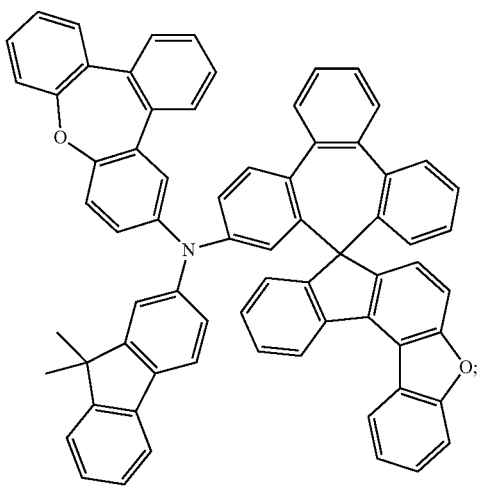
Compound 448
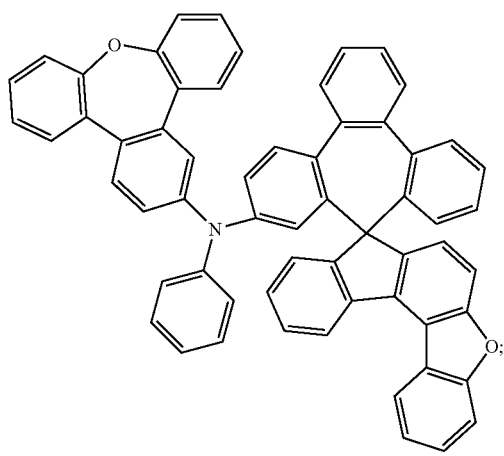
Compound 449
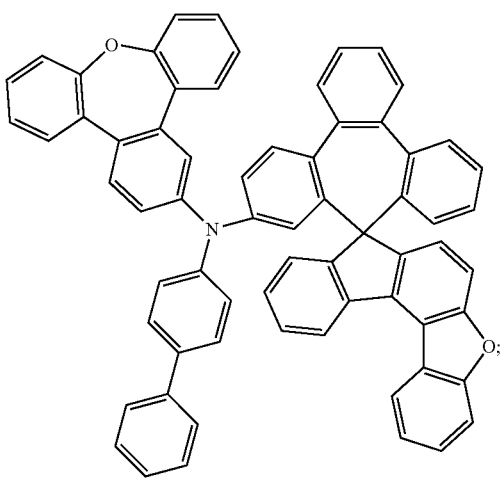

-continued
Compound 450
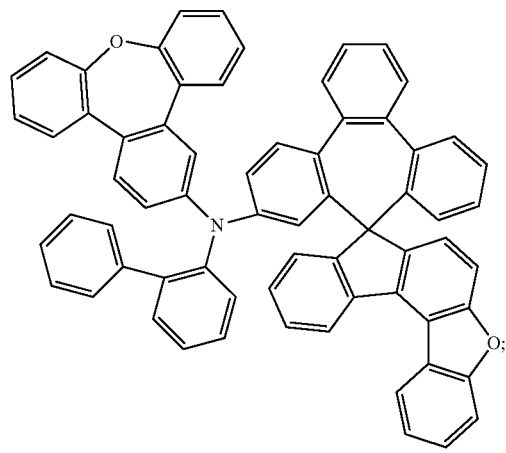
Compound 451
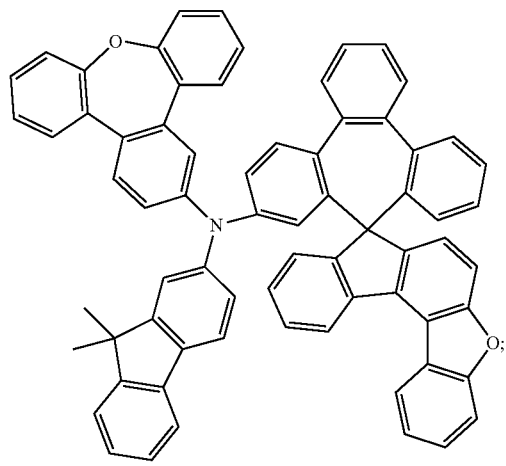
Compound 452
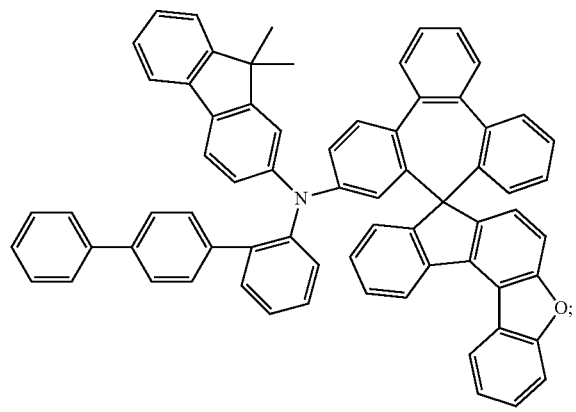
Compound 453
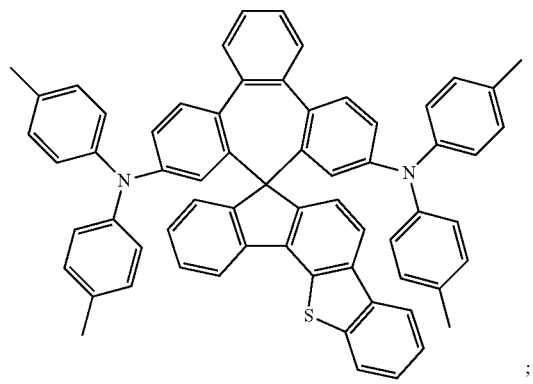
Compound 454
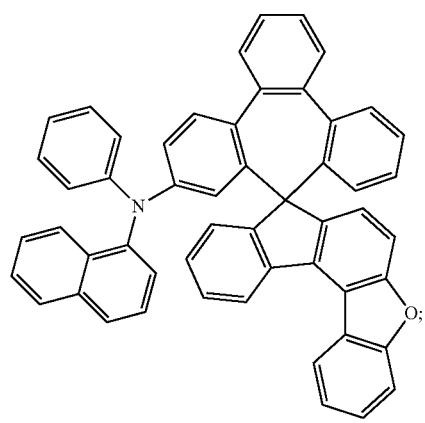
Compound 455
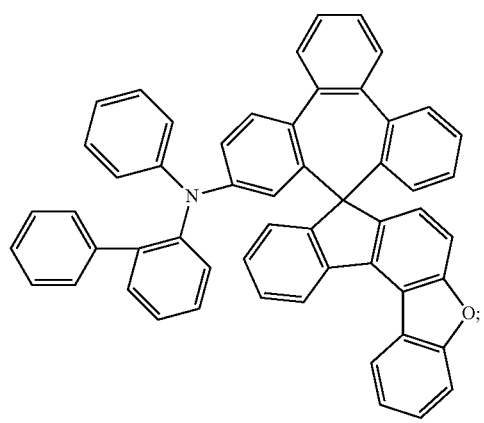

-continued
Compound 456
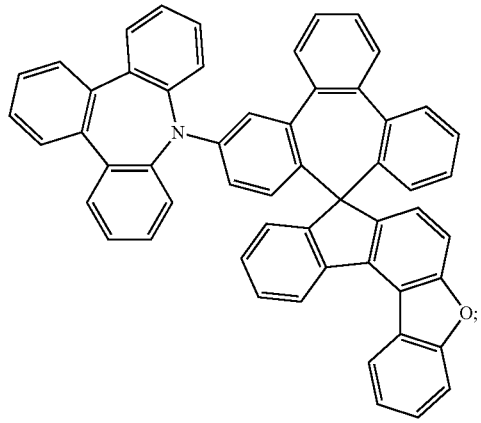
Compound 457
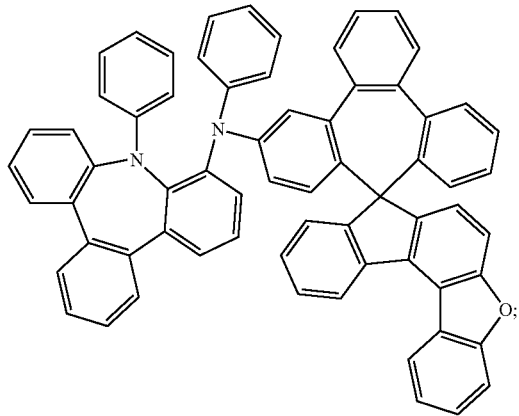
Compound 458
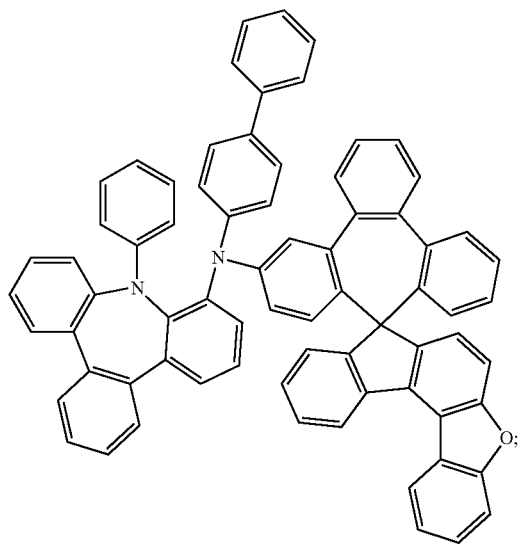
Compound 459
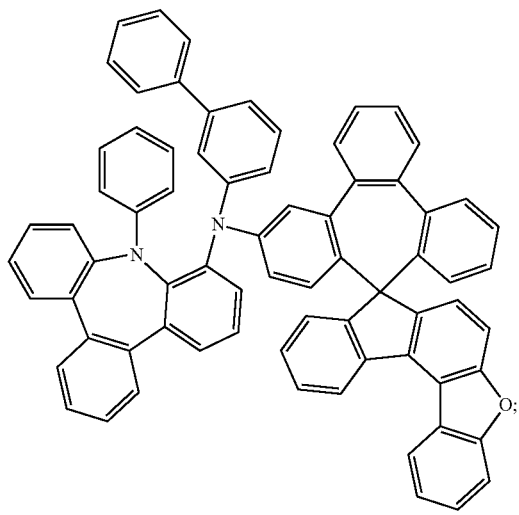
Compound 460
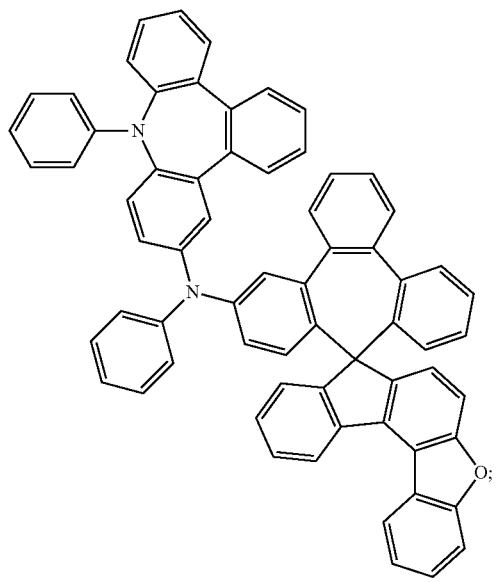
Compound 461
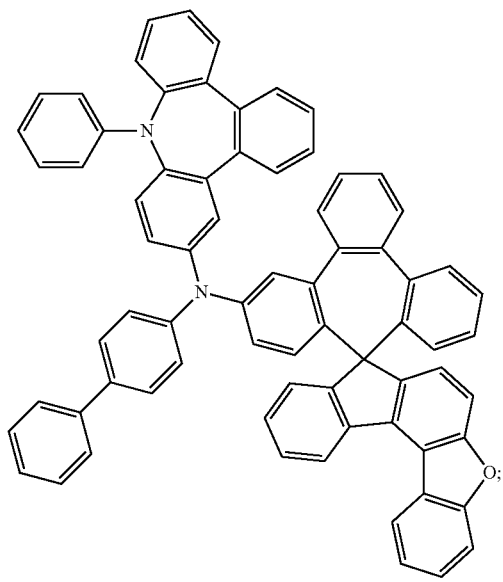

-continued
Compound 462
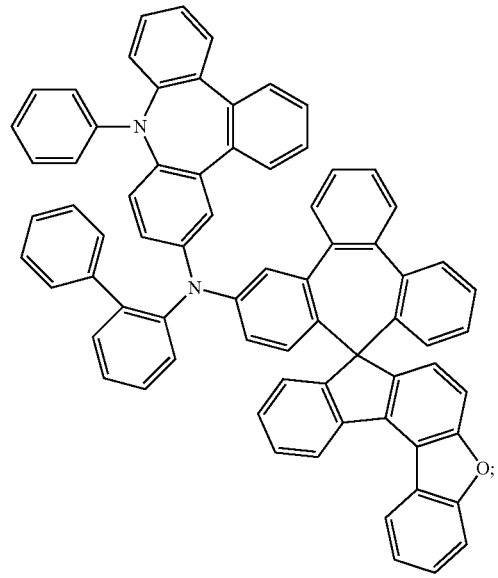
Compound 463
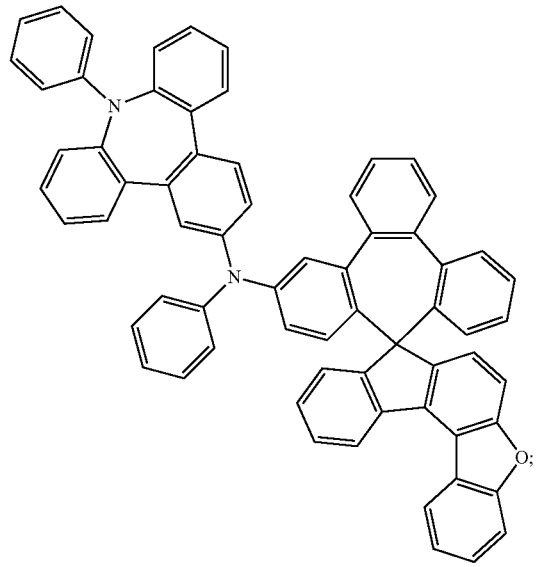
Compound 464
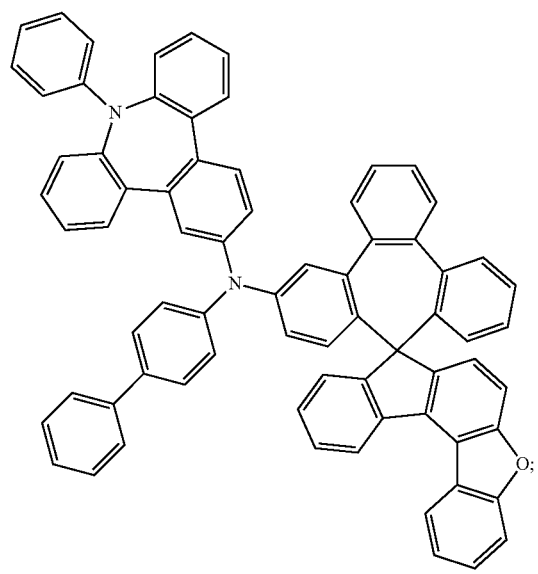
Compound 465
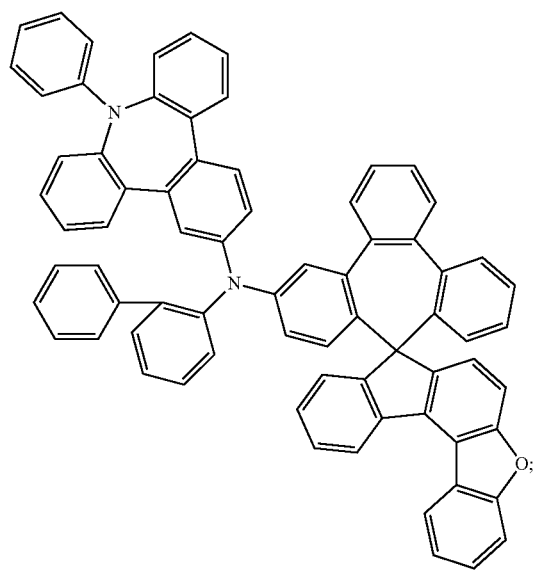

-continued
Compound 466
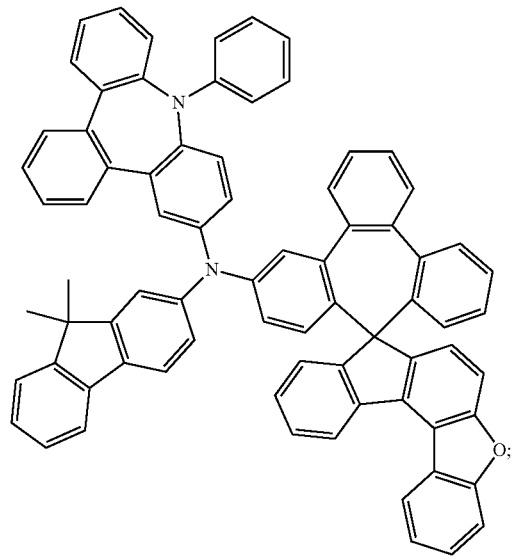
Compound 467
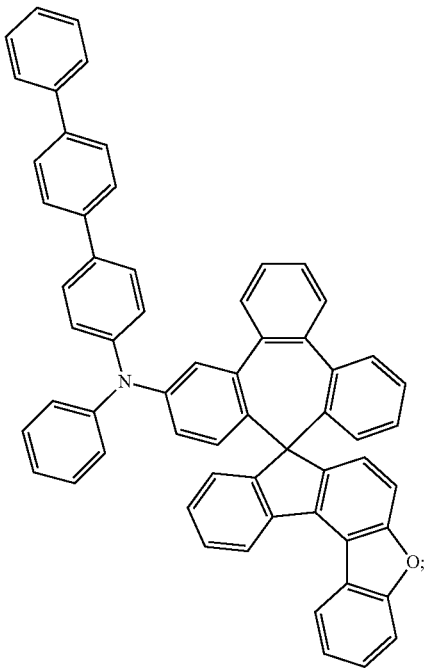
Compound 468
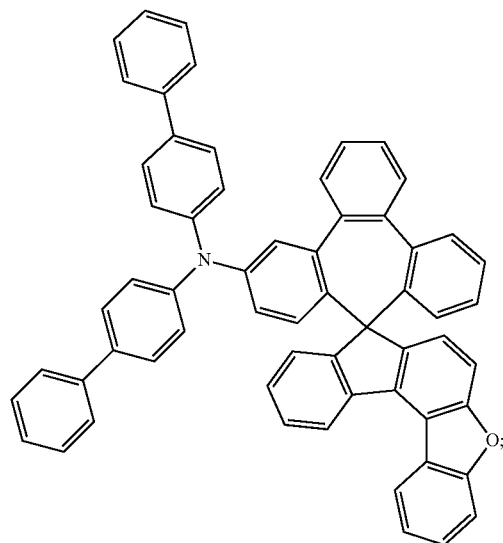
Compound 469
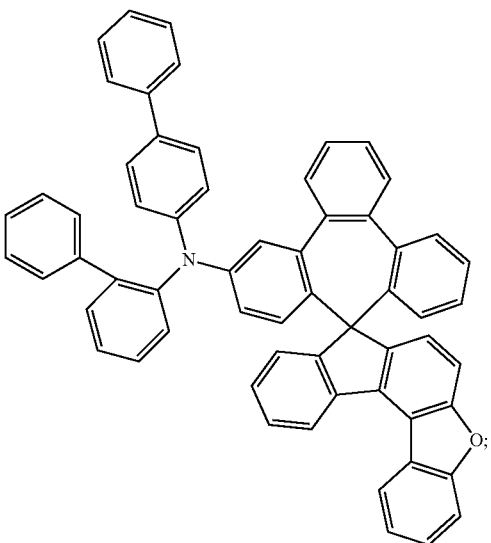

Compound 470
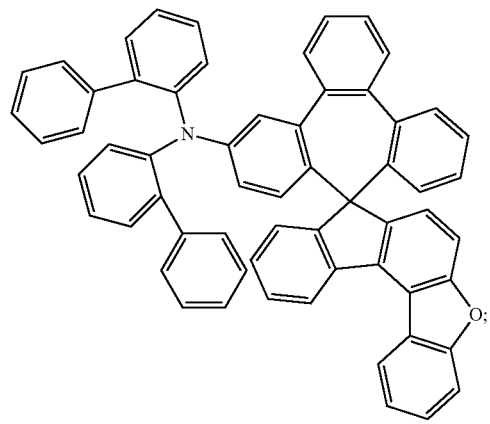
Compound 471
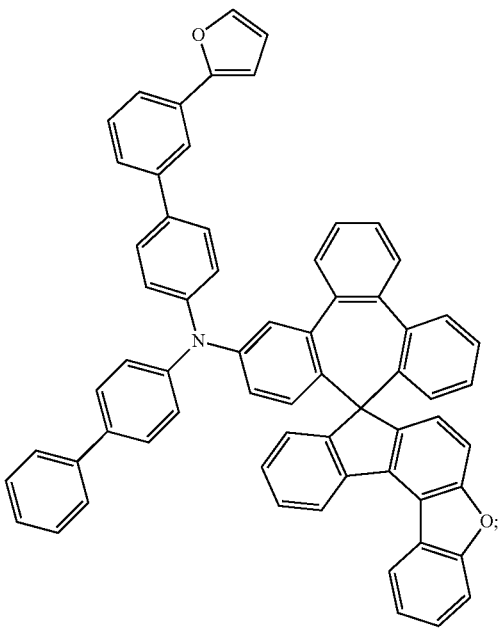
Compound 472
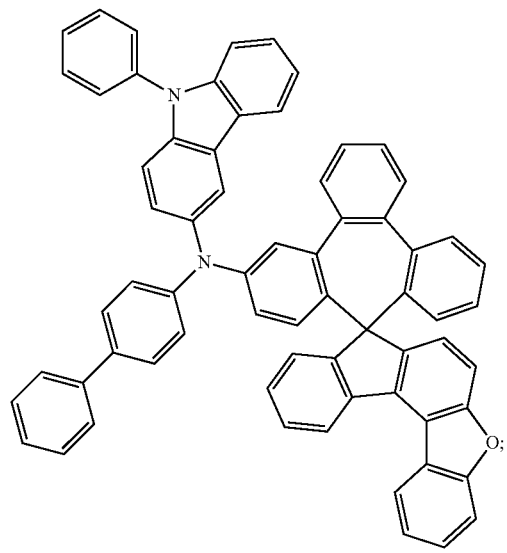
Compound 473
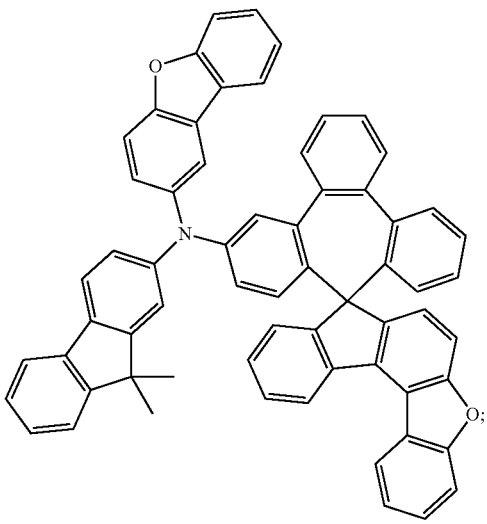

-continued
Compound 474
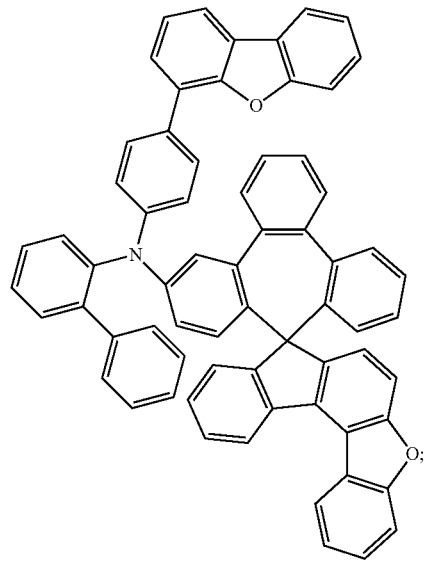
Compound 475
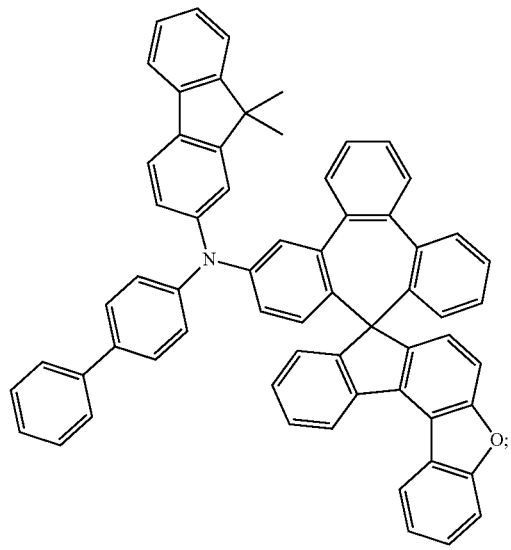
Compound 476
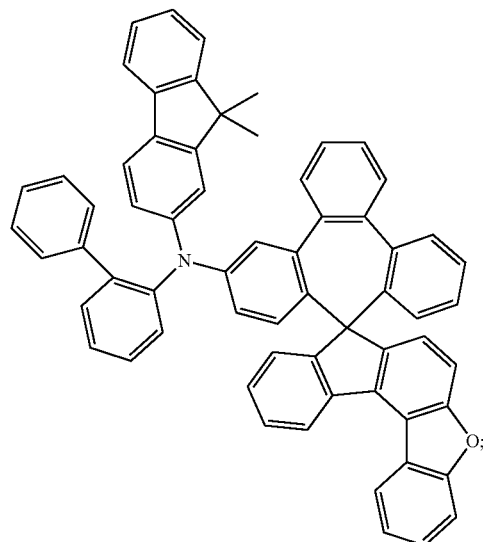
Compound 477
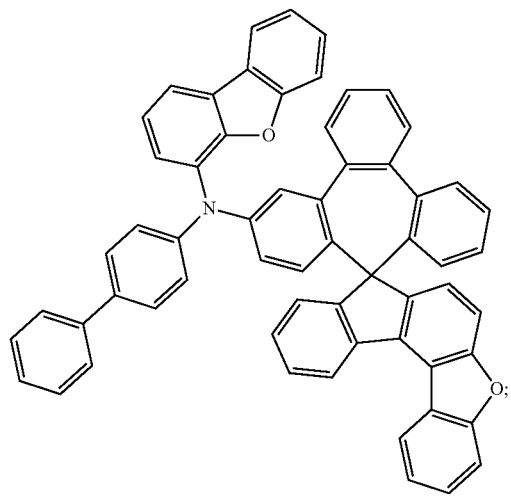
Compound 478
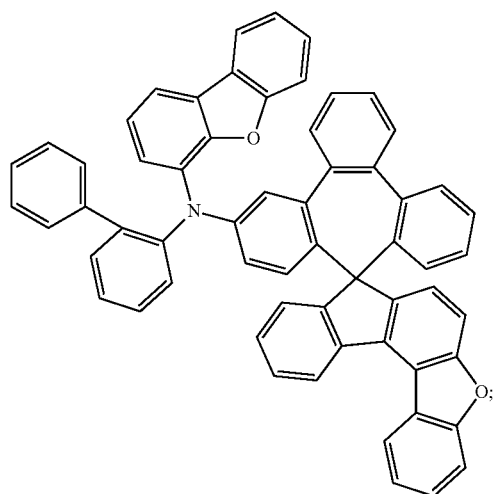
Compound 479
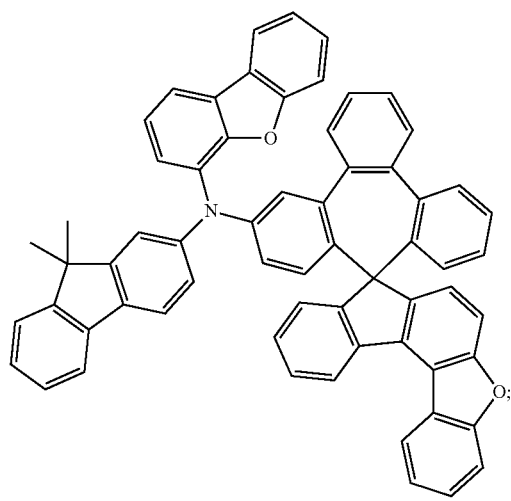

Compound 480
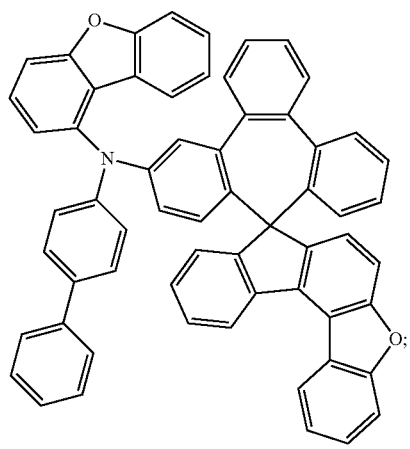
Compound 481
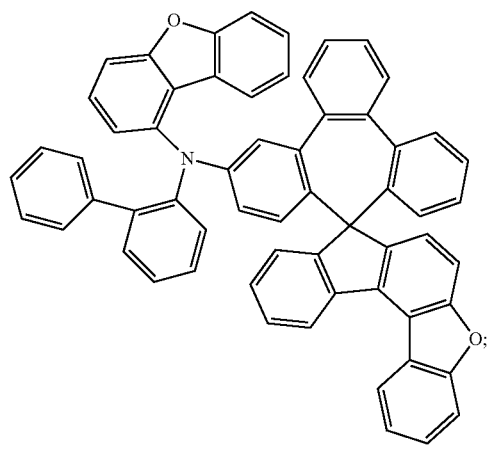
Compound 482
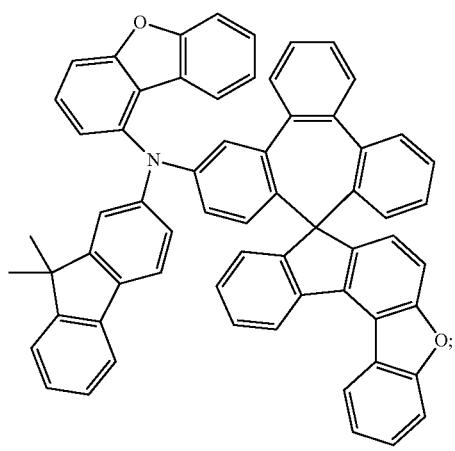
Compound 483
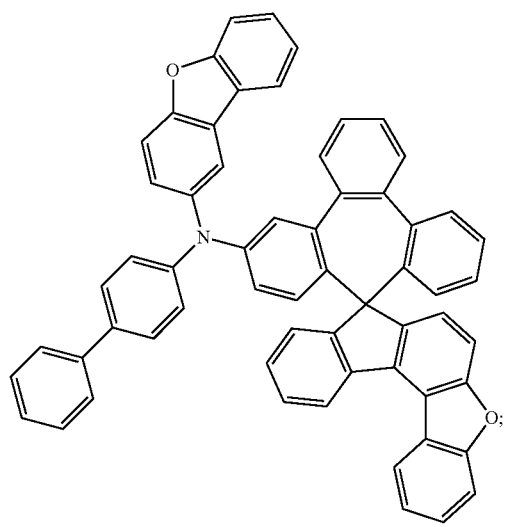
Compound 484
Compound 485
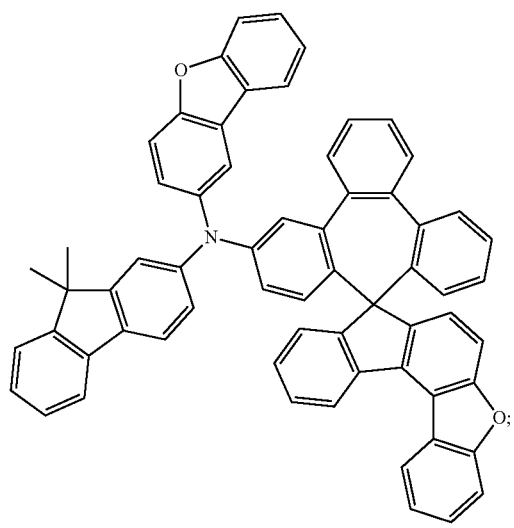

Compound 486
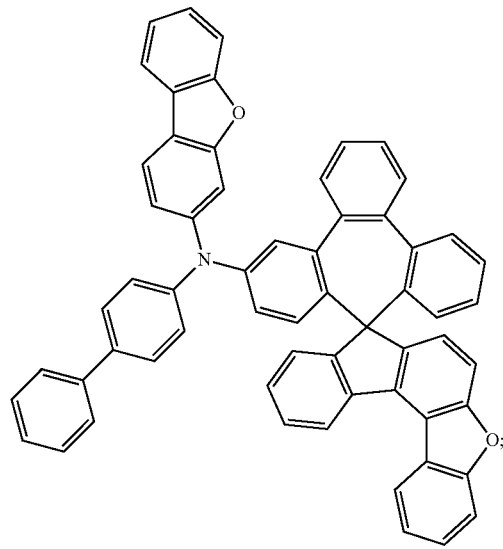
Compound 487
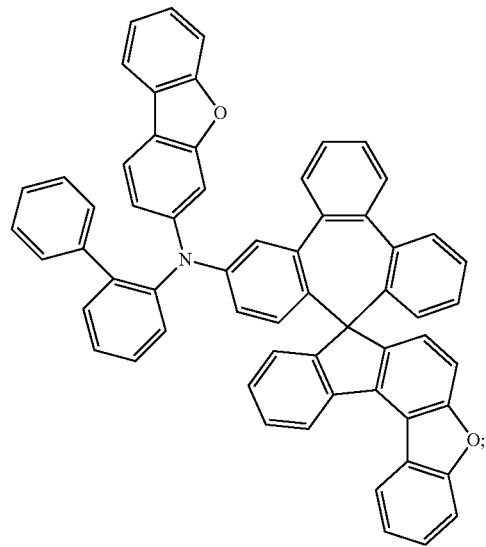
Compound 488
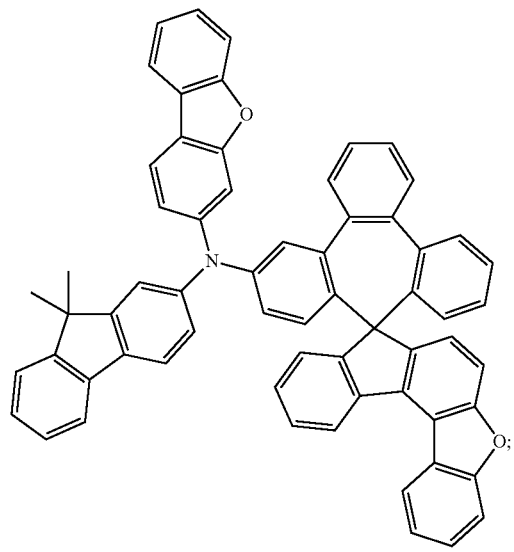
Compound 489
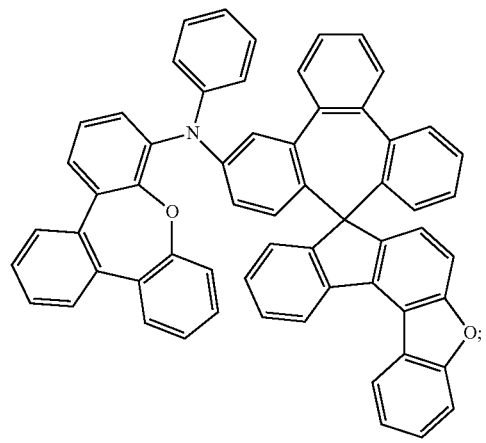

-continued
Compound 490
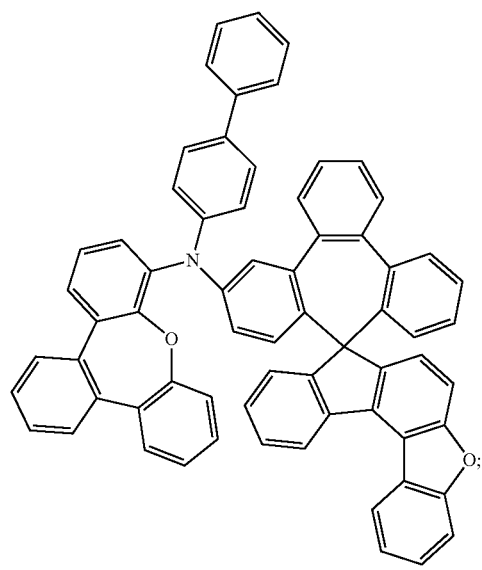
Compound 491
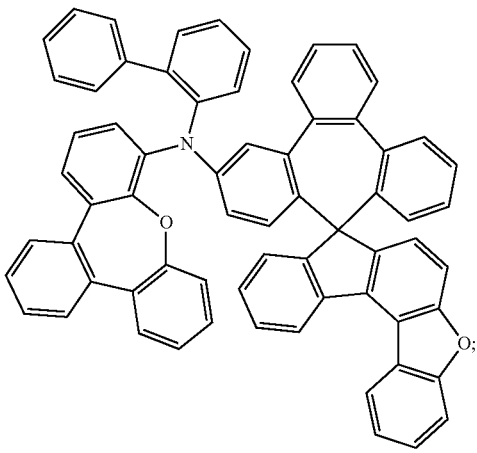
Compound 492
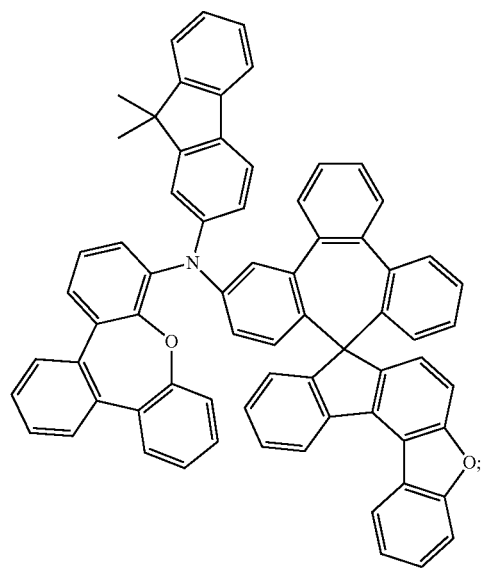
Compound 493
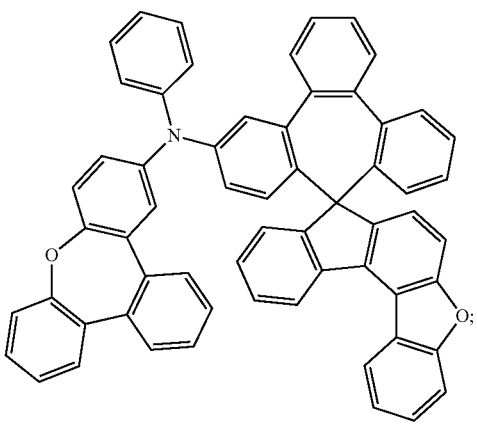

Compound 494
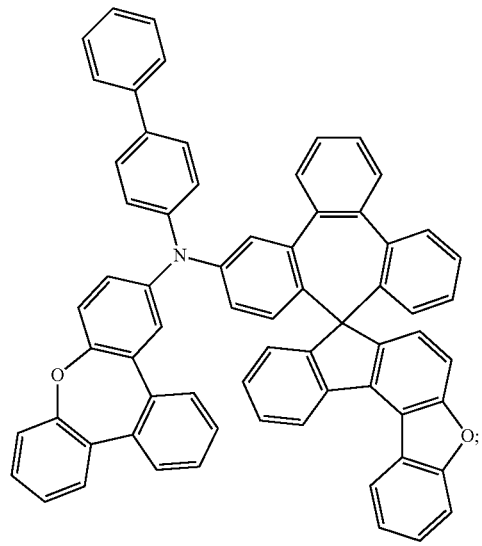
Compound 495
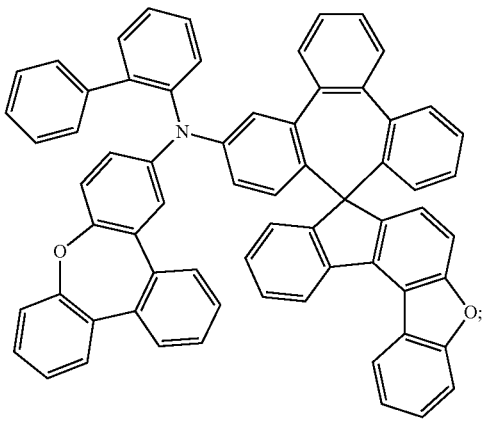
Compound 496
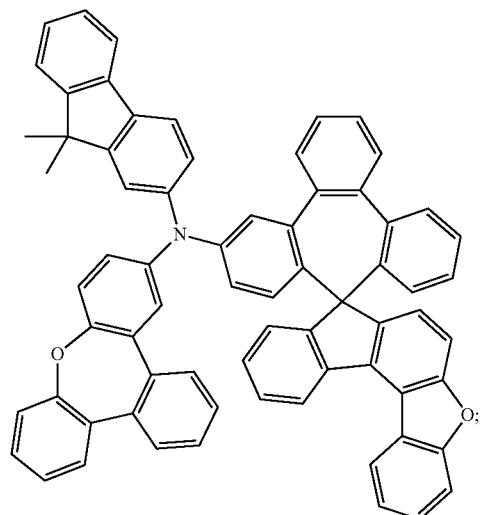
Compound 497
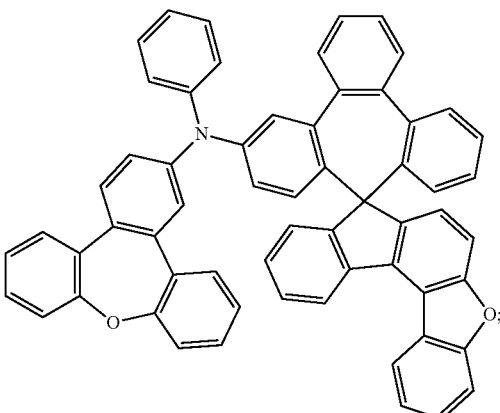
Compound 498
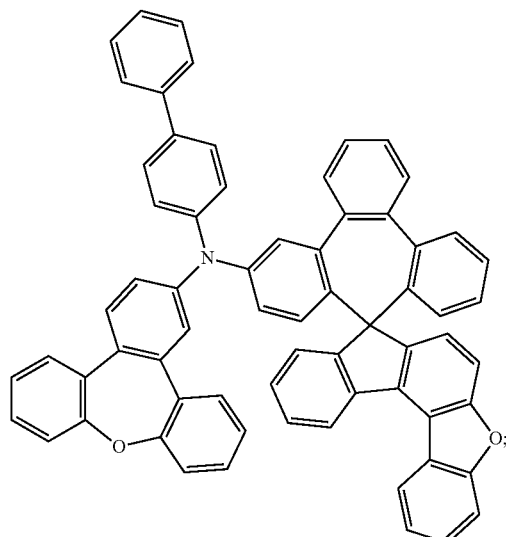
Compound 499
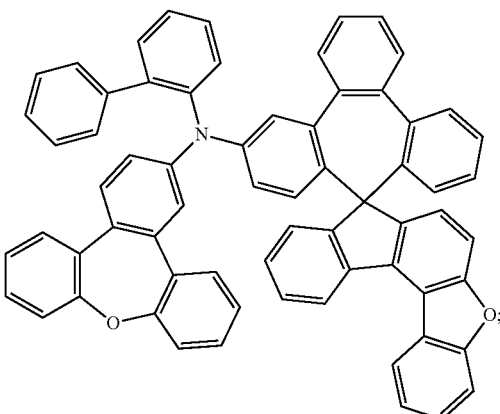

-continued
Compound 500
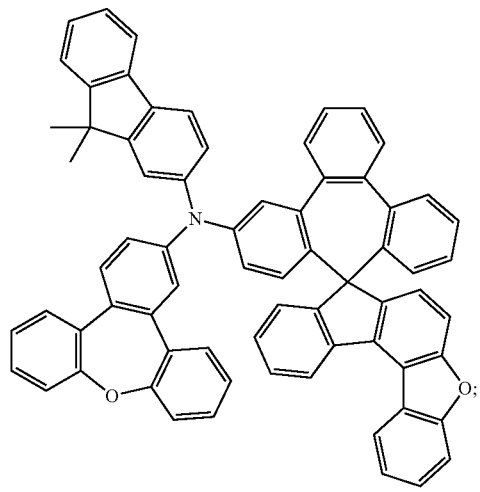
Compound 501
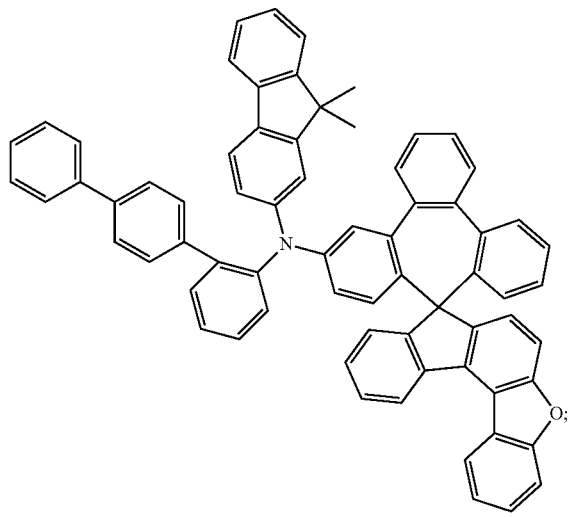
Compound 502
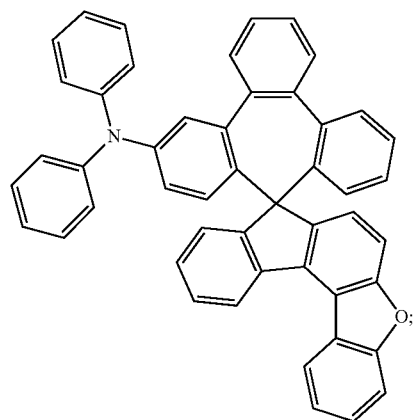
Compound 503
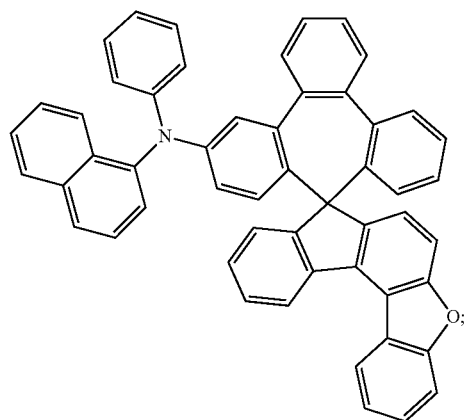
Compound 504
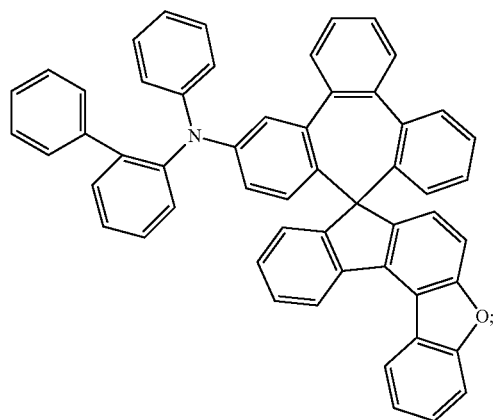
Compound 505
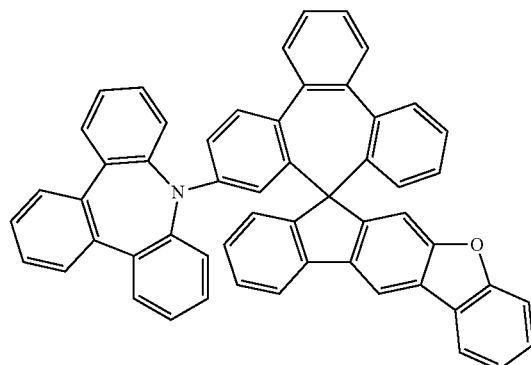

-continued
Compound 506
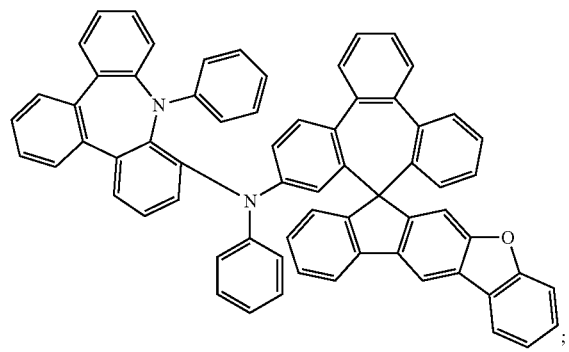
Compound 507
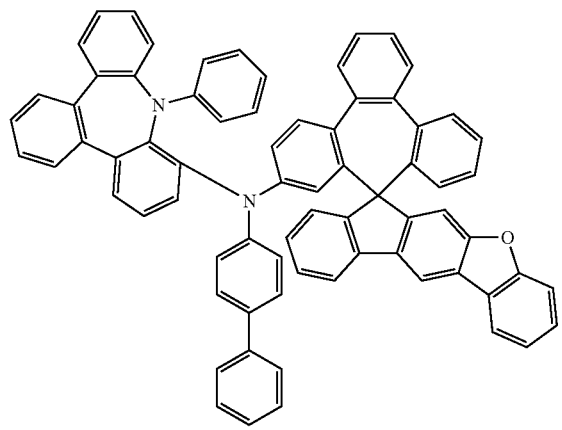
Compound 508
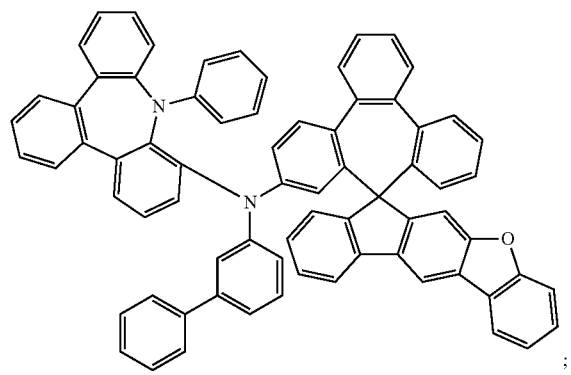
Compound 509
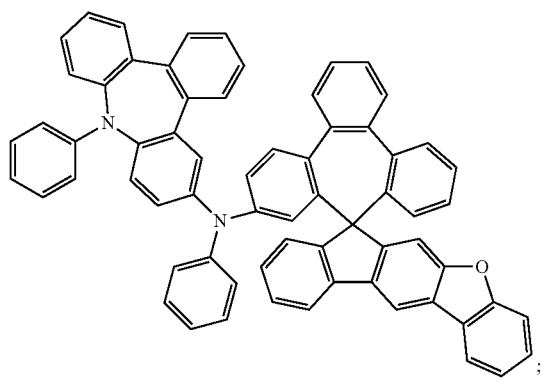
Compound 510
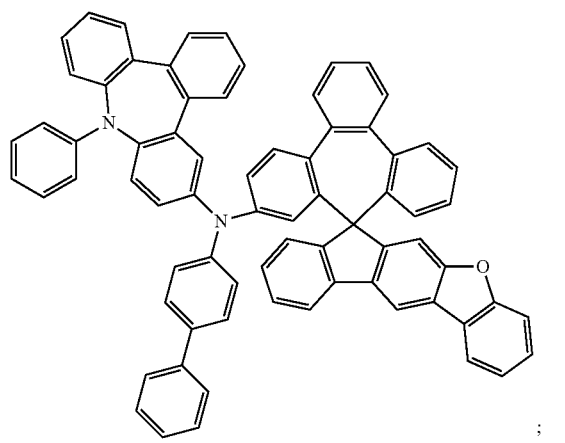
Compound 511
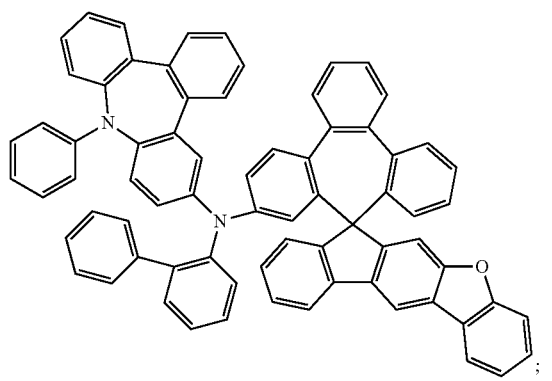

-continued
Compound 512
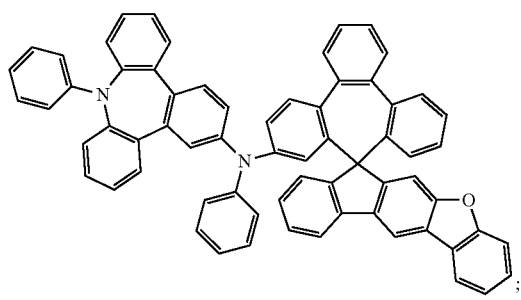
Compound 513
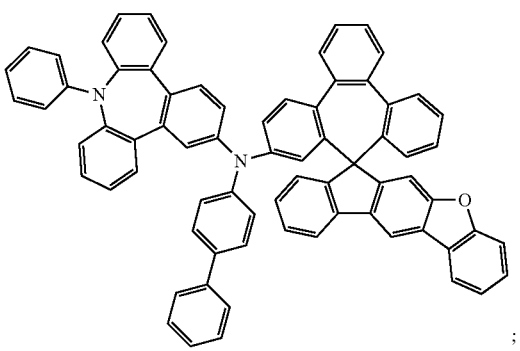
Compound 514
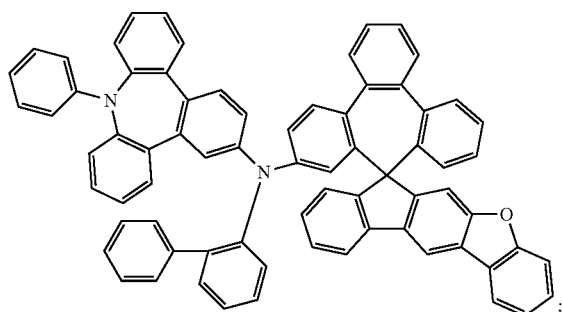
Compound 515
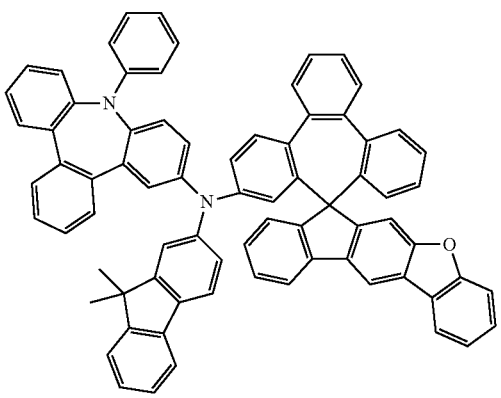
Compound 516
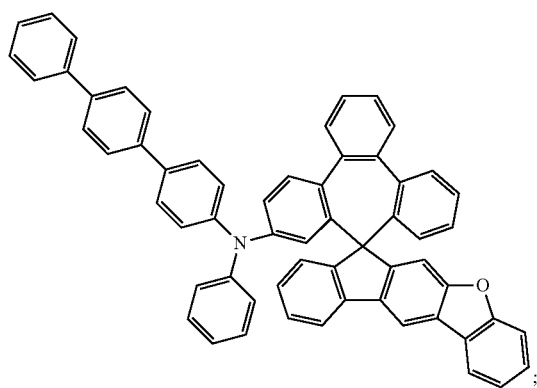
Compound 517
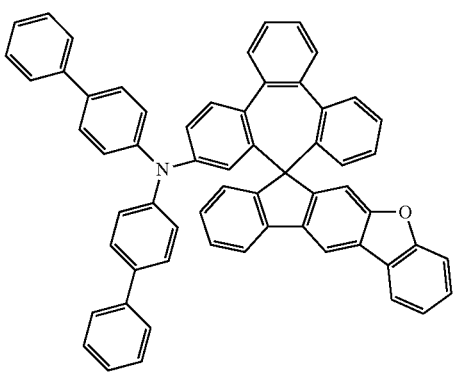
Compound 518
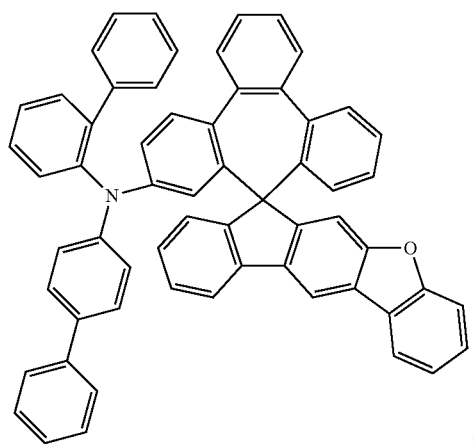
Compound 519
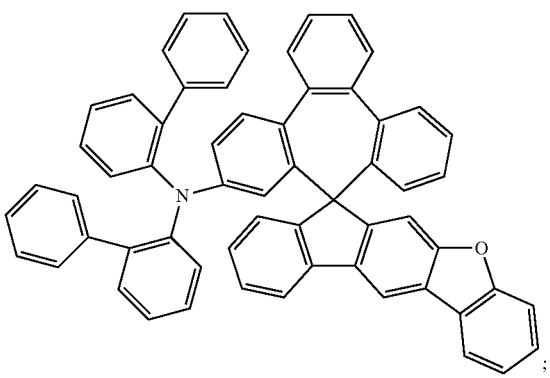

-continued
Compound 520
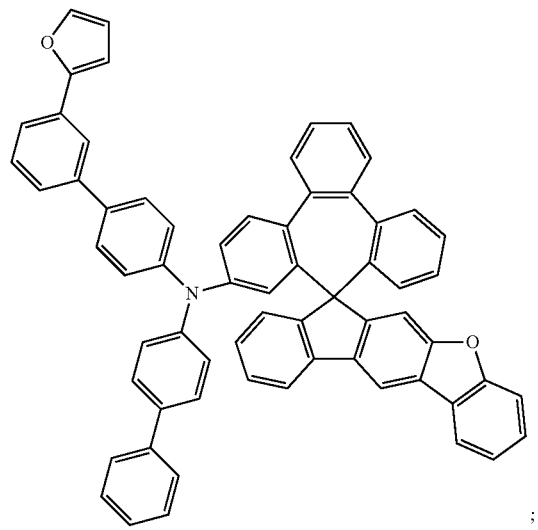
Compound 521
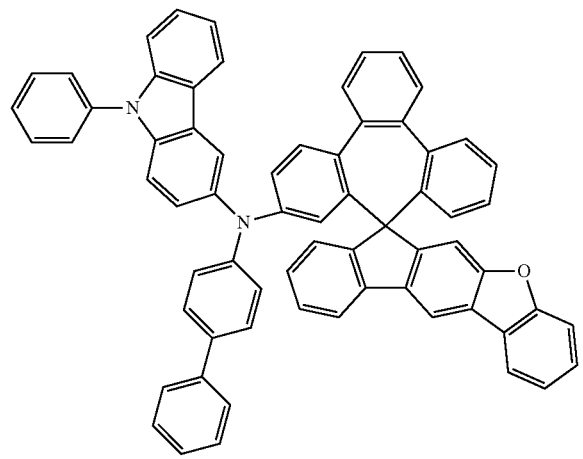
Compound 522
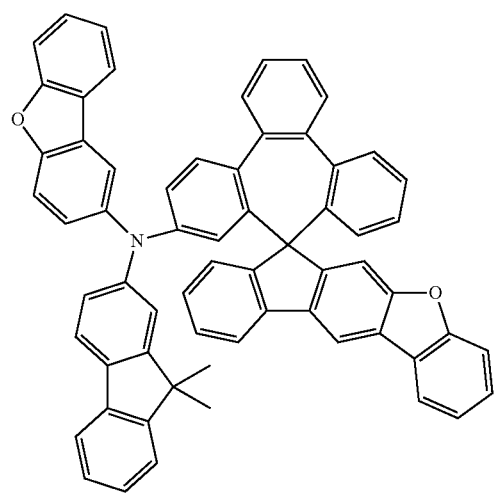
Compound 523
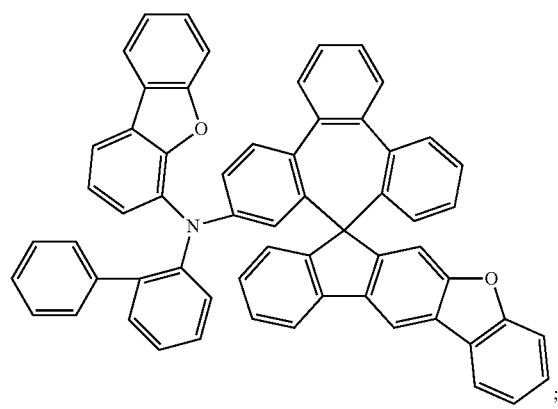
Compound 524
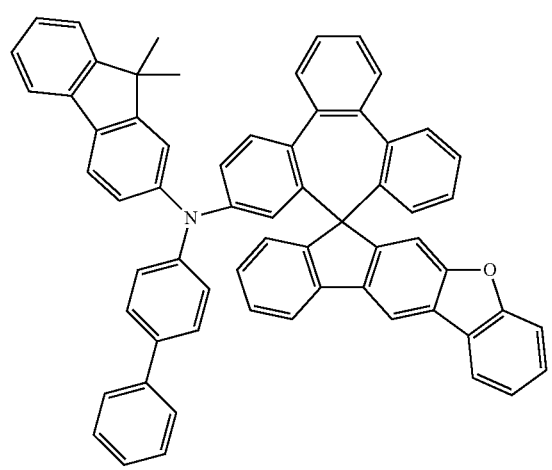
Compound 525
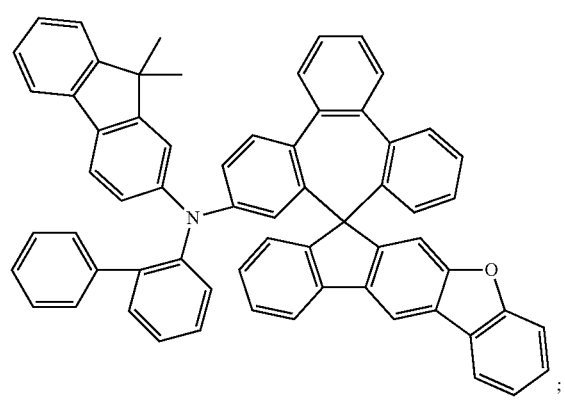

-continued
Compound 526
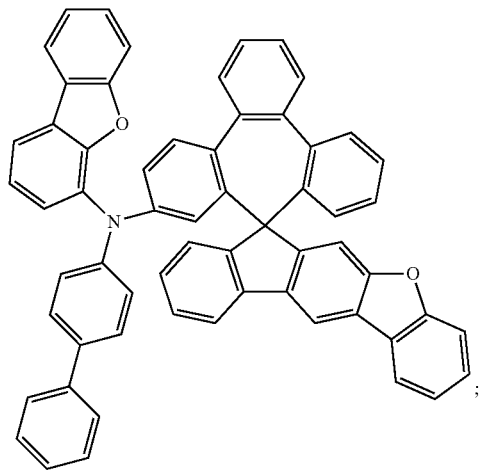
Compound 527
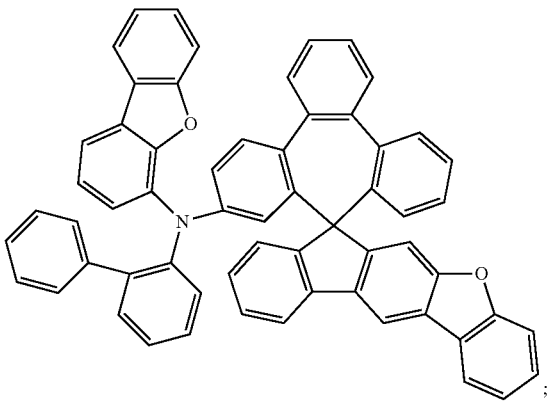
Compound 528
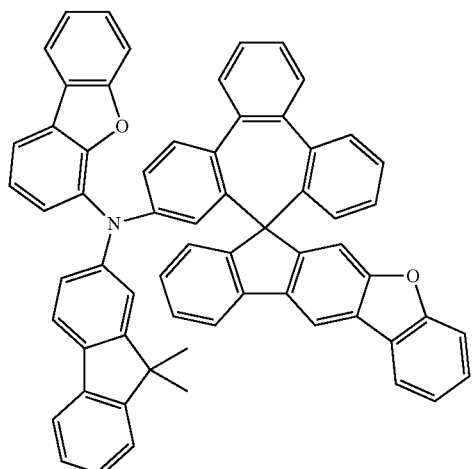
Compound 529
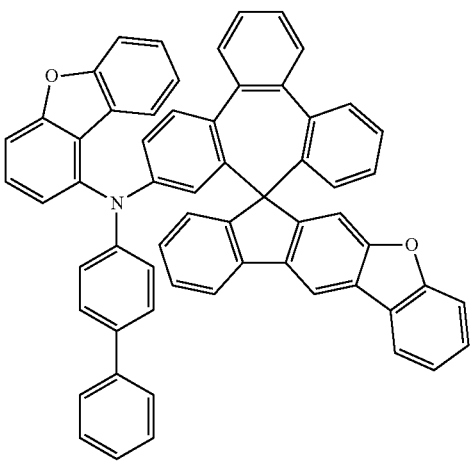
Compound 530
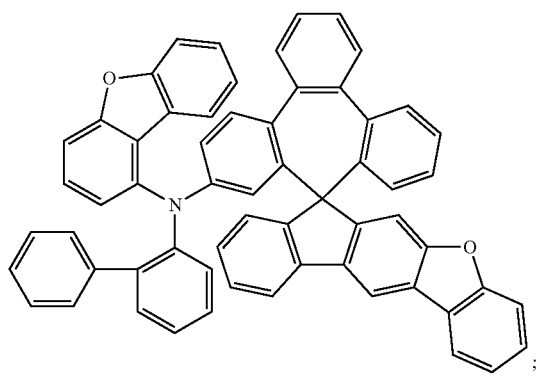
Compound 531
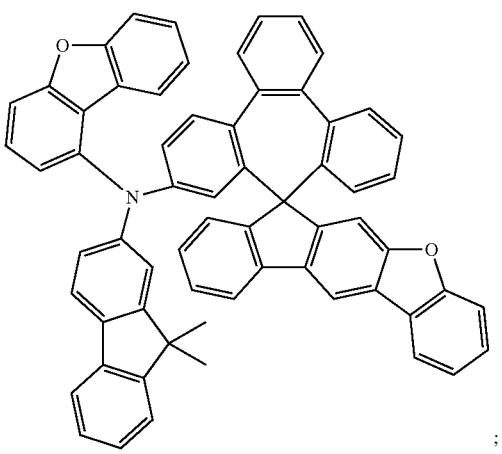

-continued
Compound 532
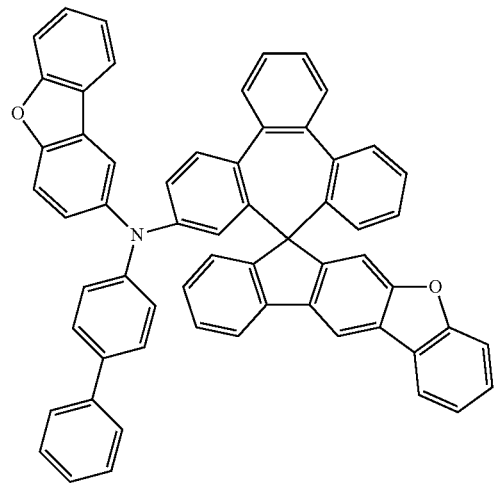
Compound 533
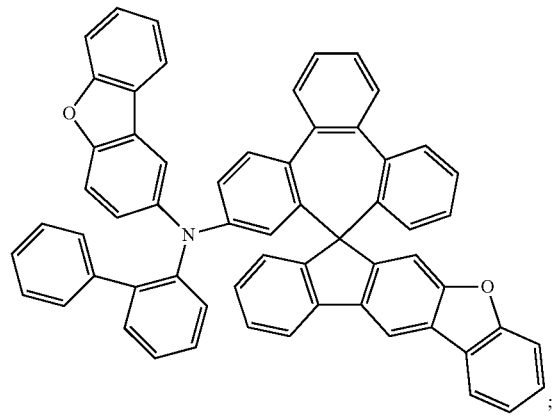
Compound 534
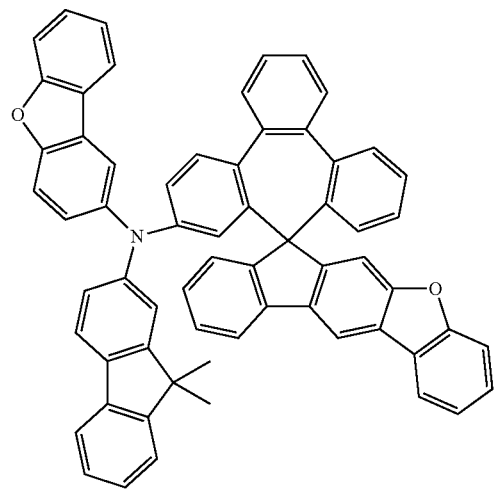
Compound 535
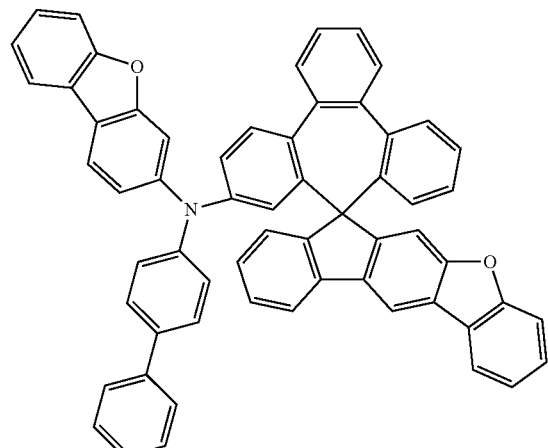
Compound 536
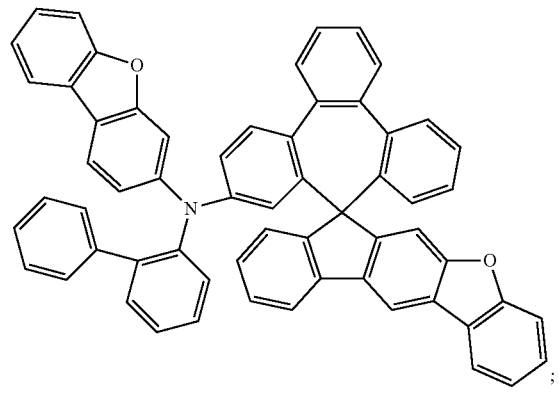
Compound 537
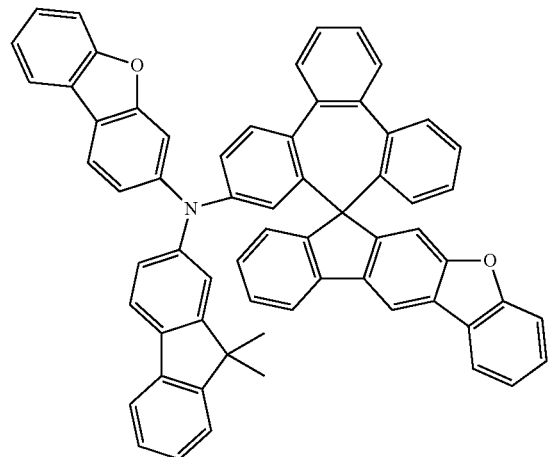

-continued
Compound 538
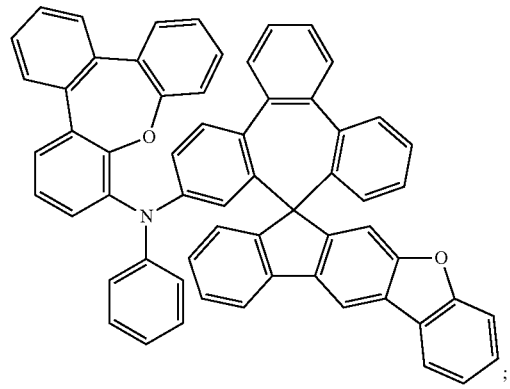
Compound 539
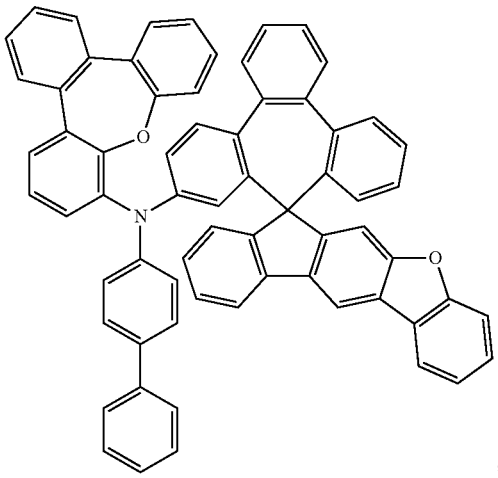
Compound 540
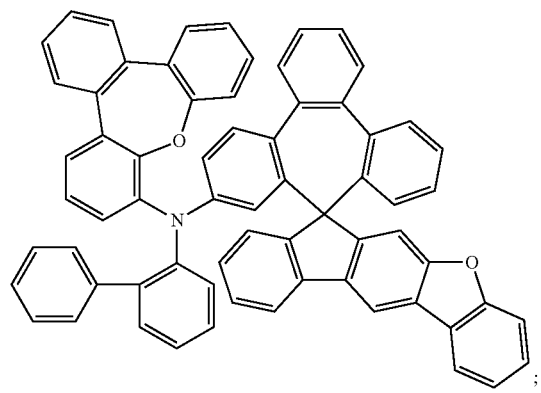
Compound 541
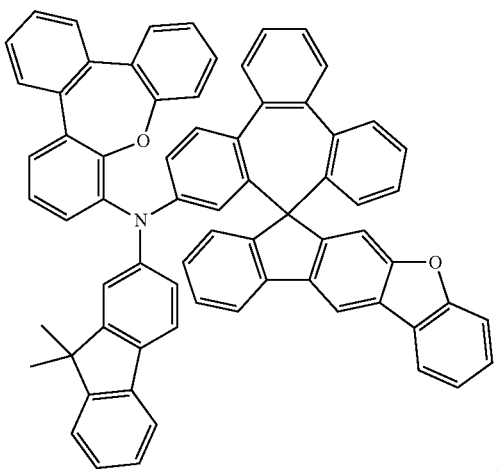
Compound 542
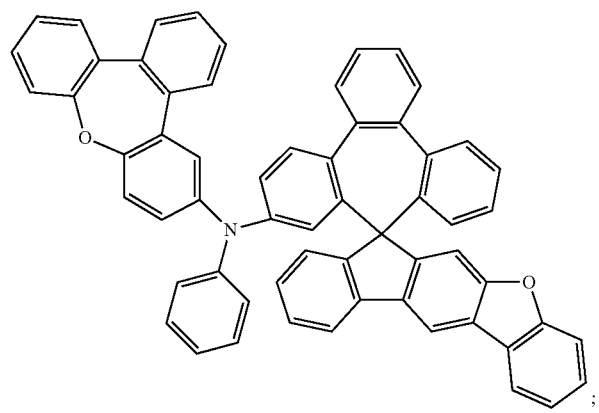
Compound 543
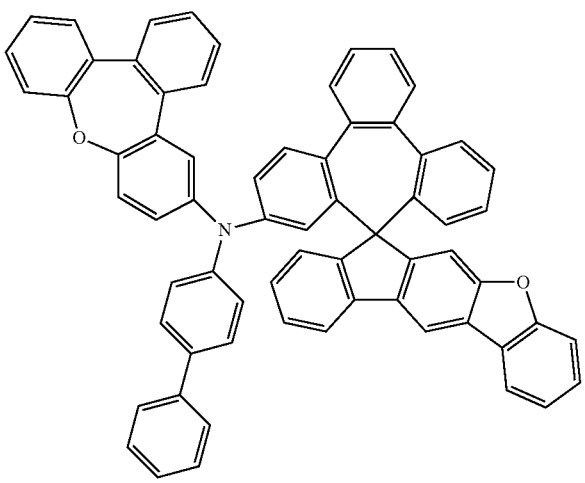

-continued
Compound 544
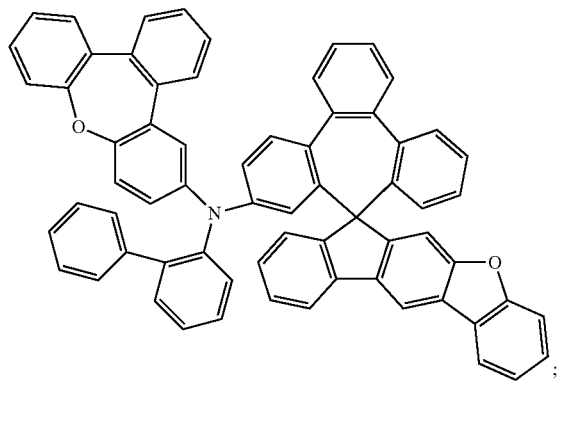
Compound 545
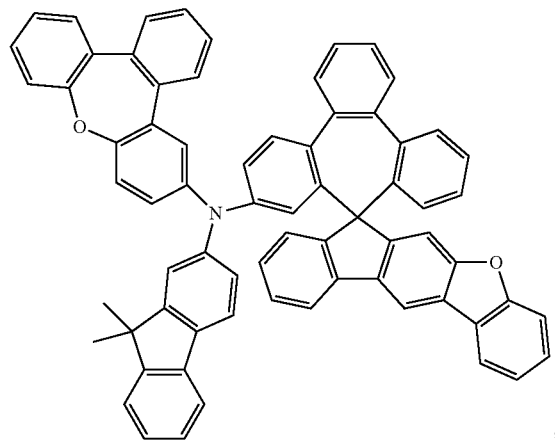
Compound 546
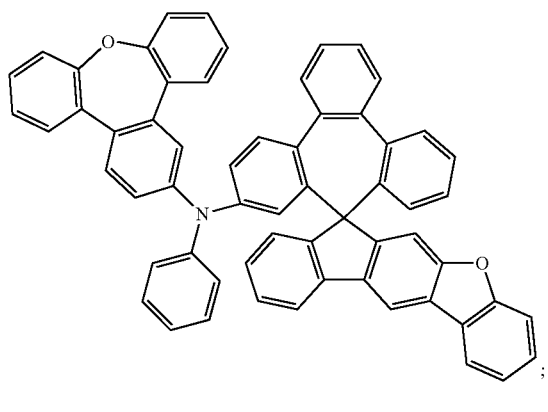
Compound 547
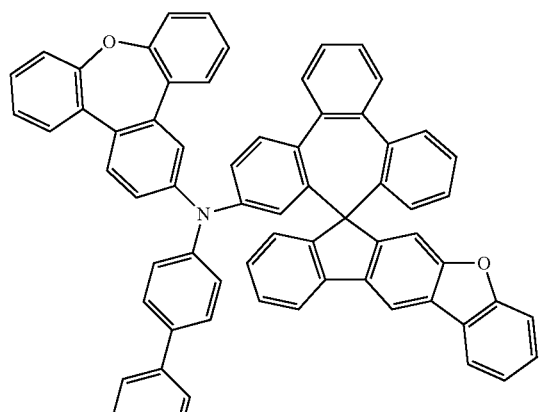
Compound 548
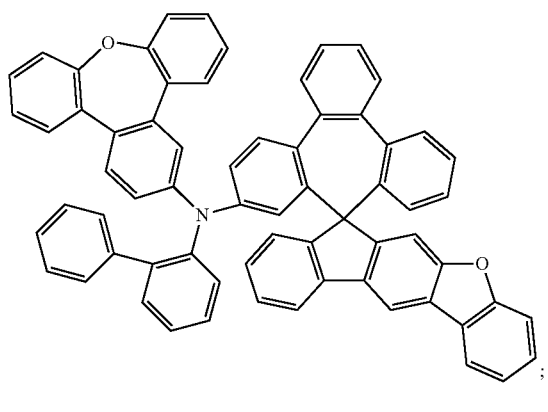
Compound 549
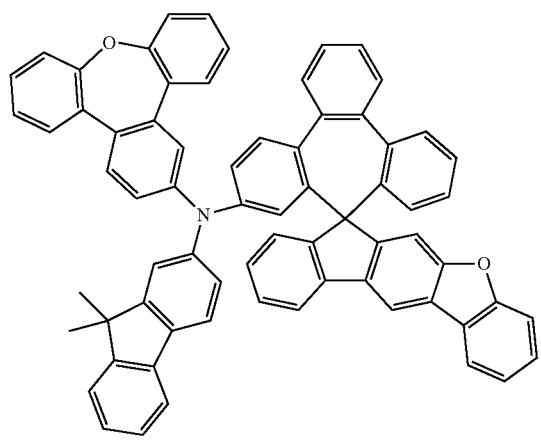

-continued
Compound 550
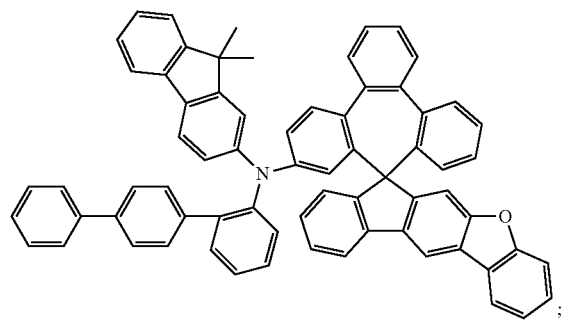
Compound 551
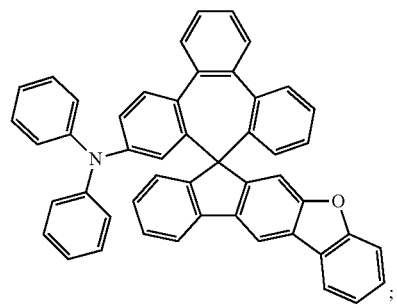
Compound 552
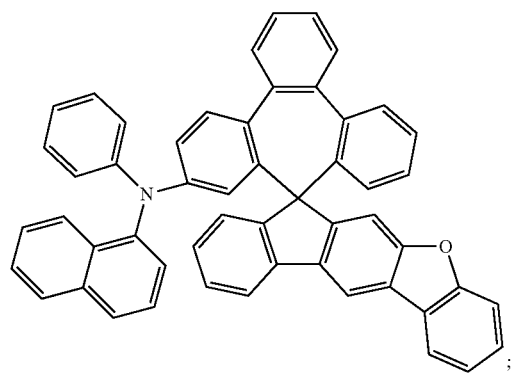
Compound 553
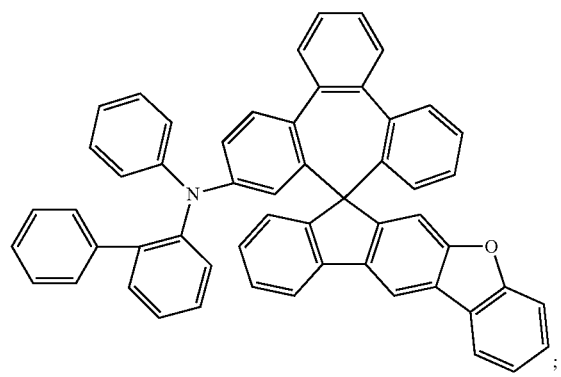
Compound 554
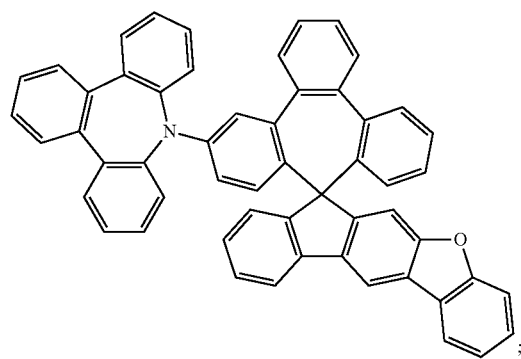
Compound 555
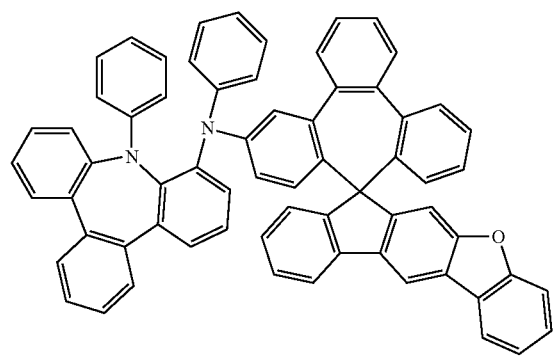
Compound 556
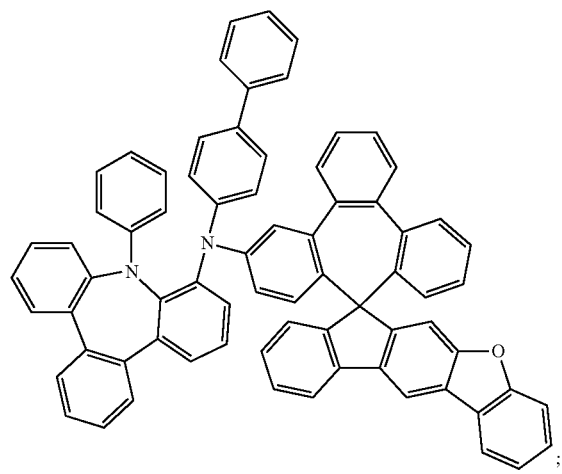
Compound 557
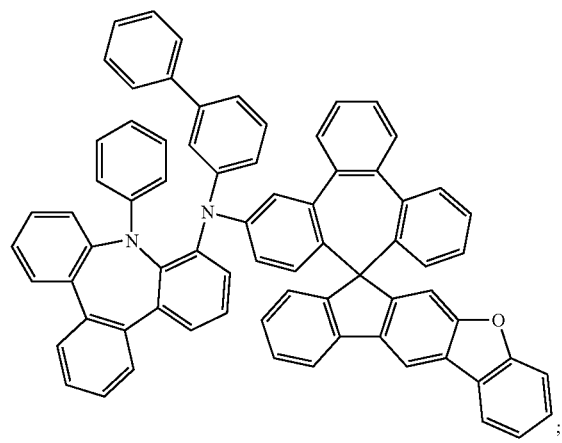

Compound 558
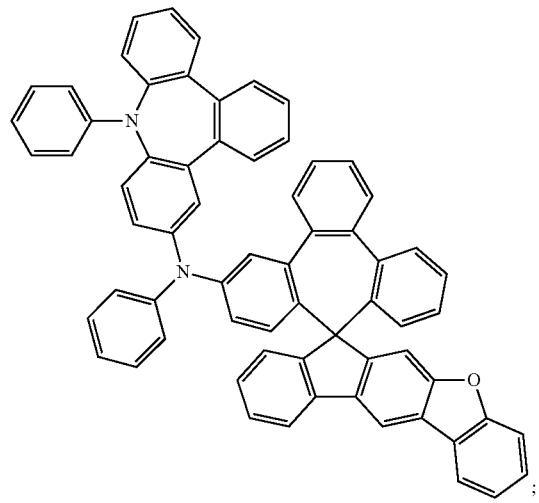
Compound 559
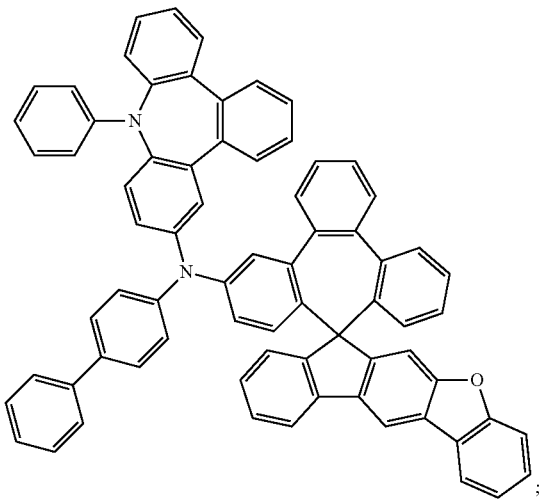
Compound 560
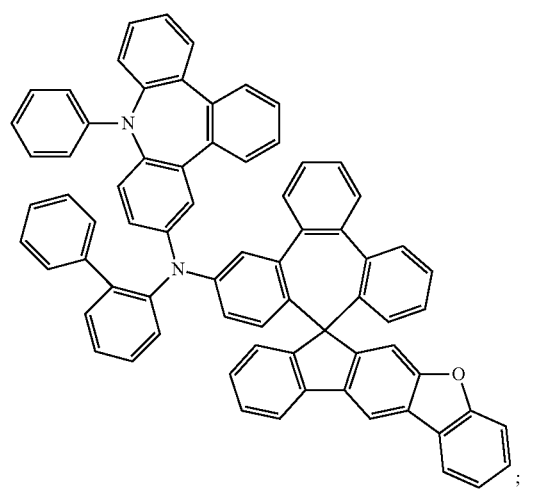
Compound 561
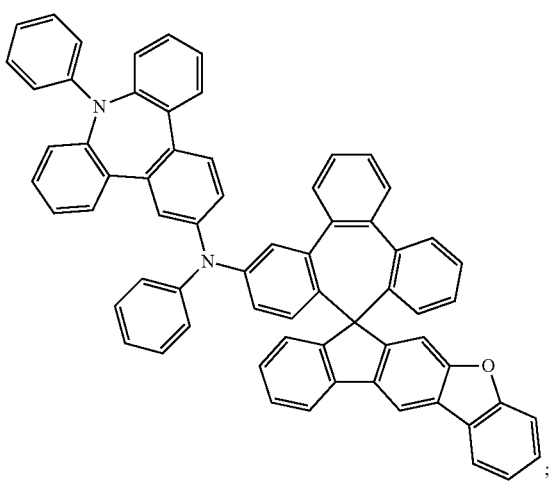
Compound 562
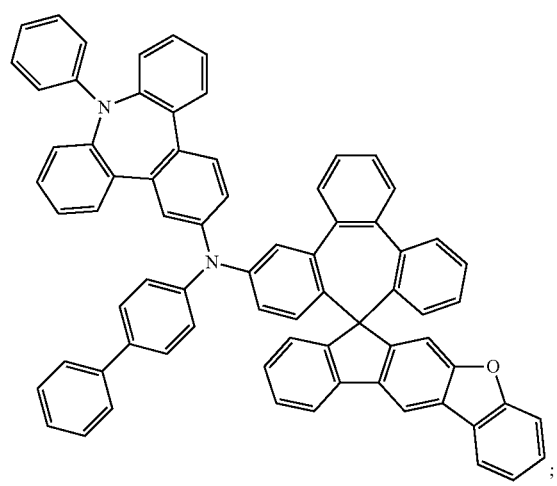
Compound 563
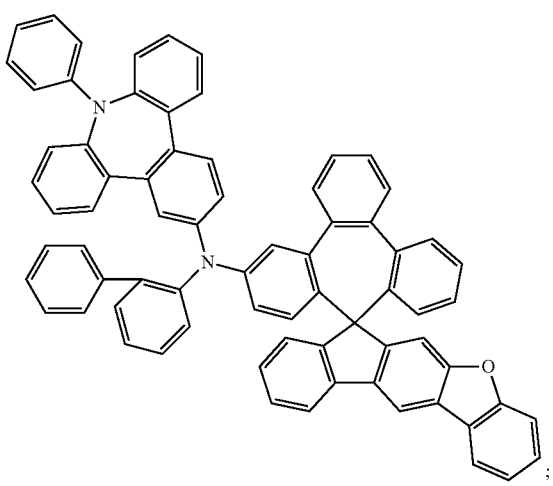

Compound 564
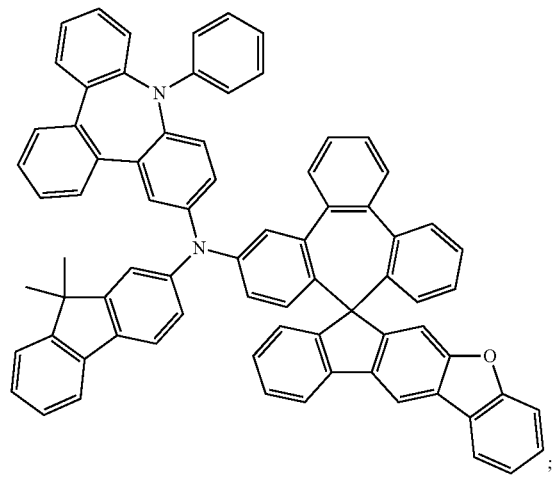
Compound 565
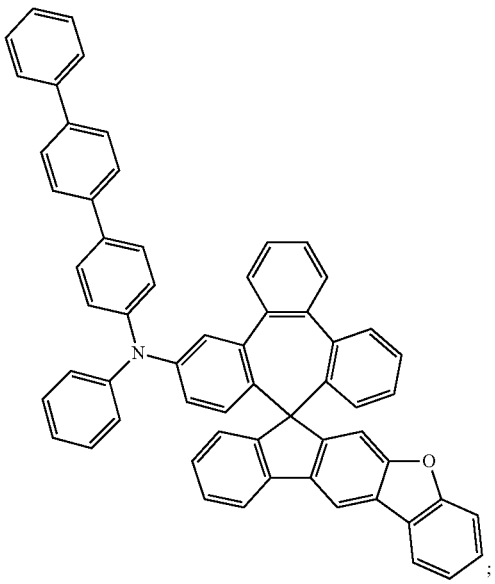
Compound 565
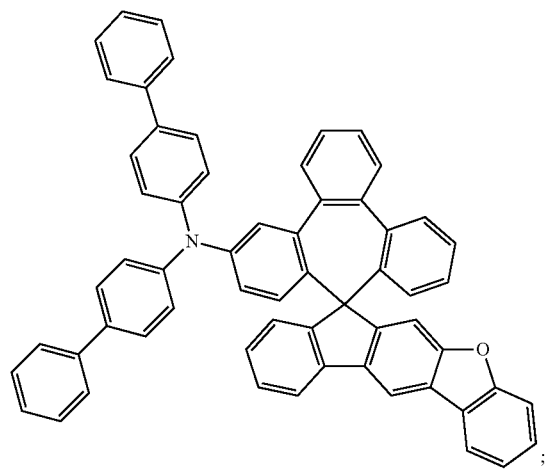
Compound 567
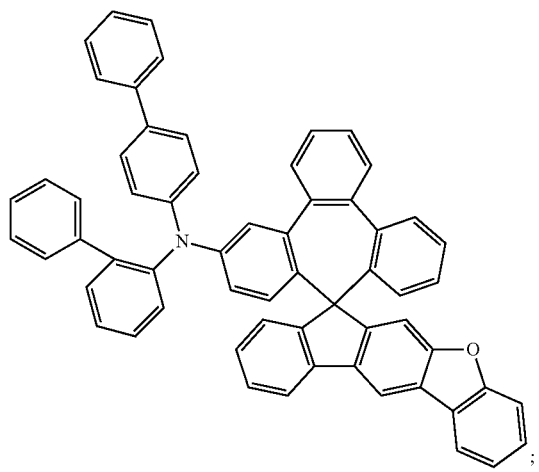

-continued
Compound 568
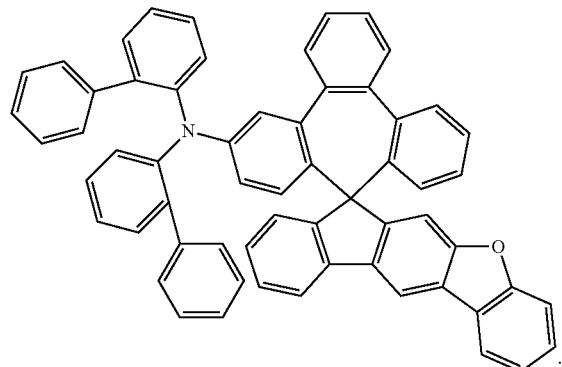
Compound 569
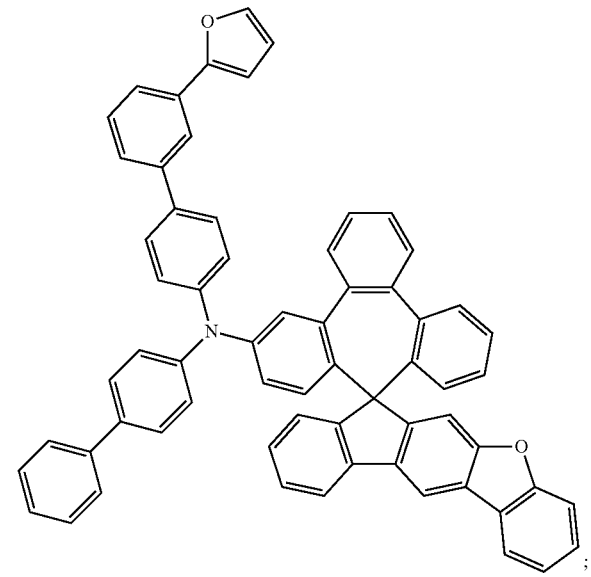
Compound 570
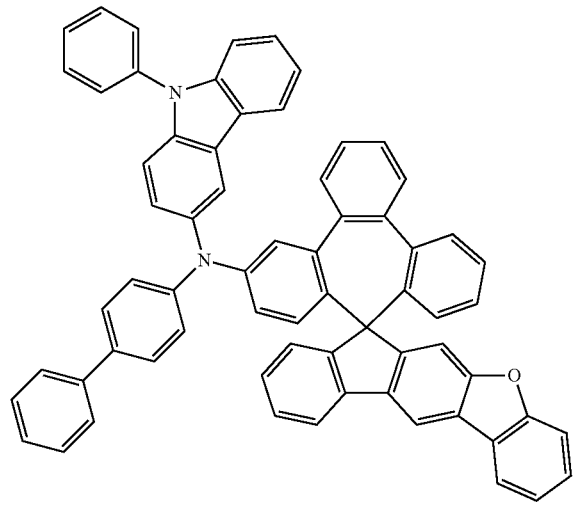
Compound 571
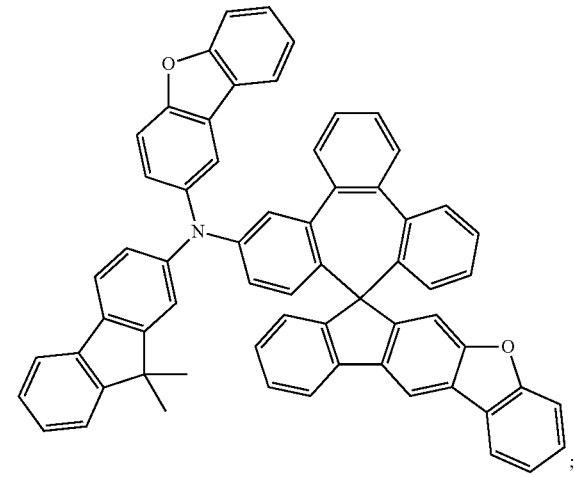
Compound 572
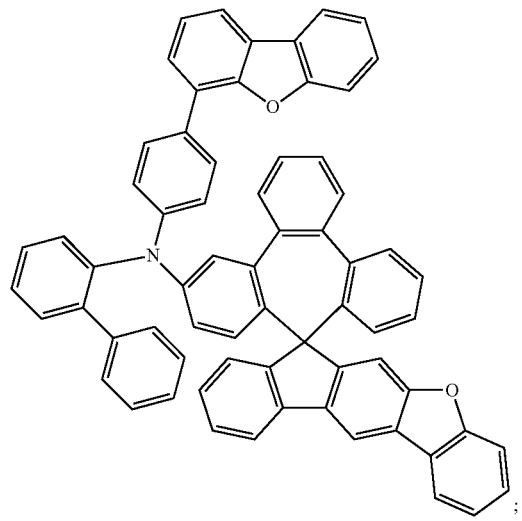
Compound 573
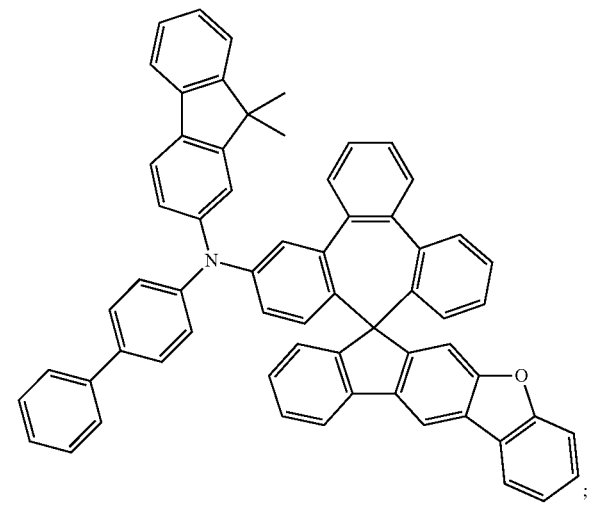

-continued
Compound 574
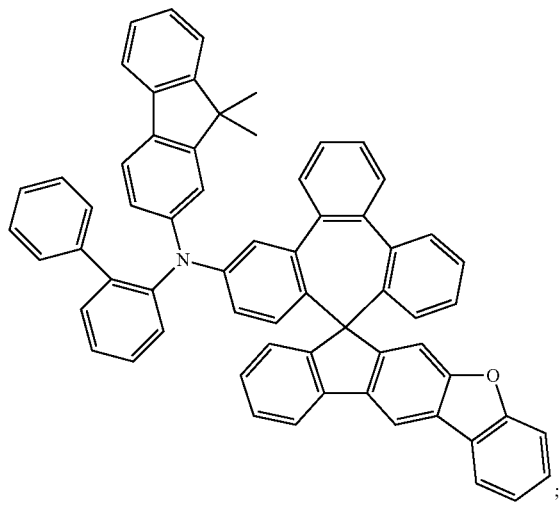
Compound 575
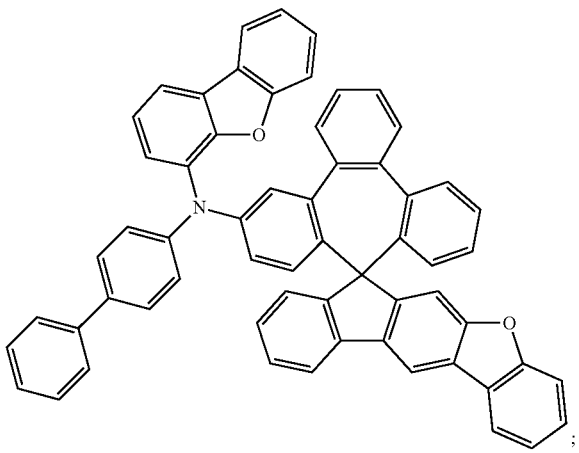
Compound 576
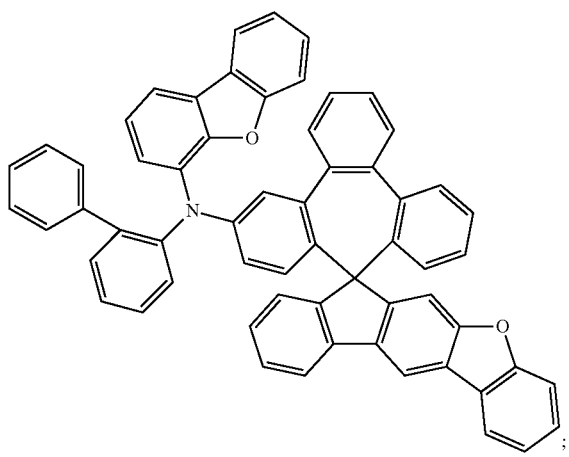
Compound 577
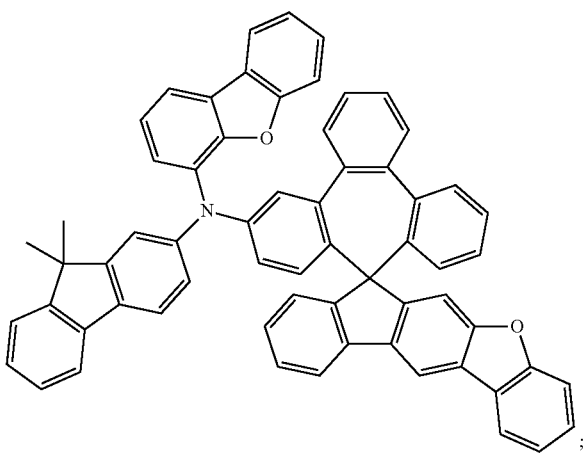
Compound 578
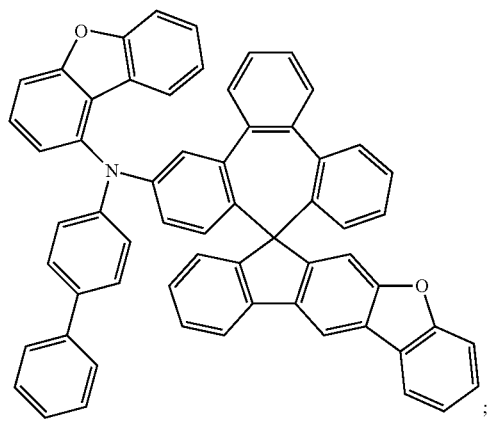
Compound 579
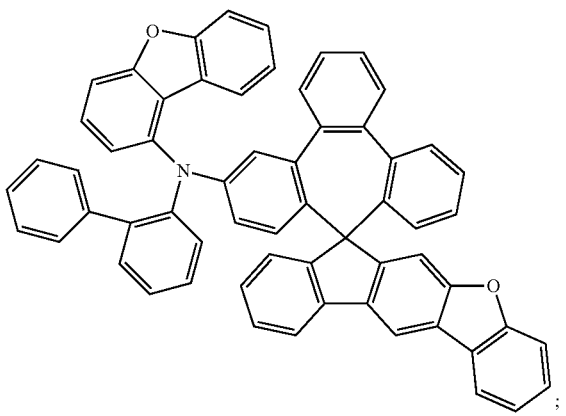

Compound 580
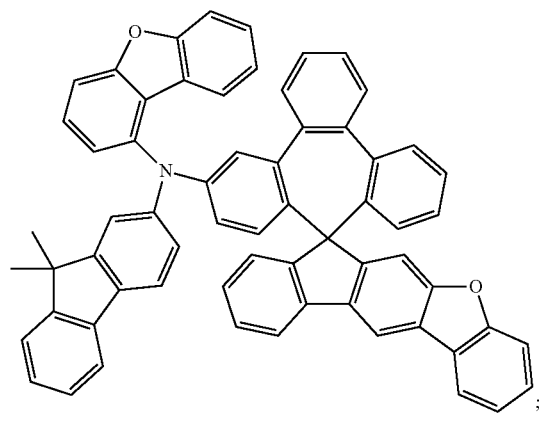
Compound 581
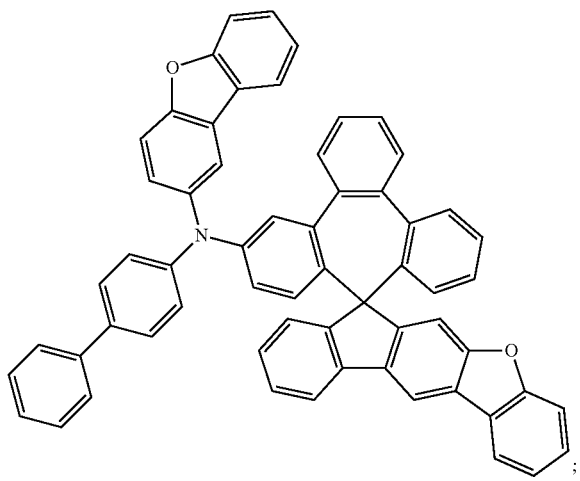
Compound 582
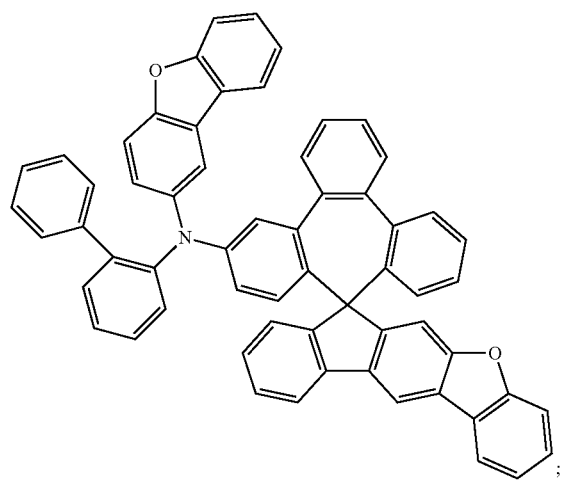
Compound 583
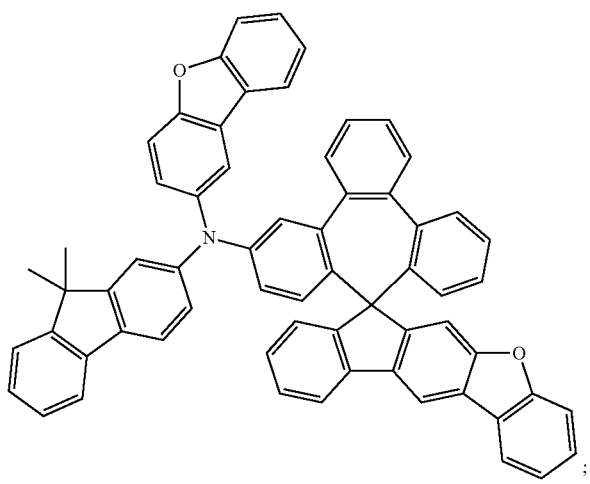
Compound 584
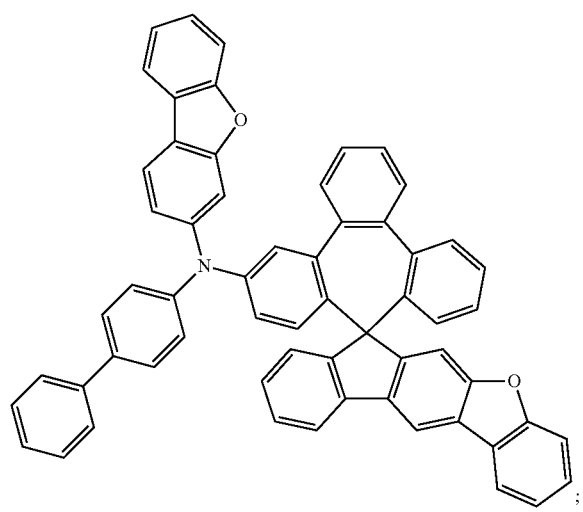
Compound 585
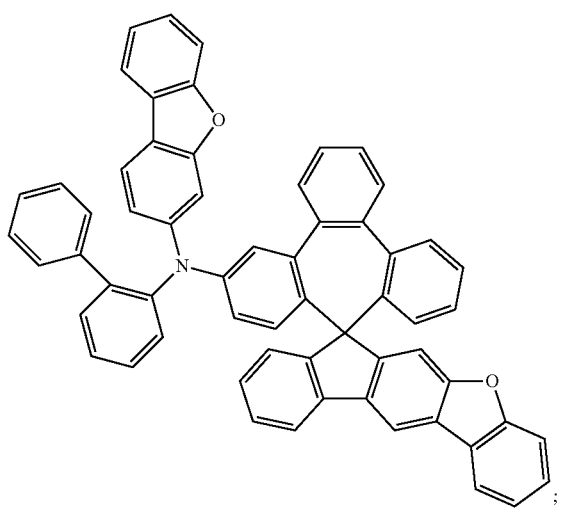

Compound 586
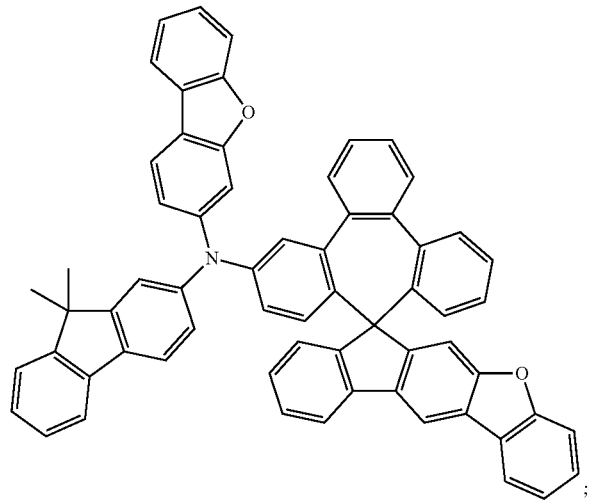
Compound 587
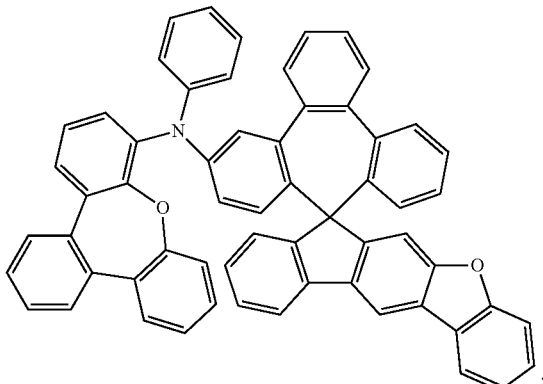
Compound 588
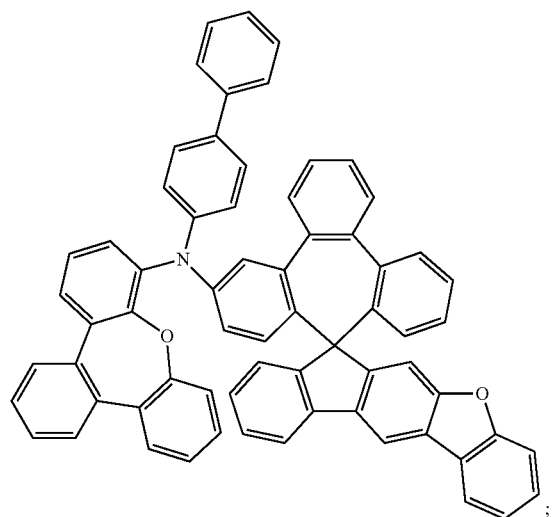
Compound 589
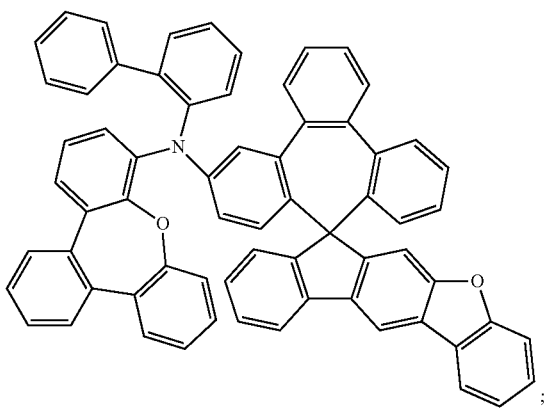
Compound 590
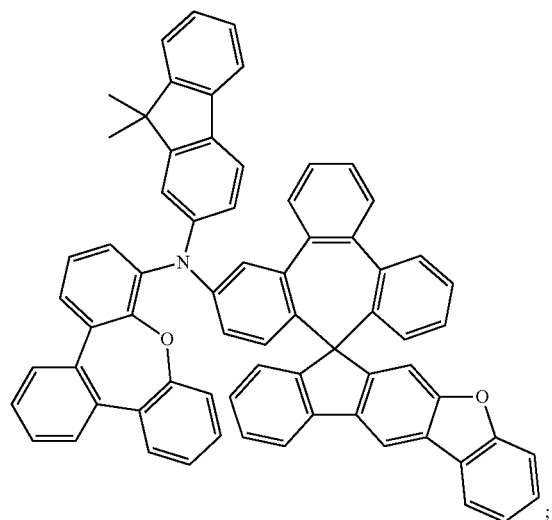
Compound 591

-continued
Compound 592
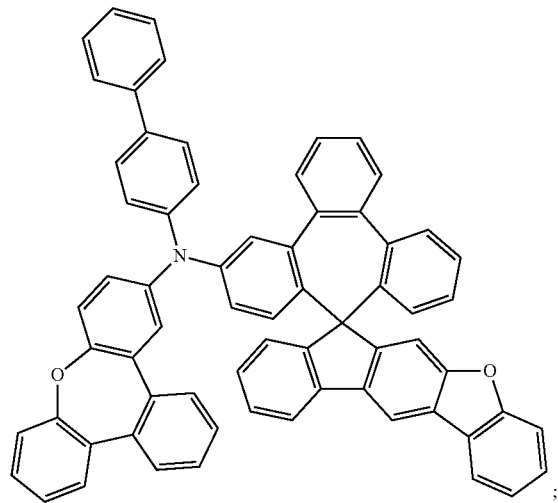
Compound 593
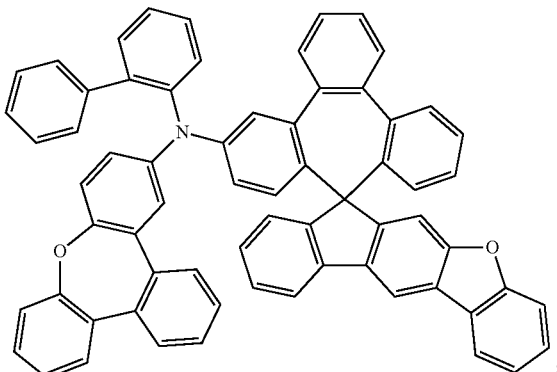
Compound 594
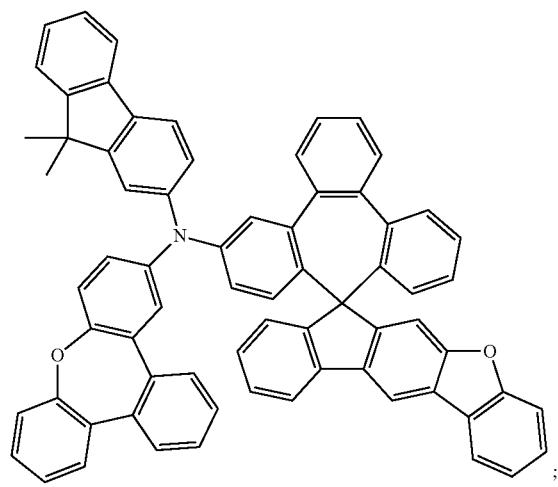
Compound 595
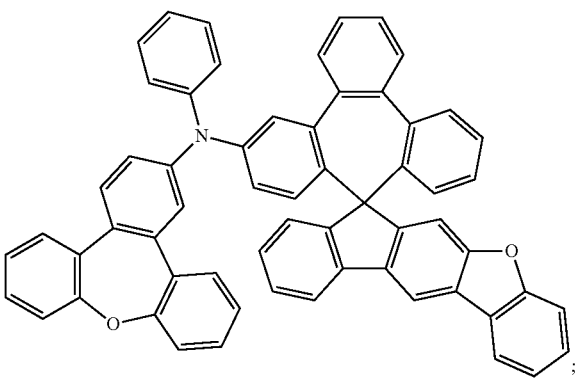
Compound 596
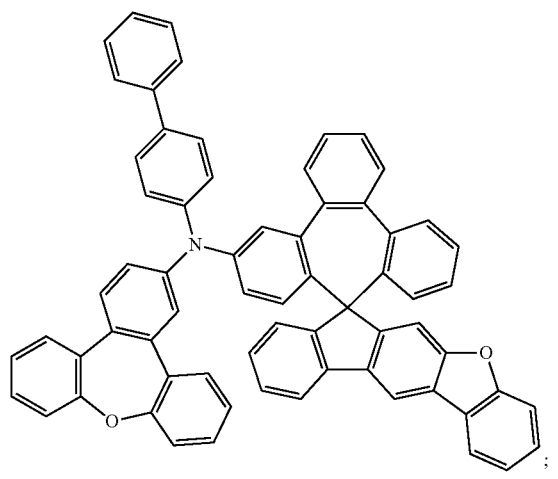
Compound 597
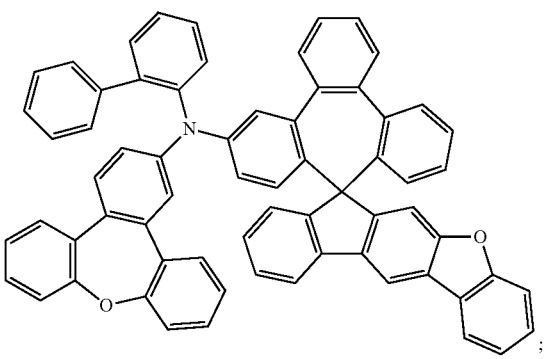

-continued
Compound 598
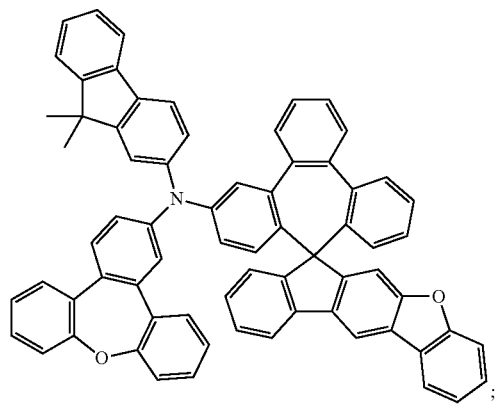
Compound 599
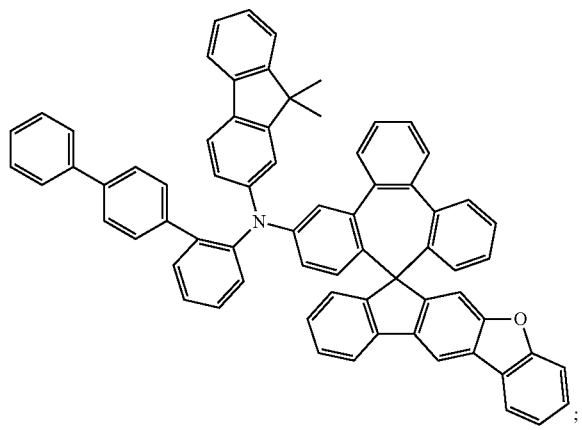
Compound 600
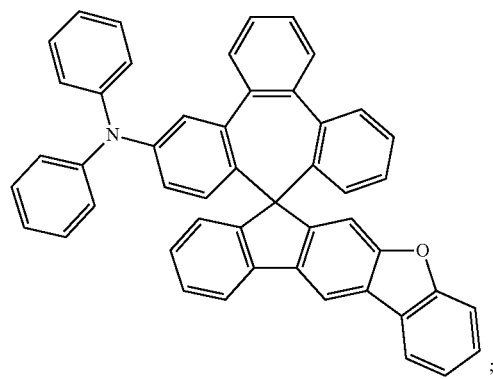
Compound 601
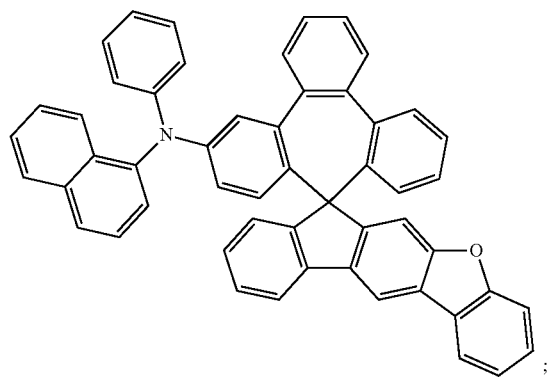
Compound 602
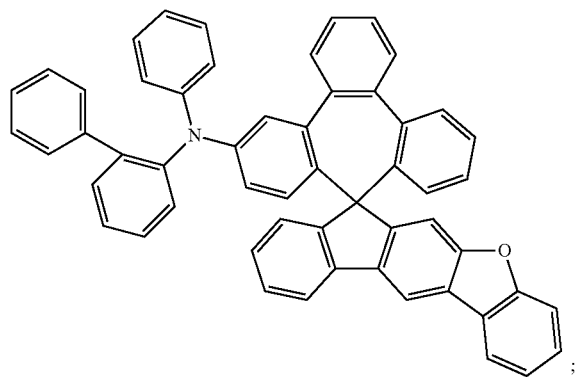
Compound 603
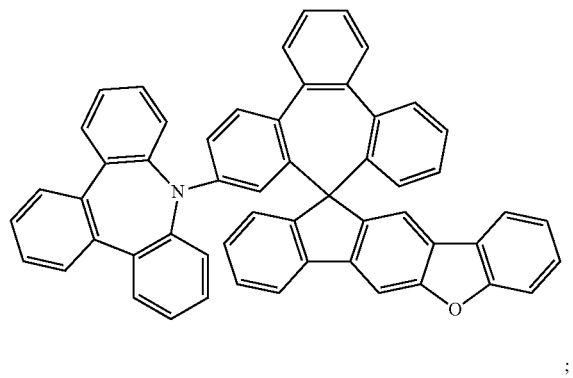

-continued
Compound 604
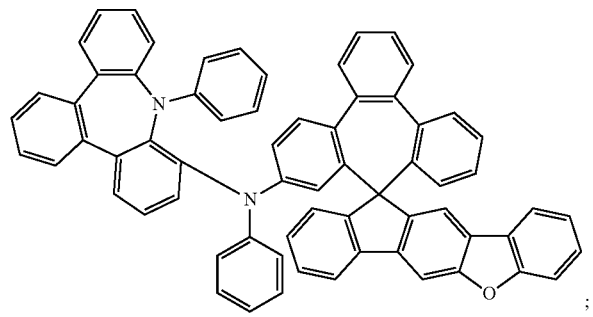
Compound 605
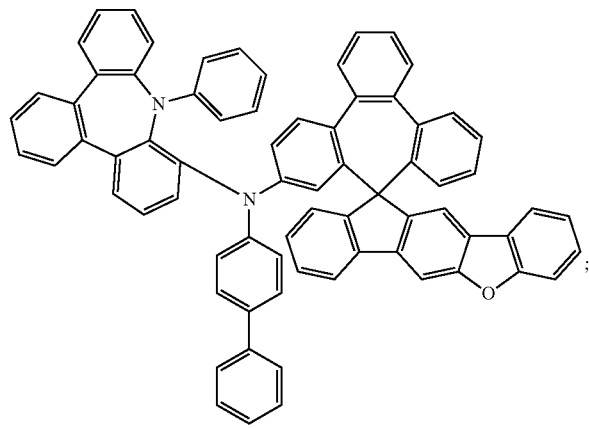
Compound 606
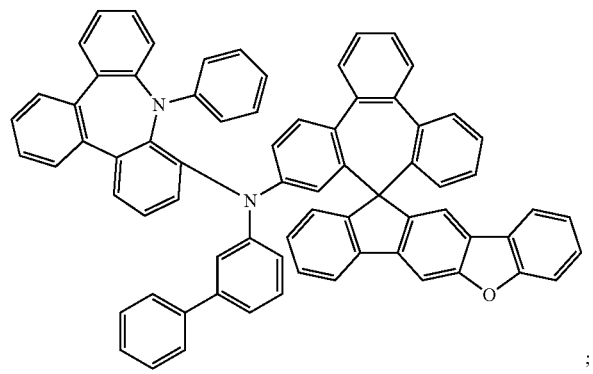
Compound 607
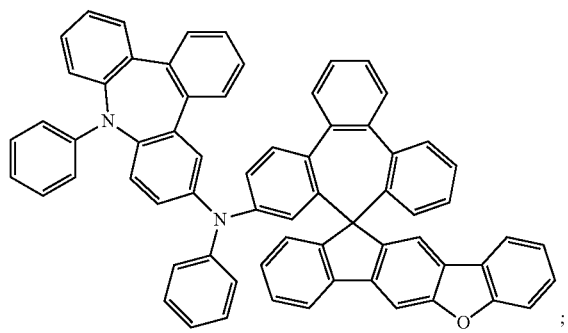
Compound 608
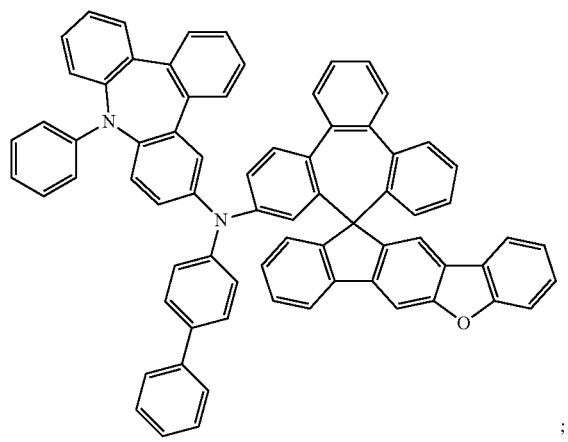
Compound 609
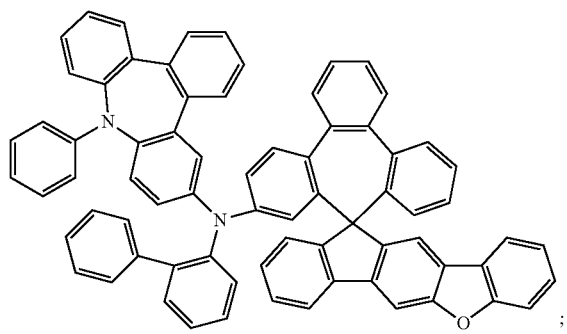

-continued
Compound 610
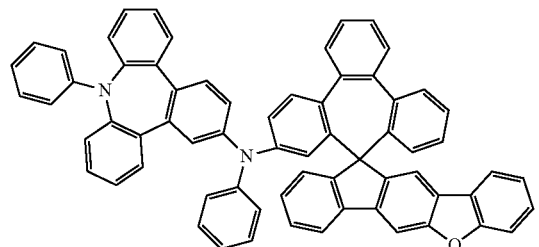
Compound 611
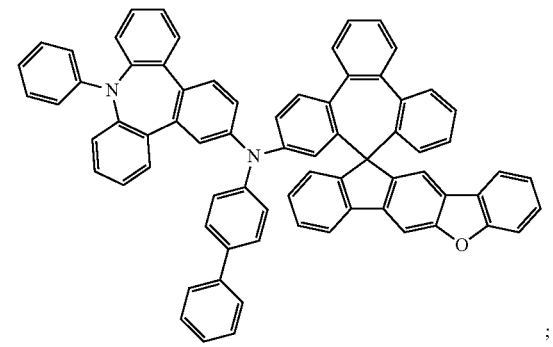
Compound 612
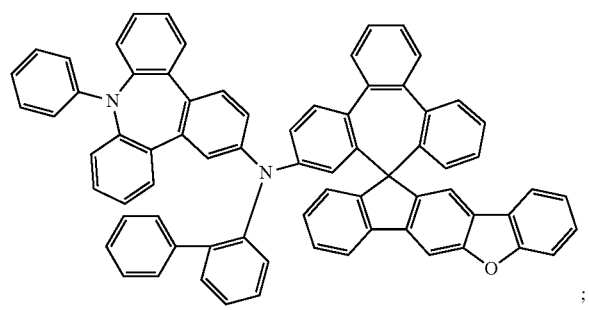
Compound 613
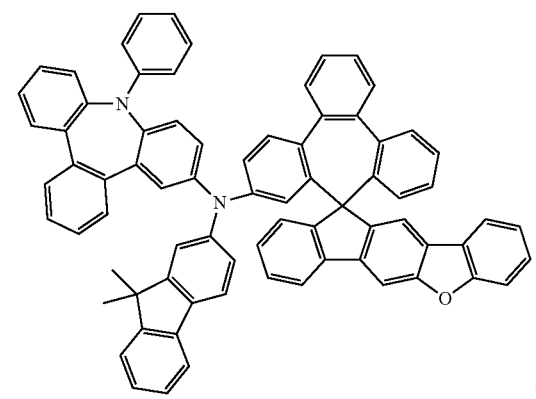
Compound 614
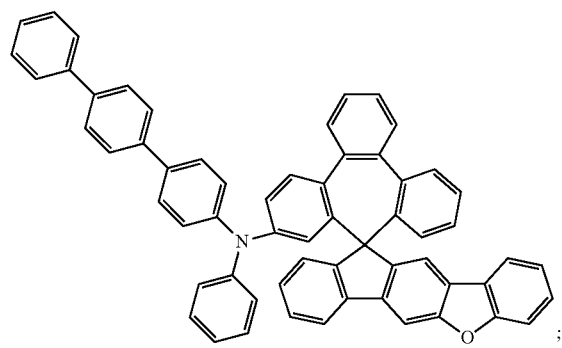
Compound 615
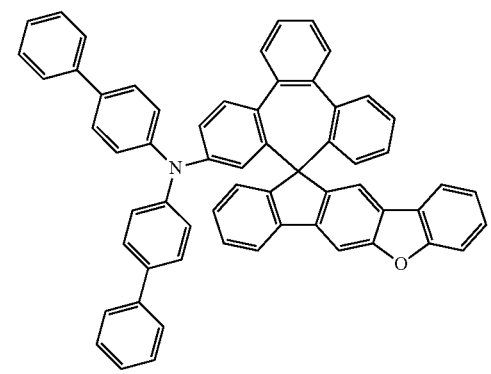
Compound 616
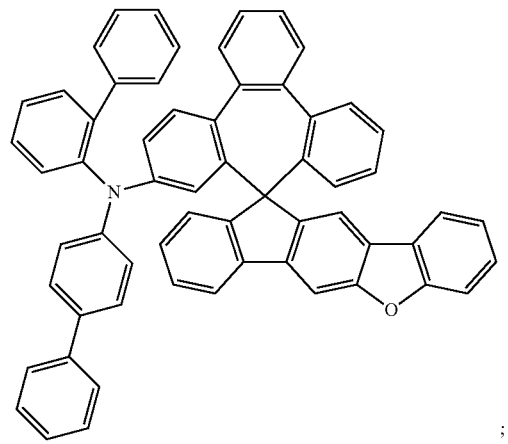
Compound 617
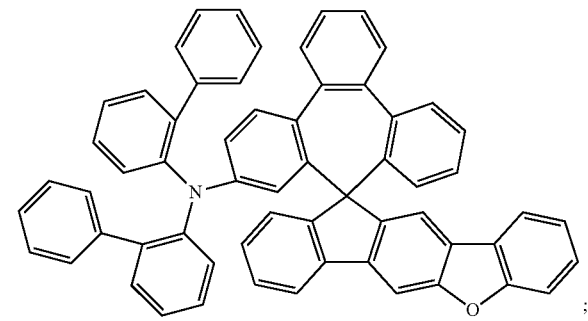

1043
-continued
Compound 618
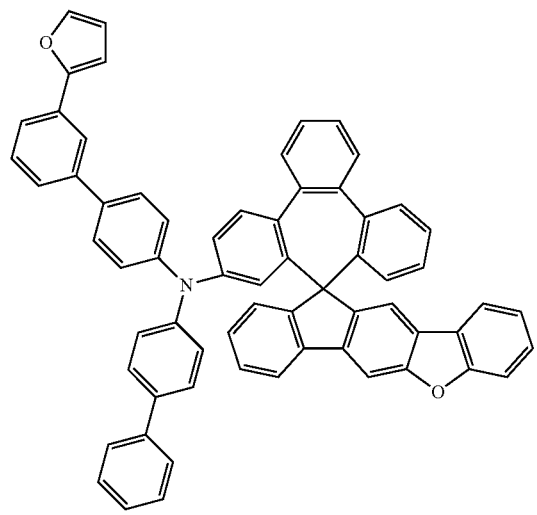
;
Compound 620
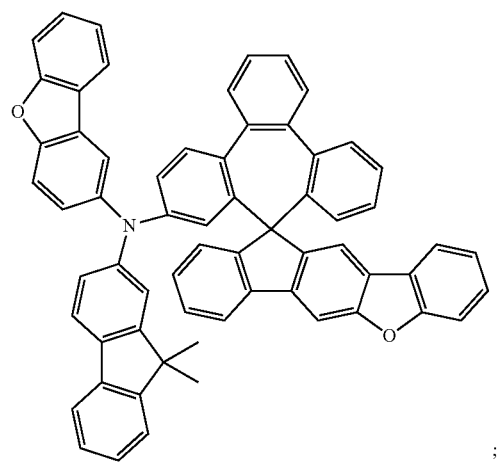
;
Compound 622
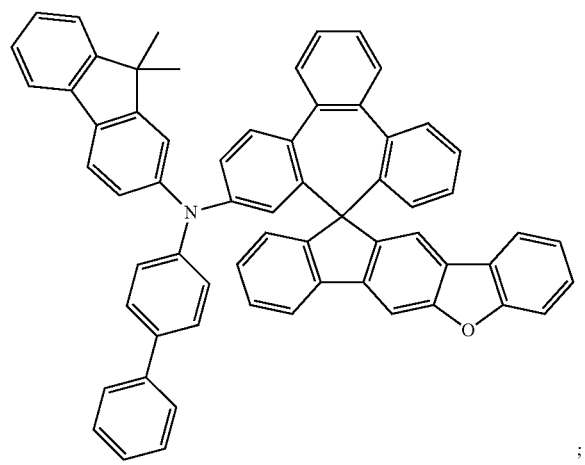
;
1044
Compound 619
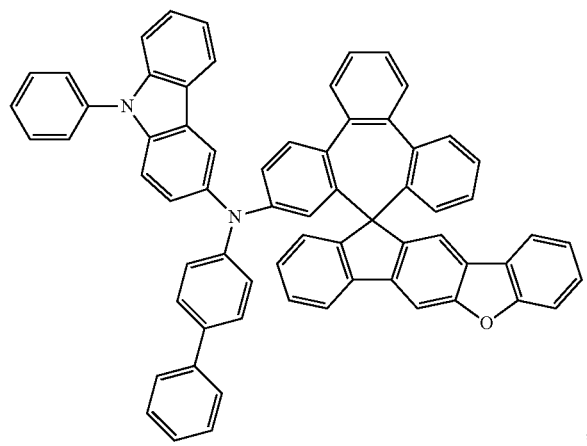
;
Compound 621
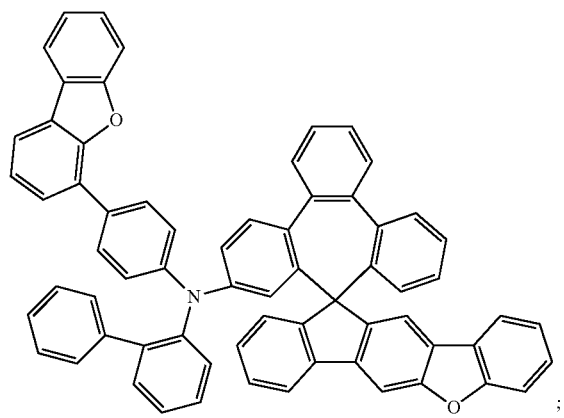
;
Compound 623
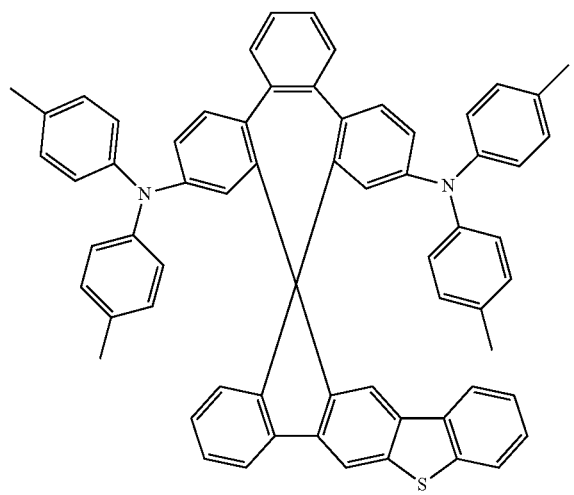
;

-continued
Compound 624
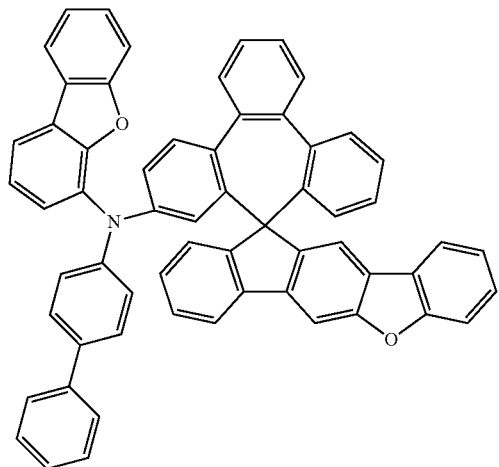
;
Compound 625
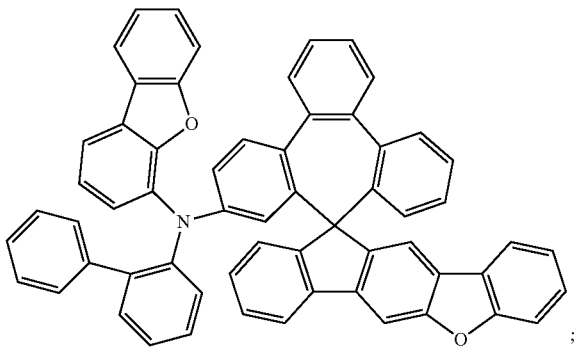
;
Compound 626
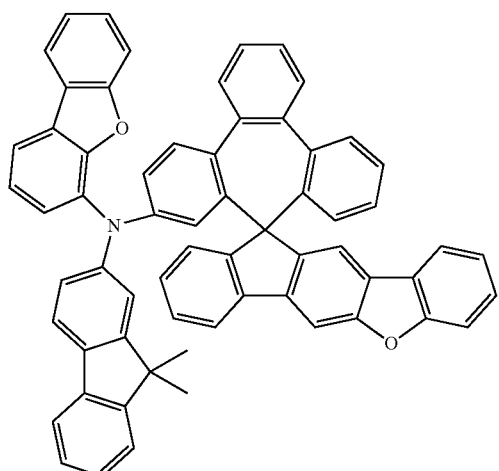
;
Compound 627
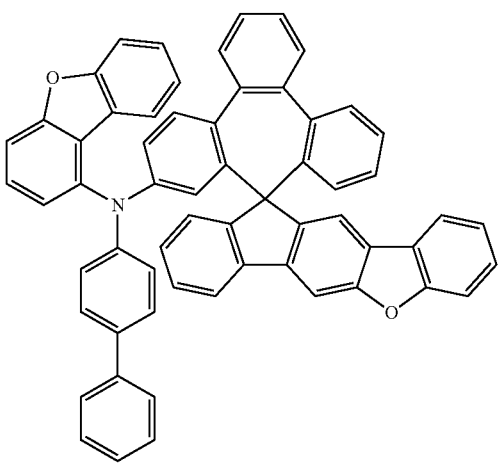
;
Compound 628
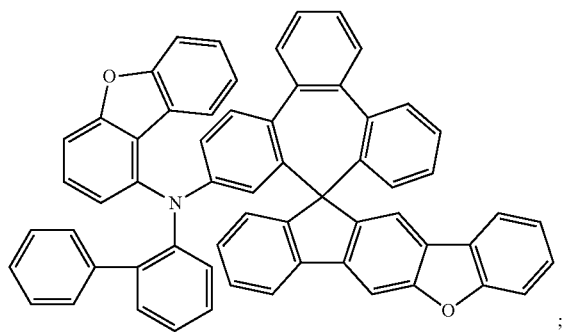
;
Compound 629
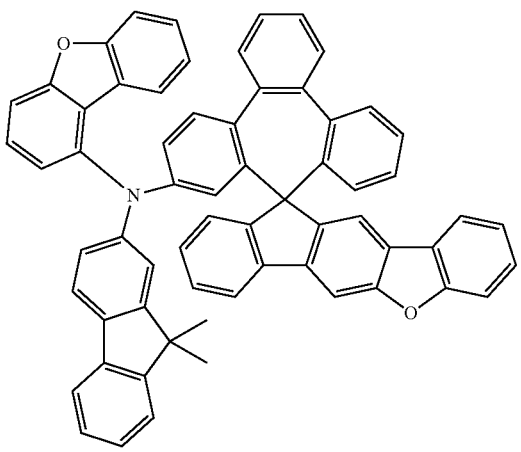
;

-continued
Compound 630
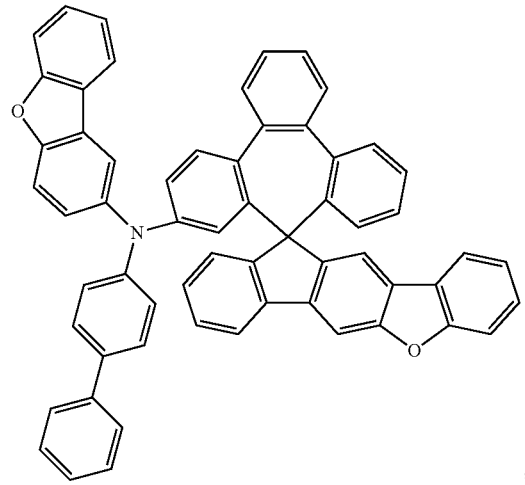
;
Compound 631
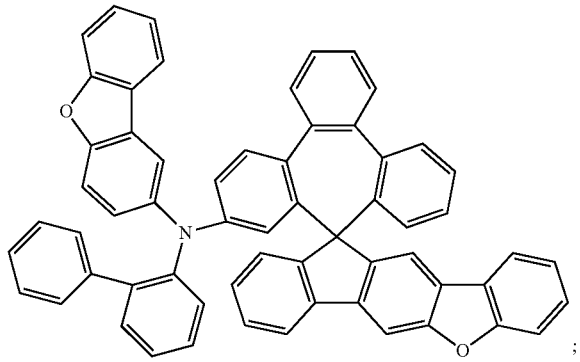
;
Compound 632
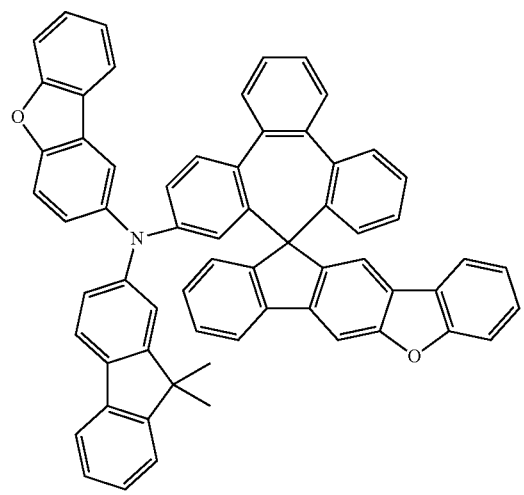
;
Compound 633
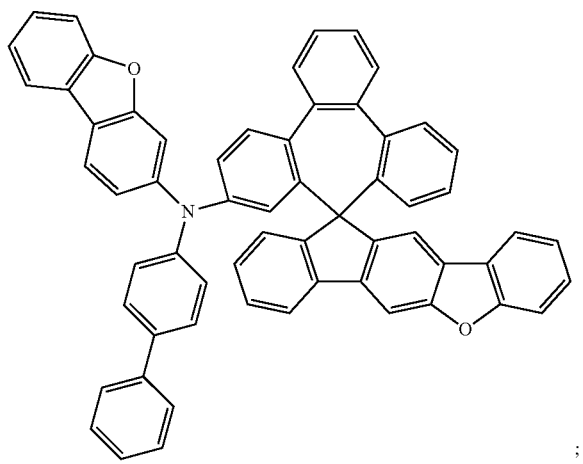
;
Compound 634
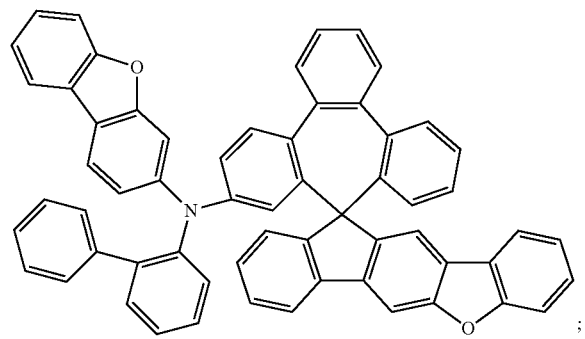
;
Compound 635
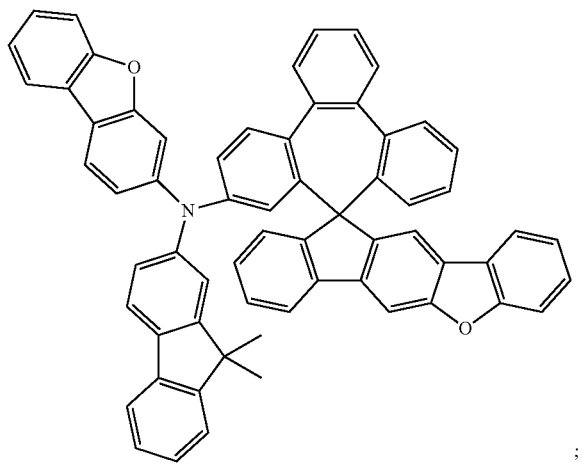
;

-continued
Compound 636
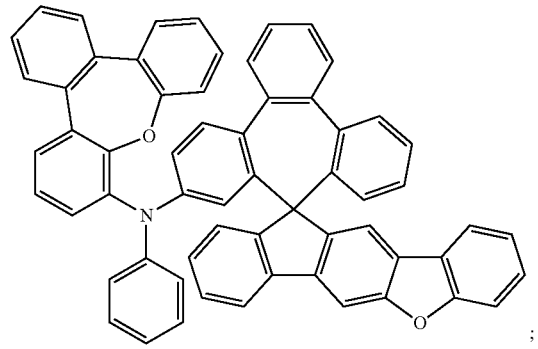
Compound 637
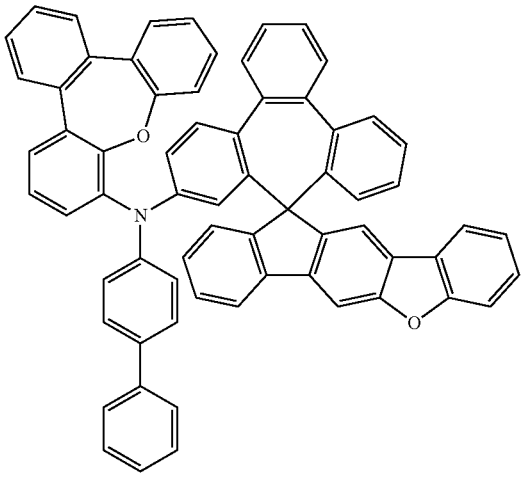
Compound 638
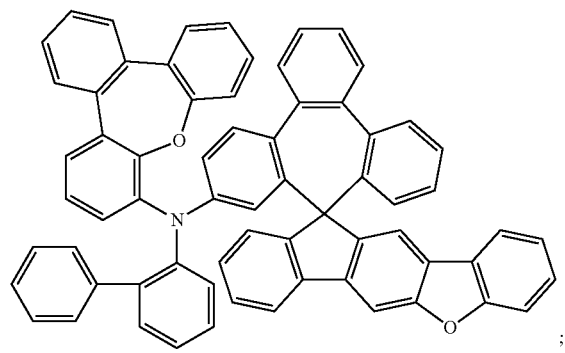
Compound 639
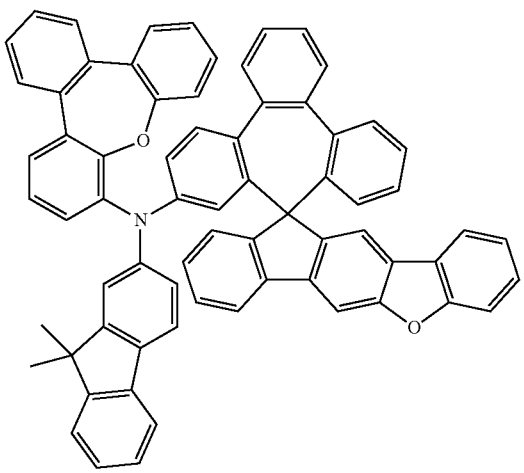
Compound 640
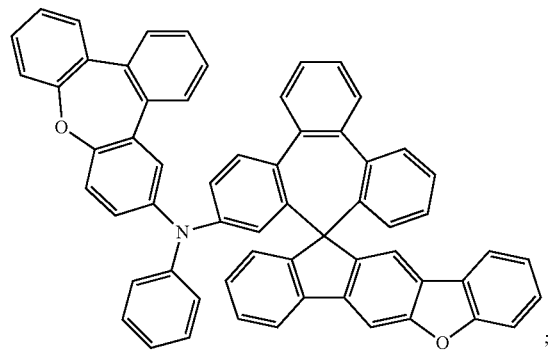
Compound 641
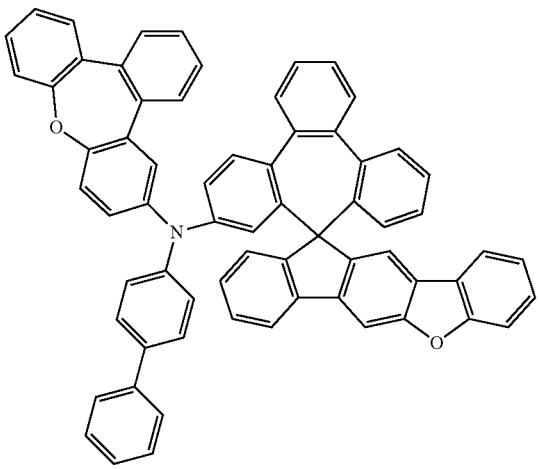

-continued
Compound 642
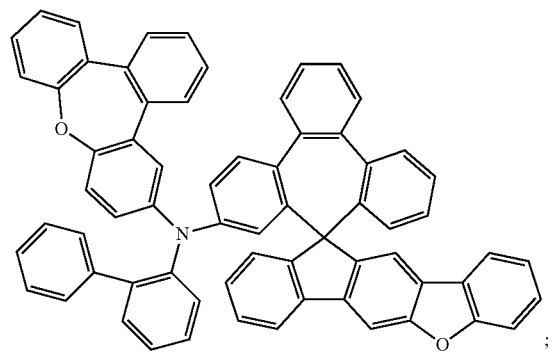
Compound 643
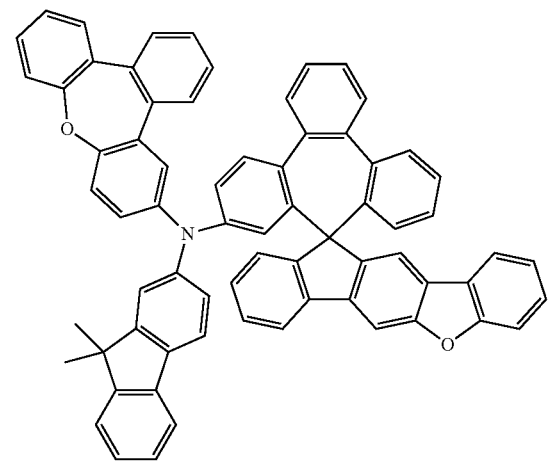
Compound 644
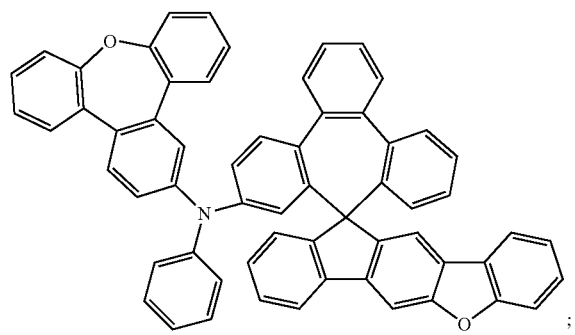
Compound 645
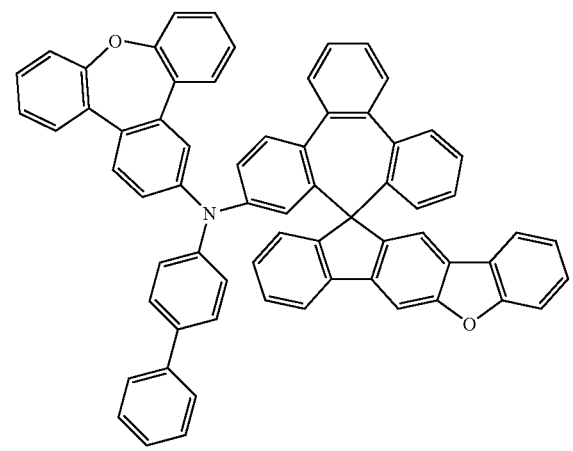
Compound 646
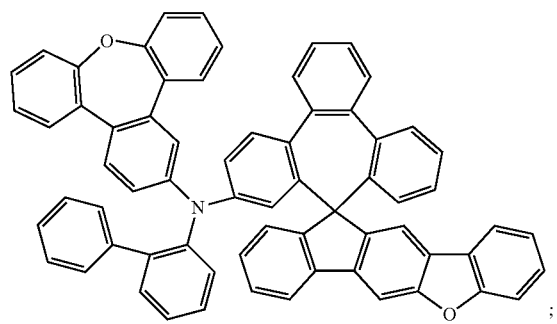
Compound 647
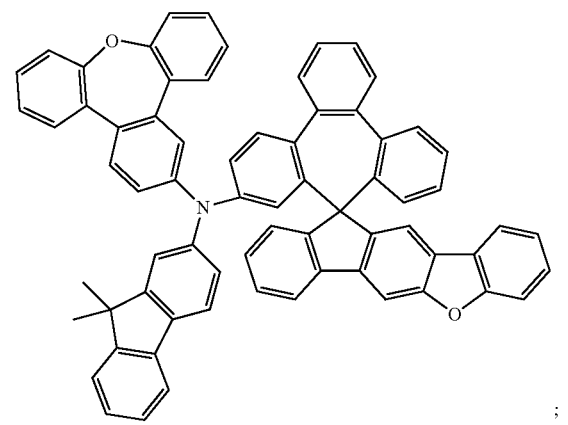

-continued
Compound 648
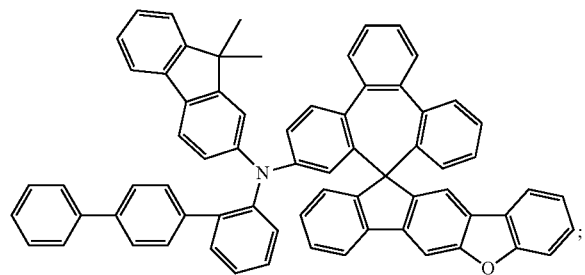
Compound 649
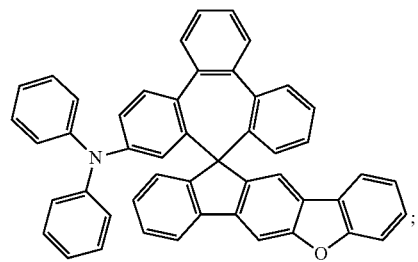
Compound 650
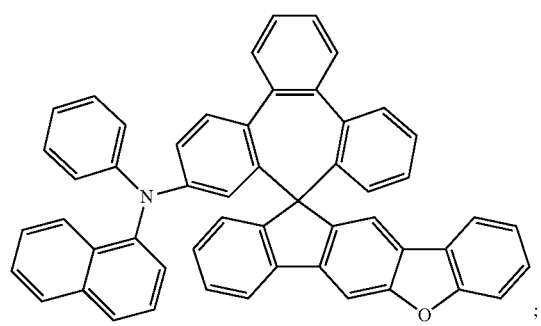
Compound 651
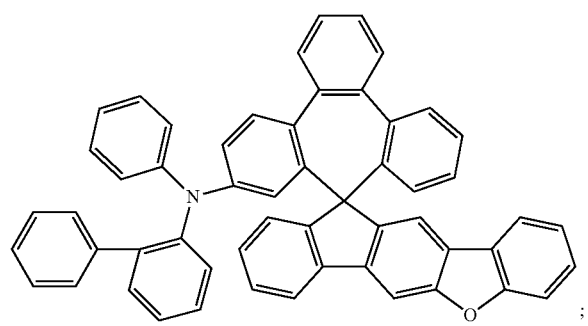
Compound 652
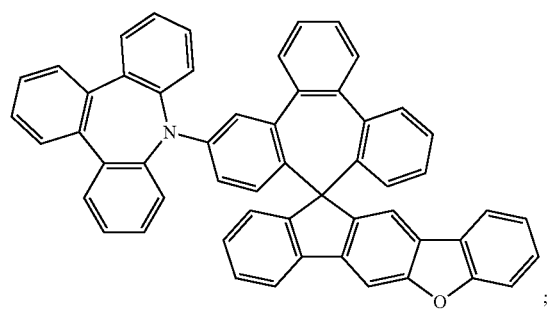
Compound 653
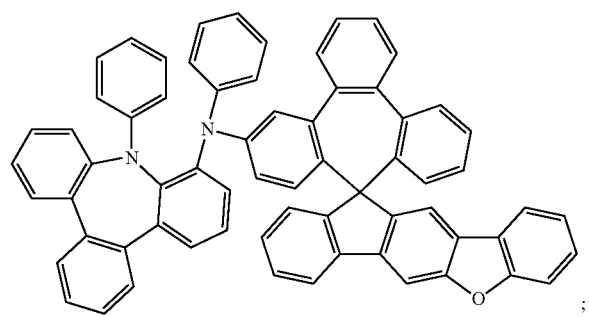
Compound 654
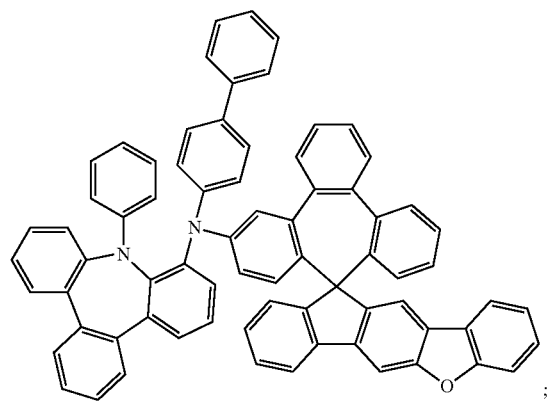
Compound 655
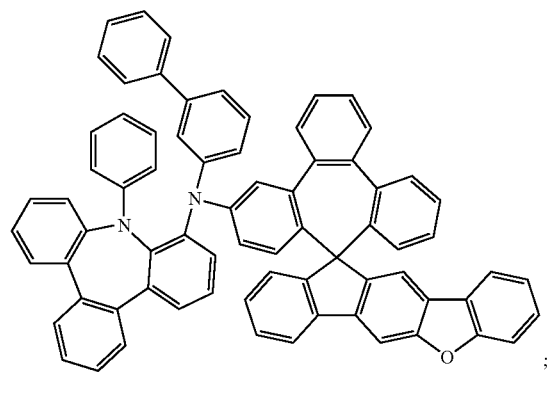

-continued
Compound 656
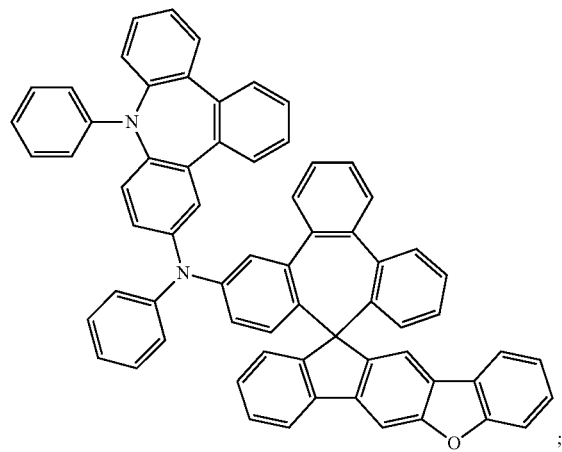
Compound 657
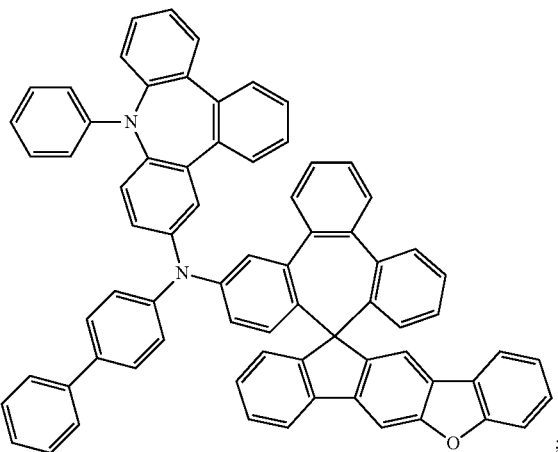
Compound 658
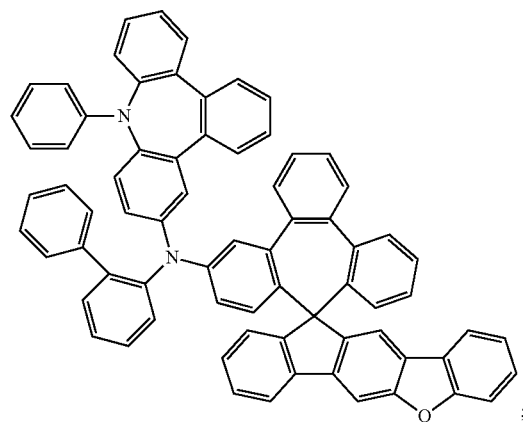
Compound 659
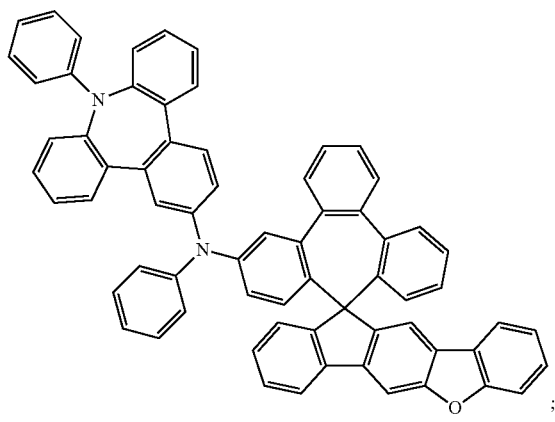
Compound 660
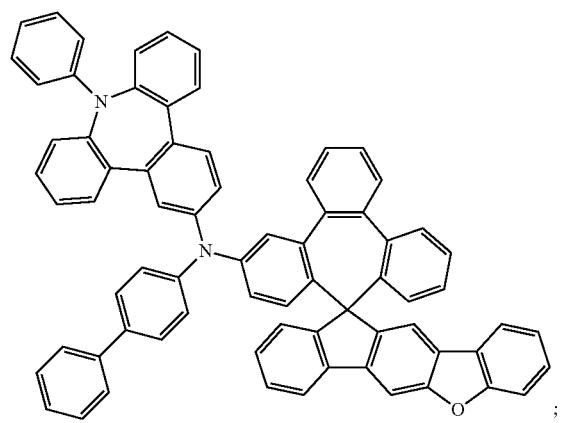
Compound 661
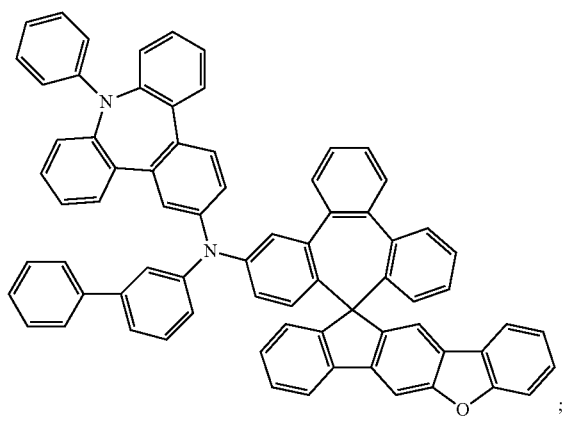

-continued
Compound 662
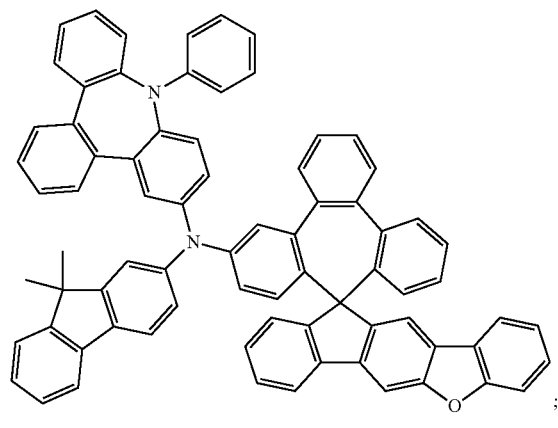
Compound 663
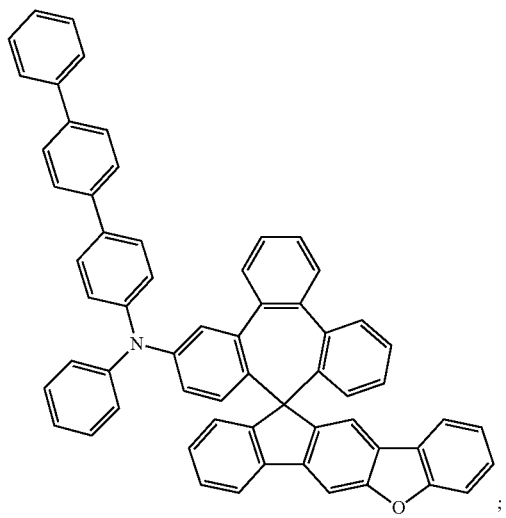
Compound 664
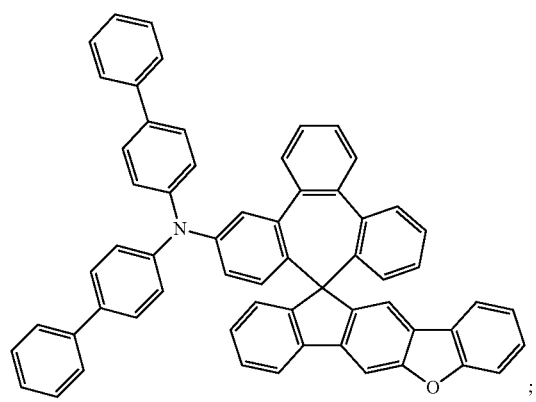
Compound 665
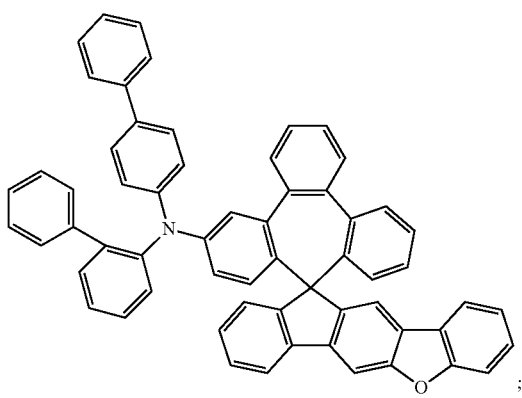
Compound 666
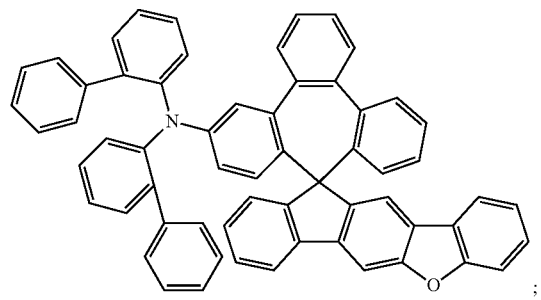
Compound 667
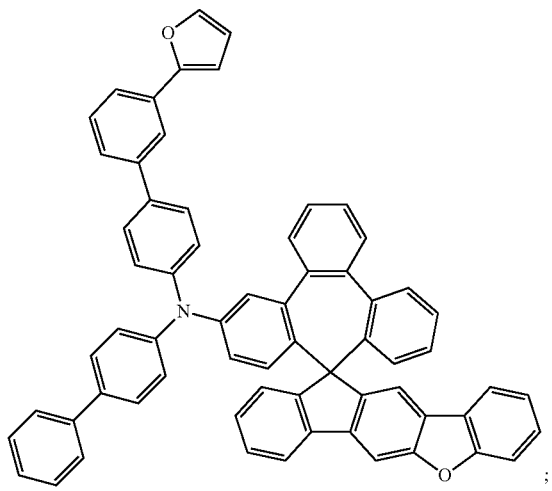

-continued
Compound 668
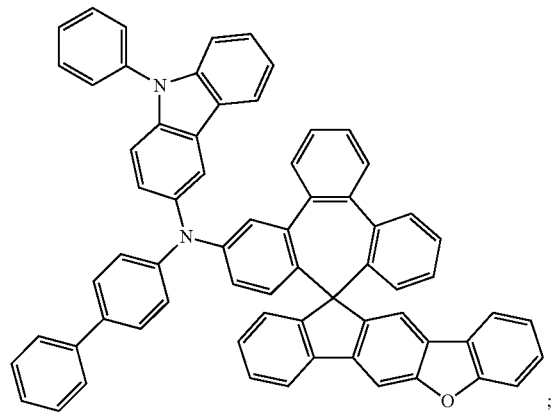
Compound 669
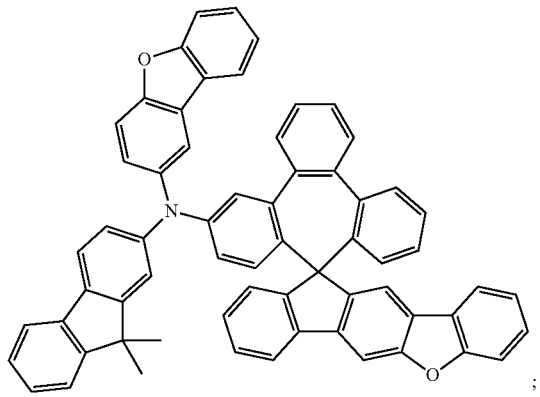
Compound 670
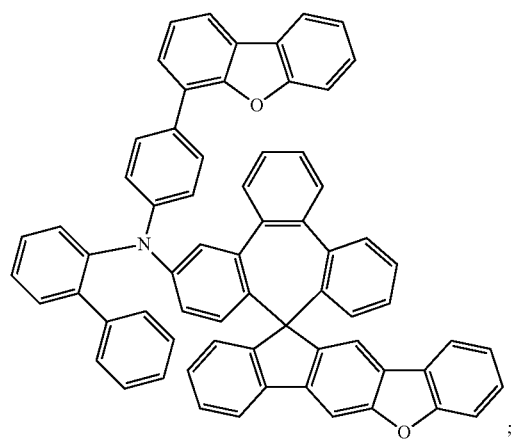
Compound 671
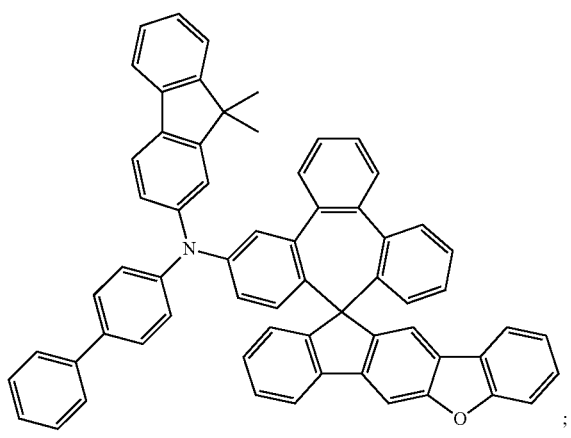
Compound 672
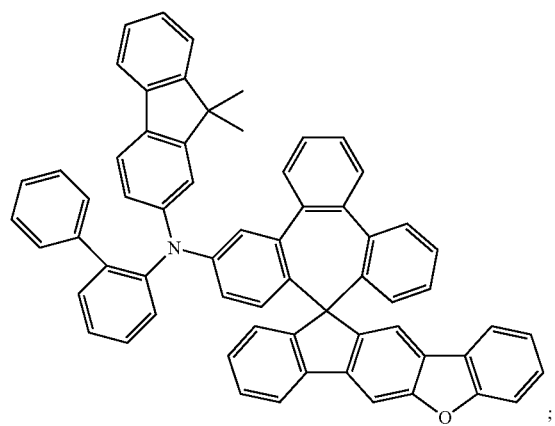
Compound 673
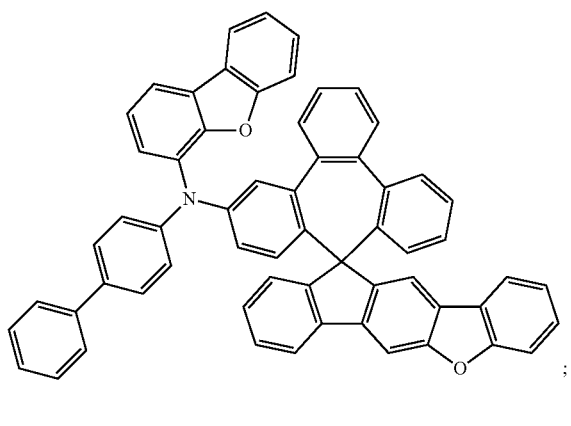

-continued
Compound 674
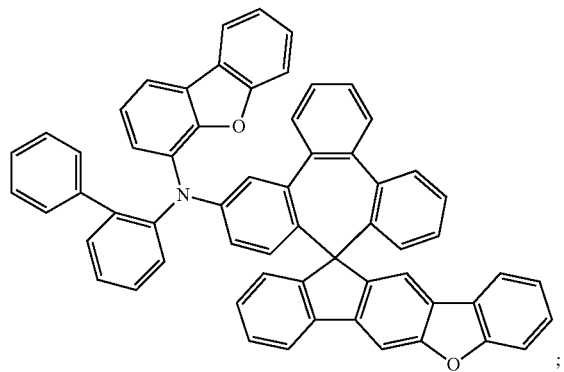
Compound 675
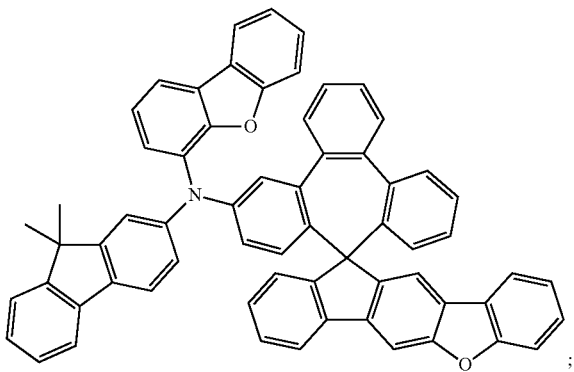
Compound 676
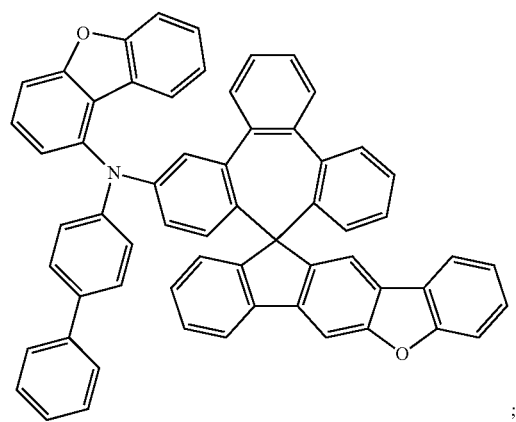
Compound 677
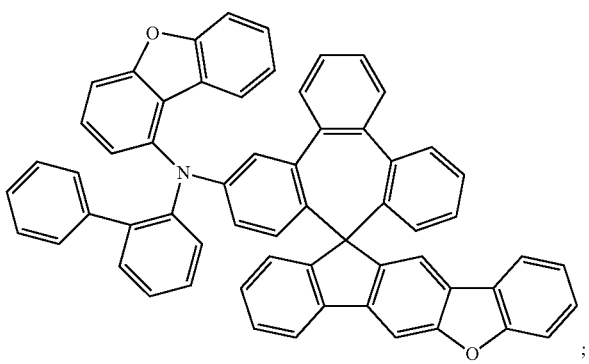
Compound 678
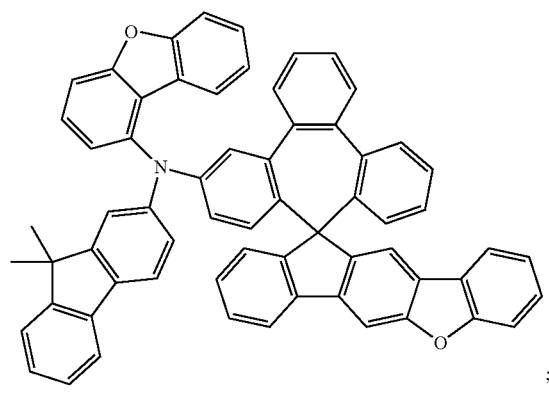
Compound 679
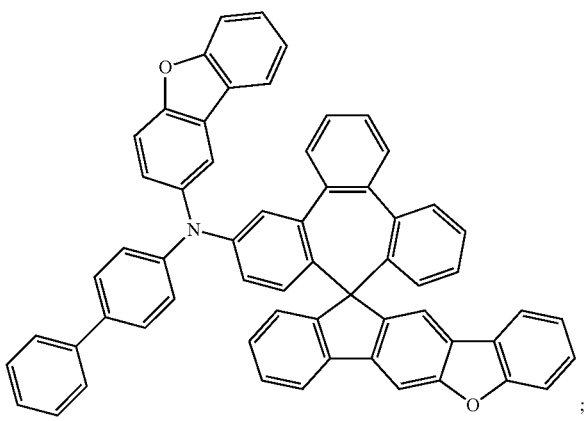

-continued
Compound 680
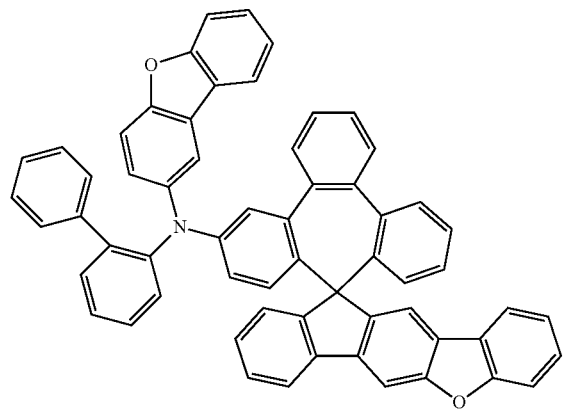
Compound 681
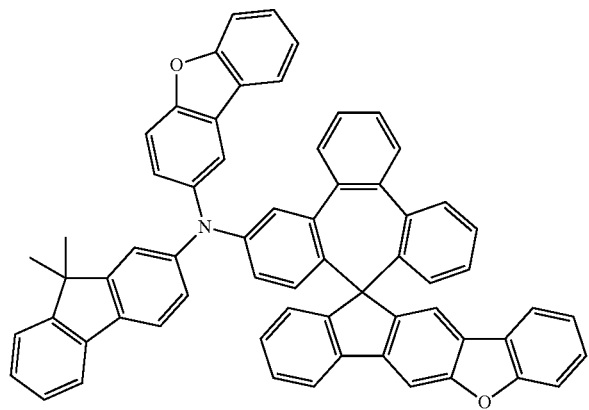
Compound 682
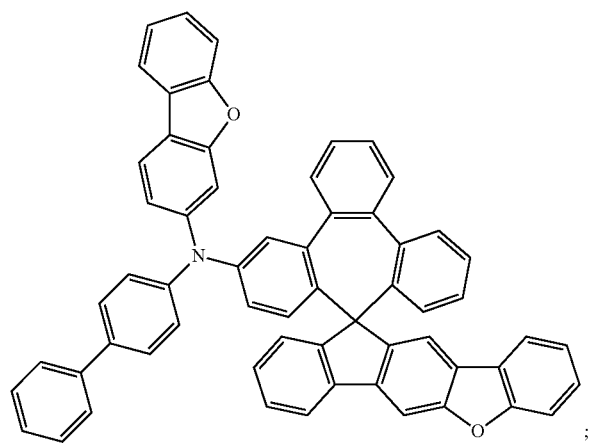
Compound 683
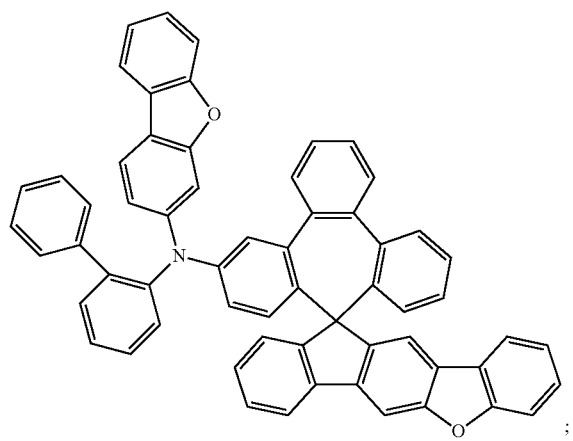
Compound 684
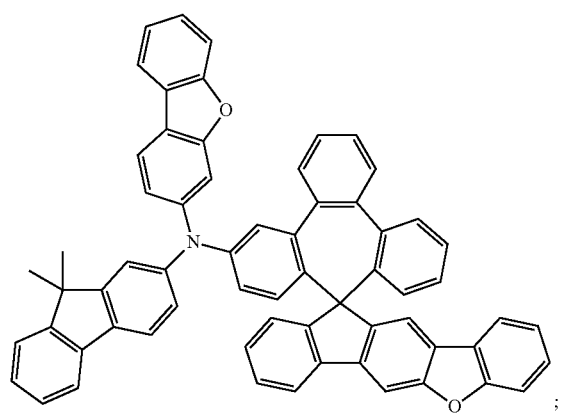
Compound 685
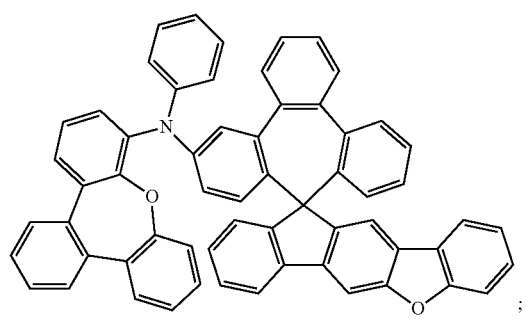

-continued
Compound 686
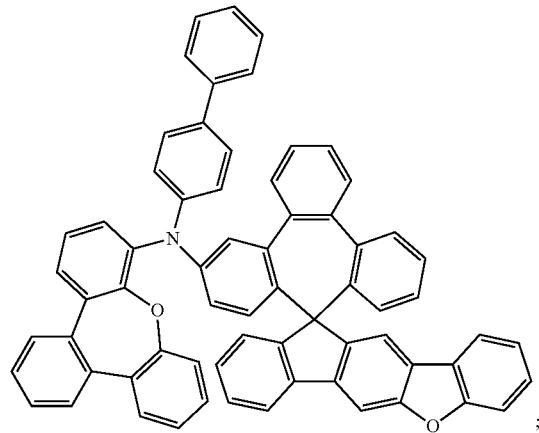
Compound 687
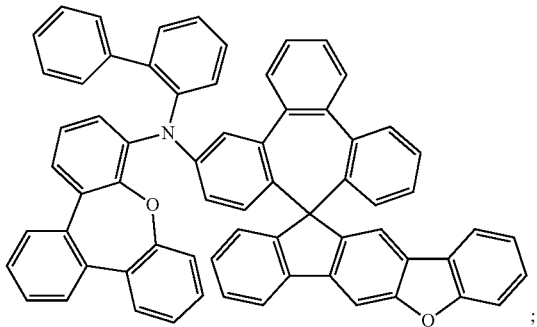
Compound 688
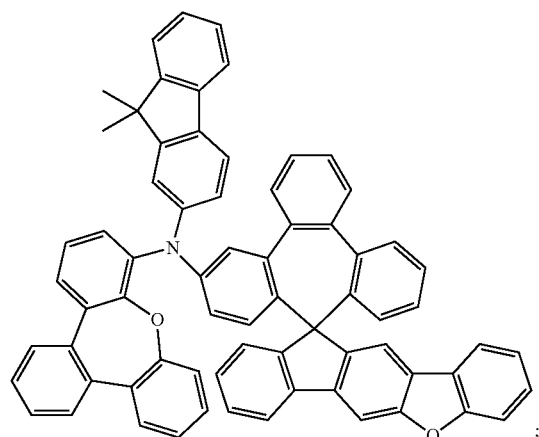
Compound 689
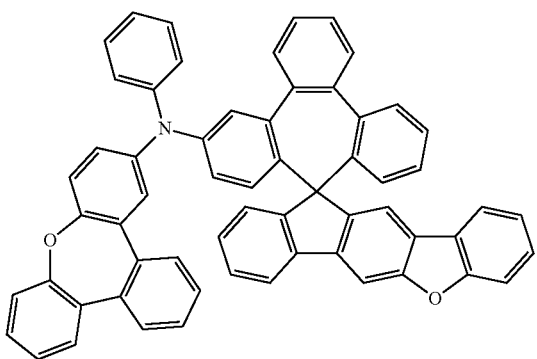
Compound 690
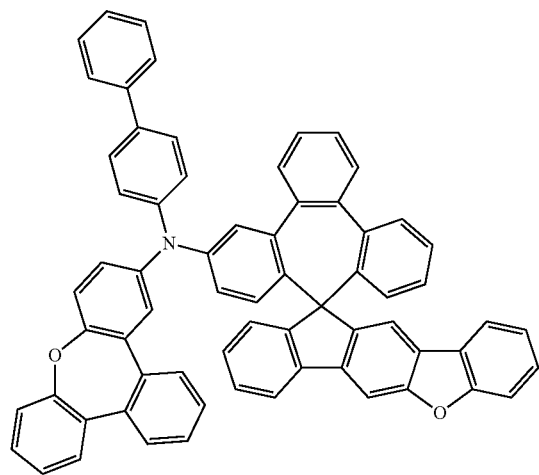
Compound 691
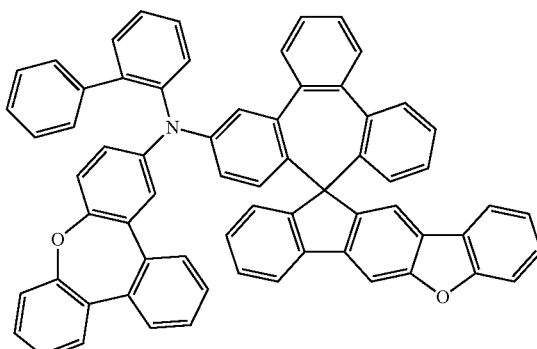

-continued
Compound 692
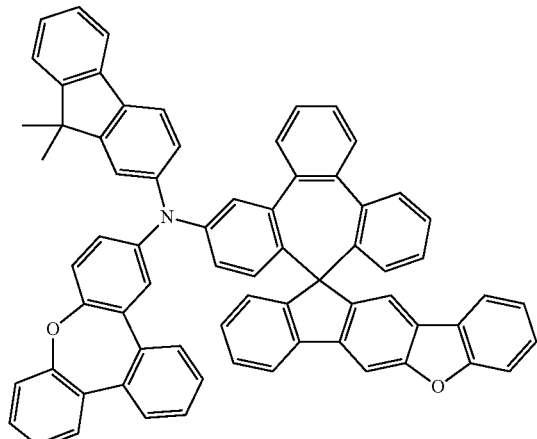
Compound 693
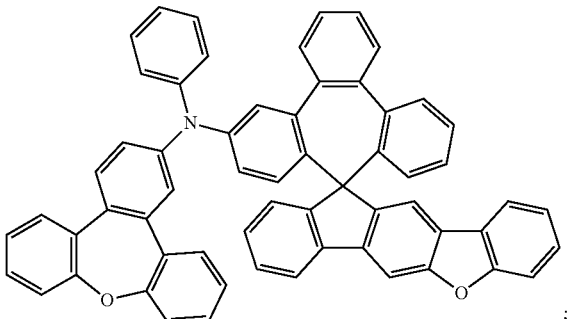
;
Compound 694
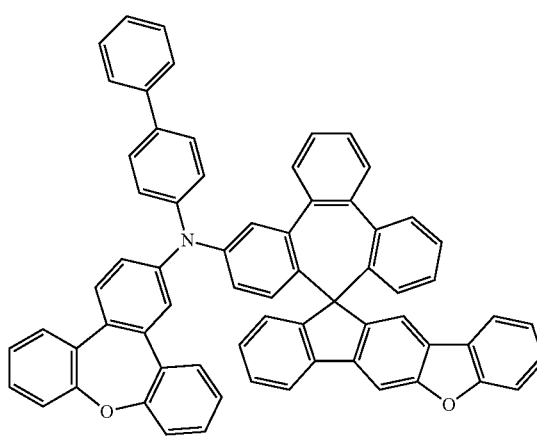
Compound 695
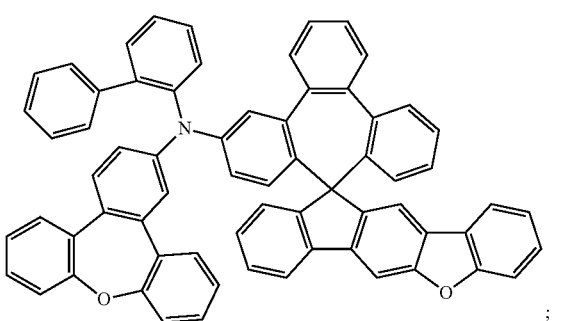
;
Compound 696
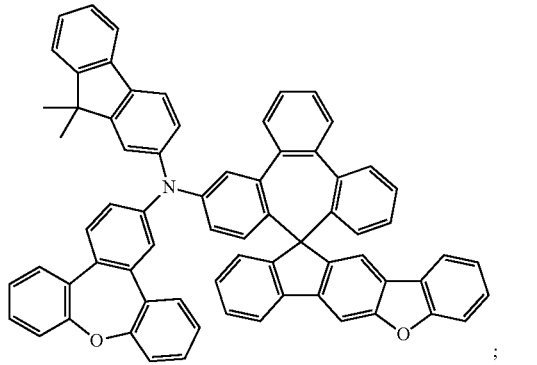
Compound 697
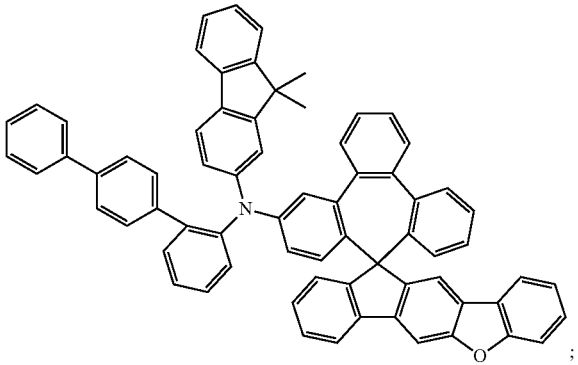
;
Compound 698
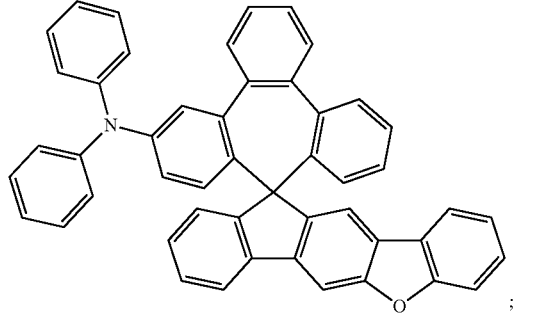
Compound 699
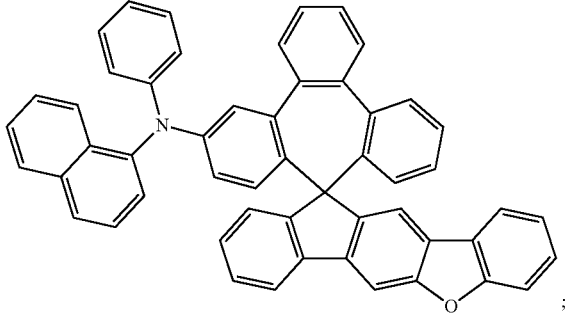
;

-continued
Compound 700
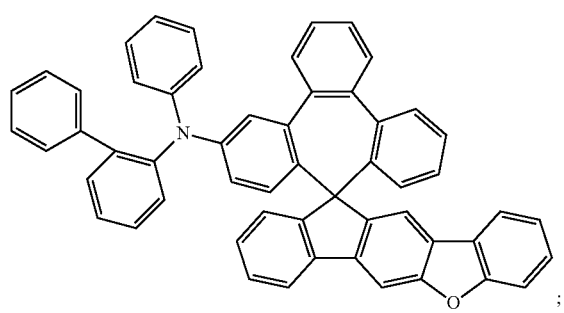
Compound 701
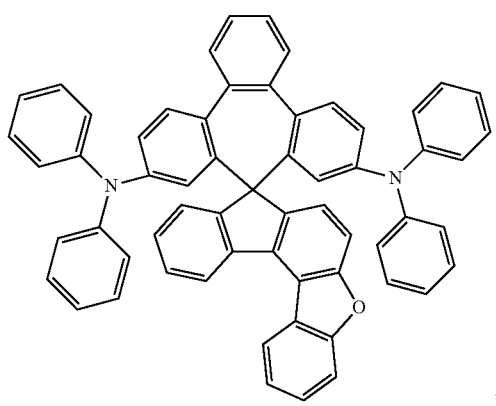
Compound 702
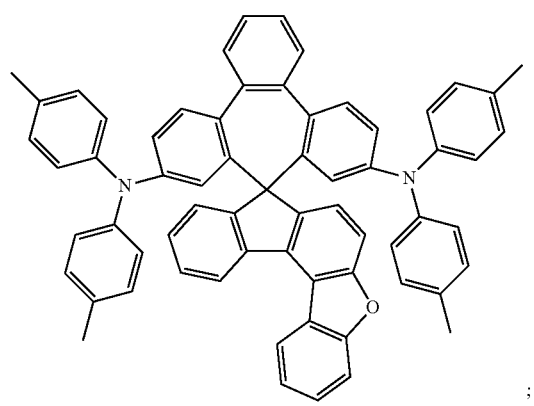
Compound 703
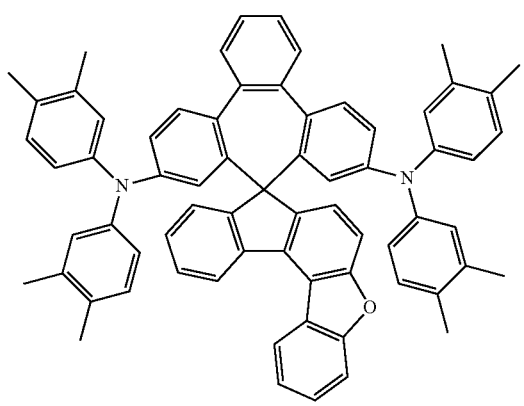
Compound 704
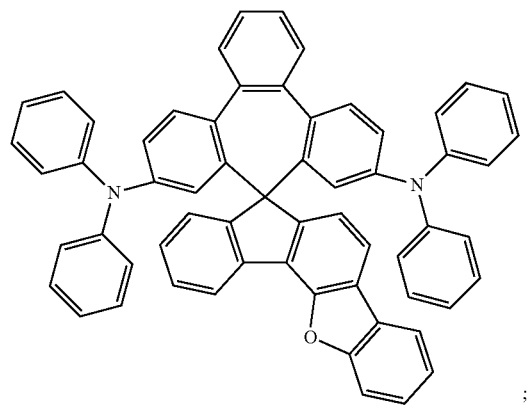
Compound 705
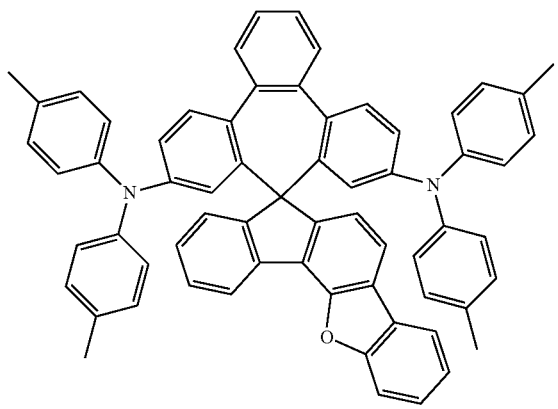

-continued
Compound 706
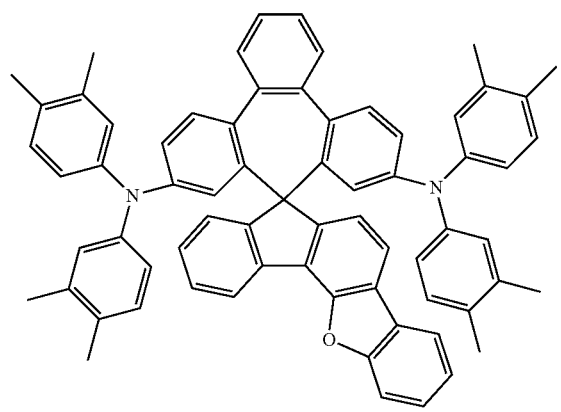
Compound 707
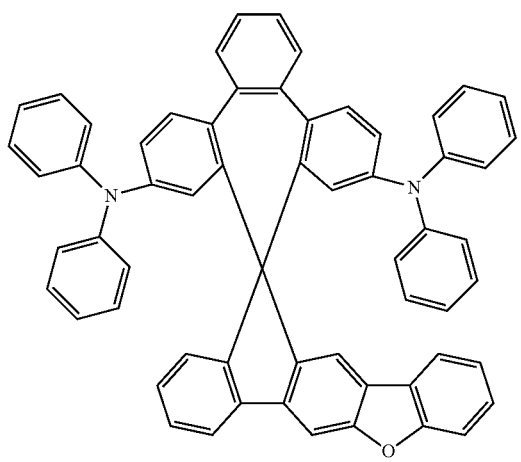
Compound 708
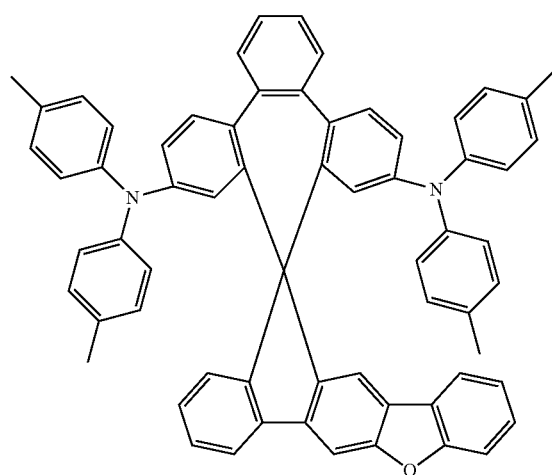
Compound 709
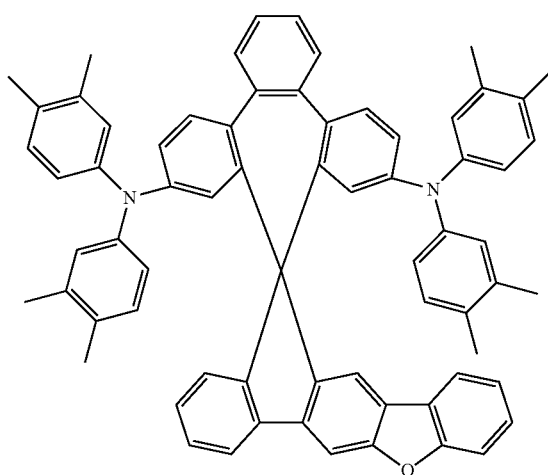
Compound 710
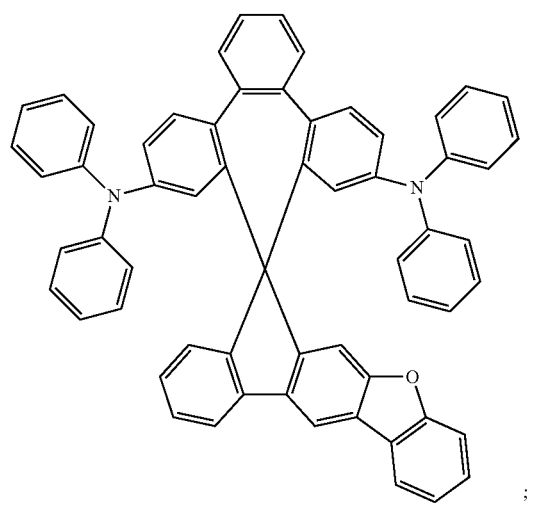
Compound 711
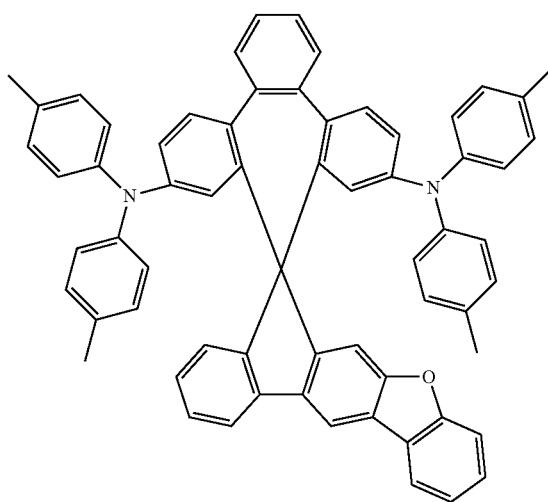

-continued
Compound 712
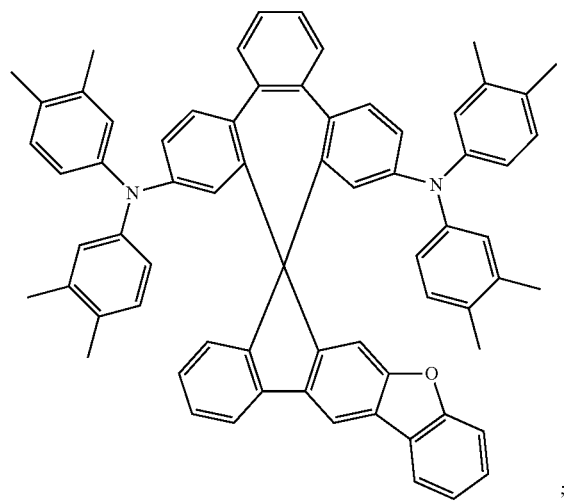
;
Compound 713
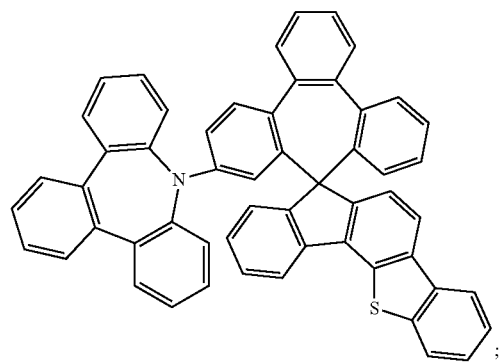
;
Compound 714
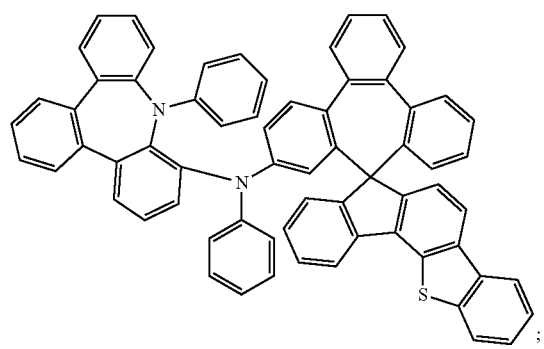
;
Compound 715
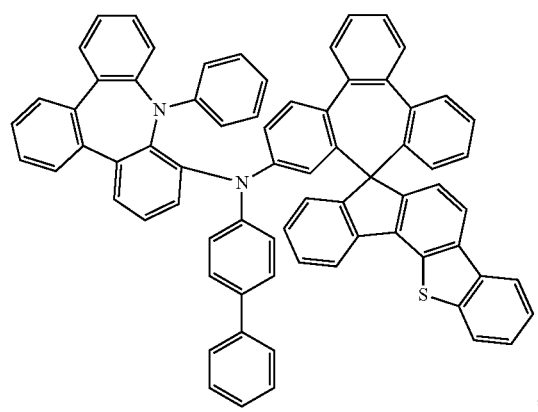
;
Compound 716
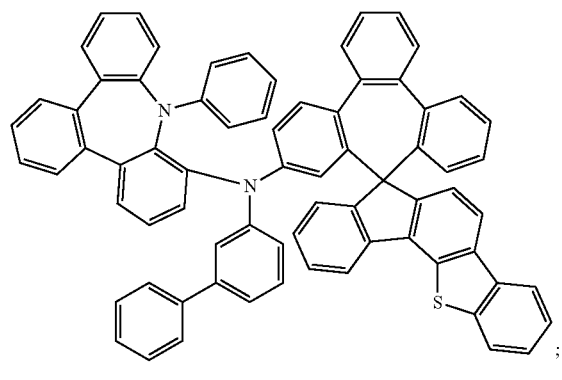
;
Compound 717
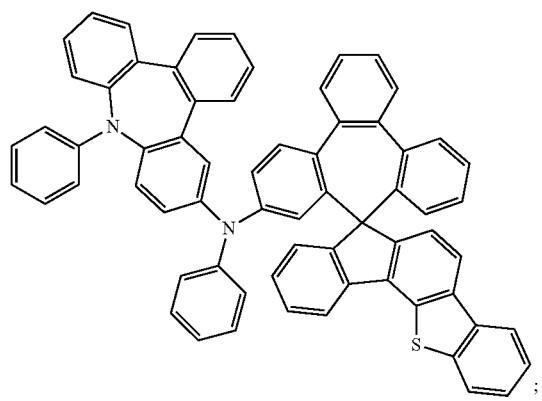
;

-continued
Compound 718
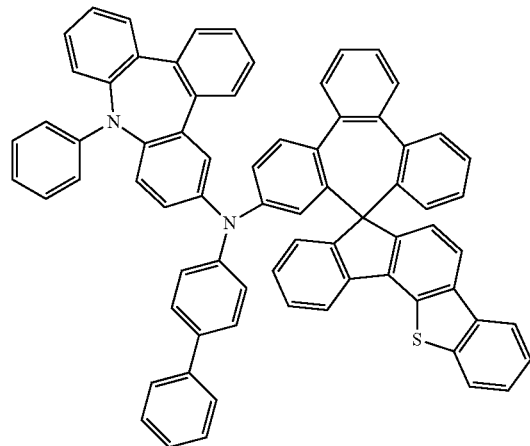
Compound 719
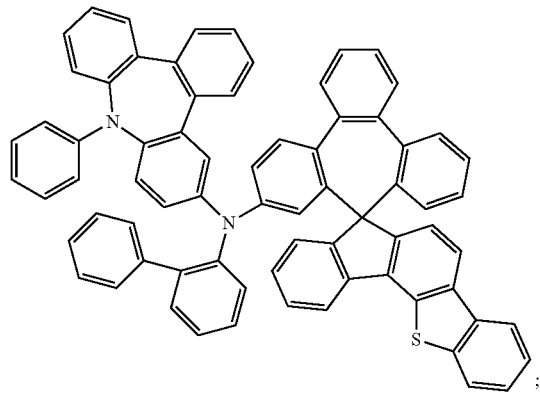
Compound 720
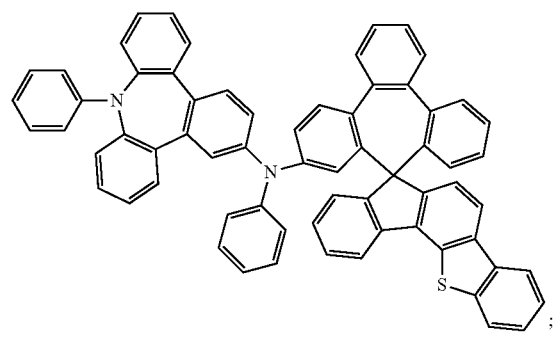
Compound 721
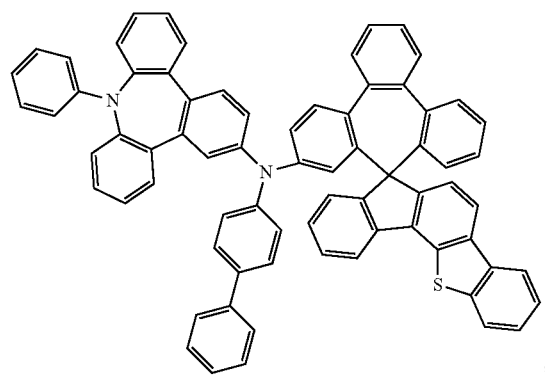
Compound 722
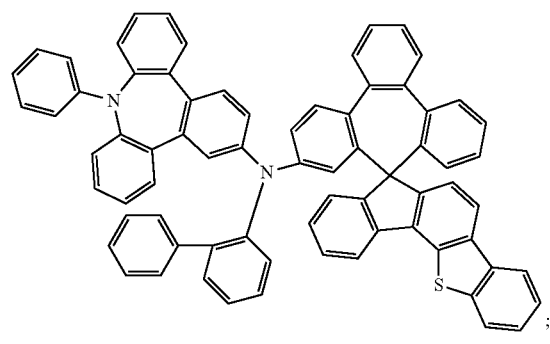
Compound 723
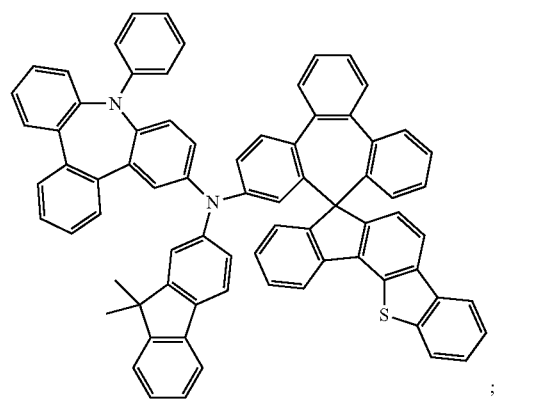

-continued
Compound 724
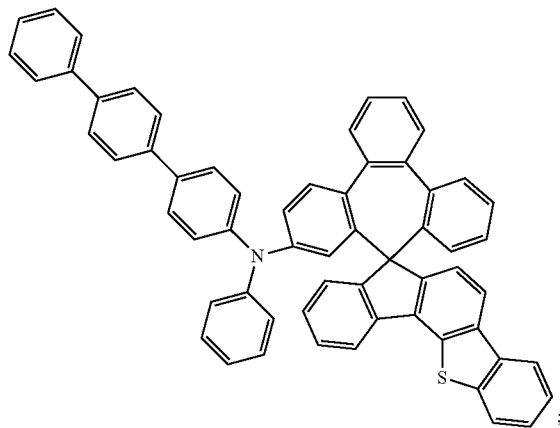
Compound 725
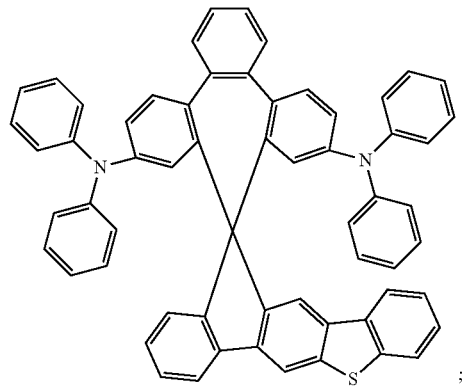
Compound 726
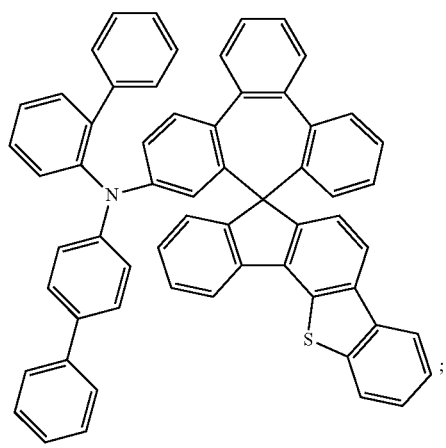
Compound 727
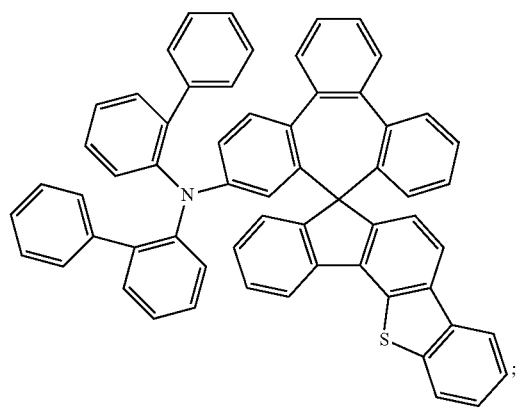
Compound 728
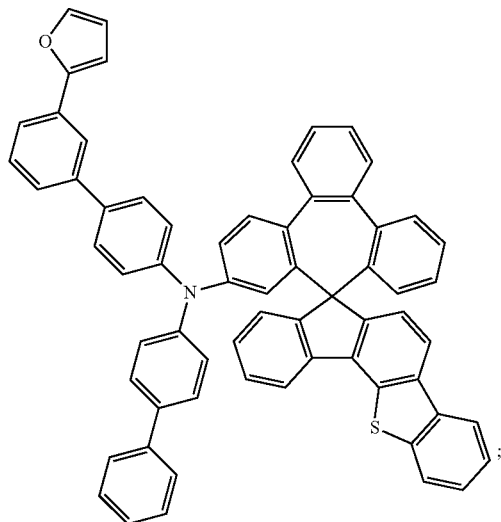
Compound 729
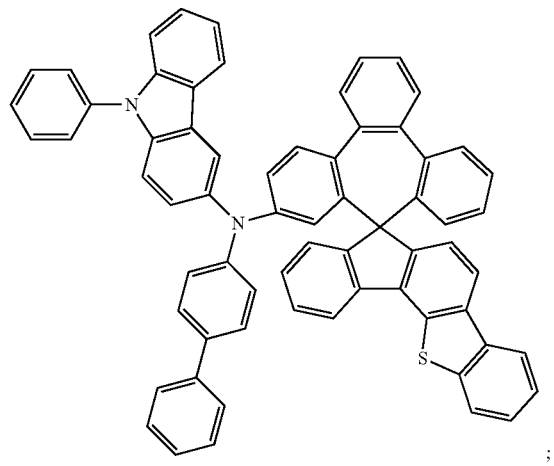

-continued
Compound 730
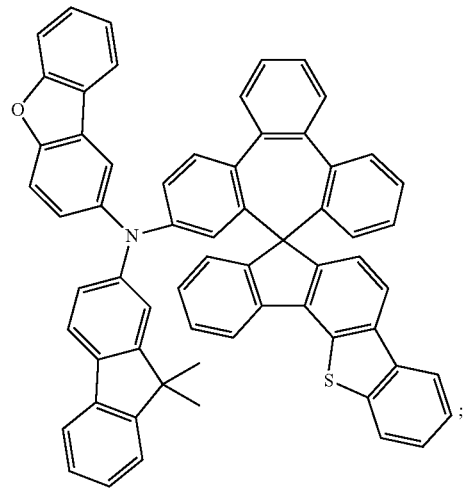
Compound 731
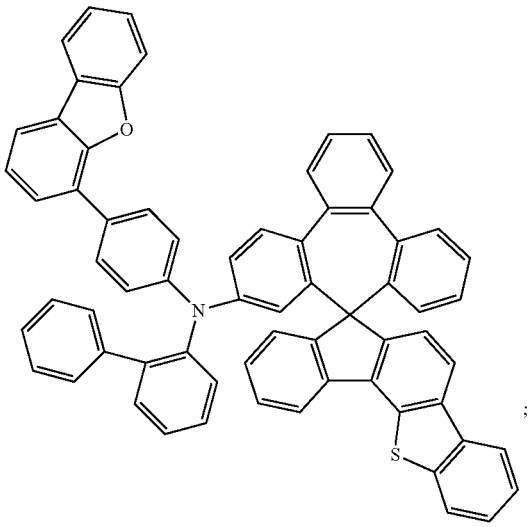
Compound 732
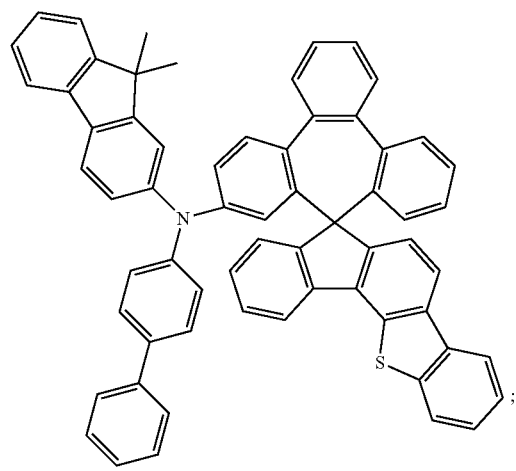
Compound 733
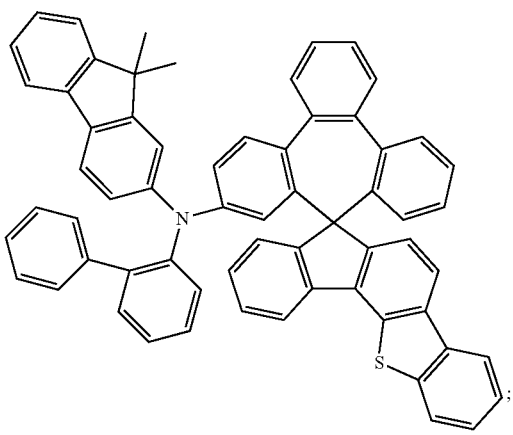
Compound 734
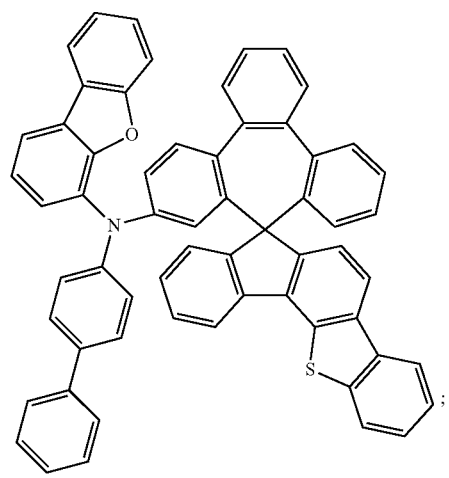
Compound 735
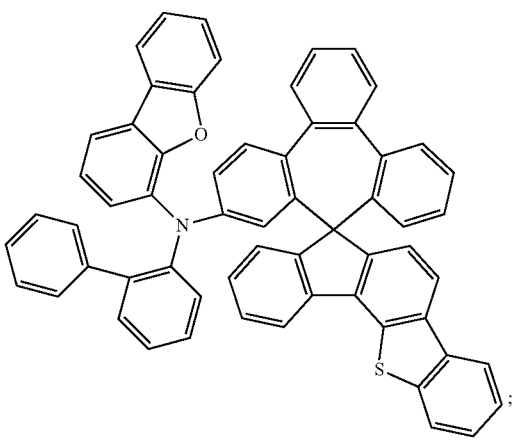

-continued
Compound 736
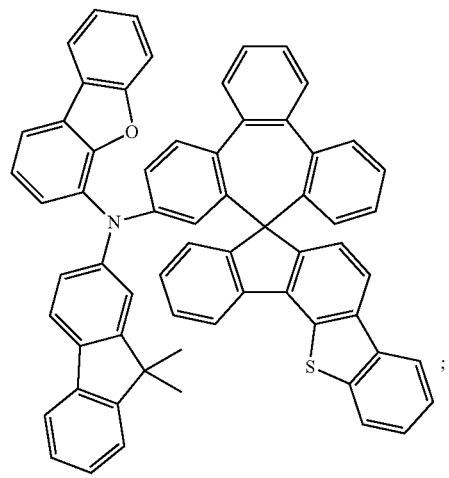
Compound 737
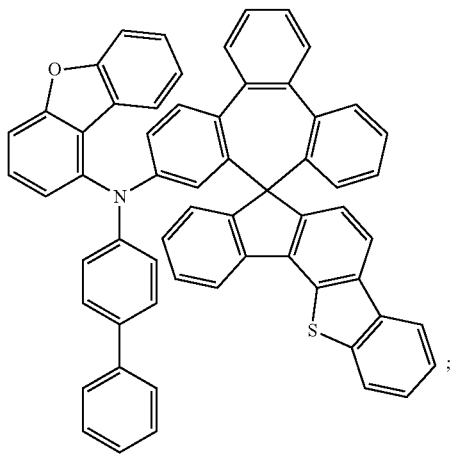
Compound 738
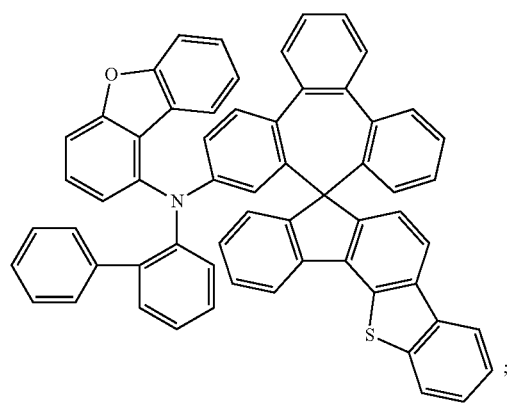
Compound 739
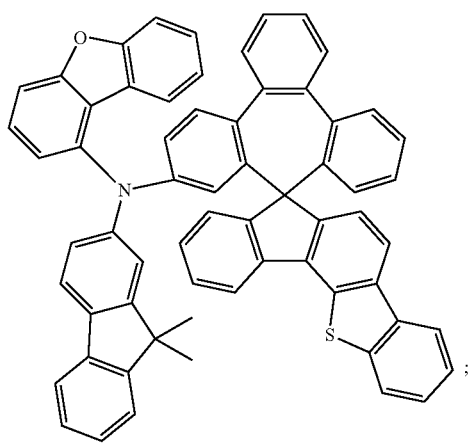
Compound 740
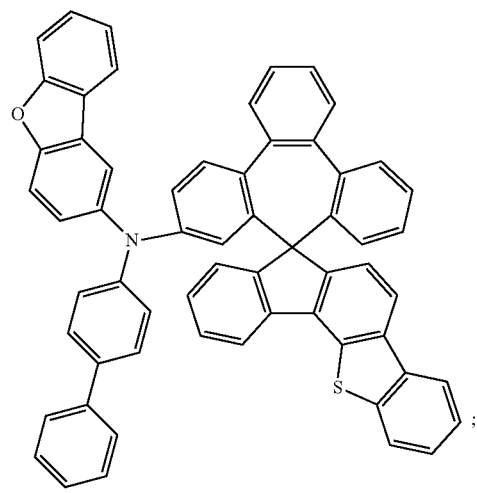
Compound 741
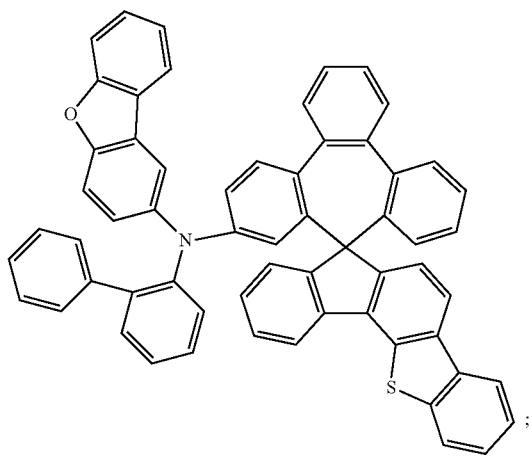

-continued
Compound 742
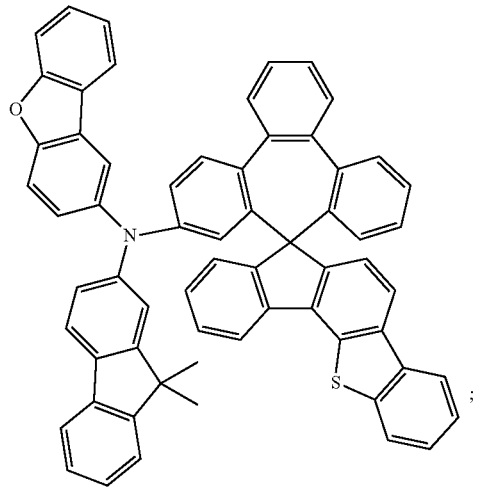
Compound 743
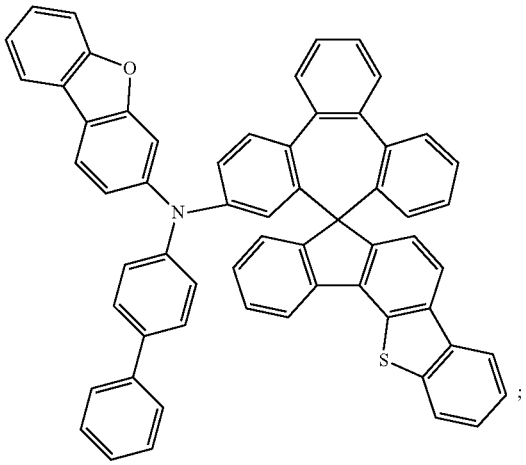
Compound 744
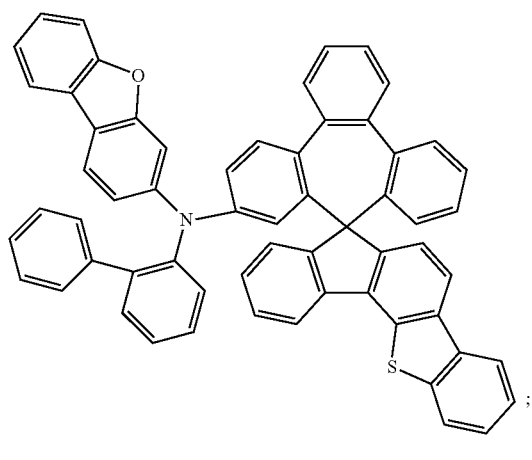
Compound 745
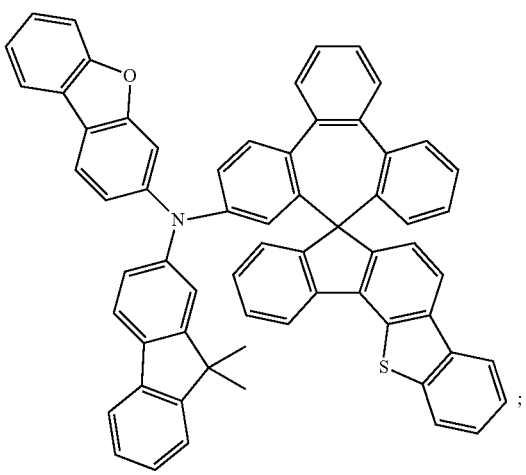
Compound 746
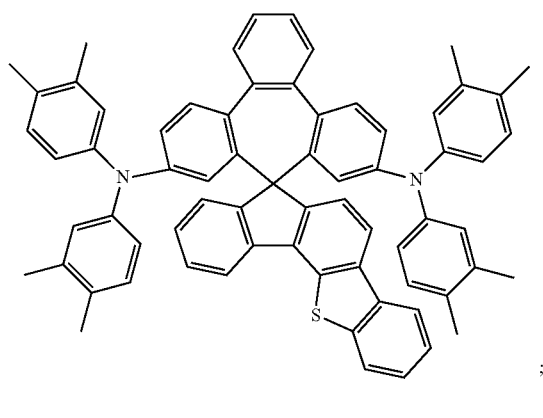
Compound 747
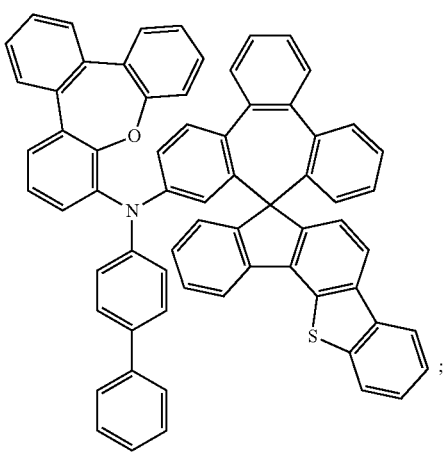

-continued
Compound 748
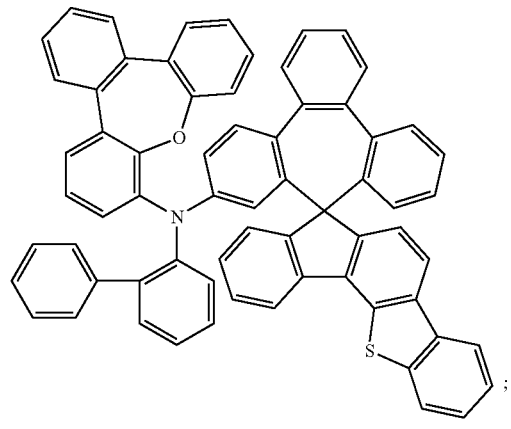
;
Compound 749
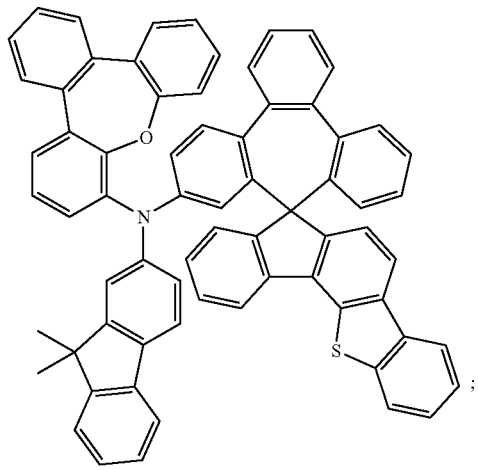
;
Compound 750
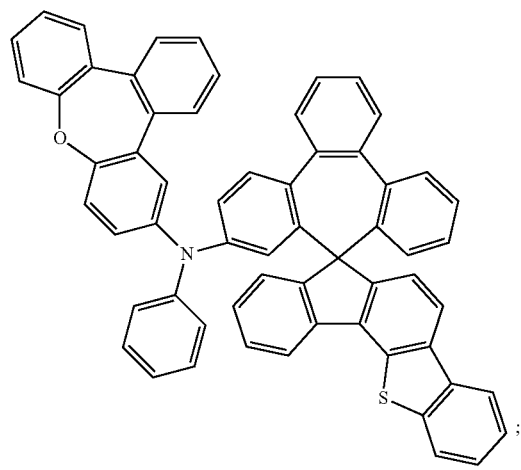
;
Compound 751
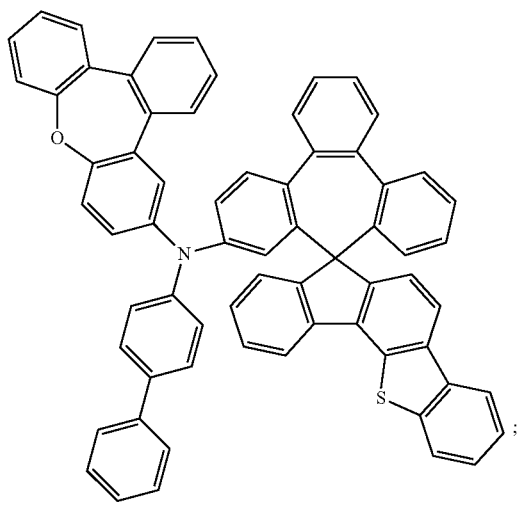
;
Compound 752
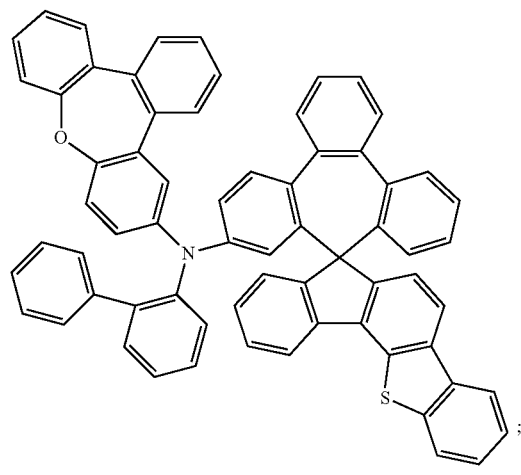
;
Compound 753
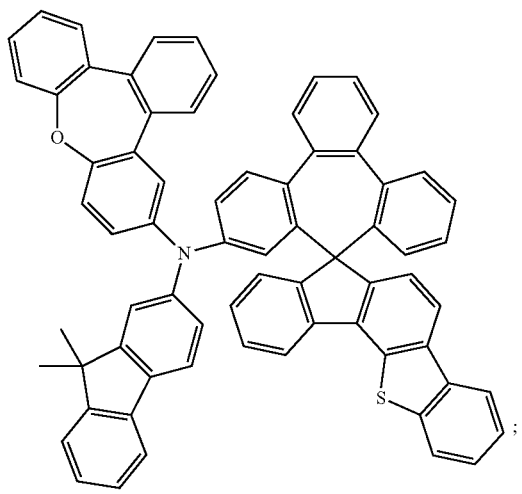
;

-continued
Compound 754
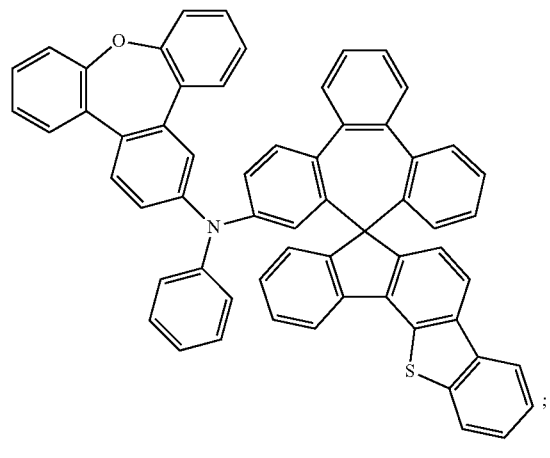
Compound 755
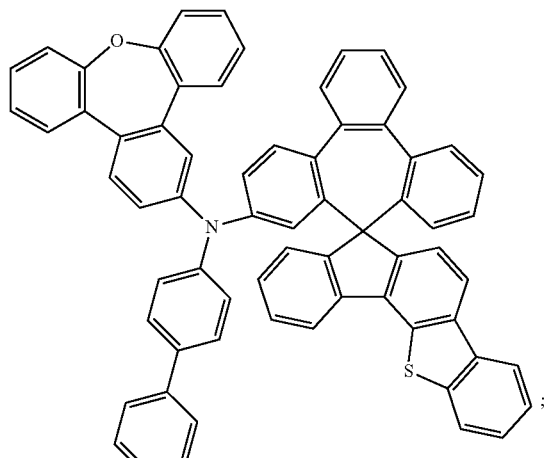
Compound 756
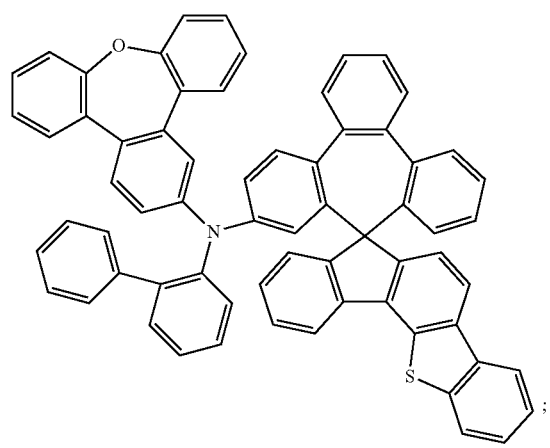
Compound 757
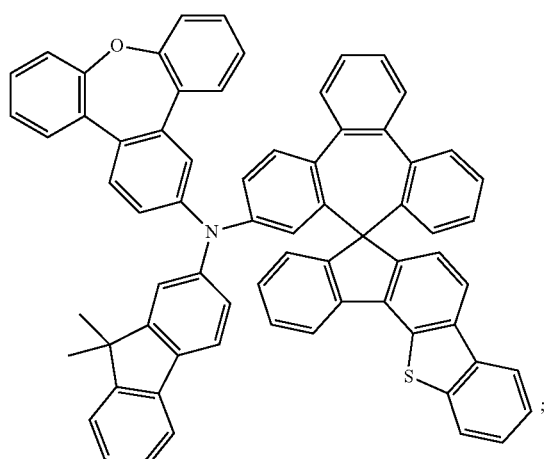
Compound 758
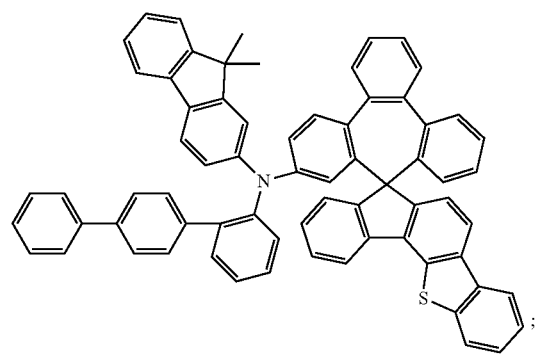
Compound 759
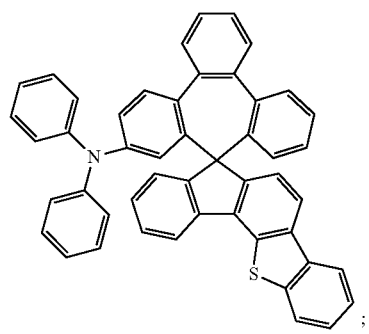

Compound 760 Compound 761

Compound 762 Compound 763

Compound 764 Compound 765

-continued
Compound 766
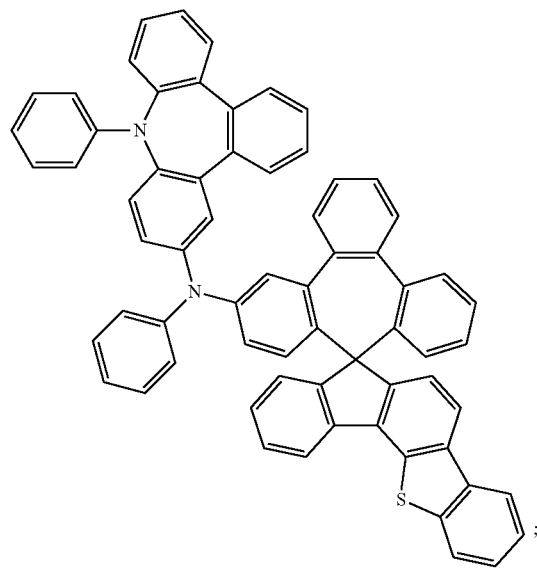
Compound 767
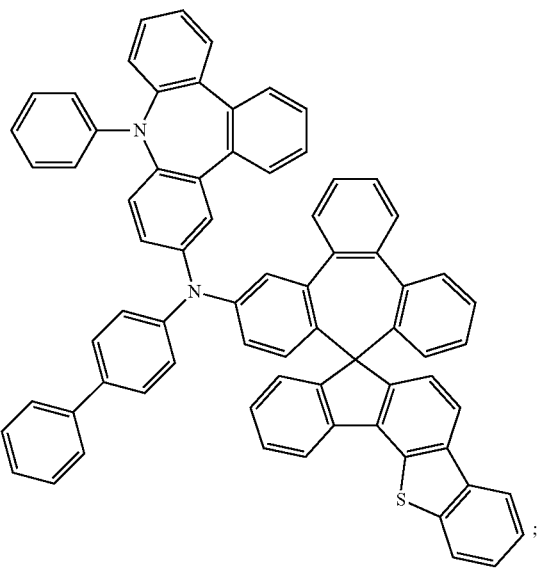
Compound 768
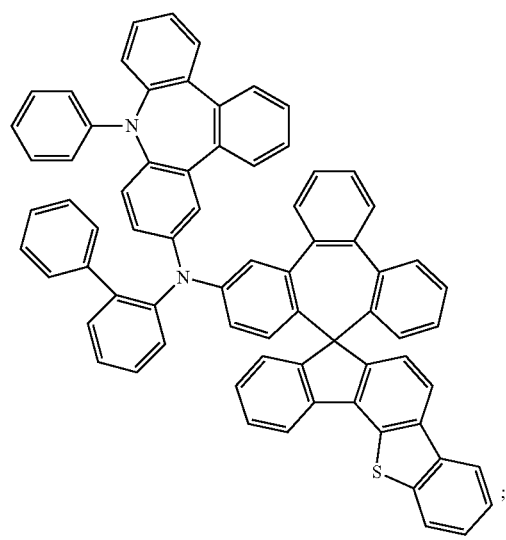
Compound 769
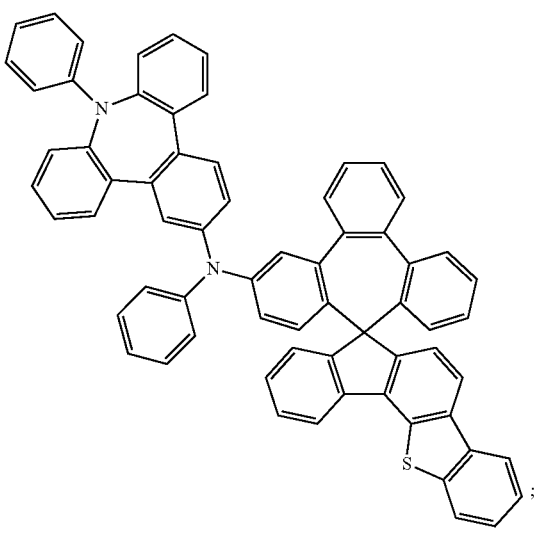

-continued
Compound 770
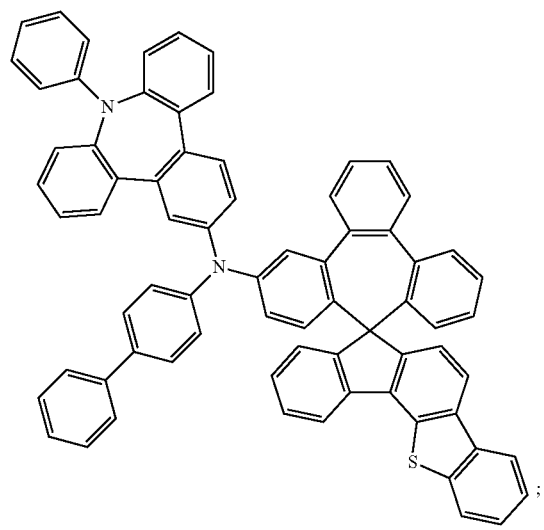
Compound 771
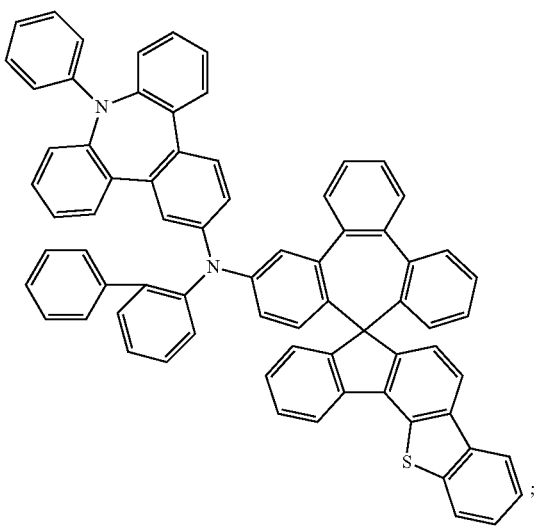
Compound 772
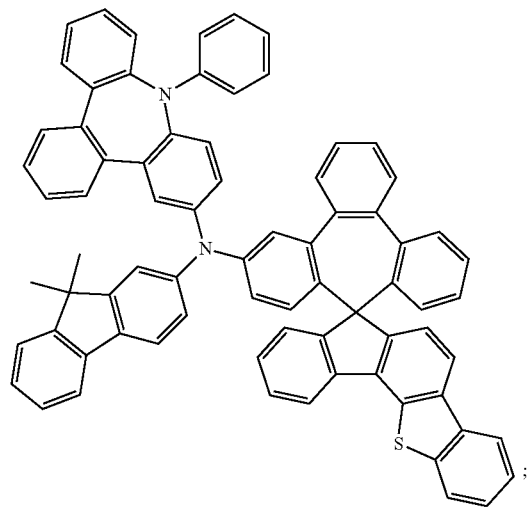
Compound 773
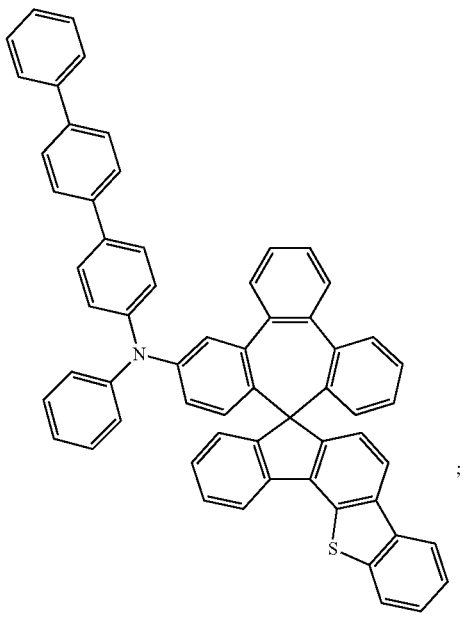

-continued
Compound 774
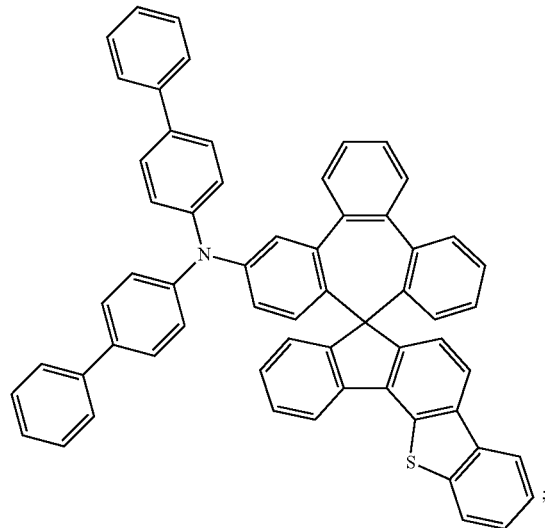
Compound 775
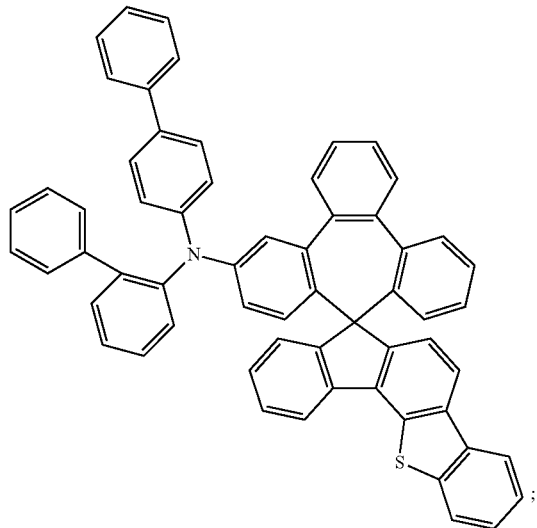
Compound 776
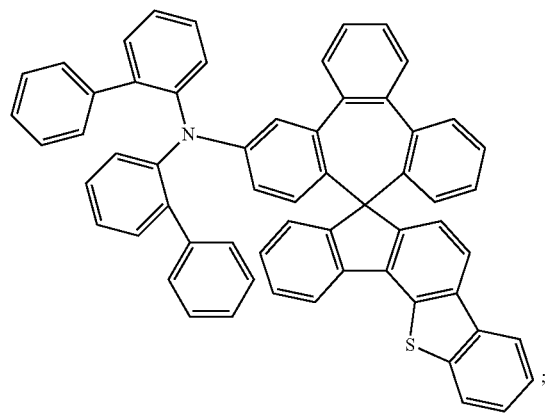
Compound 777
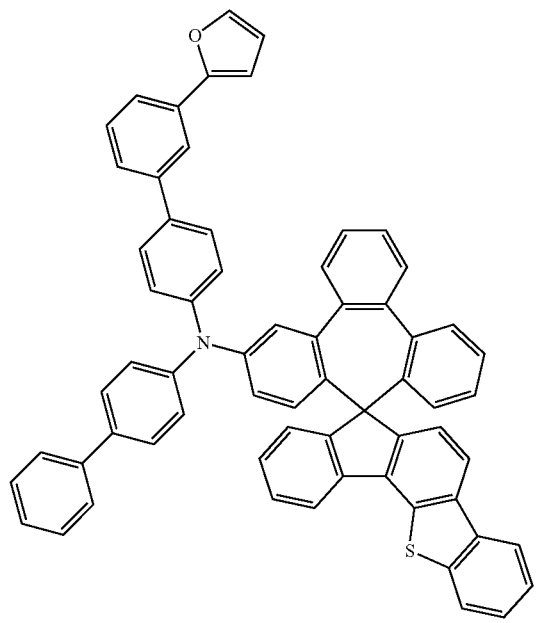

Compound 778
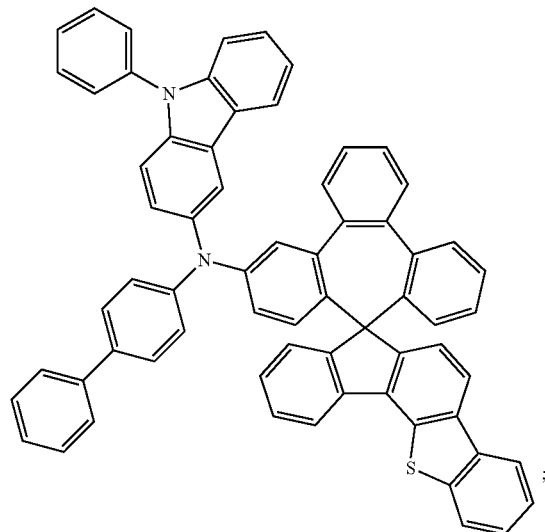
Compound 779
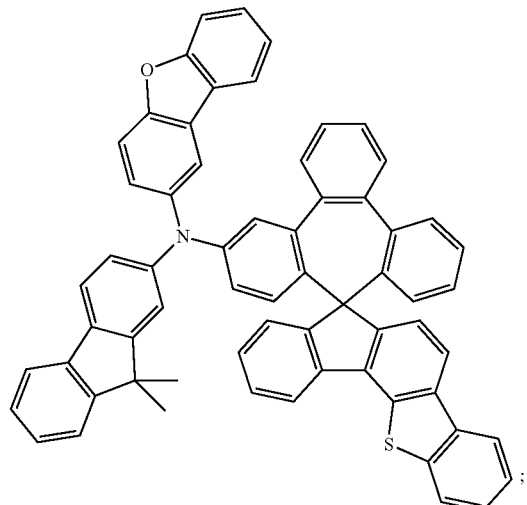
Compound 780
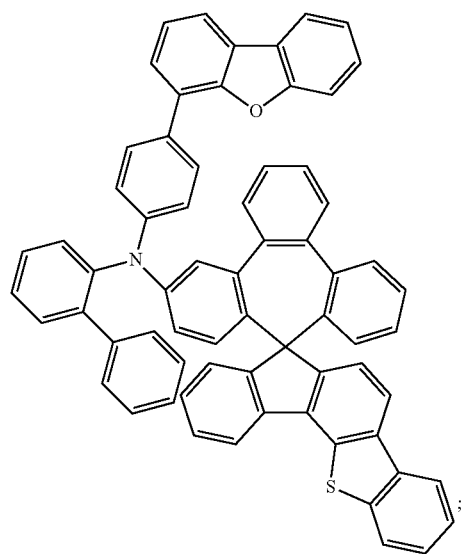
Compound 781
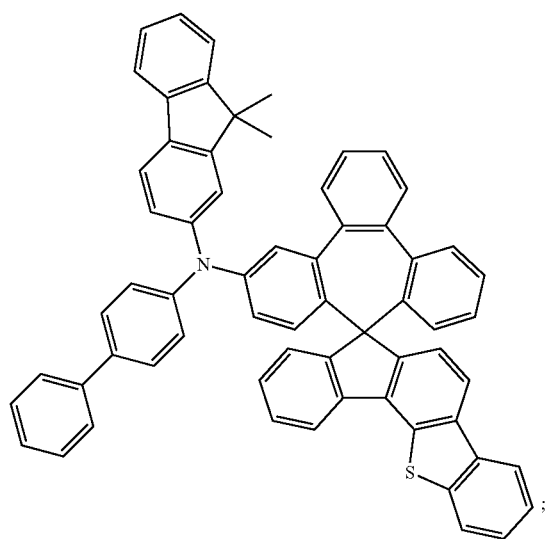

-continued
Compound 782
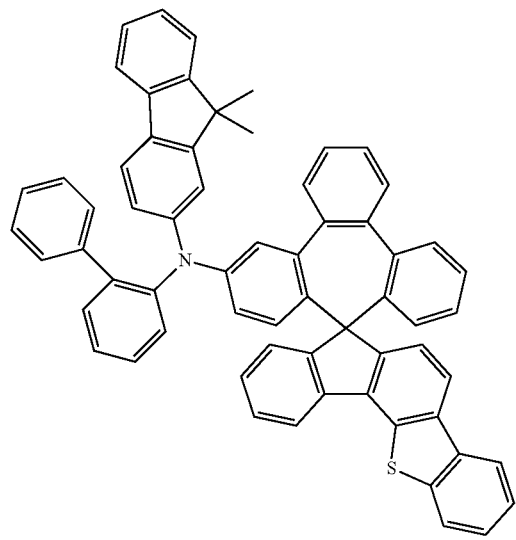
Compound 783
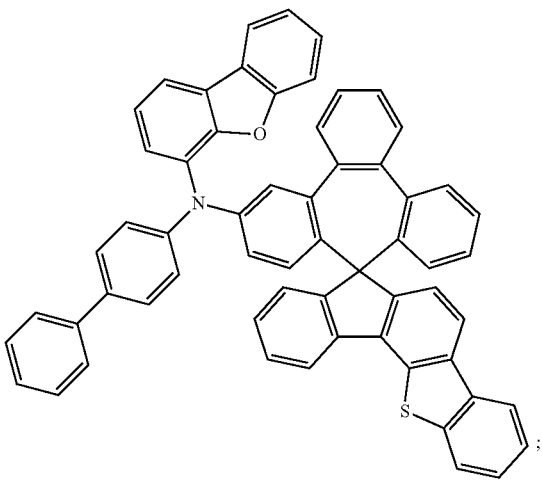
Compound 784
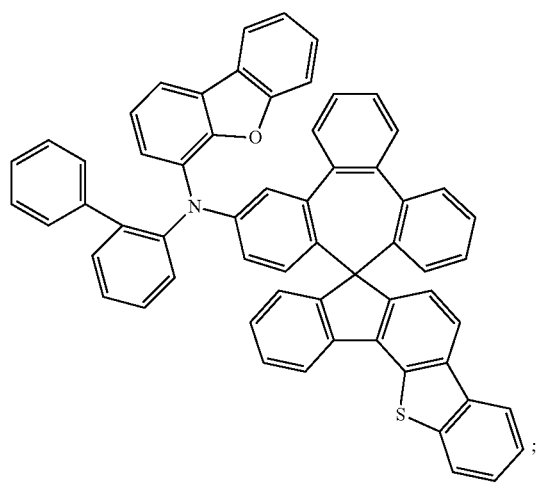
Compound 785
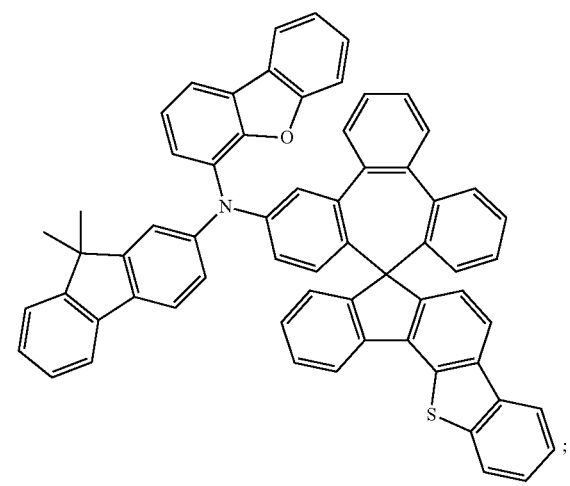
Compound 786
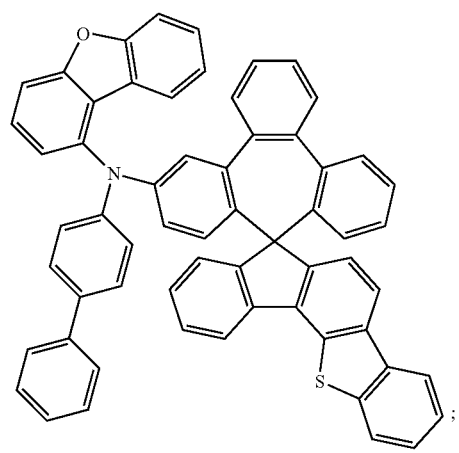
Compound 787
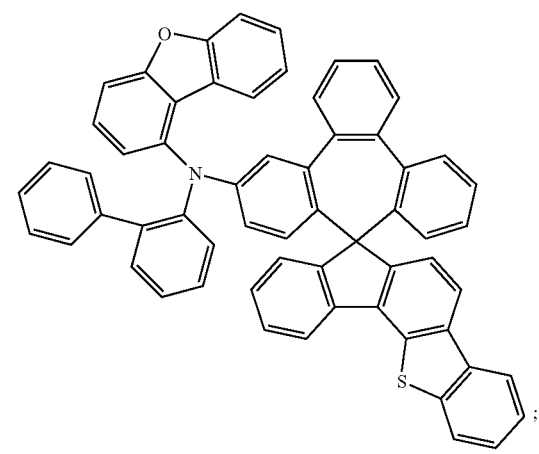

-continued
Compound 788
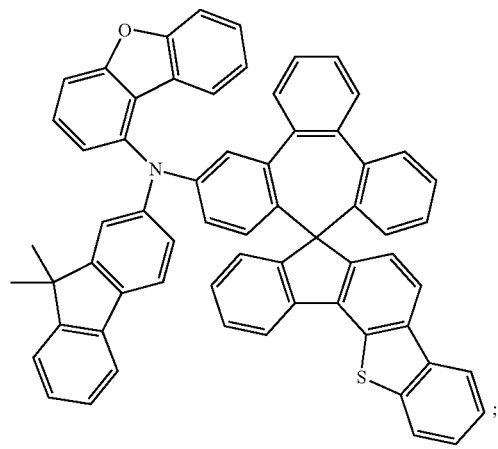
Compound 789
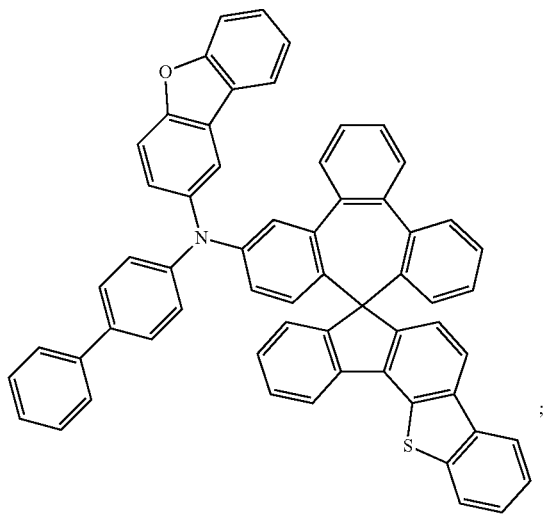
Compound 790
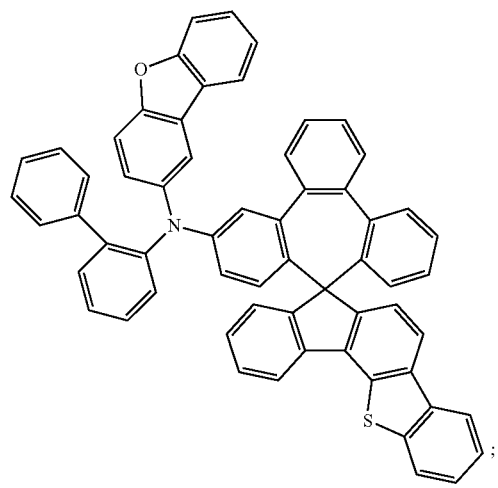
Compound 791
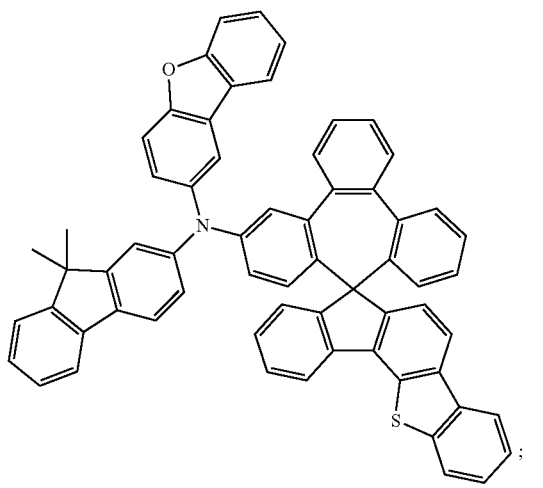
Compound 792
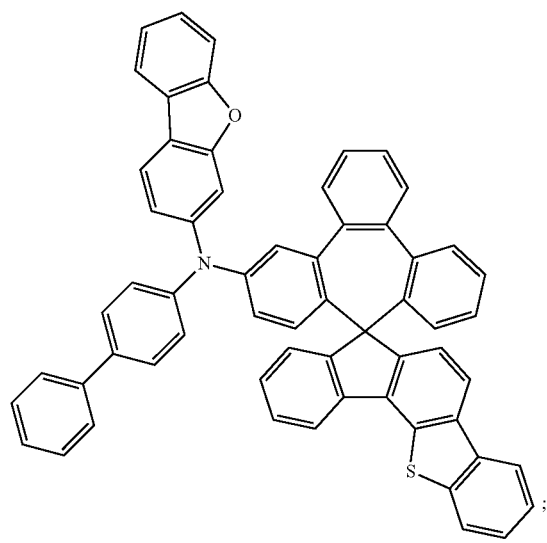
Compound 793
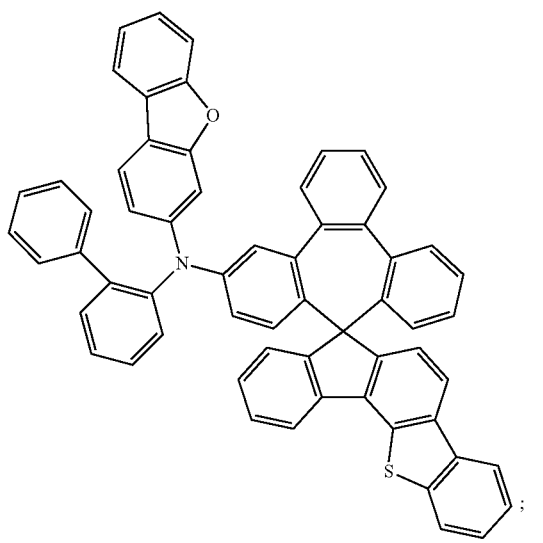

-continued
Compound 794
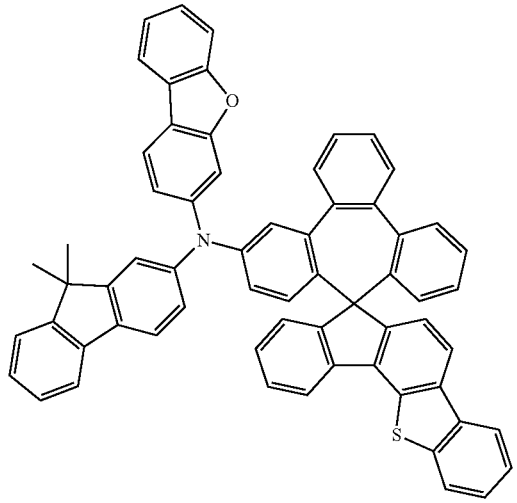
Compound 795
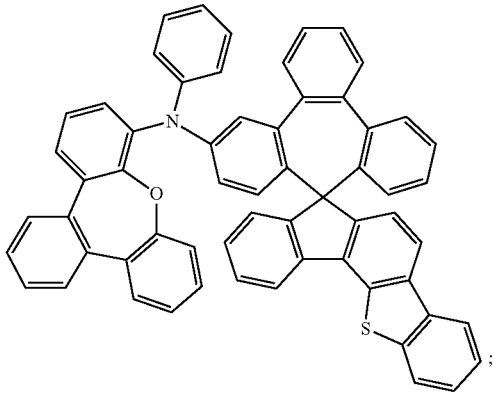
Compound 796
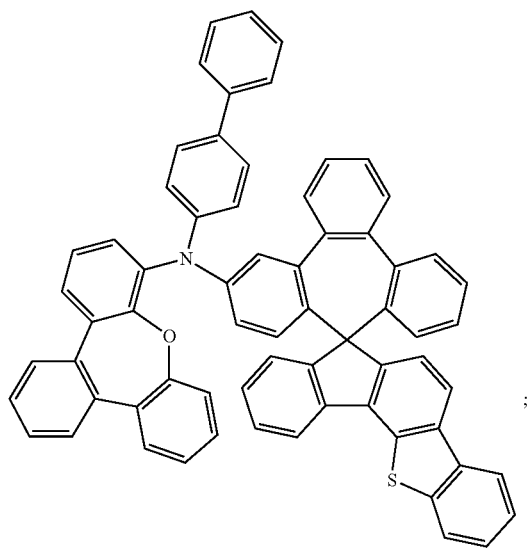
Compound 797
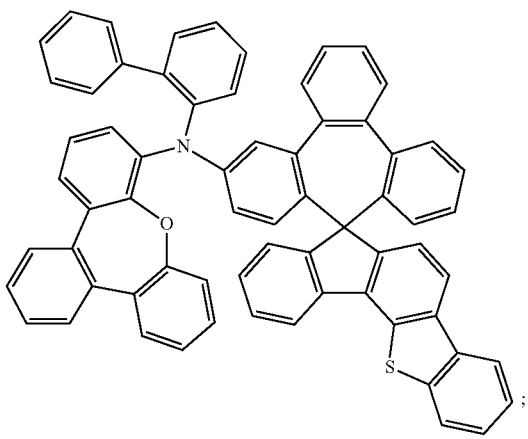
Compound 798
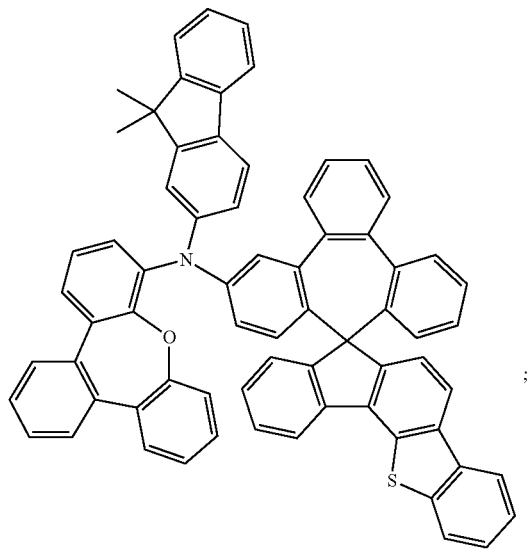
Compound 799
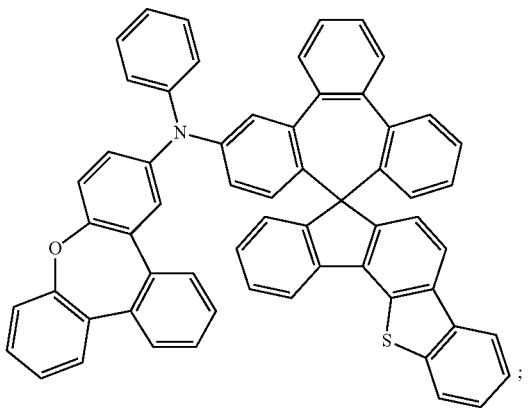

-continued
Compound 800
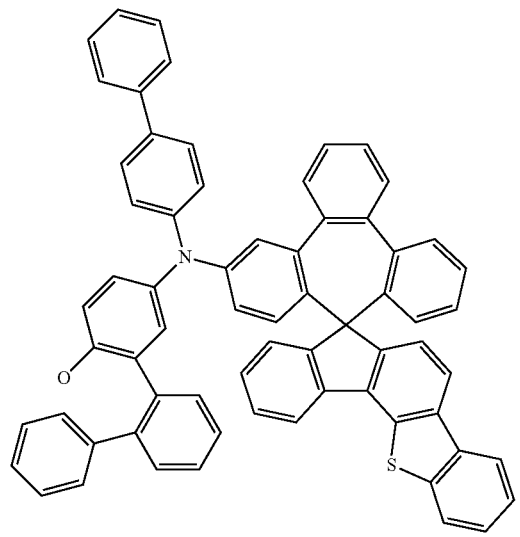
Compound 801
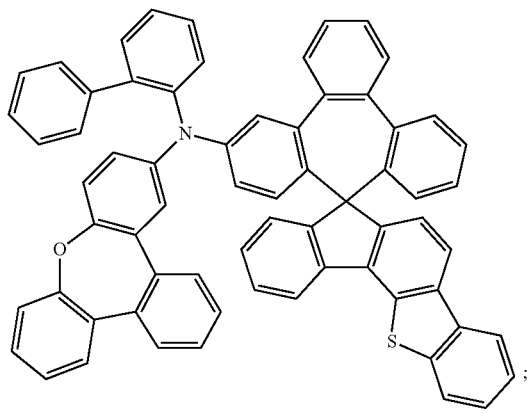
;
Compound 802
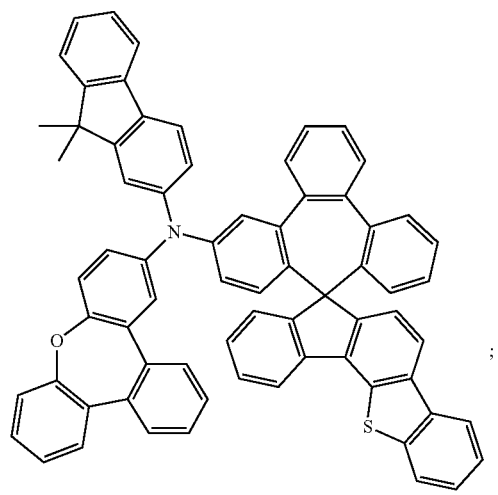
;
Compound 803
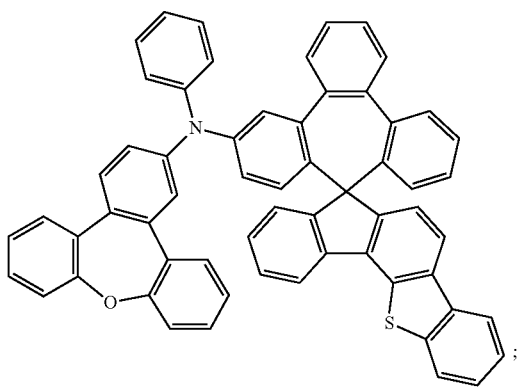
;
Compound 804
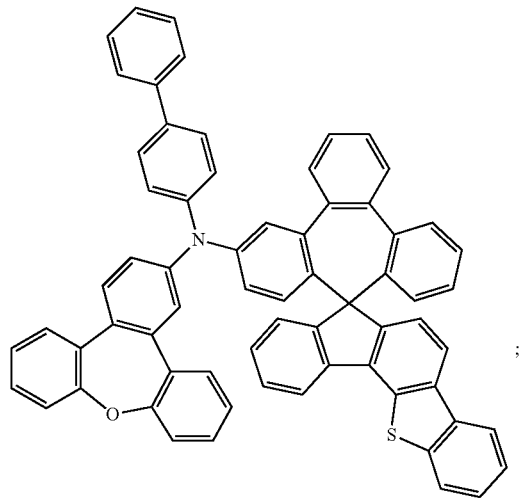
;
Compound 805
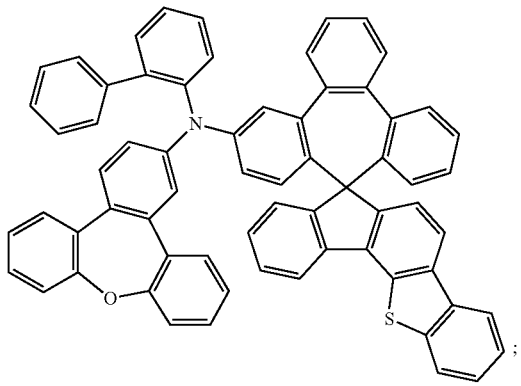
;

-continued
Compound 806
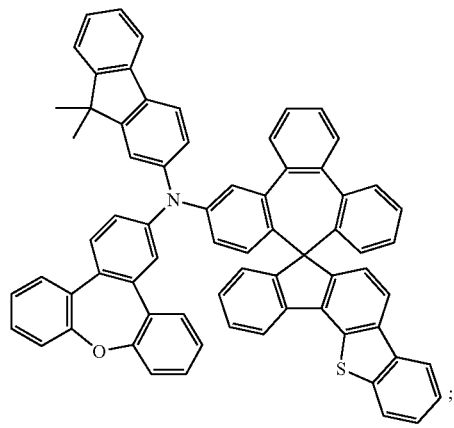
Compound 807
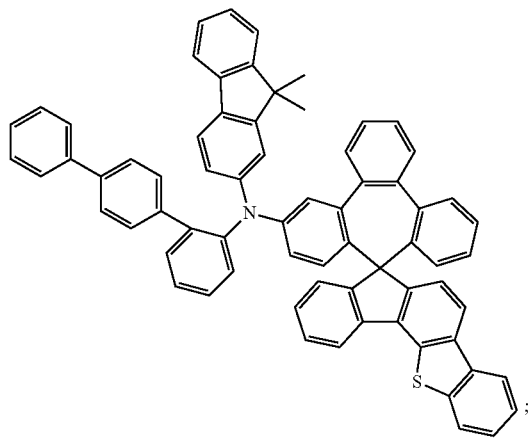
Compound 808
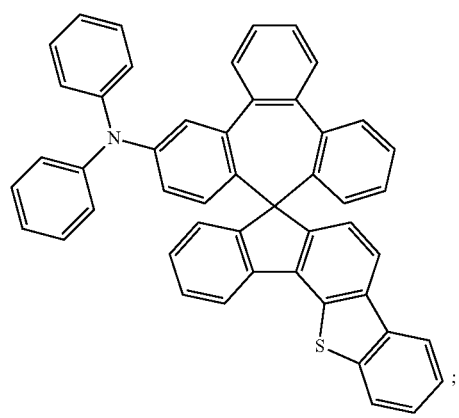
Compound 809
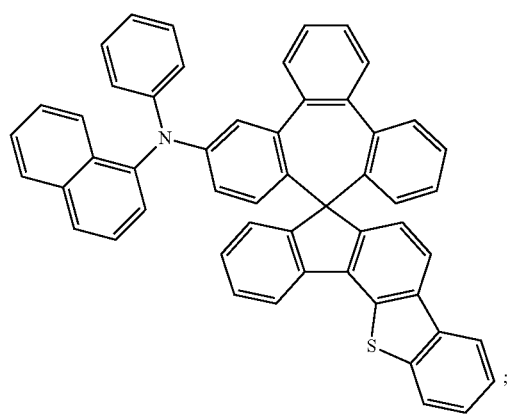
Compound 810
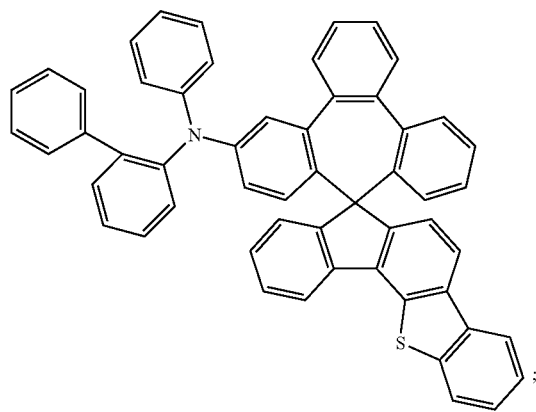
Compound 811
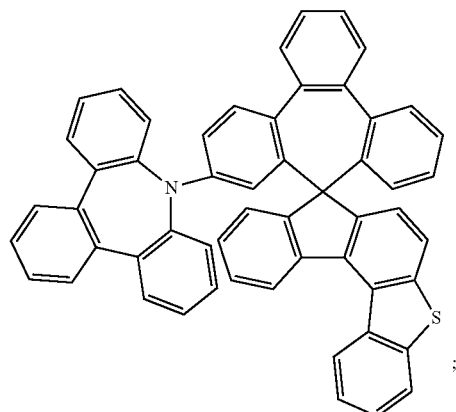

-continued
Compound 812
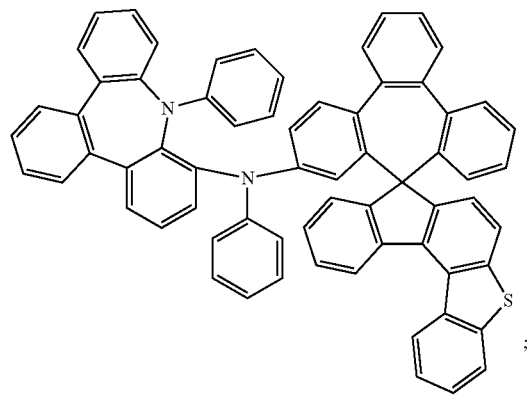
Compound 813
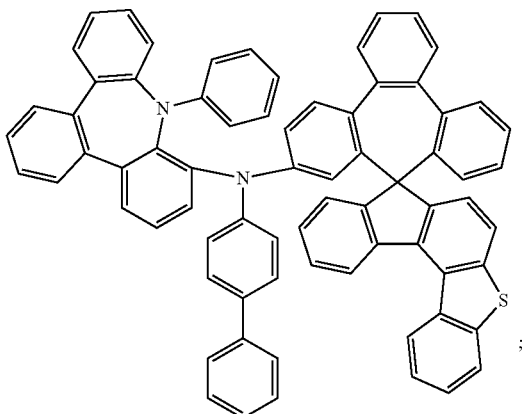
Compound 814
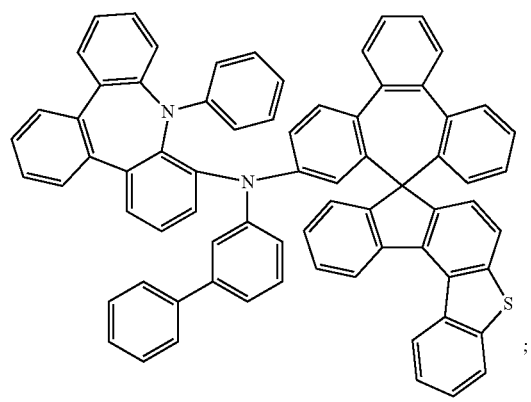
Compound 815
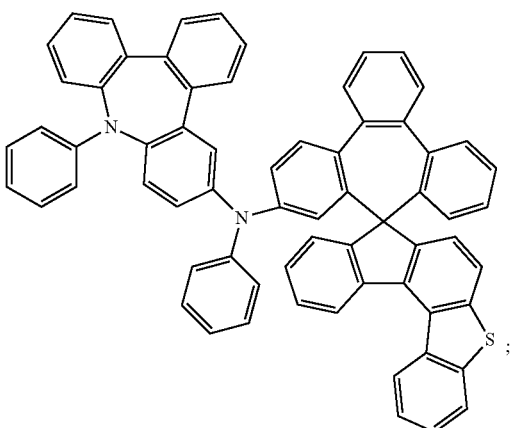
Compound 816
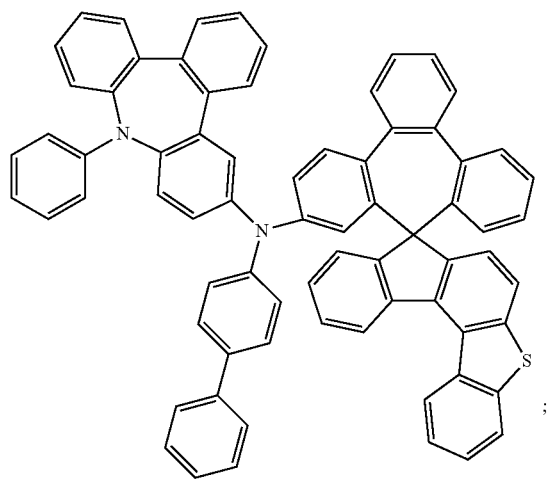
Compound 817
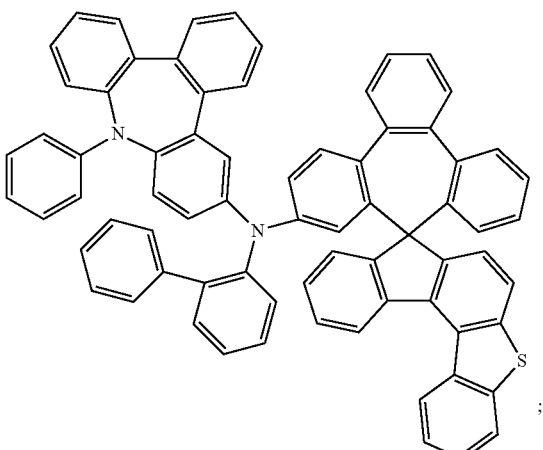

-continued
Compound 818
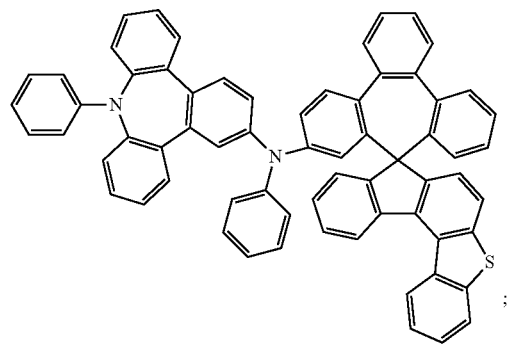
Compound 819
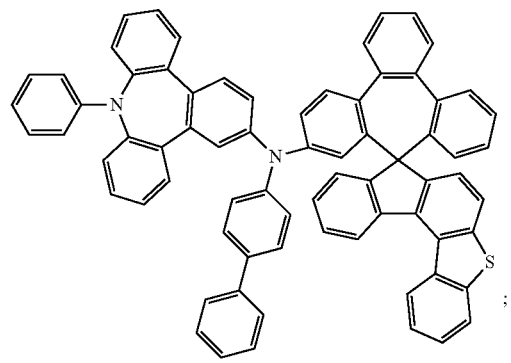
Compound 820
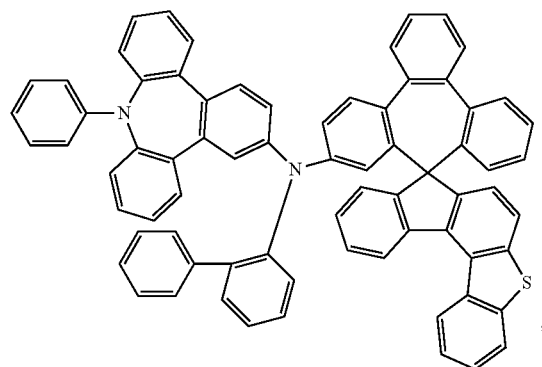
Compound 821
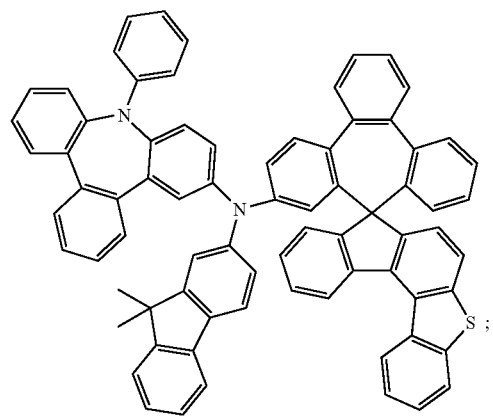
Compound 822
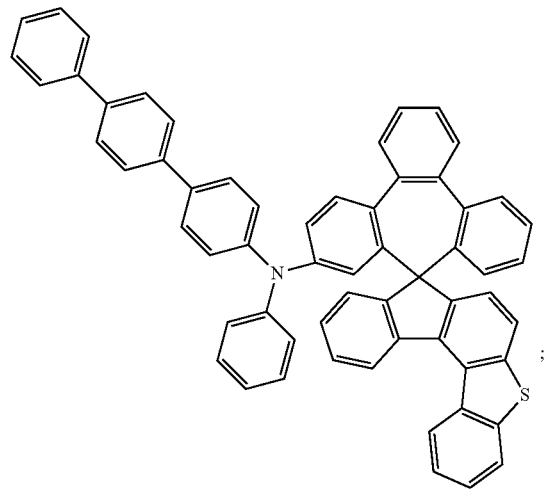
Compound 823
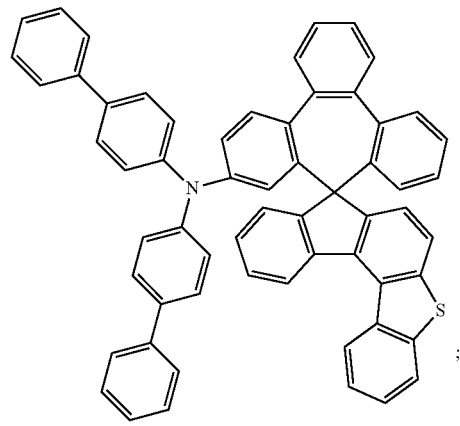

-continued
Compound 824
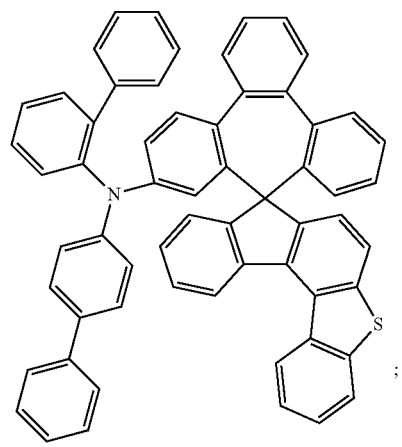
Compound 825
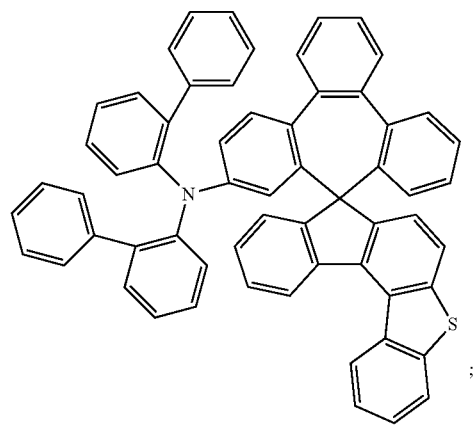
Compound 826
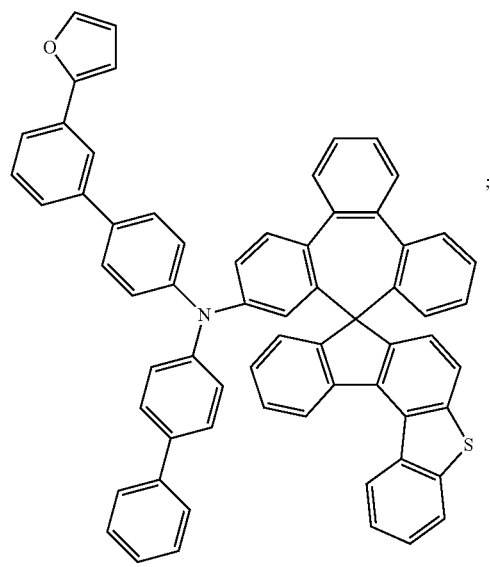
Compound 827
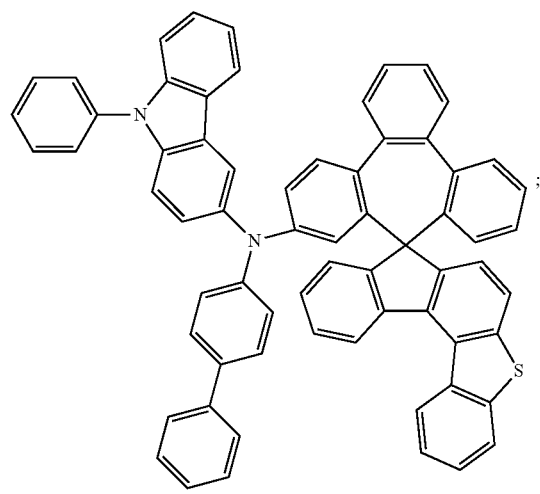
Compound 828
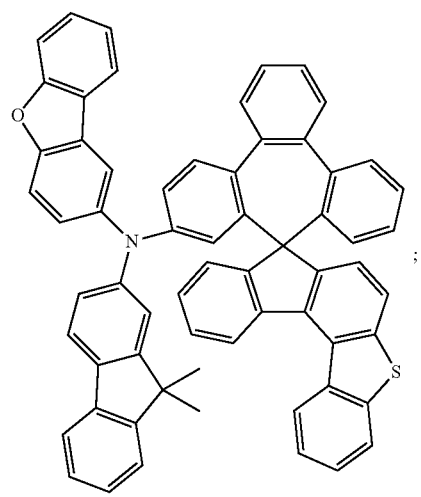
Compound 829
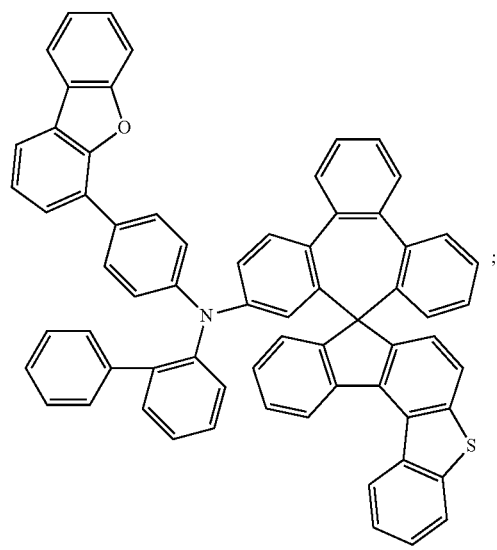

-continued
Compound 830
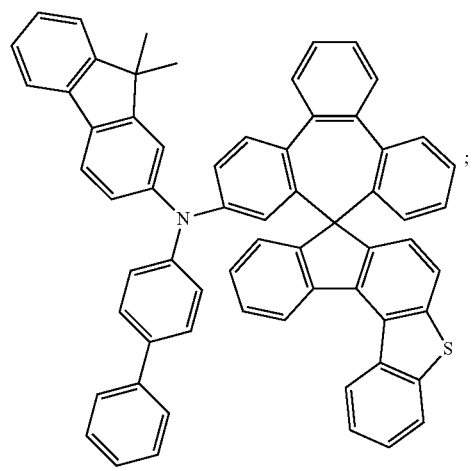
Compound 831
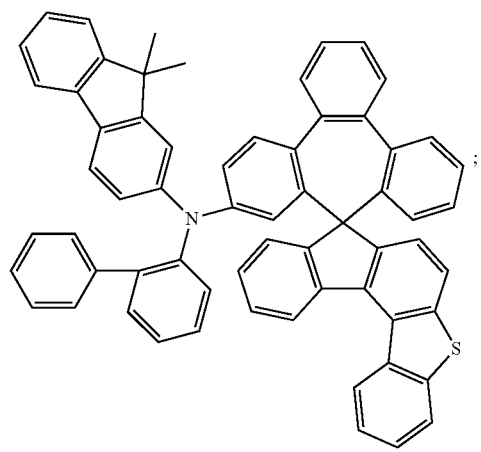
Compound 832
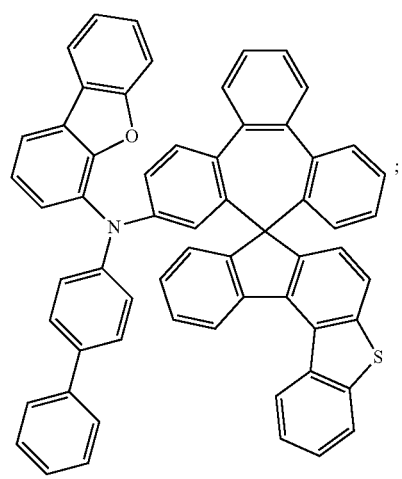
Compound 833
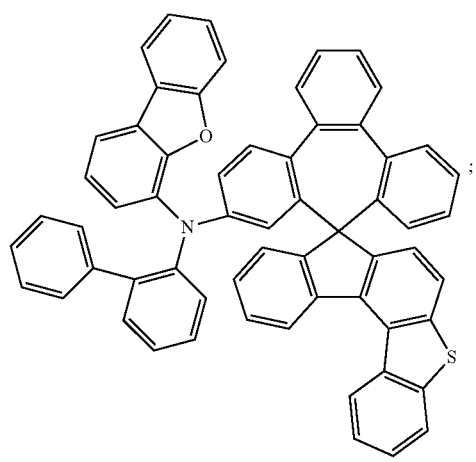
Compound 834
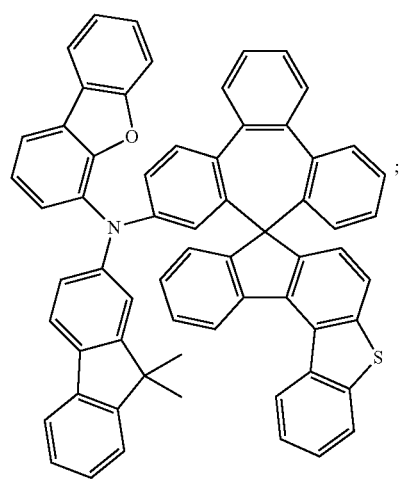
Compound 835
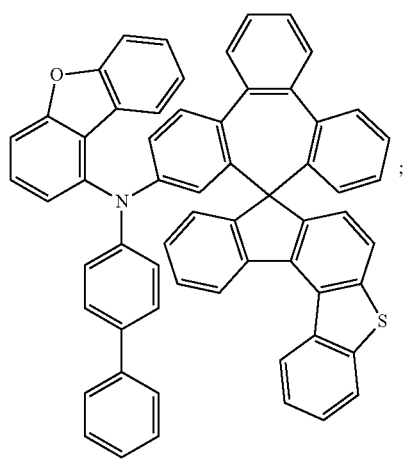

-continued
Compound 836
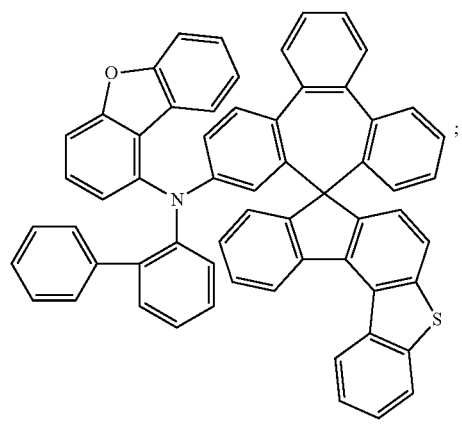
Compound 837
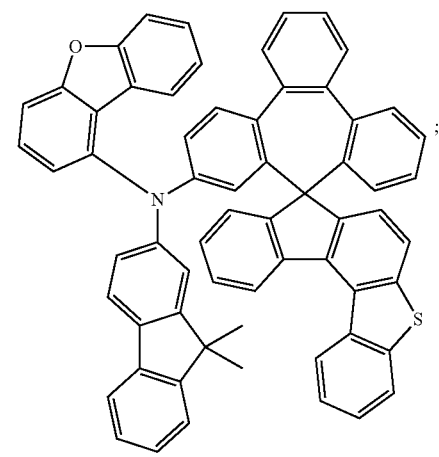
Compound 838
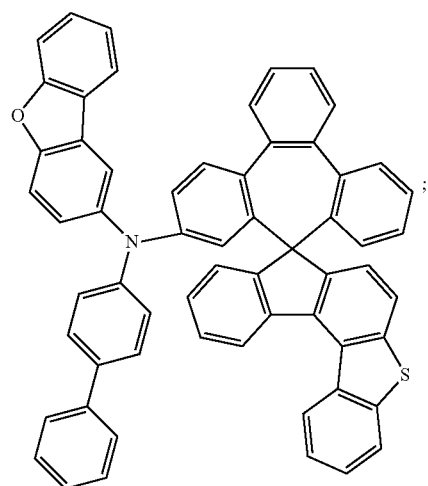
Compound 839
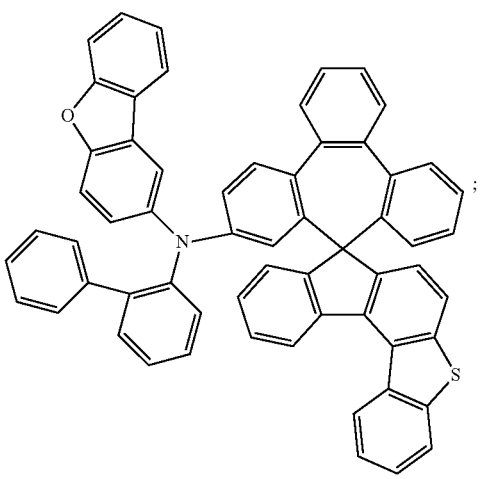
Compound 340
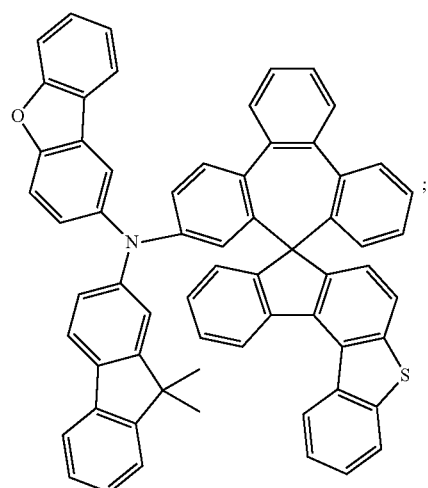
Compound 841
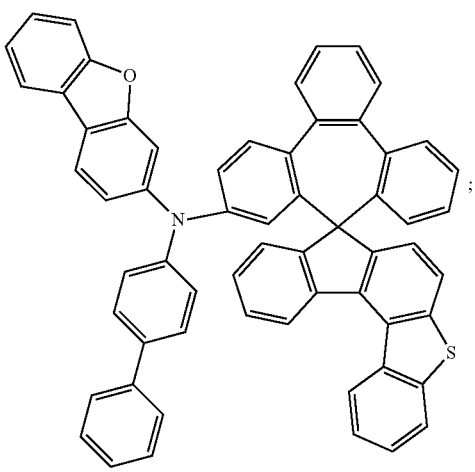

-continued
Compound 842
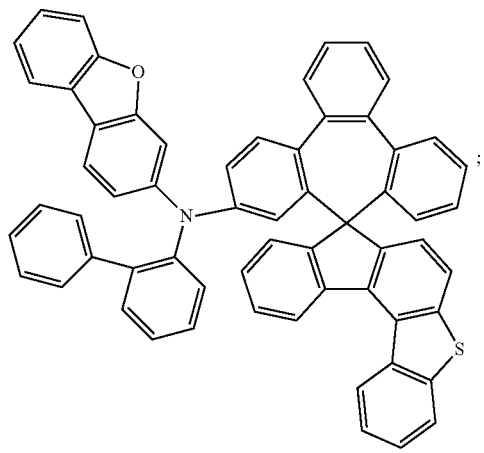
Compound 843
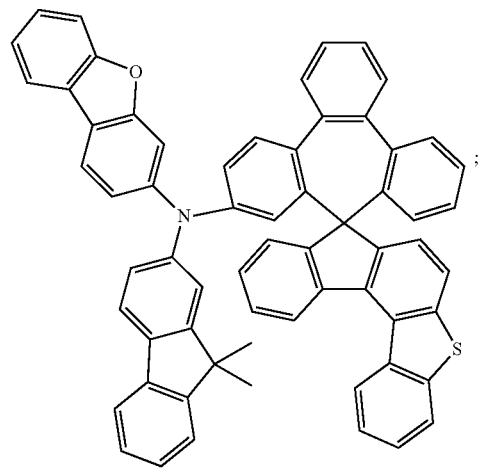
Compound 844
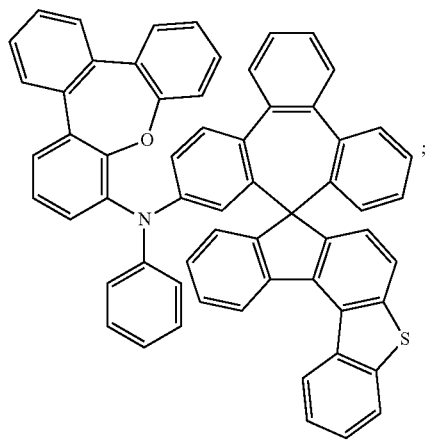
Compound 845
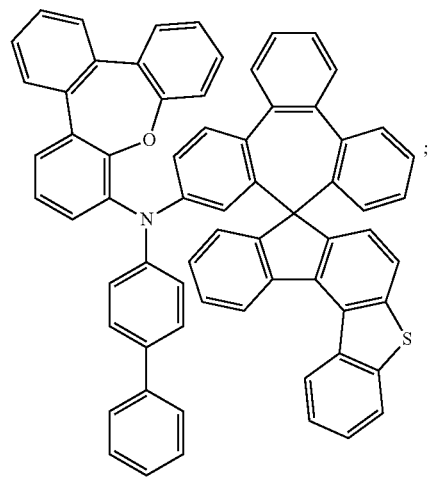
Compound 846
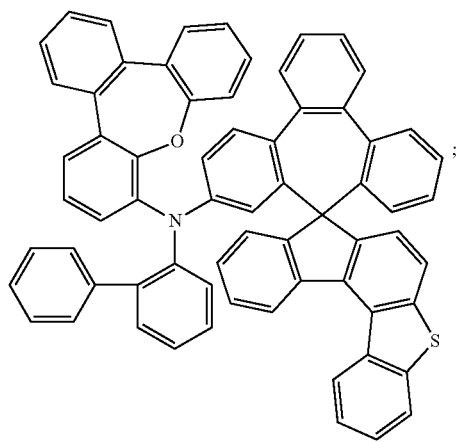
Compound 847
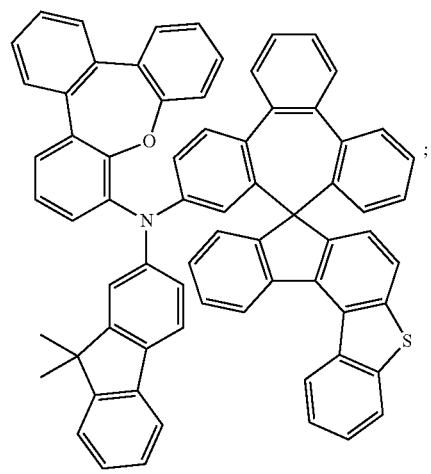

Compound 848
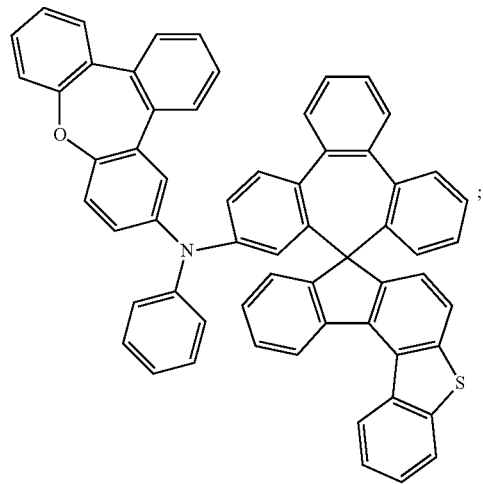
Compound 849
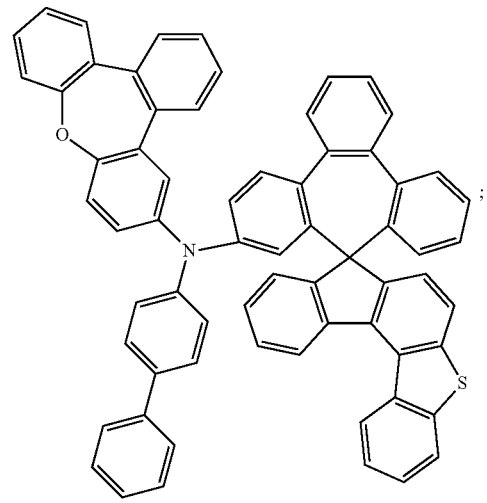
Compound 850
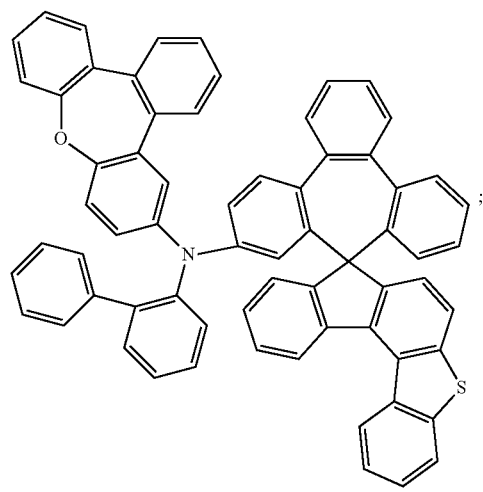
Compound 851
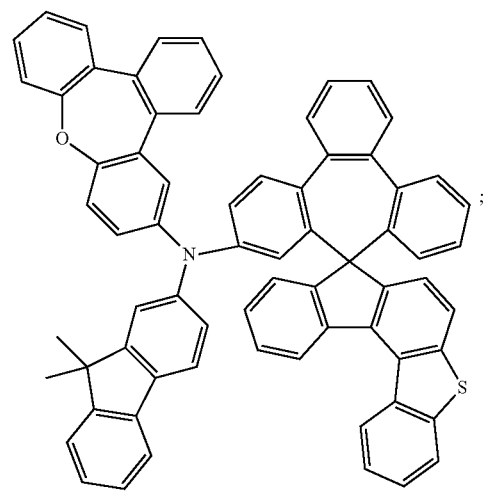
Compound 852
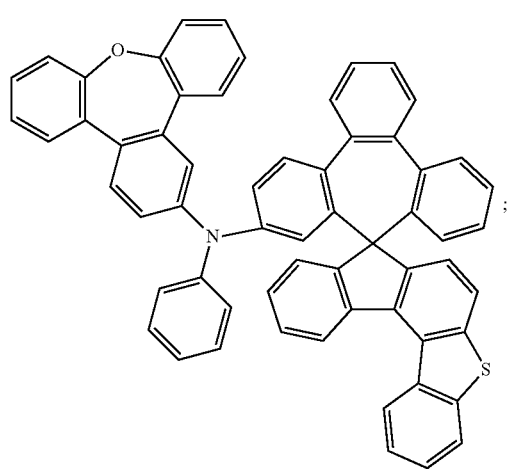

-continued
Compound 854
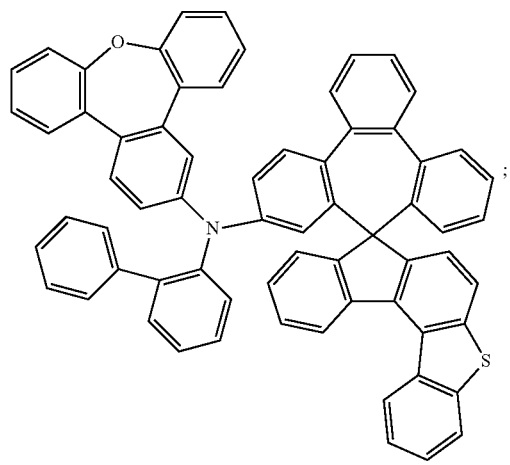
Compound 855
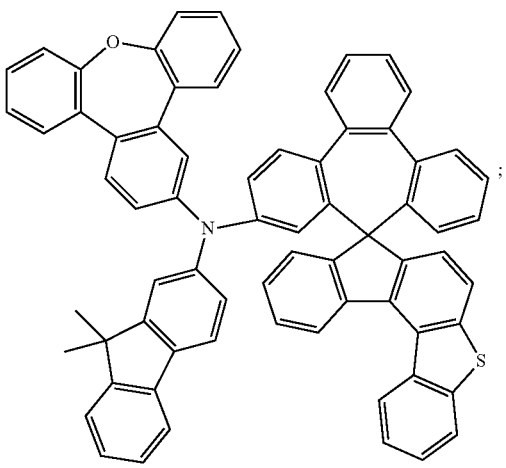
Compound 856
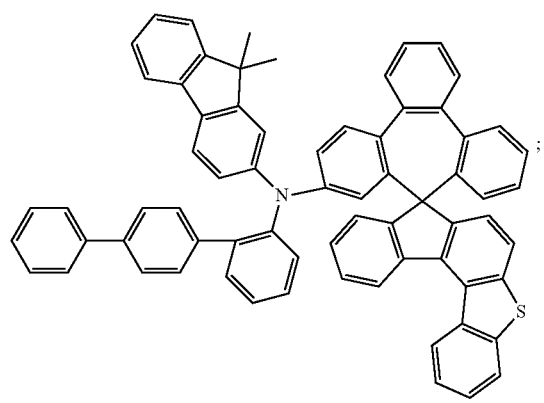
Compound 857
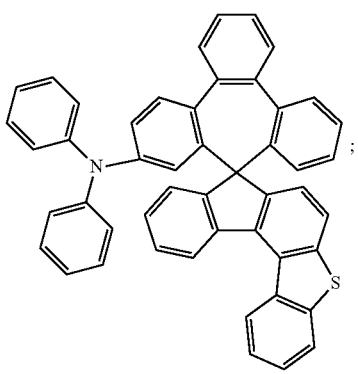
Compound 858
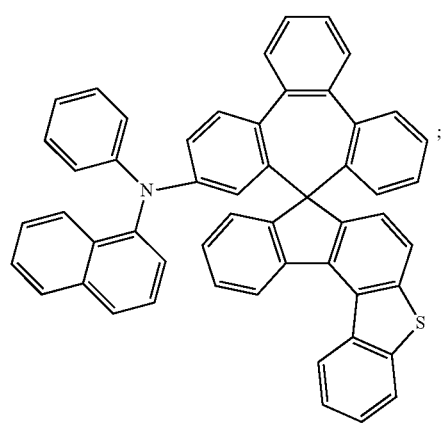
Compound 859
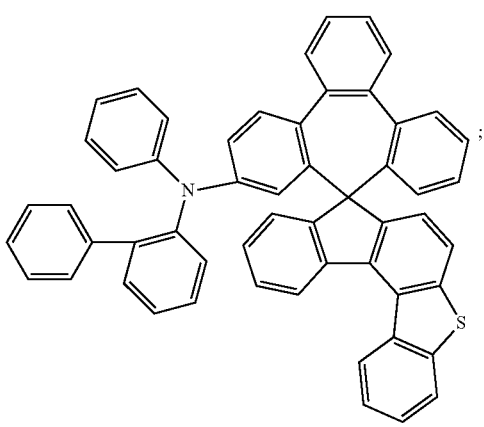

-continued
Compound 860
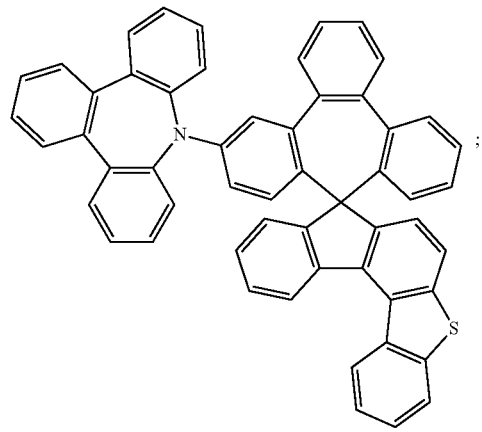
Compound 861
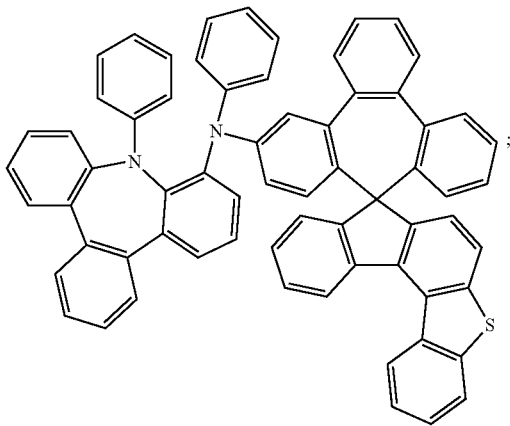
Compound 862
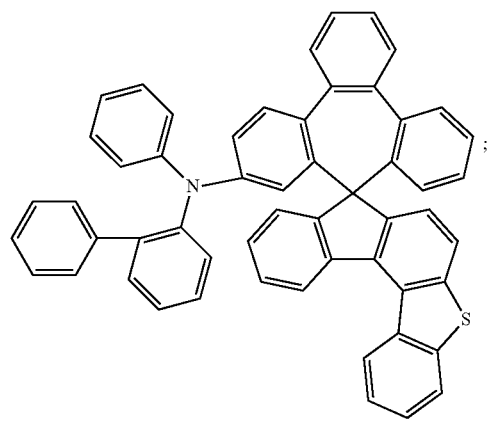
Compound 863
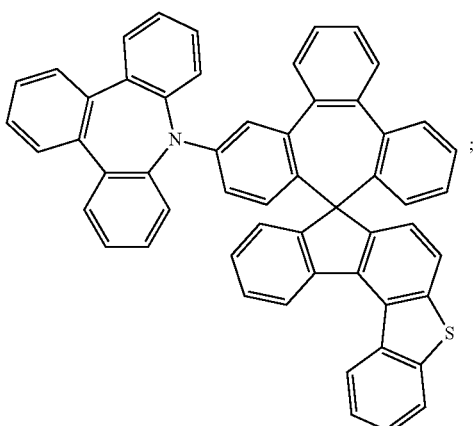
Compound 864
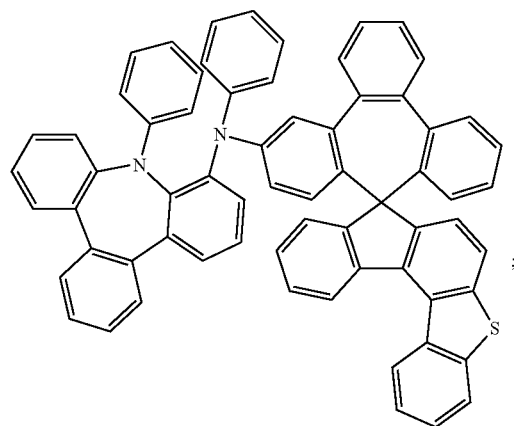
Compound 865
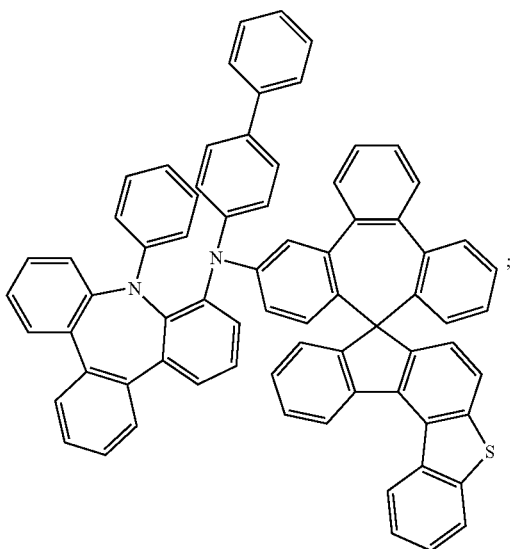

-continued
Compound 866
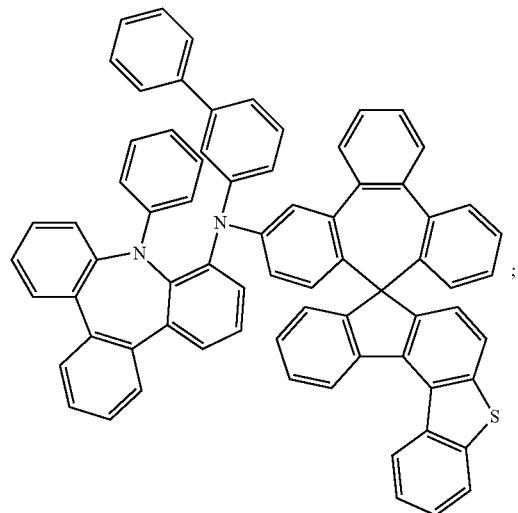
Compound 867
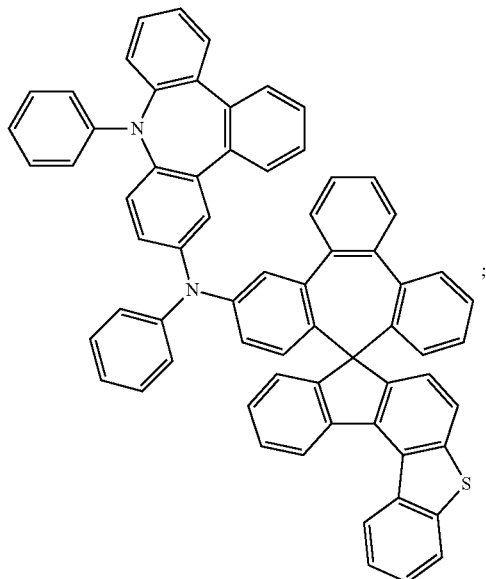
Compound 868
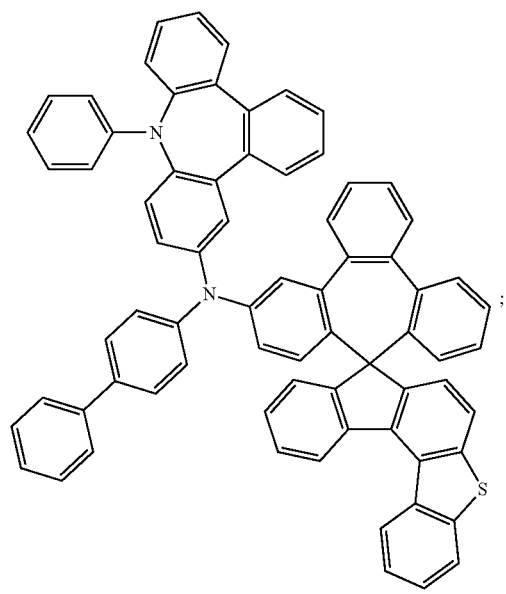
Compound 869
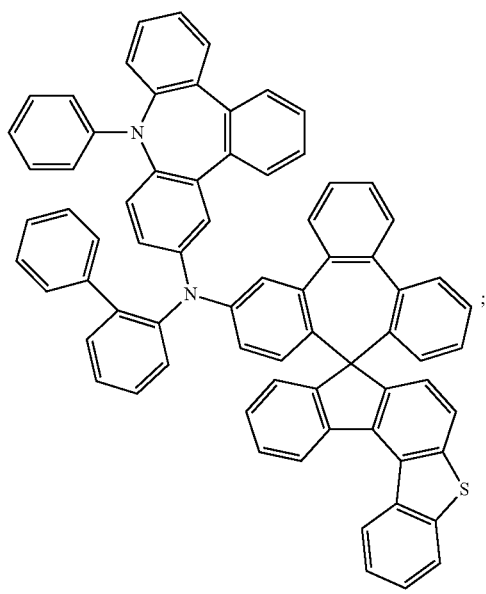

-continued
Compound 870
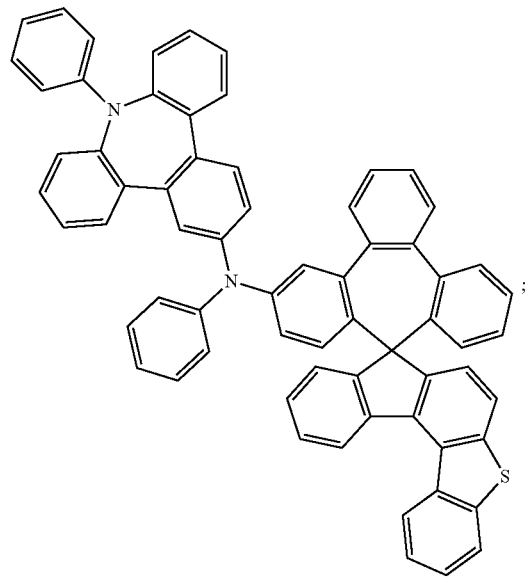
Compound 871
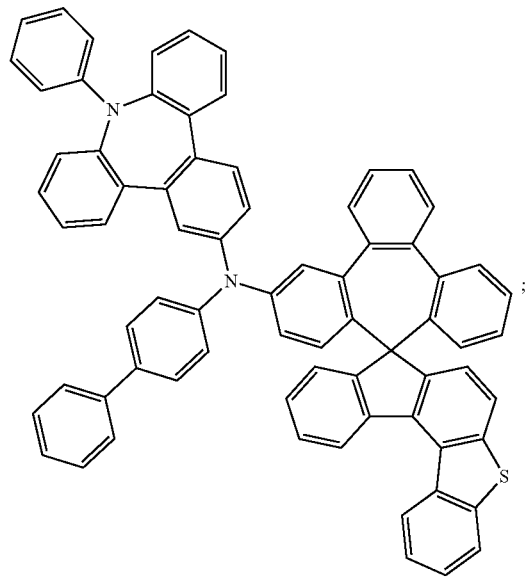
Compound 872
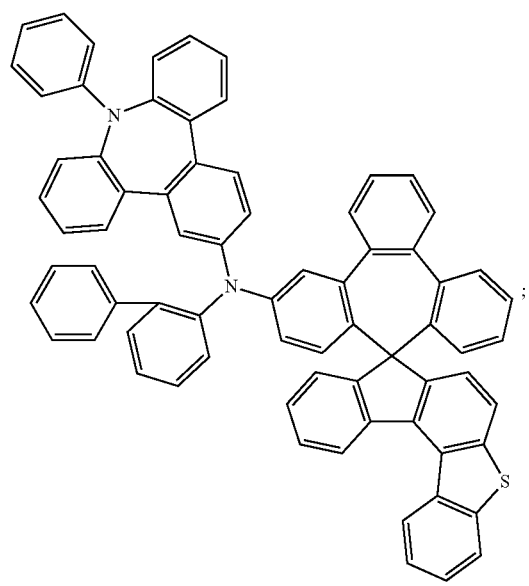
Compound 873
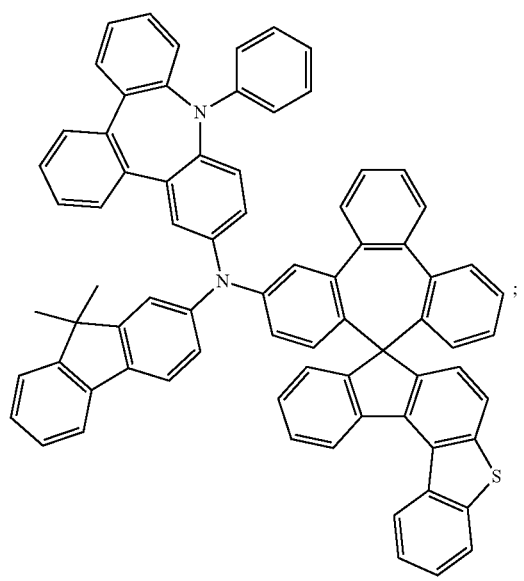

Compound 874
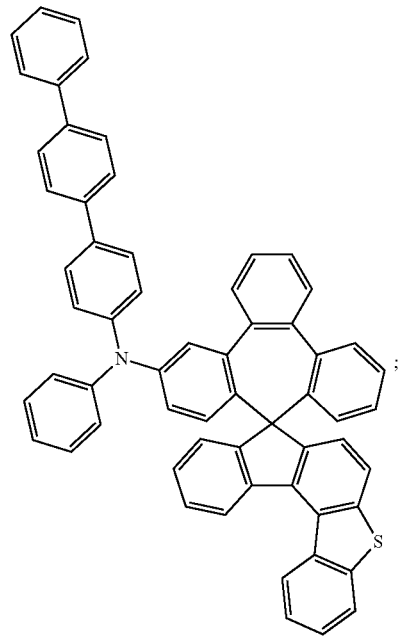
Compound 875
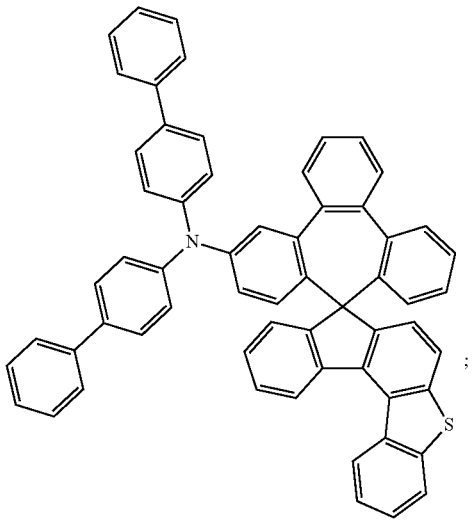
Compound 876
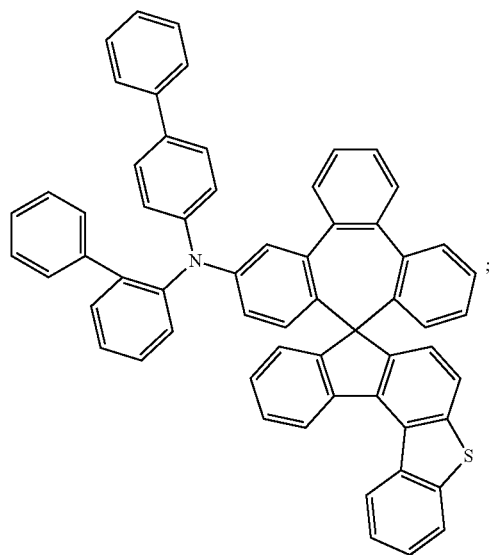
Compound 877
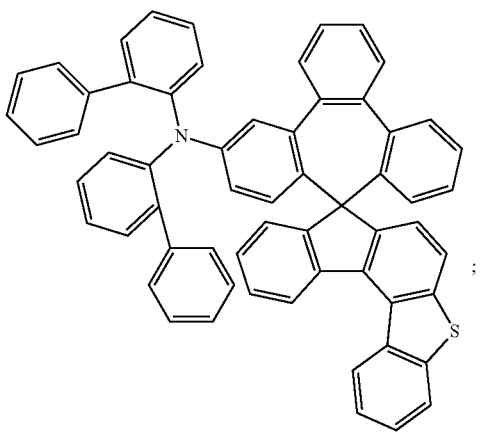

-continued
Compound 878
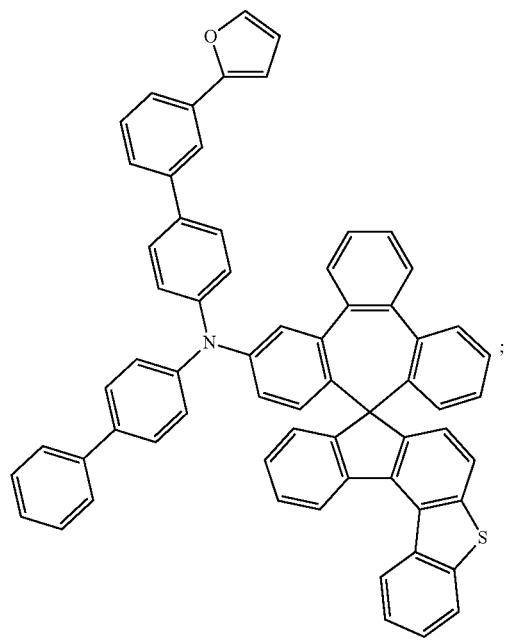
Compound 879
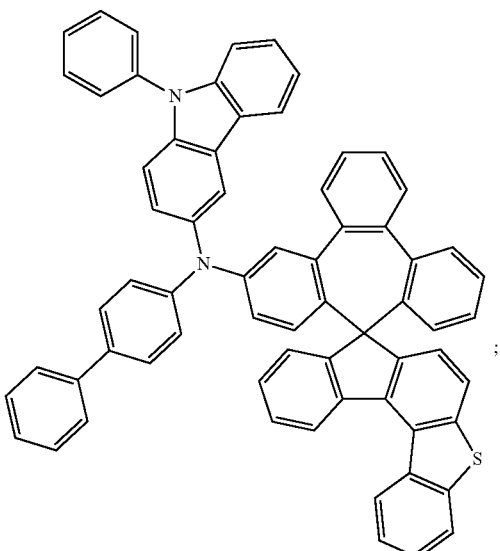
Compound 880
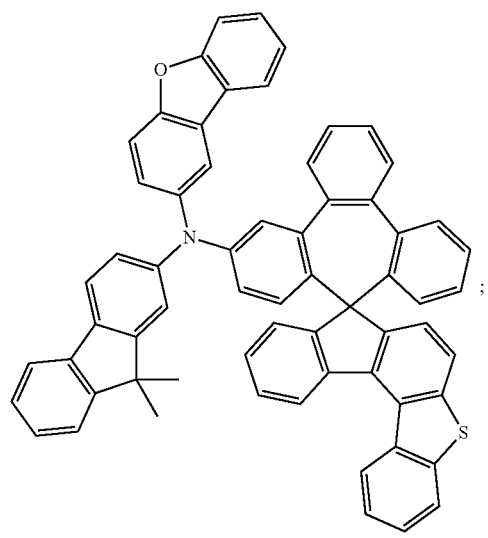
Compound 881
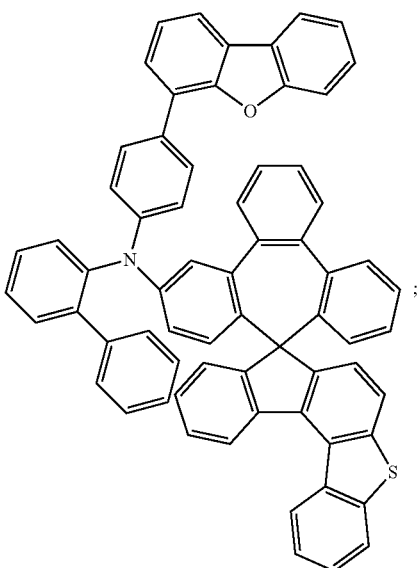

-continued
Compound 882
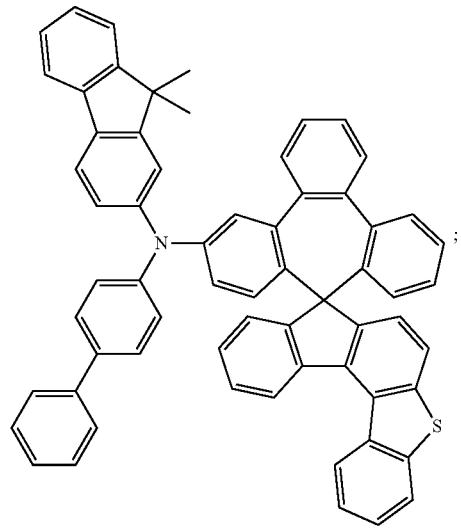
Compound 883
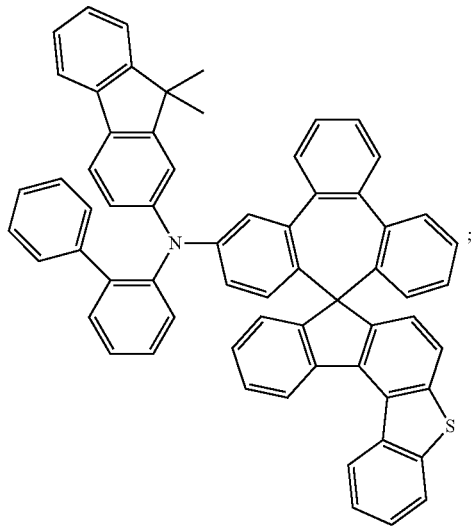
Compound 884
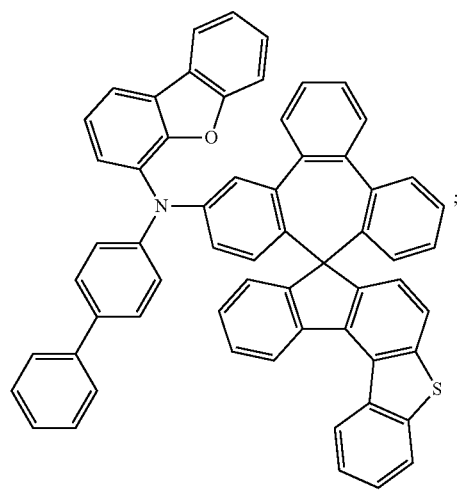
Compound 885
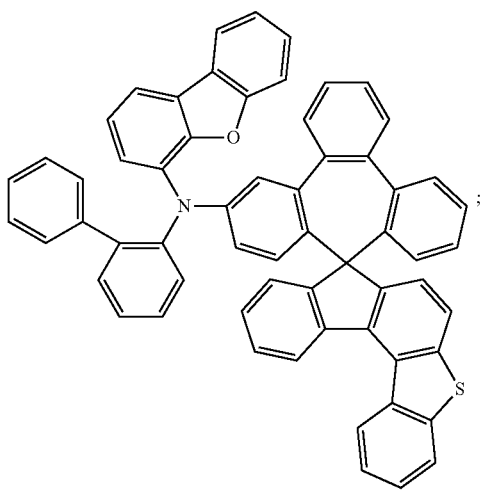
Compound 886
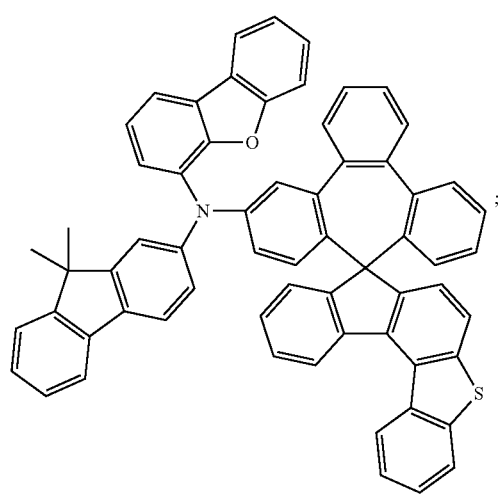
Compound 887
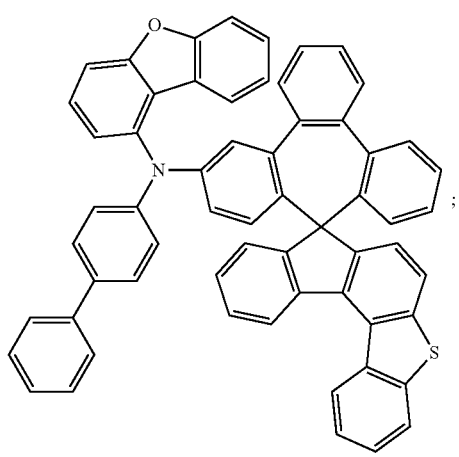

-continued
Compound 888
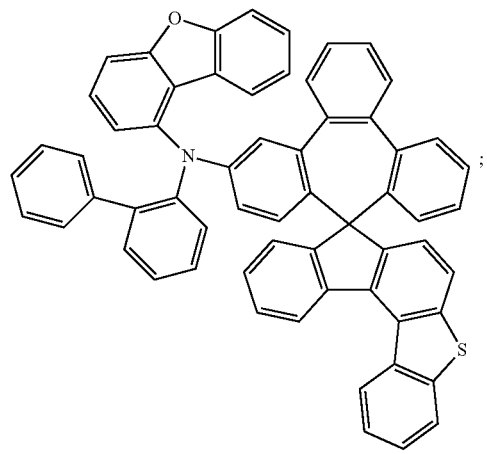
Compound 889
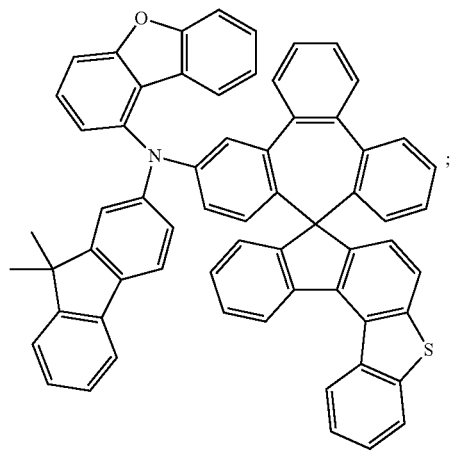
Compound 890
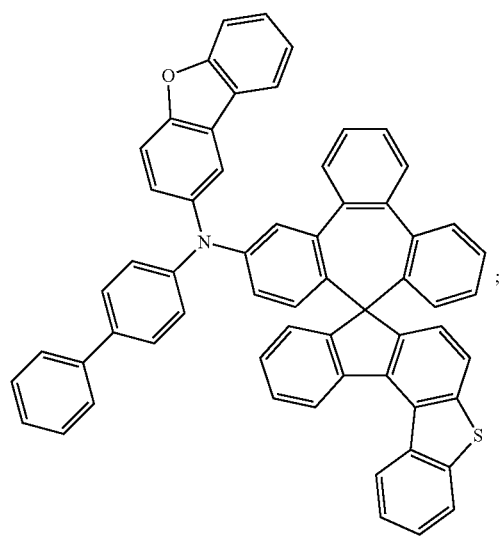
Compound 891
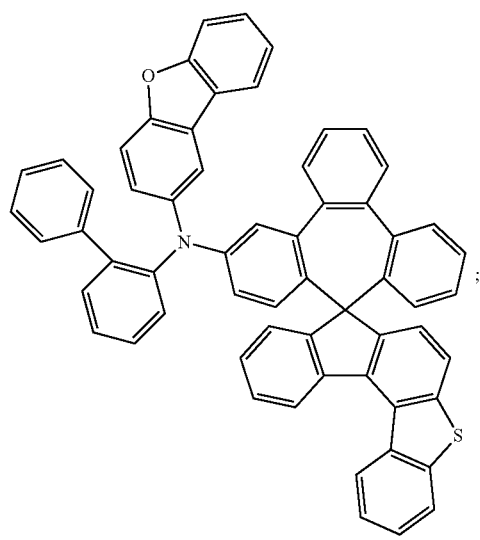
Compound 892
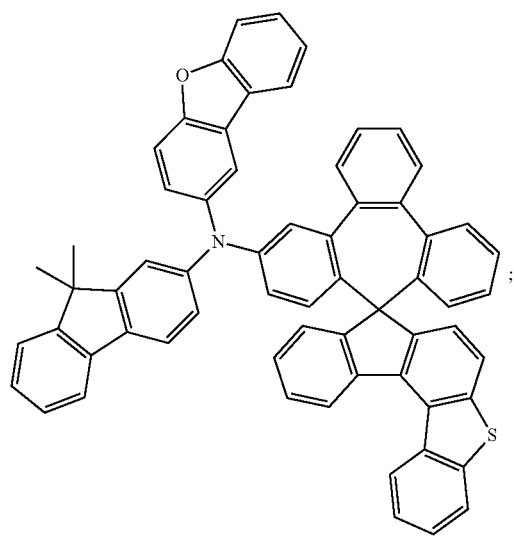
Compound 893
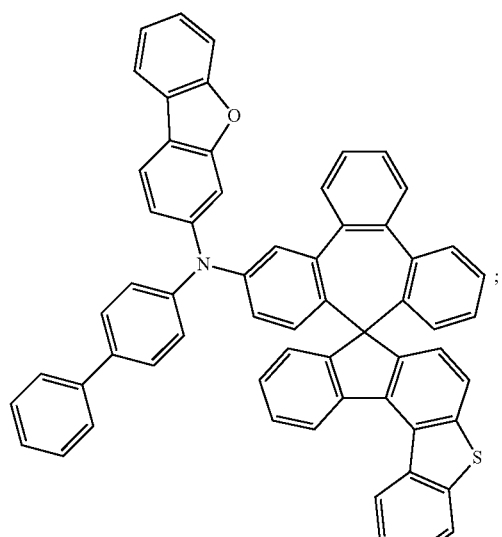

Compound 894
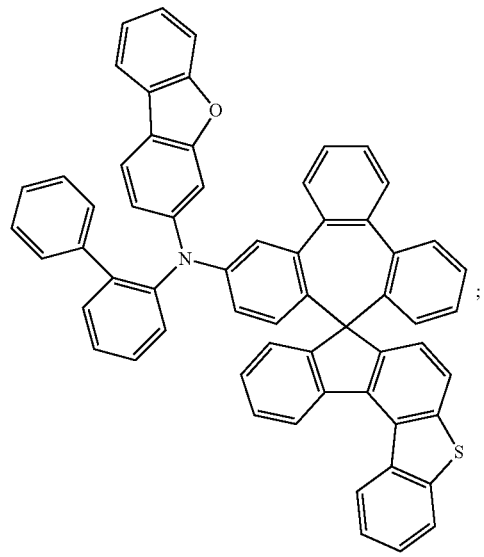
Compound 895
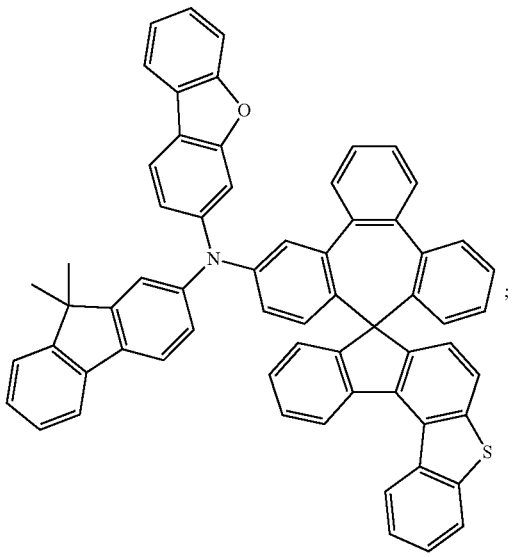
Compound 896
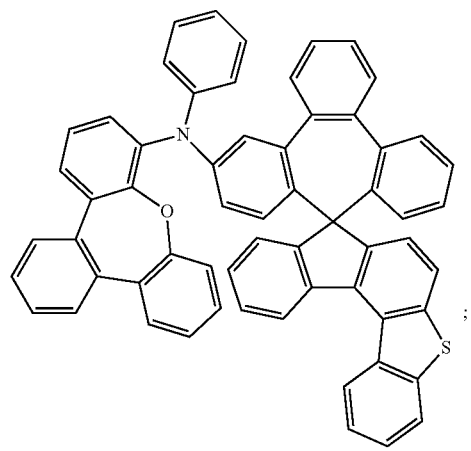
Compound 897
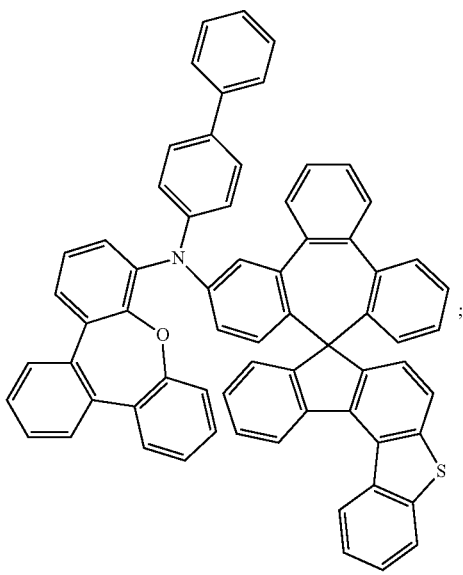

-continued
Compound 898
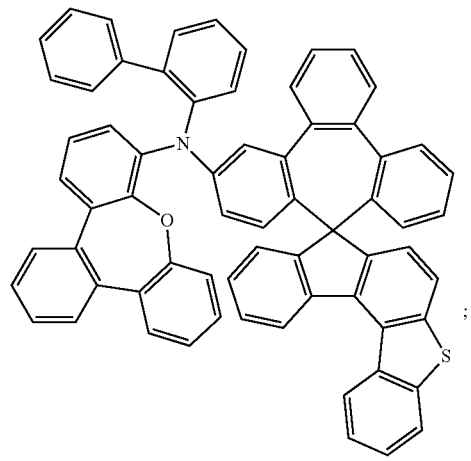
Compound 899
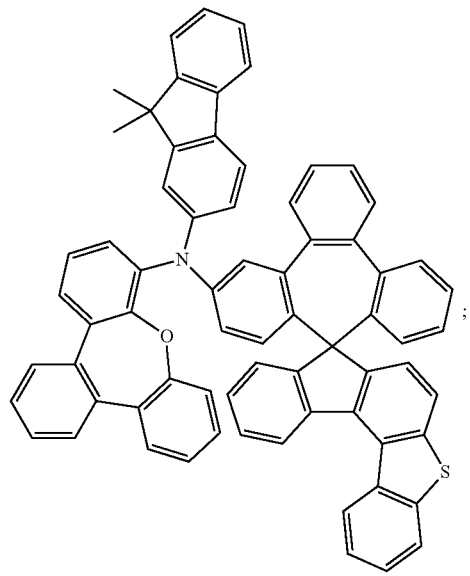
Compound 900
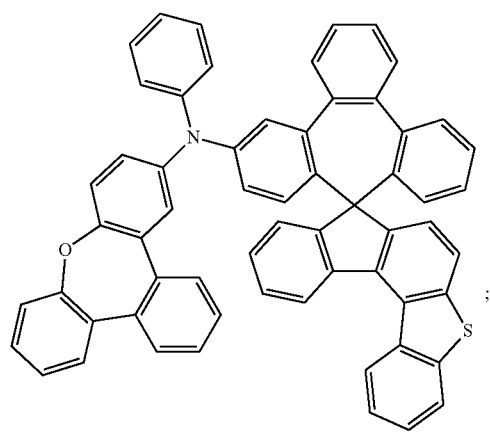
Compound 901
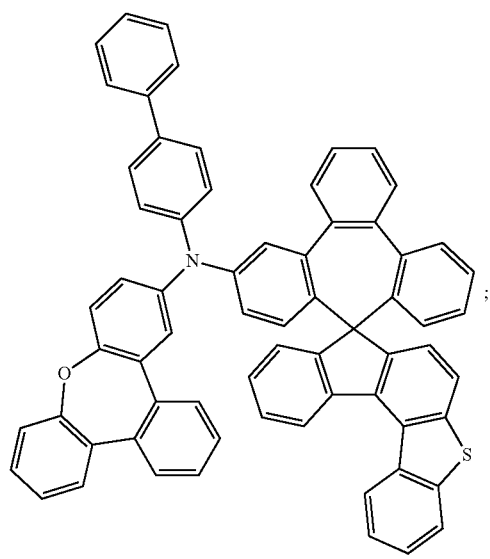

-continued
Compound 902
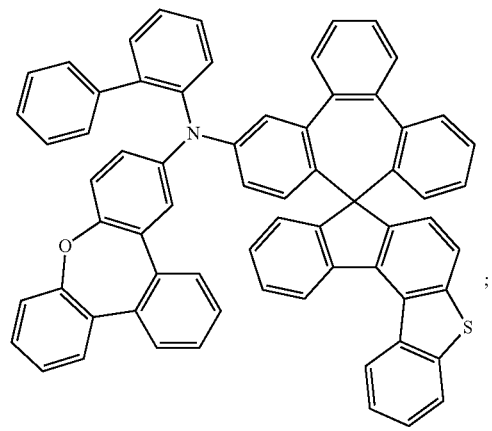
Compound 903
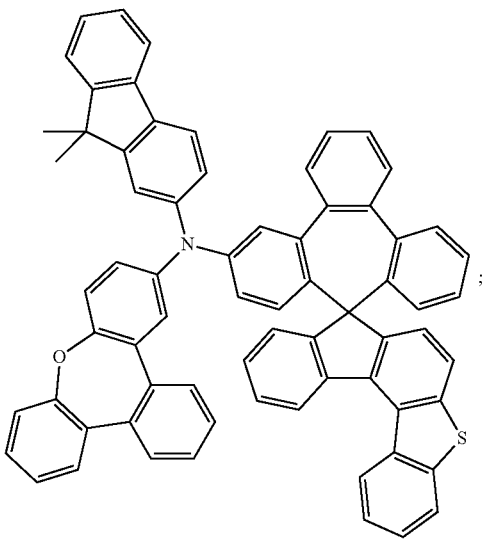
Compound 904
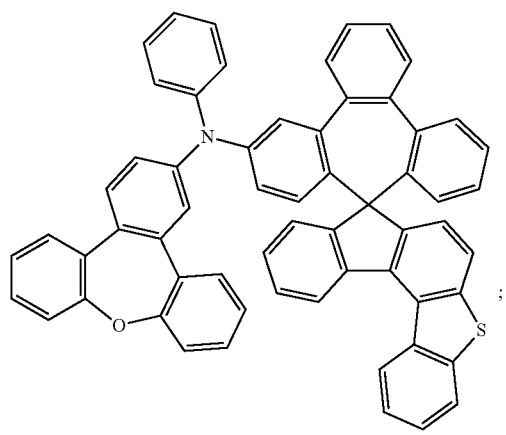
Compound 905
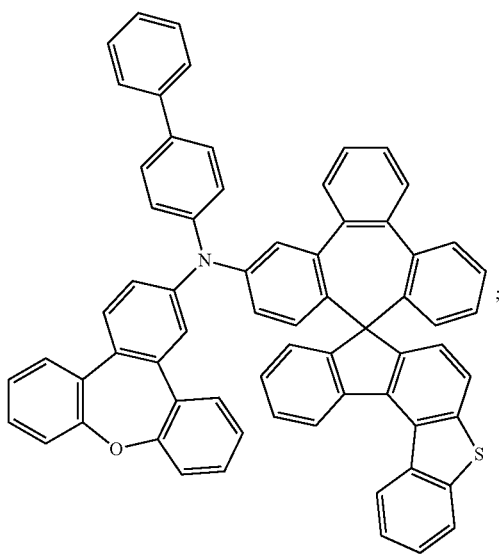

-continued
Compound 906
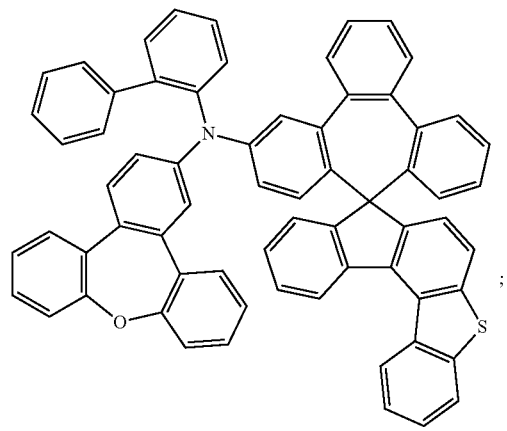
Compound 907
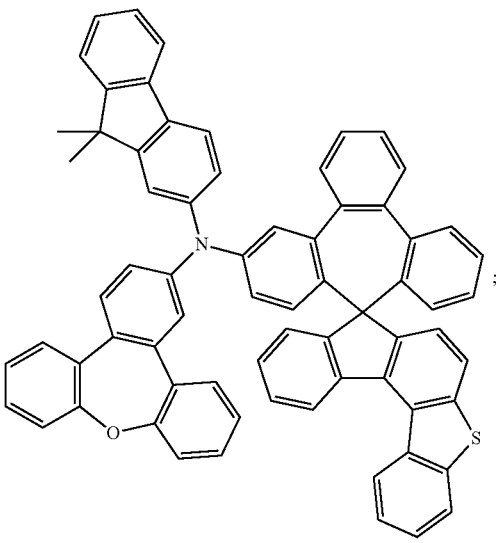
Compound 908
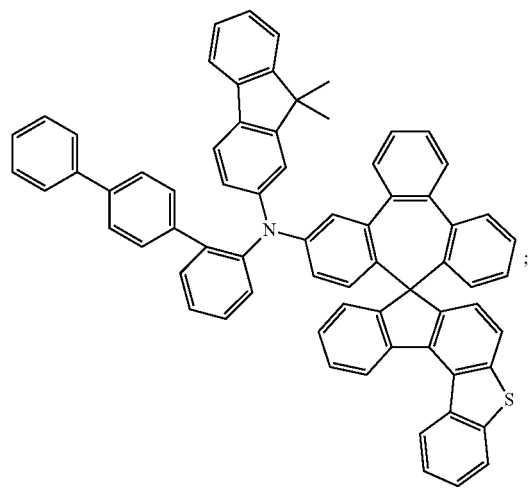
Compound 909
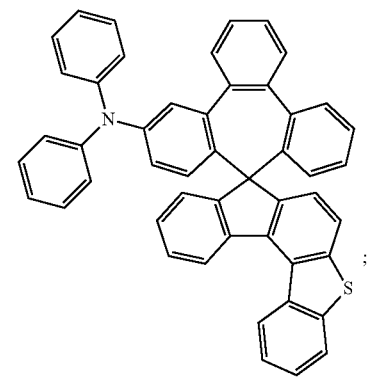
Compound 910
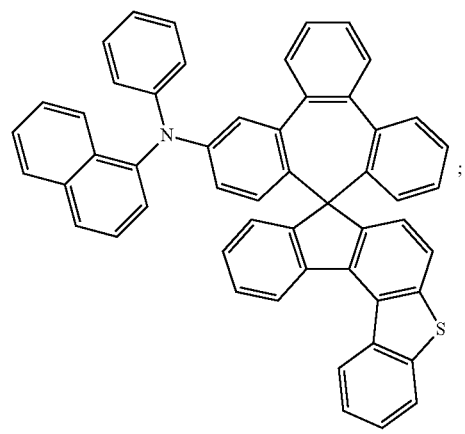
Compound 911
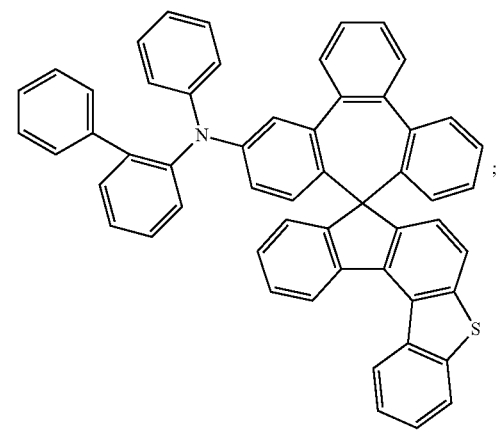

-continued
Compound 912
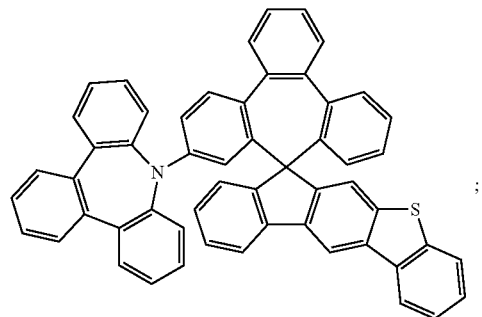
Compound 913
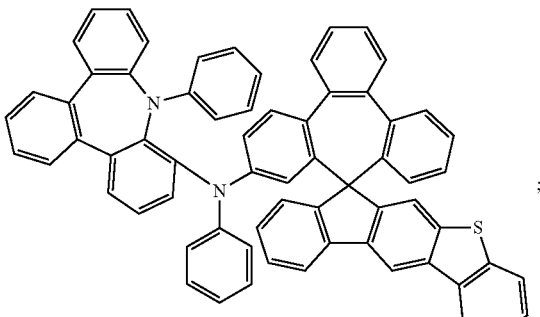
Compound 914
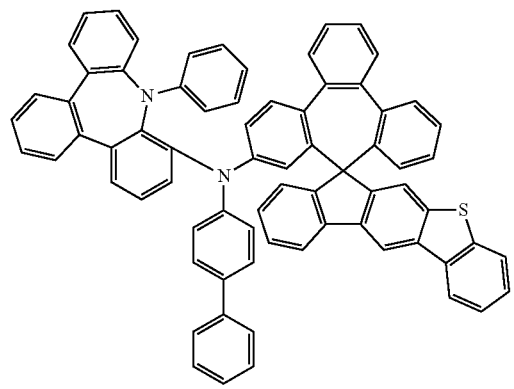
Compound 915
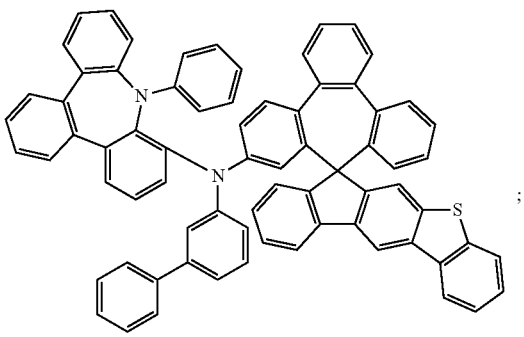
Compound 916
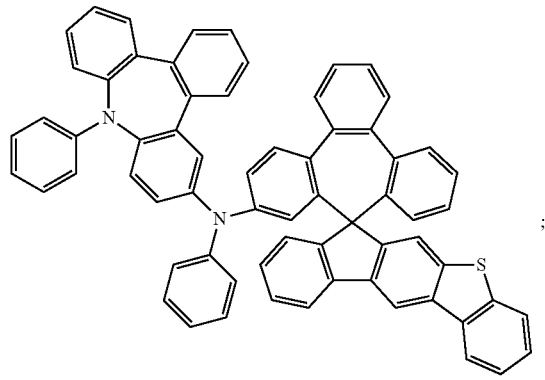
Compound 917
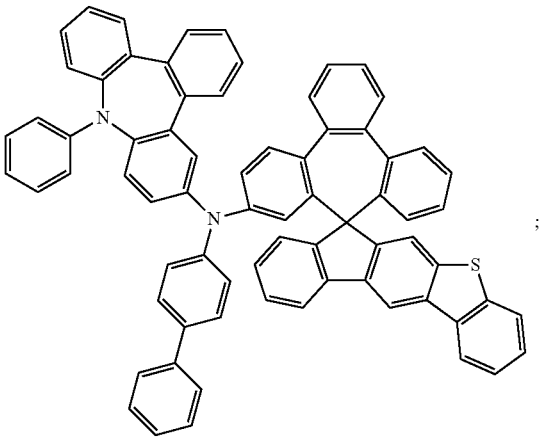
Compound 918
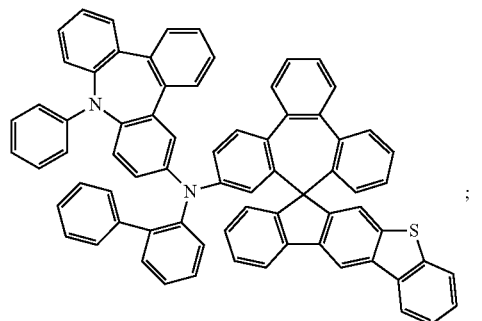
Compound 919
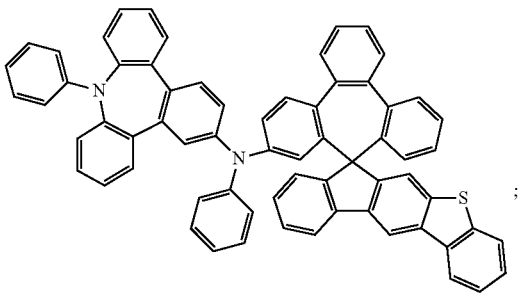

-continued
Compound 920
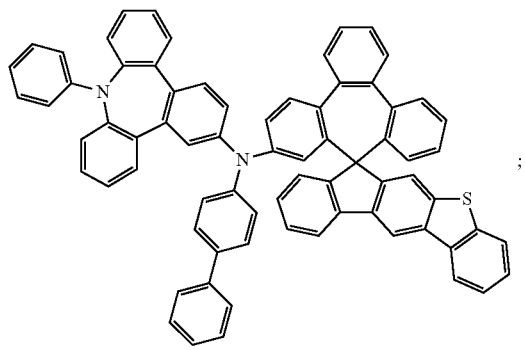
Compound 921
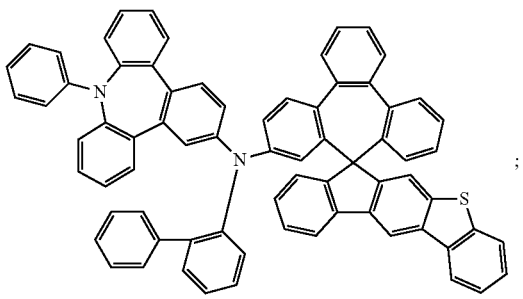
Compound 922
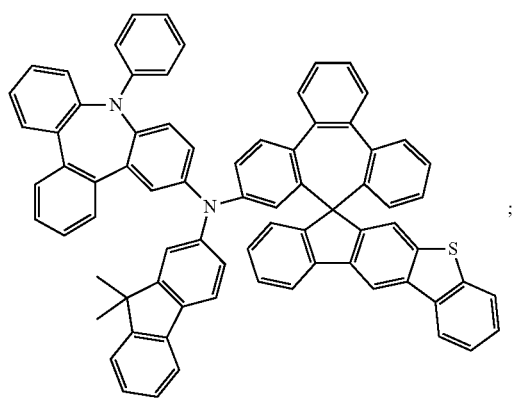
Compound 923
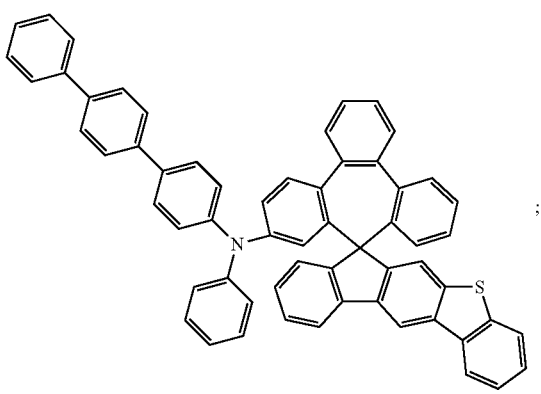
Compound 924
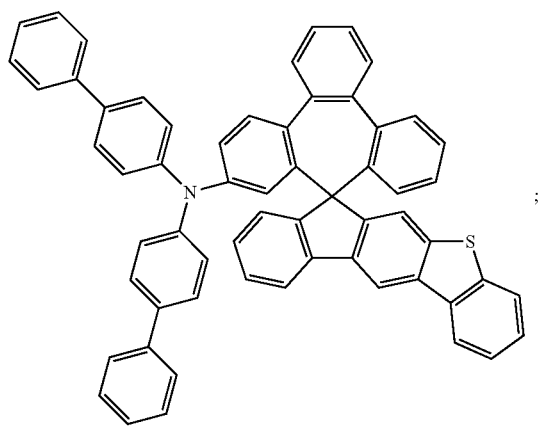
Compound 925
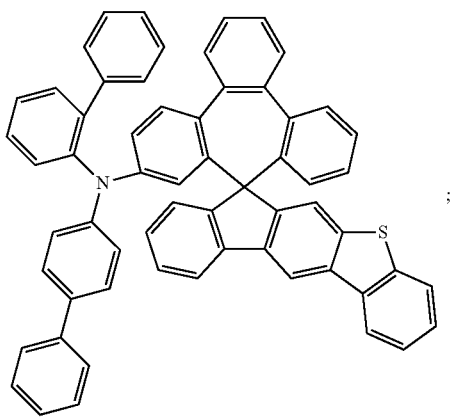

-continued
Compound 926
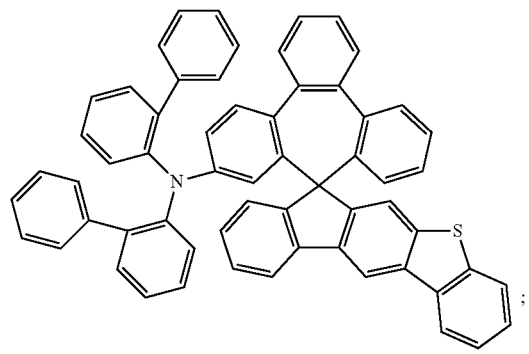
Compound 927
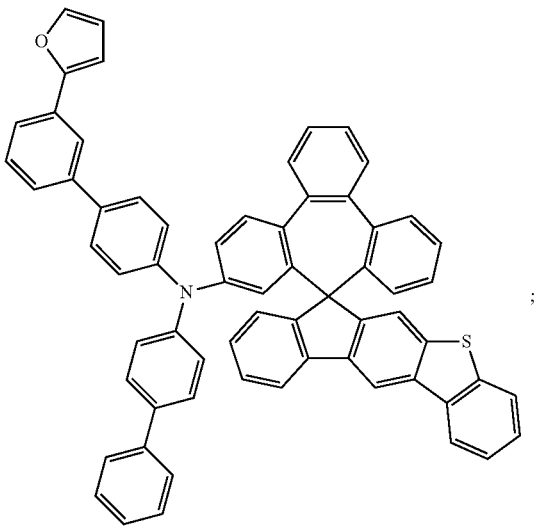
Compound 928
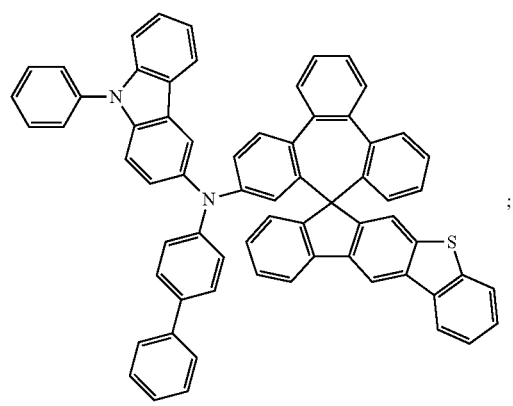
Compound 929
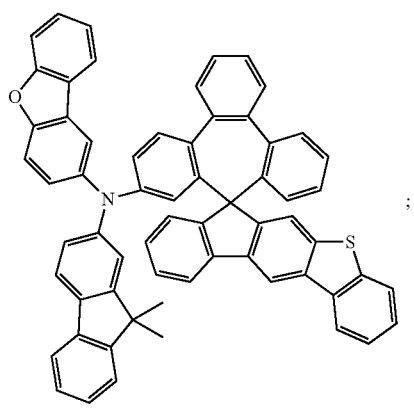
Compound 930
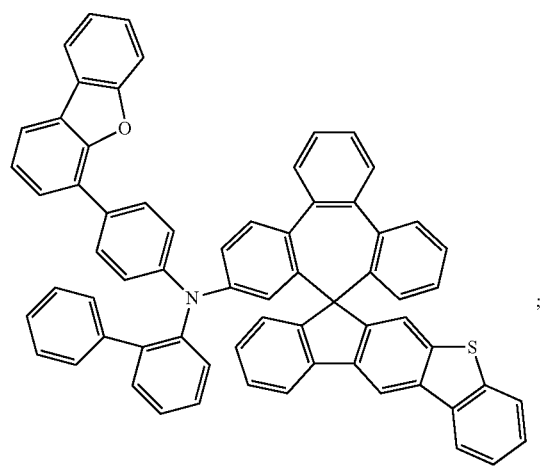
Compound 931
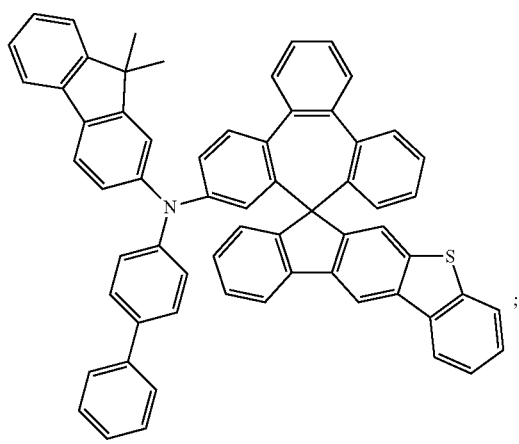

-continued
Compound 932
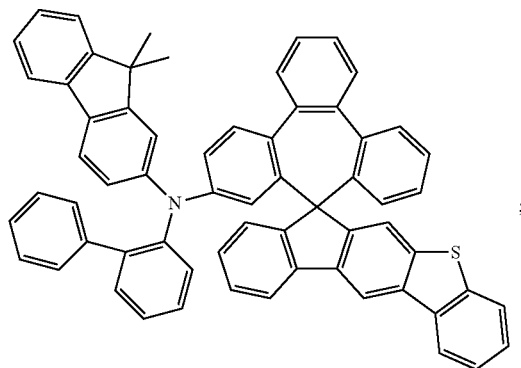
;
Compound 933
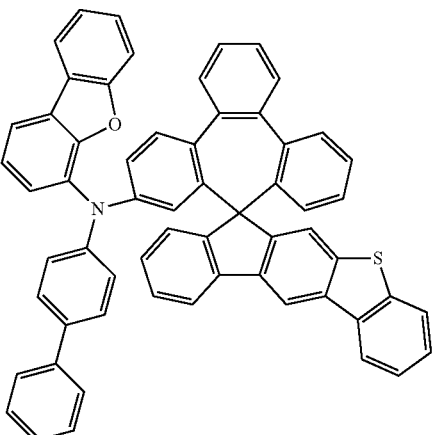
;
Compound 934
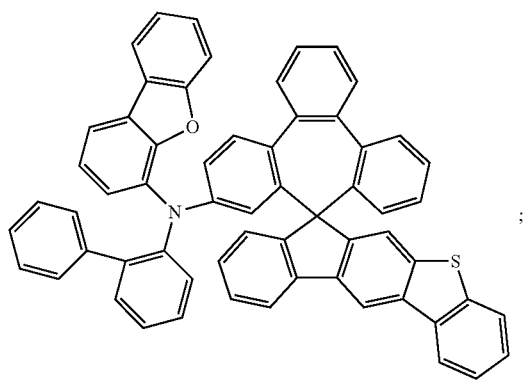
;
Compound 935
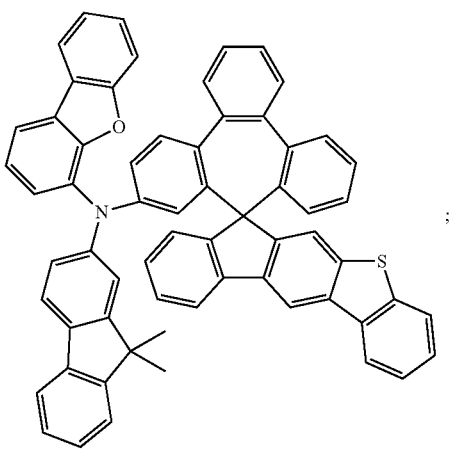
;
Compound 936
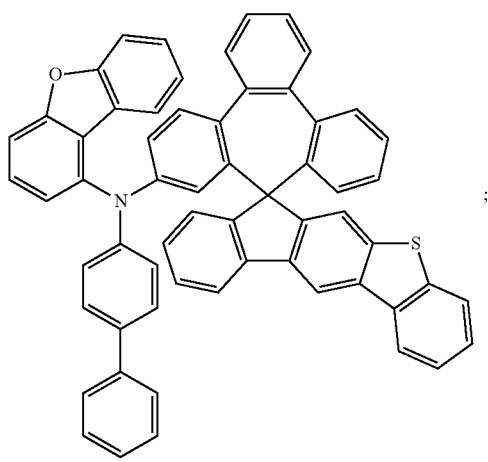
;
Compound 937
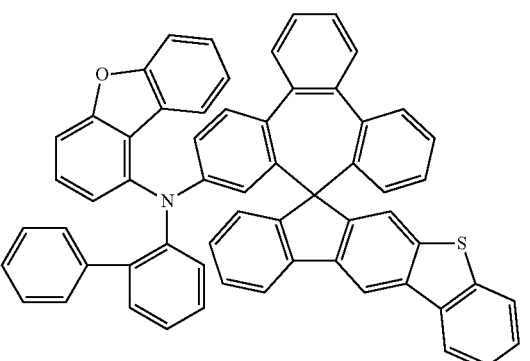
;

-continued
Compound 938
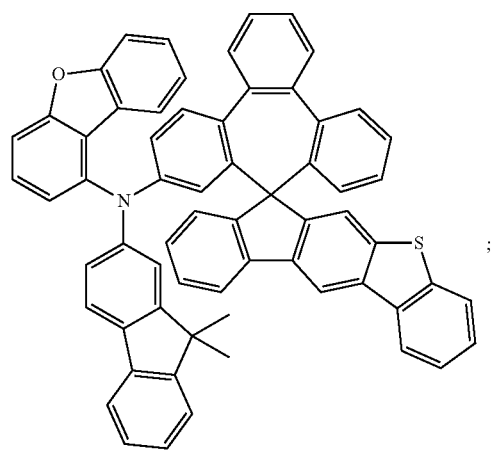
;
Compound 939
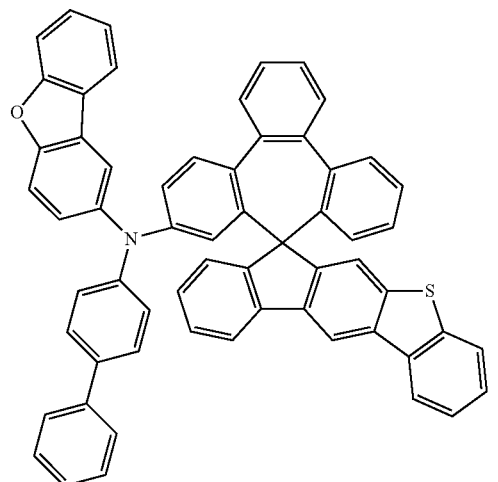
;
Compound 940
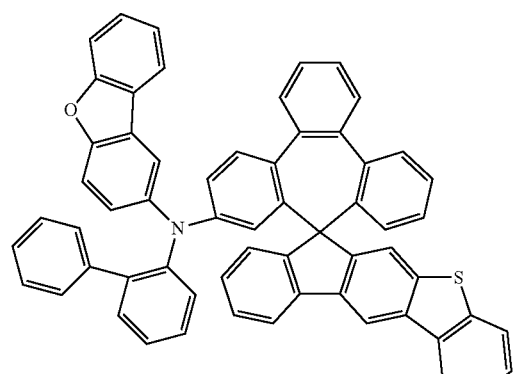
;
Compound 941
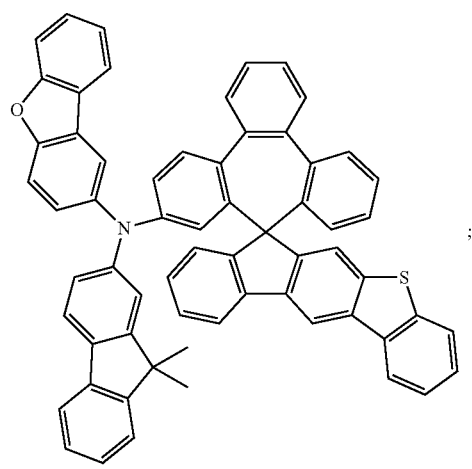
;
Compound 942
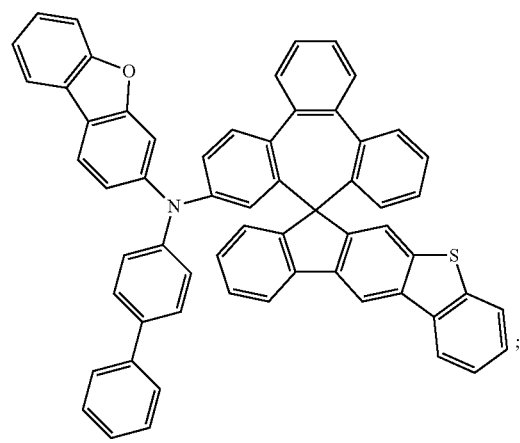
;
Compound 943
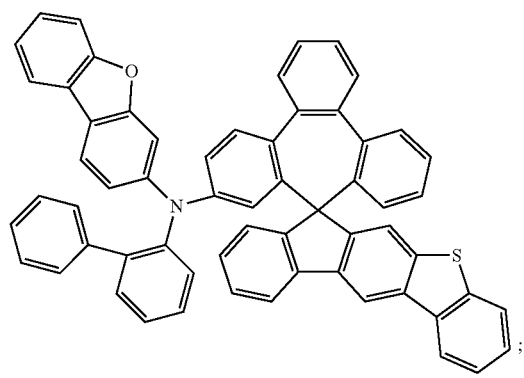
;

-continued
Compound 944
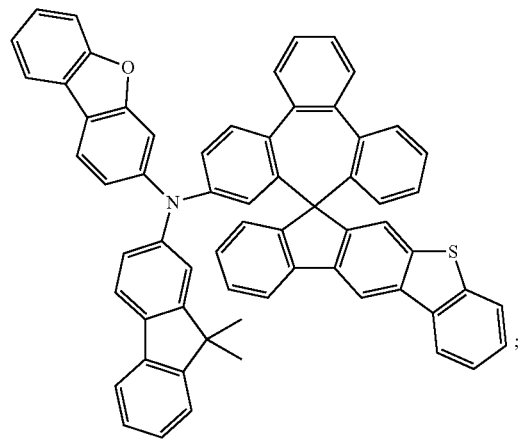
Compound 945
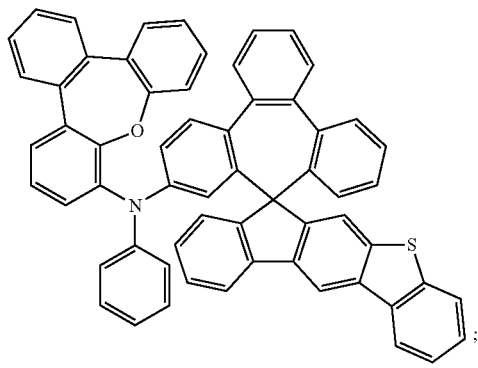
Compound 946
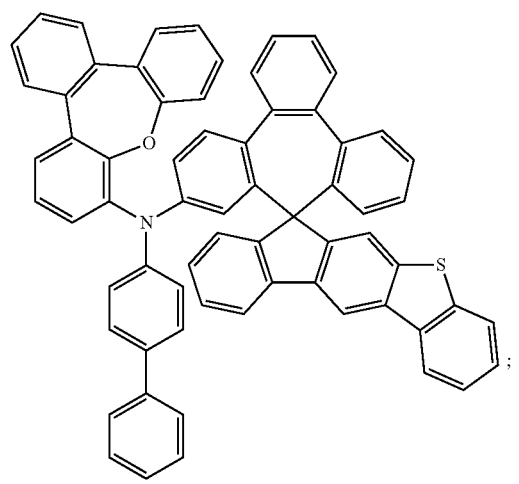
Compound 947
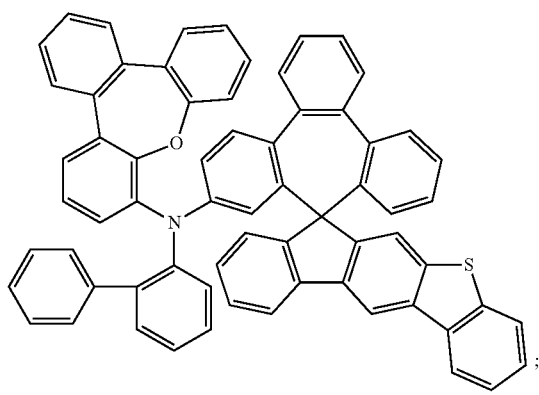
Compound 948
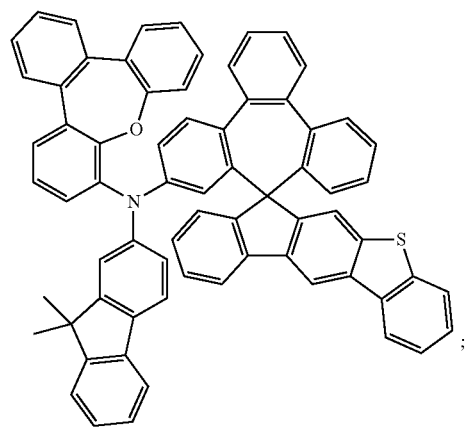
Compound 949
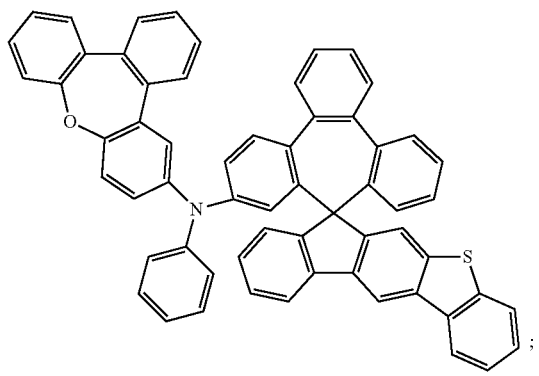

Compound 950
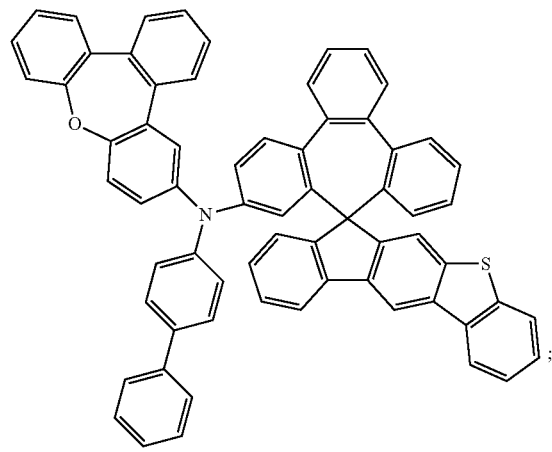
Compound 951
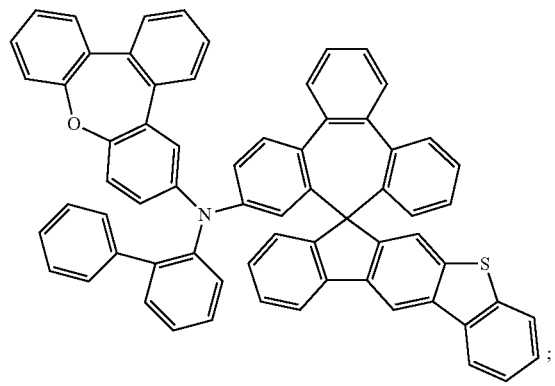
Compound 952
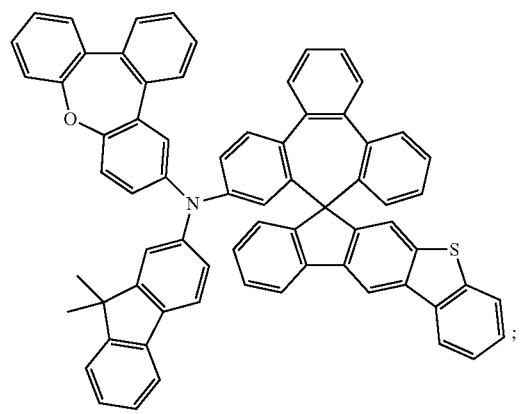
Compound 953
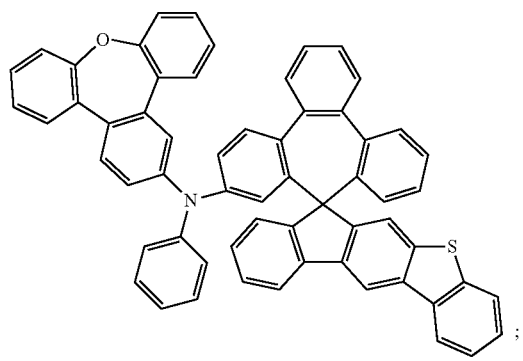
Compound 954
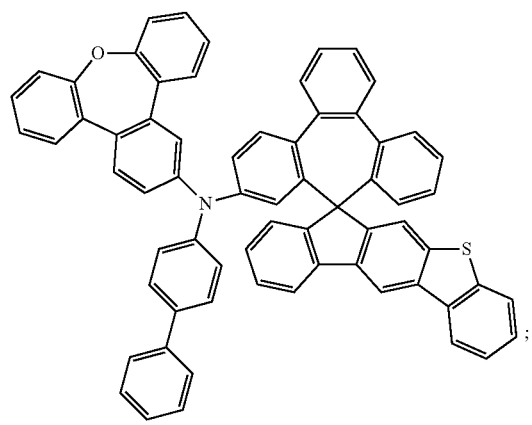
Compound 955
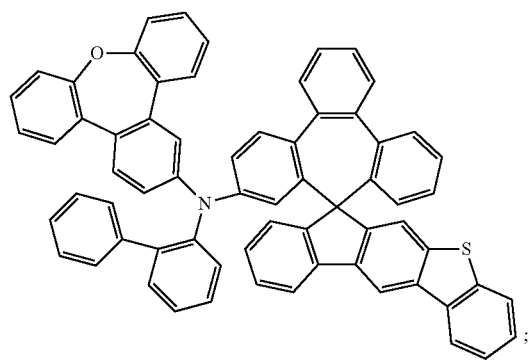

-continued
Compound 956
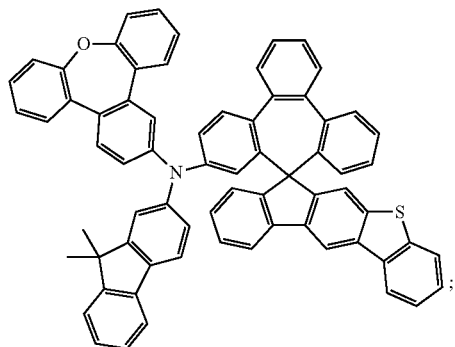
Compound 957
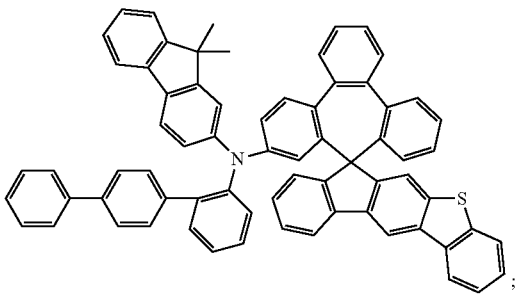
Compound 958
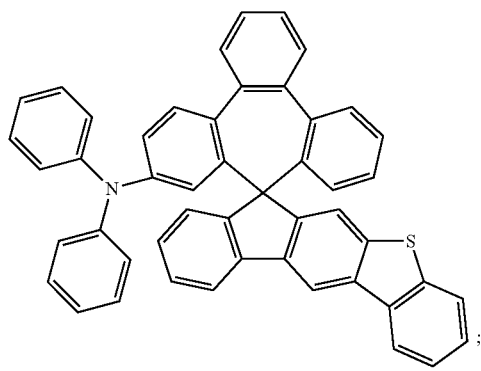
Compound 959
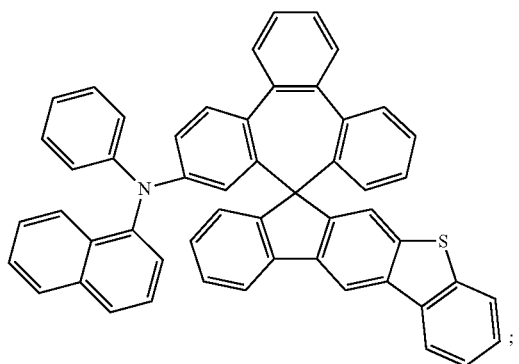
Compound 960
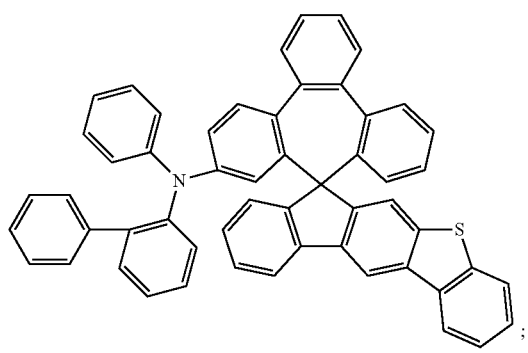
Compound 961
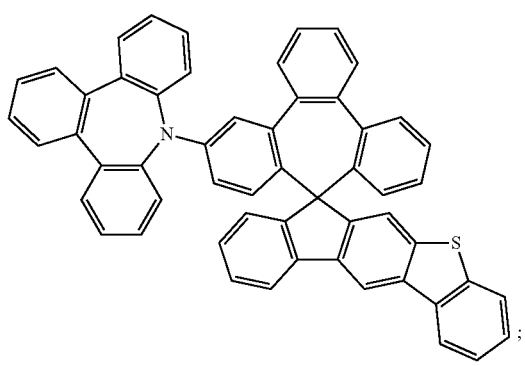
Compound 962
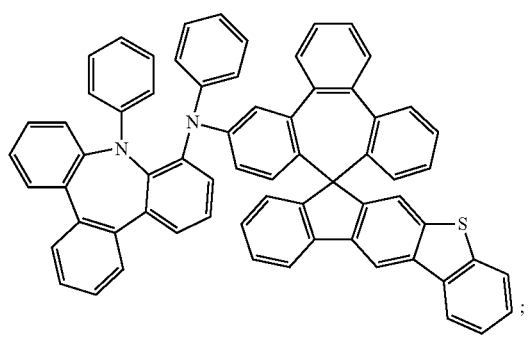
Compound 963
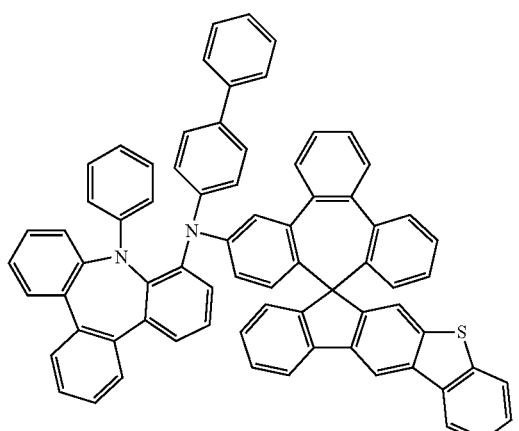

-continued
Compound 964
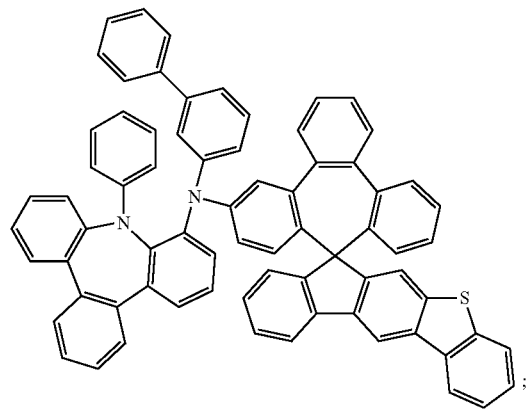
Compound 965
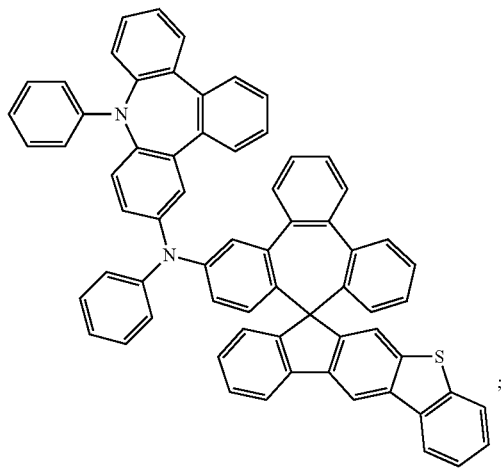
Compound 966
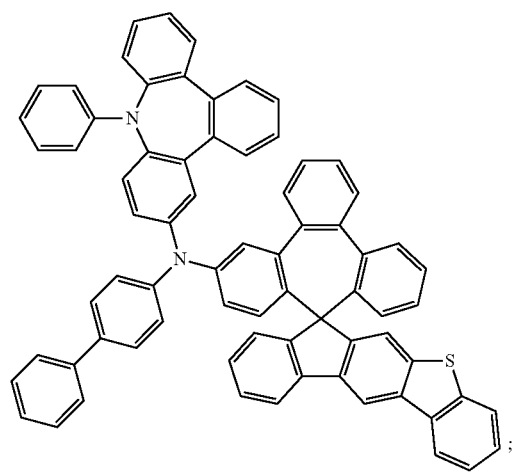
Compound 967
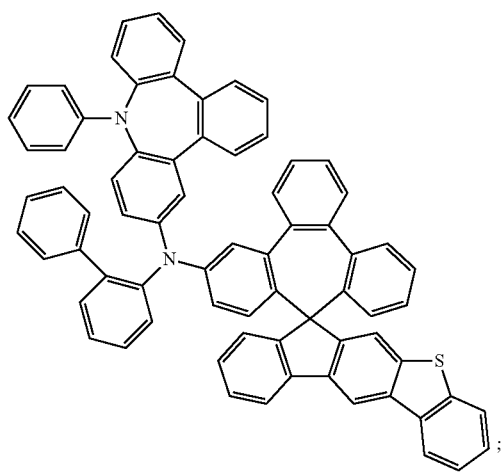
Compound 968
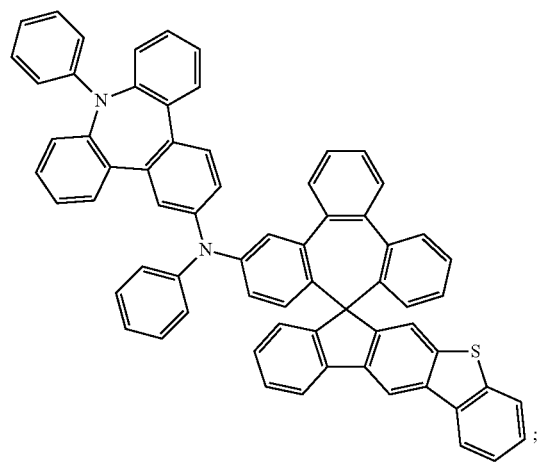
Compound 969
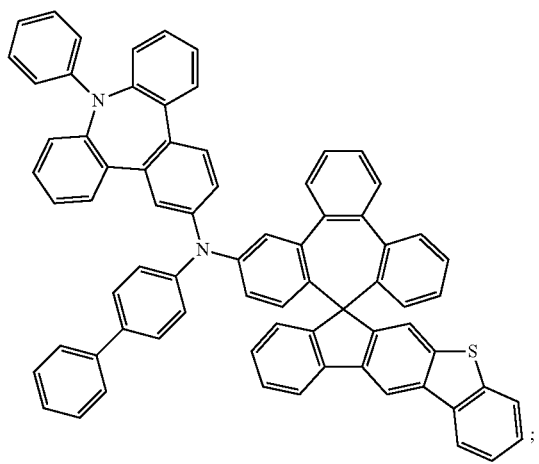

-continued
Compound 970
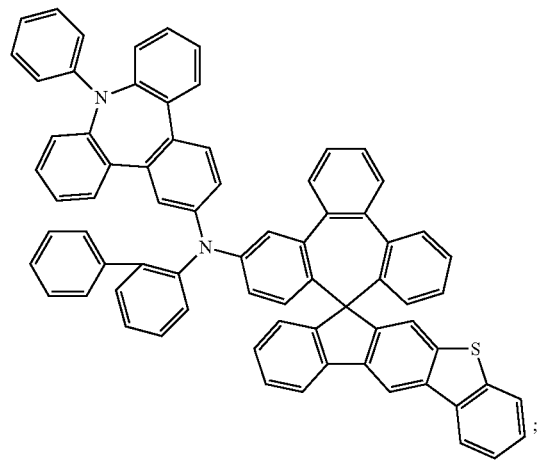
Compound 971
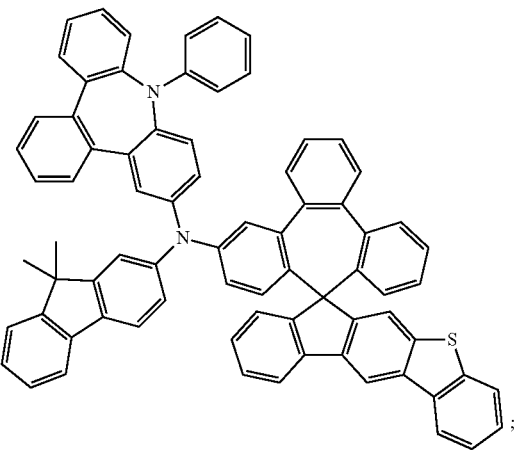
Compound 972
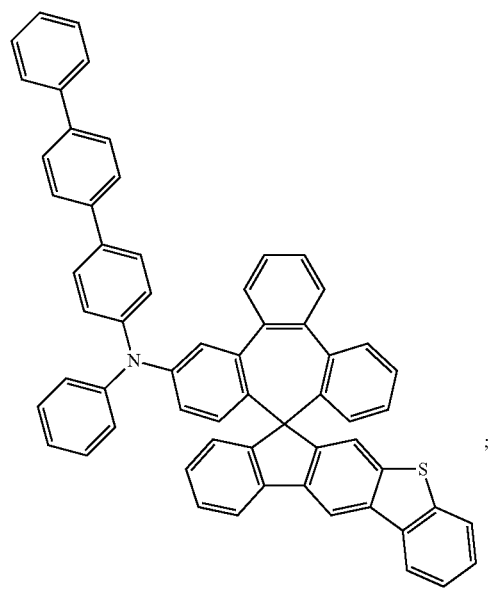
Compound 973
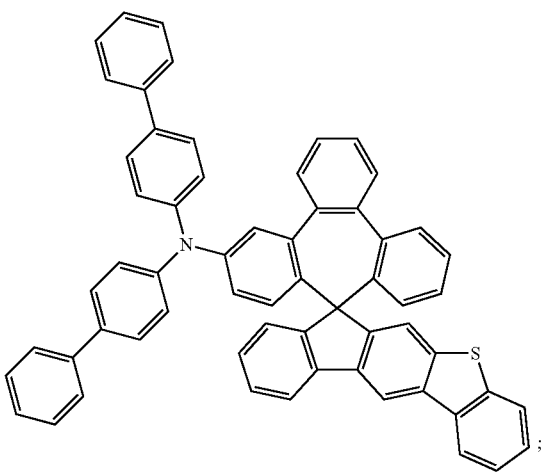
Compound 974
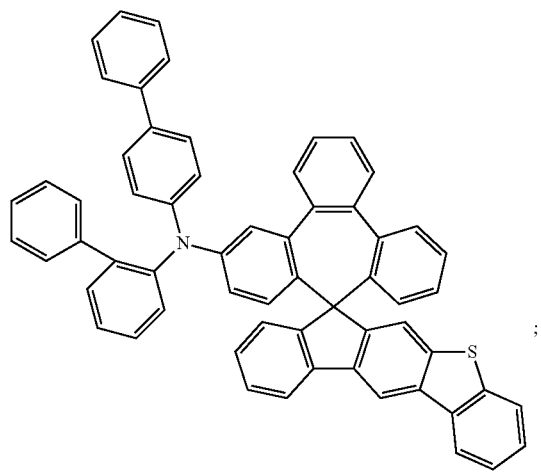
Compound 975
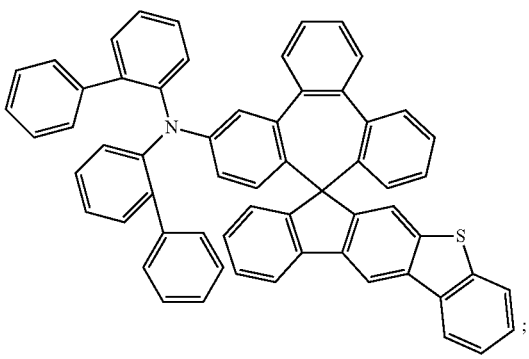

-continued
Compound 976
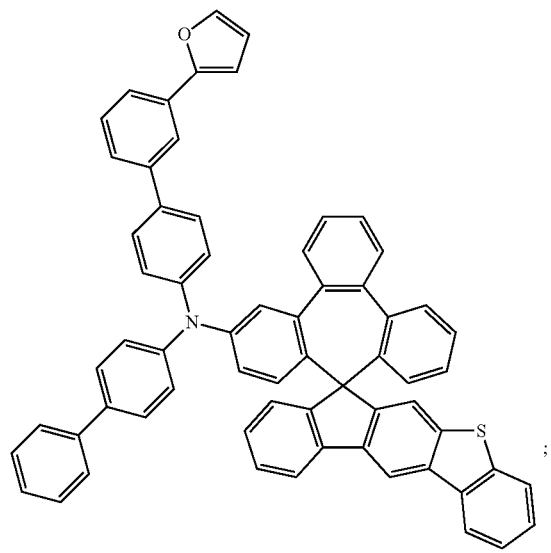
Compound 977
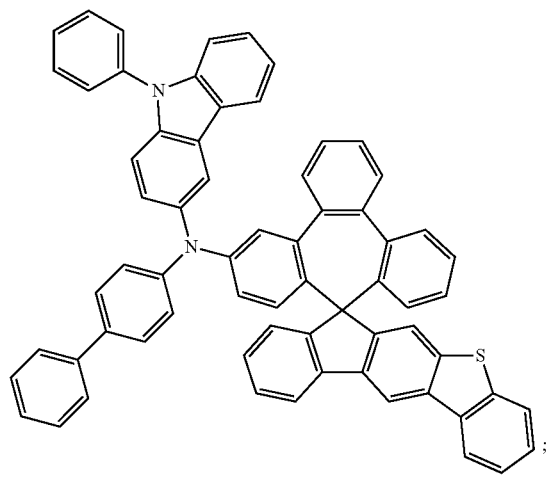
Compound 978
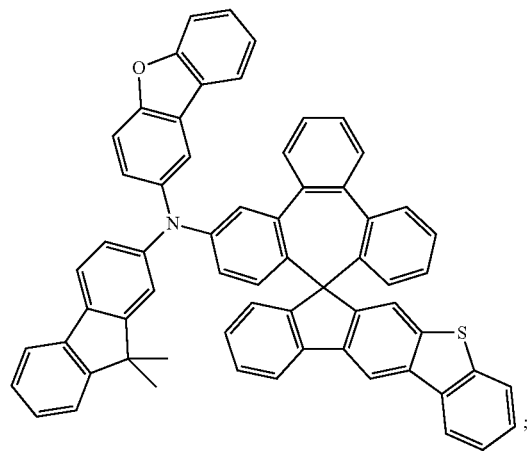
Compound 979
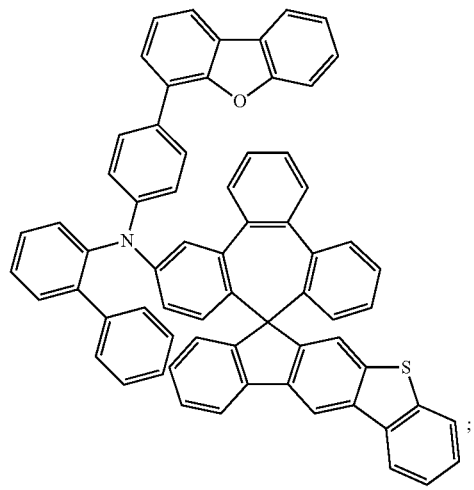
Compound 980
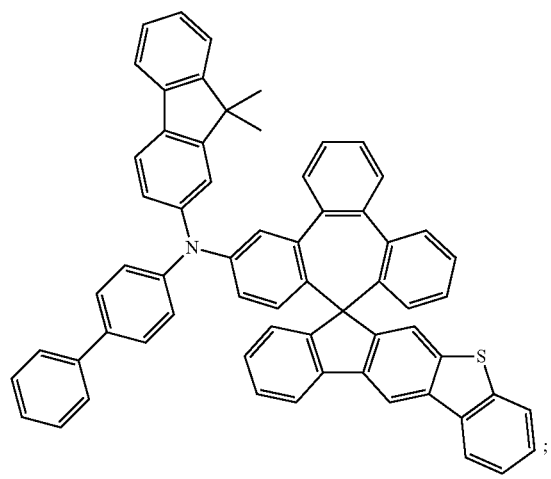
Compound 981
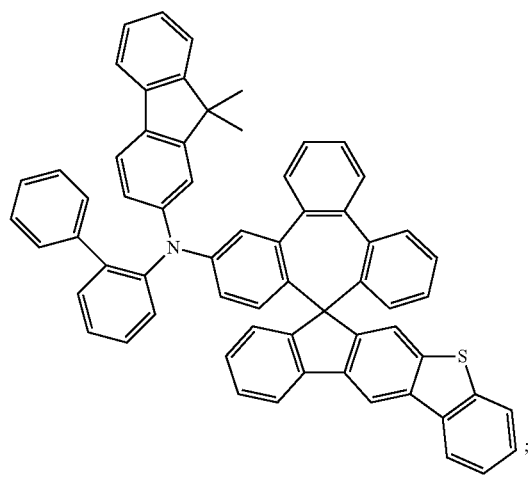

Compound 982
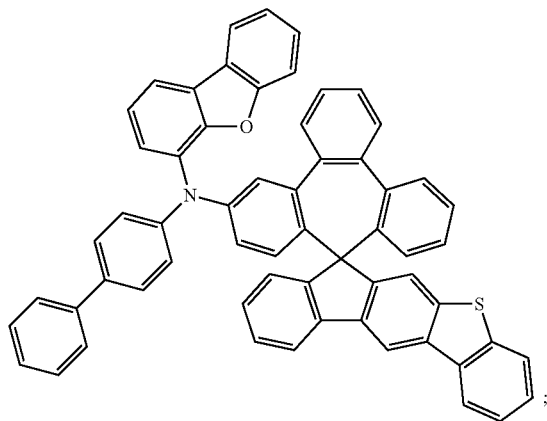
Compound 983
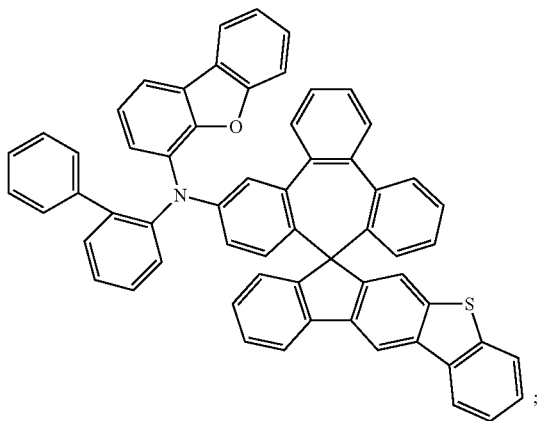
Compound 984
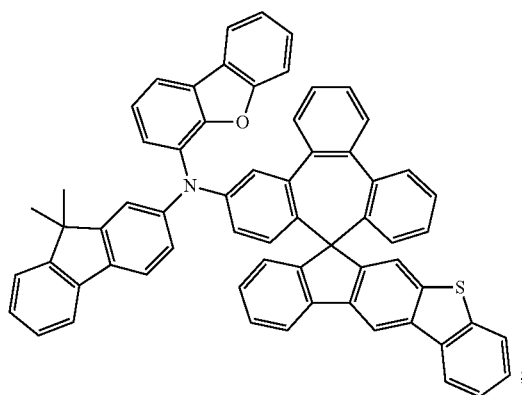
Compound 985
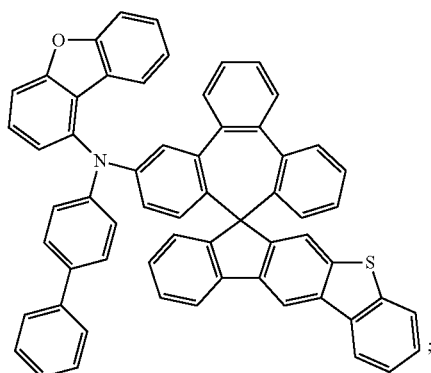
Compound 986
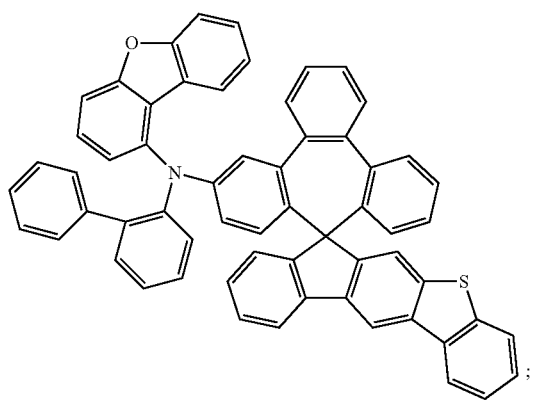
Compound 987
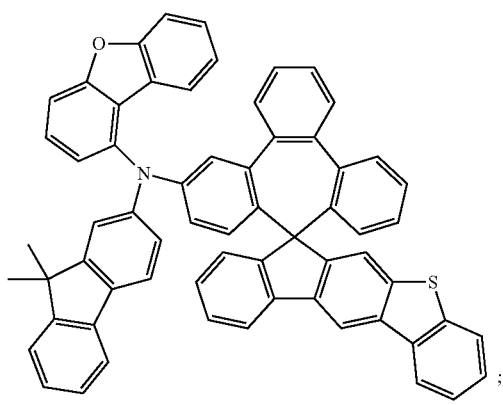

-continued
Compound 988
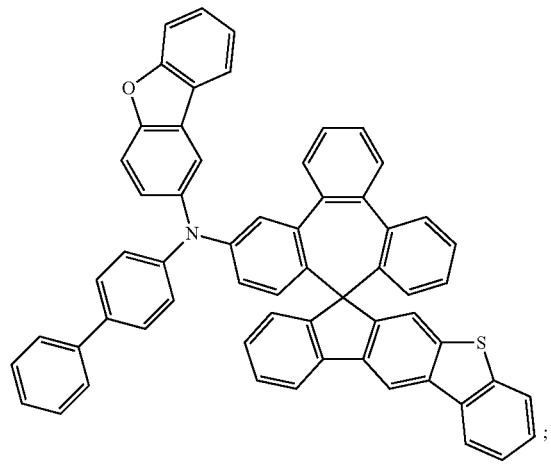
Compound 989
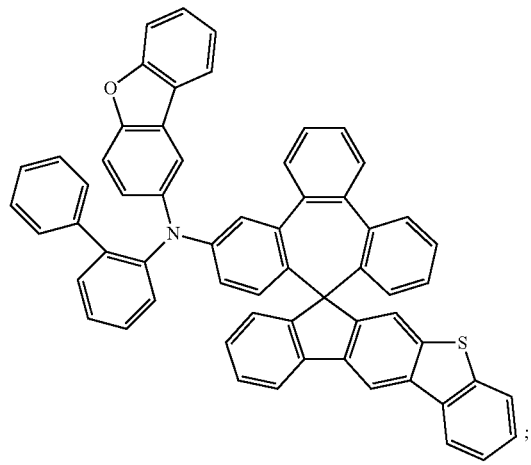
Compound 990
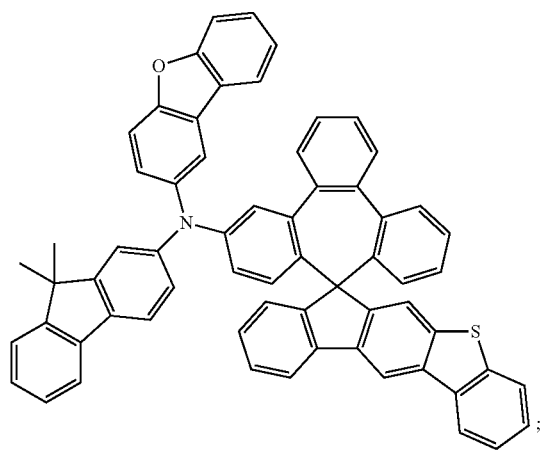
Compound 991
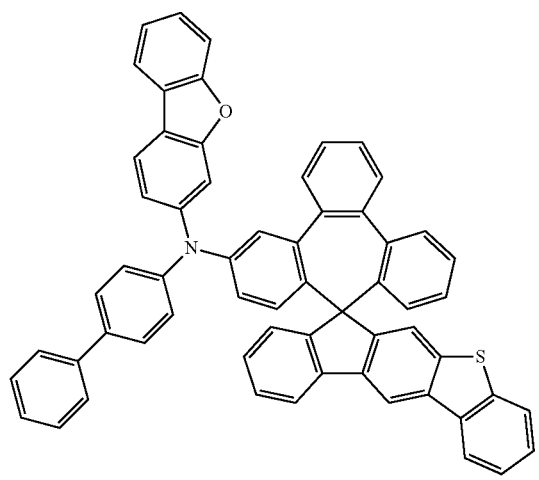
Compound 992
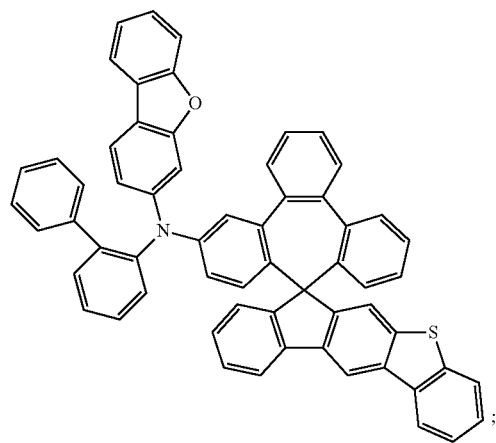
Compound 993
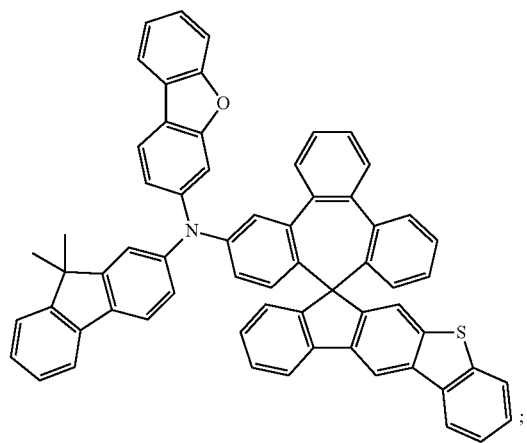

-continued
Compound 994
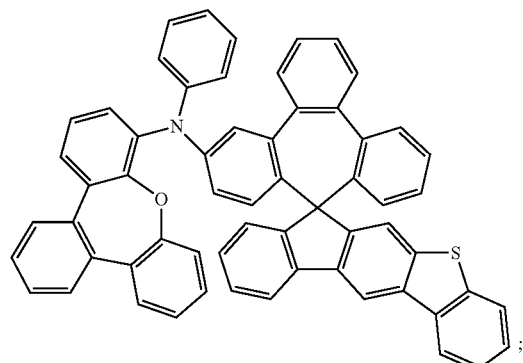
Compound 995
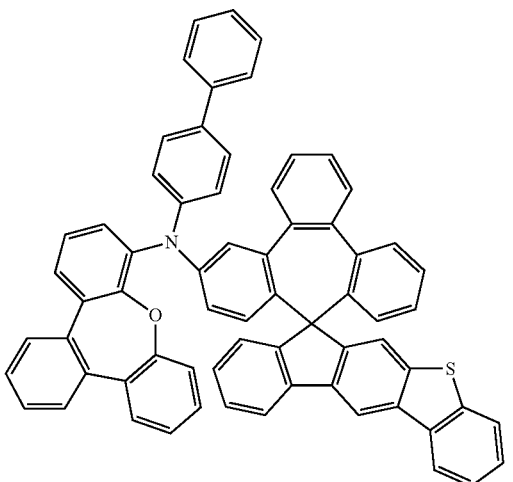
Compound 996
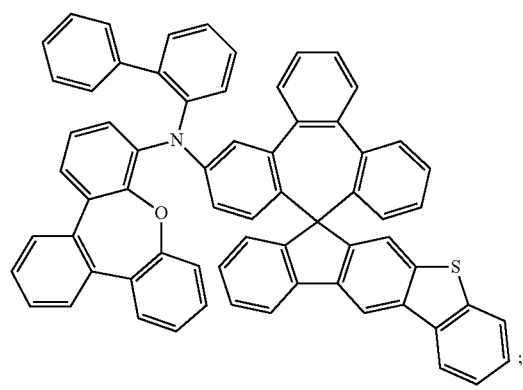
Compound 997
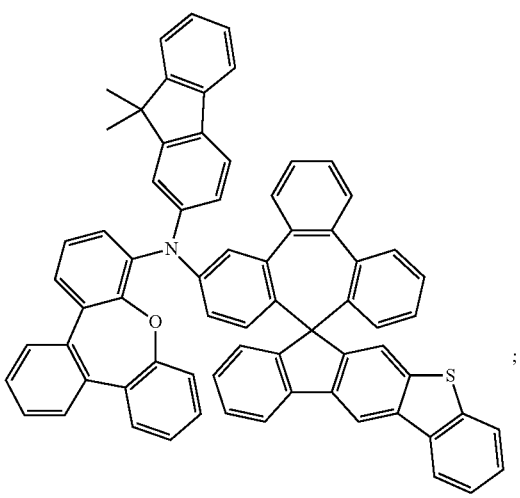
Compound 998
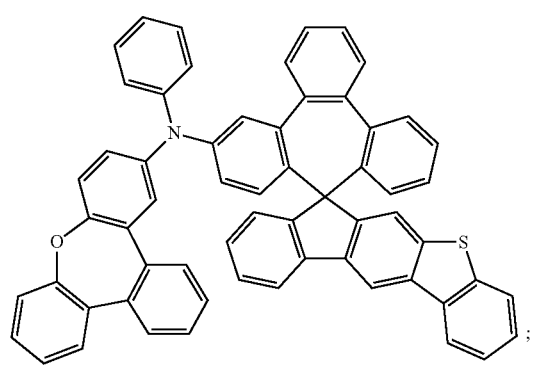
Compound 999
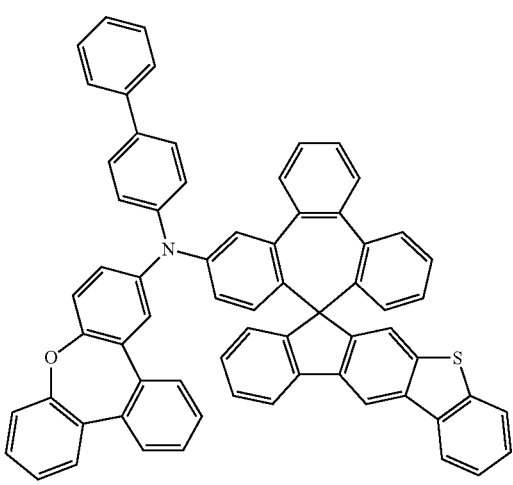

-continued
Compund 1000
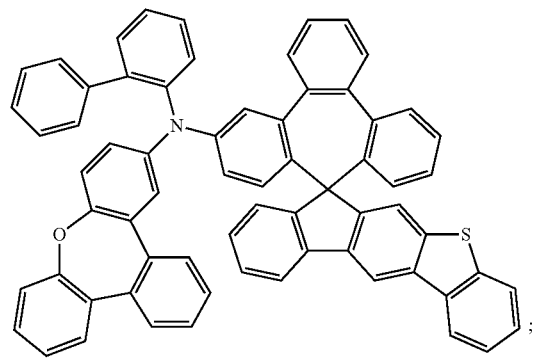
Compund 1001
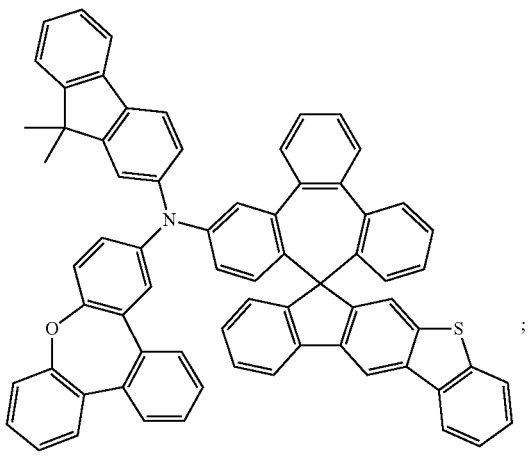
Compound 1002
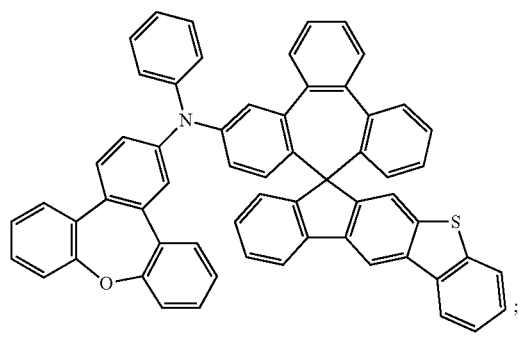
Compound 1003
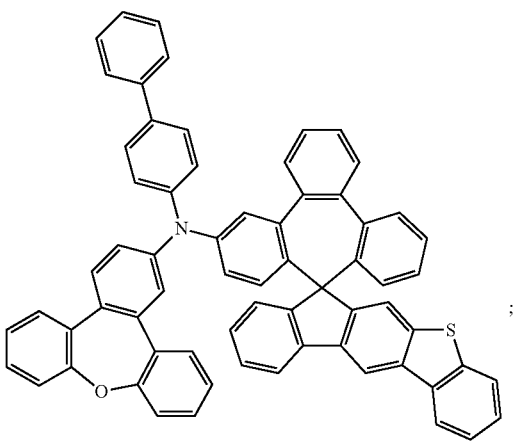
Compound 1004
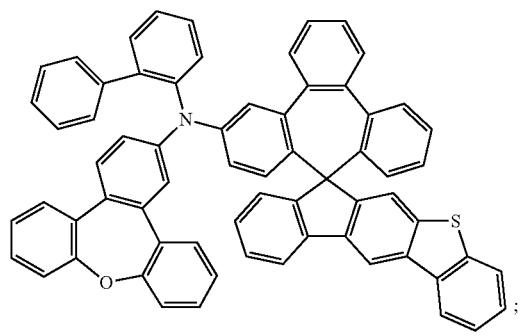
Compound 1005
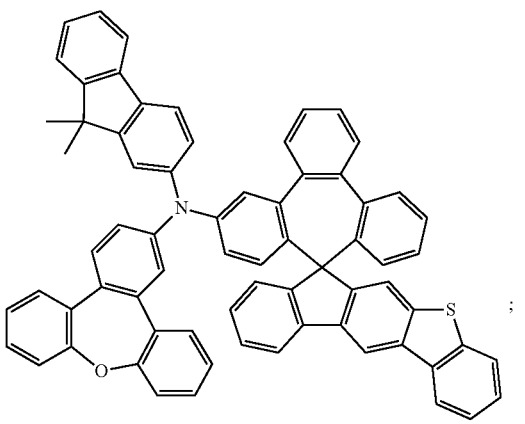

-continued
Compound 1006
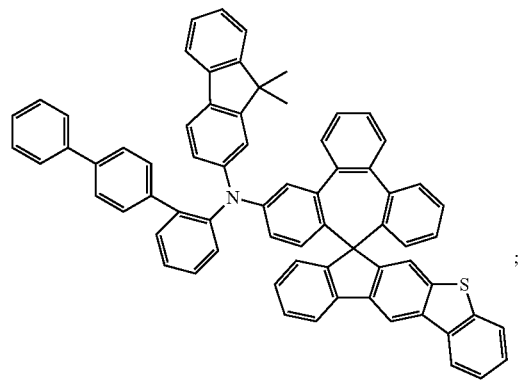
Compound 1007
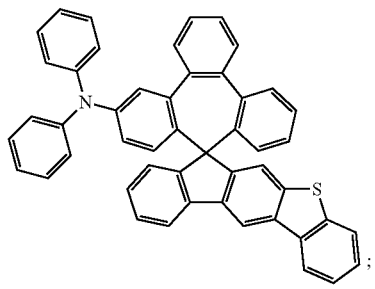
Compound 1008
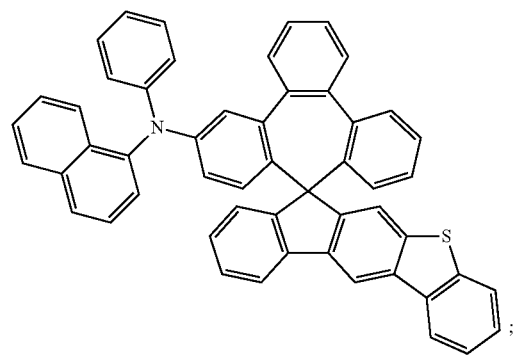
Compound 1009
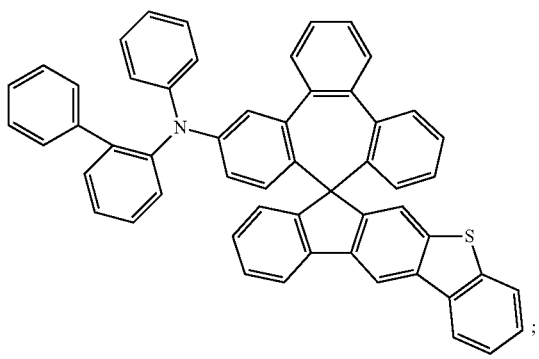
Compound 1010
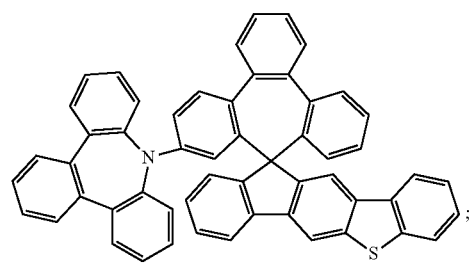
Compound 1011
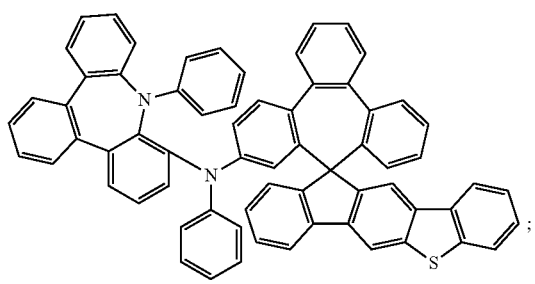
Compound 1012
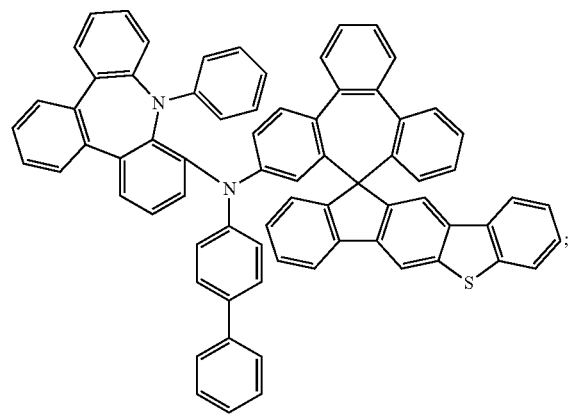
Compound 1013
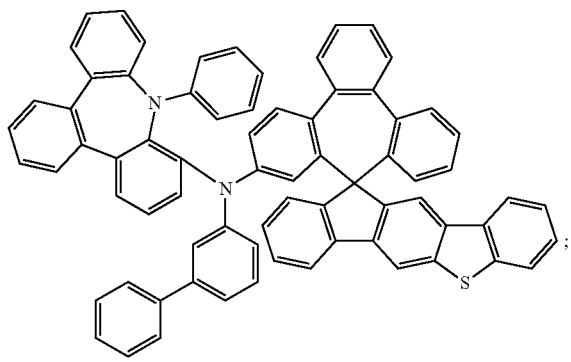

-continued
Compound 1014
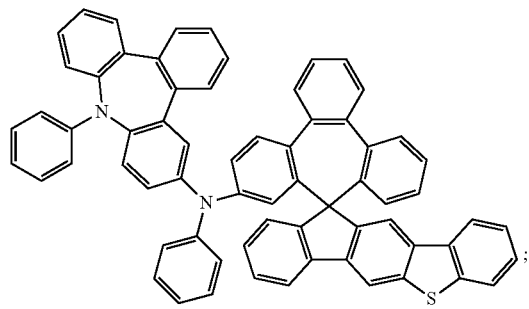
Compound 1015
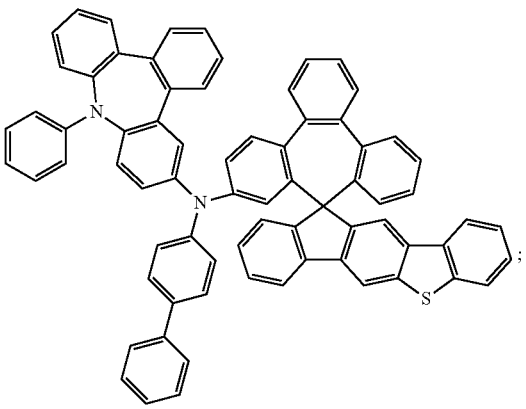
Compound 1016
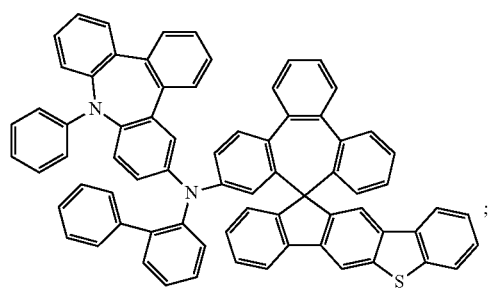
Compound 1017
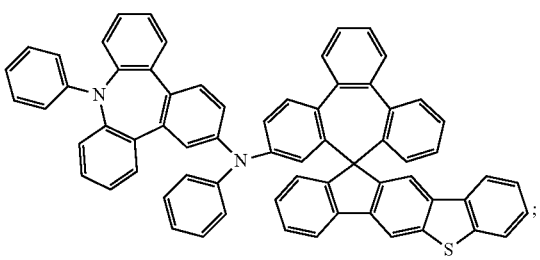
Compound 1018
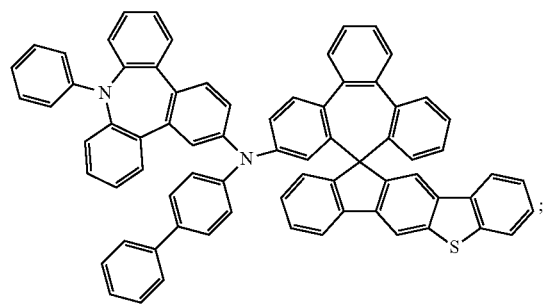
Compound 1019
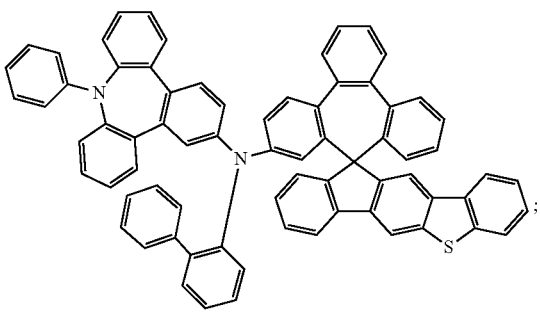
Compound 1020
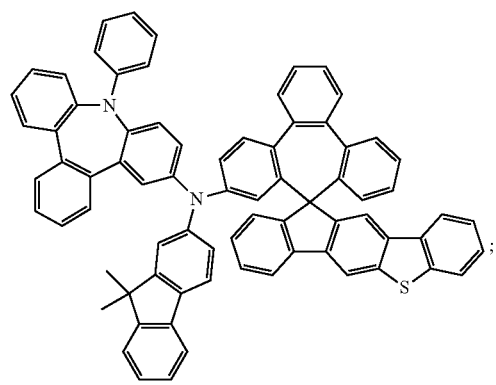
Compound 1021
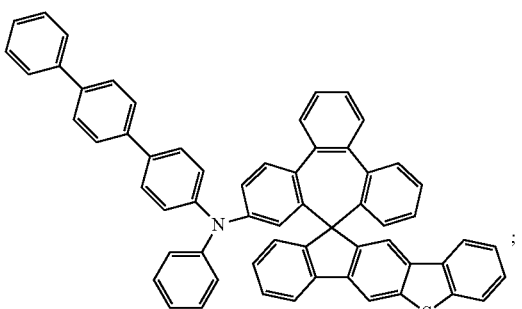

-continued
Compound 1022
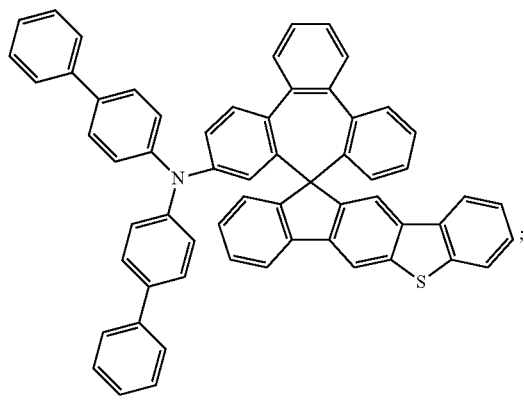
Compound 1023
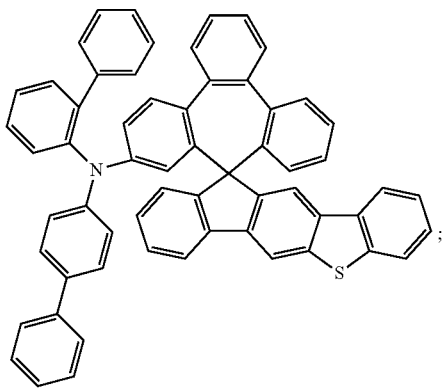
Compound 1024
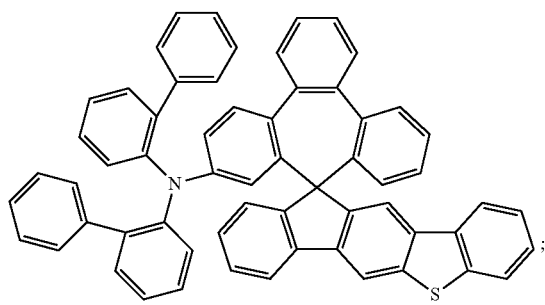
Compound 1025
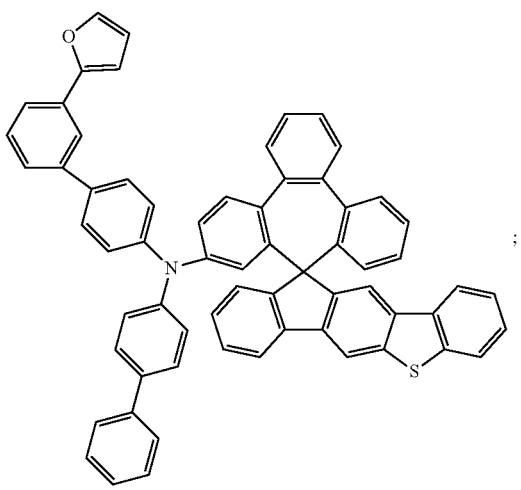
Compound 1026
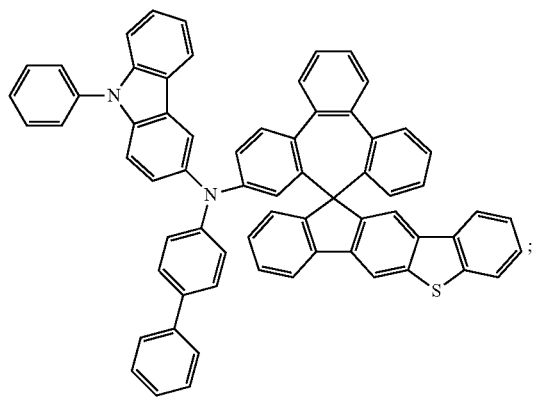
Compound 1027
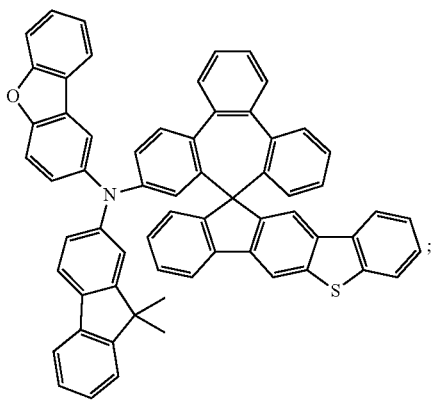

-continued
Compound 1028
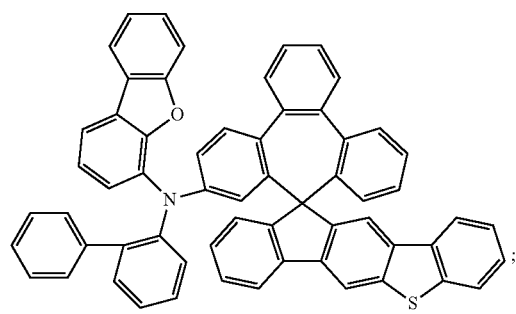
Compound 1029
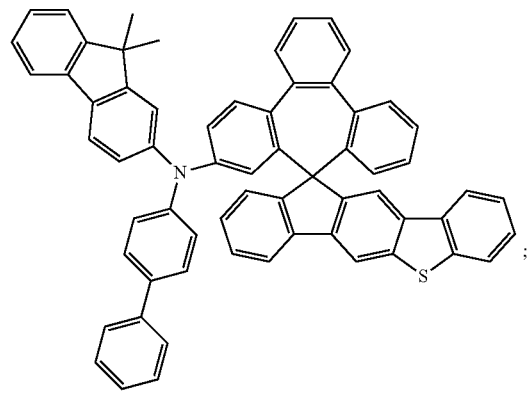
Compound 1030
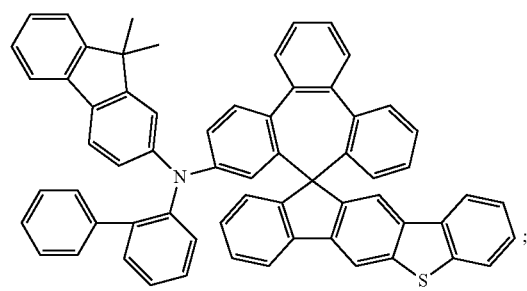
Compound 1031
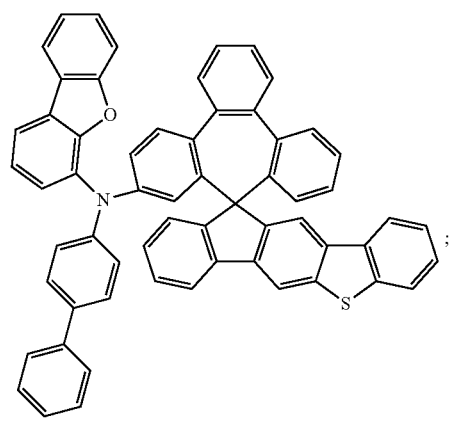
Compound 1032
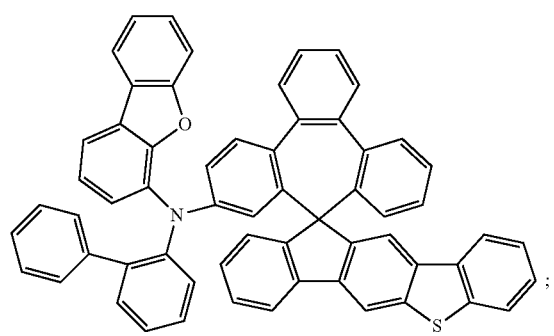
Compound 1033
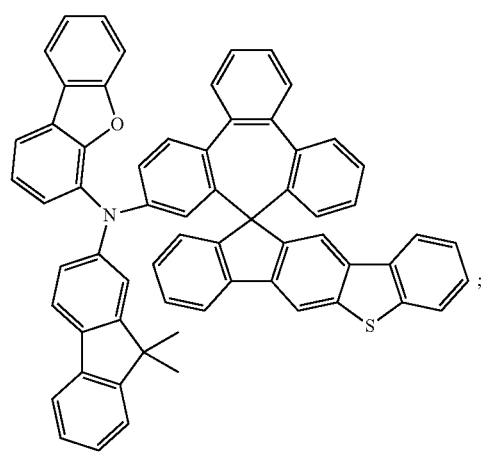

-continued
Compound 1034
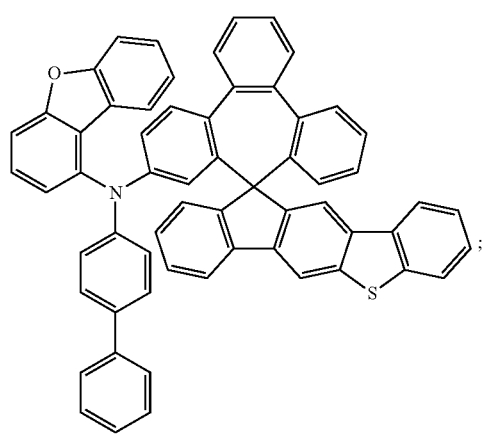
Compound 1035
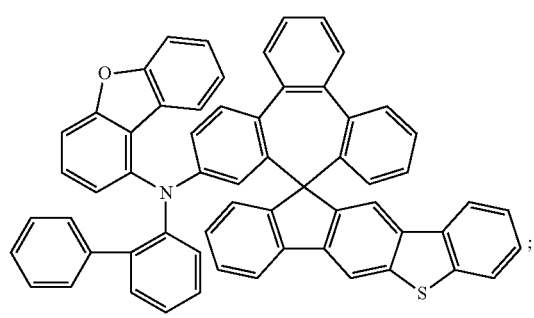
Compound 1036
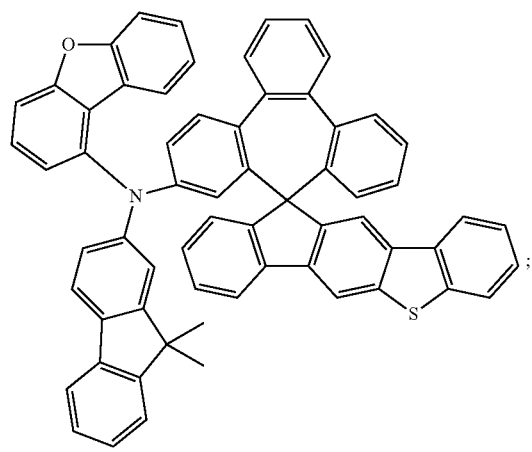
Compound 1037
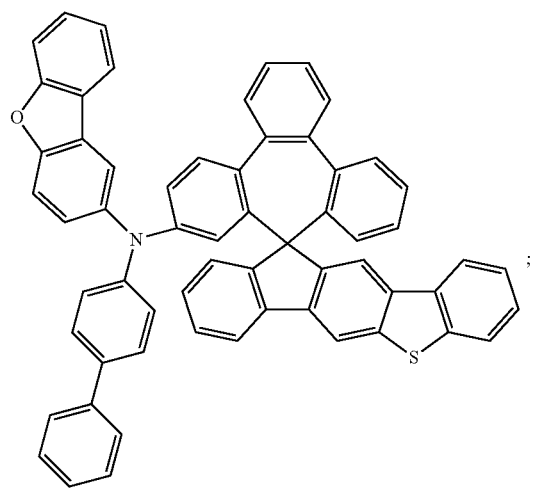
Compound 1038
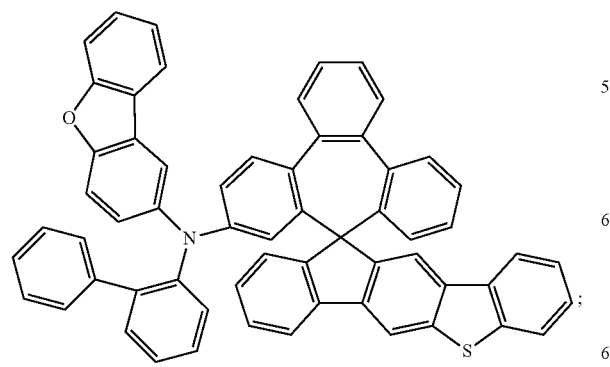

Compound 1039
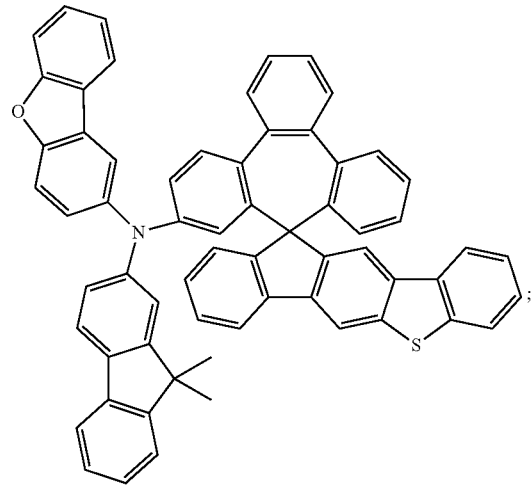
Compound 1040
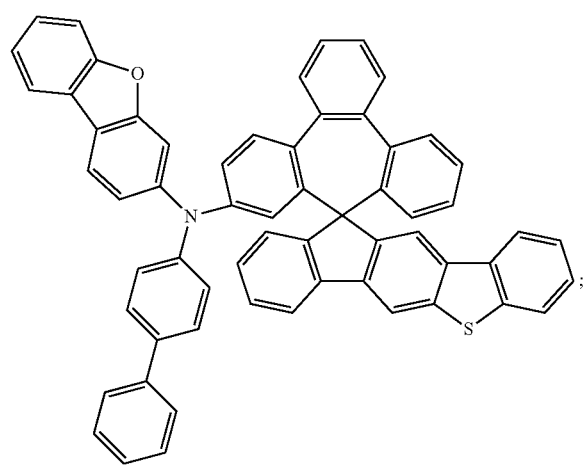
Compound 1041
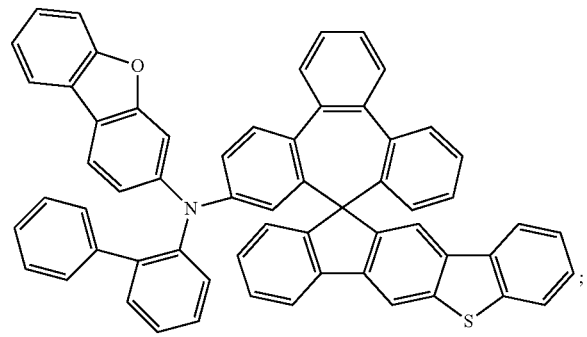
Compound 1042
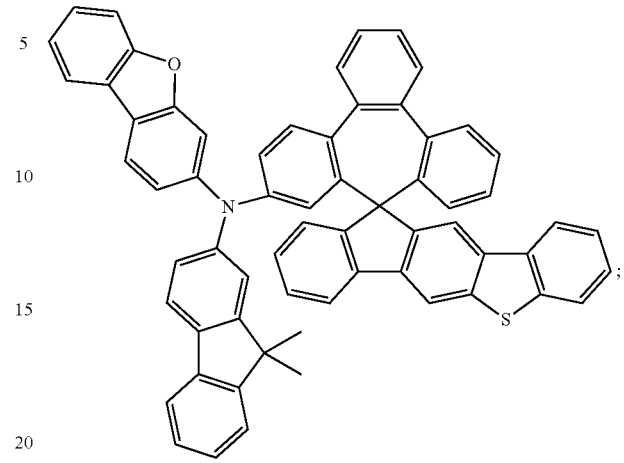
Compound 1043
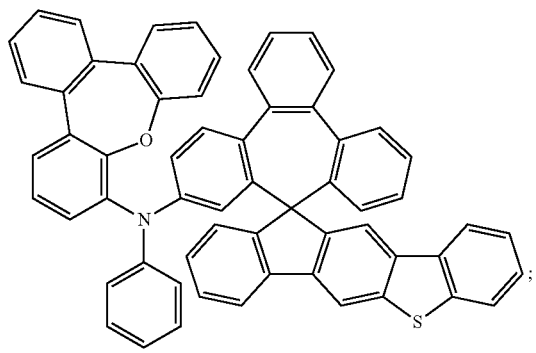
Compound 1044
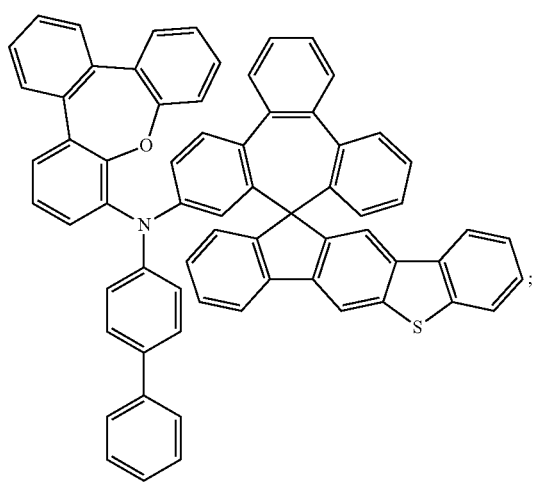

Compound 1045
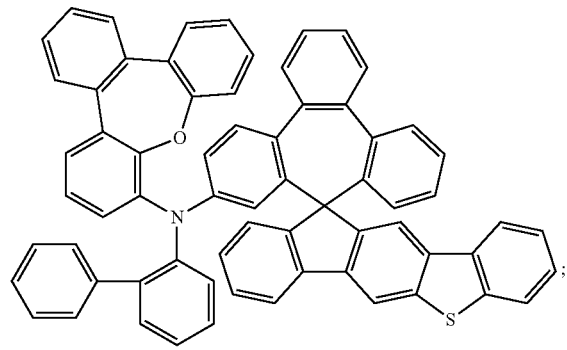
Compound 1046
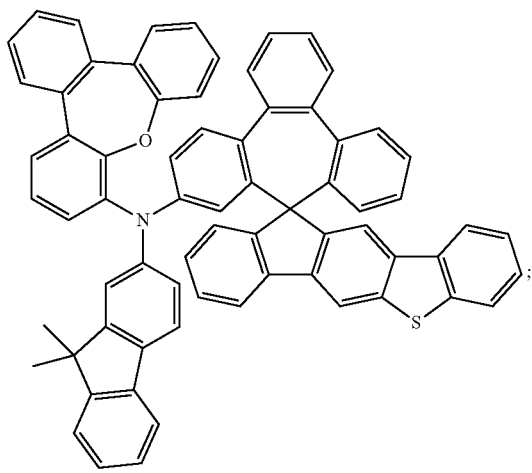
Compound 1047
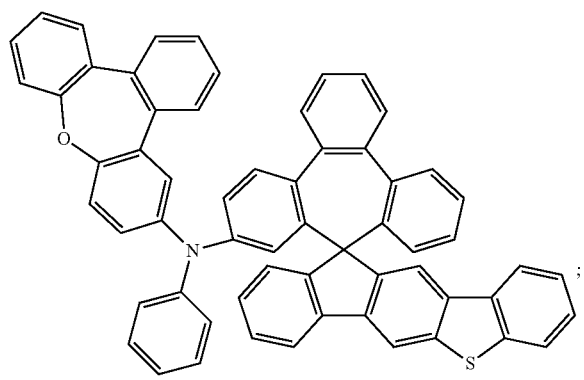
Compound 1048
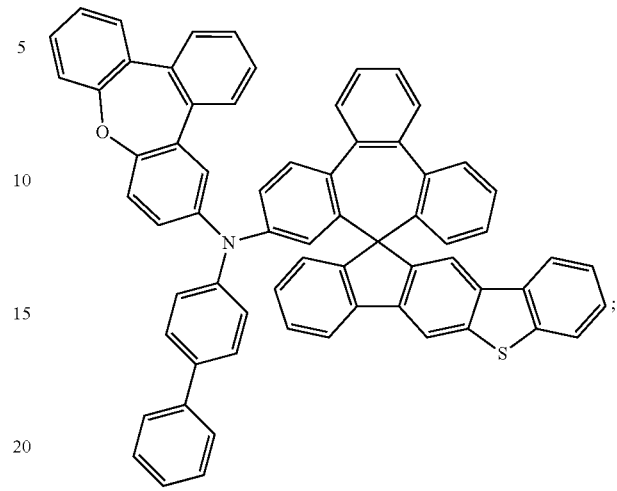
Compound 1049
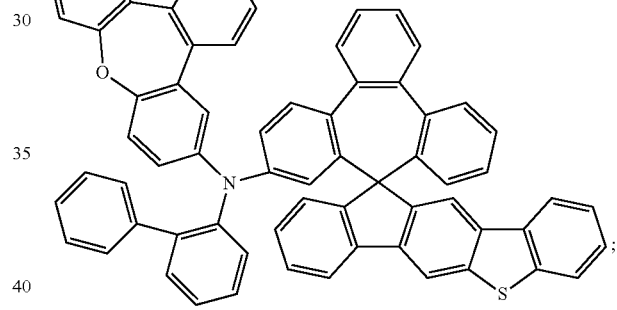
Compound 1050
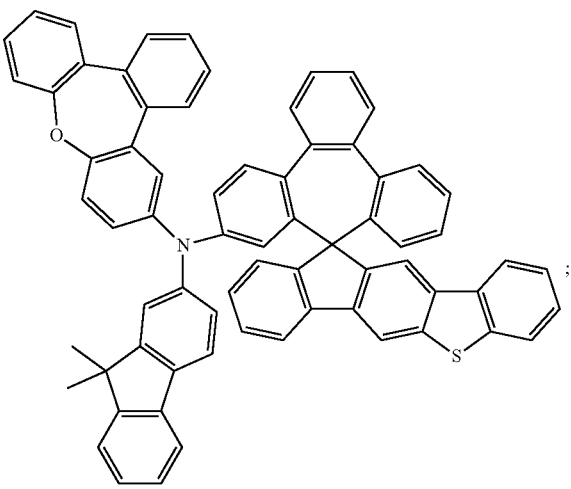

Compound 1051
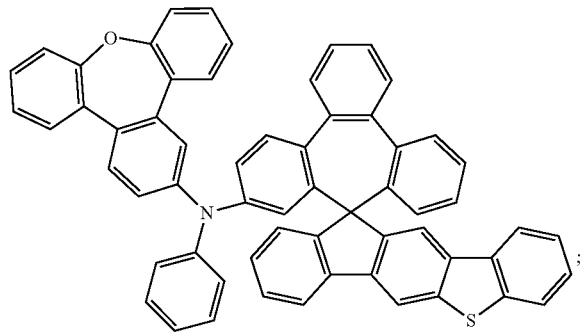
Compound 1052
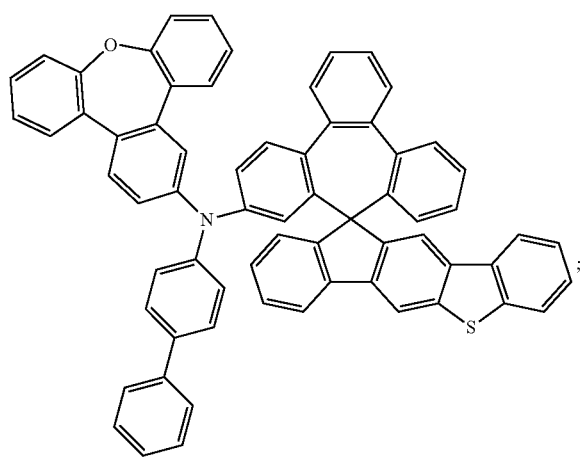
Compound 1053
Compound 1054
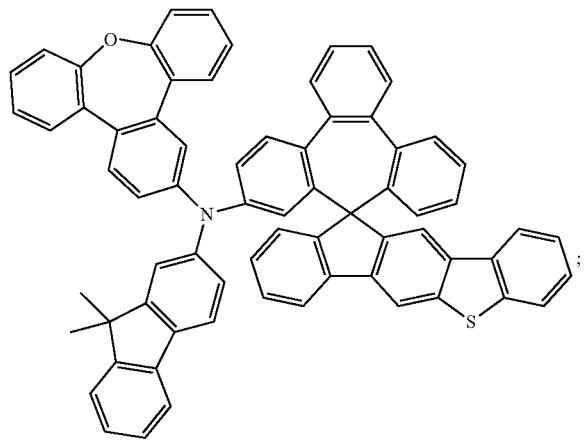
Compound 1055
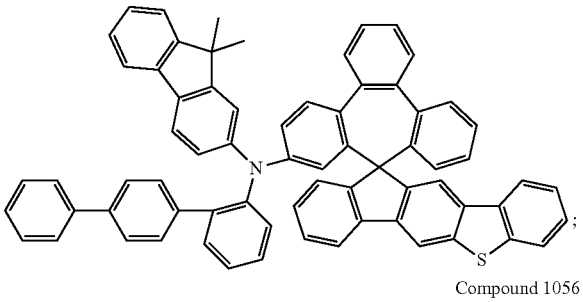
Compound 1056
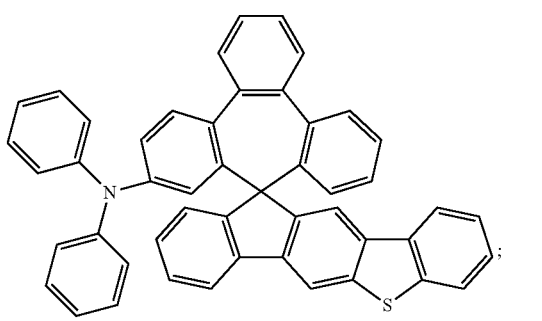
Compound 1057
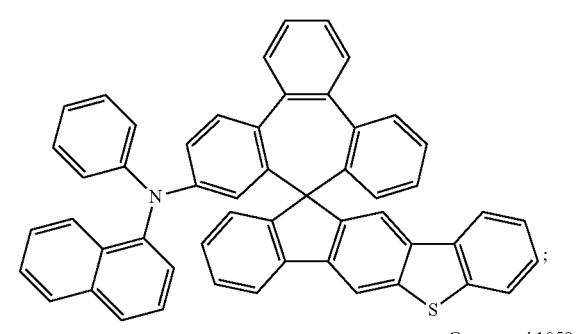
Compound 1058
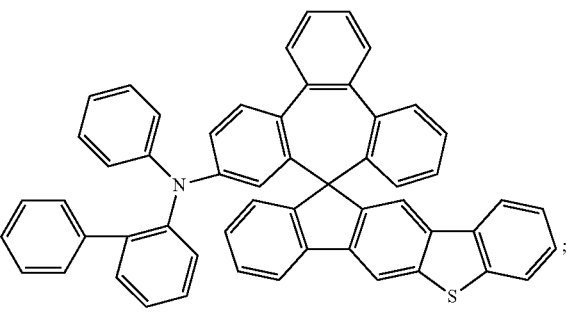
Compound 1059
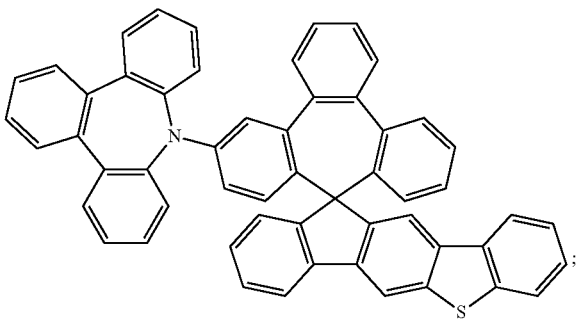

Compound 1060
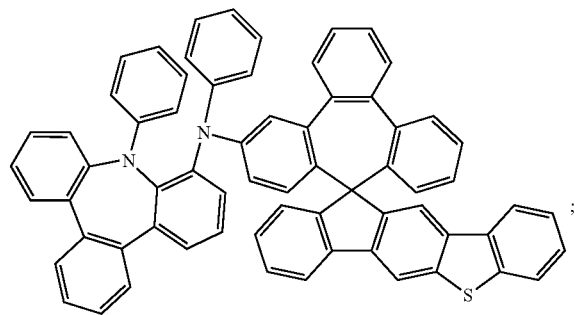
Compound 1061
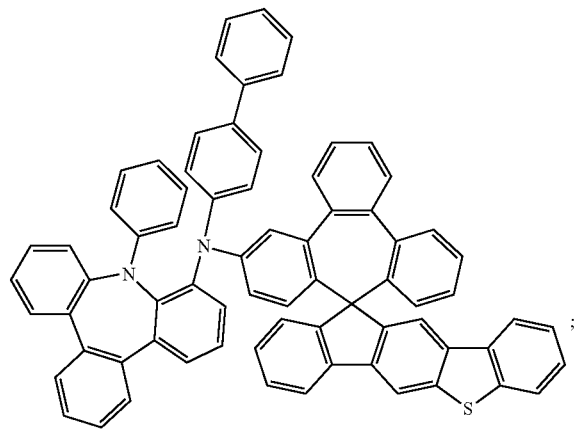
Compound 1062
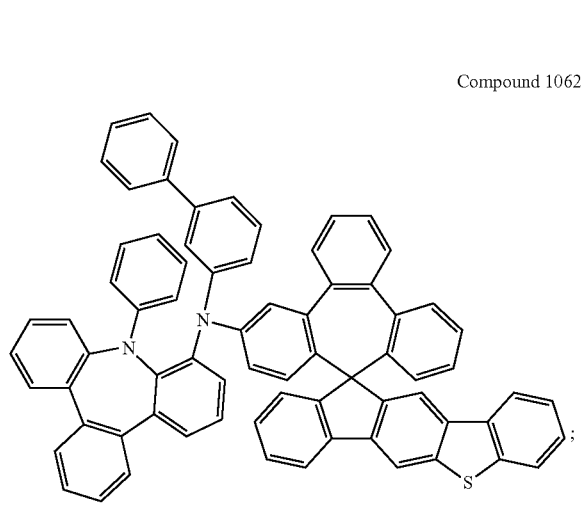
Compound 1063
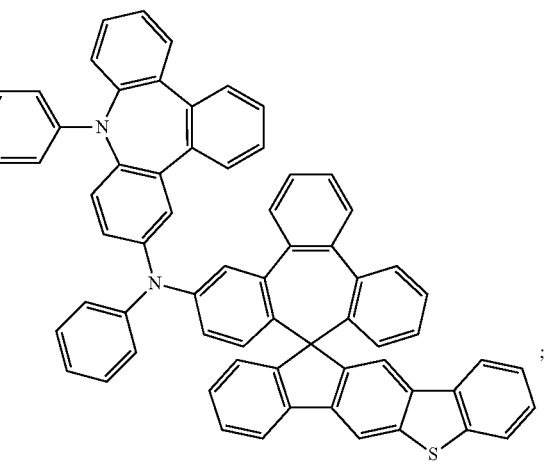
Compound 1064
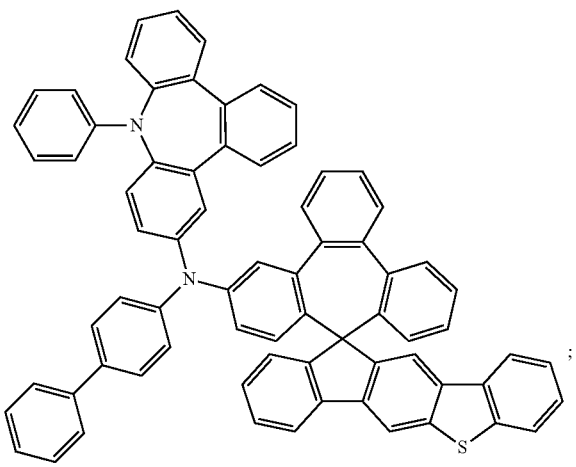
Compound 1065
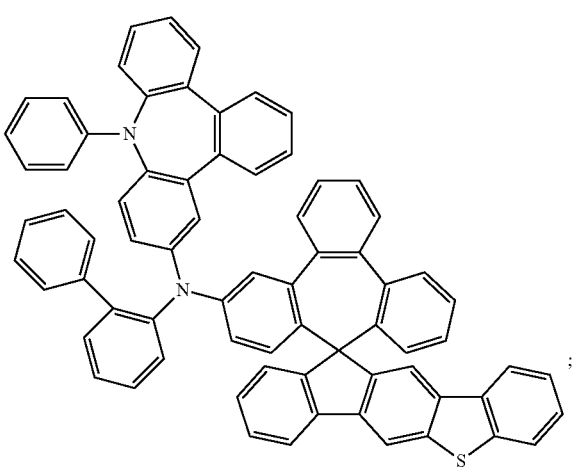

Compound 1066
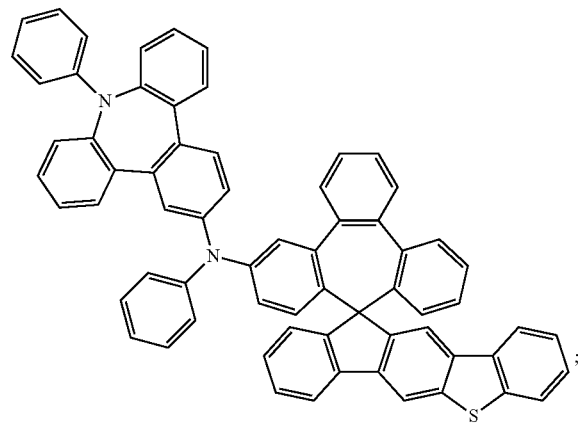
Compound 1067
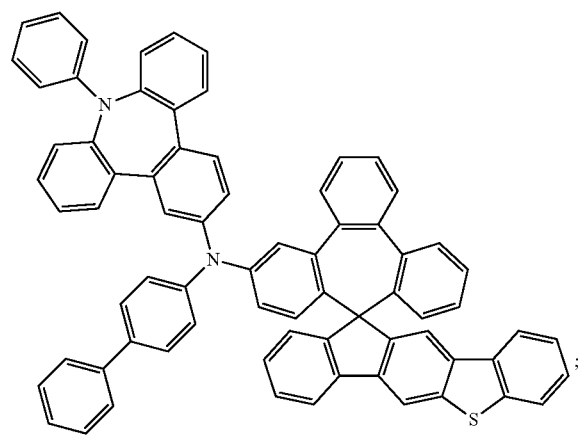
Compound 1068
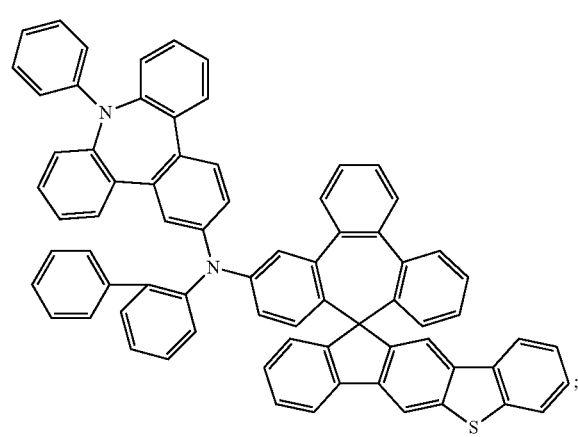
Compound 1069
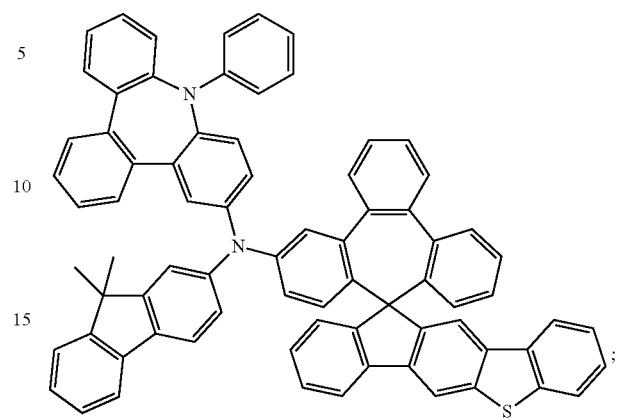
Compound 1070
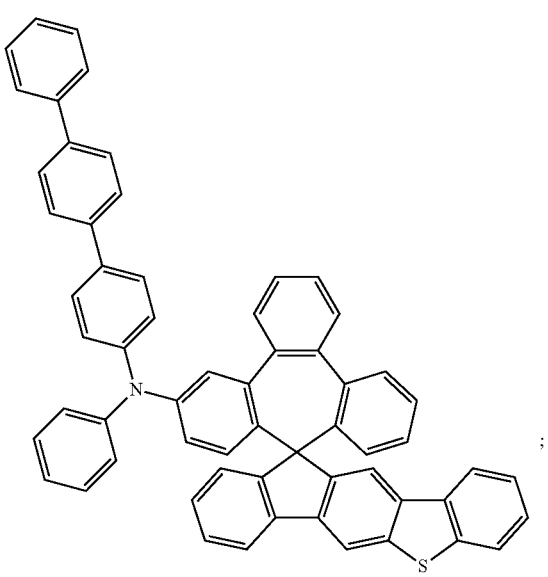
Compound 1071
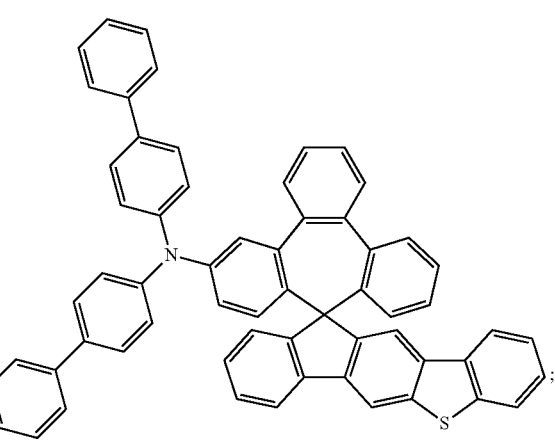

Compound 1072
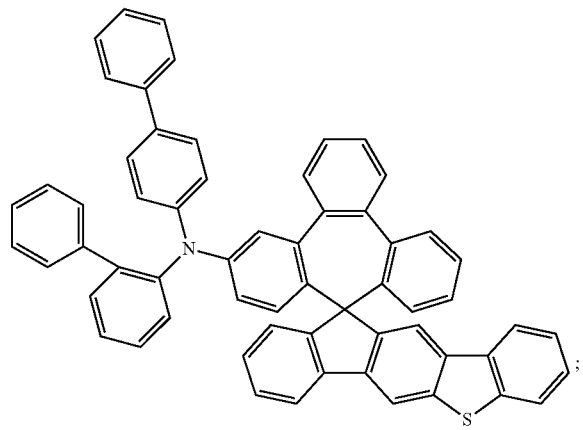
Compound 1073
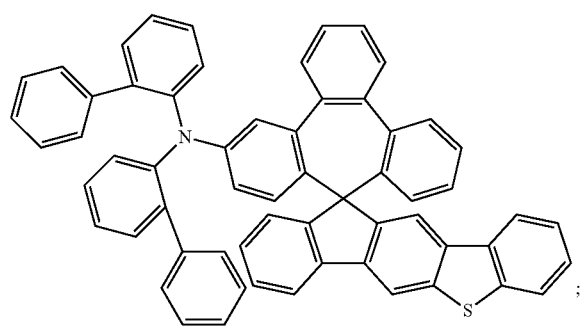
Compound 1074
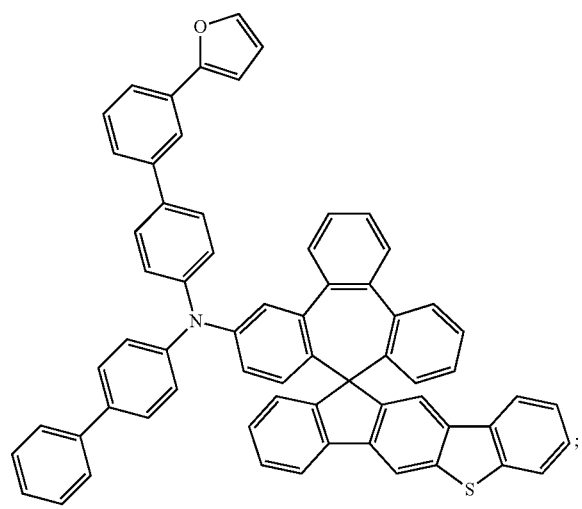
Compound 1075
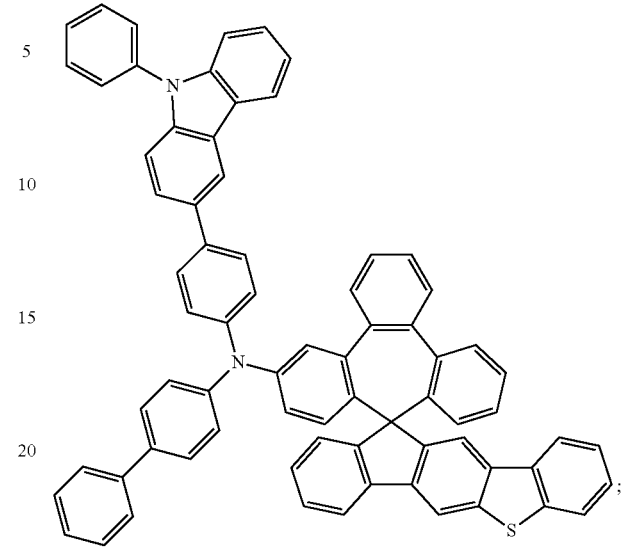
Compound 1076
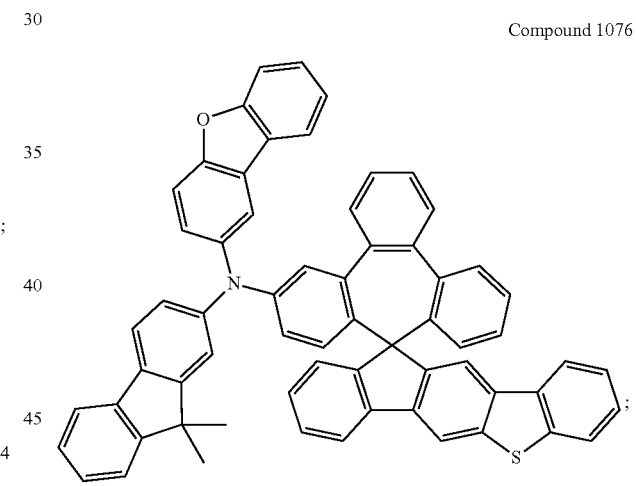
Compound 1077
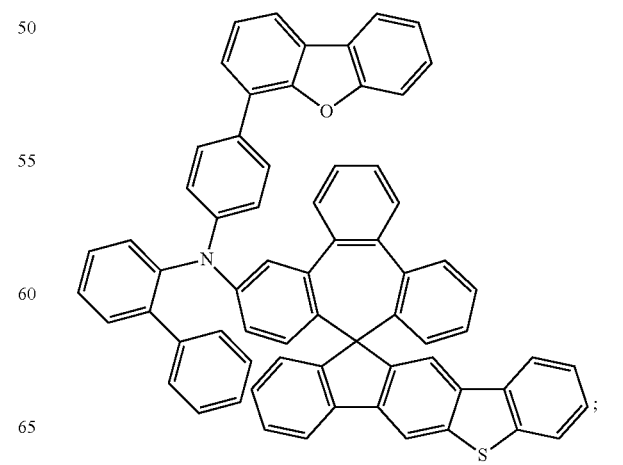

Compound 1078
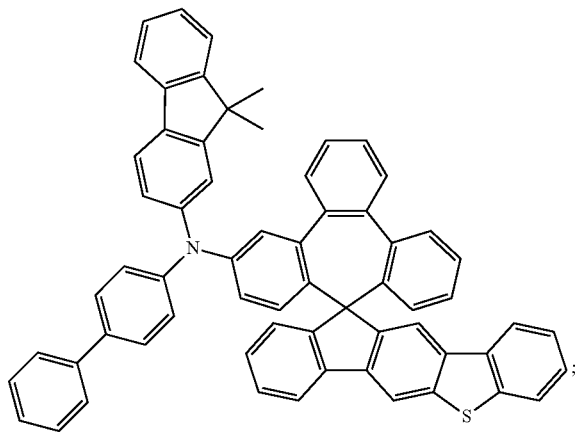
Compound 1079
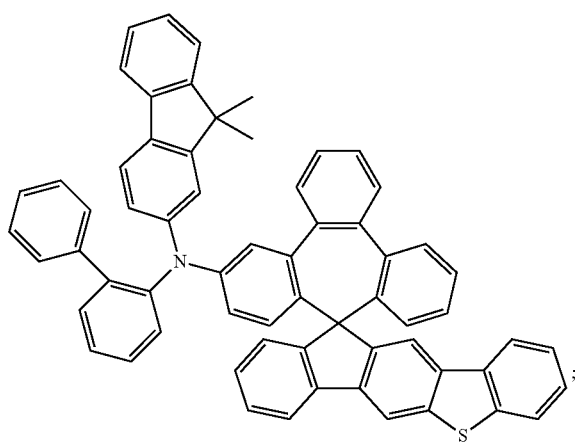
Compound 1080
Compound 1081
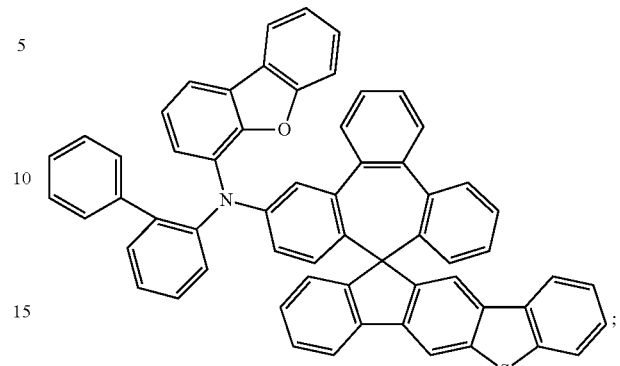
Compound 1082
Compound 1083
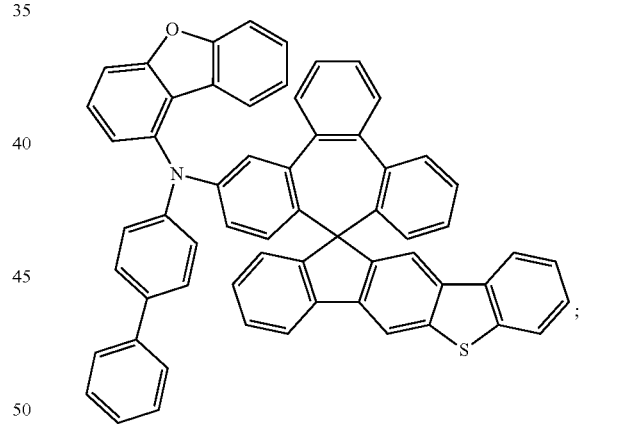
Compound 1084
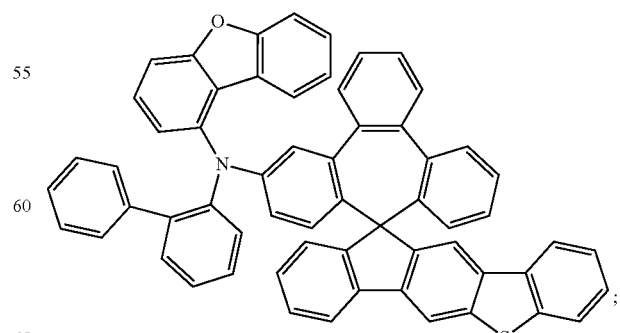

Compound 1085
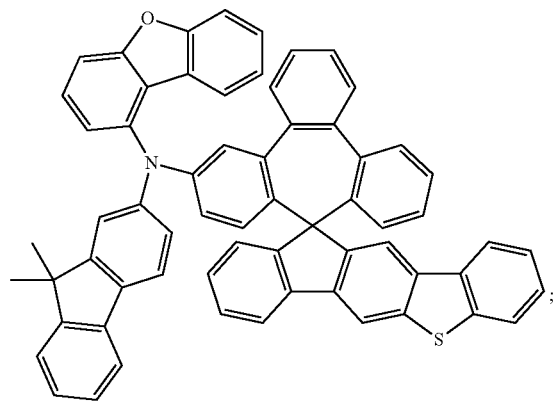
Compound 1086
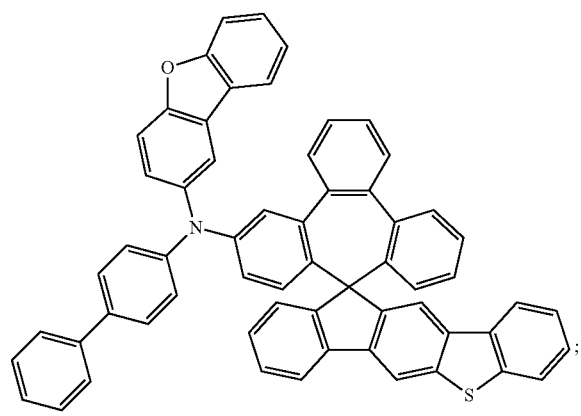
Compound 1087
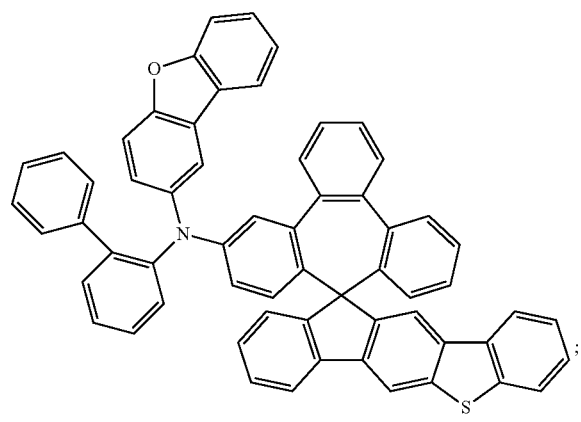
Compound 1088
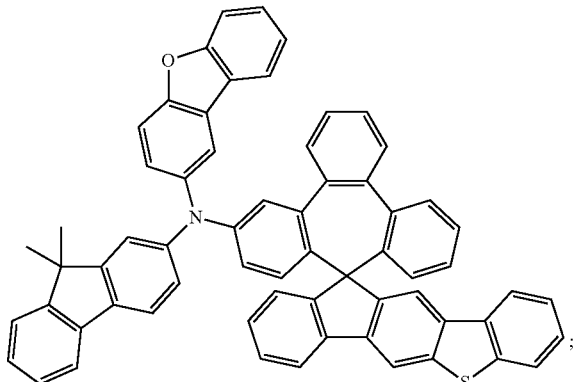
Compound 1089
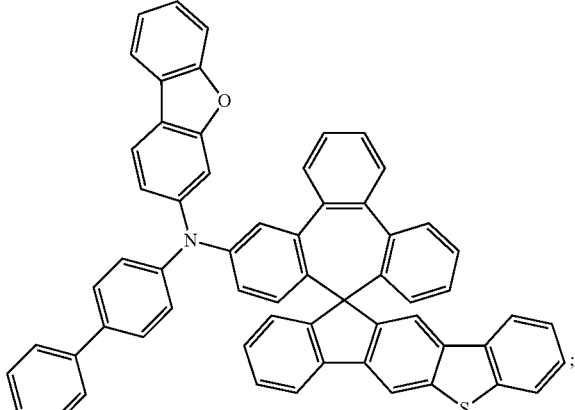
Compound 1090
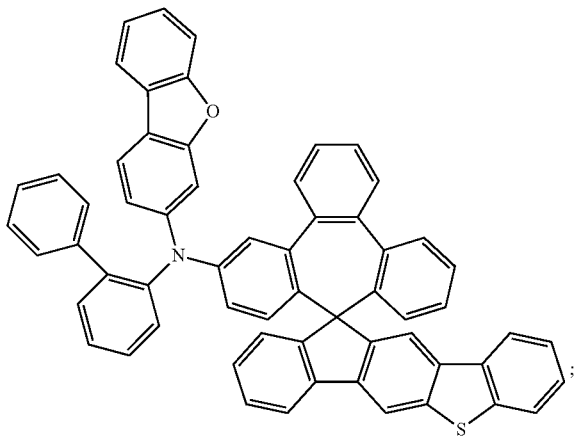

-continued
Compound 1091
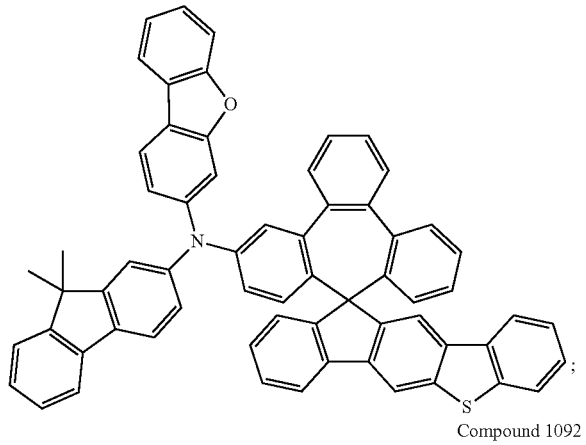
Compound 1092
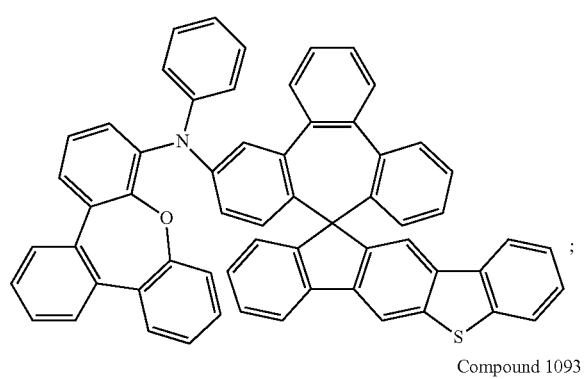
Compound 1093
Compound 1094
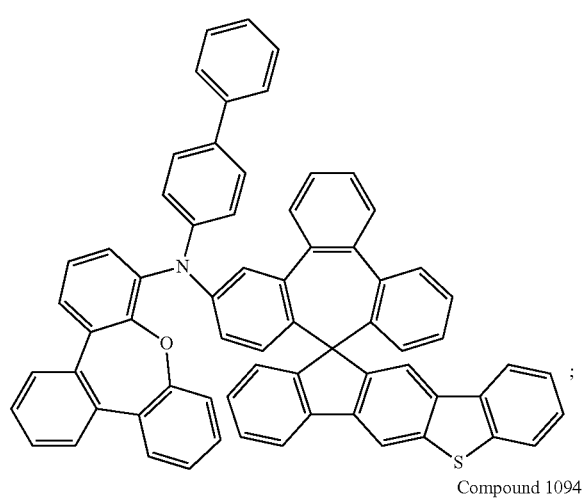
-continued
Compound 1095
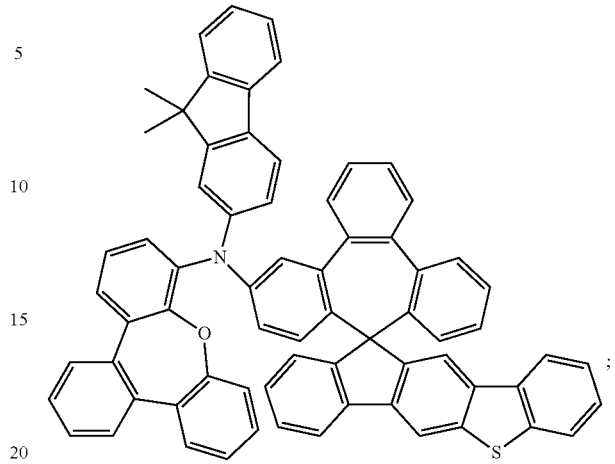
Compound 1096
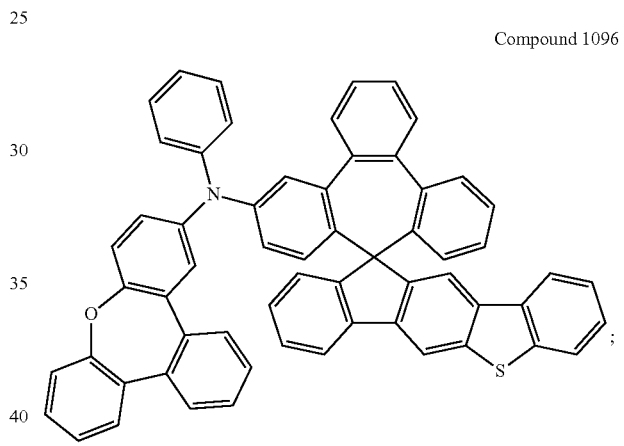
Compound 1097
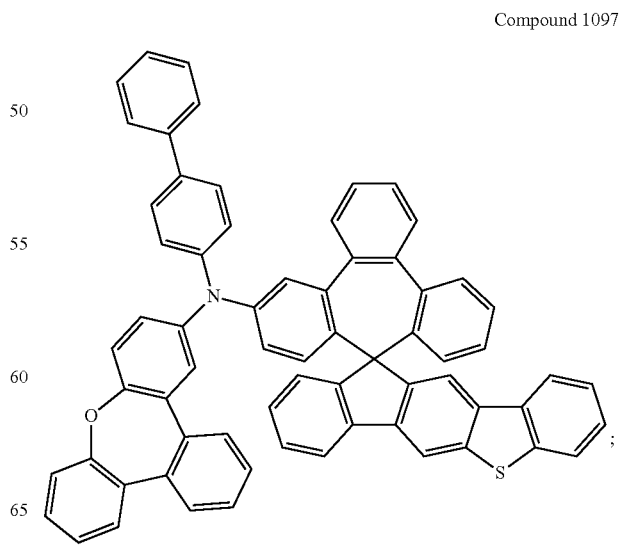

Compound 1098
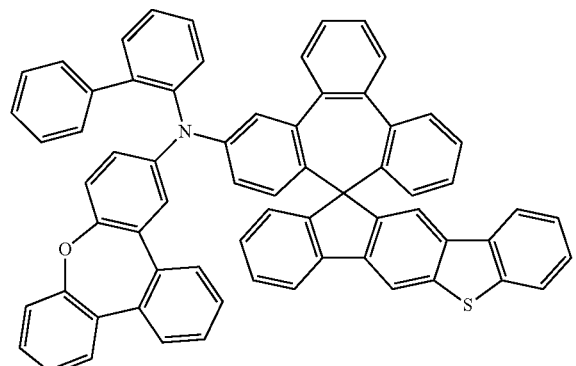
Compound 1099
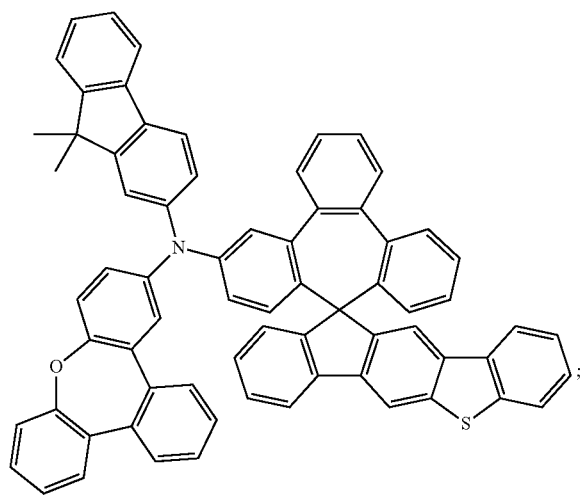
Compound 1100
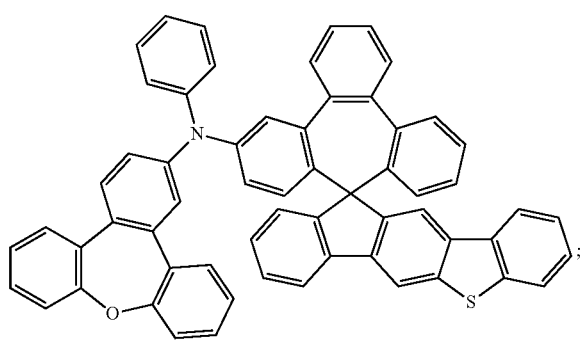
Compound 1101
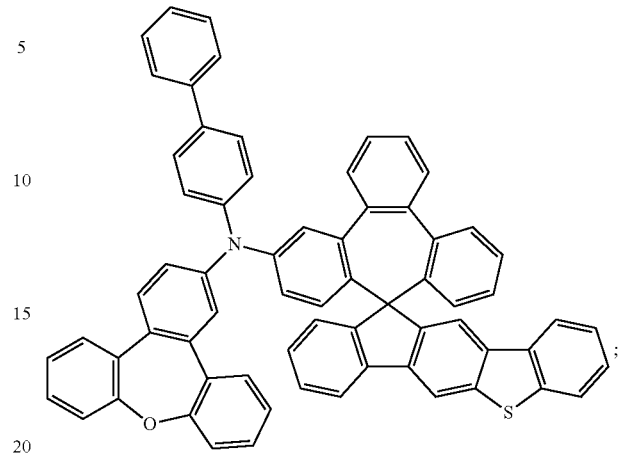
Compound 1102
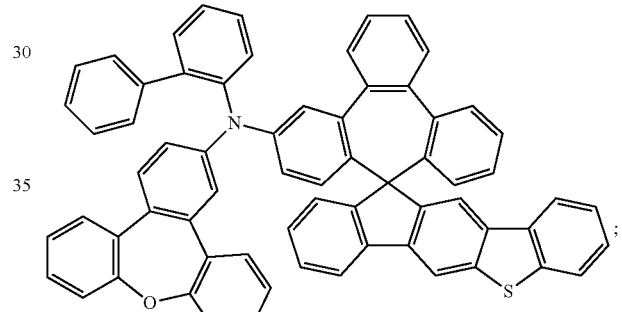
Compound 1103
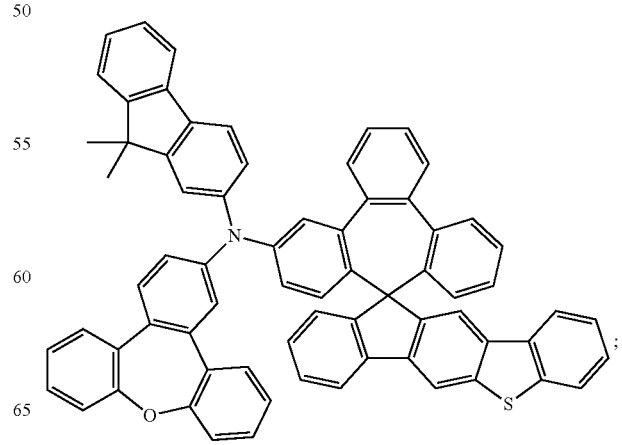

-continued
Compound 1104
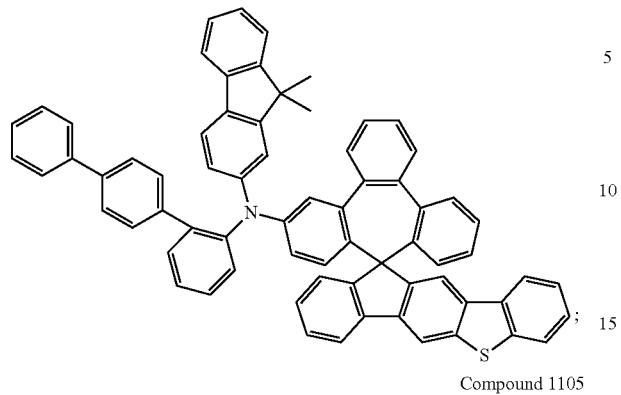
Compound 1105
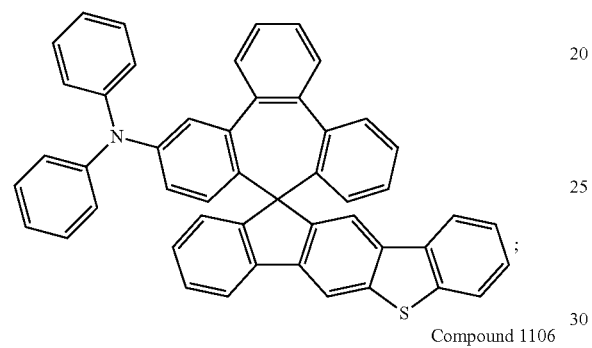
Compound 1106
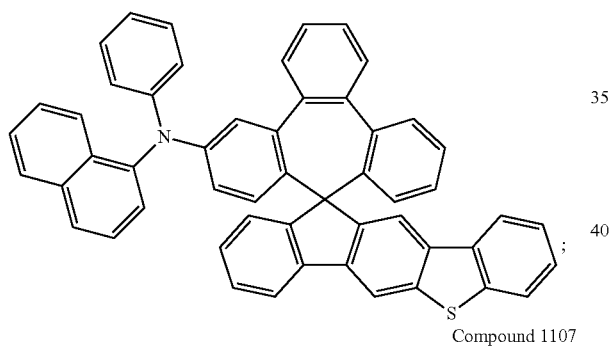
Compound 1107
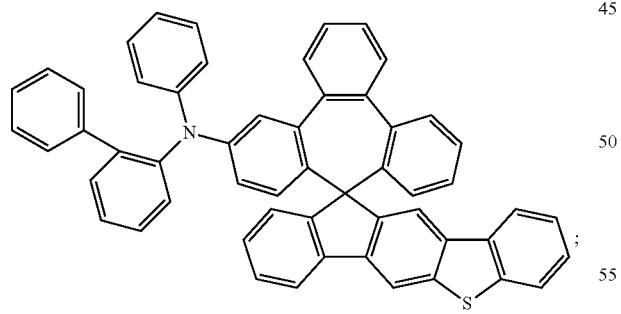
-continued
Compound 1108
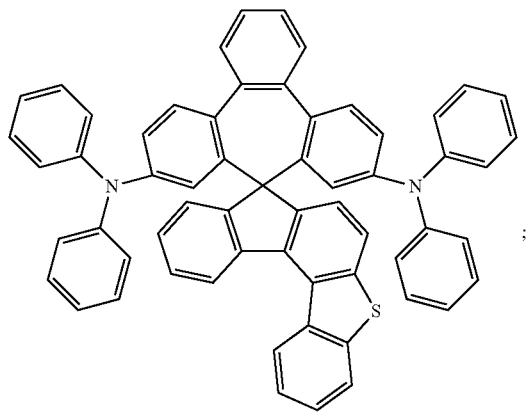
;
Compound 1109
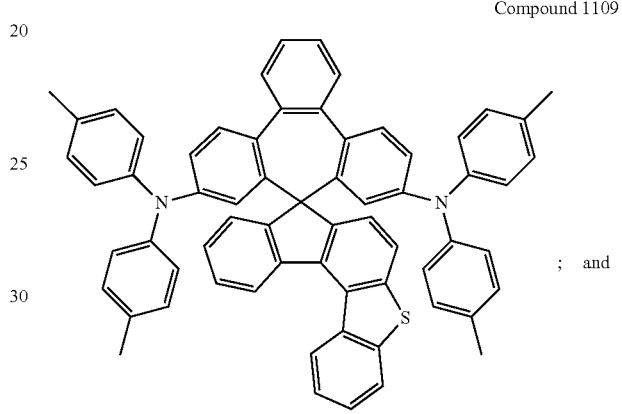
; and
Compound 1110
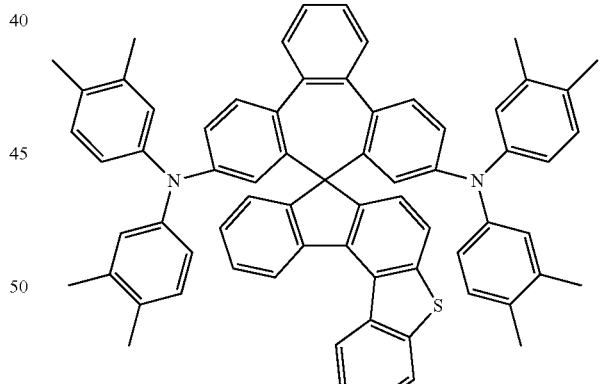
.
* * * * *